US007446176B2

(12) United States Patent
Ni et al.

(10) Patent No.: US 7,446,176 B2
(45) Date of Patent: Nov. 4, 2008

(54) 12 HUMAN SECRETED PROTEINS

(75) Inventors: Jian Ni, Germantown, MD (US); Steven M. Ruben, Brookeville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 367 days.

(21) Appl. No.: 11/246,999

(22) Filed: Oct. 11, 2005

(65) Prior Publication Data

US 2006/0099622 A1 May 11, 2006

Related U.S. Application Data

(60) Division of application No. 09/984,130, filed on Oct. 29, 2001, now abandoned, and a continuation-in-part of application No. 09/836,353, filed on Apr. 18, 2001, now abandoned, and a continuation-in-part of application No. PCT/US99/25031, filed on Oct. 27, 1999.

(60) Provisional application No. 60/243,792, filed on Oct. 30, 2000, provisional application No. 60/198,407, filed on Apr. 19, 2000, provisional application No. 60/105,971, filed on Oct. 28, 1998.

(51) Int. Cl.
*C07K 16/00* (2006.01)

(52) U.S. Cl. ................................ 530/387.1; 424/130.1

(58) Field of Classification Search ....................... None
See application file for complete search history.

(56) References Cited

U.S. PATENT DOCUMENTS

| | | | |
|---|---|---|---|
| 5,001,225 | A | 3/1991 | Taylor |
| 5,545,806 | A | 8/1996 | Lonberg et al. |
| 2003/0105000 | A1 | 6/2003 | Pero et al. |

FOREIGN PATENT DOCUMENTS

| | | | |
|---|---|---|---|
| EP | 0 869 178 A1 | 10/1998 | |
| WO | WO-82/01461 | 5/1982 | |
| WO | WO-99/51639 | 10/1999 | |
| WO | WO-02/071927 | 9/2002 | |

OTHER PUBLICATIONS

Lehnert, K. et al., "Cloning, sequence analysis, and chromosomal localization of the novel human integrin alpha11 subunit (ITGA11)", *Genomics* 60(2):179-87, Sep. 1, 1999 (abstract only).

Hillier, L. et al., "The WashU-Merck EST Project", GenBank Accession No. H16112, Jun. 27, 1995.

Adams, M.D. et al., "Initial assessment of human gene diversity and expression patterns based upon 83 million nucleotides of cDNA sequence", GenBank Accession No. AA316377, Apr. 19, 1997.

Frohme, M. et al., "Pancreatic tumor cDNAs", GenBank Accession No. U53091, Apr. 19, 1996.

Hillier, L. et al., "The WashU-Merck EST Project", GenBank Accession No. W45078, Oct. 10, 1996.

Kang, D. et al., "A peptidoglycan recognition protein in innate immunity conserved from insects to humans", GenBank Accession No. AF076483, Aug. 15, 1998.

Fraser, N.J., "Direct Submission", GenBank Accession No. AJ001016, Jun. 5, 1998.

Watson, J. D. et al., "Methods of Creating Recombinant DNA Molecules", *Recombinant DNA*, 63-77.

Zhang, WM. et al., "$\alpha_{11}\beta_1$ Integrin Recognizes the GFOGER Sequence in Interstitial Collagens", *The Journal of Biological Chemistry*, 278:(9)7270-7277 (2003).

Velling, T. et al., "cDNA Cloning and Chromosomal Localization of Human $\alpha_{11}$ Integrin", *The Journal of Biological Chemistry*, 274(36):25735-25742 (1999).

Zhang, WM. et al., "Analysis of the Human Integrin Alpha 11 gene (ITGA11) and its promoter", *Matrix Biol.* 21(6):513-523, Oct. 2002 (abstract only).

Tiger et al., "α11β1 Integrin Is a Receptor for Interstitial Collagens Involved in Cell Migration and Collagen Reorganization on Mesenchymal Nonmuscle Cells," *Devel. Biology*, 237:116-129 (2001).

Brown et al., Uniprot Accession No. Q91638, "Gene 5 protein," (Nov. 1, 1996).

Brown et al., EMBL Accession No. U37373, "*Xenopus laevis* tail-specific thyroid hormone up-regulated (gene 5) mRNA, complete cds," (Mar. 23, 1996).

Sakaguchi, M., "Eukaryotic protein secretion," *Curr. Opin. Biotech.*, 8(5):595-601 (Oct. 1997).

Supplementary Partial European Search Report, Application No. EP 99 97 2222, mailed May 24, 2005.

Bowie et al. (*Science*, 1990, 257:1306-1310).

Burgess et al. (*J. Cell Bio.*, 1990, 111:2129-2138).

Lazar et al. (*Mol Cell. Biology*, 1988, 8:1247-1252).

Scott et al. (*Nature Genetics*, 1999, 21:440-443).

Bork (*Genome Research*, 2000, 10:398-400).

Gura (*Science*, 1997, 278:1041-1042).

Jain (*Sci. Am.*, 1994, 271:58-65).

Curti (Crit. Rev. in Oncology/Hematology, 1993, 14:29-39).

Hartwell et al. (*Science*, 1997, 278:1064-1068).

Gullberg et al. (*Dev. Dyn.*, 1995, 204(1):57-65).

Johnstone and Thorpe (Immunochemistry in Practice, 2nd Ed. 1987, Blackwell Scientific Publications, Oxford, p. 30).

Alpha Diagnostic Internation, Inc. Datasheet, 1996, "Guidelines for Antibody production using SDS-gels or gel beads" electronic version available at www.4adi.com/service/sds.html.

*Primary Examiner*—Larry R. Helms
*Assistant Examiner*—Meera Natarajan

(57) ABSTRACT

The present invention relates to 12 novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

22 Claims, 67 Drawing Sheets

FIG. 1A

```
   1 GCGTCCGGGCCAAAATGCTGAGAACGTCCACTCCTAATCTGTGTGGTGGTCTGCATTGCC   60

  61 GGGCCCCCTGGCTCTCTTCTGGCATTCTCTGCCTCTGCCTCATATTCTTGTTAGGCCAGG  120

 121 TGGGCTTGCTGCAGGGACACCCCCAGTGCCTGGATTACGGGCCCCCTTTCCAGCCCCCTC  180

 181 TGCACCTTGAGTTTTGCTCTGACTATGAGTCCTTCGGCTGCTGTGATCAGCACAAGGACC  240

 241 GCCGCATCGCTGCCCGGTACTGGGACATCATGGAATATTTTGATCTGAAGAGACATGAGC  300

 301 TGTGTGGAGATTACATTAAAGACATCCTTTGCCAGGAGTGCTCGCCCTACGCAGCCCACT  360

 361 CTACGACGCCGAAAACACCCAGACGCCTCTCCGGAATCTCCCGGGCCTCTGCTCTGATTA  420

 421 CTGCTCTGCCTTCCATTCTAACTGTCACTCAGCCATTTCCCTGCTGACCAATGACCGCGG  480

 481 CCTCCAGGAGTCTCATGGAAGGGACGGTACCCGCTTCTGCCACCTCCTGGACCTTCCTGA  540

 541 CAAGGACTATTGCTTCCCTAATGTCCTGAGGAACGACTATCTCAACCGCCACCTGGGCAT  600
   1                                                            M    1

 601 GGTGGCCCAAGATCCTCAGGGCTGCCTGCAGCTCTGCCTGAGCGAGGTGGCCAACGGGCT  660
   2  V  A  Q  D  P  Q  G  C  L  Q  L  C  L  S  E  V  A  N  G  L   21

 661 GAGGAACCCCGTCTCCATGGTCCATGCTGGGGACGGCACCCATCGCTTCTTTGTTGCCGA  720
  22  R  N  P  V  S  M  V  H  A  G  D  G  T  H  R  F  F  V  A  E   41

 721 GCAGGTAGGAGTGGTGTGGGTCTACCTCCCTGATGGGAGTCGCCTGGAGCAACCCTTCCT  780
  42  Q  V  G  V  V  W  V  Y  L  P  D  G  S  R  L  E  Q  P  F  L   61

 781 GGACCTCAAGAACATCGTGTTGACCACCCCATGGATCGGGGATGAGAGAGGCTTCTTGGG  840
  62  D  L  K  N  I  V  L  T  T  P  W  I  G  D  E  R  G  F  L  G   81

 841 GTTGGCTTTTCACCCCAAATTCCGCCACAATCGCAAGTTCTATATTTATTATTCGTGCCT  900
  82  L  A  F  H  P  K  F  R  H  N  R  K  F  Y  I  Y  Y  S  C  L  101

 901 GGACAAGAAGAAGGTAGAAAAGATCCGAATTAGTGAGATGAAGGTTTCTCGGGCTGATCC  960
 102  D  K  K  K  V  E  K  I  R  I  S  E  M  K  V  S  R  A  D  P  121

 961 TAACAAAGCTGACCTGAAATCAGAGAGGGTCATCTTGGAGATTGAAGAACCAGCCTCAAA 1020
 122  N  K  A  D  L  K  S  E  R  V  I  L  E  I  E  E  P  A  S  N  141

1021 CCATAATGGCGGACAACTTCTTTTTGGCCTGGATGGCTATATGTACATATTCACTGGGGA 1080
 142  H  N  G  G  Q  L  L  F  G  L  D  G  Y  M  Y  I  F  T  G  D  161

1081 CGGGGGACAGGCTGGAGATCCCTTTGGCCTGTTTGGAAATGCTCAGAACAAAAGTTCCCT 1140
 162  G  G  Q  A  G  D  P  F  G  L  F  G  N  A  Q  N  K  S  S  L  181
```

FIG. 1B

```
1141 GCTGGGAAAAGTTTTAAGGATCGATGTGAACAGGGCAGGCTCACATGGCAAGCGGTACCG 1200
 182 L  G  K  V  L  R  I  D  V  N  R  A  G  S  H  G  K  R  Y  R  201

1201 AGTCCCCTCGGACAATCCATTTGTTTCTGAGCCAGGGGCCCACCCCGCCATCTATGCCTA 1260
 202 V  P  S  D  N  P  F  V  S  E  P  G  A  H  P  A  I  Y  A  Y  221

1261 TGGGATCAGGAACATGTGGCGTTGTGCTGTGGACCGAGGGGACCCCATCACGCGCCAGGG 1320
 222 G  I  R  N  M  W  R  C  A  V  D  R  G  D  P  I  T  R  Q  G  241

1321 CCGAGGCCGGATATTCTGTGGGGACGTGGGCCAGAACAGGTTTGAAGAGGTTGACCTCAT 1380
 242 R  G  R  I  F  C  G  D  V  G  Q  N  R  F  E  E  V  D  L  I  261

1381 TTTGAAAGGTGGAAACTATGGCTGGAGAGCAAAGGAAGGGTTTGCATGTTATGACAAAAA 1440
 262 L  K  G  G  N  Y  G  W  R  A  K  E  G  F  A  C  Y  D  K  K  281

1441 ACTTTGTCACAATGCCTCTTTGGATGATGTTCTGCCAATCTATGCTTATGGCCATGCAGT 1500
 282 L  C  H  N  A  S  L  D  D  V  L  P  I  Y  A  Y  G  H  A  V  301

1501 GGGGAAGTCAGTCACTGGAGGTTATGTCTATCGTGGTTGTGAATCCCCAAATCTCAATGG 1560
 302 G  K  S  V  T  G  G  Y  V  Y  R  G  C  E  S  P  N  L  N  G  321

1561 CCTGTATATCTTTGGAGACTTCATGAGTGGTCGACTTATGGCTTTGCAGGAAGATAGAAA 1620
 322 L  Y  I  F  G  D  F  M  S  G  R  L  M  A  L  Q  E  D  R  K  341

1621 AAACAAGAAATGGAAGAAGCAGGATCTTTGCCTGGGCAGCACCACGTCCTGTGCCTTCCC 1680
 342 N  K  K  W  K  K  Q  D  L  C  L  G  S  T  T  S  C  A  F  P  361

1681 AGGGCTGATCAGCACCCATAGCAAGTTCATCATCTCCTTTGCTGAAGATGAAGCAGGGGA 1740
 362 G  L  I  S  T  H  S  K  F  I  I  S  F  A  E  D  E  A  G  E  381

1741 GCTGTATTTCCTGGCGACCTCTTACCCAAGTGCCTATGCACCACGTGGATCTATTTACAA 1800
 382 L  Y  F  L  A  T  S  Y  P  S  A  Y  A  P  R  G  S  I  Y  K  401

1801 GTTTGTTGACCCCTCAAGGCGAGCACCCCCAGGCAAGTGCAAATACAAGCCAGTGCCCGT 1860
 402 F  V  D  P  S  R  R  A  P  P  G  K  C  K  Y  K  P  V  P  V  421

1861 GAGAACCAAGAGTAAGCGGATCCCGTTCAGACCACTCGCCAAGACAGTCTTGGACTTGCT 1920
 422 R  T  K  S  K  R  I  P  F  R  P  L  A  K  T  V  L  D  L  L  441

1921 AAAGGAACAATCAGAGAAAGCTGCTAGAAAATCTTCCAGTGCAACCTTAGCTTCTGGCCC 1980
 442 K  E  Q  S  E  K  A  A  R  K  S  S  S  A  T  L  A  S  G  P  461

1981 AGCCCAGGGTTTGTCTGAGAAAGGCTCCTCCAAGAAGCTGGCTTCTCCTACAAGCAGCAA 2040
 462 A  Q  G  L  S  E  K  G  S  S  K  K  L  A  S  P  T  S  S  K  481

2041 GAATACATTGCGAGGGCCTGGTACAAAGAAGAAAGCCAGAGTGGGGCCCCACGTCCGCCA 2100
 482 N  T  L  R  G  P  G  T  K  K  K  A  R  V  G  P  H  V  R  Q  501
```

FIG. 1C

```
2101 GGGCAAGAGGAGGAAGAGCCTGAAAAGCCACAGTGGCAGGATGAGGCCATCAGCAGAGCA 2160
502   G  K  R  R  K  S  L  K  S  H  S  G  R  M  R  P  S  A  E  Q  521

2161 GAAGCGAGCTGGCAGAAGTCTCCCTTGACCTATTGGTCAAGGTGGCCGACAGGGTGACGT 2220
522   K  R  A  G  R  S  L  P  *                                   530

2221 GAGAGAGGAGAGCCACCTCATCAAATGAAAGTCACTGCTGAATAAAGACCTTAGAAGTCT 2280

2281 GGGAAGCCAGGGTAGAGGTGGGGCAGGGCGGTTTTCCTCTCCCTGGGAAATCTTGCTGTC 2340

2341 TACTGAATAAATAAATGCACCTTCTCTGTATGCAGTGCTTCTGTGGGAGACCATATCCCA 2400

2401 GATTGCTGGTGCACCTGGGTTATGGTAAGCACTATCCATGAGCCTGCTTGGAATCACACT 2460

2461 GGATGTCTCCGTTTTGTCTTGTAAATGCCTACAACCTGAGGTAATAAATCAACATTTGCT 2520

2521 CAAACTGGCAAAAAAAAAAAAAAAAAAAAAAAAAAAAAAAAAAAAAAAAAAAAAAAAAAA 2580

2581 AAAAAAAAAAAAAAAAAAAAAAAAAAAAA 2609
```

FIG. 2A

```
                              10                  20                  30                  40
  1   M---------------------------------------                HAOAB64.aa
  1   MPKPTPNSERVSVRFPGCRTGMHMISVSLRLVFCSFIFKA                gi|1234787
  1   MLKM--------LSF-------KLLLLAVALGF----FEG                gb|AAD31172.1

                              50                  60                  70                  80
  2   ----------------------------------------                HAOAB64.aa
 41   GVLLG---------HPQCLDYGPP-------FKPLVHLEF                gi|1234787
 22   DAKFGERSEGSGARRRRCLNGNPPKRLKRRDRRVMSQLEL                gb|AAD31172.1

                              90                 100                 110                 120
  2   ----------------------------------------                HAOAB64.aa
 65   -------CSE-YETFGCCDQDRDNVIAEKYWSIMDYFDLN                gi|1234787
 62   LSGGEILCGGFYPRVSCCLQSDSPGLG---RLENKIFSAT                gb|AAD31172.1

                             130                 140                 150                 160
  2   ----------------------------------------                HAOAB64.aa
 97   NYHICGGYIKDILCQECSPYAAHLYDAEDPHTPLR---VI                gi|1234787
 99   NNSECSRLLEEIQCAPCSPHSQSLFYTPE-RDVLDGDLAL                gb|AAD31172.1

                             170                 180                 190                 200
  2   ----------------------------------------                HAOAB64.aa
134   PGLCFNYCSEFHLKCQNSITLLTEDKQIRESCDKGRDLFC                gi|1234787
138   PLLCKDYCKEFFYTCRGHIPGLLQTTA---------DEFC                gb|AAD31172.1

                             210                 220                 230                 240
  2   ---------------------------------------V                HAOAB64.aa
174   SLLNLPDEDYCFPNV-------------LHNTELNNNLGSV                gi|1234787
169   FYYARKDAGLCFPDFPRKQVRGPASNYLGQMEDYEKVGGI                gb|AAD31172.1

                             250                 260                 270                 280
  3   A-QDPQGCLQLCLSEVANGLRNPVSMVHAGDGTHRFFVAE                HAOAB64.aa
202   V-EDPEGCIKLCLIEVANGLRNPVLMLHANDGTHRMFVAE                gi|1234787
209   SRKHKHNC--LCVQEVMSGLRQPVSAVHSGDGSHRLFILE                gb|AAD31172.1

                             290                 300                 310                 320
 42   QVGVVWVYLPDGSRLEQPFLDLKNIVLTTPWIGDERGFLG                HAOAB64.aa
241   QIGFVWVYLPDGSRLYEPFLNLRRTVLATPWLGDERGLLG                gi|1234787
247   KEGYVKILTPEGELFKEPYLDIHKLVQSGIKGGDERGLLS                gb|AAD31172.1

                             330                 340                 350                 360
 82   LAFHPKFRHNRKFYIYYSCLDKK-----KVEKIRISEMKV                HAOAB64.aa
281   MAFHPKYQNNRKFYVYYSIMDEY-----RNEKIRISEFQV                gi|1234787
287   LAFHPNYKKNGKLYVSYTTNQERWAIGPHDHILRVVEYTV                gb|AAD31172.1

                             370                 380                 390                 400
117   SRADPNKADLKSERVILEIEEPASNHNGGQLLFGLDGYMY                HAOAB64.aa
316   EEHDINKADPYSERRILEIEEPAANHNGGQILFGKDGYLY                gi|1234787
327   SEKNPHQVDVRTARVFLEVAELHRKHLGGQLLFGPDGFLY                gb|AAD31172.1

                             410                 420                 430                 440
157   IFTGDGGQAGDPFGLFGNAQNKSSLLGKVLRIDVNRAGSH                HAOAB64.aa
356   IFTGDGGKAGDPFGRFGNAQNKSVLLGKVLRIDVDGRRAN                gi|1234787
367   IILGDGMIT---LDDMEEMDGLSDFTGSVLRLDVDTDMCN                gb|AAD31172.1
```

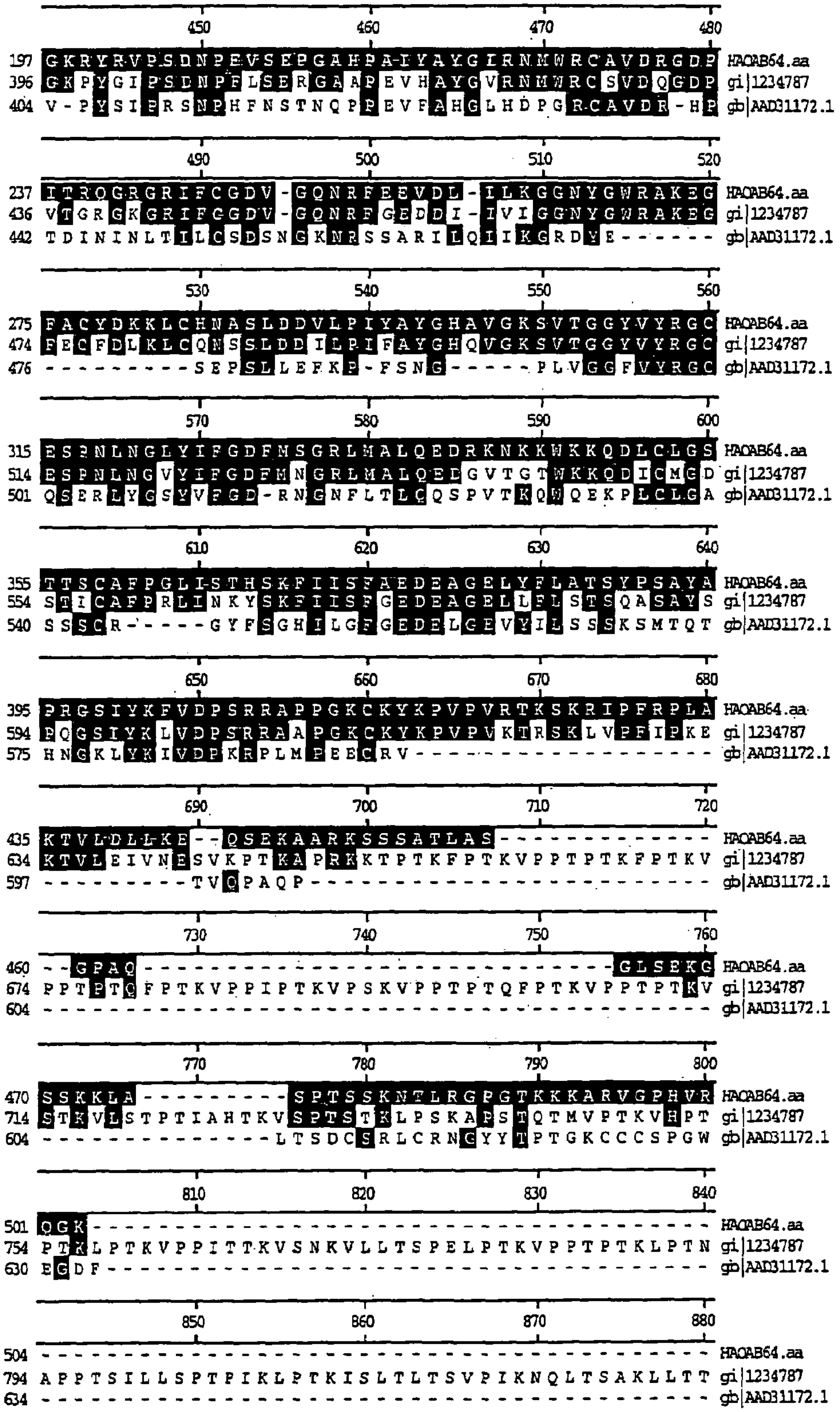

FIG. 2B

```
           450             460             470             480
197  GKRYRVPSDNPEVSEPGAHPA-IYAYGIRNMWRCAVDRGDP  HAOAB64.aa
396  GKPYGIPSDNPFLSERGAAPEVHAYGVRNMWRCSVDQGDP   gi|1234787
404  V-PYSIERSNPHFNSTNQPPEVFAHGLHDPGRCAVDR-HP   gb|AAD31172.1

           490             500             510             520
237  ITRQGRGRIFCGDV-GQNRFEEVDL-ILKGGNYGWRAKEG   HAOAB64.aa
436  VTGRGKGRIFGGDV-GQNRFGEDDI-IVIGGNYGWRAKEG   gi|1234787
442  TDININLTILCSDSNGKNRSSARILQIIKGRDYE------   gb|AAD31172.1

           530             540             550             560
275  FACYDKKLCHNASLDDVLPIYAYGHAVGKSVTGGYVYRGC   HAOAB64.aa
474  FECFDLKLCQMSSLDDILPIFAYGHQVGKSVTGGYVYRGC   gi|1234787
476  ---------SEPSLLEFKP-FSNG----PLVGGFVYRGC   gb|AAD31172.1

           570             580             590             600
315  ESPNLNGLYIFGDFMSGRLMALQEDRKNKKWKKQDLCLGS   HAOAB64.aa
514  ESPNLNGVYIFGDFMNGRLMALQEDGVTGTWKKQDICMGD   gi|1234787
501  QSERLYGSYVFGD-RNGNFLTLCQSPVTKQWQEKPLCLGA   gb|AAD31172.1

           610             620             630             640
355  TTSCAFPGLISTHSKFIISFAEDEAGELYFLATSYPSAYA   HAOAB64.aa
554  STICAFPRLINKYSKFIISFGEDEAGELLFLSTSQASAYS   gi|1234787
540  SSSCR------GYFSGHILGFGEDELGEVYILSSSKSMTQT gb|AAD31172.1

           650             660             670             680
395  PRGSIYKFVDPSRRAPPGKCKYKPVPVRTKSKRIPFRPLA   HAOAB64.aa
594  PQGSIYKLVDPSRRAAPGKCKYKPVPVKTRSKLVPFIPKE   gi|1234787
575  HNGKLYKIVDPKRPLMPEECRV-----------------  gb|AAD31172.1

           690             700             710             720
435  KTVLDLLKE--QSEKAARKSSSATLAS-------------  HAOAB64.aa
634  KTVLEIVNESVKPTKAPRKKTPTKFPTKVPPTPTKFPTKV  gi|1234787
597  --------TVCPAQP-------------------------  gb|AAD31172.1

           730             740             750             760
460  --GPAQ--------------------------GLSEKG   HAOAB64.aa
674  PPTPTCFPTKVPPIPTKVPSKVPPTPTQFPTKVPPTPTKV  gi|1234787
604  --------------------------------------   gb|AAD31172.1

           770             780             790             800
470  SSKKLA---------SPTSSKNTLRGPGTKKKARVGPHVR  HAOAB64.aa
714  STKVLSTPTIAHTKVSPTSTKLPSKAPSTQTMVPTKVHPT  gi|1234787
604  -----------LTSDCSRLCRNGYYTPTGKCCCSPGW    gb|AAD31172.1

           810             820             830             840
501  QGK------------------------------------  HAOAB64.aa
754  PTKLPTKVPPITTKVSNKVLLTSPELPTKVPPTPTKLPTN gi|1234787
630  EGDF-----------------------------------  gb|AAD31172.1

           850             860             870             880
504  ---------------------------------------  HAOAB64.aa
794  APPTSILLSPTPIKLPTKISLTLTSVPIKNQLTSAKLLTT gi|1234787
634  ---------------------------------------  gb|AAD31172.1
```

FIG. 2C

```
                      890         900         910         920
504 - - - - - - - - - - - - - - - - - - - - - - - - - - - - - - - - - - - - - - - -  HAOAB64.aa
834 T L P I S T K R A T K L P S T S T S V P S N T S C I L T H V Q P K M L P T E T R  gi|1234787
634 - - - - - - - - - C R I A K C E P A C R H G G V C V - - - - - - - - - - - - - -  gb|AAD31172.1

                      930         940         950         960
504 - - - - - - - - - - - - - - - - - - - - R R K S L K S H S G R M - - - - R P S A  HAOAB64.aa
874 V P N K M P P K P T R I P T M S M Y I T K K P P L K K N S A K K V T D K R P T K  gi|1234787
651 - - - - - - - R P N K C L C K K G Y L G P Q C E Q V D R N V E R V T - - - - - -  gb|AAD31172.1

                      970         980         990         1000
520 E Q K R A - - - - - - - - - - - - - - - - - - - - - - - - - - - - G R S L P      HAOAB64.aa
914 S P K T T K P P K P P K S K T S V V N Q P K K K E T K T G V N N K T K N L P P K  gi|1234787
678 - - - - - - - - - - - - - R A G I L D Q - - - - - - - - - I I D M T S Y L - - -  gb|AAD31172.1

                      1010        1020        1030        1040
530                                                                                HAOAB64.aa
954 A K E P K K E K K T I K V K Q P V S H Y F P P Q K P K K Q K I K K M Q K E G N E  gi|1234787
693 - - - - - - - - - - - - - - L D L T S Y I V                                      gb|AAD31172.1

530                                                                                HAOAB64.aa
994 K S                                                                            gi|1234787
700                                                                                gb|AAD31172.1
```

Decoration 'Decoration #1': Shade (with solid black) residues that match HAOAB64.aa exactly.

FIG. 4A

```
  1  CACCAGCACCCCGCCCAGAGCAGTGCCGCTGCCCAAATCCTCGCAGGCAGCTCATCAACG   60

 61  CAATTGCAACTCCGGCTGGAGCCCCGGACCTGCAAGCCTGGGTGTCCGTGGGTCCGTCTG  120

121  CCCAGCCATCTGCTGGTGGCACCTCTCCCTCCTGCCGCCTCCCTCGGTGAACCCCACCTT  180

181  GCAGAAGTGCAGCTCGCCCGGAGCAGCCCAGGAGCTCAGCATGCGTCCCCCAGGCTTCAG  240
  1                                          M  R  P  P  G  F  R    7

241  GAACTTCTTGCTGCTGGCGTCCTCCCTTCTCTTTGCTGGGTTGTCAGCTGTTCCTCAAAG  300
  8   N  F  L  L  L  A  S  S  L  L  F  A  G  L  S  A  V  P  Q  S   27

301  CTTCTCGCCATCTCTGAGGAGCTGGCCGGGCGCCGCCTGCAGGCTGTCCCGGGCCGAGTC  360
 28   F  S  P  S  L  R  S  W  P  G  A  A  C  R  L  S  R  A  E  S   47

361  GGAGCGACGCTGCCGCGCACCTGGGCAGCCCCCGGGGGCCGCGCTGTGCCACGGCCGGGG  420
 48   E  R  R  C  R  A  P  S  Q  P  P  G  A  A  L  C  H  G  R  G   67

421  CCGCTGCGACTGCGGCGTCTGCATCTGCCACGTGACTGAGCCGGGCATGTTCTTCGGGCC  480
 68   R  C  D  C  G  V  C  I  C  H  V  T  E  P  G  M  F  F  G  P   87

481  CCTGTGTGAGTGCCATGAGTGGGTGTGCGAGACCTACGACGGGAGCACCTGTGCAGGCCA  540
 88   L  C  E  C  H  E  W  V  C  E  T  Y  D  G  S  T  C  A  G  H  107

541  TGGTAAGTGTGACTGTGGCAAGTGCAAGTGTGACCAGGGATGGTATGGGGATGCTTGCCA  600
108   G  K  C  D  C  G  K  C  K  C  D  Q  G  W  Y  G  D  A  C  Q  127

601  GTACCCAACTAACTGTGACTTGACAAAGAAGAAAAGTAACCAAATGTGCAAGAATTCACA  660
128   Y  P  T  N  C  D  L  T  K  K  K  S  N  Q  M  C  K  N  S  Q  147

661  AGACATCATCTGCTCTAATGCAGGTACATGTCACTGTGGCAGGTGTAAGTGTGATAATTC  720
148   D  I  I  C  S  N  A  G  T  C  H  C  G  R  C  K  C  D  N  S  167

721  AGATGGAAGTGGACTTGTGTATGGTAAATTTTGTGAGTGTGACGATAGAGAATGCATAGA  780
168   D  G  S  G  L  V  Y  G  K  F  C  E  C  D  D  R  E  C  I  D  187

781  CGATGAAACAGAAGAAATATGTGGAGGCCATGGAAGTGTTACTGTGGAAACTGCTACTG  840
188   D  E  T  E  E  I  C  G  G  H  G  K  C  Y  C  G  N  C  Y  C  207

841  CAAGGCTGGTTGGCATGGAGATAAATGTGAATTCCAGTGCGATATCACCCCCTGGGAAAG  900
208   K  A  G  W  H  G  D  K  C  E  F  Q  C  D  I  T  P  W  E  S  227
```

FIG. 4B

```
 901  CAAGCGAAGATGCACGTCTCCAGATGGCAAAATCTGCAGTAACAGAGGGACTTGTGTATG   960
 228   K  R  R  C  T  S  P  D  G  K  I  C  S  N  R  G  T  C  V  C   247

 961  TGGTGAATGTACCTGTCACGATGTTGATCCGACTGGGGACTGGGGAGATATTCATGGGGA  1020
 248   G  E  C  T  C  H  D  V  D  P  T  G  D  W  G  D  I  H  G  D   267

1021  CACCTGTGAATGTGATGAGAGGGACTGTAGAGCTGTCTATGACCGATATTCTGATGACTT  1080
 268   T  C  E  C  D  E  R  D  C  R  A  V  Y  D  R  Y  S  D  D  F   287

1081  CTGTTCAGGTCATGGACAGTGTAATTGCGGAAGATGTGACTGCAAAGCAGGCTGGTATGG  1140
 288   C  S  G  H  G  Q  C  N  C  G  R  C  D  C  K  A  G  W  Y  G   307

1141  GAAGAAGTGTGAGCACCCACAGTCCTGCACGCTGTCAGCTGAGGAGAGCATCAGGAAGTG  1200
 308   K  K  C  E  H  P  Q  S  C  T  L  S  A  E  E  S  I  R  K  C   327

1201  CCAGGGAAGCTCGGATCTGCCTTGCTCTGGGAGGGGTAAATGTGAATGTGGCAAATGCAC  1260
 328   Q  G  S  S  D  L  P  C  S  G  R  G  K  C  E  C  G  K  C  T   347

1261  CTGCTATCCTCCAGGAGATCGCCGGGTGTATGGCAAGACTTGTGAGTGTGATGATCGCCG  1320
 348   C  Y  P  P  G  D  R  R  V  Y  G  K  T  C  E  C  D  D  R  R   367

1321  CTGTGAAGACCTCGATGGTGTGGTCTGTGGAGGCCACGGCACATGTTCCTGTGGTCGCTG  1380
 368   C  E  D  L  D  G  V  V  C  G  G  H  G  T  C  S  C  G  R  C   387

1381  TGTTTGTGAGAGAGGATGGTTTGGAAAGCTCTGCCAACATCCGCGGAAGTGTAACATGAC  1440
 388   V  C  E  R  G  W  F  G  K  L  C  Q  H  P  R  K  C  N  M  T   407

1441  GGAAGAACAAAGCAAGAATCTGTGTGAATCAGCAGATGGCATATTGTGCTCGGGGAAGGG  1500
 408   E  E  Q  S  K  N  L  C  E  S  A  D  G  I  L  C  S  G  K  G   427

1501  TTCTTGTCATTGTGGGAAGTGCATTTGTTCTGCTGAAGAGTGGTATATTTCTGGGGAGTT  1560
 428   S  C  H  C  G  K  C  I  C  S  A  E  E  W  Y  I  S  G  E  F   447

1561  CTGTGACTGTGATGACAGAGACTGCGACAAACATGATGGTCTCATTTGTACAGGGAATGG  1620
 448   C  D  C  D  D  R  D  C  D  K  H  D  G  L  I  C  T  G  N  G   467

1621  AATATGTAGCTGTGGAAACTGTGAATGCTGGGATGGATGGAATGGAAATGCATGTGAAAT  1680
 468   I  C  S  C  G  N  C  E  C  W  D  G  W  N  G  N  A  C  E  I   487

1681  CTGGCTTGGCTCAGAATATCCTTAACAATTACATGAGAGAGGTCTGGATTCTTATTTTTT  1740
 488   W  L  G  S  E  Y  P  *                                         495
```

FIG. 4C

```
1741  CTGGGCCATTAGAACATATAAATGCGAAGGAAACCATGTATATTCACCACTAGGACAGGT  1800

1801  TAAAAAGACCATTGTATGTTTTTCTATTTCTGAATTACGAATGAAATCCGAGTACCTATT  1860

1861  AGAAATGAGTTATGCAAATTTAGATGCAAATAACATTAGAAAAAAAAGATTCTTCCATAA  1920

1921  TTAACATAAGTGGTTCCTAACGAGAGCAATTTTTCCACCCAAAAGTCATTTGGCAACATC  1980

1981  TACAGACAATTTTGATTGTCACACTGGGTCGGGTAGGAAGGTATGCTGCAGACATTTGGT  2040

2041  GGGTAGAGGCCAGGGATGCTGCTGAGCATCCCGCAGTGTACAGGACAGCCCCCAAACAAG  2100

2101  GAATTATCCAGCCCCAAATGCCAATAGGGCTCAGACTGAGAAACATTGAGTTATATGGCT  2160

2161  ATTAGAAATCCACATTCTTACACAAGAAAGACCATATTAGAATCTAAGGAAAACATGCAT  2220

2221  ATTCACATTAATTAATCGATCAGATTTTTCCAGAATTCCGTATCAGTCACCATTTTAATA  2280

2281  TGGGGACAATGAAGACAAGCACACAGGAGGTAGAATATCAGAGTGGGGCTGGATCAAGGG  2340

2341  CAAAAACTGGTCATTAAGTCATCTGACATTAAATCATTTAGCCACTAAGTTATTTGTGTA  2400

2401  CTCTCACTTTAAACTCACCAAAGAAGATTCTCTTAAAGAAATTATGAAAAATGTACAATT  2460

2461  TAACATTTTAAATAAATAGTGACAGAAGTTGTTTAAAAA  2499
```

FIG. 5A

```
          10        20        30        40
1   MRPPGFRNFLLLASSLLFAGLSAVPQSFSPSLRS-WP-GA HCHCH55.aa
1   MCGSALAFF-----TAAFVCLQNDRRGPASFLWAAWVFSL gi|184521

          50        60        70        80
39  ACRLSRAESERRCRAPGQPPGAALCHGRGRCDCGVCI--- HCHCH55.aa
36  VLGLGQGE-DNRC-ASSNAASCARCLALGP-ECGWCVQED gi|184521

          90        100       110       120
76  ----------CHVTE------------------------- HCHCH55.aa
73  FISGGSRSERCDIVSNLISKGCSVDSIEYPSVHVIIPTEN gi|184521

          130       140       150       160
81  -------PG---------------------------MFFG HCHCH55.aa
113 EINTQVTPGEVSIQLRPGAEANFMLKVHPLKKYPVDLYY- gi|184521

          170       180       190       200
87  PLCECHEWVCETYDGSTCAGHG------------------ HCHCH55.aa
152 -LVDVSASMHNNIEKLNSVGNDLSRKMAFFSRDFRLGFGS gi|184521

          210       220       230       240
109 ---KCDCGKCKCDQGWYGDAC-QYPTNC----------DL HCHCH55.aa
191 YVDKTVSPYISIHPERIHNQCSDYNLDCMPPHGYIHVLSL gi|184521

          250       260       270       280
135 TKK-----KSNQMCKNSQDIICSNAG---------TC--HC HCHCH55.aa
231 TENITEFEKAVHRQKISGNIDTPEGGFDAMLQAAVCESHI gi|184521

          290       300       310       320
160 GRCKCD------------------NSDGSGLVYGKFCECDDR HCHCH55.aa
271 GWRKEAKRLLLVMTDQTSHLALDSKLAGIVVPNDGNCHLK gi|184521

          330       340       350       360
184 EC----------------------IDDETEEICGGHGKCY-- HCHCH55.aa
311 NNVYVKSTTMEHPSLGQLSEKLIDNNINVIFAVQGKQFHW gi|184521

          370       380       390       400
202 -------------CGNCYCKAGWHGDKCEFQCDITPWESKR HCHCH55.aa
351 YKDLLPLLPGTIAGEIESKAANLNNLVVEAYQKLISEVKV gi|184521

          410       420       430       440
230 RCTSPDGKICSNRGTCVCGECT-------CHDVDPTGD-W HCHCH55.aa
391 QVENQVQGIYFNI-TAICPDGSRKPGMEGCRNVTSNDEVL gi|184521

          450       460       470       480
262 GDIHGDTCECDERDCRAVYDRYSDDFCSG-----HGQCNC HCHCH55.aa
430 FNVTVTMKKCDVTGGKNYAIIKPIGFNETAKIHIHRNCSC gi|184521

          490       500       510       520
297 GRCD---------CKAGWY-GKKCEH--PQSCTLSAEE-SI HCHCH55.aa
470 -QCEDNRGPKGKCVDETFLDSKCFQCDENKCHFDELQESS gi|184521
```

FIG. 5B

```
                  530       540       550       560
325 RKCQGSSDLP-CSGRGKCECGKCTCYPPGDRRVYGKTCEC HOHCH55.aa
509 ESCKSHKDQFVCSGRGVCVCGKCSCHKIKLGKVYGKYCEK gi|184521

                  570       580       590       600
364 DDRRCEDLDGVVCGGHGTCSCGRCVCERGWFGKLCQHPRK HOHCH55.aa
549 DDFSCPYHHGNLCAGHGECEAGRCQCFSGWEGDRCQ---- gi|184521

                  610       620       630       640
404 CNMTEEQSKNLCESADGILCSGKGSCHCGKCICSAEEWYI HOHCH55.aa
585 CPSAAAQH---CVNSKGQVCSGRGTCVCGRCECTDPR--S gi|184521

                  650       660       670       680
444 SGEFCD--------CDDR----DCDKHDGLICTGNGIC-- HOHCH55.aa
620 IGRFCEHCPTCYTACKENWNCMQCLHPHNLSQAILDQCKT gi|184521

                  690       700       710       720
470 SCG----------NCECWDG-------------------- HOHCH55.aa
660 SCALMEQQHYVDQTSECFSSPSYLRIFFIIFIVTFLIGLL gi|184521

                  730       740       750       760
480 -----------WNGN----------------------AC- HOHCH55.aa
700 KVLIIRQVILQWNSNKIKSSSDYRVSASKKDKLILQSVCT gi|184521

                  770       780       790
486 -----------EIWLGSE---------YP.           HOHCH55.aa
740 RAVTYRREKPEEIKMDISKLNAHETFRCNF           gi|184521
```

Decoration 'Decoration #1': Shade (with solid black) residues that match the Consensus exactly.

FIG. 7A

```
  1  GGCACGAGAGCGTGACCCAGCTGCGGCCGGCCAGCCATGGAGACTGGAGCGCTGCGGCGC   60
  1                                      M  E  T  G  A  L  R  R      8

 61  CCGCAACTTCTCCCGTTGCTGCTGCTGCTCTGCGGTGGGTGTCCCAGAGCAGGCGGCTGC  120
  9  P  Q  L  L  P  L  L  L  L  L  C  G  G  C  P  R  A  G  G  C     28

121  AACGAGACAGGCATGTTGGAGAGGCTGCCCCTGTGTGGGAAGGCTTTCGCAGACATGATG  180
 29  N  E  T  G  M  L  E  R  L  P  L  C  G  K  A  F  A  D  M  M     48

181  GGCAAGGTGGACGTCTGGAAGTGGTGCAACCTGTCCGAGTTCATCGTGTACTATGAGAGT  240
 49  G  K  V  D  V  W  K  W  C  N  L  S  E  F  I  V  Y  Y  E  S     68

241  TTCACCAACTGCACCGAGATGGAGGCCAATGTCGTGGGCTGCTACTGGCCCAACCCCCTG  300
 69  F  T  N  C  T  E  M  E  A  N  V  V  G  C  Y  W  P  N  P  L     88

301  GCCCAGGGCTTCATCACCGGCATCCACAGGCAGTTCTTCTCCAACTGCACCGTGGACAGG  360
 89  A  Q  G  F  I  T  G  I  H  R  Q  F  F  S  N  C  T  V  D  R    108

361  GTCCACTTGGAGGACCCCCCAGACGAGGTTCTCATCCCGCTGATCGTTATACCCGTCGTT  420
109  V  H  L  E  D  P  P  D  E  V  L  I  P  L  I  V  I  P  V  V    128

421  CTGACTGTCGCCATGGCTGGCCTGGTGGTGTGGCGCAGCAAACGCACCGACACGCTGCTG  480
129  L  T  V  A  M  A  G  L  V  V  W  R  S  K  R  T  D  T  L  L    148

481  TGAGGGTCCCGGTGAGATGGAGTGGGTCACACCTGGCAAGCTGGAAGAAAGTTCCCTGGG  540
149  *                                                              149

541  GATGGGAGAGCGGGTGGGTGCTGCCAATCTCCAGCTACTGTGGCCACACCCCACCTGGTC  600

601  ATGGGCAGACCCCTCCCTTCCTGGGCTGACCTGCTCCCTCGAGGCCAGCCTGCTCCCTGG  660

661  CTGAGGCTCAGGCTATCCGCCCAAGCTCTTTGCTCATTCTAGGGCCAGTGGAGGAAAATG  720

721  TGATAAGGCCAGAGCTTGTGTGCTGGGCACAGAAATCACCTGCTGCATCCTGTGCTCCGC  780

781  AGCTGGGCCGGACCTCTGCCCGCAGGTTTCTATGCTGTTTCTTAGCACAGAATCCAGCCT  840

841  AGCCTTAGCCGCAGTCTAAGCCCTGCTTGGACTAGGACTCCTTGCTTGACCCCATCTCTG  900

901  GTTCCTGCCCTGGCTCCTGCACCAGCCCCAGCTCCTGCCTACATCCAGGCAGAAAGATAG  960
```

FIG. 7B

```
 961  CAGGGGCTCTTGGAAGACGTTCCGTGCTGTGACCTCCGAGCCCTCCTGGTGGGAAGACAG  1020
1021  CTGGAAAGGCTGGGAGGAGAAGGGAGGGGTTGGGGGTTCCCAGGAGCCATGCGTGGCCTG  1080
1081  CAGAGTCCATTCCATCATGATGCTGTGCCCGCTATGGGCTGTGTCCATGACCAGAGGCTG  1140
1141  GAGTGGGGGTGTGTTAGAGCCCCTCACCGGGACTTGCTGTGCGGATGGGGCCTGGGCCTC  1200
1201  CTTCCTACAGGGGCTCCTCTGTGGGTGAGGGGCCCTCTGGAATGGCATCCCATGAGCTTG  1260
1261  TGGCCTCTATCTGCTACCATCTGTGTTTTATCTGAGTAAAGTTACCTTACTTCTGGAAAA  1320
1321  AAAAAAAAAAAAAAAAAAA  1339
```

FIG. 8

```
                         10        20        30        40
1    METG--ALRRPQLLPLL---LLLCGGCPRAGGCNETGMLE  HTLEW81.aa
1    MAPGLRGLPRCGLWLLLAHHLFMVTACRDP----DYGTLI  gi|4587099

                         50        60        70        80
36   RLPLCGKAFADMMGKVDVWKWCNLSEFIVYYESFTNCTEM  HTLEW81.aa
37   Q-ELCLSRFKENMETIGKTLWCDWGKTIQSYGELTYCTKH  gi|4587099

                         90       100       110       120
76   EANVVGCYWPNPLAQGFITGIHRQFFSNCTVDRVHLEDPP  HTLEW81.aa
76   VAHTIGCFWPNPEVDRFFIAVHHRYFSKCPISGRALRDPP  gi|4587099

                        130       140       150
116  DEVLIPLIVIPVVLTVAMAGLVVWRSKRTDTLL.        HTLEW81.aa
116  NSILCPFIALPITVTLLMTALVVWRSKRTEGI-V        gi|4587099
```

Decoration 'Decoration #1': Shade (with solid black) residues that match the Consensus exactly.

FIG. 10A

1 GGCACGAGGACAGCCTCCACCAGAGTCCCCACCTTTCTGGAAGCTGCAGGGCTCTCCATC 60

61 CAGGATCCAGAAGCATTGAAGGGGACCAGCCGCTGAAGGGATTCTCAGTCCCATCTGACT 120

121 CCCCATGAGGCTCCTGGCTTTCCTGAGTCTGCTGGCCTTGGTGCTGCAGGAGACAGGGAC 180
1 M R L L A F L S L L A L V L Q E T G T 19

181 AGCTTCTCTCCCAAGGAAGGAGAGGAAGAGGAGAGAGGAGCAGATGCCCAGGGAAGGCGA 240
20 A S L P R K E R K R R E E Q M P R E G D 39

241 TTCCTTTGAAGTTCTGCCTCTGCGGAATGATGTCCTGAACCCAGACAACTATGGTGAAGT 300
40 S F E V L P L R N D V L N P D N Y G E V 59

301 CATTGACCTGAGCAACTATGAGGAGCTCACAGATTATGGGGACCAACTCCCCGAGGTTAA 360
60 I D L S N Y E E L T D Y G D Q L P E V K 79

361 GGTGACTAGCCTCGCTCCTGCAACCAGCATCAGTCCCGCCAAGAGCACTACGGCTCCAGG 420
80 V T S L A P A T S I S P A K S T T A P G 99

421 GACACCCTCGTCAAACCCCACGATGACCAGACCTACTACAGCAGGGCTGCTACTGAGTTC 480
100 T P S S N P T M T R P T T A G L L L S S 119

481 CCAGCCCAACCATGGTCTGCCCACCTGCCTGGTCTGCGTGTGCCTCGGTTCCTCTGTGTA 540
120 Q P N H G L P T C L V C V C L G S S V Y 139

541 TTGCGATGACATTGACCTAGAGGACATTCCTCCTCTTCCTCGGAGGACTGCCTACCTGTA 600
140 C D D I D L E D I P P L P R R T A Y L Y 159

601 TGCACGCTTCAACCGCATCAGCCGTATCAGGGCCGAAGACTTCAAAGGGCTGACAAAGTT 660
160 A R F N R I S R I R A E D F K G L T K L 179

661 GAAGAGGATTGACCTCTCCAACAACCTCATTTCCTCCATCGATAATGATGCCTTCCGCCT 720
180 K R I D L S N N L I S S I D N D A F R L 199

721 GCTACATGCCCTCCAGGACCTCATCCTCCCAGAGAACCAGTTGGAAGCTCTGCCCGTGCT 780
200 L H A L Q D L I L P E N Q L E A L P V L 219

781 GCCCAGTGGCATTGAGTTCCTGGATGTCCGCCTAAATCGGCTCCAGAGCTCGGGGATACA 840
220 P S G I E F L D V R L N R L Q S S G I Q 239

841 GCCTGCAGCCTTCAGGGCAATGGAGAAGCTGCAGTTCCTTTACCTGTCAGACAACCTGCT 900
240 P A A F R A M E K L Q F L Y L S D N L L 259

FIG. 10B

```
901   GGATTCTATCCCGGGGCCTTTGCCCCCGAGCCTGCGCTCTGTACACCTGCAGAATAACCT   960
260    D  S  I  P  G  P  L  P  P  S  L  R  S  V  H  L  Q  N  N  L    279

961   GATAGAGACCATGCAGAGAGACGTCTTCTGTGACCCCGAGGAGCACAAACACACCCGCAG   1020
280    I  E  T  M  Q  R  D  V  F  C  D  P  E  E  H  K  H  T  R  R    299

1021  GCAGCTGGAAGACATCCGCCTGGATGGCAACCCCATCAACCTCAGCCTCTTCCCCAGCGC   1080
300    Q  L  E  D  I  R  L  D  G  N  P  I  N  L  S  L  F  P  S  A    319

1081  CTACTTCTGCCTGCCTCGGCTCCCCATCGGCCGCTTCACGTAGCTCGGAGCGCTTCCACT   1140
320    Y  F  C  L  P  R  L  P  I  G  R  F  T                          333

1141  CCTCCCAGGTCATCTCTTGGACCAGCGGGCATCACATTCTCCAGCAGCCGCCATCTCACA   1200

1201  CGCCTCCCTCCTGTGGCCGCCGGCAGCATGGACAAAGGTCTCCATGCAGGGGGAGGAGGC   1260

1261  CTGCTTCTTTCCCCACAGCTCTCACGTCTCCCTTCTCCCTGCGGGTGACAAAGAAGCCCA   1320

1321  AGGACCACCTCCTTCCTGCCTCATTGTAATAAAATTCCCCACACTGAAAAAAAAAAAAAA   1380

1381  AAAAAAAAA  1389
```

FIG. 11

```
                10        20        30        40
1    MRLLAFLSLLALVLQE---TGTASLPRKERKRREEQMPRE HARAO44.aa
1    MGMLARVALGLIIIDAVLAAPTTELFNYDSEVYDAILEDT gi|1620005

                50        60        70        80
38   GDSFEVLPERNDVLNPDNYGEVIDLSNYEELTDYGDQLPE HARAO44.aa
41   GTFYNYEHIPDNHVENEKVSE--RLSGNRELLTPGPQLGD gi|1620005

                90       100       110       120
78   VKVTSLAPATSISPAKSTTAPGTPSSNPTMTRPTTAGLLL HARAO44.aa
79   NQ----------DEDKDEESTPRLIDGSSPQEPEFPGLL- gi|1620005

               130       140       150       160
118  SSQPNHGLPTCLVCVCLGSSVYCDDIDLEDIPPLPRRTAY HARAO44.aa
108  GPHTNEDFPTCLLCTCISTTVYCDDHELDAIPPLPKKTTY gi|1620005

               170       180       190       200
158  LYARFNRISRIRAEDFKGLTKLKRIDLSNNLISSIDNDAF HARAO44.aa
148  FYSRFNRIKKINKNDFASLNDLKRIDLTSNLISEIDEDAF gi|1620005

               210       220       230       240
198  RLLHALQDLILPENQLEALPVLPSGIEFLDVRLNRLQSSG HARAO44.aa
188  RKLPHLQELVLRDNKIKQLPELPNTLTFIDISNNRLGRKG gi|1620005

               250       260       270       280
238  IQPAAFRAMEKLQFLYLSDNLLDSIPGPLPPSLRSVHLQN HARAO44.aa
228  IKQEAFKDMYDLHHLYITDNSLDHIPLPLPESLRALHLQN gi|1620005

               290       300       310       320
278  NLIETMQRDVFCDPEEHKHTRRQLEDIRLDGNPINLSLFP HARAO44.aa
268  NDILEMHEDTFCNVKNLTYVRKALEDIRLDGNPINLSRTP gi|1620005

               330
318  SAYFCLPRLPIGRFT.                         HARAO44.aa
308  QAYMCLPRLPIGSF-I                         gi|1620005
```

Decoration 'Decoration #1': Shade (with solid black) residues that match the Consensus exactly.

FIG. 13A

```
  1  CCACGCGTCCGAGAGAACAGGCCTGTCTCAGGCAGGCCCTGCGCCTCCTATGCGGAGATG   60
  1                                                           M    1

 61  CTACTGCCACTGCTGCTGTCCTCGCTGCTGGGCGGGTCCCAGGCTATGGATGGGAGATTC  120
  2  L  L  P  L  L  L  S  S  L  L  G  G  S  Q  A  M  D  G  R  F    21

121  TGGATACGAGTGCAGGAGTCAGTGATGGTGCCGGAGGCCTGTGACATCTCTGTGCCCTGC  180
 22  W  I  R  V  Q  E  S  V  M  V  P  E  A  C  D  I  S  V  P  C    41

181  TCTTTCTCCTACCCCCGACAAGACTGGACAGGGTCTACCCCAGCTTATGGCTACTGGTTC  240
 42  S  F  S  Y  P  R  Q  D  W  T  G  S  T  P  A  Y  G  Y  W  F    61

241  AAAGCAGTGACTGAGACAACCAAGGGTGCTCCTGTGGCCACAAACCACCAGAGTCGAGAG  300
 62  K  A  V  T  E  T  T  K  G  A  P  V  A  T  N  H  Q  S  R  E    81

301  GTGGAAATGAGCACCCGGGGCCGATTCCAGCTCACTGGGGATCCCGCCAAGGGGAACTGC  360
 82  V  E  M  S  T  R  G  R  F  Q  L  T  G  D  P  A  K  G  N  C   101

361  TCCTTGGTGATCAGAGACGCGCAGATGCAGGATGAGTCACAGTACTTCTTTCGGGTGGAG  420
102  S  L  V  I  R  D  A  Q  M  Q  D  E  S  Q  Y  F  F  R  V  E   121

421  AGAGGAAGCTATGTGAGATATAATTTCATGAACGATGGGTTCTTTCTAAAAGTAACAGTG  480
122  R  G  S  Y  V  R  Y  N  F  M  N  D  G  F  F  L  K  V  T  V   141

481  CTCAGCTTCACGCCCAGACCCCAGGACCACAACACCGACCTCACCTGCCATGTGGACTTC  540
142  L  S  F  T  P  R  P  Q  D  H  N  T  D  L  T  C  H  V  D  F   161

541  TCCAGAAAGGGTGTGAGCGCACAGAGGACCGTCCGACTCCGTGTGGCCTATGCCCCCAGA  600
162  S  R  K  G  V  S  A  Q  R  T  V  R  L  R  V  A  Y  A  P  R   181

601  GACCTTGTTATCAGCATTTCACGTGACAACACGCCAGCCCTGGAGCCCCAGCCCCAGGGA  660
182  D  L  V  I  S  I  S  R  D  N  T  P  A  L  E  P  Q  P  Q  G   201

661  AATGTCCCATACCTGGAAGCCCAAAAAGGCCAGTTCCTGCGGCTCCTCTGTGCTGCTGAC  720
202  N  V  P  Y  L  E  A  Q  K  G  Q  F  L  R  L  L  C  A  A  D   221

721  AGCCAGCCCCCTGCCACACTGAGCTGGGTCCTGCAGAACAGAGTCCTCTCCTCGTCCCAT  780
222  S  Q  P  P  A  T  L  S  W  V  L  Q  N  R  V  L  S  S  S  H   241

781  CCCTGGGGCCCTAGACCCCTGGGGCTGGAGCTGCCCGGGGTGAAGGCTGGGGATTCAGGG  840
242  P  W  G  P  R  P  L  G  L  E  L  P  G  V  K  A  G  D  S  G   261
```

FIG. 13B

841 CGCTACACCTGCCGAGCGGAGAACAGGCTTGGCTCCCAGCAGCGAGCCCTGGACCTCTCT 900
262 R Y T C R A E N R L G S Q Q R A L D L S 281

901 GTGCAGTATCCTCCAGAGAACCTGAGAGTGATGGTTTCCCAAGCAAACAGGACAGTCCTG 960
282 V Q Y P P E N L R V M V S Q A N R T V L 301

961 GAAAACCTTGGGAACGGCACGTCTCTCCCAGTACTGGAGGGCCAAAGCCTGTGCCTGGTC 1020
302 E N L G N G T S L P V L E G Q S L C L V 321

1021 TGTGTCACACACAGCAGCCCCCCAGCCAGGCTGAGCTGGACCCAGAGGGGACAGGTTCTG 1080
322 C V T H S S P P A R L S W T Q R G Q V L 341

1081 AGCCCCTCCCAGCCCTCAGACCCCGGGGTCCTGGAGCTGCCTCGGGTTCAAGTGGAGCAC 1140
342 S P S Q P S D P G V L E L P R V Q V E H 361

1141 GAAGGAGAGTTCACCTGCCACGCTCGGCACCCACTGGGCTCCCAGCACGTCTCTCTCAGC 1200
362 E G E F T C H A R H P L G S Q H V S L S 381

1201 CTCTCCGTGCACTACTCCCCGAAGCTGCTGGGCCCCTCCTGCTCCTGGGAGGCTGAGGGT 1260
382 L S V H Y S P K L L G P S C S W E A E G 401

1261 CTGCACTGCAGCTGCTCCTCCCAGGCCAGCCCGGCCCCCTCTCTGCGCTGGTGGCTTGGG 1320
402 L H C S C S S Q A S P A P S L R W W L G 421

1321 GAGGAGCTGCTGGAGGGGAACAGCAGCCAGGACTCCTTCGAGGTCACCCCCAGCTCAGCC 1380
422 E E L L E G N S S Q D S F E V T P S S A 441

1381 GGGCCCTGGGCCAACAGCTCCCTGAGCCTCCATGGAGGGCTCAGCTCCGGCCTCAGGCTC 1440
442 G P W A N S S L S L H G G L S S G L R L 461

1441 CGCTGTGAGGCCTGGAACGTCCATGGGGCCCAGAGTGGATCCATCCTGCAGCTGCCAGAT 1500
462 R C E A W N V H G A Q S G S I L Q L P D 481

1501 AAGAAGGGACTCATCTCAACGGCATTCTCCAACGGAGCGTTTCTGGGAATCGGCATCACG 1560
482 K K G L I S T A F S N G A F <u>L G I G I T</u> 501

1561 GCTCTTCTTTTCCTCTGCCTGGCCCTGATCATCATGAAGATTCTACCGAAGAGACGGACT 1620
502 <u>A L L F L C L A L L I I</u> M K I L P K R R T 521

1621 CAGACAGAAACCCCGAGGCCCAGGTTCTCCCGGCACAGCACGATCCTGGATTACATCAAT 1680
522 Q T E T P R P R F S R H S T I L D Y I N 541

FIG. 13C

```
1681 GTGGTCCCGACGGCTGGCCCCCTGGCTCAGAAGCGGAATCAGAAAGCCACACCAAACAGT 1740
542  V  V  P  T  A  G  P  L  A  Q  K  R  N  Q  K  A  T  P  N  S  561

1741 CCTCGGACCCCTCTTCCACCAGGTGCTCCCTCCCCAGAATCAAAGAAGAACCAGAAAAAG 1800
562  P  R  T  P  L  P  P  G  A  P  S  P  E  S  K  K  N  Q  K  K  581

1801 CAGTATCAGTTGCCCAGTTTCCCAGAACCCAAATCATCCACTCAAGCCCCAGAATCCCAG 1860
582  Q  Y  Q  L  P  S  F  P  E  P  K  S  S  T  Q  A  P  E  S  Q  601

1861 GAGAGCCAAGAGGAGCTCCATTATGCCACGCTCAACTTCCCAGGCGTCAGACCCAGGCCT 1920
602  E  S  Q  E  E  L  H  Y  A  T  L  N  F  P  G  V  R  P  R  P  621

1921 GAGGCCCGGATGCCCAAGGGCACCCAGGCGGATTATGCAGAAGTCAAGTTCCAATGAGGG 1980
622  E  A  R  M  P  K  G  T  Q  A  D  Y  A  E  V  K  F  Q  *     640

1981 TCTCTTAGGCTTTAGGACTGGGACTTCGGCTAGGAGGAAGGTAGAGTAGAAGTTGAAGAT 2040

2041 AACCGAGTGCAAGAGTTTCCTTCTCTCCCTCTCTCTCTCTCTTTCTCTCTCTCTCTCTCT 2100

2101 TTCTCTCTCTTTTTAAAAAAACTCTGGCCACGGCACAGTGGCTCACGCCTGTAATCCCAG 2160

2161 CACTTTGGGAAGTTGAAGTTGGGCCAAATCCCCTGAGTCCGGATTCGAAAACAGCCTGGC 2220

2221 CAACTTGTGAAAACCCGTCTCTACTTAAAAATACCCAAATTACCTGGGCATTGTGGCAGG 2280

2281 GGCCTGTTTATCCTT 2295
```

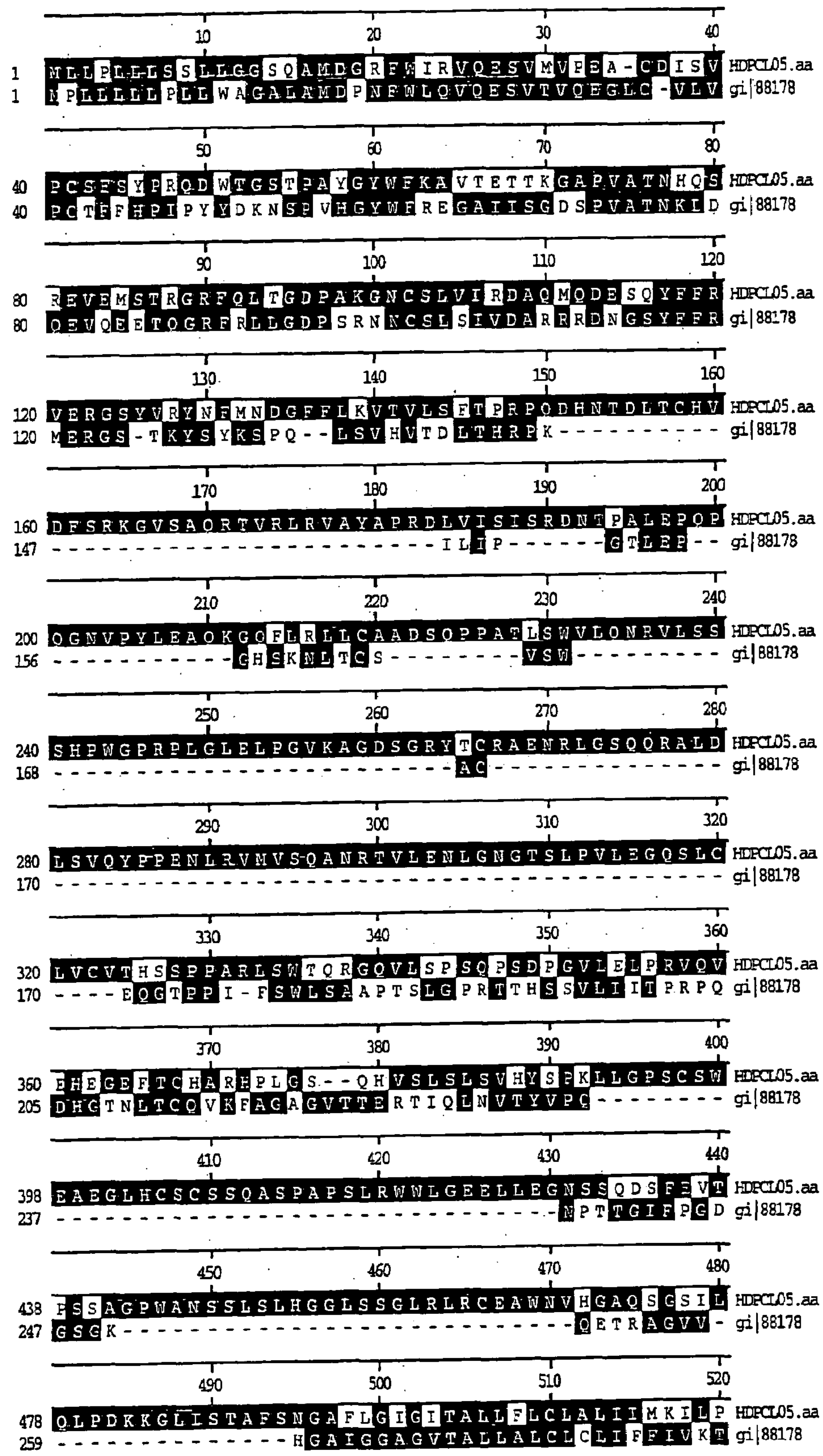

FIG. 14A

```
                    10              20              30              40
  1  MLLPLLLSSLLGGSQAMDGRFWIRVQESVMVEEA-CDISV   HDPCL05.aa
  1  MPLLLLLPLLWAGALAMDPNFWLQVQESVTVQEGLC-VLV   gi|88178

                    50              60              70              80
 40  PCSFSYPRQDWTGSTPAYGYWFKAVTETTKGAPVATNHQS   HDPCL05.aa
 40  PCTFHPIPYYDKNSPVHGYWFREGAIISGDSPVATNKID   gi|88178

                    90             100             110             120
 80  REVEMSTRGRFQLTGDPAKGNCSLVIRDAQMODESQYFFR   HDPCL05.aa
 80  QEVQEETQGRFRLLGDPSRNNCSLSIVDARRRDNGSYFFR   gi|88178

                   130             140             150             160
120  VERGSVVRYNFMNDGFFLKVTVLSETPRPQDHNTDLTCHV   HDPCL05.aa
120  MERGS-TKYSYKSPQ--LSVHVTDLTHRPK----------  gi|88178

                   170             180             190             200
160  DFSRKGVSAQRTVRLRVAYAPRDLVISISRDNTPALEPQP   HDPCL05.aa
147  -------------------ILIP-----GTLEP--       gi|88178

                   210             220             230             240
200  QGNVPYLEAQKGQFLRLLCAADSQPPATLSWVLQNRVLSS   HDPCL05.aa
156  --------GHSKNLTCS--------VSW-----------   gi|88178

                   250             260             270             280
240  SHPWGPRPLGLELPGVKAGDSGRYTCRAENRLGSQQRALD   HDPCL05.aa
168  ----------------------AC--------------   gi|88178

                   290             300             310             320
280  LSVQYPPENLRVMVSQANRTVLENLGNGTSLPVLEGQSLC   HDPCL05.aa
170  --------------------------------------   gi|88178

                   330             340             350             360
320  LVCVTHSSPPARLSWTQRGQVLSPSQPSDPGVLELPRVQV   HDPCL05.aa
170  ----EQGTPPI-FSWLSAAPTSLGPRTTHSSVLIITPRPQ  gi|88178

                   370             380             390             400
360  EHEGEFTCHAREPLGS--QHVSLSLSVHYSPKLLGPSCSW   HDPCL05.aa
205  DHGTNLTCQVKFAGAGVTTERTIQLNVTYVPC-------  gi|88178

                   410             420             430             440
398  EAEGLHCSCSSQASPAPSLRWWLGEELLEGNSSQDSFEVT   HDPCL05.aa
237  -----------------------------NPTTGIFPGD  gi|88178

                   450             460             470             480
438  PSSAGPWANSSLSLHGGLSSGLRLRCEAWNVHGAQSGSIL   HDPCL05.aa
247  GSGK-------------------------QETRAGVV-   gi|88178

                   490             500             510             520
478  QLPDKKGLISTAFSNGAFLGIGITALLFLCLALIIMKILP   HDPCL05.aa
259  ------------HGAIGGAGVTALLALCLCLIFFIVKT   gi|88178
```

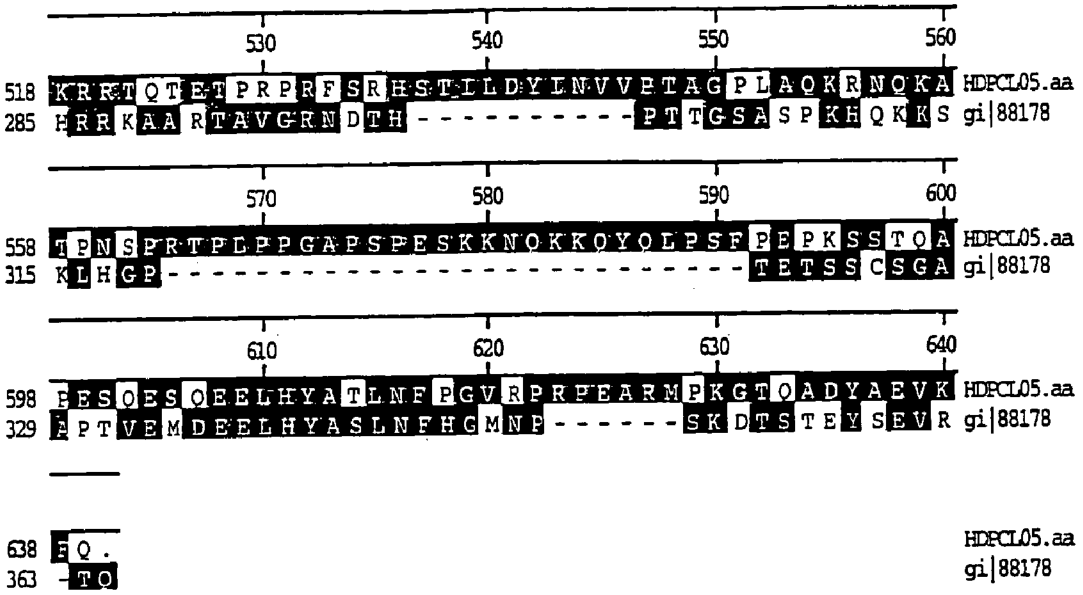

FIG. 14B

```
                530            540            550            560
518 KRRTQTETPRPRFSRHSTILDYINVVETAGPLAQKRNQKA HDPCL05.aa
285 HRRKAARTAVGRNDTH----------PTTGSASPKHQKKS gi|88178

                570            580            590            600
558 TPNSPRTPLPPGAPSPESKKNQKKQYQLPSFPEPKSSTQA HDPCL05.aa
315 KLHGP----------------------TETSSCSGA gi|88178

                610            620            630            640
598 PESQESQEELHYATLNFPGVRPRPEARMPKGTQADYAEVK HDPCL05.aa
329 APTVEMDEELHYASLNFHGMNP------SKDTSTEYSEVR gi|88178

638 EQ.  HDPCL05.aa
363 -TQ  gi|88178
```

Decoration 'Decoration #1': Shade (with solid black) residues that match the Consensus exactly.

FIG. 16A

```
  1  AGACGTTCCCTCGCGGCCCTGGCACCTCCAACCCCAGATATGCTGCTGCTGCTGCTGCTG   60
  1                                          M  L  L  L  L  L  L    7

 61  CCCCTGCTCTGGGGGAGGGAGAGGGTGGAAGGACAGAAGAGTAACCGGAAGGATTACTCG  120
  8  P  L  L  W  G  R  E  R  V  E  G  Q  K  S  N  R  K  D  Y  S   27

121  CTGACGATGCAGAGTTCCGTGACCGTGCAAGAGGGCATGTGTGTCCATGTGCGCTGCTCC  180
 28  L  T  M  Q  S  S  V  T  V  Q  E  G  M  C  V  H  V  R  C  S   47

181  TTCTCCTACCCAGTGGACAGCCAGACTGACTCTGACCCAGTTCATGGCTACTGGTTCCGG  240
 48  F  S  Y  P  V  D  S  Q  T  D  S  D  P  V  H  G  Y  W  F  R   67

241  GCAGGGAATGATATAAGCTGGAAGGCTCCAGTGGCCACAAACAACCCAGCTTGGGCAGTG  300
 68  A  G  N  D  I  S  W  K  A  P  V  A  T  N  N  P  A  W  A  V   87

301  CAGGAGGAAACTCGGGACCGATTCCACCTCCTTGGGGACCCACAGACCAAAAATTGCACC  360
 88  Q  E  E  T  R  D  R  F  H  L  L  G  D  P  Q  T  K  N  C  T  107

361  CTGAGCATCAGAGATGCCAGAATGAGTGATGCGGGGAGATACTTCTTTCGTATGGAGAAA  420
108  L  S  I  R  D  A  R  M  S  D  A  G  R  Y  F  F  R  M  E  K  127

421  GGAAATATAAAATGGAATTATAAATATGACCAGCTCTCTGTGAACGTGACAGCCTTGACC  480
128  G  N  I  K  W  N  Y  K  Y  D  Q  L  S  V  N  V  T  A  L  T  147

481  CACAGGCCCAACATCCTTATCCCCGGTACCCTGGAGTCTGGCTGCTTCCAGAATCTGACC  540
148  H  R  P  N  I  L  I  P  G  T  L  E  S  G  C  F  Q  N  L  T  167

541  TGCTCTGTGCCCTGGGCCTGTGAGCAGGGGACGCCCCCTATGATCTCCTGGATGGGGACC  600
168  C  S  V  P  W  A  C  E  Q  G  T  P  P  M  I  S  W  M  G  T  187

601  TCTGTGTCCCCCCTGCACCCCTCCACCACCCGCTCCTCAGTGCTCACCCTCATCCCACAG  660
188  S  V  S  P  L  H  P  S  T  T  R  S  S  V  L  T  L  I  P  Q  207

661  CCCCAGCACCACGGCACCAGCCTCACCTGTCAGGTGACCTTGCCTGGGGCCGGCGTGACC  720
208  P  Q  H  H  G  T  S  L  T  C  Q  V  T  L  P  G  A  G  V  T  227

721  ACGAACAGGACCATCCAACTCAATGTGTCCTACCCTCCTCAGAACTTGACTGTGACTGTC  780
228  T  N  R  T  I  Q  L  N  V  S  Y  P  P  Q  N  L  T  V  T  V  247

781  TTCCAAGGAGAAGGCACAGCATCCACAGCTCTGGGGAACAGCTCATCTCTTTCAGTCCTA  840
248  F  Q  G  E  G  T  A  S  T  A  L  G  N  S  S  S  L  S  V  L  267
```

FIG. 16B

```
841   GAGGGCCAGTCTCTGCGCTTGGTCTGTGCTGTTGACAGCAATCCCCCTGCCAGGCTGAGC   900
268   E  G  Q  S  L  R  L  V  C  A  V  D  S  N  P  P  A  R  L  S     287

901   TGGACCTGGAGGAGTCTGACCCTGTACCCCTCACAGCCCTCAAACCCTCTGGTACTGGAG   960
288   W  T  W  R  S  L  T  L  Y  P  S  Q  P  S  N  P  L  V  L  E     307

961   CTGCAAGTGCACCTGGGGGATGAAGGGGAATTCACCTGTCGAGCTCAGAACTCTCTGGGT   1020
308   L  Q  V  H  L  G  D  E  G  E  F  T  C  R  A  Q  N  S  L  G     327

1021  TCCCAGCACGTTTCCCTGAACCTCTCCCTGCAACAGGAGTACACAGGCAAAATGAGGCCT   1080
328   S  Q  H  V  S  L  N  L  S  L  Q  Q  E  Y  T  G  K  M  R  P     347

1081  GTATCAGGAGTGTTGCTGGGGGCGGTCGGGGGAGCTGGAGCCACAGCCCTGGTCTTCCTC   1140
348   V  S  G  V  L  L  G  A  V  G  G  A  G  A  T  A  L  V  F  L     367

1141  TCCTTCTGTGTCATCTTCATTGTAGTGAGGTCCTGCAGGAAGAAATCGGCAAGGCCAGCA   1200
368   S  F  C  V  I  F  I  V  V  R  S  C  R  K  K  S  A  R  P  A     387

1201  GCGGACGTGGGAGACATAGGCATGAAGGATGCAAACACCATCAGGGGCTCAGCCTCTCAG   1260
388   A  D  V  G  D  I  G  M  K  D  A  N  T  I  R  G  S  A  S  Q     407

1261  GGTAACCTGACTGAGTCCTGGGCAGATGATAACCCCCGACACCATGGCCTGGCTGCCCAC   1320
408   G  N  L  T  E  S  W  A  D  D  N  P  R  H  H  G  L  A  A  H     427

1321  TCCTCAGGGGAGGAAAGAGAGATCCAGTATGCACCCCTCAGCTTTCATAAGGGGGAGCCT   1380
428   S  S  G  E  E  R  E  I  Q  Y  A  P  L  S  F  H  K  G  E  P     447

1381  CAGGACCTATCAGGTCAAGAAGCCACCAACAATGAGTACTCAGAGATCAAGATCCCCAAG   1440
448   Q  D  L  S  G  Q  E  A  T  N  N  E  Y  S  E  I  K  I  P  K     467

1441  TAAGAAAATGCAGAGGCTCGGGCTTGTTTGAGGGTTCACGACCCCTCCAGCAAAGGAGTC   1500
468   *                                                              468

1501  TGAGGCTGATTCCAGTAGAATTAGCAGCCCTCAATGCTGTGCAACAAGACATCAGAACTT   1560

1561  ATTCCTCTTGTCTAACTGAAAATGCATGCCTGATGACCAAACTCTCCCTTTCCCCATCCA   1620

1621  ATCGGTCCACACTCCCCGCCCTGGCCTCTGGTACCCACCATTCTCCTCTGTACTTCTCTA   1680

1681  AGGATGACTACTTTAGATTCCGAATATAGTGAGATTGTAACGTGAAAAAAAAAAAAAAAA   1740

1741  AAAAAAAA  1748
```

FIG. 17

```
                  10        20        30        40
1    MLLLLLLPLLWGRERVEGQKSNRKDYSLTMQSSVTVQEGM HDPUW68.aa
1    MLPLLL-PLLWA-----GALAQERRFQLEGPESLTVQEGL gi|2913995

                  50        60        70        80
41   CVHVRCSFSYPVDSQTDSDPVHGYWFRAGNDISWKAPVAT HDPUW68.aa
35   CVLVPCRLPTTLPASYYG---YGYWFLEGADV----PVAT gi|2913995

                  90       100       110       120
81   NNPAWAVQEETRDRFHLLGDPQTKNCTLSIRDARMSDAGR HDPUW68.aa
68   NDPDEEVQEETRGRFHLLWDPRRKNCSLSIRDARRRDNAA gi|2913995

                 130       140       150       160
121  YFFRMEKGNIKWNYKYDQLSVNVTALTHRPNILIPGTLES HDPUW68.aa
108  YFFRLKSKWMKYGYTSSKLSVRVMALTHRPNISIPGTLES gi|2913995

                 170       180       190       200
161  GCFQNLTCSVPWACEQGTPPMISWMGTSVSPLHPSTTRSS HDPUW68.aa
148  GHPSNLTCSVPWVCEQGTPPIFSWMSAAPTSLGPRTTQSS gi|2913995

                 210       220       230       240
201  VLTLIPQPQHHGTSLTCQVTLPGAGVTTNRTIQLNVSYPP HDPUW68.aa
188  VLTITPRPQDHSTNLTCQVTFPGAGVTMERTIQLNVSYAP gi|2913995

                 250       260       270       280
241  QNLTVTVFQGEGTASTALGNSSSLSVLEGQSLRLVCAVDS HDPUW68.aa
228  QKVAISIFQGNSAAFKILQNTSSLPVLEGQALRLLCDADG gi|2913995

                 290       300       310       320
281  NPPARLSWTWRSLTLYPSQPSNPLVLEL-QVHLGDEGEFT HDPUW68.aa
268  NPPAHLSWFQGFPALNATPISNTGVLELPQVGSAEEGDFT gi|2913995

                 330       340       350       360
320  CRAQNSLGSQHVSLNLSLQQEYTGKMRPVSGVLLGAVGGA HDPUW68.aa
308  CRAQHPLGSLQISLSLFVHWKPEGR----AGGVLGAVWGA gi|2913995

                 370       380       390       400
360  GATALVFLSFCVIFIVVRSCRKKSARPAADVGDIGMKDAN HDPUW68.aa
344  SITTLVFLCVCFIFRV-KTRRKKAAQPVQNTDDV-----N gi|2913995

                 410       420       430       440
400  TIRGSASQGNLTESWADDNPRHHGLAAHSSGEEREIQYAP HDPUW68.aa
378  PVMVSGSRGHQHQFQTGIVSDHPAEAGPISEDEQELHYAV gi|2913995

                 450       460
440  LSFHKGEPQDLSGQEATNNEYSEIKIPK.            HDPUW68.aa
413  LHFHKVQPQE---PKVTDTEYSEIKIH-K            gi|2913995
```

Decoration 'Decoration #1': Shade (with solid black) residues that match the Consensus exactly.

FIG. 19A

1 GCCGCGCCGAGGAGGCTGCCGCTCTGGCTTGCCGCCCCCCGCCGCCGCTGCACACCGGAC 60

61 CCAGCCGCCGTGCCGCGGGCCATGGACCTGCCCAGGGGCCTGGTGGTGGCCTGGGCGCTC 120
1 M D L P R G L V V A W A L 13

121 AGCCTGTGGCCAGGGTTCACGGACACCTTCAACATGGACACCAGGAAGCCCCGGGTCATC 180
14 S L W P G F T D T F N M D T R K P R V I 33

181 CCTGGCTCCAGGACCGCCTTCTTTGGCTACACAGTGCAGCAGCACGACATCAGTGGCAAT 240
34 P G S R T A F F G Y T V Q Q H D I S G N 53

241 AAGTGGCTGGTCGTGGGCGCCCCACTGGAAACCAATGGCTACCAGAAGACGGGAGACGTG 300
54 K W L V V G A P L E T N G Y Q K T G D V 73

301 TACAAGTGTCCAGTGATCCACGGGAACTGCACCAAACTCAACCTGGGAAGGGTCACCCTG 360
74 Y K C P V I H G N C T K L N L G R V T L 93

361 TCCAACGTGTCCGAGCGGAAAGACAACATGCGCCTCGGCCTTAGTCTCGCCACCAACCCC 420
94 S N V S E R K D N M R L G L S L A T N P 113

421 AAGGACAACAGCTTCCTGGCCTGCAGCCCCCTCTGGTCTCATGAGTGTGGGAGCTCCTAC 480
114 K D N S F L A C S P L W S H E C G S S Y 133

481 TACACCACAGGGATGTGTTCAAGAGTCAACTCCAACTTCAGGTTCTCCAAGACCGTGGCC 540
134 Y T T G M C S R V N S N F R F S K T V A 153

541 CCAGCTCTCCAAAGGTGCCAGACCTACATGGACATCGTCATTGTCCTGGATGGCTCCAAC 600
154 P A L Q R C Q T Y M D I V I V L D G S N 173

601 AGCATCTACCCCTGGGTGGAGGTTCAGCACTTCCTCATCAACATCCTGAAAAAGTTTTAC 660
174 S I Y P W V E V Q H F L I N I L K K F Y 193

661 ATTGGCCCAGGGCAGATCCAGGTTGGAGTTGTGCAGTATGGCGAAGATGTGGTGCATGAG 720
194 I G P G Q I Q V G V V Q Y G E D V V H E 213

721 TTTCACCTCAATGACTACAGGTCTGTAAAAGATGTGGTGGAAGCTGCCAGCCACATTGAG 780
214 F H L N D Y R S V K D V V E A A S H I E 233

781 CAGAGAGGAGGAACAGAGACCCGGACGGCATTTGGCATTGAATTTGCACGCTCAGAGGCT 840
234 Q R G G T E T R T A F G I E F A R S E A 253

FIG. 19B

```
841  TTCCAGAAGGGTGGAAGGAAAGGAGCCAAGAAGGTGATGATTGTCATCACAGATGGGGAG  900
254  F  Q  K  G  G  R  K  G  A  K  K  V  M  I  V  I  T  D  G  E   273

901  TCCCACGACAGCCCAGACCTGGAGAAGGTGATCCAGCAAAGCGAAAGAGACAACGTAACA  960
274  S  H  D  S  P  D  L  E  K  V  I  Q  Q  S  E  R  D  N  V  T   293

961  AGATATGCGGTGGCCGTCCTGGGCTACTACAACCGCAGGGGGATCAATCCAGAAACTTTT  1020
294  R  Y  A  V  A  V  L  G  Y  Y  N  R  R  G  I  N  P  E  T  F   313

1021 CTAAATGAAATCAAATACATCGCCAGTGACCCTGATGACAAGCACTTCTTCAATGTCACT  1080
314  L  N  E  I  K  Y  I  A  S  D  P  D  D  K  H  F  F  N  V  T   333

1081 GATGAGGCTGCCTTGAAGGACATTGTCGATGCCCTGGGGGACAGAATCTTCAGCCTGGAA  1140
334  D  E  A  A  L  K  D  I  V  D  A  L  G  D  R  I  F  S  L  E   353

1141 GGCACCAACAAGAACGAGACCTCCTTTGGGCTGGAGATGTCACAGACGGGCTTTTCCTCG  1200
354  G  T  N  K  N  E  T  S  F  G  L  E  M  S  Q  T  G  F  S  S   373

1201 CACGTGGTGGAGGATGGGGTTCTGCTGGGAGCCGTCGGTGCCTATGACTGGAATGGAGCT  1260
374  H  V  V  E  D  G  V  L  L  G  A  V  G  A  Y  D  W  N  G  A   393

1261 GTGCTAAAGGAGACGAGTGCCGGGAAGGTCATTCCTCTCCGCGAGTCCTACCTGAAAGAG  1320
394  V  L  K  E  T  S  A  G  K  V  I  P  L  R  E  S  Y  L  K  E   413

1321 TTCCCCGAGGAGCTCAAGAACCATGGTGCATACCTGGGGTACACAGTCACATCGGTCGTG  1380
414  F  P  E  E  L  K  N  H  G  A  Y  L  G  Y  T  V  T  S  V  V   433

1381 TCCTCCAGGCAGGGGCGAGTGTACGTGGCCGGAGCCCCCCGGTTCAACCACACGGGCAAG  1440
434  S  S  R  Q  G  R  V  Y  V  A  G  A  P  R  F  N  H  T  G  K   453

1441 GTCATCCTGTTCACCATGCACAACAACCGGAGCCTCACCATCCACCAGGCTATGCGGGGC  1500
454  V  I  L  F  T  M  H  N  N  R  S  L  T  I  H  Q  A  M  R  G   473

1501 CAGCAGATAGGCTCTTACTTTGGGAGTGAAATCACCTCGGTGGACATCGACGGCGACGGC  1560
474  Q  Q  I  G  S  Y  F  G  S  E  I  T  S  V  D  I  D  G  D  G   493

1561 GTGACTGATGTCCTGCTGGTGGGCGCACCCATGTACTTCAACGAGGGCCGTGAGCGAGGC  1620
494  V  T  D  V  L  L  V  G  A  P  M  Y  F  N  E  G  R  E  R  G   513

1621 AAGGTGTACGTCTATGAGCTGAGACAGAACCGGTTTGTTTATAACGGAACGCTAAAGGAT  1680
514  K  V  Y  V  Y  E  L  R  Q  N  R  F  V  Y  N  G  T  L  K  D   533
```

FIG. 19C

```
1681 TCACACAGTTACCAGAATGCCCGATTTGGGTCCTCCATTGCCTCAGTTCGAGACCTCAAC 1740
534  S H S Y Q N A R F G S S I A S V R D L N                      553

1741 CAGGATTCCTACAATGACGTGGTGGTGGGAGCCCCCCTGGAGGACAACCACGCAGGAGCC 1800
554  Q D S Y N D V V V G A P L E D N H A G A                      573

1801 ATCTACATCTTCCACGGCTTCCGAGGCAGCATCCTGAAGACACCTAAGCAGAGAATCACA 1860
574  I Y I F H G F R G S I L K T P K Q R I T                      593

1861 GCCTCAGAGCTGGCTACCGGCCTCCAGTATTTTGGCTGCAGCATCCACGGGCAATTGGAC 1920
594  A S E L A T G L Q Y F G C S I H G Q L D                      613

1921 CTCAATGAGGATGGGCTCATCGACCTGGCAGTGGGAGCCCTTGGCAACGCTGTGATTCTG 1980
614  L N E D G L I D L A V G A L G N A V I L                      633

1981 TGGTCCCGCCCAGTGGTTCAGATCAATGCCAGCCTCCACTTTGAGCCATCCAAGATCAAC 2040
634  W S R P V V Q I N A S L H F E P S K I N                      653

2041 ATCTTCCACAGAGACTGCAAGCGCAGTGGCAGGGATGCCACCTGCCTGGCCGCCTTCCTC 2100
654  I F H R D C K R S G R D A T C L A A F L                      673

2101 TGCTTCACGCCCATCTTCCTGGCACCCCATTTCCAAACAACAACTGTTGGCATCAGATAC 2160
674  C F T P I F L A P H F Q T T T V G I R Y                      693

2161 AACGCCACCATGGATGAGAGGCGGTATACACCGAGGGCCCACCTGGACGAGGGCGGGGAC 2220
694  N A T M D E R R Y T P R A H L D E G G D                      713

2221 CGATTCACCAACAGAGCCGTACTGCTCTCCTCCGGCCAGGAGCTCTGTGAGCGGATCAAC 2280
714  R F T N R A V L L S S G Q E L C E R I N                      733

2281 TTCCATGTCCTGGACACTGCTGACTACGTGAAGCCAGTGACCTTCTCAGTCGAGTATTCC 2340
734  F H V L D T A D Y V K P V T F S V E Y S                      753

2341 CTGGAGGACCCTGACCATGGCCCCATGCTGGACGACGGCTGGCCCACCACTCTCAGAGTC 2400
754  L E D P D H G P M L D D G W P T T L R V                      773

2401 TCGGTGCCCTTCTGGAACGGCTGCAATGAGGATGAGCACTGTGTCCCTGACCTTGTGTTG 2460
774  S V P F W N G C N E D E H C V P D L V L                      793

2461 GATGCCCGGAGTGACCTGCCCACGGCCATGGAGTACTGCCAGAGGGTGCTGAGGAAGCCT 2520
794  D A R S D L P T A M E Y C Q R V L R K P                      813
```

FIG. 19D

```
2521 GCGCAGGACTGCTCCGCATACACGCTGTCCTTCGACACCACAGTCTTCATCATAGAGAGC 2580
 814 A Q D C S A Y T L S F D T T V F I I E S 833

2581 ACACGCCAGCGAGTGGCGGTGGAGGCCACACTGGAGAACAGGGGCGAGAACGCCTACAGC 2640
 834 T R Q R V A V E A T L E N R G E N A Y S 853

2641 ACGGTCCTAAATATCTCGCAGTCAGCAAACCTGCAGTTTGCCAGCTTGATCCAGAAGGAG 2700
 854 T V L N I S Q S A N L Q F A S L I Q K E 873

2701 GACTCAGACGGTAGCATTGAGTGTGTGAACGAGGAGAGGAGGCTCCAGAAGCAAGTCTGC 2760
 874 D S D G S I E C V N E E R R L Q K Q V C 893

2761 AACGTCAGCTATCCCTTCTTCCGGGCCAAGGCCAAGGTGGCTTTCCGTCTTGATTTTGAG 2820
 894 N V S Y P F F R A K A K V A F R L D F E 913

2821 TTCAGCAAATCCATCTTCCTACACCACCTGGAGATCGAGCTCGCTGCAGGCAGTGACAGT 2880
 914 F S K S I F L H H L E I E L A A G S D S 933

2881 AATGAGCGGGACAGCACCAAGGAAGACAACGTGGCCCCCTTACGCTTCCACCTCAAATAC 2940
 934 N E R D S T K E D N V A P L R F H L K Y 953

2941 GAGGCTGACGTCCTCTTCACCAGGAGCAGCAGCCTGAGCCACTACGAGGTCAAGCTCAAC 3000
 954 E A D V L F T R S S S L S H Y E V K L N 973

3001 AGCTCGCTGGAGAGATACGATGGTATCGGGCCTCCCTTCAGCTGCATCTTCAGGATCCAG 3060
 974 S S L E R Y D G I G P P F S C I F R I Q 993

3061 AACTTGGGCTTGTTCCCCATCCACGGGATTATGATGAAGATCACCATTCCCATCGCCACC 3120
 994 N L G L F P I H G I M M K I T I P I A T 1013

3121 AGGAGCGGCAACCGCCTACTGAAGCTGAGGGACTTCCTCACGGACGAGGTAGCGAACACG 3180
1014 R S G N R L L K L R D F L T D E V A N T 1033

3181 TCCTGTAACATCTGGGGCAATAGCACTGAGTACCGGCCCACCCCAGTGGAGGAAGACTTG 3240
1034 S C N I W G N S T E Y R P T P V E E D L 1053

3241 CGTCGTGCTCCACAGCTGAATCACAGCAACTCTGATGTCGTCTCCATCAACTGCAATATA 3300
1054 R R A P Q L N H S N S D V V S I N C N I 1073

3301 CGGCTGGTCCCCAACCAGGAAATCAATTTCCATCTACTGGGGAACCTGTGGTTGAGGTCC 3360
1074 R L V P N Q E I N F H L L G N L W L R S 1093
```

FIG. 19E

```
3361 CTAAAAGCACTCAAGTACAAATCCATGAAAATCATGGTCAACGCAGCCTTGCAGAGGCAG 3420
1094 L K A L K Y K S M K I M V N A A L Q R Q 1113

3421 TTCCACAGCCCCTTCATCTTCCGTGAGGAGGATCCCAGCCGCCAGATCGTGTTTGAGATC 3480
1114 F H S P F I F R E E D P S R Q I V F E I 1133

3481 TCCAAGCAAGAGGACTGGCAGGTCCCCATCTGGATCATTGTAGGCAGCACCCTGGGGGGC 3540
1134 S K Q E D W Q V P I W I I V G S T L G G 1153

3541 CTCCTACTGCTGGCCCTGCTGGTCCTGGCACTGTGGAAGCTCGGCTTCTTTAGAAGTGCC 3600
1154 L L L L A L L V L A L W K L G F F R S A 1173

3601 AGGCGCAGGAGGGAGCCTGGTCTGGACCCCACCCCCAAAGTGCTGGAGTGAGGCTCCAGA 3660
1174 R R R R E P G L D P T P K V L E * 1190

3661 GGAGACTTTGAGTTGATGGGGGCCAGGACACCAGTCCAGGTAGTGTTGAGACCCAGGCCT 3720

3721 GTGGCCCCACCGAGCTGGAGCGGAGAGGAAGCCAGCTGGCTTTGCACTTGACCTCATCTC 3780

3781 CCGAGCAATGGCGCCTGCTCCCTCCAGAATGGAACTCAAGCTGGTTTTAAGTGGAACTGC 3840

3841 CCTACTGGGAGACTGGGACACCTTTAACACAGACCCCTAGGGATTTAAAGGGACACCCCT 3900

3901 ACACACACCCAGGCCCACGCCAAGGCCTCCCTCAGGCTCTGTGGAGGGCATTTGCTGCCC 3960

3961 CAGCTACTAAGGTGCTAGGAATTCGTAATCATCCCCATCCTCCAGAGAAACCCAGGGAGG 4020

4021 AAGACTGTAAATACGAACCCAATCTGCACACTCCAGGCCTCTAGTTCCAGAAGGATCCAA 4080

4081 GACAAAACAGATCTGAATTCTGCCCTTTTCTCTCACCCATCCCACCCCTCCATTGGCTCC 4140

4141 CAAGTCACACCCACTCCCTTCCCCATAGATAGGCCCCTGGGGCTCCCGAAGAATGAACCC 4200

4201 AAGAGCAAGGGCTTGATGGTGACAGCTGCAAGCCAGGGATGAAGAAAGACTCTGAGATGT 4260

4261 GGAGACTGATGGCCAGGCAAGTGGGACCAGGATACTGGACGCTGTCCTGAGATGAGAGGT 4320

4321 AGCCGGGCTCTGCACCCACGTGCATTCACATTGACCGCAACTCACACATTCCCCCACCAG 4380
```

FIG. 19F

4381 CTGCAGCCCCTTGCTCTCAGCTGCCAACCCTCCCGGGTCACTTTTGTTCCCAGGTACCTC 4440

4441 ATGGGAAGCATGTGGATGACACAATCCCTGGGGCTGTGCATTCCCACGTCTTCTTGCTGC 4500

4501 AGCCTGCCCCTAGACATGGACGCACCGGCCTGGCTGCAGCTGGGCAGCAGGGGTAGGGGT 4560

4561 AGGGAGCCTCCCCTCCCTGTATCACCCCCTCCCTACACACACACACACACACACACACAC 4620

4621 ACACTGCCTCCCATCCTTCCCTCATGCCCGCCAGTGCACAGGGAAGGGCTTGGCCAGCGC 4680

4681 TGTTGAGGGGTCCCCTCTGGAATGCACTGAATAAAGCACGTGCAAGGACTCCCGGAGCCT 4740

4741 GTGCAGCCTTGGTGGCAAATATCTCATCTGCCGGCCCCCAGGACAAGTGGTATGACCAGT 4800

4801 GATAATGCCCCAAGGACAAGGGGCGTGCCTGGCGCCCAGTGGAGTAATTTATGCCTTAGT 4860

4861 CTTGTTTTGAGGTAGAAATGCAAGGGGGACACATGAAAGGCATCAGTCCCCCTGTGCATA 4920

4921 GTACGACCTTTACTGTCGTATTTTTGAAAAATTAAAAATACAGTGTTTAAAAACAAAAAA 4980

4981 AAAAAAAAAAAAAAA 4995

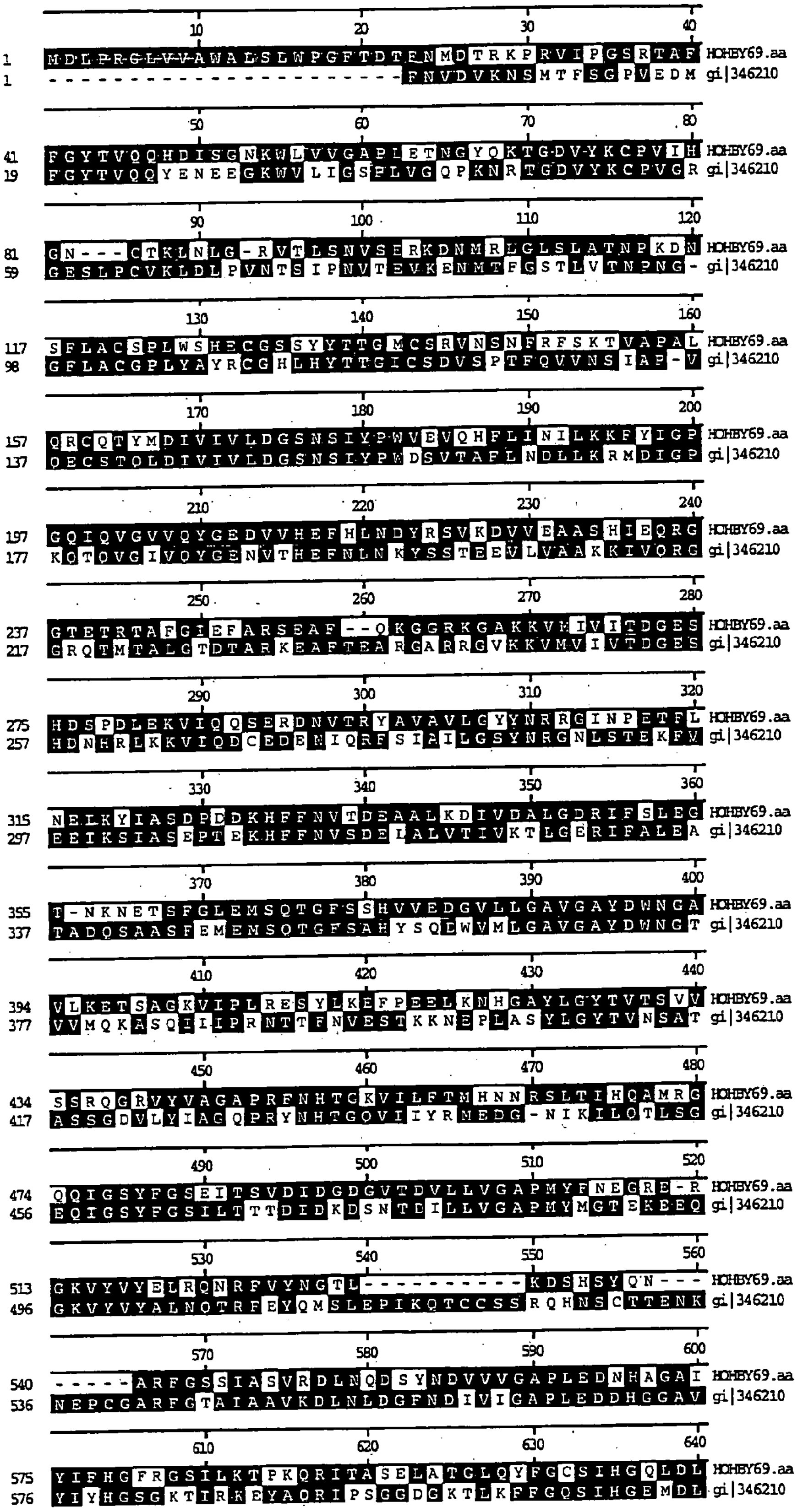

FIG. 20A

```
                10              20              30              40
1   MDLPRGLVVAWALSLWPGFTDTENMDTRKPRVIPGSRTAF HOHBY69.aa
1   --------------------FNVDVKNSMTFSGPVEDM  gi|346210

                50              60              70              80
41  FGYTVQQHDISGNKWLVVGAPLETNGYQKTGDVYKCPVIH HOHBY69.aa
19  FGYTVQQYENEEGKWVLIGSPLVGQPKNRTGDVYKCPVGR gi|346210

                90             100             110             120
81  GN---CTKLNLG-RVTLSNVSERKDNMRLGLSLATNPKDN HOHBY69.aa
59  GESLPCVKLDLPVNTSIPNVTEVKENMTFGSTLVTNPNG- gi|346210

               130             140             150             160
117 SFLACSPLWSHEGSSYYTTGMCSRVNSNFRFSKTVAPAL  HOHBY69.aa
98  GFLACGPLYAYRCGHLHYTTGICSDVSPTFQVVNSIAP-V gi|346210

               170             180             190             200
157 QRCQTYMDIVIVLDGSNSIYPWVEVQHFLINILKKFYIGP HOHBY69.aa
137 QECSTQLDIVIVLDGSNSIYPWDSVTAFLNDLLKRMDIGP gi|346210

               210             220             230             240
197 GQIQVGVVQYGEDVVHEFHLNDYRSVKDVVEAASHIEQRC HOHBY69.aa
177 KQTQVGIVQYGENVTHEFNLNKYSSTEEVLVAAKKIVQRC gi|346210

               250             260             270             280
237 GTETRTAFGIEFARSEAF--QKGGRKGAKKVMIVITDGES HOHBY69.aa
217 GRQTMTALGTDTARKEAFTEARGARRGVKKVMVIVTDGES gi|346210

               290             300             310             320
275 HDSPDLEKVIQQSERDNVTRYAVAVLGYYNRGINPETFL  HOHBY69.aa
257 HDNHRLKKVIQDCEDENIQRFSIPILGSYNRGNLSTEKFV gi|346210

               330             340             350             360
315 NELKYIASDPCDKHFFNVTDEAALKDIVDALGDRIFSLEG HOHBY69.aa
297 EEIKSIASEPTEKHFFNVSDELALVTIVKTLGERIFALEA gi|346210

               370             380             390             400
355 T-NKNETSFGLEMSQTGFSSHVVEDGVLLGAVGAYDWNGA HOHBY69.aa
337 TADQSAASFEMEMSQTGFSAHYSQLWVMLGAVGAYDWNGT gi|346210

               410             420             430             440
394 VLKETSAGKVIPLRESYLKEFPEELKNHGAYLGYTVTSVV HOHBY69.aa
377 VVMQKASQIIIPRNTTFNVESTKKNEPLASYLGYTVNSAT gi|346210

               450             460             470             480
434 SSRQGRVYVAGAPRFNHTGKVILFTMHNNRSLTIHQAMRG HOHBY69.aa
417 ASSGDVLYIAGQPRYNHTGQVIIYRMEDG-NIKILQTLSG gi|346210

               490             500             510             520
474 QQIGSYFGSEITSVDIDGDGVTDVLLVGAPMYFNEGRE-R HOHBY69.aa
456 EQIGSYFGSILTTTDIDKDSNTEILLVGAPMYMGTEKEEQ gi|346210

               530             540             550             560
513 GKVYVYELRQNRFVYNGTL----------KDSHSYQN--- HOHBY69.aa
496 GKVYVYALNQTRFEYQMSLEPIKQTCCSSRQHNSCTTENK gi|346210

               570             580             590             600
540 -----ARFGSSIASVRDLNQDSYNDVVVGAPLEDNHAGAI HOHBY69.aa
536 NEPCGARFGTAIAAVKDLNLDGFNDIVIGAPLEDDHGGAV gi|346210

               610             620             630             640
575 YIFHGFRGSILKTPKQRITASELATGLQYFGCSIHGQLDL HOHBY69.aa
576 YIYHGSGKTIRKEYAQRIPSGGDGKTLKFFGQSIHGEMDL gi|346210
```

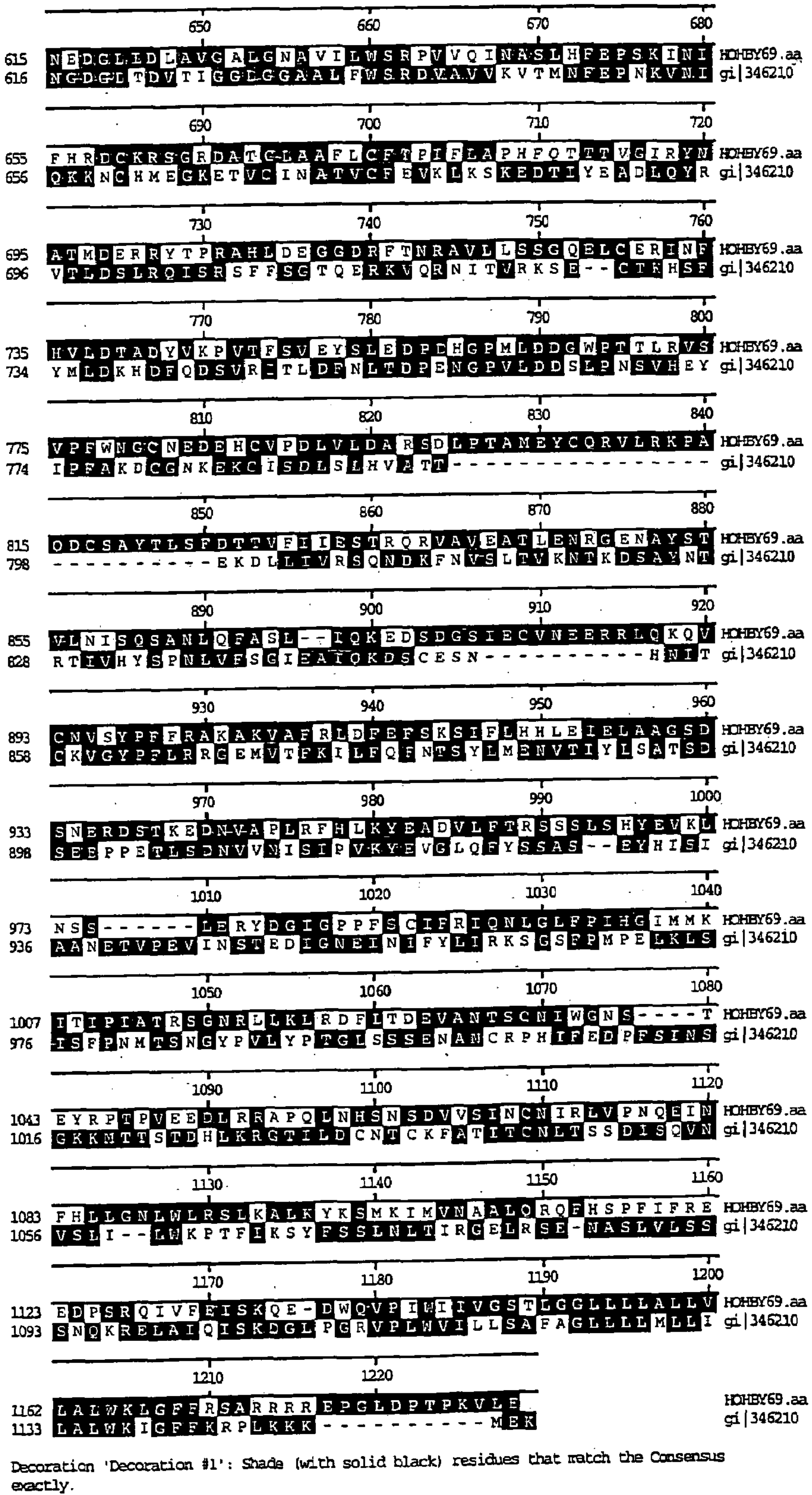

FIG. 20B

```
                    650             660             670             680
 615  N E D G L I D L A V G A L G N A V I L W S R P V V Q I N A S L H F E P S K I N I  HOHBY69.aa
 616  N G D G L T D V T I G G L G G A A L F W S R D V A V V K V T M N F E P N K V N I  gi|346210

                    690             700             710             720
 655  F H R D C K R S G R D A T G L A A F L C F T P I F L A P H F Q T T T V G I R Y N  HOHBY69.aa
 656  Q K K N C H M E G K E T V C I N A T V C F E V K L K S K E D T I Y E A D L Q Y R  gi|346210

                    730             740             750             760
 695  A T M D E R Y T P R A H L D E G G D R F T N R A V L S S G Q E L C E R I N F     HOHBY69.aa
 696  V T L D S L R Q I S R S F F S G T Q E R K V Q R N I T V R K S E - - C T H H S F  gi|346210

                    770             780             790             800
 735  H V L D T A D Y V K P V T F S V E Y S L E D P L H G P M L D D G W P T T L R V S  HOHBY69.aa
 734  Y M L D K H D F Q D S V R E T L D F N L T D P E N G P V L D D S L P N S V H E Y  gi|346210

                    810             820             830             840
 775  V P F W N G C N E D E H C V P D L V L D A R S D L P T A M E Y C Q R V L R K P A  HOHBY69.aa
 774  I P F A K D C G N K E K C I S D L S L H V A T T - - - - - - - - - - - - - - -   gi|346210

                    850             860             870             880
 815  O D C S A Y T L S F D T T V F I I E S T R Q R V A V E A T L E N R G E N A Y S T  HOHBY69.aa
 798  - - - - - - - - E K D L L I V R S Q N D K F N V S L T V K N T K D S A Y N T     gi|346210

                    890             900             910             920
 855  V L N I S Q S A N L Q F A S L - - I Q K E D S D G S I E C V N E E R R L Q K Q V  HOHBY69.aa
 828  R T I V H Y S P N L V F S G I E A T Q K D S C E S N - - - - - - - - - - H N I T  gi|346210

                    930             940             950             960
 893  C N V S Y P F F R A K A K V A F R L D F B F S K S I F L H H L E I E L A A G S D  HOHBY69.aa
 858  C K V G Y P F L R R G E M V T F K I L F Q F N T S Y L M E N V T I Y L S A T S D  gi|346210

                    970             980             990             1000
 933  S N E R D S T K E D N V A P L R F H L K Y E A D V L F T R S S S L S H Y E V K L  HOHBY69.aa
 898  S E E P P E T L S D N V V N I S I P V K Y E V G L Q F Y S S A S - - E Y H I S I  gi|346210

                    1010            1020            1030            1040
 973  N S S - - - - - - L E R Y D G I G P P F S C I F R I Q N L G L F P I H G I M M K  HOHBY69.aa
 936  A A N E T V P E V I N S T E D I G N E I N I F Y L I R K S G S F P M P E L K L S  gi|346210

                    1050            1060            1070            1080
1007  I T I P I A T R S G N R L L K L R D F I T D E V A N T S C N I W G N S - - - - T  HOHBY69.aa
 976  I S F P N M T S N G Y P V L Y P T G I S S S E N A M C R P H I F E D P F S I N S  gi|346210

                    1090            1100            1110            1120
1043  E Y R P T P V E E D L R R A P Q L N H S N S D V V S I N C N I R L V P N Q E I N  HOHBY69.aa
1016  G K K M T T S T D H L K R G T I L D C N T C K F A T I T C N L T S S D I S Q V N  gi|346210

                    1130            1140            1150            1160
1083  F H L L G N L W L R S L K A L K Y K S M K I M V N A A L Q R Q F H S P F I F R E  HOHBY69.aa
1056  V S L I - - L W K P T F I K S Y F S S L N L T I R G E L R S F - N A S L V L S S  gi|346210

                    1170            1180            1190            1200
1123  E D P S R Q I V F E I S K Q E - D W Q V P I W I I V G S T L G G L L L L A L L V  HOHBY69.aa
1093  S N Q K R E L A I Q I S K D G L P G R V P L W V I L L S A F A G L L L L M L L I  gi|346210

                    1210            1220
1162  L A L W K L G F F R S A R R R R E P G L D P T P K V L E                          HOHBY69.aa
1133  L A L W K I G F F K R P L K K K - - - - - - - - - - M E K                        gi|346210
```

Decoration 'Decoration #1': Shade (with solid black) residues that match the Consensus exactly.

FIG. 22A

```
  1  GGCACGAGCTGTCATCCGTTTCCATGCCGTGAGGTCCATTCACAGAACACATCCATGGCT   60
  1                                                          M  A    2

 61  CTCATGCTCAGTTTGGTTCTGAGTCTCCTCAAGCTGGGATCAGGGCAGTGGCAGGTGTTT  120
  3  L  M  L  S  L  V  L  S  L  L  K  L  G  S  G  Q  W  Q  V  F    22

121  GGGCCAGACAAGCCTGTCCAGGCCTTGGTGGGGGAGGACGCAGCATTCTCCTGTTTCCTG  180
 23  G  P  D  K  P  V  Q  A  L  V  G  E  D  A  A  F  S  C  F  L    42

181  TCTCCTAAGACCAATGCAGAGGCCATGGAAGTGCGGTTCTTCAGGGGCCAGTTCTCTAGC  240
 43  S  P  K  T  N  A  E  A  M  E  V  R  F  F  R  G  Q  F  S  S    62

241  GTGGTCCACCTCTACAGGGACGGGAAGGACCAGCCATTTATGCAGATGCCACAGTATCAA  300
 63  V  V  H  L  Y  R  D  G  K  D  Q  P  F  M  Q  M  P  Q  Y  Q    82

301  GGCAGGACAAAACTGGTGAAGGATTCTATTGCGGAGGGGCGCATCTCTCTGAGGCTGGAA  360
 83  G  R  T  K  L  V  K  D  S  I  A  E  G  R  I  S  L  R  L  E   102

361  AACATTACTGTGTTGGATGCTGGCCTCTATGGGTGCAGGATTAGTTCCCAGTCTTACTAC  420
103  N  I  T  V  L  D  A  G  L  Y  G  C  R  I  S  S  Q  S  Y  Y   122

421  CAGAAGGCCATCTGGGAGCTACAGGTGTCAGCACTGGGCTCAGTTCCTCTCATTTCCATC  480
123  Q  K  A  I  W  E  L  Q  V  S  A  L  G  S  V  P  L  I  S  I   142

481  GCGGGATATGTTGATAGAGACATCCAGCTACTCTGTCAGTCCTCGGGCTGGTTCCCCCGG  540
143  A  G  Y  V  D  R  D  I  Q  L  L  C  Q  S  S  G  W  F  P  R   162

541  CCCACAGCGAAGTGGAAAGGTCCACAAGGACAGGATTTGTCCACAGACTCCAGGACAAAC  600
163  P  T  A  K  W  K  G  P  Q  G  Q  D  L  S  T  D  S  R  T  N   182

601  AGAGACATGCATGGCCTGTTTGATGTGGAGATCTCTCTGACCGTCCAAGAGAACGCCGGG  660
183  R  D  M  H  G  L  F  D  V  E  I  S  L  T  V  Q  E  N  A  G   202

661  AGCATATCCTGTTCCATGCGGCATGCTCATCTGAGCCGAGAGGTGGAATCCAGGGTACAG  720
203  S  I  S  C  S  M  R  H  A  H  L  S  R  E  V  E  S  R  V  Q   222

721  ATAGGAGACTGGAGAAGAAAGCACGGACAGGCAGGTAAAAGAAAATATTCCTCTTCACAC  780
223  I  G  D  W  R  R  K  H  G  Q  A  G  K  R  K  Y  S  S  S  H   242

781  ATTTATGACTCCTTTCCAAGTCTCTCGTTTATGGATTTTTATATCCTGAGGCCCGTGGGT  840
243  I  Y  D  S  F  P  S  L  S  F  M  D  F  Y  I  L  R  P  V  G   262
```

FIG. 22B

```
 841 CCCTGCAGAGCCAAGCTTGTGATGGGAACTCTGAAATTGCAGATTCTGGGGGAGGTGCAT  900
 263 P   C   R   A   K   L   V   M   G   T   L   K   L   Q   I   L   G   E   V   H   282

 901 TTTGTAGAGAAGCCCCATAGCCTTCTTCAGATCTCTGGAGGGTCCACAACACTCAAAAAG  960
 283 F   V   E   K   P   H   S   L   L   Q   I   S   G   G   S   T   T   L   K   K   302

 961 GGTCCCAATCCTTGGTCTTTCCCTTCTCCCTGCGCCCTGTTTCCCACGTGAGCACGGAAC  1020
 303 G   P   N   P   W   S   F   P   S   P   C   A   L   F   P   T   *   319

1021 TGCCTGCTCTCTCTGCTTGCTTTCAGAATTGAGAGACGCCCGGAAACACGCAGGTACCAA  1080

1081 CGCCTGAGAGGGTAACAGTGGGCATGGAGTAGGAAGATGACCAGTGACAGATATGGAGCC  1140

1141 CATCCAGCTTGTAGACAGCAAATCTGTGATGCCCGAATCCACCCCAGGGTGCAGCTGCCT  1200

1201 CTAAATACACTTCTTGGCCCAGGACTTGGAGGGAAAAGCGTAGGGACTGGGTCAGCTAGG  1260

1261 AGGGGTCACAGGCAAGACGCCAGGGAACTGAGGGCATTAGTAGCTGGCTTCTAGGGGTCT  1320

1321 GTGCAAAGGGGAACGAAGTGAAGTTAGCAGGAACTGGTGGGTGGAAGGAAGCTGAATCCT  1380

1381 GGAGTCACTCAAGGTCTCACAAAGTCAAATAGAGGGCTTACGTGGGAGGGCAGTGGTAGG  1440

1441 GCTGGGTGAACATCTCATGGTTGAGCATCTCCAAGCATCAGTGAGGCACGGGGGCTGCCC  1500

1501 TGGAGAAGGTACATGGCTGGTGGGATAGTGGGACTGGCCGGATCCTACCCGGAGCCAGTC  1560

1561 TGCAGTGGGAGGGTCGACCTCTTGCTCCAGCCCAGATTTCGTCTTCAGTAACTCATGCTT  1620

1621 CCTCTCTCCCCCACCGCACCCCAGTGGAGGTGACTCTGGATCCAGAGACGGCTCACCCGA  1680

1681 AGCTCTGCGTTTCTGATCTGAAAACTGTAACCCATAGAAAAGCTCCTCAGGAGGTGCCTC  1740

1741 ACTCTGAGAAGAGATTTACAAGGAAGAGTGTGGTGGCTTCTCAGGGTTTCCAAGCAGGGA  1800

1801 AACATTACTGGGAGGTGGACGTGGGACAAAATGTAGGGTGGTATGTGGGAGTGTGTCGGG  1860

1861 ATGACGTAGACAGGGGGAAGAACAATGTGACTTTGTCTCCCAACAATGGGTATTGGGTCC  1920
```

FIG. 22C

```
1921 TCAGACTGACAACAGAACATTTGTATTTCACATTCAATCCCCATTTTATCAGCCTCCCCC 1980
1981 CCAGCACCCCTCCTACACGAGTAGGGGTCTTCCTGGACTATGAGGGTGGGACCATCTCCT 2040
2041 TCTTCAATACAAATGACCAGTCCCTTATTTATACCCTGCTGACATGTCAGTTTGAAGGCT 2100
2101 TGTTGAGACCCTATATCCAGCATGCGATGTATGACGAGGAAAAGGGGACTCCCATATTCA 2160
2161 TATGTCCAGTGTCCTGGGGATGAGACAGAGAAGACCCTGCTTAAAGGGCCCCACACCACA 2220
2221 GACCCAGACACAGCCAAGGGAGAGTGCTCCCGACAGGTGGCCCCAGCTTCCTCTCCGGAG 2280
2281 CCTGCGCACAGAGAGTCACGCCCCCCACTCTCCTTTAGGGAGCTGAGGTTCTTCTGCCCT 2340
2341 GAGCCCTGCAGCAGCGGCAGTCACAGCTTCCAGATGAGGGGGGATTGGCCTGACCCTGTG 2400
2401 GGAGTCAGAAGCCATGGCTGCCCTGAAGTGGGGACGGAATAGACTCACATTAGGTTTAGT 2460
2461 TTGTGAAAACTCCATCCAGCTAAGCGATCTTGAACAAGTCACAACCTCCCAGGCTCCTCA 2520
2521 TTTGCTAGTCACGGACAGTGATTCCTGCCTCACAGGTGAAGATTAAAGAGACAACGAATG 2580
2581 TGAATCATGCTTGCAGGTTTGAGGGCCACAGTGTTTGCTAATGGATGTGTTTTTATGATT 2640
2641 ATACATTTTCCCCACCATAAAACTCTGTTTGCCTTAATTCCCACATTAATTTAACTTTTC 2700
2701 CTCCTATACCCAAATCCACCCATGGAATAGTTAATTGGAACACCTGCCTTTGTGAGGCTC 2760
2761 CAAAGAATAAAGAGGAGGTAGGATTTTTCACTGATTCTATAAGCCCAGCATTACCTGATA 2820
2821 CCAAAACCAGGCAAAGAAAACAGAAGAAGAGGAAGGAAAACTACAGGTCCATATCCCTCA 2880
2881 TTAACACAGACACAAAAATTCTAAATAAAATTTTAACAAATTAAACTAAACAATATATTT 2940
2941 AAAGATGATATATAACTACTCAGTGTGGTTTGTCCCACAAATGCAGAGTTGGTTTAATAT 3000
3001 TTAAATATCAACCAGTGTAATTCAGCACATTAATAAAGTAAAAAAAAAAAAAAAAAAA 3059
```

FIG. 23

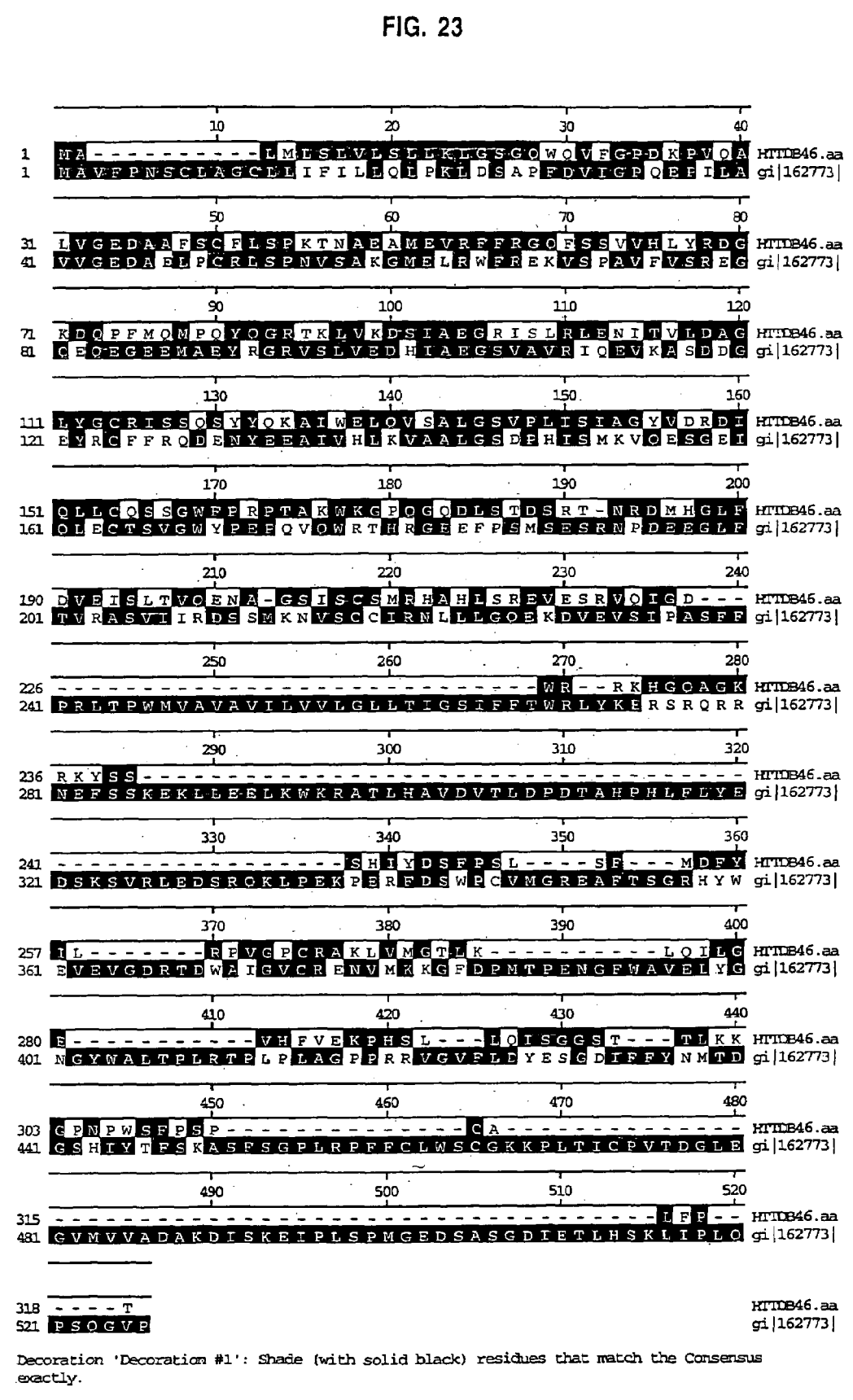

```
1    MA----------LMLSLVLSLLKLGSGQWQVFGPDKPVQA  HTTDB46.aa
1    MAVFPNSCLAGCLLIFILLQLPKLDSAPFDVIGPQEPILA  gi|162773|

31   LVGEDAAFSCFLSPKTNAEAMEVRFFRGQFSSVVHLYRDG  HTTDB46.aa
41   VVGEDAELPCRLSPNVSAKGMELRWFREKVSPAVFVSREG  gi|162773|

71   KDQPFMQMPQYQGRTKLVKDSIAEGRISLRLENITVLDAG  HTTDB46.aa
81   QEQEGEEMAEYRGRVSLVEDHIAEGSVAVRIQEVKASDDG  gi|162773|

111  LYGCRISSQSYYQKAIWELQVSALGSVPLISIAGYVDRDI  HTTDB46.aa
121  EYRCFFRQDENYEEAIVHLKVAALGSDPHISMKVQESGEI  gi|162773|

151  QLLCQSSGWFPRPTAKWKGPQGQDLSTDSRT-NRDMHGLF  HTTDB46.aa
161  QLECTSVGWYPEPQVQWRTHRGEEFPSMSESRNPDEEGLF  gi|162773|

190  DVEISLTVQENA-GSISCSMRHAHLSREVESRVQIGD---  HTTDB46.aa
201  TVRASVIIRDSSMKNVSCCIRNLLLGQEKDVEVSIPASFF  gi|162773|

226  ----------------------------WR--RKHGQAGK  HTTDB46.aa
241  PRLTPWMVAVAVILVVLGLLTIGSIFFTWRLYKERSRQRR  gi|162773|

236  RKYSS-----------------------------------  HTTDB46.aa
281  NEFSSKEKLLEELKWKRATLHAVDVTLDPDTAHPHLFLYE  gi|162773|

241  -----------------SHIYDSFPSL----SF---MDFY  HTTDB46.aa
321  DSKSVRLEDSRQKLPEKPERFDSWPCVMGREAFTSGRHYW  gi|162773|

257  IL-------RPVGPCRAKLVMGTLK----------LQILG  HTTDB46.aa
361  EVEVGDRTDWAIGVCRENVMKKGFDPMTPENGFWAVELYG  gi|162773|

280  E-----------VHFVEKPHSL---LQISGGST---TLKK  HTTDB46.aa
401  NGYWALTPLRTPLPLAGPPRRVGVFLDYESGDIFFYNMTD  gi|162773|

303  GPNPWSFPSP--------------CA--------------  HTTDB46.aa
441  GSHIYTFSKASFSGPLRPFFCLWSCGKKPLTICPVTDGLE  gi|162773|

315  -----------------------------------LFP--  HTTDB46.aa
481  GVMVVADAKDISKEIPLSPMGEDSASGDIETLHSKLIPLQ  gi|162773|

318  -----T                                    HTTDB46.aa
521  PSQGVP                                    gi|162773|
```

Decoration 'Decoration #1': Shade (with solid black) residues that match the Consensus exactly.

FIG. 25A

```
  1 GGCACGAGGGGGCAGGCATGGGAGCCGCGCTCTCTCCCGGCGCCCACACCTGTCTGAG  60

 61 CGGCGCAGCGAGCCGCGGCCCGGGCGGGCTGCTCGGCGCGGAACAGTGCTCGGCATGGCA 120
  1                                                      M  A    2

121 GGGATTCCAGGGCTCCTCTTCCTTCTCTTCTTTCTGCTCTGTGCTGTTGGGCAAGTGAGC 180
  3 G  I  P  G  L  L  F  L  L  F  F  L  L  C  A  V  G  Q  V  S   22

181 CCTTACAGTGCCCCCTGGAAACCCACTTGGCCTGCATACCGCCTCCCTGTCGTCTTGCCC 240
 23 P  Y  S  A  P  W  K  P  T  W  P  A  Y  R  L  P  V  V  L  P   42

241 CAGTCTACCCTCAATTTAGCCAAGCCAGACTTTGGAGCCGAAGCCAAATTAGAAGTATCT 300
 43 Q  S  T  L  N  L  A  K  P  D  F  G  A  E  A  K  L  E  V  S   62

301 TCTTCATGTGGACCCCAGTGTCATAAGGGAACTCCACTGCCCACTTACGAAGAGGCCAAG 360
 63 S  S  C  G  P  Q  C  H  K  G  T  P  L  P  T  Y  E  E  A  K   82

361 CAATATCTGTCTTATGAAACGCTCTATGCCAATGGCAGCCGCACAGAGACGCAGGTGGGC 420
 83 Q  Y  L  S  Y  E  T  L  Y  A  N  G  S  R  T  E  T  Q  V  G  102

421 ATCTACATCCTCAGCAGTAGTGGAGATGGGGCCCAACACCGAGACTCAGGGTCTTCAGGA 480
103 I  Y  I  L  S  S  S  G  D  G  A  Q  H  R  D  S  G  S  S  G  122

481 AAGTCTCGAAGGAAGCGGCAGATTTATGGCTATGACAGCAGGTTCAGCATTTTTGGGAAG 540
123 K  S  R  R  K  R  Q  I  Y  G  Y  D  S  R  F  S  I  F  G  K  142

541 GACTTCCTGCTCAACTACCCTTTCTCAACATCAGTGAAGTTATCCACGGGCTGCACCGGC 600
143 D  F  L  L  N  Y  P  F  S  T  S  V  K  L  S  T  G  C  T  G  162

601 ACCCTGGTGGCAGAGAAGCATGTCCTCACAGCTGCCCACTGCATACACGATGGAAAAACC 660
163 T  L  V  A  E  K  H  V  L  T  A  A  H  C  I  H  D  G  K  T  182

661 TATGTGAAAGGAACCCAGAAGCTTCGAGTGGGCTTCCTAAAGCCCAAGTTTAAAGATGGT 720
183 Y  V  K  G  T  Q  K  L  R  V  G  F  L  K  P  K  F  K  D  G  202

721 GGTCGAGGGGCCAACGACTCCACTTCAGCCATGCCCGAGCAGATGAAATTTCAGTGGATC 780
203 G  R  G  A  N  D  S  T  S  A  M  P  E  Q  M  K  F  Q  W  I  222

781 CGGGTGAAACGCACCCATGTGCCCAAGGGTTGGATCAAGGGCAATGCCAATGACATCGGC 840
223 R  V  K  R  T  H  V  P  K  G  W  I  K  G  N  A  N  D  I  G  242
```

FIG. 25B

841 ATGGATTATGATTATGCCCTCCTGGAACTCAAAAAGCCCCACAAGAGAAAATTTATGAAG 900
243 M D Y D Y A L L E L K K P H K R K F M K 262

901 ATTGGGGTGAGCCCTCCTGCTAAGCAGCTGCCAGGGGGCAGAATTCACTTCTCTGGTTAT 960
263 I G V S P P A K Q L P G G R I H F S G Y 282

961 GACAATGACCGACCAGGCAATTTGGTGTATCGCTTCTGTGACGTCAAAGACGAGACCTAT 1020
283 D N D R P G N L V Y R F C D V K D E T Y 302

1021 GACTTGCTCTACCAACAATGCGATTCCCAGCCAGGGGCCAGCGGGTCTGGGGTCTATGTG 1080
303 D L L Y Q Q C D S Q P G A S G S G V Y V 322

1081 AGGATGTGGAAGAGACAACACCAGAAGTGGGAGCGGAAAATTATTGGCATGATTTCAGGG 1140
323 R M W K R Q H Q K W E R K I I G M I S G 342

1141 CACCAGTGGGTGGACATGGATGGTTCCCCACAGGAATTCACACGTGGCTGTTCAGAGATC 1200
343 H Q W V D M D G S P Q E F T R G C S E I 362

1201 ACTCCTCTCCAATATATCCCAGATATATCTATTGGAGTATAAGGAAACTACCTGGATTGT 1260
363 T P L Q Y I P D I S I G V * 376

1261 AGGGAGGGGTGACACAGTGTCCCTCCTGCAGCAACTAAGGTCGTCATGTTCTTATTTTAG 1320

1321 GAGAGGCCAAATTGTTTTTTGTCATTGCCGTGCACACGTGTGTGTGTGTGTGTGTGTGTG 1380

1381 TGTAAGGTGTCTTATAATCTTTTACCTATTTCTTACAATTGCAAGATGACTGGCTTTACT 1440

1441 ATTTGAAAACTGGTTTGTGTATCATATCATATATCATTTAAGCAGTTTGAAGGCATACTT 1500

1501 TTGCATAGAAATAAAAAAAATACTGATTTGGGGCAATGAGGAATATTTGACAATTAAGTT 1560

1561 AATCTTCACGTTTTTGCAAACTTTGATTTTTATTTCATCTGAACTTGTTTCAAAGATTTA 1620

1621 TATTAAATATTTGGCATACAAAAAAAAAAAAAAAAAACGGGGGGGCCCGTACCCAATTCG 1680

1681 CCCTATAGTGAGGCGATAC 1699

FIG. 26

```
              10        20        30        40
1   MAGIPGLLFLLFFLLCAVGQVSPYSAPWKPTWPAYRLPVV HUSAQ05.aa
1   M--IRTLLL-----------------------------ST gi|219620

              50        60        70        80
41  LPQSTLNLAKPDFGAEAKLEVSSSCGPQCHKGTPLPTYEE HUSAQ05.aa
10  LVAGAL-----------------SCGD--------PTYPP gi|219620

              90       100       110       120
81  AKQYLSYETLYANGSRTETQVGIYILSSSGDGAQHRDSGS HUSAQ05.aa
25  -----------------------YVTRVVGGEEARPNS-- gi|219620

             130       140       150       160
121 SGKSRRKRQIYGYDSRFSIFGKDFLLNYPFSTSVKLSTGC HUSAQ05.aa
40  -----WPWQV----------------SLQYSSNGKWYHTC gi|219620

             170       180       190       200
161 TGTLVAEKHVLTAAHCIHDGKTYVKGTQKLRVGFLKPKFK HUSAQ05.aa
59  GGSLIANSWVLTAAHCISSSRTY-------RVGLGRHNLY gi|219620

             210       220       230       240
201 DGGRGANDSTSAMPEQMKFQWIRVKRTHVPKGWIKGNAND HUSAQ05.aa
92  VAESGSLA-------------VSVSKIVVHKDW---NSNQ gi|219620

             250       260       270       280
241 IGMDYDYALLELKKPHK--RKFMKIGVSPPAKQLPG---- HUSAQ05.aa
116 ISKGNDIALLKLANPVSLTDKIQLACLPPAGTILPNNYPC gi|219620

             290       300       310       320
275 -----GRIHFSGYDND--RPGNLV---YRFCD-------- HUSAQ05.aa
156 YVTGWGRLQTNGAVPDVLQQGRLLVVDYATCSSSAWWGSS gi|219620

             330       340       350       360
297 VKDETY----DLLYQQCDSQPGASGSGVYVRMWKRQHQKW HUSAQ05.aa
196 VKTSMIVAGGDGVISSCNGDSGGPLNC------QASDGRW gi|219620

             370       380       390       400
333 ERKIIGMISGHQWVDMDGSPQEFTRGCSEITPLQYIPDIS HUSAQ05.aa
230 QVHGIVSFGSRLGCNYYHKPSVFTRVSNYI---DWINSV- gi|219620

373 IGV.                                     HUSAQ05.aa
266 IANN                                     gi|219620
```

Decoration 'Decoration #1': Shade (with solid black) residues that match the Consensus exactly.

FIG. 28A

```
  1  GAATTCGGCAGAGCAGGTGCCCGACATGGCGAGTGTAGTGCTGCCGAGCGGATCCCAGTG    60
  1                         M  A  S  V  V  L  P  S  G  S  Q  C     12

 61  TGCGGCGGCAGCGGCGGCGGCGGCGCCTCCCGGGCTCCGGCTCCGGCTTCTGCTGTTGCT   120
 13   A  A  A  A  A  A  A  A  P  P  G  L  R  L  R  L  L  L  L  L   32

121  CTTCTCCGCCGCGGCACTGATCCCCACAGGTGATGGGCAGAATCTGTTTACGAAAGACGT   180
 33   F  S  A  A  A  L  I  P  T  G  D  G  Q  N  L  F  T  K  D  V   52

181  GACAGTGATCGAGGGAGAGGTTGCGACCATCAGTTGCCAAGTCAATAAGAGTGACGACTC   240
 53   T  V  I  E  G  E  V  A  T  I  S  C  Q  V  N  K  S  D  D  S   72

241  TGTGATTCAGCTACTGAATCCCAACAGGCAGACCATTTATTTCAGGGACTTCAGGCCTTT   300
 73   V  I  Q  L  L  N  P  N  R  Q  T  I  Y  F  R  D  F  R  P  L   92

301  GAAGGACAGCAGGTTTCAGTTGCTGAATTTTTCTAGCAGTGAACTCAAAGTATCATTGAC   360
 93   K  D  S  R  F  Q  L  L  N  F  S  S  S  E  L  K  V  S  L  T  112

361  AAACGTCTCAATTTCTGATGAAGGAAGATACTTTTGCCAGCTCTATACCGATCCCCCACA   420
113   N  V  S  I  S  D  E  G  R  Y  F  C  Q  L  Y  T  D  P  P  Q  132

421  GGAAAGTTACACCACCATCACAGTCCTGGTCCCACCACGTAATCTGATGATCGATATCCA   480
133   E  S  Y  T  T  I  T  V  L  V  P  P  R  N  L  M  I  D  I  Q  152

481  GAAAGACACTGCGGTGGAAGGTGAGGAGATTGAAGTCAACTGCACTGCTATGGCCAGCAA   540
153   K  D  T  A  V  E  G  E  E  I  E  V  N  C  T  A  M  A  S  K  172

541  GCCAGCCACGACTATCAGGTGGTTCAAAGGGAACACAGAGCTAAAAGGCAAATCGGAGGT   600
173   P  A  T  T  I  R  W  F  K  G  N  T  E  L  K  G  K  S  E  V  192

601  GGAAGAGTGGTCAGACATGTACACTGTGACCAGTCAGCTGATGCTGAAGGTGCACAAGGA   660
193   E  E  W  S  D  M  Y  T  V  T  S  Q  L  M  L  K  V  H  K  E  212

661  GGACGATGGGGTCCCAGTGATCTGCCAGGTGGAGCACCCTGCGGTCACTGGAAACCTGCA   720
213   D  D  G  V  P  V  I  C  Q  V  E  H  P  A  V  T  G  N  L  Q  232

721  GACCCAGCGGTATCTAGAAGTACAGTATAAGCCTCAAGTGCACATTCAGATGACTTATCC   780
233   T  Q  R  Y  L  E  V  Q  Y  K  P  Q  V  H  I  Q  M  T  Y  P  252

781  TCTACAAGGCTTAACCCGGGAAGGGGACGCGCTTGAGTTAACATGTGAAGCCATCGGGAA   840
253   L  Q  G  L  T  R  E  G  D  A  L  E  L  T  C  E  A  I  G  K  272
```

FIG. 28B

```
841  GCCCCAGCCTGTGATGGTAACTTGGGTGAGAGTCGATGATGAAATGCCTCAACACGCCGT  900
273   P  Q  P  V  M  V  T  W  V  R  V  D  D  E  M  P  Q  H  A  V   292

901  ACTGTCTGGGCCCAACCTGTTCATCAATAACCTAAACAAAACAGATAATGGTACATACCG  960
293   L  S  G  P  N  L  F  I  N  N  L  N  K  T  D  N  G  T  Y  R   312

961  CTGTGAAGCTTCAAACATAGTGGGGAAAGCTCACTCGGATTATATGCTGTATGTATACGA  1020
313   C  E  A  S  N  I  V  G  K  A  H  S  D  Y  M  L  Y  V  Y  D   332

1021 TCCCCCCACAACTATCCCTCCTCCCACAACAACCACCACCACCACCACCACCACCACCAC  1080
333   P  P  T  T  I  P  P  P  T  T  T  T  T  T  T  T  T  T  T  T   352

1081 CACCATCCTTACCATCATCACAGATTCCCGAGCCAGGTGAAGAAGGCTCGATCAGGGCAG  1140
353   T  I  L  T  I  I  T  D  S  R  A  R  *                         365

1141 TGGATCATGCCGTGATCGGTGGCGTCGTGGCGGTGGTGGTGTTCGCCATGCTGTGCTTGC  1200

1201 TCATCATTCTGGGGCGCTATTTTGCCAGACATAAAGGTACATACTTCACTCATGAAGCCA  1260

1261 AAGGAGCCGATGACGCAGCAGACGCAGACACAGCTATAATCAATGCAGAAGGAGGACAGA  1320

1321 ACAACTCCGAAGAAAAGAAAGAGTACTTCATCTAGATCAGCCTTTTTGTTTCAATGAGGT  1380

1381 GTCCAACTGGCCCTATTTAGATGATAAAGAGACAGTGATATTGGAACTTGCGAGAAATTC  1440

1441 GTGTGTTTTTTTATGAATGGGTGGAAAGGTGTGAGACTGGGAAGGCTTGGGATTTGCTGT  1500

1501 GTAAAAAAAAAAAAAAAAAA  1520
```

FIG. 29

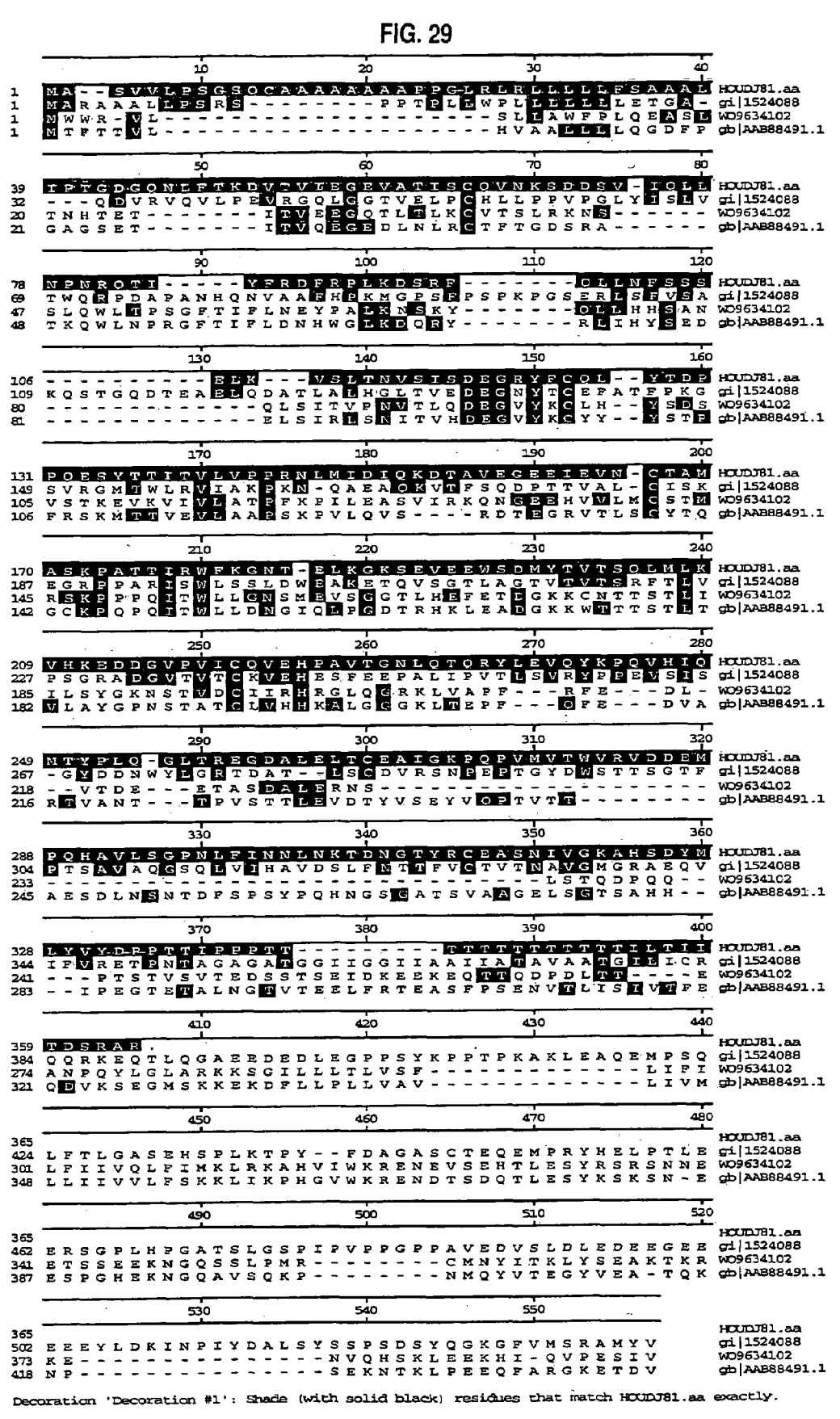

```
                10        20        30        40
1   MA--SVVLPSGSQCAAAAAAAAPPGLRLRLLLLLFSAAAL  HOUDJ81.aa
1   MARAAALLPSRS--------PPTPLLWPLLLLLLLETGA-  gi|1524088
1   MWWR-VL--------------------SLLAWFPLQEASL  WO9634102
1   MTFTTVL--------------------HVAALLLLQGDFP  gb|AAB88491.1

                50        60        70        80
39  IPTGDGQNLFTKDVTVLEGEVATISCQVNKSDDSV-IQLL  HOUDJ81.aa
32  ---QDVRVQVLPEVRGQLCGTVELPCHLLPPVPGLYISLV  gi|1524088
20  TNHTET-------ITVEEGQTLTLKCVTSLRKNS------  WO9634102
21  GAGSET-------ITVQEGEDLNLRCTFTGDSRA------  gb|AAB88491.1

                90       100       110       120
78  NPNRQTI-----YFRDFRPLKDSRF-------QLLNFSSS  HOUDJ81.aa
69  TWQRPDAPANHQNVAAFHPKMGPSFPSPKPGSERLSFVSA  gi|1524088
47  SLQWLTPSGFTIFLNEYPALKNSKY-------QLLHHSAN  WO9634102
48  TKQWLNPRGFTIFLDNHWGLKDQRY-------RLIHYSED  gb|AAB88491.1

               130       140       150       160
106 ----------ELK---VSLTNVSISDEGRYFCQL--YTDP  HOUDJ81.aa
109 KQSTGQDTEAELQDATLALHGLTVEDEGNYTCEFATEPKG  gi|1524088
80  -------------QLSITVPNVTLQDEGVYKCLH--YSDS  WO9634102
81  -------------ELSIRLSNITVHDEGVYKCYY--YSTP  gb|AAB88491.1

               170       180       190       200
131 PQESYTTITVLVPPRNLMIDIQKDTAVEGEEIEVN-CTAM  HOUDJ81.aa
149 SVRGMTWLRVIAKPKN-QAEAQKVTFSQDPTTVAL-CISK  gi|1524088
105 VSTKEVKVIVLATPFKPILEASVIRKQNGEEHVVLMCSTM  WO9634102
106 FRSKMTTVEVLAAPSKPVLQVS---RDTEGRVTLSCYTQ   gb|AAB88491.1

               210       220       230       240
170 ASKPATTIRWFKGNT-ELKGKSEVEEWSDMYTVTSQLMLK  HOUDJ81.aa
187 EGRPPARISWLSSLDWEAKETQVSGTLAGTVTVTSRFTLV  gi|1524088
145 RSKPPPQITWLLGNSMEVSGGTLHEFETDGKKCNTTSTLI  WO9634102
142 GCKPQPQITWLLDNGIQLPGDTRHKLEADGKKWTTTSTLT  gb|AAB88491.1

               250       260       270       280
209 VHKEDDGVPVICQVEHPAVTGNLQTQRYLEVQYKPQVHIQ  HOUDJ81.aa
227 PSGRADGVTVTCKVEHESFEEPALIPVTLSVRYPPEVSIS  gi|1524088
185 ILSYGKNSTVDCIIRHRGLQGRKLVAPF---RFE---DL-  WO9634102
182 VLAYGPNSTATCLVHHKALGGGKLTEPF---QFE---DVA  gb|AAB88491.1

               290       300       310       320
249 MTYPLQ-GLTREGDALELTCEAIGKPQPVMVTWVRVDDEM  HOUDJ81.aa
267 -GYDDNWYLGRTDAT--LSCDVRSNPEPTGYDWSTTSGTF  gi|1524088
218 --VTDE---ETASDALERNS--------------------  WO9634102
216 RTVANT---TPVSTTLEVDTYVSEYVQPTVTT--------  gb|AAB88491.1

               330       340       350       360
288 PQHAVLSGPNLFINNLNKTDNGTYRCEASNIVGKAHSDYM  HOUDJ81.aa
304 PTSAVAQGSQLVIHAVDSLFNTTFVCTVTNAVGMGRAEQV  gi|1524088
233 ------------------------------LSTQDPQQ--  WO9634102
245 AESDLNSNTDFSPSYPQHNGSGATSVAAGELSGTSAHH--  gb|AAB88491.1

               370       380       390       400
328 LYVYDPPTTIPPPTT----------TTTTTTTTTTTILTII  HOUDJ81.aa
344 IFVRETPNTAGAGATGGIIGGIIAAIIATAVAATGILICR  gi|1524088
241 ---PTSTVSVTEDSSTSEIDKEEKEQTTQPDPLTT----E  WO9634102
283 --IPEGTETALNGTVTEELFRTEASFPSENVTLISIVTFE  gb|AAB88491.1

               410       420       430       440
359 TDSRAR.                                   HOUDJ81.aa
384 QQRKEQTLQGAEEDEDLEGPPSYKPPTPKAKLEAQEMPSQ  gi|1524088
274 ANPQYLGLARKKSGILLLTLVSF-------------LIFI  WO9634102
321 QDVKSEGMSKKEKDFLLPLLVAV-------------LIVM  gb|AAB88491.1

               450       460       470       480
365                                           HOUDJ81.aa
424 LFTLGASEHSPLKTPY--FDAGASCTEQEMPRYHELPTLE  gi|1524088
301 LFIIVQLFIMKLRKAHVIWKRENEVSEHTLESYRSRSNNE  WO9634102
348 LLIIVVLFSKKLIKPHGVWKRENDTSDQTLESYKSKSN-E  gb|AAB88491.1

               490       500       510       520
365                                           HOUDJ81.aa
462 ERSGPLHPGATSLGSPIPVPPGPPAVEDVSLDLEDEEGEE  gi|1524088
341 ETSSEEKNGQSSLPMR--------CMNYITKLYSEAKTKR  WO9634102
387 ESPGHEKNGQAVSQKP--------NMQYVTEGYVEA-TQK  gb|AAB88491.1

               530       540       550
365                                           HOUDJ81.aa
502 EEEYLDKINPIYDALSYSSPSDSYQGKGFVMSRAMYV     gi|1524088
373 KE----------------NVQHSKLEEKHI-QVPESIV    WO9634102
418 NP----------------SEKNTKLPEEQFARGKETDV    gb|AAB88491.1
```

Decoration 'Decoration #1': Shade (with solid black) residues that match HOUDJ81.aa exactly.

FIG. 31

```
  1 TTTTTTTTTTTGAGACGGAGTCTCGCTCTTTCACCCAGGCCAGACTGAAGTGGCGCAGTC   60

 61 TCGGATCACTGAAAAGCTCAGCCTCACGGGATCACGACCATTCTCCTGCCTCAGCCTCCC  120

121 GAGTGGCTGGGACTAAAGGCGCCCGCCACCGACGCCCGGACTAATTTTTTGTATTTATAG  180

181 TAGAGACGGGGTTTCACCGTGTTAGCCAAGATGGTCTCGATCTCTTGAACTCGTGATCCG  240

241 CCCGCGTCAGCCTCCCAAAGTGCTGGGATTACAGGCGTGAGCCACAGCGCCCGGCCTGTA  300

301 AAGATTTCTTGAGCAAATGAATGAGTAAATGAAAGGAGTGCTCAAATTTCTTTTATTCTA  360

361 AAAAATGTTCCCCTTTTTTAGAAAATGCTCTGTAGCTTTTGTAGGTCTTTCCTGCACTCA  420

421 AACATCCACTCCTTACCCTTTCCAATCTCCCTTTTCTTCTCAACCCATAGAATGTACTTC  480

481 CATGTCTACCATTCCACCAGAACTACTCTAACCAAGGCTACCCAGGATATCCTTATTTCT  540

541 TTCAACTTCTTTGACATGCTCAGTCGCATTTGGCACTGTTAATGTCTTCCTCCTCTTTGA  600
  1                                         M  S  S  S  S  L  K     7

601 AACACCTCCTTTGCATGGCACTATCCTGGTTTTCTTCCTTCATTTCAGGAGAAACTTCAT  660
  8   H  L  L  C  M  A  L  S  W  F  S  S  F  I  S  G  E  T  S  F   27

661 TCTCCTTACTGAATTCTTTCTTCCTCCCCTATCCATCATCTAGATGTTGTTGTTTCTCAG  720
 28   S  L  L  N  S  F  F  L  P  Y  P  S  S  R  C  C  C  F  S  V   47

721 TGCAGTGTTCAATCCTAGACCCCTTTTCATGTAACTCAATGCGTTTTCCTTGGGAGAATT  780
 48   Q  C  S  I  L  D  P  F  S  C  N  S  M  R  F  P  W  E  N  *   67

781 AATTCCCTTCCCTGGTGTCACTNTGCC  807
```

FIG. 32

```
                            10        20        30        40
1    ----------------------------------------   HPWCM76.aa
1    SRDGFHRVSQDGEDLLTPCSSPLGLPKCWDYRGDPPRPVL   gi|1890647

                            50        60        70        80
1    ---------MSSSSLKHLL-CMA--LSW-------FSSFI   HPWCM76.aa
41   EDGSESLEYLSSSNLKEVLACRGSLHGWAQLVHLPFSAYA   gi|1890647

                            90       100       110       120
22   S-GETSFSLLNS----------------FFLPY-------   HPWCM76.aa
81   GYSSEPCTLLSAELKLHTMVLWPQFYRSILYLLYWLLRGR   gi|1890647

                           130       140       150       160
38   -----PSSRCC-----------------------------   HPWCM76.aa
121  RNNTKPKPFCCDHPPSYPLHFRLYQMEKTLSGDVHHQYYH   gi|1890647

                           170       180       190       200
44   -----------C--------------------FSVQCSIL   HPWCM76.aa
161  QDFSRKYYHPGICWLQLLLLSAPFHSINMLREFAILSNIL   gi|1890647

                           210       220       230       240
53   ---DPFSCNSMRFP------------WEN.             HPWCM76.aa
201  MHSHKLQCNSLLFMYKVRNLCLLPCWHLPLKSKSKCSYAR   gi|1890647

                           250
67                                              HPWCM76.aa
241  ESRVTLFYGSCS                               gi|1890647
```

Decoration 'Decoration #1': Shade (with solid black) residues that match the Consensus exactly.

FIG. 34

```
1   GGCACGAGCCGGACCCTGCCGCCCTGCCACTATGTCCCGCCGCTCTATGCTGCTTGCCTG   60
1                                 M  S  R  R  S  M  L  L  A  W    10

61  GGCTCTCCCCAGCCTCCTTCGACTCGGAGCGGCTCAGGAGACAGAAGACCCGGCCTGCTG   120
11   A  L  P  S  L  L  R  L  G  A  A  Q  E  T  E  D  P  A  C  C    30

121 CAGCCCCATAGTGCCCCGGAACGAGTGGAAGGCCCTGGCATCAGAGTGCGCCCAGCACCT   180
31   S  P  I  V  P  R  N  E  W  K  A  L  A  S  E  C  A  Q  H  L    50

181 GAGCCTGCCCTTACGCTATGTGGTGGTATCGCACACGGCGGGCAGCAGCTGCAACACCCC   240
51   S  L  P  L  R  Y  V  V  V  S  H  T  A  G  S  S  C  N  T  P    70

241 CGCCTCGTGCCAGCAGCAGGCCCGGAATGTGCAGCACTACCACATGAAGACACTGGGCTG   300
71   A  S  C  Q  Q  Q  A  R  N  V  Q  H  Y  H  M  K  T  L  G  W    90

301 GTGCGACGTGGGCTACAACTTCCTGATTGGAGAAGACGGGCTCGTATACGAGGGCCGTGG   360
91   C  D  V  G  Y  N  F  L  I  G  E  D  G  L  V  Y  E  G  R  G    110

361 CTGGAACTTCACGGGTGCCCACTCAGGTCACTTATGGAACCCCATGTCCATTGGCATCAG   420
111  W  N  F  T  G  A  H  S  G  H  L  W  N  P  M  S  I  G  I  S    130

421 CTTCATGGGCAACTACATGGATCGGGTGCCCACACCCCAGGCCATCCGGGCAGCCCAGGG   480
131  F  M  G  N  Y  M  D  R  V  P  T  P  Q  A  I  R  A  A  Q  G    150

481 TCTACTGGCCTGCGGTGTGGCTCAGGGAGCCCTGAGGTCCAACTATGTGCTCAAAGGACA   540
151  L  L  A  C  G  V  A  Q  G  A  L  R  S  N  Y  V  L  K  G  H    170

541 CCGGGATGTGCAGCGTACACTCTCTCCAGGCAACCAGCTCTACCACCTCATCCAGAATTG   600
171  R  D  V  Q  R  T  L  S  P  G  N  Q  L  Y  H  L  I  Q  N  W    190

601 GCCACACTACCGCTCCCCCTGAGGCCCTGCTGATCCGCACCCCATTCCTCCCCTCCCATG   660
191  P  H  Y  R  S  P  *                                          197

661 GCCAAAAACCCCACTGTCTCCTTCTCCAATAAAGATGTAGCTCAAAAAAAAAAAAAAAAA   720

721 AAAAAA   726
```

FIG. 35

```
                 10        20        30        40
1    MSRRSMLLAWALPSLLRLGAAQETEDPACCSPIVPRNEWK HCDDP40.aa
1    -----MLFACALLALLGLATS--------CSFIVPRSEWR emb|CAA60133.1

                 50        60        70        80
41   ALASECAQHLSLPLRYVVVSHTAGSSCNTPASCQQQARNV HCDDP40.aa
28   ALPSECSSRLGHPVRYVVISHTAGSFCNSPDSCEQQARNV emb|CAA60133.1

                 90       100       110       120
81   QHYHMKTLGWCDVGYNFLIGEDGLVYEGRGWNFTGAHSGH HCDDP40.aa
68   QHYHKNELGWCDVAYNFLIGEDGHVYEGRGWNIKGDHTGP emb|CAA60133.1

                130       140       150       160
121  LWNPMSIGISFMGNYMDRVPTPQAIRAAQGLLACGVAQGA HCDDP40.aa
108  IWNPMSIGITFMGNFMDRVRKAGP--------PCCPKSSG emb|CAA60133.1

                170       180       190
161  LRSNYVLKGHRDVQRTLSPGNQLYHLIQNWPHYRSP     HCDDP40.aa
140  IWG---VSGLPEIQ                           emb|CAA60133.1
```

Decoration 'Decoration #1': Shade (with solid black) residues that match the Consensus exactly.

Figure 37

```
                  Leader peptide       | D1
Siglec-10    1 M-LLPLLLSSLLGGSQAMDGR-----FWIRVQESVMVPEGLCISVPCSFSYPRQDWTGS-TPAYGYWFKAVTETTKGAPV
Siglec-5     1 M-LPLLLLPLLWGGSLQEKPV-----YELQVQKSVTVQEGLCVLVPCSFSYPWRSWYSS-PPLYVYWFRDGEIPYYAEVV
Siglec-6     1 M--LPLLLLPLLWAGALAQERR-----FQLEGPESLTVQEGLCVLVPCRLPTTLPASYYG--YGYWFLEGA------DVPV
Siglec-3     1 M-PLLLLLPLLWAGALAMDPN-----FWLQVQESVTVQEGLCVLVPCTFFHPIPYYDKN-SPVHGYWFREGAIISGDSPV
Siglec-8     1 MLLLLLLLPLLWGTKGMEGDRQYGDGYLLQVQELVTVQEGLCVHVPCSFSYPQDGWTDS-DPVHGYWFRAGDRPYQDAPV
Siglec-7     1 M-LLLLLLPLLWGRERVEGQKSNRKDYSLTMQSSVTVQEGMCVHVRCSFSYPVDSQTDS-DPVHGYWFRAGNDISWKAPV
Siglec-9     1 M--LLLLLPLLWGRERAEGQTS----KLLTMQSSVTVQEGLCVHVPCSFSYPSHGWIYPGPVVHGYWFREGANTDQDAPV

                                                                                  | D2
Siglec-10   74 ATNHQSREVEMSTRGRFQLTGDPAKGNCSLVIRDAQMQDESQYFFRVERGSYVRYN------FMNDGFFLKVTALTQKPD
Siglec-5    74 ATNNPDRRVKPETQGRFRLLGDVQKKNCSLSIGDARMEDTGSYFFRVERGRDVKYS------YQQNKLNLEVTALIEKPD
Siglec-6    66 ATNDPDEEVQEETRGRFHLLWDPRRKNCSLSIRDARRRDNAAYFFRLKSKWM-KYG------YTSSKLYVRVMALTHRPN
Siglec-3    74 ATNKLDQEVQEETQGRFRLLGDPSRNNCSLSIVDARRRDNGSYFFRMERGST-KYS------YKSPQLSVHVTDLTHRPK
Siglec-8    80 ATNNEDREVQAETQGRFQLLGDIWSNDCSLSIRDARKRDKGSYFFRLERGSM-KWSYKSQLNYKTKQLSVFVTALTHRPD
Siglec-7    79 ATNNPAWAVQEETRDRFHLLGDPQTKNCTLSIRDARMSDAGRYFFRMEKGNI-KWN------YKYDQLSVNVTALTHRPN
Siglec-9    75 ATNNPARAVWEETRDRFHLLGDPHTKNCTLSIRDARRSDAGRYFFRMEKGSI-KWN------YKHHRLSVNVTALTHRPN

Siglec-10  149 WYIPETLEPGQPVTWICVFNWAFEECPPPSFSWTGAALSSQGTKPTTSHFSVLSFTPRPQDHNTDLTCHVDFSRKGVSVQ
Siglec-5   149 IHFLEPLESGRPTRLSCSLPGSCEAGPPLTFSWTGNALSPLD--PETTRSSELTLTPRPEDHGTNLTCQMKRQGAQVTTE
Siglec-6   140 ISIPG-PGVWPSSNLTCSVPWVCEQGTPPIFSWMSAAPHLLG--PRTTQSSVLTITPRPQDHSTNLTCQVTFPGAGVTME
Siglec-3   148 ILIPGTLEPGHSKNLTCSVSWACEQGTPPIFSWLSAAPTSLG--PRTTHSSVLIITPRPQDHGTNLTCQVKFAGAGVTTE
Siglec-8   160 ILILGTLESGHSRNLTCSVPWACKQGTPPMISWIGASVSSPG--PTTARSSVLTLTPKPQDHGTSLTCQVTLPGTGVTTT
Siglec-7   153 ILIPGTLESGCFQNLTCSVPWACEQGTPPMISWMGTSVSPLH--PSTTRSSVLTLIPQPQHHGTSLTCQVTLPGAGVTTN
Siglec-9   149 ILIPGTLESGCPQNLTCSVPWACEQGTPPMISWIGTSVSPLD--PSTTRSSVLTLIPQPQDHGTSLTCQVTFPGASVTTN

                       |   Linker 1    | D3
Siglec-10  229 RTVRLRVAYAPRDLVISISRDNTPALEPQPQGNVPYLEAQKGQFLRLLCAADSQPPATLSWVLQNRVLSSSHPWGPRPLG
Siglec-5   227 RTVQLNVSYAPQ--TITIF-RNGIA-------------------------------------------------------
Siglec-6   216 RTIQLNVSYAPQKVAISIFQGNSAA-------------------------------------------------------
Siglec-3   226 RTIQLNVTYVPQNPTTGIFPGDGS--------------------------------------------------------
Siglec-8   238 STVRLDVSYPPWNLTMTVFQGDATA-------------------------------------------------------
Siglec-7   231 RTIQLNVSYPPQNLTVTVFQGEGTA-------------------------------------------------------
Siglec-9   227 KTVHLNVSYPPQNLTMTVFQGDGTV-------------------------------------------------------

                                                  |  Linker 2 ?  | D4  ?
Siglec-10  309 LELPGVKAGDSGRYTCRAENRLGSQQRALDLSVQYPPENLRVMVSQANRTVLENLGNGTSLPVLEGQSLCLVCVTHSS--
Siglec-5   246 -------------------------------------------------------LEILQNTSYLPVLEGQALRLLCDAPSN--
Siglec-6   238 -------------------------------------------------------FKILQNTSSLPVLEGQALRLLCDADGN--
Siglec-3   247 --------------------------------------------------------------------------------
Siglec-8   260 -------------------------------------------------------STALGNGSSLSVLEGQSLRLVCAVNSN--
Siglec-7   253 -------------------------------------------------------STALGNSSSLSVLEGQSLRLVCAVDSN--
Siglec-9   249 -------------------------------------------------------STVLGNGSSLSLPEGQSLRLVCAVDAVDS

                                                                          | D5
Siglec-10  386 -PPAILSWTQRGQVLSPSQPSAPGVLELPRVQVEHEGEFTCHARHPLGSQHVSLSLSVHYSPKLLGPSCSWEAEGLHCSC
Siglec-5   275 -PPAILSWFQGSPALNATPISNTGILELRRVRSAEKGGFTCRAQHPLGFLQIFLNLSVYSLPQLLGPSCSWEAEGLHCRC
Siglec-6   267 -PPAILSWFQGFPALNATPISNTGVLELPQVGSAEEGDFTCRAQHPLGSLQISLSLFVH---------------------
Siglec-3   250 --------------------------------------------------------------------------------
Siglec-8   289 -PPAILSWTRGSLTLCPSRSSNPGLLELPRVHVRDEGEFTCRAQNAQGSQHISLSLSLQ---------------------
Siglec-7   282 -PPAILSWTWRSLTLYPSQPSNPLVLEL-QVHLGDEGEFTCRAQNSLGSQHVSLNLSLQ---------------------
Siglec-9   281 NPPAILSLSWRGLTLCPSQPSNPGVLELPWVHLRDAAEFTCRAQNPLGSQQVYLNVSLQ---------------------

                            ?                   ?                                  |
Siglec-10  466 SSQPSPAPSLRVWLGEELLEGNSSQDSFEVTPSSAGPWANSSLSLHGGLSSGLRLRCEAWNVHGAQSGSILQLPDKKGLI
Siglec-6   331 S---------------------------------------------------------------------------WKPEG
Siglec-5   355 -FRAWPAPSLQWRLEEKPLEGNSSQGSFKVNSSSPGPWANSSLILHGGLNSDLKVSCKAWNIYGSQSGSVL-LLQGRSNL
Siglec-3   257 -----------------------------------------------------------------------GKQETRA
Siglec-8   353 ---------------------------------------------------------------------NEGTGTSRP
Siglec-7   345 ---------------------------------------------------------------------QEYTGKMRP
Siglec-9   343 -----------------------------------------------------------------------------SKA

                  Transmembrane       |     CT I        |Y-based motif I
Siglec-10  546 SLLPSNGAFLGIGITALLFLCLALIIIMKILPKRRTQTETPRPRFSRHSTILDYINVVPTAGPLAQKRNQKATPNSPRTPL
Siglec-5   434 RLGVVPGALGGAGVMALLCICLCLIFFLIVKARRKQA------------------------------AGRPEKMDDE
Siglec-6   331 GALGVLGALWGASITTLVFLCVCFIFRVKTRRKKA--------------------------------AQPVQNTDDV
Siglec-3   257 G-LVHGAIGG-AGVTALLALCLCLIFFIVKTHRRKA-------------------------------ARTAVGSNDT
Siglec-8   357 VLQVTLGAVGGAGATALAFLSFCIIFIIVRSCRKKS-------------------------------ARPAAGVGDT
Siglec-7   349 VLGVLLGAVGGAGATALVFLSFCVIFIVVRSCRKKS-------------------------------ARPAADVGDI
Siglec-9   343 TLGVTQGAVGGAGATALVFLSFCVIFVVVRSCRKKS-------------------------------ARPAAGVGDT

                 CT II                            Y-based motif II     Y-based motif III
Siglec-10  626 PPG-HPSPESK--KNQKKQYQLPSFPEPKSSTQAPESQESQEELHYATLNFPGVRPRPEARMPKGTQADYAEVKFQ--
Siglec-5   505 DPIMETITSG-----SRKKPWPDSPGDQASPPGDAPPLEEQKELHYASLSFSEMKSREPKDQEAPSTTEYSEIKTSK-
Siglec-3   325 NPTTASASPK-----HQKNSKLHGPTETSSCSGAAPTVEMDEELHYASLNFHGMNPSKD------TSTEYSEVRTQ--
Siglec-8   427 HMEDVKAIRGSASQVSDVGFSTPSIQPGHL-----------------------------------------------
Siglec-6   400 GPVMVSGSRG-----HQHQFQTGIVSDHPAEAGPI-SEDEQ-ELHYAVLHFHKVQPQEPKV----TDTEYSEIKIHKD
Siglec-9   413 GIEDANAVRGSASQGPLTEPWAEDSPPDQPPPASARSSVGEGELQYASLSFQMVKPWDSRGQEA-TDTEYSEIKIHR-
Siglec-7   419 GMKDTNTIRGSASQGNLTESWADDNPRHHG--LAAHSSGEERELQYAPLSFHKGEPQDLSGQEA-TNNEYSEIKIPK-
```

Figure 38
A
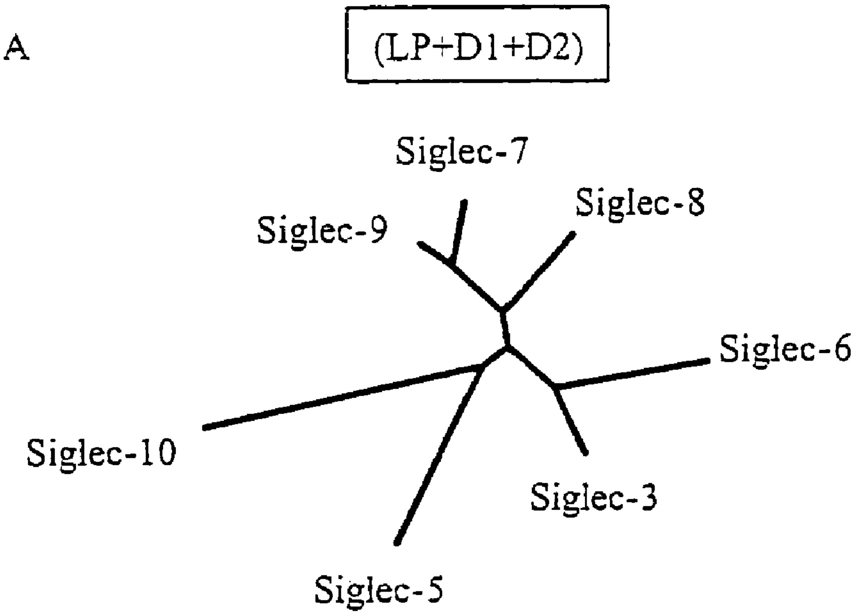
B
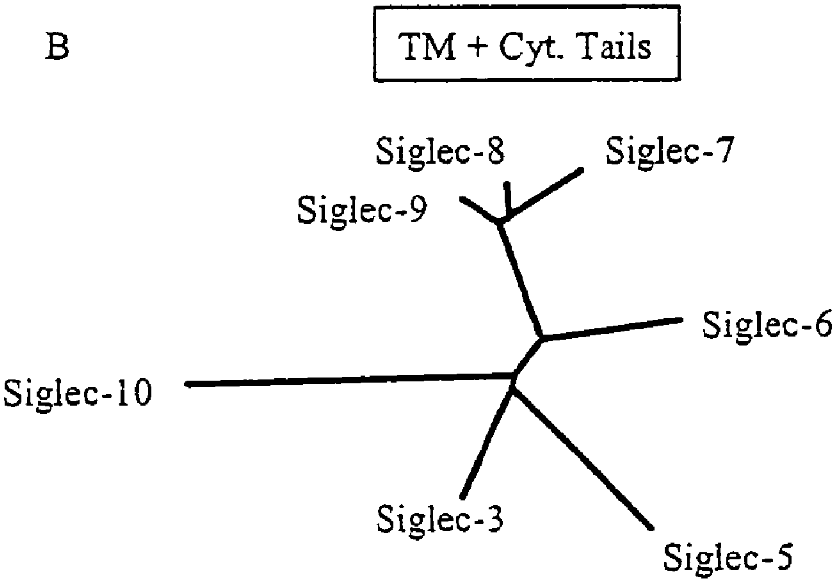

Figure 40
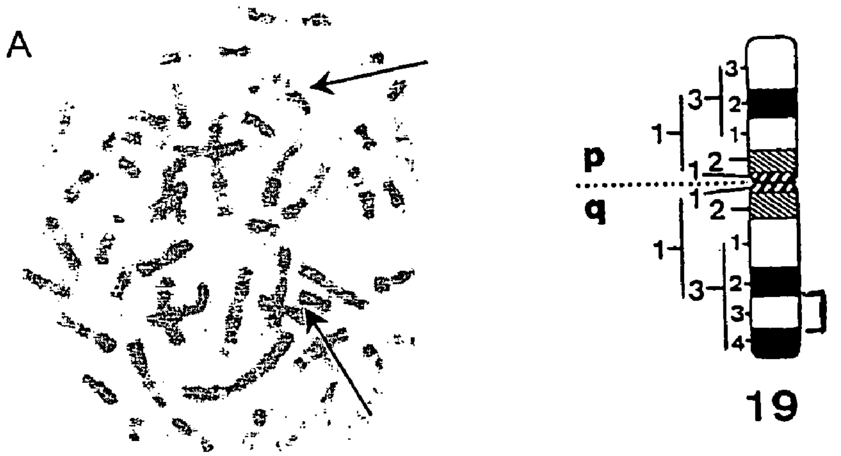
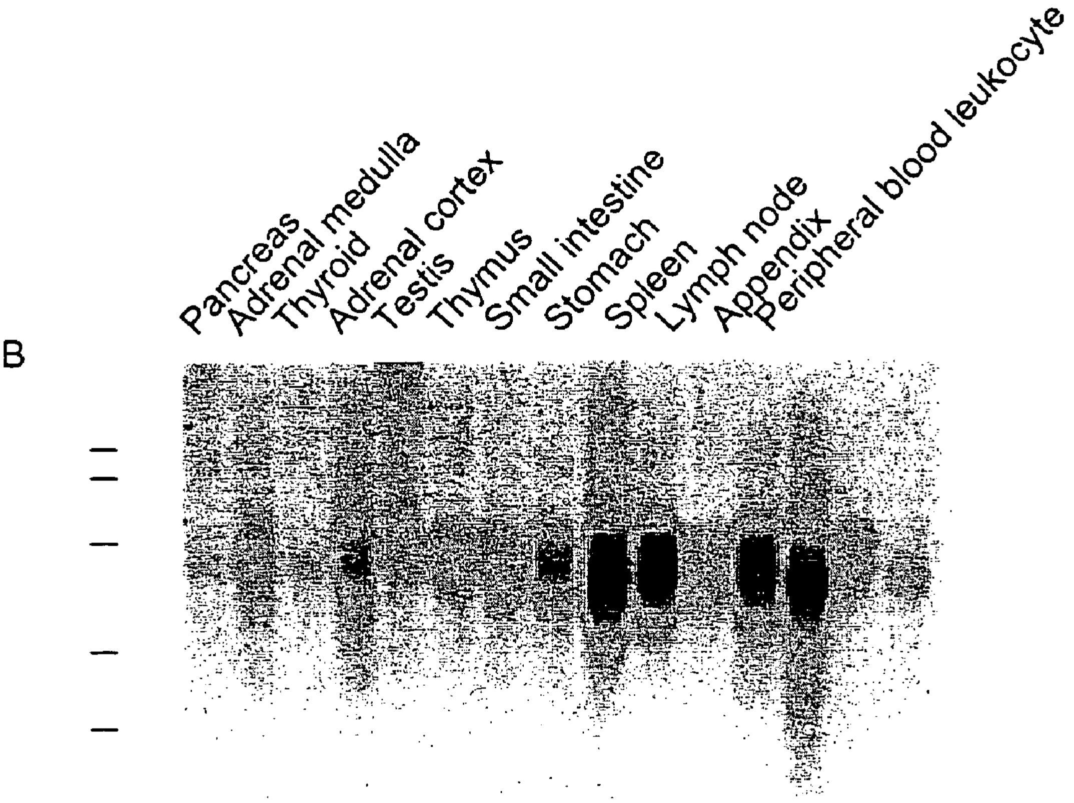

SEQUENCE LISTING

<160> NUMBER OF SEQ ID NOS: 149

<210> SEQ ID NO 1
<211> LENGTH: 733
<212> TYPE: DNA

-continued

<213> ORGANISM: Homo sapiens

<400> SEQUENCE: 1
gggatccgga gcccaaatct tctgacaaaa ctcacacatg cccaccgtgc ccagcacctg 60
aattcgaggg tgcaccgtca gtcttcctct tccccccaaa acccaaggac accctcatga 120
tctcccggac tcctgaggtc acatgcgtgg tggtggacgt aagccacgaa gaccctgagg 180
tcaagttcaa ctggtacgtg gacggcgtgg aggtgcataa tgccaagaca aagccgcggg 240
aggagcagta caacagcacg taccgtgtgg tcagcgtcct caccgtcctg caccaggact 300
ggctgaatgg caaggagtac aagtgcaagg tctccaacaa agccctccca acccccatcg 360
agaaaaccat ctccaaagcc aaagggcagc cccgagaacc acaggtgtac accctgcccc 420
catcccggga tgagctgacc aagaaccagg tcagcctgac ctgcctggtc aaaggcttct 480
atccaagcga catcgccgtg gagtgggaga gcaatgggca gccggagaac aactacaaga 540
ccacgcctcc cgtgctggac tccgacggct ccttcttcct ctacagcaag ctcaccgtgg 600
acaagagcag gtggcagcag gggaacgtct tctcatgctc cgtgatgcat gaggctctgc 660
acaaccacta cacgcagaag agcctctccc tgtctccggg taaatgagtg cgacggccgc 720
gactctagag gat 733

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring
L-amino acids

<400> SEQUENCE: 2

Trp Ser Xaa Trp Ser
1 5

<210> SEQ ID NO 3
<211> LENGTH: 86
<212> TYPE: DNA
<213> ORGANISM: Homo sapiens

<400> SEQUENCE: 3
gcgcctcgag atttccccga aatctagatt tccccgaaat gatttccccg aaatgatttc 60
cccgaaatat ctgccatctc aattag 86

<210> SEQ ID NO 4
<211> LENGTH: 27
<212> TYPE: DNA
<213> ORGANISM: Homo sapiens

<400> SEQUENCE: 4
gcggcaagct ttttgcaaag cctaggc 27

<210> SEQ ID NO 5
<211> LENGTH: 271
<212> TYPE: DNA
<213> ORGANISM: Homo sapiens

<400> SEQUENCE: 5
ctcgagattt ccccgaaatc tagatttccc cgaaatgatt tccccgaaat gatttccccg 60
aaatatctgc catctcaatt agtcagcaac catagtcccg cccctaactc cgcccatccc 120

-continued gcccctaact ccgcccagtt ccgcccattc tccgccccat ggctgactaa ttttttttat 180
ttatgcagag gccgaggccg cctcggcctc tgagctattc cagaagtagt gaggaggctt 240
ttttggaggc ctaggctttt gcaaaaagct t 271

<210> SEQ ID NO 6
<211> LENGTH: 32
<212> TYPE: DNA
<213> ORGANISM: Homo sapiens

<400> SEQUENCE: 6
gcgctcgagg gatgacagcg atagaacccc gg 32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c 31

<210> SEQ ID NO 8
<211> LENGTH: 12
<212> TYPE: DNA
<213> ORGANISM: Homo sapiens

<400> SEQUENCE: 8
ggggactttc cc 12

<210> SEQ ID NO 9
<211> LENGTH: 73
<212> TYPE: DNA
<213> ORGANISM: Homo sapiens

<400> SEQUENCE: 9
gcggcctcga ggggactttc ccggggactt tccggggact ttccgggact ttccatcctg 60
ccatctcaat tag 73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg ggactttccg ggactttcca tctgccatct 60
caattagtca gcaaccatag tcccgcccct aactccgccc atcccgcccc taactccgcc 120
cagttccgcc cattctccgc cccatggctg actaattttt tttatttatg cagaggccga 180
ggccgcctcg gcctctgagc tattccagaa gtagtgagga ggcttttttg gaggcctagg 240
cttttgcaaa aagctt 256

<210> SEQ ID NO 11
<211> LENGTH: 2609
<212> TYPE: DNA
<213> ORGANISM: Homo sapiens

<400> SEQUENCE: 11
gcgtccgggc caaaatgctg agaacgtcca ctcctaatct gtgtggtggt ctgcattgcc 60
gggccccctg gctctcttct ggcattctct gcctctgcct catattcttg ttaggccagg 120

-continued

```
tgggcttgct gcagggacac ccccagtgcc tggattacgg gccccctttc cagccccctc    180
tgcaccttga gttttgctct gactatgagt ccttcggctg ctgtgatcag cacaaggacc    240
gccgcatcgc tgcccggtac tgggacatca tggaatattt tgatctgaag agacatgagc    300
tgtgtggaga ttacattaaa gacatccttt gccaggagtg ctcgccctac gcagcccact    360
ctacgacgcc gaaaacaccc agacgcctct ccggaatctc ccgggcctct gctctgatta    420
ctgctctgcc ttccattcta actgtcactc agccatttcc ctgctgacca atgaccgcgg    480
cctccaggag tctcatggaa gggacggtac ccgcttctgc cacctcctgg accttcctga    540
caaggactat tgcttcccta atgtcctgag gaacgactat ctcaaccgcc acctgggcat    600
ggtggcccaa gatcctcagg gctgcctgca gctctgcctg agcgaggtgg ccaacgggct    660
gaggaacccc gtctccatgg tccatgctgg ggacggcacc catcgcttct ttgttgccga    720
gcaggtagga gtggtgtggg tctacctccc tgatgggagt cgcctggagc aacccttcct    780
ggacctcaag aacatcgtgt tgaccacccc atggatcggg gatgagagag gcttcttggg    840
gttggctttt caccccaaat tccgccacaa tcgcaagttc tatatttatt attcgtgcct    900
ggacaagaag aaggtagaaa agatccgaat tagtgagatg aaggtttctc gggctgatcc    960
taacaaagct gacctgaaat cagagagggt catcttggag attgaagaac cagcctcaaa   1020
ccataatggc ggacaacttc tttttggcct ggatggctat atgtacatat tcactgggga   1080
cgggggacag gctggagatc cctttggcct gtttggaaat gctcagaaca aaagttccct   1140
gctgggaaaa gttttaagga tcgatgtgaa cagggcaggc tcacatggca agcggtaccg   1200
agtcccctcg gacaatccat ttgtttctga gccaggggcc caccccgcca tctatgccta   1260
tgggatcagg aacatgtggc gttgtgctgt ggaccgaggg gaccccatca cgcgccaggg   1320
ccgaggccgg atattctgtg ggacgtgggg ccagaacagg tttgaagagg ttgacctcat   1380
tttgaaaggt ggaaactatg gctggagagc aaaggaaggg tttgcatgtt atgacaaaaa   1440
actttgtcac aatgcctctt tggatgatgt tctgccaatc tatgcttatg gccatgcagt   1500
ggggaagtca gtcactggag gttatgtcta tcgtggttgt gaatccccaa atctcaatgg   1560
cctgtatatc tttggagact tcatgagtgg tcgacttatg gctttgcagg aagatagaaa   1620
aaacaagaaa tggaagaagc aggatctttg cctgggcagc accacgtcct gtgccttccc   1680
agggctgatc agcacccata gcaagttcat catctccttt gctgaagatg aagcagggga   1740
gctgtatttc ctggcgacct cttacccaag tgcctatgca ccacgtggat ctatttacaa   1800
gtttgttgac cctcaaggcc gagcaccccc aggcaagtgc aaatacaagc cagtgcccgt   1860
gagaaccaag agtaagcgga tcccgttcag accactcgcc aagacagtct tggacttgct   1920
aaaggaacaa tcagagaaag ctgctagaaa atcttccagt gcaaccttag cttctggccc   1980
agcccagggt ttgtctgaga aaggctcctc caagaagctg gcttctccta caagcagcaa   2040
gaatacattg cgagggcctg gtacaaagaa gaaagccaga gtggggcccc acgtccgcca   2100
gggcaagagg aggaagagcc tgaaaagcca cagtggcagg atgaggccat cagcagagca   2160
gaagcgagct ggcagaagtc tcccttgacc tattggtcaa ggtggccgac agggtgacgt   2220
gagagaggag agccacctca tcaaatgaaa gtcactgctg aataaagacc ttagaagtct   2280
gggaagccag ggtagaggtg gggcagggcg gttttcctct ccctgggaaa tcttgctgtc   2340
tactgaataa ataaatgcac cttctctgta tgcagtgctt ctgtgggaga ccatatccca   2400
gattgctggt gcacctgggt tatggtaagc actatccatg agcctgcttg gaatcacact   2460
ggatgtctcc gttttgtctt gtaaatgcct acaacctgag gtaataaatc aacatttgct   2520
```

caaactggca aaaaaaaaaa aaaaaaaaaa aaaaaaaaaa aaaaaaaaaa aaaaaaaaaa 2580
aaaaaaaaaa aaaaaaaaaa aaaaaaaaa 2609

<210> SEQ ID NO 12
<211> LENGTH: 2499
<212> TYPE: DNA
<213> ORGANISM: Homo sapiens

<400> SEQUENCE: 12
caccagcacc ccgcccagag cagtgccgct gcccaaatcc tcgcaggcag ctcatcaacg 60
caattgcaac tccggctgga gccccggacc tgcaagcctg ggtgtccgtg ggtccgtctg 120
cccagccatc tgctggtggc acctctccct cctgccgcct ccctcggtga accccacctt 180
gcagaagtgc agctcgcccg gagcagccca ggagctcagc atgcgtcccc caggcttcag 240
gaacttcttg ctgctggcgt cctcccttct ctttgctggg ttgtcagctg ttcctcaaag 300
cttctcgcca tctctgagga gctggccggg cgccgcctgc aggctgtccc gggccgagtc 360
ggagcgacgc tgccgcgcac ctgggcagcc cccgggggcc gcgctgtgcc acggccgggg 420
ccgctgcgac tgcggcgtct gcatctgcca cgtgactgag ccgggcatgt tcttcgggcc 480
cctgtgtgag tgccatgagt gggtgtgcga gacctacgac gggagcacct gtgcaggcca 540
tggtaagtgt gactgtggca agtgcaagtg tgaccaggga tggtatgggg atgcttgcca 600
gtacccaact aactgtgact tgacaaagaa gaaaagtaac caaatgtgca agaattcaca 660
agacatcatc tgctctaatg caggtacatg tcactgtggc aggtgtaagt gtgataattc 720
agatggaagt ggacttgtgt atggtaaatt ttgtgagtgt gacgatagag aatgcataga 780
cgatgaaaca gaagaaatat gtggaggcca tgggaagtgt tactgtggaa actgctactg 840
caaggctggt tggcatggag ataaatgtga attccagtgc gatatcaccc cctgggaaag 900
caagcgaaga tgcacgtctc cagatggcaa aatctgcagt aacagaggga cttgtgtatg 960
tggtgaatgt acctgtcacg atgttgatcc gactggggac tggggagata ttcatgggga 1020
cacctgtgaa tgtgatgaga gggactgtag agctgtctat gaccgatatt ctgatgactt 1080
ctgttcaggt catggacagt gtaattgcgg aagatgtgac tgcaaagcag gctggtatgg 1140
gaagaagtgt gagcacccac agtcctgcac gctgtcagct gaggagagca tcaggaagtg 1200
ccagggaagc tcggatctgc cttgctctgg gaggggtaaa tgtgaatgtg gcaaatgcac 1260
ctgctatcct ccaggagatc gccgggtgta tggcaagact tgtgagtgtg atgatcgccg 1320
ctgtgaagac ctcgatggtg tggtctgtgg aggccacggc acatgttcct gtggtcgctg 1380
tgtttgtgag agaggatggt ttggaaagct ctgccaacat ccgcggaagt gtaacatgac 1440
ggaagaacaa agcaagaatc tgtgtgaatc agcagatggc atattgtgct cggggaaggg 1500
ttcttgtcat tgtgggaagt gcatttgttc tgctgaagag tggtatattt ctggggagtt 1560
ctgtgactgt gatgacagag actgcgacaa acatgatggt ctcatttgta cagggaatgg 1620
aatatgtagc tgtggaaact gtgaatgctg ggatggatgg aatggaaatg catgtgaaat 1680
ctggcttggc tcagaatatc cttaacaatt acatgagaga ggtctggatt cttatttttt 1740
ctgggccatt agaacatata aatgcgaagg aaaccatgta tattcaccac taggacaggt 1800
taaaaagacc attgtatgtt tttctatttc tgaattacga atgaaatccg agtacctatt 1860
agaaatgagt tatgcaaatt tagatgcaaa taacattaga aaaaaaagat tcttccataa 1920
ttaacataag tggttcctaa cgagagcaat tttccaccc aaaagtcatt tggcaacatc 1980

-continued

```
tacagacaat tttgattgtc acactgggtc gggtaggaag gtatgctgca gacatttggt   2040

gggtagaggc cagggatgct gctgagcatc ccgcagtgta caggacagcc cccaaacaag   2100

gaattatcca gccccaaatg ccaatagggc tcagactgag aaacattgag ttatatggct   2160

attagaaatc cacattctta cacaagaaag accatattag aatctaagga aaacatgcat   2220

attcacatta attaatcgat cagatttttc cagaattccg tatcagtcac cattttaata   2280

tggggacaat gaagacaagc acacaggagg tagaatatca gagtggggct ggatcaaggg   2340

caaaaactgg tcattaagtc atctgacatt aaatcattta gccactaagt tatttgtgta   2400

ctctcacttt aaactcacca aagaagattc tcttaaagaa attatgaaaa atgtacaatt   2460

taacatttta aataaatagt gacagaagtt gtttaaaaa                          2499
```

<210> SEQ ID NO 13
<211> LENGTH: 1339
<212> TYPE: DNA
<213> ORGANISM: Homo sapiens

<400> SEQUENCE: 13

```
ggcacgagag cgtgacccag ctgcggccgg ccagccatgg agactggagc gctgcggcgc     60

ccgcaacttc tcccgttgct gctgctgctc tgcggtgggt gtcccagagc aggcggctgc    120

aacgagacag gcatgttgga gaggctgccc ctgtgtggga aggctttcgc agacatgatg    180

ggcaaggtgg acgtctggaa gtggtgcaac ctgtccgagt tcatcgtgta ctatgagagt    240

ttcaccaact gcaccgagat ggaggccaat gtcgtgggct gctactggcc caaccccctg    300

gcccagggct tcatcaccgg catccacagg cagttcttct ccaactgcac cgtggacagg    360

gtccacttgg aggacccccc agacgaggtt ctcatcccgc tgatcgttat acccgtcgtt    420

ctgactgtcg ccatggctgg cctggtggtg tggcgcagca aacgcaccga cacgctgctg    480

tgagggtccc ggtgagatgg agtgggtcac acctggcaag ctggaagaaa gttccctggg    540

gatgggagag cgggtgggtg ctgccaatct ccagctactg tggccacacc ccacctggtc    600

atgggcagac ccctcccttc ctgggctgac ctgctccctc gaggccagcc tgctccctgg    660

ctgaggctca ggctatccgc ccaagctctt tgctcattct agggccagtg gaggaaaatg    720

tgataaggcc agagcttgtg tgctgggcac agaaatcacc tgctgcatcc tgtgctccgc    780

agctgggccg gacctctgcc cgcaggtttc tatgctgttt cttagcacag aatccagcct    840

agccttagcc gcagtctaag ccctgcttgg actaggactc cttgcttgac cccatctctg    900

gttcctgccc tggctcctgc accagcccca gctcctgcct acatccaggc agaaagatag    960

caggggctct tggaagacgt tccgtgctgt gacctccgag ccctcctggt gggaagacag   1020

ctggaaaggc tgggaggaga agggaggggt tgggggttcc caggagccat gcgtggcctg   1080

cagagtccat tccatcatga tgctgtgccc gctatgggct gtgtccatga ccagaggctg   1140

gagtgggggt gtgttagagc ccctcaccgg gacttgctgt gcggatgggg cctgggcctc   1200

cttcctacag gggctcctct gtgggtgagg ggccctctgg aatggcatcc catgagcttg   1260

tggcctctat ctgctaccat ctgtgtttta tctgagtaaa gttaccttac ttctggaaaa   1320

aaaaaaaaaa aaaaaaaaa                                                1339
```

<210> SEQ ID NO 14
<211> LENGTH: 1389
<212> TYPE: DNA
<213> ORGANISM: Homo sapiens

<400> SEQUENCE: 14

-continued

```
ggcacgagga cagcctccac cagagtcccc acctttctgg aagctgcagg gctctccatc     60

caggatccag aagcattgaa ggggaccagc cgctgaaggg attctcagtc ccatctgact    120

ccccatgagg ctcctggctt tcctgagtct gctggccttg gtgctgcagg agacagggac    180

agcttctctc ccaaggaagg agaggaagag gagagaggag cagatgccca gggaaggcga    240

ttcctttgaa gttctgcctc tgcggaatga tgtcctgaac ccagacaact atggtgaagt    300

cattgacctg agcaactatg aggagctcac agattatggg gaccaactcc ccgaggttaa    360

ggtgactagc ctcgctcctg caaccagcat cagtcccgcc aagagcacta cggctccagg    420

gacaccctcg tcaaacccca cgatgaccag acctactaca gcagggctgc tactgagttc    480

ccagcccaac catggtctgc ccacctgcct ggtctgcgtg tgcctcggtt cctctgtgta    540

ttgcgatgac attgacctag aggacattcc tcctcttcct cggaggactg cctacctgta    600

tgcacgcttc aaccgcatca gccgtatcag ggccgaagac ttcaaagggc tgacaaagtt    660

gaagaggatt gacctctcca acaacctcat ttcctccatc gataatgatg ccttccgcct    720

gctacatgcc ctccaggacc tcatcctccc agagaaccag ttggaagctc tgcccgtgct    780

gcccagtggc attgagttcc tggatgtccg cctaaatcgg ctccagagct cggggataca    840

gcctgcagcc ttcagggcaa tggagaagct gcagttcctt tacctgtcag acaacctgct    900

ggattctatc ccggggcctt tgcccccgag cctgcgctct gtacacctgc agaataacct    960

gatagagacc atgcagagag acgtcttctg tgaccccgag gagcacaaac acacccgcag   1020

gcagctggaa gacatccgcc tggatggcaa ccccatcaac ctcagcctct tccccagcgc   1080

ctacttctgc ctgcctcggc tccccatcgg ccgcttcacg tagctcggag cccttccact   1140

cctcccaggt catctcttgg accagcgggc atcacattct ccagcagccg ccatctcaca   1200

cgcctccctc ctgtggccgc cggcagcatg gacaaaggtc tccatgcagg gggaggaggc   1260

ctgcttcttt ccccacagct ctcacgtctc ccttctccct gcgggtgaca aagaagccca   1320

aggaccacct ccttcctgcc tcattgtaat aaaattcccc acactgaaaa aaaaaaaaaa   1380

aaaaaaaaa                                                           1389
```

<210> SEQ ID NO 15
<211> LENGTH: 2295
<212> TYPE: DNA
<213> ORGANISM: Homo sapiens

<400> SEQUENCE: 15

```
ccacgcgtcc gagagaacag gcctgtctca ggcaggccct gcgcctccta tgcggagatg     60

ctactgccac tgctgctgtc ctcgctgctg ggcgggtccc aggctatgga tgggagattc    120

tggatacgag tgcaggagtc agtgatggtg ccggaggcct gtgacatctc tgtgccctgc    180

tctttctcct acccccgaca agactggaca gggtctaccc cagcttatgg ctactggttc    240

aaagcagtga ctgagacaac caagggtgct cctgtggcca caaaccacca gagtcgagag    300

gtggaaatga gcacccgggg ccgattccag ctcactgggg atcccgccaa ggggaactgc    360

tccttggtga tcagagacgc gcagatgcag gatgagtcac agtacttctt tcgggtggag    420

agaggaagct atgtgagata taatttcatg aacgatgggt tctttctaaa agtaacagtg    480

ctcagcttca cgcccagacc ccaggaccac aacaccgacc tcacctgcca tgtggacttc    540

tccagaaagg gtgtgagcgc acagaggacc gtccgactcc gtgtggccta tgcccccaga    600

gaccttgtta tcagcatttc acgtgacaac acgccagccc tggagcccca gccccaggga    660
```

-continued

```
aatgtcccat acctggaagc ccaaaaaggc cagttcctgc ggctcctctg tgctgctgac    720

agccagcccc ctgccacact gagctgggtc ctgcagaaca gagtcctctc ctcgtcccat    780

ccctggggcc ctagacccct ggggctggag ctgcccgggg tgaaggctgg ggattcaggg    840

cgctacacct gccgagcgga gaacaggctt ggctcccagc agcgagccct ggacctctct    900

gtgcagtatc ctccagagaa cctgagagtg atggtttccc aagcaaacag gacagtcctg    960

gaaaaccttg ggaacggcac gtctctccca gtactggagg gccaaagcct gtgcctggtc   1020

tgtgtcacac acagcagccc cccagccagg ctgagctgga cccagagggg acaggttctg   1080

agcccctccc agccctcaga ccccggggtc ctggagctgc ctcgggttca agtggagcac   1140

gaaggagagt tcacctgcca cgctcggcac ccactgggct cccagcacgt ctctctcagc   1200

ctctccgtgc actactcccc gaagctgctg ggcccctcct gctcctggga ggctgagggt   1260

ctgcactgca gctgctcctc ccaggccagc ccggcccccct ctctgcgctg gtggcttggg   1320

gaggagctgc tggaggggaa cagcagccag gactccttcg aggtcacccc cagctcagcc   1380

gggccctggg ccaacagctc cctgagcctc catggagggc tcagctccgg cctcaggctc   1440

cgctgtgagg cctggaacgt ccatggggcc cagagtggat ccatcctgca gctgccagat   1500

aagaagggac tcatctcaac ggcattctcc aacggagcgt ttctgggaat cggcatcacg   1560

gctcttcttt tcctctgcct ggccctgatc atcatgaaga ttctaccgaa gagacggact   1620

cagacagaaa ccccgaggcc caggttctcc cggcacagca cgatcctgga ttacatcaat   1680

gtggtcccga cggctggccc cctggctcag aagcggaatc agaaagccac accaaacagt   1740

cctcggaccc ctcttccacc aggtgctccc tccccagaat caaagaagaa ccagaaaaag   1800

cagtatcagt tgcccagttt cccagaaccc aaatcatcca ctcaagcccc agaatcccag   1860

gagagccaag aggagctcca ttatgccacg ctcaacttcc caggcgtcag acccaggcct   1920

gaggcccgga tgcccaaggg cacccaggcg gattatgcag aagtcaagtt ccaatgaggg   1980

tctcttaggc tttaggactg ggacttcggc taggaggaag gtagagtaga agttgaagat   2040

aaccgagtgc aagagtttcc ttctctccct ctctctctct ctttctctct ctctctctct   2100

ttctctctct ttttaaaaaa actctggcca cggcacagtg gctcacgcct gtaatcccag   2160

cactttggga agttgaagtt gggccaaatc ccctgagtcc ggattcgaaa acagcctggc   2220

caacttgtga aaacccgtct ctacttaaaa atacccaaat tacctgggca ttgtggcagg   2280

ggcctgttta tcctt                                                    2295
```

<210> SEQ ID NO 16
<211> LENGTH: 1748
<212> TYPE: DNA
<213> ORGANISM: Homo sapiens

<400> SEQUENCE: 16

```
agacgttccc tcgcggccct ggcacctcca accccagata tgctgctgct gctgctgctg     60

cccctgctct gggggaggga gagggtggaa ggacagaaga gtaaccggaa ggattactcg    120

ctgacgatgc agagttccgt gaccgtgcaa gagggcatgt gtgtccatgt gcgctgctcc    180

ttctcctacc cagtggacag ccagactgac tctgacccag ttcatggcta ctggttccgg    240

gcagggaatg atataagctg gaaggctcca gtggccacaa acaacccagc ttgggcagtg    300

caggaggaaa ctcgggaccg attccacctc cttggggacc cacagaccaa aaattgcacc    360

ctgagcatca gagatgccag aatgagtgat gcggggagat acttctttcg tatggagaaa    420

ggaaatataa aatggaatta taaatatgac cagctctctg tgaacgtgac agccttgacc    480
```

-continued

```
cacaggccca acatccttat ccccggtacc ctggagtctg gctgcttcca gaatctgacc    540
tgctctgtgc cctgggcctg tgagcagggg acgcccccta tgatctcctg gatggggacc    600
tctgtgtccc ccctgcaccc ctccaccacc cgctcctcag tgctcaccct catcccacag    660
ccccagcacc acggcaccag cctcacctgt caggtgacct tgcctggggc cggcgtgacc    720
acgaacagga ccatccaact caatgtgtcc taccctcctc agaacttgac tgtgactgtc    780
ttccaaggag aaggcacagc atccacagct ctggggaaca gctcatctct ttcagtccta    840
gagggccagt ctctgcgctt ggtctgtgct gttgacagca atccccctgc caggctgagc    900
tggacctgga ggagtctgac cctgtacccc tcacagccct caaaccctct ggtactggag    960
ctgcaagtgc acctgggggga tgaaggggaa ttcacctgtc gagctcagaa ctctctgggt   1020
tcccagcacg tttccctgaa cctctccctg caacaggagt acacaggcaa aatgaggcct   1080
gtatcaggag tgttgctggg ggcggtcggg ggagctggag ccacagccct ggtcttcctc   1140
tccttctgtg tcatcttcat tgtagtgagg tcctgcagga agaaatcggc aaggccagca   1200
gcggacgtgg gagacatagg catgaaggat gcaaacacca tcaggggctc agcctctcag   1260
ggtaacctga ctgagtcctg ggcagatgat aaccccccgac accatggcct ggctgcccac   1320
tcctcagggg aggaaagaga gatccagtat gcacccctca gctttcataa gggggagcct   1380
caggacctat caggtcaaga agccaccaac aatgagtact cagagatcaa gatccccaag   1440
taagaaaatg cagaggctcg ggcttgtttg agggttcacg acccctccag caaaggagtc   1500
tgaggctgat tccagtagaa ttagcagccc tcaatgctgt gcaacaagac atcagaactt   1560
attcctcttg tctaactgaa aatgcatgcc tgatgaccaa actctccctt tccccatcca   1620
atcggtccac actccccgcc ctggcctctg gtacccacca ttctcctctg tacttctcta   1680
aggatgacta ctttagattc cgaatatagt gagattgtaa cgtgaaaaaa aaaaaaaaaa   1740
aaaaaaaa                                                             1748
```

<210> SEQ ID NO 17
<211> LENGTH: 4995
<212> TYPE: DNA
<213> ORGANISM: Homo sapiens

<400> SEQUENCE: 17

```
gccgcgccga ggaggctgcc gctctggctt gccgcccccc gccgccgctg cacaccggac     60
ccagccgccg tgccgcgggc catggacctg cccaggggcc tggtggtggc ctgggcgctc    120
agcctgtggc cagggttcac ggacaccttc aacatggaca ccaggaagcc ccgggtcatc    180
cctggctcca ggaccgcctt ctttggctac acagtgcagc agcacgacat cagtggcaat    240
aagtggctgg tcgtgggcgc cccactggaa accaatggct accagaagac gggagacgtg    300
tacaagtgtc cagtgatcca cgggaactgc accaaactca acctgggaag ggtcaccctg    360
tccaacgtgt ccgagcggaa agacaacatg cgcctcggcc ttagtctcgc caccaacccc    420
aaggacaaca gcttcctggc ctgcagcccc ctctggtctc atgagtgtgg gagctcctac    480
tacaccacag ggatgtgttc aagagtcaac tccaacttca ggttctccaa gaccgtggcc    540
ccagctctcc aaaggtgcca gacctacatg gacatcgtca ttgtcctgga tggctccaac    600
agcatctacc cctgggtgga ggttcagcac ttcctcatca acatcctgaa aaagttttac    660
attggcccag ggcagatcca ggttggagtt gtgcagtatg gcgaagatgt ggtgcatgag    720
tttcacctca atgactacag gtctgtaaaa gatgtggtgg aagctgccag ccacattgag    780
```

-continued

```
cagagaggag gaacagagac ccggacggca tttggcattg aatttgcacg ctcagaggct    840
ttccagaagg gtggaaggaa aggagccaag aaggtgatga ttgtcatcac agatggggag    900
tcccacgaca gcccagacct ggagaaggtg atccagcaaa gcgaaagaga caacgtaaca    960
agatatgcgg tggccgtcct gggctactac aaccgcaggg ggatcaatcc agaaactttt   1020
ctaaatgaaa tcaaatacat cgccagtgac cctgatgaca agcacttctt caatgtcact   1080
gatgaggctg ccttgaagga cattgtcgat gccctggggg acagaatctt cagcctggaa   1140
ggcaccaaca agaacgagac ctcctttggg ctggagatgt cacagacggg cttttcctcg   1200
cacgtggtgg aggatggggt tctgctggga gccgtcggtg cctatgactg gaatggagct   1260
gtgctaaagg agacgagtgc cgggaaggtc attcctctcc gcgagtccta cctgaaagag   1320
ttccccgagg agctcaagaa ccatggtgca tacctggggt acacagtcac atcggtcgtg   1380
tcctccaggc aggggcgagt gtacgtggcc ggagcccccc ggttcaacca cacgggcaag   1440
gtcatcctgt tcaccatgca caacaaccgg agcctcacca tccaccaggc tatgcggggc   1500
cagcagatag gctcttactt tgggagtgaa atcacctcgg tggacatcga cggcgacggc   1560
gtgactgatg tcctgctggt gggcgcaccc atgtacttca acgagggccg tgagcgaggc   1620
aaggtgtacg tctatgagct gagacagaac cggtttgttt ataacggaac gctaaaggat   1680
tcacacagtt accagaatgc ccgatttggg tcctccattg cctcagttcg agacctcaac   1740
caggattcct acaatgacgt ggtggtggga gccccccctgg aggacaacca cgcaggagcc   1800
atctacatct tccacggctt ccgaggcagc atcctgaaga cacctaagca gagaatcaca   1860
gcctcagagc tggctaccgg cctccagtat tttggctgca gcatccacgg gcaattggac   1920
ctcaatgagg atgggctcat cgacctggca gtgggagccc ttggcaacgc tgtgattctg   1980
tggtcccgcc cagtggttca gatcaatgcc agcctccact ttgagccatc caagatcaac   2040
atcttccaca gagactgcaa gcgcagtggc agggatgcca cctgcctggc cgccttcctc   2100
tgcttcacgc ccatcttcct ggcaccccat ttccaaacaa caactgttgg catcagatac   2160
aacgccacca tggatgagag gcggtataca ccgagggccc acctggacga gggcggggac   2220
cgattcacca acagagccgt actgctctcc tccggccagg agctctgtga gcggatcaac   2280
ttccatgtcc tggacactgc tgactacgtg aagccagtga ccttctcagt cgagtattcc   2340
ctggaggacc ctgaccatgg ccccatgctg gacgacggct ggcccaccac tctcagagtc   2400
tcggtgccct tctggaacgg ctgcaatgag gatgagcact gtgtccctga ccttgtgttg   2460
gatgcccgga gtgacctgcc cacggccatg gagtactgcc agagggtgct gaggaagcct   2520
gcgcaggact gctccgcata cacgctgtcc ttcgacacca cagtcttcat catagagagc   2580
acacgccagc gagtggcggt ggaggccaca ctggagaaca ggggcgagaa cgcctacagc   2640
acggtcctaa atatctcgca gtcagcaaac ctgcagtttg ccagcttgat ccagaaggag   2700
gactcagacg gtagcattga gtgtgtgaac gaggagagga ggctccagaa gcaagtctgc   2760
aacgtcagct atcccttctt ccgggccaag gccaaggtgg ctttccgtct tgattttgag   2820
ttcagcaaat ccatcttcct acaccacctg gagatcgagc tcgctgcagg cagtgacagt   2880
aatgagcggg acagcaccaa ggaagacaac gtggcccccct tacgcttcca cctcaaatac   2940
gaggctgacg tcctcttcac caggagcagc agcctgagcc actacgaggt caagctcaac   3000
agctcgctgg agagatacga tggtatcggg cctcccttca gctgcatctt caggatccag   3060
aacttgggct tgttccccat ccacgggatt atgatgaaga tcaccattcc catcgccacc   3120
aggagcggca accgcctact gaagctgagg gacttcctca cggacgaggt agcgaacacg   3180
```

-continued

```
tcctgtaaca tctggggcaa tagcactgag taccggccca ccccagtgga ggaagacttg   3240
cgtcgtgctc cacagctgaa tcacagcaac tctgatgtcg tctccatcaa ctgcaatata   3300
cggctggtcc ccaaccagga aatcaatttc catctactgg ggaacctgtg gttgaggtcc   3360
ctaaaagcac tcaagtacaa atccatgaaa atcatggtca acgcagcctt gcagaggcag   3420
ttccacagcc ccttcatctt ccgtgaggag gatcccagcc gccagatcgt gtttgagatc   3480
tccaagcaag aggactggca ggtccccatc tggatcattg taggcagcac cctgggggggc   3540
ctcctactgc tggccctgct ggtcctggca ctgtggaagc tcggcttctt tagaagtgcc   3600
aggcgcagga gggagcctgg tctggacccc acccccaaag tgctggagtg aggctccaga   3660
ggagactttg agttgatggg ggccaggaca ccagtccagg tagtgttgag acccaggcct   3720
gtggccccac cgagctggag cggagaggaa gccagctggc tttgcacttg acctcatctc   3780
ccgagcaatg gcgcctgctc cctccagaat ggaactcaag ctggttttaa gtggaactgc   3840
cctactggga gactgggaca cctttaacac agacccctag ggatttaaag ggacacccct   3900
acacacaccc aggcccacgc caaggcctcc ctcaggctct gtggagggca tttgctgccc   3960
cagctactaa ggtgctagga attcgtaatc atccccatcc tccagagaaa cccagggagg   4020
aagactgtaa atacgaaccc aatctgcaca ctccaggcct ctagttccag aaggatccaa   4080
gacaaaacag atctgaattc tgccctttc tctcacccat cccacccctc cattggctcc   4140
caagtcacac ccactccctt ccccatagat aggcccctgg ggctcccgaa gaatgaaccc   4200
aagagcaagg gcttgatggt gacagctgca agccagggat gaagaaagac tctgagatgt   4260
ggagactgat ggccaggcaa gtgggaccag gatactggac gctgtcctga gatgagaggt   4320
agccgggctc tgcacccacg tgcattcaca ttgaccgcaa ctcacacatt cccccaccag   4380
ctgcagcccc ttgctctcag ctgccaaccc tcccgggtca cttttgttcc caggtacctc   4440
atgggaagca tgtggatgac acaatccctg gggctgtgca ttcccacgtc ttcttgctgc   4500
agcctgcccc tagacatgga cgcaccggcc tggctgcagc tgggcagcag gggtaggggt   4560
agggagcctc ccctccctgt atcacccct ccctacacac acacacacac acacacacac   4620
acactgcctc ccatccttcc ctcatgcccg ccagtgcaca gggaagggct tggccagcgc   4680
tgttgagggg tcccctctgg aatgcactga ataaagcacg tgcaaggact cccggagcct   4740
gtgcagcctt ggtggcaaat atctcatctg ccggccccca ggacaagtgg tatgaccagt   4800
gataatgccc caaggacaag gggcgtgcct ggcgcccagt ggagtaattt atgccttagt   4860
cttgttttga ggtagaaatg caagggggac acatgaaagg catcagtccc cctgtgcata   4920
gtacgacctt tactgtcgta tttttgaaaa attaaaaata cagtgtttaa aaacaaaaaa   4980
aaaaaaaaaa aaaaa                                                      4995
```

<210> SEQ ID NO 18
<211> LENGTH: 726
<212> TYPE: DNA
<213> ORGANISM: Homo sapiens

<400> SEQUENCE: 18

```
ggcacgagcc ggaccctgcc gccctgccac tatgtcccgc cgctctatgc tgcttgcctg     60
ggctctcccc agcctccttc gactcggagc ggctcaggag acagaagacc cggcctgctg    120
cagccccata gtgccccgga acgagtggaa ggccctggca tcagagtgcg cccagcacct    180
gagcctgccc ttacgctatg tggtggtatc gcacacggcg ggcagcagct gcaacacccc    240
```

-continued

```
cgcctcgtgc cagcagcagg cccggaatgt gcagcactac cacatgaaga cactgggctg    300

gtgcgacgtg ggctacaact tcctgattgg agaagacggg ctcgtatacg agggccgtgg    360

ctggaacttc acgggtgccc actcaggtca cttatggaac cccatgtcca ttggcatcag    420

cttcatgggc aactacatgg atcgggtgcc cacaccccag gccatccggg cagcccaggg    480

tctactggcc tgcggtgtgg ctcagggagc cctgaggtcc aactatgtgc tcaaaggaca    540

ccgggatgtg cagcgtacac tctctccagg caaccagctc taccacctca tccagaattg    600

gccacactac cgctccccct gaggccctgc tgatccgcac ccccattcctc ccctcccatg    660

gccaaaaacc ccactgtctc cttctccaat aaagatgtag ctcaaaaaaa aaaaaaaaaa    720

aaaaaa                                                               726
```

<210> SEQ ID NO 19
<211> LENGTH: 3059
<212> TYPE: DNA
<213> ORGANISM: Homo sapiens

<400> SEQUENCE: 19

```
ggcacgagct gtcatccgtt tccatgccgt gaggtccatt cacagaacac atccatggct     60

ctcatgctca gtttggttct gagtctcctc aagctgggat cagggcagtg gcaggtgttt    120

gggccagaca agcctgtcca ggccttggtg ggggaggacg cagcattctc ctgtttcctg    180

tctcctaaga ccaatgcaga ggccatggaa gtgcggttct tcaggggcca gttctctagc    240

gtggtccacc tctacaggga cgggaaggac cagccattta tgcagatgcc acagtatcaa    300

ggcaggacaa aactggtgaa ggattctatt gcggaggggc gcatctctct gaggctggaa    360

aacattactg tgttggatgc tggcctctat gggtgcagga ttagttccca gtcttactac    420

cagaaggcca tctgggagct acaggtgtca gcactgggct cagttcctct catttccatc    480

gcgggatatg ttgatagaga catccagcta ctctgtcagt cctcgggctg gttcccccgg    540

cccacagcga agtggaaagg tccacaagga caggatttgt ccacagactc caggacaaac    600

agagacatgc atggcctgtt tgatgtggag atctctctga ccgtccaaga gaacgccggg    660

agcatatcct gttccatgcg gcatgctcat ctgagccgag aggtggaatc cagggtacag    720

ataggagact ggagaagaaa gcacggacag gcaggtaaaa gaaaatattc ctcttcacac    780

atttatgact cctttccaag tctctcgttt atggattttt atatcctgag gcccgtgggt    840

ccctgcagag ccaagcttgt gatgggaact ctgaaattgc agattctggg ggaggtgcat    900

tttgtagaga agccccatag ccttcttcag atctctggag ggtccacaac actcaaaaag    960

ggtcccaatc cttggtcttt cccttctccc tgcgccctgt ttcccacgtg agcacggaac   1020

tgcctgctct ctctgcttgc tttcagaatt gagagacgcc cggaaacacg caggtaccaa   1080

cgcctgagag ggtaacagtg ggcatggagt aggaagatga ccagtgacag atatggagcc   1140

catccagctt gtagacagca aatctgtgat gcccgaatcc accccagggt gcagctgcct   1200

ctaaatacac ttcttggccc aggacttgga gggaaaagcg tagggactgg gtcagctagg   1260

aggggtcaca ggcaagacgc cagggaactg agggcattag tagctggctt ctaggggtct   1320

gtgcaaaggg gaacgaagtg aagttagcag gaactggtgg gtggaaggaa gctgaatcct   1380

ggagtcactc aaggtctcac aaagtcaaat agagggctta cgtgggaggg cagtggtagg   1440

gctgggtgaa catctcatgg ttgagcatct ccaagcatca gtgaggcacg gggctgccc    1500

tggagaaggt acatggctgg tgggatagtg ggactggccg gatcctaccc ggagccagtc   1560

tgcagtggga gggtcgacct cttgctccag cccagatttc gtcttcagta actcatgctt   1620
```

-continued cctctctccc ccaccgcacc ccagtggagg tgactctgga tccagagacg gctcacccga 1680
agctctgcgt ttctgatctg aaaactgtaa cccatagaaa agctcctcag gaggtgcctc 1740
actctgagaa gagatttaca aggaagagtg tggtggcttc tcagggtttc caagcaggga 1800
aacattactg ggaggtggac gtgggacaaa atgtagggtg gtatgtggga gtgtgtcggg 1860
atgacgtaga caggggggaag aacaatgtga ctttgtctcc caacaatggg tattgggtcc 1920
tcagactgac aacagaacat ttgtatttca cattcaatcc ccattttatc agcctccccc 1980
ccagcacccc tcctacacga gtaggggtct tcctggacta tgagggtggg accatctcct 2040
tcttcaatac aaatgaccag tcccttattt ataccctgct gacatgtcag tttgaaggct 2100
tgttgagacc ctatatccag catgcgatgt atgacgagga aaaggggact cccatattca 2160
tatgtccagt gtcctgggga tgagacagag aagaccctgc ttaaagggcc ccacaccaca 2220
gacccagaca cagccaaggg agagtgctcc cgacaggtgg ccccagcttc ctctccggag 2280
cctgcgcaca gagagtcacg ccccccactc tcctttaggg agctgaggtt cttctgccct 2340
gagccctgca gcagcggcag tcacagcttc cagatgaggg gggattggcc tgaccctgtg 2400
ggagtcagaa gccatggctg ccctgaagtg gggacggaat agactcacat taggtttagt 2460
ttgtgaaaac tccatccagc taagcgatct tgaacaagtc acaacctccc aggctcctca 2520
tttgctagtc acggacagtg attcctgcct cacaggtgaa gattaaagag acaacgaatg 2580
tgaatcatgc ttgcaggttt gagggccaca gtgtttgcta atggatgtgt ttttatgatt 2640
atacattttc cccaccataa aactctgttt gccttaattc ccacattaat ttaacttttc 2700
ctcctatacc caaatccacc catggaatag ttaattggaa cacctgcctt tgtgaggctc 2760
caaagaataa agaggaggta ggatttttca ctgattctat aagcccagca ttacctgata 2820
ccaaaaccag gcaaagaaaa cagaagaaga ggaaggaaaa ctacaggtcc atatccctca 2880
ttaacacaga cacaaaaatt ctaaataaaa ttttaacaaa ttaaactaaa caatatattt 2940
aaagatgata tataactact cagtgtggtt tgtcccacaa atgcagagtt ggtttaatat 3000
ttaaatatca accagtgtaa ttcagcacat taataaagta aaaaaaaaaa aaaaaaaaa 3059

<210> SEQ ID NO 20
<211> LENGTH: 1699
<212> TYPE: DNA
<213> ORGANISM: Homo sapiens

<400> SEQUENCE: 20
ggcacgaggg ggcaggcatg ggagccgcgc gctctctccc ggcgcccaca cctgtctgag 60
cggcgcagcg agccgcggcc cgggcgggct gctcggcgcg gaacagtgct cggcatggca 120
gggattccag ggctcctctt ccttctcttc tttctgctct gtgctgttgg gcaagtgagc 180
ccttacagtg ccccctggaa acccacttgg cctgcatacc gcctccctgt cgtcttgccc 240
cagtctaccc tcaatttagc caagccagac tttggagccg aagccaaatt agaagtatct 300
tcttcatgtg gaccccagtg tcataaggga actccactgc ccacttacga agaggccaag 360
caatatctgt cttatgaaac gctctatgcc aatggcagcc gcacagagac gcaggtgggc 420
atctacatcc tcagcagtag tggagatggg gcccaacacc gagactcagg gtcttcagga 480
aagtctcgaa ggaagcggca gatttatggc tatgacagca ggttcagcat ttttgggaag 540
gacttcctgc tcaactaccc tttctcaaca tcagtgaagt tatccacggg ctgcaccggc 600
accctggtgg cagagaagca tgtcctcaca gctgcccact gcatacacga tggaaaaacc 660

-continued

```
tatgtgaaag gaacccagaa gcttcgagtg ggcttcctaa agcccaagtt taaagatggt     720

ggtcgagggg ccaacgactc cacttcagcc atgcccgagc agatgaaatt tcagtggatc     780

cgggtgaaac gcacccatgt gcccaagggt tggatcaagg gcaatgccaa tgacatcggc     840

atggattatg attatgccct cctggaactc aaaaagcccc acaagagaaa atttatgaag     900

attggggtga gccctcctgc taagcagctg ccagggggca gaattcactt ctctggttat     960

gacaatgacc gaccaggcaa tttggtgtat cgcttctgtg acgtcaaaga cgagacctat    1020

gacttgctct accaacaatg cgattcccag ccaggggcca gcgggtctgg ggtctatgtg    1080

aggatgtgga agagacaaca ccagaagtgg gagcggaaaa ttattggcat gatttcaggg    1140

caccagtggg tggacatgga tggttcccca caggaattca cacgtggctg ttcagagatc    1200

actcctctcc aatatatccc agatatatct attggagtat aaggaaacta cctggattgt    1260

agggaggggt gacacagtgt ccctcctgca gcaactaagg tcgtcatgtt cttattttag    1320

gagaggccaa attgtttttt gtcattgccg tgcacacgtg tgtgtgtgtg tgtgtgtgtg    1380

tgtaaggtgt cttataatct tttacctatt tcttacaatt gcaagatgac tggctttact    1440

atttgaaaac tggtttgtgt atcatatcat atatcattta agcagtttga aggcatactt    1500

ttgcatagaa ataaaaaaaa tactgatttg gggcaatgag gaatatttga caattaagtt    1560

aatcttcacg tttttgcaaa ctttgatttt tatttcatct gaacttgttt caaagattta    1620

tattaaatat ttggcataca aaaaaaaaaa aaaaaaacgg gggggcccgt acccaattcg    1680

ccctatagtg aggcgatac                                                 1699
```

<210> SEQ ID NO 21
<211> LENGTH: 1520
<212> TYPE: DNA
<213> ORGANISM: Homo sapiens

<400> SEQUENCE: 21

```
gaattcggca gagcaggtgc ccgacatggc gagtgtagtg ctgccgagcg gatcccagtg      60

tgcggcggca gcggcggcgg cggcgcctcc cgggctccgg ctccggcttc tgctgttgct     120

cttctccgcc gcggcactga tccccacagg tgatgggcag aatctgttta cgaaagacgt     180

gacagtgatc gagggagagg ttgcgaccat cagttgccaa gtcaataaga gtgacgactc     240

tgtgattcag ctactgaatc ccaacaggca gaccatttat ttcagggact tcaggccttt     300

gaaggacagc aggtttcagt tgctgaattt ttctagcagt gaactcaaag tatcattgac     360

aaacgtctca atttctgatg aaggaagata cttttgccag ctctataccg atcccccaca     420

ggaaagttac accaccatca cagtcctggt cccaccacgt aatctgatga tcgatatcca     480

gaaagacact gcggtggaag gtgaggagat tgaagtcaac tgcactgcta tggccagcaa     540

gccagccacg actatcaggt ggttcaaagg gaacacagag ctaaaaggca aatcggaggt     600

ggaagagtgg tcagacatgt acactgtgac cagtcagctg atgctgaagg tgcacaagga     660

ggacgatggg gtcccagtga tctgccaggt ggagcaccct gcggtcactg gaaacctgca     720

gacccagcgg tatctagaag tacagtataa gcctcaagtg cacattcaga tgacttatcc     780

tctacaaggc ttaacccggg aaggggacgc gcttgagtta acatgtgaag ccatcgggaa     840

gccccagcct gtgatggtaa cttgggtgag agtcgatgat gaaatgcctc aacacgccgt     900

actgtctggg cccaacctgt tcatcaataa cctaaacaaa acagataatg gtacataccg     960

ctgtgaagct tcaaacatag tggggaaagc tcactcggat tatatgctgt atgtatacga    1020

tcccccccaca actatccctc ctcccacaac aaccaccacc accaccacca ccaccaccac    1080
```

-continued

```
caccatcctt accatcatca cagattcccg agccaggtga agaaggctcg atcagggcag   1140

tggatcatgc cgtgatcggt ggcgtcgtgg cggtggtggt gttcgccatg ctgtgcttgc   1200

tcatcattct ggggcgctat tttgccagac ataaaggtac atacttcact catgaagcca   1260

aaggagccga tgacgcagca gacgcagaca cagctataat caatgcagaa ggaggacaga   1320

acaactccga agaaaagaaa gagtacttca tctagatcag ccttttttgtt tcaatgaggt   1380

gtccaactgg ccctatttag atgataaaga gacagtgata ttggaacttg cgagaaattc   1440

gtgtgttttt ttatgaatgg gtggaaaggt gtgagactgg gaaggcttgg gatttgctgt   1500

gtaaaaaaaa aaaaaaaaaa                                                1520
```

<210> SEQ ID NO 22
<211> LENGTH: 807
<212> TYPE: DNA
<213> ORGANISM: Homo sapiens
<220> FEATURE:
<221> NAME/KEY: SITE
<222> LOCATION: (803)
<223> OTHER INFORMATION: n equals a,t,g, or c

<400> SEQUENCE: 22

```
tttttttttt tgagacggag tctcgctctt tcacccaggc cagactgaag tggcgcagtc     60

tcggatcact gaaaagctca gcctcacggg atcacgacca ttctcctgcc tcagcctccc    120

gagtggctgg gactaaaggc gcccgccacc gacgcccgga ctaatttttt gtatttatag    180

tagagacggg gtttcaccgt gttagccaag atggtctcga tctcttgaac tcgtgatccg    240

cccgcgtcag cctcccaaag tgctgggatt acaggcgtga gccacagcgc ccggcctgta    300

aagatttctt gagcaaatga atgagtaaat gaaaggagtg ctcaaatttc ttttattcta    360

aaaaatgttc ccctttttta gaaaatgctc tgtagctttt gtaggtcttt cctgcactca    420

aacatccact ccttaccctt tccaatctcc cttttcttct caacccatag aatgtacttc    480

catgtctacc attccaccag aactactcta accaaggcta cccaggatat ccttatttct    540

ttcaacttct ttgacatgct cagtcgcatt tggcactgtt aatgtcttcc tcctctttga    600

aacacctcct ttgcatggca ctatcctggt tttcttcctt catttcagga gaaacttcat    660

tctccttact gaattctttc ttcctcccct atccatcatc tagatgttgt tgtttctcag    720

tgcagtgttc aatcctagac ccctttttcat gtaactcaat gcgttttcct tgggagaatt    780

aattcccttc cctggtgtca ctntgcc                                        807
```

<210> SEQ ID NO 23
<211> LENGTH: 2522
<212> TYPE: DNA
<213> ORGANISM: Homo sapiens

<400> SEQUENCE: 23

```
gccgctcgac accagcaccc cgcccagagc agtgccgctg cccaaatcct cgcaggcagc     60

tcatcaacgc aattgcaact ccggctggag ccccggacct gcaagcctgg gtgtccgtgg    120

gtccgtctgc ccagccatct gctggtggca cctctccctc ctgccgcctc cctcggtgaa    180

ccccaccttg cagaagtgca gctcgcccgg agcagcccag gagctcagca tgcgtccccc    240

aggcttcagg aacttcttgc tgctggcgtc ctcccttctc tttgctgggt tgtcagctgt    300

tcctcaaagc ttctcgccat ctctgaggag ctggccgggc gccgcctgca ggctgtcccg    360

ggccgagtcg gagcgacgct gccgcgcacc tgggcagccc ccgggggccg cgctgtgcca    420
```

-continued

```
cggccggggc cgctgcgact gcggcgtctg catctgccac gtgactgagc cgggcatgtt    480

cttcgggccc ctgtgtgagt gccatgagtg ggtgtgcgag acctacgacg ggagcacctg    540

tgcaggccat ggtaagtgtg actgtggcaa gtgcaagtgt gaccagggat ggtatgggga    600

tgcttgccag tacccaacta actgtgactt gacaaagaag aaaagtaacc aaatgtgcaa    660

gaattcacaa gacatcatct gctctaatgc aggtacatgt cactgtggca ggtgtaagtg    720

tgataattca gatggaagtg gacttgtgta tggtaaattt tgtgagtgtg acgatagaga    780

atgcatagac gatgaaacag aagaaaatatg tggaggccat gggaagtgtt actgtggaaa   840

ctgctactgc aaggctggtt ggcatggaga taaatgtgaa ttccagtgcg atatcacccc    900

ctgggaaagc aagcgaagat gcacgtctcc agatggcaaa atctgcagta gcagagggac    960

ttgtgtatgt ggtgaatgta cctgtcacga tgttgatccg actggggact ggggagatat   1020

tcatggggac acctgtgaat gtgatgagag ggactgtaga gctgtctatg accgatattc   1080

tgatgacttc tgttcaggtc atggacagtg taattgcgga agatgtgact gcaaagcagg   1140

ctggtatggg aagaagtgtg agcacccaca gtcctgcacg ctgtcagctg aggagagcat   1200

caggaagtgc cagggaagct cggatctgcc ttgctctggg aggggtaaat gtgaatgtgg   1260

caaatgcacc tgctatcctc caggagatcg ccgggtgtat ggcaagactt gtgagtgtga   1320

tgatcgccgc tgtgaagacc tcgatggtgt ggtctgtgga ggccacggca catgttcctg   1380

tggtcgctgt gtttgtgaga gaggatggtt tggaaagctc tgccaacatc cgcggaagtg   1440

taacatgacg gaagaacaaa gcaagaatct gtgtgaatca gcagatggca tattgtgctc   1500

ggggaagggt tcttgtcatt gtgggaagtg catttgttct gctgaagagt ggtatatttc   1560

tggggagttc tgtgactgtg atgacagaga ctgcgacaaa catgatggtc tcatttgtac   1620

cagggaatgg aatatgtagc tgtggaaact gtgaatgctg ggatggatgg aatggaaatg   1680

catgtgaaat ctggcttggc tcagaatatc cttaacaatt acatgagaga ggtctggatt   1740

cttatttttt ctgggccatt agaacatata aatgcgaagg aaaccatgta tattcaccac   1800

taggacaggt taaaaagacc attgtatgtt tttctatttc tgaattacga atgaaatccg   1860

agtacctatt agaaatgagt tatgcaaatt tagatgcaaa taacattaga aaaaaaagat   1920

tcttccataa ttaacataag tggttcctaa cgagagcaat tttccaccc aaaagtcatt   1980

tggcaacatc tacagacaat tttgattgtc acactgggtc gggtaggaag gtatgctgca   2040

gacatttggt gggtagaggc cagggatgct gctgagcatc ccgcagtgta caggacagcc   2100

cccaaacaag gaattatcca gccccaaatg ccaatagggc tcagactgag aaacattgag   2160

ttatatggct attagaaatc cacattctta cacaagaaag accatattag aatctaagga   2220

aaacatgcat attcacatta attaatcgat cagatttttc cagaattccg tatcagtcac   2280

cattttaata tggggacaat gaagacaagc acacaggagg tagaatatca gagtggggct   2340

ggatcaaggg caaaaactgg tcattaagtc atctgacatt aaatcattta gccactaagt   2400

tatttgtcta ctctcacttt aaactcacca aagaagattc tcttaaagaa attatgaaaa   2460

atgtacaatt taacatttta aataaatagt gacagaagtt gtttataaaa aaaaaaaaaa   2520

aa                                                                  2522
```

<210> SEQ ID NO 24
<211> LENGTH: 1344
<212> TYPE: DNA
<213> ORGANISM: Homo sapiens

<400> SEQUENCE: 24

-continued

```
gtccgagaga acaggcctgt ctcaggcagg ccctgcgcct cctatgcgga gatgctactg     60

ccactgctgc tgtcctcgct gctgggcggg tcccaggcta tggatgggag attctggata    120

cgagtgcagg agtcagtgat ggtgccggag ggcctgtgca tctctgtgcc ctgctctttc    180

tcctaccccc gacaagactg gacagggtct accccagctt atggctactg gttcaaagca    240

gtgactgaga caaccaaggg tgctcctgtg gccacaaacc accagagtcg agaggtggaa    300

atgagcaccc ggggccgatt tccaggctca ctgggggatc ccgccaaggg gaactgctcc    360

ttggtgatca gaagacgcgc agatgcaagg atgagtcaca gtacttcttt cgggtggaga    420

gaggaagcta tgtgagatat aatttcatga acgatgggtt ctttctaaaa gtaacagtgc    480

tcagcttcac gcccagaccc caggaccaca acaccgacct cacctgccat gtggacttct    540

ccagaaaggg tgtgagcgca cagaggaccg tccgactccg tgtggcctat gcccccagag    600

accttgttat cagcatttca cgtgacaaca cgccagccct ggagccccag ccccagggga    660

aatgtcccat acctggaagc ccaaaaaggc cagttcctgc ggctcctctg tgctgctgac    720

agccagcccc ctgccacact gagctgggtc ctgcagaaca gagtcctctc ctcgtcccat    780

ccctggggcc ctagacccct ggggctggag ctgcccgggg tgaaggctgg ggattcaggg    840

cgctacacct gccgagcgga gaacaggctt ggctcccagc agcgagccct ggacctctct    900

gtgcagtatc ctccagagaa cctgagagtg atggtttccc aagcaaacag gacagtcctg    960

gaaaaccttg ggaacggcac gtctctccca gtactggagg gccaaagcct gtgcctggtc   1020

tgtgtcacac acagcagccc cccagccagg ctgagctgga cccagagggg acaggttctg   1080

agcccctccc agccctcaga ccccggggtc ctggagctgc ctcgggttca agtggagcac   1140

gaaggagagt tcacctgcca cgctcggcac ccactgggct cccagcacgt ctctctcagc   1200

ctctccgtgc actactcccc gaagctgctg ggcccctcct gctcctggga agctgaaggt   1260

ctgcactgca actgctcctc ccaggccagc ccggccccct ctctgcgctg gtggcttggg   1320

gaggagctgc tggaagggga acaa                                          1344
```

<210> SEQ ID NO 25
<211> LENGTH: 4631
<212> TYPE: DNA
<213> ORGANISM: Homo sapiens

<400> SEQUENCE: 25

```
ccgccgcgcc gaggaggctg ccgctctggc ttgccgcccc ccgccgccgc tgcacaccgg     60

acccagccgc cgtgccgcgg gccatggacc tgcccagggg cctggtggtg gcctgggcgc    120

tcagcctgtg gccagggttc acggacacct tcaacatgga caccaggaag ccccgggtca    180

tccctggctc caggaccgcc ttctttggct acacagtgca gcagcacgac atcagtggca    240

ataagtggct ggtcgtgggc gccccactgg aaaccaatgg ctaccagaag acgggagacg    300

tgtacaagtg tccagtgatc cacgggaact gcaccaaact caacctggga agggtcaccc    360

tgtccaacgt gtccgagcgg aaagacaaca tgcgcctcgg ccttagtctc gccaccaacc    420

ccaaggacaa cagcttcctg gcctgcagcc ccctctggtc tcatgagtgt gggagctcct    480

actacaccac agggatgtgt tcaagagtca actccaactt caggttctcc aagaccgtgg    540

ccccagctct ccaaaggtgc cagacctaca tggacatcgt cattgtcctg gatggctcca    600

acagcatcta cccctgggtg gaggttcagc acttcctcat caacatcctg aaaaagtttt    660

acattggccc agggcagatc caggttggag ttgtgcagta tggcgaagat gtggtgcatg    720
```

-continued

```
agtttcacct caatgactac aggtctgtaa aagatgtggt ggaagctgcc agccacattg    780
agcagagagg aggaacagag acccggacgg catttggcat tgaatttgca cgctcagagg    840
ctttccagaa gggtggaagg aaaggagcca agaaggtgat gattgtcatc acagatgggg    900
agtcccacga cagcccagac ctggagaagg tgatccagca aagcgaaaga gacaacgtaa    960
caagatatgc ggtggccgtc ctgggctact acaaccgcag ggggatcaat ccagaaactt   1020
ttctaaatga aatcaaatac atcgccagtg accctgatga caagcacttc ttcaatgtca   1080
ctgatgaggc tgccttgaag gacattgtcg atgccctggg ggacagaatc ttcagcctgg   1140
aaggcaccaa caagaacgag acctcctttg ggctggagat gtcacagacg ggcttttcct   1200
cgcacgtggt ggaggatggg gttctgctgg gagccgtcgg tgcctatgac tggaatggag   1260
ctgtgctaaa ggagacgagt gccgggaagg tcattcctct ccgcgagtcc tacctgaaag   1320
agttccccga ggagctcaag aaccatggtg catacctggg gtacacagtc acatcggtcg   1380
tgtcctccag gcaggggcga gtgtacgtgg ccggagcccc ccggttcaac cacacgggca   1440
aggtcatcct gttcaccatg cacaacaacc ggagcctcac catccaccag gctatgcggg   1500
gccagcagat aggctcttac tttgggagtg aaatcacctc ggtggacatc gacggcgacg   1560
gcgtgactga tgtcctgctg gtgggcgcac ccatgtactt caacgagggc cgtgagcgag   1620
gcaaggtgta cgtctatgag ctgagacaga accggtttgt ttataacgga acgctaaagg   1680
attcacacag ttaccagaat gcccgatttg ggtcctccat tgcctcagtt cgagacctca   1740
accaggattc ctacaatgac gtggtggtgg gagcccccct ggaggacaac cacgcaggag   1800
ccatctacat cttccacggc ttccgaggca gcatcctgaa gacacctaag cagagaatca   1860
cagcctcaga gctggctacc ggcctccagt attttggctg cagcatccac gggcaattgg   1920
acctcaatga ggatgggctc atcgacctgg cagtgggagc ccttggcaac gctgtgattc   1980
tgtggtcccg cccagtggtt cagatcaatg ccagcctcca ctttgagcca tccaagatca   2040
acatcttcca cagagactgc aagcgcagtg gcagggatgc cacctgcctg gccgccttcc   2100
tctgcttcac gcccatcttc ctggcacccc atttccaaac aacaactgtt ggcatcagat   2160
acaacgccac catggatgag aagcggtata caccgagggc ccacctggac gaaggcgggg   2220
accgattcac caacagagcc gtactgctct cctccggcca ggagctctgt gagcggatca   2280
acttccatgt cctggacact gctgactacg tgaagccagt gaccttctca gtcgagtatt   2340
ccctggagga ccctgaccat ggccccatgc tggacgacgg ctggcccacc actctcagag   2400
tctcggtgcc cttctggaac ggctgcaatg aggatgagca ctgtgtccct gaccttgtgt   2460
tggatgcccg gagtgacctg cccacggcca tggagtactg ccagagggtg ctgaggaagc   2520
ctgcgcagga ctgctccgca tacacgctgt ccttcgacac cacagtcttc atcatagaga   2580
gcacacgcca gcgagtggcg gtggaggcca cactggagaa caggggcgag aacgcctaca   2640
gcacggtcct aaatatctcg cagtcagcaa acctgcagtt tgccagcttg atccagaagg   2700
aggactcaga cggtagcatt gagtgtgtga acgaggagag gaggctccag aagcaagtct   2760
gcaacgtcag ctatcccttc ttccgggcca aggccaaggt ggctttccgt cttgattttg   2820
agttcagcaa atccatcttc ctacaccacc tggagatcga gctcgctgca ggcagtgaca   2880
gtaatgagcg ggacagcacc aaggaagaca acgtggcccc cttacgcttc cacctcaaat   2940
acgaagctga cgtcctcttc accaggagca gcagcctgag ccactacgag gtcaagctca   3000
acagctcgct ggagagatac gatggtatcg ggcctcccct cagctgcatc ttcaggatcc   3060
agaacttggg cttgttcccc atccacggga ttatgatgaa gatcaccatt cccatcgcca   3120
```

-continued

```
ccaggagcgg caaccgccta ctgaagctga gggacttcct cacggacgag ggcgaacacg   3180
tcctgtaaca tctggggcaa tagcactgag taccggccca ccccagtgga ggaagacttg   3240
cgtcgtgctc cacagctgaa tcacagcaac tctgatgtcg tctccatcaa ctgcaatata   3300
cggctggtcc ccaaccagga aatcaatttc catctactgg ggaacctgtg gttgaggtcc   3360
gtaaaagcac tcaagtacaa atccatgaaa atcatggtca acgcagcgtt gcagaggcag   3420
ttccacagcc ccttcatctt ccgtgaggag gatcccagcc gccagatcgt gtttgagatc   3480
tccaagcaag aggactggca ggtccccatc tggatcattg taggcagcac cctgggggc    3540
ctcctactgc tggccctgct ggtcctggca ctgtggaagc tcggcttctt tagaagtgcc   3600
aggcgcagga gggagcctgg tctggacccc acccccaaag tgctggagtg aggctccaga   3660
ggagactttg agttgatggg ggccagacac cagtccaggt agtgttgaga cccaggcctg   3720
tggccccacc gagctggagc ggagaggaag ccagctggct ttgcacttga cctcatctcc   3780
cgagcaatgg cgcctgctcc ctccagaatg gaactcaagc tggttttaag tggaactgcc   3840
ctactgggag actgggacac ctttaacaca gaccccctagg gatttaaagg gacaccccta   3900
cacacaccca ggcccacgcc aaggcctccc tcaggctctg tggagggcat ttgctgcccc   3960
agctactaag gtgctaggaa ttcgtaatca tccccatcct ccagagaaac ccagggagga   4020
agactgtaaa tacgaaccca atctgcacac tccaggcctc tagttccaga aggatccaag   4080
acaaaacaga tctgaattct gcccttttct ctcacccatc ccacccctcc attggctccc   4140
aagtcacacc cactcccttc cccatagata ggcccctggg gctcccgaag atgaacccaa   4200
gagcaagggc ttgatggtga cagctgcaag ccagggatga agaaagactc tgagatgtgg   4260
agactgatgg ccaggcaagt gggaccagga tactggacgc tgtcctgaga tgagaggtag   4320
ccgggctctg cacccacgtg cattcacatt gaccgcaact cacacattcc cccaccagct   4380
gcagcccctt gctctcagct gccaaccctc ccgggtcact tttgttccca ggtacctcat   4440
gggaagcatg tggatgacac aatccctggg gctgtgcatt cccacgtctt cttgctgcag   4500
cctgccccta gacatggacg caccggcctg gctgcagctg ggcagcaggg gtaggggtag   4560
ggagcctccc ctccctgtat cacccccctcc ctacacgtcg acgcggccgc gaattcccgg   4620
gtcgacgagc t                                                        4631
```

<210> SEQ ID NO 26
<211> LENGTH: 2008
<212> TYPE: DNA
<213> ORGANISM: Homo sapiens

<400> SEQUENCE: 26

```
cgggggcttt ctaacgggaa aaactctact aaagggttca aaagctggag ctccaccgcg     60
gtggcggccg ctctagaact agtggatccc ccgggctgca ggaattcggc acgagctcgt    120
gccgaattcg gcacgagtca cagaacacat ccatggctct matgctcagt ttggttctga    180
gtctcctcaa gctgggwtca gggcagtggc aggtgtttgg gccagacaag cctgtccagg    240
ccttggtggg ggaggacgca gcattctcct gtttcctgtc tcctaagacc aatgcagagg    300
ccatggaagt gcggttcttc aggggccagt tctctagcgt ggtccacctc tacagggacg    360
ggaaggacca gccatttatg cagatgccac agtatcaagg caggacaaaa ctggtgaagg    420
attctattgc ggaggggcgc atctctctga ggctggaaaa cattactgtg ttggatgctg    480
gcctctatgg gtgcaggatt agttcccagt cttactacca gaaggccatc tgggagctac    540
```

-continued

```
aggtgtcagc actgggctca gttcctctca tttccatcac gggatatgtt gatagagaca    600

tccagctact ctgtcagtcc tcgggctggt tccccggcc cacagcgaag tggaaaggtc    660

cacaaggaca ggatttgtcc acagactcca ggacaaacag agacatgcat ggcctgtttg    720

atgtggagat ctctctgacc gtccaagaga acgccgggag catatcctgt tccatgcggc    780

atgctcatct gagccgagag gtggaatcca gggtacagat aggagatacc tttttcgagc    840

ctatatcgtg gmacctggyt accaaagtac tgggaatact ctgctgtggc ctattttttg    900

gcattgttgg actgaagatt ttcttctcca aattccagtg gaaaatccag gcggaactgg    960

actggagaag aaagcacgga caggcagaat tgagagacgc ccggaaacac gcagtggagg   1020

tgactctgga tccagagacg gctcacccga agctctgcgt ttctgatctg aaaactgtaa   1080

cccatagaaa agctccccag gaggtgcctc actctgagaa gagatttaca aggaagagtg   1140

tggtggcttc tcagagtttc caagcaggga aacattactg ggaggtggac ggaggacaca   1200

ataaaaggtg gcgcgtggga gtgtgccggg atgatgtgga caggaggaag gagtacgtga   1260

ctttgtctcc cgatcatggg tactgggtcc tcagactgaa tggagaacat ttgtatttca   1320

cattaaatcc ccgttttatc agcgtcttcc ccaggacccc acctacaaaa ataggggtct   1380

tcctggacta tgagtgtggg accatctcct tcttcaacat aaatgaccag tcccttattt   1440

ataccctgac atgtcggttt gaaggcttat tgaggcccta cattgagtat ccgtcctata   1500

atgagcaaaa tggaactccc agagacaagc aacagtgagt cctcctcaca ggcaaccacg   1560

cccttcctcc ccaggggtga aatgtaggat gaatcacatc ccacattctt ctttagggat   1620

attaaggtct ctctcccaga tccaaagtcc cgcagcagcc ggccaaggtg gcttccagat   1680

gaagggggac tggcctgtcc acatgggagt caggtgtcat ggctgccctg agctgggagg   1740

gaagaaggct gacattacat ttagtttgct ctcactccat ctggctaagt gatcttgaaa   1800

taccacctct caggtgaaga accgtcagga attcccatct cacaggctgt ggtgtagatt   1860

aagtagacaa ggaatgtgaa taatgcttag atcttattga tgacagagtg tatcctaatg   1920

gtttgttcat tatattacac tttcagtaaa aaaaaaaaaa aaaaaaaaaa aaaaaaaamc   1980

tcgagggggg gcccggtacc caattcgg                                     2008
```

<210> SEQ ID NO 27
<211> LENGTH: 1654
<212> TYPE: DNA
<213> ORGANISM: Homo sapiens

<400> SEQUENCE: 27

```
ggcacgaggg ggcaggcatg ggagccgcgc gctctctccc ggcgcccaca cctgtctgag     60

cggcgcagcg agccgcggcc cgggcgggct gctcggcgcg gaacagtgct cggcatggca    120

gggattccag ggctcctctt ccttctcttc tttctgctct gtgctgttgg gcaagtgagc    180

ccttacagtg ccccctggaa acccacttgg cctgcatacc gcctccctgt cgtcttgccc    240

cagtctaccc tcaatttagc caagccagac tttggagccg aagccaaatt agaagtatct    300

tcttcatgtg gaccccagtg tcataaggga actccactgc ccacttacga agaggccaag    360

caatatctgt cttatgaaac gctctatgcc aatggcagcc gcacagagac gcaggtgggc    420

atctacatcc tcagcagtag tggagatggg gcccaacacc gagactcagg gtcttcagga    480

aagtctcgaa ggaagcggca gatttatggc tatgacagca ggttcagcat ttttgggaag    540

gacttcctgc tcaactaccc tttctcaaca tcagtgaagt tatccacggg ctgcaccggc    600

accctggtgg cagagaagca tgtcctcaca gctgcccact gcatacacga tggaaaaacc    660
```

-continued

```
tatgtgaaag gaacccagaa gcttcgagtg ggcttcctaa agcccaagtt taaagatggt    720
ggtcgagggg ccaacgactc cacttcagcc atgcccgagc agatgaaatt tcagtggatc    780
cgggtgaaac gcacccatgt gcccaagggt tggatcaagg gcaatgccaa tgacatcggc    840
atggattatg attatgccct cctggaactc aaaaagcccc acaagagaaa atttatgaag    900
attggggtga gccctcctgc taagcagctg ccagggggca gaattcactt ctctggttat    960
gacaatgacc gaccaggcaa tttggtgtat cgcttctgtg acgtcaaaga cgagacctat   1020
gacttgctct accagcaatg cgatgcccag ccaggggcca gcgggtctgg ggtctatgtg   1080
aggatgtgga agagacagca gcagaagtgg gagcgaaaaa ttattggcat tttttcaggg   1140
caccagtggg tggacatgaa tggttcccca caggatttca acgtggctgt cagaatcact   1200
cctctcaaat atgcccagat ttgctattgg attaaaggaa actacctgga ttgtagggag   1260
gggtgacaca gtgttccctc ctggcagcaa ttaagggtct tcatgttctt attttaggag   1320
aggccaaatt gtttttgtc attggcgtgc acacgtgtgt gtgtgtgtgt gtgtgtgtgt   1380
aaggtgtctt ataatctttt acctatttct tacaattgca agatgactgg ctttactatt   1440
tgaaaactgg tttgtgtatc atatcatata tcatttaagc agtttgaagg catacttttg   1500
catagaaata aaaaaaatac tgatttgggg caatgaggaa tatttgacaa ttaagttaat   1560
cttcacgttt ttgcaaactt tgatttttat ttcatctgaa cttgtttcaa agatttatat   1620
taaatatttg gcatacaaga aaaaaaaaaa aaaa                                1654
```

<210> SEQ ID NO 28
<211> LENGTH: 1508
<212> TYPE: DNA
<213> ORGANISM: Homo sapiens

<400> SEQUENCE: 28

```
ggcacgagga catggcgtag tgtagtgctg ccgagcggat cccagtgtgc ggcggcagcg     60
gcggcggcgg cgcctcccgg gctccggctc cggcttctgc tgttgctctt ctccgccgcg    120
gcactgatcc ccacaggtga tgggcagaat ctgtttacga aagacgtgac agtgatcgag    180
ggagaggttg cgaccatcag ttgccaagtc aataagagtg acgactctgt gattcagcta    240
ctgaatccca acaggcagac catttatttc agggacttca ggcctttgaa ggacagcagg    300
tttcagttgc tgaatttttc tagcagtgaa ctcaaagtat cattgacaaa cgtctcaatt    360
tctgatgaag gaagatactt ttgccagctc tataccgatc cccccacagga aagttacacc    420
accatcacag tcctggtccc accacgtaat ctgatgatcg atatccagaa agacactgcg    480
gtggaaggtg aggagattga agtcaactgc actgctatgg ccagcaagcc agccacgact    540
atcaggtggt tcaaagggaa cacagagcta aaaggcaaat cggaggtgga agagtggtca    600
gacatgtaca ctgtgaccag tcagctgatg ctgaaggtgc acaaggagga cgatggggtc    660
ccagtgatct gccaggtgga gcaccctgcg gtcactggaa acctgcagac ccagcggtat    720
ctagaagtac agtataagcc tcaagtgcac attcagatga cttatcctct acaaggctta    780
acccgggaag ggacgcgct tgagttaaca tgtgaagcca tcgggaagcc ccagcctgtg    840
atggtaactt gggtgagagt cgatgatgaa atgcctcaac acgccgtact gtctgggccc    900
aacctgttca tcaataacct aaacaaaaca gataatggta cataccgctg tgaagcttca    960
aacatagtgg ggaaagctca ctcggattat atgctgtatg tatacgatcc ccccacaact   1020
atccctcctc ccacaacaac caccaccacc accaccacca ccaccaccac catccttacc   1080
```

-continued atcatcacag attccccgag ccaggtgaag aaggctcgat cagggcagtg gatcatgccg 1140
tgatcggtgg cgtcgtggcg gtggtggtgt tcgccatgct gtgcttgctc atcattctgg 1200
ggcgctattt tgccagacat aaaggtacat acttcactca tgaagccaaa ggagccgatg 1260
acgcagcaga cgcagacaca gctataatca atgcagaagg aggacagaac aactccgaag 1320
aaaagaaaga gtacttcatc tagatcagcc tttttgtttc aatgaggtgt ccaactggcc 1380
ctatttagat gataaagaga cagtgatatt ggaacttgcg agaaattcgt gtgttttttt 1440
atgaatgggt ggaaaggtgt gagactggga aggcttggga tttgctgtgt aaaaaaaaaa 1500
aaaaaaaa 1508

<210> SEQ ID NO 29
<211> LENGTH: 529
<212> TYPE: PRT
<213> ORGANISM: Homo sapiens

<400> SEQUENCE: 29

Met Val Ala Gln Asp Pro Gln Gly Cys Leu Gln Leu Cys Leu Ser Glu
1 5 10 15

Val Ala Asn Gly Leu Arg Asn Pro Val Ser Met Val His Ala Gly Asp
20 25 30

Gly Thr His Arg Phe Phe Val Ala Glu Gln Val Gly Val Val Trp Val
35 40 45

Tyr Leu Pro Asp Gly Ser Arg Leu Glu Gln Pro Phe Leu Asp Leu Lys
50 55 60

Asn Ile Val Leu Thr Thr Pro Trp Ile Gly Asp Glu Arg Gly Phe Leu
65 70 75 80

Gly Leu Ala Phe His Pro Lys Phe Arg His Asn Arg Lys Phe Tyr Ile
85 90 95

Tyr Tyr Ser Cys Leu Asp Lys Lys Lys Val Glu Lys Ile Arg Ile Ser
100 105 110

Glu Met Lys Val Ser Arg Ala Asp Pro Asn Lys Ala Asp Leu Lys Ser
115 120 125

Glu Arg Val Ile Leu Glu Ile Glu Glu Pro Ala Ser Asn His Asn Gly
130 135 140

Gly Gln Leu Leu Phe Gly Leu Asp Gly Tyr Met Tyr Ile Phe Thr Gly
145 150 155 160

Asp Gly Gly Gln Ala Gly Asp Pro Phe Gly Leu Phe Gly Asn Ala Gln
165 170 175

Asn Lys Ser Ser Leu Leu Gly Lys Val Leu Arg Ile Asp Val Asn Arg
180 185 190

Ala Gly Ser His Gly Lys Arg Tyr Arg Val Pro Ser Asp Asn Pro Phe
195 200 205

Val Ser Glu Pro Gly Ala His Pro Ala Ile Tyr Ala Tyr Gly Ile Arg
210 215 220

Asn Met Trp Arg Cys Ala Val Asp Arg Gly Asp Pro Ile Thr Arg Gln
225 230 235 240

Gly Arg Gly Arg Ile Phe Cys Gly Asp Val Gly Gln Asn Arg Phe Glu
245 250 255

Glu Val Asp Leu Ile Leu Lys Gly Gly Asn Tyr Gly Trp Arg Ala Lys
260 265 270

Glu Gly Phe Ala Cys Tyr Asp Lys Lys Leu Cys His Asn Ala Ser Leu
275 280 285

Asp Asp Val Leu Pro Ile Tyr Ala Tyr Gly His Ala Val Gly Lys Ser

-continued

```
    290                 295                 300

Val Thr Gly Gly Tyr Val Tyr Arg Gly Cys Glu Ser Pro Asn Leu Asn
305                 310                 315                 320

Gly Leu Tyr Ile Phe Gly Asp Phe Met Ser Gly Arg Leu Met Ala Leu
                325                 330                 335

Gln Glu Asp Arg Lys Asn Lys Lys Trp Lys Lys Gln Asp Leu Cys Leu
            340                 345                 350

Gly Ser Thr Thr Ser Cys Ala Phe Pro Gly Leu Ile Ser Thr His Ser
        355                 360                 365

Lys Phe Ile Ile Ser Phe Ala Glu Asp Glu Ala Gly Glu Leu Tyr Phe
    370                 375                 380

Leu Ala Thr Ser Tyr Pro Ser Ala Tyr Ala Pro Arg Gly Ser Ile Tyr
385                 390                 395                 400

Lys Phe Val Asp Pro Ser Arg Arg Ala Pro Pro Gly Lys Cys Lys Tyr
                405                 410                 415

Lys Pro Val Pro Val Arg Thr Lys Ser Lys Arg Ile Pro Phe Arg Pro
            420                 425                 430

Leu Ala Lys Thr Val Leu Asp Leu Leu Lys Glu Gln Ser Glu Lys Ala
        435                 440                 445

Ala Arg Lys Ser Ser Ser Ala Thr Leu Ala Ser Gly Pro Ala Gln Gly
    450                 455                 460

Leu Ser Glu Lys Gly Ser Ser Lys Lys Leu Ala Ser Pro Thr Ser Ser
465                 470                 475                 480

Lys Asn Thr Leu Arg Gly Pro Gly Thr Lys Lys Lys Ala Arg Val Gly
                485                 490                 495

Pro His Val Arg Gln Gly Lys Arg Arg Lys Ser Leu Lys Ser His Ser
            500                 505                 510

Gly Arg Met Arg Pro Ser Ala Glu Gln Lys Arg Ala Gly Arg Ser Leu
        515                 520                 525

Pro


<210> SEQ ID NO 30
<211> LENGTH: 494
<212> TYPE: PRT
<213> ORGANISM: Homo sapiens

<400> SEQUENCE: 30

Met Arg Pro Pro Gly Phe Arg Asn Phe Leu Leu Leu Ala Ser Ser Leu
  1               5                  10                  15

Leu Phe Ala Gly Leu Ser Ala Val Pro Gln Ser Phe Ser Pro Ser Leu
             20                  25                  30

Arg Ser Trp Pro Gly Ala Ala Cys Arg Leu Ser Arg Ala Glu Ser Glu
         35                  40                  45

Arg Arg Cys Arg Ala Pro Gly Gln Pro Pro Gly Ala Ala Leu Cys His
     50                  55                  60

Gly Arg Gly Arg Cys Asp Cys Gly Val Cys Ile Cys His Val Thr Glu
 65                  70                  75                  80

Pro Gly Met Phe Phe Gly Pro Leu Cys Glu Cys His Glu Trp Val Cys
                 85                  90                  95

Glu Thr Tyr Asp Gly Ser Thr Cys Ala Gly His Gly Lys Cys Asp Cys
            100                 105                 110

Gly Lys Cys Lys Cys Asp Gln Gly Trp Tyr Gly Asp Ala Cys Gln Tyr
        115                 120                 125

Pro Thr Asn Cys Asp Leu Thr Lys Lys Lys Ser Asn Gln Met Cys Lys
```

-continued

```
    130                 135                 140

Asn Ser Gln Asp Ile Ile Cys Ser Asn Ala Gly Thr Cys His Cys Gly
145                 150                 155                 160

Arg Cys Lys Cys Asp Asn Ser Asp Gly Ser Gly Leu Val Tyr Gly Lys
                165                 170                 175

Phe Cys Glu Cys Asp Asp Arg Glu Cys Ile Asp Asp Glu Thr Glu Glu
            180                 185                 190

Ile Cys Gly Gly His Gly Lys Cys Tyr Cys Gly Asn Cys Tyr Cys Lys
        195                 200                 205

Ala Gly Trp His Gly Asp Lys Cys Glu Phe Gln Cys Asp Ile Thr Pro
    210                 215                 220

Trp Glu Ser Lys Arg Arg Cys Thr Ser Pro Asp Gly Lys Ile Cys Ser
225                 230                 235                 240

Asn Arg Gly Thr Cys Val Cys Gly Glu Cys Thr Cys His Asp Val Asp
                245                 250                 255

Pro Thr Gly Asp Trp Gly Asp Ile His Gly Asp Thr Cys Glu Cys Asp
            260                 265                 270

Glu Arg Asp Cys Arg Ala Val Tyr Asp Arg Tyr Ser Asp Asp Phe Cys
        275                 280                 285

Ser Gly His Gly Gln Cys Asn Cys Gly Arg Cys Asp Cys Lys Ala Gly
    290                 295                 300

Trp Tyr Gly Lys Lys Cys Glu His Pro Gln Ser Cys Thr Leu Ser Ala
305                 310                 315                 320

Glu Glu Ser Ile Arg Lys Cys Gln Gly Ser Ser Asp Leu Pro Cys Ser
                325                 330                 335

Gly Arg Gly Lys Cys Glu Cys Gly Lys Cys Thr Cys Tyr Pro Pro Gly
            340                 345                 350

Asp Arg Arg Val Tyr Gly Lys Thr Cys Glu Cys Asp Asp Arg Arg Cys
        355                 360                 365

Glu Asp Leu Asp Gly Val Val Cys Gly Gly His Gly Thr Cys Ser Cys
    370                 375                 380

Gly Arg Cys Val Cys Glu Arg Gly Trp Phe Gly Lys Leu Cys Gln His
385                 390                 395                 400

Pro Arg Lys Cys Asn Met Thr Glu Glu Gln Ser Lys Asn Leu Cys Glu
                405                 410                 415

Ser Ala Asp Gly Ile Leu Cys Ser Gly Lys Gly Ser Cys His Cys Gly
            420                 425                 430

Lys Cys Ile Cys Ser Ala Glu Glu Trp Tyr Ile Ser Gly Glu Phe Cys
        435                 440                 445

Asp Cys Asp Asp Arg Asp Cys Asp Lys His Asp Gly Leu Ile Cys Thr
    450                 455                 460

Gly Asn Gly Ile Cys Ser Cys Gly Asn Cys Glu Cys Trp Asp Gly Trp
465                 470                 475                 480

Asn Gly Asn Ala Cys Glu Ile Trp Leu Gly Ser Glu Tyr Pro
                485                 490
```

<210> SEQ ID NO 31
<211> LENGTH: 148
<212> TYPE: PRT
<213> ORGANISM: Homo sapiens

<400> SEQUENCE: 31

```
Met Glu Thr Gly Ala Leu Arg Arg Pro Gln Leu Leu Pro Leu Leu Leu
  1               5                  10                  15
```

-continued

```
Leu Leu Cys Gly Gly Cys Pro Arg Ala Gly Gly Cys Asn Glu Thr Gly
            20                  25                  30

Met Leu Glu Arg Leu Pro Leu Cys Gly Lys Ala Phe Ala Asp Met Met
        35                  40                  45

Gly Lys Val Asp Val Trp Lys Trp Cys Asn Leu Ser Glu Phe Ile Val
    50                  55                  60

Tyr Tyr Glu Ser Phe Thr Asn Cys Thr Glu Met Glu Ala Asn Val Val
65                  70                  75                  80

Gly Cys Tyr Trp Pro Asn Pro Leu Ala Gln Gly Phe Ile Thr Gly Ile
                85                  90                  95

His Arg Gln Phe Phe Ser Asn Cys Thr Val Asp Arg Val His Leu Glu
            100                 105                 110

Asp Pro Pro Asp Glu Val Leu Ile Pro Leu Ile Val Ile Pro Val Val
        115                 120                 125

Leu Thr Val Ala Met Ala Gly Leu Val Val Trp Arg Ser Lys Arg Thr
    130                 135                 140

Asp Thr Leu Leu
145


<210> SEQ ID NO 32
<211> LENGTH: 332
<212> TYPE: PRT
<213> ORGANISM: Homo sapiens

<400> SEQUENCE: 32

Met Arg Leu Leu Ala Phe Leu Ser Leu Leu Ala Leu Val Leu Gln Glu
  1               5                  10                  15

Thr Gly Thr Ala Ser Leu Pro Arg Lys Glu Arg Lys Arg Arg Glu Glu
            20                  25                  30

Gln Met Pro Arg Glu Gly Asp Ser Phe Glu Val Leu Pro Leu Arg Asn
        35                  40                  45

Asp Val Leu Asn Pro Asp Asn Tyr Gly Glu Val Ile Asp Leu Ser Asn
    50                  55                  60

Tyr Glu Glu Leu Thr Asp Tyr Gly Asp Gln Leu Pro Glu Val Lys Val
65                  70                  75                  80

Thr Ser Leu Ala Pro Ala Thr Ser Ile Ser Pro Ala Lys Ser Thr Thr
                85                  90                  95

Ala Pro Gly Thr Pro Ser Ser Asn Pro Thr Met Thr Arg Pro Thr Thr
            100                 105                 110

Ala Gly Leu Leu Leu Ser Ser Gln Pro Asn His Gly Leu Pro Thr Cys
        115                 120                 125

Leu Val Cys Val Cys Leu Gly Ser Ser Val Tyr Cys Asp Asp Ile Asp
    130                 135                 140

Leu Glu Asp Ile Pro Pro Leu Pro Arg Arg Thr Ala Tyr Leu Tyr Ala
145                 150                 155                 160

Arg Phe Asn Arg Ile Ser Arg Ile Arg Ala Glu Asp Phe Lys Gly Leu
                165                 170                 175

Thr Lys Leu Lys Arg Ile Asp Leu Ser Asn Asn Leu Ile Ser Ser Ile
            180                 185                 190

Asp Asn Asp Ala Phe Arg Leu Leu His Ala Leu Gln Asp Leu Ile Leu
        195                 200                 205

Pro Glu Asn Gln Leu Glu Ala Leu Pro Val Leu Pro Ser Gly Ile Glu
    210                 215                 220

Phe Leu Asp Val Arg Leu Asn Arg Leu Gln Ser Ser Gly Ile Gln Pro
225                 230                 235                 240
```

-continued

```
Ala Ala Phe Arg Ala Met Glu Lys Leu Gln Phe Leu Tyr Leu Ser Asp
                245                 250                 255

Asn Leu Leu Asp Ser Ile Pro Gly Pro Leu Pro Pro Ser Leu Arg Ser
            260                 265                 270

Val His Leu Gln Asn Asn Leu Ile Glu Thr Met Gln Arg Asp Val Phe
        275                 280                 285

Cys Asp Pro Glu Glu His Lys His Thr Arg Arg Gln Leu Glu Asp Ile
    290                 295                 300

Arg Leu Asp Gly Asn Pro Ile Asn Leu Ser Leu Phe Pro Ser Ala Tyr
305                 310                 315                 320

Phe Cys Leu Pro Arg Leu Pro Ile Gly Arg Phe Thr
                325                 330


<210> SEQ ID NO 33
<211> LENGTH: 639
<212> TYPE: PRT
<213> ORGANISM: Homo sapiens

<400> SEQUENCE: 33

Met Leu Leu Pro Leu Leu Leu Ser Ser Leu Leu Gly Gly Ser Gln Ala
  1               5                  10                  15

Met Asp Gly Arg Phe Trp Ile Arg Val Gln Glu Ser Val Met Val Pro
             20                  25                  30

Glu Ala Cys Asp Ile Ser Val Pro Cys Ser Phe Ser Tyr Pro Arg Gln
         35                  40                  45

Asp Trp Thr Gly Ser Thr Pro Ala Tyr Gly Tyr Trp Phe Lys Ala Val
     50                  55                  60

Thr Glu Thr Thr Lys Gly Ala Pro Val Ala Thr Asn His Gln Ser Arg
 65                  70                  75                  80

Glu Val Glu Met Ser Thr Arg Gly Arg Phe Gln Leu Thr Gly Asp Pro
                 85                  90                  95

Ala Lys Gly Asn Cys Ser Leu Val Ile Arg Asp Ala Gln Met Gln Asp
            100                 105                 110

Glu Ser Gln Tyr Phe Phe Arg Val Glu Arg Gly Ser Tyr Val Arg Tyr
        115                 120                 125

Asn Phe Met Asn Asp Gly Phe Phe Leu Lys Val Thr Val Leu Ser Phe
    130                 135                 140

Thr Pro Arg Pro Gln Asp His Asn Thr Asp Leu Thr Cys His Val Asp
145                 150                 155                 160

Phe Ser Arg Lys Gly Val Ser Ala Gln Arg Thr Val Arg Leu Arg Val
                165                 170                 175

Ala Tyr Ala Pro Arg Asp Leu Val Ile Ser Ile Ser Arg Asp Asn Thr
            180                 185                 190

Pro Ala Leu Glu Pro Gln Pro Gln Gly Asn Val Pro Tyr Leu Glu Ala
        195                 200                 205

Gln Lys Gly Gln Phe Leu Arg Leu Leu Cys Ala Ala Asp Ser Gln Pro
    210                 215                 220

Pro Ala Thr Leu Ser Trp Val Leu Gln Asn Arg Val Leu Ser Ser Ser
225                 230                 235                 240

His Pro Trp Gly Pro Arg Pro Leu Gly Leu Glu Leu Pro Gly Val Lys
                245                 250                 255

Ala Gly Asp Ser Gly Arg Tyr Thr Cys Arg Ala Glu Asn Arg Leu Gly
            260                 265                 270

Ser Gln Gln Arg Ala Leu Asp Leu Ser Val Gln Tyr Pro Pro Glu Asn
```

-continued

```
        275                 280                 285

Leu Arg Val Met Val Ser Gln Ala Asn Arg Thr Val Leu Glu Asn Leu
    290                 295                 300

Gly Asn Gly Thr Ser Leu Pro Val Leu Glu Gly Gln Ser Leu Cys Leu
305                 310                 315                 320

Val Cys Val Thr His Ser Ser Pro Pro Ala Arg Leu Ser Trp Thr Gln
                325                 330                 335

Arg Gly Gln Val Leu Ser Pro Ser Gln Pro Ser Asp Pro Gly Val Leu
            340                 345                 350

Glu Leu Pro Arg Val Gln Val Glu His Glu Gly Glu Phe Thr Cys His
        355                 360                 365

Ala Arg His Pro Leu Gly Ser Gln His Val Ser Leu Ser Leu Ser Val
    370                 375                 380

His Tyr Ser Pro Lys Leu Leu Gly Pro Ser Cys Ser Trp Glu Ala Glu
385                 390                 395                 400

Gly Leu His Cys Ser Cys Ser Ser Gln Ala Ser Pro Ala Pro Ser Leu
                405                 410                 415

Arg Trp Trp Leu Gly Glu Glu Leu Leu Glu Gly Asn Ser Ser Gln Asp
            420                 425                 430

Ser Phe Glu Val Thr Pro Ser Ser Ala Gly Pro Trp Ala Asn Ser Ser
        435                 440                 445

Leu Ser Leu His Gly Gly Leu Ser Ser Gly Leu Arg Leu Arg Cys Glu
    450                 455                 460

Ala Trp Asn Val His Gly Ala Gln Ser Gly Ser Ile Leu Gln Leu Pro
465                 470                 475                 480

Asp Lys Lys Gly Leu Ile Ser Thr Ala Phe Ser Asn Gly Ala Phe Leu
                485                 490                 495

Gly Ile Gly Ile Thr Ala Leu Leu Phe Leu Cys Leu Ala Leu Ile Ile
            500                 505                 510

Met Lys Ile Leu Pro Lys Arg Arg Thr Gln Thr Glu Thr Pro Arg Pro
        515                 520                 525

Arg Phe Ser Arg His Ser Thr Ile Leu Asp Tyr Ile Asn Val Val Pro
    530                 535                 540

Thr Ala Gly Pro Leu Ala Gln Lys Arg Asn Gln Lys Ala Thr Pro Asn
545                 550                 555                 560

Ser Pro Arg Thr Pro Leu Pro Pro Gly Ala Pro Ser Pro Glu Ser Lys
                565                 570                 575

Lys Asn Gln Lys Lys Gln Tyr Gln Leu Pro Ser Phe Pro Glu Pro Lys
            580                 585                 590

Ser Ser Thr Gln Ala Pro Glu Ser Gln Glu Ser Gln Glu Glu Leu His
        595                 600                 605

Tyr Ala Thr Leu Asn Phe Pro Gly Val Arg Pro Arg Pro Glu Ala Arg
    610                 615                 620

Met Pro Lys Gly Thr Gln Ala Asp Tyr Ala Glu Val Lys Phe Gln
625                 630                 635


<210> SEQ ID NO 34
<211> LENGTH: 467
<212> TYPE: PRT
<213> ORGANISM: Homo sapiens

<400> SEQUENCE: 34

Met Leu Leu Leu Leu Leu Leu Pro Leu Leu Trp Gly Arg Glu Arg Val
  1               5                  10                  15
```

-continued

```
Glu Gly Gln Lys Ser Asn Arg Lys Asp Tyr Ser Leu Thr Met Gln Ser
            20                  25                  30

Ser Val Thr Val Gln Glu Gly Met Cys Val His Val Arg Cys Ser Phe
        35                  40                  45

Ser Tyr Pro Val Asp Ser Gln Thr Asp Ser Asp Pro Val His Gly Tyr
    50                  55                  60

Trp Phe Arg Ala Gly Asn Asp Ile Ser Trp Lys Ala Pro Val Ala Thr
 65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
        115                 120                 125

Asn Ile Lys Trp Asn Tyr Lys Tyr Asp Gln Leu Ser Val Asn Val Thr
    130                 135                 140

Ala Leu Thr His Arg Pro Asn Ile Leu Ile Pro Gly Thr Leu Glu Ser
145                 150                 155                 160

Gly Cys Phe Gln Asn Leu Thr Cys Ser Val Pro Trp Ala Cys Glu Gln
                165                 170                 175

Gly Thr Pro Pro Met Ile Ser Trp Met Gly Thr Ser Val Ser Pro Leu
            180                 185                 190

His Pro Ser Thr Thr Arg Ser Ser Val Leu Thr Leu Ile Pro Gln Pro
        195                 200                 205

Gln His His Gly Thr Ser Leu Thr Cys Gln Val Thr Leu Pro Gly Ala
    210                 215                 220

Gly Val Thr Thr Asn Arg Thr Ile Gln Leu Asn Val Ser Tyr Pro Pro
225                 230                 235                 240

Gln Asn Leu Thr Val Thr Val Phe Gln Gly Glu Gly Thr Ala Ser Thr
                245                 250                 255

Ala Leu Gly Asn Ser Ser Ser Leu Ser Val Leu Glu Gly Gln Ser Leu
            260                 265                 270

Arg Leu Val Cys Ala Val Asp Ser Asn Pro Pro Ala Arg Leu Ser Trp
        275                 280                 285

Thr Trp Arg Ser Leu Thr Leu Tyr Pro Ser Gln Pro Ser Asn Pro Leu
    290                 295                 300

Val Leu Glu Leu Gln Val His Leu Gly Asp Glu Gly Glu Phe Thr Cys
305                 310                 315                 320

Arg Ala Gln Asn Ser Leu Gly Ser Gln His Val Ser Leu Asn Leu Ser
                325                 330                 335

Leu Gln Gln Glu Tyr Thr Gly Lys Met Arg Pro Val Ser Gly Val Leu
            340                 345                 350

Leu Gly Ala Val Gly Gly Ala Gly Ala Thr Ala Leu Val Phe Leu Ser
        355                 360                 365

Phe Cys Val Ile Phe Ile Val Val Arg Ser Cys Arg Lys Lys Ser Ala
    370                 375                 380

Arg Pro Ala Ala Asp Val Gly Asp Ile Gly Met Lys Asp Ala Asn Thr
385                 390                 395                 400

Ile Arg Gly Ser Ala Ser Gln Gly Asn Leu Thr Glu Ser Trp Ala Asp
                405                 410                 415

Asp Asn Pro Arg His His Gly Leu Ala Ala His Ser Ser Gly Glu Glu
            420                 425                 430

Arg Glu Ile Gln Tyr Ala Pro Leu Ser Phe His Lys Gly Glu Pro Gln
```

-continued

```
        435                 440                 445

Asp Leu Ser Gly Gln Glu Ala Thr Asn Asn Glu Tyr Ser Glu Ile Lys
    450                 455                 460

Ile Pro Lys
465


<210> SEQ ID NO 35
<211> LENGTH: 1189
<212> TYPE: PRT
<213> ORGANISM: Homo sapiens

<400> SEQUENCE: 35

Met Asp Leu Pro Arg Gly Leu Val Val Ala Trp Ala Leu Ser Leu Trp
  1               5                  10                  15

Pro Gly Phe Thr Asp Thr Phe Asn Met Asp Thr Arg Lys Pro Arg Val
             20                  25                  30

Ile Pro Gly Ser Arg Thr Ala Phe Phe Gly Tyr Thr Val Gln Gln His
         35                  40                  45

Asp Ile Ser Gly Asn Lys Trp Leu Val Val Gly Ala Pro Leu Glu Thr
     50                  55                  60

Asn Gly Tyr Gln Lys Thr Gly Asp Val Tyr Lys Cys Pro Val Ile His
 65                  70                  75                  80

Gly Asn Cys Thr Lys Leu Asn Leu Gly Arg Val Thr Leu Ser Asn Val
                 85                  90                  95

Ser Glu Arg Lys Asp Asn Met Arg Leu Gly Leu Ser Leu Ala Thr Asn
            100                 105                 110

Pro Lys Asp Asn Ser Phe Leu Ala Cys Ser Pro Leu Trp Ser His Glu
        115                 120                 125

Cys Gly Ser Ser Tyr Tyr Thr Thr Gly Met Cys Ser Arg Val Asn Ser
    130                 135                 140

Asn Phe Arg Phe Ser Lys Thr Val Ala Pro Ala Leu Gln Arg Cys Gln
145                 150                 155                 160

Thr Tyr Met Asp Ile Val Ile Val Leu Asp Gly Ser Asn Ser Ile Tyr
                165                 170                 175

Pro Trp Val Glu Val Gln His Phe Leu Ile Asn Ile Leu Lys Lys Phe
            180                 185                 190

Tyr Ile Gly Pro Gly Gln Ile Gln Val Gly Val Val Gln Tyr Gly Glu
        195                 200                 205

Asp Val Val His Glu Phe His Leu Asn Asp Tyr Arg Ser Val Lys Asp
    210                 215                 220

Val Val Glu Ala Ala Ser His Ile Glu Gln Arg Gly Gly Thr Glu Thr
225                 230                 235                 240

Arg Thr Ala Phe Gly Ile Glu Phe Ala Arg Ser Glu Ala Phe Gln Lys
                245                 250                 255

Gly Gly Arg Lys Gly Ala Lys Lys Val Met Ile Val Ile Thr Asp Gly
            260                 265                 270

Glu Ser His Asp Ser Pro Asp Leu Glu Lys Val Ile Gln Gln Ser Glu
        275                 280                 285

Arg Asp Asn Val Thr Arg Tyr Ala Val Ala Val Leu Gly Tyr Tyr Asn
    290                 295                 300

Arg Arg Gly Ile Asn Pro Glu Thr Phe Leu Asn Glu Ile Lys Tyr Ile
305                 310                 315                 320

Ala Ser Asp Pro Asp Asp Lys His Phe Phe Asn Val Thr Asp Glu Ala
                325                 330                 335
```

-continued

```
Ala Leu Lys Asp Ile Val Asp Ala Leu Gly Asp Arg Ile Phe Ser Leu
            340                 345                 350

Glu Gly Thr Asn Lys Asn Glu Thr Ser Phe Gly Leu Glu Met Ser Gln
        355                 360                 365

Thr Gly Phe Ser Ser His Val Val Glu Asp Gly Val Leu Leu Gly Ala
    370                 375                 380

Val Gly Ala Tyr Asp Trp Asn Gly Ala Val Leu Lys Glu Thr Ser Ala
385                 390                 395                 400

Gly Lys Val Ile Pro Leu Arg Glu Ser Tyr Leu Lys Glu Phe Pro Glu
                405                 410                 415

Glu Leu Lys Asn His Gly Ala Tyr Leu Gly Tyr Thr Val Thr Ser Val
            420                 425                 430

Val Ser Ser Arg Gln Gly Arg Val Tyr Val Ala Gly Ala Pro Arg Phe
        435                 440                 445

Asn His Thr Gly Lys Val Ile Leu Phe Thr Met His Asn Asn Arg Ser
    450                 455                 460

Leu Thr Ile His Gln Ala Met Arg Gly Gln Gln Ile Gly Ser Tyr Phe
465                 470                 475                 480

Gly Ser Glu Ile Thr Ser Val Asp Ile Asp Gly Asp Gly Val Thr Asp
                485                 490                 495

Val Leu Leu Val Gly Ala Pro Met Tyr Phe Asn Glu Gly Arg Glu Arg
            500                 505                 510

Gly Lys Val Tyr Val Tyr Glu Leu Arg Gln Asn Arg Phe Val Tyr Asn
        515                 520                 525

Gly Thr Leu Lys Asp Ser His Ser Tyr Gln Asn Ala Arg Phe Gly Ser
    530                 535                 540

Ser Ile Ala Ser Val Arg Asp Leu Asn Gln Asp Ser Tyr Asn Asp Val
545                 550                 555                 560

Val Val Gly Ala Pro Leu Glu Asp Asn His Ala Gly Ala Ile Tyr Ile
                565                 570                 575

Phe His Gly Phe Arg Gly Ser Ile Leu Lys Thr Pro Lys Gln Arg Ile
            580                 585                 590

Thr Ala Ser Glu Leu Ala Thr Gly Leu Gln Tyr Phe Gly Cys Ser Ile
        595                 600                 605

His Gly Gln Leu Asp Leu Asn Glu Asp Gly Leu Ile Asp Leu Ala Val
    610                 615                 620

Gly Ala Leu Gly Asn Ala Val Ile Leu Trp Ser Arg Pro Val Val Gln
625                 630                 635                 640

Ile Asn Ala Ser Leu His Phe Glu Pro Ser Lys Ile Asn Ile Phe His
                645                 650                 655

Arg Asp Cys Lys Arg Ser Gly Arg Asp Ala Thr Cys Leu Ala Ala Phe
            660                 665                 670

Leu Cys Phe Thr Pro Ile Phe Leu Ala Pro His Phe Gln Thr Thr Thr
        675                 680                 685

Val Gly Ile Arg Tyr Asn Ala Thr Met Asp Glu Arg Arg Tyr Thr Pro
    690                 695                 700

Arg Ala His Leu Asp Glu Gly Gly Asp Arg Phe Thr Asn Arg Ala Val
705                 710                 715                 720

Leu Leu Ser Ser Gly Gln Glu Leu Cys Glu Arg Ile Asn Phe His Val
                725                 730                 735

Leu Asp Thr Ala Asp Tyr Val Lys Pro Val Thr Phe Ser Val Glu Tyr
            740                 745                 750

Ser Leu Glu Asp Pro Asp His Gly Pro Met Leu Asp Asp Gly Trp Pro
```

-continued

```
        755                 760                 765

Thr Thr Leu Arg Val Ser Val Pro Phe Trp Asn Gly Cys Asn Glu Asp
    770                 775                 780

Glu His Cys Val Pro Asp Leu Val Leu Asp Ala Arg Ser Asp Leu Pro
785                 790                 795                 800

Thr Ala Met Glu Tyr Cys Gln Arg Val Leu Arg Lys Pro Ala Gln Asp
                805                 810                 815

Cys Ser Ala Tyr Thr Leu Ser Phe Asp Thr Thr Val Phe Ile Ile Glu
            820                 825                 830

Ser Thr Arg Gln Arg Val Ala Val Glu Ala Thr Leu Glu Asn Arg Gly
        835                 840                 845

Glu Asn Ala Tyr Ser Thr Val Leu Asn Ile Ser Gln Ser Ala Asn Leu
    850                 855                 860

Gln Phe Ala Ser Leu Ile Gln Lys Glu Asp Ser Asp Gly Ser Ile Glu
865                 870                 875                 880

Cys Val Asn Glu Glu Arg Arg Leu Gln Lys Gln Val Cys Asn Val Ser
                885                 890                 895

Tyr Pro Phe Phe Arg Ala Lys Ala Lys Val Ala Phe Arg Leu Asp Phe
            900                 905                 910

Glu Phe Ser Lys Ser Ile Phe Leu His His Leu Glu Ile Glu Leu Ala
        915                 920                 925

Ala Gly Ser Asp Ser Asn Glu Arg Asp Ser Thr Lys Glu Asp Asn Val
    930                 935                 940

Ala Pro Leu Arg Phe His Leu Lys Tyr Glu Ala Asp Val Leu Phe Thr
945                 950                 955                 960

Arg Ser Ser Ser Leu Ser His Tyr Glu Val Lys Leu Asn Ser Ser Leu
                965                 970                 975

Glu Arg Tyr Asp Gly Ile Gly Pro Pro Phe Ser Cys Ile Phe Arg Ile
            980                 985                 990

Gln Asn Leu Gly Leu Phe Pro Ile  His Gly Ile Met Met  Lys Ile Thr
        995                 1000                1005

Ile Pro  Ile Ala Thr Arg Ser  Gly Asn Arg Leu Leu  Lys Leu Arg Asp
    1010                1015                1020

Phe  Leu Thr Asp Glu Val  Ala Asn Thr Ser Cys  Asn Ile Trp Gly Asn
1025                1030                1035                1040

Ser Thr Glu Tyr Arg  Pro Thr Pro Val Glu  Glu Asp Leu Arg Arg  Ala
                1045                1050                1055

Pro Gln Leu Asn  His Ser Asn Ser Asp  Val Val Ser Ile Asn  Cys Asn
            1060                1065                1070

Ile Arg Leu  Val Pro Asn Gln Glu  Ile Asn Phe His Leu  Leu Gly Asn
        1075                1080                1085

Leu Trp  Leu Arg Ser Leu Lys  Ala Leu Lys Tyr Lys  Ser Met Lys Ile
    1090                1095                1100

Met  Val Asn Ala Ala Leu  Gln Arg Gln Phe His  Ser Pro Phe Ile Phe
1105                1110                1115                1120

Arg Glu Glu Asp Pro  Ser Arg Gln Ile Val  Phe Glu Ile Ser Lys  Gln
                1125                1130                1135

Glu Asp Trp Gln  Val Pro Ile Trp Ile  Ile Val Gly Ser Thr  Leu Gly
            1140                1145                1150

Gly Leu Leu  Leu Leu Ala Leu Leu  Val Leu Ala Leu Trp  Lys Leu Gly
        1155                1160                1165

Phe Phe  Arg Ser Ala Arg Arg  Arg Arg Glu Pro Gly  Leu Asp Pro Thr
    1170                1175                1180
```

Pro Lys Val Leu Glu
1185

<210> SEQ ID NO 36
<211> LENGTH: 196
<212> TYPE: PRT
<213> ORGANISM: Homo sapiens

<400> SEQUENCE: 36

Met Ser Arg Arg Ser Met Leu Leu Ala Trp Ala Leu Pro Ser Leu Leu
1 5 10 15

Arg Leu Gly Ala Ala Gln Glu Thr Glu Asp Pro Ala Cys Cys Ser Pro
20 25 30

Ile Val Pro Arg Asn Glu Trp Lys Ala Leu Ala Ser Glu Cys Ala Gln
35 40 45

His Leu Ser Leu Pro Leu Arg Tyr Val Val Val Ser His Thr Ala Gly
50 55 60

Ser Ser Cys Asn Thr Pro Ala Ser Cys Gln Gln Gln Ala Arg Asn Val
65 70 75 80

Gln His Tyr His Met Lys Thr Leu Gly Trp Cys Asp Val Gly Tyr Asn
85 90 95

Phe Leu Ile Gly Glu Asp Gly Leu Val Tyr Glu Gly Arg Gly Trp Asn
100 105 110

Phe Thr Gly Ala His Ser Gly His Leu Trp Asn Pro Met Ser Ile Gly
115 120 125

Ile Ser Phe Met Gly Asn Tyr Met Asp Arg Val Pro Thr Pro Gln Ala
130 135 140

Ile Arg Ala Ala Gln Gly Leu Leu Ala Cys Gly Val Ala Gln Gly Ala
145 150 155 160

Leu Arg Ser Asn Tyr Val Leu Lys Gly His Arg Asp Val Gln Arg Thr
165 170 175

Leu Ser Pro Gly Asn Gln Leu Tyr His Leu Ile Gln Asn Trp Pro His
180 185 190

Tyr Arg Ser Pro
195

<210> SEQ ID NO 37
<211> LENGTH: 319
<212> TYPE: PRT
<213> ORGANISM: Homo sapiens
<220> FEATURE:
<221> NAME/KEY: SITE
<222> LOCATION: (319)
<223> OTHER INFORMATION: Xaa equals stop translation

<400> SEQUENCE: 37

Met Ala Leu Met Leu Ser Leu Val Leu Ser Leu Leu Lys Leu Gly Ser
1 5 10 15

Gly Gln Trp Gln Val Phe Gly Pro Asp Lys Pro Val Gln Ala Leu Val
20 25 30

Gly Glu Asp Ala Ala Phe Ser Cys Phe Leu Ser Pro Lys Thr Asn Ala
35 40 45

Glu Ala Met Glu Val Arg Phe Phe Arg Gly Gln Phe Ser Ser Val Val
50 55 60

His Leu Tyr Arg Asp Gly Lys Asp Gln Pro Phe Met Gln Met Pro Gln
65 70 75 80

Tyr Gln Gly Arg Thr Lys Leu Val Lys Asp Ser Ile Ala Glu Gly Arg

-continued

```
                85                  90                  95

Ile Ser Leu Arg Leu Glu Asn Ile Thr Val Leu Asp Ala Gly Leu Tyr
            100                 105                 110

Gly Cys Arg Ile Ser Ser Gln Ser Tyr Tyr Gln Lys Ala Ile Trp Glu
        115                 120                 125

Leu Gln Val Ser Ala Leu Gly Ser Val Pro Leu Ile Ser Ile Ala Gly
    130                 135                 140

Tyr Val Asp Arg Asp Ile Gln Leu Leu Cys Gln Ser Ser Gly Trp Phe
145                 150                 155                 160

Pro Arg Pro Thr Ala Lys Trp Lys Gly Pro Gln Gly Gln Asp Leu Ser
                165                 170                 175

Thr Asp Ser Arg Thr Asn Arg Asp Met His Gly Leu Phe Asp Val Glu
            180                 185                 190

Ile Ser Leu Thr Val Gln Glu Asn Ala Gly Ser Ile Ser Cys Ser Met
        195                 200                 205

Arg His Ala His Leu Ser Arg Glu Val Glu Ser Arg Val Gln Ile Gly
    210                 215                 220

Asp Trp Arg Arg Lys His Gly Gln Ala Gly Lys Arg Lys Tyr Ser Ser
225                 230                 235                 240

Ser His Ile Tyr Asp Ser Phe Pro Ser Leu Ser Phe Met Asp Phe Tyr
                245                 250                 255

Ile Leu Arg Pro Val Gly Pro Cys Arg Ala Lys Leu Val Met Gly Thr
            260                 265                 270

Leu Lys Leu Gln Ile Leu Gly Glu Val His Phe Val Glu Lys Pro His
        275                 280                 285

Ser Leu Leu Gln Ile Ser Gly Gly Ser Thr Thr Leu Lys Lys Gly Pro
    290                 295                 300

Asn Pro Trp Ser Phe Pro Ser Pro Cys Ala Leu Phe Pro Thr Xaa
305                 310                 315


<210> SEQ ID NO 38
<211> LENGTH: 375
<212> TYPE: PRT
<213> ORGANISM: Homo sapiens

<400> SEQUENCE: 38

Met Ala Gly Ile Pro Gly Leu Leu Phe Leu Leu Phe Phe Leu Leu Cys
  1               5                  10                  15

Ala Val Gly Gln Val Ser Pro Tyr Ser Ala Pro Trp Lys Pro Thr Trp
            20                  25                  30

Pro Ala Tyr Arg Leu Pro Val Val Leu Pro Gln Ser Thr Leu Asn Leu
        35                  40                  45

Ala Lys Pro Asp Phe Gly Ala Glu Ala Lys Leu Glu Val Ser Ser Ser
     50                  55                  60

Cys Gly Pro Gln Cys His Lys Gly Thr Pro Leu Pro Thr Tyr Glu Glu
 65                  70                  75                  80

Ala Lys Gln Tyr Leu Ser Tyr Glu Thr Leu Tyr Ala Asn Gly Ser Arg
                85                  90                  95

Thr Glu Thr Gln Val Gly Ile Tyr Ile Leu Ser Ser Ser Gly Asp Gly
            100                 105                 110

Ala Gln His Arg Asp Ser Gly Ser Ser Gly Lys Ser Arg Arg Lys Arg
        115                 120                 125

Gln Ile Tyr Gly Tyr Asp Ser Arg Phe Ser Ile Phe Gly Lys Asp Phe
    130                 135                 140
```

-continued

```
Leu Leu Asn Tyr Pro Phe Ser Thr Ser Val Lys Leu Ser Thr Gly Cys
145                 150                 155                 160

Thr Gly Thr Leu Val Ala Glu Lys His Val Leu Thr Ala Ala His Cys
                165                 170                 175

Ile His Asp Gly Lys Thr Tyr Val Lys Gly Thr Gln Lys Leu Arg Val
            180                 185                 190

Gly Phe Leu Lys Pro Lys Phe Lys Asp Gly Gly Arg Gly Ala Asn Asp
        195                 200                 205

Ser Thr Ser Ala Met Pro Glu Gln Met Lys Phe Gln Trp Ile Arg Val
    210                 215                 220

Lys Arg Thr His Val Pro Lys Gly Trp Ile Lys Gly Asn Ala Asn Asp
225                 230                 235                 240

Ile Gly Met Asp Tyr Asp Tyr Ala Leu Leu Glu Leu Lys Lys Pro His
                245                 250                 255

Lys Arg Lys Phe Met Lys Ile Gly Val Ser Pro Pro Ala Lys Gln Leu
            260                 265                 270

Pro Gly Gly Arg Ile His Phe Ser Gly Tyr Asp Asn Asp Arg Pro Gly
        275                 280                 285

Asn Leu Val Tyr Arg Phe Cys Asp Val Lys Asp Glu Thr Tyr Asp Leu
    290                 295                 300

Leu Tyr Gln Gln Cys Asp Ser Gln Pro Gly Ala Ser Gly Ser Gly Val
305                 310                 315                 320

Tyr Val Arg Met Trp Lys Arg Gln His Gln Lys Trp Glu Arg Lys Ile
                325                 330                 335

Ile Gly Met Ile Ser Gly His Gln Trp Val Asp Met Asp Gly Ser Pro
            340                 345                 350

Gln Glu Phe Thr Arg Gly Cys Ser Glu Ile Thr Pro Leu Gln Tyr Ile
        355                 360                 365

Pro Asp Ile Ser Ile Gly Val
    370                 375


<210> SEQ ID NO 39
<211> LENGTH: 364
<212> TYPE: PRT
<213> ORGANISM: Homo sapiens

<400> SEQUENCE: 39

Met Ala Ser Val Val Leu Pro Ser Gly Ser Gln Cys Ala Ala Ala Ala
  1               5                  10                  15

Ala Ala Ala Ala Pro Pro Gly Leu Arg Leu Arg Leu Leu Leu Leu Leu
             20                  25                  30

Phe Ser Ala Ala Ala Leu Ile Pro Thr Gly Asp Gly Gln Asn Leu Phe
         35                  40                  45

Thr Lys Asp Val Thr Val Ile Glu Gly Glu Val Ala Thr Ile Ser Cys
     50                  55                  60

Gln Val Asn Lys Ser Asp Asp Ser Val Ile Gln Leu Leu Asn Pro Asn
 65                  70                  75                  80

Arg Gln Thr Ile Tyr Phe Arg Asp Phe Arg Pro Leu Lys Asp Ser Arg
                 85                  90                  95

Phe Gln Leu Leu Asn Phe Ser Ser Ser Glu Leu Lys Val Ser Leu Thr
            100                 105                 110

Asn Val Ser Ile Ser Asp Glu Gly Arg Tyr Phe Cys Gln Leu Tyr Thr
        115                 120                 125

Asp Pro Pro Gln Glu Ser Tyr Thr Thr Ile Thr Val Leu Val Pro Pro
    130                 135                 140
```

-continued

```
Arg Asn Leu Met Ile Asp Ile Gln Lys Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
        195                 200                 205

Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
        275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Pro Pro Thr Thr
                325                 330                 335

Ile Pro Pro Pro Thr Thr Thr Thr Thr Thr Thr Thr Thr Thr Thr Thr
            340                 345                 350

Thr Ile Leu Thr Ile Ile Thr Asp Ser Arg Ala Arg
        355                 360
```

<210> SEQ ID NO 40
<211> LENGTH: 66
<212> TYPE: PRT
<213> ORGANISM: Homo sapiens

<400> SEQUENCE: 40

```
Met Ser Ser Ser Ser Leu Lys His Leu Leu Cys Met Ala Leu Ser Trp
  1               5                  10                  15

Phe Ser Ser Phe Ile Ser Gly Glu Thr Ser Phe Ser Leu Leu Asn Ser
             20                  25                  30

Phe Phe Leu Pro Tyr Pro Ser Ser Arg Cys Cys Cys Phe Ser Val Gln
         35                  40                  45

Cys Ser Ile Leu Asp Pro Phe Ser Cys Asn Ser Met Arg Phe Pro Trp
     50                  55                  60

Glu Asn
 65
```

<210> SEQ ID NO 41
<211> LENGTH: 469
<212> TYPE: PRT
<213> ORGANISM: Homo sapiens

<400> SEQUENCE: 41

```
Met Arg Pro Pro Gly Phe Arg Asn Phe Leu Leu Leu Ala Ser Ser Leu
  1               5                  10                  15

Leu Phe Ala Gly Leu Ser Ala Val Pro Gln Ser Phe Ser Pro Ser Leu
             20                  25                  30
```

-continued

```
Arg Ser Trp Pro Gly Ala Ala Cys Arg Leu Ser Arg Ala Glu Ser Glu
        35                  40                  45

Arg Arg Cys Arg Ala Pro Gly Gln Pro Pro Gly Ala Ala Leu Cys His
    50                  55                  60

Gly Arg Gly Arg Cys Asp Cys Gly Val Cys Ile Cys His Val Thr Glu
65                  70                  75                  80

Pro Gly Met Phe Phe Gly Pro Leu Cys Glu Cys His Glu Trp Val Cys
                85                  90                  95

Glu Thr Tyr Asp Gly Ser Thr Cys Ala Gly His Gly Lys Cys Asp Cys
            100                 105                 110

Gly Lys Cys Lys Cys Asp Gln Gly Trp Tyr Gly Asp Ala Cys Gln Tyr
        115                 120                 125

Pro Thr Asn Cys Asp Leu Thr Lys Lys Lys Ser Asn Gln Met Cys Lys
    130                 135                 140

Asn Ser Gln Asp Ile Ile Cys Ser Asn Ala Gly Thr Cys His Cys Gly
145                 150                 155                 160

Arg Cys Lys Cys Asp Asn Ser Asp Gly Ser Gly Leu Val Tyr Gly Lys
                165                 170                 175

Phe Cys Glu Cys Asp Asp Arg Glu Cys Ile Asp Asp Glu Thr Glu Glu
            180                 185                 190

Ile Cys Gly Gly His Gly Lys Cys Tyr Cys Gly Asn Cys Tyr Cys Lys
        195                 200                 205

Ala Gly Trp His Gly Asp Lys Cys Glu Phe Gln Cys Asp Ile Thr Pro
    210                 215                 220

Trp Glu Ser Lys Arg Arg Cys Thr Ser Pro Asp Gly Lys Ile Cys Ser
225                 230                 235                 240

Ser Arg Gly Thr Cys Val Cys Gly Glu Cys Thr Cys His Asp Val Asp
                245                 250                 255

Pro Thr Gly Asp Trp Gly Asp Ile His Gly Asp Thr Cys Glu Cys Asp
            260                 265                 270

Glu Arg Asp Cys Arg Ala Val Tyr Asp Arg Tyr Ser Asp Asp Phe Cys
        275                 280                 285

Ser Gly His Gly Gln Cys Asn Cys Gly Arg Cys Asp Cys Lys Ala Gly
    290                 295                 300

Trp Tyr Gly Lys Lys Cys Glu His Pro Gln Ser Cys Thr Leu Ser Ala
305                 310                 315                 320

Glu Glu Ser Ile Arg Lys Cys Gln Gly Ser Ser Asp Leu Pro Cys Ser
                325                 330                 335

Gly Arg Gly Lys Cys Glu Cys Gly Lys Cys Thr Cys Tyr Pro Pro Gly
            340                 345                 350

Asp Arg Arg Val Tyr Gly Lys Thr Cys Glu Cys Asp Asp Arg Arg Cys
        355                 360                 365

Glu Asp Leu Asp Gly Val Val Cys Gly Gly His Gly Thr Cys Ser Cys
    370                 375                 380

Gly Arg Cys Val Cys Glu Arg Gly Trp Phe Gly Lys Leu Cys Gln His
385                 390                 395                 400

Pro Arg Lys Cys Asn Met Thr Glu Glu Gln Ser Lys Asn Leu Cys Glu
                405                 410                 415

Ser Ala Asp Gly Ile Leu Cys Ser Gly Lys Gly Ser Cys His Cys Gly
            420                 425                 430

Lys Cys Ile Cys Ser Ala Glu Glu Trp Tyr Ile Ser Gly Glu Phe Cys
        435                 440                 445
```

-continued

Asp Cys Asp Asp Arg Asp Cys Asp Lys His Asp Gly Leu Ile Cys Thr
450 455 460

Arg Glu Trp Asn Met
465

<210> SEQ ID NO 42
<211> LENGTH: 127
<212> TYPE: PRT
<213> ORGANISM: Homo sapiens

<400> SEQUENCE: 42

Met Leu Leu Pro Leu Leu Leu Ser Ser Leu Leu Gly Gly Ser Gln Ala
1 5 10 15

Met Asp Gly Arg Phe Trp Ile Arg Val Gln Glu Ser Val Met Val Pro
20 25 30

Glu Gly Leu Cys Ile Ser Val Pro Cys Ser Phe Ser Tyr Pro Arg Gln
35 40 45

Asp Trp Thr Gly Ser Thr Pro Ala Tyr Gly Tyr Trp Phe Lys Ala Val
50 55 60

Thr Glu Thr Thr Lys Gly Ala Pro Val Ala Thr Asn His Gln Ser Arg
65 70 75 80

Glu Val Glu Met Ser Thr Arg Gly Arg Phe Pro Gly Ser Leu Gly Asp
85 90 95

Pro Ala Lys Gly Asn Cys Ser Leu Val Ile Arg Arg Arg Ala Asp Ala
100 105 110

Arg Met Ser His Ser Thr Ser Phe Gly Trp Arg Glu Glu Ala Met
115 120 125

<210> SEQ ID NO 43
<211> LENGTH: 1034
<212> TYPE: PRT
<213> ORGANISM: Homo sapiens

<400> SEQUENCE: 43

Met Asp Leu Pro Arg Gly Leu Val Val Ala Trp Ala Leu Ser Leu Trp
1 5 10 15

Pro Gly Phe Thr Asp Thr Phe Asn Met Asp Thr Arg Lys Pro Arg Val
20 25 30

Ile Pro Gly Ser Arg Thr Ala Phe Phe Gly Tyr Thr Val Gln Gln His
35 40 45

Asp Ile Ser Gly Asn Lys Trp Leu Val Val Gly Ala Pro Leu Glu Thr
50 55 60

Asn Gly Tyr Gln Lys Thr Gly Asp Val Tyr Lys Cys Pro Val Ile His
65 70 75 80

Gly Asn Cys Thr Lys Leu Asn Leu Gly Arg Val Thr Leu Ser Asn Val
85 90 95

Ser Glu Arg Lys Asp Asn Met Arg Leu Gly Leu Ser Leu Ala Thr Asn
100 105 110

Pro Lys Asp Asn Ser Phe Leu Ala Cys Ser Pro Leu Trp Ser His Glu
115 120 125

Cys Gly Ser Ser Tyr Tyr Thr Thr Gly Met Cys Ser Arg Val Asn Ser
130 135 140

Asn Phe Arg Phe Ser Lys Thr Val Ala Pro Ala Leu Gln Arg Cys Gln
145 150 155 160

Thr Tyr Met Asp Ile Val Ile Val Leu Asp Gly Ser Asn Ser Ile Tyr
165 170 175

-continued

```
Pro Trp Val Glu Val Gln His Phe Leu Ile Asn Ile Leu Lys Lys Phe
            180                 185                 190

Tyr Ile Gly Pro Gly Gln Ile Gln Val Gly Val Val Gln Tyr Gly Glu
        195                 200                 205

Asp Val Val His Glu Phe His Leu Asn Asp Tyr Arg Ser Val Lys Asp
    210                 215                 220

Val Val Glu Ala Ala Ser His Ile Glu Gln Arg Gly Gly Thr Glu Thr
225                 230                 235                 240

Arg Thr Ala Phe Gly Ile Glu Phe Ala Arg Ser Glu Ala Phe Gln Lys
                245                 250                 255

Gly Gly Arg Lys Gly Ala Lys Lys Val Met Ile Val Ile Thr Asp Gly
            260                 265                 270

Glu Ser His Asp Ser Pro Asp Leu Glu Lys Val Ile Gln Gln Ser Glu
        275                 280                 285

Arg Asp Asn Val Thr Arg Tyr Ala Val Ala Val Leu Gly Tyr Tyr Asn
    290                 295                 300

Arg Arg Gly Ile Asn Pro Glu Thr Phe Leu Asn Glu Ile Lys Tyr Ile
305                 310                 315                 320

Ala Ser Asp Pro Asp Asp Lys His Phe Phe Asn Val Thr Asp Glu Ala
                325                 330                 335

Ala Leu Lys Asp Ile Val Asp Ala Leu Gly Asp Arg Ile Phe Ser Leu
            340                 345                 350

Glu Gly Thr Asn Lys Asn Glu Thr Ser Phe Gly Leu Glu Met Ser Gln
        355                 360                 365

Thr Gly Phe Ser Ser His Val Val Glu Asp Gly Val Leu Leu Gly Ala
    370                 375                 380

Val Gly Ala Tyr Asp Trp Asn Gly Ala Val Leu Lys Glu Thr Ser Ala
385                 390                 395                 400

Gly Lys Val Ile Pro Leu Arg Glu Ser Tyr Leu Lys Glu Phe Pro Glu
                405                 410                 415

Glu Leu Lys Asn His Gly Ala Tyr Leu Gly Tyr Thr Val Thr Ser Val
            420                 425                 430

Val Ser Ser Arg Gln Gly Arg Val Tyr Val Ala Gly Ala Pro Arg Phe
        435                 440                 445

Asn His Thr Gly Lys Val Ile Leu Phe Thr Met His Asn Asn Arg Ser
    450                 455                 460

Leu Thr Ile His Gln Ala Met Arg Gly Gln Gln Ile Gly Ser Tyr Phe
465                 470                 475                 480

Gly Ser Glu Ile Thr Ser Val Asp Ile Asp Gly Asp Gly Val Thr Asp
                485                 490                 495

Val Leu Leu Val Gly Ala Pro Met Tyr Phe Asn Glu Gly Arg Glu Arg
            500                 505                 510

Gly Lys Val Tyr Val Tyr Glu Leu Arg Gln Asn Arg Phe Val Tyr Asn
        515                 520                 525

Gly Thr Leu Lys Asp Ser His Ser Tyr Gln Asn Ala Arg Phe Gly Ser
    530                 535                 540

Ser Ile Ala Ser Val Arg Asp Leu Asn Gln Asp Ser Tyr Asn Asp Val
545                 550                 555                 560

Val Val Gly Ala Pro Leu Glu Asp Asn His Ala Gly Ala Ile Tyr Ile
                565                 570                 575

Phe His Gly Phe Arg Gly Ser Ile Leu Lys Thr Pro Lys Gln Arg Ile
            580                 585                 590

Thr Ala Ser Glu Leu Ala Thr Gly Leu Gln Tyr Phe Gly Cys Ser Ile
```

-continued

```
        595                 600                 605

His Gly Gln Leu Asp Leu Asn Glu Asp Gly Leu Ile Asp Leu Ala Val
    610                 615                 620

Gly Ala Leu Gly Asn Ala Val Ile Leu Trp Ser Arg Pro Val Val Gln
625                 630                 635                 640

Ile Asn Ala Ser Leu His Phe Glu Pro Ser Lys Ile Asn Ile Phe His
                645                 650                 655

Arg Asp Cys Lys Arg Ser Gly Arg Asp Ala Thr Cys Leu Ala Ala Phe
            660                 665                 670

Leu Cys Phe Thr Pro Ile Phe Leu Ala Pro His Phe Gln Thr Thr Thr
        675                 680                 685

Val Gly Ile Arg Tyr Asn Ala Thr Met Asp Glu Lys Arg Tyr Thr Pro
    690                 695                 700

Arg Ala His Leu Asp Glu Gly Gly Asp Arg Phe Thr Asn Arg Ala Val
705                 710                 715                 720

Leu Leu Ser Ser Gly Gln Glu Leu Cys Glu Arg Ile Asn Phe His Val
                725                 730                 735

Leu Asp Thr Ala Asp Tyr Val Lys Pro Val Thr Phe Ser Val Glu Tyr
            740                 745                 750

Ser Leu Glu Asp Pro Asp His Gly Pro Met Leu Asp Asp Gly Trp Pro
        755                 760                 765

Thr Thr Leu Arg Val Ser Val Pro Phe Trp Asn Gly Cys Asn Glu Asp
    770                 775                 780

Glu His Cys Val Pro Asp Leu Val Leu Asp Ala Arg Ser Asp Leu Pro
785                 790                 795                 800

Thr Ala Met Glu Tyr Cys Gln Arg Val Leu Arg Lys Pro Ala Gln Asp
                805                 810                 815

Cys Ser Ala Tyr Thr Leu Ser Phe Asp Thr Thr Val Phe Ile Ile Glu
            820                 825                 830

Ser Thr Arg Gln Arg Val Ala Val Glu Ala Thr Leu Glu Asn Arg Gly
        835                 840                 845

Glu Asn Ala Tyr Ser Thr Val Leu Asn Ile Ser Gln Ser Ala Asn Leu
    850                 855                 860

Gln Phe Ala Ser Leu Ile Gln Lys Glu Asp Ser Asp Gly Ser Ile Glu
865                 870                 875                 880

Cys Val Asn Glu Glu Arg Arg Leu Gln Lys Gln Val Cys Asn Val Ser
                885                 890                 895

Tyr Pro Phe Phe Arg Ala Lys Ala Lys Val Ala Phe Arg Leu Asp Phe
            900                 905                 910

Glu Phe Ser Lys Ser Ile Phe Leu His His Leu Glu Ile Glu Leu Ala
        915                 920                 925

Ala Gly Ser Asp Ser Asn Glu Arg Asp Ser Thr Lys Glu Asp Asn Val
    930                 935                 940

Ala Pro Leu Arg Phe His Leu Lys Tyr Glu Ala Asp Val Leu Phe Thr
945                 950                 955                 960

Arg Ser Ser Ser Leu Ser His Tyr Glu Val Lys Leu Asn Ser Ser Leu
                965                 970                 975

Glu Arg Tyr Asp Gly Ile Gly Pro Pro Phe Ser Cys Ile Phe Arg Ile
            980                 985                 990

Gln Asn Leu Gly Leu Phe Pro Ile  His Gly Ile Met Met  Lys Ile Thr
        995                 1000                1005

Ile Pro  Ile Ala Thr Arg Ser  Gly Asn Arg Leu Leu  Lys Leu Arg Asp
    1010                1015                1020
```

```
Phe  Leu Thr Asp Glu Gly  Glu His Val Leu
1025                 1030


<210> SEQ ID NO 44
<211> LENGTH: 461
<212> TYPE: PRT
<213> ORGANISM: Homo sapiens
<220> FEATURE:
<221> NAME/KEY: SITE
<222> LOCATION: (234)
<223> OTHER INFORMATION: Xaa equals any of the naturally occurring
      L-amino acids
<220> FEATURE:
<221> NAME/KEY: SITE
<222> LOCATION: (236)
<223> OTHER INFORMATION: Xaa equals any of the naturally occurring
      L-amino acids

<400> SEQUENCE: 44

Met Ala Leu Met Leu Ser Leu Val Leu Ser Leu Leu Lys Leu Gly Ser
  1               5                  10                  15

Gly Gln Trp Gln Val Phe Gly Pro Asp Lys Pro Val Gln Ala Leu Val
             20                  25                  30

Gly Glu Asp Ala Ala Phe Ser Cys Phe Leu Ser Pro Lys Thr Asn Ala
         35                  40                  45

Glu Ala Met Glu Val Arg Phe Phe Arg Gly Gln Phe Ser Ser Val Val
     50                  55                  60

His Leu Tyr Arg Asp Gly Lys Asp Gln Pro Phe Met Gln Met Pro Gln
 65                  70                  75                  80

Tyr Gln Gly Arg Thr Lys Leu Val Lys Asp Ser Ile Ala Glu Gly Arg
                 85                  90                  95

Ile Ser Leu Arg Leu Glu Asn Ile Thr Val Leu Asp Ala Gly Leu Tyr
            100                 105                 110

Gly Cys Arg Ile Ser Ser Gln Ser Tyr Tyr Gln Lys Ala Ile Trp Glu
        115                 120                 125

Leu Gln Val Ser Ala Leu Gly Ser Val Pro Leu Ile Ser Ile Thr Gly
    130                 135                 140

Tyr Val Asp Arg Asp Ile Gln Leu Leu Cys Gln Ser Ser Gly Trp Phe
145                 150                 155                 160

Pro Arg Pro Thr Ala Lys Trp Lys Gly Pro Gln Gly Gln Asp Leu Ser
                165                 170                 175

Thr Asp Ser Arg Thr Asn Arg Asp Met His Gly Leu Phe Asp Val Glu
            180                 185                 190

Ile Ser Leu Thr Val Gln Glu Asn Ala Gly Ser Ile Ser Cys Ser Met
        195                 200                 205

Arg His Ala His Leu Ser Arg Glu Val Glu Ser Arg Val Gln Ile Gly
    210                 215                 220

Asp Thr Phe Phe Glu Pro Ile Ser Trp Xaa Leu Xaa Thr Lys Val Leu
225                 230                 235                 240

Gly Ile Leu Cys Cys Gly Leu Phe Phe Gly Ile Val Gly Leu Lys Ile
                245                 250                 255

Phe Phe Ser Lys Phe Gln Trp Lys Ile Gln Ala Glu Leu Asp Trp Arg
            260                 265                 270

Arg Lys His Gly Gln Ala Glu Leu Arg Asp Ala Arg Lys His Ala Val
        275                 280                 285

Glu Val Thr Leu Asp Pro Glu Thr Ala His Pro Lys Leu Cys Val Ser
    290                 295                 300
```

-continued

Asp Leu Lys Thr Val Thr His Arg Lys Ala Pro Gln Glu Val Pro His
305 310 315 320

Ser Glu Lys Arg Phe Thr Arg Lys Ser Val Val Ala Ser Gln Ser Phe
325 330 335

Gln Ala Gly Lys His Tyr Trp Glu Val Asp Gly Gly His Asn Lys Arg
340 345 350

Trp Arg Val Gly Val Cys Arg Asp Asp Val Asp Arg Arg Lys Glu Tyr
355 360 365

Val Thr Leu Ser Pro Asp His Gly Tyr Trp Val Leu Arg Leu Asn Gly
370 375 380

Glu His Leu Tyr Phe Thr Leu Asn Pro Arg Phe Ile Ser Val Phe Pro
385 390 395 400

Arg Thr Pro Pro Thr Lys Ile Gly Val Phe Leu Asp Tyr Glu Cys Gly
405 410 415

Thr Ile Ser Phe Phe Asn Ile Asn Asp Gln Ser Leu Ile Tyr Thr Leu
420 425 430

Thr Cys Arg Phe Glu Gly Leu Leu Arg Pro Tyr Ile Glu Tyr Pro Ser
435 440 445

Tyr Asn Glu Gln Asn Gly Thr Pro Arg Asp Lys Gln Gln
450 455 460

<210> SEQ ID NO 45
<211> LENGTH: 383
<212> TYPE: PRT
<213> ORGANISM: Homo sapiens

<400> SEQUENCE: 45

Met Ala Gly Ile Pro Gly Leu Leu Phe Leu Leu Phe Phe Leu Leu Cys
1 5 10 15

Ala Val Gly Gln Val Ser Pro Tyr Ser Ala Pro Trp Lys Pro Thr Trp
20 25 30

Pro Ala Tyr Arg Leu Pro Val Val Leu Pro Gln Ser Thr Leu Asn Leu
35 40 45

Ala Lys Pro Asp Phe Gly Ala Glu Ala Lys Leu Glu Val Ser Ser Ser
50 55 60

Cys Gly Pro Gln Cys His Lys Gly Thr Pro Leu Pro Thr Tyr Glu Glu
65 70 75 80

Ala Lys Gln Tyr Leu Ser Tyr Glu Thr Leu Tyr Ala Asn Gly Ser Arg
85 90 95

Thr Glu Thr Gln Val Gly Ile Tyr Ile Leu Ser Ser Ser Gly Asp Gly
100 105 110

Ala Gln His Arg Asp Ser Gly Ser Ser Gly Lys Ser Arg Arg Lys Arg
115 120 125

Gln Ile Tyr Gly Tyr Asp Ser Arg Phe Ser Ile Phe Gly Lys Asp Phe
130 135 140

Leu Leu Asn Tyr Pro Phe Ser Thr Ser Val Lys Leu Ser Thr Gly Cys
145 150 155 160

Thr Gly Thr Leu Val Ala Glu Lys His Val Leu Thr Ala Ala His Cys
165 170 175

Ile His Asp Gly Lys Thr Tyr Val Lys Gly Thr Gln Lys Leu Arg Val
180 185 190

Gly Phe Leu Lys Pro Lys Phe Lys Asp Gly Gly Arg Gly Ala Asn Asp
195 200 205

Ser Thr Ser Ala Met Pro Glu Gln Met Lys Phe Gln Trp Ile Arg Val
210 215 220

-continued

```
Lys Arg Thr His Val Pro Lys Gly Trp Ile Lys Gly Asn Ala Asn Asp
225                 230                 235                 240

Ile Gly Met Asp Tyr Asp Tyr Ala Leu Leu Glu Leu Lys Lys Pro His
                245                 250                 255

Lys Arg Lys Phe Met Lys Ile Gly Val Ser Pro Pro Ala Lys Gln Leu
            260                 265                 270

Pro Gly Gly Arg Ile His Phe Ser Gly Tyr Asp Asn Asp Arg Pro Gly
        275                 280                 285

Asn Leu Val Tyr Arg Phe Cys Asp Val Lys Asp Glu Thr Tyr Asp Leu
    290                 295                 300

Leu Tyr Gln Gln Cys Asp Ala Gln Pro Gly Ala Ser Gly Ser Gly Val
305                 310                 315                 320

Tyr Val Arg Met Trp Lys Arg Gln Gln Gln Lys Trp Glu Arg Lys Ile
                325                 330                 335

Ile Gly Ile Phe Ser Gly His Gln Trp Val Asp Met Asn Gly Ser Pro
            340                 345                 350

Gln Asp Phe Asn Val Ala Val Arg Ile Thr Pro Leu Lys Tyr Ala Gln
        355                 360                 365

Ile Cys Tyr Trp Ile Lys Gly Asn Tyr Leu Asp Cys Arg Glu Gly
    370                 375                 380


<210> SEQ ID NO 46
<211> LENGTH: 229
<212> TYPE: PRT
<213> ORGANISM: Homo sapiens

<400> SEQUENCE: 46

Met Ile Asp Ile Gln Lys Asp Thr Ala Val Glu Gly Glu Glu Ile Glu
  1               5                  10                  15

Val Asn Cys Thr Ala Met Ala Ser Lys Pro Ala Thr Thr Ile Arg Trp
             20                  25                  30

Phe Lys Gly Asn Thr Glu Leu Lys Gly Lys Ser Glu Val Glu Glu Trp
         35                  40                  45

Ser Asp Met Tyr Thr Val Thr Ser Gln Leu Met Leu Lys Val His Lys
     50                  55                  60

Glu Asp Asp Gly Val Pro Val Ile Cys Gln Val Glu His Pro Ala Val
 65                  70                  75                  80

Thr Gly Asn Leu Gln Thr Gln Arg Tyr Leu Glu Val Gln Tyr Lys Pro
                 85                  90                  95

Gln Val His Ile Gln Met Thr Tyr Pro Leu Gln Gly Leu Thr Arg Glu
            100                 105                 110

Gly Asp Ala Leu Glu Leu Thr Cys Glu Ala Ile Gly Lys Pro Gln Pro
        115                 120                 125

Val Met Val Thr Trp Val Arg Val Asp Asp Glu Met Pro Gln His Ala
    130                 135                 140

Val Leu Ser Gly Pro Asn Leu Phe Ile Asn Asn Leu Asn Lys Thr Asp
145                 150                 155                 160

Asn Gly Thr Tyr Arg Cys Glu Ala Ser Asn Ile Val Gly Lys Ala His
                165                 170                 175

Ser Asp Tyr Met Leu Tyr Val Tyr Asp Pro Pro Thr Thr Ile Pro Pro
            180                 185                 190

Pro Thr Thr Thr Thr Thr Thr Thr Thr Thr Thr Thr Thr Thr Ile Leu
        195                 200                 205

Thr Ile Ile Thr Asp Ser Pro Ser Gln Val Lys Lys Ala Arg Ser Gly
```

```
    210                 215                 220

Gln Trp Ile Met Pro
225


<210> SEQ ID NO 47
<211> LENGTH: 724
<212> TYPE: PRT
<213> ORGANISM: Homo sapiens

<400> SEQUENCE: 47

Met Leu Arg Thr Ser Thr Pro Asn Leu Cys Gly Gly Leu His Cys Arg
  1               5                  10                  15

Ala Pro Trp Leu Ser Ser Gly Ile Leu Cys Leu Cys Leu Ile Phe Leu
             20                  25                  30

Leu Gly Gln Val Gly Leu Leu Gln Gly His Pro Gln Cys Leu Asp Tyr
         35                  40                  45

Gly Pro Pro Phe Gln Pro Pro Leu His Leu Glu Phe Cys Ser Asp Tyr
     50                  55                  60

Glu Ser Phe Gly Cys Cys Asp Gln His Lys Asp Arg Arg Ile Ala Ala
 65                  70                  75                  80

Arg Tyr Trp Asp Ile Met Glu Tyr Phe Asp Leu Lys Arg His Glu Leu
                 85                  90                  95

Cys Gly Asp Tyr Ile Lys Asp Ile Leu Cys Gln Glu Cys Ser Pro Tyr
            100                 105                 110

Ala Ala His Leu Tyr Asp Ala Glu Asn Thr Gln Thr Pro Leu Arg Asn
        115                 120                 125

Leu Pro Gly Leu Cys Ser Asp Tyr Cys Ser Ala Phe His Ser Asn Cys
    130                 135                 140

His Ser Ala Ile Ser Leu Leu Thr Asn Asp Arg Gly Leu Gln Glu Ser
145                 150                 155                 160

His Gly Arg Asp Gly Thr Arg Phe Cys His Leu Leu Asp Leu Pro Asp
                165                 170                 175

Lys Asp Tyr Cys Phe Pro Asn Val Leu Arg Asn Asp Tyr Leu Asn Arg
            180                 185                 190

His Leu Gly Met Val Ala Gln Asp Pro Gln Gly Cys Leu Gln Leu Cys
        195                 200                 205

Leu Ser Glu Val Ala Asn Gly Leu Arg Asn Pro Val Ser Met Val His
    210                 215                 220

Ala Gly Asp Gly Thr His Arg Phe Phe Val Ala Glu Gln Val Gly Val
225                 230                 235                 240

Val Trp Val Tyr Leu Pro Asp Gly Ser Arg Leu Glu Gln Pro Phe Leu
                245                 250                 255

Asp Leu Lys Asn Ile Val Leu Thr Thr Pro Trp Ile Gly Asp Glu Arg
            260                 265                 270

Gly Phe Leu Gly Leu Ala Phe His Pro Lys Phe Arg His Asn Arg Lys
        275                 280                 285

Phe Tyr Ile Tyr Tyr Ser Cys Leu Asp Lys Lys Lys Val Glu Lys Ile
    290                 295                 300

Arg Ile Ser Glu Met Lys Val Ser Arg Ala Asp Pro Asn Lys Ala Asp
305                 310                 315                 320

Leu Lys Ser Glu Arg Val Ile Leu Glu Ile Glu Glu Pro Ala Ser Asn
                325                 330                 335

His Asn Gly Gly Gln Leu Leu Phe Gly Leu Asp Gly Tyr Met Tyr Ile
            340                 345                 350
```

-continued

```
Phe Thr Gly Asp Gly Gly Gln Ala Gly Asp Pro Phe Gly Leu Phe Gly
        355                 360                 365

Asn Ala Gln Asn Lys Ser Ser Leu Leu Gly Lys Val Leu Arg Ile Asp
    370                 375                 380

Val Asn Arg Ala Gly Ser His Gly Lys Arg Tyr Arg Val Pro Ser Asp
385                 390                 395                 400

Asn Pro Phe Val Ser Glu Pro Gly Ala His Pro Ala Ile Tyr Ala Tyr
                405                 410                 415

Gly Ile Arg Asn Met Trp Arg Cys Ala Val Asp Arg Gly Asp Pro Ile
            420                 425                 430

Thr Arg Gln Gly Arg Gly Arg Ile Phe Cys Gly Asp Val Gly Gln Asn
        435                 440                 445

Arg Phe Glu Glu Val Asp Leu Ile Leu Lys Gly Gly Asn Tyr Gly Trp
    450                 455                 460

Arg Ala Lys Glu Gly Phe Ala Cys Tyr Asp Lys Lys Leu Cys His Asn
465                 470                 475                 480

Ala Ser Leu Asp Asp Val Leu Pro Ile Tyr Ala Tyr Gly His Ala Val
                485                 490                 495

Gly Lys Ser Val Thr Gly Gly Tyr Val Tyr Arg Gly Cys Glu Ser Pro
            500                 505                 510

Asn Leu Asn Gly Leu Tyr Ile Phe Gly Asp Phe Met Ser Gly Arg Leu
        515                 520                 525

Met Ala Leu Gln Glu Asp Arg Lys Asn Lys Lys Trp Lys Lys Gln Asp
    530                 535                 540

Leu Cys Leu Gly Ser Thr Thr Ser Cys Ala Phe Pro Gly Leu Ile Ser
545                 550                 555                 560

Thr His Ser Lys Phe Ile Ile Ser Phe Ala Glu Asp Glu Ala Gly Glu
                565                 570                 575

Leu Tyr Phe Leu Ala Thr Ser Tyr Pro Ser Ala Tyr Ala Pro Arg Gly
            580                 585                 590

Ser Ile Tyr Lys Phe Val Asp Pro Ser Arg Arg Ala Pro Pro Gly Lys
        595                 600                 605

Cys Lys Tyr Lys Pro Val Pro Val Arg Thr Lys Ser Lys Arg Ile Pro
    610                 615                 620

Phe Arg Pro Leu Ala Lys Thr Val Leu Asp Leu Leu Lys Glu Gln Ser
625                 630                 635                 640

Glu Lys Ala Ala Arg Lys Ser Ser Ser Ala Thr Leu Ala Ser Gly Pro
                645                 650                 655

Ala Gln Gly Leu Ser Glu Lys Gly Ser Ser Lys Lys Leu Ala Ser Pro
            660                 665                 670

Thr Ser Ser Lys Asn Thr Leu Arg Gly Pro Gly Thr Lys Lys Lys Ala
        675                 680                 685

Arg Val Gly Pro His Val Arg Gln Gly Lys Arg Arg Lys Ser Leu Lys
    690                 695                 700

Ser His Ser Gly Arg Met Arg Pro Ser Ala Glu Gln Lys Arg Ala Gly
705                 710                 715                 720

Arg Ser Leu Pro
```

<210> SEQ ID NO 48
<211> LENGTH: 995
<212> TYPE: PRT
<213> ORGANISM: Homo sapiens

<400> SEQUENCE: 48

-continued

```
Met Pro Lys Pro Thr Pro Asn Ser Glu Arg Val Ser Val Arg Phe Pro
  1               5                  10                  15

Gly Cys Arg Thr Gly Met His Met Ile Ser Val Ser Leu Arg Leu Val
             20                  25                  30

Phe Cys Ser Phe Ile Phe Lys Ala Gly Val Leu Leu Gly His Pro Gln
         35                  40                  45

Cys Leu Asp Tyr Gly Pro Pro Phe Lys Pro Leu Val His Leu Glu Phe
     50                  55                  60

Cys Ser Glu Tyr Glu Thr Phe Gly Cys Cys Asp Gln Asp Arg Asp Asn
 65                  70                  75                  80

Val Ile Ala Glu Lys Tyr Trp Ser Ile Met Asp Tyr Phe Asp Leu Asn
                 85                  90                  95

Asn Tyr His Ile Cys Gly Gly Tyr Ile Lys Asp Ile Leu Cys Gln Glu
            100                 105                 110

Cys Ser Pro Tyr Ala Ala His Leu Tyr Asp Ala Glu Asp Pro His Thr
        115                 120                 125

Pro Leu Arg Val Ile Pro Gly Leu Cys Phe Asn Tyr Cys Ser Glu Phe
    130                 135                 140

His Leu Lys Cys Gln Asn Ser Ile Thr Leu Leu Thr Glu Asp Lys Gln
145                 150                 155                 160

Ile Arg Glu Ser Cys Asp Lys Gly Arg Asp Leu Phe Cys Ser Leu Leu
                165                 170                 175

Asn Leu Pro Asp Glu Asp Tyr Cys Phe Pro Asn Val Leu His Asn Thr
            180                 185                 190

Glu Leu Asn Asn Asn Leu Gly Ser Val Val Glu Asp Pro Glu Gly Cys
        195                 200                 205

Ile Lys Leu Cys Leu Ile Glu Val Ala Asn Gly Leu Arg Asn Pro Val
    210                 215                 220

Leu Met Leu His Ala Asn Asp Gly Thr His Arg Met Phe Val Ala Glu
225                 230                 235                 240

Gln Ile Gly Phe Val Trp Val Tyr Leu Pro Asp Gly Ser Arg Leu Tyr
                245                 250                 255

Glu Pro Phe Leu Asn Leu Arg Arg Thr Val Leu Ala Thr Pro Trp Leu
            260                 265                 270

Gly Asp Glu Arg Gly Leu Leu Gly Met Ala Phe His Pro Lys Tyr Gln
        275                 280                 285

Asn Asn Arg Lys Phe Tyr Val Tyr Tyr Ser Ile Met Asp Glu Tyr Arg
    290                 295                 300

Asn Glu Lys Ile Arg Ile Ser Glu Phe Gln Val Glu Glu His Asp Ile
305                 310                 315                 320

Asn Lys Ala Asp Pro Tyr Ser Glu Arg Arg Ile Leu Glu Ile Glu Glu
                325                 330                 335

Pro Ala Ala Asn His Asn Gly Gly Gln Ile Leu Phe Gly Lys Asp Gly
            340                 345                 350

Tyr Leu Tyr Ile Phe Thr Gly Asp Gly Gly Lys Ala Gly Asp Pro Phe
        355                 360                 365

Gly Arg Phe Gly Asn Ala Gln Asn Lys Ser Val Leu Leu Gly Lys Val
    370                 375                 380

Leu Arg Ile Asp Val Asp Gly Arg Arg Ala Asn Gly Lys Pro Tyr Gly
385                 390                 395                 400

Ile Pro Ser Asp Asn Pro Phe Leu Ser Glu Arg Gly Ala Ala Pro Glu
                405                 410                 415

Val His Ala Tyr Gly Val Arg Asn Met Trp Arg Cys Ser Val Asp Gln
```

-continued

```
            420                 425                 430

Gly Asp Pro Val Thr Gly Arg Gly Lys Gly Arg Ile Phe Cys Gly Asp
        435                 440                 445

Val Gly Gln Asn Arg Phe Gly Glu Asp Asp Ile Ile Val Ile Gly Gly
    450                 455                 460

Asn Tyr Gly Trp Arg Ala Lys Glu Gly Phe Glu Cys Phe Asp Leu Lys
465                 470                 475                 480

Leu Cys Gln Asn Ser Ser Leu Asp Asp Ile Leu Pro Ile Phe Ala Tyr
                485                 490                 495

Gly His Gln Val Gly Lys Ser Val Thr Gly Gly Tyr Val Tyr Arg Gly
            500                 505                 510

Cys Glu Ser Pro Asn Leu Asn Gly Val Tyr Ile Phe Gly Asp Phe Met
        515                 520                 525

Asn Gly Arg Leu Met Ala Leu Gln Glu Asp Gly Val Thr Gly Thr Trp
    530                 535                 540

Lys Lys Gln Asp Ile Cys Met Gly Asp Ser Thr Ile Cys Ala Phe Pro
545                 550                 555                 560

Arg Leu Ile Asn Lys Tyr Ser Lys Phe Ile Ile Ser Phe Gly Glu Asp
                565                 570                 575

Glu Ala Gly Glu Leu Leu Phe Leu Ser Thr Ser Gln Ala Ser Ala Tyr
            580                 585                 590

Ser Pro Gln Gly Ser Ile Tyr Lys Leu Val Asp Pro Ser Arg Arg Ala
        595                 600                 605

Ala Pro Gly Lys Cys Lys Tyr Lys Pro Val Pro Val Lys Thr Arg Ser
    610                 615                 620

Lys Leu Val Pro Phe Ile Pro Lys Glu Lys Thr Val Leu Glu Ile Val
625                 630                 635                 640

Asn Glu Ser Val Lys Pro Thr Lys Ala Pro Arg Lys Lys Thr Pro Thr
                645                 650                 655

Lys Phe Pro Thr Lys Val Pro Pro Thr Pro Thr Lys Phe Pro Thr Lys
            660                 665                 670

Val Pro Pro Thr Pro Thr Gln Phe Pro Thr Lys Val Pro Pro Ile Pro
        675                 680                 685

Thr Lys Val Pro Ser Lys Val Pro Pro Thr Pro Thr Gln Phe Pro Thr
    690                 695                 700

Lys Val Pro Pro Thr Pro Thr Lys Val Ser Thr Lys Val Leu Ser Thr
705                 710                 715                 720

Pro Thr Ile Ala His Thr Lys Val Ser Pro Thr Ser Thr Lys Leu Pro
                725                 730                 735

Ser Lys Ala Pro Ser Thr Gln Thr Met Val Pro Thr Lys Val His Pro
            740                 745                 750

Thr Pro Thr Lys Leu Pro Thr Lys Val Pro Pro Ile Thr Thr Lys Val
        755                 760                 765

Ser Asn Lys Val Leu Leu Thr Ser Pro Glu Leu Pro Thr Lys Val Pro
    770                 775                 780

Pro Thr Pro Thr Lys Leu Pro Thr Asn Ala Pro Pro Thr Ser Ile Leu
785                 790                 795                 800

Leu Ser Pro Thr Pro Ile Lys Leu Pro Thr Lys Ile Ser Leu Thr Leu
                805                 810                 815

Thr Ser Val Pro Ile Lys Asn Gln Leu Thr Ser Ala Lys Leu Leu Thr
            820                 825                 830

Thr Thr Leu Pro Ile Ser Thr Lys Arg Ala Thr Lys Leu Pro Ser Thr
        835                 840                 845
```

-continued

```
Ser Thr Ser Val Pro Ser Asn Thr Ser Cys Ile Leu Thr His Val Gln
    850                 855                 860

Pro Lys Met Leu Pro Thr Glu Thr Arg Val Pro Asn Lys Met Pro Pro
865                 870                 875                 880

Lys Pro Thr Arg Ile Pro Thr Met Ser Met Tyr Ile Thr Lys Lys Pro
                885                 890                 895

Pro Leu Lys Lys Asn Ser Ala Lys Lys Val Thr Asp Lys Arg Pro Thr
            900                 905                 910

Lys Ser Pro Lys Thr Thr Lys Pro Pro Lys Pro Pro Lys Ser Lys Thr
        915                 920                 925

Ser Val Val Asn Gln Pro Lys Lys Lys Glu Thr Lys Thr Gly Val Asn
    930                 935                 940

Asn Lys Thr Lys Asn Leu Pro Pro Lys Ala Lys Glu Pro Lys Lys Glu
945                 950                 955                 960

Lys Lys Thr Ile Lys Val Lys Gln Pro Val Ser His Tyr Phe Pro Pro
                965                 970                 975

Gln Lys Pro Lys Lys Gln Lys Ile Lys Lys Met Gln Lys Glu Gly Asn
            980                 985                 990

Glu Lys Ser
        995
```

<210> SEQ ID NO 49
<211> LENGTH: 700
<212> TYPE: PRT
<213> ORGANISM: Homo sapiens

<400> SEQUENCE: 49

```
Met Leu Lys Met Leu Ser Phe Lys Leu Leu Leu Leu Ala Val Ala Leu
  1               5                  10                  15

Gly Phe Phe Glu Gly Asp Ala Lys Phe Gly Glu Arg Ser Glu Gly Ser
             20                  25                  30

Gly Ala Arg Arg Arg Arg Cys Leu Asn Gly Asn Pro Pro Lys Arg Leu
         35                  40                  45

Lys Arg Arg Asp Arg Arg Val Met Ser Gln Leu Glu Leu Leu Ser Gly
     50                  55                  60

Gly Glu Ile Leu Cys Gly Gly Phe Tyr Pro Arg Val Ser Cys Cys Leu
 65                  70                  75                  80

Gln Ser Asp Ser Pro Gly Leu Gly Arg Leu Glu Asn Lys Ile Phe Ser
                 85                  90                  95

Ala Thr Asn Asn Ser Glu Cys Ser Arg Leu Leu Glu Glu Ile Gln Cys
            100                 105                 110

Ala Pro Cys Ser Pro His Ser Gln Ser Leu Phe Tyr Thr Pro Glu Arg
        115                 120                 125

Asp Val Leu Asp Gly Asp Leu Ala Leu Pro Leu Leu Cys Lys Asp Tyr
    130                 135                 140

Cys Lys Glu Phe Phe Tyr Thr Cys Arg Gly His Ile Pro Gly Leu Leu
145                 150                 155                 160

Gln Thr Thr Ala Asp Glu Phe Cys Phe Tyr Tyr Ala Arg Lys Asp Ala
                165                 170                 175

Gly Leu Cys Phe Pro Asp Phe Pro Arg Lys Gln Val Arg Gly Pro Ala
            180                 185                 190

Ser Asn Tyr Leu Gly Gln Met Glu Asp Tyr Glu Lys Val Gly Gly Ile
        195                 200                 205

Ser Arg Lys His Lys His Asn Cys Leu Cys Val Gln Glu Val Met Ser
```

-continued

```
    210                 215                 220

Gly Leu Arg Gln Pro Val Ser Ala Val His Ser Gly Asp Gly Ser His
225                 230                 235                 240

Arg Leu Phe Ile Leu Glu Lys Glu Gly Tyr Val Lys Ile Leu Thr Pro
                245                 250                 255

Glu Gly Glu Leu Phe Lys Glu Pro Tyr Leu Asp Ile His Lys Leu Val
            260                 265                 270

Gln Ser Gly Ile Lys Gly Gly Asp Glu Arg Gly Leu Leu Ser Leu Ala
        275                 280                 285

Phe His Pro Asn Tyr Lys Lys Asn Gly Lys Leu Tyr Val Ser Tyr Thr
    290                 295                 300

Thr Asn Gln Glu Arg Trp Ala Ile Gly Pro His Asp His Ile Leu Arg
305                 310                 315                 320

Val Val Glu Tyr Thr Val Ser Arg Lys Asn Pro His Gln Val Asp Val
                325                 330                 335

Arg Thr Ala Arg Val Phe Leu Glu Val Ala Glu Leu His Arg Lys His
            340                 345                 350

Leu Gly Gly Gln Leu Leu Phe Gly Pro Asp Gly Phe Leu Tyr Ile Ile
        355                 360                 365

Leu Gly Asp Gly Met Ile Thr Leu Asp Asp Met Glu Glu Met Asp Gly
    370                 375                 380

Leu Ser Asp Phe Thr Gly Ser Val Leu Arg Leu Asp Val Asp Thr Asp
385                 390                 395                 400

Met Cys Asn Val Pro Tyr Ser Ile Pro Arg Ser Asn Pro His Phe Asn
                405                 410                 415

Ser Thr Asn Gln Pro Pro Glu Val Phe Ala His Gly Leu His Asp Pro
            420                 425                 430

Gly Arg Cys Ala Val Asp Arg His Pro Thr Asp Ile Asn Ile Asn Leu
        435                 440                 445

Thr Ile Leu Cys Ser Asp Ser Asn Gly Lys Asn Arg Ser Ser Ala Arg
    450                 455                 460

Ile Leu Gln Ile Ile Lys Gly Arg Asp Tyr Glu Ser Glu Pro Ser Leu
465                 470                 475                 480

Leu Glu Phe Lys Pro Phe Ser Asn Gly Pro Leu Val Gly Gly Phe Val
                485                 490                 495

Tyr Arg Gly Cys Gln Ser Glu Arg Leu Tyr Gly Ser Tyr Val Phe Gly
            500                 505                 510

Asp Arg Asn Gly Asn Phe Leu Thr Leu Gln Gln Ser Pro Val Thr Lys
        515                 520                 525

Gln Trp Gln Glu Lys Pro Leu Cys Leu Gly Ala Ser Ser Ser Cys Arg
    530                 535                 540

Gly Tyr Phe Ser Gly His Ile Leu Gly Phe Gly Glu Asp Glu Leu Gly
545                 550                 555                 560

Glu Val Tyr Ile Leu Ser Ser Ser Lys Ser Met Thr Gln Thr His Asn
                565                 570                 575

Gly Lys Leu Tyr Lys Ile Val Asp Pro Lys Arg Pro Leu Met Pro Glu
            580                 585                 590

Glu Cys Arg Val Thr Val Gln Pro Ala Gln Pro Leu Thr Ser Asp Cys
        595                 600                 605

Ser Arg Leu Cys Arg Asn Gly Tyr Tyr Thr Pro Thr Gly Lys Cys Cys
    610                 615                 620

Cys Ser Pro Gly Trp Glu Gly Asp Phe Cys Arg Ile Ala Lys Cys Glu
625                 630                 635                 640
```

```
Pro Ala Cys Arg His Gly Gly Val Cys Val Arg Pro Asn Lys Cys Leu
                645                 650                 655

Cys Lys Lys Gly Tyr Leu Gly Pro Gln Cys Glu Gln Val Asp Arg Asn
            660                 665                 670

Val Arg Arg Val Thr Arg Ala Gly Ile Leu Asp Gln Ile Ile Asp Met
        675                 680                 685

Thr Ser Tyr Leu Leu Asp Leu Thr Ser Tyr Ile Val
    690                 695                 700


<210> SEQ ID NO 50
<211> LENGTH: 567
<212> TYPE: PRT
<213> ORGANISM: Homo sapiens

<400> SEQUENCE: 50

Thr Ser Thr Pro Pro Arg Ala Val Pro Leu Pro Lys Ser Ser Gln Ala
  1               5                  10                  15

Ala His Gln Arg Asn Cys Asn Ser Gly Trp Ser Pro Gly Pro Ala Ser
             20                  25                  30

Leu Gly Val Arg Gly Ser Val Cys Pro Ala Ile Cys Trp Trp His Leu
         35                  40                  45

Ser Leu Leu Pro Pro Pro Ser Val Asn Pro Thr Leu Gln Lys Cys Ser
     50                  55                  60

Ser Pro Gly Ala Ala Gln Glu Leu Ser Met Arg Pro Pro Gly Phe Arg
 65                  70                  75                  80

Asn Phe Leu Leu Leu Ala Ser Ser Leu Leu Phe Ala Gly Leu Ser Ala
                 85                  90                  95

Val Pro Gln Ser Phe Ser Pro Ser Leu Arg Ser Trp Pro Gly Ala Ala
            100                 105                 110

Cys Arg Leu Ser Arg Ala Glu Ser Glu Arg Arg Cys Arg Ala Pro Gly
        115                 120                 125

Gln Pro Pro Gly Ala Ala Leu Cys His Gly Arg Gly Arg Cys Asp Cys
    130                 135                 140

Gly Val Cys Ile Cys His Val Thr Glu Pro Gly Met Phe Phe Gly Pro
145                 150                 155                 160

Leu Cys Glu Cys His Glu Trp Val Cys Glu Thr Tyr Asp Gly Ser Thr
                165                 170                 175

Cys Ala Gly His Gly Lys Cys Asp Cys Gly Lys Cys Lys Cys Asp Gln
            180                 185                 190

Gly Trp Tyr Gly Asp Ala Cys Gln Tyr Pro Thr Asn Cys Asp Leu Thr
        195                 200                 205

Lys Lys Lys Ser Asn Gln Met Cys Lys Asn Ser Gln Asp Ile Ile Cys
    210                 215                 220

Ser Asn Ala Gly Thr Cys His Cys Gly Arg Cys Lys Cys Asp Asn Ser
225                 230                 235                 240

Asp Gly Ser Gly Leu Val Tyr Gly Lys Phe Cys Glu Cys Asp Asp Arg
                245                 250                 255

Glu Cys Ile Asp Asp Glu Thr Glu Glu Ile Cys Gly Gly His Gly Lys
            260                 265                 270

Cys Tyr Cys Gly Asn Cys Tyr Cys Lys Ala Gly Trp His Gly Asp Lys
        275                 280                 285

Cys Glu Phe Gln Cys Asp Ile Thr Pro Trp Glu Ser Lys Arg Arg Cys
    290                 295                 300

Thr Ser Pro Asp Gly Lys Ile Cys Ser Asn Arg Gly Thr Cys Val Cys
```

-continued 305 310 315 320

Gly Glu Cys Thr Cys His Asp Val Asp Pro Thr Gly Asp Trp Gly Asp
325 330 335

Ile His Gly Asp Thr Cys Glu Cys Asp Glu Arg Asp Cys Arg Ala Val
340 345 350

Tyr Asp Arg Tyr Ser Asp Asp Phe Cys Ser Gly His Gly Gln Cys Asn
355 360 365

Cys Gly Arg Cys Asp Cys Lys Ala Gly Trp Tyr Gly Lys Lys Cys Glu
370 375 380

His Pro Gln Ser Cys Thr Leu Ser Ala Glu Glu Ser Ile Arg Lys Cys
385 390 395 400

Gln Gly Ser Ser Asp Leu Pro Cys Ser Gly Arg Gly Lys Cys Glu Cys
405 410 415

Gly Lys Cys Thr Cys Tyr Pro Pro Gly Asp Arg Arg Val Tyr Gly Lys
420 425 430

Thr Cys Glu Cys Asp Asp Arg Arg Cys Glu Asp Leu Asp Gly Val Val
435 440 445

Cys Gly Gly His Gly Thr Cys Ser Cys Gly Arg Cys Val Cys Glu Arg
450 455 460

Gly Trp Phe Gly Lys Leu Cys Gln His Pro Arg Lys Cys Asn Met Thr
465 470 475 480

Glu Glu Gln Ser Lys Asn Leu Cys Glu Ser Ala Asp Gly Ile Leu Cys
485 490 495

Ser Gly Lys Gly Ser Cys His Cys Gly Lys Cys Ile Cys Ser Ala Glu
500 505 510

Glu Trp Tyr Ile Ser Gly Glu Phe Cys Asp Cys Asp Asp Arg Asp Cys
515 520 525

Asp Lys His Asp Gly Leu Ile Cys Thr Gly Asn Gly Ile Cys Ser Cys
530 535 540

Gly Asn Cys Glu Cys Trp Asp Gly Trp Asn Gly Asn Ala Cys Glu Ile
545 550 555 560

Trp Leu Gly Ser Glu Tyr Pro
565

<210> SEQ ID NO 51
<211> LENGTH: 29
<212> TYPE: PRT
<213> ORGANISM: Homo sapiens

<400> SEQUENCE: 51

Gly Lys Cys Asp Cys Gly Lys Cys Lys Cys Asp Gln Gly Trp Tyr Gly
1 5 10 15

Asp Ala Cys Gln Tyr Pro Thr Asn Cys Asp Leu Thr Lys
20 25

<210> SEQ ID NO 52
<211> LENGTH: 29
<212> TYPE: PRT
<213> ORGANISM: Homo sapiens

<400> SEQUENCE: 52

Gly Gly His Gly Lys Cys Tyr Cys Gly Asn Cys Tyr Cys Lys Ala Gly
1 5 10 15

Trp His Gly Asp Lys Cys Glu Phe Gln Cys Asp Ile Thr
20 25

-continued

<210> SEQ ID NO 53
<211> LENGTH: 29
<212> TYPE: PRT
<213> ORGANISM: Homo sapiens

<400> SEQUENCE: 53

```
His Gly Gln Cys Asn Cys Gly Arg Cys Asp Cys Lys Ala Gly Trp Tyr
  1               5                  10                  15

Gly Lys Lys Cys Glu His Pro Gln Ser Cys Thr Leu Ser
             20                  25
```

<210> SEQ ID NO 54
<211> LENGTH: 29
<212> TYPE: PRT
<213> ORGANISM: Homo sapiens

<400> SEQUENCE: 54

```
His Gly Thr Cys Ser Cys Gly Arg Cys Val Cys Glu Arg Gly Trp Phe
  1               5                  10                  15

Gly Lys Leu Cys Gln His Pro Arg Lys Cys Asn Met Thr
             20                  25
```

<210> SEQ ID NO 55
<211> LENGTH: 29
<212> TYPE: PRT
<213> ORGANISM: Homo sapiens

<400> SEQUENCE: 55

```
Gly Asn Gly Ile Cys Ser Cys Gly Asn Cys Glu Cys Trp Asp Gly Trp
  1               5                  10                  15

Asn Gly Asn Ala Cys Glu Ile Trp Leu Gly Ser Glu Tyr
             20                  25
```

<210> SEQ ID NO 56
<211> LENGTH: 29
<212> TYPE: PRT
<213> ORGANISM: Homo sapiens

<400> SEQUENCE: 56

```
Gly Asn Gly Ile Cys Ser Cys Gly Asn Cys Glu Cys Trp Asp Gly Trp
  1               5                  10                  15

Asn Gly Asn Ala Cys Glu Ile Trp Leu Gly Ser Glu Tyr
             20                  25
```

<210> SEQ ID NO 57
<211> LENGTH: 29
<212> TYPE: PRT
<213> ORGANISM: Homo sapiens

<400> SEQUENCE: 57

```
Gly Asn Gly Ile Cys Ser Cys Gly Asn Cys Glu Cys Trp Asp Gly Trp
  1               5                  10                  15

Asn Gly Asn Ala Cys Glu Ile Trp Leu Gly Ser Glu Tyr
             20                  25
```

<210> SEQ ID NO 58
<211> LENGTH: 33
<212> TYPE: PRT
<213> ORGANISM: Homo sapiens

<400> SEQUENCE: 58

```
Glu Thr Tyr Asp Gly Ser Thr Cys Ala Gly His Gly Lys Cys Asp Cys
  1               5                  10                  15
```

-continued

```
Gly Lys Cys Lys Cys Asp Gln Gly Trp Tyr Gly Asp Ala Cys Gln Tyr
            20                  25                  30

Pro


<210> SEQ ID NO 59
<211> LENGTH: 34
<212> TYPE: PRT
<213> ORGANISM: Homo sapiens

<400> SEQUENCE: 59

Met Cys Lys Asn Ser Gln Asp Ile Ile Cys Ser Asn Ala Gly Thr Cys
  1               5                  10                  15

His Cys Gly Arg Cys Lys Cys Asp Asn Ser Asp Gly Ser Gly Leu Val
            20                  25                  30

Tyr Gly


<210> SEQ ID NO 60
<211> LENGTH: 31
<212> TYPE: PRT
<213> ORGANISM: Homo sapiens

<400> SEQUENCE: 60

Ile Asp Asp Glu Thr Glu Glu Ile Cys Gly Gly His Gly Lys Cys Tyr
  1               5                  10                  15

Cys Gly Asn Cys Tyr Cys Lys Ala Gly Trp His Gly Asp Lys Cys
            20                  25                  30


<210> SEQ ID NO 61
<211> LENGTH: 34
<212> TYPE: PRT
<213> ORGANISM: Homo sapiens

<400> SEQUENCE: 61

Lys Arg Arg Cys Thr Ser Pro Asp Gly Lys Ile Cys Ser Asn Arg Gly
  1               5                  10                  15

Thr Cys Val Cys Gly Glu Cys Thr Cys His Asp Val Asp Pro Thr Gly
            20                  25                  30

Asp Trp


<210> SEQ ID NO 62
<211> LENGTH: 34
<212> TYPE: PRT
<213> ORGANISM: Homo sapiens

<400> SEQUENCE: 62

Asp Arg Tyr Ser Asp Asp Phe Cys Ser Gly His Gly Gln Cys Asn Cys
  1               5                  10                  15

Gly Arg Cys Asp Cys Lys Ala Gly Trp Tyr Gly Lys Lys Cys Glu His
            20                  25                  30

Pro Gln


<210> SEQ ID NO 63
<211> LENGTH: 33
<212> TYPE: PRT
<213> ORGANISM: Homo sapiens

<400> SEQUENCE: 63

Cys Gln Gly Ser Ser Asp Leu Pro Cys Ser Gly Arg Gly Lys Cys Glu
  1               5                  10                  15
```

-continued

```
Cys Gly Lys Cys Thr Cys Tyr Pro Pro Gly Asp Arg Arg Val Tyr Gly
            20                  25                  30

Lys


<210> SEQ ID NO 64
<211> LENGTH: 31
<212> TYPE: PRT
<213> ORGANISM: Homo sapiens

<400> SEQUENCE: 64

Cys Glu Asp Leu Asp Gly Val Val Cys Gly Gly His Gly Thr Cys Ser
  1               5                  10                  15

Cys Gly Arg Cys Val Cys Glu Arg Gly Trp Phe Gly Lys Leu Cys
            20                  25                  30


<210> SEQ ID NO 65
<211> LENGTH: 32
<212> TYPE: PRT
<213> ORGANISM: Homo sapiens

<400> SEQUENCE: 65

Ser Ala Asp Gly Ile Leu Cys Ser Gly Lys Gly Ser Cys His Cys Gly
  1               5                  10                  15

Lys Cys Ile Cys Ser Ala Glu Glu Trp Tyr Ile Ser Gly Glu Phe Cys
            20                  25                  30


<210> SEQ ID NO 66
<211> LENGTH: 33
<212> TYPE: PRT
<213> ORGANISM: Homo sapiens

<400> SEQUENCE: 66

Cys Asp Lys His Asp Gly Leu Ile Cys Thr Gly Asn Gly Ile Cys Ser
  1               5                  10                  15

Cys Gly Asn Cys Glu Cys Trp Asp Gly Trp Asn Gly Asn Ala Cys Glu
            20                  25                  30

Ile


<210> SEQ ID NO 67
<211> LENGTH: 769
<212> TYPE: PRT
<213> ORGANISM: Homo sapiens

<400> SEQUENCE: 67

Met Cys Gly Ser Ala Leu Ala Phe Phe Thr Ala Ala Phe Val Cys Leu
  1               5                  10                  15

Gln Asn Asp Arg Arg Gly Pro Ala Ser Phe Leu Trp Ala Ala Trp Val
            20                  25                  30

Phe Ser Leu Val Leu Gly Leu Gly Gln Gly Glu Asp Asn Arg Cys Ala
        35                  40                  45

Ser Ser Asn Ala Ala Ser Cys Ala Arg Cys Leu Ala Leu Gly Pro Glu
    50                  55                  60

Cys Gly Trp Cys Val Gln Glu Asp Phe Ile Ser Gly Gly Ser Arg Ser
 65                  70                  75                  80

Glu Arg Cys Asp Ile Val Ser Asn Leu Ile Ser Lys Gly Cys Ser Val
                 85                  90                  95

Asp Ser Ile Glu Tyr Pro Ser Val His Val Ile Ile Pro Thr Glu Asn
            100                 105                 110

Glu Ile Asn Thr Gln Val Thr Pro Gly Glu Val Ser Ile Gln Leu Arg
```

-continued

```
        115                 120                 125

Pro Gly Ala Glu Ala Asn Phe Met Leu Lys Val His Pro Leu Lys Lys
    130                 135                 140

Tyr Pro Val Asp Leu Tyr Tyr Leu Val Asp Val Ser Ala Ser Met His
145                 150                 155                 160

Asn Asn Ile Glu Lys Leu Asn Ser Val Gly Asn Asp Leu Ser Arg Lys
                165                 170                 175

Met Ala Phe Phe Ser Arg Asp Phe Arg Leu Gly Phe Gly Ser Tyr Val
            180                 185                 190

Asp Lys Thr Val Ser Pro Tyr Ile Ser Ile His Pro Glu Arg Ile His
        195                 200                 205

Asn Gln Cys Ser Asp Tyr Asn Leu Asp Cys Met Pro Pro His Gly Tyr
    210                 215                 220

Ile His Val Leu Ser Leu Thr Glu Asn Ile Thr Glu Phe Glu Lys Ala
225                 230                 235                 240

Val His Arg Gln Lys Ile Ser Gly Asn Ile Asp Thr Pro Glu Gly Gly
                245                 250                 255

Phe Asp Ala Met Leu Gln Ala Ala Val Cys Glu Ser His Ile Gly Trp
            260                 265                 270

Arg Lys Glu Ala Lys Arg Leu Leu Leu Val Met Thr Asp Gln Thr Ser
        275                 280                 285

His Leu Ala Leu Asp Ser Lys Leu Ala Gly Ile Val Val Pro Asn Asp
    290                 295                 300

Gly Asn Cys His Leu Lys Asn Asn Val Tyr Val Lys Ser Thr Thr Met
305                 310                 315                 320

Glu His Pro Ser Leu Gly Gln Leu Ser Glu Lys Leu Ile Asp Asn Asn
                325                 330                 335

Ile Asn Val Ile Phe Ala Val Gln Gly Lys Gln Phe His Trp Tyr Lys
            340                 345                 350

Asp Leu Leu Pro Leu Leu Pro Gly Thr Ile Ala Gly Glu Ile Glu Ser
        355                 360                 365

Lys Ala Ala Asn Leu Asn Asn Leu Val Val Glu Ala Tyr Gln Lys Leu
    370                 375                 380

Ile Ser Glu Val Lys Val Gln Val Glu Asn Gln Val Gln Gly Ile Tyr
385                 390                 395                 400

Phe Asn Ile Thr Ala Ile Cys Pro Asp Gly Ser Arg Lys Pro Gly Met
                405                 410                 415

Glu Gly Cys Arg Asn Val Thr Ser Asn Asp Glu Val Leu Phe Asn Val
            420                 425                 430

Thr Val Thr Met Lys Lys Cys Asp Val Thr Gly Gly Lys Asn Tyr Ala
        435                 440                 445

Ile Ile Lys Pro Ile Gly Phe Asn Glu Thr Ala Lys Ile His Ile His
    450                 455                 460

Arg Asn Cys Ser Cys Gln Cys Glu Asp Asn Arg Gly Pro Lys Gly Lys
465                 470                 475                 480

Cys Val Asp Glu Thr Phe Leu Asp Ser Lys Cys Phe Gln Cys Asp Glu
                485                 490                 495

Asn Lys Cys His Phe Asp Glu Asp Gln Phe Ser Ser Glu Ser Cys Lys
            500                 505                 510

Ser His Lys Asp Gln Pro Val Cys Ser Gly Arg Gly Val Cys Val Cys
        515                 520                 525

Gly Lys Cys Ser Cys His Lys Ile Lys Leu Gly Lys Val Tyr Gly Lys
    530                 535                 540
```

-continued

```
Tyr Cys Glu Lys Asp Asp Phe Ser Cys Pro Tyr His His Gly Asn Leu
545                 550                 555                 560

Cys Ala Gly His Gly Glu Cys Glu Ala Gly Arg Cys Gln Cys Phe Ser
                565                 570                 575

Gly Trp Glu Gly Asp Arg Cys Gln Cys Pro Ser Ala Ala Ala Gln His
            580                 585                 590

Cys Val Asn Ser Lys Gly Gln Val Cys Ser Gly Arg Gly Thr Cys Val
        595                 600                 605

Cys Gly Arg Cys Glu Cys Thr Asp Pro Arg Ser Ile Gly Arg Phe Cys
    610                 615                 620

Glu His Cys Pro Thr Cys Tyr Thr Ala Cys Lys Glu Asn Trp Asn Cys
625                 630                 635                 640

Met Gln Cys Leu His Pro His Asn Leu Ser Gln Ala Ile Leu Asp Gln
                645                 650                 655

Cys Lys Thr Ser Cys Ala Leu Met Glu Gln Gln His Tyr Val Asp Gln
            660                 665                 670

Thr Ser Glu Cys Phe Ser Ser Pro Ser Tyr Leu Arg Ile Phe Phe Ile
        675                 680                 685

Ile Phe Ile Val Thr Phe Leu Ile Gly Leu Leu Lys Val Leu Ile Ile
    690                 695                 700

Arg Gln Val Ile Leu Gln Trp Asn Ser Asn Lys Ile Lys Ser Ser Ser
705                 710                 715                 720

Asp Tyr Arg Val Ser Ala Ser Lys Lys Asp Lys Leu Ile Leu Gln Ser
                725                 730                 735

Val Cys Thr Arg Ala Val Thr Tyr Arg Arg Glu Lys Pro Glu Glu Ile
            740                 745                 750

Lys Met Asp Ile Ser Lys Leu Asn Ala His Glu Thr Phe Arg Cys Asn
        755                 760                 765

Phe
```

```
<210> SEQ ID NO 68
<211> LENGTH: 550
<212> TYPE: DNA
<213> ORGANISM: Homo sapiens
<220> FEATURE:
<221> NAME/KEY: SITE
<222> LOCATION: (29)
<223> OTHER INFORMATION: n equals a,t,g, or c
<220> FEATURE:
<221> NAME/KEY: SITE
<222> LOCATION: (445)
<223> OTHER INFORMATION: n equals a,t,g, or c
<220> FEATURE:
<221> NAME/KEY: SITE
<222> LOCATION: (460)
<223> OTHER INFORMATION: n equals a,t,g, or c
<220> FEATURE:
<221> NAME/KEY: SITE
<222> LOCATION: (462)
<223> OTHER INFORMATION: n equals a,t,g, or c
<220> FEATURE:
<221> NAME/KEY: SITE
<222> LOCATION: (477)
<223> OTHER INFORMATION: n equals a,t,g, or c
<220> FEATURE:
<221> NAME/KEY: SITE
<222> LOCATION: (492)
<223> OTHER INFORMATION: n equals a,t,g, or c
<220> FEATURE:
<221> NAME/KEY: SITE
<222> LOCATION: (501)
<223> OTHER INFORMATION: n equals a,t,g, or c
<220> FEATURE:
```

-continued

<221> NAME/KEY: SITE
<222> LOCATION: (513)
<223> OTHER INFORMATION: n equals a,t,g, or c
<220> FEATURE:
<221> NAME/KEY: SITE
<222> LOCATION: (523)
<223> OTHER INFORMATION: n equals a,t,g, or c
<220> FEATURE:
<221> NAME/KEY: SITE
<222> LOCATION: (534)
<223> OTHER INFORMATION: n equals a,t,g, or c

<400> SEQUENCE: 68
ggcacgagtg gaaactgcta ctgcaaggnt ggttggcatg gagataaatg tgaattccag 60
tgcgatatca ccccctggga aagcaagcga agatgcacgt ctccagatgg caaaatctgc 120
aataacagag ggacttgtgt atgtggtgaa tgtacctgtc acgatgttga tccgactggg 180
gactggggag atattcatgg ggacacctgt gaatgtgatg agagggactg tagagctgtc 240
tatgaccgat attctgatga cttctgttca ggtcatggac agtgtaattg cggaagatgt 300
gactgcaaag caggctggtt atgggaagaa gtgtgagcac ccacagtcct gcacgctgtc 360
agctgaggag agcatcagga agtgccaagg aagctcggat ctgccttgct ctgggaaggg 420
taaatgtgaa tgtggcaaat gcacntggta tcctccaggn gntccgccgg gtgtatnggc 480
aaacttgttg anttgtgatg ntcgccgctg tgnaagaccc cgnggtgtgg tctnggaagc 540
cacggcacat 550

<210> SEQ ID NO 69
<211> LENGTH: 495
<212> TYPE: DNA
<213> ORGANISM: Homo sapiens
<220> FEATURE:
<221> NAME/KEY: SITE
<222> LOCATION: (10)
<223> OTHER INFORMATION: n equals a,t,g, or c
<220> FEATURE:
<221> NAME/KEY: SITE
<222> LOCATION: (56)
<223> OTHER INFORMATION: n equals a,t,g, or c
<220> FEATURE:
<221> NAME/KEY: SITE
<222> LOCATION: (69)
<223> OTHER INFORMATION: n equals a,t,g, or c
<220> FEATURE:
<221> NAME/KEY: SITE
<222> LOCATION: (91)
<223> OTHER INFORMATION: n equals a,t,g, or c
<220> FEATURE:
<221> NAME/KEY: SITE
<222> LOCATION: (258)
<223> OTHER INFORMATION: n equals a,t,g, or c
<220> FEATURE:
<221> NAME/KEY: SITE
<222> LOCATION: (302)
<223> OTHER INFORMATION: n equals a,t,g, or c
<220> FEATURE:
<221> NAME/KEY: SITE
<222> LOCATION: (321)
<223> OTHER INFORMATION: n equals a,t,g, or c
<220> FEATURE:
<221> NAME/KEY: SITE
<222> LOCATION: (338)
<223> OTHER INFORMATION: n equals a,t,g, or c
<220> FEATURE:
<221> NAME/KEY: SITE
<222> LOCATION: (349)
<223> OTHER INFORMATION: n equals a,t,g, or c
<220> FEATURE:
<221> NAME/KEY: SITE
<222> LOCATION: (350)
<223> OTHER INFORMATION: n equals a,t,g, or c -continued
<220> FEATURE:
<221> NAME/KEY: SITE
<222> LOCATION: (355)
<223> OTHER INFORMATION: n equals a,t,g, or c
<220> FEATURE:
<221> NAME/KEY: SITE
<222> LOCATION: (359)
<223> OTHER INFORMATION: n equals a,t,g, or c
<220> FEATURE:
<221> NAME/KEY: SITE
<222> LOCATION: (362)
<223> OTHER INFORMATION: n equals a,t,g, or c
<220> FEATURE:
<221> NAME/KEY: SITE
<222> LOCATION: (363)
<223> OTHER INFORMATION: n equals a,t,g, or c
<220> FEATURE:
<221> NAME/KEY: SITE
<222> LOCATION: (369)
<223> OTHER INFORMATION: n equals a,t,g, or c
<220> FEATURE:
<221> NAME/KEY: SITE
<222> LOCATION: (378)
<223> OTHER INFORMATION: n equals a,t,g, or c
<220> FEATURE:
<221> NAME/KEY: SITE
<222> LOCATION: (386)
<223> OTHER INFORMATION: n equals a,t,g, or c
<220> FEATURE:
<221> NAME/KEY: SITE
<222> LOCATION: (387)
<223> OTHER INFORMATION: n equals a,t,g, or c
<220> FEATURE:
<221> NAME/KEY: SITE
<222> LOCATION: (388)
<223> OTHER INFORMATION: n equals a,t,g, or c
<220> FEATURE:
<221> NAME/KEY: SITE
<222> LOCATION: (395)
<223> OTHER INFORMATION: n equals a,t,g, or c
<220> FEATURE:
<221> NAME/KEY: SITE
<222> LOCATION: (401)
<223> OTHER INFORMATION: n equals a,t,g, or c
<220> FEATURE:
<221> NAME/KEY: SITE
<222> LOCATION: (423)
<223> OTHER INFORMATION: n equals a,t,g, or c
<220> FEATURE:
<221> NAME/KEY: SITE
<222> LOCATION: (448)
<223> OTHER INFORMATION: n equals a,t,g, or c
<220> FEATURE:
<221> NAME/KEY: SITE
<222> LOCATION: (468)
<223> OTHER INFORMATION: n equals a,t,g, or c
<220> FEATURE:
<221> NAME/KEY: SITE
<222> LOCATION: (494)
<223> OTHER INFORMATION: n equals a,t,g, or c

<400> SEQUENCE: 69
aattcggcan aggatttttt ctgggccatt agaacatata aatgcggagg aaaccntgta 60
tattcaccnc taggacaggt taaaaagacc nttgtatgtt tttctatttc tgaattacga 120
atgaaatccg agtacctatt agaaatgaag ttatgcaaat ttagatgcaa ataacattag 180
aaaaaaaaga ttcttccata attaacataa gtggttccta acgagagcaa tttttccacc 240
caaaagtcat ttggcaanat ctacagacca tttttgattg tcacactggg gtcgggtagg 300
angtatgctg ccagacattt nggtggggta gagggccngg gatgctgcnn gggcntccnc 360
cnnttgttnc aggccggncc ccccannnaa ggganttttt ncccggcccc aaatggccca 420
ttnggggttc aaacttgggg aacccttngg gttttttttgg gctttttngg aattccccat 480

-continued tttttcccc aggna 495

<210> SEQ ID NO 70
<211> LENGTH: 495
<212> TYPE: DNA
<213> ORGANISM: Homo sapiens
<220> FEATURE:
<221> NAME/KEY: SITE
<222> LOCATION: (10)
<223> OTHER INFORMATION: n equals a,t,g, or c
<220> FEATURE:
<221> NAME/KEY: SITE
<222> LOCATION: (126)
<223> OTHER INFORMATION: n equals a,t,g, or c
<220> FEATURE:
<221> NAME/KEY: SITE
<222> LOCATION: (182)
<223> OTHER INFORMATION: n equals a,t,g, or c
<220> FEATURE:
<221> NAME/KEY: SITE
<222> LOCATION: (192)
<223> OTHER INFORMATION: n equals a,t,g, or c
<220> FEATURE:
<221> NAME/KEY: SITE
<222> LOCATION: (248)
<223> OTHER INFORMATION: n equals a,t,g, or c
<220> FEATURE:
<221> NAME/KEY: SITE
<222> LOCATION: (350)
<223> OTHER INFORMATION: n equals a,t,g, or c
<220> FEATURE:
<221> NAME/KEY: SITE
<222> LOCATION: (370)
<223> OTHER INFORMATION: n equals a,t,g, or c
<220> FEATURE:
<221> NAME/KEY: SITE
<222> LOCATION: (377)
<223> OTHER INFORMATION: n equals a,t,g, or c
<220> FEATURE:
<221> NAME/KEY: SITE
<222> LOCATION: (380)
<223> OTHER INFORMATION: n equals a,t,g, or c
<220> FEATURE:
<221> NAME/KEY: SITE
<222> LOCATION: (389)
<223> OTHER INFORMATION: n equals a,t,g, or c
<220> FEATURE:
<221> NAME/KEY: SITE
<222> LOCATION: (399)
<223> OTHER INFORMATION: n equals a,t,g, or c
<220> FEATURE:
<221> NAME/KEY: SITE
<222> LOCATION: (406)
<223> OTHER INFORMATION: n equals a,t,g, or c
<220> FEATURE:
<221> NAME/KEY: SITE
<222> LOCATION: (408)
<223> OTHER INFORMATION: n equals a,t,g, or c
<220> FEATURE:
<221> NAME/KEY: SITE
<222> LOCATION: (412)
<223> OTHER INFORMATION: n equals a,t,g, or c
<220> FEATURE:
<221> NAME/KEY: SITE
<222> LOCATION: (414)
<223> OTHER INFORMATION: n equals a,t,g, or c
<220> FEATURE:
<221> NAME/KEY: SITE
<222> LOCATION: (424)
<223> OTHER INFORMATION: n equals a,t,g, or c
<220> FEATURE:
<221> NAME/KEY: SITE
<222> LOCATION: (441)
<223> OTHER INFORMATION: n equals a,t,g, or c
<220> FEATURE:
<221> NAME/KEY: SITE
<222> LOCATION: (444)
<223> OTHER INFORMATION: n equals a,t,g, or c -continued
<220> FEATURE:
<221> NAME/KEY: SITE
<222> LOCATION: (445)
<223> OTHER INFORMATION: n equals a,t,g, or c
<220> FEATURE:
<221> NAME/KEY: SITE
<222> LOCATION: (447)
<223> OTHER INFORMATION: n equals a,t,g, or c
<220> FEATURE:
<221> NAME/KEY: SITE
<222> LOCATION: (459)
<223> OTHER INFORMATION: n equals a,t,g, or c
<220> FEATURE:
<221> NAME/KEY: SITE
<222> LOCATION: (464)
<223> OTHER INFORMATION: n equals a,t,g, or c
<220> FEATURE:
<221> NAME/KEY: SITE
<222> LOCATION: (466)
<223> OTHER INFORMATION: n equals a,t,g, or c
<220> FEATURE:
<221> NAME/KEY: SITE
<222> LOCATION: (467)
<223> OTHER INFORMATION: n equals a,t,g, or c
<220> FEATURE:
<221> NAME/KEY: SITE
<222> LOCATION: (468)
<223> OTHER INFORMATION: n equals a,t,g, or c
<220> FEATURE:
<221> NAME/KEY: SITE
<222> LOCATION: (473)
<223> OTHER INFORMATION: n equals a,t,g, or c
<220> FEATURE:
<221> NAME/KEY: SITE
<222> LOCATION: (480)
<223> OTHER INFORMATION: n equals a,t,g, or c
<220> FEATURE:
<221> NAME/KEY: SITE
<222> LOCATION: (483)
<223> OTHER INFORMATION: n equals a,t,g, or c
<220> FEATURE:
<221> NAME/KEY: SITE
<222> LOCATION: (484)
<223> OTHER INFORMATION: n equals a,t,g, or c
<220> FEATURE:
<221> NAME/KEY: SITE
<222> LOCATION: (485)
<223> OTHER INFORMATION: n equals a,t,g, or c
<220> FEATURE:
<221> NAME/KEY: SITE
<222> LOCATION: (488)
<223> OTHER INFORMATION: n equals a,t,g, or c
<220> FEATURE:
<221> NAME/KEY: SITE
<222> LOCATION: (492)
<223> OTHER INFORMATION: n equals a,t,g, or c

<400> SEQUENCE: 70
aattcggcan agccaacatc cgcggaagtg taacatgacg gaagaacaaa gcaagaatct 60
gtgtgaatca gcagatggca tattgtgctc ggggaagggt tcttgtcatt gtgggaagtg 120
catttnttct gctgaggagt ggtatatttc tggggagttc tgtgaactgt gaatgacaga 180
gnactgcgac anacatggat ggtctcattt gtacagggaa tggaatatgt agctgtggga 240
aactgtgnaa tgctggggat ggatgggaat gggaaatgca tgtgaaaatc tgggcttggg 300
ctccagaata tccctttaac catttacatg aggagagggt cttggattcn taattttttc 360
ctgggggccn ttagggnccn tttaaatgnc ggggggaanc ctgttntntt tncnccctgg 420
gggncggttt aaaaagcccc ntgnntnttt ttccctttnc ggantnnngg gtnaaaaccn 480
ggnnnccntt tngaa 495

<210> SEQ ID NO 71

-continued

<211> LENGTH: 495
<212> TYPE: DNA
<213> ORGANISM: Homo sapiens
<220> FEATURE:
<221> NAME/KEY: SITE
<222> LOCATION: (36)
<223> OTHER INFORMATION: n equals a,t,g, or c
<220> FEATURE:
<221> NAME/KEY: SITE
<222> LOCATION: (38)
<223> OTHER INFORMATION: n equals a,t,g, or c
<220> FEATURE:
<221> NAME/KEY: SITE
<222> LOCATION: (53)
<223> OTHER INFORMATION: n equals a,t,g, or c
<220> FEATURE:
<221> NAME/KEY: SITE
<222> LOCATION: (68)
<223> OTHER INFORMATION: n equals a,t,g, or c
<220> FEATURE:
<221> NAME/KEY: SITE
<222> LOCATION: (69)
<223> OTHER INFORMATION: n equals a,t,g, or c
<220> FEATURE:
<221> NAME/KEY: SITE
<222> LOCATION: (81)
<223> OTHER INFORMATION: n equals a,t,g, or c
<220> FEATURE:
<221> NAME/KEY: SITE
<222> LOCATION: (82)
<223> OTHER INFORMATION: n equals a,t,g, or c
<220> FEATURE:
<221> NAME/KEY: SITE
<222> LOCATION: (103)
<223> OTHER INFORMATION: n equals a,t,g, or c
<220> FEATURE:
<221> NAME/KEY: SITE
<222> LOCATION: (105)
<223> OTHER INFORMATION: n equals a,t,g, or c
<220> FEATURE:
<221> NAME/KEY: SITE
<222> LOCATION: (109)
<223> OTHER INFORMATION: n equals a,t,g, or c
<220> FEATURE:
<221> NAME/KEY: SITE
<222> LOCATION: (113)
<223> OTHER INFORMATION: n equals a,t,g, or c
<220> FEATURE:
<221> NAME/KEY: SITE
<222> LOCATION: (123)
<223> OTHER INFORMATION: n equals a,t,g, or c
<220> FEATURE:
<221> NAME/KEY: SITE
<222> LOCATION: (131)
<223> OTHER INFORMATION: n equals a,t,g, or c
<220> FEATURE:
<221> NAME/KEY: SITE
<222> LOCATION: (134)
<223> OTHER INFORMATION: n equals a,t,g, or c
<220> FEATURE:
<221> NAME/KEY: SITE
<222> LOCATION: (158)
<223> OTHER INFORMATION: n equals a,t,g, or c
<220> FEATURE:
<221> NAME/KEY: SITE
<222> LOCATION: (224)
<223> OTHER INFORMATION: n equals a,t,g, or c
<220> FEATURE:
<221> NAME/KEY: SITE
<222> LOCATION: (238)
<223> OTHER INFORMATION: n equals a,t,g, or c
<220> FEATURE:
<221> NAME/KEY: SITE
<222> LOCATION: (243)
<223> OTHER INFORMATION: n equals a,t,g, or c
<220> FEATURE:
<221> NAME/KEY: SITE
<222> LOCATION: (258)
<223> OTHER INFORMATION: n equals a,t,g, or c -continued
<220> FEATURE:
<221> NAME/KEY: SITE
<222> LOCATION: (268)
<223> OTHER INFORMATION: n equals a,t,g, or c
<220> FEATURE:
<221> NAME/KEY: SITE
<222> LOCATION: (313)
<223> OTHER INFORMATION: n equals a,t,g, or c
<220> FEATURE:
<221> NAME/KEY: SITE
<222> LOCATION: (319)
<223> OTHER INFORMATION: n equals a,t,g, or c
<220> FEATURE:
<221> NAME/KEY: SITE
<222> LOCATION: (327)
<223> OTHER INFORMATION: n equals a,t,g, or c
<220> FEATURE:
<221> NAME/KEY: SITE
<222> LOCATION: (338)
<223> OTHER INFORMATION: n equals a,t,g, or c
<220> FEATURE:
<221> NAME/KEY: SITE
<222> LOCATION: (339)
<223> OTHER INFORMATION: n equals a,t,g, or c
<220> FEATURE:
<221> NAME/KEY: SITE
<222> LOCATION: (358)
<223> OTHER INFORMATION: n equals a,t,g, or c
<220> FEATURE:
<221> NAME/KEY: SITE
<222> LOCATION: (365)
<223> OTHER INFORMATION: n equals a,t,g, or c
<220> FEATURE:
<221> NAME/KEY: SITE
<222> LOCATION: (370)
<223> OTHER INFORMATION: n equals a,t,g, or c
<220> FEATURE:
<221> NAME/KEY: SITE
<222> LOCATION: (371)
<223> OTHER INFORMATION: n equals a,t,g, or c
<220> FEATURE:
<221> NAME/KEY: SITE
<222> LOCATION: (374)
<223> OTHER INFORMATION: n equals a,t,g, or c
<220> FEATURE:
<221> NAME/KEY: SITE
<222> LOCATION: (377)
<223> OTHER INFORMATION: n equals a,t,g, or c
<220> FEATURE:
<221> NAME/KEY: SITE
<222> LOCATION: (381)
<223> OTHER INFORMATION: n equals a,t,g, or c
<220> FEATURE:
<221> NAME/KEY: SITE
<222> LOCATION: (386)
<223> OTHER INFORMATION: n equals a,t,g, or c
<220> FEATURE:
<221> NAME/KEY: SITE
<222> LOCATION: (391)
<223> OTHER INFORMATION: n equals a,t,g, or c
<220> FEATURE:
<221> NAME/KEY: SITE
<222> LOCATION: (394)
<223> OTHER INFORMATION: n equals a,t,g, or c
<220> FEATURE:
<221> NAME/KEY: SITE
<222> LOCATION: (400)
<223> OTHER INFORMATION: n equals a,t,g, or c
<220> FEATURE:
<221> NAME/KEY: SITE
<222> LOCATION: (408)
<223> OTHER INFORMATION: n equals a,t,g, or c
<220> FEATURE:
<221> NAME/KEY: SITE
<222> LOCATION: (423)
<223> OTHER INFORMATION: n equals a,t,g, or c
<220> FEATURE:
<221> NAME/KEY: SITE
<222> LOCATION: (428)

-continued

<223> OTHER INFORMATION: n equals a,t,g, or c
<220> FEATURE:
<221> NAME/KEY: SITE
<222> LOCATION: (446)
<223> OTHER INFORMATION: n equals a,t,g, or c
<220> FEATURE:
<221> NAME/KEY: SITE
<222> LOCATION: (456)
<223> OTHER INFORMATION: n equals a,t,g, or c
<220> FEATURE:
<221> NAME/KEY: SITE
<222> LOCATION: (460)
<223> OTHER INFORMATION: n equals a,t,g, or c
<220> FEATURE:
<221> NAME/KEY: SITE
<222> LOCATION: (463)
<223> OTHER INFORMATION: n equals a,t,g, or c
<220> FEATURE:
<221> NAME/KEY: SITE
<222> LOCATION: (472)
<223> OTHER INFORMATION: n equals a,t,g, or c
<220> FEATURE:
<221> NAME/KEY: SITE
<222> LOCATION: (487)
<223> OTHER INFORMATION: n equals a,t,g, or c

<400> SEQUENCE: 71
aattcggcac aggatttttt ctgggccatt agaacntnta aatgcgagga aancttgtat 60
attcaccnnt tggacaggtt nnaaagaccg ttgtatgttt ttntntttnt ganttacgga 120
tgnaaatccg ngtnacctat tagaaatggg ttatgcanat ttagatgcaa ataacattag 180
aaaaaaaaga ttcttccata attaacataa gtggttccta acgngagcaa tttttccncc 240
ctnaagtcat ttggcaantc tacagacnat tttggttgtc acactgggtc gggtaggaag 300
gtatgctggc agncatttng tgggtanagg gccctggnnt gctgttgaag catccccnag 360
tgtancaggn ncgngcncca naccangggg nttnatcccn gccccaantg cccatggggg 420
ttnaaacntg gggaaacgtt ggggtntttt gggctntttn ggnaattccc cntttctttc 480
accaggnaag gcccc 495

<210> SEQ ID NO 72
<211> LENGTH: 317
<212> TYPE: DNA
<213> ORGANISM: Homo sapiens
<220> FEATURE:
<221> NAME/KEY: SITE
<222> LOCATION: (120)
<223> OTHER INFORMATION: n equals a,t,g, or c
<220> FEATURE:
<221> NAME/KEY: SITE
<222> LOCATION: (121)
<223> OTHER INFORMATION: n equals a,t,g, or c
<220> FEATURE:
<221> NAME/KEY: SITE
<222> LOCATION: (185)
<223> OTHER INFORMATION: n equals a,t,g, or c
<220> FEATURE:
<221> NAME/KEY: SITE
<222> LOCATION: (267)
<223> OTHER INFORMATION: n equals a,t,g, or c
<220> FEATURE:
<221> NAME/KEY: SITE
<222> LOCATION: (288)
<223> OTHER INFORMATION: n equals a,t,g, or c
<220> FEATURE:
<221> NAME/KEY: SITE
<222> LOCATION: (295)
<223> OTHER INFORMATION: n equals a,t,g, or c
<220> FEATURE:
<221> NAME/KEY: SITE
<222> LOCATION: (307)
<223> OTHER INFORMATION: n equals a,t,g, or c -continued
<220> FEATURE:
<221> NAME/KEY: SITE
<222> LOCATION: (308)
<223> OTHER INFORMATION: n equals a,t,g, or c

<400> SEQUENCE: 72
ggcacagtca aattttatcg tatttattta ggaatttgtc ttctcattac tcagaagaac 60
atttatatat tcttgatagg aatcctttgg caggccatgg taagtgtgac tgtggcaagn 120
ngcaagtgtg accagggatg gtatggggat gcttgccagt acccaactaa ctgtgacttg 180
acaangaaga aaagtaacca aatgtggcaa gaattcacaa gacatcatct gctctaattc 240
aggtacatgt cactgtggca gtgtaantgt gatagattca gatggaantg ggacntggtg 300
tatgggnnaa tttgtgg 317

<210> SEQ ID NO 73
<211> LENGTH: 36
<212> TYPE: PRT
<213> ORGANISM: Homo sapiens

<400> SEQUENCE: 73

Ile Cys Gly Gly His Gly Lys Cys Tyr Cys Gly Asn Cys Tyr Cys Lys
1 5 10 15

Ala Gly Trp His Gly Asp Lys Cys Glu Phe Gln Cys Asp Ile Thr Pro
20 25 30

Trp Glu Ser Lys
35

<210> SEQ ID NO 74
<211> LENGTH: 35
<212> TYPE: PRT
<213> ORGANISM: Homo sapiens

<400> SEQUENCE: 74

Gly Gln Pro Pro Gly Ala Ala Leu Cys His Gly Arg Gly Arg Cys Asp
1 5 10 15

Cys Gly Val Cys Ile Cys His Val Thr Glu Pro Gly Met Phe Phe Gly
20 25 30

Pro Leu Cys
35

<210> SEQ ID NO 75
<211> LENGTH: 148
<212> TYPE: PRT
<213> ORGANISM: Homo sapiens

<400> SEQUENCE: 75

Met Ala Pro Gly Leu Arg Gly Leu Pro Arg Cys Gly Leu Trp Leu Leu
1 5 10 15

Leu Ala His His Leu Phe Met Val Thr Ala Cys Arg Asp Pro Asp Tyr
20 25 30

Gly Thr Leu Ile Gln Glu Leu Cys Leu Ser Arg Phe Lys Glu Asn Met
35 40 45

Glu Thr Ile Gly Lys Thr Leu Trp Cys Asp Trp Gly Lys Thr Ile Gln
50 55 60

Ser Tyr Gly Glu Leu Thr Tyr Cys Thr Lys His Val Ala His Thr Ile
65 70 75 80

Gly Cys Phe Trp Pro Asn Pro Glu Val Asp Arg Phe Phe Ile Ala Val
85 90 95

-continued

```
His His Arg Tyr Phe Ser Lys Cys Pro Ile Ser Gly Arg Ala Leu Arg
            100                 105                 110

Asp Pro Pro Asn Ser Ile Leu Cys Pro Phe Ile Ala Leu Pro Ile Thr
        115                 120                 125

Val Thr Leu Leu Met Thr Ala Leu Val Val Trp Arg Ser Lys Arg Thr
    130                 135                 140

Glu Gly Ile Val
145
```

<210> SEQ ID NO 76
<211> LENGTH: 502
<212> TYPE: DNA
<213> ORGANISM: Homo sapiens
<220> FEATURE:
<221> NAME/KEY: SITE
<222> LOCATION: (10)
<223> OTHER INFORMATION: n equals a,t,g, or c
<220> FEATURE:
<221> NAME/KEY: SITE
<222> LOCATION: (170)
<223> OTHER INFORMATION: n equals a,t,g, or c
<220> FEATURE:
<221> NAME/KEY: SITE
<222> LOCATION: (209)
<223> OTHER INFORMATION: n equals a,t,g, or c
<220> FEATURE:
<221> NAME/KEY: SITE
<222> LOCATION: (284)
<223> OTHER INFORMATION: n equals a,t,g, or c
<220> FEATURE:
<221> NAME/KEY: SITE
<222> LOCATION: (304)
<223> OTHER INFORMATION: n equals a,t,g, or c
<220> FEATURE:
<221> NAME/KEY: SITE
<222> LOCATION: (338)
<223> OTHER INFORMATION: n equals a,t,g, or c
<220> FEATURE:
<221> NAME/KEY: SITE
<222> LOCATION: (347)
<223> OTHER INFORMATION: n equals a,t,g, or c
<220> FEATURE:
<221> NAME/KEY: SITE
<222> LOCATION: (356)
<223> OTHER INFORMATION: n equals a,t,g, or c
<220> FEATURE:
<221> NAME/KEY: SITE
<222> LOCATION: (367)
<223> OTHER INFORMATION: n equals a,t,g, or c
<220> FEATURE:
<221> NAME/KEY: SITE
<222> LOCATION: (379)
<223> OTHER INFORMATION: n equals a,t,g, or c
<220> FEATURE:
<221> NAME/KEY: SITE
<222> LOCATION: (405)
<223> OTHER INFORMATION: n equals a,t,g, or c
<220> FEATURE:
<221> NAME/KEY: SITE
<222> LOCATION: (415)
<223> OTHER INFORMATION: n equals a,t,g, or c
<220> FEATURE:
<221> NAME/KEY: SITE
<222> LOCATION: (420)
<223> OTHER INFORMATION: n equals a,t,g, or c
<220> FEATURE:
<221> NAME/KEY: SITE
<222> LOCATION: (424)
<223> OTHER INFORMATION: n equals a,t,g, or c
<220> FEATURE:
<221> NAME/KEY: SITE
<222> LOCATION: (448)
<223> OTHER INFORMATION: n equals a,t,g, or c
<220> FEATURE:
<221> NAME/KEY: SITE -continued
<222> LOCATION: (454)
<223> OTHER INFORMATION: n equals a,t,g, or c
<220> FEATURE:
<221> NAME/KEY: SITE
<222> LOCATION: (459)
<223> OTHER INFORMATION: n equals a,t,g, or c
<220> FEATURE:
<221> NAME/KEY: SITE
<222> LOCATION: (465)
<223> OTHER INFORMATION: n equals a,t,g, or c
<220> FEATURE:
<221> NAME/KEY: SITE
<222> LOCATION: (472)
<223> OTHER INFORMATION: n equals a,t,g, or c
<220> FEATURE:
<221> NAME/KEY: SITE
<222> LOCATION: (485)
<223> OTHER INFORMATION: n equals a,t,g, or c
<220> FEATURE:
<221> NAME/KEY: SITE
<222> LOCATION: (487)
<223> OTHER INFORMATION: n equals a,t,g, or c
<220> FEATURE:
<221> NAME/KEY: SITE
<222> LOCATION: (498)
<223> OTHER INFORMATION: n equals a,t,g, or c
<220> FEATURE:
<221> NAME/KEY: SITE
<222> LOCATION: (501)
<223> OTHER INFORMATION: n equals a,t,g, or c

<400> SEQUENCE: 76
aattcggcan agctggtcat gggcagaccc ctcccttcct gggctgacct gctccctcga 60
ggccagcctg ctccctggct gaggctcagg ctatccgccc aagctctttg ctcattctag 120
ggccagtgga ggaaaatgtg ataaggccag agcttgtgtg ctgggcaagn aaatcacctg 180
ctgcatcctg tgctccgcag ctgggccgna gcctctgccc gcagtttcta tgctgtttct 240
tagcacagaa tccagcctag ccttagccgc agtctaggcc ctgnttggga ctaggactcc 300
ttgnttgacc ccatctttgg ttcctgcctg gttcctgnaa cagcccnagt tctggntaaa 360
tccaggnaga aagttaggna agggtttttg gaagaagttc cgtgntttga acttnggagn 420
cttnttggtg ggaagaaaat tggaaagntt gggnaggana aaggngggtt tnggggtttc 480
aaggngnatg gggggttnaa na 502

<210> SEQ ID NO 77
<211> LENGTH: 505
<212> TYPE: DNA
<213> ORGANISM: Homo sapiens
<220> FEATURE:
<221> NAME/KEY: SITE
<222> LOCATION: (11)
<223> OTHER INFORMATION: n equals a,t,g, or c
<220> FEATURE:
<221> NAME/KEY: SITE
<222> LOCATION: (14)
<223> OTHER INFORMATION: n equals a,t,g, or c
<220> FEATURE:
<221> NAME/KEY: SITE
<222> LOCATION: (67)
<223> OTHER INFORMATION: n equals a,t,g, or c
<220> FEATURE:
<221> NAME/KEY: SITE
<222> LOCATION: (208)
<223> OTHER INFORMATION: n equals a,t,g, or c
<220> FEATURE:
<221> NAME/KEY: SITE
<222> LOCATION: (247)
<223> OTHER INFORMATION: n equals a,t,g, or c
<220> FEATURE:
<221> NAME/KEY: SITE
<222> LOCATION: (250)

-continued

<223> OTHER INFORMATION: n equals a,t,g, or c
<220> FEATURE:
<221> NAME/KEY: SITE
<222> LOCATION: (267)
<223> OTHER INFORMATION: n equals a,t,g, or c
<220> FEATURE:
<221> NAME/KEY: SITE
<222> LOCATION: (299)
<223> OTHER INFORMATION: n equals a,t,g, or c
<220> FEATURE:
<221> NAME/KEY: SITE
<222> LOCATION: (320)
<223> OTHER INFORMATION: n equals a,t,g, or c
<220> FEATURE:
<221> NAME/KEY: SITE
<222> LOCATION: (321)
<223> OTHER INFORMATION: n equals a,t,g, or c
<220> FEATURE:
<221> NAME/KEY: SITE
<222> LOCATION: (339)
<223> OTHER INFORMATION: n equals a,t,g, or c
<220> FEATURE:
<221> NAME/KEY: SITE
<222> LOCATION: (349)
<223> OTHER INFORMATION: n equals a,t,g, or c
<220> FEATURE:
<221> NAME/KEY: SITE
<222> LOCATION: (364)
<223> OTHER INFORMATION: n equals a,t,g, or c
<220> FEATURE:
<221> NAME/KEY: SITE
<222> LOCATION: (384)
<223> OTHER INFORMATION: n equals a,t,g, or c
<220> FEATURE:
<221> NAME/KEY: SITE
<222> LOCATION: (386)
<223> OTHER INFORMATION: n equals a,t,g, or c
<220> FEATURE:
<221> NAME/KEY: SITE
<222> LOCATION: (406)
<223> OTHER INFORMATION: n equals a,t,g, or c
<220> FEATURE:
<221> NAME/KEY: SITE
<222> LOCATION: (417)
<223> OTHER INFORMATION: n equals a,t,g, or c
<220> FEATURE:
<221> NAME/KEY: SITE
<222> LOCATION: (424)
<223> OTHER INFORMATION: n equals a,t,g, or c
<220> FEATURE:
<221> NAME/KEY: SITE
<222> LOCATION: (440)
<223> OTHER INFORMATION: n equals a,t,g, or c
<220> FEATURE:
<221> NAME/KEY: SITE
<222> LOCATION: (446)
<223> OTHER INFORMATION: n equals a,t,g, or c
<220> FEATURE:
<221> NAME/KEY: SITE
<222> LOCATION: (448)
<223> OTHER INFORMATION: n equals a,t,g, or c
<220> FEATURE:
<221> NAME/KEY: SITE
<222> LOCATION: (467)
<223> OTHER INFORMATION: n equals a,t,g, or c
<220> FEATURE:
<221> NAME/KEY: SITE
<222> LOCATION: (474)
<223> OTHER INFORMATION: n equals a,t,g, or c
<220> FEATURE:
<221> NAME/KEY: SITE
<222> LOCATION: (484)
<223> OTHER INFORMATION: n equals a,t,g, or c
<220> FEATURE:
<221> NAME/KEY: SITE
<222> LOCATION: (488)
<223> OTHER INFORMATION: n equals a,t,g, or c
<220> FEATURE:
<221> NAME/KEY: SITE -continued
<222> LOCATION: (490)
<223> OTHER INFORMATION: n equals a,t,g, or c
<220> FEATURE:
<221> NAME/KEY: SITE
<222> LOCATION: (497)
<223> OTHER INFORMATION: n equals a,t,g, or c
<220> FEATURE:
<221> NAME/KEY: SITE
<222> LOCATION: (504)
<223> OTHER INFORMATION: n equals a,t,g, or c

<400> SEQUENCE: 77
gaattcggca nagnctgcgg ccggccagcc atggagactg gagcgctgcg acgccgcaac 60
ttctccngtt gctgctgctg ctctgcggtg ggtgtcccag agcaggcggc tgcaacgaga 120
caggcatgtt ggagaggctg cccctgtgtg ggaaaggctt tcgcagacat gatgggcaag 180
gtggacgtct gggaatggtg caactgtncc gagttcatcg tgtactatga gaagtttcac 240
caactgncan cgagatggag gccaatntcg tgggctgctt actggcccaa ccccctggnc 300
ccagggcttt catcaccggn ntccacaggc agttttttnt tccaactgna acgtggacaa 360
ggtncatttg gagggacccc ccanangagg ttttaatccg ttgatngtta ttaccgnggt 420
tttnatttgg gcatggttgn ctggtngntt tggggaaaaa ggaacgnaaa gttnttttag 480
ggtnccgntn aattggnttg ggtna 505

<210> SEQ ID NO 78
<211> LENGTH: 101
<212> TYPE: DNA
<213> ORGANISM: Homo sapiens
<220> FEATURE:
<221> NAME/KEY: SITE
<222> LOCATION: (101)
<223> OTHER INFORMATION: n equals a,t,g, or c

<400> SEQUENCE: 78
aattcggcac gaggtgaggg gccctctgga atggcatccc atgagcttgt ggcctctatc 60
tgctaccatc tgtgttttat ctgagtaaag ttaccttact n 101

<210> SEQ ID NO 79
<211> LENGTH: 322
<212> TYPE: PRT
<213> ORGANISM: Homo sapiens

<400> SEQUENCE: 79

Met Gly Met Leu Ala Arg Val Ala Leu Gly Leu Ile Ile Ile Asp Ala
1 5 10 15

Val Leu Ala Ala Pro Thr Thr Glu Leu Phe Asn Tyr Asp Ser Glu Val
20 25 30

Tyr Asp Ala Ile Leu Glu Asp Thr Gly Thr Phe Tyr Asn Tyr Glu His
35 40 45

Ile Pro Asp Asn His Val Glu Asn Glu Lys Val Ser Glu Arg Leu Ser
50 55 60

Gly Asn Arg Glu Leu Leu Thr Pro Gly Pro Gln Leu Gly Asp Asn Gln
65 70 75 80

Asp Glu Asp Lys Asp Glu Glu Ser Thr Pro Arg Leu Ile Asp Gly Ser
85 90 95

Ser Pro Gln Glu Pro Glu Phe Pro Gly Leu Leu Gly Pro His Thr Asn
100 105 110

Glu Asp Phe Pro Thr Cys Leu Leu Cys Thr Cys Ile Ser Thr Thr Val
115 120 125

-continued

```
Tyr Cys Asp Asp His Glu Leu Asp Ala Ile Pro Pro Leu Pro Lys Lys
    130                 135                 140

Thr Thr Tyr Phe Tyr Ser Arg Phe Asn Arg Ile Lys Lys Ile Asn Lys
145                 150                 155                 160

Asn Asp Phe Ala Ser Leu Asn Asp Leu Lys Arg Ile Asp Leu Thr Ser
                165                 170                 175

Asn Leu Ile Ser Glu Ile Asp Glu Asp Ala Phe Arg Lys Leu Pro His
            180                 185                 190

Leu Gln Glu Leu Val Leu Arg Asp Asn Lys Ile Lys Gln Leu Pro Glu
        195                 200                 205

Leu Pro Asn Thr Leu Thr Phe Ile Asp Ile Ser Asn Asn Arg Leu Gly
    210                 215                 220

Arg Lys Gly Ile Lys Gln Glu Ala Phe Lys Asp Met Tyr Asp Leu His
225                 230                 235                 240

His Leu Tyr Ile Thr Asp Asn Ser Leu Asp His Ile Pro Leu Pro Leu
                245                 250                 255

Pro Glu Ser Leu Arg Ala Leu His Leu Gln Asn Asn Asp Ile Leu Glu
            260                 265                 270

Met His Glu Asp Thr Phe Cys Asn Val Lys Asn Leu Thr Tyr Val Arg
        275                 280                 285

Lys Ala Leu Glu Asp Ile Arg Leu Asp Gly Asn Pro Ile Asn Leu Ser
    290                 295                 300

Arg Thr Pro Gln Ala Tyr Met Cys Leu Pro Arg Leu Pro Ile Gly Ser
305                 310                 315                 320

Phe Ile
```

```
<210> SEQ ID NO 80
<211> LENGTH: 435
<212> TYPE: DNA
<213> ORGANISM: Homo sapiens
<220> FEATURE:
<221> NAME/KEY: SITE
<222> LOCATION: (85)
<223> OTHER INFORMATION: n equals a,t,g, or c
<220> FEATURE:
<221> NAME/KEY: SITE
<222> LOCATION: (248)
<223> OTHER INFORMATION: n equals a,t,g, or c

<400> SEQUENCE: 80

ggcagagcca cctttctgga agctgcaggg ctctccatcc aggatccaga agcattgaag      60

gggaccagcc gctgaaggga ttctnagtcc catctgactc cccatgaggc tcctggcttt     120

cctgagtctg ctggccttgg tgctgcagga gacagggaca gcttctctcc caaggaagga     180

gaggaagagg agagaggagc agatgcccag ggaaggcgat tcctttgaag ttctgcctct     240

gcggaatnat gtcctgaacc cagacaacta tggtgaagtc attgacctga gcaactatga     300

ggagctcaca gattatgggg accaactccc cgaggttaag gtgactagcc tcgctcctgc     360

aaccagcatc agtcccgcca agagcactac ggctccaggg acaacctcgt caaaccccac     420

ggatgaccca gacct                                                      435

<210> SEQ ID NO 81
<211> LENGTH: 449
<212> TYPE: DNA
<213> ORGANISM: Homo sapiens
<220> FEATURE:
<221> NAME/KEY: SITE
<222> LOCATION: (57)
<223> OTHER INFORMATION: n equals a,t,g, or c
```

-continued

<220> FEATURE:
<221> NAME/KEY: SITE
<222> LOCATION: (98)
<223> OTHER INFORMATION: n equals a,t,g, or c
<220> FEATURE:
<221> NAME/KEY: SITE
<222> LOCATION: (391)
<223> OTHER INFORMATION: n equals a,t,g, or c
<220> FEATURE:
<221> NAME/KEY: SITE
<222> LOCATION: (433)
<223> OTHER INFORMATION: n equals a,t,g, or c

<400> SEQUENCE: 81
gacagcctcc accagagtcc ccaccttttt ggaagctgca gggctctcca tccaggntcc 60
agaagcattg aaggggacca gccgctgaag ggattctnag tcccatctga ctccccatga 120
ggctcctggc tttcctgagt ctgctggcct tggtgctgca ggagacaggg acagcttctt 180
tcccaaggaa ggagaggaag aggagagagg agcagatgcc cagggaaggc gattcctttg 240
aagttctgcc tctgcggaat gatgtcctga acccagacaa ctatggtgaa gtcattgacc 300
tgagcaacta tgaggagctc acagattatg gggaccaact ccccgaggtt aaggtgacta 360
gcctcgctcc tgcaaccagc atcagtcccg ncaagagcac tacgggcttc aggggacaac 420
ctcgtcaaac ccnacggtga ccagaccta 449

<210> SEQ ID NO 82
<211> LENGTH: 331
<212> TYPE: DNA
<213> ORGANISM: Homo sapiens
<220> FEATURE:
<221> NAME/KEY: SITE
<222> LOCATION: (29)
<223> OTHER INFORMATION: n equals a,t,g, or c
<220> FEATURE:
<221> NAME/KEY: SITE
<222> LOCATION: (70)
<223> OTHER INFORMATION: n equals a,t,g, or c
<220> FEATURE:
<221> NAME/KEY: SITE
<222> LOCATION: (152)
<223> OTHER INFORMATION: n equals a,t,g, or c

<400> SEQUENCE: 82
ctggaagctg cagggctctc catccaggnt ccagaagcat tgaaggggac cagccgctga 60
agggattctn agtcccatct gactccccat gaggctcctg gctttcctga gtctgctggc 120
cttggtgctg caggagacag ggacagcttc tntcccaagg aaggagagga agaggagaga 180
ggagcagatg cccagggaag gcgattcctt tgaagttctg cctctgcgga atgatgtcct 240
gaacccagac aactatggtg aagtcattga cctgagcaac tatgaggagc tcacagatta 300
tggggaccaa ctccccgagg ttaaggtgac t 331

<210> SEQ ID NO 83
<211> LENGTH: 280
<212> TYPE: DNA
<213> ORGANISM: Homo sapiens
<220> FEATURE:
<221> NAME/KEY: SITE
<222> LOCATION: (19)
<223> OTHER INFORMATION: n equals a,t,g, or c
<220> FEATURE:
<221> NAME/KEY: SITE
<222> LOCATION: (58)
<223> OTHER INFORMATION: n equals a,t,g, or c
<220> FEATURE:
<221> NAME/KEY: SITE
<222> LOCATION: (115)

-continued

<223> OTHER INFORMATION: n equals a,t,g, or c

<400> SEQUENCE: 83
ctggctttcc tgagtctgnt ggccttggtg ctgcaggaga cagggacagc ttcttttnca 60
aggaaggaga ggaagaggag agaggagcag atgcccaggg aaggcgattc ctttnaagtt 120
ctgcctctgc ggaatgatgt cctgaaccca gacaactatg gtgaagtcat tgacctgagc 180
aactatgagg agctcacaga ttatggggac caactccccg aggttaaggt gactagcctc 240
gctcctgcaa ccagcatcag tcccgccaag agcactacgg 280

<210> SEQ ID NO 84
<211> LENGTH: 211
<212> TYPE: DNA
<213> ORGANISM: Homo sapiens
<220> FEATURE:
<221> NAME/KEY: SITE
<222> LOCATION: (93)
<223> OTHER INFORMATION: n equals a,t,g, or c

<400> SEQUENCE: 84
cttggaccag cgggcatcac attctccagc agccgccatc tcacacgcct ccctcctgtg 60
gccgccggca gcatggacaa aggtctccat gcngggggag gaggcctgct tctttcccca 120
cagctctcac gtctcccttc tccctgcggg tgacaaagaa gcccaaggac cacctccttc 180
ctgcctcatt gtaataaaat tccccacact g 211

<210> SEQ ID NO 85
<211> LENGTH: 208
<212> TYPE: DNA
<213> ORGANISM: Homo sapiens
<220> FEATURE:
<221> NAME/KEY: SITE
<222> LOCATION: (56)
<223> OTHER INFORMATION: n equals a,t,g, or c
<220> FEATURE:
<221> NAME/KEY: SITE
<222> LOCATION: (117)
<223> OTHER INFORMATION: n equals a,t,g, or c
<220> FEATURE:
<221> NAME/KEY: SITE
<222> LOCATION: (140)
<223> OTHER INFORMATION: n equals a,t,g, or c

<400> SEQUENCE: 85
ctggatggca accccatcaa cctcagcctc ttccccagcg cctacttctg cctgcntcgg 60
ctccccatcg gccgcttcac gtagctcgga gcccttccac tcctcccagg tcatctnttg 120
gaccagcggg catcacattn tccagcagcc gccatctcac acgcctccct cctgtggccg 180
ccggcagcat ggacaaaggt ctccatgc 208

<210> SEQ ID NO 86
<211> LENGTH: 73
<212> TYPE: DNA
<213> ORGANISM: Homo sapiens

<400> SEQUENCE: 86
cgacccacgc gtccgccgcc ttcggcttcc ccttctgcca agagccctga gccactcaca 60
gcacgaccag aga 73

<210> SEQ ID NO 87
<211> LENGTH: 305
<212> TYPE: DNA
<213> ORGANISM: Homo sapiens -continued

<400> SEQUENCE: 87
gtatggaatg gggtgggaac ccctgcctct cacactgggg agggaccctg gggacagcct 60
atgggctgag cagagagggc tctcagggac ccctgcagca caagaatctc ccaccacggt 120
ctctgtccca gccctgactc agaagcctga tgtctacatc cccgagaccc tggagcccgg 180
gcagccggtg acggtcatct gtgtgtttaa ctgggccttt gaggaatgtc cacccccttc 240
tttctcctgg acgggggctg ccctctcctc ccaaggaacc aaaccaacga cctcccactt 300
ctcag 305

<210> SEQ ID NO 88
<211> LENGTH: 175
<212> TYPE: DNA
<213> ORGANISM: Homo sapiens

<400> SEQUENCE: 88
atcctccaga gaacctgaga gtgatggttt cccaagcaaa caggacaggt aggaaagggg 60
acagaggagc caaggcctct cagtgccgaa ttgggggccc aggagtctgg agggtcccca 120
cgcaggaggg tccctgagcc ctgagctgct catcgattct gcctcttcct tccct 175

<210> SEQ ID NO 89
<211> LENGTH: 72
<212> TYPE: DNA
<213> ORGANISM: Homo sapiens

<400> SEQUENCE: 89
gtgagtgggg gaaaggggac acctgggtcc caggaagggg accctgctga gtcctgtcct 60
ccctcccctc ag 72

<210> SEQ ID NO 90
<211> LENGTH: 421
<212> TYPE: DNA
<213> ORGANISM: Homo sapiens

<400> SEQUENCE: 90
ctggccccct ggctcagaag cggaatcaga aagccacacc aaacagtcct cggacccctc 60
ttccaccagg tgctccctcc ccagaatcaa agaagaacca gaaaaagcag tatcagttgc 120
ccagtttccc agaacccaaa tcatccactc aagccccaga atcccaggag agccaagagg 180
agctccatta tgccacgctc aacttcccag gcgtcagacc caggcctgag gcccggatgc 240
ccaagggcac ccaggcggat tatgcagaag tcaagttcca atgagggtct cttaggcttt 300
aggactggga cttcggctag ggaggaaggt agagtaagag gttgaagata acagagtgca 360
aagtttcctt ctctccctct ctctctctct ttctctctct ctctctcttt ctctctcttt 420
t 421

<210> SEQ ID NO 91
<211> LENGTH: 964
<212> TYPE: DNA
<213> ORGANISM: Homo sapiens

<400> SEQUENCE: 91
aaaaaaacat ctggccaggg cacagtggct cacgcctgta atcccagcac tttgggaggt 60
tgaggtgggc agatcgcctg aggtcgggag ttcgagacca gcctggccaa cttggtgaaa 120
ccccgtctct actaaaaata caaaaattag ctgggcatgg tggcaggcgc ctgtaatcct 180

-continued

```
actacttggg aagctgaggc aggagaatca cttgaacctg ggagacggag gttgcagtga    240

gccaagatca caccattgca cgccagcttg ggcaacaaag cgagactcca tctcaaaaaa    300

aaaatcctcc aaatgggttg ggtgtctgta atcccagcac tttgggaggc taaggtgggt    360

ggattgcttg agcccaggag ttcgagacca gcctgggcaa catggtgaaa ccccatctct    420

acaaaaaata caaaacatag ctgggcttgg tggtgtgtgc ctgtagtccc agctgtcaga    480

catttaaacc agagcaactc ccatctggaa tgggagctga ataaaatgag gctgagacct    540

actgggctgc cattctcaga cagtggaggc cattctaagt cacaggatga gacaggaggt    600

ccgtacaaga tacaggtcat aaagactttg ctgataaaac agattgcagt aaagaagcca    660

accaaatccc accaaaacca agttggccac gagagtgacc tctggtcgtc ctcactgcta    720

cactcctgac agcaccatga cagtttacaa atgccatggc aacatcagga agttacccga    780

tatgtcccaa aagggggagg aatgaataat ccaccccttg tttagcaaat aagcaagaaa    840

taaccataaa agtgggcaac cagcagctct aggcgctgct cttgtctatg gagtagccat    900

tcttttgttc ctttactttc ttaataaact tgctttcacc ttaaaaaaaa aaaaaaaaaa    960

aaaa                                                                 964


<210> SEQ ID NO 92
<211> LENGTH: 364
<212> TYPE: PRT
<213> ORGANISM: Homo sapiens

<400> SEQUENCE: 92

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Gly Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
```

-continued

```
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360


<210> SEQ ID NO 93
<211> LENGTH: 397
<212> TYPE: DNA
<213> ORGANISM: Homo sapiens
<220> FEATURE:
<221> NAME/KEY: SITE
<222> LOCATION: (19)
<223> OTHER INFORMATION: n equals a,t,g, or c
<220> FEATURE:
<221> NAME/KEY: SITE
<222> LOCATION: (68)
<223> OTHER INFORMATION: n equals a,t,g, or c
<220> FEATURE:
<221> NAME/KEY: SITE
<222> LOCATION: (148)
<223> OTHER INFORMATION: n equals a,t,g, or c
<220> FEATURE:
<221> NAME/KEY: SITE
<222> LOCATION: (262)
<223> OTHER INFORMATION: n equals a,t,g, or c
<220> FEATURE:
<221> NAME/KEY: SITE
<222> LOCATION: (323)
<223> OTHER INFORMATION: n equals a,t,g, or c
<220> FEATURE:
<221> NAME/KEY: SITE
<222> LOCATION: (361)
<223> OTHER INFORMATION: n equals a,t,g, or c
<220> FEATURE:
<221> NAME/KEY: SITE
<222> LOCATION: (386)
<223> OTHER INFORMATION: n equals a,t,g, or c
<220> FEATURE:
<221> NAME/KEY: SITE
<222> LOCATION: (388)
<223> OTHER INFORMATION: n equals a,t,g, or c
<220> FEATURE:
<221> NAME/KEY: SITE
<222> LOCATION: (390)
<223> OTHER INFORMATION: n equals a,t,g, or c
<220> FEATURE:
<221> NAME/KEY: SITE
<222> LOCATION: (392)
<223> OTHER INFORMATION: n equals a,t,g, or c
<220> FEATURE:
<221> NAME/KEY: SITE
<222> LOCATION: (394)
<223> OTHER INFORMATION: n equals a,t,g, or c

<400> SEQUENCE: 93

ggcagagtgg ccccctggnt cagaagcgga atcagaaagc cacaccaaac agtcctcgga     60
```

-continued cccctctncc accaggtgct ccctccccag aatcaaagaa gaaccagaaa aagcagtatc 120
agttgcccag tttcccagaa cccaaatnat ccactcaagc cccagaatcc caggagagcc 180
aagaggagct ccattatgcc acgctcaact tcccaggcgt cagacccagg cctgaggccg 240
gtatgcccaa gggcacccag gnggattatg cagaagtcaa gttccaatga gggtctctta 300
ggctttagga ctgggacttc ggntagggag gaaggtagag taagaggttg aagttaacag 360
ntgcaaattt cctttttttc cttttntntn tntnttt 397

<210> SEQ ID NO 94
<211> LENGTH: 276
<212> TYPE: DNA
<213> ORGANISM: Homo sapiens
<220> FEATURE:
<221> NAME/KEY: SITE
<222> LOCATION: (190)
<223> OTHER INFORMATION: n equals a,t,g, or c
<220> FEATURE:
<221> NAME/KEY: SITE
<222> LOCATION: (241)
<223> OTHER INFORMATION: n equals a,t,g, or c
<220> FEATURE:
<221> NAME/KEY: SITE
<222> LOCATION: (262)
<223> OTHER INFORMATION: n equals a,t,g, or c
<220> FEATURE:
<221> NAME/KEY: SITE
<222> LOCATION: (264)
<223> OTHER INFORMATION: n equals a,t,g, or c
<220> FEATURE:
<221> NAME/KEY: SITE
<222> LOCATION: (265)
<223> OTHER INFORMATION: n equals a,t,g, or c

<400> SEQUENCE: 94
gctcctaccc ccgacaagac tggacagggt ctaccccagc ttatggctac tggttcaaag 60
cagtgactga gacaaccaag ggtgctcctg tggccacaaa ccaccagagt cgagaggtgg 120
aaatgagcac ccggggccga ttccagctca ctggggatcc cgccaagggg aactgctcct 180
tggtgatcan aagacgcgca gatgcaggat gagtcacagt acttctttcg ggtggagaga 240
ngaactatgt gagatataat gncnngaacg atgggt 276

<210> SEQ ID NO 95
<211> LENGTH: 469
<212> TYPE: DNA
<213> ORGANISM: Homo sapiens
<220> FEATURE:
<221> NAME/KEY: SITE
<222> LOCATION: (348)
<223> OTHER INFORMATION: n equals a,t,g, or c
<220> FEATURE:
<221> NAME/KEY: SITE
<222> LOCATION: (375)
<223> OTHER INFORMATION: n equals a,t,g, or c
<220> FEATURE:
<221> NAME/KEY: SITE
<222> LOCATION: (430)
<223> OTHER INFORMATION: n equals a,t,g, or c
<220> FEATURE:
<221> NAME/KEY: SITE
<222> LOCATION: (445)
<223> OTHER INFORMATION: n equals a,t,g, or c
<220> FEATURE:
<221> NAME/KEY: SITE
<222> LOCATION: (457)
<223> OTHER INFORMATION: n equals a,t,g, or c
<220> FEATURE:
<221> NAME/KEY: SITE
<222> LOCATION: (469)

-continued

<223> OTHER INFORMATION: n equals a,t,g, or c

<400> SEQUENCE: 95
gcaacgacct cccacttctc agtgctcagc ttcacgccca gaccccagga ccacaacacc 60
gacctcacct gccatgtgga cttctccaga aagggtgtga gcgtacagag gaccgtccga 120
ctccgtgtgg cctatgcccc cagagacctt gttatcagca tttcacgtga caacacgcca 180
gatcctccag agaacctgag agtgatggtt tcccaagcaa acaggacagt cctggaaaac 240
cttgggaacg gcacgtctct cccagtactg gagggccaaa gcctgtgcct ggtctgtgtc 300
acacacagca gccccccagc caggctgagc tggacccaga agggacangt tctgagcccc 360
tcccagccct caganccegg ggtcctggag tgccttcggg ttcaagtgga gcaacgaaag 420
gagagttcan ctggcaaggt tcggnaacca attgggnttc caagaaggn 469

<210> SEQ ID NO 96
<211> LENGTH: 398
<212> TYPE: DNA
<213> ORGANISM: Homo sapiens
<220> FEATURE:
<221> NAME/KEY: SITE
<222> LOCATION: (160)
<223> OTHER INFORMATION: n equals a,t,g, or c
<220> FEATURE:
<221> NAME/KEY: SITE
<222> LOCATION: (189)
<223> OTHER INFORMATION: n equals a,t,g, or c
<220> FEATURE:
<221> NAME/KEY: SITE
<222> LOCATION: (221)
<223> OTHER INFORMATION: n equals a,t,g, or c
<220> FEATURE:
<221> NAME/KEY: SITE
<222> LOCATION: (248)
<223> OTHER INFORMATION: n equals a,t,g, or c
<220> FEATURE:
<221> NAME/KEY: SITE
<222> LOCATION: (285)
<223> OTHER INFORMATION: n equals a,t,g, or c
<220> FEATURE:
<221> NAME/KEY: SITE
<222> LOCATION: (326)
<223> OTHER INFORMATION: n equals a,t,g, or c
<220> FEATURE:
<221> NAME/KEY: SITE
<222> LOCATION: (339)
<223> OTHER INFORMATION: n equals a,t,g, or c
<220> FEATURE:
<221> NAME/KEY: SITE
<222> LOCATION: (344)
<223> OTHER INFORMATION: n equals a,t,g, or c
<220> FEATURE:
<221> NAME/KEY: SITE
<222> LOCATION: (382)
<223> OTHER INFORMATION: n equals a,t,g, or c
<220> FEATURE:
<221> NAME/KEY: SITE
<222> LOCATION: (392)
<223> OTHER INFORMATION: n equals a,t,g, or c

<400> SEQUENCE: 96
acggagcgtt tctgggaatc ggcatcacgg ctcttctttt cctctgcctg gccctgatca 60
tcatgaagat tctaccgaag agacggactc agacagaaac cccgtaggcc caggttctcc 120
cggcacagca cgatcctgga ttacatcaat gtggtcccgn acggactggc cccctggctc 180
agaagcggna atcagtaaag ccacaccaaa cagtcctcgg nacccctctt gccaccaggt 240
gctccctncc ccaggaatgc aaagaagaac cagaaaaagg cagtnatgca gttgcccagt 300
ttgcccagaa cccaaatcat tccatncaag ccccagaanc ccangagagc caagaggagt 360

-continued tccattaagg ccaggttcaa antttcccag gngttcga 398

<210> SEQ ID NO 97
<211> LENGTH: 256
<212> TYPE: DNA
<213> ORGANISM: Homo sapiens
<220> FEATURE:
<221> NAME/KEY: SITE
<222> LOCATION: (18)
<223> OTHER INFORMATION: n equals a,t,g, or c
<220> FEATURE:
<221> NAME/KEY: SITE
<222> LOCATION: (40)
<223> OTHER INFORMATION: n equals a,t,g, or c
<220> FEATURE:
<221> NAME/KEY: SITE
<222> LOCATION: (52)
<223> OTHER INFORMATION: n equals a,t,g, or c
<220> FEATURE:
<221> NAME/KEY: SITE
<222> LOCATION: (68)
<223> OTHER INFORMATION: n equals a,t,g, or c
<220> FEATURE:
<221> NAME/KEY: SITE
<222> LOCATION: (73)
<223> OTHER INFORMATION: n equals a,t,g, or c
<220> FEATURE:
<221> NAME/KEY: SITE
<222> LOCATION: (85)
<223> OTHER INFORMATION: n equals a,t,g, or c
<220> FEATURE:
<221> NAME/KEY: SITE
<222> LOCATION: (91)
<223> OTHER INFORMATION: n equals a,t,g, or c
<220> FEATURE:
<221> NAME/KEY: SITE
<222> LOCATION: (126)
<223> OTHER INFORMATION: n equals a,t,g, or c
<220> FEATURE:
<221> NAME/KEY: SITE
<222> LOCATION: (127)
<223> OTHER INFORMATION: n equals a,t,g, or c
<220> FEATURE:
<221> NAME/KEY: SITE
<222> LOCATION: (162)
<223> OTHER INFORMATION: n equals a,t,g, or c
<220> FEATURE:
<221> NAME/KEY: SITE
<222> LOCATION: (164)
<223> OTHER INFORMATION: n equals a,t,g, or c
<220> FEATURE:
<221> NAME/KEY: SITE
<222> LOCATION: (184)
<223> OTHER INFORMATION: n equals a,t,g, or c
<220> FEATURE:
<221> NAME/KEY: SITE
<222> LOCATION: (251)
<223> OTHER INFORMATION: n equals a,t,g, or c
<220> FEATURE:
<221> NAME/KEY: SITE
<222> LOCATION: (256)
<223> OTHER INFORMATION: n equals a,t,g, or c

<400> SEQUENCE: 97
tcgacccacg catccgcngc cttcagcttc cccttctgcn aagagccctg anccactcac 60
agcacganca ganaacaggc ctgtntcaag naggccctgc gcctcctatg cggagatgct 120
actgcnnctg ctgctgtcct cgctgctggg cgggtcccag gntntggatg ggagattctg 180
gatncgagtg caggagtcag tgatggtgcc ggaaggcctg tgcatctctg tgccctgctc 240
tttctcctac ncccgn 256

<210> SEQ ID NO 98
<211> LENGTH: 299

-continued

<212> TYPE: DNA
<213> ORGANISM: Homo sapiens
<220> FEATURE:
<221> NAME/KEY: SITE
<222> LOCATION: (239)
<223> OTHER INFORMATION: n equals a,t,g, or c
<220> FEATURE:
<221> NAME/KEY: SITE
<222> LOCATION: (264)
<223> OTHER INFORMATION: n equals a,t,g, or c

<400> SEQUENCE: 98

```
ccaacagctc cctgagcctc catggagggc tcagctccgg cctcaggctc cgctgtaagg     60

cctggaacgt ccacggggcc cagagtggct ctgtcttcca gctgctacca gggtgaagat    120

ctgcaggaag gaagctcgca agagggcagc agctgagcag gacgtgccct ccaccctggg    180

acccatctcc cagggtcacc agcatgaatg ctcggcaggc agctcccaag accacccgnc    240

cccaggtgca gccacctaca cccngggaa gggggaagag caggagctcc actatgcct     299
```

<210> SEQ ID NO 99
<211> LENGTH: 442
<212> TYPE: PRT
<213> ORGANISM: Homo sapiens

<400> SEQUENCE: 99

```
Met Leu Pro Leu Leu Leu Pro Leu Leu Trp Ala Gly Ala Leu Ala Gln
  1               5                  10                  15

Glu Arg Arg Phe Gln Leu Glu Gly Pro Glu Ser Leu Thr Val Gln Glu
             20                  25                  30

Gly Leu Cys Val Leu Val Pro Cys Arg Leu Pro Thr Thr Leu Pro Ala
         35                  40                  45

Ser Tyr Tyr Gly Tyr Gly Tyr Trp Phe Leu Glu Gly Ala Asp Val Pro
     50                  55                  60

Val Ala Thr Asn Asp Pro Asp Glu Glu Val Gln Glu Glu Thr Arg Gly
 65                  70                  75                  80

Arg Phe His Leu Leu Trp Asp Pro Arg Arg Lys Asn Cys Ser Leu Ser
                 85                  90                  95

Ile Arg Asp Ala Arg Arg Arg Asp Asn Ala Ala Tyr Phe Phe Arg Leu
            100                 105                 110

Lys Ser Lys Trp Met Lys Tyr Gly Tyr Thr Ser Ser Lys Leu Ser Val
        115                 120                 125

Arg Val Met Ala Leu Thr His Arg Pro Asn Ile Ser Ile Pro Gly Thr
    130                 135                 140

Leu Glu Ser Gly His Pro Ser Asn Leu Thr Cys Ser Val Pro Trp Val
145                 150                 155                 160

Cys Glu Gln Gly Thr Pro Pro Ile Phe Ser Trp Met Ser Ala Ala Pro
                165                 170                 175

Thr Ser Leu Gly Pro Arg Thr Thr Gln Ser Ser Val Leu Thr Ile Thr
            180                 185                 190

Pro Arg Pro Gln Asp His Ser Thr Asn Leu Thr Cys Gln Val Thr Phe
        195                 200                 205

Pro Gly Ala Gly Val Thr Met Glu Arg Thr Ile Gln Leu Asn Val Ser
    210                 215                 220

Tyr Ala Pro Gln Lys Val Ala Ile Ser Ile Phe Gln Gly Asn Ser Ala
225                 230                 235                 240

Ala Phe Lys Ile Leu Gln Asn Thr Ser Ser Leu Pro Val Leu Glu Gly
                245                 250                 255
```

-continued

```
Gln Ala Leu Arg Leu Leu Cys Asp Ala Asp Gly Asn Pro Pro Ala His
            260                 265                 270

Leu Ser Trp Phe Gln Gly Phe Pro Ala Leu Asn Ala Thr Pro Ile Ser
        275                 280                 285

Asn Thr Gly Val Leu Glu Leu Pro Gln Val Gly Ser Ala Glu Glu Gly
    290                 295                 300

Asp Phe Thr Cys Arg Ala Gln His Pro Leu Gly Ser Leu Gln Ile Ser
305                 310                 315                 320

Leu Ser Leu Phe Val His Trp Lys Pro Glu Gly Arg Ala Gly Gly Val
                325                 330                 335

Leu Gly Ala Val Trp Gly Ala Ser Ile Thr Thr Leu Val Phe Leu Cys
            340                 345                 350

Val Cys Phe Ile Phe Arg Val Lys Thr Arg Arg Lys Lys Ala Ala Gln
        355                 360                 365

Pro Val Gln Asn Thr Asp Asp Val Asn Pro Val Met Val Ser Gly Ser
    370                 375                 380

Arg Gly His Gln His Gln Phe Gln Thr Gly Ile Val Ser Asp His Pro
385                 390                 395                 400

Ala Glu Ala Gly Pro Ile Ser Glu Asp Glu Gln Glu Leu His Tyr Ala
                405                 410                 415

Val Leu His Phe His Lys Val Gln Pro Gln Glu Pro Lys Val Thr Asp
            420                 425                 430

Thr Glu Tyr Ser Glu Ile Lys Ile His Lys
        435                 440
```

<210> SEQ ID NO 100
<211> LENGTH: 258
<212> TYPE: DNA
<213> ORGANISM: Homo sapiens
<220> FEATURE:
<221> NAME/KEY: SITE
<222> LOCATION: (111)
<223> OTHER INFORMATION: n equals a,t,g, or c
<220> FEATURE:
<221> NAME/KEY: SITE
<222> LOCATION: (193)
<223> OTHER INFORMATION: n equals a,t,g, or c
<220> FEATURE:
<221> NAME/KEY: SITE
<222> LOCATION: (196)
<223> OTHER INFORMATION: n equals a,t,g, or c
<220> FEATURE:
<221> NAME/KEY: SITE
<222> LOCATION: (230)
<223> OTHER INFORMATION: n equals a,t,g, or c

<400> SEQUENCE: 100

```
aaactcggga ccgattccac ctccttgggg acccacagac caaaaattgc accctgagca     60

tcagagatcc agaatgagtg atgcggggag atacttcttt cgtatggaga naggaaatat    120

aaaatggaat tataaatatg accagctctc tgtgaacgtg acagaccctc ctcagaactt    180

gactgtgact gtnttncaag gagaaggcac agcatccaca gctctggggn acagctcatc    240

tctttcagtc ctagaggg                                                  258
```

<210> SEQ ID NO 101
<211> LENGTH: 139
<212> TYPE: DNA
<213> ORGANISM: Homo sapiens
<220> FEATURE:
<221> NAME/KEY: SITE
<222> LOCATION: (21)
<223> OTHER INFORMATION: n equals a,t,g, or c -continued
<220> FEATURE:
<221> NAME/KEY: SITE
<222> LOCATION: (26)
<223> OTHER INFORMATION: n equals a,t,g, or c
<220> FEATURE:
<221> NAME/KEY: SITE
<222> LOCATION: (34)
<223> OTHER INFORMATION: n equals a,t,g, or c
<220> FEATURE:
<221> NAME/KEY: SITE
<222> LOCATION: (37)
<223> OTHER INFORMATION: n equals a,t,g, or c
<220> FEATURE:
<221> NAME/KEY: SITE
<222> LOCATION: (92)
<223> OTHER INFORMATION: n equals a,t,g, or c
<220> FEATURE:
<221> NAME/KEY: SITE
<222> LOCATION: (110)
<223> OTHER INFORMATION: n equals a,t,g, or c
<220> FEATURE:
<221> NAME/KEY: SITE
<222> LOCATION: (123)
<223> OTHER INFORMATION: n equals a,t,g, or c
<220> FEATURE:
<221> NAME/KEY: SITE
<222> LOCATION: (131)
<223> OTHER INFORMATION: n equals a,t,g, or c
<220> FEATURE:
<221> NAME/KEY: SITE
<222> LOCATION: (133)
<223> OTHER INFORMATION: n equals a,t,g, or c

<400> SEQUENCE: 101
ctcgctgacg atgcagagtt ncgtgnccgt gcanganggc atgtgtgtcc atgtgcgctg 60
ctccttctcc tacccagtgg acgccagact gnatctgcac acgttctggn tatggttcgg 120
gcnggaatga ntnagctgg 139

<210> SEQ ID NO 102
<211> LENGTH: 33
<212> TYPE: PRT
<213> ORGANISM: Homo sapiens

<400> SEQUENCE: 102

Thr Asn Gly Tyr Gln Lys Thr Gly Asp Val Tyr Lys Cys Pro Val Ile
1 5 10 15

His Gly Asn Cys Thr Lys Leu Asn Leu Gly Arg Val Thr Leu Ser Asn
20 25 30

Val

<210> SEQ ID NO 103
<211> LENGTH: 1151
<212> TYPE: PRT
<213> ORGANISM: Homo sapiens

<400> SEQUENCE: 103

Phe Asn Val Asp Val Lys Asn Ser Met Thr Phe Ser Gly Pro Val Glu
1 5 10 15

Asp Met Phe Gly Tyr Thr Val Gln Gln Tyr Glu Asn Glu Glu Gly Lys
20 25 30

Trp Val Leu Ile Gly Ser Pro Leu Val Gly Gln Pro Lys Asn Arg Thr
35 40 45

Gly Asp Val Tyr Lys Cys Pro Val Gly Arg Gly Glu Ser Leu Pro Cys
50 55 60

Val Lys Leu Asp Leu Pro Val Asn Thr Ser Ile Pro Asn Val Thr Glu
65 70 75 80

-continued

```
Val Lys Glu Asn Met Thr Phe Gly Ser Thr Leu Val Thr Asn Pro Asn
                85                  90                  95

Gly Gly Phe Leu Ala Cys Gly Pro Leu Tyr Ala Tyr Arg Cys Gly His
            100                 105                 110

Leu His Tyr Thr Thr Gly Ile Cys Ser Asp Val Ser Pro Thr Phe Gln
        115                 120                 125

Val Val Asn Ser Ile Ala Pro Val Gln Glu Cys Ser Thr Gln Leu Asp
    130                 135                 140

Ile Val Ile Val Leu Asp Gly Ser Asn Ser Ile Tyr Pro Trp Asp Ser
145                 150                 155                 160

Val Thr Ala Phe Leu Asn Asp Leu Leu Lys Arg Met Asp Ile Gly Pro
                165                 170                 175

Lys Gln Thr Gln Val Gly Ile Val Gln Tyr Gly Glu Asn Val Thr His
            180                 185                 190

Glu Phe Asn Leu Asn Lys Tyr Ser Ser Thr Glu Glu Val Leu Val Ala
        195                 200                 205

Ala Lys Lys Ile Val Gln Arg Gly Gly Arg Gln Thr Met Thr Ala Leu
    210                 215                 220

Gly Thr Asp Thr Ala Arg Lys Glu Ala Phe Thr Glu Ala Arg Gly Ala
225                 230                 235                 240

Arg Arg Gly Val Lys Lys Val Met Val Ile Val Thr Asp Gly Glu Ser
                245                 250                 255

His Asp Asn His Arg Leu Lys Lys Val Ile Gln Asp Cys Glu Asp Glu
            260                 265                 270

Asn Ile Gln Arg Phe Ser Ile Ala Ile Leu Gly Ser Tyr Asn Arg Gly
        275                 280                 285

Asn Leu Ser Thr Glu Lys Phe Val Glu Glu Ile Lys Ser Ile Ala Ser
    290                 295                 300

Glu Pro Thr Glu Lys His Phe Phe Asn Val Ser Asp Glu Leu Ala Leu
305                 310                 315                 320

Val Thr Ile Val Lys Thr Leu Gly Glu Arg Ile Phe Ala Leu Glu Ala
                325                 330                 335

Thr Ala Asp Gln Ser Ala Ala Ser Phe Glu Met Glu Met Ser Gln Thr
            340                 345                 350

Gly Phe Ser Ala His Tyr Ser Gln Asp Trp Val Met Leu Gly Ala Val
        355                 360                 365

Gly Ala Tyr Asp Trp Asn Gly Thr Val Val Met Gln Lys Ala Ser Gln
    370                 375                 380

Ile Ile Ile Pro Arg Asn Thr Thr Phe Asn Val Glu Ser Thr Lys Lys
385                 390                 395                 400

Asn Glu Pro Leu Ala Ser Tyr Leu Gly Tyr Thr Val Asn Ser Ala Thr
                405                 410                 415

Ala Ser Ser Gly Asp Val Leu Tyr Ile Ala Gly Gln Pro Arg Tyr Asn
            420                 425                 430

His Thr Gly Gln Val Ile Ile Tyr Arg Met Glu Asp Gly Asn Ile Lys
        435                 440                 445

Ile Leu Gln Thr Leu Ser Gly Glu Gln Ile Gly Ser Tyr Phe Gly Ser
    450                 455                 460

Ile Leu Thr Thr Thr Asp Ile Asp Lys Asp Ser Asn Thr Asp Ile Leu
465                 470                 475                 480

Leu Val Gly Ala Pro Met Tyr Met Gly Thr Glu Lys Glu Glu Gln Gly
                485                 490                 495
```

-continued

```
Lys Val Tyr Val Tyr Ala Leu Asn Gln Thr Arg Phe Glu Tyr Gln Met
            500                 505                 510

Ser Leu Glu Pro Ile Lys Gln Thr Cys Cys Ser Ser Arg Gln His Asn
        515                 520                 525

Ser Cys Thr Thr Glu Asn Lys Asn Glu Pro Cys Gly Ala Arg Phe Gly
    530                 535                 540

Thr Ala Ile Ala Ala Val Lys Asp Leu Asn Leu Asp Gly Phe Asn Asp
545                 550                 555                 560

Ile Val Ile Gly Ala Pro Leu Glu Asp Asp His Gly Gly Ala Val Tyr
                565                 570                 575

Ile Tyr His Gly Ser Gly Lys Thr Ile Arg Lys Glu Tyr Ala Gln Arg
            580                 585                 590

Ile Pro Ser Gly Gly Asp Gly Lys Thr Leu Lys Phe Phe Gly Gln Ser
        595                 600                 605

Ile His Gly Glu Met Asp Leu Asn Gly Asp Gly Leu Thr Asp Val Thr
    610                 615                 620

Ile Gly Gly Leu Gly Gly Ala Ala Leu Phe Trp Ser Arg Asp Val Ala
625                 630                 635                 640

Val Val Lys Val Thr Met Asn Phe Glu Pro Asn Lys Val Asn Ile Gln
                645                 650                 655

Lys Lys Asn Cys His Met Glu Gly Lys Glu Thr Val Cys Ile Asn Ala
            660                 665                 670

Thr Val Cys Phe Glu Val Lys Leu Lys Ser Lys Glu Asp Thr Ile Tyr
        675                 680                 685

Glu Ala Asp Leu Gln Tyr Arg Val Thr Leu Asp Ser Leu Arg Gln Ile
    690                 695                 700

Ser Arg Ser Phe Phe Ser Gly Thr Gln Glu Arg Lys Val Gln Arg Asn
705                 710                 715                 720

Ile Thr Val Arg Lys Ser Glu Cys Thr Lys His Ser Phe Tyr Met Leu
                725                 730                 735

Asp Lys His Asp Phe Gln Asp Ser Val Arg Ile Thr Leu Asp Phe Asn
            740                 745                 750

Leu Thr Asp Pro Glu Asn Gly Pro Val Leu Asp Asp Ser Leu Pro Asn
        755                 760                 765

Ser Val His Glu Tyr Ile Pro Phe Ala Lys Asp Cys Gly Asn Lys Glu
    770                 775                 780

Lys Cys Ile Ser Asp Leu Ser Leu His Val Ala Thr Thr Glu Lys Asp
785                 790                 795                 800

Leu Leu Ile Val Arg Ser Gln Asn Asp Lys Phe Asn Val Ser Leu Thr
                805                 810                 815

Val Lys Asn Thr Lys Asp Ser Ala Tyr Asn Thr Arg Thr Ile Val His
            820                 825                 830

Tyr Ser Pro Asn Leu Val Phe Ser Gly Ile Glu Ala Ile Gln Lys Asp
        835                 840                 845

Ser Cys Glu Ser Asn His Asn Ile Thr Cys Lys Val Gly Tyr Pro Phe
    850                 855                 860

Leu Arg Arg Gly Glu Met Val Thr Phe Lys Ile Leu Phe Gln Phe Asn
865                 870                 875                 880

Thr Ser Tyr Leu Met Glu Asn Val Thr Ile Tyr Leu Ser Ala Thr Ser
                885                 890                 895

Asp Ser Glu Glu Pro Pro Glu Thr Leu Ser Asp Asn Val Val Asn Ile
            900                 905                 910

Ser Ile Pro Val Lys Tyr Glu Val Gly Leu Gln Phe Tyr Ser Ser Ala
```

-continued

```
        915                 920                 925

Ser Glu Tyr His Ile Ser Ile Ala Ala Asn Glu Thr Val Pro Glu Val
    930                 935                 940

Ile Asn Ser Thr Glu Asp Ile Gly Asn Glu Ile Asn Ile Phe Tyr Leu
945                 950                 955                 960

Ile Arg Lys Ser Gly Ser Phe Pro Met Pro Glu Leu Lys Leu Ser Ile
                965                 970                 975

Ser Phe Pro Asn Met Thr Ser Asn Gly Tyr Pro Val Leu Tyr Pro Thr
            980                 985                 990

Gly Leu Ser Ser Ser Glu Asn Ala  Asn Cys Arg Pro His  Ile Phe Glu
        995                 1000                 1005

Asp Pro  Phe Ser Ile Asn Ser  Gly Lys Lys Met Thr  Thr Ser Thr Asp
    1010                 1015                 1020

His  Leu Lys Arg Gly Thr  Ile Leu Asp Cys Asn  Thr Cys Lys Phe Ala
1025                 1030                 1035                 1040

Thr Ile Thr Cys Asn  Leu Thr Ser Ser Asp  Ile Ser Gln Val Asn  Val
                1045                 1050                 1055

Ser Leu Ile Leu  Trp Lys Pro Thr Phe  Ile Lys Ser Tyr Phe  Ser Ser
            1060                 1065                 1070

Leu Asn Leu  Thr Ile Arg Gly Glu  Leu Arg Ser Glu Asn  Ala Ser Leu
        1075                 1080                 1085

Val Leu  Ser Ser Ser Asn Gln  Lys Arg Glu Leu Ala  Ile Gln Ile Ser
    1090                 1095                 1100

Lys  Asp Gly Leu Pro Gly  Arg Val Pro Leu Trp  Val Ile Leu Leu Ser
1105                 1110                 1115                 1120

Ala Phe Ala Gly Leu  Leu Leu Leu Met Leu  Leu Ile Leu Ala Leu  Trp
                1125                 1130                 1135

Lys Ile Gly Phe  Phe Lys Arg Pro Leu  Lys Lys Lys Met Glu  Lys
            1140                 1145                 1150
```

<210> SEQ ID NO 104
<211> LENGTH: 389
<212> TYPE: DNA
<213> ORGANISM: Homo sapiens
<220> FEATURE:
<221> NAME/KEY: SITE
<222> LOCATION: (256)
<223> OTHER INFORMATION: n equals a,t,g, or c
<220> FEATURE:
<221> NAME/KEY: SITE
<222> LOCATION: (279)
<223> OTHER INFORMATION: n equals a,t,g, or c
<220> FEATURE:
<221> NAME/KEY: SITE
<222> LOCATION: (302)
<223> OTHER INFORMATION: n equals a,t,g, or c
<220> FEATURE:
<221> NAME/KEY: SITE
<222> LOCATION: (310)
<223> OTHER INFORMATION: n equals a,t,g, or c
<220> FEATURE:
<221> NAME/KEY: SITE
<222> LOCATION: (347)
<223> OTHER INFORMATION: n equals a,t,g, or c
<220> FEATURE:
<221> NAME/KEY: SITE
<222> LOCATION: (349)
<223> OTHER INFORMATION: n equals a,t,g, or c
<220> FEATURE:
<221> NAME/KEY: SITE
<222> LOCATION: (382)
<223> OTHER INFORMATION: n equals a,t,g, or c

<400> SEQUENCE: 104

-continued

```
gcctccagta ttttggctgc agcatccacg ggcaattggt acctcaatga gggatgggct     60

catcgacctg gcagtgggag cccttggcaa cgctgtgatt ctgtggtccc gcccagtggt    120

tcagatcaat gccagcctcc actttgagcc atccaagatc aacatcttcc acagagactg    180

caagcgcagt ggcagggatg ccacctgcct ggccgccttc ctctgcttca cgcccatctt    240

cctggcaccc catttncaaa caacaactgt tggcatcana tacaacgcca ccatgggatg    300

anaggcggtn tacaccgagg gcccacctgg acaaggcggg gaccgantna caacagaacc    360

gtactggttt tcttcggcca gnaacttgt                                      389
```

<210> SEQ ID NO 105
<211> LENGTH: 491
<212> TYPE: DNA
<213> ORGANISM: Homo sapiens
<220> FEATURE:
<221> NAME/KEY: SITE
<222> LOCATION: (11)
<223> OTHER INFORMATION: n equals a,t,g, or c
<220> FEATURE:
<221> NAME/KEY: SITE
<222> LOCATION: (212)
<223> OTHER INFORMATION: n equals a,t,g, or c
<220> FEATURE:
<221> NAME/KEY: SITE
<222> LOCATION: (268)
<223> OTHER INFORMATION: n equals a,t,g, or c
<220> FEATURE:
<221> NAME/KEY: SITE
<222> LOCATION: (274)
<223> OTHER INFORMATION: n equals a,t,g, or c
<220> FEATURE:
<221> NAME/KEY: SITE
<222> LOCATION: (290)
<223> OTHER INFORMATION: n equals a,t,g, or c
<220> FEATURE:
<221> NAME/KEY: SITE
<222> LOCATION: (297)
<223> OTHER INFORMATION: n equals a,t,g, or c
<220> FEATURE:
<221> NAME/KEY: SITE
<222> LOCATION: (317)
<223> OTHER INFORMATION: n equals a,t,g, or c
<220> FEATURE:
<221> NAME/KEY: SITE
<222> LOCATION: (355)
<223> OTHER INFORMATION: n equals a,t,g, or c
<220> FEATURE:
<221> NAME/KEY: SITE
<222> LOCATION: (381)
<223> OTHER INFORMATION: n equals a,t,g, or c
<220> FEATURE:
<221> NAME/KEY: SITE
<222> LOCATION: (384)
<223> OTHER INFORMATION: n equals a,t,g, or c
<220> FEATURE:
<221> NAME/KEY: SITE
<222> LOCATION: (398)
<223> OTHER INFORMATION: n equals a,t,g, or c
<220> FEATURE:
<221> NAME/KEY: SITE
<222> LOCATION: (400)
<223> OTHER INFORMATION: n equals a,t,g, or c
<220> FEATURE:
<221> NAME/KEY: SITE
<222> LOCATION: (404)
<223> OTHER INFORMATION: n equals a,t,g, or c
<220> FEATURE:
<221> NAME/KEY: SITE
<222> LOCATION: (405)
<223> OTHER INFORMATION: n equals a,t,g, or c
<220> FEATURE:
<221> NAME/KEY: SITE
<222> LOCATION: (407)

-continued

<223> OTHER INFORMATION: n equals a,t,g, or c
<220> FEATURE:
<221> NAME/KEY: SITE
<222> LOCATION: (413)
<223> OTHER INFORMATION: n equals a,t,g, or c
<220> FEATURE:
<221> NAME/KEY: SITE
<222> LOCATION: (414)
<223> OTHER INFORMATION: n equals a,t,g, or c
<220> FEATURE:
<221> NAME/KEY: SITE
<222> LOCATION: (415)
<223> OTHER INFORMATION: n equals a,t,g, or c
<220> FEATURE:
<221> NAME/KEY: SITE
<222> LOCATION: (434)
<223> OTHER INFORMATION: n equals a,t,g, or c
<220> FEATURE:
<221> NAME/KEY: SITE
<222> LOCATION: (438)
<223> OTHER INFORMATION: n equals a,t,g, or c
<220> FEATURE:
<221> NAME/KEY: SITE
<222> LOCATION: (443)
<223> OTHER INFORMATION: n equals a,t,g, or c
<220> FEATURE:
<221> NAME/KEY: SITE
<222> LOCATION: (462)
<223> OTHER INFORMATION: n equals a,t,g, or c
<220> FEATURE:
<221> NAME/KEY: SITE
<222> LOCATION: (465)
<223> OTHER INFORMATION: n equals a,t,g, or c
<220> FEATURE:
<221> NAME/KEY: SITE
<222> LOCATION: (466)
<223> OTHER INFORMATION: n equals a,t,g, or c
<220> FEATURE:
<221> NAME/KEY: SITE
<222> LOCATION: (467)
<223> OTHER INFORMATION: n equals a,t,g, or c
<220> FEATURE:
<221> NAME/KEY: SITE
<222> LOCATION: (482)
<223> OTHER INFORMATION: n equals a,t,g, or c
<220> FEATURE:
<221> NAME/KEY: SITE
<222> LOCATION: (483)
<223> OTHER INFORMATION: n equals a,t,g, or c

<400> SEQUENCE: 105
gaattcggca naggcagaca ctgctccttg ggtagccata actgtgtccc cactttccag 60
ggtgccagac ctacatggac atcgtcattg tcctggatgg gtccaacagc atctacccct 120
gggtgggggt tcagcacttc ctcatcaaca tcctgaaaaa gttttacatt ggcccagggc 180
agatccaggt tggagttgtg cagtatggcg angatgtggt gcatgagttt cacctcaatg 240
actacaggtc tgtaaaagat gtggtggnag ctgncagcca cattgagccn gagaggnggg 300
acagagaccc ggacggnatt tggcattgga atttggcacg gttaaaaaaa aagtngggcc 360
aaaaaaattt tttttgggtc ncanatgctt ttgtagtnan tccnntnggc ttnnnaacaa 420
atttccccaa attnggtncc ctngggccat atttttttat tnccnnnaat tttggggttt 480
gnntgggtca a 491

<210> SEQ ID NO 106
<211> LENGTH: 340
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c -continued
<220> FEATURE:
<221> NAME/KEY: SITE
<222> LOCATION: (188)
<223> OTHER INFORMATION: n equals a,t,g, or c
<220> FEATURE:
<221> NAME/KEY: SITE
<222> LOCATION: (251)
<223> OTHER INFORMATION: n equals a,t,g, or c
<220> FEATURE:
<221> NAME/KEY: SITE
<222> LOCATION: (292)
<223> OTHER INFORMATION: n equals a,t,g, or c
<220> FEATURE:
<221> NAME/KEY: SITE
<222> LOCATION: (308)
<223> OTHER INFORMATION: n equals a,t,g, or c
<220> FEATURE:
<221> NAME/KEY: SITE
<222> LOCATION: (312)
<223> OTHER INFORMATION: n equals a,t,g, or c
<220> FEATURE:
<221> NAME/KEY: SITE
<222> LOCATION: (327)
<223> OTHER INFORMATION: n equals a,t,g, or c

<400> SEQUENCE: 106
ggcanaggag taaatgagcg ggacagcacc aaggaagaca acgtggcccc cttacgcttc 60
cacctcaaat acgaggctga cgtcctcttc accaggagca gcagcctgag ccactacgaa 120
ggtcaagctc aacagctcgc tggagagata cgatggtatc gggcctccct tcagctgcat 180
cttcaggntc cagaacttgg gcttgttccc catccacggg atgatggatg gaagatcacc 240
attcccatcg ncaccaggag cggcaaccgc cttactgaag ttgagggact tnctcaagga 300
cgaggcgnac angtcctgta aacattnggg gcaatagcat 340

<210> SEQ ID NO 107
<211> LENGTH: 356
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<220> FEATURE:
<221> NAME/KEY: SITE
<222> LOCATION: (9)
<223> OTHER INFORMATION: n equals a,t,g, or c
<220> FEATURE:
<221> NAME/KEY: SITE
<222> LOCATION: (84)
<223> OTHER INFORMATION: n equals a,t,g, or c
<220> FEATURE:
<221> NAME/KEY: SITE
<222> LOCATION: (298)
<223> OTHER INFORMATION: n equals a,t,g, or c
<220> FEATURE:
<221> NAME/KEY: SITE
<222> LOCATION: (311)
<223> OTHER INFORMATION: n equals a,t,g, or c
<220> FEATURE:
<221> NAME/KEY: SITE
<222> LOCATION: (312)
<223> OTHER INFORMATION: n equals a,t,g, or c
<220> FEATURE:
<221> NAME/KEY: SITE
<222> LOCATION: (336)
<223> OTHER INFORMATION: n equals a,t,g, or c
<220> FEATURE:
<221> NAME/KEY: SITE
<222> LOCATION: (339)
<223> OTHER INFORMATION: n equals a,t,g, or c
<220> FEATURE:
<221> NAME/KEY: SITE
<222> LOCATION: (342)

-continued

<223> OTHER INFORMATION: n equals a,t,g, or c
<220> FEATURE:
<221> NAME/KEY: SITE
<222> LOCATION: (343)
<223> OTHER INFORMATION: n equals a,t,g, or c

<400> SEQUENCE: 107
ggcanaggng aaatcaattt ccatctactg gggaacctgt ggttgaggtc cctaaaagca 60
ctcaagtaca gatccatgaa aatnatggtc aacgcagcct tgcagaggca ggttgcacag 120
ccccttcatc ttccgtgaag gaggtatccc agccgccaga tcgtgtttga gaatctccaa 180
gcaagaggac tggcaggtcc ccatctggat cattgtaggc agcaccctgg ggggcctcct 240
actgctggcc ctgctggttc ctgggcactg tgggaagctt cggtttcttt aagaagtntc 300
caggtcgcag nnggggtagc ctggttctgg gacccnaanc cnnaaaattg ctgggt 356

<210> SEQ ID NO 108
<211> LENGTH: 262
<212> TYPE: DNA
<213> ORGANISM: Homo sapiens
<220> FEATURE:
<221> NAME/KEY: SITE
<222> LOCATION: (76)
<223> OTHER INFORMATION: n equals a,t,g, or c
<220> FEATURE:
<221> NAME/KEY: SITE
<222> LOCATION: (216)
<223> OTHER INFORMATION: n equals a,t,g, or c
<220> FEATURE:
<221> NAME/KEY: SITE
<222> LOCATION: (234)
<223> OTHER INFORMATION: n equals a,t,g, or c
<220> FEATURE:
<221> NAME/KEY: SITE
<222> LOCATION: (248)
<223> OTHER INFORMATION: n equals a,t,g, or c
<220> FEATURE:
<221> NAME/KEY: SITE
<222> LOCATION: (257)
<223> OTHER INFORMATION: n equals a,t,g, or c
<220> FEATURE:
<221> NAME/KEY: SITE
<222> LOCATION: (259)
<223> OTHER INFORMATION: n equals a,t,g, or c

<400> SEQUENCE: 108
ctgcacaccg gacccagccg ccgtgccgcg ggccatggta cctgcccagg ggcctggtgg 60
tggcctgggc gctcancctg tggccagggt tcacggacac cttcaacatg gtacaccagg 120
aagccccggg tcatccctgg ctccaggacc gccttctttg gctacacagt gcagcagcac 180
gacatcagtg gcaataagtg gctggtcctt ggggcncccc actggaaacc aatngctaca 240
aaaaaaangg aaaactntnc aa 262

<210> SEQ ID NO 109
<211> LENGTH: 327
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c
<220> FEATURE:
<221> NAME/KEY: SITE
<222> LOCATION: (33)
<223> OTHER INFORMATION: n equals a,t,g, or c
<220> FEATURE:
<221> NAME/KEY: SITE
<222> LOCATION: (47)
<223> OTHER INFORMATION: n equals a,t,g, or c -continued
<220> FEATURE:
<221> NAME/KEY: SITE
<222> LOCATION: (55)
<223> OTHER INFORMATION: n equals a,t,g, or c
<220> FEATURE:
<221> NAME/KEY: SITE
<222> LOCATION: (67)
<223> OTHER INFORMATION: n equals a,t,g, or c
<220> FEATURE:
<221> NAME/KEY: SITE
<222> LOCATION: (98)
<223> OTHER INFORMATION: n equals a,t,g, or c
<220> FEATURE:
<221> NAME/KEY: SITE
<222> LOCATION: (153)
<223> OTHER INFORMATION: n equals a,t,g, or c
<220> FEATURE:
<221> NAME/KEY: SITE
<222> LOCATION: (186)
<223> OTHER INFORMATION: n equals a,t,g, or c
<220> FEATURE:
<221> NAME/KEY: SITE
<222> LOCATION: (259)
<223> OTHER INFORMATION: n equals a,t,g, or c
<220> FEATURE:
<221> NAME/KEY: SITE
<222> LOCATION: (283)
<223> OTHER INFORMATION: n equals a,t,g, or c
<220> FEATURE:
<221> NAME/KEY: SITE
<222> LOCATION: (293)
<223> OTHER INFORMATION: n equals a,t,g, or c
<220> FEATURE:
<221> NAME/KEY: SITE
<222> LOCATION: (316)
<223> OTHER INFORMATION: n equals a,t,g, or c
<220> FEATURE:
<221> NAME/KEY: SITE
<222> LOCATION: (326)
<223> OTHER INFORMATION: n equals a,t,g, or c

<400> SEQUENCE: 109
ggcagancta cagcacggtc ctaaatatct cgnagtcagc aaacctncag tttcnagctt 60
aatccanaag gaggactcaa acggtagcat tgagtgtntg aacgaggaga ggaggctcca 120
gaagcaagtt tgcaacgtca gctatccctt ctnccgggcc aaggccaagg tggctttccg 180
tcttgnattt taagttcagc aaatccatct tcctacacca cctggagatc gagcctcgct 240
gcagcagtga cagtaatgng atgaggggtt agccggggtt tgnacccaag tgnatttcac 300
attggccgga aatttnaaaa tttccnc 327

<210> SEQ ID NO 110
<211> LENGTH: 301
<212> TYPE: DNA
<213> ORGANISM: Homo sapiens
<220> FEATURE:
<221> NAME/KEY: SITE
<222> LOCATION: (71)
<223> OTHER INFORMATION: n equals a,t,g, or c
<220> FEATURE:
<221> NAME/KEY: SITE
<222> LOCATION: (72)
<223> OTHER INFORMATION: n equals a,t,g, or c
<220> FEATURE:
<221> NAME/KEY: SITE
<222> LOCATION: (90)
<223> OTHER INFORMATION: n equals a,t,g, or c
<220> FEATURE:
<221> NAME/KEY: SITE
<222> LOCATION: (194)
<223> OTHER INFORMATION: n equals a,t,g, or c
<220> FEATURE:
<221> NAME/KEY: SITE
<222> LOCATION: (212)

-continued

<223> OTHER INFORMATION: n equals a,t,g, or c
<220> FEATURE:
<221> NAME/KEY: SITE
<222> LOCATION: (241)
<223> OTHER INFORMATION: n equals a,t,g, or c
<220> FEATURE:
<221> NAME/KEY: SITE
<222> LOCATION: (245)
<223> OTHER INFORMATION: n equals a,t,g, or c
<220> FEATURE:
<221> NAME/KEY: SITE
<222> LOCATION: (268)
<223> OTHER INFORMATION: n equals a,t,g, or c
<220> FEATURE:
<221> NAME/KEY: SITE
<222> LOCATION: (275)
<223> OTHER INFORMATION: n equals a,t,g, or c
<220> FEATURE:
<221> NAME/KEY: SITE
<222> LOCATION: (290)
<223> OTHER INFORMATION: n equals a,t,g, or c
<220> FEATURE:
<221> NAME/KEY: SITE
<222> LOCATION: (296)
<223> OTHER INFORMATION: n equals a,t,g, or c

<400> SEQUENCE: 110
cccatagata ggcccctggg gctcctgaaa gaatgaaccc aagagcaagg gcttaatggt 60
aacagctgca nnaagggaat gaagaaagan tctaagaatg tggagactga tggccaggca 120
agtgggacca ggatactgaa cgctgtcctg aagaatgaga aggtagccgg gctctgcacc 180
cacgtgcatt gcanattgaa ccgcaactga anacattccc ccaccagctg cagccccttg 240
ntctncagtt gccaaccctc ccgggtgnaa ttttnttccc aggtaccttn atgggnaagc 300
a 301

<210> SEQ ID NO 111
<211> LENGTH: 478
<212> TYPE: DNA
<213> ORGANISM: Homo sapiens
<220> FEATURE:
<221> NAME/KEY: SITE
<222> LOCATION: (96)
<223> OTHER INFORMATION: n equals a,t,g, or c
<220> FEATURE:
<221> NAME/KEY: SITE
<222> LOCATION: (285)
<223> OTHER INFORMATION: n equals a,t,g, or c
<220> FEATURE:
<221> NAME/KEY: SITE
<222> LOCATION: (359)
<223> OTHER INFORMATION: n equals a,t,g, or c
<220> FEATURE:
<221> NAME/KEY: SITE
<222> LOCATION: (387)
<223> OTHER INFORMATION: n equals a,t,g, or c
<220> FEATURE:
<221> NAME/KEY: SITE
<222> LOCATION: (407)
<223> OTHER INFORMATION: n equals a,t,g, or c
<220> FEATURE:
<221> NAME/KEY: SITE
<222> LOCATION: (433)
<223> OTHER INFORMATION: n equals a,t,g, or c
<220> FEATURE:
<221> NAME/KEY: SITE
<222> LOCATION: (452)
<223> OTHER INFORMATION: n equals a,t,g, or c
<220> FEATURE:
<221> NAME/KEY: SITE
<222> LOCATION: (469)
<223> OTHER INFORMATION: n equals a,t,g, or c

<400> SEQUENCE: 111

-continued ggcacagtgg ccgtgggcag gtcactccgg gcatccaaca caaggtcagg gacacagtgc 60
tcatcctcat tgcagccgtt ccagaagggc acctgngcca gggagagcca ggtgtgggca 120
gctgggtagg gacccgcagc ccctcgccct caatgtacac cagctctgtc tccaccacac 180
tagacatggg ctggctttcc tgcactgtcc ccagacacca cactgctctg tcttgtgctt 240
ttccatagat gcttccctct ttaaaacgat gctcaaagct tcagntcctc ctggctcccc 300
tccagtttca tgaatggagc tgatggcaca gaacccccaa ccccattcaa ccagcagang 360
gttctggttc aacatttatt gatcaanaat gtgtgtgggg caagggnttg gtaatggggg 420
ttacaaaaca agnaagttgg cagttttggc cntcagttca aggggaaant ggtgtttg 478

<210> SEQ ID NO 112
<211> LENGTH: 224
<212> TYPE: DNA
<213> ORGANISM: Homo sapiens
<220> FEATURE:
<221> NAME/KEY: SITE
<222> LOCATION: (12)
<223> OTHER INFORMATION: n equals a,t,g, or c
<220> FEATURE:
<221> NAME/KEY: SITE
<222> LOCATION: (21)
<223> OTHER INFORMATION: n equals a,t,g, or c
<220> FEATURE:
<221> NAME/KEY: SITE
<222> LOCATION: (49)
<223> OTHER INFORMATION: n equals a,t,g, or c
<220> FEATURE:
<221> NAME/KEY: SITE
<222> LOCATION: (66)
<223> OTHER INFORMATION: n equals a,t,g, or c
<220> FEATURE:
<221> NAME/KEY: SITE
<222> LOCATION: (176)
<223> OTHER INFORMATION: n equals a,t,g, or c
<220> FEATURE:
<221> NAME/KEY: SITE
<222> LOCATION: (184)
<223> OTHER INFORMATION: n equals a,t,g, or c
<220> FEATURE:
<221> NAME/KEY: SITE
<222> LOCATION: (197)
<223> OTHER INFORMATION: n equals a,t,g, or c
<220> FEATURE:
<221> NAME/KEY: SITE
<222> LOCATION: (212)
<223> OTHER INFORMATION: n equals a,t,g, or c
<220> FEATURE:
<221> NAME/KEY: SITE
<222> LOCATION: (221)
<223> OTHER INFORMATION: n equals a,t,g, or c

<400> SEQUENCE: 112
ctattgcccc anatgttaca ngacgtgttc gcctcgtccg tgtaggaant ccctcagctt 60
cagtangcgg ttgccgctcc tggtggcgag ggaatggtga atcttcatca tcatcccgtg 120
gtatggggaa caaacccaag ttctggatcc tgaaaaatca actgaaagga aggccnatac 180
atcntatctc tccaacnaac tgttggcttg anctcctaat ngtt 224

<210> SEQ ID NO 113
<211> LENGTH: 126
<212> TYPE: DNA
<213> ORGANISM: Homo sapiens
<220> FEATURE:
<221> NAME/KEY: SITE
<222> LOCATION: (72)
<223> OTHER INFORMATION: n equals a,t,g, or c -continued

<400> SEQUENCE: 113
ggcacgagct gacatctctc tgtcactctg ttgcaggcac caacaagaac gagacctcct 60
ttgggctgtg gnagtcacag acgggctttt cctcgcacgt ggtggaggta tgtggtggag 120
gtacgg 126

<210> SEQ ID NO 114
<211> LENGTH: 150
<212> TYPE: PRT
<213> ORGANISM: Homo sapiens

<400> SEQUENCE: 114

Met Leu Phe Ala Cys Ala Leu Leu Ala Leu Leu Gly Leu Ala Thr Ser
1 5 10 15

Cys Ser Phe Ile Val Pro Arg Ser Glu Trp Arg Ala Leu Pro Ser Glu
20 25 30

Cys Ser Ser Arg Leu Gly His Pro Val Arg Tyr Val Val Ile Ser His
35 40 45

Thr Ala Gly Ser Phe Cys Asn Ser Pro Asp Ser Cys Glu Gln Gln Ala
50 55 60

Arg Asn Val Gln His Tyr His Lys Asn Glu Leu Gly Trp Cys Asp Val
65 70 75 80

Ala Tyr Asn Phe Leu Ile Gly Glu Asp Gly His Val Tyr Glu Gly Arg
85 90 95

Gly Trp Asn Ile Lys Gly Asp His Thr Gly Pro Ile Trp Asn Pro Met
100 105 110

Ser Ile Gly Ile Thr Phe Met Gly Asn Phe Met Asp Arg Val Arg Lys
115 120 125

Ala Gly Pro Pro Cys Cys Pro Lys Ser Ser Gly Ile Trp Gly Val Ser
130 135 140

Gly Leu Pro Glu Ile Gln
145 150

<210> SEQ ID NO 115
<211> LENGTH: 285
<212> TYPE: DNA
<213> ORGANISM: Homo sapiens
<220> FEATURE:
<221> NAME/KEY: SITE
<222> LOCATION: (18)
<223> OTHER INFORMATION: n equals a,t,g, or c
<220> FEATURE:
<221> NAME/KEY: SITE
<222> LOCATION: (263)
<223> OTHER INFORMATION: n equals a,t,g, or c
<220> FEATURE:
<221> NAME/KEY: SITE
<222> LOCATION: (270)
<223> OTHER INFORMATION: n equals a,t,g, or c
<220> FEATURE:
<221> NAME/KEY: SITE
<222> LOCATION: (273)
<223> OTHER INFORMATION: n equals a,t,g, or c
<220> FEATURE:
<221> NAME/KEY: SITE
<222> LOCATION: (276)
<223> OTHER INFORMATION: n equals a,t,g, or c
<220> FEATURE:
<221> NAME/KEY: SITE
<222> LOCATION: (283)
<223> OTHER INFORMATION: n equals a,t,g, or c

<400> SEQUENCE: 115
accccaggcc atccgggnag cccagggtct actggcctgc ggtgtggctc agggagcctg 60

-continued

```
aggtccaact atgtgctcaa aggacaccgg gatgtgcagc gtacactctc tccaggcaac    120

cagctctacc acctcatcca gaattggcca cactaccgct ccccctgagg ccctgctgat    180

ccgcacccca ttcctcccct cccatggcca aaaaccccac tgtctccttc tccaataaag    240

atgtagctca aaaaaaaaaa aanaaaaaan ccnggngggg ggncc                    285
```

<210> SEQ ID NO 116
<211> LENGTH: 457
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<220> FEATURE:
<221> NAME/KEY: SITE
<222> LOCATION: (9)
<223> OTHER INFORMATION: n equals a,t,g, or c
<220> FEATURE:
<221> NAME/KEY: SITE
<222> LOCATION: (27)
<223> OTHER INFORMATION: n equals a,t,g, or c
<220> FEATURE:
<221> NAME/KEY: SITE
<222> LOCATION: (57)
<223> OTHER INFORMATION: n equals a,t,g, or c
<220> FEATURE:
<221> NAME/KEY: SITE
<222> LOCATION: (70)
<223> OTHER INFORMATION: n equals a,t,g, or c
<220> FEATURE:
<221> NAME/KEY: SITE
<222> LOCATION: (75)
<223> OTHER INFORMATION: n equals a,t,g, or c
<220> FEATURE:
<221> NAME/KEY: SITE
<222> LOCATION: (80)
<223> OTHER INFORMATION: n equals a,t,g, or c
<220> FEATURE:
<221> NAME/KEY: SITE
<222> LOCATION: (110)
<223> OTHER INFORMATION: n equals a,t,g, or c
<220> FEATURE:
<221> NAME/KEY: SITE
<222> LOCATION: (173)
<223> OTHER INFORMATION: n equals a,t,g, or c
<220> FEATURE:
<221> NAME/KEY: SITE
<222> LOCATION: (176)
<223> OTHER INFORMATION: n equals a,t,g, or c
<220> FEATURE:
<221> NAME/KEY: SITE
<222> LOCATION: (212)
<223> OTHER INFORMATION: n equals a,t,g, or c
<220> FEATURE:
<221> NAME/KEY: SITE
<222> LOCATION: (237)
<223> OTHER INFORMATION: n equals a,t,g, or c
<220> FEATURE:
<221> NAME/KEY: SITE
<222> LOCATION: (300)
<223> OTHER INFORMATION: n equals a,t,g, or c
<220> FEATURE:
<221> NAME/KEY: SITE
<222> LOCATION: (310)
<223> OTHER INFORMATION: n equals a,t,g, or c
<220> FEATURE:
<221> NAME/KEY: SITE
<222> LOCATION: (318)
<223> OTHER INFORMATION: n equals a,t,g, or c
<220> FEATURE:
<221> NAME/KEY: SITE
<222> LOCATION: (320)
<223> OTHER INFORMATION: n equals a,t,g, or c
<220> FEATURE:

-continued

<221> NAME/KEY: SITE
<222> LOCATION: (326)
<223> OTHER INFORMATION: n equals a,t,g, or c
<220> FEATURE:
<221> NAME/KEY: SITE
<222> LOCATION: (337)
<223> OTHER INFORMATION: n equals a,t,g, or c
<220> FEATURE:
<221> NAME/KEY: SITE
<222> LOCATION: (348)
<223> OTHER INFORMATION: n equals a,t,g, or c
<220> FEATURE:
<221> NAME/KEY: SITE
<222> LOCATION: (396)
<223> OTHER INFORMATION: n equals a,t,g, or c
<220> FEATURE:
<221> NAME/KEY: SITE
<222> LOCATION: (399)
<223> OTHER INFORMATION: n equals a,t,g, or c
<220> FEATURE:
<221> NAME/KEY: SITE
<222> LOCATION: (436)
<223> OTHER INFORMATION: n equals a,t,g, or c
<220> FEATURE:
<221> NAME/KEY: SITE
<222> LOCATION: (439)
<223> OTHER INFORMATION: n equals a,t,g, or c
<220> FEATURE:
<221> NAME/KEY: SITE
<222> LOCATION: (444)
<223> OTHER INFORMATION: n equals a,t,g, or c
<220> FEATURE:
<221> NAME/KEY: SITE
<222> LOCATION: (451)
<223> OTHER INFORMATION: n equals a,t,g, or c
<220> FEATURE:
<221> NAME/KEY: SITE
<222> LOCATION: (453)
<223> OTHER INFORMATION: n equals a,t,g, or c

<400> SEQUENCE: 116
ggcanagcng gaccctgccg ccctgcnact atgtcccgcc gctctatgct gcttgcntgg 60
gctctccccn gcctncttcn actcgaagcg gctcaggaga cagaagaccn ggcctgctgc 120
agccccatag tgccccggaa acagtggaag gccctggtat caaagtgcgc ccngcnctga 180
agacctgccc ttacgctatg tggtggtatc gnacacggcg ggcagcagct gcaacanccc 240
cgatttgttg ccagcagcaa gcccggaatg tgcagcacta cccacatgaa gacactgggn 300
tggtgcgaan gtggggtnan aaattnctga tttgggngaa agaagggntt cttataagag 360
ggggcctttg gtttgggaat ttaaagggtt gccccnttna ggtgaatttt tgggaaaccc 420
ttgttccatt gggatnaant ttcntgggca ntnacat 457

<210> SEQ ID NO 117
<211> LENGTH: 1833
<212> TYPE: DNA
<213> ORGANISM: Homo sapiens

<400> SEQUENCE: 117
acatccatgg ctctaatgct cagtttggtt ctgagtctcc tcaagctggg atcagggcag 60
tggcaggtgt ttgggccaga caagcctgtc caggccttgg tgggggagga cgcagcattc 120
tcctgtttcc tgtctcctaa gaccaatgca gaggccatgg aagtgcggtt cttcaggggc 180
cagttctcta gcgtggtcca cctctacagg gacgggaagg accagccatt tatgcagatg 240
ccacagtatc aaggcaggac aaaactggtg aaggattcta ttgcggaggg gcgcatctct 300
ctgaggctgg aaaacattac tgtgttggat gctggcctct atgggtgcag gattagttcc 360
cagtcttact accagaaggc catctgggag ctacaggtgt cagcactggg ctcagttcct 420

-continued

```
ctcatttcca tcacgggata tgttgataga gacatccagc tactctgtca gtcctcgggc    480
tggttccccc ggcccacagc gaagtggaaa ggtccacaag gacaggattt gtccacagac    540
tccaggacaa acagagacat gcatggcctg tttgatgtgg agatctctct gaccgtccaa    600
gagaacgccg ggagcatatc ctgttccatg cggcatgctc atctgagccg agaggtggaa    660
tccagggtac agataggaga taccttttc gagcctatat cgtggcacct ggctaccaaa    720
gtactgggaa tactctgctg tggcctattt tttggcattg ttggactgaa gattttcttc    780
tccaaattcc agtggaaaat ccaggcggaa ctggactgga gaagaaagca cggacaggca    840
gaattgagag acgcccggaa acacgcagtg gaggtgactc tggatccaga gacggctcac    900
ccgaagctct gcgtttctga tctgaaaact gtaacccata gaaaagctcc ccaggaggtg    960
cctcactctg agaagagatt tacaaggaag agtgtggtgg cttctcagag tttccaagca   1020
gggaaacatt actgggaggt ggacggagga cacaataaaa ggtggcgcgt gggagtgtgc   1080
cgggatgatg tggacaggag gaaggagtac gtgactttgt ctcccgatca tgggtactgg   1140
gtcctcagac tgaatggaga acatttgtat ttcacattaa atccccgttt tatcagcgtc   1200
ttccccagga ccccacctac aaaaataggg gtcttcctgg actatgagtg tgggaccatc   1260
tccttcttca acataaatga ccagtccctt atttataccc tgacatgtcg gtttgaaggc   1320
ttattgaggc cctacattga gtatccgtcc tataatgagc aaaatggaac tcccagagac   1380
aagcaacagt gagtcctcct cacaggcaac cacgcccttc ctccccaggg gtgaaatgta   1440
ggatgaatca catcccacat tcttctttag ggatattaag gtctctctcc cagatccaaa   1500
gtcccgcagc agccggccaa ggtggcttcc agatgaaggg ggactggcct gtccacatgg   1560
gagtcaggtg tcatggctgc cctgagctgg gagggaagaa ggctgacatt acatttagtt   1620
tgctctcact ccatctggct aagtgatctt gaaataccac ctctcaggtg aagaaccgtc   1680
aggaattccc atctcacagg ctgtggtgta gattaagtag acaaggaatg tgaataatgc   1740
ttagatctta ttgatgacag agtgtatcct aatggtttgt tcattatatt acactttcag   1800
taaaaaaaaa aaaaaaaaaa aaaaaaaaaa aaa                                1833
```

<210> SEQ ID NO 118
<211> LENGTH: 1386
<212> TYPE: DNA
<213> ORGANISM: Homo sapiens

<400> SEQUENCE: 118

```
atggctctaa tgctcagttt ggttctgagt ctcctcaagc tgggatcagg gcagtggcag     60
gtgtttgggc cagacaagcc tgtccaggcc ttggtggggg aggacgcagc attctcctgt    120
ttcctgtctc ctaagaccaa tgcagaggcc atggaagtgc ggttcttcag gggccagttc    180
tctagcgtgg tccacctcta cagggacggg aaggaccagc catttatgca gatgccacag    240
tatcaaggca ggacaaaact ggtgaaggat tctattgcgg aggggcgcat ctctctgagg    300
ctggaaaaca ttactgtgtt ggatgctggc ctctatgggt gcaggattag ttcccagtct    360
tactaccaga aggccatctg ggagctacag gtgtcagcac tgggctcagt tcctctcatt    420
tccatcacgg gatatgttga tagagacatc cagctactct gtcagtcctc gggctggttc    480
cccggccca cagcgaagtg gaaaggtcca caaggacagg atttgtccac agactccagg    540
acaaacagag acatgcatgg cctgtttgat gtggagatct ctctgaccgt ccaagagaac    600
gccgggagca tatcctgttc catgcggcat gctcatctga gccgagaggt ggaatccagg    660
```

-continued

```
gtacagatag gagatacctt tttcgagcct atatcgtggc acctggctac caaagtactg    720

ggaatactct gctgtggcct attttttggc attgttggac tgaagatttt cttctccaaa    780

ttccagtgga aaatccaggc ggaactggac tggagaagaa agcacggaca ggcagaattg    840

agagacgccc ggaaacacgc agtggaggtg actctggatc cagagacggc tcacccgaag    900

ctctgcgttt ctgatctgaa aactgtaacc catagaaaag ctccccagga ggtgcctcac    960

tctgagaaga gatttacaag gaagagtgtg gtggcttctc agagtttcca agcagggaaa   1020

cattactggg aggtggacgg aggacacaat aaaaggtggc gcgtgggagt gtgccgggat   1080

gatgtggaca ggaggaagga gtacgtgact ttgtctcccg atcatgggta ctgggtcctc   1140

agactgaatg gagaacattt gtatttcaca ttaaatcccc gttttatcag cgtcttcccc   1200

aggaccccac ctacaaaaat aggggtcttc ctggactatg agtgtgggac catctccttc   1260

ttcaacataa atgaccagtc ccttatttat accctgacat gtcggtttga aggcttattg   1320

aggccctaca ttgagtatcc gtcctataat gagcaaaatg gaactcccag agacaagcaa   1380

cagtga                                                              1386


<210> SEQ ID NO 119
<211> LENGTH: 461
<212> TYPE: PRT
<213> ORGANISM: Homo sapiens

<400> SEQUENCE: 119

Met Ala Leu Met Leu Ser Leu Val Leu Ser Leu Leu Lys Leu Gly Ser
1               5                   10                  15

Gly Gln Trp Gln Val Phe Gly Pro Asp Lys Pro Val Gln Ala Leu Val
            20                  25                  30

Gly Glu Asp Ala Ala Phe Ser Cys Phe Leu Ser Pro Lys Thr Asn Ala
        35                  40                  45

Glu Ala Met Glu Val Arg Phe Phe Arg Gly Gln Phe Ser Ser Val Val
    50                  55                  60

His Leu Tyr Arg Asp Gly Lys Asp Gln Pro Phe Met Gln Met Pro Gln
65                  70                  75                  80

Tyr Gln Gly Arg Thr Lys Leu Val Lys Asp Ser Ile Ala Glu Gly Arg
                85                  90                  95

Ile Ser Leu Arg Leu Glu Asn Ile Thr Val Leu Asp Ala Gly Leu Tyr
            100                 105                 110

Gly Cys Arg Ile Ser Ser Gln Ser Tyr Tyr Gln Lys Ala Ile Trp Glu
        115                 120                 125

Leu Gln Val Ser Ala Leu Gly Ser Val Pro Leu Ile Ser Ile Thr Gly
    130                 135                 140

Tyr Val Asp Arg Asp Ile Gln Leu Leu Cys Gln Ser Ser Gly Trp Phe
145                 150                 155                 160

Pro Arg Pro Thr Ala Lys Trp Lys Gly Pro Gln Gly Gln Asp Leu Ser
                165                 170                 175

Thr Asp Ser Arg Thr Asn Arg Asp Met His Gly Leu Phe Asp Val Glu
            180                 185                 190

Ile Ser Leu Thr Val Gln Glu Asn Ala Gly Ser Ile Ser Cys Ser Met
        195                 200                 205

Arg His Ala His Leu Ser Arg Glu Val Glu Ser Arg Val Gln Ile Gly
    210                 215                 220

Asp Thr Phe Phe Glu Pro Ile Ser Trp His Leu Ala Thr Lys Val Leu
225                 230                 235                 240
```

-continued

```
Gly Ile Leu Cys Cys Gly Leu Phe Phe Gly Ile Val Gly Leu Lys Ile
                245                 250                 255

Phe Phe Ser Lys Phe Gln Trp Lys Ile Gln Ala Glu Leu Asp Trp Arg
            260                 265                 270

Arg Lys His Gly Gln Ala Glu Leu Arg Asp Ala Arg Lys His Ala Val
        275                 280                 285

Glu Val Thr Leu Asp Pro Glu Thr Ala His Pro Lys Leu Cys Val Ser
    290                 295                 300

Asp Leu Lys Thr Val Thr His Arg Lys Ala Pro Gln Glu Val Pro His
305                 310                 315                 320

Ser Glu Lys Arg Phe Thr Arg Lys Ser Val Val Ala Ser Gln Ser Phe
                325                 330                 335

Gln Ala Gly Lys His Tyr Trp Glu Val Asp Gly Gly His Asn Lys Arg
            340                 345                 350

Trp Arg Val Gly Val Cys Arg Asp Asp Val Asp Arg Arg Lys Glu Tyr
        355                 360                 365

Val Thr Leu Ser Pro Asp His Gly Tyr Trp Val Leu Arg Leu Asn Gly
    370                 375                 380

Glu His Leu Tyr Phe Thr Leu Asn Pro Arg Phe Ile Ser Val Phe Pro
385                 390                 395                 400

Arg Thr Pro Pro Thr Lys Ile Gly Val Phe Leu Asp Tyr Glu Cys Gly
                405                 410                 415

Thr Ile Ser Phe Phe Asn Ile Asn Asp Gln Ser Leu Ile Tyr Thr Leu
            420                 425                 430

Thr Cys Arg Phe Glu Gly Leu Leu Arg Pro Tyr Ile Glu Tyr Pro Ser
        435                 440                 445

Tyr Asn Glu Gln Asn Gly Thr Pro Arg Asp Lys Gln Gln
    450                 455                 460
```

<210> SEQ ID NO 120
<211> LENGTH: 1152
<212> TYPE: DNA
<213> ORGANISM: Homo sapiens

<400> SEQUENCE: 120

```
acctttttcg agcctatatc gtggcacctg gctaccaaag tactgggaat actctgctgt     60

ggcctatttt ttggcattgt tggactgaag attttcttct ccaaattcca gtggaaaatc    120

caggcggaac tggactggag aagaaagcac ggacaggcag aattgagaga cgcccggaaa    180

cacgcagtgg aggtgactct ggatccagag acggctcacc cgaagctctg cgtttctgat    240

ctgaaaactg taacccatag aaaagctccc caggaggtgc ctcactctga gaagagattt    300

acaaggaaga gtgtggtggc ttctcagagt ttccaagcag ggaaacatta ctgggaggtg    360

gacggaggac acaataaaag gtggcgcgtg ggagtgtgcc gggatgatgt ggacaggagg    420

aaggagtacg tgactttgtc tcccgatcat gggtactggg tcctcagact gaatggagaa    480

catttgtatt tcacattaaa tccccgtttt atcagcgtct tccccaggac cccacctaca    540

aaaatagggg tcttcctgga ctatgagtgt gggaccatct ccttcttcaa cataaatgac    600

cagtccctta tttataccct gacatgtcgg tttgaaggct tattgaggcc ctacattgag    660

tatccgtcct ataatgagca aaatggaact cccagagaca agcaacagtg agtcctcctc    720

acaggcaacc acgcccttcc tccccagggg tgaaatgtag gatgaatcac atcccacatt    780

cttctttagg gatattaagg tctctctccc agatccaaag tcccgcagca gccggccaag    840

gtggcttcca gatgaagggg gactggcctg tccacatggg agtcaggtgt catggctgcc    900
```

```
ctgagctggg agggaagaag gctgacatta catttagttt gctctcactc catctggcta    960

agtgatcttg aaataccacc tctcaggtga agaaccgtca ggaattccca tctcacaggc   1020

tgtggtgtag attaagtaga caaggaatgt gaataatgct tagatcttat tgatgacaga   1080

gtgtatccta atggtttgtt cattatatta cactttcagt aaaaaaaaaa aaaaaaaaaa   1140

aaaaaaaaaa aa                                                       1152


<210> SEQ ID NO 121
<211> LENGTH: 526
<212> TYPE: PRT
<213> ORGANISM: Homo sapiens

<400> SEQUENCE: 121

Met Ala Val Phe Pro Asn Ser Cys Leu Ala Gly Cys Leu Leu Ile Phe
  1               5                  10                  15

Ile Leu Leu Gln Leu Pro Lys Leu Asp Ser Ala Pro Phe Asp Val Ile
             20                  25                  30

Gly Pro Gln Glu Pro Ile Leu Ala Val Val Gly Glu Asp Ala Glu Leu
         35                  40                  45

Pro Cys Arg Leu Ser Pro Asn Val Ser Ala Lys Gly Met Glu Leu Arg
     50                  55                  60

Trp Phe Arg Glu Lys Val Ser Pro Ala Val Phe Val Ser Arg Glu Gly
 65                  70                  75                  80

Gln Glu Gln Glu Gly Glu Glu Met Ala Glu Tyr Arg Gly Arg Val Ser
                 85                  90                  95

Leu Val Glu Asp His Ile Ala Glu Gly Ser Val Ala Val Arg Ile Gln
            100                 105                 110

Glu Val Lys Ala Ser Asp Asp Gly Glu Tyr Arg Cys Phe Phe Arg Gln
        115                 120                 125

Asp Glu Asn Tyr Glu Glu Ala Ile Val His Leu Lys Val Ala Ala Leu
    130                 135                 140

Gly Ser Asp Pro His Ile Ser Met Lys Val Gln Glu Ser Gly Glu Ile
145                 150                 155                 160

Gln Leu Glu Cys Thr Ser Val Gly Trp Tyr Pro Glu Pro Gln Val Gln
                165                 170                 175

Trp Arg Thr His Arg Gly Glu Glu Phe Pro Ser Met Ser Glu Ser Arg
            180                 185                 190

Asn Pro Asp Glu Glu Gly Leu Phe Thr Val Arg Ala Ser Val Ile Ile
        195                 200                 205

Arg Asp Ser Ser Met Lys Asn Val Ser Cys Cys Ile Arg Asn Leu Leu
    210                 215                 220

Leu Gly Gln Glu Lys Asp Val Glu Val Ser Ile Pro Ala Ser Phe Phe
225                 230                 235                 240

Pro Arg Leu Thr Pro Trp Met Val Ala Val Ala Val Ile Leu Val Val
                245                 250                 255

Leu Gly Leu Leu Thr Ile Gly Ser Ile Phe Phe Thr Trp Arg Leu Tyr
            260                 265                 270

Lys Glu Arg Ser Arg Gln Arg Arg Asn Glu Phe Ser Ser Lys Glu Lys
        275                 280                 285

Leu Leu Glu Glu Leu Lys Trp Lys Arg Ala Thr Leu His Ala Val Asp
    290                 295                 300

Val Thr Leu Asp Pro Asp Thr Ala His Pro His Leu Phe Leu Tyr Glu
305                 310                 315                 320
```

-continued

```
Asp Ser Lys Ser Val Arg Leu Glu Asp Ser Arg Gln Lys Leu Pro Glu
                325                 330                 335

Lys Pro Glu Arg Phe Asp Ser Trp Pro Cys Val Met Gly Arg Glu Ala
            340                 345                 350

Phe Thr Ser Gly Arg His Tyr Trp Glu Val Glu Val Gly Asp Arg Thr
        355                 360                 365

Asp Trp Ala Ile Gly Val Cys Arg Glu Asn Val Met Lys Lys Gly Phe
    370                 375                 380

Asp Pro Met Thr Pro Glu Asn Gly Phe Trp Ala Val Glu Leu Tyr Gly
385                 390                 395                 400

Asn Gly Tyr Trp Ala Leu Thr Pro Leu Arg Thr Pro Leu Pro Leu Ala
                405                 410                 415

Gly Pro Pro Arg Arg Val Gly Val Phe Leu Asp Tyr Glu Ser Gly Asp
            420                 425                 430

Ile Phe Phe Tyr Asn Met Thr Asp Gly Ser His Ile Tyr Thr Phe Ser
        435                 440                 445

Lys Ala Ser Phe Ser Gly Pro Leu Arg Pro Phe Phe Cys Leu Trp Ser
    450                 455                 460

Cys Gly Lys Lys Pro Leu Thr Ile Cys Pro Val Thr Asp Gly Leu Glu
465                 470                 475                 480

Gly Val Met Val Val Ala Asp Ala Lys Asp Ile Ser Lys Glu Ile Pro
                485                 490                 495

Leu Ser Pro Met Gly Glu Asp Ser Ala Ser Gly Asp Ile Glu Thr Leu
            500                 505                 510

His Ser Lys Leu Ile Pro Leu Gln Pro Ser Gln Gly Val Pro
        515                 520                 525
```

```
<210> SEQ ID NO 122
<211> LENGTH: 469
<212> TYPE: DNA
<213> ORGANISM: Homo sapiens
<220> FEATURE:
<221> NAME/KEY: SITE
<222> LOCATION: (63)
<223> OTHER INFORMATION: n equals a,t,g, or c
<220> FEATURE:
<221> NAME/KEY: SITE
<222> LOCATION: (289)
<223> OTHER INFORMATION: n equals a,t,g, or c
<220> FEATURE:
<221> NAME/KEY: SITE
<222> LOCATION: (338)
<223> OTHER INFORMATION: n equals a,t,g, or c
<220> FEATURE:
<221> NAME/KEY: SITE
<222> LOCATION: (357)
<223> OTHER INFORMATION: n equals a,t,g, or c
<220> FEATURE:
<221> NAME/KEY: SITE
<222> LOCATION: (358)
<223> OTHER INFORMATION: n equals a,t,g, or c
<220> FEATURE:
<221> NAME/KEY: SITE
<222> LOCATION: (362)
<223> OTHER INFORMATION: n equals a,t,g, or c
<220> FEATURE:
<221> NAME/KEY: SITE
<222> LOCATION: (364)
<223> OTHER INFORMATION: n equals a,t,g, or c
<220> FEATURE:
<221> NAME/KEY: SITE
<222> LOCATION: (381)
<223> OTHER INFORMATION: n equals a,t,g, or c
<220> FEATURE:
<221> NAME/KEY: SITE
<222> LOCATION: (389)
```

-continued

<223> OTHER INFORMATION: n equals a,t,g, or c
<220> FEATURE:
<221> NAME/KEY: SITE
<222> LOCATION: (391)
<223> OTHER INFORMATION: n equals a,t,g, or c
<220> FEATURE:
<221> NAME/KEY: SITE
<222> LOCATION: (437)
<223> OTHER INFORMATION: n equals a,t,g, or c
<220> FEATURE:
<221> NAME/KEY: SITE
<222> LOCATION: (447)
<223> OTHER INFORMATION: n equals a,t,g, or c
<220> FEATURE:
<221> NAME/KEY: SITE
<222> LOCATION: (454)
<223> OTHER INFORMATION: n equals a,t,g, or c
<220> FEATURE:
<221> NAME/KEY: SITE
<222> LOCATION: (458)
<223> OTHER INFORMATION: n equals a,t,g, or c

<400> SEQUENCE: 122
ggcagagcct gtcatccgtt tccatgccgt gaggtccatt cacagaacac atccatggct 60
ctnatgctca gtttggttct gagtctcctc aagctgggat cagggcagtg gcaggtgttt 120
gggccagaca agcctgtcca ggccttggtg ggggaggacg cagcattctc ctgtttcctg 180
tctcctaaga accaatgcag aggccatggt aagtgcggtt cttcaggggc cagtttctct 240
agcgtggtcc acctcttaca gggacgggaa ggaccagccc attttatgnc agatggccac 300
agtattcaag gccaggacaa aaaatgggtg gaaggttnct atttgcggag gggcgcnntt 360
tntnttgagg gtgggaaaaa natttactnt ntttggattg ctgggcccct tatgggtgcc 420
agggttaagt ttcccanttt ttaattnacc cganaggncc atttggggg 469

<210> SEQ ID NO 123
<211> LENGTH: 368
<212> TYPE: DNA
<213> ORGANISM: Homo sapiens
<220> FEATURE:
<221> NAME/KEY: SITE
<222> LOCATION: (81)
<223> OTHER INFORMATION: n equals a,t,g, or c
<220> FEATURE:
<221> NAME/KEY: SITE
<222> LOCATION: (109)
<223> OTHER INFORMATION: n equals a,t,g, or c
<220> FEATURE:
<221> NAME/KEY: SITE
<222> LOCATION: (133)
<223> OTHER INFORMATION: n equals a,t,g, or c
<220> FEATURE:
<221> NAME/KEY: SITE
<222> LOCATION: (210)
<223> OTHER INFORMATION: n equals a,t,g, or c
<220> FEATURE:
<221> NAME/KEY: SITE
<222> LOCATION: (228)
<223> OTHER INFORMATION: n equals a,t,g, or c
<220> FEATURE:
<221> NAME/KEY: SITE
<222> LOCATION: (242)
<223> OTHER INFORMATION: n equals a,t,g, or c
<220> FEATURE:
<221> NAME/KEY: SITE
<222> LOCATION: (245)
<223> OTHER INFORMATION: n equals a,t,g, or c
<220> FEATURE:
<221> NAME/KEY: SITE
<222> LOCATION: (249)
<223> OTHER INFORMATION: n equals a,t,g, or c
<220> FEATURE:
<221> NAME/KEY: SITE -continued
<222> LOCATION: (251)
<223> OTHER INFORMATION: n equals a,t,g, or c
<220> FEATURE:
<221> NAME/KEY: SITE
<222> LOCATION: (268)
<223> OTHER INFORMATION: n equals a,t,g, or c
<220> FEATURE:
<221> NAME/KEY: SITE
<222> LOCATION: (329)
<223> OTHER INFORMATION: n equals a,t,g, or c
<220> FEATURE:
<221> NAME/KEY: SITE
<222> LOCATION: (335)
<223> OTHER INFORMATION: n equals a,t,g, or c
<220> FEATURE:
<221> NAME/KEY: SITE
<222> LOCATION: (339)
<223> OTHER INFORMATION: n equals a,t,g, or c
<220> FEATURE:
<221> NAME/KEY: SITE
<222> LOCATION: (353)
<223> OTHER INFORMATION: n equals a,t,g, or c
<220> FEATURE:
<221> NAME/KEY: SITE
<222> LOCATION: (362)
<223> OTHER INFORMATION: n equals a,t,g, or c

<400> SEQUENCE: 123
ggcagagagg atttgtccac agactccagg acaaacagag acatgcatgg cctgtttgat 60
gtggagatct ctctgaccgt ncaagagaac gccgggagca tatcctgtnc catgcggcat 120
gctcatctaa gcncgagaag gtgggaatcc agggtacaga taggagatac cttttcgaag 180
cctatatcgt ggcacctggc taccaaagtn ctgggaaata ctctgctngt ggcctatttt 240
tnggnattnt nggactaaag atattttnct ccaaattcca gtgtaagcaa gggagaaggg 300
gcatgggccc gtgccttatt ccatggttnc cagcngggnc aggatcagag atngctccca 360 cntccagt 368

<210> SEQ ID NO 124
<211> LENGTH: 27
<212> TYPE: PRT
<213> ORGANISM: Homo sapiens

<400> SEQUENCE: 124

Gly Thr Leu Val Ala Glu Lys His Val Leu Thr Ala Ala His Cys Ile
1 5 10 15

His Asp Gly Lys Thr Tyr Val Lys Gly Thr Gln
20 25

<210> SEQ ID NO 125
<211> LENGTH: 413
<212> TYPE: PRT
<213> ORGANISM: Homo sapiens

<400> SEQUENCE: 125

Gly Thr Arg Gly Gln Ala Trp Glu Pro Arg Ala Leu Ser Arg Arg Pro
1 5 10 15

His Leu Ser Glu Arg Arg Ser Glu Pro Arg Pro Gly Arg Ala Ala Arg
20 25 30

Arg Gly Thr Val Leu Gly Met Ala Gly Ile Pro Gly Leu Leu Phe Leu
35 40 45

Leu Phe Phe Leu Leu Cys Ala Val Gly Gln Val Ser Pro Tyr Ser Ala
50 55 60

Pro Trp Lys Pro Thr Trp Pro Ala Tyr Arg Leu Pro Val Val Leu Pro
65 70 75 80

-continued

Gln Ser Thr Leu Asn Leu Ala Lys Pro Asp Phe Gly Ala Glu Ala Lys
85 90 95

Leu Glu Val Ser Ser Ser Cys Gly Pro Gln Cys His Lys Gly Thr Pro
100 105 110

Leu Pro Thr Tyr Glu Glu Ala Lys Gln Tyr Leu Ser Tyr Glu Thr Leu
115 120 125

Tyr Ala Asn Gly Ser Arg Thr Glu Thr Gln Val Gly Ile Tyr Ile Leu
130 135 140

Ser Ser Ser Gly Asp Gly Ala Gln His Arg Asp Ser Gly Ser Ser Gly
145 150 155 160

Lys Ser Arg Arg Lys Arg Gln Ile Tyr Gly Tyr Asp Ser Arg Phe Ser
165 170 175

Ile Phe Gly Lys Asp Phe Leu Leu Asn Tyr Pro Phe Ser Thr Ser Val
180 185 190

Lys Leu Ser Thr Gly Cys Thr Gly Thr Leu Val Ala Glu Lys His Val
195 200 205

Leu Thr Ala Ala His Cys Ile His Asp Gly Lys Thr Tyr Val Lys Gly
210 215 220

Thr Gln Lys Leu Arg Val Gly Phe Leu Lys Pro Lys Phe Lys Asp Gly
225 230 235 240

Gly Arg Gly Ala Asn Asp Ser Thr Ser Ala Met Pro Glu Gln Met Lys
245 250 255

Phe Gln Trp Ile Arg Val Lys Arg Thr His Val Pro Lys Gly Trp Ile
260 265 270

Lys Gly Asn Ala Asn Asp Ile Gly Met Asp Tyr Asp Tyr Ala Leu Leu
275 280 285

Glu Leu Lys Lys Pro His Lys Arg Lys Phe Met Lys Ile Gly Val Ser
290 295 300

Pro Pro Ala Lys Gln Leu Pro Gly Gly Arg Ile His Phe Ser Gly Tyr
305 310 315 320

Asp Asn Asp Arg Pro Gly Asn Leu Val Tyr Arg Phe Cys Asp Val Lys
325 330 335

Asp Glu Thr Tyr Asp Leu Leu Tyr Gln Gln Cys Asp Ser Gln Pro Gly
340 345 350

Ala Ser Gly Ser Gly Val Tyr Val Arg Met Trp Lys Arg Gln His Gln
355 360 365

Lys Trp Glu Arg Lys Ile Ile Gly Met Ile Ser Gly His Gln Trp Val
370 375 380

Asp Met Asp Gly Ser Pro Gln Glu Phe Thr Arg Gly Cys Ser Glu Ile
385 390 395 400

Thr Pro Leu Gln Tyr Ile Pro Asp Ile Ser Ile Gly Val
405 410

<210> SEQ ID NO 126
<211> LENGTH: 383
<212> TYPE: PRT
<213> ORGANISM: Homo sapiens

<400> SEQUENCE: 126

Met Ala Gly Ile Pro Gly Leu Leu Phe Leu Leu Phe Phe Leu Leu Cys
1 5 10 15

Ala Val Gly Gln Val Ser Pro Tyr Ser Ala Pro Trp Lys Pro Thr Trp
20 25 30

Pro Ala Tyr Arg Leu Pro Val Val Leu Pro Gln Ser Thr Leu Asn Leu

-continued

```
         35                  40                  45

Ala Lys Pro Asp Phe Gly Ala Glu Ala Lys Leu Glu Val Ser Ser Ser
     50                  55                  60

Cys Gly Pro Gln Cys His Lys Gly Thr Pro Leu Pro Thr Tyr Glu Glu
 65                  70                  75                  80

Ala Lys Gln Tyr Leu Ser Tyr Glu Thr Leu Tyr Ala Asn Gly Ser Arg
                 85                  90                  95

Thr Glu Thr Gln Val Gly Ile Tyr Ile Leu Ser Ser Ser Gly Asp Gly
            100                 105                 110

Ala Gln His Arg Asp Ser Gly Ser Ser Gly Lys Ser Arg Arg Lys Arg
        115                 120                 125

Gln Ile Tyr Gly Tyr Asp Ser Arg Phe Ser Ile Phe Gly Lys Asp Phe
    130                 135                 140

Leu Leu Asn Tyr Pro Phe Ser Thr Ser Val Lys Leu Ser Thr Gly Cys
145                 150                 155                 160

Thr Gly Thr Leu Val Ala Glu Lys His Val Leu Thr Ala Ala His Cys
                165                 170                 175

Ile His Asp Gly Lys Thr Tyr Val Lys Gly Thr Gln Lys Leu Arg Val
            180                 185                 190

Gly Phe Leu Lys Pro Lys Phe Lys Asp Gly Gly Arg Gly Ala Asn Asp
        195                 200                 205

Ser Thr Ser Ala Met Pro Glu Gln Met Lys Phe Gln Trp Ile Arg Val
    210                 215                 220

Lys Arg Thr His Val Pro Lys Gly Trp Ile Lys Gly Asn Ala Asn Asp
225                 230                 235                 240

Ile Gly Met Asp Tyr Asp Tyr Ala Leu Leu Glu Leu Lys Lys Pro His
                245                 250                 255

Lys Arg Lys Phe Met Lys Ile Gly Val Ser Pro Pro Ala Lys Gln Leu
            260                 265                 270

Pro Gly Gly Arg Ile His Phe Ser Gly Tyr Asp Asn Asp Arg Pro Gly
        275                 280                 285

Asn Leu Val Tyr Arg Phe Cys Asp Val Lys Asp Glu Thr Tyr Asp Leu
    290                 295                 300

Leu Tyr Gln Gln Cys Asp Ala Gln Pro Gly Ala Ser Gly Ser Gly Val
305                 310                 315                 320

Tyr Val Arg Met Trp Lys Arg Gln Gln Gln Lys Trp Glu Arg Lys Ile
                325                 330                 335

Ile Gly Ile Phe Ser Gly His Gln Trp Val Asp Met Asn Gly Ser Pro
            340                 345                 350

Gln Asp Phe Asn Val Ala Val Arg Ile Thr Pro Leu Lys Tyr Ala Gln
        355                 360                 365

Ile Cys Tyr Trp Ile Lys Gly Asn Tyr Leu Asp Cys Arg Glu Gly
    370                 375                 380


<210> SEQ ID NO 127
<211> LENGTH: 269
<212> TYPE: PRT
<213> ORGANISM: Homo sapiens

<400> SEQUENCE: 127

Met Ile Arg Thr Leu Leu Leu Ser Thr Leu Val Ala Gly Ala Leu Ser
  1               5                  10                  15

Cys Gly Asp Pro Thr Tyr Pro Pro Tyr Val Thr Arg Val Val Gly Gly
             20                  25                  30
```

-continued

```
Glu Glu Ala Arg Pro Asn Ser Trp Pro Trp Gln Val Ser Leu Gln Tyr
         35                  40                  45

Ser Ser Asn Gly Lys Trp Tyr His Thr Cys Gly Gly Ser Leu Ile Ala
     50                  55                  60

Asn Ser Trp Val Leu Thr Ala Ala His Cys Ile Ser Ser Ser Arg Thr
 65                  70                  75                  80

Tyr Arg Val Gly Leu Gly Arg His Asn Leu Tyr Val Ala Glu Ser Gly
                 85                  90                  95

Ser Leu Ala Val Ser Val Ser Lys Ile Val Val His Lys Asp Trp Asn
            100                 105                 110

Ser Asn Gln Ile Ser Lys Gly Asn Asp Ile Ala Leu Leu Lys Leu Ala
        115                 120                 125

Asn Pro Val Ser Leu Thr Asp Lys Ile Gln Leu Ala Cys Leu Pro Pro
    130                 135                 140

Ala Gly Thr Ile Leu Pro Asn Asn Tyr Pro Cys Tyr Val Thr Gly Trp
145                 150                 155                 160

Gly Arg Leu Gln Thr Asn Gly Ala Val Pro Asp Val Leu Gln Gln Gly
                165                 170                 175

Arg Leu Leu Val Val Asp Tyr Ala Thr Cys Ser Ser Ser Ala Trp Trp
            180                 185                 190

Gly Ser Ser Val Lys Thr Ser Met Ile Val Ala Gly Gly Asp Gly Val
        195                 200                 205

Ile Ser Ser Cys Asn Gly Asp Ser Gly Gly Pro Leu Asn Cys Gln Ala
    210                 215                 220

Ser Asp Gly Arg Trp Gln Val His Gly Ile Val Ser Phe Gly Ser Arg
225                 230                 235                 240

Leu Gly Cys Asn Tyr Tyr His Lys Pro Ser Val Phe Thr Arg Val Ser
                245                 250                 255

Asn Tyr Ile Asp Trp Ile Asn Ser Val Ile Ala Asn Asn
            260                 265
```

<210> SEQ ID NO 128
<211> LENGTH: 328
<212> TYPE: DNA
<213> ORGANISM: Homo sapiens
<220> FEATURE:
<221> NAME/KEY: SITE
<222> LOCATION: (30)
<223> OTHER INFORMATION: n equals a,t,g, or c
<220> FEATURE:
<221> NAME/KEY: SITE
<222> LOCATION: (216)
<223> OTHER INFORMATION: n equals a,t,g, or c

<400> SEQUENCE: 128

```
tgaaacgcac ccatgtgccc aagggttggn tcaagggcaa tgccaatgac atcggcatgg     60

attatgatta tgccctcctg gaactcaaaa agccccacaa gagaaaattt atgaagattg    120

gggtgagccc tcctgctaag cagctgccag ggggcagaat tcacttctct ggttatgaca    180

atgaccgacc aggcaatttg gtgtatcgct tctgtnacgt caaagacgag acctatgact    240

tgctctacca gcaatgcgat gcccagccag gggccagcgg gtctggggtc tatgttagga    300

tgtgggagag acagcagcat gaagtggg                                       328
```

<210> SEQ ID NO 129
<211> LENGTH: 495
<212> TYPE: DNA
<213> ORGANISM: Homo sapiens
<220> FEATURE:

-continued

<221> NAME/KEY: SITE
<222> LOCATION: (23)
<223> OTHER INFORMATION: n equals a,t,g, or c
<220> FEATURE:
<221> NAME/KEY: SITE
<222> LOCATION: (260)
<223> OTHER INFORMATION: n equals a,t,g, or c
<220> FEATURE:
<221> NAME/KEY: SITE
<222> LOCATION: (291)
<223> OTHER INFORMATION: n equals a,t,g, or c
<220> FEATURE:
<221> NAME/KEY: SITE
<222> LOCATION: (295)
<223> OTHER INFORMATION: n equals a,t,g, or c
<220> FEATURE:
<221> NAME/KEY: SITE
<222> LOCATION: (305)
<223> OTHER INFORMATION: n equals a,t,g, or c
<220> FEATURE:
<221> NAME/KEY: SITE
<222> LOCATION: (319)
<223> OTHER INFORMATION: n equals a,t,g, or c
<220> FEATURE:
<221> NAME/KEY: SITE
<222> LOCATION: (331)
<223> OTHER INFORMATION: n equals a,t,g, or c
<220> FEATURE:
<221> NAME/KEY: SITE
<222> LOCATION: (352)
<223> OTHER INFORMATION: n equals a,t,g, or c
<220> FEATURE:
<221> NAME/KEY: SITE
<222> LOCATION: (364)
<223> OTHER INFORMATION: n equals a,t,g, or c
<220> FEATURE:
<221> NAME/KEY: SITE
<222> LOCATION: (390)
<223> OTHER INFORMATION: n equals a,t,g, or c
<220> FEATURE:
<221> NAME/KEY: SITE
<222> LOCATION: (400)
<223> OTHER INFORMATION: n equals a,t,g, or c
<220> FEATURE:
<221> NAME/KEY: SITE
<222> LOCATION: (402)
<223> OTHER INFORMATION: n equals a,t,g, or c
<220> FEATURE:
<221> NAME/KEY: SITE
<222> LOCATION: (406)
<223> OTHER INFORMATION: n equals a,t,g, or c
<220> FEATURE:
<221> NAME/KEY: SITE
<222> LOCATION: (428)
<223> OTHER INFORMATION: n equals a,t,g, or c
<220> FEATURE:
<221> NAME/KEY: SITE
<222> LOCATION: (429)
<223> OTHER INFORMATION: n equals a,t,g, or c
<220> FEATURE:
<221> NAME/KEY: SITE
<222> LOCATION: (448)
<223> OTHER INFORMATION: n equals a,t,g, or c
<220> FEATURE:
<221> NAME/KEY: SITE
<222> LOCATION: (461)
<223> OTHER INFORMATION: n equals a,t,g, or c
<220> FEATURE:
<221> NAME/KEY: SITE
<222> LOCATION: (463)
<223> OTHER INFORMATION: n equals a,t,g, or c
<220> FEATURE:
<221> NAME/KEY: SITE
<222> LOCATION: (465)
<223> OTHER INFORMATION: n equals a,t,g, or c
<220> FEATURE:
<221> NAME/KEY: SITE
<222> LOCATION: (469)
<223> OTHER INFORMATION: n equals a,t,g, or c -continued
<220> FEATURE:
<221> NAME/KEY: SITE
<222> LOCATION: (470)
<223> OTHER INFORMATION: n equals a,t,g, or c
<220> FEATURE:
<221> NAME/KEY: SITE
<222> LOCATION: (476)
<223> OTHER INFORMATION: n equals a,t,g, or c
<220> FEATURE:
<221> NAME/KEY: SITE
<222> LOCATION: (482)
<223> OTHER INFORMATION: n equals a,t,g, or c
<220> FEATURE:
<221> NAME/KEY: SITE
<222> LOCATION: (489)
<223> OTHER INFORMATION: n equals a,t,g, or c

<400> SEQUENCE: 129
aattcggcac aggctcggcc cgnaggactc aggggcttca ggaaagtctc gaaggaagcg 60
gcagatttat ggctatgaca gcaggttcag catttttggg aaggacttcc tgctcaacta 120
ccctttctca acatcagtga agttatccac gggctgcacc ggcaccctgg tgggcagaga 180
agcatgtcct cacagctgcc cactgcatac acgatggaaa aacctatgtg aaaggaaccc 240
agaagcttcg agtgggcttn ctaaagccca agtttaaaga tggtggtcga ngggncaacg 300
acttncactt cagccatgnc cgagcagatg nattttcagt gggtccggtg gnaaggaacc 360
ctgntgccca agggtttggg ttcagggggn atggcatgan cnaggnatgg gtttatgatt 420
atgcctcnng ggaattcaaa aggcccanaa ggggaaattt ntnanggtnn gggtgnggcc 480
tnctgttang aaatt 495

<210> SEQ ID NO 130
<211> LENGTH: 288
<212> TYPE: DNA
<213> ORGANISM: Homo sapiens
<220> FEATURE:
<221> NAME/KEY: SITE
<222> LOCATION: (12)
<223> OTHER INFORMATION: n equals a,t,g, or c
<220> FEATURE:
<221> NAME/KEY: SITE
<222> LOCATION: (24)
<223> OTHER INFORMATION: n equals a,t,g, or c
<220> FEATURE:
<221> NAME/KEY: SITE
<222> LOCATION: (31)
<223> OTHER INFORMATION: n equals a,t,g, or c
<220> FEATURE:
<221> NAME/KEY: SITE
<222> LOCATION: (69)
<223> OTHER INFORMATION: n equals a,t,g, or c
<220> FEATURE:
<221> NAME/KEY: SITE
<222> LOCATION: (102)
<223> OTHER INFORMATION: n equals a,t,g, or c
<220> FEATURE:
<221> NAME/KEY: SITE
<222> LOCATION: (200)
<223> OTHER INFORMATION: n equals a,t,g, or c

<400> SEQUENCE: 130
cccacacctg tntgagcggc gcangagccg nggcccgggc gggctgctcg gcgcggaaca 60
gtgctcggna tggcagggat tccagggctc ctcttccttc tnttctttct gctctgtgct 120
gttgggcaag taagccctta cagtgccccc tggaaaccca cttggcctgc ataccgcctc 180
cctgtcgtct tgccccagtn taccctcaat ttagccaagc cagactttgg agccgaagcc 240
aaattagaag tatcttcttc atgtggaccc cagtgtcata agggaact 288

<210> SEQ ID NO 131
<211> LENGTH: 423
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<220> FEATURE:
<221> NAME/KEY: SITE
<222> LOCATION: (49)
<223> OTHER INFORMATION: n equals a,t,g, or c
<220> FEATURE:
<221> NAME/KEY: SITE
<222> LOCATION: (61)
<223> OTHER INFORMATION: n equals a,t,g, or c
<220> FEATURE:
<221> NAME/KEY: SITE
<222> LOCATION: (79)
<223> OTHER INFORMATION: n equals a,t,g, or c
<220> FEATURE:
<221> NAME/KEY: SITE
<222> LOCATION: (90)
<223> OTHER INFORMATION: n equals a,t,g, or c
<220> FEATURE:
<221> NAME/KEY: SITE
<222> LOCATION: (224)
<223> OTHER INFORMATION: n equals a,t,g, or c
<220> FEATURE:
<221> NAME/KEY: SITE
<222> LOCATION: (251)
<223> OTHER INFORMATION: n equals a,t,g, or c
<220> FEATURE:
<221> NAME/KEY: SITE
<222> LOCATION: (272)
<223> OTHER INFORMATION: n equals a,t,g, or c
<220> FEATURE:
<221> NAME/KEY: SITE
<222> LOCATION: (300)
<223> OTHER INFORMATION: n equals a,t,g, or c
<220> FEATURE:
<221> NAME/KEY: SITE
<222> LOCATION: (308)
<223> OTHER INFORMATION: n equals a,t,g, or c
<220> FEATURE:
<221> NAME/KEY: SITE
<222> LOCATION: (315)
<223> OTHER INFORMATION: n equals a,t,g, or c
<220> FEATURE:
<221> NAME/KEY: SITE
<222> LOCATION: (363)
<223> OTHER INFORMATION: n equals a,t,g, or c
<220> FEATURE:
<221> NAME/KEY: SITE
<222> LOCATION: (375)
<223> OTHER INFORMATION: n equals a,t,g, or c
<220> FEATURE:
<221> NAME/KEY: SITE
<222> LOCATION: (392)
<223> OTHER INFORMATION: n equals a,t,g, or c
<220> FEATURE:
<221> NAME/KEY: SITE
<222> LOCATION: (396)
<223> OTHER INFORMATION: n equals a,t,g, or c
<220> FEATURE:
<221> NAME/KEY: SITE
<222> LOCATION: (405)
<223> OTHER INFORMATION: n equals a,t,g, or c

<400> SEQUENCE: 131
ggcanagggt ggtcgagggg ccaacgactc cacttcagcc atgcccganc agatgaaatt 60
ncagtggatc cgggtgaang cacccatgtn gccaagggtt ggatcaaggg caatgccaat 120
gaacatcggc atggattatg aattatgccc ctcctgggaa ctgcaaaaag ccccacaaga 180
gaaaatttat gaaagattgg ggtggagccc tcctgcttaa gcanctgcca gggggcagaa 240

-continued ttgcacttct ntggttatga acaatgaacc gnccagggca atttggtgtg atcgcttctn 300
tgaacgtnca aagangagga cctatggact tggttcttac ccagcaatgg ggattgcccc 360
agnccagggg gccancgggg tttggggggt tntttntttt aaggnttttt gggaaggggg 420
cca 423

<210> SEQ ID NO 132
<211> LENGTH: 145
<212> TYPE: DNA
<213> ORGANISM: Homo sapiens
<220> FEATURE:
<221> NAME/KEY: SITE
<222> LOCATION: (66)
<223> OTHER INFORMATION: n equals a,t,g, or c
<220> FEATURE:
<221> NAME/KEY: SITE
<222> LOCATION: (76)
<223> OTHER INFORMATION: n equals a,t,g, or c
<220> FEATURE:
<221> NAME/KEY: SITE
<222> LOCATION: (104)
<223> OTHER INFORMATION: n equals a,t,g, or c
<220> FEATURE:
<221> NAME/KEY: SITE
<222> LOCATION: (112)
<223> OTHER INFORMATION: n equals a,t,g, or c
<220> FEATURE:
<221> NAME/KEY: SITE
<222> LOCATION: (134)
<223> OTHER INFORMATION: n equals a,t,g, or c

<400> SEQUENCE: 132
ttgcatagaa ataaaaaaaa tactgatttg gggcaatgag gaatatttga caattaagtt 60
aatctncacg tttttncaaa ctttggattt ttatttcatc tgancttgtt tnaaagattt 120
atattaaata tttngcatac aagag 145

<210> SEQ ID NO 133
<211> LENGTH: 340
<212> TYPE: DNA
<213> ORGANISM: Homo sapiens
<220> FEATURE:
<221> NAME/KEY: SITE
<222> LOCATION: (260)
<223> OTHER INFORMATION: n equals a,t,g, or c
<220> FEATURE:
<221> NAME/KEY: SITE
<222> LOCATION: (295)
<223> OTHER INFORMATION: n equals a,t,g, or c
<220> FEATURE:
<221> NAME/KEY: SITE
<222> LOCATION: (313)
<223> OTHER INFORMATION: n equals a,t,g, or c
<220> FEATURE:
<221> NAME/KEY: SITE
<222> LOCATION: (314)
<223> OTHER INFORMATION: n equals a,t,g, or c

<400> SEQUENCE: 133
cagaagtggg agcgaaaaat tattggcatt ttttcagggc accagtgggt ggacatgaat 60
ggttccccac aggatttcaa cgtggctgtc agaatcactc ctctcaaata tgcccagatt 120
tgctattgga ttaaaggaaa ctacctggat tgtagggagg ggtgacacag tgttccctcc 180
tggcagcaat taagggtctt catgttctta ttttaggaga ggccaaattg ttttttgtca 240
ttggcgtgca cacgtgtgtn tggtgtgtgt ggtgtgtgtg taaaggtgtc ttatnaatct 300
ttttacccat ttnnttacaa ttgcaagatg actggcttta 340

-continued

<210> SEQ ID NO 134
<211> LENGTH: 99
<212> TYPE: DNA
<213> ORGANISM: Homo sapiens
<220> FEATURE:
<221> NAME/KEY: SITE
<222> LOCATION: (51)
<223> OTHER INFORMATION: n equals a,t,g, or c
<220> FEATURE:
<221> NAME/KEY: SITE
<222> LOCATION: (56)
<223> OTHER INFORMATION: n equals a,t,g, or c
<220> FEATURE:
<221> NAME/KEY: SITE
<222> LOCATION: (57)
<223> OTHER INFORMATION: n equals a,t,g, or c
<220> FEATURE:
<221> NAME/KEY: SITE
<222> LOCATION: (59)
<223> OTHER INFORMATION: n equals a,t,g, or c
<220> FEATURE:
<221> NAME/KEY: SITE
<222> LOCATION: (79)
<223> OTHER INFORMATION: n equals a,t,g, or c

<400> SEQUENCE: 134
ggagccgcgc gctctctccc ggcgcccaca cctgtctgag cggcgcacga ngccgnngnc 60
ccgggcgggc tgctcggcnc ggaacagtgc tcggcatgg 99

<210> SEQ ID NO 135
<211> LENGTH: 161
<212> TYPE: DNA
<213> ORGANISM: Homo sapiens
<220> FEATURE:
<221> NAME/KEY: SITE
<222> LOCATION: (4)
<223> OTHER INFORMATION: n equals a,t,g, or c
<220> FEATURE:
<221> NAME/KEY: SITE
<222> LOCATION: (12)
<223> OTHER INFORMATION: n equals a,t,g, or c
<220> FEATURE:
<221> NAME/KEY: SITE
<222> LOCATION: (28)
<223> OTHER INFORMATION: n equals a,t,g, or c
<220> FEATURE:
<221> NAME/KEY: SITE
<222> LOCATION: (58)
<223> OTHER INFORMATION: n equals a,t,g, or c
<220> FEATURE:
<221> NAME/KEY: SITE
<222> LOCATION: (101)
<223> OTHER INFORMATION: n equals a,t,g, or c
<220> FEATURE:
<221> NAME/KEY: SITE
<222> LOCATION: (109)
<223> OTHER INFORMATION: n equals a,t,g, or c
<220> FEATURE:
<221> NAME/KEY: SITE
<222> LOCATION: (152)
<223> OTHER INFORMATION: n equals a,t,g, or c
<220> FEATURE:
<221> NAME/KEY: SITE
<222> LOCATION: (156)
<223> OTHER INFORMATION: n equals a,t,g, or c
<220> FEATURE:
<221> NAME/KEY: SITE
<222> LOCATION: (157)
<223> OTHER INFORMATION: n equals a,t,g, or c

<400> SEQUENCE: 135
gcancgagcc gnggcccggg cgggctgntc ggcgcggaac agtgctccgg catggcanta 60
tattccaggg ctcctcttcc ttctgttctt tctgcttatg ngctgttgng caagtagagc 120
ccttacagtt gcccactgta aacccacttg gnctgnntac c 161

<210> SEQ ID NO 136
<211> LENGTH: 442
<212> TYPE: PRT
<213> ORGANISM: Homo sapiens

<400> SEQUENCE: 136

Met Ala Ser Val Val Leu Pro Ser Gly Ser Gln Cys Ala Ala Ala Ala
1 5 10 15

Ala Ala Ala Ala Pro Pro Gly Leu Arg Leu Arg Leu Leu Leu Leu Leu
20 25 30

Phe Ser Ala Ala Ala Leu Ile Pro Thr Gly Asp Gly Gln Asn Leu Phe
35 40 45

Thr Lys Asp Val Thr Val Ile Glu Gly Glu Val Ala Thr Ile Ser Cys
50 55 60

Gln Val Asn Lys Ser Asp Asp Ser Val Ile Gln Leu Leu Asn Pro Asn
65 70 75 80

Arg Gln Thr Ile Tyr Phe Arg Asp Phe Arg Pro Leu Lys Asp Ser Arg
85 90 95

Phe Gln Leu Leu Asn Phe Ser Ser Ser Glu Leu Lys Val Ser Leu Thr
100 105 110

Asn Val Ser Ile Ser Asp Glu Gly Arg Tyr Phe Cys Gln Leu Tyr Thr
115 120 125

Asp Pro Pro Gln Glu Ser Tyr Thr Thr Ile Thr Val Leu Val Pro Pro
130 135 140

Arg Asn Leu Met Ile Asp Ile Gln Lys Asp Thr Ala Val Glu Gly Glu
145 150 155 160

Glu Ile Glu Val Asn Cys Thr Ala Met Ala Ser Lys Pro Ala Thr Thr
165 170 175

Ile Arg Trp Phe Lys Gly Asn Thr Glu Leu Lys Gly Lys Ser Glu Val
180 185 190

Glu Glu Trp Ser Asp Met Tyr Thr Val Thr Ser Gln Leu Met Leu Lys
195 200 205

Val His Lys Glu Asp Asp Gly Val Pro Val Ile Cys Gln Val Glu His
210 215 220

Pro Ala Val Thr Gly Asn Leu Gln Thr Gln Arg Tyr Leu Glu Val Gln
225 230 235 240

Tyr Lys Pro Gln Val His Ile Gln Met Thr Tyr Pro Leu Gln Gly Leu
245 250 255

Thr Arg Glu Gly Asp Ala Leu Glu Leu Thr Cys Glu Ala Ile Gly Lys
260 265 270

Pro Gln Pro Val Met Val Thr Trp Val Arg Val Asp Asp Glu Met Pro
275 280 285

Gln His Ala Val Leu Ser Gly Pro Asn Leu Phe Ile Asn Asn Leu Asn
290 295 300

Lys Thr Asp Asn Gly Thr Tyr Arg Cys Glu Ala Ser Asn Ile Val Gly
305 310 315 320

Lys Ala His Ser Asp Tyr Met Leu Tyr Val Tyr Asp Pro Pro Thr Thr
325 330 335

Ile Pro Pro Pro Thr Thr Thr Thr Thr Thr Thr Thr Thr Thr Thr Thr
340 345 350

Thr Ile Leu Thr Ile Ile Thr Asp Ser Arg Ala Gly Glu Glu Gly Ser
355 360 365

-continued

```
Ile Arg Ala Val Asp His Ala Val Ile Gly Gly Val Val Ala Val Val
    370                 375                 380

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
                405                 410                 415

Ala Ala Asp Ala Asp Thr Ala Ile Ile Asn Ala Glu Gly Gly Gln Asn
            420                 425                 430

Asn Ser Glu Glu Lys Lys Glu Tyr Phe Ile
        435                 440


<210> SEQ ID NO 137
<211> LENGTH: 1329
<212> TYPE: DNA
<213> ORGANISM: Homo sapiens

<400> SEQUENCE: 137

atggcgagtg tagtgctgcc gagcggatcc cagtgtgcgg cggcagcggc ggcggcggcg     60

cctcccgggc tccggctccg gcttctgctg ttgctcttct ccgccgcggc actgatcccc    120

acaggtgatg ggcagaatct gtttacgaaa gacgtgacag tgatcgaggg agaggttgcg    180

accatcagtt gccaagtcaa taagagtgac gactctgtga ttcagctact gaatcccaac    240

aggcagacca tttatttcag ggacttcagg cctttgaagg acagcaggtt tcagttgctg    300

aatttttcta gcagtgaact caaagtatca ttgacaaacg tctcaatttc tgatgaagga    360

agatactttt gccagctcta taccgatccc ccacaggaaa gttacaccac catcacagtc    420

ctggtcccac cacgtaatct gatgatcgat atccagaaag acactgcggt ggaaggtgag    480

gagattgaag tcaactgcac tgctatggcc agcaagccag ccacgactat caggtggttc    540

aaagggaaca cagagctaaa aggcaaatcg gaggtggaag agtggtcaga catgtacact    600

gtgaccagtc agctgatgct gaaggtgcac aaggaggacg atggggtccc agtgatctgc    660

caggtggagc accctgcggt cactggaaac ctgcagaccc agcggtatct agaagtacag    720

tataagcctc aagtgcacat tcagatgact tatcctctac aaggcttaac ccgggaaggg    780

gacgcgcttg agttaacatg tgaagccatc gggaagcccc agcctgtgat ggtaacttgg    840

gtgagagtcg atgatgaaat gcctcaacac gccgtactgt ctgggcccaa cctgttcatc    900

aataacctaa acaaaacaga taatggtaca taccgctgtg aagcttcaaa catagtgggg    960

aaagctcact cggattatat gctgtatgta tacgatcccc ccacaactat ccctcctccc   1020

acaacaacca ccaccaccac caccaccacc accaccacca tccttaccat catcacagat   1080

tcccgagcag gtgaagaagg ctcgatcagg gcagtggatc atgccgtgat cggtggcgtc   1140

gtggcggtgg tggtgttcgc catgctgtgc ttgctcatca ttctggggcg ctattttgcc   1200

agacataaag gtacatactt cactcatgaa gccaaaggag ccgatgacgc agcagacgca   1260

gacacagcta taatcaatgc agaaggagga cagaacaact ccgaagaaaa gaaagagtac   1320

ttcatctag                                                           1329


<210> SEQ ID NO 138
<211> LENGTH: 538
<212> TYPE: PRT
<213> ORGANISM: Homo sapiens

<400> SEQUENCE: 138

Met Ala Arg Ala Ala Ala Leu Leu Pro Ser Arg Ser Pro Pro Thr Pro
```

-continued

```
 1               5                  10                  15

Leu Leu Trp Pro Leu Leu Leu Leu Leu Leu Leu Glu Thr Gly Ala Gln
            20                  25                  30

Asp Val Arg Val Gln Val Leu Pro Glu Val Arg Gly Gln Leu Gly Gly
        35                  40                  45

Thr Val Glu Leu Pro Cys His Leu Leu Pro Pro Val Pro Gly Leu Tyr
    50                  55                  60

Ile Ser Leu Val Thr Trp Gln Arg Pro Asp Ala Pro Ala Asn His Gln
65                  70                  75                  80

Asn Val Ala Ala Phe His Pro Lys Met Gly Pro Ser Phe Pro Ser Pro
                85                  90                  95

Lys Pro Gly Ser Glu Arg Leu Ser Phe Val Ser Ala Lys Gln Ser Thr
            100                 105                 110

Gly Gln Asp Thr Glu Ala Glu Leu Gln Asp Ala Thr Leu Ala Leu His
        115                 120                 125

Gly Leu Thr Val Glu Asp Glu Gly Asn Tyr Thr Cys Glu Phe Ala Thr
    130                 135                 140

Phe Pro Lys Gly Ser Val Arg Gly Met Thr Trp Leu Arg Val Ile Ala
145                 150                 155                 160

Lys Pro Lys Asn Gln Ala Glu Ala Gln Lys Val Thr Phe Ser Gln Asp
                165                 170                 175

Pro Thr Thr Val Ala Leu Cys Ile Ser Lys Glu Gly Arg Pro Pro Ala
            180                 185                 190

Arg Ile Ser Trp Leu Ser Ser Leu Asp Trp Glu Ala Lys Glu Thr Gln
        195                 200                 205

Val Ser Gly Thr Leu Ala Gly Thr Val Thr Val Thr Ser Arg Phe Thr
    210                 215                 220

Leu Val Pro Ser Gly Arg Ala Asp Gly Val Thr Val Thr Cys Lys Val
225                 230                 235                 240

Glu His Glu Ser Phe Glu Glu Pro Ala Leu Ile Pro Val Thr Leu Ser
                245                 250                 255

Val Arg Tyr Pro Pro Glu Val Ser Ile Ser Gly Tyr Asp Asp Asn Trp
            260                 265                 270

Tyr Leu Gly Arg Thr Asp Ala Thr Leu Ser Cys Asp Val Arg Ser Asn
        275                 280                 285

Pro Glu Pro Thr Gly Tyr Asp Trp Ser Thr Thr Ser Gly Thr Phe Pro
    290                 295                 300

Thr Ser Ala Val Ala Gln Gly Ser Gln Leu Val Ile His Ala Val Asp
305                 310                 315                 320

Ser Leu Phe Asn Thr Thr Phe Val Cys Thr Val Thr Asn Ala Val Gly
                325                 330                 335

Met Gly Arg Ala Glu Gln Val Ile Phe Val Arg Glu Thr Pro Asn Thr
            340                 345                 350

Ala Gly Ala Gly Ala Thr Gly Gly Ile Ile Gly Gly Ile Ile Ala Ala
        355                 360                 365

Ile Ile Ala Thr Ala Val Ala Ala Thr Gly Ile Leu Ile Cys Arg Gln
    370                 375                 380

Gln Arg Lys Glu Gln Thr Leu Gln Gly Ala Glu Glu Asp Glu Asp Leu
385                 390                 395                 400

Glu Gly Pro Pro Ser Tyr Lys Pro Pro Thr Pro Lys Ala Lys Leu Glu
                405                 410                 415

Ala Gln Glu Met Pro Ser Gln Leu Phe Thr Leu Gly Ala Ser Glu His
            420                 425                 430
```

```
Ser Pro Leu Lys Thr Pro Tyr Phe Asp Ala Gly Ala Ser Cys Thr Glu
        435                 440                 445

Gln Glu Met Pro Arg Tyr His Glu Leu Pro Thr Leu Glu Glu Arg Ser
    450                 455                 460

Gly Pro Leu His Pro Gly Ala Thr Ser Leu Gly Ser Pro Ile Pro Val
465                 470                 475                 480

Pro Pro Gly Pro Pro Ala Val Glu Asp Val Ser Leu Asp Leu Glu Asp
                485                 490                 495

Glu Glu Gly Glu Glu Glu Glu Glu Tyr Leu Asp Lys Ile Asn Pro Ile
            500                 505                 510

Tyr Asp Ala Leu Ser Tyr Ser Ser Pro Ser Asp Ser Tyr Gln Gly Lys
        515                 520                 525

Gly Phe Val Met Ser Arg Ala Met Tyr Val
    530                 535


<210> SEQ ID NO 139
<211> LENGTH: 499
<212> TYPE: DNA
<213> ORGANISM: Homo sapiens
<220> FEATURE:
<221> NAME/KEY: SITE
<222> LOCATION: (76)
<223> OTHER INFORMATION: n equals a,t,g, or c
<220> FEATURE:
<221> NAME/KEY: SITE
<222> LOCATION: (188)
<223> OTHER INFORMATION: n equals a,t,g, or c
<220> FEATURE:
<221> NAME/KEY: SITE
<222> LOCATION: (203)
<223> OTHER INFORMATION: n equals a,t,g, or c
<220> FEATURE:
<221> NAME/KEY: SITE
<222> LOCATION: (238)
<223> OTHER INFORMATION: n equals a,t,g, or c
<220> FEATURE:
<221> NAME/KEY: SITE
<222> LOCATION: (342)
<223> OTHER INFORMATION: n equals a,t,g, or c
<220> FEATURE:
<221> NAME/KEY: SITE
<222> LOCATION: (347)
<223> OTHER INFORMATION: n equals a,t,g, or c
<220> FEATURE:
<221> NAME/KEY: SITE
<222> LOCATION: (359)
<223> OTHER INFORMATION: n equals a,t,g, or c
<220> FEATURE:
<221> NAME/KEY: SITE
<222> LOCATION: (382)
<223> OTHER INFORMATION: n equals a,t,g, or c
<220> FEATURE:
<221> NAME/KEY: SITE
<222> LOCATION: (393)
<223> OTHER INFORMATION: n equals a,t,g, or c
<220> FEATURE:
<221> NAME/KEY: SITE
<222> LOCATION: (395)
<223> OTHER INFORMATION: n equals a,t,g, or c
<220> FEATURE:
<221> NAME/KEY: SITE
<222> LOCATION: (405)
<223> OTHER INFORMATION: n equals a,t,g, or c
<220> FEATURE:
<221> NAME/KEY: SITE
<222> LOCATION: (406)
<223> OTHER INFORMATION: n equals a,t,g, or c
<220> FEATURE:
<221> NAME/KEY: SITE
<222> LOCATION: (431)
<223> OTHER INFORMATION: n equals a,t,g, or c
```

-continued

<220> FEATURE:
<221> NAME/KEY: SITE
<222> LOCATION: (440)
<223> OTHER INFORMATION: n equals a,t,g, or c
<220> FEATURE:
<221> NAME/KEY: SITE
<222> LOCATION: (444)
<223> OTHER INFORMATION: n equals a,t,g, or c
<220> FEATURE:
<221> NAME/KEY: SITE
<222> LOCATION: (446)
<223> OTHER INFORMATION: n equals a,t,g, or c
<220> FEATURE:
<221> NAME/KEY: SITE
<222> LOCATION: (449)
<223> OTHER INFORMATION: n equals a,t,g, or c
<220> FEATURE:
<221> NAME/KEY: SITE
<222> LOCATION: (469)
<223> OTHER INFORMATION: n equals a,t,g, or c
<220> FEATURE:
<221> NAME/KEY: SITE
<222> LOCATION: (471)
<223> OTHER INFORMATION: n equals a,t,g, or c

<400> SEQUENCE: 139
gacacgaggc aaatcggagg tggaagagtg gtcagacatg tacactgtga ccagtcagct 60
gatgctgaag gtgcanaagg aggacgatgg ggtcccagtg atctgccagg tggagcaccc 120
tgcggtcact ggaaacctgc agacccagcg gtatctagaa gtacagtata agcctcaagt 180
gcacattnag atgacttatc ctntacaagg cttaacccgg gaaggggacg cgcttgantt 240
aacatgtgaa gccatcggga agccccagcc tgtgaatggt aaacttgggt gagaagtgcg 300
atgatgaaat gcctcaacac gccgtactgt ttgggcccaa cntgttncat tcattaacnt 360
aaacaaaaca gttaatggta cntaccgttg tgnangtttc aaacnnagtg ggggaaagtt 420
cattcgggtt ntatgctgtn tgtntnagnt tccccccaca attttcctnc ntcccacaac 480
aaccaccacc accaccacc 499

<210> SEQ ID NO 140
<211> LENGTH: 245
<212> TYPE: DNA
<213> ORGANISM: Homo sapiens
<220> FEATURE:
<221> NAME/KEY: SITE
<222> LOCATION: (44)
<223> OTHER INFORMATION: n equals a,t,g, or c
<220> FEATURE:
<221> NAME/KEY: SITE
<222> LOCATION: (46)
<223> OTHER INFORMATION: n equals a,t,g, or c
<220> FEATURE:
<221> NAME/KEY: SITE
<222> LOCATION: (152)
<223> OTHER INFORMATION: n equals a,t,g, or c
<220> FEATURE:
<221> NAME/KEY: SITE
<222> LOCATION: (154)
<223> OTHER INFORMATION: n equals a,t,g, or c

<400> SEQUENCE: 140
caagttccaa tatcactgtc tctttatcat ctaaataggg ccantnggac acctcattga 60
aacaaaaagg ctgatctaga tgaagtactc tttcttttct tcggagttgt tctgtcctcc 120
ttctgcattg attatagctg tgtctgcgtc tncngcgtca tcggctcctt tggcttcatg 180
agtgaagtat gtacctttat gtctggcaaa atagcgcccc agaatgatga gcaagcacag 240
catgg 245

-continued

<210> SEQ ID NO 141
<211> LENGTH: 324
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<220> FEATURE:
<221> NAME/KEY: SITE
<222> LOCATION: (94)
<223> OTHER INFORMATION: n equals a,t,g, or c
<220> FEATURE:
<221> NAME/KEY: SITE
<222> LOCATION: (148)
<223> OTHER INFORMATION: n equals a,t,g, or c
<220> FEATURE:
<221> NAME/KEY: SITE
<222> LOCATION: (256)
<223> OTHER INFORMATION: n equals a,t,g, or c
<220> FEATURE:
<221> NAME/KEY: SITE
<222> LOCATION: (316)
<223> OTHER INFORMATION: n equals a,t,g, or c
<220> FEATURE:
<221> NAME/KEY: SITE
<222> LOCATION: (317)
<223> OTHER INFORMATION: n equals a,t,g, or c
<220> FEATURE:
<221> NAME/KEY: SITE
<222> LOCATION: (322)
<223> OTHER INFORMATION: n equals a,t,g, or c
<220> FEATURE:
<221> NAME/KEY: SITE
<222> LOCATION: (324)
<223> OTHER INFORMATION: n equals a,t,g, or c

<400> SEQUENCE: 141
ggcanaggga acacagagct aaaaggcaaa tcggaggtgg aagagtggtc agacatgtac 60
actgtgaacc agtcagctga tgctgaaggt gcanaaggag gacgatgggg tcccagtgaa 120
tctgccaggt ggagcaccct gcggtcantg gaaacctgca gacccagcgg tatctagaag 180
tacagtataa gcctcaagtg cacatttcag atgacttatc ctgtacaagg cttaacccgg 240
aaggggacgc gctttnagtt taacatgtga agccatcggg gaagccccca gcctgtgaat 300
ggtaaatttg ggttannagt cngn 324

<210> SEQ ID NO 142
<211> LENGTH: 468
<212> TYPE: DNA
<213> ORGANISM: Homo sapiens
<220> FEATURE:
<221> NAME/KEY: SITE
<222> LOCATION: (89)
<223> OTHER INFORMATION: n equals a,t,g, or c
<220> FEATURE:
<221> NAME/KEY: SITE
<222> LOCATION: (226)
<223> OTHER INFORMATION: n equals a,t,g, or c
<220> FEATURE:
<221> NAME/KEY: SITE
<222> LOCATION: (242)
<223> OTHER INFORMATION: n equals a,t,g, or c
<220> FEATURE:
<221> NAME/KEY: SITE
<222> LOCATION: (245)
<223> OTHER INFORMATION: n equals a,t,g, or c
<220> FEATURE:
<221> NAME/KEY: SITE
<222> LOCATION: (298)
<223> OTHER INFORMATION: n equals a,t,g, or c
<220> FEATURE:
<221> NAME/KEY: SITE

```
<222> LOCATION: (314)
<223> OTHER INFORMATION: n equals a,t,g, or c
<220> FEATURE:
<221> NAME/KEY: SITE
<222> LOCATION: (322)
<223> OTHER INFORMATION: n equals a,t,g, or c
<220> FEATURE:
<221> NAME/KEY: SITE
<222> LOCATION: (343)
<223> OTHER INFORMATION: n equals a,t,g, or c
<220> FEATURE:
<221> NAME/KEY: SITE
<222> LOCATION: (348)
<223> OTHER INFORMATION: n equals a,t,g, or c
<220> FEATURE:
<221> NAME/KEY: SITE
<222> LOCATION: (377)
<223> OTHER INFORMATION: n equals a,t,g, or c
<220> FEATURE:
<221> NAME/KEY: SITE
<222> LOCATION: (385)
<223> OTHER INFORMATION: n equals a,t,g, or c
<220> FEATURE:
<221> NAME/KEY: SITE
<222> LOCATION: (408)
<223> OTHER INFORMATION: n equals a,t,g, or c
<220> FEATURE:
<221> NAME/KEY: SITE
<222> LOCATION: (414)
<223> OTHER INFORMATION: n equals a,t,g, or c
<220> FEATURE:
<221> NAME/KEY: SITE
<222> LOCATION: (421)
<223> OTHER INFORMATION: n equals a,t,g, or c
<220> FEATURE:
<221> NAME/KEY: SITE
<222> LOCATION: (423)
<223> OTHER INFORMATION: n equals a,t,g, or c
<220> FEATURE:
<221> NAME/KEY: SITE
<222> LOCATION: (426)
<223> OTHER INFORMATION: n equals a,t,g, or c
<220> FEATURE:
<221> NAME/KEY: SITE
<222> LOCATION: (428)
<223> OTHER INFORMATION: n equals a,t,g, or c
<220> FEATURE:
<221> NAME/KEY: SITE
<222> LOCATION: (432)
<223> OTHER INFORMATION: n equals a,t,g, or c
<220> FEATURE:
<221> NAME/KEY: SITE
<222> LOCATION: (439)
<223> OTHER INFORMATION: n equals a,t,g, or c
<220> FEATURE:
<221> NAME/KEY: SITE
<222> LOCATION: (442)
<223> OTHER INFORMATION: n equals a,t,g, or c
<220> FEATURE:
<221> NAME/KEY: SITE
<222> LOCATION: (461)
<223> OTHER INFORMATION: n equals a,t,g, or c

<400> SEQUENCE: 142

gaattcggca gagcaggtgc ccgacatggc gagtgtactg ctgccgagcg gatcccagtg      60

tgcggcggca cggcggcggc ggcgctgcnc gggctccggc tccggcttct gctgttgctc     120

ttctccgccg cggcactgat ccccacaggt gatgggcaga atctgtttac gaaagacgtg     180

acagtgatcg agggagaggt tgcgaccatc agttgccaag tcaatnaaga gtgacgactc     240

tntgnattca gctactgaat cccaacaggc agaccattta tttcagggga cttcaggnct     300

ttgaaggaca gcangttttc anttgcttga aatttttcta gcnattgnaa ctcaaaagtg     360

ttcatttgac aaacgtntca atttntgatg aagggaggtt aatttttngc caantttttt     420
```

-continued

```
nanccntncc cnaacaggna anttacaacc acctttaaaa ntcctggt                468


<210> SEQ ID NO 143
<211> LENGTH: 279
<212> TYPE: DNA
<213> ORGANISM: Homo sapiens
<220> FEATURE:
<221> NAME/KEY: SITE
<222> LOCATION: (23)
<223> OTHER INFORMATION: n equals a,t,g, or c
<220> FEATURE:
<221> NAME/KEY: SITE
<222> LOCATION: (118)
<223> OTHER INFORMATION: n equals a,t,g, or c
<220> FEATURE:
<221> NAME/KEY: SITE
<222> LOCATION: (190)
<223> OTHER INFORMATION: n equals a,t,g, or c
<220> FEATURE:
<221> NAME/KEY: SITE
<222> LOCATION: (201)
<223> OTHER INFORMATION: n equals a,t,g, or c
<220> FEATURE:
<221> NAME/KEY: SITE
<222> LOCATION: (223)
<223> OTHER INFORMATION: n equals a,t,g, or c
<220> FEATURE:
<221> NAME/KEY: SITE
<222> LOCATION: (238)
<223> OTHER INFORMATION: n equals a,t,g, or c
<220> FEATURE:
<221> NAME/KEY: SITE
<222> LOCATION: (260)
<223> OTHER INFORMATION: n equals a,t,g, or c

<400> SEQUENCE: 143

aaatgcctca acacgccgta ctntctgggc ccaacctgtt catcaataac ctaaacaaaa     60

cagataatgg tacataccgc tgtgaagctt caaacatagt ggggaaagct cactcggntt    120

atatgctgta tgtatacgat ccccccacaa ctatccctcc tcccacaaca accaccacca    180

ccaccaccan caccaccacc nccatcctta ccatcatcac agnttcccga gcaggtgnag    240

aaggctcgat cagggcagtn gatcatgccg tgatcggtg                          279


<210> SEQ ID NO 144
<211> LENGTH: 393
<212> TYPE: PRT
<213> ORGANISM: Homo sapiens

<400> SEQUENCE: 144

Met Trp Trp Arg Val Leu Ser Leu Leu Ala Trp Phe Pro Leu Gln Glu
1               5                   10                  15

Ala Ser Leu Thr Asn His Thr Glu Thr Ile Thr Val Glu Glu Gly Gln
            20                  25                  30

Thr Leu Thr Leu Lys Cys Val Thr Ser Leu Arg Lys Asn Ser Ser Leu
        35                  40                  45

Gln Trp Leu Thr Pro Ser Gly Phe Thr Ile Phe Leu Asn Glu Tyr Pro
    50                  55                  60

Ala Leu Lys Asn Ser Lys Tyr Gln Leu Leu His His Ser Ala Asn Gln
65                  70                  75                  80

Leu Ser Ile Thr Val Pro Asn Val Thr Leu Gln Asp Glu Gly Val Tyr
                85                  90                  95

Lys Cys Leu His Tyr Ser Asp Ser Val Ser Thr Lys Glu Val Lys Val
            100                 105                 110

Ile Val Leu Ala Thr Pro Phe Lys Pro Ile Leu Glu Ala Ser Val Ile
        115                 120                 125
```

```
Arg Lys Gln Asn Gly Glu Glu His Val Val Leu Met Cys Ser Thr Met
    130                 135                 140

Arg Ser Lys Pro Pro Pro Gln Ile Thr Trp Leu Leu Gly Asn Ser Met
145                 150                 155                 160

Glu Val Ser Gly Gly Thr Leu His Glu Phe Glu Thr Asp Gly Lys Lys
                165                 170                 175

Cys Asn Thr Thr Ser Thr Leu Ile Ile Leu Ser Tyr Gly Lys Asn Ser
            180                 185                 190

Thr Val Asp Cys Ile Ile Arg His Arg Gly Leu Gln Gly Arg Lys Leu
        195                 200                 205

Val Ala Pro Phe Arg Phe Glu Asp Leu Val Thr Asp Glu Glu Thr Ala
    210                 215                 220

Ser Asp Ala Leu Glu Arg Asn Ser Leu Ser Thr Gln Asp Pro Gln Gln
225                 230                 235                 240

Pro Thr Ser Thr Val Ser Val Thr Glu Asp Ser Ser Thr Ser Glu Ile
                245                 250                 255

Asp Lys Glu Glu Lys Glu Gln Thr Thr Gln Asp Pro Asp Leu Thr Thr
            260                 265                 270

Glu Ala Asn Pro Gln Tyr Leu Gly Leu Ala Arg Lys Lys Ser Gly Ile
        275                 280                 285

Leu Leu Leu Thr Leu Val Ser Phe Leu Ile Phe Ile Leu Phe Ile Ile
    290                 295                 300

Val Gln Leu Phe Ile Met Lys Leu Arg Lys Ala His Val Ile Trp Lys
305                 310                 315                 320

Arg Glu Asn Glu Val Ser Glu His Thr Leu Glu Ser Tyr Arg Ser Arg
                325                 330                 335

Ser Asn Asn Glu Glu Thr Ser Ser Glu Glu Lys Asn Gly Gln Ser Ser
            340                 345                 350

Leu Pro Met Arg Cys Met Asn Tyr Ile Thr Lys Leu Tyr Ser Glu Ala
        355                 360                 365

Lys Thr Lys Arg Lys Glu Asn Val Gln His Ser Lys Leu Glu Glu Lys
    370                 375                 380

His Ile Gln Val Pro Glu Ser Ile Val
385                 390


<210> SEQ ID NO 145
<211> LENGTH: 439
<212> TYPE: PRT
<213> ORGANISM: Homo sapiens

<400> SEQUENCE: 145

Met Thr Phe Thr Thr Val Leu His Val Ala Ala Leu Leu Leu Leu Gln
  1               5                  10                  15

Gly Asp Phe Pro Gly Ala Gly Ser Glu Thr Ile Thr Val Gln Glu Gly
             20                  25                  30

Glu Asp Leu Asn Leu Arg Cys Thr Phe Thr Gly Asp Ser Arg Ala Thr
         35                  40                  45

Lys Gln Trp Leu Asn Pro Arg Gly Phe Thr Ile Phe Leu Asp Asn His
     50                  55                  60

Trp Gly Leu Lys Asp Gln Arg Tyr Arg Leu Ile His Tyr Ser Glu Asp
 65                  70                  75                  80

Glu Leu Ser Ile Arg Leu Ser Asn Ile Thr Val His Asp Glu Gly Val
                 85                  90                  95

Tyr Lys Cys Tyr Tyr Tyr Ser Thr Pro Phe Arg Ser Lys Met Thr Thr
```

-continued

```
            100                 105                 110

Val Glu Val Leu Ala Ala Pro Ser Lys Pro Val Leu Gln Val Ser Arg
        115                 120                 125

Asp Thr Glu Gly Arg Val Thr Leu Ser Cys Tyr Thr Gln Gly Cys Lys
    130                 135                 140

Pro Gln Pro Gln Ile Thr Trp Leu Leu Asp Asn Gly Ile Gln Leu Pro
145                 150                 155                 160

Gly Asp Thr Arg His Lys Leu Glu Ala Asp Gly Lys Lys Trp Thr Thr
                165                 170                 175

Thr Ser Thr Leu Thr Val Leu Ala Tyr Gly Pro Asn Ser Thr Ala Thr
            180                 185                 190

Cys Leu Val His His Lys Ala Leu Gly Gly Gly Lys Leu Thr Glu Pro
        195                 200                 205

Phe Gln Phe Glu Asp Val Ala Arg Thr Val Ala Asn Thr Thr Pro Val
    210                 215                 220

Ser Thr Thr Leu Glu Val Asp Thr Tyr Val Ser Glu Tyr Val Gln Pro
225                 230                 235                 240

Thr Val Thr Thr Ala Glu Ser Asp Leu Asn Ser Asn Thr Asp Phe Ser
                245                 250                 255

Pro Ser Tyr Pro Gln His Asn Gly Ser Gly Ala Thr Ser Val Ala Ala
            260                 265                 270

Gly Glu Leu Ser Gly Thr Ser Ala His His Ile Pro Glu Gly Thr Glu
        275                 280                 285

Thr Ala Leu Asn Gly Thr Val Thr Glu Glu Leu Phe Arg Thr Glu Ala
    290                 295                 300

Ser Phe Pro Ser Glu Asn Val Thr Leu Ile Ser Ile Val Thr Phe Glu
305                 310                 315                 320

Gln Asp Val Lys Ser Glu Gly Met Ser Lys Lys Glu Lys Asp Phe Leu
                325                 330                 335

Leu Pro Leu Leu Val Ala Val Leu Ile Val Met Leu Leu Ile Ile Val
            340                 345                 350

Val Leu Phe Ser Lys Lys Leu Ile Lys Pro His Gly Val Trp Lys Arg
        355                 360                 365

Glu Asn Asp Thr Ser Asp Gln Thr Leu Glu Ser Tyr Lys Ser Lys Ser
    370                 375                 380

Asn Glu Glu Ser Pro Gly His Glu Lys Asn Gly Gln Ala Val Ser Gln
385                 390                 395                 400

Lys Pro Asn Met Gln Tyr Val Thr Glu Gly Tyr Val Glu Ala Thr Gln
                405                 410                 415

Lys Asn Pro Ser Glu Lys Asn Thr Lys Leu Pro Glu Glu Gln Phe Ala
            420                 425                 430

Arg Gly Lys Glu Thr Asp Val
        435


<210> SEQ ID NO 146
<211> LENGTH: 252
<212> TYPE: PRT
<213> ORGANISM: Homo sapiens

<400> SEQUENCE: 146

Ser Arg Asp Gly Phe His Arg Val Ser Gln Asp Gly Leu Asp Leu Leu
  1               5                  10                  15

Thr Pro Cys Ser Ser Pro Leu Gly Leu Pro Lys Cys Trp Asp Tyr Arg
             20                  25                  30
```

-continued

```
Gly Asp Pro Pro Arg Pro Val Leu Glu Asp Gly Ser Glu Ser Leu Glu
        35                  40                  45

Tyr Leu Ser Ser Ser Asn Leu Lys Glu Val Leu Ala Cys Arg Gly Ser
    50                  55                  60

Leu His Gly Trp Ala Gln Leu Val His Leu Pro Phe Ser Ala Tyr Ala
65                  70                  75                  80

Gly Tyr Ser Ser Glu Pro Gly Thr Leu Leu Ser Ala Glu Leu Lys Leu
                85                  90                  95

His Thr Met Val Leu Trp Pro Gln Phe Tyr Arg Ser Ile Leu Tyr Leu
            100                 105                 110

Leu Tyr Trp Leu Leu Arg Gly Arg Arg Asn Asn Thr Lys Pro Lys Pro
        115                 120                 125

Phe Cys Cys Asp His Pro Pro Ser Tyr Pro Leu His Phe Arg Leu Tyr
    130                 135                 140

Gln Met Glu Lys Thr Leu Ser Gly Asp Val His His Gln Tyr Tyr His
145                 150                 155                 160

Gln Asp Phe Ser Arg Lys Tyr Tyr His Pro Gly Ile Cys Trp Leu Gln
                165                 170                 175

Leu Leu Leu Leu Ser Ala Pro Phe His Ser Ile Asn Met Leu Arg Glu
            180                 185                 190

Phe Ala Ile Leu Ser Asn Ile Leu Met His Ser His Lys Leu Gln Cys
        195                 200                 205

Asn Ser Leu Leu Phe Met Tyr Lys Val Arg Asn Leu Cys Leu Leu Pro
    210                 215                 220

Cys Trp His Leu Pro Leu Lys Ser Lys Ser Lys Cys Ser Tyr Ala Arg
225                 230                 235                 240

Glu Ser Arg Val Thr Leu Phe Tyr Gly Ser Cys Ser
                245                 250
```

<210> SEQ ID NO 147
<211> LENGTH: 369
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<220> FEATURE:
<221> NAME/KEY: SITE
<222> LOCATION: (19)
<223> OTHER INFORMATION: n equals a,t,g, or c
<220> FEATURE:
<221> NAME/KEY: SITE
<222> LOCATION: (80)
<223> OTHER INFORMATION: n equals a,t,g, or c
<220> FEATURE:
<221> NAME/KEY: SITE
<222> LOCATION: (152)
<223> OTHER INFORMATION: n equals a,t,g, or c
<220> FEATURE:
<221> NAME/KEY: SITE
<222> LOCATION: (251)
<223> OTHER INFORMATION: n equals a,t,g, or c
<220> FEATURE:
<221> NAME/KEY: SITE
<222> LOCATION: (255)
<223> OTHER INFORMATION: n equals a,t,g, or c
<220> FEATURE:
<221> NAME/KEY: SITE
<222> LOCATION: (286)
<223> OTHER INFORMATION: n equals a,t,g, or c
<220> FEATURE:
<221> NAME/KEY: SITE
<222> LOCATION: (301)
<223> OTHER INFORMATION: n equals a,t,g, or c -continued
<220> FEATURE:
<221> NAME/KEY: SITE
<222> LOCATION: (346)
<223> OTHER INFORMATION: n equals a,t,g, or c
<220> FEATURE:
<221> NAME/KEY: SITE
<222> LOCATION: (350)
<223> OTHER INFORMATION: n equals a,t,g, or c
<220> FEATURE:
<221> NAME/KEY: SITE
<222> LOCATION: (368)
<223> OTHER INFORMATION: n equals a,t,g, or c

<400> SEQUENCE: 147
ggcanagtga caccagggna gggaattaat tctcccaagg aaaacgcatt gagttacatg 60
aaaaggggtc taggattgan cactgcactg agaaacaaca acatctagat gatggatagg 120
ggaggaagaa agatttcagt taaggagaat gnaagtttct cctgaaatga aaggaagaaa 180
accaggatag tgccatgcaa aggaaggtgt ttcaaagagg aggaagagat taacagtgcc 240
aaatgcgact ncgantgtca aagaagtttg aaagaaataa gggttntcct gggtagcctt 300
ngttagagta gttctggtgg aatggtagac atgggagtta cctttntatn ggttgggaag 360 gaaagggng 369

<210> SEQ ID NO 148
<211> LENGTH: 2338
<212> TYPE: DNA
<213> ORGANISM: Homo sapiens
<220> FEATURE:
<221> NAME/KEY: SITE
<222> LOCATION: (3)
<223> OTHER INFORMATION: n equals a,t,g, or c
<220> FEATURE:
<221> NAME/KEY: SITE
<222> LOCATION: (6)
<223> OTHER INFORMATION: n equals a,t,g, or c
<220> FEATURE:
<221> NAME/KEY: SITE
<222> LOCATION: (9)
<223> OTHER INFORMATION: n equals a,t,g, or c
<220> FEATURE:
<221> NAME/KEY: SITE
<222> LOCATION: (11)
<223> OTHER INFORMATION: n equals a,t,g, or c
<220> FEATURE:
<221> NAME/KEY: SITE
<222> LOCATION: (12)
<223> OTHER INFORMATION: n equals a,t,g, or c
<220> FEATURE:
<221> NAME/KEY: SITE
<222> LOCATION: (17)
<223> OTHER INFORMATION: n equals a,t,g, or c
<220> FEATURE:
<221> NAME/KEY: SITE
<222> LOCATION: (18)
<223> OTHER INFORMATION: n equals a,t,g, or c
<220> FEATURE:
<221> NAME/KEY: SITE
<222> LOCATION: (21)
<223> OTHER INFORMATION: n equals a,t,g, or c
<220> FEATURE:
<221> NAME/KEY: SITE
<222> LOCATION: (23)
<223> OTHER INFORMATION: n equals a,t,g, or c
<220> FEATURE:
<221> NAME/KEY: SITE
<222> LOCATION: (25)
<223> OTHER INFORMATION: n equals a,t,g, or c
<220> FEATURE:
<221> NAME/KEY: SITE
<222> LOCATION: (26)
<223> OTHER INFORMATION: n equals a,t,g, or c
<220> FEATURE:

-continued

<221> NAME/KEY: SITE
<222> LOCATION: (27)
<223> OTHER INFORMATION: n equals a,t,g, or c
<220> FEATURE:
<221> NAME/KEY: SITE
<222> LOCATION: (28)
<223> OTHER INFORMATION: n equals a,t,g, or c
<220> FEATURE:
<221> NAME/KEY: SITE
<222> LOCATION: (29)
<223> OTHER INFORMATION: n equals a,t,g, or c
<220> FEATURE:
<221> NAME/KEY: SITE
<222> LOCATION: (30)
<223> OTHER INFORMATION: n equals a,t,g, or c
<220> FEATURE:
<221> NAME/KEY: SITE
<222> LOCATION: (31)
<223> OTHER INFORMATION: n equals a,t,g, or c
<220> FEATURE:
<221> NAME/KEY: SITE
<222> LOCATION: (32)
<223> OTHER INFORMATION: n equals a,t,g, or c
<220> FEATURE:
<221> NAME/KEY: SITE
<222> LOCATION: (33)
<223> OTHER INFORMATION: n equals a,t,g, or c
<220> FEATURE:
<221> NAME/KEY: SITE
<222> LOCATION: (34)
<223> OTHER INFORMATION: n equals a,t,g, or c
<220> FEATURE:
<221> NAME/KEY: SITE
<222> LOCATION: (37)
<223> OTHER INFORMATION: n equals a,t,g, or c
<220> FEATURE:
<221> NAME/KEY: SITE
<222> LOCATION: (38)
<223> OTHER INFORMATION: n equals a,t,g, or c

<400> SEQUENCE: 148
crnatndwnd nnsdaynnct nbnrnnnnnn nnnnamnnta cggtgggagg tctatataag 60
cagagctctc tggctaacta gagaacccac tgcttactgg cttatcgaaa ttaatacgac 120
tcactatagg gagacccaag cttgatatcg aattcgcggc cgctcctgtc tcaggcaggc 180
cctgcgcctc ctatgcggag atgctactgc cactgctgct gtcctcgctg ctgggcgggt 240
cccaggctat ggatgggaga ttctggatac gagtgcagga gtcagtgatg gtgccggagg 300
gcctgtgcat ctctgtgccc tgctctttct cctacccccg acaagactgg acagggtcta 360
ccccagctta tggctactgg ttcaaagcag tgactgagac aaccaagggt gctcctgtgg 420
ccacaaacca ccagagtcga gaggtggaaa tgagcacccg gggccgattc cagctcactg 480
gggatcccgc caaggggaac tgctccttgg tgatcagaga cgcgcagatg caggatgagt 540
cacagtactt ctttcgggtg gagagaggaa gctatgtgag atataatttc atgaacgatg 600
ggttctttct aaaagtaaca gccctgactc agaagcctga tgtctacatc cccgagaccc 660
tggagcccgg gcagccggtg acggtcatct gtgtgtttaa ctgggccttt gaggaatgtc 720
cacccccttc tttctcctgg acgggggctg ccctctcctc ccaaggaacc aaaccaacga 780
cctcccactt ctcagtgctc agcttcacgc ccagacccca ggaccacaac accgacctca 840
cctgccatgt ggacttctcc agaaagggtg tgagcgtaca gaggaccgtc cgactccgtg 900
tggcctatgc ccccagagac cttgttatca gcatttcacg tgacaacacg ccagccctgg 960
agccccagcc ccagggaaat gtcccatacc tggaagccca aaaaggccag ttcctgcggc 1020
tcctctgtgc tgctgacagc cagcccccctg ccacactgag ctgggtcctg cagaacagag 1080
tcctctcctc gtcccatccc tggggcccta gacccctggg gctggagctg cccggggtga 1140

-continued

```
aggctgggga ttcagggcgc tacacctgcc gagcggagaa caggcttggc tcccagcagc   1200
gagccctgga cctctctgtg cagtatcctc cagagaacct gagagtgatg gtttcccaag   1260
caaacaggac agtcctggaa aaccttggga acggcacgtc tctcccagta ctggagggcc   1320
aaagcctgtg cctggtctgt gtcacacaca gcagcccccc agccaggctg agctggaccc   1380
agaggggaca ggttctgagc cctcccagc cctcagaccc cggggtcctg gagctgcctc    1440
gggttcaagt ggagcacgaa ggagagttca cctgccacgc tcggcaccca ctgggctccc   1500
agcacgtctc tctcagcctc tccgtgcact actccccgaa gctgctgggc ccctcctgct   1560
cctgggaggc tgagggtctg cactgcagct gctcctccca ggccagcccg gccccctctc   1620
tgcgctggtg gcttggggag gagctgctgg aggggaacag cagccaggac tccttcgagg   1680
tcacccccag ctcagccggg ccctgggcca acagctccct gagcctccat ggagggctca   1740
gctctggcct caggctccgc tgtgaggcct ggaacgtcca tggggcccag agtggatcca   1800
tcctgcagct gccagataag aagggactca tctcaacggc attctccaac ggagcgtttc   1860
tgggaatcgg catcacggct cttcttttcc tctgcctggc cctgatcatc atgaagattc   1920
taccgaagag acggactcag acagaaaccc cgaggcccag gttctcccgg cacagcacga   1980
tcctggatta catcaatgtg gtcccgacgg ctggcccccct ggctcagaag cggaatcaga  2040
aagccacacc aaacagtcct cggacccctc ttccaccagg tgctccctcc ccagaatcaa   2100
agaagaacca gaaaaagcag tatcagttgc ccagtttccc agaacccaaa tcatccactc   2160
aagccccaga atcccaggag agccaagagg agctccatta tgccacgctc aacttcccag   2220
gcgtcagacc caggcctgag gcccggatgc ccaagggcac ccaggcggat tatgcagaag   2280
tcaagttcca atgagggtct cttaggcttt aggactggga cttcggctag ggaggaag     2338
```

<210> SEQ ID NO 149
<211> LENGTH: 697
<212> TYPE: PRT
<213> ORGANISM: Homo sapiens

<400> SEQUENCE: 149

```
Met Leu Leu Pro Leu Leu Leu Ser Ser Leu Leu Gly Gly Ser Gln Ala
  1               5                  10                  15

Met Asp Gly Arg Phe Trp Ile Arg Val Gln Glu Ser Val Met Val Pro
             20                  25                  30

Glu Gly Leu Cys Ile Ser Val Pro Cys Ser Phe Ser Tyr Pro Arg Gln
         35                  40                  45

Asp Trp Thr Gly Ser Thr Pro Ala Tyr Gly Tyr Trp Phe Lys Ala Val
     50                  55                  60

Thr Glu Thr Thr Lys Gly Ala Pro Val Ala Thr Asn His Gln Ser Arg
 65                  70                  75                  80

Glu Val Glu Met Ser Thr Arg Gly Arg Phe Gln Leu Thr Gly Asp Pro
                 85                  90                  95

Ala Lys Gly Asn Cys Ser Leu Val Ile Arg Asp Ala Gln Met Gln Asp
            100                 105                 110

Glu Ser Gln Tyr Phe Phe Arg Val Glu Arg Gly Ser Tyr Val Arg Tyr
        115                 120                 125

Asn Phe Met Asn Asp Gly Phe Phe Leu Lys Val Thr Ala Leu Thr Gln
    130                 135                 140

Lys Pro Asp Val Tyr Ile Pro Glu Thr Leu Glu Pro Gly Gln Pro Val
145                 150                 155                 160
```

-continued

```
Thr Val Ile Cys Val Phe Asn Trp Ala Phe Glu Glu Cys Pro Pro Pro
                165                 170                 175

Ser Phe Ser Trp Thr Gly Ala Ala Leu Ser Ser Gln Gly Thr Lys Pro
            180                 185                 190

Thr Thr Ser His Phe Ser Val Leu Ser Phe Thr Pro Arg Pro Gln Asp
        195                 200                 205

His Asn Thr Asp Leu Thr Cys His Val Asp Phe Ser Arg Lys Gly Val
    210                 215                 220

Ser Val Gln Arg Thr Val Arg Leu Arg Val Ala Tyr Ala Pro Arg Asp
225                 230                 235                 240

Leu Val Ile Ser Ile Ser Arg Asp Asn Thr Pro Ala Leu Glu Pro Gln
                245                 250                 255

Pro Gln Gly Asn Val Pro Tyr Leu Glu Ala Gln Lys Gly Gln Phe Leu
            260                 265                 270

Arg Leu Leu Cys Ala Ala Asp Ser Gln Pro Pro Ala Thr Leu Ser Trp
        275                 280                 285

Val Leu Gln Asn Arg Val Leu Ser Ser Ser His Pro Trp Gly Pro Arg
    290                 295                 300

Pro Leu Gly Leu Glu Leu Pro Gly Val Lys Ala Gly Asp Ser Gly Arg
305                 310                 315                 320

Tyr Thr Cys Arg Ala Glu Asn Arg Leu Gly Ser Gln Gln Arg Ala Leu
                325                 330                 335

Asp Leu Ser Val Gln Tyr Pro Pro Glu Asn Leu Arg Val Met Val Ser
            340                 345                 350

Gln Ala Asn Arg Thr Val Leu Glu Asn Leu Gly Asn Gly Thr Ser Leu
        355                 360                 365

Pro Val Leu Glu Gly Gln Ser Leu Cys Leu Val Cys Val Thr His Ser
    370                 375                 380

Ser Pro Pro Ala Arg Leu Ser Trp Thr Gln Arg Gly Gln Val Leu Ser
385                 390                 395                 400

Pro Ser Gln Pro Ser Asp Pro Gly Val Leu Glu Leu Pro Arg Val Gln
                405                 410                 415

Val Glu His Glu Gly Glu Phe Thr Cys His Ala Arg His Pro Leu Gly
            420                 425                 430

Ser Gln His Val Ser Leu Ser Leu Ser Val His Tyr Ser Pro Lys Leu
        435                 440                 445

Leu Gly Pro Ser Cys Ser Trp Glu Ala Glu Gly Leu His Cys Ser Cys
    450                 455                 460

Ser Ser Gln Ala Ser Pro Ala Pro Ser Leu Arg Trp Trp Leu Gly Glu
465                 470                 475                 480

Glu Leu Leu Glu Gly Asn Ser Ser Gln Asp Ser Phe Glu Val Thr Pro
                485                 490                 495

Ser Ser Ala Gly Pro Trp Ala Asn Ser Ser Leu Ser Leu His Gly Gly
            500                 505                 510

Leu Ser Ser Gly Leu Arg Leu Arg Cys Glu Ala Trp Asn Val His Gly
        515                 520                 525

Ala Gln Ser Gly Ser Ile Leu Gln Leu Pro Asp Lys Lys Gly Leu Ile
    530                 535                 540

Ser Thr Ala Phe Ser Asn Gly Ala Phe Leu Gly Ile Gly Ile Thr Ala
545                 550                 555                 560

Leu Leu Phe Leu Cys Leu Ala Leu Ile Ile Met Lys Ile Leu Pro Lys
                565                 570                 575

Arg Arg Thr Gln Thr Glu Thr Pro Arg Pro Arg Phe Ser Arg His Ser
```

-continued

| | | | | | | | | | | | | | | | |
|---|---|---|---|---|---|---|---|---|---|---|---|---|---|---|---|
| | | | 580 | | | | | 585 | | | | | 590 | | |
| Thr | Ile | Leu | Asp | Tyr | Ile | Asn | Val | Val | Pro | Thr | Ala | Gly | Pro | Leu | Ala |
| | | 595 | | | | | 600 | | | | | 605 | | | |
| Gln | Lys | Arg | Asn | Gln | Lys | Ala | Thr | Pro | Asn | Ser | Pro | Arg | Thr | Pro | Leu |
| | 610 | | | | | 615 | | | | | 620 | | | | |
| Pro | Pro | Gly | Ala | Pro | Ser | Pro | Glu | Ser | Lys | Lys | Asn | Gln | Lys | Lys | Gln |
| 625 | | | | | 630 | | | | | 635 | | | | | 640 |
| Tyr | Gln | Leu | Pro | Ser | Phe | Pro | Glu | Pro | Lys | Ser | Ser | Thr | Gln | Ala | Pro |
| | | | | 645 | | | | | 650 | | | | | 655 | |
| Glu | Ser | Gln | Glu | Ser | Gln | Glu | Glu | Leu | His | Tyr | Ala | Thr | Leu | Asn | Phe |
| | | | 660 | | | | | 665 | | | | | 670 | | |
| Pro | Gly | Val | Arg | Pro | Arg | Pro | Glu | Ala | Arg | Met | Pro | Lys | Gly | Thr | Gln |
| | | 675 | | | | | 680 | | | | | 685 | | | |
| Ala | Asp | Tyr | Ala | Glu | Val | Lys | Phe | Gln | | | | | | | |
| | 690 | | | | | 695 | | | | | | | | | |

12 HUMAN SECRETED PROTEINS

This application is a division of U.S. application Ser. No. 09/984,130, filed Oct. 29, 2001 (now abandoned), which claims benefit under 35 U.S.C. § 119(e) of U.S. Provisional Application No. 60/243,792, filed on Oct. 30, 2000, and which is also a continuation-in-part of U.S. application Ser. No. 09/836,353, filed Apr. 18, 2001 (now abandoned), which claims benefit under 35 U.S.C. § 119(e) of U.S. Provisional Application No. 60/198,407, filed Apr. 19, 2000, and which is a continuation-in-part of PCT International Application No. PCT/US99/25031 (published in English), filed Oct. 27, 1999, which claims benefit under 35 U.S.C. § 119(e) of U.S. Provisional Application No. 60/105,971, filed Oct. 28, 1998. Each of the above referenced patent applications is hereby incorporated by reference herein.

STATEMENT UNDER 37 C.F.R. § 1.77(b)(4)

This application refers to a "Sequence Listing" listed below, which is provided as an electronic document on two identical compact discs (CD-R), labeled "Copy 1" and "Copy 2." These compact discs each contain the file "PF489P2D1 Seq list.txt" (288,736 bytes, created on Oct. 5, 2005), which is hereby incorporated by reference in its entirety herein. The Sequence Listing may be viewed on an IBM-PC machine running the MS-Windows operating system.

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant and synthetic methods for producing the polypeptides and polynucleotides. Also provided are diagnostic methods for detecting disorders and conditions related to the polypeptides and polynucleotides, and therapeutic methods for treating such disorders and conditions. The invention further relates to screening methods for identifying binding partners of the polypeptides.

BRIEF DESCRIPTION OF THE FIGURES

FIGS. 1A-C show the nucleotide (SEQ ID NO:11) and deduced amino acid sequence (SEQ ID NO:29) of this protein.

FIG. 2 shows the regions of similarity between the amino acid sequences of SEQ ID NO:29, the *Xenopus laevis* tail resorption protein (gi|1234787) (SEQ ID NO:48), and the Hedgehog Interacting Protein ("HIP"; gi|AAD31172.1) (SEQ ID NO:49).

FIGS. 4A-C shows the nucleotide (SEQ ID NO:12) and deduced amino acid sequence (SEQ ID NO:30) of TIDE. Predicted amino acids from about 1 to about 23 constitute the predicted signal peptide (amino acid residues from about 1 to about 23 in SEQ ID NO:30) and are represented by the underlined amino acid regions; amino acids from about 108 to about 136, from about 195 to about 223, from about 291 to about 319, from about 379 to about 407, and/or from about 465 to about 493 constitute the predicted EGF-like domain signature 1 and 2 domains (amino acids from about 108 to about 136, from about 195 to about 223, from about 291 to about 319, from about 379 to about 407, and/or from about 465 to about 493 in SEQ ID NO:30) and are represented by the double underlined amino acids; and amino acids from about 55 to about 89, from about 97 to about 129, from about 142 to about 175, from about 186 to about 216, from about 228 to about 261, from about 281 to about 314, from about 327 to about 359, from about 368 to about 398, from about 417 to about 448, and/or from about 455 to about 487 constitute the predicted integrins beta chain cysteine-rich domains (amino acids from about 55 to about 89, from about 97 to about 129, from about 142 to about 175, from about 186 to about 216, from about 228 to about 261, from about 281 to about 314, from about 327 to about 359, from about 368 to about 398, from about 417 to about 448, and/or from about 455 to about 487 in SEQ ID NO:30) and are represented by the shaded amino acids.

FIG. 5 shows the regions of similarity between the amino acid sequences of the Ten Integrin Domains with EGF homology (TIDE) protein (SEQ ID NO:30) and the human integrin beta-8 subunit (SEQ ID NO: 67).

FIGS. 7A-B show the nucleotide (SEQ ID NO:13) and deduced amino acid sequence (SEQ ID NO:31) of the Intestine derived extracellular protein. Predicted amino acids from about 1 to about 27 constitute the predicted signal peptide (amino acid residues from about 1 to about 27 in SEQ ID NO:31) and are represented by the underlined amino acid regions; and amino acids from about 122 to about 138 constitute the predicted transmembrane domain (amino acid residues from about 122 to about 138 in SEQ ID NO:31) and are represented by the double-underlined amino acids.

FIG. 8 shows the regions of similarity between the amino acid sequences of the Intestine derived extracellular protein SEQ ID NO:31, and the RAMP3 protein (gi|4587099) (SEQ ID NO: 75).

FIGS. 10A-B shows the nucleotide (SEQ ID NO:14) and deduced amino acid sequence (SEQ ID NO:32) of the retinal specific protein. Predicted amino acids from about 1 to about 21 constitute the predicted signal peptide (amino acid residues from about 1 to about 21 in SEQ ID NO:32) and are represented by the underlined amino acid regions.

FIG. 11 shows the regions of similarity between the amino acid sequences of the retinal specific protein SEQ ID NO:32, and the *Gallus gallus* proteoglycan (SEQ ID NO:79).

FIGS. 13A-C shows the nucleotide (SEQ ID NO:15) and deduced amino acid sequence (SEQ ID NO:33) of the CD33-like protein. Predicted amino acids from about 1 to about 16 constitute the predicted signal peptide (amino acid residues from about 1 to about 16 in SEQ ID NO:33) and are represented by the underlined amino acid regions; and amino acids from about 496 to about 512 constitute the predicted transmembrane domain (amino acid residues from about 496 to about 512 in SEQ ID NO:33) and are represented by the double-underlined amino acid regions.

FIG. 14 shows the regions of similarity between the amino acid sequences of the CD33-like protein SEQ ID NO:33, and the CD33L1 protein (gi|88178) (SEQ ID NO: 92).

FIGS. 16A-B show the nucleotide (SEQ ID NO:16) and deduced amino acid sequence (SEQ ID NO:34) of CD33-like 3. Predicted amino acids from about 1 to about 18 constitute the predicted signal peptide (amino acid residues from about 1 to about 18 in SEQ ID NO:34) and are represented by the underlined amino acid regions; and amino acids from about 360 to about 376 constitute the predicted transmembrane domain (amino acids from about 360 to about 376 in SEQ ID NO:34) and are represented by the double underlined amino acids.

FIG. 17 shows the regions of similarity between the amino acid sequences of the CD33-like 3 protein (SEQ ID NO:34) and the human CD33L1 protein (SEQ ID NO:99).

FIGS. 19A-F show the nucleotide (SEQ ID NO:17) and deduced amino acid sequence (SEQ ID NO:35) of a11. Predicted amino acids from about 1 to about 22 constitute the predicted signal peptide (amino acid residues from about 1 to about 22 in SEQ ID NO:35) and are represented by the underlined amino acid regions; amino acids from about 666 to about 682, and/or amino acids from about 1145 to about 1161 constitute the predicted transmembrane domains (amino acids from about 666 to about 682, and/or amino acids from about 1145 to about 1161 in SEQ ID NO:35) and are represented by the double underlined amino acids; and amino acids from about 64 to about 96 constitute the predicted immunoglobulin and major histocompatibility complex protein domain (amino acids from about 64 to about 96 in SEQ ID NO:35) and are represented by the bold amino acids.

FIG. 20 shows the regions of similarity between the amino acid sequences of the integrin alpha 11 subunit (a11) protein (SEQ ID NO:35) and the human integrin alpha 1 subunit (SEQ ID NO: 103).

FIGS. 22A-C show the nucleotide (SEQ ID NO:19) and deduced amino acid sequence (SEQ ID NO:37) of BBIR II. Predicted amino acids from about 1 to about 17 constitute the predicted signal peptide (amino acid residues from about 1 to about 17 in SEQ ID NO:37) and are represented by the underlined amino acid regions.

FIG. 23 shows the regions of similarity between the amino acid sequences of the Butyrophlin and B7-like IgG superfamily receptor (BBIR II) protein (SEQ ID NO:37) and the bovine butyrophilin precursor (SEQ ID NO:121)

FIGS. 25 A-B show the nucleotide (SEQ ID NO:20) and deduced amino acid sequence (SEQ ID NO:38) of the present invention. Predicted amino acids from about 1 to about 19 constitute the predicted signal peptide (amino acid residues from about 1 to about 19 in SEQ ID NO:38) and are represented by the underlined amino acid regions; amino acids from about 162 to about 188 constitutes the predicted serine protease histidine active site domain (amino acids residues from about 162 to about 188 in SEQ ID NO:38) and are represented by the double underlined amino acid regions; and amino acid residue 175 (amino acid residue 175 in SEQ ID NO:38) constitutes the predicted histidine active site residue and is represented by the bold amino acid.

FIG. 26 shows the regions of similarity between the amino acid sequences of the present invention SEQ ID NO:38, and the Human Pancreatic Elastase 2 protein (gi|219620)(SEQ ID NO: 127).

FIGS. 28A-B shows the nucleotide (SEQ ID NO:21) and deduced amino acid sequence (SEQ ID NO:39) of the present invention. Predicted amino acids from about 1 to about 44 constitute the predicted signal peptide (amino acid residues from about 1 to about 44 in SEQ ID NO:39) and are represented by the underlined amino acid regions.

FIG. 29 shows the regions of similarity between the amino acid sequences of the present invention SEQ ID NO:39, the human poliovirus receptor protein (gi|1524088) (SEQ ID NO: 138), the human class-I MHC-restricted T cell associated molecule (WO9634102) (SEQ ID NO:144), and the *Gallus gallus* thymocyte activation and developmental protein (gb|AAB88491.1) (SEQ ID NO: 145).

Figure 30:
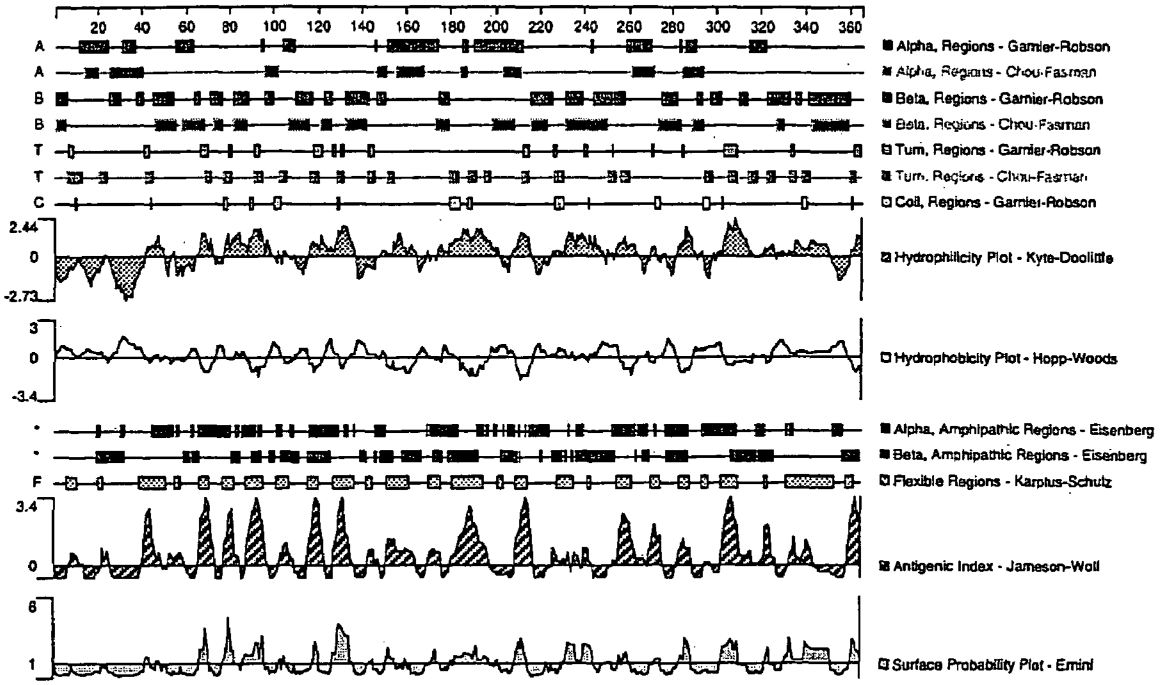

FIG. 30 shows an analysis of the amino acid sequence of SEQ ID NO:39. Alpha, beta, turn and coil regions; hydrophilicity and hydrophobicity; amphipathic regions; flexible regions; antigenic index and surface probability are shown.

FIG. 31 shows the nucleotide (SEQ ID NO:22) and deduced amino acid sequence (SEQ ID NO:40) of the present invention. Predicted amino acids from about 1 to about 23 constitute the predicted signal peptide (amino acid residues from about 1 to about 23 in SEQ ID NO:40) and are represented by the underlined amino acid regions.

FIG. 32 shows the regions of similarity between the amino acid sequences of the present invention SEQ ID NO:40 and the human FAP protein (gi|1890647) (SEQ ID NO:146).

Figure 33:
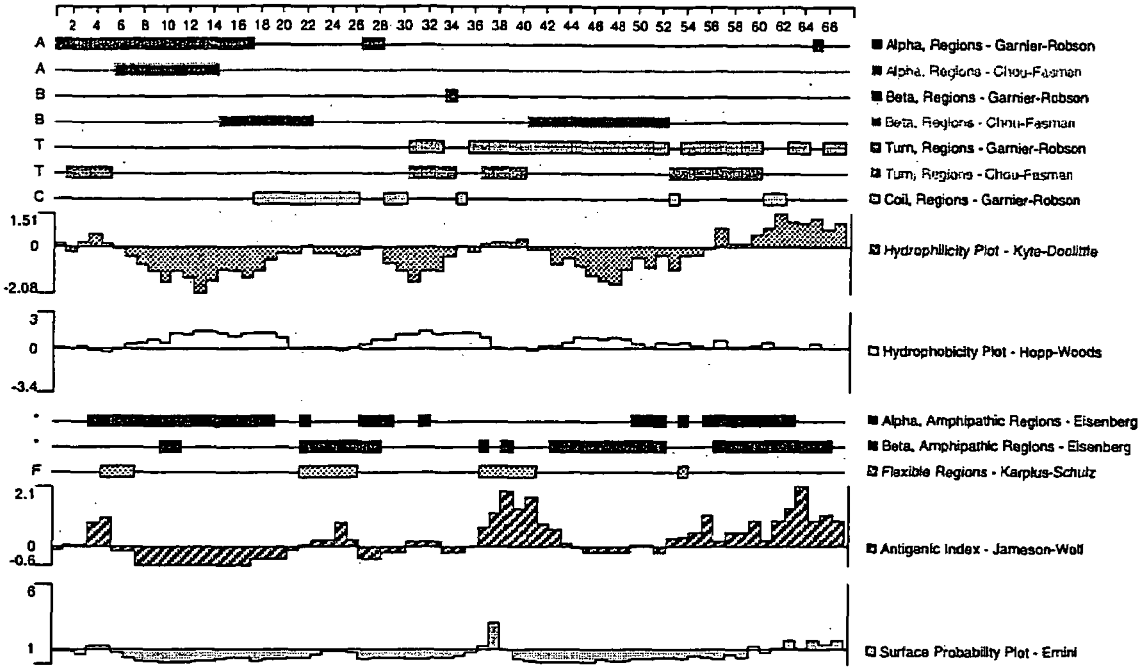

FIG. 33 shows an analysis of the amino acid sequence of SEQ ID NO:40. Alpha, beta, turn and coil regions; hydrophilicity and hydrophobicity; amphipathic regions; flexible regions; antigenic index and surface probability are shown.

FIG. 34 shows the nucleotide (SEQ ID NO:18) and deduced amino acid sequence (SEQ ID NO:36) of htag7. Predicted amino acids from about 1 to about 21 constitute the predicted signal peptide (amino acid residues from about 1 to about 21 in SEQ ID NO:36) and are represented by the underlined amino acid regions; and amino acids from about 34 to about 117 constitute the predicted PGRP-like domain (amino acids from about 34 to about 117 in SEQ ID NO:36) and are represented by the double underlined amino acids.

FIG. 35 shows the regions of similarity between the amino acid sequences of the htag7 protein (SEQ ID NO:36) and the mouse tag7 protein (SEQ ID NO:114).

Figure 36:
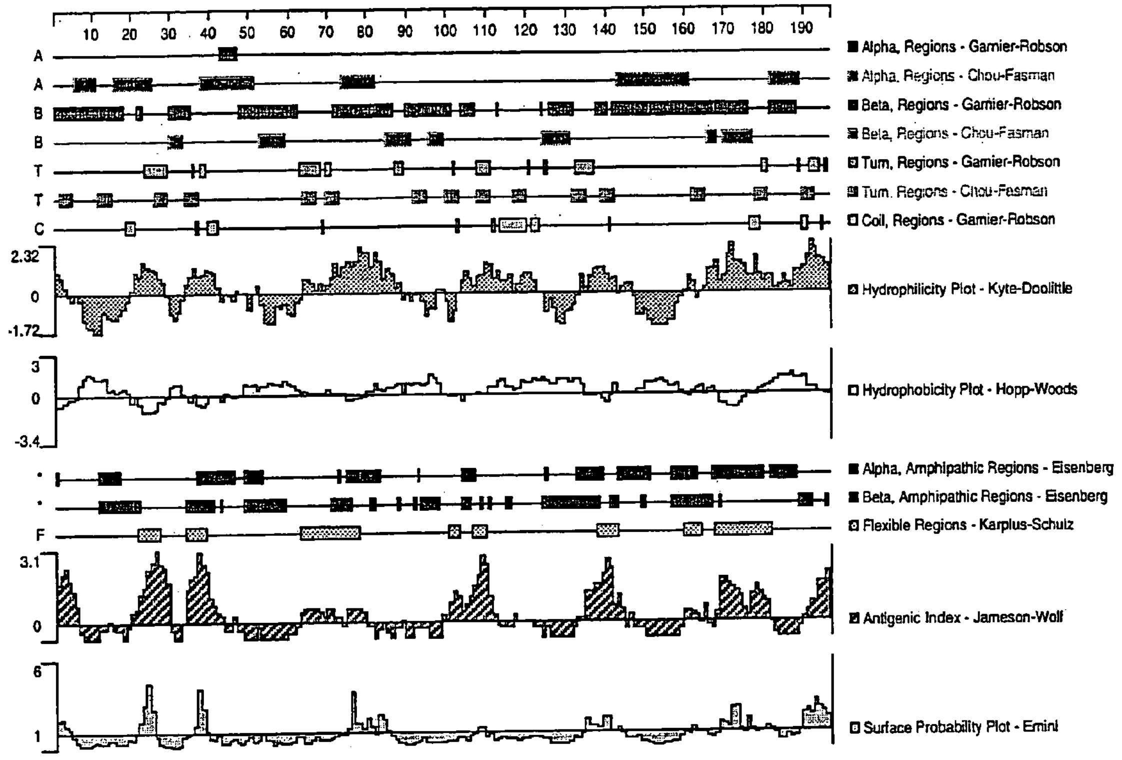

FIG. 36 shows an analysis of the htag7 amino acid sequence. Alpha, beta, turn and coil regions; hydrophilicity and hydrophobicity; amphipathic regions; flexible regions; antigenic index and surface probability are shown.

FIG. 37 shows the predicted protein sequence of CD33-likeSV protein (identified in FIG. 37 as "Siglec-10") and alignment with closely-related Siglecs. Alignment was performed with the ClustalW multiple sequence alignment program. Residues that are identical in more than half the proteins are boxed in black, similar residues in grey. Asterisks indicate positions of the cysteine residues characteristic of Siglecs. Filled circles overlay residues important for sialic acid binding. Vertical lines indicate positions of intron-exon boundaries, as deduced from the sequence of the gene encoding CD33-likeSV. Positions of the domain boundaries, transmembrane region, cytoplasmic tail (encoded by two exons) and the tyrosine based motifs are indicated. Genbank accession numbers are as follows: CD33/Siglec-3, Siglec-5: AAD50978; Siglec-6, NP001236; Siglec-7 AAF12759; Siglec-8, AAF27622; and Siglec-9, AAF87223.

FIG. 38 provides a phylogenetic analysis of CD33-related Siglecs and CD33-likeSV protein (identified in FIG. 38 as "Siglec-10"). The leader peptide, domain 1, and domain 2, or the transmembrane and cytoplasmic tails were aligned using the Clustal W multiple sequence alignment program and analyzed for phylogenetic relationship using the PHYLIP 3.6. Unrooted phylograms were constructed using the neighbor joining method.

Figure 39:
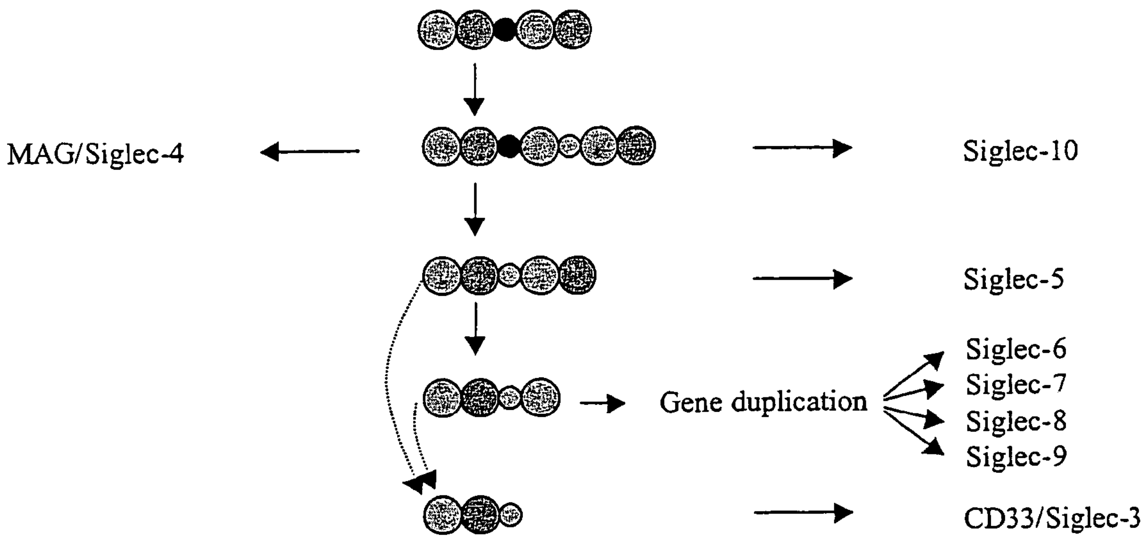

FIG. 39 provides a sequential deletion model for evolution of CD33-related Siglecs. Based on the phylogenetic analysis and sequence comparisons, this model predicts that MAG and CD33-likeSV (identified in FIG. 39 as "Siglec-10") are both derived from a common 4-domain progenitor. CD33-likeSV then gave rise to Siglec-5 involving a deletion of the exons encoding domain 3 and its associated linker. Siglec-5 then gave rise to a three domain siglec by deletion of domain 4. The other 3-domain Siglecs then arose through gene duplication. CD33 may have been derived in a single deletion event either from Siglec-5 or one of the three domain Siglecs.

FIGS. 40A & B provides the localization and expression of the CD33-likeSV gene.

Human lymphocyte metaphase spreads were hybridized with a 3 kb biotinylated insert from HEONM10 followed by fluorescein-avidin and the chromosomes counterstained with propidium iodide. The digital image is reversed to illustrate the hybridization signals (arrows) on the long arm of chromosome 19. The position of CD33-likeSV on chromosome 19 band q13.3 is also shown schematically.

Northern blot analysis of CD33-likeSV mRNA in human tissues. Each lane of the Multiple Tissue Northern (MTN) Blot (Clontech) contains approximately 2 μg poly A+ RNA from the tissue indicated and is normalized for levels of β-actin mRNA. A major form of CD33-likeSV mRNA is seen at around 3.0 kb in most tissues.

Figure 41:
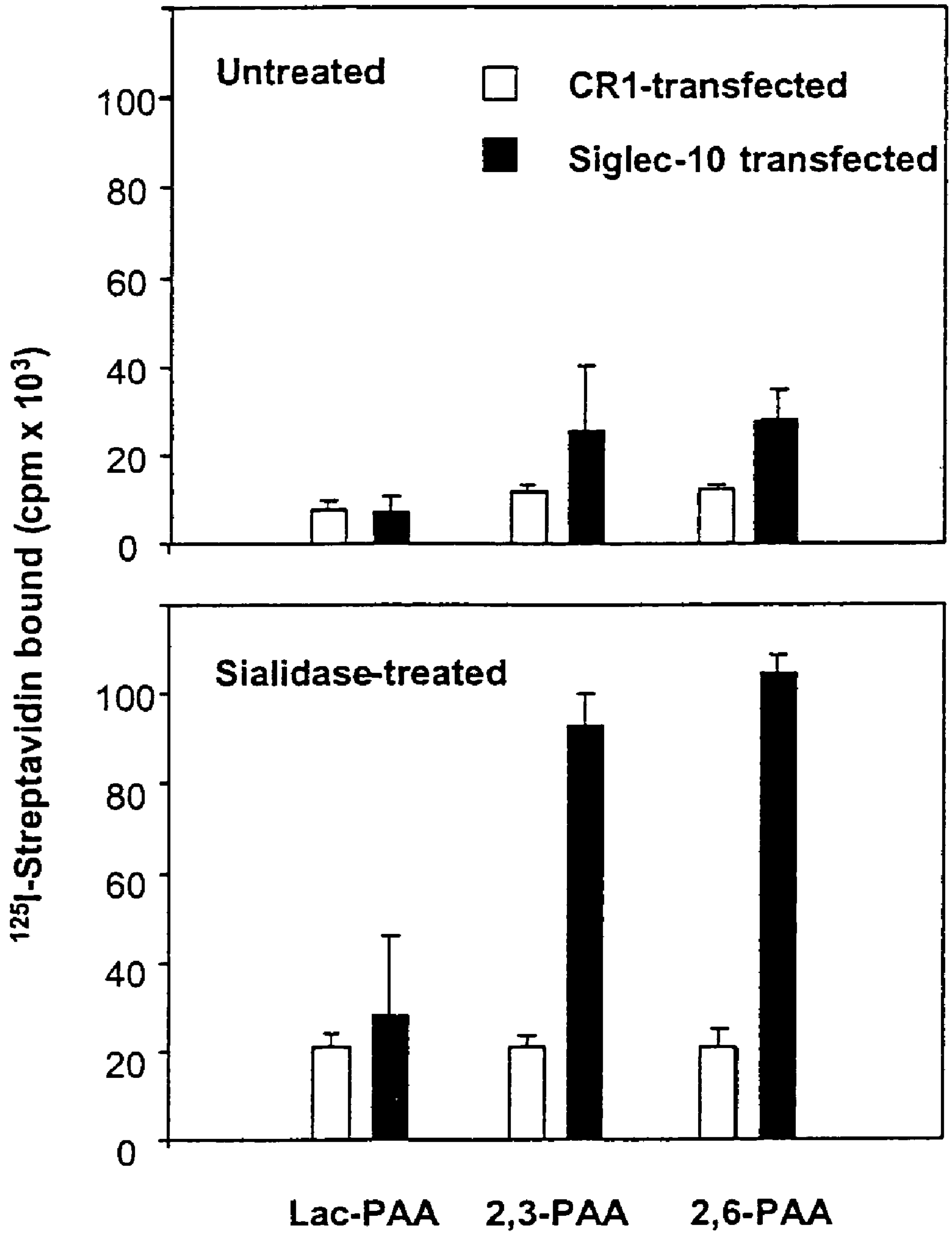

FIG. 41 disclosed the binding of CD33-likeSV (identified in FIG. 41 as "Siglec-10") expressed on COS cells to polyacrylamide conjugates. CR1 was included as a negative control to measure non-specific binding. Three days after transient transfection, COS cells expressing the indicated proteins were incubated with biotinylated polyacrylamide (PAA) glycoconjugates linked either to 3' sialyllactose (2,3-PAA) or 6' sialyllactose (2,6-PAA) or lactose (Lac-PAA) at 20 μg/ml or with buffer alone. Unbound conjugate was washed off and binding detected with $^{125}$I-streptavidin. Data show means standard deviations of quadruplicates and are representative of 3 experiments performed.

Figure 42:
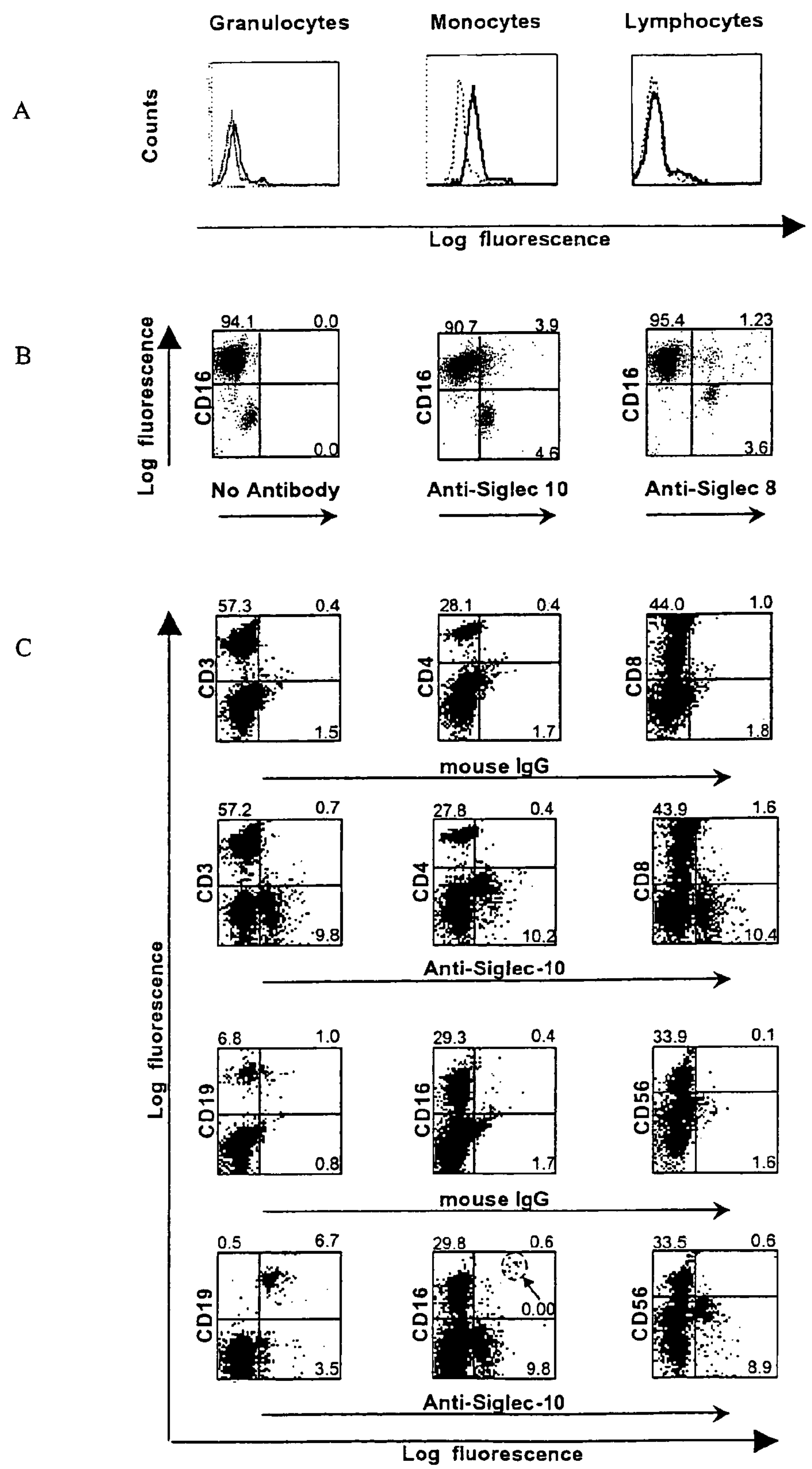

FIGS. 42A, B & C show the expression of CD33-likeSV (identified in FIG. 42 as "Siglec-10") on human peripheral blood leukocyte subsets.

FACS histograms showing expression of CD33-likeSV on granulocytes, monocytes and lymphocytes, gated in each case according to their characteristic side and forward scatter properties. Thick lines show staining with affinity purified mouse anti-CD33-likeSV polyclonal antibody. Thin lines show staining in the presence of mouse IgG used as a negative control. CD33-likeSV is expressed on a minor subset of granulocytes, most monocytes and a subset of lymphocytes Double labeling of granulocytes with anti-CD 16 (neutrophils) and anti-CD33-likeSV mAb compared with anti-Siglec-8 mAb. Compared to the isotype matched control mAb, CD33-likeSV shows clear labeling of the eosinophils and some of the neutrophils are also weakly stained. Values represent the percentages of total granulocytes analyzed.

Double labeling of the lymphocyte fraction with antibodies to CD 19 (B cells), CD3 (pan T cell), CD4 and CD8 (T cell subsets) and CD56 (NK cells). CD33-likeSV is expressed by most CD 19+ B cells and a small subset of CD16+ cells that do not express the CD56 natural killer cell marker. Values represent the percentages of the total lymphocytes analyzed. Similar results were obtained using the mouse anti-CD33-likeSV mAb, 5G6.

Figure 43:
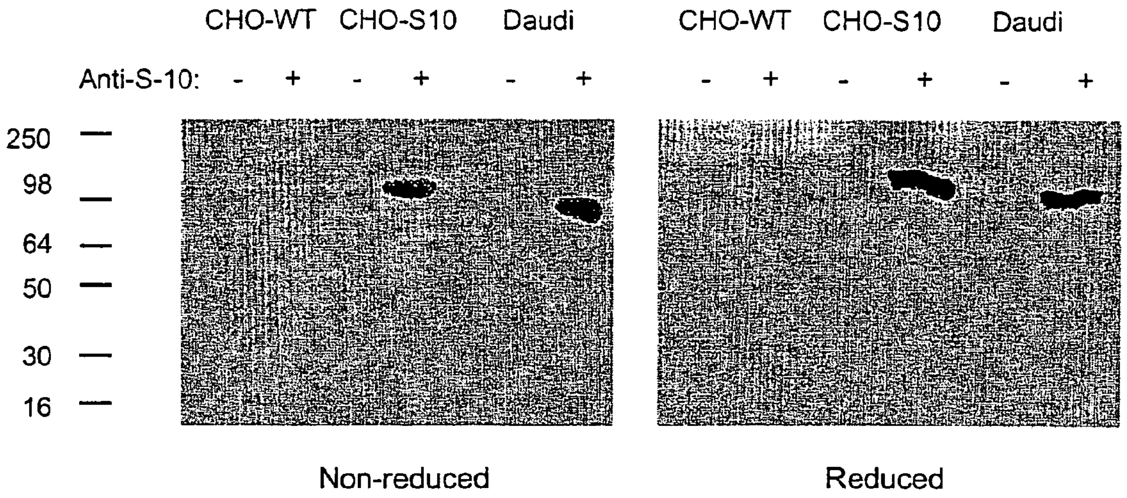

FIG. 43 provides a molecular characterization of CD33-likeSV (identified in FIG. 43 as "S10"). Stably-transfected CHO cells expressing CD33-likeSV, wild-type CHO cells, or Daudi cells were surface biotinylated, lysed and immunoprecipitations performed with mouse anti-CD33-likeSV polyclonal antibody. Precipitates were run either under reducing or non-reducing conditions on 4-12% gradient SDS polyacrylamide gels, transferred to nitrocellulose and probed with streptavidin-horse radish peroxidase. CD33-likeSV migrates as a single monomeric species at around 120 kDa in CHO cells and around 100 kDa in Daudi cells.

Figure 44:
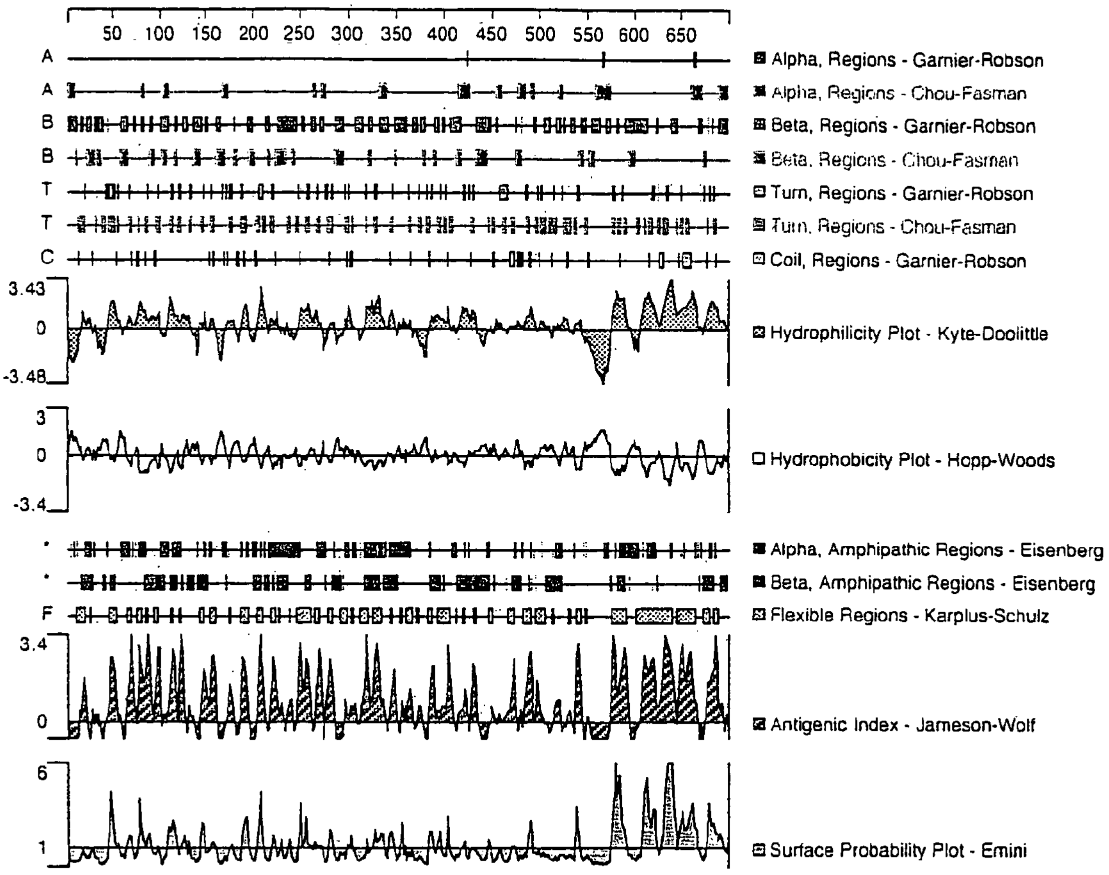

FIG. 44 shows an analysis of the amino acid sequence of CD33-likeSV protein (SEQ ID NO: 149). Alpha, beta, turn and coil regions; hydrophilicity and hydrophobicity; amphipathic regions; flexible regions; antigenic index and surface probability are shown.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table XIV, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X the complement thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

"SEQ ID NO:X" refers to a polynucleotide sequence while "SEQ ID NO:Y" refers to a polypeptide sequence, both sequences identified by an integer specified in Table XIV.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about ten-fold less activity, and most preferably, not more than about three-fold less activity relative to the polypeptide of the present invention.)

Polynucleotides and Polypeptides of the Invention

Features of Protein Encoded by Gene No: 1

Translation products corresponding to this gene share sequence homology with a protein from *Xenopus laevis* that is described as upregulated in response to thyroid hormone in tadpoles, and is thought to be important in the tail resorption process during *Xenopus laevis* metamorphosis (See Proc. Natl. Acad. Sci. USA (Mar. 5, 1996):93(5):1924-9, which is herein incorporated by reference). In addition, translation products corresponding to this gene share sequence homology with a recently described group of proteins, called hedgehog interacting proteins (HIPs) (See International Publication No. WO98/12326, which is herein incorporated by reference). These proteins bind to hedgehog polypeptides such as Shh and Dhh with high affinity (Kd approx. 1 nM). HIPs exhibit spatially and temporally restricted expression domains indicative of important roles in hedgehog-mediated induction. They regulate differentiation of neuronal cells, regulate survival of differentiated neuronal cells, proliferation of chondrocytes, proliferation of testicular germ line cells and/or expression of patched or hedgehog genes. The biological activity of this polypeptide is assayed by techniques known in the art, otherwise disclosed herein and as described in International Publication No. WO98/12326, which is herein incorporated by reference.

Preferred polypeptides of the invention comprise, or alternatively consist of, the following amino acid sequence: MLRTSTPNLCGGLHCRAPWLSSGILCLCLIFLLGQVGLLQGHPQCLDYGPPFQPPLHLEFCSDYESFGCCDQHKDRRIAA RYWDIMEYFDLKRHELCGDYIKDILCQECSPYAAHLYDAENT QTPLRNLPGLCSDYCSAFHSNCHSAISLLTNDRGLQE SHGRDGTRFCHLLDLPDKDYCFPNVLRNDYLNRHLGMVAQDPQGCLQLCLSEVANGLRNPVSMVHAGDGTHRFFVA EQVGVVWVYLPDGSRLEQPFLDLKNIVLTTPWIGDERGFL GLAFHPKFRHNRKFYIYYSCLDKKKVEKIRISEMKVSRA DPNKADLKSERVILEIEEPASNHNGGQLLFGLDGYMYIFTGDGGQAGDPFGLFGNAQNKSSLLGKVLRIDVNRAGSHG KRYRVPSDNPFVSEPGAHPAIYAYGIRNMWRCAVDRGDPITRQGRGRIFCGDVGQNRFEEVDLILKGGNYGWRAKEGF ACYDKKLCHNASLDDVLPIYAYGHAVGKSVTGGYVYRGCESPN LNGLYIFGDFMSGRLMALQEDRKNKKWKKQDLC LGSTTSCAFPGLISTHSKFIISFAEDEAGELYFLATSYPSAYAPRGSIYKFVDPSRRAPPGKCKYKPVPVRTKSKRIPFRPLA KTVLDLLKEQSEKAARKSSSATLASGPAQGLSEKGSSK KLASPTSSKNTLRGPGTKKKARVGPHVRQGKRRKSLKSHS GRMRPSAEQKRAGRSLP (SEQ ID NO: 47). Also preferred are polypeptides comprising the mature polypeptide which is predicted to consist of residues 42-724 of the foregoing sequence, and biologically active fragments of the mature polypeptide. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred polypeptides of the present invention comprise, or alternatively consist of, one, two, three, four, five, six, seven, eight, nine, ten, eleven, twelve, thirteen, fourteen, fifteen, sixteen, or all sixteen of the immunogenic epitopes shown in SEQ ID NO: 29 as residues: Asp-52 to Glu-57, Arg-89 to Tyr-95, Asp-102 to Glu-107, Ser-117 to Ser-128, Glu-137 to Gly-145, Arg-192 to Arg-199, Val-231 to Gly-243, Val-250 to Glu-256, Arg-312 to Asn-318, Glu-338 to Asp-349, Pro-405 to Lys-417, Thr-423 to Ile-428, Lys-442 to Ser-453, Glu-467 to Ala-475, Thr-478 to Arg-494, and/or Pro-497 to Arg-526. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

FIGS. 1A-C show the nucleotide (SEQ ID NO:11) and deduced amino acid sequence (SEQ ID NO:29) of this protein.

FIG. 2 shows the regions of similarity between the amino acid sequences of SEQ ID NO:29, the *Xenopus laevis* tail resorption protein (gi|1234787) (SEQ ID NO:48), and the Hedgehog Interacting Protein ("HIP"; gi|AAD31172.1) (SEQ ID NO:49).

Figure 3:
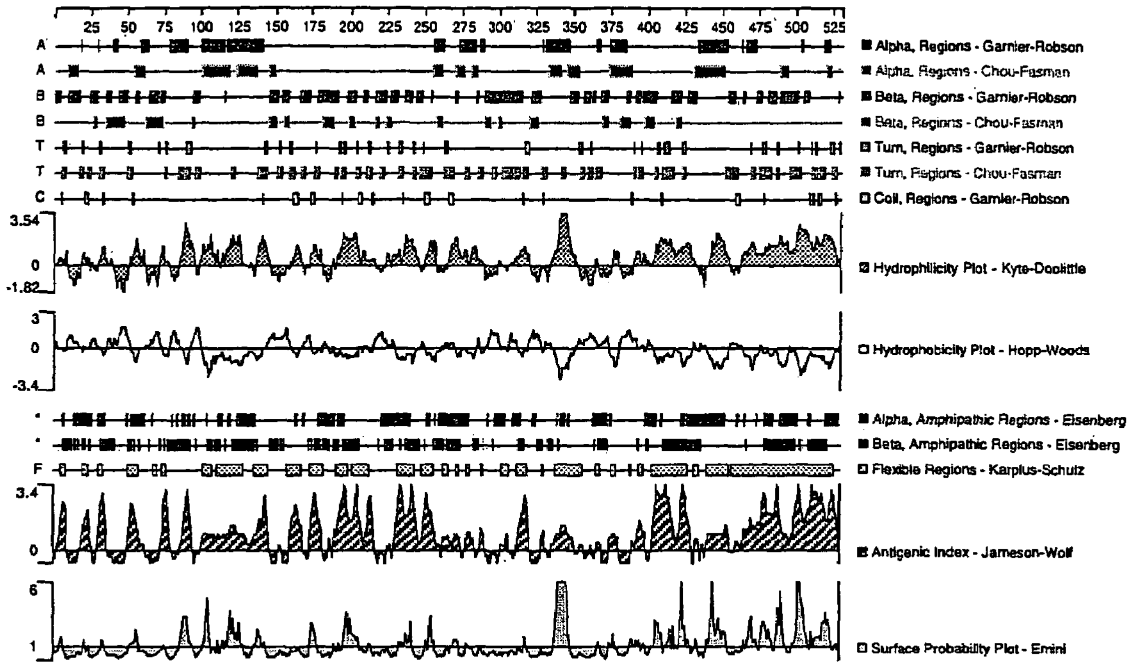
FIG. 3 shows an analysis of the amino acid sequence of SEQ ID NO: 29. Alpha, beta, turn and coil regions; hydrophilicity and hydrophobicity; amphipathic regions; flexible regions; antigenic index and surface probability are shown.

FIG. 3 shows an analysis of the amino acid sequence of SEQ ID NO: 29. Alpha, beta, turn and coil regions; hydrophilicity and hydrophobicity; amphipathic regions; flexible regions; antigenic index and surface probability are shown.

The present invention provides isolated nucleic acid molecules comprising a polynucleotide encoding the polypeptide having the amino acid sequence shown in FIGS. 1A-C (SEQ ID NO:29), which was determined by sequencing a cloned cDNA. The nucleotide sequence shown in FIGS. 1A-C (SEQ ID NO:11) was obtained by sequencing a cloned cDNA, which was deposited on Nov. 17, 1998 at the American Type Culture Collection, and given Accession Number 203484. The deposited gene is inserted in the pSport plasmid (Life Technologies, Rockville, Md.) using the SalI/NotI restriction endonuclease cleavage sites.

The present invention is further directed to fragments of the isolated nucleic acid molecules described herein. By a fragment of an isolated DNA molecule having the nucleotide sequence of the deposited cDNA or the nucleotide sequence shown in SEQ ID NO:11 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:11. By a fragment at least 20 nt in length, for example, is intended fragments which include 20 or more contiguous bases from the nucleotide sequence of the deposited cDNA or the nucleotide sequence as shown in SEQ ID NO:11. In this context "about" includes the particularly recited size, larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 570 of SEQ ID NO:11, or the complementary strand thereto, or the cDNA contained in the deposited gene. In this context "about" includes the particularly recited ranges, larger or smaller by several (5, 4, 3, 2, or 1) nucleotides, at either terminus or at both termini. In additional embodiments, the polynucleotides of the invention encode functional attributes of the corresponding protein.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 3 and/or Table I, as described above, was generated using the various modules and algorithms of the DNA*STAR set on default parameters. In a preferred embodiment, the data presented in columns VIII, IX, XIII, and XIV of Table I can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 is used to easily determine specific boundaries of a preferred region. The above-mentioned preferred regions set out in FIG. 3 and in Table I include, but are not limited to, regions of the aforementioned types identified by analysis of the amino acid sequence set out in FIGS. 1A-C (SEQ ID NO:29). As set out in FIG. 3 and in Table I, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein other functional activities (e.g., biological activities, ability to multimerize, etc.) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, the present invention further provides polypeptides having one or more residues deleted from the amino terminus of the amino acid sequence shown in FIGS. 1A-C, up to the alanine residue at position number 524 and polynucleotides encoding such polypeptides. In particular, the present invention provides polypeptides comprising the amino acid sequence of residues n1-524 of FIGS. 1A-C, where n1 is an integer from 1 to 524 corresponding to the position of the amino acid residue in FIGS. 1A-C (which is identical to the sequence shown as SEQ ID NO:29). N-terminal deletions of the polypeptide of the invention shown as SEQ ID NO:29 include polypeptides comprising the amino acid sequence of residues: V-2 to P-529; A-3 to P-529; Q-4 to P-529; D-5 to P-529; P-6 to P-529; Q-7 to P-529; C-9 to P-529; L-10 to P-529; Q-11 to P-529; L-12 to P-529; C-13 to P-529; L-14 to P-529; S-15 to P-529; E-16 to P-529; V-17 to P-529; A-18 to P-529; N-19 to P-529; G-20 to P-529; L-21 to P-529; R-22 to P-529; N-23 to P-529; P-24 to P-529; V-25 to P-529; S-26 to P-529; M-27 to P-529; V-28 to P-529; H-29 to P-529; A-30 to P-529; G-31 to P-529; D-32 to P-529; G-33 to P-529; T-34 to P-529; H-35 to P-529; R-36 to P-529; F-37 to P-529; F-38 to P-529; V-39 to P-529; A-40 to P-529; E-41 to P-529; Q-42 to P-529; V-43 to P-529; G-44 to P-529; V-45 to P-529; V-46 to P-529; W-47 to P-529; V-48 to P-529; Y-49 to P-529; L-50 to P-529; P-51 to P-529; D-52 to P-529; G-53 to P-529; S-54 to P-529; R-55 to P-529; L-56 to P-529; E-57 to P-529; Q-58 to P-529; P-59 to P-529; F-60 to P-529; L-61 to P-529; D-62 to P-529; L-63 to P-529; K-64 to P-529; N-65 to P-529; I-66 to P-529; V-67 to P-529; L-68 to P-529; T-69 to P-529; T-70 to P-529; P-71 to P-529; W-72 to P-529; I-73 to P-529; G-74 to P-529; D-75 to P-529; E-76 to P-529; R-77 to P-529; G-78 to P-529; F-79 to P-529; L-80 to P-529; G-81 to P-529; L-82 to P-529; A-83 to P-529; F-84 to P-529; H-85 to P-529; P-86 to P-529; K-87 to P-529; F-88 to P-529; R-89 to P-529; H-90 to P-529; N-91 to P-529; R-92 to P-529; K-93 to P-529; F-94 to P-529; Y-95 to P-529; I-96 to P-529; Y-97 to P-529; Y-98 to P-529; S-99 to P-529; C-100 to P-529; L-101 to P-529; D-102 to P-529; K-103 to P-529; K-104 to P-529; K-105 to P-529; V-106 to P-529; E-107 to P-529; K-108 to P-529; I-109 to P-529; R-110 to P-529; I-111 to P-529; S-112 to P-529; E-113 to P-529; M-114 to P-529; K-115 to P-529; V-116 to P-529; S-117 to P-529; R-118 to P-529; A-119 to P-529; D-120 to P-529; P-121 to P-529; N-122 to P-529; K-123 to P-529; A-124 to P-529; D-125 to P-529; L-126 to P-529; K-127 to P-529; S-128 to P-529; E-129 to P-529; R-130 to P-529; V-131 to P-529; I-132 to P-529; L-133 to P-529; E-134 to P-529; I-135 to P-529; E-136 to P-529; E-137 to P-529; P-138 to P-529; A-139 to P-529; S-140 to P-529; N-141 to P-529; H-142 to P-529; N-143 to P-529; G-144 to P-529; G-145 to P-529; Q-146 to P-529; L-147 to P-529; L-148 to P-529; F-149 to P-529; G-150 to P-529; L-151 to P-529; D-152 to P-529; G-153 to P-529; Y-154 to P-529; M-155 to P-529; Y-156 to P-529; I-157 to P-529; F-158 to P-529; T-159 to P-529; G-160 to P-529; D-161 to P-529; G-162 to P-529; G-163 to P-529; Q-164 to P-529; A-165 to P-529; G-166 to P-529; D-167 to P-529; P-168 to P-529; F-169 to P-529; G-170 to P-529; L-171 to P-529; F-172 to P-529; G-173 to P-529; N-174 to P-529; A-175 to P-529; Q-176 to P-529; N-177 to P-529; K-178 to P-529; S-179 to P-529; S-180 to P-529; L-181 to P-529; L-182 to P-529; G-183 to P-529; K-184 to P-529; V-185 to P-529; L-186 to P-529; R-187 to P-529; I-188 to P-529; D-189 to P-529; V-190 to P-529; N-191 to P-529; R-192 to P-529; A-193 to P-529; G-194 to P-529; S-195 to P-529; H-196 to P-529; G-197 to P-529; K-198 to P-529; R-199 to P-529; Y-200 to P-529; R-201 to P-529; V-202 to P-529; P-203 to P-529; S-204 to P-529; D-205 to P-529; N-206 to P-529; P-207 to P-529; F-208 to P-529; V-209 to P-529; S-210 to P-529; E-211 to P-529; P-212 to P-529; G-213 to P-529; A-214 to P-529; H-215 to P-529; P-216 to P-529; A-217 to P-529; I-218 to P-529; Y-219 to P-529; A-220 to P-529; Y-221 to P-529; G-222 to P-529; I-223 to P-529; R-224 to P-529; N-225 to P-529; M-226 to P-529; W-227 to P-529; R-228 to P-529; C-229 to P-529; A-230 to P-529; V-231 to P-529; D-232 to P-529; R-233 to P-529; G-234 to P-529; D-235 to P-529; P-236 to P-529; I-237 to P-529; T-238 to P-529; R-239 to P-529; Q-240 to P-529; G-241 to P-529; R-242 to P-529; G-243 to P-529; R-244 to P-529; I-245 to P-529; F-246 to P-529; C-247 to P-529; G-248 to P-529; D-249 to P-529; V-250 to P-529; G-251 to P-529; Q-252 to P-529; N-253 to P-529; R-254 to P-529; F-255 to P-529; E-256 to P-529; E-257 to P-529; V-258 to P-529; D-259 to P-529; L-260 to P-529; I-261 to P-529; L-262 to P-529; K-263 to P-529; G-264 to P-529; G-265 to P-529; N-266 to P-529; Y-267 to P-529; G-268 to P-529; W-269 to P-529; R-270 to P-529; A-271 to P-529; K-272 to P-529; E-273 to P-529; G-274 to P-529; F-275 to P-529; A-276 to P-529; C-277 to P-529; Y-278 to P-529; D-279 to P-529; K-280 to P-529; K-281 to P-529; L-282 to P-529; C-283 to P-529; H-284 to P-529; N-285 to P-529; A-286 to P-529; S-287 to P-529; L-288 to P-529; D-289 to P-529; D-290 to P-529; V-291 to P-529; L-292 to P-529; P-293 to P-529; I-294 to P-529; Y-295 to P-529; A-296 to P-529; Y-297 to P-529; G-298 to P-529; H-299 to P-529; A-300 to P-529; V-301 to P-529; G-302 to P-529; K-303 to P-529; S-304 to P-529; V-305 to P-529; T-306 to P-529; G-307 to P-529; G-308 to P-529; Y-309 to P-529; V-310 to P-529; Y-311 to P-529; R-312 to P-529; G-313 to P-529; C-314 to P-529; E-315 to P-529; S-316 to P-529; P-317 to P-529; N-318 to P-529; L-319 to P-529; N-320 to P-529; G-321 to P-529; L-322 to P-529; Y-323 to P-529; I-324 to P-529; F-325 to P-529; G-326 to P-529; D-327 to P-529; F-328 to P-529; M-329 to P-529; S-330 to P-529; G-331 to P-529; R-332 to P-529; L-333 to P-529; M-334 to P-529; A-335 to P-529; L-336 to P-529; Q-337 to P-529; E-338 to P-529; D-339 to P-529; R-340 to P-529; K-341 to P-529; N-342 to P-529; K-343 to P-529; K-344 to P-529; W-345 to P-529; K-346 to P-529; K-347 to P-529; Q-348 to P-529; D-349 to P-529; L-350 to P-529; C-351 to P-529; L-352 to P-529; G-353 to P-529; S-354 to P-529; T-355 to P-529; T-356 to P-529; S-357 to P-529; C-358 to P-529; A-359 to P-529; F-360 to P-529; P-361 to P-529; G-362 to P-529; L-363 to P-529; I-364 to P-529; S-365 to P-529; T-366 to P-529; H-367 to P-529; S-368 to P-529; K-369 to P-529; F-370 to P-529; I-371 to P-529; I-372 to P-529; S-373 to P-529; F-374 to P-529; A-375 to P-529; E-376 to P-529; D-377 to P-529; E-378 to P-529; A-379 to P-529; G-380 to P-529; E-381 to P-529; L-382 to P-529; Y-383 to P-529; F-384 to P-529; L-385 to P-529; A-386 to P-529; T-387 to P-529; S-388 to P-529; Y-389 to P-529; P-390 to P-529; S-391 to P-529; A-392 to P-529; Y-393 to P-529; A-394 to P-529; P-395 to P-529; R-396 to P-529; G-397 to P-529; S-398 to P-529; I-399 to P-529; Y-400 to P-529; K-401 to P-529; F-402 to P-529; V-403 to P-529; D-404 to P-529;

P-405 to P-529; S-406 to P-529; R-407 to P-529; R-408 to P-529; A-409 to P-529; P-410 to P-529; P-411 to P-529; G-412 to P-529; K-413 to P-529; C-414 to P-529; K-415 to P-529; Y-416 to P-529; K-417 to P-529; P-418 to P-529; V-419 to P-529; P-420 to P-529; V-421 to P-529; R-422 to P-529; T-423 to P-529; K-424 to P-529; S-425 to P-529; K-426 to P-529; R-427 to P-529; I-428 to P-529; P-429 to P-529; F-430 to P-529; R-431 to P-529; P-432 to P-529; L-433 to P-529; A-434 to P-529; K-435 to P-529; T-436 to P-529; V-437 to P-529; L-438 to P-529; D-439 to P-529; L-440 to P-529; L-441 to P-529; K-442 to P-529; E-443 to P-529; Q-444 to P-529; S-445 to P-529; E-446 to P-529; K-447 to P-529; A-448 to P-529; A-449 to P-529; R-450 to P-529; K-451 to P-529; S-452 to P-529; S-453 to P-529; S-454 to P-529; A-455 to P-529; T-456 to P-529; L-457 to P-529; A-458 to P-529; S-459 to P-529; G-460 to P-529; P-461 to P-529; A-462 to P-529; Q-463 to P-529; G-464 to P-529; L-465 to P-529; S-466 to P-529; E-467 to P-529; K-468 to P-529; G-469 to P-529; S-470 to P-529; S-471 to P-529; K-472 to P-529; K-473 to P-529; L-474 to P-529; A-475 to P-529; S-476 to P-529; P-477 to P-529; T-478 to P-529; S-479 to P-529; S-480 to P-529; K-481 to P-529; N-482 to P-529; T-483 to P-529; L-484 to P-529; R-485 to P-529; G-486 to P-529; P-487 to P-529; G-488 to P-529; T-489 to P-529; K-490 to P-529; K-491 to P-529; K-492 to P-529; A-493 to P-529; R-494 to P-529; V-495 to P-529; G-496 to P-529; P-497 to P-529; H-498 to P-529; V-499 to P-529; R-500 to P-529; Q-501 to P-529; G-502 to P-529; K-503 to P-529; R-504 to P-529; R-505 to P-529; K-506 to P-529; S-507 to P-529; L-508 to P-529; K-509 to P-529; S-510 to P-529; H-511 to P-529; S-512 to P-529; G-513 to P-529; R-514 to P-529; M-515 to P-529; R-516 to P-529; P-517 to P-529; S-518 to P-529; A-519 to P-529; E-520 to P-529; Q-521 to P-529; K-522 to P-529; R-523 to P-529; A-524 to P-529; of SEQ ID NO:29. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities (e.g., biological activities (e.g., ability to illicit mitogenic activity, induce differentiation of normal or malignant cells, bind to EGF receptors, etc.)), may still be retained. For example the ability to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a mutein with a large number of deleted C-terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the polypeptide shown in FIGS. 1A-C, up to the glutamine residue at position number 7, and polynucleotides encoding such polypeptides. In particular, the present invention provides polypeptides comprising the amino acid sequence of residues 1-m1 of FIGS. 1A-C, where m1 is an integer from 7 to 528 corresponding to the position of the amino acid residue in FIGS. 1A-C. Moreover, the invention provides polynucleotides encoding polypeptides comprising, or alternatively consisting of, the amino acid sequence of C-terminal deletions of the polypeptide of the invention shown as SEQ ID NO:29 include polypeptides comprising the amino acid sequence of residues: M-1 to L-528; M-1 to S-527; M-1 to R-526; M-1 to G-525; M-1 to A-524; M-1 to R-523; M-1 to K-522; M-1 to Q-521; M-1 to E-520; M-1 to A-519; M-1 S-518; M-1 to P-517; M-1 to R-516; M-1 to M-515; M-1 to R-514; M-1 to G-513; M-1 to S-512; M-1 to H-511; M-1 to S-510; M-1 to K-509; M-1 to L-508; M-1 to S-507; M-1 to K-506; M-1 to R-505; M-1 to R-504; M-1 to K-503; M-1 to G-502; M-1 to Q-501; M-1 to R-500; M-1 to V-499; M-1 to H-498; M-1 to P-497; M-1 to G-496; M-1 to V-495; M-1 to R-494; M-1 to A-493; M-1 to K-492; M-1 to K-491; M-1 to K-490; M-1 to T-489; M-1 to G-488; M-1 to P-487; M-1 to G-486; M-1 to R-485; M-1 to L-484; M-1 to T-483; M-1 to N-482; M-1 to K-481; M-1 to S-480; M-1 to S-479; M-1 to T-478; M-1 to P-477; M-1 to S-476; M-1 to A-475; M-1 to L-474; M-1 to K-473; M-1 to K-472; M-1 to S-471; M-1 to S-470; M-1 to G-469; M-1 to K-468; M-1 to E-467; M-1 to S-466; M-1 to L-465; M-1 to G-464; M-1 to Q-463; M-1 to A-462; M-1 to P-461; M-1 to G-460; M-1 to S-459; M-1 to A-458; M-1 to L-457; M-1 to T-456; M-1 to A-455; M-1 to S-454; M-1 to S-453; M-1 to S-452; M-1 to K-451; M-1 to R-450; M-1 to A-449; M-1 to A-448; M-1 to K-447; M-1 to E-446; M-1 to S-445; M-1 to Q-444; M-1 to E-443; M-1 to K-442; M-1 to L-441; M-1 to L-440; M-1 to D-439; M-1 to L-438; M-1 to V-437; M-1 to T-436; M-1 to K-435; M-1 to A-434; M-1 to L-433; M-1 to P-432; M-1 to R-431; M-1 to F-430; M-1 to P-429; M-1 to I-428; M-1 to R-427; M-1 to K-426; M-1 to S-425; M-1 to K-424; M-1 to T-423; M-1 to R-422; M-1 to V-421; M-1 to P-420; M-1 to V-419; M-1 to P-418; M-1 to K-417; M-1 to Y-416; M-1 to K-415; M-1 to C-414; M-1 to K-413; M-1 to G-412; M-1 to P-411; M-1 to P-410; M-1 to A-409; M-1 to R-408; M-1 to R-407; M-1 to S-406; M-1 to P-405; M-1 to D-404; M-1 to V-403; M-1 to F-402; M-1 to K-401; M-1 to Y-400; M-1 to I-399; M-1 to S-398; M-1 to G-397; M-1 to R-396; M-1 to P-395; M-1 to A-394; M-1 to Y-393; M-1 to A-392; M-1 to S-391; M-1 to P-390; M-1 to Y-389; M-1 to S-388; M-1 to T-387; M-1 to A-386; M-1 to L-385; M-1 to F-384; M-1 to Y-383; M-1 to L-382; M-1 to E-381; M-1 to G-380; M-1 to A-379; M-1 to E-378; M-1 to D-377; M-1 to E-376; M-1 to A-375; M-1 to F-374; M-1 to S-373; M-1 to I-372; M-1 to I-371; M-1 to F-370; M-1 to K-369; M-1 to S-368; M-1 to H-367; M-1 to T-366; M-1 to S-365; M-1 to I-364; M-1 to L-363; M-1 to G-362; M-1 to P-361; M-1 to F-360; M-1 to A-359; M-1 to C-358; M-1 to S-357; M-1 to T-356; M-1 to T-355; M-1 to S-354; M-1 to G-353; M-1 to L-352; M-1 to C-351; M-1 to L-350; M-1 to D-349; M-1 to Q-348; M-1 to K-347; M-1 to K-346; M-1 to W-345; M-1 to K-344; M-1 to K-343; M-1 to N-342; M-1 to K-341; M-1 to R-340; M-1 to D-339; M-1 to E-338; M-1 to Q-337; M-1 to L-336; M-1 to A-335; M-1 to M-334; M-1 to L-333; M-1 to R-332; M-1 to G-331; M-1 to S-330; M-1 to M-329; M-1 to F-328; M-1 to D-327; M-1 to G-326; M-1 to F-325; M-1 to I-324; M-1 to Y-323; M-1 to L-322; M-1 to G-321; M-1 to N-320; M-1 to L-319; M-1 to N-318; M-1 to P-317; M-1 to S-316; M-1 to E-315; M-1 to C-314; M-1 to G-313; M-1 to R-312; M-1 to Y-311; M-1 to V-310; M-1 to Y-309; M-1 to G-308; M-1 to G-307; M-1 to T-306; M-1 to V-305; M-1 to S-304; M-1 to K-303; M-1 to G-302; M-1 to V-301; M-1 to A-300; M-1 to H-299; M-1 to G-298; M-1 to Y-297; M-1 to A-296; M-1 to Y-295; M-1 to I-294; M-1 to P-293; M-1 to L-292; M-1 to V-291; M-1 to D-290; M-1 to D-289; M-1 to L-288; M-1 to S-287; M-1 to A-286; M-1 to N-285; M-1 to H-284; M-1 to C-283; M-1 to L-282; M-1 to K-281; M-1 to K-280; M-1 to D-279; M-1 to Y-278; M-1 to C-277; M-1 to A-276; M-1 to F-275; M-1 to G-274; M-1 to E-273; M-1 to K-272; M-1 to A-271; M-1 to R-270; M-1 to W-269; M-1 to G-268; M-1 to Y-267; M-1 to N-266; M-1 to G-265; M-1 to G-264; M-1 to K-263; M-1 to L-262; M-1 to I-261; M-1 to L-260; M-1 to D-259; M-1 to V-258; M-1 to E-257; M-1 to E-256; M-1 to F-255; M-1 to R-254; M-1 to N-253; M-1 to Q-252; M-1 to G-251; M-1 to V-250; M-1 to D-249; M-1 to G-248; M-1 to C-247; M-1 to F-246; M-1 to I-245; M-1 to R-244; M-1 to G-243; M-1 to R-242; M-1 to G-241; M-1 to Q-240; M-1 to R-239; M-1 to T-238; M-1 to I-237; M-1 to P-236; M-1 to D-235; M-1 to G-234; M-1 to R-233; M-1 to D-232; M-1 to V-231; M-1 to A-230; M-1 to C-229; M-1 to R-228; M-1 to W-227; M-1 to M-226; M-1 to N-225; M-1 to R-224; M-1 to I-223; M-1 to G-222; M-1 to Y-221; M-1 to A-220; M-1 to Y-219; M-1 to I-218; M-1 to A-217; M-1 to P-216; M-1 to H-215; M-1 to A-214; M-1 to G-213; M-1 to P-212; M-1 to E-211; M-1 to S-210; M-1 to V-209; M-1 to F-208; M-1 to P-207; M-1 to N-206; M-1 to D-205; M-1 to S-204; M-1 to P-203; M-1 to V-202; M-1 to R-201; M-1 to Y-200; M-1 to R-199; M-1 to K-198; M-1 to G-197; M-1 to H-196; M-1 to S-195; M-1 to G-194; M-1 to A-193; M-1 to R-192; M-1 to N-191; M-1 to V-190; M-1 to D-189; M-1 to I-188; M-1 to R-187; M-1 to L-186; M-1 to V-185; M-1 to K-184; M-1 to G-183; M-1 to L-182; M-1 to L-181; M-1 to S-180; M-1 to S-179; M-1 to K-178; M-1 to N-177; M-1 to Q-176; M-1 to A-175; M-1 to N-174; M-1 to G-173; M-1 to F-172; M-1 to L-171; M-1 to G-170; M-1 to F-169; M-1 to P-168; M-1 to D-167; M-1 to G-166; M-1 to A-165; M-1 to Q-164; M-1 to G-163; M-1 to G-162; M-1 to D-161; M-1 to G-160; M-1 to T-159; M-1 to F-158; M-1 to I-157; M-1 to Y-156; M-1 to M-155; M-1 to Y-154; M-1 to G-153; M-1 to D-152; M-1 to L-151; M-1 to G-150; M-1 to F-149; M-1 to L-148; M-1 to L-147; M-1 to Q-146; M-1 to G-145; M-1 to G-144; M-1 to N-143; M-1 to H-142; M-1 to N-141; M-1 to S-140; M-1 to A-139; M-1 to P-138; M-1 to E-137; M-1 to E-136; M-1 to I-135; M-1 to E-134; M-1 to L-133; M-1 to I-132; M-1 to V-131; M-1 to R-130; M-1 to E-129; M-1 to S-128; M-1 to K-127; M-1 to L-126; M-1 to D-125; M-1 to A-124; M-1 to K-123; M-1 to N-122; M-1 to P-121; M-1 to D-120; M-1 to A-119; M-1 to R-118; M-1 to S-117; M-1 to V-116; M-1 to K-115; M-1 to M-114; M-1 to E-113; M-1 to S-112; M-1 to I-111; M-1 to R-110; M-1 to I-109; M-1 to K-108; M-1 to E-107; M-1 to V-106; M-1 to K-105; M-1 to K-104; M-1 to K-103; M-1 to D-102; M-1 to L-101; M-1 to C-100; M-1 to S-99; M-1 to Y-98; M-1 to Y-97; M-1 to I-96; M-1 to Y-95; M-1 to F-94; M-1 to K-93; M-1 to R-92; M-1 to N-91; M-1 to H-90; M-1 to R-89; M-1 to F-88; M-1 to K-87; M-1 to P-86; M-1 to H-85; M-1 to F-84; M-1 to A-83; M-1 to L-82; M-1 to G-81; M-1 to L-80; M-1 to F-79; M-1 to G-78; M-1 to R-77; M-1 to E-76; M-1 to D-75; M-1 to G-74; M-1 to I-73; M-1 to W-72; M-1 to P-71; M-1 to T-70; M-1 to T-69; M-1 to L-68; M-1 to V-67; M-1 to I-66; M-1 to N-65; M-1 to K-64; M-1 to L-63; M-1 to D-62; M-1 to L-61; M-1 to F-60; M-1 to P-59; M-1 to Q-58; M-1 to E-57; M-1 to L-56; M-1 to R-55; M-1 to S-54; M-1 to G-53; M-1 to D-52; M-1 to P-51; M-1 to L-50; M-1 to Y-49; M-1 to V-48; M-1 to W-47; M-1 to V-46; M-1 to V-45; M-1 to G-44; M-1 to V-43; M-1 to Q-42; M-1 to E-41; M-1 to A-40; M-1 to V-39; M-1 to F-38; M-1 to F-37; M-1 to R-36; M-1 to H-35; M-1 to T-34; M-1 to G-33; M-1 to D-32; M-1 to G-31; M-1 to A-30; M-1 to H-29; M-1 to V-28; M-1 to M-27; M-1 to S-26; M-1 to V-25; M-1 to P-24; M-1 to N-23; M-1 to R-22; M-1 to L-21; M-1 to G-20; M-1 to N-19; M-1 to A-18; M-1 to V-17; M-1 to E-16; M-1 to S-15; M-1 to L-14; M-1 to C-13; M-1 to L-12; M-1 to Q-11; M-1 to L-10; M-1 to C-9; M-1 to G-8; M-1 to Q-7; of SEQ ID NO:29. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Northern analysis indicates that a 2.5-3.0 kb transcript of this gene is expressed primarily in testes tissue and A549 lung carcinoma tissue, but interestingly is absent from normal lung tissue. This gene is also expressed in osteoarthritis tissue and human fetal tissues.

Therefore, polynucleotides and polypeptides of the invention, including antibodies, are useful as reagents for differential identification of the tissue(s) or cell type(s) present in a biological sample and for diagnosis of diseases and conditions which include, but are not limited to, developmental disorders, and degenerative disorders; osteoarthritis, and lung cancer. Similarly, polypeptides and antibodies directed to these polypeptides are useful in providing immunological probes for differential identification of the tissue(s) or cell type(s). For a number of disorders of the above tissues or cells, particularly of developing tissues, cartilage, and bone, expression of this gene at significantly higher or lower levels is routinely detected in certain tissues or cell types (e.g. bone, lung, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Based upon the tissue distribution in testes tissue, lung carcinoma tissue, and osteoarthritic and fetal tissues, and the homology to several proteins involved in the development, differentiation, and/or proliferation of various cells, polynucleotides, translation products and antibodies corresponding to this gene may be useful for the diagnosis, detection and/or treatment of diseases and/or disorders involving the proliferation of cells, particularly cancers cells such as lung carcinoma cells, as well as for diseases and/or disorders of the testes, fetal tissues and for the diagnosis, detection and/or treatment of osteoarthritis.

The expression in lung carcinoma tissue indicates that polynucleotides, translation products and antibodies corresponding to this gene are useful for the diagnosis, detection and/or treatment of lung carcinomas. Polynucleotides, translation products and antibodies corresponding to this gene may be useful for the prevention of the growth of lung carcinomas. Alternatively, polynucleotides, translation products and antibodies corresponding to this gene may be useful in the detection of lung carcinomas. Accordingly, preferred are antibodies and or small molecules which specifically bind a portion of the translation product of this gene. Also provided is a kit for detecting lung carcinomas. Such a kit comprises in one embodiment an antibody specific for translation products corresponding to this gene bound to a solid support. Also provided is a method of detecting lung carcinomas in an individual which comprises a step of contacting an antibody specific for translation products corresponding to this gene to a bodily fluid or biological sample from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein.

More generally, tissue distribution in testes tissue indicates that polynucleotides, translation products and antibodies corresponding to this gene are useful for the treatment and/or diagnosis of conditions concerning proper testicular function (e.g. endocrine function, sperm maturation), as well as cancer. Therefore, polynucleotides, translation products and antibodies corresponding to this gene are useful in the treatment of male infertility and/or impotence. Polynucleotides, translation products and antibodies corresponding to this gene are also useful in assays designed to identify binding agents, as such agents (antagonists) are useful as male contraceptive agents. Similarly, polynucleotides, translation products and antibodies corresponding to this gene are useful in the treatment and/or diagnosis of testicular cancer. The testes are also a site of active gene expression of transcripts that may be expressed, particularly at low levels, in other tissues of the body. Therefore, translation products corresponding to this gene may be expressed in other specific tissues or organs where it may play related functional roles in other processes, such as hematopoiesis, inflammation, bone formation, and kidney function, to name a few possible target indications.

Furthermore, the tissue distribution in osteoarthritic tissue suggests that polynucleotides, translation products and antibodies corresponding to this gene are useful for the treatment and/or diagnosis of diseases of connective tissue, particularly osteoarthritis, including but not limited to inflammation, rheumatoid arthritis, and cartilage tears and physical injury. Additionally, translation products corresponding to this gene, as well as antibodies directed against these translation products, may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 2595 of SEQ ID NO:11, b is an integer of 15 to 2609, where both a and b correspond to the positions of nucleotide residues shown in SEQ ID NO:11, and where b is greater than or equal to a+14.

Features of Protein Encoded by Gene No: 2

Translation products corresponding to this gene, sometimes referred to herein as TIDE (for Ten Integrin Domains with EGF homology), share sequence homology with integrins, which are a superfamily of dimeric ab cell-surface glycoproteins that mediate the adhesive functions of many cell types, enabling cells to interact with one another and with the extracellular matrix (See *Genomics* 56, 169-178 (1999); all information and references contained within this publication are hereby incorporated herein by reference). Eight human integrin 'b' subunits have been described to date, and in combination with the 12 known 'a' subunits form a large family of heterodimeric cell surface receptors that mediate cell adhesion to counter-receptors on neighboring cells, and to ECM proteins (reviewed by Hynes, 1992). Integrin-ligand interactions are crucial for fundamental biological processes such as cell migration and motility, and lymphocyte extravasation.

In another embodiment, polypeptides comprising the amino acid sequence of the open reading frame upstream of the predicted signal peptide are contemplated by the present invention. Specifically, polypeptides of the invention comprise, or alternatively consist of, the following amino acid sequence: TSTPPRAVPLPKSSQAAHQRNCNSG-
WSPGPASLGVRGSVCPAICWWHLS
LLPPPSVNPTLQKCSSPGAAQELSMRP-
PGFRNFLLLASSLLFAGLSAVPQSF-
SPSLRSWPGAACRLSRAESERR CRAPGQPPGAALCH-
GRGRCDCGVCICHVTEPGMFFGPLCECHEWVC
ETYDGSTCAGHGKCDCGKCKCDQGWYGDAC QYPT-
NCDLTKKKSNQMCKNSQDIICSNAGTCH-
CGRCKCDNSDGSGLVYGKFCECD-
DRECIDDETEEICGGHGKCYCGN
CYCKAGWHGDKCEFQCDITP-
WESKRRCTSPDGKICSNRGTC VCGECTCHDVDPT-
GDWGDIHGDTCECDERDCRAVYD RYSDDFCSGH-
GQCNCGRCDCKAGWYGKKCEHPQSCTLSAEES
IRKCQGSSDLPCSGRGKCECGKCTCYPPGDRRVYG
KTCECDDRRCEDLDGVVCGGHGTC-
SCGRCVCERGWFGKLCQHPRKCNMTE-
EQSKNLCESADGILCSGKGSCHCGKCI CSAEEWYIS-
GEFCDCDDRDCDKHDGLICTGNGICSCGNCEC
WDGWNGNACEI WLGSEYP (SEQ ID NO:50). Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Included in this invention as preferred domains are EGF-like domain signature 1 and 2 domains, which were identified using the ProSite analysis tool (Swiss Institute of Bioinformatics). A sequence of about thirty to forty amino-acid residues long found in the sequence of epidermal growth factor (EGF) has been shown [1 to 6] to be present, in a more or less conserved form, in a large number of other, mostly animal proteins. The functional significance of EGF domains in what appear to be unrelated proteins is not yet clear. However, a common feature is that these repeats are found in the extracellular domain of membrane-bound proteins or in proteins known to be secreted (exception: prostaglandin G/H synthase). The EGF domain includes six cysteine residues which have been shown (in EGF) to be involved in disulfide bonds. The main structure is a two-stranded beta-sheet followed by a loop to a C-terminal short two-stranded sheet. Subdomains between the conserved cysteines strongly vary in length as shown in the following schematic representation of the EGF-like domain:

```
               +-----------------------+     +------------------------------+
               |                       |     |                              |
x(4)-C-x(0,48)-C-x(3,12)-C-x(1,70)-C-x(1,6)-C-x(2)-G-a-x(0,21)-G-x(2)-C-x
     |                   |                  ***************************
     +-------------------+
```

'C': conserved cysteine involved in a disulfide bond. 'G': often conserved glycine 'a': often conserved aromatic amino acid '*': position of both patterns. 'x': any residue The region between the 5th and 6th cysteine contains two conserved glycines of which at least one is present in most EGF-like domains. The consensus pattern is as follows: C-x-C-x(5)-G-x(2)-C [The 3 C's are involved in disulfide bonds].

Preferred polypeptides of the invention comprise, or alternatively consist of, an amino acid sequence selected from the group consisting of GKCDCGKCKCDQGWYGDACQYPTNCDLTK (SEQ ID NO: 51), GGHGKCYCGNCYCKAGWHGDKCEFQCDIT (SEQ ID NO: 52), HGQCNCGRCDCKAGWYGKKCEHPQSCTLS (SEQ ID NO: 53), HGTCSCGRCVCERGWFGKLCQHPRKCNMT (SEQ ID NO: 54), GNGICSCGNCECWDGWNGNACEIWLGSEY (SEQ ID NO: 55), and ICGGHGKCYCGNCYCKAGWHGDKCEFQCDITPWESK (SEQ ID NO: 73). Polynucleotides encoding these polypeptides are also encompassed by the invention.

Further preferred are polypeptides comprising the EGF-like domain signature 1 and 2 domains of the sequence referenced in Table I for this gene, and at least 5, 10, 15, 20, 25, 30, 50, or 75 additional contiguous amino acid residues of this referenced sequence. The additional contiguous amino acid residues is N-terminal or C-terminal to the EGF-like domain signature 1 and 2 domains.

Alternatively, the additional contiguous amino acid residues is both N-terminal and C-terminal to the EGF-like domain signature 1 and 2 domains, wherein the total N- and C-terminal contiguous amino acid residues equal the specified number. The above preferred polypeptide domain is characteristic of a signature specific to EGF-like domain 1 and 2 containing proteins. Based on the sequence similarity, the translation product of this gene is expected to share at least some biological activities with EGF-like containing proteins. Such activities are known in the art, some of which are described elsewhere herein.

Included in this invention as preferred domains are integrins beta chain cysteine-rich domains, which were identified using the ProSite analysis tool (Swiss Institute of Bioinformatics). Integrins [7,8] are a large family of cell surface receptors that mediate cell to cell as well as cell to matrix adhesion. Some integrins recognize the R-G-D sequence in their extracellular matrix protein ligand. Structurally, integrins consist of a dimer of an alpha and a beta chain. Each subunit has a large N-terminal extracellular domain followed by a transmembrane domain and a short C-terminal cytoplasmic region. Some receptors share a common beta chain while having different alpha chains. All the integrin beta chains contain four repeats of a forty amino acid region in the C-terminal extremity of their extracellular domain. Each of the repeats contains eight cysteines. The consensus pattern is as follows: C-x-[GNQ]-x(1,3)-G-x-C-x-C-x(2)-C-x-C [The five C's are probably involved in disulfide bonds].

Preferred polypeptides of the invention comprise, or alternatively consist of, an amino acid sequence selected from the group consisting of: GQPPGAALCHGRGRCDCGVCICHVTEPGMFFGPLC (SEQ ID NO: 74), ETYDGSTCAGHGKCDCGKCKCDQGWYGDACQYP (SEQ ID NO: 58), MCKNSQDIICSNAGTCHCGRCKCDNSDGSGLVYG (SEQ ID NO: 59), IDDETEEICGGHGKCYCGNCYCKAGWHGDKC (SEQ ID NO: 60), KRRCTSPDGKICSNRGTCVCGECTCHDVDPTGDW (SEQ ID NO: 61), DRYSDDFCSGHGQCNCGRCDCKAGWYGKKCEHPQ (SEQ ID NO: 62), CQGSSDLPCSGRGKCECGKCTCYPPGDRRVYGK (SEQ ID NO: 63), CEDLDGVVCGGHGTCSCGRCVCERGWFGKLC (SEQ ID NO: 64), SADGILCSGKGSCHCGKCICSAEEWYISGEFC (SEQ ID NO: 65), and CDKHDGLICTGNGICSCGNCECWDGWNGNACEI (SEQ ID NO: 66). Polynucleotides encoding these polypeptides are also encompassed by the invention.

Further preferred are polypeptides comprising the integrins beta chain cysteine-rich domain of the sequence referenced in Table XIV for this gene, and at least 5, 10, 15, 20, 25, 30, 50, or 75 additional contiguous amino acid residues of this referenced sequence. The additional contiguous amino acid residues is N-terminal or C-terminal to the integrins beta chain cysteine-rich domain.

Alternatively, the additional contiguous amino acid residues is both N-terminal and C-terminal to the integrins beta chain cysteine-rich domain, wherein the total N- and C-terminal contiguous amino acid residues equal the specified number. The above preferred polypeptide domain is characteristic of a signature specific to integrin proteins. Based on the sequence similarity, the translation product of this gene is expected to share at least some biological activities with integrin proteins, and specifically those containing an integrins beta chain cysteine-rich domain. Such activities are known in the art, some of which are described elsewhere herein. The following publications were referenced above and are hereby incorporated herein by reference: [1] Davis C. G., New Biol. 2:410-419(1990); [2] Blomquist M. C., Hunt L. T., Barker W. C., Proc. Natl. Acad. Sci. U.S.A. 81:7363-7367 (1984); [3] Barker W. C., Johnson G. C., Hunt L. T., George D. G., Protein Nucl. Acid Enz. 29:54-68(1986); [4] Doolittle R. F., Feng D. F., Johnson M. S., Nature 307:558-560(1984); [5] Appella E., Weber I. T., Blasi F., FEBS Lett. 231:1-4 (1988); [6] Campbell I. D., Bork P., Curr. Opin. Struct. Biol. 3:385-392(1993); [7] Hynes R. O., Cell 48:549-554(1987); and [8] Albelda S. M., Buck C. A., FASEB J. 4:2868-2880 (1990).

The polypeptide of the present invention has been putatively identified as a member of the integrin family and has been termed Ten Integrin Domains with EGF homology ("TIDE"). This identification has been made as a result of amino acid sequence homology to the human integrin beta-8 subunit (See Genbank Accession No. gi|184521).

Preferred polypeptides of the present invention comprise, or alternatively consist of, one, two, three, four, five, six, seven, eight, nine, ten, eleven, twelve, thirteen, fourteen, fifteen, sixteen, seventeen, eighteen, nineteen, or all nineteen of the immunogenic epitopes shown in SEQ ID NO: 30 as residues: Met-1 to Phe-6, Arg-44 to Arg-52, His-64 to Cys-69, Tyr-99 to Gln-147, His-158 to Gly-169, Phe-177 to Asp-182, Cys-194 to Cys-202, Gly-213 to Phe-218, Pro-224 to Gly-236, Asp-254 to Trp-261, Asp-263 to Ala-303, Trp-305 to Cys-316, Lys-326 to Asp-332, Pro-334 to Cys-343, Pro-350 to Asp-370, Thr-407 to Asn413, Gly-425 to Cys431, Asp-449 to Asp-459, and/or Gly472 to Asn-483. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

FIGS. 4A-C shows the nucleotide (SEQ ID NO:12) and deduced amino acid sequence (SEQ ID NO:30) of TIDE. Predicted amino acids from about 1 to about 23 constitute the predicted signal peptide (amino acid residues from about 1 to about 23 in SEQ ID NO:30) and are represented by the underlined amino acid regions; amino acids from about 108 to about 136, from about 195 to about 223, from about 291 to about 319, from about 379 to about 407, and/or from about 465 to about 493 constitute the predicted EGF-like domain signature 1 and 2 domains (amino acids from about 108 to about 136, from about 195 to about 223, from about 291 to about 319, from about 379 to about 407, and/or from about 465 to about 493 in SEQ ID NO:30) and are represented by the double underlined amino acids; and amino acids from about 55 to about 89, from about 97 to about 129, from about 142 to about 175, from about 186 to about 216, from about 228 to about 261, from about 281 to about 314, from about 327 to about 359, from about 368 to about 398, from about 417 to about 448, and/or from about 455 to about 487 constitute the predicted integrins beta chain cysteine-rich domains (amino acids from about 55 to about 89, from about 97 to about 129, from about 142 to about 175, from about 186 to about 216, from about 228 to about 261, from about 281 to about 314, from about 327 to about 359, from about 368 to about 398, from about 417 to about 448, and/or from about 455 to about 487 in SEQ ID NO:30) and are represented by the shaded amino acids.

FIG. 5 shows the regions of similarity between the amino acid sequences of the Ten Integrin Domains with EGF homology (TIDE) protein (SEQ ID NO:30) and the human integrin beta-8 subunit (SEQ ID NO: 67).

Figure 6:
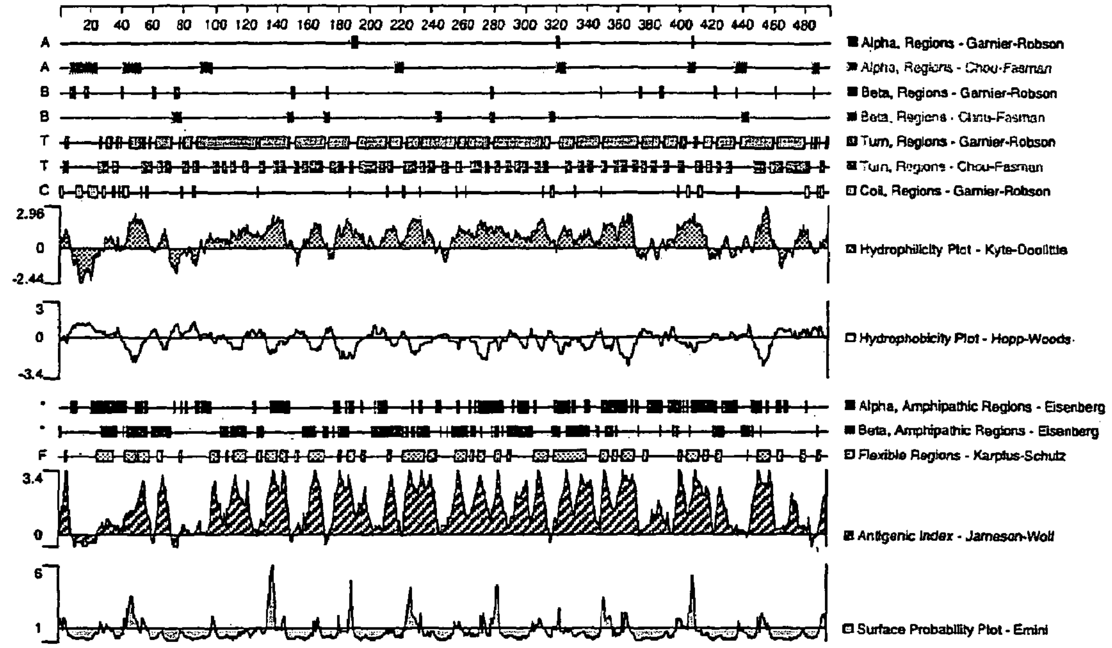
FIG. 6 shows an analysis of the Ten Integrin Domains with EGF homology (TIDE) amino acid sequence. Alpha, beta, turn and coil regions; hydrophilicity and hydrophobicity; amphipathic regions; flexible regions; antigenic index and surface probability are shown.

FIG. 6 shows an analysis of the Ten Integrin Domains with EGF homology (TIDE) amino acid sequence. Alpha, beta, turn and coil regions; hydrophilicity and hydrophobicity; amphipathic regions; flexible regions; antigenic index and surface probability are shown.

Translation products corresponding to this gene share homology to the characteristic integrins beta chain cysteine-rich domains of integrin family members. The polynucleotide contains an open reading frame encoding the TIDE polypeptide of 494 amino acids. TIDE exhibits a high degree of homology at the amino acid level to the human integrin beta-8 subunit (as shown in FIG. 5).

The present invention provides isolated nucleic acid molecules comprising a polynucleotide encoding the TIDE polypeptide having the amino acid sequence shown in FIGS. 4A-C (SEQ ID NO:30). The nucleotide sequence shown in FIGS. 4A-C (SEQ ID NO:12) was obtained by sequencing a cloned cDNA (HOHCH55), which was deposited on November 17 at the American Type Culture Collection, and given Accession Number 203484. The present invention is further directed to fragments of the isolated nucleic acid molecules described herein. By a fragment of an isolated DNA molecule having the nucleotide sequence of the deposited cDNA or the nucleotide sequence shown in SEQ ID NO:12 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:12. By a fragment at least 20 nt in length, for example, is intended fragments which include 20 or more contiguous bases from the nucleotide sequence of the deposited cDNA or the nucleotide sequence as shown in SEQ ID NO:12. In this context "about" includes the particularly recited size, larger or smaller by several (5, 4, 3, 2, or 1) nucleotides, at either terminus or at both termini. Representative examples of TIDE polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, from about 501 to about 550, from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1350, from about 1351 to about 1400, from about 1401 to about 1450, from about 1451 to about 1500, from about 1501 to about 1550, from about 1551 to about 1600, from about 1601 to about 1650, from about 1651 to about 1700, from about 1701 to about 1750, from about 1751 to about 1800, from about 1801 to about 1850, from about 1851 to about 1900, from about 1901 to about 1950, from about 1951 to about 2000, from about 2001 to about 2050, from about 2051 to about 2100, from about 2101 to about 2150, from about 2151 to about 2200, from about 2201 to about 2250, from about 2251 to about 2300, from about 2301 to about 2350, from about 2351 to about 2400, from about 2401 to about 2450, from about 2451 to about 2499, from about 289 to about 1705, and/or from about 221 to about 1705 of SEQ ID NO:12, or the complementary strand thereto, or the cDNA contained in the deposited gene. In this context "about" includes the particularly recited ranges, larger or smaller by several (5, 4, 3, 2, or 1) nucleotides, at either terminus or at both termini.

Preferred nucleic acid fragments of the present invention include nucleic acid molecules encoding a member selected from the group: a polypeptide comprising or alternatively, consisting of, the mature TIDE protein (amino acid residues from about 221 to about 1705 in FIGS. 4AC (amino acids from about 221 to about 1705 in SEQ ID NO:30). Since the location of these domains have been predicted by computer analysis, one of ordinary skill would appreciate that the amino acid residues constituting these domains may vary slightly (e.g., by about 1 to 15 amino acid residues) depending on the criteria used to define each domain. In additional embodiments, the polynucleotides of the invention encode functional attributes of TIDE.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of TIDE. The data representing the structural or functional attributes of TIDE set forth in FIG. 6 and/or Table II, as described above, was generated using the various modules and algorithms of the DNA*STAR set on default parameters. In a preferred embodiment, the data presented in columns VIII, IX XIII, and XIV of Table II can be used to determine regions of TIDE which exhibit a high degree of potential for antigenicity. Regions of high antigenicity are determined from the data presented in columns VIII, IX XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 6, but may, as shown in Table II, be represented or identified by using tabular representations of the data presented in FIG. 6. The DNA*STAR computer algorithm used to generate FIG. 6 (set on the original default parameters) was used to present the data in FIG. 6 in a tabular format (See Table II). The tabular format of the data in FIG. 6 is used to easily determine specific boundaries of a preferred region. The above-mentioned preferred regions set out in FIG. 6 and in Table II include, but are not limited to, regions of the aforementioned types identified by analysis of the amino acid sequence set out in FIGS. 4A-C. As set out in FIG. 6 and in Table II, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, etc.) may still be retained. For example, the ability of shortened TIDE muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an TIDE mutein with a large number of deleted N-terminal amino acid residues may retain some biological or immunogenic activities. In fact, peptides composed of as few as six TIDE amino acid residues may often evoke an immune response.

Accordingly, the present invention further provides polypeptides having one or more residues deleted from the amino terminus of the TIDE amino acid sequence shown in FIGS. 4A-C, up to the leucine residue at position number 489 and polynucleotides encoding such polypeptides. In particular, the present invention provides polypeptides comprising the amino acid sequence of residues n1-494 of FIGS. 4A-C, where n1 is an integer from 2 to 489 corresponding to the position of the amino acid residue in FIGS. 4A-C (which is identical to the sequence shown as SEQ ID NO:30). In another embodiment, N-terminal deletions of the TIDE polypeptide can be described by the general formula n2-494, where n2 is a number from 2 to 489, corresponding to the position of amino acid identified in FIGS. 4A-C. N-terminal deletions of the TIDE polypeptide of the invention shown as SEQ ID NO:30 include polypeptides comprising the amino acid sequence of residues: N-terminal deletions of the TIDE polypeptide of the invention shown as SEQ ID NO:30 include polypeptides comprising the amino acid sequence of residues: R-2 to P494; P-3 to P-494; P-4 to P-494; G-5 to P-494; F-6 to P-494; R-7 to P-494; N-8 to P-494; F-9 to P-494; L-10 to P-494; L-11 to P-494; L-12 to P-494; A-13 to P-494; S-14 to P-494; S-15 to P-494; L-16 to P-494; L-17 to P-494; F-18 to P-494; A-19 to P-494; G-20 to P-494; L-21 to P-494; S-22 to P-494; A-23 to P-494; V-24 to P-494; P-25 to P-494; Q-26 to P-494; S-27 to P-494; F-28 to P-494; S-29 to P-494; P-30 to P-494; S-31 to P-494; L-32 to P-494; R-33 to P-494; S-34 to P-494; W-35 to P-494; P-36 to P-494; G-37 to P-494; A-38 to P-494; A-39 to P-494; C-40 to P-494; R-41 to P-494; L-42 to P-494; S-43 to P-494; R-44 to P-494; A-45 to P-494; E-46 to P-494; S-47 to P-494; E-48 to P-494; R-49 to P-494; R-50 to P-494; C-51 to P-494; R-52 to P-494; A-53 to P-494; P-54 to P-494; G-55 to P-494; Q-56 to P-494; P-57 to P-494; P-58 to P-494; G-59 to P-494; A-60 to P-494; A-61 to P-494; L-62 to P-494; C-63 to P-494; H-64 to P-494; G-65 to P-494; R-66 to P-494; G-67 to P-494; R-68 to P-494; C-69 to P-494; D-70 to P-494; C-71 to P-494; G-72 to P-494; V-73 to P-494; C-74 to P-494; I-75 to P-494; C-76 to P-494; H-77 to P-494; V-78 to P-494; T-79 to P-494; E-80 to P-494; P-81 to P-494; G-82 to P-494; M-83 to P-494; F-84 to P-494; F-85 to P-494; G-86 to P-494; P-87 to P-494; L-88 to P-494; C-89 to P-494; E-90 to P-494; C-91 to P-494; H-92 to P-494; E-93 to P-494; W-94 to P-494; V-95 to P-494; C-96 to P-494; E-97 to P-494; T-98 to P-494; Y-99 to P-494; D-100 to P-494; G-101 to P-494; S-102 to P-494; T-103 to P-494; C-104 to P-494; A-105 to P-494; G-106 to P-494; H-107 to P-494; G-108 to P-494; K-109 to P-494; C-110 to P-494; D-111 to P-494; C-112 to P-494; G-113 to P-494; K-114 to P-494; C-115 to P-494; K-116 to P-494; C-117 to P-494; D-118 to P-494; Q-119 to P-494; G-120 to P-494; W-121 to P-494; Y-122 to P-494; G-123 to P-494; D-124 to P-494; A-125 to P-494; C-126 to P-494; Q-127 to P-494; Y-128 to P-494; P-129 to P 494; T-130 to P-494; N-131 to P-494; C-132 to P-494; D-133 to P-494; L-134 to P-494; T-135 to P-494; K-136 to P-494; K-137 to P-494; K-138 to P-494; S-139 to P-494; N-140; to P-494; Q-141 to P-494; M-142 to P-494; C-143 to P-494; K-144 to P-494; N-145 to P-494; S-146 to P-494; Q-147 to P-494; D-148 to P-494; I-149 to P-494; I-150 to P-494; C-151 to P-494; S-152to P-494; N-153 to P-494; A-154 to P-494; G-155 to P-494; T-156 to P-494; C-157 to P-494; H-158 to P-494; C-159 to P-494; G-160 to P-494; R-161 to P-494; C-162 to P-494; K-163 to P-494; C-164 to P-494; D-165 to P-494; N-166 to P-494; S-167 to P-494; D-168 to P-494; G-169 to P-494; S-170 to P-494; G-171 to P-494; L-172 to P-494; V-173 to P-494; Y-174 to P-494; G-175 to P-494; K-176 to P-494; F-177 to P-494; C-178 to P-494; E-179 to P-494; C-180 to P-494; D-181 to P-494; D-182 to P-494; R-183 to P-494; E-184 to P-494; C-185 to P-494; I-186 to P-494; D-187 to P-494; D-188 to P-494; E-189 to P-494; T-190 to P-494; E-191 to P-494; E-192 to P-494; I-193 to P-494; C-194 to P-494; G-195 to P-494; G-196 to P-494; H-197 to P-494; G-198 to P-494; K-199 to P-494; C-200 to P-494; Y-201 to P-494; C-202 to P-494; G-203 to P-494; N-204 to P-494; C-205 to P-494; Y-206 to P-494; C-207 to P-494; K-208 to P-494; A-209 to P-494; G-210 to P-494; W-211 to P-494; H-212 to P-494; G-213 to P-494; D-214 to P-494; K-215 to P-494; C-216 to P-494; E-217 to P-494; F-218 to P-494; Q-219 to P-494; C-220 to P-494; D-221 to P-494; I-222 to P-494; T-223 to P-494; P-224 to P-494; W-225 to P-494; E-226 to P-494; S-227 to P-494; K-228 to P-494; R-229 to P-494; R-230 to P-494; C-231 to P-494; T-232 to P-494; S-233 to P-494; P-234 to P-494; D-235 to P-494; G-236 to P-494; K-237 to P-494; I-238 to P-494; C-239 to P-494; S-240 to P-494; N-241 to P-494; R-242 to P-494; G-243 to P-494; T-244 to P-494; C-245 to P-494; V-246 to P-494; C-247 to P-494; G-248 to P-494; E-249 to P-494; C-250 to P-494; T-251 to P-494; C-252 to P-494; H-253 to P-494; D-254 to P-494; V-255 to P-494; D-256 to P-494; P-257 to P-494; T-258 to P-494; G-259 to P-494; D-260 to P-494; W-261 to P-494; G-262 to P-494; D-263 to P-494; I-264 to P-494; H-265 to P494; G-266 to P-494; D-267 to P-494; T-268 to P-494; C-269 to P-494; E-270 to P-494; C-271 to P-494; D-272 to P-494; E-273 to P-494; R-274 to P-494; D-275 to P-494; C-276 to P-494; R-277 to P-494; A-278 to P-494; V-279 to P-494; Y-280 to P-494; D-281 to P-494; R-282 to P-494; Y-283 to P-494; S-284 to P-494; D-285 to P-494; D-286 to P-494; F-287 to P-494; C-288 to P-494; S-289 to P-494; G-290 to P-494; H-291 to P-494; G-292 to P-494; Q-293 to P-494; C-294 to P-494; N-295 to P-494; C-296 to P-494; G-297 to P-494; R-298 to P-494; C-299 to P-494; D-300 to P-494; C-301 to P-494; K-302 to P-494; A-303 to P-494; G-304 to P-494; W-305 to P-494; Y-306 to P-494; G-307 to P-494; K-308 to P-494; K-309 to P-494; C-310 to P-494; E-311 to P-494; H-312 to P-494; P-313 to P-494; Q-314 to P-494; S-315 to P-494; C-316 to P-494; T-317 to P-494; L-318 to P-494; S-319 to P-494; A-320 to P-494; E-321 to P-494; E-322 to P-494; S-323 to P-494; I-324 to P-494; R-325 to P-494; K-326 to P-494; C-327 to P-494; Q-328 to P-494; G-329 to P494; S-330 to P-494; S-331 to P-494; D-332 to P-494; L-333 to P-494; P-334 to P-494; C-335 to P-494; S-336 to P-494; G-337 to P-494; R-338 to P-494; G-339 to P-494; K-340 to P-494; C-341 to P-494; E-342 to P-494; C-343 to P-494; G-344 to P-494; K-345 to P-494; C-346 to P-494; T-347 to P-494; C-348 to P-494; Y-349 to P-494; P-350 to P-494; P-351 to P-494; G-352 to P-494; D-353 to P-494; R-354 to P-494; R-355 to P-494; V-356 to P-494; Y-357 to P-494; G-358 to P-494; K-359 to P-494; T-360 to P-494; C-361 to P-494; E-362 to P-494; C-363 to P-494; D-364 to P-494; D-365 to P-494; R-366 to P-494; R-367 to P-494; C-368 to P-494; E-369 to P-494; D-370 to P-494; L-371 to P-494; D-372 to P-494; G-373 to P-494; V-374 to P-494; V-375 to P-494; C-376 to P-494; G-377 to P-494; G-378 to P-494; H-379 to P-494; G-380 to P-494; T-381 to P-494; C-382 to P-494; S-383 to P-494; C-384 to P-494; G-385 to P-494; R-386 to P-494; C-387 to P-494; V-388 to P-494; C-389 to P-494; E-390 to P-494; R-391 to P-494; G-392 to P-494; W-393 to P-494; F-394 to P-494; G-395 to P-494; K-396 to P-494; L-397 to P-494; C-398 to P-494; Q-399 to P-494; H-400 to P-494; P-401 to P-494; R-402 to P-494; K-403 to P-494; C-404 to P-494; N-405 to P-494; M-406 to P-494; T-407 to P-494; E-408 to P-494; E-409 to P-494; Q-410 to P-494; S-411 to P-494; K-412 to P-494; N-413 to P-494; L-414 to P-494; C-415 to P-494; E-416 to P-494; S-417 to P-494; A-418 to P-494; D-419 to P-494; G-420 to P-494; I-421 to P-494; L-422 to P-494; C-423 to P-494; S-424 to P-494; G-425 to P-494; K-426 to P-494; G-427 to P-494; S-428 to P-494; C-429 to P-494; H-430 to P-494; C-431 to P-494; G-432 to P-494; K-433 to P-494; C-434 to P-494; I-435 to P-494; C-436 to P-494; S-437 to P-494; A-438 to P-494; E-439 to P-494; E-440 to P-494; W-441 to P-494; Y-442 to P-494; I-443 to P-494; S-444 to P-494; G-445 to P-494; E-446 to P-494; F-447 to P-494; C-448 to P-494; D-449 to P-494; C-450 to P-494; D-451 to P-494; D-452 to P-494; R-453 to P-494; D-454 to P-494; C-455 to P-494; D-456 to P-494; K-457 to P-494; H-458 to P-494; D-459 to P-494; G-460 to P-494; L-461 to P-494; I-462 to P-494; C-463 to P-494; T-464 to P-494; G-465 to P-494; N-466 to P-494; G-467 to P-494; I-468 to P-494; C-469 to P-494; S-470 to P-494; C-471 to P-494; G-472 to P-494; N-473 to P-494; C-474 to P-494; E-475 to P-494; C-476 to P-494; W-477 to P-494; D-478 to P-494; G-479 to P-494; W-480 to P-494; N-481 to P-494; G-482 to P-494; N-483 to P-494; A-484 to P-494; C-485 to P-494; E-486 to P-494; I-487 to P-494; W-488 to P-494; L-489 to P-494; of SEQ ID NO:30. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities may still be retained. For example the ability of the shortened TIDE mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an TIDE mutein with a large number of deleted C-terminal amino acid residues may retain some biological or immunogenic activities. In fact, peptides composed of as few as six TIDE amino acid residues may often evoke an immune response.

Accordingly, the present invention further provides polypeptides having one or more residues deleted from the carboxy terminus of the amino acid sequence of the TIDE polypeptide shown in FIGS. 4A-C, up to the phenylalanine residue at position number 6, and polynucleotides encoding such polypeptides. In particular, the present invention provides polypeptides comprising the amino acid sequence of residues 1-m1 of FIG. 1, where m1 is an integer from 6 to 494 corresponding to the position of the amino acid residue in FIGS. 4A-C. Moreover, the invention provides polynucleotides encoding polypeptides comprising, or alternatively consisting of, the amino acid sequence of C-terminal deletions of the TIDE polypeptide of the invention shown as SEQ ID NO:30 include polypeptides comprising the amino acid sequence of residues: M-1 to Y-493; M-1 to E-492; M-1 to S-491; M-1 to G-490; M-1 to L-489; M-1 to W-488; M-1 to I-487; M-1 to E-486; M-1 to C-485; M-1 to A-484; M-1 to N-483; M-1 to G-482; M-1 to N-481; M-1 to W-480; M-1 to G-479; M-1 to D-478; M-1 to W-477; M-1 to C-476; M-1 to E-475; M-1 to C-474; M-1 to N-473; M-1 to G-472; M-1 to C-471; M-1 to S-470; M-1 to C-469; M-1 to I-468 to M-1 to G-467; M-1 to N-466; M-1 to G-465; M-1 to T-464; M-1 to C-463; M-1 to I-462; M-1 to L-461; M-1 to G-460; M-1 to D-459; M-1 to H-458; M-1 to K-457; M-1 to D-456; M-1 to C-455; M-1 to D-454; M-1 to R-453; M-1 to D-452; M-1 to D-451; M-1 to C-450; M-1 to D-449; M-1 to C-448; M-1 to F-447; M-1 to E-446; M-1 to G-445; M-1 to S-444; M-1 to I-443; M-1 to Y-442; M-1 to W-441; M-1 to E-440; M-1 to E-439; M-1 to A-438; M-1 to S-437; M-1 to C-436; M-1 to I-435; M-1 to C-434; M-1 to K-433; M-1 to G-432; M-1 to C-431; M-1 to H-430; M-1 to C-429; M-1 to S-428; M-1 to G-427; M-1 to K-426; M-1 to G-425; M-1 to S-424; M-1 to C-423; M-1 to L-422; M-1 to I-421; M-1 to G-420; M-1 to D-419; M-1 to A-418; M-1 to S-417; M-1 to E-416; M-1 to C-415; M-1 to L-414; M-1 to N-413; M-1 to K-412; M-1 to S-411; M-1 to Q-410; M-1 to E-409; M-1 to E-408; M-1 to T-407; M-1 to M-406; M-1 to N-405; M-1 to C-404; M-1 to K-403; M-1 to R-402; M-1 to P-401; M-1 to H-400; M-1 to Q-399; M-1 to C-398; M-1 to L-397; M-1 to K-396; M-1 to G-395; M-1 to F-394; M-1 to W-393; M-1 to G-392; M-1 to R-391; M-1 to E-390; M-1 to C-389; M-1 to V-388; M-1 to C-387; M-1 to R-386; M-1 to G-385; M-1 to C-384; M-1 to S-383; M-1 to C-382; M-1 to T-381; M-1 to G-380; M-1 to H-379; M-1 to G-378; M-1 to G-377; M-1 to C-376; M-1 to V-375; M-1 to V-374; M-1 to G-373; M-1 to D-372; M-1 to L-371; M-1 to D-370; M-1 to E-369; M-1 to C-368; M-1 to R-367; M-1 to R-366; M-1 to D-365; M-1 to D-364; M-1 to C-363; M-1 to E-362; M-1 to C-361; M-1 to T-360; M-1 to K-359; M-1 to G-358; M-1 to Y-357; M-1 to V-356; M-1 to R-355; M-1 to R-354; M-1 to D-353; M-1 to G-352; M-1 to P-351; M-1 to P-350; M-1 to Y-349; M-1 to C-348; M-1 to T-347; M-1 to C-346; M-1 to K-345; M-1 to G-344; M-1 to C-343; M-1 to E-342; M-1 to C-341; M-1 to K-340; M-1 to G-339; M-1 to R-338; M-1 to G-337; M-1 to S-336; M-1 to C-335; M-1 to P-334; M-1 to L-333; M-1 to D-332; M-1 to S-331; M-1 to S-330; M-1 to G-329; M-1 to Q-328; M-1 to C-327; M-1 to K-326; M-1 to R-325; M-1 to I-324; M-1 to S-323; M-1 to E-322; M-1 to E-321; M-1 to A-320; M-1 to S-319; M-1 to L-318; M-1 to T-317; M-1 to C-316; M-1 to S-315; M-1 to Q-314; M-1 to P-313; M-1 to H-312; M-1 to E-311; M-1 to C-310; M-1 to K-309; M-1 to K-308; M-1 to G-307; M-1 to Y-306; M-1 to W-305; M-1 to G-304; M-1 to A-303; M-1 to K-302; M-1 to C-301; M-1 to D-300; M-1 to C-299; M-1 to R-298; M-1 to G-297; M-1 to C-296; M-1 to N-295; M-1 to C-294; M-1 to Q-293; M-1 to G-292; M-1 to H-291; M-1 to G-290; M-1 to S-289; M-1 to C-288; M-1 to F-287; M-1 to D-286; M-1 to D-285; M-1 to S-284; M-1 to Y-283; M-1 to R-282; M-1 to D-281; M-1 to Y-280; M-1 to V-279; M-1 to A-278; M-1 to R-277; M-1 to C-276; M-1 to D-275; M-1 to R-274; M-1 to E-273; M-1 to D-272; M-1 to C-271; M-1 to E-270; M-1 to C-269; M-1 to T-268; M-1 to D-267; M-1 to G-266; M-1 to H-265; M-1 to I-264; M-1 to D-263; M-1 to G-262; M-1 to W-261; M-1 to D-260; M-1 to G-259; M-1 to T-258; M-1 to P-257; M-1 to D-256; M-1 to V-255; M-1 to D-254; M-1 to H-253; M-1 to C-252; M-1 to T-251; M-1 to C-250; M-1 to E-249; M-1 to G-248; M-1 to C-247; M-1 to V-246; M-1 to C-245; M-1 to T-244; M-1 to G-243; M-1 to R-242; M-1 to N-241; M-1 to S-240; M-1 to C-239; M-1 to I-238; M-1 to K-237; M-1 to G-236; M-1 to D-235; M-1 to P-234; M-1 to S-233; M-1 to T-232; M-1 to C-231; M-1 to R-230; M-1 to R-229; M-1 to K-228; M-1 to S-227; M-1 to E-226; M-1 to W-225; M-1 to P-224; M-1 to T-223; M-1 to I-222; M-1 to D-221; M-1 to C-220; M-1 to Q-219; M-1 to F-218; M-1 to E-217; M-1 to C-216; M-1 to K-215; M-1 to D-214; M-1 to G-213; M-1 to H-212; M-1 to W-211; M-1 to G-210; M-1 to A-209; M-1 to K-208; M-1 to C-207; M-1 to Y-206; M-1 to C-205; M-1 to N-204; M-1 to G-203; M-1 to C-202; M-1 to Y-201; M-1 to C-200; M-1 to K-199; M-1 to G-198; M-1 to H-197; M-1 to G-196; M-1 to G-195; M-1 to C-194; M-1 to I-193; M-1 to E-192; M-1 to E-191; M-1 to T-190; M-1 to E-189; M-1 to D-188; M-1 to D-187; M-1 to I-186; M-1 to C-185; M-1 to E-184; M-1 to R-183; M-1 to D-182; M-1 to D-181; M-1 to C-180; M-1 to E-179; M-1 to C-178; M-1 to F-177; M-1 to K-176; M-1 to G-175; M-1 to Y-174; M-1 to V-173; M-1 to L-172; M-1 to G-171; M-1 to S-170; M-1 to G-169; M-1 to D-168; M-1 to S-167; M-1 to N-166; M-1 to D-165; M-1 to C-164; M-1 to K-163; M-1 to C-162; M-1 to R-161; M-1 to G-160; M-1 to C-159; M-1 to H-158; M-1 to C-157; M-1 to T-156; M-1 to G-155; M-1 to A-154; M-1 to N-153; M-1 to S-152; M-1 to C-151; M-1 to I-150; M-1 to I-149; M-1 to D-148; M-1 to Q-147; M-1 to S-146; M-1 to N-145; M-1 to K-144; M-1 to C-143; M-1 to M-142; M-1 to Q-141; M-1 to N-140; M-1 to S-139; M-1 to K-138; M-1 to K-137; M-1 to K-136; M-1 to T-135; M-1 to L-134; M-1 to D-133; M-1 to C-132; M-1 to N-131; M-1 to T-130; M-1 to P-129; M-1 to Y-128; M-1 to Q-127; M-1 to C-126; M-1 to A-125; M-1 to D-124; M-1 to G-123; M-1 to Y-122; M-1 to W-121; M-1 to G-120; M-1 to Q-119; M-1 to D-118; M-1 to C-117; M-1 to K-116; M-1 to C-115; M-1 to K-114; M-1 to G-113; M-1 to C-112; M-1 to D-111; M-1 to C-110; M-1 to K-109; M-1 to G-108; M-1 to H-107; M-1 to G-106; M-1 to A-105; M-1 to C-104; M-1 to T-103; M-1 to S-102; M-1 to G-101; M-1 to D-100; M-1 to Y-99; M-1 to T-98; M-1 to E-97; M-1 to C-96; M-1 to V-95; M-1 to W-94; M-1 to E-93; M-1 to H-92; M-1 to C-91; M-1 to E-90; M-1 to C-89; M-1 to L-88; M-1 to P-87; M-1 to G-86; M-1 to F-85; M-1 to F-84; M-1 to M-83; M-1 to G-82; M-1 to P-81; M-1 to E-80; M-1 to T-79; M-1 to V-78; M-1 to H-77; M-1 to C-76; M-1 to I-75; M-1 to C-74; M-1 to V-73; M-1 to G-72; M-1 to C-71; M-1 to D-70; M-1 to C-69; M-1 to R-68; M-1 to G-67; M-1 to R-66; M-1 to G-65; M-1 to H-64; M-1 to C-63; M-1 to L-62; M-1 to A-61; M-1 to A-60; M-1 to G-59; M-1 to P-58; M-1 to P-57; M-1 to Q-56; M-1 to G-55; M-1 to P-54; M-1 to A-53; M-1 to R-52; M-1 to C-51; M-1 to R-50; M-1 to R-49; M-1 to E-48; M-1 to S-47; M-1 to E-46; M-1 to A-45; M-1 to R-44; M-1 to S-43; M-1 to L-42; M-1 to R-41; M-1 to C-40; M-1 to A-39; M-1 to A-38; M-1 to G-37; M-1 to P-36; M-1 to W-35; M-1 to S-34; M-1 to R-33; M-1 to L-32; M-1 to S-31; M-1 to P-30; M-1 to S-29; M-1 to F-28; M-1 to S-27; M-1 to Q-26; M-1 to P-25; M-1 to V-24; M-1 to A-23; M-1 to S-22; M-1 to L-21; M-1 to G-20; M-1 to A-19; M-1 to F-18; M-1 to L-17; M-1 to L-16; M-1 to S-15; M-1 to S-14; M-1 to A-13; M-1 to L-12; M-1 to L-11; M-1 to L-10; M-1 to F-9; M-1 to N-8; M-1 to R-7; M-1 to F-6; of SEQ ID NO:30. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 990% identical to these polypeptides and polypeptides encoded by the polynucleotide which hybrdizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nucleotide sequences related to extensive portions of SEQ ID NO:12 which have been determined from the following related cDNA genes: HLHFV34R (SEQ ID NO:68), HSRDA85R (SEQ ID NO:69), HSRAZ62R (SEQ ID NO:70), HSRDA17R (SEQ ID NO:71), and HSLEC45R (SEQ ID NO:72).

A polynucleotide encoding a polypeptide of the present invention is obtained from human osteoblasts, synovial hypoxia tissue, osteoblast and osteoclast, bone marrow stromal cells, umbilical vein, smooth muscle, placenta, and fetal lung. The polynucleotide of this invention was discovered in a human osteoblast II cDNA library.

This gene is expressed primarily in synovial hypoxia tissue, osteoblast and osteoclast, bone marrow stromal cells, and to a lesser extent in umbilical vein, smooth muscle, placenta, and fetal lung cDNA libraries. Therefore, polynucleotides and polypeptides of the invention, including antibodies, are useful as reagents for differential identification of the tissue(s) or cell type(s) present in a biological sample and for diagnosis of diseases and conditions which include, but are not limited to, disorders of bone and connective tissues, immune and hematopoietic diseases and/or disorders, vascular disorders, and other disorders involving aberrations in cell-surface interactions. Similarly, polypeptides and antibodies directed to these polypeptides are useful in providing immunological probes for differential identification of the tissue(s) or cell type(s). For a number of disorders of the above tissues or cells, particularly of the connective tissue and skeletal system, expression of this gene at significantly higher or lower levels is routinely detected in certain tissues or cell types (e.g., cartilage, bone, vascular, hypoxic tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Based on the sequence similarity to the human integrin beta-8 subunit, translation product of this gene is expected to share at least some biological activities with integrin proteins, and specifically the human integrin beta-8 subunit. Such activities are known in the art, some of which are described elsewhere herein.

Specifically, polynucleotides, translation products and antibodies corresponding to this gene are also useful for modulating the differentiation of normal and malignant cells, modulating the proliferation and/or differentiation of cancer and neoplastic cells, and modulating the immune response. Polynucleotides and polypeptides of the invention may represent a diagnostic marker for hematopoietic and immune diseases and/or disorders. The full-length protein should be a secreted protein, based upon homology to the integrin family. Therefore, it is secreted into serum, urine, or feces and thus the levels is assayable from patient samples. Assuming specific expression levels are reflective of the presence of immune disorders, this protein would provide a convenient diagnostic for early detection. In addition, expression of this gene product may also be linked to the progression of immune diseases, and therefore may itself actually represent a therapeutic or therapeutic target for the treatment of cancer. Polynucleotides and polypeptides of the invention may play an important role in the pathogenesis of human cancers and cellular transformation, particularly those of the immune and hematopoietic systems. Polynucleotides and polypeptides of the invention may also be involved in the pathogenesis of developmental abnormalities based upon its potential effects on proliferation and differentiation of cells and tissue cell types. Due to the potential proliferating and differentiating activity of said polynucleotides and polypeptides, the invention is useful as a therapeutic agent in inducing tissue regeneration, for treating inflammatory conditions (e.g., inflammatory bowel syndrome, diverticulitis, etc.). Moreover, the invention is useful in modulating the immune response to aberrant polypeptides, as may exist in rapidly proliferating cells and tissue cell types, particularly in adenocarcinoma cells, and other cancers.

Alternatively, the expression within cellular sources marked by proliferating cells indicates polynucleotides, translation products and antibodies corresponding to this gene may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA).

Alternatively, this gene product is involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, polynucleotides, translation products and antibodies corresponding to this gene may have applications in the adult for tissue regeneration and the treatment of cancers. It may also act as a morphogen to control cell and tissue type specification. Therefore, polynucleotides, translation products and antibodies corresponding to this gene are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The translation product of this gene, sometimes referred to herein as TIDE (for Ten Integrin Domains with EGF homology), shares sequence homology with integrins, which are a superfamily of dimeric ab cell-surface glycoproteins that mediate the adhesive functions of many cell types, enabling cells to interact with one another and with the extracellular matrix (See Genomics 56, 169-178 (1999); all information and references contained within this publication are hereby incorporated herein by reference).

The gene encoding the disclosed cDNA is believed to reside on chromosome 13, at locus 13q33. Accordingly, polynucleotides related to this invention are useful as a marker in linkage analysis for chromosome 13, generally, and particularly at locus 13q33.

The tissue distribution and homology to the human integrin beta-8 subunit indicates polynucleotides and polypeptides corresponding to this gene are useful for the diagnosis and treatment of a variety of immune system disorders. Representative uses are described in the "Immune Activity" and "infectious disease" sections below, in Example 11, 13, 14, 16, 18, 19, 20, and 27, and elsewhere herein.

Briefly, the expression indicates a role in regulating the proliferation; survival; differentiation; and/or activation of hematopoietic cell lineages, including blood stem cells. Involvement in the regulation of cytokine production antigen presentation, or other processes indicates a usefulness for treatment of cancer (e.g. by boosting immune responses). Expression in cells of lymphoid origin, indicates the natural gene product is involved in immune functions. Therefore it would also be useful as an agent for immunological disorders including arthritis, asthma, immunodeficiency diseases such as AIDS, leukemia, rheumatoid arthritis, granulomatous Disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's Disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Based upon the tissue distribution of this protein, antagonists directed against this protein is useful in blocking the activity of this protein. Accordingly, preferred are antibodies which specifically bind a portion of the translation product of this gene.

Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid or biological sample from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein.

Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 2485 of SEQ ID NO:12, b is an integer of 15 to 2499, where both a and b correspond to the positions of nucleotide residues shown in SEQ ID NO:12, and where b is greater than or equal to a+14.

Features of Protein Encoded by Gene No: 3

Translation products corresponding to this gene share sequence homology with RAMP-3 (receptor-activity-modifying proteins), which another group has recently published, which is thought to be important in the transport of the calcitonin-receptor-like receptor (CRLR) to the plasma membrane. RAMPs regulate the transport and ligand specificity of the calcitonin-receptor-like-receptor. There are two other related receptor-activity-modifying proteins, known as RAMP1 and RAMP-2 (*Nature* 1998 May 28;393(6683):333-9). RAMP1 is thought to present the receptor at the cell surface as a mature glycoprotein and a Calcitonin-gene-related peptide (CGRP) receptor.

Alternatively, RAMP-2-transported receptors are core-glycosylated and are adrenomedullin receptors. CGRP (a 37-amino-acid neuropeptide) and its receptors are widely distributed in the body, and it is the most potent endogenous vasodilatory peptide discovered so far (*Crit Rev Neurobiol* 1997;11(2-3):167-239). Specific binding sites for adrenomedullin were present in every region of human brain (cerebral cortex, cerebellum, thalamus, hypothalamus, pons and medulla oblongata), suggesting that a novel neurotransmitter/neuromodulator role may exist for adrenomedullin in human brain (*Peptides* 1997;18(8):1125-9).

FIGS. 7A-B show the nucleotide (SEQ ID NO:13) and deduced amino acid sequence (SEQ ID NO:31) of the intestine derived extracellular protein. Predicted amino acids from about 1 to about 27 constitute the predicted signal peptide (amino acid residues from about 1 to about 27 in SEQ ID NO:31) and are represented by the underlined amino acid regions; and amino acids from about 122 to about 138 constitute the predicted transmembrane domain (amino acid residues from about 122 to about 138 in SEQ ID NO:31) and are represented by the double-underlined amino acids.

FIG. 8 shows the regions of similarity between the amino acid sequences of the Intestine derived extracellular protein SEQ ID NO:31, and the RAMP3 protein (gi|4587099) (SEQ ID NO: 75).

Figure 9:
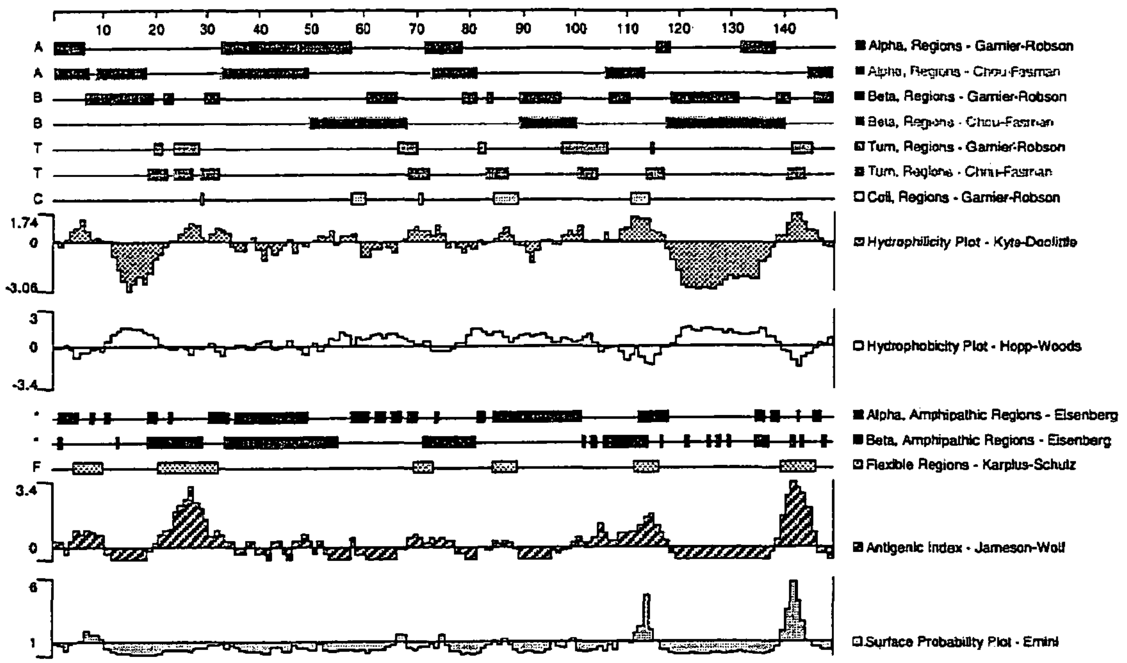
FIG. 9 shows an analysis of the amino acid sequence of SEQ ID NO: 31. Alpha, beta, turn and coil regions; hydrophilicity and hydrophobicity; amphipathic regions; flexible regions; antigenic index and surface probability are shown.

FIG. 9 shows an analysis of the amino acid sequence of SEQ ID NO: 31.

Alpha, beta, turn and coil regions; hydrophilicity and hydrophobicity; amphipathic regions; flexible regions; antigenic index and surface probability are shown.

Preferred polypeptides of the present invention comprise, or alternatively consist of, one, two, three, or all three of the immunogenic epitopes shown in SEQ ID NO: 31 as residues: Ala-5 to Gln-10, Pro-23 to Cys-28, and/or Arg-140 to Asp-145. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

The present invention provides isolated nucleic acid molecules comprising a polynucleotide encoding the polypeptide having the amino acid sequence shown in FIG. 1 (SEQ ID NO:31), which was determined by sequencing a cloned cDNA (HTLEW81). The nucleotide sequence shown in FIGS. 7A-B (SEQ ID NO:13) was obtained by sequencing a cloned cDNA (HTLEW81), which was deposited on Nov. 17, 1998 at the American Type Culture Collection, and given Accession Number 203484. The deposited gene is inserted in the pSport plasmid (Life Technologies, Rockville, Md.) using the SalI/NotI restriction endonuclease cleavage sites. The present invention is further directed to fragments of the isolated nucleic acid molecules described herein.

By a fragment of an isolated DNA molecule having the nucleotide sequence of the deposited cDNA or the nucleotide sequence shown in SEQ ID NO:13 is intended DNA fragments at least about 15nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:13. By a fragment at least 20 nt in length, for example, is intended fragments which include 20 or more contiguous bases from the nucleotide sequence of the deposited cDNA or the nucleotide sequence as shown in SEQ ID NO:13. In this context "about" includes the particularly recited size, larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1339 of SEQ ID NO:13, or the complementary strand thereto, or the cDNA contained in the deposited gene. In this context "about" includes the particularly recited ranges, larger or smaller by several (5, 4, 3, 2, or 1) nucleotides, at either terminus or at both termini. In additional embodiments, the polynucleotides of the invention encode functional attributes of the corresponding protein.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 9 and/or Table III, as described above, was generated using the various modules and algorithms of the DNA*STAR set on default parameters. In a preferred embodiment, the data presented in columns VIII, IX, XIII, and XIV of Table III can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 9, but may, as shown in Table III, be represented or identified by using tabular representations of the data presented in FIG. 9. The DNA*STAR computer algorithm used to generate FIG. 9 (set on the original default parameters) was used to present the data in FIG. 9 in a tabular format (See Table III). The tabular format of the data in FIG. 9 is used to easily determine specific boundaries of a preferred region. The above-mentioned preferred regions set out in FIG. 9 and in Table III include, but are not limited to, regions of the aforementioned types identified by analysis of the amino acid sequence set out in FIGS. 7A-B. As set out in FIG. 9 and in Table III, such preferred regions include Gamier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, etc.) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, the present invention further provides polypeptides having one or more residues deleted from the amino terminus of the amino acid sequence shown in FIGS. 7A-B, up to the arginine residue at position number 143 and polynucleotides encoding such polypeptides. In particular, the present invention provides polypeptides comprising the amino acid sequence of residues n1-148 of FIGS. 7A-B, where n1 is an integer from 2 to 143 corresponding to the position of the amino acid residue in FIGS. 7A-B (which is identical to the sequence shown as SEQ ID NO:31). N-terminal deletions of the polypeptide of the invention shown as SEQ ID NO:31 include polypeptides comprising the amino acid sequence of residues: E-2 to L-148; T-3 to L-148; G-4 to L-148; A-5 to L-148; L-6 to L-148; R-7 to L-148; R-8 to L-148; P-9 to L-148; Q-10 to L-148; L-11 to L-148; L-12 to L-148; P-13to L-148; L-14 to L-148; L-15 to L-148; L-16 to L-148; L-17 to L-148; L-18 to L-148; C-19 to L-148; G-20 to L-148; G-21 to L-148; C-22 to L-148; P-23 to L-148; R-24 to L-148; A-25 to L-148; G-26 to L-148; G-27 to L-148; C-28 to L-148; N-29 to L-148; E-30 to L-148; T-31 to L-148; G-32 to L-148; M-33 to L-148; L-34 to L-148; E-35 to L-148; R-36 to L-148; L-37 to L-148; P-38 to L-148; L-39 to L-148; C-40 to L-148; G-41 to L-148; K-42 to L-148; A-43 to L-148; F-44 to L-148; A-45 to L-148; D-46 to L-148; M-47 to L-148; M-48 to L-148; G-49 to L-148; K-50 to L-148; V-51 to L-148; D-52 to L-148; V-53 to L-148; W-54 to L-148; K-55 to L-148; W-56 to L-148; C-57 to L-148; N-58 to L-148; L-59 to L-148; S-60 to L-148; E-61 to L-148; F-62 to L-148; I-63 to L-148; V-64 to L-148; Y-65 to L-148; Y-66 to L-148; E-67 to L-148; S-68 to L-148; F-69 to L-148; T-70 to L-148; N-71 to L-148; C-72 to L-148; T-73 to L-148; E-74 to L-148; M-75 to L-148; E-76 to L-148; A-77 to L-148; N-78 to L-148; V-79 to L-148; V-80 to L-148; G-81 to L-148; C-82 to L-148; Y-83 to L-148; W-84 to L-148; P-85 to L-148; N-86 to L-148; P-87 to L-148; L-88 to L-148; A-89 to L-148; Q-90 to L-148; G-91 to L-148; F-92 to L-148; I-93 to L-148; T-94 to L-148; G-95 to L-148; I-96 to L-148; H-97 to L-148; R-98 to L-148; Q-99 to L-148; F-100 to L-148; F-101 to L-148; S-102 to L-148; N-103 to L-148; C-104 to L-148; T-105 to L-148; V-106 to L-148; D-107 to L-148; R-108 to L-148; V-109 to L-148; H-110 to L-148; L-111 to L-148; E-112 to L-148; D-113 to L-148; P-114 to L-148; P-115 to L-148; D-116 to L-148; E-117 to L-148; V-118 to L-148; L-119 to L-148; I-120 to L-148; P-121 to L-148; L-122 to L-148; I-123 to L-148; V-124 to L-148; I-125 to L-148; P-126 to L-148; V-127 to L-148; V-128 to L-148; L-129 to L-148; T-130 to L-148; V-131 to L-148; A-132 to L-148; M-133 to L-148; A-134 to L-148; G-135 to L-148; L-136 to L-148; V-137 to L-148; V-138 to L-148; W-139 to L-148; R-140 to L-148; S-141 to L-148; K-142 to L-148; R-143 to L-148; of SEQ ID NO:31. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities (e.g., biological activities (e.g., ability to illicit mitogenic activity, induce differentiation of normal or malignant cells, bind to EGF receptors, etc.)), may still be retained. For example the ability to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a mutein with a large number of deleted C-terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the polypeptide shown in FIGS. 7A-B, up to the arginine residue at position number 7, and polynucleotides encoding such polypeptides. In particular, the present invention provides polypeptides comprising the amino acid sequence of residues 1-m1 of FIGS. 7A-B, where m1 is an integer from 7 to 147 corresponding to the position of the amino acid residue in FIGS. 7A-B. Moreover, the invention provides polynucleotides encoding polypeptides comprising, or alternatively consisting of, the amino acid sequence of C-terminal deletions of the polypeptide of the invention shown as SEQ ID NO:31 include polypeptides comprising the amino acid sequence of residues: M-1 to L-147; M-1 to T-146; M-1 to D-145; M-1 to T-144; M-1 to R-143; M-1 to K-142; M-1 to S-141; M-1 to R-140; M-1 to W-139; M-1 to V-138; M-1 to V-137; M-1 to L-136; M-1 to G-135; M-1 to A-134; M-1 to M-133; M-1 to A-132; M-1 to V-131; M-1 to T-130; M-1 to L-129; M-1 V-128; M-1 to V-127; M-1 to P-126; M-1 to I-125; M-1 to V-124; M-1 to I-123; M-1 to L-122; M-1 to P-121; M-1 to I-120; M-1 to L-119; M-1 to V-118; M-1 to E-117; M-1 to D-116; M-1 to P-115; M-1 to P-114; M-1 to D-113; M-1 to E-112; M-1 to L-111; M-1 to H-110; M-1 to V-109; M-1 to R-108; M-1 to D-107; M-1 to V-106; M-1 to T-105; M-1 to C-104; M-1 to N-103; M-1 to S-102; M-1 to F-101; M-1 to F-100; M-1 to Q-99; M-1 to R-98; M-1 to H-97; M-1 to I-96; M-1 to G-95; M-1 to T-94; M-1 to I-93; M-1 to F-92; M-1 to G-91; M-1 to Q-90; M-1 to A-89; M-1 to L-88; M-1 to P-87; M-1 to N-86; M-1 to P-85; M-1 to W-84; M-1 to Y-83; M-1 to C-82; M-1 to G-81; M-1 to V-80; M-1 to V-79; M-1 to N-78; M-1 to A-77; M-1 to E-76; M-1 to M-75; M-1 to E-74; M-1 to T-73; M-1 to C-72; M-1 to N-71; M-1 to T-70; M-1 to F-69; M-1 to S-68; M-1 to E-67; M-1 to Y-66; M-1 to Y-65; M-1 to V-64; M-1 to I-63; M-1 to F-62; M-1 to E-61; M-1 to S-60; M-1 to L-59; M-1 to N-58; M-1 to C-57; M-1 to W-56; M-1 to K-55; M-1 to W-54; M-1 to V-53; M-1 to D-52; M-1 to V-51; M-1 to K-50; M-1 to G-49; M-1 to M-48; M-1 to M-47; M-1 to D-46; M-1 to A-45; M-1 to F-44; M-1 to A-43; M-1 to K-42; M-1 to G-41; M-1 to C-40; M-1 to L-39; M-1 to P-38; M-1 to L-37; M-1 to R-36; M-1 to E-35; M-1 to L-34; M-1 to M-33; M-1 to G-32; M-1 to T-31; M-1 to E-30; M-1 to N-29; M-1 to C-28; M-1 to G-27; M-1 to G-26; M-1 to A-25; M-1 to R-24; M-1 to P-23; M-1 to C-22; M-1 to G-21; M-1 to G-20; M-1 to C-19; M-1 to L-18; M-1 to L-17; M-1 to L-16; M-1 to L-15; M-1 to L-14; M-1 to P-13; M-1 to L-12; M-1 to L-11; M-1 to Q-10; M-1 to P-9; M-1 to R-8; M-1 to R-7; of SEQ ID NO:31. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nucleotide sequences related to extensive portions of SEQ ID NO:31 which have been determined from the following related cDNA genes: HLHCH17RA (SEQ ID NO:76), HTOAT51R (SEQ ID NO:77), and/or HBNBO41R (SEQ ID NO:78).

The polypeptide of this gene has been determined to have a transmembrane domain at about amino acid position 122-138 of the amino acid sequence referenced in Table XIV for this gene. Moreover, a cytoplasmic tail encompassing amino acids 139 to 149 of this protein has also been determined. Based upon these characteristics, it is believed that the protein product of this gene shares structural features to type Ia membrane proteins.

Northern analysis indicates that a 1.4 kb transcript of this gene is primarily expressed in small intestine tissue, and to a lesser extent in colon and prostate tissue.

Therefore, polynucleotides and polypeptides of the invention, including antibodies, are useful as reagents for differential identification of the tissue(s) or cell type(s) present in a biological sample and for diagnosis of diseases and conditions which include, but are not limited to, gastrointestinal and neurodegenerative diseases and disorders. Similarly, polypeptides and antibodies directed to these polypeptides are useful in providing immunological probes for differential identification of the tissue(s) or cell type(s). For a number of disorders of the above tissues or cells, particularly of the central nervous and gastrointestinal systems, expression of this gene at significantly higher or lower levels is routinely detected in certain tissues or cell types (e.g., brain, CNS, gastrointestinal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution and homology to RAMP-3 suggest that polynucleotides, translation products and antibodies corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo.

Alternatively, the tissue distribution in small intestine and colon tissues indicates that polynucleotides, translation products and antibodies corresponding to this gene are useful for the diagnosis and/or treatment of disorders involving the small intestine. This may include diseases associated with digestion and food absorption, as well as hematopoietic disorders involving the Peyer's patches of the small intestine, or other hematopoietic cells and tissues within the body. Similarly, expression of this gene product in colon tissue indicates again involvement in digestion, processing, and elimination of food, as well as a potential role for this gene as a diagnostic marker or causative agent in the development of colon cancer, and cancer in general. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 1325 of SEQ ID NO:13, b is an integer of 15 to 1339, where both a and b correspond to the positions of nucleotide residues shown in SEQ ID NO:13, and where b is greater than or equal to a+14.

Features of Protein Encoded by Gene No: 4

Translation products corresponding to this gene share sequence homology with a proteoglycan from *Gallus gallus*, and this proteoglycan is believed to participate in the osteogenic processes of cartilage ossification (See Genbank Accession No. gi|222847). Based on the sequence similarity, translation products corresponding to this gene are expected to share biological activities with the *Gallus gallus* proteoglycan polypeptide.

Preferred polypeptides of the present invention comprise, or alternatively consist of, one, two, three, four, or all four of the immunogenic epitopes shown in SEQ ID NO: 32 as residues: Leu-22 to Asp-39, Asn-64 to Pro-76, Pro-98 to Thr-111, and/or Pro-291 to Glu-302. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

FIGS. 10A-B shows the nucleotide (SEQ ID NO:14) and deduced amino acid sequence (SEQ ID NO:32) of the retinal specific protein. Predicted amino acids from about 1 to about 21 constitute the predicted signal peptide (amino acid residues from about 1 to about 21 in SEQ ID NO:32) and are represented by the underlined amino acid regions.

FIG. 11 shows the regions of similarity between the amino acid sequences of the retinal specific protein SEQ ID NO:32, and the *Gallus gallus* proteoglycan (SEQ ID NO:79).

Figure 12:
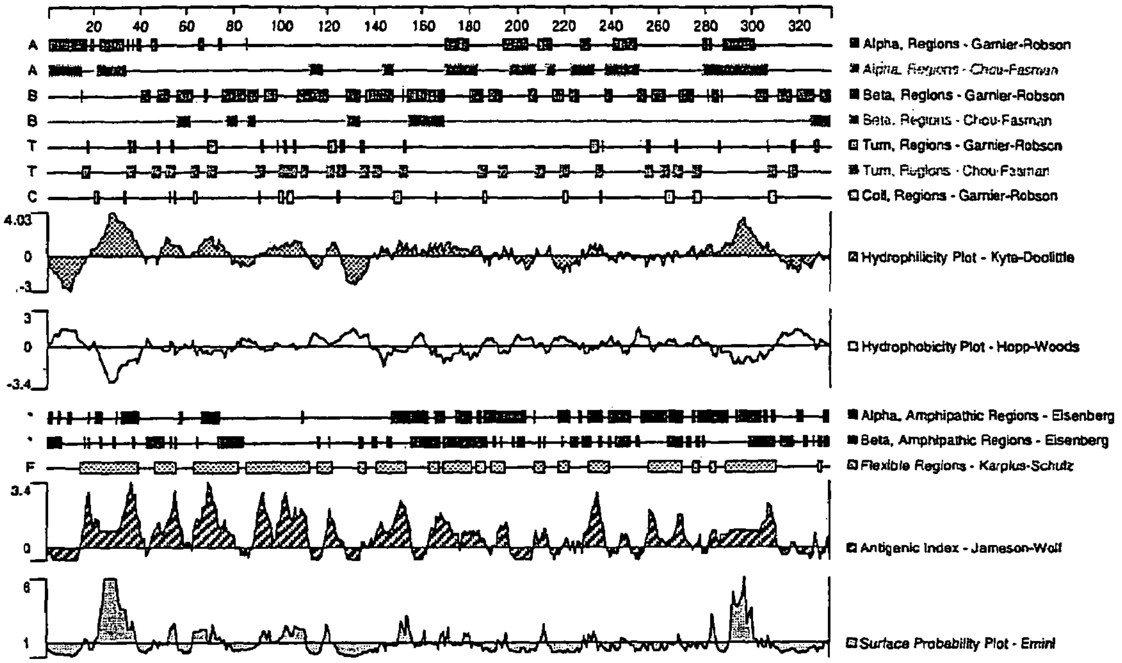
FIG. 12 shows an analysis of the amino acid sequence of SEQ ID NO: 32. Alpha, beta, turn and coil regions; hydrophilicity and hydrophobicity; amphipathic regions; flexible regions; antigenic index and surface probability are shown.

FIG. 12 shows an analysis of the amino acid sequence of SEQ ID NO: 32. Alpha, beta, turn and coil regions; hydrophilicity and hydrophobicity; amphipathic regions; flexible regions; antigenic index and surface probability are shown.

The present invention provides isolated nucleic acid molecules comprising a polynucleotide encoding the polypeptide having the amino acid sequence shown in FIGS. 10A-B (SEQ ID NO:32), which was determined by sequencing a cloned cDNA (HARAO44). The nucleotide sequence shown in FIGS. 10A-B (SEQ ID NO:14) was obtained by sequencing a cloned cDNA (HARAO44), which was deposited on Nov. 17, 1998 at the American Type Culture Collection, and given Accession Number 203484. The deposited gene is inserted in the pSport plasmid (Life Technologies, Rockville, Md.) using the SalI/NotI restriction endonuclease cleavage sites.

The present invention is further directed to fragments of the isolated nucleic acid molecules described herein. By a fragment of an isolated DNA molecule having the nucleotide sequence of the deposited cDNA or the nucleotide sequence shown in SEQ ID NO:14 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:14. By a fragment at least 20 nt in length, for example, is intended fragments which include 20 or more contiguous bases from the nucleotide sequence of the deposited cDNA or the nucleotide sequence as shown in SEQ ID NO:14. In this context "about" includes the particularly recited size, larger or smaller by several (5, 4, 3, 2, or 1) nucleotides, at either terminus or at both termini.

Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1350, from about 1351 to about 1389, and from about 187 to about 1119 of SEQ ID NO:14, or the complementary strand thereto, or the cDNA contained in the deposited gene. In this context "about"includes the particularly recited ranges, larger or smaller by several (5, 4, 3, 2, or 1) nucleotides, at either terminus or at both termini. In additional embodiments, the polynucleotides of the invention encode functional attributes of the corresponding protein.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 12 and/or Table IV, as described above, was generated using the various modules and algorithms of the DNA*STAR set on default parameters. In a preferred embodiment, the data presented in columns VIII, IX, XIII, and XIV of Table IV can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 12, but may, as shown in Table IV, be represented or identified by using tabular representations of the data presented in FIG. 12. The DNA*STAR computer algorithm used to generate FIG. 12 (set on the original default parameters) was used to present the data in FIG. 12 in a tabular format (See Table IV). The tabular format of the data in FIG. 12 is used to easily determine specific boundaries of a preferred region. The above-mentioned preferred regions set out in FIG. 12 and in Table IV include, but are not limited to, regions of the aforementioned types identified by analysis of the amino acid sequence set out in FIGS. 10A-B. As set out in FIG. 12 and in Table IV, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, etc.) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, the present invention further provides polypeptides having one or more residues deleted from the amino terminus of the amino acid sequence shown in FIGS. 10A-B, up to the proline residue at position number 327 and polynucleotides encoding such polypeptides. In particular, the present invention provides polypeptides comprising the amino acid sequence of residues n1-332 of FIGS. 10A-B, where n1 is an integer from 2 to 327 corresponding to the position of the amino acid residue in FIGS. 10A-B (which is identical to the sequence shown as SEQ ID NO:32). N-terminal deletions of the polypeptide of the invention shown as SEQ ID NO:32 include polypeptides comprising the amino acid sequence of residues: R-2 to T-332; L-3 to T-332; L-4 to T-332; A-5 to T-332; F-6 to T-332; L-7 to T-332; S-8 to T-332; L-9 to T-332; L-10 to T-332; A-11 to T-332; L-12 to T-332; V-13 to T-332; L-14 to T-332; Q-15 to T-332; E-16 to T-332; T-17 to T-332; G-18 to T-332; T-19 to T-332; A-20 to T-332; S-21 to T-332; L-22 to T-332; P-23 to T-332; R-24 to T-332; K-25 to T-332; E-26 to T-332; R-27 to T-332; K-28 to T-332; R-29 to T-332; R-30 to T-332; E-31 to T-332; E-32 to T-332; Q-33 to T-332; M-34 to T-332; P-35 to T-332; R-36 to T-332; E-37 to T-332; G-38 to T-332; D-39 to T-332; S-40 to T-332; F-41 to T-332; E-42 to T-332; V-43 to T-332; L-44 to T-332; P-45 to T-332; L-46 to T-332; R-47 to T-332; N-48 to T-332; D-49 to T-332; V-50 to T-332; L-51 to T-332; N-52 to T-332; P-53 to T-332; D-54 to T-332; N-55 to T-332; Y-56 to T-332; G-57 to T-332; E-58 to T-332; V-59 to T-332; I-60 to T-332; D-61 to T-332; L-62 to T-332; S-63 to T-332; N-64 to T-332; Y-65 to T-332; E-66 to T-332; E-67 to T-332; L-68 to T-332; T-69 to T-332; D-70 to T-332; Y-71 to T-332; G-72 to T-332; D-73 to T-332; Q-74 to T-332; L-75 to T-332; P-76 to T-332; E-77 to T-332; V-78 to T-332; K-79 to T-332; V-80 to T-332; T-81 to T-332; S-82 to T-332; L-83 to T-332; A-84 to T-332; P-85 to T-332; A-86 to T-332; T-87 to T-332; S-88 to T-332; I-89 to T-332; S-90 to T-332; P-91 to T-332; A-92 to T-332; K-93 to T-332; S-94 to T-332; T-95 to T-332; T-96 to T-332; A-97 to T-332; P-98 to T-332; G-99 to T-332; T-100 to T-332; P-101 to T-332; S-102 to T-332; S-103 to T-332; N-104 to T-332; P-105 to T-332; T-106 to T-332; M-107 to T-332; T-108 to T-332; R-109 to T-332; P-110 to T-332; T-111 to T-332; T-112 to T-332; A-113 to T-332; G-114 to T-332; L-115 to T-332; L-116 to T-332; L-117 to T-332; S-118 to T-332; S-119 to T-332; Q-120 to T-332; P-121 to T-332; N-122 to T-332; H-123 to T-332; G-124 to T-332; L-125 to T-332; P-126 to T-332; T-127 to T-332; C-128 to T-332; L-129 to T-332; V-130 to T-332; C-131 to T-332; V-132 to T-332; C-133 to T-332; L-134 to T-332; G-135 to T-332; S-136 to T-332; S-137 to T-332; V-138 to T-332; Y-139 to T-332; C-140 to T-332; D-141 to T-332; D-142 to T-332; I-143 to T-332; D-144 to T-332; L-145 to T-332; E-146 to T-332; D-147 to T-332; I-148 to T-332; P-149 to T-332; P-150 to T-332; L-151 to T-332; P-152 to T-332; R-153 to T-332; R-154 to T-332; T-155 to T-332; A-156 to T-332; Y-157 to T-332; L-158 to T-332; Y-159 to T-332; A-160 to T-332; R-161 to T-332;

F-162 to T-332; N-163 to T-332; R-164 to T-332; I-165 to T-332; S-166 to T-332; R-167 to T-332; I-168 to T-332; R-169 to T-332; A-170 to T-332; E-171 to T-332; D-172 to T-332; F-173 to T-332; K-174 to T-332; G-175 to T-332; L-176 to T-332; T-177 to T-332; K-178 to T-332; L-179 to T-332; K-180 to T-332; R-181 to T-332; I-182 to T-332; D-183 to T-332; L-184 to T-332; S-185 to T-332; N-186 to T-332; N-187 to T-332; L-188 to T-332; I-189 to T-332; S-190 to T-332; S-191 to T-332; I-192 to T-332; D-193 to T-332; N-194 to T-332; D-195 to T-332; A-196 to T-332; F-197 to T-332; R-198 to T-332; L-199 to T-332; L-200 to T-332; H-201 to T-332; A-202 to T-332; L-203 to T-332; Q-204 to T-332; D-205 to T-332; L-206 to T-332; I-207 to T-332; L-208 to T-332; P-209 to T-332; E-210 to T-332; N-211 to T-332; Q-212 to T-332; L-213 to T-332; E-214 to T-332; A-215 to T-332; L-216 to T-332; P-217 to T-332; V-218 to T-332; L-219 to T-332; P-220 to T-332; S-221 to T-332; G-222 to T-332; I-223 to T-332; E-224 to T-332; F-225 to T-332; L-226 to T-332; D-227 to T-332; V-228 to T-332; R-229 to T-332; L-230 to T-332; N-231 to T-332; R-232 to T-332; L-233 to T-332; Q-234 to T-332; S-235 to T-332; S-236 to T-332; G-237 to T-332; I-238 to T-332; Q-239 to T-332; P-240 to T-332; A-241 to T-332; A-242 to T-332; F-243 to T-332; R-244 to T-332; A-245 to T-332; M-246 to T-332; E-247 to T-332; K-248 to T-332; L-249 to T-332; Q-250 to T-332; F-251 to T-332; L-252 to T-332; Y-253 to T-332; L-254 to T-332; S-255 to T-332; D-256 to T-332; N-257 to T-332; L-258 to T-332; L-259 to T-332; D-260 to T-332; S-261 to T-332; I-262 to T-332; P-263 to T-332; G-264 to T-332; P-265 to T-332; L-266 to T-332; P-267 to T-332; P-268 to T-332; S-269 to T-332; L-270 to T-332; R-271 to T-332; S-272 to T-332; V-273 to T-332; H-274 to T-332; L-275 to T-332; Q-276 to T-332; N-277 to T-332; N-278 to T-332; L-279 to T-332; I-280 to T-332; E-281 to T-332; T-282 to T-332; M-283 to T-332; Q-284 to T-332; R-285 to T-332; D-286 to T-332; V-287 to T-332; F-288 to T-332; C-289 to T-332; D-290 to T-332; P-291 to T-332; E-292 to T-332; E-293 to T-332; H-294 to T-332; K-295 to T-332; H-296 to T-332; T-297 to T-332; R-298 to T-332; R-299 to T-332; Q-300 to T-332; L-301 to T-332; E-302 to T-332; D-303 to T-332; I-304 to T-332; R-305 to T-332; L-306 to T-332; D-307 to T-332; G-308 to T-332; N-309 to T-332; P-310 to T-332; I-311 to T-332; N-312 to T-332; L-313 to T-332; S-314 to T-332; L-315 to T-332; F-316 to T-332; P-317 to T-332; S-318 to T-332; A-319 to T-332; Y-320 to T-332; F-321 to T-332; C-322 to T-332; L-323 to T-332; P-324 to T-332; R-325 to T-332; L-326 to T-332; P-327 to T-332; of SEQ ID NO:32. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities (e.g., biological activities (e.g., ability to illicit mitogenic activity, induce differentiation of normal or malignant cells, bind to EGF receptors, etc.)), may still be retained. For example the ability to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a mutein with a large number of deleted C-terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the polypeptide shown in FIGS. 10A-B, up to the glutamine residue at position number 7, and polynucleotides encoding such polypeptides. In particular, the present invention provides polypeptides comprising the amino acid sequence of residues 1-m1 of FIGS. 10A-B, where m1 is an integer from 7 to 331 corresponding to the position of the amino acid residue in FIGS. 10A-B. Moreover, the invention provides polynucleotides encoding polypeptides comprising, or alternatively consisting of the amino acid sequence of C-terminal deletions of the polypeptide of the invention shown as SEQ ID NO:32 include polypeptides comprising the amino acid sequence of residues: M-1 to F-331; M-1 to R-330; M-1 to G-329; M-1 to I-328; M-1 to P-327; M-1 to L-326; M-1 to R-325; M-1 to P-324; M-1 to L-323; M-1 to C-322; M-1 to F-321; M-1 to Y-320; M-1 to A-319; M-1 to S-318; M-1 to P-317; M-1 to F-316; M-1 to L-315; M-1 to S-314; M-1 to L-313; M-1 to N-312; M-1 to I-311; M-1 to P-310; M-1 to N-309; M-1 to G-308; M-1 to D-307; M-1 to L-306; M-1 to R-305; M-1 to I-304; M-1 to D-303; M-1 to E-302; M-1 to L-301; M-1 to Q-300; M-1 to R-299; M-1 to R-298; M-1 to T-297; M-1 to H-296; M-1 to K-295; M-1 to H-294; M-1 to E-293; M-1 to E-292; M-1 to P-291; M-1 to D-290; M-1 to C-289; M-1 to F-288; M-1 to V-287; M-1 to D-286; M-1 to R-285; M-1 to Q-284; M-1 to M-283; M-1 to T-282; M-1 to E-281; M-1 to I-280; M-1 to L-279; M-1 to N-278; M-1 to N-277; M-1 to Q-276; M-1 to L-275; M-1 to H-274; M-1 to V-273; M-1 to S-272; M-1 to R-271; M-1 to L-270; M-1 to S-269; M-1 to P-268; M-1 to P-267; M-1 to L-266; M-1 to P-265; M-1 to G-264; M-1 to P-263; M-1 to I-262; M-1 to S-261; M-1 to D-260; M-1 to L-259; M-1 to L-258; M-1 to N-257; M-1 to D-256; M-1 to S-255; M-1 to L-254; M-1 to Y-253; M-1 to L-252; M-1 to F-251; M-1 to Q-250; M-1 to L-249; M-1 to K-248; M-1 to E-247; M-1 to M-246; M-1 to A-245; M-1 to R-244; M-1 to F-243; M-1 to A-242; M-1 to A-241; M-1 to P-240; M-1 to Q-239; M-1 to I-238; M-1 to G-237; M-1 to S-236; M-1 to S-235; M-1 to Q-234; M-1 to L-233; M-1 to R-232; M-1 to N-231; M-1 to L-230; M-1 to R-229; M-1 to V-228; M-1 to D-227; M-1 to L-226; M-1 to F-225; M-1 to E-224; M-1 to I-223; M-1 to G-222; M-1 to S-221; M-1 to P-220; M-1 to L-219; M-1 to V-218; M-1 to P-217; M-1 to L-216; M-1 to A-215; M-1 to E-214; M-1 to L-213; M-1 to Q-212; M-1 to N-211; M-1 to E-210; M-1 to P-209; M-1 to L-208; M-1 to I-207; M-1 to L-206; M-1 to D-205; M-1 to Q-204; M-1 to L-203; M-1 to A-202; M-1 to H-201; M-1 to L-200; M-1 to L-199; M-1 to R-198; M-1 to F-197; M-1 to A-196; M-1 to D-195; M-1 to N-194; M-1 to D-193; M-1 to I-192; M-1 to S-191; M-1 to S-190; M-1 to I-189; M-1 to L-188; M-1 to N-187; M-1 to N-186; M-1 to S-185; M-1 to L-184; M-1 to D-183; M-1 to I-182; M-1 to R-181; M-1 to K-180; M-1 to L-179; M-1 to K-178; M-1 to T-177; M-1 to L-176; M-1 to G-175; M-1 to K-174; M-1 to F-173; M-1 to D-172; M-1 to E-171; M-1 to A-170; M-1 to R-169; M-1 to I-168; M-1 to R-167; M-1 to S-166; M-1 to I-165; M-1 to R-164; M-1 to N-163; M-1 to F-162; M-1 to R-161; M-1 to A-160; M-1 to Y-159; M-1 to L-158; M-1 to Y-157; M-1 to A-156; M-1 to T-155; M-1 to R-154; M-1 to R-153; M-1 to P-152; M-1 to L-151; M-1 to P-150; M-1 to P-149; M-1 to I-148; M-1 to D-147; M-1 to E-146; M-1 to L-145; M-1 to D-144; M-1 to I-143; M-1 to D-142; M-1 to D-141; M-1 to C-140; M-1 to Y-139; M-1 to V-138; M-1 to S-137; M-1 to S-136; M-1 to G-135; M-1 to L-134; M-1 to C-133; M-1 to V-132; M-1 to C-131; M-1 to V-130; M-1 to L-129; M-1 to C-128; M-1 to T-127; M-1 to P-126; M-1 to L-125; M-1 to G-124; M-1 to H-123; M-1 to N-122; M-1 to P-121; M-1 to Q-120; M-1 to S-119; M-1 to S-118; M-1 to L-117; M-1 to L-116; M-1 to L-115; M-1 to G-114; M-1 to A-113; M-1 to T-112; M-1 to T-111; M-1 to P-110; M-1 to R-109; M-1 to T-108; M-1 to M-107; M-1 to T-106; M-1 to P-105; M-1 to N-104; M-1 to S-103; M-1 to S-102; M-1 to P-101; M-1 to T-100; M-1 to G-99; M-1 to P-98; M-1 to A-97; M-1 to T-96; M-1 to T-95; M-1 to S-94; M-1 to K-93; M-1 to A-92; M-1 to P-91; M-1 to S-90; M-1 to I-89; M-1 to S-88; M-1 to T-87; M-1 to A-86; M-1 to P-85; M-1 to A-84; M-1 to L-83; M-1 to S-82; M-1 to T-81; M-1 to V-80; M-1 to K-79; M-1 to V-78; M-1 to E-77; M-1 to P-76; M-1 to L-75; M-1 to Q-74; M-1 to D-73; M-1 to G-72; M-1 to Y-71; M-1 to D-70; M-1 to T-69; M-1 to L-68; M-1 to E-67; M-1 to E-66; M-1 to Y-65; M-1 to N-64; M-1 to S-63; M-1 to L-62; M-1 to D-61; M-1 to I-60; M-1 to V-59; M-1 to E-58; M-1 to G-57; M-1 to Y-56; M-1 to N-55; M-1 to D-54; M-1 to P-53; M-1 to N-52; M-1 to L-51; M-1 to V-50; M-1 to D-49; M-1 to N-48; M-1 to R-47; M-1 to L-46; M-1 to P-45; M-1 to L-44; M-1 to V-43; M-1 to E-42; M-1 to F-41; M-1 to S-40; M-1 to D-39; M-1 to G-38; M-1 to E-37; M-1 to R-36; M-1 to P-35; M-1 to M-34; M-1 to Q-33; M-1 to E-32; M-1 to E-31; M-1 to R-30; M-1 to R-29; M-1 to K-28; M-1 to R-27; M-1 to E-26; M-1 to K-25; M-1 to R-24; M-1 to P-23; M-1 to L-22; M-1 to S-21; M-1 to A-20; M-1 to T-19; M-1 to G-18; M-1 to T-17; M-1 to E-16; M-1 to Q-15; M-1 to L-14; M-1 to V-13; M-1 to L-12; M-1 to A-11; M-1 to L-10; M-1 to L-9; M-1 to S-8; M-1 to L-7; of SEQ ID NO:32. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nucleotide sequences related to extensive portions of SEQ ID NO:14 which have been determined from the following related cDNA genes: HARAY79R (SEQ ID NO:80), HARAO44R (SEQ ID NO:81), HARAJ74R (SEQ ID NO:82), HARAO66R (SEQ ID NO:83), HARAN19R (SEQ ID NO:84), and HARAT78R (SEQ ID NO:85).

Northern analysis indicates that this gene is expressed in adrenal cortex and adrenal medulla tissues. This gene is also expressed in retinal tissue.

Therefore, polynucleotides and polypeptides of the invention, including antibodies, are useful as reagents for differential identification of the tissue(s) or cell type(s) present in a biological sample and for diagnosis of diseases and conditions which include, but are not limited to, retinal disorders. Similarly, polypeptides and antibodies directed to these polypeptides are useful in providing immunological probes for differential identification of the tissue(s) or cell type(s). For a number of disorders of the above tissues or cells, particularly of the retina, expression of this gene at significantly higher or lower levels is routinely detected in certain tissues or cell types (e.g., retinal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in retinal tissue, and the homology to a *Gallus gallus* proteoglycan involved in the ossification process indicates that polynucleotides, translation products and antibodies corresponding to this gene are useful for the treatment of disorders of the retina which involve the adhesion of tissues, or the binding of certain proteins to the cell surface. Polynucleotides, translation products and antibodies corresponding to this gene are useful for the treatment of retinal disorders such as retinal detachment in individuals suffering from myopia, or in the treatment of macular degeneration. Furthermore, this gene may serve as a tumor marker for retinoblastomas, or related tumors. More generally, the tissue distribution in retinal tissue indicates that polynucleotides, translation products and antibodies corresponding to this gene are useful for the diagnosis, detection and/or treatment of eye disorders including blindness, color blindness, impaired vision, short and long sightedness, retinitis pigmentosa, retinitis proliferans, and retinoblastoma, retinochoroiditis, retinopathy and retinoschisis. Based upon the tissue distribution of this protein, antagonists directed against this protein are useful in blocking the activity of this protein. Accordingly, preferred are antibodies which specifically bind a portion of the translation product of this gene.

Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 1375 of SEQ ID NO:14, b is an integer of 15 to 1389, where both a and b correspond to the positions of nucleotide residues shown in SEQ ID NO:14, and where b is greater than or equal to a+14.

Features of Protein Encoded by Gene No: 5

Translation products corresponding to the CD33-like gene (SEQ ID NOs: 33 and/or 149) share sequence homology with the CD33 protein (See Genbank Accession BAA24983). The expression pattern of CD33 within the hematopoietic system indicates a potential role in the regulation of myeloid cell differentiation. However, this expression is absent from hematopoietic stem cells.

CD33 is expressed in clonogenic leukemia cells in about 90% of patients suffering from acute myeloid leukemia (AML). While about 60-70% of adults suffering from AML experience complete remission due to chemotherapy application, most of these patients will ultimately die of relapsed leukemia It is believed that, like CD33, the CD33-like protein of the present invention is also expressed by clonogenic leukemia cells from the vast majority of patients with AML. Thus, there is a clear need to identify and isolate nucleic acid molecules encoding additional polypeptides having CD33-like protein activity. It is believed that cancerous tissue contains significantly greater amounts of CD33-like protein gene copy number and expresses significantly enhanced levels of CD33-like protein and mRNA encoding the CD33-like protein when compared to a "standard" mammal, i.e.—a mammal of the same species not having the cancer or inflammatory disease. Thus, enhanced levels of the CD33-like protein will be detected in certain bodily fluids (e.g., serum, plasma, urine, synovial fluid and spinal fluid) from mammals when compared to sera from mammals of the same species not having the cancer or inflammatory disease.

Translation products corresponding to the CD33-like and CD33-likeSV (a splice variant of CD33-like) (SEQ ID NOs: 33 and/or 149) share sequence homology with a number of CD33-related Siglecs, namely Siglecs-3, -5 (See Genbank Accession AAD50978), -6 (See Genbank Accession NP001236), -7 (See Genbank Accession AAF12759), -8 (See Genbank Accession AAF27622), and -9 (See Genbank Accession AAF87223). Siglecs are sialic acid binding proteins, and are members of the Ig superfamily which are expressed at the cellular surface. Each Siglec member exhibits distinct sialic acid binding properties, and has a characteristic tissue expression profile. Based upon the homology, it is thought that CD33-like and CD33-likeSV will share at least some of the biological activities of other Siglecs (e.g., sialic acid binding). CD33-likeSV is thought to exist as a monomer in the plasma membrane (See FIG. 43 and/or Example 54). CD33-likeSV was mapped by in situ hybridization to the long arm of chromosome 19, in the 19q13.3 band, which is closely linked to other CD33-related Siglecs.

Two related cDNAs, HDPIB36 and HEOMH10, have been isolated. These cDNAs appear to encode splice variants of the same gene. Preferred polynucleotides comprise, or alternatively consist of, a polynucleotide sequence selected from the following sequences: CGACCCACGCGTCCGCCGCCT-TCGGCTTCCCCTTCTGC

CAAGAGCCCTGAGCCACTCACAGCAC-GACCAGAGA (SEQ ID NO: 86),

GTATGGAATGGGGTGGGAACCCCTGC-CTCTCACACTGGGGAGGGACCCTGGGGA-CAGCCTATGGGCTG AGCAGAGAGGGCTCTCAGG-GACCCCTGCAGCACAAGAATCTCCCACCACGG TTCTGTCCCAGCCCTGACTCAGA AGCCTGATGTC-TACATCCCCGAGACCCTGGAGC-CCGGGCAGCCGGTGACGGTCATCTGTGT-GTTTAACTGGGCCTT TGAGGAATGTCCACCCCCTTCTTTCTC-CTGGACGGGGGCTGCCC TCTCCTCCCAAGGAAC-CAAACCAACGACCTCC CACTTCTCAG (SEQ ID NO: 87),

ATCCTCCAGAGAACCTGAGAGTGATG-GTTTCCCAAGCAAACAGGACAGGTAG-GAAAGGGGACAGAGG AGCCAAGGCCTCTCAGTGC-CGAATTGGGGGCCCAGGAGTCTGGAGGGTCC CCACGCAGGAGGGTCCCTGAGCCCT GAGCTGCT-CATCGATTCTGCCTCTTCCTTCCCT (SEQ ID NO: 88),

GTGAGTGGGGGAAAGGGGACAC-CTGGGTCCCAGGAAGGGGACCCTGCT-GAGTCCTGTCCTCCCTCCCCT CAG (SEQ ID NO: 89),

CTGGCCCCCTGGCTCAGAAGCGGAATCA-GAAAGCCACACCAAACAGTCCTCGGAC-CCCTCTTCCACCAG GTGCTCCCTCCCCAGAAT-CAAAGAAGAACCAGAAAAAGCAGTATCAGTT GCCCAGTTTCCCAGAACCCAAATCAT CCACT-CAAGCCCCAGAATCCCAGGAGAGCCAA-GAGGAGCTCCATTATGCCACGCTCAACT-TCCCAGGCGTCAGAC CCAGGCCTGAGGCCCGGATGC-CCAAGGGCACCCAGGCGGATTATGCA-GAAGTCAAGTTCCAATGAGGGTCTCTTA GGCTT-TAGGACTGGGACTTCGGCTAGGGAGGAAGGTAG AGTAAGAGGTTGAAGATAACAGAGTG-CAAAGTTTCCT TCTCTC-CCTCTCTCTCTCTCTTTCTCTCTCTCTCTCT TTCTCTCTCTTTT (SEQ ID NO: 90), and/or AAAAAAACATCTGGCCAGGGCACAGTG-GCTCACGCCTGTAATCCCAGCACTTTGG-GAGGTTGAGGTGG GCAGATCGCCTGAGGTCGG-GAGTTCGAGACCAGCCTGGCCAACTTGGTG AAACCCCGTCTCTACTAAAAATACAA AAATT-AGCTGGGCATGGTGGCAGGCGCCTG-TAATCCTACTACTTGGGAAGCTGAG-GCAGGAGAATCACTTGAACC TGGGAGACGGAGGTTGCAGTGAGCCAA-GATCACACCATTGCACGCCAGCT-TGGGCAACAAAGCGAGACTCCATCT CAAAAAAAAAATCCTCCAAATGGGT-TGGGTGTCTGTAATCCCAGCACTTTGG-GAGGCTAAGGTGGGTGGATTGCT TGAGCCCAG-GAGTTCGAGACCAGCCTGGGCAACATGGTG AAACCCCATCTCTACAAAAAATACAAAACATAGCTG GGCTTGGTGGTGTGTGCCTGTAGTC-CCAGCTGTCAGACATTTAAACCAGAG-CAACTCCCATCTGGAATGGGAGCTG AATAAAAT-GAGGCTGAGACCTACTGGGCTGCCATTCTCA GACAGTGGAGGCCATTCTAAGTCACAG-GATGAGACA GGAGGTCCGTACAAGATACAGGTCAT-AAAGACTTTGCTGATAAAACAGATTG-CAGTAAAGAAGCCAACCAAATCC CACCA AAACCAAGTTGGCCACGAGAGTGAC-CTCTGGTCGTCCTCACTGCTACACTCCT-GACAGCACCATGACAGTT TACAAATGCCATGGCAA-CATCAGGAAGTTACCCGATATGTCCCAAAAG GGGGAGGAATGAATAATCCACCCCTTG TTTAG-CAAATAAGCAAGAAATAACCAT-AAAAGTGGGCAACCAGCAGCTCTAG-GCGCTGCTCTTGTCTATGGAGTA GCCATTCTTTTGTTCCTI TACTTTCTTAATAAACT-TGCTTTCACCTT (SEQ ID NO:91). Also preferred are the polypeptides encoded by these polynucleotides.

Preferred CD33-like polypeptides of the present invention comprise, or alternatively consist of, one, two, three, four, five, six, seven, eight, nine, ten, eleven, twelve, thirteen, fourteen, fifteen, sixteen, seventeen, eighteen, nineteen, twenty, or all twenty of the predicted immunogenic epitopes shown in SEQ ID NO: 33 as residues: Pro-46 to Gly-52, Asn-76 to Val-82, Ser-85 to Phe-90, Gly-94 to Asn-100, Gln-111 to Tyr-116, Pro-146 to Leu-155, Ser-188 to Asn-202, Ser-240 to Arg-246, Gly-258 to Tyr-263, Ala-267 to Arg-276, Ser-326 to Arg-331, Ser-333 to Gln-339, Pro-343 to Asp-348, Glu-426 to Asp-432, Pro-517 to His-533, Ala-550 to Pro-565, Gly-569 to Gln-582, Pro-589 to Glu-606, Gly-616 to Ala-623, and/or Met-625 to Ala-631. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred CD33-likeSV polypeptides of the present invention comprise, or alternatively consist of, one, two, three, four, five, six, seven, eight, nine, ten, eleven, twelve, thirteen, fourteen, fifteen, sixteen, seventeen, eighteen, nineteen, twenty, twenty-one, twenty-two, or all twenty-two of the predicted immunogenic epitopes shown in SEQ ID NO: 149 as residues: Pro-46 to Gly-52, Asn-76 to Val-82, Ser-85 to Phe-90, Gly-94 to Asn-100, Gln-111 to Tyr-116, Cys-173 to Ser-179, Gln-188 to Ser-195, Pro-204 to Leu-213, Ser-246 to Asn-260, Ser-298 to Arg-304, Gly-316 to Tyr-321, Ala-325 to Arg-334, Ser-384 to Arg-389, Ser-391 to Gln-397, Pro-401 to Asp-406, Glu-484 to Asp-490, Pro-575 to His-591, Ala-608 to Pro-623, Gly-627 to Gln-640, Pro-647 to Glu-664, Gly-674 to Ala-681, and Met-683 to Ala-689. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

FIGS. 13A-C show the nucleotide (SEQ ID NO:15) and deduced amino acid sequence (SEQ ID NO:33) of the CD33-like protein. Predicted amino acids from about 1 to about 16 constitute the predicted signal peptide (amino acid residues from about 1 to about 16 in SEQ ID NO:33) and are represented by the underlined amino acid regions; and amino acids from about 496 to about 512 constitute the predicted transmembrane domain (amino acid residues from about 496 to about 512 in SEQ ID NO:33) and are represented by the double-underlined amino acid regions.

FIG. 14 shows the regions of similarity between the amino acid sequences of the CD33-like protein SEQ ID NO:33, and the CD33L1 protein (See Genbank Accession A30521) (SEQ ID NO: 92).

Figure 15:
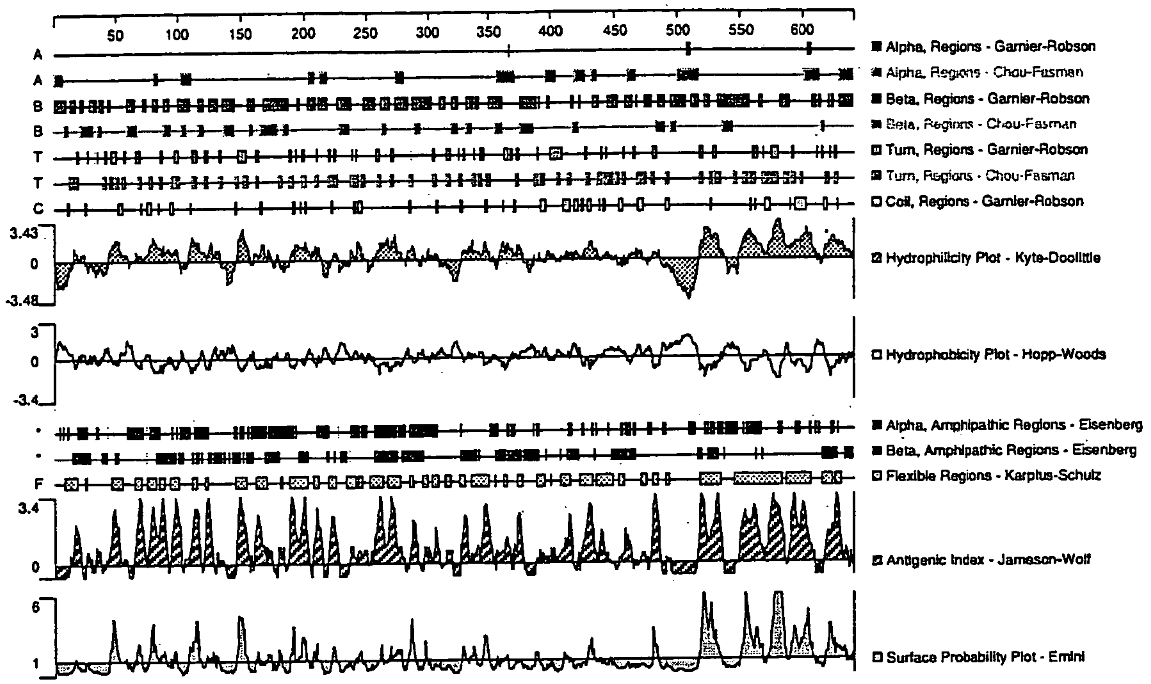
FIG. 15 shows an analysis of the amino acid sequence of SEQ ID NO:33. Alpha, beta, turn and coil regions; hydrophilicity and hydrophobicity; amphipathic regions; flexible regions; antigenic index and surface probability are shown.

FIG. 15 shows an analysis of the amino acid sequence of CD33-like protein (SEQ ID NO:33). Alpha, beta, turn and coil regions; hydrophilicity and hydrophobicity; amphipathic regions; flexible regions; antigenic index and surface probability are shown.

FIG. 37 shows the predicted protein sequence of CD33-likeSV protein (identified in FIG. 37 as "Siglec-10") and alignment with closely-related Siglecs. Alignment was performed with the ClustalW multiple sequence alignment program. Residues that are identical in more than half the proteins are boxed in black, similar residues in grey. Asterisks indicate positions of the cysteine residues characteristic of Siglecs. Filled circles overlay residues important for sialic acid binding. Vertical lines indicate positions of intron-exon boundaries, as deduced from the sequence of the gene encoding CD33-likeSV. Positions of the domain boundaries, transmembrane region, cytoplasmic tail (encoded by two exons) and the tyrosine based motifs are indicated. Genbank accession numbers are as follows: CD33/Siglec-3, Siglec-5: AAD50978; Siglec-6, NP001236; Siglec-7 AAF12759; Siglec-8, AAF27622; and Siglec-9, AAF87223.

FIG. 38 provides a phylogenetic analysis of CD33-related Siglecs and CD33-likeSV protein (identified in FIG. 38 as "Siglec-10"). The leader peptide, domain 1, and domain 2, or the transmembrane and cytoplasmic tails were aligned using the Clustal W multiple sequence alignment program and analyzed for phylogenetic relationship using the PHYLIP 3.6. Unrooted phylograms were constructed using the neighbor joining method.

FIG. 39 provides a sequential deletion model for evolution of CD33-related Siglecs. Based on the phylogenetic analysis and sequence comparisons, this model predicts that MAG and CD33-likeSV (identified in FIG. 39 as "Siglec-10") are both derived from a common 4-domain progenitor. CD33-likeSV then gave rise to Siglec-5 involving a deletion of the exons encoding domain 3 and its associated linker. Siglec-5 then gave rise to a three domain siglec by deletion of domain 4. The other 3-domain Siglecs then arose through gene duplication. CD33 may have been derived in a single deletion event either from Siglec-5 or one of the three domain Siglecs.

FIGS. 40A & B provides the localization and expression of the CD33-likeSV gene.

Human lymphocyte metaphase spreads were hybridized with a 3 kb biotinylated insert from HEONM10 followed by fluorescein-avidin and the chromosomes counterstained with propidium iodide. The digital image is reversed to illustrate the hybridization signals (arrows) on the long arm of chromosome 19. The position of CD33-likeSV on chromosome 19 band q13.3 is also shown schematically.

Northern blot analysis of CD33-likeSV mRNA in human tissues. Each lane of the Multiple Tissue Northern (MTN) Blot (Clontech) contains approximately 2 gg poly A+ RNA from the tissue indicated and is normalized for levels of β-actin mRNA. A major form of CD33-likeSV mRNA is seen at around 3.0 kb in most tissues.

FIG. 41 disclosed the binding of CD33-likeSV (identified in FIG. 41 as "Siglec-10") expressed on COS cells to polyacrylamide conjugates. CR1 was included as a negative control to measure non-specific binding. Three days after transient transfection, COS cells expressing the indicated proteins were incubated with biotinylated polyacrylamide (PAA) glycoconjugates linked either to 3' sialyllactose (2,3-PAA) or 6' sialyllactose (2,6-PAA) or lactose (Lac-PAA) at 20 μg/ml or with buffer alone. Unbound conjugate was washed off and binding detected with $^{125}$I-streptavidin. Data show means standard deviations of quadruplicates and are representative of 3 experiments performed.

FIGS. 42A, B & C show the expression of CD33-likeSV (identified in FIG. 42 as "Siglec-10") on human peripheral blood leukocyte subsets.

FACS histograms showing expression of CD33-likeSV on granulocytes, monocytes and lymphocytes, gated in each case according to their characteristic side and forward scatter properties. Thick lines show staining with affinity purified mouse anti-CD33-likeSV polyclonal antibody. Thin lines show staining in the presence of mouse IgG used as a negative control. CD33-likeSV is expressed on a minor subset of granulocytes, most monocytes and a subset of lymphocytes Double labeling of granulocytes with anti-CD 16 (neutrophils) and anti-CD33-likeSV mAb compared with anti-Siglec-8 mAb. Compared to the isotype matched control mAb, CD33-likeSV shows clear labeling of the eosinophils and some of the neutrophils are also weakly stained. Values represent the percentages of total granulocytes analyzed.

Double labeling of the lymphocyte fraction with antibodies to CD 19 (B cells), CD3 (pan T cell), CD4 and CD8 (T cell subsets) and CD56 (NK cells). CD33-likeSV is expressed by most CD 19+ B cells and a small subset of CD16+ cells that do not express the CD56 natural killer cell marker. Values represent the percentages of the total lymphocytes analyzed. Similar results were obtained using the mouse anti-CD33-likeSV mAb, 5G6.

FIG. 43 provides a molecular characterization of CD33-likeSV (identified in FIG. 43 as "S10"). Stably-transfected CHO cells expressing CD33-likeSV, wild-type CHO cells, or Daudi cells were surface biotinylated, lysed and immunoprecipitations performed with mouse anti-CD33-likeSV polyclonal antibody. Precipitates were run either under reducing or non-reducing conditions on 4-12% gradient SDS polyacrylamide gels, transferred to nitrocellulose and probed with streptavidin-horse radish peroxidase. CD33-likeSV migrates as a single monomeric species at around 120 kDa in CHO cells and around 100 kDa in Daudi cells.

FIG. 44 shows an analysis of the amino acid sequence of CD33-likeSV protein (SEQ ID NO: 149). Alpha, beta, turn and coil regions; hydrophilicity and hydrophobicity; amphipathic regions; flexible regions; antigenic index and surface probability are shown.

The present invention provides isolated nucleic acid molecules comprising a polynucleotide encoding the polypeptide having the amino acid sequence shown in FIGS. 13A-C (SEQ ID NO:33), which was determined by sequencing a cloned cDNA (HDPCL05). The nucleotide sequence shown in FIGS. 13A-C (SEQ ID NO:15) was obtained by sequencing a cloned cDNA (HDPCL05), which was deposited on Nov. 17, 1998 at the American Type Culture Collection, and given Accession Number 203484. The deposited gene is inserted in the pSport plasmid (Life Technologies, Rockville, Md.) using the SalI/NotI restriction endonuclease cleavage sites.

The present invention provides isolated nucleic acid molecules comprising a polynucleotide encoding the polypeptide having the amino acid sequence shown in FIG. 37 (SEQ ID NO:149).

The present invention is further directed to fragments of the isolated nucleic acid molecules described herein. By a fragment of an isolated DNA molecule having the nucleotide sequence of the deposited cDNA, the nucleotide sequence shown in SEQ ID NO:15, or the nucleotide sequence shown in SEQ ID NO: 148, is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA, as shown in SEQ ID NO:15, or as shown in SEQ ID NO: 148. By a fragment at least 20 nt in length, for example, is intended fragments which include 20 or more contiguous bases from the nucleotide sequence of the deposited cDNA or the nucleotide sequence as shown in SEQ ID NO:15. In this context "about" includes the particularly recited size, larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, from about 501 to about 550, from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1350, from about 1351 to about 1400, from about 1401 to about 1450, from about 1451 to about 1500, from about 1501 to about 1550, from about 1551 to about 1600, from about 1601 to about 1650, from about 1651 to about 1700, from about 1701 to about 1750, from about 1751 to about 1800, from about 1801 to about 1850, from about 1851 to about 1900, from about 1901 to about 1950, from about 1951 to about 2000, from about 2001 to about 2050, from about 2051 to about 2100, from about 2101 to about 2150, from about 2151 to about 2200, from about 2201 to about 2250, from about 2251 to about 2295, from about 307 to about 1977, and from about 106 to about 1977, of SEQ ID NO:15, of SEQ ID NO: 148, or the complementary strand thereto, or the cDNA contained in the deposited gene. In this context "about" includes the particularly recited ranges, larger or smaller by several (5, 4, 3, 2, or 1) nucleotides, at either terminus or at both termini. In additional embodiments, the polynucleotides of the invention encode functional attributes of the corresponding protein.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 15, FIG. 44, and/or Tables V or XIII, as described above, was generated using the various modules and algorithms of the DNA*STAR set on default parameters. In a preferred embodiment, the data presented in columns VII, IX, XIII, and XIV of Tables V and XIII can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIGS. 15 and 44, but may, as shown in Tables V and XIII, be represented or identified by using tabular representations of the data presented in FIGS. 15 and 44. The DNA*STAR computer algorithm used to generate FIGS. 15 and 44, (set on the original default parameters) was used to present the data in FIGS. 15 and 44 in a tabular format (See Tables V and XIII). The tabular format of the data in FIGS. 15 and 44 is used to easily determine specific boundaries of a preferred region. The above-mentioned preferred regions set out in FIGS. 15 and 44 and in Tables V and XIII include, but are not limited to, regions of the aforementioned types identified by analysis of the amino acid sequences set out in FIGS. 13A-C and FIG. 37. As set out in FIGS. 15 and 44, and in Tables V and XIII, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, etc.) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, the present invention further provides polypeptides having one or more residues deleted from the amino terminus of the amino acid sequence shown in FIGS. 13A-C, up to the alanine residue at position number 634 and polynucleotides encoding such polypeptides. In particular, the present invention provides polypeptides comprising the amino acid sequence of residues n1-639 of FIGS. 13A-C, where n1 is an integer from 2 to 634 corresponding to the position of the amino acid residue in FIGS. 13A-C (which is identical to the sequence shown as SEQ ID NO:33). N-terminal deletions of the polypeptide of the invention shown as SEQ ID NO:33 include polypeptides comprising, or alternatively consisting of, an amino acid sequence selected from residues: L-2 to Q-639; L-3 to Q-639; P-4 to Q-639; L-5 to Q-639; L-6 to Q-639; L-7 to Q-639; S-8 to Q-639; S-9 to Q-639; L-10 to Q-639; L-11 to Q-639; G-12 to Q-639; G-13 to Q-639; S-14 to Q-639; Q-15 to Q-639; A-16 to Q-639; M-17 to Q-639; D-18 to Q-639; G-19 to Q-639; R-20 to Q-639; F-21 to Q-639; W-22 to Q-639; I-23 to Q-639; R-24 to Q-639; V-25 to Q-639; Q-26 to Q-639; E-27 to Q-639; S-28 to Q-639; V-29 to Q-639; M-30 to Q-639; V-31 to Q-639; P-32 to Q-639; E-33 to Q-639; A-34 to Q-639; C-35 to Q-639; D-36 to Q-639; I-37 to Q-639; S-38 to Q-639; V-39 to Q-639; P-40 to Q-639; C41 to Q-639; S-42 to Q-639; F-43 to Q-639; S-44 to Q-639; Y-45 to Q-639; P-46 to Q-639; R-47 to Q-639; Q-48 to Q-639; D-49 to Q-639; W-50 to Q-639; T-51 to Q-639; G-52 to Q-639; S-53 to Q-639; T-54 to Q-639; P-55 to Q-639; A-56 to Q-639; Y-57 to Q-639; G-58 to Q-639; Y-59 to Q-639; W-60 to Q-639; F-61 to Q-639; K-62 to Q-639; A-63 to Q-639; V-64 to Q-639; T-65 to Q-639; E-66 to Q-639; T-67 to Q-639; T-68 to Q-639; K-69 to Q-639; G-70 to Q-639; A-71 to Q-639; P-72 to Q-639; V-73 to Q-639; A-74 to Q-639; T-75 to Q-639; N-76 to Q-639; H-77 to Q-639; Q-78 to Q-639; S-79 to Q-639; R-80 to Q-639; E-81 to Q-639; V-82 to Q-639; E-83 to Q-639; M-84 to Q-639; S-85 to Q-639; T-86 to Q-639; R-87 to Q-639; G-88 to Q-639; R-89 to Q-639; F-90 to Q-639; Q-91 to Q-639; L-92 to Q-639; T-93 to Q-639; G-94 to Q-639; D-95 to Q-639; P-96 to Q-639; A-97 to Q-639; K-98 to Q-639; G-99 to Q-639; N-100 to Q-639; C-101 to Q-639; S-102 to Q-639; L-103 to Q-639; V-104 to Q-639; I-105 to Q-639; R-106 to Q-639; D-107 to Q-639; A-108 to Q-639; Q-109to Q-639; M-110 to Q-639; Q-111 to Q-639; D-112 to Q-639; E-113 to Q-639; S-114 to Q-639; Q-115 to Q-639; Y-116 to Q-639; F-117 to Q-639; F-118 to Q-639; R-119 to Q-639; V-120 to Q-639; E-121 to Q-639; R-122 to Q-639; G-123 to Q-639; S-124 to Q-639; Y-125 to Q-639; V-126 to Q-639; R-127 to Q-639; Y-128 to Q-639; N-129 to Q-639; F-130 to Q-639; M-131 to Q-639; N-132 to Q-639; D-133 to Q-639; G-134 to Q-639; F-135 to Q-639; F-136 to Q-639; L-137 to Q-639; K-138 to Q-639; V-139to Q-639; T-140 to Q-639; V-141 to Q-639; L-142 to Q-639; S-143 to Q-639; F-144 to Q-639; T-145 to Q-639; P-146 to Q-639; R-147to Q-639; P-148 to Q-639; Q-149 to Q-639; D-150 to Q-639; H-151 to Q-639; N-152 to Q-639; T-153 to Q-639; D-154 to Q-639; L-155 to Q-639; T-156 to Q-639; C-157 to Q-639; H-158 to Q-639; V-159 to Q-639; D-160 to Q-639; F-161 to Q-639; S-162to Q-639; R-163 to Q-639; K-164 to Q-639; G-165 to Q-639; V-166 to Q-639; S-167 to Q-639; A-168 to Q-639; Q-169 to Q-639; R-170 to Q-639; T-171 to Q-639; V-172 to Q-639; R-173 to Q-639; L-174 to Q-639; R-175 to Q-639; V-176 to Q-639; A-177 to Q-639; Y-178 to Q-639; A-179 to Q-639; P-180 to Q-639; R-181 to Q-639; D-182 to Q-639; L-183 to Q-639; V-184to Q-639; I-185 to Q-639; S-186 to Q-639; I-187 to Q-639; S-188 to Q-639; R-189 to Q-639; D-190 to Q-639; N-191 to Q-639; T-192 to Q-639; P-193 to Q-639; A-194 to Q-639; L-195 to Q-639; E-196 to Q-639; P-1 97 to Q-639; Q-198 to Q-639; P-199 to Q-639; Q-200 to Q-639; G-201 to Q-639; N-202 to Q-639; V-203 to Q-639; P-204 to Q-639; Y-205 to Q-639; L-206 to Q-639; E-207 to Q-639; A-208 to Q-639; Q-209 to Q-639; K-210 to Q-639; G-211 to Q-639; Q-212 to Q-639; F-213 to Q-639; L-214 to Q-639; R-215 to Q-639; L-216 to Q-639; L-217 to Q-639; C-218 to Q-639; A-219 to Q-639; A-220 to Q-639; D-221 to Q-639; S-222 to Q-639; Q-223 to Q-639; P-224 to Q-639; P-225 to Q-639; A-226 to Q-639; T-227 to Q-639; L-228 to Q-639; S-229 to Q-639; W-230 to Q-639; V-231 to Q-639; L-232 to Q-639; Q-233 to Q-639; N-234 to Q-639; R-235 to Q-639; V-236 to Q-639; L-237 to Q-639; S-238 to Q-639; S-239 to Q-639; S-240 to Q-639; H-241 to Q-639; P-242to Q-639; W-243 to Q-639; G-244 to Q-639; P-245 to Q-639; R-246 to Q-639; P-247 to Q-639; L-248 to Q-639; G-249 to Q-639; L-250 to Q-639; E-251 to Q-639; L-252 to Q-639; P-253 to Q-639; G-254 to Q-639; V-255 to Q-639; K-256 to Q-639; A-257 to Q-639; G-258 to Q-639; D-259 to Q-639; S-260 to Q-639; G-261 to Q-639; R-262 to Q-639; Y-263 to Q-639; T-264 to Q-639; C-265 to Q-639; R-266 to Q-639; A-267 to Q-639; E-268 to Q-639; N-269 to Q-639; R-270 to Q-639; L-271 to Q-639; G-272 to Q-639; S-273 to Q-639; Q-274 to Q-639; Q-275 to Q-639; R-276 to Q-639; A-277 to Q-639; L-278 to Q-639; D-279 to Q-639; L-280 to Q-639; S-281 to Q-639; V-282 to Q-639; Q-283 to Q-639; Y-284 to Q-639; P-285 to Q-639; P-286 to Q-639; E-287to Q-639; N-288 to Q-639; L-289 to Q-639; R-290 to Q-639; V-291 to Q-639; M-292 to Q-639; V-293 to Q-639; S-294 to Q-639; Q-295 to Q-639; A-296 to Q-639;

N-297 to Q-639; R-298 to Q-639; T-299 to Q-639; V-300 to Q-639; L-301 to Q-639; E-302 to Q-639; N-303 to Q-639; L-304 to Q-639; G-305 to Q-639; N-306 to Q-639; G-307 to Q-639; T-308 to Q-639; S-309 to Q-639; L-310 to Q-639; P-311 to Q-639; V-312 to Q-639; L-313 to Q-639; E-314 to Q-639; G-315 to Q-639; Q-316 to Q-639; S-317 to Q-639; L-318 to Q-639; C-319 to Q-639; L-320 to Q-639; V-321 to Q-639; C-322 to Q-639; V-323 to Q-639; T-324 to Q-639; H-325 to Q-639; S-326 to Q-639; S-327 to Q-639; P-328 to Q-639; P-329 to Q-639; A-330 to Q-639; R-331 to Q-639; L-332 to Q-639; S-333 to Q-639; W-334 to Q-639; T-335 to Q-639; Q-336 to Q-639; R-337 to Q-639; G-338 to Q-639; Q-339 to Q-639; V-340 to Q-639; L-341 to Q-639; S-342 to Q-639; P-343 to Q-639; S-344 to Q-639; Q-345 to Q-639; P-346 to Q-639; S-347 to Q-639; D-348 to Q-639; P-349 to Q-639; G-350 to Q-639; V-351 to Q-639; L-352 to Q-639; E-353 to Q-639; L-354 to Q-639; P-355 to Q-639; R-356 to Q-639; V-357 to Q-639; Q-358 to Q-639; V-359 to Q-639; E-360 to Q-639; H-361 to Q-639; E-362 to Q-639; G-363 to Q-639; E-364 to Q-639; F-365 to Q-639; T-366 to Q-639; C-367 to Q-639; H-368 to Q-639; A-369 to Q-639; R-370 to Q-639; H-371 to Q-639; P-372 to Q-639; L-373 to Q-639; G-374 to Q-639; S-375 to Q-639; Q-376 to Q-639; H-377 to Q-639; V-378 to Q-639; S-379 to Q-639; L-380 to Q-639; S-381 to Q-639; L-382 to Q-639; S-383 to Q-639; V-384 to Q-639; H-385 to Q-639; Y-386 to Q-639; S-387 to Q-639; P-388 to Q-639; K-389 to Q-639; L-390 to Q-639; L-391 to Q-639; G-392 to Q-639; P-393 to Q-639; S-394 to Q-639; C-395 to Q-639; S-396 to Q-639; W-397 to Q-639; E-398 to Q-639; A-399 to Q-639; E-400 to Q-639; G-401 to Q-639; L-402 to Q-639; H-403 to Q-639; C-404 to Q-639; S-405 to Q-639; C-406 to Q-639; S-407 to Q-639; S-408 to Q-639; Q-409 to Q-639; A-410 to Q-639; S-411 to Q-639; P-412 to Q-639; A-413 to Q-639; P-414 to Q-639; S-415 to Q-639; L-416 to Q-639; R-417 to Q-639; W-418 to Q-639; W-419 to Q-639; L-420 to Q-639; G-421 to Q-639; E-422 to Q-639; E-423 to Q-639; L-424to Q-639; L-425 to Q-639; E-426 to Q-639; G-427 to Q-639; N-428 to Q-639; S-429 to Q-639; S-430 to Q-639; Q-431 to Q-639; D-432 to Q-639; S-433 to Q-639; F-434 to Q-639; E-435 to Q-639; V-436 to Q-639; T-437 to Q-639; P-438 to Q-639; S-439 to Q-639; S-440 to Q-639; A-441 to Q-639; G-442 to Q-639; P-443 to Q-639; W-444 to Q-639; A-445 to Q-639; N-446 to Q-639; S-447 to Q-639; S-448 to Q-639; L-449 to Q-639; S-450 to Q-639; L-451 to Q-639; H-452 to Q-639; G-453 to Q-639; G-454 to Q-639; L-455 to Q-639; S-456 to Q-639; S-457 to Q-639; G-458 to Q-639; L-459 to Q-639; R-460 to Q-639; L-461 to Q-639; R-462 to Q-639; C-463 to Q-639; E-464 to Q-639; A-465 to Q-639; W-466 to Q-639; N-467 to Q-639; V-468 to Q-639; H-469 to Q-639; G-470 to Q-639; A-471 to Q-639; Q-472 to Q-639; S-473 to Q-639; G-474 to Q-639; S-475 to Q-639; I-476 to Q-639; L-477 to Q-639; Q-478 to Q-639; L-479 to Q-639; P-480 to Q-639; D-481 to Q-639; K-482 to Q-639; K-483 to Q-639; G-484 to Q-639; L-485to Q-639; I-486 to Q-639; S-487 to Q-639; T-488 to Q-639; A-489 to Q-639; F-490 to Q-639; S-491 to Q-639; N-492 to Q-639; G-493 to Q-639; A-494 to Q-639; F-495 to Q-639; L-496 to Q-639; G-497 to Q-639; 1498 to Q-639; G-499 to Q-639; I-500 to Q-639; T-501 to Q-639; A-502 to Q-639; L-503 to Q-639; L-504 to Q-639; F-505 to Q-639; L-506 to Q-639; C-507 to Q-639; L-508 to Q-639; A-509 to Q-639; L-510 to Q-639; I-511 to Q-639; I-512 to Q-639; M-513 to Q-639; K-514 to Q-639; I-515 to Q-639; L-516 to Q-639; P-517 to Q-639; K-518 to Q-639; R-519 to Q-639; R-520 to Q-639; T-521 to Q-639; Q-522 to Q-639; T-523 to Q-639; E-524 to Q-639; T-525 to Q-639; P-526 to Q-639; R-527 to Q-639; P-528to Q-639; R-529 to Q-639; F-530 to Q-639; S-531 to Q-639; R-532 to Q-639; H-533 to Q-639; S-534 to Q-639; T-535 to Q-639; I-536to Q-639; L-537 to Q-639; D-538 to Q-639; Y-539 to Q-639; I-540 to Q-639; N-541 to Q-639; V-542 to Q-639; V-543 to Q-639; P-544 to Q-639; T-545 to Q-639; A-546 to Q-639; G-547 to Q-639; P-548 to Q-639; L-549 to Q-639; A-550 to Q-639; Q-551 to Q-639; K-552 to Q-639; R-553 to Q-639; N-554 to Q-639; Q-555 to Q-639; K-556 to Q-639; A-557 to Q-639; T-558 to Q-639; P-559 to Q-639; N-560 to Q-639; S-561 to Q-639; P-562 to Q-639; R-563 to Q-639; T-564 to Q-639; P-565 to Q-639; L-566 to Q-639; P-567 to Q-639; P-568 to Q-639; G-569 to Q-639; A-570 to Q-639; P-571 to Q-639; S-572 to Q-639; P-573 to Q-639; E-574 to Q-639; S-575 to Q-639; K-576 to Q-639; K-577 to Q-639; N-578 to Q-639; Q-579 to Q-639; K-580 to Q-639; K-581 to Q-639; Q-582 to Q-639; Y-583 to Q-639; Q-584 to Q-639; L-585 to Q-639; P-586 to Q-639; S-587 to Q-639; F-588 to Q-639; P-589 to Q-639; E-590 to Q-639; P-591 to Q-639; K-592 to Q-639; S-593 to Q-639; S-594 to Q-639; T-595 to Q-639; Q-596 to Q-639; A-597 to Q-639; P-598 to Q-639; E-599 to Q-639; S-600 to Q-639; Q-601 to Q-639; E-602 to Q-639; S-603 to Q-639; Q-604 to Q-639; E-605 to Q-639; E-606 to Q-639; L-607 to Q-639; H-608 to Q-639; Y-609 to Q-639; A-610 to Q-639; T-611 to Q-639; L-612 to Q-639; N-613 to Q-639; F-614 to Q-639; P-615 to Q-639; G-616 to Q-639; V-617 to Q-639; R-618 to Q-639; P-619 to Q-639; R-620to Q-639; P-621 to Q-639; E-622 to Q-639; A-623 to Q-639; R-624 to Q-639; M-625 to Q-639; P-626 to Q-639; K-627 to Q-639; G-628 to Q-639; T-629 to Q-639; Q-630 to Q-639; A-631 to Q-639; D-632 to Q-639; Y-633 to Q-639; and A-634 to Q-639 of SEQ ID NO:33. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities (e.g., biological activities (e.g., ability to illicit mitogenic activity, induce differentiation of normal or malignant cells, bind to EGF receptors, etc.)), may still be retained. For example the ability to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a mutein with a large number of deleted C-terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the polypeptide shown in FIGS. 13A-C, up to the leucine residue at position number 7, and polynucleotides encoding such polypeptides. In particular, the present invention provides polypeptides comprising the amino acid sequence of residues 1-m1 of FIGS. 13A-C, where m1 is an integer from 7 to 638 corresponding to the position of the amino acid residue in FIGS. 13A-C. Moreover, the invention provides polynucleotides encoding polypeptides comprising, or alternatively consisting of, the amino acid sequence of C-terminal deletions of the polypeptide of the invention shown as SEQ ID NO:33 include polypeptides comprising, or alternatively consisting of, an amino acid sequence selected from residues: M-1 to F-638; M-1 to K-637; M-1 to V-636; M-1 to E-635; M-1 to A-634; M-1 to Y-633; M-1 to D-632; M-1 to A-631; M-1 to Q-630; M-1 to T-629; M-1 to G-628; M-1 to K-627; M-1 to P-626; M-1 to M-625; M-1 to R-624; M-1 to A-623; M-1 to E-622; M-1 to P-621; M-1 to R-620; M-1 to P-619; M-1 to R-618; M-1 to V-617; M-1 to G-616; M-1 to P-615; M-1 to F-614; M-1 to N-613; M-1 to L-612; M-1 to T-611; M-1 to A-610; M-1 to Y-609; M-1 to H-608; M-1 to L-607; M-1 to E-606; M-1 to E-605; M-1 to Q-604; M-1 to S-603; M-1 to E-602; M-1 to Q-601; M-1 to S-600; M-1 to E-599; M-1 to P-598; M-1 to A-597; M-1 to Q-596; M-1 to T-595; M-1 to S-594; M-1 to S-593; M-1 to K-592; M-1 to P-591; M-1 to E-590; M-1 to P-589; M-1 to F-588; M-1 to S-587; M-1 to P-586; M-1 to L-585; M-1 to Q-584; M-1 to Y-583; M-1 to Q-582; M-1 to K-581; M-1 to K-580; M-1 to Q-579; M-1 to N-578; M-1 to K-577; M-1 to K-576; M-1 to S-575; M-1 to E-574; M-1 to P-573; M-1 to S-572; M-1 to P-571; M-1 to A-570; M-1 to G-569; M-1 to P-568; M-1 to P-567; M-1 to L-566; M-1 to P-565; M-1 to T-564; M-1 to R-563; M-1 to P-562; M-1 to S-561; M-1 to N-560; M-1 to P-559; M-1 to T-558; M-1 to A-557; M-1 to K-556; M-1 to Q-555; M-1 to N-554; M-1 to R-553; M-1 to K-552; M-1 to Q-551; M-1 to A-550; M-1 to L-549; M-1 to P-548; M-1 to G-547; M-1 A-546; M-1 to T-545; M-1 to P-544; M-1 to V-543; M-1 to V-542; M-1 to N-541; M-1 to I-540; M-1 to Y-539; M-1 to D-538; M-1 to L-537; M-1 to I-536; M-1 to T-535; M-1 to S-534; M-1 to H-533; M-1 to R-532; M-1 to S-531; M-1 to F-530; M-1 to R-529; M-1 to P-528; M-1 to R-527; M-1 to P-526; M-1 to T-525; M-1 to E-524; M-1 to T-523; M-1 to Q-522; M-1 to T-521; M-1 to R-520; M-1 to R-519; M-1 to K-518; M-1 to P-517; M-1 to L-516; M-1 to I-515; M-1 to K-514; M-1 to M-513; M-1 to I-512; M-1 to I-511; M-1 to L-510; M-1 to A-509; M-1 to L-508; M-1 to C-507; M-1 to L-506; M-1 to F-505; M-1 to L-504; M-1 to L-503; M-1 to A-502; M-1 to T-501; M-1 to I-500; M-1 to G-499; M-1 to I-498; M-1 to G-497; M-1 to L-496; M-1 to F-495; M-1 to A-494; M-1 to G-493; M-1 to N-492; M-1 to S-491; M-1 to F-490; M-1 to A-489; M-1 to T-488; M-1 to S-487; M-1 to I-486; M-1 to L-485; M-1 to G-484; M-1 to K-483; M-1 to K-482; M-1 to D-481; M-1 to P-480; M-1 to L-479; M-1 to Q-478; M-1 to L-477; M-1 to I-476; M-1 to S-475; M-1 to G-474; M-1 to S-473; M-1 to Q-472; M-1 to A-471; M-1 to G-470; M-1 to H-469; M-1 to V-468; M-1 to N-467; M-1 to W-466; M-1 to A-465; M-1 to E-464; M-1 to C-463; M-1 to R-462; M-1 to L-461; M-1 to R-460; M-1 to L-459; M-1 to G-458; M-1 to S-457; M-1 to S-456; M-1 to L-455; M-1 to G-454; M-1 to G-453; M-1 to H-452; M-1 to L-451; M-1 to S-450; M-1 to L-449; M-1 to S-448; M-1 to S-447; M-1 to N-446; M-1 to A-445; M-1 to W-444; M-1 to P-443; M-1 to G-442; M-1 to A-441; M-1 to S-440; M-1 to S-439; M-1 to P-438; M-1 to T-437; M-1 to V-436; M-1 to E-435; M-1 to F-434; M-1 to S-433; M-1 to D-432; M-1 to Q-431; M-1 to S-430; M-1 to S-429; M-1 to N-428; M-1 to G-427; M-1 to E-426; M-1 to L-425; M-1 to L-424; M-1 to E-423; M-1 to E-422; M-1 to G-421; M-1 to L-420; M-1 to W-419; M-1 to W-418; M-1 to R-417; M-1 to L-416; M-1 to S-415; M-1 to P-414; M-1 to A-413; M-1 to P-412; M-1 to S-411; M-1 to A-410; M-1 to Q-409; M-1 to S-408; M-1 to S-407; M-1 to C-406; M-1 to S-405; M-1 to C-404; M-1 to H-403; M-1 to L-402; M-1 to G-401; M-1 to E-400; M-1 to A-399; M-1 to E-398; M-1 to W-397; M-1 to S-396; M-1 to C-395; M-1 to S-394; M-1 to P-393; M-1 to G-392; M-1 to L-391; M-1 to L-390; M-1 to K-389; M-1 to P-388; M-1 to S-387; M-1 to Y-386; M-1 to H-385; M-1 to V-384; M-1 to S-383; M-1 to L-382; M-1 to S-381; M-1 to L-380; M-1 to S-379; M-1 to V-378; M-1 to H-377; M-1 to Q-376; M-1 to S-375; M-1 to G-374; M-1 to L-373; M-1 to P-372; M-1 to H-371; M-1 to R-370; M-1 to A-369; M-1 to H-368; M-1 to C-367; M-1 to T-366; M-1 to F-365; M-1 to E-364; M-1 to G-363; M-1 to E-362; M-1 to H-361; M-1 to E-360; M-1 to V-359; M-1 to Q-358; M-1 to V-357; M-1 to R-356; M-1 to P-355; M-1 to L-354; M-1 to E-353; M-1 to L-352; M-1 to V-351; M-1 to G-350; M-1 to P-349; M-1 to D-348; M-1 to S-347; M-1 to P-346; M-1 to Q-345; M-1 to S-344; M-1 to P-343; M-1 to S-342; M-1 to L-341; M-1 to V-340; M-1 to Q-339; M-1 to G-338; M-1 to R-337; M-1 to Q-336; M-1 to T-335; M-1 to W-334; M-1 to S-333; M-1 to L-332; M-1 to R-331; M-1 to A-330; M-1 to P-329; M-1 to P-328; M-1 to S-327; M-1 to S-326; M-1 to H-325; M-1 to T-324; M-1 to V-323; M-1 to C-322; M-1 to V-321; M-1 to L-320; M-1 to C-319; M-1 to L-318; M-1 to S-317; M-1 to Q-316; M-1 to G-315; M-1 to E-314; M-1 to L-313; M-1 to V-312; M-1 to P-311; M-1 to L-310; M-1 to S-309; M-1 to T-308; M-1 to G-307; M-1 to N-306; M-1 to G-305; M-1 to L-304; M-1 to N-303; M-1 to E-302; M-1 to L-301; M-1 to V-300; M-1 to T-299; M-1 to R-298; M-1 to N-297; M-1 to A-296; M-1 to Q-295; M-1 to S-294; M-1 to V-293; M-1 to M-292; M-1 to V-291; M-1 to R-290; M-1 to L-289; M-1 to N-288; M-1 to E-287; M-1 to P-286; M-1 to P-285; M-1 to Y-284; M-1 to Q-283; M-1 to V-282; M-1 to S-281; M-1 to L-280; M-1 to D-279; M-1 to L-278; M-1 to A-277; M-1 to R-276; M-1 to Q-275; M-1 to Q-274; M-1 to S-273; M-1 to G-272; M-1 to L-271; M-1 to R-270; M-1 to N-269; M-1 to E-268; M-1 to A-267; M-1 to R-266; M-1 to C-265; M-1 to T-264; M-1 to Y-263; M-1 to R-262; M-1 to G-261; M-1 to S-260; M-1 to D-259; M-1 to G-258; M-1 to A-257; M-1 to K-256; M-1 to V-255; M-1 to G-254; M-1 to P-253; M-1 to L-252; M-1 to E-251; M-1 to L-250; M-1 to G-249; M-1 to L-248; M-1 to P-247; M-1 to R-246; M-1 to P-245; M-1 to G-244; M-1 to W-243; M-1 to P-242; M-1 to H-241; M-1 to S-240; M-1 to S-239; M-1 to S-238; M-1 to L-237; M-1 to V-236; M-1 to R-235; M-1 to N-234; M-1 to Q-233; M-1 to L-232; M-1 to V-231; M-1 to W-230; M-1 to S-229; M-1 to L-228; M-1 to T-277; M-1 to A-226; M-1 to P-225; M-1 to P-224; M-1 to Q-223; M-1 to S-222; M-1 to D-221; M-1 to A-220; M-1 to A-219; M-1 to C-218; M-1 to L-217; M-1 to L-216; M-1 to R-215; M-1 to L-214; M-1 to F-213; M-1 to Q-212; M-1 to G-211; M-1 to K-210; M-1 to Q-209; M-1 to A-208; M-1 to E-207; M-1 to L-206; M-1 to Y-205; M-1 to P-204; M-1 to V-203; M-1 to N-202; M-1 to G-201; M-1 to Q-200; M-1 to P-199; M-1 to Q-198; M-1 to P-197; M-1 to E-196; M-1 to L-195; M-1 to A-194; M-1 to P-193; M-1 to T-192; M-1 to N-191; M-1 to D-190; M-1 to R-189; M-1 to S-188; M-1 to I-187; M-1 to S-186; M-1 to I-185; M-1 to V-184; M-1 to L-183; M-1 to D-182; M-1 to R-181; M-1 to P-180; M-1 to A-179; M-1 to Y-178; M-1 to A-177; M-1 to V-176; M-1 to R-175; M-1 to L-174; M-1 to R-173; M-1 to V-172; M-1 to T-171; M-1 to R-170; M-1 to Q-169; M-1 to A-168; M-1 to S-167; M-1 to V-166; M-1 to G-165; M-1 to K-164; M-1 to R-163; M-1 to S-162; M-1 to F-161; M-1 to D-160; M-1 to V-159; M-1 to H-158; M-1 to C-157; M-1 to T-156; M-1 to L-155; M-1 to D-154; M-1 to T-153; M-1 to N-152; M-1 to H-151; M-1 to D-150; M-1 to Q-149; M-1 to P-148; M-1 to R-147; M-1 to P-146; M-1 to T-145; M-1 to F-144; M-1 to S-143; M-1 to L-142; M-1 to V-141; M-1 to T-140; M-1 to V-139; M-1 to K-138; M-1 to L-137; M-1 to F-136; M-1 to F-135; M-1 to G-134; M-1 to D-133; M-1 to N-132; M-1 to M-131; M-1 to F-130; M-1 to N-129; M-1 to Y-128; M-1 to R-127; M-1 to V-126; M-1 to Y-125; M-1 to S-124; M-1 to G-123; M-1 to R-122; M-1 to E-121; M-1 to V-120; M-1 to R-119; M-1 to F-118; M-1 to F-117; M-1 to Y-116; M-1 to Q-115; M-1 to S-114; M-1 to E-113; M-1 to D-112; M-1 to Q-111; M-1 to M-110; M-1 to Q-109; M-1 to A-108; M-1 to D-107; M-1 to R-106; M-1 to I-105; M-1 to V-104; M-1 to L-103; M-1 to S-102; M-1 to C-101; M-1 to N-100; M-1 to G-99; M-1 to K-98; M-1 to A-97; M-1 to P-96; M-1 to D-95; M-1 to G-94; M-1 to T-93; M-1 to L-92; M-1 to Q-91; M-1 to F-90; M-1 to R-89; M-1 to G-88; M-1 to R-87; M-1 to T-86; M-1 to S-85; M-1 to M-84; M-1 to E-83; M-1 to V-82; M-1 to E-81; M-1 to R-80; M-1 to S-79; M-1 to Q-78; M-1 to H-77; M-1 to N-76; M-1 to T-75; M-1 to A-74; M-1 to V-73; M-1 to P-72; M-1 to A-71; M-1 to G-70; M-1 to K-69; M-1 to T-68; M-1 to T-67; M-1 to E-66; M-1 to T-65; M-1 to V-64; M-1 to A-63; M-1 to K-62; M-1 to F-61; M-1 to W-60; M-1 to Y-59; M-1 to G-58; M-1 to Y-57; M-1 to A-56; M-1 to P-55; M-1 to T-54; M-1 to S-53; M-1 to G-52; M-1 to T-51; M-1 to W-50; M-1 to D-49; M-1 to Q-48; M-1 to R-47; M-1 to P-46; M-1 to Y-45; M-1 to S-44; M-1 to F-43; M-1 to S-42; M-1 to C-41; M-1 to P-40; M-1 to V-39; M-1 to S-38; M-1 to I-37; M-1 to D-36; M-1 to C-35; M-1 to A-34; M-1 to E-33; M-1 to P-32; M-1 to V-31; M-1 to M-30; M-1 to V-29; M-1 to S-28; M-1 to E-27; M-1 to Q-26; M-1 to V-25; M-1 to R-24; M-1 to I-23; M-1 to W-22; M-1 to F-21; M-1 to R-20; M-1 to G-19; M-1 to D-18; M-1 to M-17; M-1 to A-16; M-1 to Q-15; M-1 to S-14; M-1 to G-13; M-1 to G-12; M-1 to L-11; M-1 to L-10; M-1 to S-9; M-1 to S-8; and M-1 to L-7 of SEQ ID NO:33. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Further preferred polypeptides of the invention include N-terminal deletions of CD33-likeSV (SEQ ID NO: 149), these deletions comprising, or alternatively consisting of, an amino acid sequence selected from residues: L-2 to Q-697; L-3 to Q-697; P-4 to Q-697; L-5 to Q-697; L-6 to Q-697; L-7 to Q-697; S-8 to Q-697; S-9 to Q-697; L-10 to Q-697; L-11 to Q-697; G-12 to Q-697; G-13 to Q-697; S-14 to Q-697; Q-15 to Q-697; A-16 to Q-697; M-17 to Q-697; D-18 to Q-697; G-19 to Q-697; R-20 to Q-697; F-21 to Q-697; W-22 to Q-697; I-23 to Q-697; R-24 to Q-697; V-25 to Q-697; Q-26 to Q-697; E-27 to Q-697; S-28 to Q-697; V-29 to Q-697; M-30 to Q-697; V-31 to Q-697; P-32 to Q-697; E-33 to Q-697; G-34 to Q-697; L-35 to Q-697; C-36 to Q-697; I-37 to Q-697; S-38 to Q-697; V-39 to Q-697; P-40 to Q-697; C-41 to Q-697; S-42 to Q-697; F-43 to Q-697; S-44 to Q-697; Y-45 to Q-697; P-46 to Q-697; R-47 to Q-697; Q-48 to Q-697; D-49 to Q-697; W-50 to Q-697; T-51 to Q-697; G-52 to Q-697; S-53 to Q-697; T-54 to Q-697; P-55 to Q-697; A-56 to Q-697; Y-57 to Q-697; G-58 to Q-697; Y-59 to Q-697; W-60 to Q-697; F-61 to Q-697; K-62 to Q-697; A-63 to Q-697; V-64 to Q-697; T-65 to Q-697; E-66 to Q-697; T-67 to Q-697; T-68 to Q-697; K-69 to Q-697; G-70 to Q-697; A-71 to Q-697; P-72 to Q-697; V-73 to Q-697; A-74 to Q-697; T-75 to Q-697; N-76 to Q-697; H-77 to Q-697; Q-78 to Q-697; S-79 to Q-697; R-80 to Q-697; E-81 to Q-697; V-82 to Q-697; E-83 to Q-697; M-84 to Q-697; S-85 to Q-697; T-86 to Q-697; R-87 to Q-697; G-88 to Q-697; R-89 to Q-697; F-90 to Q-697; Q-91 to Q-697; L-92 to Q-697; T-93 to Q-697; G-94 to Q-697; D-95 to Q-697; P-96 to Q-697; A-97 to Q-697; K-98 to Q-697; G-99 to Q-697; N-100 to Q-697; C-101 to Q-697; S-102 to Q-697; L-103 to Q-697; V-104 to Q-697; I-105 to Q-697; R-106 to Q-697; D-107 to Q-697; A-108 to Q-697; Q-109 to Q-697; M-110 to Q-697; Q-111 to Q-697; D-112 to Q-697; E-113 to Q-697; S-114 to Q-697; Q-115 to Q-697; Y-116 to Q-697; F-117 to Q-697; F-118 to Q-697; R-119 to Q-697; V-120 to Q-697; E-121 to Q-697; R-122 to Q-697; G-123 to Q-697; S-124 to Q-697; Y-125 to Q-697; V-126 to Q-697; R-127 to Q-697; Y-128 to Q-697; N-129 to Q-697; F-130 to Q-697; M-131 to Q-697; N-132 to Q-697; D-133 to Q-697; G-134 to Q-697; F-135 to Q-697; F-136 to Q-697; L-137 to Q-697; K-138 to Q-697; V-139 to Q-697; T-140 to Q-697; A-141 to Q-697; L-142 to Q-697; T-143 to Q-697; Q-144 to Q-697; K-145 to Q-697; P-146 to Q-697; D-147 to Q-697; V-148 to Q-697; Y-149 to Q-697; I-150 to Q-697; P-151 to Q-697; E-152 to Q-697; T-153 to Q-697; L-154 to Q-697; E-155 to Q-697; P-156 to Q-697; G-157 to Q-697; Q-158 to Q-697; P-159 to Q-697; V-160 to Q-697; T-161 to Q-697; V-162 to Q-697; I-163 to Q-697; C-164 to Q-697; V-165 to Q-697; F-166 to Q-697; N-167 to Q-697; W-168 to Q-697; A-169 to Q-697; F-170 to Q-697; E-171 to Q-697; E-172 to Q-697; C-173 to Q-697; P-174 to Q-697; P-175 to Q-697; P-176 to Q-697; S-177 to Q-697; F-178 to Q-697; S-179 to Q-697; W-180 to Q-697; T-181 to Q-697; G-182 to Q-697; A-183 to Q-697; A-184 to Q-697; L-185 to Q-697; S-186 to Q-697; S-187 to Q-697; Q-188 to Q-697; G-189 to Q-697; T-190 to Q-697; K-191 to Q-697; P-192 to Q-697; T-193 to Q-697; T-194 to Q-697; S-195 to Q-697; H-196 to Q-697; F-197 to Q-697; S-198 to Q-697; V-199 to Q-697; L-200 to Q-697; S-201 to Q-697; F-202 to Q-697; T-203 to Q-697; P-204 to Q-697; R-205 to Q-697; P-206 to Q-697; Q-207 to Q-697; D-208 to Q-697; H-209 to Q-697; N-210 to Q-697; T-211 to Q-697; D-212 to Q-697; L-213 to Q-697; T-214 to Q-697; C-215 to Q-697; H-216 to Q-697; V-217 to Q-697; D-218 to Q-697; F-219 to Q-697; S-220 to Q-697; R-221 to Q-697; K-222 to Q-697; G-223 to Q-697; V-224 to Q-697; S-224 to Q-697; S-225 to Q-697; V-226 to Q-697; Q-227 to Q-697; R-228 to Q-697; T-229 to Q-697; V-230 to Q-697; R-231 to Q-697; L-232 to Q-697; R-233 to Q-697; V-234 to Q-697; A-235 to Q-697; Y-236 to Q-697; A-237 to Q-697; P-238 to Q-697; R-239 to Q-697; D-240 to Q-697; L-241 to Q-697; V-242 to Q-697; I-243 to Q-697; S-244 to Q-697; I-245 to Q-697; S-246 to Q-697; R-247 to Q-697; D-248 to Q-697; N-249 to Q-697; T-250 to Q-697; P-251 to Q-697; A-252 to Q-697; L-253 to Q-697; E-254 to Q-697; P-255 to Q-697; Q-256 to Q-697; P-257 to Q-697; Q-258 to Q-697; G-259 to Q-697; N-260 to Q-697; V-261 to Q-697; P-262 to Q-697; Y-263 to Q-697; L-264 to Q-697; E-265 to Q-697; A-266 to Q-697; Q-267 to Q-697; K-268 to Q-697; G-269 to Q-697; Q-270 to Q-697; F-271 to Q-697; L-272 to Q-697; R-273 to Q-697; L-274 to Q-697; L-275 to Q-697; C-276 to Q-697; A-277 to Q-697; A-278 to Q-697; D-279 to Q-697; S-280 to Q-697; Q-281 to Q-697; P-282 to Q-697; P-283 to Q-697; A-284 to Q-697; T-285 to Q-697; L-286 to Q-697; S-287 to Q-697; W-288 to Q-697; V-289 to Q-697; L-290 to Q-697; Q-291 to Q-697; N-292 to Q-697; R-293 to Q-697; V-294 to Q-697; L-295 to Q-697; S-296 to Q-697; S-297 to Q-697; S-298 to Q-697; H-299 to Q-697; P-300 to Q-697; W-301 to Q-697; G-302 to Q-697; P-303 to Q-697; R-304 to Q-697; P-305 to Q-697; L-306 to Q-697; G-307 to Q-697; L-308 to Q-697;

E-309 to Q-697; L-310 to Q-697; P-311 to Q-697; G-312 to Q-697; V-313 to Q-697; K-314 to Q-697; A-315 to Q-697; G-316 to Q-697; D-317 to Q-697; S-318 to Q-697; G-319 to Q-697; R-320 to Q-697; Y-321 to Q-697; T-322 to Q-697; C-323 to Q-697; R-324 to Q-697; A-325 to Q-697; E-326 to Q-697; N-327 to Q-697; R-328 to Q-697; L-329 to Q-697; G-330 to Q-697; S-331 to Q-697; Q-332 to Q-697; Q-333 to Q-697; R-334 to Q-697; A-335 to Q-697; L-336 to Q-697; D-337 to Q-697; L-338 to Q-697; S-339 to Q-697; V-340 to Q-697; Q-341 to Q-697; Y-342 to Q-697; P-343 to Q-697; P-344 to Q-697; E-345 to Q-697; N-346 to Q-697; L-347 to Q-697; R-348 to Q-697; V-349 to Q-697; M-350 to Q-697; V-351 to Q-697; S-352 to Q-697; Q-353 to Q-697; A-354 to Q-697; N-355 to Q-697; R-356 to Q-697; T-357 to Q-697; V-358 to Q-697; L-359 to Q-697; E-360 to Q-697; N-361 to Q-697; L-362 to Q-697; G-363 to Q-697; N-364 to Q-697; G-365 to Q-697; T-366 to Q-697; S-367 to Q-697; L-368 to Q-697; P-369 to Q-697; V-370 to Q-697; L-371 to Q-697; E-372 to Q-697; G-373 to Q-697; Q-374 to Q-697; S-375 to Q-697; L-376 to Q-697; C-377 to Q-697; L-378 to Q-697; V-379 to Q-697; C-380 to Q-697; V-381 to Q-697; T-382 to Q-697; H-383 to Q-697; S-384 to Q-697; S-385 to Q-697; P-386 to Q-697; P-387 to Q-697; A-388 to Q-697; R-389 to Q-697; L-390 to Q-697; S-391 to Q-697; W-392 to Q-697; T-393 to Q-697; Q-394 to Q-697; R-395 to Q-697; G-396 to Q-697; Q-397 to Q-697; V-398 to Q-697; L-399 to Q-697; S-400 to Q-697; P-401 to Q-697; S-402 to Q-697; Q-403 to Q-697; P-404 to Q-697; S-405 to Q-697; D-406 to Q-697; P-407 to Q-697; G-408 to Q-697; V-409 to Q-697; L-410 to Q-697; E-411 to Q-697; L-412 to Q-697; P-413 to Q-697; R-414 to Q-697; V-415 to Q-697; Q-416 to Q-697; V-417 to Q-697; E-418 to Q-697; H-419 to Q-697; E-420 to Q-697; G-421 to Q-697; E-422 to Q-697; F-423 to Q-697; T-424 to Q-697; C-425 to Q-697; H-426 to Q-697; A-427 to Q-697; R-428 to Q-697; H-429 to Q-697; P-430 to Q-697; L-431 to Q-697; G-432 to Q-697; S-433 to Q-697; Q-434 to Q-697; H-435 to Q-697; V-436 to Q-697; S-437 to Q-697; L-438 to Q-697; S-439 to Q-697; L-440 to Q-697; S-441 to Q-697; V-442 to Q-697; H-443 to Q-697; Y-444 to Q-697; S-445 to Q-697; P-446 to Q-697; K-447 to Q-697; L-448 to Q-697; L-449 to Q-697; G-450 to Q-697; P-451 to Q-697; S-452 to Q-697; C-453 to Q-697; S-454 to Q-697; W-455 to Q-697; E-456 to Q-697; A-457 to Q-697; E-458 to Q-697; G-459 to Q-697; L-460 to Q-697; H-461 to Q-697; C-462 to Q-697; S-463 to Q-697; C-464 to Q-697; S-465 to Q-697; S-466 to Q-697; Q-467 to Q-697; A-468 to Q-697; S-469 to Q-697; P-470 to Q-697; A-471 to Q-697; P-472 to Q-697; S-473 to Q-697; L-474 to Q-697; R-475 to Q-697; W-476 to Q-697; W-477 to Q-697; L-478 to Q-697; G-479 to Q-697; E-480 to Q-697; E-481 to Q-697; L-482 to Q-697; L-483 to Q-697; E-484 to Q-697; G-485 to Q-697; N-486 to Q-697; S-487 to Q-697; S-488 to Q-697; Q-489 to Q-697; D-490 to Q-697; S-491 to Q-697; F-492 to Q-697; E-493 to Q-697; V-494 to Q-697; T-495 to Q-697; P-496 to Q-697; S-497 to Q-697; S-498 to Q-697; A-499 to Q-697; G-500 to Q-697; P-501 to Q-697; W-502 to Q-697; A-503 to Q-697; N-504 to Q-697; S-505 to Q-697; S-506 to Q-697; L-507 to Q-697; S-508 to Q-697; L-509 to Q-697; H-510 to Q-697; G-511 to Q-697; G-512 to Q-697; L-513 to Q-697; S-514 to Q-697; S-515 to Q-697; G-516 to Q-697; L-517 to Q-697; R-518 to Q-697; L-519 to Q-697; R-520 to Q-697; C-521 to Q-697; E-522 to Q-697; A-523 to Q-697; W-524 to Q-697; N-525 to Q-697; V-526 to Q-697; H-527 Q-697; G-528 to Q-697; A-529 to Q-697; Q-530 to Q-697; S-531 to Q-697; G-532 to Q-697; S-533 to Q-697; I-534 to Q-697; L-535 to Q-697; Q-536 to Q-697; L-537 to Q-697; P-538 to Q-697; D-539 to Q-697; K-540 to Q-697; K-541 to Q-697; G-542 to Q-697; L-543 to Q-697; I-544 to Q-697; S-545 to Q-697; T-546 to Q-697; A-547 to Q-697; F-548 to Q-697; S-549 to Q-697; N-550 to Q-697; G-551 to Q-697; A-552 to Q-697; F-553 to Q-697; L-554 to Q-697; G-555 to Q-697; I-556 to Q-697; G-557 to Q-697; I-558 to Q-697; T-559 to Q-697; A-560 to Q-697; L-561 to Q-697; L-562 to Q-697; F-563 to Q-697; L-564 to Q-697; C-565 to Q-697; L-566 to Q-697; A-567 to Q-697; L-568 to Q-697; I-569 to Q-697; I-570 to Q-697; M-571 to Q-697; K-572 to Q-697; I-573 to Q-697; L-574 to Q-697; P-575 to Q-697; K-576 to Q-697; R-577 to Q-697; R-578 to Q-697; T-579 to Q-697; Q-580 to Q-697; T-581 to Q-697; E-582 to Q-697; T-583 to Q-697; P-584 to Q-697; R-585 to Q-697; P-586 to Q-697; R-587 to Q-697; F-588 to Q-697; S-589 to Q-697; R-590 to Q-697; H-591 to Q-697; S-592 to Q-697; T-593 to Q-697; I-594 to Q-697; L-595 to Q-697; D-596 to Q-697; Y-597 to Q-697; I-598 to Q-697; N-599 to Q-697; V-600 to Q-697; V-601 to Q-697; P-602 to Q-697; T-603 to Q-697; A-604 to Q-697; G-605 to Q-697; P-606 to Q-697; L-607 to Q-697; A-608 to Q-697; Q-609 to Q-697; K-610 to Q-697; R-611 to Q-697; N-612 to Q-697; Q-613 to Q-697; K-614 to Q-697; A-615 to Q-697; T-616 to Q-697; P-617 to Q-697; N-618 to Q-697; S-619 to Q-697; P-620 to Q-697; R-621 to Q-697; T-622 to Q-697; P-623 to Q-697; L-624 to Q-697; P-625 to Q-697; P-626 to Q-697; G-627 to Q-697; A-628 to Q-697; P-629 to Q-697; S-630 to Q-697; P-631 to Q-697; E-632 to Q-697; S-633 to Q-697; K-634 to Q-697; K-635 to Q-697; N-636 to Q-697; Q-637 to Q-697; K-638 to Q-697; K-639 to Q-697; Q-640 to Q-697; Y-641 to Q-697; Q-642 to Q-697; L-643 to Q-697; P-644 to Q-697; S-645 to Q-697; F-646 to Q-697; P-647 to Q-697; E-648 to Q-697; P-649 to Q-697; K-650 to Q-697; S-651 to Q-697; S-652 to Q-697; T-653 to Q-697; Q-654 to Q-697; A-655 to Q-697; P-656 to Q-697; E-657 to Q-697; S-658 to Q-697; Q-659 to Q-697; E-660 to Q-697; S-661 to Q-697; Q-662 to Q-697; E-663 to Q-697; E-664 to Q-697; L-665 to Q-697; H-666 to Q-697; Y-667 to Q-697; A-668 to Q-697; T-669 to Q-697; L-670 to Q-697; N-671 to Q-697; F-672 to Q-697; P-673 to Q-697; G-674 to Q-697; V-675 to Q-697; R-676 to Q-697; P-677 to Q-697; R-678 to Q-697; P-679 to Q-697; E-680 to Q-697; A-681 to Q-697; R-682 to Q-697; M-683 to Q-697; P-684 to Q-697; K-685 to Q-697; G-686 to Q-697; T-687 to Q-697; Q-688 to Q-697; A-689 to Q-697; D-690 to Q-697; Y-691 to Q-697; A-692 to Q-697 of SEQ ID NO: 149. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Moreover, the invention provides C-terminal amino acid deletions of CD33-likeSV (SEQ ID NO: 149) comprising, or alternatively consisting of, an amino acid sequence selected from residues: M-1 to F-696; M-1 to K-695; M-1 to V-694; M-1 to E-693; M-1 to A-692; M-1 to Y-691; M-1 to D-690; M-1 to A-689; M-1 to Q-688; M-1 to T-687; M-1 to G-686; M-1 to K-685; M-1 to P-684; M-1 to M-683; M-1 to R-682; M-1 to A-681; M-1 to E-680; M-1 to P-679; M-1 to R-678; M-1 to P-677; M-1 to R-676; M-1 to V-675; M-1 to G-674; M-1 to P-673; M-1 to F-672; M-1 to N-671; M-1 to L-670; M-1 to T-669; M-1 to A-668; M-1 to Y-667; M-1 to H-666;

M-1 to L-665; M-1 to E-664; M-1 to E-663; M-1 to Q-662; M-1 to S-661; M-1 to E-660; M-1 to Q-659; M-1 to S-658; M-1 to E-657; M-1 to P-656; M-1 to A-655; M-1 to Q-654; M-1 to T-653; M-1 to S-652; M-1 to S-651; M-1 to K-650; M-1 to P-649; M-1 to E-648; M-1 to P-647; M-1 to F-646; M-1 to S-645; M-1 to P-644; M-1 to L-643; M-1 to Q-642; M-1 to Y-641; M-1 to Q-640; M-1 to K-639; M-1 to K-638; M-1 to Q-637; M-1 to N-636; M-1 to K-635; M-1 to K-634; M-1 to S-633; M-1 to E-632; M-1 to P-631; M-1 to S-630; M-1 to P-629; M-1 to A-628; M-1 to G-627; M-1 to P-626; M-1 to P-625; M-1 to L-624; M-1 to P-623; M-1 to T-622; M-1 to R-621; M-1 to P-620; M-1 to S-619; M-1 to N-618; M-1 to P-617; M-1 to T-616; M-1 to A-615; M-1 to K-614; M-1 to Q-613; M-1 to N-612; M-1 to R-611; M-1 to K-610; M-1 to Q-609; M-1 to A-608; M-1 to L-607; M-1 to P-606; M-1 to G-605; M-1 to A-604; M-1 to T-603; M-1 to P-602; M-1 to V-601; M-1 to V-600; M-1 to N-599; M-1 to I-598; M-1 to Y-597; M-1 to D-596; M-1 to L-595; M-1 to I-594; M-1 to T-593; M-1 to S-592; M-1 to H-591; M-1 to R-590; M-1 to S-589; M-1 to F-588; M-1 to R-587; M-1 to P-586; M-1 to R-585; M-1 to P-584; M-1 to T-583; M-1 to E-582; M-1 to T-581; M-1 to Q-580; M-1 to T-579; M-1 to R-578; M-1 to R-577; M-1 to K-576; M-1 to P-575; M-1 to L-574; M-1 to I-573; M-1 to K-572; M-1 to M-571; M-1 to I-570; M-1 to I-569; M-1 to L-568; M-1 to A-567; M-1 to L-566; M-1 to C-565; M-1 to L-564; M-1 to F-563; M-1 to L-562; M-1 to L-561; M-1 to A-560; M-1 to T-559; M-1 to I-558; M-1 to G-557; M-1 to I-556; M-1 to G-555; M-1 to L-554; M-1 to F-553; M-1 to A-552; M-1 to G-551; M-1 to N-550; M-1 to S-549; M-1 to F-548; M-1 to A-547; M-1 to T-546; M-1 to S-545; M-1 to I-544; M-1 to L-543; M-1 to G-542; M-1 to K-541; M-1 to K-540; M-1 to D-539; M-1 to P-538; M-1 to L-537; M-1 to Q-536; M-1 to L-535; M-1 to I-534; M-1 to S-533; M-1 to G-532; M-1 to S-531; M-1 to Q-530; M-1 to A-529; M-1 to G-528; M-1 to H-527; M-1 to V-526; M-1 to N-525; M-1 to W-524; M-1 to A-523; M-1 to E-522; M-1 to C-521; M-1 to R-520; M-1 to L-519; M-1 to R-518; M-1 to L-517; M-1 to G-516; M-1 to S-515; M-1 to S-514; M-1 to L-513; M-1 to G-512; M-1 to G-511; M-1 to H-510; M-1 to L-509; M-1 to S-508; M-1 to L-507; M-1 to S-506; M-1 to S-505; M-1 to N-504; M-1 to A-503; M-1 to W-502; M-1 to P-501; M-1 to G-500; M-1 to A-499; M-1 to S-498; M-1 to S-497; M-1 to P-496; M-1 to T495; M-1 to V-494; M-1 to E-493; M-1 to F-492; M-1 to S-491; M-1 to D-490; M-1 to Q-489; M-1 to S-488; M-1 to S-487; M-1 to N-486; M-1 to G-485; M-1 to E-484; M-1 to L-483; M-1 to L-482; M-1 to E-481; M-1 to E-480; M-1 to G-479; M-1 to L-478; M-1 to W-477; M-1 to W-476; M-1 to R-475; M-1 to L-474; M-1 to S-473; M-1 to P-472; M-1 to A-471; M-1 to P-470; M-1 to S-469; M-1 to A-468; M-1 to Q-467; M-1 to S-466; M-1 to S-465; M-1 to C-464; M-1 to S-463; M-1 to C-462; M-1 to H-461; M-1 to L-460; M-1 to G-459; M-1 to E-458; M-1 to A-457; M-1 to E-456; M-1 to W-455; M-1 to S-454; M-1 to C-453; M-1 to S-452; M-1 to P-451; M-1 to G-450; M-1 to L-449; M-1 to L-448; M-1 to K-447; M-1 to P-446; M-1 to S-445; M-1 to Y-444; M-1 to H-443; M-1 to V-442; M-1 to S-441; M-1 to L-440; M-1 to S-439; M-1 to L-438; M-1 to S-437; M-1 to V-436; M-1 to H-435; M-1 to Q-434; M-1 to S-433; M-1 to G-432; M-1 to L-431; M-1 to P-430; M-1 to H-429; M-1 to R-428; M-1 to A-427; M-1 to H-426; M-1 to C-425; M-1 to T-424; M-1 to F-423; M-1 to E-422; M-1 to G-421; M-1 to E-420; M-1 to H-419; M-1 to E-418; M-1 to V-417; M-1 to Q-416; M-1 to V-415; M-1 to R-414; M-1 to P-413; M-1 to L-412; M-1 to E-411; M-1 to L-410; M-1 to V-409; M-1 to G-408; M-1 to P-407; M-1 to D-406; M-1 to S-405; M-1 to P-404; M-1 to Q-403; M-1 to S-402; M-1 to P-401; M-1 to S-400; M-1 to L-399; M-1 to V-398; M-1 to Q-397; M-1 to G-396; M-1 to R-395; M-1 to Q-394; M-1 to T-393; M-1 to W-392; M-1 to S-391; M-1 to L-390; M-1 to R-389; M-1 to A-388; M-1 to P-387; M-1 to P-386; M-1 to S-385; M-1 to S-384; M-1 to H-383; M-1 to T-382; M-1 to V-381; M-1 to C-380; M-1 to V-379; M-1 to L-378; M-1 to C-377; M-1 to L-376; M-1 to S-375; M-1 to Q-374; M-1 to G-373; M-1 to E-372; M-1 to L-371; M-1 to V-370; M-1 to P-369; M-1 to L-368; M-1 to S-367; M-1 to T-366; M-1 to G-365; M-1 to N-364; M-1 to G-363; M-1 to L-362; M-1 to N-361; M-1 to E-360; M-1 to L-359; M-1 to V-358; M-1 to T-357; M-1 to R-356; M-1 to N-355; M-1 to A-354; M-1 to Q-353; M-1 to S-352; M-1 to V-351; M-1 to M-350; M-1 to V-349; M-1 to R-348; M-1 to L-347; M-1 to N-346; M-1 to E-345; M-1 to P-344; M-1 to P-343; M-1 to Y-342; M-1 to Q-341; M-1 to V-340; M-1 to S-339; M-1 to L-338; M-1 to D-337; M-1 to L-336; M-1 to A-335; M-1 to R-334; M-1 to Q-333; M-1 to Q-332; M-1 to S-331; M-1 to G-330; M-1 to L-329; M-1 to R-328; M-1 to N-327; M-1 to E-326; M-1 to A-325; M-1 to R-324; M-1 to C-323; M-1 to T-322; M-1 to Y-321; M-1 to R-320; M-1 to G-319; M-1 to S-318; M-1 to D-317; M-1 to G-316; M-1 to A-315; M-1 to K-314; M-1 to V-313; M-1 to G-312; M-1 to P-311; M-1 to L-310; M-1 to E-309; M-1 to L-308; M-1 to G-307; M-1 to L-306; M-1 to P-305; M-1 to R-304; M-1 to P-303; M-1 to G-302; M-1 to W-301; M-1 to P-300; M-1 to H-299; M-1 to S-298; M-1 to S-297; M-1 to S-296; M-1 to L-295; M-1 to V-294; M-1 to R-293; M-1 to N-292; M-1 to Q-291; M-1 to L-290; M-1 to V-289; M-1 to W-288; M-1 to S-287; M-1 to L-286; M-1 to T-285; M-1 to A-284; M-1 to P-283; M-1 to P-282; M-1 to Q-281; M-1 to S-280; M-1 to D-279; M-1 to A-278; M-1 to A-277; M-1 to C-276; M-1 to L-275; M-1 to L-274; M-1 to R-273; M-1 to L-272; M-1 to F-271; M-1 to Q-270; M-1 to G-269; M-1 to K-268; M-1 to Q-267; M-1 to A-266; M-1 to E-265; M-1 to L-264; M-1 to Y-263; M-1 to P-262; M-1 to V-261; M-1 to N-260; M-1 to G-259; M-1 to Q-258; M-1 to P-257; M-1 to Q-256; M-1 to P-255; M-1 to E-254; M-1 to L-253; M-1 to A-252; M-1 to P-251; M-1 to T-250; M-1 to N-249; M-1 to D-248; M-1 to R-247; M-1 to S-246; M-1 to I-245; M-1 to S-244; M-1 to I-243; M-1 to V-242; M-1 to L-241; M-1 to D-240; M-1 to R-239; M-1 to P-238; M-1 to A-237; M-1 to Y-236; M-1 to A-235; M-1 to V-234; M-1 to R-233; M-1 to M-1 to L-232; M-1 to R-231; M-1 to V-230; M-1 to T-229; M-1 to R-228; M-1 to Q-227; M-1 to V-226; M-1 to S-225; M-1 to V-224; M-1 to G-223; M-1 to K-222; M-1 to R-221; M-1 to S-220; M-1 to F-219; M-1 to D-218; M-1 to V-217; M-1 to H-216; M-1 to M-1 to C-215; M-1 to T-214; M-1 to L-213; M-1 to D-212; M-1 to T-211; M-1 to N-210; M-1 to H-209; M-1 to D-208; M-1 to Q-207; M-1 to P-206; M-1 to R-205; M-1 to P-204; M-1 to T-203; M-1 to F-202; M-1 to S-201; M-1 to L-200; M-1 to V-199; M-1 to S-198; M-1 to F-197; M-1 to H-196; M-1 to S-195; M-1 to T-194; M-1 to T-193; M-1 to P-192; M-1 to K-191; M-1 to T-190; M-1 to G-189; M-1 to Q-188; M-1 to S-187; M-1 to S-186; M-1 to L-185; M-1 to A-184; M-1 to A-183; M-1 to G-182; M-1 to T-181; M-1 to W-180; M-1 to S-179; M-1 to F-178; M-1 to S-177; M-1 to P-176; M-1 to P-175; M-1 to P-174; M-1 to C-173; M-1 to E-172; M-1 to E-171; M-1 to F-170; M-1 to A-169; M-1 to W-168; M-1 to N-167; M-1 to F-166; M-1 to V-165; M-1 to C-164; M-1 to I-163; M-1 to V-162; M-1 to T-161; M-1 to V-160; M-1 to P-159; M-1 to Q-158; M-1 to G-157; M-1 to P-156; M-1 to E-155; M-1 to L-154; M-1 to T-153; M-1 to E-152; M-1 to P-151; M-1 to I-150; M-1 to Y-149; M-1 to V-148; M-1 to D-147; M-1 to P-146; M-1 to K-145; M-1 to Q-144; M-1 to T-143; M-1 to L-142; M-1 to A-141; M-1 to T-140; M-1 to V-139; M-1 to K-138; M-1 to L-137; M-1 to F-136; M-1 to F-135; M-1 to G-134; M-1 to D-133; M-1 to N-132; M-1 to M-131; M-1 to

F-130; M-1 to N-129; M-1 to Y-128; M-1 to R-127; M-1 to V-126; M-1 to Y-125; M-1 to S-124; M-1 to G-123; M-1 to R-122; M-1 to E-121; M-1 to V-120; M-1 to R-119; M-1 to F-118; M-1 to F-117; M-1 to Y-116; M-1 to Q-115; M-1 to S-114; M-1 to E-113; M-1 to D-112; M-1 to Q-111; M-1 to M-110; M-1 to Q-109; M-1 to A-108; M-1 to D-107; M-1 to R-106; M-1 to I-105; M-1 to V-104; M-1 to L-103; M-1 to S-102; M-1 to C-101; M-1 to N-100; M-1 to G-99; M-1 to K-98; M-1 to A-97; M-1 to P-96; M-1 to D-95; M-1 to G-94; M-1 to T-93; M-1 to L-92; M-1 to Q-91; M-1 to F-90; M-1 to R-89; M-1 to G-88; M-1 to R-87; M-1 to T-86; M-1 to S-85; M-1 to M-84; M-1 to E-83; M-1 to V-82; M-1 to E-81; M-1 to R-80; M-1 to S-79; M-1 to Q-78; M-1 to H-77; M-1 to N-76; M-1 to T-75; M-1 to A-74; M-1 to V-73; M-1 to P-72; M-1 to A-71; M-1 to G-70; M-1 to K-69; M-1 to T-68; M-1 to T-67; M-1 to E-66; M-1 to T-65; M-1 to V-64; M-1 to A-63; M-1 to K-62; M-1 to F-61; M-1 to W-60; M-1 to Y-59; M-1 to G-58; M-1 to Y-57; M-1 to A-56; M-1 to P-55; M-1 to T-54; M-1 to S-53; M-1 to G-52; M-1 to T-51; M-1 to W-50; M-1 to D-49; M-1 to Q-48; M-1 to R-47; M-1 to P-46; M-1 to Y-45; M-1 to S-44; M-1 to F-43; M-1 to S-42; M-1 to C-41; M-1 to P-40; M-1 to V-39; M-1 to S-38; M-1 to I-37; M-1 to C-36; M-1 to L-35; M-1 to G-34; M-1 to E-33; M-1 to P-32; M-1 to V-31; M-1 to M-30; M-1 to V-29; M-1 to S-28; M-1 to E-27; M-1 to Q-26; M-1 to V-25; M-1 to R-24; M-1 to I-23; M-1 to W-22; M-1 to F-21; M-1 to R-20; M-1 to G-19; M-1 to D-18; M-1 to M-17; M-1 to A-16; M-1 to Q-15; M-1 to S-14; M-1 to G-13; M-1 to G-12; M-1 to L-11; M-1 to L-10; M-1 to S-9; M-1 to S-8; and M-1 to L-7 of SEQ ID NO: 149. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nucleotide sequences related to extensive portions of SEQ ID NO:15 and/or SEQ ID NO: 148, which have been determined in part from the following related cDNA genes: HTOFA26R (SEQ ID NO:93), HWAEM43R (SEQ ID NO:94), HDPMQ69R (SEQ ID NO:95), HDPGA09RA (SEQ ID NO:96), HEOMH10R (SEQ ID NO:97), and HFKCT73F (SEQ ID NO:98).

The CD33-like polypeptide sequence corresponding to SEQ ID NO: 33 of this gene has been determined to have a transmembrane domain at about amino acid position 496-512 of the amino acid sequence referenced in Table XIV for this gene. Moreover, a cytoplasmic tail encompassing amino acids 513 to 639 of this protein has also been determined. Based upon these characteristics, it is believed that the protein product of this gene shares structural features to type Ia membrane proteins.

The CD33-likeSV polypeptide sequence corresponding to SEQ ID NO: 149 has been determined to have a transmembrane domain at about amino acid position 539-572 of SEQ ID NO: 149. Moreover, a cytoplasmic tail encompassing amino acids 573-697 of SEQ ID NO: 149 has also been determined. Additionally, polypeptides encompassed by the invention comprise, or alternatively consist of, one, two, three, four, or all five of the CD33-likeSV Ig-like domains represented in SEQ ID NO: 149 as amino acids Phe-21 to Ala-141; Leu-142 to Tyr-236; Leu-253 to Gln-341; Val-358 to Val-442; and His-443 to Pro-538 (See FIG. 37 for domains).

Northern analysis indicates that CD33-like is expressed highest in spleen tissue and peripheral blood leukocytes, and to a lesser extent in ovary and lung tissue.

Additionally, Northern blot analysis reveals the presence of a major CD33-likeSV mRNA transcript of approximately 3.0 kb, with highest levels in spleen, lymph node, blood leukocytes, and appendix. CD33-likeSV is also expressed in eosinophils, B cells and monocytes.

Therefore, CD33-like polynucleotides and polypeptides, including antibodies, are useful as reagents for differential identification of the tissue(s) or cell type(s) present in a biological sample and for diagnosis of the following diseases and conditions which include, but are not limited to, disorders of the immune system, in particular the immunodiagnosis of acute leukemias. Similarly, polypeptides and antibodies directed to these polypeptides are useful to provide immunological probes for differential identification of the tissue(s) or cell type(s). For a number of disorders of the above tissues or cells, particularly of the immune system, expression of this gene at significantly higher or lower levels is detected in certain tissues or cell types (e.g., immune, cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue from an individual not having the disorder.

Similarly, CD33-likeSV polynucleotides and polypeptides, including antibodies, are useful as reagents for differential identification of the tissue(s) or cell type(s) present in a biological sample and for diagnosis of the following diseases and conditions which include, but are not limited to, disorders of the immune system, including inflammatory and allergic disorders. Similarly, polypeptides and antibodies directed to these polypeptides are useful to provide immunological probes for differential identification of the tissue(s) or cell type(s). For a number of disorders of the above tissues or cells, particularly of the immune system, expression of this gene at significantly higher or lower levels is detected in certain tissues or cell types (e.g., immune, cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue from an individual not having the disorder.

CD33 monoclonal antibodies (MoAB) are important in the immunodiagnosis of AML. CD33 MoABs have been used in preliminary therapeutic trials for purging bone marrow of AML patients, either before transplantation or for diseases resistant to chemotherapy. To prevent AML patients in remission from suffering relapse, or due to the lack of an appropriate allogenic bone marrow donor, a method is necessary for purging leukemia cells from the autografts of patients with advanced AML. By the invention, this method is provided by which bone marrow from an AML patient is obtained by, for example, percutaneous aspirations from the posterior iliac crest, isolating bone marrow mononuclear by Ficoll-hypaque density gradient centrifugation, and incubating with an anti-CD33-like protein MoAB, for example, 3-5 times for 15-30 min. at 4-6 degrees C., followed by incubation with rabbit complement at about 37 degrees C. for 30 minutes. The patient is then subject to myeloablative chemotherapy, followed by reinfusion of the treated autologous bone marrow according to standard techniques. By the invention, clonogenic tumor cells are depleted from the bone marrow while sparing hematopoietic cells necessary for engraftment.

In a further embodiment,the invention provides an in vivo method for selectively killing or inhibiting growth of tumor cells expressing CD33-like protein antigen of the present invention. The method involves administering to the patient an effective amount of an antagonist to inhibit the CD33-like protein receptor signaling pathway. By the invention, administering such antagonist of the CD33-like protein to a patient may also be useful for treating inflammatory diseases including arthritis and colitis. Antagonists for use in the present invention include polyclonal and monoclonal antibodies raised against the CD33-like protein or a fragment thereof, antisense molecules which control gene expression through antisense DNA or RNA or through triple-helix formation, proteins or other compounds which bind the CD33-like protein domains, or soluble forms of the CD33-like protein, such as protein fragments including the extracellular region from the full length receptor, which antagonize CD33-like protein mediated signaling by competing with the cell surface CD33-like protein for binding to CD33 receptor ligands.

The tissue distribution of CD33-likeSV in blood leukocytes, B cells and eosinophils, and the homology to other CD33 related Siglecs, indicates that polynucleotides, translation products and antibodies corresponding to CD33-like and CD33-likeSV are useful for the diagnosis, detection and/or treatment of diseases and/or disorders of the immune system.

The homology to a number of CD33 related Siglec proteins indicates that polynucleotides, translation products and antibodies corresponding to CD33-like and CD33-likeSV may be useful as a target for immunotherapy in diseases and/or disorders involving the immune system, and more particularly diseases and/or disorders related to leukocytes. The expression in eosinophils indicates that polynucleotides, translation products and antibodies corresponding to CD33-like and/or CD33-likeSV are useful for the diagnosis, detection and/or treatment of diseases and/or disorders related to eosinophils, such as, for example, eosinophil adenoma, eosinophilic granuloma, eosinophilic leukemia, and eosinophilic nonallergic rhinitis, allergic disorders, and/or hypereosinophilic disorders. Additionally, the expression in blood leukocytes indicates that polynucleotides, translation products and antibodies corresponding to CD33-like and CD33-likeSV are useful for the diagnosis, detection and/or treatment of diseases and/or disorders relating to other blood leukocytes, such as monocytes, for example.

Alternatively, the homology to other CD33 related Siglec proteins indicates that translation products corresponding to CD33-like and CD33-likeSV may play a useful role in the activation of cells involved in the destruction of pathogens. This may occur, by way of a non-limiting hypothesis, through an interaction between CD33-like and/or CD33-likeSV translation products and non-sialylated pathogens. Furthermore, the binding of CD33-like and/or CD33-likeSV translation products to erythrocytes suggests that these translation products may function in the elimination of erythrocytes from the blood stream and/or self-recognition, and may play a role in the recognition of sialic acid on the surface of erythrocytes. Sialidase treated erythrocytes were not bound by translation products corresponding to CD33-like and/or CD33-likeSV. Thus, translation products corresponding to CD33-like and/or CD33-likeSV may be involved in the clearance of erythrocytes from the blood stream, self-recognition and/or immune system activation.

Polynucleotides or polypeptides, or agonists or antagonists of the present invention, can be used in assays to test for one or more biological activities. If these polynucleotides or polypeptides, or agonists or antagonists of the present invention, do exhibit activity in a particular assay, it is likely that these molecules may be involved in the diseases associated with the biological activity. Thus, the polynucleotides and polypeptides, and agonists or antagonists could be used to treat the associated disease.

CD33-like and CD33-likeSV polypeptides are believed to be involved in biological activities associated with immune cell activation, pathogen recognition, erythrocyte binding, and/or eosinophilic and other immune cell disorders. Accordingly, compositions of the invention (including polynucleotides, polypeptides and antibodies of the invention, and fragments and variants thereof) may be used in the diagnosis, detection and/or treatment of diseases and/or disorders associated with aberrant CD33-like and CD33-likeSV activity. In preferred embodiments, compositions of the invention (including polynucleotides, polypeptides and antibodies of the invention, and fragments and variants thereof) may be used in the diagnosis, detection and/or treatment of diseases and/or disorders relating to blood disorders (e.g., polycythemia, and/or as described under "Immune activity" and "Cardiovascular Disorders" below), hypereosinophilic disorders, allergic disorders, pathogen recognition, erythrocyte binding, and immune system disorders (e.g., pathogen infections, and/or as described under "Immune activity" below). Thus, polynucleotides, translation products and antibodies of the invention are useful in the diagnosis, detection and/or treatment of diseases and/or disorders associated with activities that include, but are not limited to, blood disorders, hypereosinophilic disorders, allergic disorders, pathogen recognition, erythrocyte binding, and immune system disorders.

Many polynucleotide sequences, such as EST sequences, are publicly available and accessible through sequence databases. Some of these sequences are related to SEQ ID NO: 15 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 2281 of SEQ ID NO:15, b is an integer of 15 to 2295, where both a and b correspond to the positions of nucleotide residues shown in SEQ ID NO:15, and where b is greater than or equal to a+14.

Many polynucleotide sequences, such as EST sequences, are publicly available and accessible through sequence databases. Some of these sequences are related to SEQ ID NO:148 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2324 of SEQ ID NO:148, b is an integer of 15 to 2338, where both a and b correspond to the positions of nucleotide residues shown in SEQ ID NO:148, and where b is greater than or equal to a+14.

Features of Protein Encoded by Gene No: 6

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as a CD33 homolog derived from a human primary dendritic cells cDNA library. More particularly, the polypeptide of the present invention has been putatively identified as a human siglec homolog, sometimes hereafter referred to as "CD33-like 3" and/or "siglec 7". The invention also relates to inhibiting the action of such polypeptides.

The siglecs (sialic acid binding Ig-like lectins) are type I membrane proteins that constitute a distinct subset of the Ig superfamily, characterised by their sequence similarities and abilities to bind sialic acids in glycoproteins and glycolipid (Crocker, P. R., et al., Glycobiology: 8 (1998)). Members of the Ig Superfamily of proteins are defined as molecules that share domains of sequence similarity with the variable or constant domains of antibodies.

Many Ig superfamily proteins consist of multiple tandem Ig-like domains connected to other domains, such as Fn-III repeat domains (Vaughn, D. E., and P. J. Bjorkman, Neuron, 16:261-73 (1996)). At the primary structural level, traditional Ig-like domains can be identified by the presence of two cysteine residues separated by approximately 55-75 amino acid residues, and an "invariant"tryptophan residue located 10-15 residues C-terminal to the first of the two conserved cysteine residues. The two conserved cysteine residues are thought to be involved in disulfide bonding to form the folded Ig structures (Vaughn, D. E., (1996)).

Ig-like domains further share a common folding pattern, that of a sandwich or fold structure of two b-sheets consisting of antiparallel b-strands containing 5-10 amino acids (Huang, Z., et al., Biopolymers, 43:367-82 (1997)). Ig-like domains are divided, based upon sequence and structural similarities, into four classifications known as C1, C2, I and V-like domains.

The functional determinants of the Ig-like domains are presented on the faces of b-sheets or the loop regions of the Ig-fold. Accordingly, protein-protein interactions can occur either between the faces of the b-sheets, or the loop regions of the Ig-fold (Huang, Z., (1998)). These Ig-like domains are involved in mediating a diversity of biological functions such as intermolecular binding and protein-protein homophilic or heterophilic interactions.

Thus, Ig-like domains play an integral role in facilitating the activities of proteins of the Ig superfamily. In mammals, the group currently comprises sialoadhesin/siglec-1, CD22/siglec-2, CD33/siglec-3, myelin associated glycoprotein (MAG/siglec-4), siglecs-5, -6 and -7 (Crocker, P. R., et al., EMBO J., 13:4490-503 (1994); Sgroi, D., et al., J Biol. Chem. 268:7011-18 (1993); Freeman, D. S., et al., Blood, 85:2005-12 (1995); Kelm, S., et al., Curr Biol., 4:965-72 (1994); Cornish, A. L., et al., Blood, 92:2123-132 (1998); Patel, N., et al., J Biol. Chem, 274:22729-738 (1999); Nicol, G., et al., J Biol. Chem, In Press (1999)). Siglec-7 has also recently been characterised independently as the NK receptor p75/AIRM1 (Falco, M., et al., J Exp. Med., 190:793-802 (1999)). In addition, the gene encoding another siglec-like sequence, OBBP-like protein has been reported but there is no information on its binding activity (Yousef, G. M., et al., Biochem. Biophys. Res. Commun., In Press (1999)).

Each of these proteins has an extracellular region made up of a membrane distal V-set domain followed by varying numbers of C2 set domains which range from 16 in sialoadhesin to 1 in CD33. In the cases of sialoadhesin, CD22, MAG and CD33, the sialic acid binding site has been mapped to the V-set domain and for sialoadhesin it has been further characterised at the molecular level by X-ray crystallography 11 (Nath, D., et al., J Biol. Chem., 270:26184-91 (1995); van der Merwe, P. A., et al., J. Biol. Chem., 271:9273-80 (1996); Tang, S., et al., J. Cell Biol., 138:1355-66 (1997); Taylor, V. C., et al., J. Biol. Chem., 274:11505-12 (1999); May, A. P., et al., Molecular Cell, 1:719-28 (1998)).

Apart from MAG and SMP that are found exclusively in the nervous system, all siglecs characterised to date are expressed on discrete subsets of hemopoietic cells and can provide useful lineage-restricted markers. Thus, CD22 is present only on mature B cells, sialoadhesin is on macrophage subsets, CD33 is a marker of early committed myeloid progenitor cells, siglec-5 is expressed by monocytes and mature neutrophils, siglec-6 is on B cells and siglec-7 is expressed by NK cells and monocytes (Dorken, B., et al., J. Immunology, 136:4470-79 (1986); Crocker, P. R., et al., J. Exp. Med., 164:1862-75 (1986); Peiper, S. C., et al., In Leukocyte Typing IV. Oxford University Press, Oxford. 814-16 (1989); Cornish, A. L., et al., Blood, 92:2123-132 (1998); Patel, N., et al., J Biol. Chem, 274:22729-738 (1999); Nicol, G., et al., J Biol. Chem, In Press (1999)).

These expression patterns indicate discrete functions amongst hemopoietic cell subsets, but apart from CD22, a well-characterised negative regulator of B cell activation (reviewed in Cyster, J. G. and C. C. Goodnow, Immunity, 6:509-17 (1997)), the biological functions of siglecs expressed in the hemopoietic system are unknown. Proposed functions include cell-cell interactions through recognition of sialylated glycoconjugates on other cells. However, a number of studies have also shown that cell-cell adhesion mediated by siglecs can be modulated by cis-interactions with sialic acids present in the host plasma membrane. This is particularly striking for CD22, CD33 and siglec-5, whose binding activities can be greatly increased if host cells are pretreated with sialidase to remove the cis-competing sialic acids (Freeman, D. S., et al., Blood, 85:2005-12 (1995); Cornish, A. L., et al., Blood, 92:2123-132 (1998); Sgroi, D., et al., P.N.A.S., 92:4026-30 (1995)).

Besides potential roles in cellular interactions, there is growing evidence that, similar to CD22, the more recently characterised siglecs are involved in signalling functions. The cytoplasmic tails of CD33 and siglecs-5, -6 and -7 have two well-conserved tyrosine-based motifs that are similar to well-characterised signaling motifs in other leukocyte receptors (Gergely, J., et al., Immun. Lett., 68:3-15 (1999)). Where studied, both tyrosine residues can be phosphorylated by src-like kinase(s) and, in the case of the membrane proximal tyrosine, this leads to subsequent recruitment of the tyrosine phosphatases, SHP-1 and SHP-2 (Falco, M., et al., J. Exp. Med., 190:793-802 (1999); Taylor, V. C., et al., J. Biol. Chem., 274:11505-12 (1999)).

Thus there exists a clear need for identifying and exploiting novel members of the siglec family of immunoglobulin proteins. Although structurally related, such proteins may possess diverse and multifaceted functions in a variety of cell and tissue types. The purified siglec proteins of the invention are research tools useful for the identification, characterization and purification of cell signaling molecules. Furthermore, the identification of new siglecs permits the development of a range of derivatives, agonists and antagonists at the nucleic acid and protein levels which in turn have applications in the treatment and diagnosis of a range of conditions such as cancer, inflammation, neurological disorders and immunological disorders, amongst many other conditions. The polypeptide of the present invention has been putatively identified as a member of the siglec family and has been termed CD33-like 3. This identification has been made as a result of amino acid sequence homology to the human cd3311 (See Genbank Accession No. gi|2913995).

Preferred polypeptides of the present invention comprise, or alternatively consist of, one, two, three, four, five, six, seven, eight, nine, ten, eleven, twelve, or all twelve of the immunogenic epitopes shown in SEQ ID NO: 34 as residues: Gly-12 to Tyr-26, Val-52 to Asp-59, Gln-88 to Asp-93, Arg-124 to Asn-129, His-193 to Arg-198, Gln-207 to Thr-213, Gln-338 to Arg-346, Ser-378 to Ala-384, Ser-413 to Arg-420, Ser-428 to Glu-434, His-443 to Ser-451, and/or Glu-454 to Ser-461. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

FIGS. 16A-B show the nucleotide (SEQ ID NO:16) and deduced amino acid sequence (SEQ ID NO:34) of CD33-like 3. Predicted amino acids from about 1 to about 18 constitute the predicted signal peptide (amino acid residues from about 1 to about 18 in SEQ ID NO:34) and are represented by the underlined amino acid regions; and amino acids from about 360 to about 376 constitute the predicted transmembrane domain (amino acids from about 360 to about 376 in SEQ ID NO:34) and are represented by the double underlined amino acids.

FIG. 17 shows the regions of similarity between the amino acid sequences of the CD33-like 3 protein (SEQ ID NO:34) and the human CD33L1 protein (SEQ ID NO:99).

Figure 18:
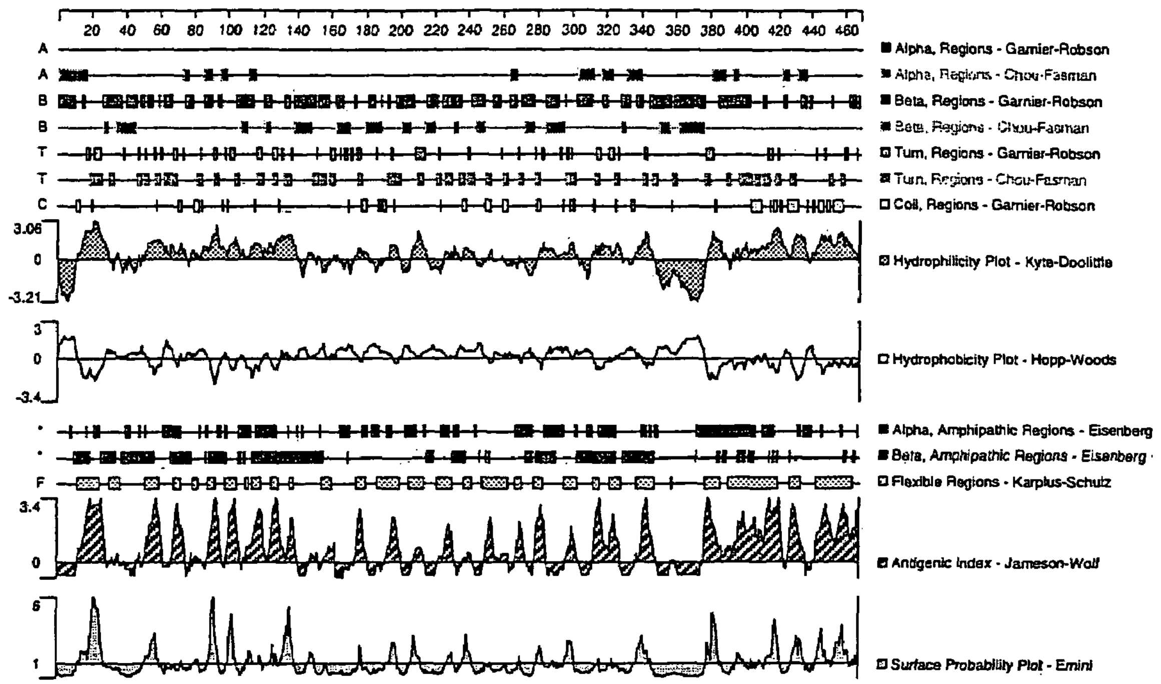
FIG. 18 shows an analysis of the CD33-like 3 amino acid sequence. Alpha, beta, turn and coil regions; hydrophilicity and hydrophobicity; amphipathic regions; flexible regions; antigenic index and surface probability are shown.

FIG. 18 shows an analysis of the CD33-like 3 amino acid sequence. Alpha, beta, turn and coil regions; hydrophilicity and hydrophobicity; amphipathic regions; flexible regions; antigenic index and surface probability are shown.

As shown in FIGS. 16A-B, CD33-like 3 has a transmembrane domain (the transmembrane domains comprise amino acids from about 360 to about 376 of SEQ ID NO:34; which correspond to amino acids from about 360 to about 376 of FIGS. 16A-B). The polynucleotide contains an open reading frame encoding the CD33-like 3 polypeptide of 467 amino acids. CD33-like 3 exhibits a high degree of homology at the amino acid level to the human CD33L1 (as shown in FIG. 18).

The present invention provides isolated nucleic acid molecules comprising a polynucleotide encoding the CD33-like 3 polypeptide having the amino acid sequence shown in FIGS. 16A-B (SEQ ID NO:34). The nucleotide sequence shown in FIGS. 16A-B (SEQ ID NO:16) was obtained by sequencing a cloned cDNA (HDPUW68), which was deposited on November 17 at the American Type Culture Collection, and given Accession Number 203484.

The present invention is further directed to fragments of the isolated nucleic acid molecules described herein. By a fragment of an isolated DNA molecule having the nucleotide sequence of the deposited cDNA or the nucleotide sequence shown in SEQ ID NO:16 is intended DNA fragments at least about 15nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:16. By a fragment at least 20 nt in length, for example, is intended fragments which include 20 or more contiguous bases from the nucleotide sequence of the deposited cDNA or the nucleotide sequence as shown in SEQ ID NO:16. In this context "about" includes the particularly recited size, larger or smaller by several (5, 4, 3, 2, or 1) nucleotides, at either terminus or at both termini. Representative examples of CD33-like 3 polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, from about 501 to about 550, from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1350, from about 1351 to about 1400, from about 1401 to about 1450, from about 1451 to about 1500, from about 1501 to about 1550, from about 1551 to about 1600, from about 1601 to about 1650, from about 1651 to about 1700, from about 1701 to about 1748 of SEQ ID NO:16, or the complementary strand thereto, or the cDNA contained in the deposited gene. In this context "about" includes the particularly recited ranges, larger or smaller by several (5, 4, 3, 2, or 1) nucleotides, at either terminus or at both termini.

Preferred nucleic acid fragments of the present invention include nucleic acid molecules encoding a member selected from the group: a polypeptide comprising or alternatively, consisting of, the transmembrane domain (amino acid residues from about 360 to about 376 in FIGS. 16A-B (amino acids from about 360 to about 376 in SEQ ID NO:34). Since the location of these domains have been predicted by computer analysis, one of ordinary skill would appreciate that the amino acid residues constituting these domains may vary slightly (e.g., by about 1 to 15 amino acid residues) depending on the criteria used to define each domain.

In additional embodiments, the polynucleotides of the invention encode functional attributes of CD33-like 3.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of CD33-like 3. The data representing the structural or functional attributes of CD33-like 3 set forth in FIG. 18 and/or Table VI, as described above, was generated using the various modules and algorithms of the DNA*STAR set on default parameters. In a preferred embodiment, the data presented in columns VIII, IX, XIII, and XIV of Table VI can be used to determine regions of CD33-like 3 which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 18, but may, as shown in Table VI, be represented or identified by using tabular representations of the data presented in FIG. 18. The DNA*STAR computer algorithm used to generate FIG. 18 (set on the original default parameters) was used to present the data in FIG. 18 in a tabular format (See Table VI). The tabular format of the data in FIG. 18 is used to easily determine specific boundaries of a preferred region. The above-mentioned preferred regions set out in FIG. 18 and in Table VI include, but are not limited to, regions of the aforementioned types identified by analysis of the amino acid sequence set out in FIGS. 16A-B. As set out in FIG. 18 and in Table VI, such preferred regions include Garnier-Robson alpha-regions, beta-regions, turn-regions, and coil-regions, Chou-Fasman alpha-regions, beta-regions, and turn-regions, Kyte-Doolitle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, modulate cellular interaction, or signalling pathways, etc.) may still be retained. For example, the ability of shortened CD33-like 3 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an CD33-like 3 mutein with a large number of deleted N-terminal amino acid residues may retain some biological or immunogenic activities. In fact, peptides composed of as few as six CD33-like 3 amino acid residues may often evoke an immune response.

Accordingly, the present invention further provides polypeptides having one or more residues deleted from the amino terminus of the CD33-like 3 amino acid sequence shown in FIGS. 16A-B, up to the glutamic acid residue at position number 462 and polynucleotides encoding such polypeptides. In particular, the present invention provides polypeptides comprising the amino acid sequence of residues n1-467 of FIGS. 16A-B, where n1 is an integer from 2 to 462 corresponding to the position of the amino acid residue in FIGS. 16A-B (which is identical to the sequence shown as SEQ ID NO:34). In another embodiment, N-terminal deletions of the CD33-like 3 polypeptide can be described by the general formula n2-467, where n2 is a number from 2 to 462, corresponding to the position of amino acid identified in FIGS. 16A-B . N-terminal deletions of the CD33-like 3 polypeptide of the invention shown as SEQ ID NO:34 include polypeptides comprising the amino acid sequence of residues: N-terminal deletions of the CD33-like 3 polypeptide of the invention shown as SEQ ID NO:34 include polypeptides comprising the amino acid sequence of residues: L-2 to K-467; L-3 to K-467; L-4 to K-467; L-5 to K-467; L-6 to K-467; L-7 to K-467; P-8 to K-467; L-9 to K-467; L-10 to K-467; W-11 to K-467; G-12 to K-467; R-13 to K-467; E-14 to K-467; R-15 to K-467; V-16 to K-467; E-17 to K-467; G-18 to K-467; Q-19 to K-467; K-20 to K-467; S-21 to K-467; N-22 to K-467; R-23 to K-467; K-24 to K-467; D-25 to K-467; Y-26 to K-467; S-27 to K-467; L-28 to K-467; T-29 to K-467; M-30 to K-467; Q-31 to K-467; S-32 to K-467; S-33 to K-467; V-34 to K-467; T-35 to K-467; V-36 to K-467; Q-37 to K-467; E-38 to K-467; G-39 to K-467; M-40 to K-467; C-41 to K-467; V-42 to K-467; H-43 to K-467; V-44 to K-467; R-45 to K-467; C-46 to K-467; S-47 to K-467; F-48 to K-467; S-49 to K-467; Y-50 to K-467; P-51 to K-467; V-52 to K-467; D-53 to K-467; S-54 to K-467; Q-55 to K-467; T-56 to K-467; D-57 to K-467; S-58 to K-467; D-59 to K-467; P-60 to K-467; V-61 to K-467; H-62 to K-467; G-63 to K-467; Y-64 to K-467; W-65 to K-467; F-66 to K-467; R-67 to K-467; A-68 to K-467; G-69 to K-467; N-70 to K-467; D-71 to K-467; I-72 to K-467; S-73 to K-467; W-74 to K-467; K-75 to K-467; A-76 to K-467; P-77 to K-467; V-78 to K-467; A-79 to K-467; T-80 to K-467; N-81 to K-467; N-82 to K-467; P-83 to K-467; A-84 to K-467; W-85 to K-467; A-86 to K-467; V-87 to K-467; Q-88 to K-467; E-89 to K-467; E-90 to K-467; T-91 to K-467; R-92 to K-467; D-93 to K-467; R-94 to K-467; F-95 to K-467; H-96 to K-467; L-97 to K-467; L-98 to K-467; G-99 to K-467; D-100 to K-467; P-101 to K-467; Q-102 to K-467; T-103 to K-467; K-104 to K-467; N-105 to K-467; C-106 to K-467; T-107 to K-467; L-108 to K-467; S-109 to K-467; I-110 to K-467; R-111 to K-467; D-112 to K-467; A-113 to K-467; R-114 to K-467; M-115 to K-467; S-116 to K-467; D-117 to K-467; A-118 to K-467; G-119 to K-467; R-120 to K-467; Y-121 to K-467; F-122 to K-467; F-123 to K-467; R-124 to K-467; M-125 to K-467; E-126 to K-467; K-127 to K-467; G-128 to K-467; N-129 to K-467; I-130 to K-467; K-131 to K-467; W-132 to K-467; N-133 to K-467; Y-134 to K-467; K-135 to K-467; Y-136 to K-467; D-137 to K-467; Q-138 to K-467; L-139 to K-467; S-140 to K-467; V-141 to K-467; N-142 to K-467; V-143 to K-467; T-144 to K-467; A-145 to K-467; L-146 to K-467; T-147 to K-467; H-148 to K-467; R-149 to K-467; P-150 to K-467; N-151 to K-467; I-152 to K-467; L-153 to K-467; I-154 to K-467; P-155 to K-467; G-156 to K-467; T-157 to K-467; L-158 to K-467; E-159 to K-467; S-160 to K-467; G-161 to K-467; C-162 to K-467; F-163 to K-467; Q-164 to K-467; N-165 to K-467; L-166 to K-467; T-167 to K-467; C-168 to K-467; S-169 to K-467; V-170 to K-467; P-171 to K-467; W-172 to K-467; A-173 to K-467; C-174 to K-467; E-175 to K-467; Q-176 to K-467; G-177 to K-467; T-178 to K-467; P-179 to K-467; P-180 to K-467; M-181 to K-467; I-182 to K-467; S-183 to K-467; W-184 to K-467; M-185 to K-467; G-186 to K-467; T-187 to K-467; S-188 to K-467; V-189 to K-467; S-190 to K-467; P-191 to K-467; L-192 to K-467; H-193 to K-467; P-194 to K-467; S-195 to K-467; T-196 to K-467; T-197 to K-467; R-198 to K-467; S-199 to K-467; S-200 to K-467; V-201 to K-467; L-202 to K-467; T-203 to K-467; L-204 to K-467; I-205 to K-467; P-206 to K-467; Q-207 to K-467; P-208 to K-467; Q-209 to K-467; H-210 to K-467; H-211 to K-467; G-212 to K-467; T-213 to K-467; S-214 to K-467; L-215 to K-467; T-216 to K-467; C-217 to K-467; Q-218 to K-467; V-219 to K-467; T-220 to K-467; L-221 to K-467; P-222 to K-467; G-223 to K-467; A-224 to K-467; G-225 to K-467; V-226 to K-467; T-227 to K-467; T-228 to K-467; N-229 to K-467; R-230 to K-467; T-231 to K-467; I-232 to K-467; Q-233 to K-467; L-234 to K-467; N-235 to K-467; V-236 to K-467; S-237 to K-467; Y-238 to K-467; P-239 to K-467; P-240 to K-467; Q-241 to K-467; N-242 to K-467; L-243 to K-467; T-244 to K-467; V-245 to K-467; T-246 to K-467; V-247 to K-467; F-248 to K-467; Q-249 to K-467; G-250 to K-467; E-251 to K-467; G-252 to K-467; T-253 to K-467; A-254 to K-467; S-255 to K-467; T-256 to K-467; A-257 to K-467; L-258 to K-467; G-259 to K-467; N-260 to K-467; S-261 to K-467; S-262 to K-467; S-263 to K-467; L-264 to K-467; S-265 to K-467; V-266 to K-467; L-267 to K-467; E-268 to K-467; G-269 to K-467; Q-270 to K-467; S-271 to K-467; L-272 to K-467; R-273 to K-467; L-274 to K-467; V-275 to K-467; C-276 to K-467; A-277 to K-467; V-278 to K-467; D-279 to K-467; S-280 to K-467; N-281 to K-467; P-282 to K-467; P-283 to K-467; A-284 to K-467; R-285 to K-467; L-286 to K-467; S-287 to K-467; W-288 to K-467; T-289 to K-467; W-290 to K-467; R-291 to K-467; S-292 to K-467; L-293 to K-467; T-294 to K-467; L-295 to K-467; Y-296 to K-467; P-297 to K-467; S-298 to K-467; Q-299 to K-467; P-300 to K-467; S-301 to K-467; N-302 to K-467; P-303 to K-467; L-304 to K-467; V-305 to K-467; L-306 to K-467; E-307 to K-467; L-308 to K-467; Q-309 to K-467; V-3 10 to K-467; H-311 to K-467; L-312 to K-467; G-313 to K-467; D-314 to K-467; E-315 to K-467; G-316 to K-467; E-317 to K-467; F-318 to K-467; T-319 to K-467; C-320 to K-467; R-321 to K-467; A-322 to K-467; Q-323 to K-467; N-324 to K-467; S-325 to K-467; L-326 to K-467; G-327 to K-467; S-328 to K-467; Q-329 to K-467; H-330 to K-467; V-331 to K-467; S-332 to K-467; L-333 to K-467; N-334 to K-467; L-335 to K-467; S-336 to K-467; L-337 to K-467; Q-338 to K-467; Q-339 to K-467; E-340 to K-467; Y-341 to K-467; T-342 to K-467; G-343 to K-467; K-344 to K-467; M-345 to K-467; R-346 to K-467; P-347 to K-467; V-348 to K-467; S-349 to K-467; G-350 to K-467; V-351 to K-467; L-352 to K-467; L-353 to K-467; G-354 to K-467; A-355 to K-467; V-356 to K-467; G-357 to K-467; G-358 to K-467; A-359 to K-467; G-360 to K-467; A-361 to K-467; T-362 to K-467; A-363 to K-467; L-364 to K-467; V-365 to K-467; F-366 to K-467; L-367 to K-467; S-368 to K-467; F-369 to K-467; C-370 to K-467; V-371 to K-467; I-372 to K-467; F-373 to K-467; I-374 to K-467; V-375 to K-467; V-376 to K-467; R-377 to K-467; S-378 to K-467; C-379 to K-467; R-380 to K-467; K-381 to K-467; K-382 to K-467; S-383 to K-467; A-384 to K-467; R-385 to K-467; P-386 to K-467; A-387 to K-467; A-388 to K-467; D-389 to K-467; V-390 to K-467; G-391 to K-467; D-392 to K-467; I-393 to K-467; G-394 to K-467; M-395 to K-467; K-396 to K-467; D-397 to K-467; A-398 to K-467; N-399 to K-467; T-400 to K-467; I-401 to K-467; R-402 to K-467; G-403 to K-467; S-404 to K-467; A-405 to K-467; S-406 to K-467; Q-407 to K-467; G-408 to K-467; N-409 to K-467; L-410 to K-467; T-411 to K-467; E-412 to K-467; S-413 to K-467; W-414 to K-467; A-415 to K-467; D-416 to K-467; D-417 to K-467; N-418 to K-467; P-419 to K-467; R-420 to K-467; H-421 to K-467; H-422 to K-467; G-423to K-467; L-424 to K-467; A-425 to K-467; A-426 to K-467; H-427 to K-467; S-428 to K-467; S-429 to K-467; G-430 to K-467; E-431 to K-467; E-432 to K-467; R-433 to K-467; E-434 to K-467; I-435 to K-467; Q-436 to K-467; Y-437 to K-467; A-438 to K-467; P-439 to K-467; L-440 to K-467; S-441 to K-467; F-442 to K-467; H-443 to K-467; K-444 to K-467; G-445 to K-467; E-446 to K-467; P-447 to K-467; Q-448 to K-467; D-449 to K-467; L-450 to K-467; S-451 to K-467; G-452 to K-467; Q-453 to K-467; E-454 to K-467; A-455 to K-467; T-456 to K-467; N-457 to K-467; N-458 to K-467; E-459 to K-467; Y-460 to K-467; S-461 to K-467; E-462 to K-467; of SEQ ID NO:34. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities may still be retained. For example the ability of the shortened CD33-like 3 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a CD33-like 3 mutein with a large number of deleted C-terminal amino acid residues may retain some biological or immunogenic activities. In fact, peptides composed of as few as six CD33-like 3 amino acid residues may often evoke an immune response.

Accordingly, the present invention further provides polypeptides having one or more residues deleted from the carboxy terminus of the amino acid sequence of the CD33-like 3 polypeptide shown in FIGS. 16A-B, up to the leucine residue at position number 6, and polynucleotides encoding such polypeptides. In particular, the present invention provides polypeptides comprising the amino acid sequence of residues 1-m1 of FIG. 1, where m1 is an integer from 6 to 467 corresponding to the position of the amino acid residue in FIGS. 16A-B.

Moreover, the invention provides polynucleotides encoding polypeptides comprising, or alternatively consisting of, the amino acid sequence of C-terminal deletions of the CD33-like 3 polypeptide of the invention shown as SEQ ID NO:34 include polypeptides comprising the amino acid sequence of residues: M-1 to P-466; M-1 to I-465; M-1 to K-464; M-1 to I-463; M-1 to E-462; M-1 to S-461; M-1 to Y-460; M-1 to E-459; M-1 to N-458; M-1 to N-457; M-1 to T-456; M-1 to A-455; M-1 to E-454; M-1 to Q-453; M-1 to G-452; M-1 to S-451; M-1 to L-450; M-1 to D-449; M-1 to Q-448; M-1 to P-477; M-1 to E-446; M-1 to G-445; M-1 to K-444; M-1 to H-443; M-1 to F-442; M-1 to S-441; M-1 to L-440; M-1 to P-339; M-1 to A-438; M-1 to Y-437; M-1 to Q-436; M-1 to I-435; M-1 to E-434; M-1 to R-433; M-1 to E-432; M-1 to E-431; M-1 to G-430; M-1 to S-429; M-1 to S-428; M-1 to H-427; M-1 to A-426; M-1 to A-425; M-1 to L-424; M-1 to G-423; M-1 to H-422; M-1 to H-421; M-1 to R-420; M-1 to P-419; M-1 to N-418; M-1 to D-417; M-1 to D-416; M-1 to A-415; M-1 to W-414; M-1 to S-413; M-1 to E-412; M-1 to T-411; M-1 to L-410; M-1 to N-409; M-1 to G-408; M-1 to Q-407; M-1 to S-406; M-1 to A-405; M-1 to S-404; M-1 to G-403; M-1 to R-402; M-1 to I-401; M-1 to T-400; M-1 to N-399; M-1 to A-398; M-1 to D-397; M-1 to K-396; M-1 to M-395; M-1 to G-394; M-1 to I-393; M-1 to D-392; M-1 to G-391; M-1 to V-390; M-1 to D-389; M-1 to A-388; M-1 to A-387; M-1 to P-386; M-1 to R-385; M-1 to A-384; M-1 to S-383; M-1 to K-382; M-1 to K-381; M-1 to R-380; M-1 to C-379; M-1 to S-378; M-1 to R-377; M-1 to V-376; M-1 to V-375; M-1 to I-374; M-1 to F-373; M-1 to I-372; M-1 to V-371; M-1 to C-370; M-1 to F-369; M-1 to S-368; M-1 to L-367; M-1 to F-366; M-1 to V-365; M-1 to L-364; M-1 to A-363; M-1 to T-362; M-1 to A-361; M-1 to G-360; M-1 to A-359; M-1 to G-358; M-1 to G-357; M-1 to V-356; M-1 to A-355; M-1 to G-354; M-1 to L-353; M-1 to L-352; M-1 to V-351; M-1 to G-350; M-1 to S-349; M-1 to V-348; M-1 to P-347; M-1 to R-346; M-1 to M-345; M-1 to K-344; M-1 to G-343; M-1 to T-342; M-1 to Y-341; M-1 to E-340; M-1 to Q-339; M-1 to Q-338; M-1 to L-337; M-1 to S-336; M-1 to L-335; M-1 to N-334; M-1 to L-333; M-1 to S-332; M-1 to V-331; M-1 to H-330; M-1 to Q-329; M-1 to S-328; M-1 to G-327; M-1 to L-326; M-1 to S-325; M-1 to N-324; M-1 to Q-323; M-1 to A-322; M-1 to R-321; M-1 to C-320; M-1 to T-319; M-1 to F-318; M-1 to E-317; M-1 to G-316; M-1 to E-315; M-1 to D-314; M-1 to G-313; M-1 to L-312; M-1 to H-311; M-1 to V-310; M-1 to Q-309; M-1 to L-308; M-1 to E-307; M-1 to L-306; M-1 to V-305; M-1 to L-304; M-1 to P-303; M-1 to N-302; M-1 to S-301; M-1 to P-300; M-1 to Q-299; M-1 to S-298; M-1 to P-297; M-1 to Y-296; M-1 to L-295; M-1 to T-294; M-1 to L-293; M-1 to S-292; M-1 to R-291; M-1 to W-290; M-1 to T-289; M-1 to W-288; M-1 to S-287; M-1 to L-286; M-1 to R-285; M-1 to A-284; M-1 to P-283; M-1 to P-282; M-1 to N-281; M-1 to S-280; M-1 to D-279; M-1 to V-278; M-1 to A-277; M-1 to C-276; M-1 to V-275; M-1 to L-274; M-1 to R-273; M-1 to L-272; M-1 to S-271; M-1 to Q-270; M-1 to G-269; M-1 to E-268; M-1 to L-267; M-1 to V-266; M-1 to S-265; M-1 to L-264; M-1 to S-263; M-1 to S-262; M-1 to S-261; M-1 to N-260; M-1 to G-259; M-1 to L-258; M-1 to A-257; M-1 to T-256; M-1 to S-255; M-1 to A-254; M-1 to T-253; M-1 to G-252; M-1 to E-251; M-1 to G-250; M-1 to Q-249; M-1 to F-248; M-1 to V-247; M-1 to T-246; M-1 to V-245; M-1 to T-244; M-1 to L-243; M-1 to N-242; M-1 to Q-241; M-1 to P-240; M-1 to P-239; M-1 to Y-238; M-1 to S-237; M-1 to V-236; M-1 to N-235; M-1 to L-234; M-1 to Q-233; M-1 to I-232; M-1 to T-231; M-1 to R-230; M-1 to N-229; M-1 to T-228; M-1 to T-227; M-1 to V-226; M-1 to G-225; M-1 to A-224; M-1 to G-223; M-1 to P-222; M-1 to L-221; M-1 to T-220; M-1 to V-219; M-1 to Q-218; M-1 to C-217; M-1 to T-216; M-1 to L-215; M-1 to S-214; M-1 to T-213; M-1 to G-212; M-1 to H-211; M-1 to H-210; M-1 to Q-209; M-1 to P-208; M-1 to Q-207; M-1 to P-206; M-1 to I-205; M-1 to L-204; M-1 to T-203; M-1 to L-202; M-1 to V-201; M-1 to S-200; M-1 to S-199; M-1 to R-198; M-1 to T-197; M-1 to T-196; M-1 to S-195; M-1 to P-194; M-1 to H-193; M-1 to L-192; M-1 to P-191; M-1 to S-190; M-1 to V-189; M-1 to S-188; M-1 to T-187; M-1 to G-186; M-1 to M-185; M-1 to W-184; M-1 to S-183; M-1 to I-182; M-1 to M-181; M-1 to P-180; M-1 to P-179; M-1 to T-178; M-1 to G-177; M-1 to Q-176; M-1 to E-175; M-1 to C-174; M-1 to A-173; M-1 to W-172; M-1 to P-171; M-1 to V-170; M-1 to S-169; M-1 to C-168; M-1 to T-167; M-1 to L-166; M-1 to N-165; M-1 to Q-164; M-1 to F-163; M-1 to C-162; M-1 to G-161; M-1 to S-160; M-1 to E-159; M-1 to L-158; M-1 to T-157; M-1 to G-156; M-1 to P-155; M-1 to I-154; M-1 to L-153; M-1 to I-152; M-1 to N-151; M-1 to P-150; M-1 to R-149; M-1 to H-148; M-1 to T-147; M-1 to L-146; M-1 to A-145; M-1 to T-144; M-1 to V-143; M-1 to N-142; M-1 to V-141; M-1 to S-140; M-1 to L-139; M-1 to Q-138; M-1 to D-137; M-1 to Y-136; M-1 to K-135; M-1 to Y-134; M-1 to N-133; M-1 to W-132; M-1 to K-131; M-1 to I-130; M-1 to N-129; M-1 to G-128; M-1 to K-127; M-1 to E-126; M-1 to M-125; M-1 to R-124; M-1 to F-123; M-1 to F-122; M-1 to Y-121; M-1 to R-120; M-1 to G-119; M-1 to A-118; M-1 to D-117; M-1 to S-116; M-1 to M-115; M-1 to R-114; M-1 to A-113; M-1 to D-112; M-1 to R-111; M-1 to I-110; M-1 to S-109; M-1 to L-108; M-1 to T-107; M-1 to C-106; M-1 to N-105; M-1 to K-104; M-1 to T-103; M-1 to Q-102; M-1 to P-101; M-1 to D-100; M-1 to G-99; M-1 to L-98; M-1 to L-97; M-1 to H-96; M-1 to F-95; M-1 to R-94; M-1 to D-93; M-1 to R-92; M-1 to T-91; M-1 to E-90; M-1 to E-89; M-1 to Q-88; M-1 to V-87; M-1 to A-86; M-1 to W-85; M-1 to A-84; M-1 to P-83; M-1 to N-82; M-1 to N-81; M-1 to T-80; M-1 to A-79; M-1 to V-78; M-1 to P-77; M-1 to A-76; M-1 to K-75; M-1 to W-74; M-1 to S-73; M-1 to I-72; M-1 to D-71; M-1 to N-70; M-1 to G-69; M-1 to A-68; M-1 to R-67; M-1 to R-66; M-1 to W-65; M-1 to Y-64; M-1 to G-63; M-1 to H-62; M-1 to V-61; M-1 to P-60; M-1 to D-59; M-1 to S-58; M-1 to D-57; M-1 to T-56; M-1 to Q-55; M-1 to S-54; M-1 to D-53; M-1 to V-52; M-1 to P-51; M-1 to Y-50; M-1 to S-49; M-1 to F-48; M-1 to S-47; M-1 to C-46; M-1 to R-45; M-1 to V-44; M-1 to H-43; M-1 to V-42; M-1 to C-41; M-1 to M-40; M-1 to G-39; M-1 to E-38; M-1 to Q-37; M-1 to V-36; M-1 to T-35; M-1 to V-34; M-1 to S-33; M-1 to S-32; M-1 to Q-31; M-1 to M-30; M-1 to T-29; M-1 to L-28; M-1 to S-27; M-1 to Y-26; M-1 to D-25; M-1 to K-24; M-1 to R-23; M-1 to N-22; M-1 to S-21; M-1 to K-20; M-1 to Q-19; M-1 to G-18; M-1 to E-17; M-1 to V-16; M-1 to R-15; M-1 to E-14; M-1 to R-13; M-1 to G-12; M-1 to W-11; M-1 to L-10; M-1 to L-9; M-1 to P-8; M-1 to L-7; M-1 to L-6; of SEQ ID NO:34. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nrucleotide sequences related to extensive portions of SEQ ID NO:16 which have been determined from the following related cDNA genes: HGBAY02R (SEQ ID NO:100) and HLYBY62R (SEQ ID NO:101).

A polynucleotide encoding a polypeptide of the present invention is obtained from human NK cells, T-cells, primary dendritic cells, placenta, spleen, primary breast cancer, gall bladder, apoptotic t-cells, macrophage, and chronic lymphocytic leukemia spleen. The polynucleotide of this invention was discovered in a human primary dendritic cell cDNA library.

Based on the sequence similarity to the human CD33L1, translation product of this gene is expected to share at least some biological activities with CD33 proteins, and specifically myeloid modulatory proteins and/or siglec proteins. Such activities are known in the art, some of which are described elsewhere herein.

Specifically, polynucleotides and polypeptides of the invention, including antibodies, are also useful for modulating the differentiation of normal and malignant cells, modulating the proliferation and/or differentiation of cancer and neoplastic cells, and modulating the immune response. Polynucleotides and polypeptides of the invention may represent a diagnostic marker for hematopoietic and immune diseases and/or disorders. The full-length protein should be a secreted protein, based upon homology to the CD33 family. Therefore, it is secreted into serum, urine, or feces and thus the levels is assayable from patient samples. Assuming specific expression levels are reflective of the presence of immune disorders, this protein would provide a convenient diagnostic for early detection. In addition, expression of this gene product may also be linked to the progression of immune diseases, and therefore may itself actually represent a therapeutic or therapeutic target for the treatment of cancer.

Polynucleotides and polypeptides of the invention may play an important role in the pathogenesis of human cancers and cellular transformation, particularly those of the immune and hematopoietic systems. Polynucleotides and polypeptides of the invention may also be involved in the pathogenesis of developmental abnormalities based upon its potential effects on proliferation and differentiation of cells and tissue cell types. Due to the potential proliferating and differentiating activity of said polynucleotides and polypeptides, polynucleotides, translation products and antibodies corresponding to this gene are useful as a therapeutic agent(s) in inducing tissue regeneration, for treating inflammatory conditions (e.g., inflammatory bowel syndrome, diverticulitis, etc.). Moreover, the invention is useful in modulating the immune response to aberrant polypeptides, as may exist in rapidly proliferating cells and tissue cell types, particularly in adenocarcinoma cells, and other cancers.

This gene is expressed predominantly on NK cells, and to a lesser extent on T-cells. Therefore, polynucleotides, translation products and antibodies corresponding to this gene are useful as reagents for differential identification of the tissue(s) or cell type(s) present in a biological sample and for diagnosis of the following diseases and conditions which include, but are not limited to, immune disorders and cancer, as well as the immunodiagnosis of acute leukemias. Similarly, polynucleotides, translation products and antibodies corresponding to this gene are useful to provide immunological probes for differential identification of the tissue(s) or cell type(s). For a number of disorders of the above tissues or cells, particularly of the immune system, and breast tissue, expression of this gene at significantly higher or lower levels is detected in certain tissues or cell types (e.g. immune, cancerous and wounded tissues) or bodily fluids (e.g., serum, plasma, urine, synovial fluid or spinal fluid) or another tissue or cell sample taken from an individual having such a disorder, relative to the standard gene expression level, i.e., the expression level in healthy tissue from an individual not having the disorder.

The tissue distribution in NK cells, in combination with the homology to siglec family of proteins, indicates that polynucleotides, translation products and antibodies corresponding to this gene are useful for the diagnosis and treatment of a variety of immune system disorders. NK cells are bone-marrow derived granular lymphocytes that play an important role in natural immunity to infectious diseases and have the capacity to kill certain virally-infected cells and tumor cells that have down-regulated MHC Class-I antigen expression. The killing and proinflammatory activities of NK cells are regulated through a variety of cell surface receptors that can mediate either activity or inhibitory signals. The best understood receptors are those that recognize MHC Class I molecules at the cell surface and deliver a negative signal, thereby protecting normal host cells from cytotoxicity. These receptors can belong either to the C-type lectin superfamily or the Ig superfamily, although in humans the majority are members of the Ig superfamily known as killer cell Ig-like receptors (KIRs). Representative uses are described in the "Immune Activity" and "infectious disease" sections below, in Example 11, 13, 14, 16, 18, 19, 20, and 27, and elsewhere herein.

Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g. by boosting immune responses). Expression in cells of lymphoid origin, indicates the natural gene product is involved in immune functions. Therefore it would also be useful as an agent for immunological disorders including arhritis, asthma, immunodeficiency diseases such as AIDS, leukemia, rheumatoid arthritis, granulomatous Disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's Disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Based upon the tissue distribution of this protein, antagonists directed against this protein is useful in blocking the activity of this protein. Accordingly, preferred are antibodies which specifically bind a portion of the translation product of this gene.

Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 1734 of SEQ ID NO:16, b is an integer of 15 to 1748, where both a and b correspond to the positions of nucleotide residues shown in SEQ ID NO:16, and where b is greater than or equal to a+14.

Features of Protein Encoded by Gene No: 7

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as a human integrin alpha 11 homolog derived from a human osteoblast II cDNA library. More particularly, the polypeptide of the present invention has been putatively identified as a human integrin alpha 11-subunit homolog, sometimes hereafter referred to as "integrin alpha 11", "integrin alpha 11-subunit", "a11", "A11-subunit", and/or "Integrin a11-subunit". The invention also relates to inhibiting the action of such polypeptides. The integrins are a large family of cell adhesion molecules consisting of noncovalently associated ab heterodimers.

We have cloned and sequenced a novel human integrin a-subunit cDNA, designated a11. The a11 cDNA encodes a protein with a 22 amino acid signal peptide, a large 1120 residue extracellular domain that contains an I-domain of 207 residues and is linked by a transmembrane domain to a short cytoplasmic domain of 24 amino acids. The deduced a11 protein shows the typical structural features of integrin a-subunits and is similar to a distinct group of a-subunits from collagen-binding integrins. However, it differs from most integrin a-chains by an incompletetely preserved cytoplasmic GFFKR motif.

The human ITGA11 gene was located to bands q22.3-23 on chromosome 15, and its transcripts were found predominantly in bone, cartilage as well as in cardiac and skeletal muscle. Expression of the 5.5 kilobase a11 mRNA was also detectable in ovary and small intestine.

All vertebrate cells express members of the integrin family of cell adhesion molecules, which mediate cellular adhesion to other cells and extracellular subtratum, cell migration and participate in important physiologic processes from signal transduction to cell proliferation and differentiation (Hynes, 92; Springer, 92).

Integrins are structurally homologous heterodimeric type-I membrane glycoproteins formed by the noncovalent association of one of eight b-subunits with one of the 17 different a-subunits described to date, resulting in at least 22 different ab complexes. Their binding specificities for cellular and extracellular ligands are determined by both subunits and are dynamically regulated in a cell-type-specific mode by the cellular environment as well as by the developmental and activation state of the cell {Diamond and Springer, 94}. In integrin a-subunits, the aminoterminal region of the large extracellular domain consists of a seven-fold repeated structure which is predicted to fold into a b-propeller domain {Corbi et al., 1987; Springer, 1997}. The three or four C-terminal repeats contain putative divalent cation binding motifs that are thought to be important for ligand binding and subunit association {Diamond and Springer, 94}. The a1, a2, a 10, aD, aE, aL, aM and aX-subunits contain an approximately 200 amino acid I-domain inserted between the second and third repeat that is not present in other a-chains {Larson et al., 1989}. Several isolated I-domains have been shown to independently bind the ligands of the parent integrin heterodimer {Kamata and Takada, 1994; Randi and Hogg, 1994}. The a3, a5-8, a11b and aV-subunits are proteolytically processed at a conserved site into disulphide-linked heavy and light chains, while the a4-subunit is cleaved at a more aminoterminal site into two fragments that remain noncovalently associated {Hemler et al., 90}. Additional a-subunit variants are generated by alternative splicing of primary transcripts {Ziober et al., 93; Delwel et al., 95; Leung et al., 98}.

The extracellular domains of a-integrin subunits are connected by a single spanning transmembrane domain to short, diverse cytoplasmic domains whose only conserved feature is a membrane-proximal KXGFF(K/R)R motif {Sastry and Horwitz, 1993}. The cytoplasmic domains have been implicated in the cell-type-specific modulation of integrin affinity states {Williams et al., 1994}.

The polypeptide of the present invention has been putatively identified as a member of the integrin family and has been termed integrin alpha 11 subunit ("a11"). This identification has been made as a result of amino acid sequence homology to the human integrin alpha 1 subunit (See Genbank Accession No. gi|346210).

FIGS. 19A-F show the nucleotide (SEQ ID NO:17) and deduced amino acid sequence (SEQ ID NO:35) of a11. Predicted amino acids from about 1 to about 22 constitute the predicted signal peptide (amino acid residues from about 1 to about 22 in SEQ ID NO:35) and are represented by the underlined amino acid regions; amino acids from about 666 to about 682, and/or amino acids from about 1145 to about 1161 constitute the predicted transmembrane domains (amino acids from about 666 to about 682, and/or amino acids from about 1145 to about 1161 in SEQ ID NO:35) and are represented by the double underlined amino acids; and amino acids from about 64 to about 96 constitute the predicted immunoglobulin and major histocompatibility complex protein domain (amino acids from about 64 to about 96 in SEQ ID NO:35) and are represented by the bold amino acids.

FIG. 20 shows the regions of similarity between the amino acid sequences of the integrin alpha 11 subunit (a11) protein (SEQ ID NO:35) and the human integrin alpha 1 subunit (SEQ ID NO: 103).

Figure 21:
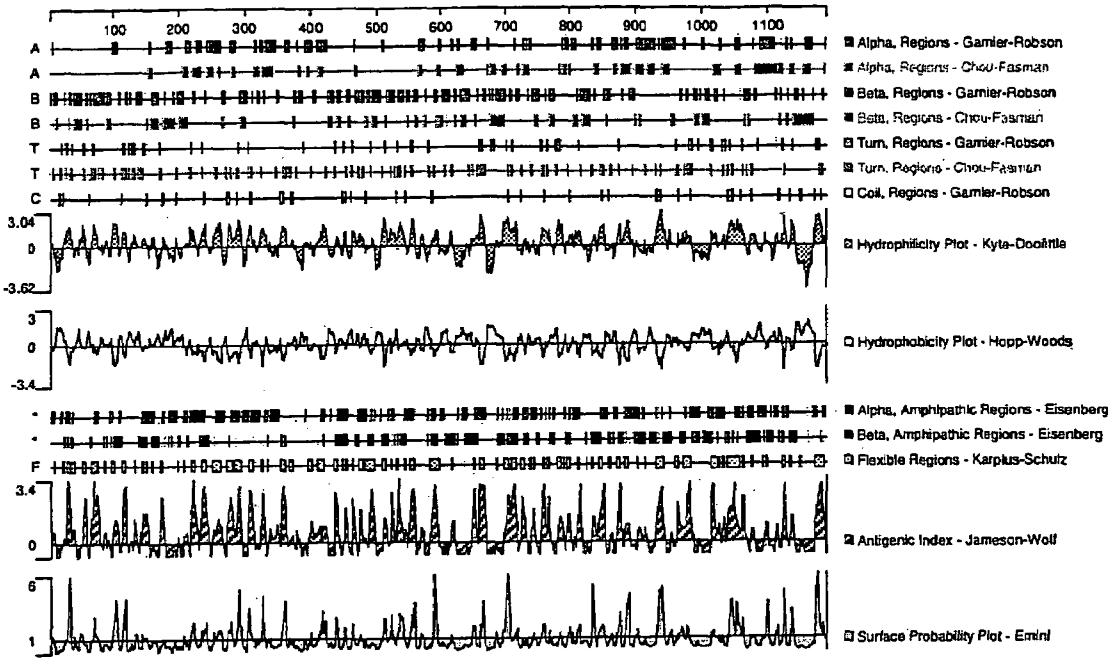
FIG. 21 shows an analysis of the integrin alpha 11 subunit (a11) amino acid sequence. Alpha, beta, turn and coil regions; hydrophilicity and hydrophobicity; amphipathic regions; flexible regions; antigenic index and surface probability are shown.

FIG. 21 shows an analysis of the integrin alpha 11 subunit (a11) amino acid sequence. Alpha, beta, turn and coil regions; hydrophilicity and hydrophobicity; amphipathic regions; flexible regions; antigenic index and surface probability are shown.

Its translation product has homology to the characteristic immunoglobulin and major histocompatibility complex protein domain of integrin family members. As shown in FIGS. 19A-F, a11 has transmembrane domains (the transmembrane domains comprise amino acids 666-682 and/or 1145-1161 of SEQ ID NO:35; which correspond to amino acids 666-682 and/or 1145-1161 of FIGS. 19A-F) with strong conservation between other members of the integrin family. The polynucleotide contains an open reading frame encoding the a11 polypeptide of 1189 amino acids. The present invention exhibits a high degree of homology at the amino acid level to the human integrin alpha 1 subunit (as shown in FIG. 20).

Preferred polypeptides of the invention comprise, or alternatively consist of, the following amino acid sequence: TNGYQKTGDVYKCPVIHGNCTKLNLGRVT LSNV (SEQ ID NO:102). Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred polypeptides of the present invention comprise, or alternatively consist of, one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, or all thirty-three of the immunogenic epitopes shown in SEQ ID NO: 35 as residues: Phe-23 to Arg-31, Leu-62 to Asp-72, Val-96 to Asp-101, Thr-111 to Asn-116, Glu-128 to Thr-135, Val-142 to Ser-149, Asn-217 to Val-222, Glu-233 to Arg-241, Gly-272 to Leu-280, Gln-286 to Thr-293, Tyr-303 to Ile-308, Gly-354 to Thr-360, Glu-408 to Lys-419, Glu-508 to Lys-514, Arg-521 to Val-526, Gly-529 to Phe-542, Asp-551 to Tyr-557, Thr-587 to Thr-593, His-656 to Asp-665, Met-697 to Arg-705, Asp-709 to Thr-716, Glu-755 to Gly-760, Asn-779 to His-786, Leu-810 to Asp-816, Leu-844 to Ala-851, Gln-871 to Gly- 877, Glu-884 to Gln-889, Ser-931 to Asn-943, Ser-974 to Ile-982, Gly-1039 to Gln-1058, Arg-1121 to Arg-1127, Ser-1134 to Trp-1139, and/or Ser-1172 to Pro-1183. Polynucleotides encoding these polypeptides are also encompassed by the invention as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

The present invention provides isolated nucleic acid molecules comprising a polynucleotide encoding the a11 polypeptide having the amino acid sequence shown in FIGS. 19A-F (SEQ ID NO:35). The nucleotide sequence shown in FIGS. 19A-F (SEQ ID NO:35) was obtained by sequencing a cloned cDNA (HOHBY69), which was deposited on Nov. 17 at the American Type Culture Collection, and given Accession Number 203484.

The present invention is further directed to fragments of the isolated nucleic acid molecules described herein. By a fragment of an isolated DNA molecule having the nucleotide sequence of the deposited cDNA or the nucleotide sequence shown in SEQ ID NO:17 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:17. By a fragment at least 20 nt in length, for example, is intended fragments which include 20 or more contiguous bases from the nucleotide sequence of the deposited cDNA or the nucleotide sequence as shown in SEQ ID NO:17. In this context "about" includes the particularly recited size, larger or smaller by several (5, 4, 3, 2, or 1) nucleotides, at either terminus or at both termini. Representative examples of all polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, from about 501 to about 550, from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1350, from about 1351 to about 1400, from about 1401 to about 1450, from about 1451 to about 1500, from about 1501 to about 1550, from about 1551 to about 1600, from about 1601 to about 1650, from about 1651 to about 1700, from about 1701 to about 1750, from about 1751 to about 1800, from about 1801 to about 1850, from about 1851 to about 1900, from about 1901 to about 1950, from about 1951 to about 2000, from about 2001 to about 2050, from about 2051 to about 2100, from about 2101 to about 2150, from about 2151 to about 2200, from about 2201 to about 2250, from about 2251 to about 2300, from about 2301 to about 2350, from about 2351 to about 2400, from about 2401 to about 2450, from about 2451 to about 2500, from about 2501 to about 2550, from about 2551 to about 2600, from about 2601 to about 2650, from about 2651 to about 2700, from about 2701 to about 2750, from about 2751 to about 2800, from about 2801 to about 2850, from about 2851 to about 2900, from about 2901 to about 2950, from about 2951 to about 3000, from about 3001 to about 3050, from about 3051 to about 3100, from about 3101 to about 3150, from about 3151 to about 3200, from about 3201 to about 3250, from about 3251 to about 3300, from about 3301 to about 3350, from about 3351 to about 3400, from about 3401 to about 3450, from about 3451 to about 3500, from about 3501 to about 3550, from about 3551 to about 3600, from about 3601 to about 3650, from about 3651 to about 3700, from about 3701 to about 3750, from about 3751 to about 3800, from about 3801 to about 3850, from about 3851 to about 3900, from about 3901 to about 3950, from about 3951 to about 4000, from about 4001 to about 4050, from about 4051 to about 4100, from about 4101 to about 4150, from about 4151 to about 4200, from about 4201 to about 4250, from about 4251 to about 4300, from about 4301 to about 4350, from about 4351 to about 4400, from about 4401 to about 4450, from about 4451 to about 4500, from about 4501 to about 4550, from about 4551 to about 4600, from about 4601 to about 4650, from about 4651 to about 4700, from about 4701 to about 4750, from about 4751 to about 4800, from about 4801 to about 4850, from about 4851 to about 4900, from about 4901 to about 4950, from about 4951 to about 4995, from about, from about 1 to about 236, from about 144 to about 188, from about 231 to about 276 of SEQ ID NO:17, or the complementary strand thereto, or the cDNA contained in the deposited gene. In this context "about" includes the particularly recited ranges, larger or smaller by several (5, 4, 3, 2, or 1) nucleotides, at either terminus or at both termini.

Preferred nucleic acid fragments of the present invention include nucleic acid molecules encoding a member selected from the group: a polypeptide comprising or alternatively, consisting of, any one of the transmembrane domains (amino acid residues from about 666 to about 682 and/or 1145 to about 1161 in FIGS. 19A-F (amino acids from about 666 to about 682 and/or 1145 to about 1161 in SEQ ID NO:35), in addition to the immunoglobulin and major histocompatibility complex protein domain (amino acid residues from about 64 to about 96 in FIGS. 19A-F (amino acids from about 64 to about 96 in SEQ ID NO:35). Since the location of these domains have been predicted by computer analysis, one of ordinary skill would appreciate that the amino acid residues constituting these domains may vary slightly (e.g., by about 1 to 15 amino acid residues) depending on the criteria used to define each domain. In additional embodiments, the polynucleotides of the invention encode functional attributes of a11.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of the present invention.

The data representing the structural or functional attributes of a11 set forth in FIG. 21 and/or Table VII, as described above, was generated using the various modules and algorithms of the DNA*STAR set on default parameters. In a preferred embodiment, the data presented in columns VIII, IX XIII, and XIV of Table VII can be used to determine regions of a11 which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 21, but may, as shown in Table VII, be represented or identified by using tabular representations of the data presented in FIG. 21. The DNA*STAR computer algorithm used to generate FIG. 21 (set on the original default parameters) was used to present the data in FIG. 21 in a tabular format (See Table VII). The tabular format of the data in FIG. 21 is used to easily determine specific boundaries of a preferred region. The above-mentioned preferred regions set out in FIG. 21 and in Table VII include, but are not limited to, regions of the aforementioned types identified by analysis of the amino acid sequence set out in FIGS. 19A-F. As set out in FIG. 21 and in Table VII, such preferred regions include Gamier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, etc.) may still be retained. For example, the ability of shortened a11 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an a11 mutein with a large number of deleted N-terminal amino acid residues may retain some biological or immunogenic activities. In fact, peptides composed of as few as six a11 amino acid residues may often evoke an immune response.

Accordingly, the present invention further provides polypeptides having one or more residues deleted from the amino terminus of the a11 amino acid sequence shown in FIGS. 19A-F, up to the threonine residue at position number 1184 and polynucleotides encoding such polypeptides. In particular, the present invention provides polypeptides comprising the amino acid sequence of residues n1-1189 of FIGS. 19A-F, where n1 is an integer from 2 to 1184 corresponding to the position of the amino acid residue in FIGS. 19A-F (which is identical to the sequence shown as SEQ ID NO:35). In another embodiment, N-terminal deletions of the all polypeptide can be described by the general formula n2-1189, where n2 is a number from 2 to 1184, corresponding to the position of amino acid identified in FIG. 19. N-terminal deletions of the a11 polypeptide of the invention shown as SEQ ID NO:35 include polypeptides comprising the amino acid sequence of residues: N-terminal deletions of the a11 polypeptide of the invention shown as SEQ ID NO:35 include polypeptides comprising the amino acid sequence of residues: D-2 to E-1189; L-3 to E-1189; P-4 to E-1189; R-5 to E-1189; G-6 to E-1189; L-7 to E-1189; V-9 to E-1189; A-10 to E-1189; W-11 to E-1189; A-12 to E-1189; L-13 to E-1189; S-14 to E-1189; L-15 to E-1189; W-16 to E-1189; P-17 to E-1189; G-18 to E-1189; F-19 to E-1189; T-20 to E-1189; D-21 to E-1189; T-22 to E-1189; F-23 to E-1189; N-24 to E-1189; M-25 to E-1189; D-26 to E-1189; T-27 to E-1189; R-28 to E-1189; K-29 to E-1189; P-30 to E-1189; R-31 to E-1189; V-32 to E-1189; I-33 to E-1189; P-34 to E-1189; G-35 to E-1189; S-36 to E-1189; R-37 to E-1189; T-38 to E-1189; A-39 to E-1189; F-40 to E-1189; F-41 to E-1189; G-42 to E-1189; Y-43 to E-1189; T44 to E-1189; V-45 to E-1189; Q-46 to E-1189; Q-47 to E-1189; H-48 to E-1189; D-49 to E-1189; I-50 to E-1189; S-51 to E-1189; G-52 to E-1189; N-53 to E-1189; K-54 to E-1189; W-55 to E-1189; L-56 to E-1189; V-57 to E-1189; V-58 to E-1189; G-59 to E-1189; A-60 to E-1189; P-61 to E-1189; L-62 to E-1189; E-63 to E-1189; T-64 to E-1189; N-65 to E-1189; G-66 to E-1189; Y-67 to E-1189; Q-68 to E-1189; K-69 to E-1189; T-70 to E-1189; G-71 to E-1189; D-72 to E-1189; V-73 to E-1189; Y-74 to E-1189; K-75 to E-1189; C-76 to E-1189; P-77 to E-1189; V-78 to E-1189; I-79 to E-1189; H-80 to E-1189; G-81 to E-1189; N-82 to E-1189; C-83 to E-1189; T-84 to E-1189; K-85 to E-1189; L-86 to E-1189; N-87 to E-1189; L-88 to E-1189; G-89 to E-1189; R-90 to E-1189; V-91 to E-1189; T-92 to E-1189; L-93 to E-1189; S-94 to E-1189; N-95 to E-1189; V-96 to E-1189; S-97 to E-1189; E-98 to E-1189; R-99 to E-1189; K-100 to E-1189; D-101 to E-1189; N-102 to E-1189; M-103 to E-1189; R-104 to E-1189; L-105 to E-1189; G-106 to E-1189; L-107 to E-1189; S-108 to E-1189; L-109 to E-1189; A-110 to E-1189; T-111 to E-1189; N-112 to E-1189; P-113 to E-1189; K-114 to E-1189; D-115 to E-1189; N-116 to E-1189; S-117 to E-1189; F-118 to E-1189; L-119 to E-1189; A-120 to E-1189; C-121 to E-1189; S-122 to E-1189; P-123 to E-1189; L-124 to E-1189; W-125 to E-1189; S-126 to E-1189; H-127 to E-1189; E-128 to E-1189; C-129 to E-1189; G-130 to E-1189; S-131to E-1189; S-132 to E-1189; Y-133 to E-1189; Y-134 to E-1189; T-135 to E-1189; T-136 to E-1189; G-137 to E-1189; M-138 to E-1189; C-139 to E-1189; S-140 to E-1189; R-141 to E-1189; V-142 to E-1189; N-143 to E-1189; S-144 to E-1189; N-145 to E-1189; F-146 to E-1189; R-147 to E-1189; F-148 to E-1189; S-149 to E-1189; K-150 to E-1189; T-151 to E-1189; V-152 to E-1189; A-153 to E-1189; P-154 to E-1189; A-155 to E-1189; L-156 to E-1189; Q-157 to E-1189; R-158 to E-1189; C-159 to E-1189; Q-160 to E-1189; T-161 to E-1189; Y-162 to E-1189; M-163 to E-1189; D-164 to E-1189; I-165 to E-1189; V-166 to E-1189; I-167 to E-1189; V-168 to E-1189; L-169 to E-1189; D-170 to E-1189; G-171 to E-1189; S-172 to E-1189; N-173 to E-1189; S-174 to E-1189; I-175 to E-1189; Y-176 to E-1189; P-177 to E-1189; W-178 to E-1189; V-179 to E-1189; E-180 to E-1189; V-181 to E-1189; Q-182 to E-1189; H-183 to E-1189; F-184 to E-1189; L-185 to E-1189; I-186 to E-1189; N-187 to E-1189; I-188 to E-1189; L-189 to E-1189; K-190 to E-1189; K-191 to E-1189; F-192 to E-1189; Y-193 to E-1189; I-194 to E-1189; G-195 to E-1189; P-196 to E-1189; G-197 to E-1189; Q-198 to E-1189; I-199 to E-1189; Q-200 to E-1189; V-201 to E-1189; G-202 to E-1189; V-203 to E-1189; V-204 to E-1189; Q-205 to E-1189; Y-206 to E-1189; G-207 to E-1189; E-208 to E-1189; D-209 to E-1189; V-210 to E-1189; V-211 to E-1189; H-212 to E-1189; E-213 to E-1189; F-214 to E-1189; H-215 to E-1189; L-216 to E-1189; N-217 to E-1189; D-218 to E-1189; Y-219 to E-1189; R-220 to E-1189; S-221 to E-1189; V-222 to E-1189; K-223 to E-1189; D-224 to E-1189; V-225 to E-1189; V-226 to E-1189; E-227 to E-1189; A-228 to E-1189; A-229 to E-1189; S-230 to E-1189; H-231 to E-1189; I-232 to E-1189; E-233 to E-1189; Q-234 to E-1189; R-235 to E-1189; G-236 to E-1189; G-237 to E-1189; T-238 to E-1189; E-239 to E-1189; T-240 to E-1189; R-241 to E-1189; T-242 to E-1189; A-243 to E-1189; F-244 to E-1189; G-245 to E-1189; I-246 to E-1189; E-247 to E-1189; F-248 to E-1189; A-249 to E-1189; R-250 to E-1189; S-251 to E-1189; E-252 to E-1189; A-253 to E-1189; F-254 to E-1189; Q-255 to E-1189; K-256 to E-1189; G-257 to E-1189; G-258 to E-1189; R-259 to E-1189; K-260 to E-1189; G-261 to E-1189; A-262 to E-1189; K-263 to E-1189; K-264 to E-1189; V-265 to E-1189; M-266 to E-1189; I-267 to E-1189; V-268 to E-1189; I-269 to E-1189; T-270 to E-1189; D-271 to E-1189; G-272 to E-1189; E-273 to E-1189; S-274 to E-1189; H-275 to E-1189; D-276 to E-1189; S-277 to E-1189; P-278 to E-1189; D-279 to E-1189; L-280 to E-1189; E-281 to E-1189; K-282 to E-1189; V-283 to E-1189; I-284 to E-1189; Q-285 to E-1189; Q-286 to E-1189; S-287 to E-1189; E-288 to E-1189; R-289 to E-1189; D-290 to E-1189; N-291 to E-1189; V-292 to E-1189; T-293 to E-1189; R-294 to E-1189; Y-295 to E-1189; A-296 to E-1189; V-297 to E-1189; A-298 to E-1189; V-299 to E-1189; L-300 to E-1189; G-301 to E-1189; Y-302 to E-1189; Y-303 to E-1189; N-304 to E-1189; R-305 to E-1189; R-306 to E-1189; G-307 to E-1189; I-308 to E-1189; N-309 to E-1189; P-310 to E-1189; E-311 to E-1189; T-312 to E-1189; F-313 to E-1189; L-314 to E-1189; N-315 to E-1189; E-316 to E-1189; I-317 to E-1189; K-318 to E-1189; Y-319 to E-1189; I-320 to E-1189; A-321 to E-1189; S-322 to E-1189; D-323 to E-1189; P-324 to E-1189; D-325 to E-1189; D-326 to E-1189; K-327 to E-1189; H-328 to E-1189; F-329 to E-1189; F-330 to E-1189; N-331 to E-1189; V-332 to E-1189; T-333 to E-1189; D-334 to E-1189; E-335 to E-1189; A-336 to E-1189; A-337 to E-1189; L-338 to E-1189; K-339 to E-1189; D-340 to E-1189; I-341 to E-1189; V-342 to E-1189; D-343 to E-1189; A-344 to E-1189; L-345 to E-1189; G-346 to E-1189; D-347 to E-1189; R-348 to E-1189; I-349 to E-1189; F-350 to E-1189; S-351 to E-1189; L-352 to E-1189; E-353 to E-1189; G-354 to E-1189; T-355 to E-1189; N-356 to E-1189; K-357 to E-1189; N-358 to E-1189; E-359 to E-1189; T-360 to E-1189; S-361 to E-1189; F-362 to E-1189; G-363 to E-1189; L-364 to E-1189; E-365 to E-1189; M-366 to E-1189; S-367 to E-1189; Q-368 to E-1189; T-369 to E-1189; G-370 to E-1189; F-371 to E-1189; S-372 to E-1189; S-373 to E-1189; H-374 to E-1189; V-375 to E-1189; V-376 to E-1189; E-377 to E-1189; D-378 to E-1189; G-379 to E-1189; V-380 to E-1189; L-381 to E-1189; L-382 to E-1189; G-383 to E-1189; A-384 to E-1189; V-385 to E-1189; G-386 to E-1189; A-387 to E-1189; Y-388 to E-1189; D-389 to E-1189; W-390 to E-1189; N-391 to E-1189; G-392 to E-1189; A-393 to E-1189; V-394 to E-1189; L-395 to E-1189; K-396 to E-1189; E-397 to E-1189; T-398 to E-1189; S-399 to E-1189; A-400 to E-1189; G-401 to E-1189; K-402 to E-1189; V-403 to E-1189; I-404 to E-1189; P-405 to E-1189; L-406 to E-1189; R-407 to E-1189; E-408 to E-1189; S-409 to E-1189; Y-410 to E-1189; L-411 to E-1189; K-412 to E-1189; E-413 to E-1189; F-414 to E-1189; P-415 to E-1189; E-416 to E-1189; E-417 to E-1189; L-418 to E-1189; K-419 to E-1189; N-420 to E-1189; H-421 to E-1189; G-422 to E-1189; A-423 to E-1189; Y-424 to E-1189; L-425 to E-1189; G-426 to E-1189; Y-427 to E-1189; T-428 to E-1189; V-429 to E-1189; T-430 to E-1189; S-431 to E-1189; V-432 to E-1189; V-433 to E-1189; S-434 to E-1189; S-435 to E-1189; R-436 to E-1189; Q-437 to E-1189; G-438 to E-1189; R-439 to E-1189; V-440 to E-1189; Y-441 to E-1189; V-442 to E-1189; A-443 to E-1189; G-444 to E-1189; A-445 to E-1189; P-446 to E-1189; R-447 to E-1189; F-448 to E-1189; N-449 to E-1189; H-450 to E-1189; T-451 to E-1189; G-452 to E-1189; K-453 to E-1189; V-454 to E-1189; I-455 to E-1189; L-456 to E-1189; F-457 to E-1189; T-458 to E-1189; M-459 to E-1189; H-460 to E-1189; N-461 to E-1189; N-462 to E-1189; R-463 to E-1189; S-464 to E-1189; L-465 to E-1189; T-466 to E-1189; I-467 to E-1189; H-468 to E-1189; Q-469 to E-1189; A-470 to E-1189; M-471 to E-1189; R-472 to E-1189; G-473 to E-1189; Q-474 to E-1189; Q-475 to E-1189; I-476 to E-1189; G-477 to E-1189; S-478 to E-1189; Y-479 to E-1189; F-480 to E-1189; G-481 to E-1189; S-482 to E-1189; E-483 to E-1189; I-484 to E-1189; T-485 to E-1189; S-486 to E-1189; V-487 to E-1189; D-488 to E-1189; I-489 to E-1189; D-490 to E-1189; G-491 to E-1189; D-492 to E-1189; G-493 to E-1189; V-494 to E-1189; T-495 to E-1189; D-496 to E-1189; V-497 to E-1189; L-498 to E-1189; L-499 to E-1189; V-500 to E-1189; G-501 to E-1189; A-502 to E-1189; P-503 to E-1189; M-504 to E-1189; Y-505 to E-1189; F-506 to E-1189; N-507 to E-1189; E-508 to E-1189; G-509 to E-1189; R-510 to E-1189; E-511 to E-1189; R-512 to E-1189; G-513 to E-1189; K-514 to E-1189; V-515 to E-1189; Y-516 to E-1189; V-517 to E-1189; Y-518 to E-1189; E-519 to E-1189; L-520 to E-1189; R-521 to E-1189; Q-522 to E-1189; N-523 to E-1189; R-524 to E-1189; F-525 to E-1189; V-526 to E-1189; Y-527 to E-1189; N-528 to E-1189; G-529 to E-1189; T-530 to E-1189; L-531 to E-1189; K-532 to E-1189; D-533 to E-1189; S-534 to E-1189; H-535 to E-1189; S-536 to E-1189; Y-537 to E-1189; Q-538 to E-1189; N-539 to E-1189; A-540 to E-1189; R-541 to E-1189; F-542 to E-1189; G-543 to E-1189; S-544 to E-1189; S-545 to E-1189; I-546 to E-1189; A-547 to E-1189; S-548 to E-1189; V-549 to E-1189; R-550 to E-1189; D-551 to E-1189; L-552 to E-1189; N-553 to E-1189; Q-554 to E-1189; D-555 to E-1189; S-556 to E-1189; Y-557 to E-1189; N-558 to E-1189; D-559 to E-1189; V-560 to E-1189; V-561 to E-1189; V-562 to E-1189; G-563 to E-1189; A-564 to E-1189; P-565 to E-1189; L-566 to E-1189; E-567 to E-1189; D-568 to E-1189; N-569 to E-1189; H-570 to E-1189; A-571 to E-1189; G-572 to E-1189; A-573 to E-1189; I-574 to E-1189; Y-575 to E-1189; I-576 to E-1189; F-577 to E-1189; H-578 to E-1189; G-579 to E-1189; F-580 to E-1189; R-581 to E-1189; G-582 to E-1189; S-583 to E-1189; I-584 to E-1189; L-585 to E-1189; K-586 to E-1189; T-587 to E-1189; P-588 to E-1189; K-589 to E-1189; Q-590 to E-1189; R-591 to E-1189; I-592 to E-1189; T-593 to E-1189; A-594 to E-1189; S-595 to E-1189; E-596 to E-1189; L-597 to E-1189; A-598 to E-1189; T-599 to E-1189; G-600 to E-1189; L-601 to E-1189; Q-602 to E-1189; Y-603 to E-1189; F-604 to E-1189; G-605 to E-1189; C-606 to E-1189; S-607 to E-1189; I-608 to E-1189; H-609 to E-1189; G-610 to E-1189; Q-611 to E-1189; L-612 to E-1189; D-613 to E-1189; L-614 to E-1189; N-615 to E-1189; E-616 to E-1189; D-617 to E-1189; G-618 to E-1189; L-619 to E-1189; I-620 to E-1189; D-621 to E-1189; L-622 to E-1189; A-623 to E-1189; V-624 to E-1189; G-625 to E-1189; A-626 to E-1189; L-627 to E-1189; G-628 to E-1189; N-629 to E-1189; A-630 to E-1189; V-631 to E-1189; I-632 to E-1189; L-633 to E-1189; W-634 to E-1189; S-635 to E-1189; R-636 to E-1189; P-637 to E-1189; V-638 to E-1189; V-639 to E-1189; Q-640 to E-1189; I-641 to E-1189; N-642 to E-1189; A-643 to E-1189; S-644 to E-1189; L-645 to E-1189; H-646 to E-1189; F-647 to E-1189; E-648 to E-1189; P-649 to E-1189; S-650 to E-1189; K-651 to E-1189; I-652 to E-1189; N-653 to E-1189; I-654 to E-1189; F-655 to E-1189; H-656 to E-1189; R-657 to E-1189; D-658 to E-1189; C-659 to E-1189; K-660 to E-1189; R-661 to E-1189; S-662 to E-1189; G-663 to E-1189; R-664 to E-1189; D-665 to E-1189; A-666 to

E-1189; T-667 to E-1189; C-668 to E-1189; L-669 to E-1189; A-670 to E-1189; A-671 to E-1189; F-672 to E-1189; L-673 to E-1189; C-674 to E-1189; F-675 to E-1189; T-676 to E-1189; P-677 to E-1189; I-678 to E-1189; F-679 to E-1189; L-680 to E-1189; A-681 to E-1189; P-682 to E-1189; H-683 to E-1189; F-684 to E-1189; Q-685 to E-1189; T-686 to E-1189; T-687 to E-1189; T-688 to E-1189; V-689 to E-1189; G-690 to E-1189; I-691 to E-1189; R-692 to E-1189; Y-693 to E-1189; N-694 to E-1189; A-695 to E-1189; T-696 to E-1189; M-697 to E-1189; D-698 to E-1189; E-699 to E-1189; R-700 to E-1189; R-701 to E-1189; Y-702 to E-1189; T-703 to E-1189; P-704 to E-1189; R-705 to E-1189; A-706 to E-1189; H-707 to E-1189; L-708 to E-1189; D-709 to E-1189; E-710 to E-1189; G-711 to E-1189; G-712 to E-1189; D-713 to E-1189; R-714 to E-1189; F-715 to E-1189; T-716 to E-1189; N-717 to E-1189; R-718 to E-1189; A-719 to E-1189; V-720 to E-1189; L-721 to E-1189; L-722 to E-1189; S-723 to E-1189; S-724 to E-1189; G-725 to E-1189; Q-726 to E-1189; E-727 to E-1189; L-728 to E-1189; C-729 to E-1189; E-730 to E-1189; R-731 to E-1189; I-732 to E-1189; N-733 to E-1189; F-734 to E-1189; H-735 to E-1189; V-736 to E-1189; L-737 to E-1189; D-738 to E-1189; T-739 to E-1189; A-740 to E-1189; D-741 to E-1189; Y-742 to E-1189; V-743 to E-1189; K-744 to E-1189; P-745 to E-1189; V-746 to E-1189; T-747 to E-1189; F-748 to E-1189; S-749 to E-1189; V-750 to E-1189; E-751 to E-1189; Y-752 to E-1189; S-753 to E-1189; L-754 to E-1189; E-755 to E-1189; D-756 to E-1189; P-757 to E-1189; D-758 to E-1189; H-759 to E-1189; G-760 to E-1189; P-761 to E-1189; M-762 to E-1189; L-763 to E-1189; D-764 to E-1189; D-765 to E-1189; G-766 to E-1189; W-767 to E-1189; P-768 to E-1189; T-769 to E-1189; T-770 to E-1189; L-771 to E-1189; R-772 to E-1189; V-773 to E-1189; S-774 to E-1189; V-775 to E-1189; P-776 to E-1189; F-777 to E-1189; W-778 to E-1189; N-779 to E-1189; G-780 to E-1189; C-781 to E-1189; N-782 to E-1189; E-783 to E-1189; D-784 to E-1189; E-785 to E-1189; H-786 to E-1189; C-787 to E-1189; V-788 to E-1189; P-789 to E-1189; D-790 to E-1189; L-791 to E-1189; V-792 to E-1189; L-793 to E-1189; D-794 to E-1189; A-795 to E-1189; R-796 to E-1189; S-797 to E-1189; D-798 to E-1189; L-799 to E-1189; P-800 to E-1189; T-801 to E-1189; A-802 to E-1189; M-803 to E-1189; E-804 to E-1189; Y-805 to E-1189; C-806 to E-1189; Q-807 to E-1189; R-808 to E-1189; V-809 to E-1189; L-810 to E-1189; R-811 to E-1189; K-812 to E-1189; P-813 to E-1189; A-814 to E-1189; Q-815 to E-1189; D-816 to E-1189; C-817 to E-1189; S-818 to E-1189; A-819 to E-1189; Y-820 to E-1189; T-821 to E-1189; L-822 to E-1189; S-823 to E-1189; F-824 to E-1189; D-825 to E-1189; T-826 to E-1189; T-827 to E-1189; V-828 to E-1189; F-829 to E-1189; I-830 to E-1189; I-831 to E-1189; E-832 to E-1189; S-833 to E-1189; T-834 to E-1189; R-835 to E-1189; Q-836 to E-1189; R-837 to E-1189; V-838 to E-1189; A-839 to E-1189; V-840to E-1189; E-841 to E-1189; A-842 to E-1189; T-843 to E-1189; L-844 to E-1189; E-845 to 1189; N-846 to E-1189; R-847 to E-1189; G-848 to E-1189; E-849 to E-1189; N-850 to E-1189; A-851 to E-1189; Y-852 to E-1189; S-853 to E-1189; T-854 to E-1189; V-855 to E-1189; L-856 to E-1189; N-857 to E-1189; I-858 to E-1189; S-859 to E-1189; Q-860 to E-1189; S-861 to E-1189; A-862 to E-1189; N-863 to E-1189; L-864 to E-1189; Q-865 to E-1189; F-866 to E-1189; A-867 to E-1189; S-868 to E-1189; L-869 to E-1189; I-870 to E-1189; Q-871 to E-1189; K-872 to E-1189; E-873 to E-1189; D-874 to E-1189; S-875 to E-1189; D-876 to E-1189; G-877 to E-1189; S-878 to E-1189; I-879 to E-1189; E-880 to E-1189; C-881 to E-1189; V-882 to E-1189; N-883 to E-1189; E-884 to E-1189; E-885 to E-1189; R-886 to E-1189; R-887 to E-1189; L-888 to E-1189; Q-889 to E-1189; K-890 to E-1189; Q-891 to E-1189; V-892 to E-1189; C-893 to E-1189; N-894 to E-1189; V-895 to E-1189; S-896 to E-1189; Y-897 to E-1189; P-898 to E-1189; F-899 to E-1189; F-900 to E-1189; R-901 to E-1189; A-902 to E-1189; K-903 to E-1189; A-904 to E-1189; K-905 to E-1189; V-906 to E-1189; A-907 to E-1189; F-908 to E-1189; R-909 to E-1189; L-910 to E-1189; D-911 to E-1189; F-912 to E-1189; E-913 to E-1189; F-914 to E-1189; S-915 to E-1189; K-916 to E-1189; S-917 to E-1189; I-918 to E-1189; F-919 to E-1189; L-920 to E-1189; H-921 to E-1189; H-922 to E-1189; L-923 to E-1189; E-924 to E-1189; I-925 to E-1189; E-926 to E-1189; L-927 to E-1189; A-928 to E-1189; A-929 to E-1189; G-930 to E-1189; S-931 to E-1189; D-932 to E-1189; S-933 to E-1189; N-934 to E-1189; E-935 to E-1189; R-936 to E-1189; D-937 to E-1189; S-938 to E-1189; T-939 to E-1189; K-940 to E-1189; E-941 to E-1189; D-942 to E-1189; N-943 to E-1189; V-944 to E-1189; A-945 to E-1189; P-946 to E-1189; L-947 to E-1189; R-948 to E-1189; F-949 to E-1189; H-950 to E-1189; L-951 to E-1189; K-952 to E-1189; Y-953 to E-1189; E-954 to E-1189; A-955 to E-1189; D-956 to E-1189; V-957 to E-1189; L-958 to E-1189; F-959 to E-1189; T-960 to E-1189; R-961 to E-1189; S-962 to E-1189; S-963 to E-1189; S-964 to E-1189; L-965 to E-1189; S-966 to E-1189; H-967 to E-1189; Y-968 to E-1189; E-969 to E-1189; V-970 to E-1189; K-971 to E-1189; L-972 to E-1189; N-973 to E-1189; S-974 to E-1189; S-975 to E-1189; L-976 to E-1189; E-977 to E-1189; R-978 to E-1189; Y-979 to E-1189; D-980 to E-1189; G-981 to E-1189; I-982 to E-1189; G-983 to E-1189; P-984 to E-1189; P-985 to E-1189; F-986 to E-1189; S-987 to E-1189; C-988 to E-1189; I-989 to E-1189; F-990 to E-1189; R-991 to E-1189; I-992 to E-1189; Q-993 to E-1189; N-994 to E-1189; L-995 to E-1189; G-996 to E-1189; L-997 to E-1189; F-998 to E-1189; P-999 to E-1189; I-1000 to E-1189; H-1001 to E-1189; G-1002 to E-1189; I-1003 to E-1189; M-1004 to E-1189; M-1005 to E-1189; K-1006 E-1189; I-1007 to E-1189; T-1008 to E-1189; I-1009 to E-1189; P-1010 to E-1189; I-1011 to E-1189; A-1012 to E-1189; T-1013 to E-1189; R-1014 to E-1189; S-1015 to E-1189; G-1016 to E-1189; N-1017 to E-1189; R-1018 to E-1189; L-1019 to E-1189; L-1020 to E-1189; K-1021 to E-1189; L-1022 to E-1189; R-1023 to E-1189; D-1024 to E-1189; F-1025 to E-1189; L-1026 to E-1189; T-1027 to E-1189; D-1028 to E-1189; E-1029 to E-1189; V-1030 to E-1189; A-1031 to E-1189; N-1032 to E-1189; T-1033 to E-1189; S-1034 to E-1189; C-1035 to E-1189; N-1036 to E-1189; I-1037 to E-1189; W-1038 to E-1189; G-1039 to E-1189; N-1040 to E-1189; S-1041 to E-1189; T-1042 to E-1189; E-1043 to E-1189; Y-1044 to E-1189; R-1045 to E-1189; P-1046 to E-1189; T-1047 to E-1189; P-1048 to E-1189; V-1049 to E-1189; E-1050 to E-1189; E-1051 to E-1189; D-1052 to E-1189; L-1053 to E-1189; R-1054 to E-1189; R-1055 to E-1189; A-1056 to E-1189; P-1057 to E-1189; Q-1058 to E-1189; L-1059 to E-1189; N-1060 to E-1189; H-1061 to E-1189; S-1062 to E-1189; N-1063to E-1189; S-1064to E-1189; D-1065 to E-1189; V-1066 to E-1189; V-1067 to E-1189; S-1068 to E-1189; I-1069 to E-1189; N-1070 to E-1189; C-1071 to E-1189; N-1072 to E-1189; I-1073 to E-1189; R-1074 to E-1189; L-1075 to E-1189; V-1076 to E-1189; P-1077 to E-1189; N-1078 to E-1189; Q-1079 to E-1189; E-1080 to E-1189; I-1081 to E-1189; N-1082 to E-1189; F-1083 to E-1189; H-1084 to E-1189; L-1085 to E-1189; L-1086 to E-1189; G-1087 to E-1189; N-1088 to E-1189; L-1089 to E-1189; W-1090to E-1189; L-1091 to E-1189; R-1092 to E-1189; S-1093 to E-1189; L-1094 to E-1189; K-1095 to E-1189; A-1096 to E-1189; L-1097 to E-1189; K-1098 to E-1189; Y-1099 to

E-1189; K-1100 to E-1189; S-1101 to E-1189; M-1102 to E-1189; K-1103 to E-1189; I-1104 to E-1189; M-1105 to E-1189; V-1106 to E-1189; N-1107 to E-1189; A-1108 to E-1189; A-1109 to E-1189; L-1110to E-1189; Q-1111 to E-1189; R-1112 to E-1189; Q-1113 to E-1189; F-1114 to E-1189; H-1115 to E-1189; S-1116 to E-1189; P-1117 to E-1189; F-1118 to E-1189; I-1119 to E-1189; F-1120 to E-1189; R-1121 to E-1189; E-1122 to E-1189; E-1123 to E-1189; D-1124 to E-1189; P-1125 to E-1189; S-1126 to E-1189; R-1127 to E-1189; Q-1128 to E-1189; I-1129 to E-1189; V-1130 to E-1189; F-1131 to E-1189; E-1132 to E-1189; I-1133 to E-1189; S-1134 to E-1189; K-1135 to E-1189; Q-1136 to E-1189; E-1137 to E-1189; D-1138 to E-1189; W-1139 to E-1189; Q-1140 to E-1189; V-1141 to E-1189; P-1142 to E-1189; I-1143 to E-1189; W-1144 to E-1189; I-1145 to E-1189; I-1146 to E-1189; V-1147 to E-1189; G-1148 to E-1189; S-1149 to E-1189; T-1150 to E-1189; L-1151 to E-1189; G-1152 to E-1189; G-1153 to E-1189; L-1154 to E-1189; L-1155 to E-1189; L-1156 to E-1189; L-1157 to E-1189; A-1158 to E-1189; L-1159 to E-1189; L-1160 to E-1189; V-1161 to E-1189; L-1162 to E-1189; A-1163 to E-1189; L-1164 to E-1189; W-1165 to E-1189; K-1166 to E-1189; L-1167 to E-1189; G-1168 to E-1189; F-1169 to E-1189; F-1170 to E-1189; R-1171 to E-1189; S-1172 to E-1189; A-1173 to E-1189; R-1174 to E-1189; R-1175 to E-1189; R-1176 to E-1189; R-1177 to E-1189; E-1178 to E-1189; P-1179 to E-1189; G-1180 to E-1189; L-1181 to E-1189; D-1182 to E-1189; P-1183 to E-1189; T-1184 to E-1189; of SEQ ID NO:35. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities (e.g., biological activities (e.g., ability to illicit mitogenic activity, induce differentiation of normal or malignant cells, ability to multimerize, etc.) may still be retained. For example the ability of the shortened a11 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an a11 mutein with a large number of deleted C-terminal amino acid residues may retain some biological or immunogenic activities. In fact, peptides composed of as few as six a11 amino acid residues may often evoke an immune response.

Accordingly, the present invention further provides polypeptides having one or more residues deleted from the carboxy terminus of the amino acid sequence of the all polypeptide shown in FIGS. 19A-F, up to the glycine residue at position number 6, and polynucleotides encoding such polypeptides. In particular, the present invention provides polypeptides comprising the amino acid sequence of residues 1-m1 of FIGS. 19A-F, where m1 is an integer from 6 to 1189 corresponding to the position of the amino acid residue in FIGS. 19A-F. Moreover, the invention provides polynucleotides encoding polypeptides comprising, or alternatively consisting of, the amino acid sequence of C-terminal deletions of the al I polypeptide of the invention shown as SEQ ID NO:35 include polypeptides comprising the amino acid sequence of residues: M-1 to L-1188; M-1 to V-1187; M-1 to K-1186; M-1 to P-1185; M-1 to T-1184; M-1 to P-1183; M-1 to D-1182; M-1 to L-1181; M-1 to G-1180; M-1 to P-1179; M-1 to E-1178; M-1 to R-1177; M-1 to R-1176; M-1 to R-1175; M-1 to R-1174; M-1 to A-1173; M-1 to S-1172; M-1 to R-1171; M-1 to F-1170; M-1 to F-1169; M-1 to G-1168; M-1 to L-1167; M-1 to K-1166; M-1 to W-1165; M-1 to L-1164; M-1 to A-1163; M-1 to L-1162; M-1 to V-1161; M-1 to L-1160; M-1 to L-1159; M-1 to A-1158; M-1 to L-1157; M-1 to L-1156; M-1 to L-1155; M-1 to L-1154; M-1 to G-1153; M-1 to G-1152; M-1 to L-1151; M-1 to T-1150; M-1 to S-1149; M-1 to G-1148; M-1 to V-1147; M-1 to I-1146; M-1 to I-1145; M-1 to W-1144; M-1 to I-1143; M-1 to P-1142; M-1 to V-1141; M-1 to Q-1140; M-1 to W-1139; M-1 to D-1138; M-1 to E-1137; M-1 to Q-1136; M-1 to K-1135; M-1 to S-1134; M-1 to I-1133; M-1 to E-1132; M-1 to F-1131; M-1 to V-1130; M-1 to I-1129; M-1 to Q-1128; M-1 to R-1127; M-1 to S-1126; M-1 to P-1125; M-1 to D-1124; M-1 to E-1123; M-1 to E-1122; M-1 to R-1121; M-1 to F-1120; M-1 to I-1119; M-1 to F-1118; M-1 to P-1117; M-1 to S-1116; M-1 to H-1115; M-1 to F-1114; M-1 to Q-1113; M-1 to R-1112; M-1 to Q-1111; M-1 to L-1110; M-1 to A-1109; M-1 to A-1108; M-1 to N-1107; M-1 to V-1106; M-1 to M-1105; M-1 to I-1104; M-1 to K-1103; M-1 to M-1102; M-1 to S-1101; M-1 to K-1100; M-1 to Y-1099; M-1 to K-1098; M-1 to L-1097; M-1 to A-1096; M-1 to K-1095; M-1 to L-1094; M-1 to S-1093; M-1 to R-1092; M-1 to L-1091; M-1 to W-1090; M-1 to L-1089; M-1 to N-1088; M-1 to G-1087; M-1 to L-1086; M-1 to L-1085; M-1 to H-1084; M-1 to F-1083; M-1 to N-1082; M-1 to I-1081; M-1 to E-1080; M-1 to Q-1079; M-1 to N-1078; M-1 to P-1077; M-1 to V-1076; M-1 to L-1075; M-1 to R-1074; M-1 to I-1073; M-1 to N-1072; M-1 to C-1071; M-1 to N-1070; M-1 to I-1069; M-1 to S-1068; M-1 to V-1067; M-1 to V-1066; M-1 to D-1065; M-1 to S-1064; M-1 to N-1063; M-1 to S-1062; M-1 to H-1061; M-1 to N-1060; M-1 to L-1059; M-1 to Q-1058; M-1 to P-1057; M-1 to A-1056; M-1 to R-1055; M-1 to R-1054; M-1 to L-1053; M-1 to D-1052; M-1 to E-1051; M-1 to E-1050; M-1 to V-1049; M-1 to P-1048; M-1 to T-1047; M-1 to P-1046; M-1 to R-1045; M-1 to Y-1044; M-1 to E-1043; M-1 to T-1042; M-1 to S-1041; M-1 to N-1040; M-1 to G-1039; M-1 to W-1038; M-1 to I-1037; M-1 to N-1036; M-1 to C-1035; M-1 to S-1034; M-1 to T-1033; M-1 *to N*-1032; M-1 to A-1031; M-1 to V-1030; M-1 to E-1029; M-1 to D-1028; M-1 to T-1027; M-1 to L-1026; M-1 to F-1025; M-1 to D-1024; M-1 to R-1023; M-1 to L-1022; M-1 to K-1021; M-1 to L-1020; M-1 to L-1019; M-1 to R-1018; M-1 to N-1017; M-1 to G-1016; M-1 to S-1015; M-1 to R-1014; M-1 to T-1013; M-1 to A-1012; M-1 to I-1011; M-1 to P-1010; M-1 to I-1009; M-1 to T-1008; M-1 to I-1007; M-1 to K-1006; M-1 to M-1005; M-1 to M-1004; M-1 to I-1003; M-1 to G-1002; M-1 to H-1001; M-1 to I-1000; M-1 to P-999; M-1 to F-998; M-1 to L-997; M-1 to G-996; M-1 to L-995; M-1 to N-994; M-1 to Q-993; M-1 to I-992; M-1 to R-991; M-1 to F-990; M-1 to I-989; M-1 to C-988; M-1 to S-987; M-1 to F-986; M-1 to P-985; M-1 to P-984; M-1 to G-983; M-1 to I-982; M-1 to G-981; M-1 to D-980; M-1 to Y-979; M-1 to R-978; M-1 to E-977; M-1 to L-976; M-1 to S-975; M-1 to S-974; M-1 to N-973; M-1 to L-972; M-1 to K-971; M-1 to V-970; M-1 to E-969; M-1 to Y-968; M-1 to H-967; M-1 to S-966; M-1 to L-965; M-1 to S-964; M-1 to S-963; M-1 to S-962; M-1 to R-961; M-1 to T-960; M-1 to F-959; M-1 to L-958; M-1 to V-957; M-1 to D-956; M-1 to A-955; M-1 to E-954; M-1 to Y-953; M-1 to K-952; M-1 to L-951; M-1 to H-950; M-1 to F-949; M-1 to R-948; M-1 to L-947; M-1 to A-946; M-1 to A-945; M-1 to V-944; M-1 to N-943; M-1 to D-942; M-1 to E-941; M-1 to K-940; M-1 to T-939; M-1 to S-938; M-1 to D-937; M-1 to R-936; M-1 to E-935; M-1 to N-934; M-1 to S-933; M-1 to D-932; M-1 to S-931; M-1 to G-930; M-1 to A-929; M-1 to A-928; M-1 to L-927; M-1 to E-926; M-1 to I-925; M-1 to E-924; M-1 to L-923; M-1 to H-922; M-1 to H-921; M-1 to L-920; M-1 to F-919; M-1 to I-918; M-1 to S-917; M-1 to K-916; M-1 to S-915; M-1 to F-914; M-1 to E-913; M-1 to F-912; M-1 to D-911; M-1 to L-910; M-1 to R-909; M-1 to F-908; M-1 to A-907; M-1 to V-906; M-1 to K-905; M-1 to A-904; M-1 to K-903; M-1 to A-902; M-1 to R-901; M-1 to F-900; M-1 to F-899; M-1 to P-898; M-1 to Y-897; M-1 to S-896; M-1 to V-895; M-1 to N-894; M-1 to C-893; M-1 to V-892; M-1 to Q-891; M-1 to K-890; M-1 to Q-889; M-1 to L-888; M-1 to R-887; M-1 to R-886; M-1 to E-885; M-1 to E-884; M-1 to N-883; M-1 to V-882; M-1 to C-881; M-1 to E-880; M-1 to I-879; M-1 to S-878; M-1 to G-877; M-1 to D-876; M-1 to S-875; M-1 to D-874; M-1 to E-873; M-1 to K-872; M-1 to Q-871; M-1 to I-870; M-1 to L-869; M-1 to S-868; M-1 to A-867; M-1 to F-866; M-1 to Q-865; M-1 to L-864; M-1 to N-863; M-1 to A-862; M-1 to S-861; M-1 to Q-860; M-1 to S-859; M-1 to I-858; M-1 to N-857; M-1 to L-856; M-1 to V-855; M-1 to T-854; M-1 to S-853; M-1 to Y-852; M-1 to A-851; M-1 to N-850; M-1 to E-849; M-1 to G-848; M-1 to R-847; M-1 to N-846; M-1 to E-845; M-1 to L-844; M-1 to T-843; M-1 to A-842; M-1 to E-841; M-1 to V-840; M-1 to A-839; M-1 to V-838; M-1 to R-837; M-1 to Q-836; M-1 to R-835; M-1 to T-834; M-1 to S-833; M-1 to E-832; M-1 to I-831; M-1 to I-830; M-1 to F-829; M-1 to V-828; M-1 to T-827; M-1 to T-826; M-1 to D-825; M-1 to F-824; M-1 to S-823; M-1 to L-822; M-1 to T-821; M-1 to Y-820; M-1 to A-819; M-1 to S-818; M-1 to C-817; M-1 to D-816; M-1 to Q-815; M-1 to A-814; M-1 to P-813; M-1 to K-812; M-1 to R-811; M-1 to L-810; M-1 to V-809; M-1 to R-808; M-1 to Q-807; M-1 to C-806; M-1 to Y-805; M-1 to E-804; M-1 to M-803; M-1 to A-802; M-1 to T-801; M-1 to P-800; M-1 to L-799; M-1 to D-798; M-1 to S-797; M-1 to R-796; M-1 to A-795; M-1 to D-794; M-1 to L-793; M-1 to V-792; M-1 to L-791; M-1 to D-790; M-1 to P-789; M-1 to V-788; M-1 to C-787; M-1 to H-786; M-1 to E-785; M-1 to D-784; M-1 to E-783; M-1 to N-782; M-1 to C-781; M-1 to G-780; M-1 to N-779; M-1 to W-778; M-1 to F-777; M-1 to P-776; M-1 to V-775; M-1 to S-774; M-1 to V-773; M-1 to R-772; M-1 to L-771; M-1 to T-770; M-1 to T-769; M-1 to P-768; M-1 to W-767; M-1 to G-766; M-1 to D-765; M-1 to D-764; M-1 to L-763; M-1 to M-762; M-1 to P-761; M-1 to G-760; M-1 to H-759; M-1 to D-758; M-1 to P-757; M-1 to D-756; M-1 to E-755; M-1 to L-754; M-1 to S-753; M-1 to Y-752; M-1 to E-751; M-1 to V-750; M-1 to S-749; M-1 to F-748; M-1 to T-747; M-1 to V-746; M-1 to P-745; M-1 to K-744; M-1 to V-743; M-1 to Y-742; M-1 to D-741; M-1 to A-740; M-1 to T-739; M-1 to D-738; M-1 to L-737; M-1 to V-736; M-1 to H-735; M-1 to F-734; M-1 to N-733; M-1 to I-732; M-1 to R-731; M-1 to E-730; M-1 to C-729; M-1 to L-728; M-1 to E-727; M-1 to Q-726; M-1 to G-725; M-1 to S-724; M-1 to S-723; M-1 to L-722; M-1 to L-721; M-1 to V-720; M-1 to A-719; M-1 to R-718; M-1 to N-717; M-1 to T-716; M-1 to F-715; M-1 to R-714; M-1 to D-713; M-1 to G-712; M-1 to G-711; M-1 to E-710; M-1 to D-709; M-1 to L-708; M-1 to H-707; M-1 to A-706; M-1 to R-705; M-1 to P-704; M-1 to T-703; M-1 to Y-702; M-1 to R-701; M-1 to R-700; M-1 to E-699; M-1 to D-698; M-1 to M-697; M-1 to T-696; M-1 to A-695; M-1 to N-694; M-1 to Y-693; M-1 to R-692; M-1 to I-691; M-1 to G-690; M-1 to V-689; M-1 T-688; M-1 to T-687; M-1 to T-686; M-1 to Q-685; M-1 to F-684; M-1 to H-683; M-1 to P-682; M-1 to A-681; M-1 to L-680; M-1 to F-679; M-1 to I-678; M-1 to P-677; M-1 to T-676; M-1 to F-675; M-1 to C-674; M-1 to L-673; M-1 to F-672; M-1 to A-671; M-1 to A-670; M-1 to L-669; M-1 to C-668; M-1 to T-667; M-1 to A-666; M-1 to D-665; M-1 to R-664; M-1 to G-663; M-1 to S-662; M-1 to R-661; M-1 to K-660; M-1 to C-659; M-1 to D-658; M-1 to R-657; M-1 to H-656; M-1 to F-655; M-1 to I-654; M-1 to N-653; M-1 to I-652; M-1 to K-651; M-1 to S-650; M-1 to P-649; M-1 to E-648; M-1 to F-647; M-1 to H-646; M-1 to L-645; M-1 to S-644; M-1 to A-643; M-1 to N-642; M-1 to I-641; M-1 to Q-640; M-1 to V-639; M-1 to V-638; M-1 to P-637; M-1 to R-636; M-1 to S-635; M-1 to W-634; M-1 to L-633; M-1 to I-632; M-1 to V-631; M-1 to A-630; M-1 to N-629; M-1 to G-628; M-1 to L-627; M-1 to A-626; M-1 to G-625; M-1 to V-624; M-1 to A-623; M-1 to L-622; M-1 to D-621; M-1 to I-620; M-1 to L-619; M-1 to G-618; M-1 to D-617; M-1 to E-616; M-1 to N-615; M-1 to L-614; M-1 to D-613; M-1 to L-612; M-1 to Q-611; M-1 to G-610; M-1 to H-609; M-1 to I-608; M-1 to S-607; M-1 to C-606; M-1 to G-605; M-1 to F-604; M-1 to Y-603; M-1 to Q-602; M-1 to L-601; M-1 to G-600; M-1 to T-599; M-1 to A-598; M-1 to L-597; M-1 to E-596; M-1 to S-595; M-1 to A-594; M-1 to T-593; M-1 to I-592; M-1 to R-591; M-1 to Q-590; M-1 to K-589; M-1 to P-588; M-1 to T-587; M-1 to K-586; M-1 to L-585; M-1 to I-584; M-1 to S-583; M-1 to G-582; M-1 to R-581; M-1 to F-580; M-1 to G-579; M-1 to H-578; M-1 to F-577; M-1 to I-576; M-1 to Y-575; M-1 to I-574; M-1 to A-573; M-1 to G-572; M-1 to A-571; M-1 to H-570; M-1 to N-569; M-1 to D-568; M-1 to E-567; M-1 to L-566; M-1 to P-565; M-1 to A-564; M-1 to G-563; M-1 to V-562; M-1 to V-561; M-1 to V-560; M-1 to D-559; M-1 to N-558; M-1 to Y-557; M-1 to S-556; M-1 to D-555; M-1 to Q-554; M-1 to N-553; M-1 to L-552; M-1 to D-551; M-1 to R-550; M-1 to V-549; M-1 to S-548; M-1 to A-547; M-1 to I-546; M-1 to S-545; M-1 to S-544; M-1 to G-543; M-1 to F-542; M-1 to R-541; M-1 to A-540; M-1 to N-539; M-1 to Q-538; M-1 to Y-537; M-1 to S-536; M-1 to H-535; M-1 to S-534; M-1 to D-533; M-1 to K-532; M-1 to L-531; M-1 to T-530; M-1 to G-529; M-1 to N-528; M-1 to Y-527; M-1 to V-526; M-1 to F-525; M-1 to R-524; M-1 to N-523; M-1 to Q-522; M-1 to R-521; M-1 to L-520; M-1 to E-519; M-1 to Y-518; M-1 to V-517; M-1 to Y-516; M-1 to V-515; M-1 to K-514; M-1 to G-513; M-1 to R-512; M-1 to E-511; M-1 to R-510; M-1 to G-509; M-1 to E-508; M-1 to N-507; M-1 to F-506; M-1 to Y-505; M-1 to M-504; M-1 to P-503; M-1 to A-502; M-1 to G-501; M-1 to V-500; M-1 to L-499; M-1 to L-498; M-1 to V-497; M-1 to D-496; M-1 to T-495; M-1 to V-494; M-1 to G-493; M-1 to D-492; M-1 to G-491; M-1 to D-490; M-1 to I-489; M-1 to D-488; M-1 to V-487; M-1 to S-486; M-1 to T-485; M-1 to I-484; M-1 to E-483; M-1 to S-482; M-1 to G-481; M-1 to F-480; M-1 to Y-479; M-1 to S-478; M-1 to G-477; M-1 to I-476; M-1 to Q-474; M-1 to G-474; M-1 to G-473; M-1 to R-472; M-1 to M-471; M-1 to A-470; M-1 to Q-469; M-1 to H-468; M-1 to I-467; M-1 to T-466; M-1 to L-465; M-1 to S-464; M-1 to R-463; M-1 to N-462; M-1 to N-461; M-1 to H-460; M-1 to M-459; M-1 to T-458; M-1 to F-457; M-1 to L-456; M-1 to I-455; M-1 to V-454; M-1 to K-453; M-1 to G-452; M-1 to T-451; M-1 to H-450; M-1 to N-449; M-1 to F-448; M-1 to R-447; M-1 to P-446; M-1 to A-445; M-1 to G-444; M-1 to A-443; M-1 to V-442; M-1 to Y-441; M-1 to V-440; M-1 to R-439; M-1 to G-438; M-1 to Q-437; M-1 to R-436; M-1 to S-435; M-1 to S-434; M-1 to V-433; M-1 to V-432; M-1 to S-431; M-1 to T-430; M-1 to V-429; M-1 to T-428; M-1 to Y-427; M-1 to G-426; M-1 to L-425; M-1 to Y-424; M-1 to A-423; M-1 to G-422; M-1 to H-421; M-1 to N-420; M-1 to K-419; M-1 to L-418; M-1 to E-417; M-1 to E-416; M-1 to P-415; M-1 to F-414; M-1 to E-413; M-1 to K-412; M-1 to L-411; M-1 to Y-410; M-1 to S-409; M-1 to E-408; M-1 to R-407; M-1 to L-406; M-1 to P-405; M-1 to I-404; M-1 to V-403; M-1 to K-402; M-1 to G-401; M-1 to A-400; M-1 to S-399; M-1 to T-398; M-1 to E-397; M-1 to K-396; M-1 to L-395; M-1 to V-394; M-1 to A-393; M-1 to G-392; M-1 to N-391; M-1 to W-390; M-1 to D-389; M-1 to Y-388; M-1 to A-387; M-1 to G-386; M-1 to V-385; M-1 to A-384; M-1 to G-383; M-1 to L-382; M-1 to L-381; M-1 to V-380; M-1 to G-379; M-1 to D-378; M-1 to E-377; M-1 to V-376; M-1 to V-375; M-1 to H-374; M-1 to S-373; M-1 to S-372; M-1 to F-371; M-1 to G-370; M-1 to T-369; M-1 to Q-368; M-1 to S-367; M-1 to M-366; M-1 to E-365; M-1 to L-364; M-1 to G-363; M-1 to F-362; M-1 to S-361; M-1 to T-360; M-1 to E-359; M-1 to N-358; M-1 to K-357; M-1 to N-356; M-1 to T-355; M-1 to G-354; M-1 to E-353; M-1 to L-352; M-1 to S-351; M-1 to F-350; M-1 to I-349; M-1 to R-348; M-1 to D-347; M-1 to G-346; M-1 to L-345; M-1 to A-344; M-1 to D-343; M-1 to V-342; M-1 to I-341; M-1 to D-340; M-1 to K-339; M-1 to L-338; M-1 to A-337; M-1 to A-336; M-1 to E-335; M-1 to D-334; M-1 to T-333; M-1 to V-332; M-1 to N-331; M-1 to F-330; M-1 to F-329; M-1 to H-328; M-1 to K-327; M-1 to D-326; M-1 to D-325; M-1 to P-324; M-1 to D-323; M-1 to S-322; M-1 to A-321; M-1 to I-320; M-1 to Y-319; M-1 to K-318; M-1 to I-317; M-1 to E-316; M-1 to N-315; M-1 to L-314; M-1 to F-313; M-1 to T-312; M-1 to E-311; M-1 to P-310; M-1 to N-309; M-1 to I-308; M-1 to G-307; M-1 to R-306; M-1 to R-305; M-1 to N-304; M-1 to Y-303; M-1 to Y-302; M-1 to G-301; M-1 to L-300; M-1 to V-299; M-1 to A-298; M-1 to V-297; M-1 to A-296; M-1 to Y-295; M-1 to R-294; M-1 to T-293; M-1 to V-292; M-1 to N-291; M-1 to D-290; M-1 to R-289; M-1 to E-288; M-1 to S-287; M-1 to Q-286; M-1 to Q-285; M-1 to I-284; M-1 to V-283; M-1 to K-282; M-1 to E-281; M-1 to L-280; M-1 to D-279; M-1 to P-278; M-1 to S-277; M-1 to D-276; M-1 to H-275; M-1 to S-274; M-1 to E-273; M-1 to G-272; M-1 to D-271; M-1 to T-270; M-1 to I-269; M-1 to V-268; M-1 to I-267; M-1 to M-266; M-1 to V-265; M-1 to K-264; M-1 to K-263; M-1 to A-262; M-1 to G-261; M-1 to K-260; M-1 to R-259; M-1 to G-258; M-1 to G-257; M-1 to K-256; M-1 to Q-255; M-1 to F-254; M-1 to A-253; M-1 to E-252; M-1 to S-251; M-1 to R-250; M-1 to A-249; M-1 to F-248; M-1 to E-247; M-1 to I-246; M-1 to G-245; M-1 to F-244; M-1 to A-243; M-1 to T-242; M-1 to R-241; M-1 to T-240; M-1 to E-239; M-1 to T-238; M-1 to G-237; M-1 to G-236; M-1 to R-235; M-1 to Q-234; M-1 to E-233; M-1 to I-232; M-1 to H-231; M-1 to S-230; M-1 to A-229; M-1 to A-228; M-1 to E-227; M-1 to V-226; M-1 to V-225; M-1 to D-224; M-1 to K-223; M-1 to V-222; M-1 to S-221; M-1 to R-220; M-1 to Y-219; M-1 to D-218; M-1 to N-217; M-1 to L-216; M-1 to H-215; M-1 to F-214; M-1 to E-213; M-1 to H-212; M-1 to V-211; M-1 to V-210; M-1 to D-209; M-1 to E-208; M-1 to G-207; M-1 to Y-206; M-1 to Q-205; M-1 to V-204; M-1 to V-203; M-1 to G-202; M-1 to V-201; M-1 to Q-200; M-1 to I-199; M-1 to Q-198; M-1 to G-197; M-1 to P-196; M-1 to G-195; M-1 to I-194; M-1 to Y-193; M-1 to F-192; M-1 to K-191; M-1 to K-190; M-1 to L-189; M-1 to I-188; M-1 to N-187; M-1 to I-186; M-1 to L-185; M-1 to F-184; M-1 to H-183; M-1 to Q-182; M-1 to V-181; M-1 to E-180; M-1 to V-179; M-1 to W-178; M-1 to P-177; M-1 to Y-176; M-1 to I-175; M-1 to S-174; M-1 to N-173; M-1 to S-172; M-1 to G-171; M-1 to D-170; M-1 to L-169; M-1 to V-168; M-1 to I-167; M-1 to V-166; M-1 to I-165; M-1 to 164; M-1 to M-163; M-1 to Y-162; M-1 to T-161; M-1 to Q-160; M-1 to C-159; M-1 to R-158; M-1 to Q-157; M-1 to L-156; M-1 to A-155; M-1 to P-154; M-1 to A-153; M-1 to V-152; M-1 to T-151; M-1 to K-150; M-1 to S-149; M-1 to F-148; M-1 to R-147; M-1 to F-146; M-1 to N-145; M-1 to S-144; M-1 to N-143; M-1 to V-142; M-1 to R-141; M-1 to S-140; M-1 to C-139; M-1 to M-138; M-1 to G-137; M-1 to T-136; M-1 to T-135; M-1 to Y-134; M-1 to Y-133; M-1 to S-132; M-1 to S-131; M-1 to G-130; M-1 to C-129; M-1 to E-128; M-1 to H-127; M-1 to S-126; M-1 to W-125; M-1 to L-124; M-1 to P-123; M-1 to S-122; M-1 to C-121; M-1 to A-120; M-1 to L-119; M-1 to F-118; M-1 to S-117; M-1 to N-116; M-1 to D-115; M-1 to K-114; M-1 to P-113; M-1 to N-112; M-1 to T-111; M-1 to A-110; M-1 to L-109; M-1 to S-108; M-1 to L-107; M-1 to G-106; M-1 to L-105; M-1 to R-104; M-1 to M-103; M-1 to N-102; M-1 to D-101; M-1 to K-100; M-1 to R-99; M-1 to E-98; M-1 to S-97; M-1 to V-96; M-1 to N-95; M-1 to S-94; M-1 to L-93; M-1 to T-92; M-1 to V-91; M-1 to R-90; M-1 to G-89; M-1 to L-88; M-1 to N-87; M-1 to K-86; M-1 to K-85; M-1 to T-84; M-1 to C-83; M-1 to N-82; M-1 to G-81; M-1 to H-80; M-1 to I-79; M-1 to V-78; M-1 to P-77; M-1 to C-76; M-1 to K-75; M-1 to Y-74; M-1 to V-73; M-1 to D-72; M-1 to G-71; M-1 to T-70; M-1 to K-69; M-1 to Q-68; M-1 to Y-67; M-1 to G-66; M-1 to N-65; M-1 to T-64; M-1 to E-63; M-1 to L-62; M-1 to P-61; M-1 to A-60; M-1 to G-59; M-1 to V-58; M-1 to V-57; M-1 to L-56; M-1 to W-55; M-1 to K-54; M-1 to N-53; M-1 to G-52; M-1 to S-51; M-1 to I-50; M-1 to D-49; M-1 to H-48; M-1 to Q-47; M-1 to Q-46; M-1 to V-45; M-1 to T-44; M-1 to Y-43; M-1 to G-42; M-1 to F-41; M-1 to F-40; M-1 to A-39; M-1 to T-38; M-1 to R-37; M-1 to S-36; M-1 to G-35; M-1 to P-34; M-1 to I-33; M-1 to V-32; M-1 to R-31; M-1 to P-30; M-1 to K-29; M-1 to R-28; M-1 to T-27; M-1 to D-26; M-1 to M-25; M-1 to N-24; M-1 to F-23; M-1 to T-22; M-1 to D-21; M-1 to T-20; M-1 to F-19; M-1 to G-18; M-1 to P-17; M-1 to W-16; M-1 to L-15; M-1 to S-14; M-1 to L-13; M-1 to A-12; M-1 to W-11; M-1 to A-10; M-1 to V-9; M-1 to V-8; M-1 to L-7; M-1 to G-6; of SEQ ID NO:35. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nucleotide sequences related to extensive portions of SEQ ID NO:17 which have been determined from the following related cDNA genes: HEEAB54R (SEQ ID NO:104), HRDAF83R (SEQ ID NO:105), HOUBC62R (SEQ ID NO:106), HCDBI19R (SEQ ID NO:107), HOHCU94R (SEQ ID NO:108), HOACC13R (SEQ ID NO:109), HCDAP21R (SEQ ID NO:110), HNHHA34R (SEQ ID NO:111), HOHEA75R (SEQ ID NO:112) and HNGEL59R (SEQ ID NO:113).

A polynucleotide encoding a polypeptide of the present invention is obtained from human ovary small intestine, fetal heart, fetal brain, large intestine, osteoblasts, human trabelcular bone cells, messangial cells, adipocytes, osteosarcoma, chondrosarcoma, breast cancer cells, and bone marrow tissues and cells. The polynucleotide of this invention was discovered in a human osteoblast n cDNA library.

Based on the sequence similarity to the human integrin alpha 1 subunit, translation product of this gene is expected to share at least some biological activities with integrin proteins, and specifically the integrin alpha 1 protein. Such activities are known in the art, some of which are described elsewhere herein.

Specifically, polynucleotides and polypeptides of the invention, including antibodies, are also useful for modulating the differentiation of normal and malignant cells, modulating the proliferation and/or differentiation of cancer and neoplastic cells, and modulating the immune response. Polynucleotides and polypeptides of the invention may represent a diagnostic marker for hematopoietic and immune diseases and/or disorders. The full-length protein should be a secreted protein, based upon homology to the integrin family. Therefore, it is secreted into serum, urine, or feces and thus the levels is assayable from patient samples. Assuming specific expression levels are reflective of the presence of immune disorders, this protein would provide a convenient diagnostic for early detection. In addition, expression of this gene product may also be linked to the progression of immune diseases, and therefore may itself actually represent a therapeutic or therapeutic target for the treatment of cancer.

Polynucleotides and polypeptides of the invention may play an important role in the pathogenesis of human cancers and cellular transformation, particularly those of the immune and hematopoietic systems. Polynucleotides and polypeptides of the invention may also be involved in the pathogenesis of developmental abnormalities based upon its potential effects on proliferation and differentiation of cells and tissue cell types. Due to the potential proliferating and differentiating activity of said polynucleotides and polypeptides, the invention is useful as a therapeutic agent in inducing tissue regeneration, for treating inflammatory conditions (e.g., inflammatory bowel syndrome, diverticulitis, etc.). Moreover, the invention is useful in modulating the immune response to aberrant polypeptides, as may exist in rapidly proliferating cells and tissue cell types, particularly in adenocarcinoma cells, and other cancers.

Alternatively, the expression within cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA).

Alternatively, this gene product is involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus, this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

This gene is expressed almost exclusively in osteoblasts, human trabelcular bone cells, messangial cells, adipocytes, and to a lesser extent in osteosarcoma, chondrosarcoma, breast cancer cells, and bone marrow.

Therefore, polynucleotides and polypeptides of the invention, including antibodies, are useful as reagents for differential identification of the tissue(s) or cell type(s) present in a biological sample and for diagnosis of the following diseases and conditions which include, but are not limited to, disorders of the skeletal system, connective tissues, and immune and hematpoietic diseases and/or disorders. Similarly, polypeptides and antibodies directed to these polypeptides are useful to provide immunological probes for differential identification of the tissue(s) or cell type(s). For a number of disorders of the above tissues or cells, particularly of the connective tissue and skeletal system, expression of this gene at significantly higher or lower levels is detected in certain tissues or cell types (e.g. immune, hematopoietic, skeletal, bone, cartilage, developmental, reproductive, secretory, and cancerous and wounded tissues) or bodily fluids or cell types (e.g., lymph, serum, plasma, urine, synovial fluid or spinal fluid) or another tissue or cell sample taken from an individual having such a disorder, relative to the standard gene expression level, i.e., the expression level in healthy tissue from an individual not having the disorder.

The tissue distribution in osteoblasts and homology to integrin alpha subunit 10 indicates that the protein products of this gene are useful for the treatment of disorders and conditions affecting the skeletal system, in particular osteoporosis as well as disorders afflicting connective tissues (e.g., arthritis, trauma, tendonitis, chrondomalacia and inflammation), such as in the diagnosis and treatment of various autoimmune disorders such as rheumatoid arthritis, lupus, scleroderma, and dermatomyositis as well as dwarfism, spinal deformation, and specific joint abnormalities as well as chondrodysplasias (i.e., spondyloepiphyseal dysplasia congenita, familial osteoarthritis, Atelosteogenesis type II, metaphyseal chondrodysplasia type Schmid). polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. Such a use is consistent with the observed homology to integrin family members, in conjunction with the tissue distribution in bone marrow cells.

Integrins play pivotal roles in cell migration, inflammation, proliferation, and cellular infiltration. Thus, the present invention is expected to share at least some of these activities.

Representative uses are described in the "Immune Activity" and "infectious disease" sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Based upon the tissue distribution of this protein, antagonists directed against this protein is useful in blocking the activity of this protein. Accordingly, preferred are antibodies which specifically bind a portion of the translation product of this gene.

Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein.

Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 4981 of SEQ ID NO:17, b is an integer of 15 to 4995, where both a and b correspond to the positions of nucleotide residues shown in SEQ ID NO:17, and where b is greater than or equal to a+14.

Features of Protein Encoded by Gene No: 8

The present invention relates to a novel peptidoglycan recognition binding proteins expressed by chondrosarcoma tissue. More specifically, isolated nucleic acid molecules are provided encoding a human peptidoglycan recognition protein-related protein, sometimes referred to herein as "human tag7" or "tag7" or "htag7". Further provided are vectors, host cells and recombinant methods for producing the same. The invention also relates to both the inhibition and enhancement of activities of the tag7 protein, polypeptides and diagnostic methods for detecting tag7 gene expression.

Peptidoglycan, as well as Lipopolysaccharide (LPS), is a surface component of many bacteria which illicit a wide range of physiological and immune responses in humans. Specifically, peptidoglycan has been shown to manifest itself clinically by reproducing most of the symptoms of bacterial infection, including fever, acute-phase response, inflammation, septic shock, leukocytosis, sleepiness, malaise, abcess formation, and arthritis (see Dziarski et al., JBC, 273 (15): 8680 (1998)). Furthermore, the type of peptidoglycan (i.e.—the specific stereoisomers or analogs of muramyl dipeptide, N-acetylglucosaminyl-beta(1-4)-N-acteylmuramyl tetrapeptides, etc.), were shown to elicit a broad range of activities, including exhibiting greater pyrogenicity, inducing acute joint inflammation, stimulating macrophages, and causing hemorrhagic necrosis at a primed site (See Kotani et al., Fed Proc, 45(11):2534 (1986)). It has been demonstrated in humans that a lipopolysaccharide binding protein exists that was discovered as a trace plasma protein (See Schumann et al., Science, 249(4975):1429 (1990)). It is thought that one of the modes of action by which this lipopolysaccharide binding protein functions is by forming high-affinity complexes with lipopolysaccharide, that then bind to macrophages and monocytes, inducing the secretion of tumor necrosis factor. Dziarski and Gupta (See Dziarski et al., JBC, 269(3):2100 (1994)) demonstrated that a 70 kDa receptor protein present on the surface of mouse lymphocytes served to bind heparin, heparinoids, bacterial lipoteichoic acids, peptidoglycan, and lipopolysaccharides. Recently, Dziarski et al. demonstrated that the CD14, a glycosylphosphatidylinositol-linked protein present on the surface of macrophage and polymorphonuclear leukocytes, bound peptidoglycan and lipopolysaccharide.

Furthermore, the binding affinity of CD14 for lipopolysaccharide was significantly increased in the presence of a LPS-binding protein present in plasma. It is thought that the LPS-binding protein functions as a transfer molecule, whereby it binds LPS and presents it to the CD14 receptor (See Dziarski et al., JBC, 273(15):8680 (1998)). Yoshida et al. isolated a peptidoglycan binding protein from the hemolymph of the Silkworm, *Bombyx mori*, using column chromatography. This protein was found to have a very specific affinity for peptidoglycan (See Yoshida et al., JBC, 271(23):13854 (1996)).

Additionally, Kang et al. recently cloned a peptidoglycan binding protein from the moth *Trichoplusia ni*. The peptidoglycan binding protein was shown to bind strongly to insoluble peptidoglycan (See Kang et al., PNAS, 95(17): 10078 (1998)). In this study the peptidoglycan binding protein was upregulated by a bacterial infection in *T. ni*. The insect immune system is regarded as a model for innate immunity. Thus, Kang et al were able to gene both mouse and human homologs of the *T. ni* peptidoglycan binding protein. All of these peptidoglycan binding proteins shared regions of homology, as well as four conserved cysteine residues which may function in the tertiary structure of the protein, possibly in helping to form binding domains. Given that peptidoglycan is an integral component of bacterial cell walls, and that it induces many physiological responses from cytokine secretion to inflammation and macrophage activation, it appears as if this family of proteins is a ubiquitous group involved in the binding and recognition of peptidoglycan, the presentation of antigens (e.g., cell wall components, etc.), and the activation of the immune system, such as the secretion of cytokines, such as TNF. TNF is noted for its pro-inflammatory actions which result in tissue injury, such as induction of procoagulant activity on vascular endothelial cells (Pober, J. S. et al., J. Immunol. 136:1680 (1986)), increased adherence of neutrophils and lymphocytes (Pober, J. S. et al., J. Immunol. 138: 3319 (1987)), and stimulation of the release of platelet activating factor from macrophages, neutrophils and vascular endothelial cells (Camussi, G. et al., J. Exp. Med. 166:1390 (1987)).

Recent evidence implicates TNF in the pathogenesis of many infections (Cerami, A. et al., Immunol. Today 9:28 (1988)), immune disorders, neoplastic pathology, e.g., in cachexia accompanying some malignancies (Oliff, A. et al., Cell 50:555 (1987)), and in autoimmune pathologies and graft-versus host pathology (Piguet, P.-F. et al., J. Exp. Med. 166:1280 (1987)). The association of TNF with cancer and infectious pathologies is often related to the host's catabolic state. A major problem in cancer patients is weight loss, usually associated with anorexia. The extensive wasting which results is known as "cachexia" (Kem, K. A. et al. J. Parent. Enter. Nutr. 12:286-298 (1988)). Cachexia includes progressive weight loss, anorexia, and persistent erosion of body mass in response to a malignant growth. The cachectic state is thus associated with significant morbidity and is responsible for the majority of cancer mortality.

A number of studies have suggested that TNF is an important mediator of the cachexia in cancer, infectious pathology, and in other catabolic states. TNF is thought to play a central role in the pathophysiological consequences of Gram-negative sepsis and endotoxic shock (Michie, H. R. et al., Br. J. Surg. 76:670-671 (1989); Debets, J. M. H. et al., Second Vienna Shock Forum, p. 463-466 (1989); Simpson, S. Q. et al., Crit. Care Clin. 5:27-47 (1989)), including fever, malaise, anorexia, and cachexia. Endotoxin is a potent monocyte/macrophage activator which stimulates production and secretion of TNF (Kombluth, S. K. et al., J. Immunol. 137:2585-2591 (1986)) and other cytokines. Because TNF could mimic many biological effects of endotoxin, it was concluded to be a central mediator responsible for the clinical manifestations of endotoxin-related illness. TNF and other monocyte-derived cytokines mediate the metabolic and neurohormonal responses to endotoxin (Michie, H. R. et al., N. Eng. J. Med. 318:1481-1486 (1988)). Endotoxin administration to human volunteers produces acute illness with flu-like symptoms including fever, tachycardia, increased metabolic rate and stress hormone release (Revhaug, A. et al., Arch. Surg. 123: 162-170 (1988)). Elevated levels of circulating TNF have also been found in patients suffering from Gram-negative sepsis (Waage, A. et al., Lancet 1:355-357 (1987); Hammerle, A. F. et al., Second Vienna Shock Forum p. 715-718 (1989); Debets, J. M. H. et al., Crit. Care Med. 17:489-497 (1989); Calandra, T. et al., J. Infec. Dis. 161:982-987 (1990)). Passive immunotherapy directed at neutralizing TNF may have a beneficial effect in Gram-negative sepsis and endotoxemia, based on the increased TNF production and elevated TNF levels in these pathology states, as discussed above.

Antibodies to a "modulator" material which was characterized as cachectin (later found to be identical to TNF) were disclosed by Cerami et al. (EPO Patent Publication 0,212, 489, Mar. 4, 1987). Such antibodies were said to be useful in diagnostic immunoassays and in therapy of shock in bacterial infections. Rubin et al. (EPO Patent Publication 0,218,868, Apr. 22, 1987) disclosed monoclonal antibodies to human TNF, the hybridomas secreting such antibodies, methods of producing such antibodies, and the use of such antibodies in immunoassay of TNF. Yone et al. (EPO Patent Publication 0,288,088, Oct. 26, 1988) disclosed anti-TNF antibodies, including mAbs, and their utility in immunoassay diagnosis of pathologies, in particular Kawasaki's pathology and bacterial infection. The body fluids of patients with Kawasaki's pathology (infantile acute febrile mucocutaneous lymph node syndrome; Kawasaki, T., Allergy 16:178 (1967); Kawasaki, T., Shonica (Pediatrics) 26:935 (1985)) were said to contain elevated TNF levels which were related to progress of the pathology (Yone et al., supra).

Accordingly, there is a need to provide molecules that are involved in pathological conditions. Such novel proteins could be useful in augmenting the immune system in such areas as immune recognition, antigen presentation, and immune system activation. Antibodies or antagonists directed against these proteins is useful in reducing or eliminating disorders associated with TNF and TNF-like cytokines, such as endotoxic shock and auto-immune disorders, for example.

The polypeptide of the present invention has been putatively identified as a member of the novel peptidoglycan recognition binding protein family and has been termed human tag7. This identification has been made as a result of amino acid sequence homology to the mouse tag7 (See Genbank Accession No. emb|CAA60133).

The translation product of this gene also shares sequence homology with antimicrobial BGP-A, a bovine antimicrobial peptide from bovine neutrophils. Preferred polypeptides of this invention comprise residues 184 to 196 shown in SEQ ID NO: 36. This polypeptide is believed to be the active mature form of the translation product of this gene.

Preferred polypeptides of the present invention comprise, or alternatively consist of, one, two, three, four, five, or all five of the immunogenic epitopes shown in SEQ ID NO: 36 as residues: Ala-63 to Asn-68, Ala-71 to Gln-81, Tyr-135 to Thr-141, Leu-167 to Gln-174, and/or Pro-191 to Pro-196. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

FIG. 34 shows the nucleotide (SEQ ID NO:18) and deduced amino acid sequence (SEQ ID NO:36) of htag7. Predicted amino acids from about 1 to about 21 constitute the predicted signal peptide (amino acid residues from about 1 to about 21 in SEQ ID NO:36) and are represented by the underlined amino acid regions; and amino acids from about 34 to about 117 constitute the predicted PGRP-like domain (amino acids from about 34 to about 117 in SEQ ID NO:36) and are represented by the double underlined amino acids.

FIG. 35 shows the regions of similarity between the amino acid sequences of the htag7 protein (SEQ ID NO:36) and the mouse tag7 protein (SEQ ID NO:114).

FIG. 36 shows an analysis of the htag7 amino acid sequence. Alpha, beta, turn and coil regions; hydrophilicity and hydrophobicity; amphipathic regions; flexible regions; antigenic index and surface probability are shown.

As shown in FIG. 34, htag7 has a PGRP domain (the PGRP domain comprise amino acids from about 34 to about 117 of SEQ ID NO:36; which correspond to amino acids from about 34 to about 117 of FIG. 34). The polynucleotide contains an open reading frame encoding the htag7 polypeptide of 198 amino acids. htag7 exhibits a high degree of homology at the amino acid level to the mouse tag7 (as shown in FIG. 35). The present invention provides isolated nucleic acid molecules comprising a polynucleotide encoding the htag7 polypeptide having the amino acid sequence shown in FIG. 34 (SEQ ID NO:36). The nucleotide sequence shown in FIG. 34 (SEQ ID NO:18) was obtained by sequencing a cloned cDNA (HCDDP40), which was deposited on November 17 at the American Type Culture Collection, and given Accession Number 203484.

The present invention is further directed to fragments of the isolated nucleic acid molecules described herein. By a fragment of an isolated DNA molecule having the nucleotide sequence of the deposited cDNA or the nucleotide sequence shown in SEQ ID NO:18 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:18. By a fragment at least 20 nt in length, for example, is intended fragments which include 20 or more contiguous bases from the nucleotide sequence of the deposited cDNA or the nucleotide sequence as shown in SEQ ID NO:18. In this context "about" includes the particularly recited size, larger or smaller by several (5, 4, 3, 2, or 1) nucleotides, at either terminus or at both termini. Representative examples of htag7 polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, from about 501 to about 550, from about 551 to about 600, from about 601 to about 650, from about 651 to about 700, from about 701 to about 726, and from about 130 to about 379 of SEQ ID NO:18, or the complementary strand thereto, or the cDNA contained in the deposited gene. In this context "about" includes the particularly recited ranges, larger or smaller by several (5, 4, 3, 2, or 1) nucleotides, at either terminus or at both termini.

Preferred nucleic acid fragments of the present invention include nucleic acid molecules encoding a member selected from the group: a polypeptide comprising or alternatively, consisting of, the PGRP-like domain (amino acid residues from about 34 to about 117 in FIG. 34 (amino acids from about 34 to about 117 in SEQ ID NO:36). Since the location of these domains have been predicted by computer analysis, one of ordinary skill would appreciate that the amino acid residues constituting these domains may vary slightly (e.g., by about 1 to 15 amino acid residues) depending on the criteria used to define each domain. As indicated, nucleic acid molecules of the present invention which encode a htag7 polypeptide may include, but are not limited to those encoding the amino acid sequence of the PGRP-like domain of the polypeptide, by itself, and the coding sequence for the PGRP-like domain of the polypeptide and additional sequences, such as a pre-, or pro or prepro-protein sequence. In additional embodiments, the polynucleotides of the invention encode functional attributes of htag7.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of htag7. The data representing the structural or functional attributes of htag7 set forth in FIG. 36 and/or Table XII, as described above, was generated using the various modules and algorithms of the DNA*STAR set on default parameters. In a preferred embodiment, the data presented in columns VIII, IX, XIII, and XIV of Table XII can be used to determine regions of htag7 which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 36, but may, as shown in Table XII, be represented or identified by using tabular representations of the data presented in FIG. 36. The DNA*STAR computer algorithm used to generate FIG. 36 (set on the original default parameters) was used to present the data in FIG. 36 in a tabular format (See Table XII). The tabular format of the data in FIG. 36 is used to easily determine specific boundaries of a preferred region. The above-mentioned preferred regions set out in FIG. 36 and in Table XII include, but are not limited to, regions of the aforementioned types identified by analysis of the amino acid sequence set out in FIG. 34. As set out in FIG. 36 and in Table XII, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, modulate cellular interaction, or signalling pathways, etc.) may still be retained. For example, the ability of shortened htag7 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an htag7 mutein with a large number of deleted N-terminal amino acid residues may retain some biological or immunogenic activities. In fact, peptides composed of as few as six htag7 amino acid residues may often evoke an immune response.

Accordingly, the present invention further provides polypeptides having one or more residues deleted from the amino terminus of the htag7 amino acid sequence shown in FIG. 34, up to the proline residue at position number 191 and polynucleotides encoding such polypeptides. In particular, the present invention provides polypeptides comprising the amino acid sequence of residues n1-196 of FIG. 34, where n1 is an integer from 2 to 191 corresponding to the position of the amino acid residue in FIG. 34 (which is identical to the sequence shown as SEQ ID NO:36). In another embodiment, N-terminal deletions of the htag7 polypeptide can be described by the general formula n2-196, where n2 is a number from 2 to 191, corresponding to the position of amino acid identified in FIG. 34. N-terminal deletions of the htag7 polypeptide of the invention shown as SEQ ID NO:36 include polypeptides comprising the amino acid sequence of residues: N-terminal deletions of the htag7 polypeptide of the invention shown as SEQ ID NO:36 include polypeptides comprising the amino acid sequence of residues: S-2 to P-196; R-3 to P-196; R-4 to P-196; S-5 to P-196; M-6 to P-196; L-8 to P-196; A-9 to P-196; W-10 to P-196; A-11 to P-196; L-12 to P-196; P-13 to P-196; S-14 to P-196; L-15 to P-196; L-16 to P-196; R-17 to P-196; L-18 to P-196; G-19 to P-196; A-20 to P-196; A-21 to P-196; Q-22 to P-196; E-23 to P-196; T-24 to P-196; E-25 to P-196; D-26 to P-196; P-27 to P-196; A-28 to P-196; C-29 to P-196; C-30 to P-196; S-31 to P-196; P-32 to P-196; I-33 to P-196; V-34 to P-196; P-35 to P-196; R-36 to P-196; N-37 to P-196; E-38 to P-196; W-39 to P-196; K-40 to P-196; A-41 to P-196; L-42 to P-196; A-43 to P-196; S-44 to P-196; E-45 to P-196; C-46 to P-196; A-47 to P-196; Q-48 to P-196; H-49 to P-196; L-50 to P-196; S-51 to P-196; L-52 to P-196; P-53 to P-196; L-54 to P-196; R-55 to P-196; Y-56 to P-196; V-57 to P-196; V-58 to P-196; V-59 to P-196; S-60 to P-196; H-61 to P-196; T-62 to P-196; A-63 to P-196; G-64 to P-196; S-65 to P-196; S-66 to P-196; C-67 to P-196; N-68 to P-196; T-69 to P-196; P-70 to P-196; A-71 to P-196; S-72 to P-196; C-73 to P-196; Q-74 to P-196; Q-75 to P-196; Q-76 to P-196; A-77 to P-196; R-78 to P-196; N-79 to P-196; V-80 to P-196; Q-81 to P-196; H-82 to P-196; Y-83 to P-196; H-84 to P-196; M-85 to P-196; K-86 to P-196; T-87 to P-196; L-88 to P-196; G-89 to P-196; W-90 to P-196; C-91 to P-196; D-92 to P-196; V-93 to P-196; G-94 to P-196; Y-95 to P-196; N-96 to P-196; F-97 to P-196; L-98 to P-196; I-99 to P-196; G-100 to P-196; E-101 to P-196; D-102 to P-196; G-103 to P-196; L-104 to P-196; V-105 to P-196; Y-106 to P-196; E-107 to P-196; G-108 to P-196; R-109 to P-196; G-110 to P-196; W-111 to P-196; N-112 to P-196; F-113 to P-196; T-114 to P-196; G-115 to P-196; A-116 to P-196; H-117 to P-196; S-118 to P-196; G-119 to P-196; H-120 to P-196; L-121 to P-196; W-122 to P-196; N-123 to P-196; P-124 to P-196; M-125 to P-196; S-126 to P-196; I-127 to P-196; G-128 to P-196; I-129 to P-196; S-130 to P-196; F-131 to P-196; M-132 to P-196; G-133 to P-196; N-134 to P-196; Y-135 to P-196; M-136 to P-196; D-137 to P-196; R-138 to P-196; V-139 to P-196; P-140 to P-196; T-141 to P-196; P-142 to P-196; Q-143 to P-196; A-144 to P-196; I-145 to P-196; R-146 to P-196; A-147 to P-196; A-148 to P-196; Q-149 to P-196; G-150 to P-196; L-151 to P-196; L-152 to P-196; A-153 to P-196; C-154 to P-196; G-155 to P-196; V-156 to P-196; A-157 to P-196; Q-158 to P-196; G-159 to P-196; A-160 to P-196; L-161 to P-196; R-162 to P-196; S-163 to P-196; N-164 to P-196; Y-165 to P-196; V-166 to P-196; L-167 to P-196; K-168 to P-196; G-169 to P-196; H-170 to P-196; R-171 to P-196; D-172 to P-196; V-173 to P-196; Q-174 to P-196; R-175 to P-196; T-176 to P-196; L-177 to P-196; S-178 to P-196; P-179 to P-196; G-180 to P-196; N-181 to P-196; Q-182 to P-196; L-183 to P-196; Y-184 to P-196; H-185 to P-196; L-186 to P-196; I-187 to P-196; Q-188 to P-196; N-189 to P-196; W-190 to P-196; P-191 to P-196; of SEQ ID NO:36. Polynucleotides encoding these polypeptides are also encompassed by the invention.

Also as mentioned above, even if deletion of one or more amino acids from the C-terminus of a protein results in modification or loss of one or more biological functions of the protein, other functional activities (e.g., biological activities ) may still be retained. For example the ability of the shortened htag7 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a htag7 mutein with a large number of deleted C-terminal amino acid residues may retain some biological or immunogenic activities. In fact, peptides composed of as few as six htag7 amino acid residues may often evoke an immune response.

Accordingly, the present invention further provides polypeptides having one or more residues deleted from the carboxy terminus of the amino acid sequence of the htag7 polypeptide shown in FIG. 34, up to the methionine residue at position number 6, and polynucleotides encoding such polypeptides. In particular, the present invention provides polypeptides comprising the amino acid sequence of residues 1-ml of FIG. 1, where ml is an integer from 6 to 196 corresponding to the position of the amino acid residue in FIG. 34. Moreover, the invention provides polynucleotides encoding polypeptides comprising, or alternatively consisting of, the amino acid sequence of C-terminal deletions of the htag7 polypeptide of the invention shown as SEQ ID NO:36 include polypeptides comprising the amino acid sequence of residues: M-1 to S-195; M-1 to R-194; M-1 to Y-193; M-1 to H-192; M-1 to P-191; M-1 to W-190; M-1 to N-189; M-1 to Q-188; M-1 to I-187; M-1 to L-186; M-1 to H-185; M-1 to Y-184; M-1 to L-183; M-1 to Q-182; M-1 to N-181; M-1 to G-180; M-1 to P-179; M-1 to S-178; M-1 to L-177; M-1 to T-176; M-1 to R-175; M-1 to Q-174; M-1 to V-173; M-1 to D-172; M-1 to R-171; M-1 to H-170; M-1 to G-169; M-1 to K-168; M-1 to L-167; M-1 to V-166; M-1 to Y-165; M-1 to N-164; M-1 to S-163; M-1 to R-162; M-1 to L-161; M-1 to A-160; M-1 to G-159; M-1 to Q-158; M-1 to A-157; M-1 to V-156; M-1 to G-155; M-1 to C-154; M-1 to A-153; M-1 to L-152; M-1 to L-151; M-1 to G-150; M-1 to Q-149; M-1 to A-148; M-1 to A-147; M-1 to R-146; M-1 to I-145; M-1 to A-144; M-1 to Q-143; M-1 to P-142; M-1 to T-141; M-1 to P-140; M-1 to V-139; M-1 to R-138; M-1 to D-137; M-1 to M-136; M-1 to Y-135; M-1 to N-134; M-1 to G-133; M-1 to M-132; M-1 to F-131; M-1 to S-130; M-1 to l-129; M-1 to G-128; M-1 to I-127; M-1 to S-126; M-1 to M-125; M-1 to P-124; M-1 to N-123; M-1 to W-122; M-1 to L-121; M-1 to H-120; M-1 to G-119; M-1 to S-118; M-1 to H-117; M-1 to A-116; M-1 to G-115; M-1 to T-114; M-1 to F-113; M-1 to N-112; M-1 to W-111; M-1 to G-110; M-1 to R-109; M-1 to G-108; M-1 to E-107; M-1 to Y-106; M-1 to V-105; M-1 to L-104; M-1 to G-103; M-1 to D-102; M-1 to E-101; M-1 to G-100; M-1 to I-99; M-1 to L-98; M-1 to F-97; M-1 to N-96; M-1 to Y-95; M-1 to G-94; M-1 to V-93; M-1 to D-92; M-1 to C-91; M-1 to W-90; M-1 to G-89; M-1 to L-88; M-1 to T-87; M-1 to K-86; M-1 to M-85; M-1 to H-84; M-1 to Y-83; M-1 to H-82; M-1 to Q-81; M-1 to V-80; M-1 to N-79; M-1 to R-78; M-1 to A-77; M-1 to Q-76; M-1 to Q-75; M-1 to Q-74; M-1 to C-73; M-1 to S-72; M-1 to A-71; M-1 to P-70; M-1 to T-69; M-1 to N-68; M-1 to C-67; M-1 to S-66; M-1 to S-65; M-1 to G-64; M-1 to A-63; M-1 to T-62; M-1 to H-61; M-1 to S-60; M-1 to V-59; M-1 to V-58; M-1 to V-57; M-1 to Y-56; M-1 to R-55; M-1 to L-54; M-1 to P-53; M-1 to L-52; M-1 to S-51; M-1 to L-50; M-1 to H-49; M-1 to Q-48; M-1 to A-47; M-1 to C-46; M-1 to E-45; M-1 to S-44; M-1 to A-43; M-1 to L-42; M-1 to A-41; M-1 to K-40; M-1 to W-39; M-1 to E-38; M-1 to N-37; M-1 to R-36; M-1 to P-35; M-1 to V-34; M-1 to I-33; M-1 to P-32; M-1 to S-31; M-1 to C-30; M-1 to C-29; M-1 to A-28; M-1 to P-27; M-1 to D-26; M-1 to E-25; M-1 to T-24; M-1 to E-23; M-1 to Q-22; M-1 to A-21; M-1 to A-20; M-1 to G-19; M-1 to L-18; M-1 to R-17; M-1 to L-16; M-1 to L-15; M-1 to S-14; M-1 to P-13; M-1 to L-12; M-1 to A-11; M-1 to W-10; M-1 to A-9; M-1 to L-8; M-1 to L-7; M-1 to M-6; of SEQ ID NO:36. Polynucleotides encoding these polypeptides are also encompassed by the invention.

In addition, the invention provides nucleic acid molecules having nucleotide sequences related to extensive portions of SEQ ID NO:36 which have been determined from the following related cDNA genes: HBMTB79R (SEQ ID NO:115) and HCDDP-40R (SEQ ID NO:116).

A polynucleotide encoding a polypeptide of the present invention is obtained from human chondrosarcoma cells, bone marrow, and neutrophils. The polynucleotide of this invention was discovered in a human chondrosarcoma cDNA library. This gene is expressed primarily in bone marrow and to a lesser extent in human chondrosarcoma and neutrophils.

Therefore, polynucleotides and polypeptides of the invention, including antibodies, are useful as reagents for differential identification of the tissue(s) or cell type(s) present in a biological sample and for diagnosis of diseases and conditions which include, but are not limited to, infections, cancer, and disorders of the immune system. Similarly, polypeptides and antibodies directed to these polypeptides are useful in providing immunological probes for differential identification of the tissue(s) or cell type(s). For a number of disorders of the above tissues or cells, particularly of infected tissues and the immune system, expression of this gene at significantly higher or lower levels is routinely detected in certain tissues or cell types (e.g. immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Based on the sequence similarity to the mouse tag7 and the PGRP-like domain, translation product of this gene is expected to share at least some biological activities with tag7 proteins, and specifically cytokine modulatory proteins. Such activities are known in the art, some of which are described elsewhere herein. Specifically, polynucleotides and polypeptides of the invention are also useful for modulating the differentiation of normal and malignant cells, modulating the proliferation and/or differentiation of cancer and neoplastic cells, such as chondrosarcomas, and modulating the immune response. Polynucleotides and polypeptides of the invention may represent a diagnostic marker for hematopoietic and immune diseases and/or disorders. The full-length protein should be a secreted protein, based upon homology to the tag7 protein. Therefore, it is secreted into serum, urine, or feces and thus the levels is assayable from patient samples. Assuming specific expression levels are reflective of the presence of immune disorders, this protein would provide a convenient diagnostic for early detection. In addition, expression of this gene product may also be linked to the progression of immune diseases, and therefore may itself actually represent a therapeutic or therapeutic target for the treatment of cancer.

Polynucleotides and polypeptides of the invention may play an important role in the pathogenesis of human cancers and cellular transformation, particularly those of the immune and hematopoietic systems. Polynucleotides and polypeptides of the invention may also be involved in the pathogenesis of developmental abnormalities based upon its potential effects on proliferation and differentiation of cells and tissue cell types. Due to the potential proliferating and differentiating activity of said polynucleotides and polypeptides, the invention is useful as a therapeutic agent in inducing tissue regeneration, for treating inflammatory conditions (e.g., inflammatory bowel syndrome, diverticulitis, etc.).

Moreover, the invention is useful in modulating the immune response to aberrant polypeptides, as may exist in rapidly proliferating cells and tissue cell types, particularly in adenocarcinoma cells, and other cancers. The translation product of this gene shares sequence homology with Tag7, which is a mouse cytokine that, in soluble form, triggers apoptosis in mouse L929 cells in vitro.

Features of Protein Encoded by Gene No: 9

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as a human butyrophilin homolog derived from a human testes tumor cDNA library. The polypeptide of the present invention is sometimes hereafter referred to as "Butyrophlin and B7-like IgG superfamily receptor", and/or "BBIR II". The invention also relates to inhibiting the action of such polypeptides.

Butyrophilin is a glycoprotein of the immunoglobulin superfamily that is secreted in association with the milk-fat-globule membrane from mammary epithelial cells. The butyrophilin gene appears to have evolved from a subset of genes in the immunoglobulin superfamily and genes encoding the B30.2 domain, which is conserved in a family of zinc-finger proteins. Furthermore, expression analysis of butyrophilin genes has shown that butyrophilin expression increases during lactation in conjunction with an increase in milk fat content. These results suggest that the stage-specific expression of milk fat globule membrane glycoproteins in mammary epithelial cells is regulated in a similar but not necessarily identical mechanism to that of a major milk protein, beta-casein.

The polypeptide of the present invention has been putatively identified as a member of the milk fat globule membrane glycoprotein family, and more particularly the butyrophilin family, and has been termed Butyrophlin and B7-like IgG superfamily receptor ("BBIR II"). This identification has been made as a result of amino acid sequence homology to the bovine butyrophilin precursor (See Genbank Accession No. gi|162773).

Preferred polynucleotides of the invention comprise, or alternatively consist of, a nucleic acid sequence selected from the group consisting of: ACATCCATGGCTCTAATGCT-
CAGTTTGGTTCTGAGTCTCCT-
CAAGCTGGGATCAGGGCAGTGGCAGGTGTTTGGGC
CAGACAAGCCTGTCCAGGCCTTG-
GTGGGGGAGGACGCAGCATTCTCCT-
GTTTCCTGTCTCCTAAGACCAATGCAGA GGCCATG-
GAAGTGCGGTTCTTCAGGGGCCAGTTCTCTA
GCGTGGTCCACCTCTACAGGGACGG-
GAAGGACCAGCC ATTTATGCAGATGCCACAGTAT-
CAAGGCAGGACAAAACTGGTGAAGGAT-
TCTATTGCGGAGGGGCGCATCTCTCT
GAGGCTGGAAAACATTACTGTGTTGGAT-
GCTGGCCTCTATGGGT GCAGGATTAGTTC-
CCAGTCTTACTACCAGAAG GCCATCTGGGAGCTA-
CAGGTGTCAGCACTGGGCTCAGTrCCTCTCAT
TTCCATCACGGGATATGTTGATAGAGACA TCCAGC-
TACTCTGTCAGTCCTCGGGCTGGTTC-
CCCCGGCCCACAGCGAAGTGGAAAGGTC-
CACAAGGACAGGATT
TGTCCACAGACTCCAGGACAAACAGAGA-
CATGCATGGCC TGTTTGATGTGGAGATCTCTCT-
GACCGTCCAAGAGA ACGCCGGGAGCATATCCTGT-
TCCATGCGGCATGCTCATCTGAGCCGAGAGG
TGGAATCCAGGGTACAGATAGGAG ATACCTTTTTC-
GAGCCTATATCGTGGCACCTGGCTAC-
CAAAGTACTGGGAATACTCTGCTGTGGC- CTATTTTTTGGC ATTGTTGGACTGAAGATTTrCTTCTC-CAAATTCCAGTG GAAAATCCAGGCGGAACTG-GACTGGAGAAGAAAGCAC GGACAGGCAGAAT-TGAGAGACGCCCGGAAACACGCAGTGGAGGTGA CTCTGGATCCAGAGACGGCTCACCCGAA GCTCT-GCGTTTCTGATCTGAAAACTGTAAC-CCATAGAAAAGCTCCCCAGGAGGTGCCT-CACTCTGAGAAGAGATTT ACAAGGAAGAGTGTGGTGGCTTCTCA-GAGTTTCCAAGCAGGGAAACATTACTGG-GAGGTGGACGGAGGACACAA TAAAAGCGTG-GCGCGTGTGGAGTGTGCCGGGATGATGTGGAC AGGAGGAAGGAGTACGTGACTTTGTCTCCCGATCA TGGGTACTGGGTCCTCAGACTGAATG-GAGAACATTTGTATTTCACATTAAATC-CCCGTTTTATCAGCGTCTTCCCCA GGACCCCAC-CTACAAAAATAGGGGTCTTCCTGGACTATGAGT GTGGGACCATCTCCTTCTTCAACATAAATGACCA GTCCCTTATTTATACCCTGACATGTCG-GTTTGAAGGCTTATTGAGGCCCTACAT-TGAGTATCCGTCCTATAATGAGC AAAATGGAACTC-CCAGAGACAAGCAACAGTGAGTCCTCCTCACA GGCAACCACGCCCTTCCTCCCCAGGGGTGAA ATG-TAGGATGAATCACATCCCACATTCT-TCTTTAGGGATATTAAGGTCTCTCTC-CCAGATCCAAAGTCCCGCAGCA GCCGGCCAAGGTGGCTTCCAGAT-GAAGGGGGACTGGCCTGT CCACATGGGAGTCAG-GTGTCATGGCTGCCCTGAG CTGGGAGGGAAGAAG-GCTGACATTACATTTAGTTTGCTCTCACTCCAT CTGGCTAAGTGATCTTGAAATACCACCT CTCAGGT-GAAGAACCGTCAGGAATTCCCATCTCA-CAGGCTGTGGTGTAGATTAAGTAGA-CAAGGAATGTGAATAA TGCTTAGATCTTATTGATGACAGAGTG-TATCCTAATGGTTTGTTCATTATATTA-CACTTTCAGTAAAAAAAAAAAA AAAAAAAAAAAAAAAAAAA (SEQ ID NO:117), and/or ATGGCTCTAATGCTCAGTTTGGTTCT-GAGTCTCCTCAAGCTGGGAT-CAGGGCAGTGGCAGGTGTTTGGGCCAGACA AGCCTGTCCAGGCCTTGGTGGGGGAG-GACGCAGCATTCTCCTGTTTCCTGTCTC-CTAAGACCAATGCAGAGGCCAT GGAAGTGCGGT-TCTTCAGGGGCCAGTTCTCTAGCGTGGTCCACC TCTACAGGGACGGGAAGGACCAGCCATTTAT GCA-GATGCCACAGTATCAAGGCAGGA-CAAAACTGGTGAAGGATTCTATTGCG-GAGGGGCGCATCTCTCTGAGGCT GGAAAACATTACTGTGTTGGATGCTGGC-CTCTATGGGTGCA GGATTAGTTCCCAGTCTTACTAC-CAGAAGGCCATC TGGGAGCTACAGGTGTCAG-CACTGGGCTCAGTTCCTCTCATTTCCATCACG GGATATGTTGATAGAGACATCCAGC TACTCTGT-CAGTCCTCGGGCTGGTTCCCCCGGCCCA-CAGCGAAGTGGAAAGGTCCACAAGGA-CAGGATTTGTCCA CAGACTCCAGGACAAACAGAGACATG-CATGGCCTGTTTGATGTG GAGATCTCTCTGAC-CGTCCAAGAGAACGCCG GGAGCATATCCTGTTC-CATGCGGCATGCTCATCTGAGCCGAGAGGTGG AATCCAGGGTACAGATAGGAGATACCT TTTTC-GAGCCTATATCGTGGCACCTGGCTAC-CAAAGTACTGGGAATACTCTGCTGTGGC-CTATTTTTTGGCATTGTT GGACT GAAGATTTTCTTCTCCAAATTCCAGTG-GAAAATCCAGGCGGAACTGGACTG-GAGAAGAAAGCACGGACAG GCAGAAT-TGAGAGACGCCCGGAAACACGCAGTGGAGGT GACTCTGGATCCAGAGACGGCTCAC-CCGAAGCTCTG CGTTTCTGATCTGAAAACTGTAAC-CCATAGAAAAGCTCCCCAGGAGGTGCCT-CACTCTGAGAAGAGATTTACAAG GAAGAGTGTGGTGGCTTCTCAGAGTTTC-CAAGCAGGGAAAC ATTACTGGGAGGTGGACGGAG-GACACAATAAAA GGTGGCGCGTGGGAGTGTGC-CGGGATGATGTGGACAGGAGGAAGGAGTACGTG ACTTTGTCTCCCGATCATGGGT ACTGGGTCCTCA-GACTGAATGGAGAACATTTGTATTTCACATTAAA TCCCCGTTTTATCAGCGTCTTCCCCAGGAC CCCAC-CTACAAAA ATAGGGGTCTTCCTGGACTATGAGT-GTGGGACCATCTCCT-CTTCAACATAAATGAC-CAGTCC CTTATTTATACCCTGACATG TCGGTTTGAAGGCTTATTGAGGCCCTA-CATTGAGTATCCGTCCTATAATGAGCAAA ATG-GAACTCCCAGAGACAAGCAACAGTGA (SEQ ID NO:118). Polypeptides encoded by these polynucleotides are also encompassed by the invention.

Preferred polypeptides of the invention comprise, or alternatively consist of the following amino acid sequence: MALMLSLVLSLLKLGSGQWQVFGPDK-PVQALVGEDAAFSCFLSPKTNAEAMEVR-FFRGQFSSVVHLYRDG KDQPFMQMPQYQGRT-KLVKDSIAEGRISLRLENITVLDAGLYGCRISSQS YYQKAIWELQVSALGSVPLISITGYVDRDI QLLCQSS-GWFPRPTAKWKGPQGQDLSTDSRTNRDM-HGLFDVEISLTVQENAGSISCSMRHAHL-SREVESRVQIGDTFFE PISWHLATKVLGILCCGLFF-GIVGLKIFFSKFQWKIQAELDWRR KHGQAELRD-ARKHAVEVTLDPETAHPKLCVSDLKT VTHRKAPQEVPHSEKRFTRKSVVASQS-FQAGKHYWEVDGGHNKRWRVGVCRD-DVDRRKEYVTLSPDHGYWVLRLN GEHLYFTLN-PRFISVFPRTPPTKIGVFLDYECGTISFFNINDQSLI YTLTCRFEGLLRPYIEYPSYNEQNGTPRDKQQ (SEQ ID NO:119). Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

A preferred polynucleotide splice variant of the invention comprises the following nucleic acid sequence: ACCTTTTTCGAGCCTATATCGTGGCAC-CTGGCTACCAAAGTACTGGGAATACTCT-GCTGTGGCCTATTTT TTGGCATTGTFGGAC TGAA-GATTTTCTTCTCCAAATTCCAGTGGAAAATCCA GGCGGAACTGGACTGGAGAAGAA AGCACGGA-CAGGCAGAATTGAGAGACGCCCGGAAA-CACGCAGTGGAGGTGACTCTGGATCCA-GAGACGGCTCAC CCGAAG CTCTGCGTTTCTGATCTGAAAACTG-TAACCCATAGAA AAGCTCCCCAGGAGGTGCCT-CACTCTGAGAAG AGATTTACAAGGAAGAGTGTG-GTGGCTTCTCAGAGTTTCCAAGCAGGGAAACA TTACTGGGAGGTGGACGGAGGA CACAATAAAAG-GTGGCGCGTGGGAGTGTGCCGGGATGAT-GTGGACAGGAGGAAGGAGTACGTGAC-TYTGTCTCCC GATCATGGGTACTGGGTCCTCAGACT-GAATGGAGAACATTFGTATTTCACAT-TAAATCCCCGTTTTATCAGCGTCTT CCCCAGGAC-CCCACCTACAAAAATAGGGGTCTTCCTGGACTAT GAGTGTGGGACCATCTCCTTCTTCAACATAAAT GACCAGTCCCTTATTTATACCCTGACAT-GTCGGTTTGAAGGCTTATTGAGGCCCTA-CATTGAGTATCCGTCCTATAA TGAGCAAAATG-GAACTCCCAGAGACAAGCAACAGTGAGTCCTCC TCACAGGCAACCACGCCCTfCCTCCCCAGGG GTGAAATGTAGGATGAATCACATCCCA-CATTCTTCTTTAGGGATATTAAG-GTCTCTCTCCCAGATCCAAAGTCCCG CAGCAGCCG-GCCAAGGTGGCTTCCAGATGAAGGGGGACTGGC CTGTCCACATGGGAGTCAGGTGTCATGGCTGCC CTGAGCTGGGAGGGAAGAAGGCTGACAT-TACATTTAGTTTGCTCTCACTCCATCTG-GCTAAGTGATCTTGAAATAC CACCTCTCAGGTGAA-GAACCGTCAGGAATTCCCATCTCACAGGCTGTG GTGTAGATTAAGTAGACAAGGAATGTG AATAAT-GCTTAGATCTTATTGATGACAGAGTG-TATCCTAATGGTTTGTTCATTATATTA-CACTTTCAGTAAAAAAA AAAAAAAAAAAAAAAAAAAAAAAAA (SEQ ID NO:120). Polypeptides encoded by these polynucleotides are also encompassed by the invention.

Preferred polypeptides of the present invention comprise, or alternatively consist of, one, two, three, four, five, or all five of the immunogenic epitopes shown in SEQ ID NO: 37 as residues: Tyr-67 to Pro-74, Ser-1 17 to Gln-123, Pro-161 to Met-185, Gly-224 to His-242, and/or Thr-299 to Trp-307. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

FIGS. 22A-C show the nucleotide (SEQ ID NO:19) and deduced amino acid sequence (SEQ ID NO:37) of BBIR II. Predicted amino acids from about 1 to about 17 constitute the predicted signal peptide (amino acid residues from about 1 to about 17 in SEQ ID NO:37) and are represented by the underlined amino acid regions.

FIG. 23 shows the regions of similarity between the amino acid sequences of the Butyrophlin and B7-like IgG superfamily receptor (BBIR II) protein (SEQ ID NO:37) and the bovine butyrophilin precursor (SEQ ID NO:121)

Figure 24:
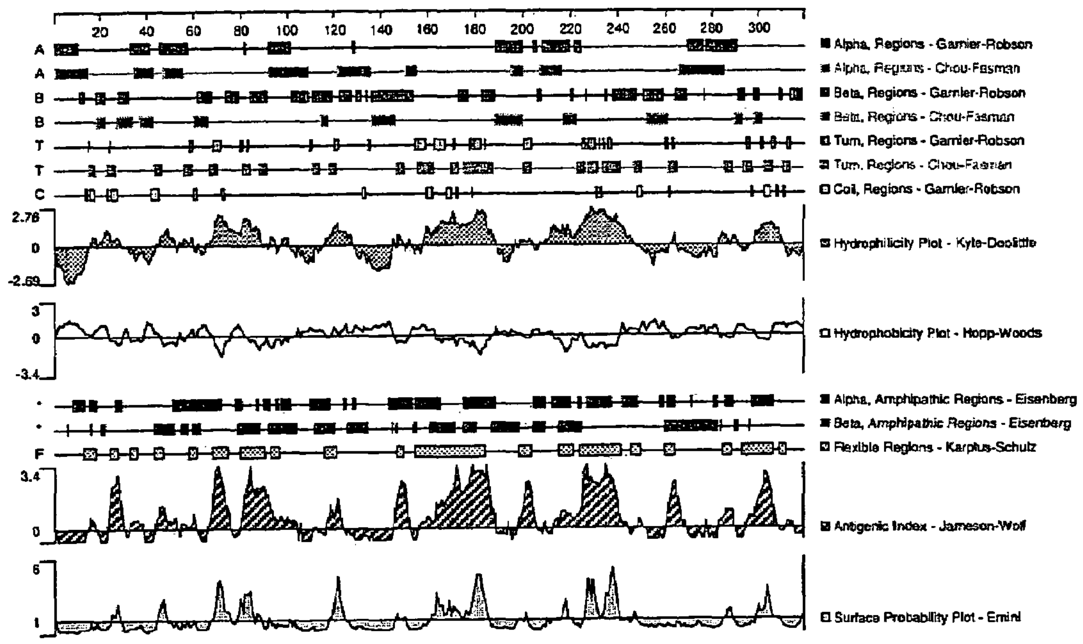
FIG. 24 shows an analysis of the integrin alpha 11 subunit (BBIR II) amino acid sequence.

FIG. 24 shows an analysis of the integrin alpha 11 subunit (BBIR 11) amino acid sequence. Alpha, beta, turn and coil regions; hydrophilicity and hydrophobicity; amphipathic regions; flexible regions; antigenic index and surface probability are shown.

Translation products corresponding to this gene share homology to the B30.2-like domain which is characteristic of proteins containing zinc-binding B-box motifs, and particularly for butyrophilin family members. The polynucleotide contains an open reading frame encoding the BBIR II polypeptide of 318 amino acids. BBIR II exhibits a high degree of homology at the amino acid level to the bovine butyrophilin precursor (as shown in FIG. 23). The present invention provides isolated nucleic acid molecules comprising a polynucleotide encoding the BBIR II polypeptide having the amino acid sequence shown in FIGS. 22A-C (SEQ ID NO:37). The nucleotide sequence shown in FIGS. 22A-C (SEQ ID NO:19) was obtained by sequencing a cloned cDNA (HTTDB46), which was deposited on November 17 at the American Type Culture Collection, and given Accession Number 203484.

The present invention is further directed to fragments of the isolated nucleic acid molecules described herein. By a fragment of an isolated DNA molecule having the nucleotide sequence of the deposited cDNA or the nucleotide sequence shown in SEQ ID NO: 19 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:19. By a fragment at least 20 nt in length, for example, is intended fragments which include 20 or more contiguous bases from the nucleotide sequence of the deposited cDNA or the nucleotide sequence as shown in SEQ ID NO:19. In this context "about" includes the particularly recited size, larger or smaller by several (5, 4, 3, 2, or 1) nucleotides, at either terminus or at both termini. Representative examples of BBIR II polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, from about 501 to about 550, from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1350, from about 1351 to about 1400, from about 1401 to about 1450, from about 1451 to about 1500, from about 1501 to about 1550, from about 1551 to about 1600, from about 1601 to about 1650, from about 1651 to about 1700, from about 1701 to about 1750, from about 1751 to about 1800, from about 1801 to about 1850, from about 1851 to about 1900, from about 1901 to about 1950, from about 1951 to about 2000, from about 2001 to about 2050, from about 2051 to about 2100, from about 2101 to about 2150, from about 2151 to about 2200, from about 2201 to about 2250, from about 2251 to about 2300, from about 2301 to about 2350, from about 2351 to about 2400, from about 2401 to about 2450, from about 2451 to about 2500, from about 2501 to about 2550, from about 2551 to about 2600, from about 2601 to about 2650, from about 2651 to about 2700, from about 2701 to about 2750, from about 2751 to about 2800, from about 2801 to about 2850, from about 2851 to about 2900, from about 2901 to about 2950, from about 2951 to about 3000, from about 3001 to about 3050, from about 3051 to about 3059 of SEQ ID NO:19, or the complementary strand thereto, or the cDNA contained in the deposited gene. In this context "about" includes the particularly recited ranges, larger or smaller by several (5, 4, 3, 2, or 1) nucleotides, at either terminus or at both termini.

Preferred nucleic acid fragments of the present invention include nucleic acid molecules encoding a member selected from the group: a polypeptide comprising or alternatively, consisting of, the mature BBIR II protein (amino acid residues from about 18 to about 318 in FIGS. 22A-C (amino acids from about 18 to about 318 in SEQ ID NO:37). Since the location of this form of the protein has been predicted by computer analysis, one of ordinary skill would appreciate that the amino acid residues constituting these domains may vary slightly (e.g., by about 1 to 15 amino acid residues) depending on the criteria used to define this location. In additional embodiments, the polynucleotides of the invention encode functional attributes of BBIR II.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of BBIR II. The data representing the structural or functional attributes of BBIR II set forth in FIG. 24 and/or Table VIII, as described above, was generated using the various modules and algorithms of the DNA*STAR set on default parameters. In a preferred embodiment, the data presented in columns VIII, IX, XIII, and XIV of Table VIII can be used to determine regions of BBIR II which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 24, but may, as shown in Table VIII, be represented or identified by using tabular representations of the data presented in FIG. 24. The DNA*STAR computer algorithm used to generate FIG. 24 (set on the original default parameters) was used to present the data in FIG. 24 in a tabular format (See Table VIII). The tabular format of the data in FIG. 24 is used to easily determine specific boundaries of a preferred region. The above-mentioned preferred regions set out in FIG. 24 and in Table VIII include, but are not limited to, regions of the aforementioned types identified by analysis of the amino acid sequence set out in FIGS. 22A-C. As set out in FIG. 24 and in Table VIII, such preferred regions include Gamier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, etc.) may still be retained. For example, the ability of shortened BBIR II muteins to induce and/or bind to antibodies which recognize the complete or mature forms of the polypeptides generally will be retained when less than the majority of the residues of the complete or mature polypeptide are removed from the N terminus. Whether a particular polypeptide lacking N-terminal residues of a complete polypeptide retains such immunologic activities can readily be determined by routine methods described herein and otherwise known in the art. It is not unlikely that an BBIR II mutein with a large number of deleted N-terminal amino acid residues may retain some biological or immunogenic activities. In fact, peptides composed of as few as six BBIR II amino acid residues may often evoke an immune response.

Accordingly, the present invention further provides polypeptides having one or more residues deleted from the amino terminus of the BBIR II amino acid sequence shown in FIGS. 22A-C, up to the cystein residue at position number 313 and polynucleotides encoding such polypeptides. In particular, the present invention provides polypeptides comprising the amino acid sequence of residues n1-318 of FIGS. 22A-C, where n1 is an integer from 2 to 313 corresponding to the position of the amino acid residue in FIGS. 22A-C (which is identical to the sequence shown as SEQ ID NO:37). In another embodiment, N-terminal deletions of the BBIR II polypeptide can be described by the general formula n2-318, where n2 is a number from 2 to 313, corresponding to the position of amino acid identified in FIGS. 22A-C. N-terminal deletions of the BBIR II polypeptide of the invention shown as SEQ ID NO:37 include polypeptides comprising the amino acid sequence of residues: N-terminal deletions of the BBIR II polypeptide of the invention shown as SEQ ID NO:37 include polypeptides comprising the amino acid sequence of residues: A-2 to T-318; L-3 to T-318; M4 to T-318; L-5 to T-318; S-6to T-318; L-7 to T-318; V-8 to T-318; L-9 to T-318; S-10 to T-318; L-11 to T-318; L-12 to T-318; K-13 to T-318; L-14 to T-318; G-15 to T-318; S-16 to T-318; G-17 to T-318; Q-18 to T-318; W-19 to T-318; Q-20 to T-318; V-21 to T-318; F-22 to T-318; G-23 to T-318; P-24 to T-318; D-25 to T-318; K-26 to T-318; P-27 to T-318; V-28 to T-318; Q-29 to T-318; A-30 to T-318; L-31 to T-318; V-32 to T-318; G-33 to T-318; E-34 to T-318; D-35 to T-318; A-36 to T-318; A-37 to T-318; F-38 to T-318; S-39 to T-319; C-40 to T-319; F-41 to T-318; L-42 to T-318; S-43 to T-318; P-44 to T-318; K-45 to T-318; T-46 to T-318; N-47 to T-318; A-48 to T-318; E-49 to T-318; A-50 to T-318; M-51 to T-318; E-52 to T-318; V-53 to T-318; R-54 to T-318; F-55 to T-318; F-56 to T-318; R-57 to T-318; G-58 to T-318; Q-59 to T-318; F-60 to T-318; S-61 to T-318; S-62 to T-318; V-63 to T-318; V-64 to T-318; H-65 to T-318; L-66 to T-318; Y-67 to T-318; R-68 to T-318; D-69 to T-318; G-70 to T-318; K-71 to T-318; D-72 to T-318; Q-73 to T-318; P-74 to T-318; F-75 to T-318; M-76 to T-318; Q-77 to T-318; M-78 to T-318; P-79 to T-318; Q-80 to T-318; Y-81 to T-318; Q-82 to T-318; G-83 to T-318; R-84 to T-318; T-85 to T-318; K-86 to T-318; L-87 to T-318; V-88 to T-318; K-89 to T-318; D-90 to T-318; S-91 to T-318; I-92 to T-318; A-93 to T-318; E-94 to T-318; G-95 to T-318; R-96 to T-318; I-97 to T-318; S-98 to T-318; L-99 to T-318; R-100 to T-318; L-101 to T-318; E-102 to T-318; N-103 to T-318; I-104 to T-318; T-105 to T-318; V-106 to T-318; L-107 to T-318; D-108 to T-318; A-109 to T-318; G-110 to T-318; L-111 to T-318; Y-112 to T-318; G-113 to T-318; C-114 to T-318; R-115 to T-318; I-116 to T-318; S-117 to T-318; S-118 to T-318; Q-119 to T-318; S-120to T-318; Y-121 to T-318; Y-122 to T-318; Q-123 to T-318; K-124 to T-318; A-125 to T-318; I-126 to T-318; W-127 to T-318; E-128 to T-318; L-129 to T-318; Q-130 to T-318; V-131 to T-318; S-132 to T-318; A-133 to T-318; L-134 to T-318; G-135 to T-318; S-136 to T-318; V-137 to T-318; P-138 to T-318; L-139 to T-318; I-140 to T-318; S-141 to T-318; I-142 to T-318; A-143 to T-318; G-144 to T-318; Y-145 to T-318; V-146 to T-318; D-147 to T-318; R-148 to T-318; D-149 to T-318; I-150 to T-318; Q-151 to T-318; L-152 to T-318; L-153 to T-318; C-154 to T-318; Q-155 to T-318; S-156 to T-318; S-157 to T-318; G-158 to T-318; W-159 to T-318; F-160 to T-318; P-161 to T-318; R-162 to T-318; P-163 to T-318; T-164 to T-318; A-165 to T-318; K-166 to T-318; W-167 to T-318; K-168 to T-318; G-169 to T-318; P-170 to T-318; Q-171 to T-318; G-172 to T-318; Q-173 to T-318; D-174 to T-318; L-175 to T-318; S-176 to T-318; T-177 to T-318; D-178 to T-318; S-179 to T-318; R-180 to T-318; T-181 to T-318; N-182 to T-318; R-183 to T-318; D-184 to T-318; M-185 to T-318; H-186 to T-318; G-187 to T-318; L-188 to T-318; F-189 to T-318; D-190 to T-318; V-191 to T-318; E-192 to T-318; I-193 to T-318; S-194 to T-318; L-195 to T-318; T-196 to T-318; V-197 to T-318; Q-198 to T-318; E-199 to T-318; N-200 to T-318; A-201 to T-318; G-202 to T-318; S-203 to T-318; I-204 to T-318; S-205 to T-318; C-206 to T-318; S-207 to T-318; M-208 to T-318; R-209 to T-318; H-210 to T-318; A-211 to T-318; H-212 to T-318; L-213 to T-318; S-214 to T-318; R-215 to T-318; E-216 to T-318; V-217 to T-318; E-218 to T-318; S-219 to T-318; R-220 to T-318; V-221 to T-318; Q-222 to T-318; I-223 to T-318; G-224 to T-318; D-225 to T-318; W-226 to T-318; R-227 to T-318; R-228 to T-318; K-229 to T-318; H-230 to T-318; G-231 to T-318; Q-232 to T-318; A-233 to T-318; G-234 to T-318; K-235 to T-318; R-236 to T-318; K-237 to T-318; Y-238 to T-318; S-239 to T-318; S-240 to T-318; S-241 to T-318; H-242 to T-318; I-243 to T-318; Y-244 to T-318; D-245 to T-318; S-246 to T-318; F-247 to T-318; P-248 to T-318; S-249 to T-318; L-250 to T-318; S-251 to T-318; F-252 to T-318; M-253 to T-318; D-254 to T-318; F-255 to T-318; Y-256 to T-318; I-257 to T-318; L-258 to T-318; R-259 to T-318; P-260 to T-318; V-261 to T-318; G-262 to T-318; P-263 to T-318; C-264 to T-318; R-265 to T-318; A-266 to T-318; K-267 to T-318; L-268 to T-318; V-269 to T-318; M-270 to T-318; G-271 to T-318; T-272 to T-318; L-273 to T-318; K-274 to T-318; L-275 to T-318; Q-276 to T-318; I-277 to T-318; L-278 to T-318; G-279 to T-318; E-280 to T-318; V-281 to T-318; H-282 to T-318; F-283 to T-318; V-284 to T-318; E-285 to T-318; K-286 to T-318; P-287 to T-318; H-288 to T-318; S-289 to T-318; L-290 to T-318; L-291 to T-318; Q-292 to T-318; I-293 to T-318; S-294 to T-318; G-295 to T-318; G-296 to T-318; S-297 to T-318; T-298 to T-318; T-299 to T-318; L-300 to T-318; K-301 to T-318; K-302 to T-318; G-303 to T-318; P-304 to T-318; N-305 to T-318; P-306 to T-318; W-307 to T-318; S-308 to T-318; F-309 to T-318; P-310 to T-318; S-311 to T-318; P-312 to T-318; C-313 to T-318; of SEQ ID NO:37. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities (e.g., biological activities (e.g., ability to illicit mitogenic activity, induce differentiation of normal or malignant cells, ability to multimerize, etc.) may still be retained. For example the ability of the shortened BBIR II mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an BBIR II mutein with a large number of deleted C-terminal amino acid residues may retain some biological or immunogenic activities. In fact, peptides composed of as few as six BBIR II amino acid residues may often evoke an immune response.

Accordingly, the present invention further provides polypeptides having one or more residues deleted from the carboxy terminus of the amino acid sequence of the BBIR II polypeptide shown in FIGS. 22A-C, up to the serine residue at position number 6,, and polynucleotides encoding such polypeptides. In particular, the present invention provides polypeptides comprising the amino acid sequence of residues 1-m1 of FIG. 1, where m1 is an integer from 6 to 318 corresponding to the position of the amino acid residue in FIGS. 22A-C. Moreover, the invention provides polynucleotides encoding polypeptides comprising, or alternatively consisting of, the amino acid sequence of C-terminal deletions of the BBIR II polypeptide of the invention shown as SEQ ID NO:37 include polypeptides comprising the amino acid sequence of residues M-1 to P-317; M-1 to F-316; M-1 to L-315; M-1 to A-314; M-1 to C-313; M-1 to P-312; M-1 to S-311; M-1 to P-310; M-1 to F-309; M-1 to S-308; M-1 to W-307; M-1 to P-306; M-1 to N-305; M-1 to P-304; M-1 to G-303; M-1 to K-302; M-1 to K-301; M-1 to L-300; M-1 to T-299; M-1 to T-298; M-1 to S-297; M-1 to G-296; M-1 to G-295; M-1 to S-294; M-1 to I-293; M-1 to Q-292; M-1 to L-291; M-1 to L-290; M-1 to S-289; M-1 to H-288; M-1 to P-287; M-1 to K-286; M-1 to E-285; M-1 to V-284; M-1 to F-283; M-1 to H-282; M-1 to V-281; M-1 to E-280; M-1 to G-279; M-1 to L-278; M-1 to I-277; M-1 to Q-276; M-1 to L-275; M-1 to K-274; M-1 to L-273; M-1 to T-272; M-1 to G-271; M-1 to M-270; M-1 to V-269; M-1 to L-268; M-1 to K-267; M-1 to A-266; M-1 to R-265; M-1 to C-264; M-1 to P-263; M-1 to G-262; M-1 to V-261; M-1 to P-260; M-1 to R-259; M-1 to L-258; M-1 to I-257; M-1 to Y-256; M-1 to F-255; M-1 to D-254; M-1 to M-253; M-1 to F-252; M-1 to S-251; M-1 to L-250; M-1 to S-249; M-1 to P-248; M-1 to F-247; M-1 to S-246; M-1 to D-245; M-1 to Y-244; M-1 to I-243; M-1 to H-242; M-1 to S-241; M-1 to S-240; M-1 to S-239; M-1 to Y-238; M-1 to K-237; M-1 to R-236; M-1 to K-235; M-1 to G-234; M-1 to A-233; M-1 to Q-232; M-1 to G-231; M-1 to H-230; M-1 to K-229; M-1 to R-228; M-1 to R-227; M-1 to W-226; M-1 to D-225; M-1 to G-224; M-1 to I-223; M-1 to Q-222; M-1 to V-221; M-1 to R-220; M-1 to S-219; M-1 to E-218; M-1 to V-217; M-1 to E-216; M-1 to R-215; M-1 to S-214; M-1 to L-213; M-1 to H-212; M-1 to A-211; M-1 to H-210; M-1 to R-209; M-1 to M-208; M-1 to S-207; M-1 to C-206; M-1 to S-205; M-1 to I-204; M-1 to S-203; M-1 to G-202; M-1 to A-201; M-1 to N-200; M-1 to E-199; M-1 to Q-198; M-1 to V-197; M-1 to T-196; M-1 to L-195; M-1 to S-194; M-1 to I-193; M-1 to E-192; M-1 to V-191; M-1 to D-190; M-1 to F-189; M-1 to L-188; M-1 to G-187; M-1 to H-186; M-1 to M-185; M-1 to D-184; M-1 to R-183; M-1 to N-182; M-1 to T-181; M-1 to R-180; M-1 to S-179; M-1 to D-178; M-1 to T-177; M-1 to S-176; M-1 to L-175; M-1 to D-174; M-1 to Q-173; M-1 to G-172; M-1 to Q-171; M-1 to P-170; M-1 to G-169; M-1 to K-168; M-1 to W-167; M-1 to K-166; M-1 to A-165; M-1 to T-164; M-1 to P-163; M-1 to R-162; M-1 to P-161; M-1 to F-160; M-1 to W-159; M-1 to G-158; M-1 to S-157; M-1 to S-156; M-1 to Q-155; M-1 C-154; M-1 to L-153; M-1 to L-152; M-1 to Q-151; M-1 to I-150; M-1 to D-149; M-1 to R-148; M-1 to D-147; M-1 to V-146; M-1 to Y-145; M-1 to G-144; M-1 to A-143; M-1 to I-142; M-1 to S-141; M-1 to I-140; M-1 to L-139; M-1 to P-138; M-1 to V-137; M-1 to S-136; M-1 to G-135; M-1 to L-134; M-1 to A-133; M-1 to S-132; M-1 to V-131; M-1 to Q-130; M-1 to L-129; M-1 to E-128; M-1 to W-127; M-1 to I-126; M-1 to A-125; M-1 to K-124; M-1 to Q-123; M-1 to Y-122; M-1 to Y-121; M-1 to S-120; M-1 to Q-119; M-1 to S-118; M-1 to S-117; M-1 to I-116; M-1 to R-115; M-1 to C-114; M-1 to G-113; M-1 to Y-112; M-1 to L-111; M-1 to G-110; M-1 to A-109; M-1 to D-108; M-1 to L-107; M-1 to V-106; M-1 to T-105; M-1 to I-104; M-1 to N-103; M-1 to E-102; M-1 to L-101; M-1 to R-100; M-1 to L-99; M-1 to S-98; M-1 to I-97; M-1 to R-96; M-1 to G-95; M-1 to E-94; M-1 to A-93; M-1 to I-92; M-1 to S-91; M-1 to D-90; M-1 to K-89; M-1 to V-88; M-1 to L-87; M-1 to K-86; M-1 to T-85; M-1 to R-84; M-1 to G-83; M-1 to Q-82; M-1 to Y-81; M-1 to Q-80; M-1 to P-79; M-1 to M-78; M-1 to Q-77; M-1 to M-76; M-1 to F-75; M-1 to P-74; M-1 to Q-73; M-1 to D-72; M-1 to K-71; M-1 to G-70; M-1 to D-69; M-1 to R-68; M-1 to Y-67; M-1 to L-66; M-1 to H-65; M-1 to V-64; M-1 to V-63; M-1 to S-62; M-1 to S-61; M-1 to F-60; M-1 to Q-59; M-1 to G-58; M-1 to R-57; M-1 to F-56; M-1 to F-55; M-1 to R-54; M-1 to V-53; M-1 to E-52; M-1 to M-51; M-1 to A-50; M-1 to E-49; M-1 to A-48; M-1 to N-47; M-1 to T-46; M-1 to K-45; M-1 to P-44; M-1 to S-43; M-1 to L-42; M-1 to F-41; M-1 to C-40; M-1 to S-39; M-1 to F-38; M-1 to A-37; M-1 to A-36; M-1 to D-35; M-1 to E-34; M-1 to G-33; M-1 to V-32; M-1 to L-31; M-1 to A-30; M-1 to Q-29; M-1 to V-28; M-1 to P-27; M-1 to K-26; M-1 to D-25; M-1 to P-24; M-1 to G-23; M-1 to F-22; M-1 to V-21; M-1 to Q-20; M-1 to W-19; M-1 to Q-18; M-1 to G-17; M-1 to S-16; M-1 to G-15; M-1 to L-14; M-1 to K-13; M-1 to L-11; M-1 to S-10; M-1 to L-9; M-1 to V-8; M-1 to L-7; M-1 to S-6; of SEQ ID NO:37. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nucleotide sequences related to extensive portions of SEQ ID NO:19 which have been determined from the following related cDNA genes: HTTDB46R (SEQ ID NO:122), and HSIEA44R (SEQ ID NO:123).

A polynucleotide encoding a polypeptide of the present invention is obtained from human small intestine, colon tumor, and human testes tumor cells and tissues. The polynucleotide of this invention was discovered in a human testes tumor cDNA library.

Based on the sequence similarity to the bovin butyrophilin precursor, translation product of this gene is expected to share at least some biological activities with B30.2-like domain containing proteins, and specifically butyrophilin proteins. Such activities are known in the art, some of which are described elsewhere herein. Specifically, polynucleotides and polypeptides of the invention are also useful for modulating the differentiation of normal and malignant cells, modulating the proliferation and/or differentiation of cancer and neoplastic cells, and regulation of cell growth and differentiation. Polynucleotides and polypeptides of the invention may represent a diagnostic marker for breast diseases and/or disorders, in addition to disorders of secretory organs and tissues (which include, testicular and gastrointestinal disorders, particularly those cells which serve secretory functions for seminal fluid or gastrointestinal hormones, and disorders of the mucosal membranes of such cells and tissues, etc.).

The full-length protein should be a secreted protein, based upon homology to the butyrophilin family of proteins. Therefore, it is secreted into milk, serum, urine, seminal fluid, or feces and thus the levels is assayable from patient samples. Assuming specific expression levels are reflective of the presence of breast disorders (i.e., breast cancer, breast dysfunction, etc.) this protein would provide a convenient diagnostic for early detection of such disorders In addition, expression of this gene product may also be linked to the progression of breast diseases, and therefore may itself actually represent a therapeutic or therapeutic target for the treatment of breast cancer. Polynucleotides and polypeptides of the invention may play an important role in the pathogenesis of human cancers and cellular transformation, particularly those of secretory cells and tissues. Polynucleotides and polypeptides of the invention may also be involved in the pathogenesis of developmental abnormalities based upon its potential effects on proliferation and differentiation of cells and tissue cell types.

Due to the potential proliferating and differentiating activity of said polynucleotides and polypeptides, the invention is useful as a therapeutic agent in inducing tissue regeneration, for treating inflammatory conditions. Moreover, the invention is useful in modulating the immune response to aberrant polypeptides, as may exist in rapidly proliferating cells and tissue cell types, particularly in cancers. The invention, including agonists and/or antagonists thereof, is useful in modulating the nutritional value of milk, its caloric content, its fat content, and may conceivably be useful in mediating the adaption of breast secretory function as a delivery vehicle for therapeutics (i.e., transgenic breast secretory tissue for transferring therapeutically active proteins to infants).

Alternatively, the expression within cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA).

Alternatively, this gene product is involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

This gene is expressed primarily in small intestine, colon tumor, and to a lesser extent in human testes tumor cells.

Therefore, polynucleotides and polypeptides of the invention are useful as reagents for differential identification of the tissue(s) or cell type(s) present in a biological sample and for diagnosis of diseases and conditions which include, but are not limited to, gastrointestinal diseases and/or disorders, in addition to lactation disorders, and tumors of the testes. Similarly, polypeptides and antibodies directed to these polypeptides are useful in providing immunological probes for differential identification of the tissue(s) or cell type(s). For a number of disorders of the above tissues or cells, particularly of the immune and reproductive systems, expression of this gene at significantly higher or lower levels is routinely detected in certain tissues or cell types (e.g. immune, testicular, gastrointestinal, and cancerous and wounded tissues) or bodily fluids (e.g. lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Features of Protein Encoded by Gene No: 10

The translation product of this gene contains a serine protease motif and accordingly is believed to possess serine protease activity. Assays for determining such activity are well known in the art. Preferred polypeptides of this invention possess such activity.

Included in this invention as preferred domains are serine protease histidine active site domains, which were identified using the ProSite analysis tool (Swiss Institute of Bioinformatics). The catalytic activity of the serine proteases from the trypsin family is provided by a charge relay system involving an aspartic acid residue hydrogen-bonded to a histidine, which itself is hydrogen-bonded to a serine. The sequences in the vicinity of the active site serine and histidine residues are well conserved in this family of proteases [1]. Consensus pattern: [LIVM]-[ST]-A-[STAG]-H-C, H is the active site residue.

Preferred polypeptides of the invention comprise, or alternatively consist of, the following amino acid sequence: GTLVAEKHVLTAAHCIHDGKTYVKGTQ (SEQ ID NO: 124). Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Further preferred are polypeptides comprising the serine protease histidine active site domain of the sequence referenced in Table XIV for this gene, and at least 5, 10, 15, 20, 25, 30, 50, or 75 additional contiguous amino acid residues of this referenced sequence. The additional contiguous amino acid residues is N-terminal or C-terminal to the serine protease histidine active site domain.

Alternatively, the additional contiguous amino acid residues is both N-terminal and C-terminal to the serine protease histidine active site domain, wherein the total N- and C-terminal contiguous amino acid residues equal the specified number. The above preferred polypeptide domain is characteristic of a signature specific to serine protease proteins. Based on the sequence similarity, the translation product of this gene is expected to share at least some biological activities with serine proteases. Such activities are known in the art, some of which are described elsewhere herein.

In another embodiment, polypeptides comprising the amino acid sequence of the open reading frame upstream of the predicted signal peptide are contemplated by the present invention. Specifically, polypeptides of the invention comprise, or alternatively consist of, the following amino acid sequence: GTRGQAWEPRALSRRPHLSERRSEPRPGRAARRGTVLGMAGIPGLLFLLFF LLCAVGQVSPYSAPWKPTWPAYRLPVVLPQSTLNLAKPDFGAEAKLEVSSSCGPQCHKGTPLPTYEEAKQY LSYETLYANGSRTETQVGIYILSSSGDGAQHRDSGSSGKSRRK RQIYGYDSRFSIFGKDFLLNYPFSTSVKLSTGCTGTLV AEKHVLTAAHCIHDGKTYVKGTQKLRVGFLKPKFKDGGRGANDSTSAMPEQMKFQWIRVKRTHVPKGWIKGNANDI GMDYDYALLELKKPHKRKFMKIGVSPPAKQLPGGRIHFSG YNDRPGNLVYRFCDVKDETYDLLYQQCDSQPGASGS GVYYVRMWKRQHQKWERKIIGMISGHQWVDMDGSPQEFTRGCSEITPLQYIPDISIGV (SEQ ID NO: 125). Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

A preferred polypeptide variant of the invention comprises, or alternatively consists of, the following amino acid sequence: MAGIPGLLFLLFFLLCAVGQVSPYSAPWKPTWPAYRLPVVLPQSTLNLAKPD FGAEAKLEVSSSCGPQCHKGTPLPTYEEAKQYLSYETLYANGSRTETQVGIYILSSSGDGAQHRDSGSSGKSR RKRQIYGYDSRFSIFGKDFLLNYPFSTSVKLSTGCTGTLVAEKHVLT AAHCIHDGKTYVKGTQKLRVGFLKPKFKDGGRGANDSTSAMPEQMKFQWIRVKRTHVPKGWIKGNANDIGMDYDY ALLELKKPHKRKFMKIGVSPPAKQLPG- GRIHFSGYDNDRPGNLVYRFCDVKDETY-DLLYQQCDAQPGASGSGVYVRM WKRQQQKWERKI-IGIFSGHQWVDMNGSPQDFNVAVRITPLKYAQIC YWIKGNYLDCRE G (SEQ ID NO: 126). Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred polypeptides of the present invention comprise, or alternatively consist of, one, two, three, four, five, six, seven, eight, nine, ten, eleven, twelve, thirteen, or all thirteen of the immunogenic epitopes shown in SEQ ID NO: 38 as residues: Pro-67 to Thr-73, Pro-76 to Gln-83, Asn-93 to Thr-99, His-115 to Arg-128, His-178 to Lys-189, Pro-197 to Ala-212, Val-224 to Trp-233, Lys-253 to Lys-259, Ser-280 to Asn-289, Asp-296 to Tyr-302, Gln-308 to Ala-315, Arg-327 to Lys-335, and/or Asp-349 to Gly-358. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

FIGS. 25 A-B show the nucleotide (SEQ ID NO:20) and deduced amino acid sequence (SEQ ID NO:38) of the present invention. Predicted amino acids from about 1 to about 19 constitute the predicted signal peptide (amino acid residues from about 1 to about 19 in SEQ ID NO:38) and are represented by the underlined amino acid regions; amino acids from about 162 to about 188 constitutes the predicted serine protease histidine active site domain (amino acids residues from about 162 to about 188 in SEQ ID NO:38) and are represented by the double underlined amino acid regions; and amino acid residue 175 (amino acid residue 175 in SEQ ID NO:38) constitutes the predicted histidine active site residue and is represented by the bold amino acid.

FIG. 26 shows the regions of similarity between the amino acid sequences of the present invention SEQ ID NO:38, and the Human Pancreatic Elastase 2 protein (gi|219620)(SEQ ID NO: 127).

Figure 27:
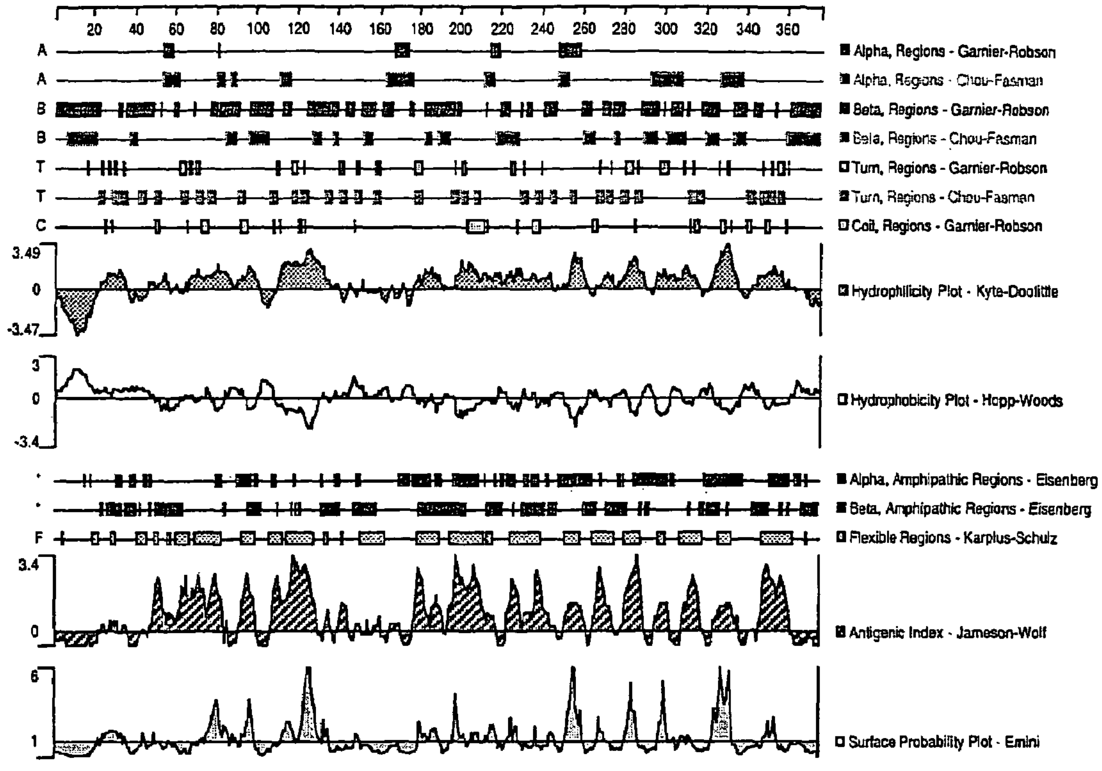
FIG. 27 shows an analysis of the amino acid sequence of SEQ ID NO:38. Alpha, beta, turn and coil regions; hydrophilicity and hydrophobicity; amphipathic regions; flexible regions; antigenic index and surface probability are shown.

FIG. 27 shows an analysis of the amino acid sequence of SEQ ID NO:38. Alpha, beta, turn and coil regions; hydrophilicity and hydrophobicity; amphipathic regions; flexible regions; antigenic index and surface probability are shown.

The present invention provides isolated nucleic acid molecules comprising a polynucleotide encoding the polypeptide having the amino acid sequence shown in FIGS. 25A-B (SEQ ID NO:38), which was determined by sequencing a cloned cDNA. The nucleotide sequence shown in FIGS. 25A-B (SEQ ID NO:20) was obtained by sequencing a cloned cDNA (HUSAQ05), which was deposited on Nov. 17, 1998 at the American Type Culture Collection, and given Accession Number 203484. The deposited gene is inserted in the pSport plasmid (Life Technologies, Rockville, Md.) using the SalI/NotI restriction endonuclease cleavage sites.

The present invention is further directed to fragments of the isolated nucleic acid molecules described herein. By a fragment of an isolated DNA molecule having the nucleotide sequence of the deposited cDNA or the nucleotide sequence shown in SEQ ID NO:20 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:20. By a fragment at least 20 nt in length, for example, is intended fragments which include 20 or more contiguous bases from the nucleotide sequence of the deposited cDNA or the nucleotide sequence as shown in SEQ ID NO:20. In this context "about" includes the particularly recited size, larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1350, from about 1351 to about 1400, from about 1401 to about 1450, from about 1451 to about 1500, from about 1501 to about 1550, from about 1551 to about 1600, from about 1601 to about 1650, from about 1651 to about 1699 of SEQ ID NO:20, or the complementary strand thereto, or the cDNA contained in the deposited gene. In this context "about" includes the particularly recited ranges, larger or smaller by several (5, 4, 3, 2, or 1) nucleotides, at either terminus or at both termini. In additional embodiments, the polynucleotides of the invention encode functional attributes of the corresponding protein.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 27 and/or Table IX, as described above, was generated using the various modules and algorithms of the DNA*STAR set on default parameters. In a preferred embodiment, the data presented in columns VIII, IX, XIII, and XIV of Table IX can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 27, but may, as shown in Table IX, be represented or identified by using tabular representations of the data presented in FIG. 27. The DNA*STAR computer algorithm used to generate FIG. 27 (set on the original default parameters) was used to present the data in FIG. 27 in a tabular format (See Table IX). The tabular format of the data in FIG. 27 is used to easily determine specific boundaries of a preferred region. The above-mentioned preferred regions set out in FIG. 27 and in Table IX include, but are not limited to, regions of the aforementioned types identified by analysis of the amino acid sequence set out in FIG. 1. As set out in FIG. 27 and in Table IX, such preferred regions include Gamier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, etc.) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, the present invention further provides polypeptides having one or more residues deleted from the amino terminus of the amino acid sequence shown in FIGS. 25A-B, up to the aspartic acid residue at position number 370 and polynucleotides encoding such polypeptides. In particular, the present invention provides polypeptides comprising the amino acid sequence of residues n1-375 of FIGS. 25A-B, where n1 is an integer from 2 to 370 corresponding to the position of the amino acid residue in FIGS. 25A-B (which is identical to the sequence shown as SEQ ID NO:38). N-terminal deletions of the polypeptide of the invention shown as SEQ ID NO:38 include polypeptides comprising the amino acid sequence of residues: A-2 to V-375; G-3 to V-375; 14 to V-375; P-5 to V-375; G-6 to V-375; L-7 to V-375; L-8 to V-375; F-9 to V-375; L-10 to V-375; L-11 to V-375; F-12 to V-375; F-13 to V-375; L-14 to V-375; L-15 to V-375; C-16 to V-375; A-17 to V-375; V-18 to V-375; G-19 to V-375; Q-20 to V-375; V-21 to V-375; S-22 to V-375; P-23 to V-375; Y-24 to V-375; S-25 to V-375; A-26 to V-375; P-27 to V-375; W-28 to V-375; K-29 to V-375; P-30 to V-375; T-31 to V-375; W-32 to V-375; P-33 to V-375; A-34 to V-375; Y-35 to V-375; R-36 to V-375; L-37 to V-375; P-38 to V-375; V-39 to V-375; V-40 to V-375; L-41 to V-375; P-42 to V-375; Q-43 to V-375; S-44 to V-375; T-45 to V-375; L-46 to V-375; N-47 to V-375; L-48 to V-375; A-49 to V-375; K-50 to V-375; P-51 to V-375; D-52 to V-375; F-53 to V-375; G-54 to V-375; A-55 to V-375; E-56 to V-375; A-57 to V-375; K-58 to V-375; L-59 to V-375; E-60 to V-375; V-61 to V-375; S-62 to V-375; S-63 to V-375; S-64 to V-375; C-65 to V-375; G-66 to V-375; P-67 to V-375; Q-68 to V-375; C-69 to V-375; H-70 to V-375; K-71 to V-375; G-72 to V-375; T-73 to V-375; P-74 to V-375; L-75 to V-375; P-76 to V-375; T-77 to V-375; Y-78 to V-375; E-79 to V-375; E-80 to V-375; A-81 to V-375; K-82 to V-375; Q-83 to V-375; Y-84 to V-375; L-85 to V-375; S-86 to V-375; Y-87 to V-375; E-88 to V-375; T-89 to V-375; L-90 to V-375; Y-91 to V-375; A-92 to V-375; N-93 to V-375; G-94 to V-375; S-95 to V-375; R-96 to V-375; T-97 to V-375; E-98 to V-375; T-99 to V-375; Q-100 to V-375; V-101 to V-375; G-102 to V-375; I-103 to V-375; Y-104 to V-375; I-105 to V-375; L-106 to V-375; S-107 to V-375; S-108 to V-375; S-109 to V-375; G-110 to V-375; D-111 to V-375; G-112 to V-375; A-113 to V-375; Q-114 to V-375; H-115 to V-375; R-116 to V-375; D-117 to V-375; S-118 to V-375; G-119 to V-375; S-120 to V-375; S-121 to V-375; G-122 to V-375; K-123 to V-375; S-124 to V-375; R-125 to V-375; R-126 to V-375; K-127 to V-375; R-128 to V-375; Q-129 to V-375; I-130 to V-375; Y-131 to V-375; G-132 to V-375; Y-133 to V-375; D-134 to V-375; S-135 to V-375; R-136 to V-375; F-137 to V-375; S-138 to V-375; I-139 to V-375; F-140 to V-375; G-141 to V-375; K-142 to V-375; D-143 to V-375; F-144 to V-375; L-145 to V-375; L-146 to V-375; N-147 to V-375; Y-148 to V-375; P-149 to V-375; F-150 to V-375; S-151 to V-375; T-152 to V-375; S-153 to V-375; V-154 to V-375; K-155 to V-375; L-156 to V-375; S-157 to V-375; T-158 to V-375; G-159 to V-375; C-160 to V-375; T-161 to V-375; G-162 to V-375; T-163 to V-375; L-164 to V-375; V-165 to V-375; A-166 to V-375; E-167 to V-375; K-168 to V-375; H-169 to V-375; V-170 to V-375; L-171 to V-375; T-172 to V-375; A-173 to V-375; A-174 to V-375; H-175 to V-375; C-176 to V-375; I-177 to V-375; H-178 to V-375; D-179 to V-375; G-180 to V-375; K-181 to V-375; T-182 to V-375; Y-183 to V-375; V-184 to V-375; K-185 to V-375; G-186 to V-375; T-187 to V-375; Q-188 to V-375; K-189 to V-375; L-190 to V-375; R-191 to V-375; V-192 to V-375; G-193 to V-375; F-194 to V-375; L-195 to V-375; K-196 to V-375; P-197 to V-375; K-198 to V-375; F-199 to V-375; K-200 to V-375; D-201 to V-375; G-202 to V-375; G-203 to V-375; R-204 to V-375; G-205 to V-375; A-206 to V-375; N-207 to V-375; D-208 to V-375; S-209 to V-375; T-210 to V-375; S-211 to V-375; A-212 to V-375; M-213 to V-375; P-214 to V-375; E-215 to V-375; Q-216 to V-375; M-217 to V-375; K-218 to V-375; F-219 to V-375; Q-220 to V-375; W-221 to V-375; I-222 to V-375; R-223 to V-375; V-224 to V-375; K-225 to V-375; R-226 to V-375; T-227 to V-375; H-228 to V-375; V-229 to V-375; P-230 to V-375; K-231 to V-375; G-232 to V-375; W-233 to V-375; I-234 to V-375; K-235 to V-375; G-236 to V-375; N-237 to V-375; A-238 to V-375; N-239 to V-375; D-240 to V-375; I-241 to V-375; G-242 to V-375; M-243 to V-375; D-244 to V-375; Y-245 to V-375; D-246 to V-375; Y-247 to V-375; A-248 to V-375; L-249 to V-375; L-250 to V-375; E-251 to V-375; L-252 to V-375; K-253 to V-375; K-254 to V-375; P-255 to V-375; H-256 to V-375; K-257 to V-375; R-258 to V-375; K-259 to V-375; F-260 to V-375; M-261 to V-375; K-262 to V-375; I-263 to V-375; G-264 to V-375; V-265 to V-375; S-266 to V-375; P-267 to V-375; P-268 to V-375; A-269 to V-375; K-270 to V-375; Q-271 to V-375; L-272 to V-375; P-273 to V-375; G-274 to V-375; G-275 to V-375; R-276 to V-375; I-277 to V-375; H-278 to V-375; F-279 to V-375; S-280 to V-375; G-281 to V-375; Y-282 to V-375; D-283 to V-375; N-284 to V-375; D-285 to V-375; R-286 to V-375; P-287 to V-375; G-288 to V-375; N-289 to V-375; L-290 to V-375; V-291 to V-375; Y-292 to V-375; R-293 to V-375; F-294 to V-375; C-295 to V-375; D-296 to V-375; V-297 to V-375; K-298 to V-375; D-299 to V-375; E-300 to V-375; T-301 to V-375; Y-302 to V-375; D-303 to V-375; L-304 to V-375; L-305 to V-375; Y-306 to V-375; Q-307 to V-375; Q-308 to V-375; C-309 to V-375; D-310 to V-375; S-311 to V-375; Q-312 to V-375; P-313 to V-375; G-314 to V-375; A-315 to V-375; S-316 to V-375; G-317 to V-375; S-318 to V-375; G-319 to V-375; V-320 to V-375; Y-321 to V-375; V-322 to V-375; R-323 to V-375; M-324 to V-375; W-325 to V-375; K-326 to V-375; R-327 to V-375; Q-328 to V-375; H-329 to V-375; Q-330 to V-375; K-331 to V-375; W-332 to V-375; E-333 to V-375; R-334 to V-375; K-335 to V-375; I-336 to V-375; I-337 to V-375; G-338 to V-375; M-339 to V-375; I-340 to V-375; S-341 to V-375; G-342 to V-375; H-343 to V-375; Q-344 to V-375; W-345 to V-375; V-346 to V-375; D-347 to V-375; M-348 to V-375; D-349 to V-375; G-350 to V-375; S-351 to V-375; P-352 to V-375; Q-353 to V-375; E-354 to V-375; F-355 to V-375; T-356 to V-375; R-357 to V-375; G-358 to V-375; C-359 to V-375; S-360 to V-375; E-361 to V-375; I-362 to V-375; T-363 to V-375; P-364 to V-375; L-365 to V-375; Q-366 to V-365; Y-367 to V-375; I-368 to V-375; P-369 to V-375; D-370 to V-375; of SEQ ID NO:38. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities (e.g., biological activities such as ability to modulate the extracellular matrix etc.) may still be retained. For example the ability to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a mutein with a large number of deleted C-terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the polypeptide shown in FIGS. 25A-B, up to the glycine residue at position number 6, and polynucleotides encoding such polypeptides. In particular, the present invention provides polypeptides comprising the amino acid sequence of residues 1-m1 of FIGS. 25A-B, where m1 is an integer from 6 to 375 corresponding to the position of the amino acid residue in FIGS. 25A-B. Moreover, the invention provides polynucleotides encoding polypeptides comprising, or alternatively consisting of, the amino acid sequence of C-terminal deletions of the polypeptide of the invention shown as SEQ ID NO:38 include polypeptides comprising the amino acid sequence of residues: M-1 to G-374; M-1 to I-373; M-1 to S-372; M-1 to I-371; M-1 to D-370; M-1 to P-369; M-1 to I-368; M-1 to Y-367; M-1 to Q-366; M-1 to L-365; M-1 to P-364; M-1 to T-363; M-1 to I-362; M-1 to E-361; M-1 to S-360; M-1 to C-359; M-1 to G-358; M-1 to R-357; M-1 to T-356; M-1 to F-355; M-1 to E-354; M-1 to Q-353; M-1 to P-352; M-1 to S-351; M-1 to G-350; M-1 to D-349; M-1 to M-348; M-1 to D-347; M-1 to V-346; M-1 to W-345; M-1 to Q-344; M-1 to H-343; M-1 to G-342; M-1 to S-341; M-1 to I-340; M-1 to M-339; M-1 to G-338; M-1 to I-337; M-1 to I-336; M-1 to K-335; M-1 to R-334; M-1 to E-333; M-1 to W-332; M-1 to K-331; M-1 to Q-330; M-1 to H-329; M-1 to Q-328; M-1 to R-327; M-1 to K-326; M-1 to W-325; M-1 to M-324; M-1 to R-323; M-1 to V-322; M-1 to Y-321; M-1 to V-320; M-1 to G-319; M-1 to S-318; M-1 to G-317; M-1 to S-316; M-1 to A-315; M-1 to G-314; M-1 to P-313; M-1 to Q-312; M-1 to S-311; M-1 to D-310; M-1 to C-309; M-1 to Q-308; M-1 to Q-307; M-1 to Y-306; M-1 to L-305; M-1 to L-304; M-1 to D-303; M-1 to Y-302; M-1 to T-301; M-1 to E-300; M-1 to D-299; M-1 to K-298; M-1 to V-297; M-1 to D-296; M-1 to C-295; M-1 to F-294; M-1 to R-293; M-1 to Y-292; M-1 to V-291; M-1 to L-290; M-1 to N-289; M-1 to G-288; M-1 to P-287; M-1 to R-286; M-1 to D-285; M-1 to N-284; M-1 to D-283; M-1 to Y-282; M-1 to G-281; M-1 to S-280; M-1 to F-279; M-1 to H-278; M-1 to I-277; M-1 to R-276; M-1 to G-275; M-1 to G-274; M-1 to P-273; M-1 to L-272; M-1 to Q-271; M-1 to K-270; M-1 to A-269; M-1 to P-268; M-1 to P-267; M-1 to S-266; M-1 to V-265; M-1 to G-264; M-1 to I-263; M-1 to K-262; M-1 to M-261; M-1 to F-260; M-1 to K-259; M-1 to R-258; M-1 to K-257; M-1 to H-256; M-1 to P-255; M-1 to K-254; M-1 to K-253; M-1 to L-252; M-1 to E-251; M-1 to L-250; M-1 to L-249; M-1 to A-248; M-1 to Y-247; M-1 to D-246; M-1 to Y-245; M-1 to D-244; M-1 to M-243; M-1 to G-242; M-1 to I-241; M-1 to D-240; M-1 to N-239; M-1 to A-238; M-1 to N-237; M-1 to G-236; M-1 to K-235; M-1 to I-234; M-1 to W-233; M-1 to G-232; M-1 to K-231; M-1 to P-230; M-1 to V-229; M-1 to H-228; M-1 to T-227; M-1 to R-226; M-1 to K-225; M-1 to V-224; M-1 to R-223; M-1 to I-222; M-1 to W-221; M-1 to Q-220; M-1 to F-219; M-1 to K-218; M-1 to M-217; M-1 to Q-216; M-1 to E-215; M-1 to P-214; M-1 to M-213; M-1 to A-212; M-1 to S-211; M-1 to T-210; M-1 to S-209; M-1 to D-208; M-1 to N-207; M-1 to A-206; M-1 to G-205; M-1 to R-204; M-1 to G-203; M-1 to G-202; M-1 to D-201; M-1 to K-200; M-1 to F-199; M-1 to K-198; M-1 to P-197; M-1 to K-196; M-1 to L-195; M-1 to F-194; M-1 to G-193; M-1 to V-192; M-1 to R-191; M-1 to L-190; M-1 to K-189; M-1 to Q-188; M-1 to T-187; M-1 to G-186; M-1 to K-185; M-1 to V-184; M-1 to Y-183; M-1 to T-182; M-1 to K-181; M-1 to G-180; M-1 to D-179; M-1 to H-178; M-1 to I-177; M-1 to C-176; M-1 to H-175; M-1 to A-174; M-1 to A-173; M-1 to T-172; M-1 to L-171; M-1 to V-170; M-1 to H-169; M-1 to K-168; M-1 to E-167; M-1 to A-166; M-1 to V-165; M-1 to L-164; M-1 to T-163; M-1 to G-162; M-1 to T-161; M-1 to C-160; M-1 to G-159; M-1 to T-158; M-1 to S-157; M-1 to L-156; M-1 to K-155; M-1 to V-154; M-1 to S-153; M-1 to T-152; M-1 to S-151; M-1 to F-150; M-1 to P-149; M-1 to Y-148; M-1 to N-147; M-1 to L-146; M-1 to L-145; M-1 to F-144; M-1 to D-143; M-1 to K-142; M-1 to G-141; M-1 to F-140; M-1 to I-139; M-1 to S-138; M-1 to F-137; M-1 to R-136; M-1 to S-135; M-1 to D-134; M-1 to Y-133; M-1 to G-132; M-1 to Y-131; M-1 to I-130; M-1 to Q-129; M-1 to R-128; M-1 to K-127; M-1 to R-126; M-1 to R-125; M-1 to S-124; M-1 to K-123; M-1 to G-122; M-1 to S-121; M-1 to S-120; M-1 to G-119; M-1 to S-118; M-1 to D-117; M-1 to R-116; M-1 to H-115; M-1 to Q-114; M-1 to A-113; M-1 to G-112; M-1 to D-111; M-1 to G-110; M-1 to S-109; M-1 to S-108; M-1 to S-107; M-1 to L-106; M-1 to I-105; M-1 to Y-104; M-1 to I-103; M-1 to G-102; M-1 to V-101; M-1 to Q-100; M-1 to T-99; M-1 to E-98; M-1 to T-97; M-1 to R-96; M-1 to S-95; M-1 to G-94; M-1 to N-93; M-1 to A-92; M-1 to Y-91; M-1 to L-90; M-1 to T-89; M-1 to E-88; M-1 to Y-87; M-1 to S-86; M-1 to L-85; M-1 to Y-84; M-1 to Q-83; M-1 to K-82; M-1 to A-81; M-1 to E-80; M-1 to E-79; M-1 to Y-78; M-1 to T-77; M-1 to P-76; M-1 to L-75; M-1 to P-74; M-1 to T-73; M-1 to G-72; M-1 to K-71; M-1 to H-70; M-1 to C-69; M-1 to Q-68; M-1 to P-67; M-1 to G-66; M-1 to C-65; M-1 to S-64; M-1 to S-63 M-1 to S-62; M-1 to V-61; M-1 to E-60; M-1 to L-59; M-1 to K-58; M-1 to A-57; M-1 to E-56; M-1 to A-55; M-1 to G-54; M-1 to F-53; M-1 to D-52; M-1 to P-51; M-1 to K-50; M-1 to A-49; M-1 to L-48; M-1 to N-47; M-1 to L-46; M-1 to T-45; M-1 to S-44; M-1 to Q-43; M-1 to P-42; M-1 to L-41; M-1 to V-40; M-1 to V-39; M-1 to P-38; M-1 to L-37; M-1 R-36; M-1 to Y-35; M-1 to A-34; M-1 to P-33; M-1 to W-32; M-1 to T-31; M-1 to P-30; M-1 to K-29; M-1 TO W-28; M-1 to P-27; M-1 to A-26; M-1 to S-25; M-1 to Y-24; M-1 to P-23; M-1 to S-22; M-1 to V-21; M-1 to Q-20; M-1 to M-1 G-19; M-1 to V-18; M-1 to A-17; M-1 to C-16; M-1 to L-15; M-1 to L-14; M-1 to F-13; M-1 to F-12; M-1 to L-11; M-1 to L-10; M-1 to F-9; M-1 to L-8; M-1 to L-7; M-1 to G-6; of SEQ ID NO:38. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nucleotide sequences related to extensive portions of SEQ ID NO:20 which have been determined from the following related cDNA genes: HFKCF40F (SEQ ID NO:128), HSRDF26R (SEQ ID NO:129), HTEBE07R (SEQ ID NO:130), HFTBP-82R (SEQ ID NO:131), HAQBJ11R (SEQ ID NO:132), HAFBB11R (SEQ ID NO:133), HOEFO85R (SEQ ID NO:134), and HUVGY95R (SEQ ID NO:135).

The gene encoding the disclosed cDNA is believed to reside on chromosome 12. Accordingly, polynucleotides related to this invention are useful as a marker in linkage analysis for chromosome 12.

This gene is expressed primarily in endothelial cells, fibroblasts, smooth muscle, and osteoblasts, and to a lesser extent in brain, heart, placental tissues, lung, and many other tissues. Moreover, the transcript is present in HUVEC, HUVEC+LPS, smooth muscle, fibroblasts; present in heart, brain, placenta, lung, liver, muscle, kidney, pancreas, spleen, thymus, prostate, testes, ovary, small intestine, colon and weakly in PBLs.

Northern analysis indicates that this gene is expressed highest in HUVEC, HUVEC+LPS, smooth muscle, fibroblasts, present in heart, brain, placenta, lung, liver, muscle, kidney, pancreas, spleen, thymus, prostate, testes, ovary, small intestine, colon and weakly in PBLs.

Therefore, polynucleotides and polypeptides of the invention, including antibodies, are useful as reagents for differential identification of the tissue(s) or cell type(s) present in a biological sample and for diagnosis of diseases and conditions which include, but are not limited to, disorders of vascularized tissues. Similarly, polypeptides and antibodies directed to these polypeptides are useful in providing immunological probes for differential identification of the tissue(s) or cell type(s). For a number of disorders of the above tissues or cells, particularly of the vascular tissues, expression of this gene at significantly higher or lower levels is routinely detected in certain tissues or cell types (e.g. vascular, skeletal, developmental, neural, cardiovascular, pulmonary, renal, immune, hematopoietic, reproductive, gastrointestinal, and cancerous and wounded tissues) or bodily fluids (e.g., lymph, seminal, fluid, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in the vascularized endothelial cells indicates that polynucleotides and polypeptides corresponding to this gene are useful for the diagnosis and treatment of diseases of vascularized tissues, such as atherosclerosis, ataxia malabsortion, and hyperlipidemia. These and other factors often result in other cardiovascular disease. Furthermore, translation product of this gene is useful for the treatment of wounds, and may facilitate the wound healing process. Moreover, the protein is useful in the detection, treatment, and/or prevention of a variety of vascular disorders and conditions, which include, but are not limited to, miscrovascular disease, vascular leak syndrome, aneurysm, stroke, embolism, thrombosis, coronary artery disease, arteriosclerosis, and/or atherosclerosis. Based upon the tissue distribution of this protein, antagonists directed against this protein is useful in blocking the activity of this protein. Accordingly, preferred are antibodies which specifically bind a portion of the translation product of this gene.

Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 1685 of SEQ ID NO:20, b is an integer of 15 to 1699, where both a and b correspond to the positions of nucleotide residues shown in SEQ ID NO:20, and where b is greater than or equal to a+14.

Features of Protein Encoded by Gene No: 11

Translation products corresponding to this gene share sequence homology with Cytotoxic-Regulatory T-Cell Associated Molecule (CRTAM) protein, which is thought to be important in the regulation of celluar physiology, development, differentiation or function of various cell types, including haematopoietic cells and various T-cell progenitors. See for example, International Publication No. WO 96/34102 incorporated herein by reference in its entirety. Moreover, translation products corresponding to this gene also share sequence homology with the thymocyte activation and developmental protein and the class-I MHC-restricted T cell associated molecule (See Genbank Accession Nos. gi|2665790, gb|AAB88491.1, gb|AAC80267.1, and gi|3930163; all information and references contained within these accessions are hereby incorporated herein by reference). Based on the sequence similarity, the translation product of this gene is expected to share at least some biological activities with T-cell modulatory proteins. Such activities are known in the art, some of which are described elsewhere herein.

Preferred polypeptides of the invention comprise, or alternatively consist of, the following amino acid sequence: MASVVLPSGSQCAAAAAAAAPPGLRLRLLLLLFSAAALIPTGDGQNLFTKDVTVIEGEVATI SCQVNKSDDSVIQLLNPN RQTIYFRDFRPLKDSRFQLLNFSSSELKVSLTNVSISDEGRYFCQLYTDPPQESYTTITVLVPPRNLMIDIQKDTAVEGEEI EVNCTAMASKPATTIRWFKGNTELKGKSEVEEWSDMYT VTSQLMLKVHKEDDGVPVICQVEHPAVTGNLQTQRYLE VQYKPQVHIQMTYPLQGLTREGDALELTCEAIGKPQPVMVTWVRVDDEMPQ HAVLSGPNLFINNLNKTDNGTYRCEA SNIVGKAHSDYMLYVYDPPTTIPPPTTrTTTTTrTILTIITDSRAGEEGSRAVDHAVIGGVVAVVVFAMLCLLIILGR YFARHKGTYFTHEAKGADDAADADTAIINAEGGQNNSEEKKEYFI (SEQ ID NO: 136). Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

The polypeptide of this latter embodiment has been determined to have a transmembrane domain at about amino acid position 379-395 of the amino acid sequence referenced in Table XIV for this gene. Moreover, a cytoplasmic tail encompassing amino acids 396 to 442 of this protein has also been determined. Based upon these characteristics, it is believed that the protein product of this gene shares structural features to type la membrane proteins.

Preferred polynucleotides comprise, or alternatively consist of, the following nucleic acid sequence: ATGGCGAGTGTAGTGC TGCCGAGCGGATCCCAGTGTGCGGCGGCAGCGGCGGCGGCGGCGCCTCCCGGGCTCCGGCTCCGGCTTC TGCTGTTGCT CTTCTCCGCCGCGGCACTGATCCCCACAGGTGATGGGCAGAATCTGTTTACGAAAGACGTGACAGT GATCGAGGGAGAGGTTGCGACCATCAGTTGCCAAGTCAATAAGAGTGACG ACTCTGTGATTCAGCTACTGAATCC CAACAGGCAGACCATTTATTTCAGGGACTTCAGGCCTTTGAAGGACAGCAGGTTTCAGTTGCTGAATFTTTCTAGC AGTGAACTCAAAGTATCATTGACAAACGTCTCAATTTCTG ATGAAGGAAGATACTTTTGCCAGCTCTATACCGATC CCCCACAGGAAAGTTACACCACCATCACAGTCCTGGTC CCACCACGTAATCTGATGATCGATATCCAGAAAGACA CTGCGGTGGAAGGTGAGGAGATTGAAGTCAACTGCACTGCTATGGCCAGCAAGCCAGCCACGACTATCAGGTGGT TCAAAGGGAACACAGAGCTAAAAGGCAAATCGGAGGTGGAAGAGTGGTCAGACATGTACACTGTGACCAGTCAG CTGATGCTGAAGGTGCACAAGGAGGACGATGGGGTCCCAGTG ATCTGCCAGGTGGAGCACCCTGCGGTCACTGGA AACCTGCAGACCCAGCGGTATCTAGAAGTACAGTATAAGCCTCAAGTGCACATTCAGATGACTTATCCTCTACAA GGCTTAACCCGGGAAGGGGACGCGCTTGAGTTAACATGTGAAGC CATCGGGAAGCCCCAGCCTGTGATGGTAACT TGGGTGAGAGTCGATGATGAAATGCCTCAACACGCCGTACTGTCTGGGCCCAACCTGTTCATCAATAACCTAAAC AAAACAGATAATGGTACATACCGCTGTGAAGCTTCAAACATAGTGGG GAAAGCTCACTCGGATTATATGCTGTAT GTATACGATCCCCCCACAACTATCCCTCCTCCCACAACAACCACCACCACCACCACCACCACCACCACCACCACCATCC TTACCATCATCACAGATTCCCGAGCAGGTGAAGAAGGCTCGATCAGGGCAGTGGATCATGCCGTGATCGGTGGCG TCGTGGCGGTGGTGGTGTTCGCCATGCTGTGCTTGCTCATCATT CTGGGGCGCTATmGCCAGACATAAAGGTAC ATACTTCACTCATGAAGCCAAAGGAGCCGATGACGCAGCAGACGCAGACACAGCTATAATCAATGCAGAAGGAG GACAGAACAACTCCGAAGAAAAGAAAGAGTACTTCATCTAG (SEQ ID NO:137). Also preferred are the polypeptides encoded by these polynucleotides.

Preferred polypeptides of the present invention comprise, or alternatively consist of, one, two, three, four, five, six, seven, eight, nine, or all nine of the immunogenic epitopes shown in SEQ ID NO: 39 as residues: Gly-42 to Phe-48, Val-66 to Asp-71, Asn-78 to Thr-83, Asp-88 to Arg-96, Tyr-127 to Tyr-135, Lys-181 to Trp-195, His-210 to Gly-215, Leu-303 to Thr-310, and/or Thr-341 to Thr-350. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

FIGS. 28A-B shows the nucleotide (SEQ ID NO:21) and deduced amino acid sequence (SEQ ID NO:39) of the present invention. Predicted amino acids from about 1 to about 44 constitute the predicted signal peptide (amino acid residues from about 1 to about 44 in SEQ ID NO:39) and are represented by the underlined amino acid regions.

FIG. 29 shows the regions of similarity between the amino acid sequences of the present invention SEQ ID NO:39, the human poliovirus receptor protein (gi|1524088) (SEQ ID NO: 138), the human class-I MHC-restricted T cell associated molecule (WO9634102) (SEQ ID NO:144), and the *Gallus gallus* thymocyte activation and developmental protein (gb|AAB88491.1)(SEQ ID NO:145).

FIG. 30 shows an analysis of the amino acid sequence of SEQ ID NO:39. Alpha, beta, turn and coil regions; hydrophilicity and hydrophobicity; amphipathic regions; flexible regions; antigenic index and surface probability are shown.

The present invention provides isolated nucleic acid molecules comprising a polynucleotide encoding the polypeptide having the amino acid sequence shown in FIGS. 28A-B (SEQ ID NO:39), which was determined by sequencing a cloned cDNA. The nucleotide sequence shown in FIGS. 28A-B (SEQ ID NO:21) was obtained by sequencing a cloned cDNA (HOUDJ81), which was deposited on Nov. 17, 1998 at the American Type Culture Collection, and given Accession Number 203484. The deposited gene is inserted in the pSport plasmid (Life Technologies, Rockville, Md.) using the SalI/NotI restriction endonuclease cleavage sites.

The present invention is further directed to fragments of the isolated nucleic acid molecules described herein. By a fragment of an isolated DNA molecule having the nucleotide sequence of the deposited cDNA or the nucleotide sequence shown in SEQ ID NO:21 is intended DNA fragments at least about 15 nt, and more preferably at least about 20 nt; still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:21. By a fragment at least 20 nt in length, for example, is intended fragments which include 20 or more contiguous bases from the nucleotide sequence of the deposited cDNA or the nucleotide sequence as shown in SEQ ID NO:21. In this context "about" includes the particularly recited size, larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1350, from about 1351 to about 1400, from about 1401 to about 1450, from about 1451 to about 1500, from about 1501 to about 1520 of SEQ ID NO:21, or the complementary strand thereto, or the cDNA contained in the deposited gene. In this context "about" includes the particularly recited ranges, larger or smaller by several (5, 4, 3, 2, or 1) nucleotides, at either terminus or at both termini. In additional embodiments, the polynucleotides of the invention encode functional attributes of the corresponding protein.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 30 and/or Table X as described above, was generated using the various modules and algorithms of the DNA*STAR set on default parameters. In a preferred embodiment, the data presented in columns VIII, IX, XIII, and XIV of Table X can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 30, but may, as shown in Table X, be represented or identified by using tabular representations of the data presented in FIG. 30. The DNA*STAR computer algorithm used to generate FIG. 30 (set on the original default parameters) was used to present the data in FIG. 30 in a tabular format (See Table X). The tabular format of the data in FIG. 30 is used to easily determine specific boundaries of a preferred region. The above-mentioned preferred regions set out in FIG. 30 and in Table X include, but are not limited to, regions of the aforementioned types identified by analysis of the amino acid sequence set out in FIGS. 28A-B. As set out in FIG. 30 and in Table X such preferred regions include Gamier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, etc.) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact peptides composed of as few as six amino acid residues may often evoke an immune response.

Accordingly, the present invention further provides polypeptides having one or more residues deleted from the amino terminus of the amino acid sequence shown in FIGS. 28A-B, up to the threonine residue at position number 359 and polynucleotides encoding such polypeptides. In particular, the present invention provides polypeptides comprising the amino acid sequence of residues n1-364 of FIGS. 28A-B, where n1 is an integer from 2 to 359 corresponding to the position of the amino acid residue in FIGS. 28A-B (which is identical to the sequence shown as SEQ ID NO:39). N-terminal deletions of the polypeptide of the invention shown as SEQ ID NO:39 include polypeptides comprising the amino acid sequence of residues: A-2 to R-364; S-3 to R-364; V-4 to R-364; V-5 to R-364; L-6 to R-364; P-7 to R-364; S-8 to R-364; G-9 to R-364; S-10 to R-364; Q-11 to R-364; C-12 to R-364; A-13 to R-364; A-14 to R-364; A-15 to R-364; A-16 to R-364; A-17 to R-364; A-18 to R-364; A-19 to R-364; A-20 to R-364; P-21 to R-364; P-22 to R-364; G-23 to R-364; L-24 to R-364; R-25 to R-364; L-26 to R-364; R-27 to R-364; L-28 to R-364; L-29 to R-364; L-30 to R-364; L-31 to R-364; L-32 to R-364; F-33 to R-364; S-34 to R-364; A-35 to R-364; A-36 to R-364; A-37 to R-364; L-38 to R-364; I-39 to R-364; P-40 to R-364; T-41 to R-364; G-42 to R-364; D-43 to R-364; G-44 to R-364; Q-45 to R-364; N-46 to R-364; L-47 to R-364; F-48 to R-364; T-49 to R-364; K-50 to R-364; D-51 to R-364; V-52 to R-364; T-53 to R-364; V-54 to R-364; I-55 to R-364; E-56 to R-364; G-57 to R-364; E-58 to R-364; V-59 to R-364; A-60 to R-364; T-61 to R-364; I-62 to R-364; S-63 to R-364; C-64 to R-364; Q-65 to R-364; V-66 to R-364; N-67 to R-364; K-68 to R-364; S-69 to R-364; D-70 to R-364; D-71 to R-364; S-72 to R-364; V-73 to R-364; I-74 to R-364; Q-75 to R-364; L-76 to R-364; L-77 to R-364; N-78 to R-364; P-79 to R-364; N-80 to R-364; R-81 to R-364; Q-82 to R-364; T-83 to R-364; I-84 to R-364; Y-85 to R-364; F-86 to R-364; R-87 to R-364; D-88 to R-364; F-89 to R-364; R-90 to R-364; P-91 to R-364; L-92 to R-364; K-93 to R-364; D-94 to R-364; S-95 to R-364; R-96 to R-364; F-97 to R-364; Q-98 to R-364; L-99 to R-364; L-100 to R-364; N-101 to R-364; F-102 to R-364; S-103 to R-364; S-104 to R-364; S-105 to R-364; E-106 to R-364; L-107 to R-364; K-108 to R-364; V-109 to R-364; S-110 to R-364; L-111 to R-364; T-112 to R-364; N-113 to R-364; V-114 to R-364; S-115 to R-364; I-116 to R-364; S-117 to R-364; D-118 to R-364; E-119 to R-364; G-120 to R-364; R-121 to R-364; Y-122 to R-364; F-123 to R-364; C-124 to R-364; Q-125 to R-364; L-126 to R-364; Y-127 to R-364; T-128 to R-364; D-129 to R-364; P-130 to R-364; P-131 to R-364; Q-132 to R-364; E-133 to R-364; S-134 to R-364; Y-135 to R-364; T-136 to R-364; T-137 to R-364; I-138 to R-364; T-139 to R-364; V-140 to R-364; L-141 to R-364; V-142 to R-364; P-143 to R-364; P-144 to R-364; R-145 to R-364; N-146 to R-364; L-147 to R-364; M-148 to R-364; I-149 to R-364; D-150 to R-364; I-151 to R-364; Q-152 to R-364; K-153 to R-364; D-154 to R-364; T-155 to R-364; A-156 to R-364; V-157 to R-364; E-158 to R-364; G-159 to R-364; E-160 to R-364; E-161 to R-364; I-162 to R-364; E-163 to R-364; V-164 to R-364; N-165 to R-364; C-166 to R-364; T-167 to R-364; A-168 to R-364; M-169 to R-364; A-170 to R-364; S-171 to R-364; K-172 to R-364; P-173 to R-364; A-174 to R-364; T-175 to R-364; T-176 to R-364; I-177 to R-364; R-178 to R-364; W-179 to R-364; F-180 to R-364; K-181 to R-364; G-182 to R-364; N-183 to R-364; T-184 to R-364; E-185 to R-364; L-186 to R-364; K-187 to R-364; G-188 to R-364; K-189 to R-364; S-190 to R-364; E-191 to R-364; V-192 to R-364; E-193 to R-364; E-194 to R-364; W-195 to R-364; S-196 to R-364; D-197 to R-364; M-198 to R-364; Y-199 to R-364; T-200 to R-364; V-201 to R-364; T-202 to R-364; S-203 to R-364; Q-204 to R-364; L-205 to R-364; M-206 to R-364; L-207 to R-364; K-208 to R-364; V-209 to R-364; H-210 to R-364; K-211 to R-364; E-212 to R-364; D-213 to R-364; D-214 to R-364; G-215 to R-364; V-216 to R-364; P-217 to R-364; V-218 to R-364; I-219 to R-364; C-220 to R-364; Q-221 to R-364; V-222 to R-364; E-223 to R-364; H-224 to R-364; P-225 to R-364; A-226 to R-364; V-227 to R-364; T-228 to R-364; G-229 to R-364; N-230 to R-364; L-231 to R-364; Q-232 to R-364; T-233 to R-364; Q-234 to R-364; R-235 to R-364; Y-236 to R-364; L-237 to R-364; E-238 to R-364; V-239 to R-364; Q-240 to R-364; Y-241 to R-364; K-242 to R-364; P-243 to R-364; Q-244 to R-364; V-245 to R-364; H-246 to R-364; I-247 to R-364; Q-248 to R-364; M-249 to R-364; T-250 to R-364; Y-251 to R-364; P-252 to R-364; L-253 to R-364; Q-254 to R-364; G-255 to R-364; L-256.to R-364; T-257 to R-364; R-258 to R-364; E-259 to R-364; G-260 to R-364; D-261 to R-364; A-262 to R-364; L-263 to R-364; E-264 to R-364; L-265 to R-364; T-266 to R-364; C-267 to R-364; E-268 to R-364; A-269 to R-364; I-270 to R-364; G-271 to R-364; K-272 to R-364; P-273 to R-364; Q-274 to R-364; P-275 to R-364; V-276 to R-364; M-277 to R-364; V-278 to R-364; T-279 to R-364; W-280 to R-364; V-281 to R-364; R-282 to R-364; V-283 to R-364; D-284 to R-364; D-285 to R-364; E-286 to R-364; M-287 to R-364; P-288 to R-364; Q-289 to R-364; H-290 to R-364; A-291 to R-364; V-292 to R-364; L-293 to R-364; S-294 to R-364; G-295 to R-364; P-296 to R-364; N-297 to R-364; L-298 to R-364; F-299 to R-364; I-300 to R-364; N-301 to R-364; N-302 to R-364; L-303 to R-364; N-304 to R-364; K-305 to R-364; T-306 to R-364; D-307 to R-364; N-308 to R-364; G-309 to R-364; T-310 to R-364; Y-311 to R-364; R-312 to R-364; C-313 to R-364; E-314 to R-364; A-315 to R-364; S-316 to R-364; N-317 to R-364; I-318 to R-364; V-319 to R-364; G-320 to R-364; K-321 to R-364; A-322 to R-364; H-323 to R-364; S-324 to R-364; D-325 to R-364; Y-326 to R-364; M-327 to R-364; L-328 to R-364; Y-329 to R-364; V-330 to R-364; Y-331 to R-364; D-332 to R-364; P-333 to R-364; P-334 to R-364; T-335 to R-364; T-336 to R-364; I-337 to R-364; P-338 to R-364; P-339 to R-364; P-340 to R-364; T-341 to R-364; T-342 to R-364; T-343 to R-364; T-344 to R-364; T-345 to R-364; T-346 to R-364; T-347 to R-364; T-348 to R-364; T-349 to R-364; T-350 to R-364; T-351 to R-364; T-352 to R-364; T-353 to R-364; 1-354 to R-364; L-355 to R-364; T-356 to R-364; 1-357 to R-364; 1-358 to R-364; T-359 to R-364; of SEQ ID NO:39. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities (e.g., biological activities such as ability to modulate the extracellular matrix, etc.) may still be retained. For example the ability to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a mutein with a large number of deleted C-terminal amino acid residues may retain some biological or immunogenic activities.

In fact, peptides composed of as few as six amino acid residues may often evoke an immune response.

Accordingly, the present invention further provides polypeptides having one or more residues deleted from the carboxy terminus of the amino acid sequence of the polypeptide shown in FIGS. 28A-B, up to the leucine residue at position number 6, and polynucleotides encoding such polypeptides. In particular, the present invention provides polypeptides comprising the amino acid sequence of residues 1-m1of FIGS. 28A-B, where m1 integer from 6 to 364 corresponding to the position of the amino acid residue in FIGS. 28A-B. Moreover, the invention provides polynucleotides encoding polypeptides comprising, or alternatively consisting of, the amino acid sequence of C-terminal deletions of the polypeptide of the invention shown as SEQ ID NO:39 include polypeptides comprising the amino acid sequence of residues: M-1 to A-363; M-1 to R-362; M-1 to S-361; M-1 to D-360; M-1 to T-359; M-1 to I-358; M-1 to I-357; M-1 to T-356; M-1 to L-355; M-1 to I-354; M-1 to T-353; M-1 to T-352; M-1 to T-351; M-1 to T-350; M-1 to T-349; M-1 to T-348; M-1 to T-347; M-1 to T-346; M-1 to T-345; M-1 to T-344; M-1 to T-343; M-1 to T-342; M-1 to T-341; M-1 to P-340; M-1 to P-339; M-1 to P-338; M-1 to I-337; M-1 to T-336; M-1 to T-335; M-1 to P-334; M-1 to P-333; M-1 to D-332; M-1 to Y-331; M-1 to V-330; M-1 to Y-329; M-1 to L-328; M-1 to M-327; M-1 to Y-326; M-1 to D-325; M-1 to S-324; M-1 to H-323; M-1 to A-322; M-1 to K-321; M-1 to G-320; M-I to V-319; M-1 to I-318; M-1 to N-317; M-1 to S-316; M-1 to A-315; M-1 to E-314; M-1 to C-313; M-1 to R-312; M-1 to Y-311; M-1 to T-310; M-1 to G-309; M-1 to N-308; M-1 to D-307; M-1 to T-306; M-1 to K-305; M-1 to N-304;M-1 to L-303; M-1 to N-302; M-1 to N-301; M-1 to I-300; M-1 to F-299; M-1 to L-298; M-1 to N-297; M-1 to P-296; M-1 to G-295; M-1 to S-294; M-1 to L-293; M-1 to V-292; M-1 to A-291; M-1 to H-290; M-1 to Q-289; M-1 to P-288; M-1 to M-287; M-1 to E-286; M-1 to D-285; M-1 to D-284; M-1 to V-283; M-1 to R-282; M-1 to V-281; M-1 to W-280; M-1 to T-279; M-1 to V-278; M-1 to M-277; M-1 to V-276; M-1 to P-275; M-1 to Q-274; M-1 to P-273; M-1 to K-272; M-1 to G-271; M-1 to I-270; M-1 to A-269; M-1 to E-268; M-1 to C-267; M-1 to T-266; M-1 to L-265; M-1 to E-264; M-1 to L-263; M-1 to A-262; M-1 to D-261; M-1 to G-260; M-1 to E-259; M-1 to R-258; M-1 to T-257; M-1 to L-256; M-1 to G-255; M-1 to Q-254; M-1 to L-253; M-1 to P-252; M-1 to Y-251; M-1 to T-250; M-1 to M-249; M-1 to Q-248; M-1 to I-247; M-1 to H-246; M-1 to V-245; M-1 to Q-244; M-1 to P-243; M-1 to K-242; M-1 to Y-241; M-1 to Q-240; M-1 to V-239; M-1 to E-238; M-1 to L-237; M-1 to Y-236; M-1 to R-235; M-1 to Q-234; M-1 to T-233; M-1 to Q-232; M-1 to L-231; M-1 to N-230; M-1 to G-229; M-1 to T-228; M-1 to V-227; M-1 to A-226; M-1 to P-225; M-1 to H-224; M-1 to E-223; M-1 to V-222; M-1 to Q-221; M-1 to C-220; M-1 to 1-219; M-1 to V-218; M-1 to P-217; M-1 to V-216; M-1 to G-215; M-1 to D-214; M-1 to D-213; M-1 to E-212; M-1 to K-211; M-1 to H-210; M-1 to V-209; M-1 to K-208; M-1 to L-207; M-1 to M-206; M-1 to L-205; M-1 to Q-204; M-1 to S-203; M-1 to T-202; M-1 to V-201; M-1 to T-200; M-1 to Y-199; M-1 to M-198; M-1 to D-197; M-1 to S-196; M-1 to W-195; M-1 to E-194; M-1 to E-193; M-1 to V-192; M-1 to E-191; M-1 to S-190; M-1 to K-189; M-1 to G-188; M-1 to K-187; M-1 to L-186; M-1 to E-185; M-1 to T-184; M-1 to N-183; M-1 to G-1 82; M-1 to K-181; M-1 to F-180; M-1 to W-179; M-1 to R-178; M-1 to 1-177; M-1 to T-176; M-1 to T-175; M-1 to A-174; M-1 to P-173; M-1 to K-172; M-1 to S-1 71; M-1 to A-1 70; M-1 to M-169; M-1 to A-168; M-1 to T-167; M-1 to C-166; M-1 to N-165; M-1 to V-164; M-1 to E-163; M-1 to I-162; M-1 to E-161; M-1 to E-160; M-1 to G-159; M-1 to E-158; M-1 to V-157; M-1 to A-156; M-1 to T-155; M-1 to D-154; M-1 to K-1 53; M-1 to Q-152; M-1 to I-151; M-1 to D-150; M-1 to 1-149; M-1 to M-148; M-1 to L-147; M-1 to N-146; M-1 to R-145; M-1 to P-144; M-1 to P-143; M-1 to V-142; M-1 to L-141; M-1 to V-140; M-1 to T-139; M-1 to I-138; M-1 to T-137; M-1 to T-136; M-1 to Y-135; M-1 to S-134; M-1 to E-133; M-1 to Q-132; M-1 to P-131; M-1 to P-130; M-1 to D-129; M-1 to T-128; M-1 to Y-127; M-1 to L-126; M-1 to Q-125; M-1 to C-124; M-1 to F-123; M-1 to Y-122; M-1 to R-121; M-1 to G-120; M-1 to E-119; M-1 to D-118; M-1 to S-117; M-1 to I-116; M-1 to S-115; M-1 to V-114; M-1 to N-113; M-1 to T-112; M-1 to L-111; M-1 to S-110; M-1 to V-109; M-1 to K-108; M-1 to L-107; M-1 to E-106; M-1 to S-105; M-1 to S-104; M-1 to S-103; M-1 to F-102; M-1 to N-101; M-1 to L-100; M-1 to L-99; M-1 to Q-98; M-1 to F-97; M-1 to R-96; M-1 to S-95; M-1 to D-94; M-1 to K-93; M-1 to L-92; M-1 to P-91; M-1 to R-90; M-1 to F-89; M-1 to D-88; M-1 to R-87; M-1 to F-86; M-1 to Y-85; M-1 to I-84; M-1 to T-83; M-1 to Q-82; M-1 to R-81; M-1 to N-80; M-1 to P-79; M-1 to N-78; M-1 to L-77; M-1 to L-76; M-1 to Q-75; M-1 to I-74; M-1 to V-73; M-1 to S-72; M-1 to D-71; M-1 to D-70; M-1 to S-69; M-1 to K-68; M-1 to N-67; M-1 to V-66; M-1 to Q-65; M-1 to C-64; M-1 to S-63; M-1 to I-62; M-1 to T-61; M-1 to A-60; M-1 to V-59; M-1 to E-58; M-1 to G-57; M-1 to E-56; M-1 to I-55; M-1 to V-54; M-1 to T-53; M-1 to V-52; M-1 to D-51; M-1 to K-50; M-1 to T-49; M-1 to F-48; M-1 to L-47; M-1 to N-46; M-1 to Q-45; M-1 to G-44; M-1 to D-43; M-1 to G-42; M-1 to T-41; M-1 to P-40; M-1 to I-39; M-1 to L-38; M-1 to A-37; M-1 to A-36; M-1 to A-35; M-1 to S-34; M-1 to F-33; M-1 to L-32; M-1 to L-31; M-1 to L-30; M-1 to L-29; M-1 to L-28; M-1 to R-27; M-1 to L-26; M-1 to R-25; M-1 to L-24; M-1 to G-23; M-1 to P-22; M-1 to P-21; M-1 to A-20; M-1 to A-19; M-1 to A-18; M-1 to A-17; M-1 to A-16; M-1 to A-15; M-1 to A-14; M-1 to A-13; M-1 to C-12; M-1 to Q-11; M-1 to S-10; M-1 to G-9; M-1 to S-8; M-1 to P-7; M-1 to L-6; of SEQ ID NO:39. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nucleotide sequences related to extensive portions of SEQ ID NO:21 which have been determined from the following related cDNA genes: HSQFJ92R (SEQ ID NO:139), HFLAB18F (SEQ ID NO:140), HAQBH82R (SEQ ID NO:141), HLHTM10R (SEQ ID NO:142), and HLHAL65R (SEQ ID NO: 143).

This gene is expressed primarily in immune system related tissues such as ulcerative colitis, rejected kidney tissues, and to a lesser extent in thymus and bone marrow.

Therefore, polynucleotides and polypeptides of the invention, including antibodies, are useful as reagents for differential identification of the tissue(s) or cell type(s) present in a biological sample and for diagnosis of diseases and conditions which include, but are not limited to, immune and hematopoietic diseases and/or disorders, particularly ulcerative colitis and rejected organs. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels is routinely detected in certain tissues or cell types (e.g. transplanted kidney, immune, hematopoeitic, renal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution primarily in immune cells and tissues, combined with the homology to the CRTAM, thymocyte activation and developmental protein, the class-I MHC-restricted T cell associated molecule protein, and the polivirus receptor, indicates that the protein products of this gene are useful for the regulation of celluar physiology, development, differentiation or function of various cell types, including haematopoietic cells and particularly T-cell progenitors. Representative uses are described in the "Immune Activity" and "infectious disease" sections below, in Example 11, 13, 14, 16, 18, 19, 20, and 27, and elsewhere herein. The proteins can be used to develop products for the diagnosis and treatment of conditions associated with abnormal physiology or development, including abnormal proliferation, e.g. cancers, or degenerative conditions. The physiology or development of a cell can be modulated by contacting the cell with an agonist or antagonist (i.e. an anti-CRTAM-like peptide antibody). Further the CRTAM-like polypeptides of the present invention include treatment of ulcerative colitis, organ rejection and other immune system related disorders. Agonists or antagonists may treat or prevent such disorders as ulcerative colitis and rejected organs, such as kidney. Based upon the tissue distribution of this protein, antagonists directed against this protein is useful in blocking the activity of this protein. Accordingly, preferred are antibodies which specifically bind a portion of the translation product of this gene.

Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 1506 of SEQ ID NO:21, b is an integer of 15 to 1520, where both a and b correspond to the positions of nucleotide residues shown in SEQ ID NO:21, and where b is greater than or equal to a+14.

Features of Protein Encoded by Gene No: 12

FIG. 31 shows the nucleotide (SEQ ID NO:22) and deduced amino acid sequence (SEQ ID NO:40) of the present invention. Predicted amino acids from about 1 to about 23 constitute the predicted signal peptide (amino acid residues from about 1 to about 23 in SEQ ID NO:40) and are represented by the underlined amino acid regions.

FIG. 32 shows the regions of similarity between the amino acid sequences of the present invention SEQ ID NO:40 and the human FAP protein (gi|1890647) (SEQ ID NO:146).

FIG. 33 shows an analysis of the amino acid sequence of SEQ ID NO:40. Alpha, beta, turn and coil regions; hydrophilicity and hydrophobicity; amphipathic regions; flexible regions; antigenic index and surface probability are shown.

The present invention provides isolated nucleic acid molecules comprising a polynucleotide encoding the polypeptide having the amino acid sequence shown in FIG. 31 (SEQ ID NO:40), which was determined by sequencing a cloned cDNA. The nucleotide sequence shown in FIG. 31 (SEQ ID NO:22) was obtained by sequencing a cloned cDNA (HPWCM76), which was deposited on Nov. 17, 1998 at the American Type Culture Collection, and given Accession Number 203484. The deposited gene is inserted in the pSport plasmid (Life Technologies, Rockville, Md.) using the SalI/NotI restriction endonuclease cleavage sites.

The present invention is further directed to fragments of the isolated nucleic acid molecules described herein. By a fragment of an isolated DNA molecule having the nucleotide sequence of the deposited cDNA or the nucleotide sequence shown in SEQ ID NO:22 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:22. By a fragment at least 20 nt in length, for example, is intended fragments which include 20 or more contiguous bases from the nucleotide sequence of the deposited cDNA or the nucleotide sequence as shown in SEQ ID NO:22. In this context "about" includes the particularly recited size, larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, from about 601 to about 650, from about 651 to about 700, from about 701 to about 750, from about 751 to about 800, from about 801 to about 807 of SEQ ID NO:22, or the complementary strand thereto, or the cDNA contained in the deposited gene. In this context "about" includes the particularly recited ranges, larger or smaller by several (5, 4, 3, 2, or 1) nucleotides, at either terminus or at both termini. In additional embodiments, the polynucleotides of the invention encode functional attributes of the corresponding protein.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 33 and/or Table XI, as described above, was generated using the various modules and algorithms of the DNA*STAR set on default parameters. In a preferred embodiment, the data presented in columns VIII, IX, XIII, and XIV of Table XI can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 33, but may, as shown in Table XI, be represented or identified by using tabular representations of the data presented in FIG. 33. The DNA*STAR computer algorithm used to generate FIG. 33 (set on the original default parameters) was used to present the data in FIG. 33 in a tabular format (See Table XI). The tabular format of the data in FIG. 33 is used to easily determine specific boundaries of a preferred region. The above-mentioned preferred regions set out in FIG. 33 and in Table XI include, but are not limited to, regions of the aforementioned types identified by analysis of the amino acid sequence set out in FIG. 31. As set out in FIG. 33 and in Table XI, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, etc.) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, the present invention further provides polypeptides having one or more residues deleted from the amino terminus of the amino acid sequence shown in FIG. 31, up to the arginine residue at position number 61 and polynucleotides encoding such polypeptides. In particular, the present invention provides polypeptides comprising the amino acid sequence of residues n1-66 of FIG. 31, where n1 is an integer from 2 to 61 corresponding to the position of the amino acid residue in FIG. 31 (which is identical to the sequence shown as SEQ ID NO:40). N-terminal deletions of the polypeptide of the invention shown as SEQ ID NO:40 include polypeptides comprising the amino acid sequence of residues: S-2 to N-66; S-3 to N-66; S-4 to N-66; S-5 to N-66; L-6 to N-66; K-7 to N-66; H-8 to N-66; L-9 to N-66; L-10 to N-66; C-11 to N-66; M-12 to N-66; A-13 to N-66; L-14 to N-66; S-15 to N-66; W-16 to N-66; F-17 to N-66; S-18 to N-66; S-19 to N-66; F-20 to N-66; I-21 to N-66; S-22 to N-66; G-23 to N-66; E-24 to N-66; T-25 to N-66; S-26 to N-66; F-27 to N-66; S-28 to N-66; L-29 to N-66; L-30 to N-66; N-31 to N-66; S-32 to N-66; F-33 to N-66; F-34 to N-66; L-35 to N-66; P-36 to N-66; Y-37 to N-66; P-38 to N-66; S-39 to N-66; S-40 to N-66; R-41 to N-66; C-42 to N-66; C-43 to N-66; C-44 to N-66; F-45 to N-66; S-46 to N-66; V-47 to N-66; Q-48 to N-66; C-49 to N-66; S-50 to N-66; I-51 to N-66; L-52 to N-66; D-53 to N-66; P-54 to N-66; F-55 to N-66; S-56 to N-66; C-57 to N-66; N-58 to N-66; S-59 to N-66; M-60 to N-66; R-61 to N-66; of SEQ ID NO:40. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities (e.g., biological activities such as ability to modulate the extracellular matrix, etc.) may still be retained. For example the ability to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a mutein with a large number of deleted C-terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the polypeptide shown in FIG. 31, up to the leucine residue at position number 6, and polynucleotides encoding such polypeptides. In particular, the present invention provides polypeptides comprising the amino acid sequence of residues 1-ml of FIG. 31, where ml is an integer from 6 to 66 corresponding to the position of the amino acid residue in FIG. 31. Moreover, the invention provides polynucleotides encoding polypeptides comprising, or alternatively consisting of, the amino acid sequence of C-terminal deletions of the polypeptide of the invention shown as SEQ ID NO:40 include polypeptides comprising the amino acid sequence of residues: M-1 to E-65; M-1 to W-64; M-1 to P-63; M-1 to F-62; M-1 to R-61;

M-1 to M-60; M-1 to S-59; M-1 to N-58; M-1 to C-57; M-1 to S-56; M-1 to F-55; M-1 to P-54; M-1 to D-53; M-1 to L-52; M-1 to I-51; M-1 to S-50; M-1 to C-49; M-1 to Q-48; M-1 to V-47; M-1 to S-46; M-1 to F-45; M-1 to C-44; M-1 to C-43; M-1 to C-42; M-1 to R-41; M-1 to S-40; M-1 to S-39; M-1 to P-38; M-1 to Y-37; M-1 to P-36; M-1 to L-35; M-1 to F-34; M-1 to F-33; M-1 to S-32; M-1 to N-31; M-1 to L-30; M-1 to L-29; M-1 to S-28; M-1 to F-27; M-1 to S-26; M-1 to T-25; M-1 to E-24; M-1 to G-23; M-1 to S-22; M-1 to I-21; M-1 to F-20; M-1 to S-19; M-1 to S-18; M-1 to F-17; M-1 to W-16; M-1 to S-15; M-1 to L-14; M-1 to A-13; M-1 to M-12; M-1 to C-11; M-1 to L-10; M-1 to L-9; M-1 to H-8; M-1 to K-7; M-1 to L-6; of SEQ ID NO:40. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99%, identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nucleotide sequences related to extensive portions of SEQ ID NO:22 which have been determined from the following related cDNA genes: HPWCM76R (SEQ ID NO: 147).

This gene is expressed primarily in prostate BPH (benign prostatic hyperplasia) tissue.

Therefore, polynucleotides and polypeptides of the invention, including antibodies, are useful as reagents for differential identification of the tissue(s) or cell type(s) present in a biological sample and for diagnosis of diseases and conditions which include, but are not limited to, inflammation of the prostate, or related tissues. Similarly, polypeptides and antibodies directed to these polypeptides are useful in providing immunological probes for differential identification of the tissue(s) or cell type(s). For a number of disorders of the above tissues or cells, particularly of the prostate, expression of this gene at significantly higher or lower levels is routinely detected in certain tissues or cell types (e.g. prostate, cancerous and wounded tissues) or bodily fluids (e.g., serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in prostate BPH tissue indicates that polynucleotides and polypeptides corresponding to this gene are useful for the treatment of inflammatory conditions which result in an enlargement of the prostate, or related tissues. Polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that is expressed, particularly at low levels, in other tissues of the body. Therefore, this gene product is expressed in other specific tissues or organs where it may play related functional roles in other processes, such as hematopoiesis, inflammation, bone formation, and kidney function, to name a few possible target indications. Based upon the tissue distribution of this protein, antagonists directed against this protein is useful in blocking the activity of this protein. Accordingly, preferred are antibodies which specifically bind a portion of the translation product of this gene.

Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein.

Shared homology to the FAP protein indicates that the protein product of this gene is useful in treating, detecting, and/or preventing iron metabolism disorders, particularly those resulting in high oxidative states, tissue damage, athersclerosis, free radical damage, vascular disorders, iron binding protein dysfunction, nitric oxide synthase dysfunction or aberration, vasodilation disorders, and tissue edema. Based on the sequence similarity, the translation product of this gene is expected to share at least some biological activities with iron metabolism modulatory proteins. Such activities are known in the art, some of which are described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 793 of SEQ ID NO:22, b is an integer of 15 to 807, where both a and b correspond to the positions of nucleotide residues shown in SEQ ID NO:22, and where b is greater than or equal to a +14.

TABLE I

| Res | | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | −0.10 | 0.44 | . | . | . | −0.40 | 0.48 |
| Val | 2 | . | . | B | . | . | . | . | 0.08 | 0.01 | . | . | . | 0.15 | 0.63 |
| Ala | 3 | . | . | B | . | . | . | . | 0.47 | 0.01 | . | . | . | 0.40 | 0.76 |
| Gln | 4 | . | . | B | . | . | . | . | 0.51 | −0.01 | . | . | . | 1.40 | 1.33 |
| Asp | 5 | . | . | . | . | . | T | C | 0.23 | −0.20 | . | . | F | 2.20 | 1.77 |
| Pro | 6 | . | . | . | . | T | T | . | 0.02 | −0.27 | * | * | F | 2.50 | 0.94 |
| Gln | 7 | . | . | . | . | T | T | . | 0.88 | −0.09 | * | * | F | 2.25 | 0.45 |
| Gly | 8 | . | . | . | . | T | T | . | 0.66 | −0.09 | . | * | F | 2.00 | 0.47 |
| Cys | 9 | . | A | B | . | . | . | . | −0.01 | 0.60 | . | * | . | −0.10 | 0.25 |
| Leu | 10 | . | A | B | . | . | . | . | −0.82 | 0.74 | . | * | . | −0.35 | 0.08 |
| Gln | 11 | . | A | B | . | . | . | . | −0.91 | 1.03 | . | * | . | −0.60 | 0.06 |
| Leu | 12 | . | A | B | . | . | . | . | −0.91 | 0.99 | . | * | . | −0.60 | 0.16 |
| Cys | 13 | . | A | B | . | . | . | . | −1.42 | 0.41 | . | * | . | −0.60 | 0.34 |
| Leu | 14 | . | A | B | . | . | . | . | −1.34 | 0.37 | * | . | . | −0.30 | 0.14 |
| Ser | 15 | . | A | B | . | . | . | . | −0.53 | 0.47 | * | * | . | −0.60 | 0.18 |
| Glu | 16 | . | A | B | . | . | . | . | −0.88 | 0.19 | * | . | . | −0.30 | 0.53 |
| Val | 17 | . | . | B | . | . | T | . | −0.88 | 0.04 | * | * | . | 0.10 | 0.63 |
| Ala | 18 | A | . | . | . | . | T | . | −0.10 | 0.04 | * | . | . | 0.10 | 0.39 |
| Asn | 19 | . | . | . | . | T | T | . | 0.71 | −0.34 | * | . | . | 1.31 | 0.44 |
| Gly | 20 | . | . | . | . | T | T | . | 0.80 | 0.06 | * | * | F | 1.07 | 0.96 |
| Leu | 21 | . | . | . | . | . | . | C | −0.06 | −0.16 | * | * | F | 1.63 | 1.47 |
| Arg | 22 | . | . | . | . | . | . | C | 0.50 | −0.01 | * | * | F | 1.69 | 0.68 |
| Asn | 23 | . | . | . | . | . | T | C | 0.49 | −0.03 | * | . | F | 2.10 | 0.92 |
| Pro | 24 | . | . | B | . | . | T | . | −0.37 | 0.16 | * | . | F | 1.24 | 1.10 |
| Val | 25 | . | . | B | . | . | T | . | −0.06 | 0.11 | * | * | . | 0.73 | 0.42 |
| Ser | 26 | . | . | B | . | . | T | . | 0.17 | 0.61 | * | * | . | 0.22 | 0.35 |
| Met | 27 | . | . | B | B | . | . | . | −0.29 | 0.71 | * | . | . | −0.39 | 0.23 |
| Val | 28 | . | . | B | B | . | . | . | −0.29 | 0.71 | . | . | . | −0.60 | 0.31 |
| His | 29 | . | . | B | B | . | . | . | −0.42 | 0.07 | . | . | . | 0.00 | 0.38 |
| Ala | 30 | A | . | B | . | . | . | . | 0.12 | 0.11 | . | . | . | 0.50 | 0.38 |
| Gly | 31 | . | . | . | . | T | T | . | 0.39 | −0.01 | * | . | F | 2.15 | 0.74 |
| Asp | 32 | . | . | . | . | T | T | . | 1.10 | −0.16 | * | * | F | 2.45 | 0.74 |
| Gly | 33 | . | . | . | . | . | T | C | 1.26 | −0.66 | * | * | F | 3.00 | 1.44 |
| Thr | 34 | . | . | . | . | . | T | C | 0.59 | −0.37 | * | * | F | 2.40 | 1.26 |
| His | 35 | . | . | B | B | . | . | . | 0.32 | −0.01 | * | * | . | 1.20 | 0.65 |
| Arg | 36 | . | . | B | B | . | . | . | 0.08 | 0.63 | . | * | . | 0.00 | 0.49 |
| Phe | 37 | . | . | B | B | . | . | . | 0.08 | 0.70 | . | * | . | −0.30 | 0.34 |
| Phe | 38 | . | . | B | B | . | . | . | 0.42 | 0.21 | . | * | . | −0.30 | 0.44 |
| Val | 39 | A | . | . | B | . | . | . | −0.12 | 0.11 | . | * | . | −0.30 | 0.39 |
| Ala | 40 | A | . | . | B | . | . | . | −0.43 | 0.76 | . | * | . | −0.60 | 0.33 |
| Glu | 41 | A | . | . | B | . | . | . | −1.40 | 0.40 | . | * | . | −0.60 | 0.38 |
| Gln | 42 | A | . | . | B | . | . | . | −1.56 | 0.26 | . | . | . | −0.30 | 0.38 |
| Val | 43 | A | . | . | B | . | . | . | −1.14 | 0.26 | . | . | . | −0.30 | 0.28 |
| Gly | 44 | . | . | B | B | . | . | . | −1.14 | 0.67 | . | . | . | −0.60 | 0.17 |
| Val | 45 | . | . | B | B | . | . | . | −0.80 | 1.31 | . | . | . | −0.60 | 0.07 |
| Val | 46 | . | . | B | B | . | . | . | −1.61 | 1.67 | . | . | . | −0.60 | 0.15 |
| Trp | 47 | . | . | B | B | . | . | . | −1.82 | 1.71 | . | . | . | −0.60 | 0.13 |
| Val | 48 | . | . | B | B | . | . | . | −0.97 | 1.71 | . | . | . | −0.60 | 0.27 |
| Tyr | 49 | . | . | B | . | . | . | . | −0.97 | 1.07 | . | . | . | −0.16 | 0.60 |
| Leu | 50 | . | . | B | . | . | T | . | −0.41 | 0.86 | * | . | . | 0.28 | 0.56 |
| Pro | 51 | . | . | . | . | T | T | . | 0.56 | 0.33 | * | * | F | 1.52 | 1.01 |
| Asp | 52 | . | . | . | . | T | T | . | 0.03 | −0.31 | . | * | F | 2.36 | 1.27 |
| Gly | 53 | . | . | . | . | . | T | C | 0.89 | −0.39 | * | * | F | 2.40 | 1.27 |
| Ser | 54 | . | A | . | . | . | . | C | 1.13 | −1.07 | * | . | F | 2.06 | 1.42 |
| Arg | 55 | . | A | B | . | . | . | . | 1.73 | −1.10 | * | * | F | 1.62 | 1.47 |
| Leu | 56 | . | A | B | . | . | . | . | 1.24 | −0.67 | * | . | F | 1.38 | 2.30 |
| Glu | 57 | . | A | B | . | . | . | . | 0.43 | −0.31 | * | . | F | 0.84 | 1.49 |
| Gln | 58 | . | A | B | . | . | . | . | 0.78 | −0.01 | * | * | F | 0.45 | 0.63 |
| Pro | 59 | A | A | . | . | . | . | . | 0.27 | −0.01 | * | * | F | 0.60 | 1.27 |
| Phe | 60 | A | A | . | . | . | . | . | 0.20 | −0.01 | * | * | . | 0.30 | 0.60 |
| Leu | 61 | A | A | . | . | . | . | . | 1.01 | −0.01 | * | . | . | 0.30 | 0.70 |
| Asp | 62 | A | A | . | . | . | . | . | 0.12 | −0.01 | * | . | . | 0.30 | 0.73 |
| Leu | 63 | A | . | . | B | . | . | . | −0.73 | 0.24 | * | . | . | −0.30 | 0.59 |
| Lys | 64 | A | . | . | B | . | . | . | −1.33 | 0.10 | . | . | . | −0.30 | 0.53 |
| Asn | 65 | . | . | B | B | . | . | . | −0.94 | 0.10 | . | . | . | −0.30 | 0.26 |
| Ile | 66 | . | . | B | B | . | . | . | −0.44 | 0.59 | . | * | . | −0.60 | 0.46 |
| Val | 67 | . | . | B | B | . | . | . | −0.66 | 0.39 | . | . | . | −0.30 | 0.33 |
| Leu | 68 | . | . | B | B | . | . | . | −0.13 | 0.81 | * | . | . | −0.60 | 0.32 |
| Thr | 69 | . | . | B | B | . | . | . | −1.07 | 1.33 | . | . | F | −0.45 | 0.48 |
| Thr | 70 | . | . | B | B | . | . | . | −1.41 | 1.33 | . | . | F | −0.45 | 0.45 |
| Pro | 71 | . | . | B | B | . | . | . | −0.52 | 1.11 | . | . | F | −0.45 | 0.54 |
| Trp | 72 | . | . | . | B | T | . | . | 0.33 | 0.43 | . | . | . | −0.20 | 0.62 |
| Ile | 73 | . | . | B | B | . | . | . | 1.26 | −0.06 | . | * | . | 0.61 | 0.75 |
| Gly | 74 | . | . | B | B | . | . | . | 1.22 | −0.54 | . | . | F | 1.37 | 0.95 |
| Asp | 75 | . | . | . | . | . | T | C | 0.83 | −0.54 | . | . | F | 2.28 | 0.89 |
| Glu | 76 | . | . | B | . | . | T | . | 0.23 | −0.67 | . | . | F | 2.54 | 1.10 |
| Arg | 77 | . | . | . | . | T | T | . | 0.18 | −0.67 | . | * | F | 3.10 | 0.92 |

TABLE I-continued

| Res | | I | II | III | IV | V | VI | VII | VIII | IX | X | XI | XII | XIII | XIV |
|---|---|---|---|---|---|---|---|---|---|---|---|---|---|---|---|
| Gly | 78 | . | . | . | . | T | T | . | 0.26 | −0.67 | . | . | F | 2.79 | 0.54 |
| Phe | 79 | A | . | . | . | . | . | . | 0.01 | 0.01 | . | * | . | 0.83 | 0.26 |
| Leu | 80 | A | . | . | . | . | . | . | −0.69 | 0.51 | . | * | . | 0.22 | 0.13 |
| Gly | 81 | A | . | . | . | . | . | . | −0.72 | 1.30 | . | * | . | −0.09 | 0.12 |
| Leu | 82 | A | . | . | . | . | . | . | −1.04 | 1.37 | * | * | . | −0.40 | 0.18 |
| Ala | 83 | A | . | . | . | . | . | . | −0.66 | 1.01 | . | * | . | −0.40 | 0.34 |
| Phe | 84 | A | . | . | . | . | . | . | −0.66 | 0.33 | . | * | . | −0.10 | 0.70 |
| His | 85 | A | . | . | . | . | T | . | 0.27 | 0.69 | * | * | . | −0.20 | 0.73 |
| Pro | 86 | A | . | . | . | . | T | . | 0.58 | 0.00 | . | * | . | 0.25 | 1.42 |
| Lys | 87 | A | . | . | . | . | T | . | 1.39 | 0.00 | . | * | . | 0.56 | 2.23 |
| Phe | 88 | A | . | . | . | . | T | . | 2.09 | −0.39 | * | * | . | 1.47 | 2.63 |
| Arg | 89 | A | . | . | . | . | . | . | 2.83 | −0.89 | * | * | . | 1.88 | 3.33 |
| His | 90 | A | . | . | . | T | T | . | 2.17 | −1.31 | * | * | . | 2.79 | 3.33 |
| Asn | 91 | . | . | . | . | T | T | . | 2.13 | −0.53 | . | * | . | 3.10 | 3.33 |
| Arg | 92 | . | . | . | . | T | T | . | 1.20 | −0.56 | . | * | . | 2.79 | 2.67 |
| Lys | 93 | . | . | . | . | T | T | . | 1.66 | 0.13 | * | * | . | 1.58 | 1.37 |
| Phe | 94 | . | . | . | B | T | . | . | 1.30 | 0.39 | * | * | . | 0.87 | 1.34 |
| Tyr | 95 | . | . | B | B | . | . | . | 1.03 | 0.74 | . | . | . | −0.14 | 1.07 |
| Ile | 96 | . | . | B | B | . | . | . | 0.37 | 1.13 | * | . | . | −0.60 | 0.72 |
| Tyr | 97 | . | . | B | . | . | T | . | −0.56 | 1.70 | * | . | . | −0.20 | 0.44 |
| Tyr | 98 | . | . | B | . | . | T | . | −0.60 | 1.60 | . | * | . | −0.20 | 0.23 |
| Ser | 99 | . | . | B | . | . | T | . | 0.14 | 0.84 | . | . | . | −0.20 | 0.56 |
| Cys | 100 | A | . | . | . | . | T | . | 0.43 | 0.16 | . | . | . | 0.10 | 0.71 |
| Leu | 101 | A | A | . | . | . | . | . | 1.37 | −0.60 | . | . | . | 0.60 | 0.91 |
| Asp | 102 | A | A | . | . | . | . | . | 0.76 | −1.36 | . | . | F | 0.90 | 1.35 |
| Lys | 103 | A | A | . | . | . | . | . | 1.00 | −1.10 | . | . | F | 0.90 | 1.87 |
| Lys | 104 | A | A | . | . | . | . | . | 1.34 | −1.67 | . | . | F | 0.90 | 3.94 |
| Lys | 105 | A | A | . | . | . | . | . | 1.12 | −2.36 | * | * | F | 0.90 | 4.71 |
| Val | 106 | A | A | . | . | . | . | . | 2.04 | −1.67 | . | * | F | 0.90 | 1.65 |
| Glu | 107 | A | A | . | . | . | . | . | 1.16 | −1.67 | . | * | F | 0.90 | 1.62 |
| Lys | 108 | A | A | . | . | . | . | . | 0.81 | −0.99 | . | * | F | 0.75 | 0.57 |
| Ile | 109 | A | A | . | . | . | . | . | 0.77 | −0.60 | . | * | F | 0.90 | 1.02 |
| Arg | 110 | A | A | . | . | . | . | . | 0.12 | −1.24 | . | . | . | 0.75 | 1.02 |
| Ile | 111 | A | A | . | . | . | . | . | 1.02 | −0.63 | . | * | . | 0.60 | 0.51 |
| Ser | 112 | A | A | . | . | . | . | . | 0.17 | −0.63 | . | * | F | 0.90 | 1.45 |
| Glu | 113 | A | A | . | . | . | . | . | −0.18 | −0.67 | * | * | F | 0.75 | 0.55 |
| Met | 114 | A | A | . | . | . | . | . | 0.82 | −0.29 | * | * | F | 0.60 | 1.05 |
| Lys | 115 | A | A | . | . | . | . | . | 0.12 | −0.97 | * | . | F | 0.90 | 1.53 |
| Val | 116 | . | A | B | . | . | . | . | 1.01 | −0.86 | . | . | F | 0.75 | 0.89 |
| Ser | 117 | A | A | . | . | . | . | . | 1.10 | −0.86 | . | * | F | 0.90 | 1.51 |
| Arg | 118 | A | A | . | . | . | . | . | 1.10 | −1.04 | . | . | F | 0.90 | 1.17 |
| Ala | 119 | A | A | . | . | . | . | . | 1.74 | −0.64 | * | . | F | 0.90 | 2.52 |
| Asp | 120 | A | . | . | . | . | T | . | 1.11 | −1.29 | * | . | F | 1.30 | 3.77 |
| Pro | 121 | A | . | . | . | . | T | . | 1.97 | −1.17 | * | . | F | 1.30 | 1.94 |
| Asn | 122 | A | . | . | . | . | T | . | 1.46 | −1.17 | . | * | F | 1.30 | 3.21 |
| Lys | 123 | A | . | . | . | . | T | . | 1.39 | −0.99 | . | * | F | 1.30 | 1.59 |
| Ala | 124 | A | A | . | . | . | . | . | 1.68 | −0.99 | . | * | F | 0.90 | 2.05 |
| Asp | 125 | A | A | . | . | . | . | . | 1.68 | −1.03 | * | . | F | 0.90 | 1.71 |
| Leu | 126 | A | A | . | . | . | . | . | 2.00 | −1.43 | * | * | F | 0.90 | 1.48 |
| Lys | 127 | A | A | . | . | . | . | . | 1.14 | −1.43 | * | * | F | 0.90 | 2.87 |
| Ser | 128 | A | A | . | . | . | . | . | 0.21 | −1.29 | * | * | F | 0.90 | 1.28 |
| Glu | 129 | A | A | . | . | . | . | . | −0.01 | −0.60 | * | * | F | 0.90 | 1.08 |
| Arg | 130 | A | A | . | . | . | . | . | −0.01 | −0.60 | * | * | F | 0.75 | 0.45 |
| Val | 131 | A | A | . | . | . | . | . | −0.09 | −0.60 | * | * | . | 0.60 | 0.58 |
| Ile | 132 | A | A | . | . | . | . | . | −0.13 | −0.30 | * | * | . | 0.30 | 0.23 |
| Leu | 133 | A | A | . | . | . | . | . | 0.17 | −0.30 | * | * | . | 0.30 | 0.21 |
| Glu | 134 | A | A | . | . | . | . | . | −0.04 | −0.30 | * | * | . | 0.30 | 0.48 |
| Ile | 135 | A | A | . | . | . | . | . | −0.74 | −0.51 | * | * | . | 0.75 | 1.06 |
| Glu | 136 | A | A | . | . | . | . | . | −0.19 | −0.70 | * | * | F | 0.90 | 1.30 |
| Glu | 137 | A | A | . | . | . | . | . | 0.70 | −1.00 | * | . | F | 0.90 | 1.01 |
| Pro | 138 | A | . | . | . | . | T | . | 1.48 | −0.60 | . | * | F | 1.30 | 2.31 |
| Ala | 139 | A | . | . | . | . | T | . | 1.48 | −0.79 | . | . | F | 1.58 | 1.82 |
| Ser | 140 | A | . | . | . | . | T | . | 2.02 | −0.39 | . | . | F | 1.56 | 1.69 |
| Asn | 141 | . | . | . | . | . | T | C | 1.68 | 0.04 | . | . | F | 1.44 | 1.08 |
| His | 142 | . | . | . | . | . | T | C | 1.68 | 0.04 | . | . | F | 1.72 | 1.06 |
| Asn | 143 | . | . | . | . | T | T | . | 1.08 | −0.06 | . | . | F | 2.80 | 1.37 |
| Gly | 144 | . | . | . | . | T | T | . | 0.86 | 0.24 | . | . | F | 1.77 | 0.70 |
| Gly | 145 | . | . | . | . | T | T | . | 0.46 | 0.53 | . | . | F | 1.19 | 0.43 |
| Gln | 146 | . | A | B | B | . | . | . | 0.11 | 0.81 | . | . | F | 0.11 | 0.23 |
| Leu | 147 | . | A | B | B | . | . | . | −0.67 | 0.84 | . | * | . | −0.32 | 0.23 |
| Leu | 148 | . | A | B | B | . | . | . | −0.67 | 1.10 | . | * | . | −0.60 | 0.19 |
| Phe | 149 | . | A | B | B | . | . | . | −0.67 | 0.67 | . | * | . | −0.60 | 0.18 |
| Gly | 150 | . | . | B | B | . | . | . | −0.57 | 0.70 | . | * | . | −0.60 | 0.22 |
| Leu | 151 | . | . | B | . | . | T | . | −1.17 | 0.77 | . | * | . | −0.20 | 0.42 |
| Asp | 152 | . | . | . | . | T | T | . | −0.60 | 0.70 | . | * | . | 0.20 | 0.48 |
| Gly | 153 | . | . | . | . | T | T | . | −0.68 | 0.67 | . | . | . | 0.20 | 0.76 |
| Tyr | 154 | . | . | B | . | . | T | . | −0.68 | 0.93 | . | * | . | −0.20 | 0.65 |

TABLE I-continued

| Res | | I | II | III | IV | V | VI | VII | VIII | IX | X | XI | XII | XIII | XIV |
|---|---|---|---|---|---|---|---|---|---|---|---|---|---|---|---|
| Met | 155 | . | . | B | B | . | . | . | −0.64 | 1.03 | . | . | . | −0.60 | 0.33 |
| Tyr | 156 | . | . | B | B | . | . | . | −0.18 | 1.51 | . | * | . | −0.60 | 0.49 |
| Ile | 157 | . | . | B | B | . | . | . | −0.18 | 1.51 | . | . | . | −0.60 | 0.31 |
| Phe | 158 | . | . | B | B | . | . | . | −0.18 | 0.76 | . | . | . | −0.60 | 0.52 |
| Thr | 159 | . | . | B | B | . | . | . | −0.28 | 0.57 | . | . | F | −0.45 | 0.33 |
| Gly | 160 | . | . | . | . | T | T | . | 0.32 | 0.24 | . | . | F | 0.88 | 0.46 |
| Asp | 161 | . | . | . | . | T | T | . | −0.02 | −0.04 | . | . | F | 1.71 | 0.93 |
| Gly | 162 | . | . | . | . | . | T | C | 0.52 | −0.33 | . | . | F | 1.74 | 0.65 |
| Gly | 163 | . | . | . | . | . | T | C | 1.22 | −0.39 | . | . | F | 1.97 | 0.65 |
| Gln | 164 | . | . | . | . | . | . | C | 1.32 | −0.81 | * | . | F | 2.30 | 0.65 |
| Ala | 165 | . | . | . | . | . | . | C | 0.97 | −0.39 | * | . | F | 1.92 | 1.01 |
| Gly | 166 | . | . | B | . | . | . | . | 0.62 | −0.03 | . | . | F | 1.34 | 0.89 |
| Asp | 167 | . | . | B | . | . | T | . | 0.16 | −0.03 | . | . | F | 1.31 | 0.51 |
| Pro | 168 | . | . | B | . | . | T | . | −0.20 | 0.26 | . | . | F | 0.48 | 0.41 |
| Phe | 169 | . | . | B | . | . | T | . | −0.54 | 0.54 | * | . | . | −0.20 | 0.36 |
| Gly | 170 | . | . | B | . | . | T | . | 0.04 | 0.54 | * | . | . | −0.20 | 0.21 |
| Leu | 171 | . | . | B | . | . | . | . | −0.20 | 0.94 | . | . | . | −0.40 | 0.22 |
| Phe | 172 | . | . | B | . | . | . | . | −0.20 | 1.01 | . | . | . | −0.40 | 0.26 |
| Gly | 173 | . | . | B | . | . | . | . | 0.01 | 0.63 | . | * | . | −0.10 | 0.46 |
| Asn | 174 | . | . | . | . | . | . | C | 0.76 | 0.60 | . | * | F | 0.55 | 0.89 |
| Ala | 175 | . | . | . | . | . | . | C | 0.80 | −0.09 | . | . | F | 1.90 | 2.05 |
| Gln | 176 | . | . | . | . | . | . | C | 1.31 | −0.49 | . | * | F | 2.20 | 2.78 |
| Asn | 177 | . | . | . | . | . | T | C | 1.20 | −0.53 | . | . | F | 3.00 | 2.32 |
| Lys | 178 | . | . | . | . | T | T | . | 0.73 | −0.24 | . | * | F | 2.60 | 1.89 |
| Ser | 179 | . | . | B | . | . | T | . | 0.39 | −0.06 | . | * | F | 1.75 | 0.90 |
| Ser | 180 | . | . | B | . | . | T | . | 1.02 | −0.03 | * | * | F | 1.45 | 0.55 |
| Leu | 181 | . | . | B | . | . | . | . | 0.17 | −0.43 | * | * | F | 0.95 | 0.55 |
| Leu | 182 | . | . | B | B | . | . | . | −0.64 | 0.21 | * | . | F | −0.15 | 0.31 |
| Gly | 183 | . | . | B | B | . | . | . | −0.58 | 0.51 | * | * | F | −0.45 | 0.19 |
| Lys | 184 | . | . | B | B | . | . | . | −1.17 | 0.13 | * | * | . | −0.30 | 0.45 |
| Val | 185 | . | . | B | B | . | . | . | −0.87 | 0.13 | * | * | . | −0.30 | 0.38 |
| Leu | 186 | . | . | B | B | . | . | . | −0.91 | −0.56 | * | * | . | 0.60 | 0.64 |
| Arg | 187 | . | . | B | B | . | . | . | −0.10 | −0.34 | * | * | . | 0.30 | 0.24 |
| Ile | 188 | . | . | B | B | . | . | . | 0.36 | 0.06 | * | . | . | −0.30 | 0.52 |
| Asp | 189 | . | . | B | . | . | T | . | −0.28 | −0.59 | * | * | . | 1.15 | 1.23 |
| Val | 190 | . | . | B | . | . | T | . | 0.23 | −0.77 | * | * | . | 1.00 | 0.63 |
| Asn | 191 | . | . | B | . | . | T | . | 0.74 | −0.34 | * | * | F | 0.85 | 0.89 |
| Arg | 192 | . | . | B | . | . | T | . | 0.60 | −0.64 | . | * | F | 1.49 | 0.72 |
| Ala | 193 | . | . | . | . | T | . | . | 1.14 | −0.14 | * | * | F | 1.88 | 1.32 |
| Gly | 194 | . | . | . | . | T | T | . | 1.19 | −0.36 | * | . | F | 2.27 | 0.81 |
| Ser | 195 | . | . | . | . | . | T | C | 2.16 | −0.76 | * | . | F | 2.71 | 0.83 |
| His | 196 | . | . | . | . | T | T | . | 1.91 | −0.76 | * | * | F | 3.40 | 1.60 |
| Gly | 197 | . | . | . | . | T | T | . | 1.91 | −0.50 | * | * | F | 3.06 | 2.54 |
| Lys | 198 | . | . | B | . | . | . | . | 1.64 | −0.93 | . | * | F | 2.12 | 3.71 |
| Arg | 199 | . | . | B | B | . | . | . | 1.78 | −0.67 | . | * | F | 1.58 | 2.02 |
| Tyr | 200 | . | . | B | B | . | . | . | 1.78 | −0.74 | . | * | . | 1.43 | 3.16 |
| Arg | 201 | . | . | B | B | . | . | . | 1.81 | −0.79 | . | * | . | 1.43 | 2.12 |
| Val | 202 | . | . | B | B | . | . | . | 2.16 | −0.79 | . | * | F | 1.92 | 1.81 |
| Pro | 203 | . | . | B | . | . | T | . | 1.90 | −0.39 | . | * | F | 2.36 | 1.85 |
| Ser | 204 | . | . | . | . | T | T | . | 1.09 | −0.71 | . | * | F | 3.40 | 1.46 |
| Asp | 205 | . | . | . | . | . | T | C | 0.48 | 0.07 | . | * | F | 1.96 | 1.71 |
| Asn | 206 | . | . | . | . | . | T | C | 0.07 | 0.07 | . | * | F | 1.47 | 0.82 |
| Pro | 207 | . | . | . | . | . | . | C | 0.92 | 0.03 | . | . | F | 0.93 | 0.82 |
| Phe | 208 | . | . | B | . | . | . | . | 0.92 | −0.36 | . | . | F | 0.99 | 0.85 |
| Val | 209 | . | . | B | . | . | . | . | 0.88 | 0.07 | . | . | F | 0.33 | 0.82 |
| Ser | 210 | . | . | B | . | . | . | . | 0.29 | 0.10 | . | . | F | 0.61 | 0.52 |
| Glu | 211 | . | . | B | . | . | T | . | 0.26 | 0.17 | . | . | F | 1.09 | 0.61 |
| Pro | 212 | . | . | . | . | T | T | . | 0.26 | −0.11 | . | . | F | 2.52 | 1.12 |
| Gly | 213 | . | . | . | . | T | T | . | 0.37 | −0.33 | . | . | F | 2.80 | 1.29 |
| Ala | 214 | . | . | . | . | . | T | C | 0.33 | −0.21 | . | . | . | 2.02 | 0.75 |
| His | 215 | . | . | . | . | . | . | C | 0.39 | 0.47 | . | . | . | 0.64 | 0.34 |
| Pro | 216 | . | . | B | B | . | . | . | −0.20 | 0.80 | . | . | . | −0.04 | 0.54 |
| Ala | 217 | . | . | B | B | . | . | . | −0.23 | 0.87 | . | . | . | −0.32 | 0.54 |
| Ile | 218 | . | . | B | B | . | . | . | −0.23 | 1.13 | . | . | . | −0.60 | 0.62 |
| Tyr | 219 | . | . | B | . | . | T | . | −0.53 | 1.06 | . | * | . | −0.20 | 0.40 |
| Ala | 220 | . | . | B | . | . | T | . | −0.39 | 1.31 | . | . | . | −0.20 | 0.28 |
| Tyr | 221 | . | . | B | . | . | T | . | −0.18 | 0.81 | * | . | . | −0.20 | 0.77 |
| Gly | 222 | . | . | B | . | . | T | . | −0.19 | 0.53 | * | . | . | −0.20 | 0.79 |
| Ile | 223 | . | . | B | B | . | . | . | 0.41 | 0.39 | * | * | . | −0.30 | 0.78 |
| Arg | 224 | . | . | B | B | . | . | . | 0.77 | 0.80 | * | * | . | −0.60 | 0.52 |
| Asn | 225 | . | . | . | B | T | . | . | 0.69 | 0.04 | * | * | . | 0.25 | 1.03 |
| Met | 226 | . | . | . | B | T | . | . | 0.34 | 0.19 | * | * | . | 0.10 | 0.79 |
| Trp | 227 | . | . | B | B | . | . | . | −0.17 | 0.00 | * | * | . | 0.30 | 0.41 |
| Arg | 228 | . | . | B | . | . | . | . | 0.72 | 0.64 | * | * | . | −0.40 | 0.19 |
| Cys | 229 | . | . | B | . | . | . | . | 0.72 | 0.24 | * | * | . | 0.24 | 0.32 |
| Ala | 230 | . | . | B | . | . | . | . | 0.38 | −0.37 | * | . | . | 1.18 | 0.59 |
| Val | 231 | . | . | B | . | . | . | . | 0.98 | −0.86 | * | . | . | 1.82 | 0.30 |

TABLE I-continued

| Res | | I | II | III | IV | V | VI | VII | VIII | IX | X | XI | XII | XIII | XIV |
|---|---|---|---|---|---|---|---|---|---|---|---|---|---|---|---|
| Asp | 232 | . | . | . | . | T | T | . | 1.06 | −0.86 | * | . | F | 2.91 | 0.93 |
| Arg | 233 | . | . | . | . | T | T | . | 0.06 | −1.00 | * | . | F | 3.40 | 1.42 |
| Gly | 234 | . | . | . | . | T | T | . | 0.41 | −0.81 | * | * | F | 3.06 | 1.34 |
| Asp | 235 | . | . | . | . | . | T | C | 1.11 | −0.97 | * | . | F | 2.52 | 1.16 |
| Pro | 236 | . | . | B | . | . | . | . | 1.97 | −0.97 | * | . | F | 1.78 | 1.16 |
| Ile | 237 | . | . | B | . | . | . | . | 1.62 | −0.57 | * | * | F | 1.78 | 2.03 |
| Thr | 238 | . | . | B | . | . | . | . | 1.62 | −0.57 | * | * | F | 1.78 | 1.20 |
| Arg | 239 | . | . | B | . | . | . | . | 1.62 | −0.57 | * | * | F | 2.12 | 1.52 |
| Gln | 240 | . | . | B | . | . | . | . | 1.73 | −0.57 | * | * | F | 2.46 | 2.15 |
| Gly | 241 | . | . | . | . | T | T | . | 1.06 | −1.26 | . | * | F | 3.40 | 2.92 |
| Arg | 242 | . | . | . | . | T | T | . | 1.24 | −1.06 | . | * | F | 3.06 | 1.05 |
| Gly | 243 | . | . | . | . | T | T | . | 0.89 | −0.27 | . | * | F | 2.27 | 0.52 |
| Arg | 244 | . | . | B | . | . | T | . | 0.43 | −0.10 | . | * | F | 1.53 | 0.28 |
| Ile | 245 | . | . | B | . | . | . | . | 0.43 | −0.10 | . | * | . | 0.84 | 0.14 |
| Phe | 246 | . | . | B | . | . | . | . | −0.08 | −0.10 | . | * | . | 0.50 | 0.24 |
| Cys | 247 | . | . | B | . | . | T | . | −0.53 | 0.11 | . | * | . | 0.40 | 0.09 |
| Gly | 248 | . | . | B | . | . | T | . | −0.19 | 0.54 | . | . | . | 0.40 | 0.13 |
| Asp | 249 | . | . | . | . | T | T | . | −0.30 | 0.26 | . | . | F | 1.55 | 0.26 |
| Val | 250 | . | . | . | . | . | T | C | 0.70 | −0.13 | . | . | F | 2.25 | 0.77 |
| Gly | 251 | . | . | . | . | . | T | C | 0.70 | −0.70 | . | * | F | 3.00 | 1.53 |
| Gln | 252 | . | . | . | . | . | T | C | 1.37 | −0.34 | * | . | F | 2.25 | 0.80 |
| Asn | 253 | . | . | . | . | . | T | C | 1.71 | −0.34 | * | . | F | 2.10 | 1.86 |
| Arg | 254 | . | . | B | . | . | T | . | 0.86 | −0.99 | * | . | F | 1.90 | 3.25 |
| Phe | 255 | A | A | . | . | . | . | . | 1.71 | −0.77 | . | . | F | 1.20 | 1.39 |
| Glu | 256 | A | A | . | . | . | . | . | 1.24 | −1.17 | . | * | F | 0.90 | 1.45 |
| Glu | 257 | A | A | . | . | . | . | . | 0.36 | −0.89 | . | * | . | 0.60 | 0.61 |
| Val | 258 | A | A | . | B | . | . | . | −0.46 | −0.20 | * | * | . | 0.30 | 0.49 |
| Asp | 259 | A | A | . | B | . | . | . | −0.52 | −0.30 | . | * | . | 0.30 | 0.23 |
| Leu | 260 | A | A | . | B | . | . | . | −0.17 | −0.30 | * | * | . | 0.30 | 0.27 |
| Ile | 261 | A | A | . | B | . | . | . | −0.51 | 0.13 | * | * | . | −0.30 | 0.36 |
| Leu | 262 | A | . | . | . | . | T | . | −0.51 | −0.09 | * | * | . | 0.70 | 0.21 |
| Lys | 263 | . | . | . | . | T | T | . | 0.10 | 0.31 | * | * | F | 0.65 | 0.42 |
| Gly | 264 | . | . | . | . | T | T | . | −0.24 | 0.39 | * | . | F | 0.65 | 0.93 |
| Gly | 265 | . | . | . | . | T | T | . | 0.28 | 0.13 | * | * | F | 0.80 | 1.12 |
| Asn | 266 | . | . | . | . | . | T | C | 1.28 | 0.36 | * | * | F | 0.45 | 0.59 |
| Tyr | 267 | . | . | . | . | . | T | C | 1.50 | 0.36 | * | * | . | 0.45 | 1.17 |
| Gly | 268 | . | . | . | . | . | T | C | 1.50 | 0.43 | * | * | . | 0.15 | 1.19 |
| Trp | 269 | . | . | B | . | . | T | . | 1.84 | 0.00 | * | * | . | 0.85 | 1.48 |
| Arg | 270 | . | A | B | . | . | . | . | 1.84 | −0.40 | * | * | . | 0.45 | 1.63 |
| Ala | 271 | . | A | B | . | . | . | . | 1.14 | −0.73 | * | * | F | 0.90 | 1.63 |
| Lys | 272 | A | A | . | . | . | . | . | 0.80 | −0.37 | * | * | F | 0.60 | 1.35 |
| Glu | 273 | A | A | . | . | . | . | . | 0.48 | −0.79 | * | * | F | 0.75 | 0.69 |
| Gly | 274 | A | A | . | . | . | . | . | 0.52 | −0.21 | . | * | F | 0.45 | 0.37 |
| Phe | 275 | A | A | . | . | . | . | . | 0.41 | 0.04 | * | * | . | −0.30 | 0.29 |
| Ala | 276 | A | A | . | . | . | . | . | 1.04 | 0.04 | * | . | . | −0.30 | 0.28 |
| Cys | 277 | A | . | . | . | . | T | . | 1.04 | 0.04 | * | . | . | 0.10 | 0.56 |
| Tyr | 278 | A | . | . | . | . | T | . | 0.23 | −0.39 | * | . | . | 0.85 | 1.30 |
| Asp | 279 | A | . | . | . | . | T | . | −0.09 | −0.49 | * | . | F | 1.00 | 1.06 |
| Lys | 280 | A | . | . | . | . | T | . | 0.58 | −0.41 | * | . | F | 1.00 | 1.06 |
| Lys | 281 | A | A | . | . | . | . | . | 1.17 | −0.49 | . | . | F | 0.45 | 0.92 |
| Leu | 282 | A | A | . | . | . | . | . | 1.24 | −0.84 | . | . | . | 0.60 | 0.89 |
| Cys | 283 | A | A | . | . | . | . | . | 1.19 | −0.34 | . | * | . | 0.30 | 0.45 |
| His | 284 | . | A | B | . | . | . | . | 0.38 | 0.04 | . | * | . | −0.30 | 0.30 |
| Asn | 285 | . | . | B | . | . | T | . | 0.33 | 0.73 | . | * | . | −0.20 | 0.30 |
| Ala | 286 | A | . | . | . | . | T | . | 0.29 | 0.04 | . | * | . | 0.10 | 0.94 |
| Ser | 287 | A | . | . | . | . | T | . | 0.24 | −0.53 | . | . | . | 1.15 | 1.15 |
| Leu | 288 | A | . | . | . | . | T | . | 0.10 | −0.39 | . | . | F | 0.85 | 0.53 |
| Asp | 289 | . | . | B | B | . | . | . | −0.08 | −0.10 | . | . | F | 0.45 | 0.43 |
| Asp | 290 | . | . | B | B | . | . | . | −0.97 | −0.17 | . | * | F | 0.45 | 0.50 |
| Val | 291 | . | . | B | B | . | . | . | −0.62 | 0.13 | . | . | . | −0.30 | 0.42 |
| Leu | 292 | . | . | B | B | . | . | . | −0.91 | 0.20 | . | . | . | −0.30 | 0.40 |
| Pro | 293 | . | . | B | B | . | . | . | −0.34 | 0.70 | * | . | . | −0.60 | 0.24 |
| Ile | 294 | . | . | B | B | . | . | . | −0.69 | 1.46 | . | . | . | −0.60 | 0.51 |
| Tyr | 295 | . | . | B | . | . | T | . | −0.72 | 1.24 | . | . | . | −0.20 | 0.61 |
| Ala | 296 | . | . | B | . | . | T | . | −0.46 | 1.06 | . | . | . | −0.20 | 0.54 |
| Tyr | 297 | . | . | B | . | . | T | . | −0.50 | 1.13 | . | * | . | −0.20 | 0.77 |
| Gly | 298 | . | . | B | . | . | T | . | −0.63 | 1.09 | * | . | . | −0.20 | 0.37 |
| His | 299 | . | . | B | B | . | . | . | 0.30 | 0.76 | * | . | . | −0.60 | 0.36 |
| Ala | 300 | . | . | B | B | . | . | . | 0.24 | 0.26 | * | . | . | −0.30 | 0.46 |
| Val | 301 | . | . | B | B | . | . | . | −0.02 | −0.11 | * | . | . | 0.30 | 0.62 |
| Gly | 302 | . | . | B | . | . | T | . | −0.09 | 0.10 | * | . | F | 0.25 | 0.34 |
| Lys | 303 | . | . | B | . | . | T | . | −0.09 | 0.09 | * | . | F | 0.25 | 0.48 |
| Ser | 304 | . | . | B | . | . | T | . | −0.40 | 0.01 | * | . | F | 0.25 | 0.64 |
| Val | 305 | . | . | B | . | . | T | . | −0.06 | −0.20 | . | . | F | 0.85 | 0.64 |
| Thr | 306 | . | . | B | . | . | T | . | −0.06 | 0.13 | . | . | F | 0.25 | 0.50 |
| Gly | 307 | . | . | B | . | . | T | . | 0.04 | 0.77 | . | . | F | −0.05 | 0.28 |
| Gly | 308 | . | . | B | . | . | T | . | 0.11 | 1.14 | . | . | F | −0.05 | 0.59 |

TABLE I-continued

| Res | | I | II | III | IV | V | VI | VII | VIII | IX | X | XI | XII | XIII | XIV |
|---|---|---|---|---|---|---|---|---|---|---|---|---|---|---|---|
| Tyr | 309 | . | . | B | . | . | T | . | 0.07 | 0.50 | . | . | . | −0.20 | 0.80 |
| Val | 310 | . | . | B | . | . | . | . | 0.26 | 0.44 | * | . | . | −0.40 | 0.80 |
| Tyr | 311 | . | . | B | . | . | T | . | 0.57 | 0.59 | * | . | . | −0.20 | 0.43 |
| Arg | 312 | . | . | B | . | . | T | . | 0.61 | 0.16 | * | . | . | 0.10 | 0.48 |
| Gly | 313 | . | . | B | . | . | T | . | 0.74 | −0.21 | * | . | F | 1.13 | 0.87 |
| Cys | 314 | . | . | B | . | . | T | . | 0.99 | −0.43 | * | * | F | 1.41 | 0.85 |
| Glu | 315 | . | . | B | . | . | . | . | 1.03 | −0.79 | * | * | F | 1.79 | 0.70 |
| Ser | 316 | . | . | . | . | . | T | C | 1.28 | −0.10 | . | * | F | 2.17 | 0.58 |
| Pro | 317 | . | . | . | . | T | T | . | 0.82 | −0.13 | . | * | F | 2.80 | 1.75 |
| Asn | 318 | . | . | . | . | T | T | . | 0.36 | −0.27 | . | . | F | 2.52 | 1.00 |
| Leu | 319 | . | . | . | . | T | T | . | 0.78 | 0.41 | . | . | F | 1.19 | 0.62 |
| Asn | 320 | . | . | . | B | T | . | . | −0.11 | 0.79 | . | . | . | 0.36 | 0.63 |
| Gly | 321 | . | . | B | B | . | . | . | −0.51 | 1.04 | . | . | . | −0.32 | 0.27 |
| Leu | 322 | . | . | B | B | . | . | . | −0.64 | 1.43 | . | . | . | −0.60 | 0.29 |
| Tyr | 323 | . | . | B | B | . | . | . | −0.64 | 1.17 | . | * | . | −0.60 | 0.18 |
| Ile | 324 | . | . | B | B | . | . | . | −0.53 | 0.77 | * | . | . | −0.60 | 0.30 |
| Phe | 325 | . | . | B | B | . | . | . | −1.13 | 1.13 | * | . | . | −0.60 | 0.31 |
| Gly | 326 | . | . | B | B | . | . | . | −1.09 | 1.06 | * | . | . | −0.60 | 0.20 |
| Asp | 327 | . | . | B | . | . | . | . | −0.62 | 0.69 | . | * | . | −0.40 | 0.38 |
| Phe | 328 | . | . | B | . | . | . | . | −0.27 | 0.43 | . | * | . | −0.40 | 0.43 |
| Met | 329 | A | . | . | . | . | T | . | −0.19 | −0.36 | . | * | . | 0.70 | 0.85 |
| Ser | 330 | . | . | . | . | . | T | C | −0.09 | −0.10 | . | * | F | 1.05 | 0.42 |
| Gly | 331 | A | . | . | . | . | T | . | −0.33 | 0.51 | . | . | F | −0.05 | 0.48 |
| Arg | 332 | A | . | . | . | . | T | . | −1.14 | 0.23 | . | . | . | 0.10 | 0.49 |
| Leu | 333 | A | A | . | . | . | . | . | −0.44 | 0.30 | . | . | . | −0.30 | 0.30 |
| Met | 334 | A | A | . | . | . | . | . | 0.16 | 0.31 | . | * | . | −0.30 | 0.53 |
| Ala | 335 | A | A | . | . | . | . | . | 0.46 | −0.11 | . | * | . | 0.30 | 0.47 |
| Leu | 336 | A | A | . | . | . | . | . | 0.91 | −0.11 | . | * | . | 0.30 | 0.95 |
| Gln | 337 | A | A | . | . | . | . | . | 0.84 | −0.80 | . | . | . | 0.75 | 1.87 |
| Glu | 338 | A | A | . | . | . | . | . | 1.66 | −1.41 | . | . | F | 0.90 | 3.71 |
| Asp | 339 | A | A | . | . | . | . | . | 2.30 | −1.51 | * | . | F | 0.90 | 7.23 |
| Arg | 340 | A | A | . | . | . | . | . | 2.93 | −2.20 | * | . | F | 0.90 | 8.35 |
| Lys | 341 | A | A | . | . | . | . | . | 3.46 | −2.60 | . | * | F | 0.90 | 9.64 |
| Asn | 342 | A | . | . | . | . | T | . | 3.50 | −1.69 | * | . | F | 1.30 | 6.07 |
| Lys | 343 | A | . | . | . | . | T | . | 3.54 | −1.69 | * | . | F | 1.30 | 6.20 |
| Lys | 344 | A | . | . | . | . | T | . | 3.54 | −1.69 | * | . | F | 1.30 | 6.20 |
| Trp | 345 | A | . | . | . | . | T | . | 3.43 | −1.29 | * | . | F | 1.30 | 6.68 |
| Lys | 346 | A | A | . | . | . | . | . | 2.58 | −1.69 | . | . | F | 0.90 | 5.58 |
| Lys | 347 | A | A | . | . | . | . | . | 1.91 | −1.00 | . | . | F | 0.90 | 2.30 |
| Gln | 348 | . | A | B | . | . | . | . | 1.06 | −0.43 | * | . | F | 0.60 | 1.17 |
| Asp | 349 | . | A | B | . | . | . | . | 0.67 | −0.66 | . | . | F | 0.75 | 0.48 |
| Leu | 350 | . | A | B | . | . | . | . | 0.66 | −0.23 | . | . | F | 0.45 | 0.24 |
| Cys | 351 | . | A | B | . | . | . | . | 0.30 | 0.16 | . | . | F | −0.15 | 0.19 |
| Leu | 352 | . | A | B | . | . | . | . | −0.06 | 0.24 | . | . | F | −0.15 | 0.16 |
| Gly | 353 | . | A | . | . | T | . | . | −0.36 | 0.73 | . | . | F | −0.05 | 0.28 |
| Ser | 354 | . | . | . | . | T | T | . | −1.02 | 0.43 | . | . | F | 0.35 | 0.70 |
| Thr | 355 | . | . | . | . | T | T | . | −0.80 | 0.43 | . | . | F | 0.35 | 0.45 |
| Thr | 356 | . | . | B | . | . | T | . | −0.83 | 0.24 | . | . | F | 0.25 | 0.46 |
| Ser | 357 | . | . | B | . | . | T | . | −0.23 | 0.60 | . | . | F | −0.05 | 0.30 |
| Cys | 358 | . | . | B | . | . | . | . | −0.23 | 0.64 | . | . | . | −0.40 | 0.32 |
| Ala | 359 | . | . | B | . | . | . | . | −0.74 | 0.59 | . | . | . | −0.40 | 0.22 |
| Phe | 360 | . | . | B | . | . | T | . | −1.32 | 0.79 | . | . | . | −0.20 | 0.14 |
| Pro | 361 | . | . | B | . | . | T | . | −1.31 | 1.09 | . | . | . | −0.20 | 0.18 |
| Gly | 362 | . | . | . | . | T | T | . | −1.32 | 0.90 | . | . | . | 0.20 | 0.24 |
| Leu | 363 | . | . | B | . | . | T | . | −0.69 | 0.89 | . | . | . | −0.20 | 0.39 |
| Ile | 364 | . | . | B | . | . | . | . | −0.40 | 0.60 | * | . | . | −0.40 | 0.35 |
| Ser | 365 | A | . | . | . | . | T | . | 0.34 | 0.56 | * | * | . | −0.20 | 0.47 |
| Thr | 366 | A | . | . | . | . | T | . | −0.14 | 0.13 | * | . | F | 0.40 | 1.13 |
| His | 367 | A | . | . | . | . | T | . | −0.69 | 0.23 | * | * | F | 0.40 | 1.40 |
| Ser | 368 | . | . | B | . | . | T | . | −0.77 | 0.23 | * | * | F | 0.25 | 0.73 |
| Lys | 369 | . | . | B | B | . | . | . | −0.18 | 0.53 | * | * | . | −0.60 | 0.36 |
| Phe | 370 | . | . | B | B | . | . | . | −0.58 | 0.43 | * | * | . | −0.60 | 0.35 |
| Ile | 371 | . | . | B | B | . | . | . | −0.86 | 0.71 | * | * | . | −0.60 | 0.23 |
| Ile | 372 | . | . | B | B | . | . | . | −0.82 | 0.83 | * | * | . | −0.60 | 0.11 |
| Ser | 373 | . | A | B | . | . | . | . | −0.52 | 0.83 | * | . | . | −0.60 | 0.23 |
| Phe | 374 | A | A | . | . | . | . | . | −0.57 | 0.04 | * | * | . | −0.30 | 0.54 |
| Ala | 375 | A | A | . | . | . | . | . | −0.46 | −0.64 | . | . | . | 0.75 | 1.35 |
| Glu | 376 | A | A | . | . | . | . | . | 0.09 | −0.83 | * | . | . | 0.75 | 1.01 |
| Asp | 377 | A | A | . | . | . | . | . | 0.98 | −0.79 | * | . | F | 0.90 | 1.16 |
| Glu | 378 | A | A | . | . | . | . | . | 0.47 | −1.57 | . | . | F | 0.90 | 1.99 |
| Ala | 379 | A | A | . | . | . | . | . | 0.92 | −1.39 | . | . | F | 0.75 | 0.95 |
| Gly | 380 | A | A | . | . | . | . | . | 0.81 | −0.63 | . | . | F | 0.75 | 0.89 |
| Glu | 381 | A | A | . | B | . | . | . | 0.00 | 0.16 | . | . | . | −0.30 | 0.44 |
| Leu | 382 | A | A | . | B | . | . | . | −0.59 | 0.84 | . | . | . | −0.60 | 0.36 |
| Tyr | 383 | A | A | . | B | . | . | . | −0.90 | 0.84 | . | . | . | −0.60 | 0.37 |
| Phe | 384 | A | A | . | B | . | . | . | −0.61 | 0.90 | . | . | . | −0.60 | 0.31 |
| Leu | 385 | . | A | B | B | . | . | . | −0.51 | 1.29 | . | . | . | −0.60 | 0.50 |

TABLE I-continued

| Res | | I | II | III | IV | V | VI | VII | VIII | IX | X | XI | XII | XIII | XIV |
|---|---|---|---|---|---|---|---|---|---|---|---|---|---|---|---|
| Ala | 386 | . | A | B | B | . | . | . | −0.72 | 1.36 | . | . | . | −0.60 | 0.50 |
| Thr | 387 | . | A | B | B | . | . | . | −0.21 | 1.03 | . | . | . | −0.60 | 0.89 |
| Ser | 388 | . | A | . | . | . | . | C | −0.56 | 0.63 | . | . | F | −0.10 | 1.45 |
| Tyr | 389 | . | . | . | . | . | T | C | −0.10 | 0.44 | . | . | F | 0.30 | 1.45 |
| Pro | 390 | . | . | . | . | T | T | . | 0.12 | 0.70 | . | . | F | 0.50 | 1.58 |
| Ser | 391 | . | . | . | . | T | T | . | 0.50 | 0.71 | . | . | . | 0.35 | 1.19 |
| Ala | 392 | . | . | B | . | . | T | . | 0.92 | 0.76 | . | . | . | 0.08 | 1.17 |
| Tyr | 393 | . | . | B | . | . | . | . | 0.88 | 0.00 | . | . | . | 0.91 | 1.49 |
| Ala | 394 | . | . | B | . | . | T | . | 0.82 | 0.00 | . | * | . | 1.24 | 1.10 |
| Pro | 395 | . | . | B | . | . | T | . | 0.14 | 0.00 | . | * | F | 1.52 | 1.46 |
| Arg | 396 | . | . | . | . | T | T | . | 0.20 | 0.19 | . | . | F | 1.30 | 0.65 |
| Gly | 397 | . | . | B | . | . | T | . | 0.83 | 0.19 | . | . | F | 0.92 | 1.01 |
| Ser | 398 | . | . | B | B | . | . | . | 0.38 | −0.31 | . | . | F | 0.99 | 1.31 |
| Ile | 399 | . | . | B | B | . | . | . | 0.11 | 0.04 | * | . | . | −0.04 | 0.58 |
| Tyr | 400 | . | . | B | B | . | . | . | 0.32 | 0.69 | * | * | . | −0.47 | 0.43 |
| Lys | 401 | . | . | B | B | . | . | . | 0.00 | 0.26 | * | * | . | −0.30 | 0.54 |
| Phe | 402 | . | . | B | B | . | . | . | 0.04 | 0.30 | * | . | . | 0.19 | 1.19 |
| Val | 403 | . | . | B | B | . | . | . | 0.46 | 0.00 | * | . | F | 1.28 | 1.02 |
| Asp | 404 | . | . | B | . | . | T | . | 1.46 | −0.76 | * | . | F | 2.17 | 1.00 |
| Pro | 405 | . | . | B | . | . | T | . | 1.11 | −0.76 | * | . | F | 2.66 | 2.26 |
| Ser | 406 | . | . | . | . | T | T | . | 0.86 | −1.04 | * | . | F | 3.40 | 3.07 |
| Arg | 407 | . | . | . | . | T | T | . | 1.34 | −1.26 | * | . | F | 3.06 | 2.85 |
| Arg | 408 | . | . | . | . | T | . | . | 1.86 | −0.83 | . | . | F | 2.86 | 2.85 |
| Ala | 409 | . | . | . | . | . | . | C | 1.90 | −0.83 | . | . | F | 2.66 | 2.10 |
| Pro | 410 | . | . | . | . | . | T | C | 1.44 | −1.21 | * | . | F | 2.86 | 2.15 |
| Pro | 411 | . | . | . | . | T | T | . | 1.79 | −0.64 | * | * | F | 2.91 | 0.59 |
| Gly | 412 | . | . | . | . | T | T | . | 1.43 | −0.64 | . | * | F | 3.40 | 1.16 |
| Lys | 413 | . | . | . | . | T | T | . | 1.37 | −0.39 | . | * | F | 2.76 | 1.18 |
| Cys | 414 | . | . | . | . | T | T | . | 1.74 | −0.81 | . | * | F | 2.72 | 1.52 |
| Lys | 415 | . | . | B | . | . | T | . | 1.10 | −0.81 | . | * | F | 1.98 | 2.38 |
| Tyr | 416 | . | . | B | . | . | T | . | 1.10 | −0.60 | . | * | F | 1.49 | 0.88 |
| Lys | 417 | . | . | B | . | . | T | . | 0.59 | −0.17 | . | * | F | 1.00 | 2.55 |
| Pro | 418 | . | . | B | B | . | . | . | 0.66 | −0.10 | . | * | F | 0.45 | 0.95 |
| Val | 419 | . | . | B | B | . | . | . | 1.01 | −0.10 | . | * | F | 0.60 | 1.18 |
| Pro | 420 | . | . | B | B | . | . | . | 1.01 | −0.37 | . | * | F | 0.79 | 0.85 |
| Val | 421 | . | . | B | B | . | . | . | 0.96 | −0.37 | . | * | F | 1.28 | 1.10 |
| Arg | 422 | . | . | B | B | . | . | . | 0.96 | −0.41 | . | * | F | 1.62 | 1.99 |
| Thr | 423 | . | . | B | . | . | T | . | 1.28 | −1.06 | * | * | F | 2.66 | 2.58 |
| Lys | 424 | . | . | . | . | T | T | . | 1.24 | −1.49 | * | * | F | 3.40 | 6.80 |
| Ser | 425 | . | . | . | . | T | T | . | 1.24 | −1.44 | * | * | F | 3.06 | 2.43 |
| Lys | 426 | . | . | . | . | T | T | . | 1.40 | −1.01 | * | * | F | 2.72 | 2.61 |
| Arg | 427 | . | . | B | . | . | . | . | 1.40 | −0.71 | . | * | F | 1.78 | 1.13 |
| Ile | 428 | . | . | B | . | . | . | . | 1.50 | −0.71 | * | * | F | 1.44 | 1.65 |
| Pro | 429 | . | . | B | . | . | . | . | 0.64 | −0.67 | * | * | . | 0.95 | 1.28 |
| Phe | 430 | . | . | B | . | . | . | . | 0.36 | 0.01 | * | * | . | −0.10 | 0.54 |
| Arg | 431 | . | A | B | . | . | . | . | 0.36 | 0.51 | * | * | . | −0.60 | 0.77 |
| Pro | 432 | . | A | B | . | . | . | . | −0.07 | −0.17 | * | * | F | 0.60 | 1.00 |
| Leu | 433 | A | A | . | . | . | . | . | −0.03 | −0.11 | * | * | F | 0.60 | 1.67 |
| Ala | 434 | A | A | . | . | . | . | . | −0.63 | −0.26 | * | * | F | 0.45 | 0.63 |
| Lys | 435 | A | A | . | . | . | . | . | 0.07 | 0.43 | * | * | F | −0.45 | 0.34 |
| Thr | 436 | A | A | . | . | . | . | . | −0.86 | 0.00 | * | * | . | 0.30 | 0.68 |
| Val | 437 | A | A | . | . | . | . | . | −1.46 | 0.00 | * | . | . | 0.30 | 0.56 |
| Leu | 438 | A | A | . | . | . | . | . | −0.60 | 0.19 | * | . | . | −0.30 | 0.23 |
| Asp | 439 | A | A | . | . | . | . | . | −0.01 | 0.19 | * | . | . | −0.30 | 0.32 |
| Leu | 440 | A | A | . | . | . | . | . | −0.06 | −0.30 | * | . | . | 0.30 | 0.74 |
| Leu | 441 | A | A | . | . | . | . | . | −0.04 | −0.54 | * | . | F | 0.90 | 1.56 |
| Lys | 442 | A | A | . | . | . | . | . | 0.81 | −0.84 | * | . | F | 0.90 | 1.25 |
| Glu | 443 | A | A | . | . | . | . | . | 1.67 | −0.84 | * | . | F | 0.90 | 2.63 |
| Gln | 444 | A | A | . | . | . | . | . | 1.08 | −1.53 | * | . | F | 0.90 | 6.38 |
| Ser | 445 | A | A | . | . | . | . | . | 1.30 | −1.71 | * | . | F | 0.90 | 3.22 |
| Glu | 446 | A | A | . | . | . | . | . | 2.22 | −1.21 | * | . | F | 0.90 | 1.88 |
| Lys | 447 | A | A | . | . | . | . | . | 2.22 | −1.21 | * | . | F | 0.90 | 2.13 |
| Ala | 448 | A | A | . | . | . | . | . | 1.92 | −1.61 | * | . | F | 0.90 | 3.17 |
| Ala | 449 | A | A | . | . | . | . | . | 1.62 | −1.61 | * | . | F | 0.90 | 2.46 |
| Arg | 450 | A | A | . | . | . | . | . | 1.62 | −1.23 | * | . | F | 0.90 | 1.65 |
| Lys | 451 | A | A | . | . | . | . | . | 1.03 | −0.84 | * | . | F | 0.90 | 2.18 |
| Ser | 452 | A | . | . | . | . | T | . | 0.68 | −0.84 | * | . | F | 1.30 | 2.18 |
| Ser | 453 | A | . | . | . | . | T | . | 0.46 | −0.86 | . | . | F | 1.30 | 1.61 |
| Ser | 454 | . | . | B | . | . | T | . | 0.46 | −0.17 | . | . | F | 0.85 | 0.66 |
| Ala | 455 | . | . | B | . | . | T | . | 0.04 | 0.33 | . | . | F | 0.25 | 0.50 |
| Thr | 456 | . | . | B | . | . | . | . | −0.34 | 0.33 | . | . | . | −0.10 | 0.50 |
| Leu | 457 | . | . | B | . | . | . | . | −0.26 | 0.37 | . | . | . | −0.10 | 0.37 |
| Ala | 458 | . | . | B | . | . | T | . | −0.54 | 0.41 | . | . | F | −0.05 | 0.57 |
| Ser | 459 | . | . | B | . | . | T | . | −0.24 | 0.41 | . | . | F | −0.05 | 0.40 |
| Gly | 460 | . | . | . | . | . | T | C | 0.00 | 0.33 | . | . | F | 0.45 | 0.83 |
| Pro | 461 | . | . | . | . | . | T | C | −0.50 | 0.07 | * | . | F | 0.45 | 0.81 |
| Ala | 462 | . | . | . | . | . | . | C | 0.01 | 0.26 | * | . | F | 0.25 | 0.50 |

TABLE I-continued

| Res | | I | II | III | IV | V | VI | VII | VIII | IX | X | XI | XII | XIII | XIV |
|---|---|---|---|---|---|---|---|---|---|---|---|---|---|---|---|
| Gln | 463 | A | . | . | . | . | . | . | 0.60 | 0.26 | . | . | F | 0.05 | 0.68 |
| Gly | 464 | . | . | B | . | . | . | . | 0.94 | −0.17 | . | . | F | 0.65 | 0.76 |
| Leu | 465 | . | . | B | . | . | . | . | 0.94 | −0.60 | . | . | F | 1.10 | 1.50 |
| Ser | 466 | A | . | . | . | . | . | . | 0.86 | −0.67 | * | . | F | 0.95 | 0.86 |
| Glu | 467 | A | . | . | . | . | . | . | 1.14 | −0.69 | . | * | F | 1.10 | 1.16 |
| Lys | 468 | A | . | . | . | . | . | . | 1.19 | −0.73 | . | . | F | 1.10 | 1.89 |
| Gly | 469 | A | . | . | . | T | T | . | 1.58 | −1.41 | . | . | F | 1.70 | 2.82 |
| Ser | 470 | A | . | . | . | . | T | . | 1.58 | −1.80 | . | . | F | 1.30 | 3.26 |
| Ser | 471 | A | . | . | . | . | T | . | 1.29 | −1.11 | . | . | F | 1.30 | 1.34 |
| Lys | 472 | A | . | . | . | . | T | . | 0.99 | −0.61 | . | . | F | 1.30 | 1.37 |
| Lys | 473 | . | . | B | . | . | . | . | 0.73 | −0.66 | . | . | F | 1.10 | 1.37 |
| Leu | 474 | . | . | B | . | . | . | . | 0.77 | −0.61 | . | . | F | 1.10 | 1.58 |
| Ala | 475 | . | . | B | . | . | . | . | 0.77 | −0.51 | * | . | F | 1.40 | 1.14 |
| Ser | 476 | . | . | B | . | . | T | . | 0.77 | −0.13 | . | . | F | 1.45 | 0.77 |
| Pro | 477 | . | . | B | . | . | T | . | 0.77 | 0.26 | . | . | F | 1.30 | 1.24 |
| Thr | 478 | . | . | . | . | T | T | . | 0.72 | −0.43 | . | . | F | 2.60 | 2.46 |
| Ser | 479 | . | . | . | . | . | T | C | 1.22 | −0.53 | . | . | F | 3.00 | 2.95 |
| Ser | 480 | . | . | . | . | T | T | . | 1.00 | −0.43 | * | * | F | 2.60 | 2.76 |
| Lys | 481 | . | . | B | . | . | T | . | 1.41 | −0.17 | * | * | F | 1.90 | 1.58 |
| Asn | 482 | . | . | B | . | . | T | . | 1.28 | −0.66 | * | * | F | 1.90 | 2.30 |
| Thr | 483 | . | . | B | . | . | T | . | 1.38 | −0.61 | * | * | F | 1.94 | 1.70 |
| Leu | 484 | . | . | B | . | . | . | . | 1.33 | −0.57 | * | * | F | 1.78 | 1.32 |
| Arg | 485 | . | . | B | . | . | . | . | 1.32 | −0.14 | * | * | F | 1.67 | 0.81 |
| Gly | 486 | . | . | B | . | . | T | . | 1.32 | −0.06 | . | * | F | 2.21 | 0.81 |
| Pro | 487 | . | . | . | . | T | T | . | 1.37 | −0.54 | . | * | F | 3.40 | 1.96 |
| Gly | 488 | . | . | . | . | T | T | . | 1.72 | −1.23 | . | * | F | 3.06 | 2.00 |
| Thr | 489 | . | . | . | . | . | T | C | 1.94 | −1.23 | . | * | F | 2.52 | 4.05 |
| Lys | 490 | . | A | B | . | . | . | . | 1.94 | −1.16 | . | * | F | 1.58 | 2.65 |
| Lys | 491 | . | A | B | . | . | . | . | 1.43 | −1.59 | * | * | F | 1.24 | 5.24 |
| Lys | 492 | . | A | B | . | . | . | . | 1.30 | −1.37 | * | * | F | 0.90 | 2.69 |
| Ala | 493 | . | A | B | . | . | . | . | 1.43 | −1.43 | * | * | F | 0.90 | 1.33 |
| Arg | 494 | . | A | B | . | . | . | . | 1.71 | −1.00 | * | * | F | 0.90 | 1.03 |
| Val | 495 | . | A | B | . | . | . | . | 0.81 | −0.50 | * | * | F | 0.75 | 0.70 |
| Gly | 496 | . | . | B | . | . | T | . | 0.88 | 0.14 | * | * | F | 0.25 | 0.52 |
| Pro | 497 | . | . | B | . | . | T | . | 0.83 | −0.36 | * | * | F | 0.85 | 0.52 |
| His | 498 | . | . | B | . | . | T | . | 1.08 | 0.04 | * | * | F | 0.74 | 1.20 |
| Val | 499 | . | . | B | . | . | T | . | 1.01 | −0.17 | * | * | F | 1.68 | 1.20 |
| Arg | 500 | . | . | B | . | . | T | . | 1.98 | −0.60 | * | * | F | 2.32 | 1.55 |
| Gln | 501 | . | . | B | . | . | T | . | 2.43 | −1.03 | * | . | F | 2.66 | 2.24 |
| Gly | 502 | . | . | . | . | T | T | . | 2.69 | −1.53 | * | . | F | 3.40 | 5.90 |
| Lys | 503 | A | . | . | . | . | T | . | 2.42 | −2.17 | . | . | F | 2.66 | 6.03 |
| Arg | 504 | A | . | . | . | . | . | . | 2.47 | −1.79 | . | * | F | 2.12 | 4.66 |
| Arg | 505 | . | . | B | . | . | . | . | 2.40 | −1.50 | . | . | F | 1.78 | 3.89 |
| Lys | 506 | . | . | B | . | . | . | . | 2.10 | −1.93 | . | * | F | 1.44 | 3.89 |
| Ser | 507 | . | . | B | . | . | . | . | 2.41 | −1.54 | . | . | F | 1.44 | 2.66 |
| Leu | 508 | . | . | B | . | . | . | . | 2.07 | −1.04 | . | . | F | 1.78 | 1.85 |
| Lys | 509 | . | . | B | . | . | . | . | 1.61 | −0.66 | . | . | F | 2.12 | 1.24 |
| Ser | 510 | . | . | . | . | . | . | C | 1.61 | −0.23 | * | * | F | 2.21 | 0.91 |
| His | 511 | . | . | . | . | T | T | . | 0.97 | −0.61 | * | * | F | 3.40 | 2.17 |
| Ser | 512 | . | . | . | . | . | T | C | 1.38 | −0.69 | . | * | F | 2.86 | 1.07 |
| Gly | 513 | . | . | . | . | T | T | . | 1.98 | −0.69 | . | * | F | 3.02 | 1.57 |
| Arg | 514 | . | . | . | . | T | T | . | 1.63 | −0.64 | . | * | F | 2.98 | 1.78 |
| Met | 515 | . | . | . | . | . | . | C | 1.34 | −0.76 | . | * | F | 2.54 | 1.78 |
| Arg | 516 | . | . | . | . | . | T | C | 1.38 | −0.64 | . | * | F | 2.70 | 1.82 |
| Pro | 517 | . | . | . | . | . | T | C | 1.68 | −1.07 | . | * | F | 3.00 | 1.61 |
| Ser | 518 | A | . | . | . | . | T | . | 2.07 | −0.67 | . | * | F | 2.50 | 2.82 |
| Ala | 519 | A | . | . | . | . | T | . | 2.07 | −1.29 | . | * | F | 2.20 | 2.88 |
| Glu | 520 | A | A | . | . | . | . | . | 2.08 | −1.29 | * | * | F | 1.50 | 3.65 |
| Gln | 521 | A | A | . | . | . | . | . | 1.62 | −1.21 | * | * | F | 1.51 | 2.75 |
| Lys | 522 | A | A | . | . | . | . | . | 1.94 | −1.17 | * | . | F | 1.52 | 2.69 |
| Arg | 523 | A | A | . | . | . | . | . | 1.94 | −1.67 | * | . | F | 1.83 | 3.04 |
| Ala | 524 | . | A | . | . | T | . | . | 1.72 | −1.29 | * | . | F | 2.54 | 2.36 |
| Gly | 525 | . | . | . | . | T | T | . | 1.51 | −1.00 | * | . | F | 3.10 | 0.97 |
| Arg | 526 | . | . | . | . | T | T | . | 1.12 | −0.57 | * | . | F | 2.79 | 0.77 |
| Ser | 527 | . | . | . | . | . | T | C | 0.69 | −0.14 | * | . | F | 1.98 | 0.97 |
| Leu | 528 | . | . | . | . | . | T | C | 0.19 | −0.21 | * | . | . | 1.67 | 1.25 |
| Pro | 529 | . | . | B | . | . | . | . | 0.39 | −0.21 | * | . | . | 0.81 | 0.82 |

TABLE II

| Res | | I | II | III | IV | V | VI | VII | VIII | IX | X | XI | XII | XIII | XIV |
|---|---|---|---|---|---|---|---|---|---|---|---|---|---|---|---|
| Met | 1 | . | . | . | . | . | . | C | 0.69 | −0.24 | . | * | . | 1.19 | 1.74 |
| Arg | 2 | . | . | . | . | . | . | C | 0.38 | −0.24 | . | * | . | 1.53 | 1.34 |

TABLE II-continued

| Res | | I | II | III | IV | V | VI | VII | VIII | IX | X | XI | XII | XIII | XIV |
|---|---|---|---|---|---|---|---|---|---|---|---|---|---|---|---|
| Pro | 3 | . | . | . | . | . | T | C | 0.88 | 0.11 | . | . | . | 1.32 | 0.91 |
| Pro | 4 | . | . | . | . | T | T | . | 1.27 | −0.31 | . | . | . | 2.61 | 1.80 |
| Gly | 5 | . | . | . | . | T | T | . | 0.96 | −0.53 | . | . | F | 3.40 | 1.48 |
| Phe | 6 | . | . | . | . | T | T | . | 0.74 | 0.26 | . | . | F | 2.01 | 0.83 |
| Arg | 7 | . | A | B | . | . | . | . | −0.18 | 0.51 | . | . | . | 0.42 | 0.44 |
| Asn | 8 | . | A | B | . | . | . | . | −0.78 | 0.77 | * | . | . | 0.08 | 0.37 |
| Phe | 9 | . | A | B | . | . | . | . | −1.16 | 1.03 | * | . | . | −0.26 | 0.35 |
| Leu | 10 | . | A | B | . | . | . | . | −1.11 | 0.74 | * | . | . | −0.60 | 0.18 |
| Leu | 11 | . | A | . | . | . | . | C | −0.71 | 1.13 | * | . | . | −0.40 | 0.15 |
| Leu | 12 | . | A | . | . | . | . | C | −1.63 | 1.11 | * | . | . | −0.40 | 0.23 |
| Ala | 13 | . | A | . | . | . | . | C | −2.44 | 1.01 | . | . | . | −0.40 | 0.23 |
| Ser | 14 | . | A | . | . | . | . | C | −2.44 | 1.01 | . | . | . | −0.40 | 0.23 |
| Ser | 15 | . | A | . | . | . | . | C | −2.22 | 1.11 | . | . | . | −0.40 | 0.24 |
| Leu | 16 | . | A | B | . | . | . | . | −1.76 | 0.93 | . | . | . | −0.60 | 0.24 |
| Leu | 17 | . | A | B | . | . | . | . | −1.76 | 0.86 | . | . | . | −0.60 | 0.18 |
| Phe | 18 | . | A | B | . | . | . | . | −1.47 | 1.16 | . | . | . | −0.60 | 0.11 |
| Ala | 19 | . | A | . | . | . | . | C | −1.76 | 1.16 | . | . | . | −0.40 | 0.18 |
| Gly | 20 | . | A | . | . | . | . | C | −2.31 | 0.97 | . | . | . | −0.40 | 0.22 |
| Leu | 21 | . | A | . | . | . | . | C | −1.71 | 0.93 | * | . | . | −0.40 | 0.19 |
| Ser | 22 | . | A | . | . | . | . | C | −0.90 | 0.57 | * | . | . | −0.40 | 0.29 |
| Ala | 23 | . | A | . | . | . | . | C | −0.50 | 0.47 | * | . | . | −0.40 | 0.51 |
| Val | 24 | . | A | . | . | . | . | C | −0.61 | 0.43 | * | . | . | −0.40 | 0.83 |
| Pro | 25 | . | . | . | . | . | T | C | −0.57 | 0.53 | * | . | F | 0.15 | 0.53 |
| Gln | 26 | . | . | . | . | T | T | . | 0.03 | 0.53 | * | . | F | 0.35 | 0.71 |
| Ser | 27 | . | . | . | . | T | T | . | 0.03 | 0.46 | * | . | F | 0.50 | 1.48 |
| Phe | 28 | . | . | . | . | . | T | C | −0.19 | 0.20 | * | * | F | 0.60 | 1.28 |
| Ser | 29 | . | . | . | . | . | T | C | 0.78 | 0.46 | * | * | F | 0.15 | 0.61 |
| Pro | 30 | . | . | . | . | . | T | C | 0.69 | 0.06 | * | * | F | 0.45 | 0.89 |
| Ser | 31 | . | . | . | . | T | T | . | 0.40 | 0.06 | * | * | F | 0.80 | 1.38 |
| Leu | 32 | . | . | . | . | T | T | . | 0.49 | 0.19 | * | * | F | 0.80 | 1.08 |
| Arg | 33 | . | . | . | . | T | . | . | 0.84 | 0.23 | * | * | F | 0.60 | 1.08 |
| Ser | 34 | . | . | . | . | T | . | . | 0.56 | 0.23 | * | * | F | 0.45 | 0.80 |
| Trp | 35 | . | . | . | . | . | T | C | 0.18 | 0.34 | * | * | F | 0.45 | 0.98 |
| Pro | 36 | . | . | . | . | . | T | C | −0.19 | 0.16 | * | * | F | 0.45 | 0.50 |
| Gly | 37 | . | . | . | . | T | T | . | 0.73 | 0.73 | * | * | . | 0.20 | 0.20 |
| Ala | 38 | . | . | . | . | T | T | . | −0.19 | 0.34 | * | * | . | 0.50 | 0.38 |
| Ala | 39 | . | . | . | . | . | . | C | −0.19 | 0.11 | * | . | . | 0.10 | 0.20 |
| Cys | 40 | . | . | B | . | T | . | . | 0.21 | 0.07 | * | . | . | 0.30 | 0.27 |
| Arg | 41 | . | A | B | . | . | . | . | −0.17 | −0.36 | * | . | . | 0.30 | 0.53 |
| Leu | 42 | . | A | . | . | . | . | C | 0.18 | −0.36 | * | . | . | 0.50 | 0.53 |
| Ser | 43 | . | A | . | . | . | . | C | 0.47 | −0.86 | * | * | . | 0.95 | 1.70 |
| Arg | 44 | . | A | . | . | . | . | C | 1.06 | −1.04 | * | . | F | 1.10 | 1.16 |
| Ala | 45 | . | A | . | . | . | . | C | 1.83 | −1.04 | . | * | F | 1.10 | 2.44 |
| Glu | 46 | . | A | . | . | T | . | . | 1.83 | −1.73 | . | * | F | 1.30 | 3.57 |
| Ser | 47 | . | A | . | . | T | . | . | 1.98 | −2.11 | . | * | F | 1.30 | 3.57 |
| Glu | 48 | . | A | . | . | T | . | . | 2.39 | −1.54 | . | * | F | 1.30 | 1.89 |
| Arg | 49 | . | A | . | . | T | . | . | 1.69 | −2.04 | . | * | F | 1.30 | 2.14 |
| Arg | 50 | . | A | . | . | T | . | . | 2.07 | −1.54 | * | * | F | 1.58 | 1.62 |
| Cys | 51 | . | A | . | . | T | . | . | 1.72 | −1.50 | * | * | . | 1.71 | 1.44 |
| Arg | 52 | . | A | . | . | T | . | . | 2.02 | −1.07 | * | * | F | 1.99 | 0.73 |
| Ala | 53 | . | . | . | . | . | T | C | 1.81 | −0.67 | * | * | F | 2.47 | 0.64 |
| Pro | 54 | . | . | . | . | T | T | . | 1.49 | −0.24 | * | * | F | 2.80 | 1.86 |
| Gly | 55 | . | . | . | . | T | T | . | 1.03 | −0.39 | . | * | F | 2.52 | 1.47 |
| Gln | 56 | . | . | . | . | . | T | C | 1.11 | 0.04 | * | * | F | 1.44 | 1.44 |
| Pro | 57 | . | . | . | . | . | T | C | 0.41 | 0.04 | * | * | F | 1.01 | 0.94 |
| Pro | 58 | . | . | . | . | T | T | . | 0.19 | 0.11 | . | . | F | 0.93 | 0.96 |
| Gly | 59 | . | . | . | . | T | T | . | −0.27 | 0.37 | . | . | F | 0.65 | 0.46 |
| Ala | 60 | . | . | B | . | . | T | . | 0.04 | 0.54 | . | . | . | −0.20 | 0.16 |
| Ala | 61 | . | . | B | . | . | . | . | −0.30 | 0.61 | . | * | . | −0.40 | 0.14 |
| Leu | 62 | . | . | B | . | . | . | . | 0.02 | 0.61 | . | * | . | −0.40 | 0.14 |
| Cys | 63 | . | . | . | . | T | . | . | −0.11 | 0.19 | . | * | . | 0.61 | 0.27 |
| His | 64 | . | . | . | . | T | T | . | 0.34 | 0.11 | . | * | . | 1.12 | 0.26 |
| Gly | 65 | . | . | . | . | T | T | . | 0.27 | −0.39 | . | * | F | 2.18 | 0.63 |
| Arg | 66 | . | . | . | . | T | T | . | 0.86 | −0.50 | . | * | F | 2.49 | 0.63 |
| Gly | 67 | . | . | . | . | T | T | . | 1.00 | −1.07 | . | * | F | 3.10 | 0.77 |
| Arg | 68 | . | . | . | . | T | . | . | 1.32 | −1.00 | . | * | F | 2.59 | 0.42 |
| Cys | 69 | . | . | . | . | T | T | . | 0.50 | −1.00 | . | * | . | 2.33 | 0.21 |
| Asp | 70 | . | . | . | . | T | T | . | 0.18 | −0.36 | . | * | . | 1.72 | 0.16 |
| Cys | 71 | . | . | . | . | T | T | . | −0.82 | −0.21 | . | * | . | 1.41 | 0.04 |
| Gly | 72 | . | . | . | . | T | T | . | −1.14 | 0.47 | . | * | . | 0.20 | 0.06 |
| Val | 73 | . | . | . | B | T | . | . | −1.29 | 0.47 | . | * | . | −0.20 | 0.02 |
| Cys | 74 | . | . | B | B | . | . | . | −1.48 | 0.97 | . | . | . | −0.60 | 0.05 |
| Ile | 75 | . | . | B | B | . | . | . | −1.79 | 1.04 | * | . | . | −0.60 | 0.03 |
| Cys | 76 | . | . | B | B | . | . | . | −1.12 | 1.10 | . | . | . | −0.60 | 0.07 |
| His | 77 | . | . | B | B | . | . | . | −0.99 | 0.46 | . | . | . | −0.60 | 0.22 |
| Val | 78 | . | . | . | B | T | . | . | −0.48 | 0.31 | . | . | . | 0.10 | 0.48 |
| Thr | 79 | . | . | . | B | . | . | C | −0.41 | 0.06 | . | . | F | 0.05 | 0.89 |

TABLE II-continued

| Res | | I | II | III | IV | V | VI | VII | VIII | IX | X | XI | XII | XIII | XIV |
|---|---|---|---|---|---|---|---|---|---|---|---|---|---|---|---|
| Glu | 80 | . | . | . | . | . | T | C | −0.22 | 0.10 | * | . | F | 0.45 | 0.64 |
| Pro | 81 | . | . | . | . | T | T | . | −0.26 | 0.39 | . | . | F | 0.65 | 0.75 |
| Gly | 82 | . | . | . | . | T | T | . | −0.57 | 0.53 | . | . | . | 0.20 | 0.45 |
| Met | 83 | . | . | . | . | T | T | . | 0.08 | 0.47 | * | . | . | 0.20 | 0.26 |
| Phe | 84 | . | . | . | . | T | . | . | −0.42 | 0.90 | . | . | . | 0.00 | 0.26 |
| Phe | 85 | . | . | . | . | T | . | . | −1.09 | 1.16 | . | . | . | 0.00 | 0.21 |
| Gly | 86 | . | . | . | . | . | T | C | −0.88 | 1.30 | . | . | . | 0.00 | 0.12 |
| Pro | 87 | . | . | . | . | . | T | C | −1.20 | 0.69 | . | . | . | 0.00 | 0.23 |
| Leu | 88 | . | . | . | . | T | T | . | −0.63 | 0.47 | * | . | . | 0.20 | 0.14 |
| Cys | 89 | . | . | . | . | T | T | . | 0.07 | 0.19 | * | . | . | 0.50 | 0.20 |
| Glu | 90 | . | A | . | . | T | . | . | 0.48 | −0.24 | * | . | . | 0.70 | 0.22 |
| Cys | 91 | . | A | . | . | T | . | . | −0.03 | 0.24 | . | . | . | 0.10 | 0.28 |
| His | 92 | . | A | . | . | T | . | . | −0.49 | 0.20 | * | . | . | 0.10 | 0.39 |
| Glu | 93 | . | A | . | . | T | . | . | 0.32 | 0.20 | * | . | . | 0.10 | 0.12 |
| Trp | 94 | . | A | . | . | T | . | . | 0.68 | 0.20 | * | . | . | 0.10 | 0.39 |
| Val | 95 | . | A | . | . | T | . | . | 0.43 | 0.11 | * | . | . | 0.10 | 0.42 |
| Cys | 96 | . | A | . | . | T | . | . | 1.10 | 0.37 | * | . | . | 0.38 | 0.38 |
| Glu | 97 | . | A | . | . | T | . | . | 0.79 | 0.37 | * | . | . | 0.66 | 0.60 |
| Thr | 98 | . | A | . | . | T | . | . | 0.49 | −0.11 | * | . | F | 1.69 | 0.80 |
| Tyr | 99 | . | . | . | . | T | T | . | 0.47 | −0.37 | . | . | F | 2.52 | 1.99 |
| Asp | 100 | . | . | . | . | T | T | . | 0.66 | −0.46 | . | . | F | 2.80 | 1.66 |
| Gly | 101 | . | . | . | . | T | T | . | 0.73 | 0.11 | . | . | F | 1.77 | 0.62 |
| Ser | 102 | . | . | . | . | T | T | . | 0.39 | 0.13 | . | . | F | 1.49 | 0.40 |
| Thr | 103 | . | . | . | . | T | . | . | 0.67 | −0.20 | . | . | F | 1.61 | 0.24 |
| Cys | 104 | . | . | . | . | T | T | . | 0.57 | 0.30 | . | * | . | 0.78 | 0.32 |
| Ala | 105 | . | . | . | . | T | T | . | 0.61 | 0.30 | . | * | . | 0.50 | 0.24 |
| Gly | 106 | . | . | . | . | T | T | . | 0.29 | −0.09 | . | * | . | 1.10 | 0.33 |
| His | 107 | . | . | . | . | T | T | . | 0.59 | 0.00 | . | * | . | 0.50 | 0.33 |
| Gly | 108 | . | . | . | . | T | . | . | 0.23 | −0.57 | . | * | F | 1.35 | 0.55 |
| Lys | 109 | . | . | . | . | T | . | . | 0.56 | −0.50 | . | * | F | 1.36 | 0.30 |
| Cys | 110 | . | . | . | . | T | T | . | 1.19 | −0.50 | . | . | . | 1.72 | 0.22 |
| Asp | 111 | . | . | . | . | T | T | . | 0.87 | −1.00 | . | * | . | 2.33 | 0.44 |
| Cys | 112 | . | . | . | . | T | T | . | 0.94 | −0.86 | . | * | . | 2.64 | 0.12 |
| Gly | 113 | . | . | . | . | T | T | . | 0.62 | −0.86 | . | * | F | 3.10 | 0.44 |
| Lys | 114 | . | . | . | . | T | . | . | 0.58 | −0.86 | . | * | F | 2.59 | 0.14 |
| Cys | 115 | . | . | . | . | T | . | . | 1.24 | −0.86 | . | * | F | 2.28 | 0.44 |
| Lys | 116 | . | . | . | . | T | . | . | 0.90 | −1.03 | . | * | F | 1.97 | 0.76 |
| Cys | 117 | . | . | . | . | T | . | . | 1.28 | −1.03 | . | * | F | 1.94 | 0.38 |
| Asp | 118 | . | . | . | . | T | T | . | 1.38 | −0.11 | . | * | F | 1.81 | 0.74 |
| Gln | 119 | . | . | . | . | T | T | . | 0.99 | 0.07 | . | * | F | 1.49 | 0.58 |
| Gly | 120 | . | . | . | . | T | T | . | 1.66 | 0.50 | . | * | F | 1.62 | 1.07 |
| Trp | 121 | . | . | . | . | T | T | . | 1.02 | −0.07 | . | * | F | 2.80 | 1.07 |
| Tyr | 122 | . | . | . | . | T | . | . | 1.02 | 0.43 | . | . | . | 1.12 | 0.62 |
| Gly | 123 | . | . | . | . | T | . | . | 1.02 | 0.60 | . | . | . | 0.84 | 0.34 |
| Asp | 124 | . | . | . | . | T | . | . | 0.78 | 0.57 | . | . | . | 0.56 | 0.56 |
| Ala | 125 | . | . | . | . | T | . | . | 0.91 | 0.41 | . | . | . | 0.28 | 0.56 |
| Cys | 126 | . | . | . | . | T | . | . | 0.89 | 0.09 | * | . | . | 0.30 | 0.87 |
| Gln | 127 | . | . | . | . | T | . | . | 1.13 | 0.14 | * | . | . | 0.30 | 0.75 |
| Tyr | 128 | . | . | . | . | . | . | C | 0.81 | 0.54 | . | . | . | −0.05 | 1.20 |
| Pro | 129 | . | . | . | . | T | T | . | 0.81 | 0.61 | . | * | F | 0.50 | 1.20 |
| Thr | 130 | . | . | . | . | T | T | . | 0.59 | 0.04 | . | * | F | 0.80 | 1.15 |
| Asn | 131 | . | . | . | . | T | T | . | 0.94 | 0.33 | . | * | F | 0.65 | 0.61 |
| Cys | 132 | . | . | . | . | T | T | . | 0.99 | 0.06 | . | * | . | 0.50 | 0.57 |
| Asp | 133 | . | . | . | . | T | . | . | 1.28 | −0.37 | . | . | . | 0.90 | 0.79 |
| Leu | 134 | . | . | . | . | T | . | . | 1.53 | −0.86 | . | . | F | 1.69 | 0.98 |
| Thr | 135 | . | . | . | . | T | . | . | 1.54 | −1.26 | . | . | F | 2.18 | 3.64 |
| Lys | 136 | . | . | . | . | T | . | . | 1.54 | −1.44 | . | . | F | 2.52 | 2.92 |
| Lys | 137 | . | . | . | . | T | . | . | 2.21 | −1.04 | * | . | F | 2.86 | 5.70 |
| Lys | 138 | . | . | . | . | T | T | . | 1.61 | −1.33 | * | . | F | 3.40 | 6.84 |
| Ser | 139 | . | . | . | . | T | T | . | 1.76 | −1.20 | * | . | F | 3.06 | 3.39 |
| Asn | 140 | . | . | . | . | T | T | . | 2.11 | −0.63 | * | . | F | 2.57 | 0.91 |
| Gln | 141 | . | . | . | . | T | T | . | 2.07 | −0.63 | * | . | F | 2.57 | 0.91 |
| Met | 142 | . | . | . | . | T | . | . | 1.72 | −0.23 | * | . | . | 2.07 | 1.09 |
| Cys | 143 | . | . | . | . | T | T | . | 1.68 | −0.23 | * | . | . | 2.12 | 0.91 |
| Lys | 144 | . | . | . | . | T | T | . | 1.98 | −0.23 | * | . | F | 2.61 | 0.91 |
| Asn | 145 | . | . | . | . | T | T | . | 1.09 | −0.63 | * | . | F | 3.40 | 1.53 |
| Ser | 146 | . | . | . | . | T | T | . | 0.20 | −0.56 | * | . | F | 3.06 | 2.00 |
| Gln | 147 | . | . | . | B | T | . | . | 0.13 | −0.44 | * | . | F | 1.87 | 0.70 |
| Asp | 148 | . | . | . | B | T | . | . | 0.50 | 0.13 | * | . | F | 0.93 | 0.23 |
| Ile | 149 | . | . | B | B | . | . | . | 0.46 | 0.11 | * | . | . | 0.04 | 0.23 |
| Ile | 150 | . | . | B | B | . | . | . | −0.13 | 0.13 | . | . | . | −0.30 | 0.22 |
| Cys | 151 | . | . | B | . | . | T | . | −0.18 | 0.23 | . | . | . | 0.10 | 0.13 |
| Ser | 152 | . | . | . | . | T | T | . | −0.49 | 0.66 | . | . | . | 0.20 | 0.19 |
| Asn | 153 | . | . | . | . | T | T | . | −1.16 | 0.46 | . | . | F | 0.35 | 0.38 |
| Ala | 154 | . | . | . | . | T | T | . | −0.30 | 0.34 | . | . | F | 0.65 | 0.38 |
| Gly | 155 | . | . | . | . | T | . | . | −0.08 | 0.27 | . | . | F | 0.45 | 0.39 |
| Thr | 156 | . | . | . | . | T | . | . | 0.24 | 0.46 | . | . | . | 0.00 | 0.13 |

TABLE II-continued

| Res | | I | II | III | IV | V | VI | VII | VIII | IX | X | XI | XII | XIII | XIV |
|---|---|---|---|---|---|---|---|---|---|---|---|---|---|---|---|
| Cys | 157 | . | . | . | . | T | T | . | 0.66 | 0.49 | . | . | . | 0.20 | 0.13 |
| His | 158 | . | . | . | . | T | T | . | −0.01 | −0.01 | . | * | . | 1.10 | 0.25 |
| Cys | 159 | . | . | . | . | T | T | . | 0.62 | 0.13 | . | * | . | 0.50 | 0.09 |
| Gly | 160 | . | . | . | . | T | T | . | 0.30 | −0.36 | . | * | . | 1.10 | 0.35 |
| Arg | 161 | . | . | . | . | T | . | . | 0.61 | −0.36 | . | * | . | 1.24 | 0.14 |
| Cys | 162 | . | . | . | . | T | T | . | 1.28 | −0.86 | . | * | F | 2.23 | 0.43 |
| Lys | 163 | . | . | . | . | T | T | . | 1.01 | −1.03 | . | * | F | 2.57 | 0.69 |
| Cys | 164 | . | . | . | . | T | T | . | 1.68 | −1.07 | . | * | F | 2.91 | 0.47 |
| Asp | 165 | . | . | . | . | T | T | . | 1.68 | −1.07 | . | * | F | 3.40 | 1.48 |
| Asn | 166 | . | . | . | . | T | T | . | 1.27 | −1.21 | . | * | F | 2.91 | 0.73 |
| Ser | 167 | . | . | . | . | T | T | . | 1.59 | −0.83 | . | . | F | 2.72 | 1.83 |
| Asp | 168 | . | . | . | . | T | T | . | 0.73 | −0.97 | . | . | F | 2.38 | 1.08 |
| Gly | 169 | . | . | . | . | T | T | . | 0.54 | −0.29 | . | . | F | 1.59 | 0.56 |
| Ser | 170 | . | . | . | B | T | . | . | 0.30 | −0.04 | . | . | F | 0.85 | 0.31 |
| Gly | 171 | . | . | . | B | T | . | . | −0.04 | 0.33 | . | * | F | 0.25 | 0.29 |
| Leu | 172 | . | . | B | B | . | . | . | 0.30 | 0.76 | . | * | F | −0.45 | 0.29 |
| Val | 173 | . | . | B | B | . | . | . | −0.40 | 0.33 | . | * | . | −0.30 | 0.43 |
| Tyr | 174 | . | . | . | B | T | . | . | −0.72 | 0.73 | . | * | . | −0.20 | 0.38 |
| Gly | 175 | . | . | . | . | T | T | . | −0.42 | 0.87 | . | . | . | 0.20 | 0.24 |
| Lys | 176 | . | . | . | . | T | T | . | −0.74 | 0.19 | . | . | . | 0.50 | 0.57 |
| Phe | 177 | . | . | . | . | T | T | . | 0.07 | 0.11 | . | . | . | 0.84 | 0.20 |
| Cys | 178 | . | . | . | . | T | T | . | 0.92 | −0.64 | * | * | . | 2.08 | 0.33 |
| Glu | 179 | . | . | . | . | T | . | . | 1.28 | −1.07 | * | . | . | 2.22 | 0.28 |
| Cys | 180 | . | . | . | . | T | T | . | 1.62 | −1.07 | * | . | . | 2.76 | 0.62 |
| Asp | 181 | . | . | . | . | T | T | . | 0.91 | −1.86 | * | * | F | 3.40 | 2.01 |
| Asp | 182 | . | . | . | . | T | T | . | 0.72 | −1.86 | * | * | F | 2.91 | 0.62 |
| Arg | 183 | . | . | . | . | T | T | . | 1.39 | −1.17 | . | * | F | 2.88 | 0.81 |
| Glu | 184 | . | . | . | . | T | . | . | 1.39 | −1.74 | . | * | . | 2.50 | 0.81 |
| Cys | 185 | . | . | . | . | T | . | . | 2.06 | −1.74 | . | * | . | 2.47 | 0.81 |
| Ile | 186 | . | . | . | . | T | . | . | 1.74 | −1.74 | * | * | . | 2.44 | 0.72 |
| Asp | 187 | . | . | . | . | T | T | . | 1.74 | −1.26 | . | * | F | 3.10 | 0.60 |
| Asp | 188 | . | . | . | . | . | T | C | 1.63 | −1.26 | * | * | F | 2.74 | 1.94 |
| Glu | 189 | A | . | . | . | . | T | . | 0.74 | −1.83 | * | . | F | 2.23 | 4.79 |
| Thr | 190 | A | . | . | . | . | T | . | 0.74 | −1.83 | * | . | F | 1.92 | 2.01 |
| Glu | 191 | A | . | . | . | . | . | . | 1.29 | −1.26 | * | . | F | 1.26 | 0.65 |
| Glu | 192 | A | . | . | . | . | . | . | 0.94 | −0.83 | . | . | F | 0.95 | 0.37 |
| Ile | 193 | . | . | . | . | T | . | . | 0.91 | −0.40 | . | . | . | 1.15 | 0.25 |
| Cys | 194 | . | . | . | . | T | T | . | 0.57 | −0.39 | . | . | . | 1.60 | 0.20 |
| Gly | 195 | . | . | . | . | T | T | . | 0.92 | 0.04 | . | . | . | 1.25 | 0.11 |
| Gly | 196 | . | . | . | . | T | T | . | 0.26 | 0.04 | * | . | F | 1.65 | 0.32 |
| His | 197 | . | . | . | . | T | T | . | 0.01 | −0.07 | . | . | F | 2.50 | 0.32 |
| Gly | 198 | . | . | . | . | T | T | . | 0.23 | 0.11 | . | . | F | 1.65 | 0.51 |
| Lys | 199 | . | . | . | . | T | T | . | 0.56 | 0.26 | . | . | . | 1.25 | 0.28 |
| Cys | 200 | . | . | . | . | T | T | . | 0.90 | 0.26 | . | . | . | 1.00 | 0.20 |
| Tyr | 201 | . | . | . | . | T | T | . | 0.58 | 0.16 | . | . | . | 0.75 | 0.33 |
| Cys | 202 | . | . | . | . | T | T | . | 0.37 | 0.30 | . | . | . | 0.50 | 0.09 |
| Gly | 203 | . | . | . | . | T | T | . | 0.04 | 1.06 | . | * | . | 0.20 | 0.26 |
| Asn | 204 | . | . | . | . | T | T | . | 0.04 | 1.06 | . | * | . | 0.20 | 0.09 |
| Cys | 205 | . | . | . | . | T | T | . | 0.12 | 0.30 | * | * | . | 0.50 | 0.33 |
| Tyr | 206 | . | . | . | . | T | . | . | 0.02 | 0.23 | . | * | . | 0.30 | 0.34 |
| Cys | 207 | . | . | . | . | T | T | . | 0.40 | 0.23 | * | * | . | 0.50 | 0.21 |
| Lys | 208 | . | . | . | . | T | T | . | 0.71 | 0.74 | * | * | . | 0.20 | 0.40 |
| Ala | 209 | . | . | . | . | T | T | . | 0.37 | 0.67 | * | * | . | 0.20 | 0.35 |
| Gly | 210 | . | . | . | . | T | T | . | 1.03 | 0.34 | * | * | . | 0.81 | 0.65 |
| Trp | 211 | . | . | . | . | T | . | . | 1.32 | −0.23 | * | * | . | 1.52 | 0.54 |
| His | 212 | . | . | . | . | . | T | C | 1.32 | −0.23 | * | * | . | 1.98 | 1.07 |
| Gly | 213 | . | . | . | . | T | T | . | 1.28 | −0.16 | . | * | F | 2.49 | 0.58 |
| Asp | 214 | . | . | . | . | T | T | . | 1.17 | −0.59 | . | * | F | 3.10 | 0.96 |
| Lys | 215 | . | . | . | . | T | T | . | 1.51 | −0.71 | . | * | F | 2.79 | 0.61 |
| Cys | 216 | . | A | . | . | T | . | . | 1.13 | −0.81 | . | * | . | 2.08 | 1.07 |
| Glu | 217 | . | A | . | . | T | . | . | 1.17 | −0.67 | . | * | . | 1.62 | 0.34 |
| Phe | 218 | . | A | . | . | T | . | . | 0.62 | −0.67 | . | * | . | 1.31 | 0.29 |
| Gln | 219 | . | A | . | . | T | . | . | 0.31 | 0.01 | . | * | . | 0.10 | 0.37 |
| Cys | 220 | . | A | . | . | T | . | . | 0.06 | −0.07 | . | * | . | 0.70 | 0.31 |
| Asp | 221 | . | A | . | . | T | . | . | 0.43 | 0.36 | . | * | . | 0.10 | 0.56 |
| Ile | 222 | . | A | . | . | . | . | C | 0.43 | 0.49 | . | * | . | −0.06 | 0.34 |
| Thr | 223 | . | . | . | . | . | T | C | 0.83 | 0.09 | . | * | F | 1.28 | 1.09 |
| Pro | 224 | . | . | . | . | T | T | . | 0.88 | −0.10 | . | . | F | 2.27 | 0.88 |
| Trp | 225 | . | . | . | . | T | T | . | 1.66 | −0.10 | . | * | F | 2.76 | 2.50 |
| Glu | 226 | . | . | . | . | T | T | . | 1.77 | −0.79 | . | * | F | 3.40 | 3.39 |
| Ser | 227 | . | . | . | . | T | T | . | 1.99 | −1.27 | . | . | F | 3.06 | 4.29 |
| Lys | 228 | . | . | . | . | T | T | . | 1.99 | −1.13 | * | * | F | 2.72 | 2.19 |
| Arg | 229 | . | . | . | . | T | T | . | 1.90 | −1.56 | * | * | F | 2.38 | 1.82 |
| Arg | 230 | . | . | . | . | T | T | . | 1.98 | −1.17 | . | * | F | 2.38 | 1.82 |
| Cys | 231 | . | . | . | . | T | . | . | 1.98 | −1.13 | . | . | F | 2.18 | 1.41 |
| Thr | 232 | . | . | . | . | T | . | . | 1.93 | −1.13 | . | * | F | 2.52 | 1.20 |
| Ser | 233 | . | . | . | . | . | T | C | 1.93 | −0.70 | * | * | F | 2.71 | 0.61 |

TABLE II-continued

| Res | | I | II | III | IV | V | VI | VII | VIII | IX | X | XI | XII | XIII | XIV |
|---|---|---|---|---|---|---|---|---|---|---|---|---|---|---|---|
| Pro | 234 | . | . | . | . | T | T | . | 0.93 | −0.70 | * | * | F | 3.40 | 2.27 |
| Asp | 235 | . | . | . | . | T | T | . | 0.16 | −0.59 | * | * | F | 3.06 | 1.10 |
| Gly | 236 | . | . | . | . | T | T | . | 0.52 | −0.50 | . | * | F | 2.58 | 0.44 |
| Lys | 237 | . | . | . | . | T | . | . | 0.83 | −0.50 | . | * | F | 2.35 | 0.38 |
| Ile | 238 | . | . | . | . | T | . | . | 1.24 | −0.53 | . | * | . | 2.47 | 0.37 |
| Cys | 239 | . | . | . | . | T | T | . | 1.11 | −0.53 | . | * | . | 2.64 | 0.73 |
| Ser | 240 | . | . | . | . | T | T | . | 0.80 | −0.53 | . | * | F | 3.10 | 0.36 |
| Asn | 241 | . | . | . | . | T | T | . | 0.48 | −0.04 | . | . | F | 2.49 | 0.74 |
| Arg | 242 | . | . | . | . | T | T | . | −0.42 | −0.16 | . | . | F | 2.18 | 0.74 |
| Gly | 243 | . | . | . | B | T | . | . | −0.20 | −0.09 | . | . | F | 1.47 | 0.41 |
| Thr | 244 | . | . | . | B | T | . | . | 0.12 | 0.10 | * | . | F | 0.56 | 0.14 |
| Cys | 245 | . | . | . | B | T | . | . | 0.42 | 0.13 | * | . | . | 0.10 | 0.07 |
| Val | 246 | . | . | . | B | T | . | . | −0.24 | 0.13 | * | . | . | 0.10 | 0.12 |
| Cys | 247 | . | . | . | . | T | T | . | −0.67 | 0.27 | * | * | . | 0.50 | 0.04 |
| Gly | 248 | . | . | . | . | T | T | . | −0.99 | 0.27 | . | . | . | 0.50 | 0.12 |
| Glu | 249 | . | . | . | . | T | T | . | −0.71 | 0.27 | . | . | . | 0.50 | 0.09 |
| Cys | 250 | . | . | . | . | T | T | . | −0.04 | 0.13 | . | . | . | 0.50 | 0.22 |
| Thr | 251 | . | . | . | . | T | . | . | −0.04 | −0.44 | . | * | . | 0.90 | 0.37 |
| Cys | 252 | . | . | . | . | T | . | . | 0.62 | −0.23 | . | . | . | 0.90 | 0.16 |
| His | 253 | . | . | . | . | T | . | . | 0.76 | −0.23 | . | . | . | 1.24 | 0.50 |
| Asp | 254 | . | . | . | . | T | . | . | 0.44 | −0.37 | . | * | . | 1.58 | 0.54 |
| Val | 255 | . | . | . | . | T | . | . | 0.77 | −0.37 | . | * | . | 2.07 | 1.44 |
| Asp | 256 | . | . | . | . | . | T | C | 1.08 | −0.51 | . | * | F | 2.86 | 1.05 |
| Pro | 257 | . | . | . | . | T | T | . | 1.46 | −1.01 | * | * | F | 3.40 | 1.05 |
| Thr | 258 | . | . | . | . | T | T | . | 1.14 | −0.10 | * | * | F | 2.76 | 1.48 |
| Gly | 259 | . | . | . | . | T | T | . | 1.14 | −0.31 | . | * | F | 2.27 | 0.88 |
| Asp | 260 | . | . | . | . | T | . | . | 1.11 | −0.31 | . | * | F | 1.73 | 0.95 |
| Trp | 261 | . | . | . | . | T | . | . | 1.08 | −0.06 | . | * | F | 1.39 | 0.46 |
| Gly | 262 | . | . | . | . | . | . | C | 0.94 | −0.04 | . | * | F | 0.85 | 0.63 |
| Asp | 263 | . | . | . | . | T | . | . | 1.26 | −0.04 | . | * | F | 1.05 | 0.38 |
| Ile | 264 | . | . | . | . | T | . | . | 1.29 | −0.04 | . | * | . | 0.90 | 0.60 |
| His | 265 | . | . | . | . | T | T | . | 0.62 | −0.47 | * | . | . | 1.10 | 0.87 |
| Gly | 266 | . | . | . | . | T | T | . | 0.91 | −0.33 | * | * | F | 1.25 | 0.28 |
| Asp | 267 | . | . | . | . | T | T | . | 0.59 | −0.33 | . | * | F | 1.56 | 0.69 |
| Thr | 268 | . | . | . | . | T | T | . | 0.59 | −0.44 | . | * | F | 1.87 | 0.27 |
| Cys | 269 | . | . | . | . | T | T | . | 1.48 | −0.94 | * | * | . | 2.33 | 0.46 |
| Glu | 270 | . | . | . | . | T | T | . | 1.62 | −1.37 | . | . | . | 2.64 | 0.48 |
| Cys | 271 | . | . | . | . | T | T | . | 1.97 | −1.37 | * | . | F | 3.10 | 0.65 |
| Asp | 272 | . | . | . | . | T | T | . | 1.30 | −1.86 | * | . | F | 2.94 | 2.01 |
| Glu | 273 | . | . | . | . | T | . | . | 1.72 | −1.86 | * | * | F | 2.28 | 0.62 |
| Arg | 274 | . | . | . | . | T | T | . | 1.80 | −1.86 | * | . | F | 2.32 | 2.28 |
| Asp | 275 | . | . | . | . | T | T | . | 0.94 | −1.93 | * | . | F | 2.01 | 1.38 |
| Cys | 276 | . | . | . | . | T | T | . | 1.37 | −1.29 | * | . | . | 1.40 | 0.59 |
| Arg | 277 | . | . | . | . | T | T | . | 1.37 | −0.53 | * | . | . | 1.40 | 0.47 |
| Ala | 278 | . | . | B | B | . | . | . | 1.48 | −0.53 | * | . | . | 0.60 | 0.47 |
| Val | 279 | . | . | B | B | . | . | . | 1.12 | −0.53 | * | . | . | 1.09 | 1.73 |
| Tyr | 280 | . | . | . | B | T | . | . | 0.82 | −0.34 | * | * | . | 1.53 | 1.38 |
| Asp | 281 | . | . | . | . | T | T | . | 1.49 | 0.04 | * | . | . | 1.67 | 1.83 |
| Arg | 282 | . | . | . | . | T | T | . | 1.38 | −0.46 | * | * | F | 2.76 | 4.12 |
| Tyr | 283 | . | . | . | . | T | T | . | 1.27 | −1.10 | * | * | F | 3.40 | 4.39 |
| Ser | 284 | . | . | . | . | T | T | . | 1.46 | −1.07 | * | * | F | 3.06 | 2.28 |
| Asp | 285 | . | . | . | . | T | . | . | 1.40 | −0.50 | * | . | F | 2.07 | 0.62 |
| Asp | 286 | . | . | . | . | T | . | . | 1.06 | −0.11 | * | . | F | 1.73 | 0.53 |
| Phe | 287 | . | . | . | . | T | . | . | 0.91 | −0.44 | * | * | . | 1.24 | 0.39 |
| Cys | 288 | . | . | . | . | T | T | . | 0.81 | −0.33 | . | . | . | 1.10 | 0.32 |
| Ser | 289 | . | . | . | . | T | T | . | 1.11 | 0.10 | . | . | . | 0.50 | 0.19 |
| Gly | 290 | . | . | . | . | T | T | . | 0.44 | 0.50 | . | * | F | 0.35 | 0.38 |
| His | 291 | . | . | . | . | T | T | . | 0.44 | 0.29 | . | * | F | 0.87 | 0.38 |
| Gly | 292 | . | . | . | . | T | . | . | 0.48 | 0.11 | . | * | F | 0.89 | 0.46 |
| Gln | 293 | . | . | . | . | T | . | . | 0.80 | 0.30 | * | * | . | 0.96 | 0.25 |
| Cys | 294 | . | . | . | . | T | T | . | 1.21 | 0.30 | * | * | . | 1.38 | 0.18 |
| Asn | 295 | . | . | . | . | T | T | . | 0.89 | −0.20 | . | * | . | 2.20 | 0.36 |
| Cys | 296 | . | . | . | . | T | T | . | 0.92 | −0.06 | . | * | . | 1.98 | 0.11 |
| Gly | 297 | . | . | . | . | T | T | . | 0.60 | −0.46 | * | * | . | 2.04 | 0.34 |
| Arg | 298 | . | . | . | . | T | . | . | 0.64 | −0.46 | * | * | . | 1.90 | 0.11 |
| Cys | 299 | . | . | . | . | T | T | . | 0.72 | −0.86 | * | * | . | 2.46 | 0.43 |
| Asp | 300 | . | . | . | . | T | T | . | 0.38 | −0.93 | * | * | . | 2.52 | 0.44 |
| Cys | 301 | . | . | . | . | T | T | . | 0.76 | −0.93 | * | * | . | 2.80 | 0.22 |
| Lys | 302 | . | . | . | . | T | T | . | 0.86 | −0.01 | * | * | . | 2.22 | 0.43 |
| Ala | 303 | . | . | . | . | T | . | . | 0.40 | 0.17 | * | * | . | 1.14 | 0.40 |
| Gly | 304 | . | . | . | . | T | . | . | 1.11 | 0.60 | . | * | . | 0.56 | 0.75 |
| Trp | 305 | . | . | . | . | T | . | . | 1.16 | 0.03 | . | * | . | 0.92 | 0.75 |
| Tyr | 306 | . | . | . | . | T | . | . | 1.16 | 0.03 | . | * | . | 1.13 | 1.48 |
| Gly | 307 | . | . | . | . | T | T | . | 1.11 | 0.10 | * | . | F | 1.67 | 0.80 |
| Lys | 308 | . | . | . | . | T | T | . | 1.67 | −0.33 | * | . | F | 2.76 | 1.32 |
| Lys | 309 | . | . | . | . | T | T | . | 1.80 | −0.74 | . | . | F | 3.40 | 1.15 |
| Cys | 310 | . | . | . | . | T | T | . | 2.09 | −1.07 | . | . | F | 3.06 | 1.79 |

TABLE II-continued

| Res | | I | II | III | IV | V | VI | VII | VIII | IX | X | XI | XII | XIII | XIV |
|---|---|---|---|---|---|---|---|---|---|---|---|---|---|---|---|
| Glu | 311 | . | . | . | . | T | . | . | 2.03 | −1.10 | . | . | F | 2.52 | 1.55 |
| His | 312 | . | . | . | . | . | T | C | 1.71 | −0.71 | . | . | F | 2.18 | 1.04 |
| Pro | 313 | . | . | . | . | T | T | . | 1.36 | −0.14 | . | . | F | 1.74 | 1.04 |
| Gln | 314 | . | . | . | . | T | T | . | 0.50 | −0.23 | . | . | F | 1.25 | 0.87 |
| Ser | 315 | . | . | . | . | T | T | . | 0.87 | 0.46 | . | . | F | 0.35 | 0.52 |
| Cys | 316 | . | . | . | B | T | . | . | 0.28 | 0.34 | . | . | F | 0.25 | 0.45 |
| Thr | 317 | . | . | . | B | . | . | C | 0.31 | 0.41 | . | . | . | −0.40 | 0.27 |
| Leu | 318 | . | . | . | B | . | . | C | 0.52 | 0.01 | . | . | . | −0.10 | 0.34 |
| Ser | 319 | . | . | . | B | . | . | C | 0.22 | −0.37 | . | * | . | 0.65 | 1.11 |
| Ala | 320 | A | A | . | . | . | . | . | −0.37 | −0.56 | * | * | F | 0.90 | 1.03 |
| Glu | 321 | A | A | . | . | . | . | . | 0.41 | −0.36 | * | * | F | 0.45 | 0.87 |
| Glu | 322 | A | A | . | . | . | . | . | 0.77 | −1.04 | * | * | F | 0.90 | 1.28 |
| Ser | 323 | . | A | . | . | T | . | . | 0.91 | −1.43 | * | * | F | 1.64 | 2.53 |
| Ile | 324 | . | A | . | . | T | . | . | 1.21 | −1.36 | * | * | F | 1.83 | 0.78 |
| Arg | 325 | . | A | . | . | T | . | . | 1.46 | −0.96 | * | . | F | 2.17 | 0.78 |
| Lys | 326 | . | A | . | . | T | . | . | 1.16 | −0.53 | * | . | F | 2.51 | 0.58 |
| Cys | 327 | . | . | . | . | T | T | . | 0.86 | −0.53 | * | . | F | 3.40 | 1.11 |
| Gln | 328 | . | . | . | . | T | T | . | 1.16 | −0.83 | * | * | F | 2.91 | 0.76 |
| Gly | 329 | . | . | . | . | T | T | . | 1.23 | −0.83 | * | * | F | 2.57 | 0.63 |
| Ser | 330 | . | . | . | . | T | T | . | 0.91 | −0.14 | * | * | F | 1.93 | 0.97 |
| Ser | 331 | . | . | . | . | T | . | . | 0.20 | −0.29 | . | * | F | 1.39 | 0.87 |
| Asp | 332 | . | . | . | . | T | . | . | 0.57 | −0.11 | * | * | F | 1.05 | 0.47 |
| Leu | 333 | . | . | . | . | . | . | C | 0.22 | −0.16 | * | * | F | 1.16 | 0.47 |
| Pro | 334 | . | . | . | . | T | . | . | 0.68 | −0.11 | * | * | F | 1.67 | 0.35 |
| Cys | 335 | . | . | . | . | T | T | . | 0.63 | −0.50 | . | * | F | 2.18 | 0.41 |
| Ser | 336 | . | . | . | . | T | T | . | 0.98 | −0.07 | . | * | F | 2.49 | 0.49 |
| Gly | 337 | . | . | . | . | T | T | . | 0.31 | −0.76 | . | * | F | 3.10 | 0.63 |
| Arg | 338 | . | . | . | . | T | T | . | 1.12 | −0.61 | . | * | F | 2.79 | 0.63 |
| Gly | 339 | . | . | . | . | T | . | . | 0.67 | −1.19 | . | * | F | 2.56 | 0.82 |
| Lys | 340 | . | . | . | . | T | . | . | 0.99 | −1.00 | * | * | F | 2.53 | 0.44 |
| Cys | 341 | . | . | . | . | T | T | . | 1.33 | −1.00 | * | * | F | 2.70 | 0.22 |
| Glu | 342 | . | . | . | . | T | T | . | 1.01 | −1.00 | * | * | . | 2.52 | 0.45 |
| Cys | 343 | . | . | . | . | T | T | . | 0.59 | −0.86 | * | * | . | 2.80 | 0.12 |
| Gly | 344 | . | . | . | . | T | T | . | 0.27 | −0.37 | . | . | . | 2.22 | 0.33 |
| Lys | 345 | . | . | . | . | T | . | . | −0.02 | −0.37 | . | . | . | 1.74 | 0.10 |
| Cys | 346 | . | . | . | . | T | . | . | 0.43 | 0.39 | . | . | . | 0.86 | 0.29 |
| Thr | 347 | . | . | . | . | T | . | . | 0.22 | 0.24 | . | . | . | 0.58 | 0.46 |
| Cys | 348 | . | . | . | . | T | . | . | 0.54 | 0.24 | . | * | . | 0.64 | 0.36 |
| Tyr | 349 | . | . | B | . | . | . | . | 0.89 | 0.67 | . | * | . | 0.28 | 0.66 |
| Pro | 350 | . | . | . | . | . | T | C | 0.96 | 0.10 | . | . | F | 1.47 | 0.76 |
| Pro | 351 | . | . | . | . | T | T | . | 1.73 | −0.39 | * | . | F | 2.76 | 2.78 |
| Gly | 352 | . | . | . | . | T | T | . | 1.19 | −0.96 | * | . | F | 3.40 | 3.47 |
| Asp | 353 | . | . | . | . | T | T | . | 1.61 | −1.07 | * | . | F | 3.06 | 1.67 |
| Arg | 354 | . | . | . | . | T | . | . | 1.51 | −0.74 | * | * | F | 2.52 | 1.69 |
| Arg | 355 | . | . | . | . | T | . | . | 1.77 | −0.74 | * | * | F | 2.18 | 1.69 |
| Val | 356 | . | . | . | . | T | . | . | 1.67 | −1.17 | * | * | . | 1.69 | 2.02 |
| Tyr | 357 | . | . | . | . | T | . | . | 1.34 | −0.69 | * | * | . | 1.35 | 1.49 |
| Gly | 358 | . | . | . | . | T | T | . | 1.34 | −0.11 | * | * | F | 1.25 | 0.41 |
| Lys | 359 | . | . | . | . | T | T | . | 0.57 | −0.11 | * | . | F | 1.25 | 0.95 |
| Thr | 360 | . | . | . | . | T | T | . | 0.46 | −0.19 | * | * | F | 1.59 | 0.33 |
| Cys | 361 | . | . | . | . | T | T | . | 1.31 | −0.94 | * | * | F | 2.23 | 0.55 |
| Glu | 362 | . | . | . | . | T | . | . | 1.67 | −1.37 | * | . | . | 2.22 | 0.46 |
| Cys | 363 | . | . | . | . | T | T | . | 2.12 | −1.37 | * | . | . | 2.76 | 0.62 |
| Asp | 364 | . | . | . | . | T | T | . | 1.41 | −1.86 | * | . | F | 3.40 | 2.28 |
| Asp | 365 | . | . | . | . | T | T | . | 1.72 | −1.86 | * | . | F | 2.91 | 0.70 |
| Arg | 366 | . | . | . | . | T | T | . | 2.39 | −1.86 | * | . | F | 3.03 | 2.28 |
| Arg | 367 | . | . | . | . | T | . | . | 1.58 | −2.43 | * | . | F | 2.80 | 2.28 |
| Cys | 368 | . | . | . | . | T | . | . | 2.24 | −1.74 | . | . | F | 2.77 | 1.12 |
| Glu | 369 | . | . | . | . | T | . | . | 1.90 | −1.74 | . | . | F | 2.59 | 0.96 |
| Asp | 370 | . | . | . | . | T | T | . | 1.04 | −1.31 | * | . | F | 3.10 | 0.48 |
| Leu | 371 | . | . | . | . | T | T | . | 0.08 | −0.67 | * | . | F | 2.79 | 0.67 |
| Asp | 372 | . | . | . | . | T | T | . | −0.70 | −0.60 | . | . | F | 2.48 | 0.29 |
| Gly | 373 | . | . | . | . | T | T | . | −0.38 | −0.03 | * | . | . | 1.72 | 0.09 |
| Val | 374 | . | . | B | . | . | . | . | −0.72 | 0.40 | * | . | . | 0.21 | 0.11 |
| Val | 375 | . | . | B | . | . | . | . | −0.76 | 0.14 | . | * | . | −0.10 | 0.07 |
| Cys | 376 | . | . | . | . | T | T | . | −0.29 | 0.64 | . | . | . | 0.20 | 0.09 |
| Gly | 377 | . | . | . | . | T | T | . | −0.60 | 0.64 | . | . | . | 0.20 | 0.12 |
| Gly | 378 | . | . | . | . | T | T | . | −0.92 | 0.49 | . | . | F | 0.35 | 0.23 |
| His | 379 | . | . | . | . | T | T | . | −0.37 | 0.41 | . | . | F | 0.35 | 0.23 |
| Gly | 380 | . | . | . | . | T | . | . | −0.18 | 0.23 | . | . | F | 0.45 | 0.32 |
| Thr | 381 | . | . | . | . | T | . | . | 0.14 | 0.37 | * | . | F | 0.45 | 0.17 |
| Cys | 382 | . | . | . | . | T | T | . | 0.60 | 0.37 | * | . | . | 0.50 | 0.12 |
| Ser | 383 | . | . | . | . | T | T | . | 0.28 | −0.13 | * | . | . | 1.28 | 0.25 |
| Cys | 384 | . | . | . | . | T | T | . | −0.54 | 0.01 | * | . | . | 0.86 | 0.09 |
| Gly | 385 | . | . | . | . | T | T | . | −0.87 | 0.17 | * | . | . | 1.04 | 0.13 |
| Arg | 386 | . | . | . | . | T | . | . | −0.56 | 0.17 | * | . | . | 1.02 | 0.05 |
| Cys | 387 | . | . | B | . | T | . | . | 0.22 | −0.21 | * | . | . | 1.80 | 0.16 |

TABLE II-continued

| Res | | I | II | III | IV | V | VI | VII | VIII | IX | X | XI | XII | XIII | XIV |
|---|---|---|---|---|---|---|---|---|---|---|---|---|---|---|---|
| Val | 388 | . | . | B | . | . | . | . | 0.18 | −0.79 | * | . | . | 1.52 | 0.32 |
| Cys | 389 | . | . | B | . | . | . | . | 0.56 | −0.79 | * | * | . | 1.34 | 0.16 |
| Glu | 390 | . | . | . | . | T | T | . | 0.20 | 0.13 | * | . | . | 0.86 | 0.32 |
| Arg | 391 | . | . | . | . | T | T | . | −0.26 | 0.34 | . | . | . | 0.68 | 0.38 |
| Gly | 392 | . | . | . | . | T | T | . | 0.46 | 0.13 | . | . | . | 0.50 | 0.69 |
| Trp | 393 | . | . | . | . | T | T | . | 0.50 | −0.44 | . | . | . | 1.10 | 0.80 |
| Phe | 394 | . | . | . | . | T | . | . | 0.50 | 0.24 | * | . | . | 0.30 | 0.34 |
| Gly | 395 | . | . | . | . | T | . | . | 0.50 | 0.81 | * | . | . | 0.00 | 0.18 |
| Lys | 396 | . | . | . | . | T | . | . | 0.36 | 0.79 | * | . | . | 0.00 | 0.30 |
| Leu | 397 | . | . | . | . | T | . | . | 0.49 | 0.37 | * | * | . | 0.64 | 0.47 |
| Cys | 398 | . | . | . | . | T | . | . | 0.89 | 0.01 | * | * | . | 0.98 | 0.74 |
| Gln | 399 | . | . | . | . | T | . | . | 1.63 | −0.41 | * | . | . | 1.92 | 0.72 |
| His | 400 | . | . | . | . | . | T | C | 1.31 | −0.41 | * | * | . | 2.41 | 1.75 |
| Pro | 401 | . | . | . | . | T | T | . | 1.27 | −0.53 | * | * | F | 3.40 | 1.75 |
| Arg | 402 | . | . | . | . | T | T | . | 1.48 | −0.70 | * | . | F | 3.06 | 1.63 |
| Lys | 403 | . | . | . | . | T | T | . | 1.83 | −0.49 | . | . | F | 2.42 | 1.18 |
| Cys | 404 | . | . | . | . | T | . | . | 1.83 | −0.50 | * | . | . | 2.03 | 1.11 |
| Asn | 405 | . | A | . | . | . | . | C | 1.87 | −0.93 | . | . | . | 1.14 | 0.98 |
| Met | 406 | . | A | . | . | . | . | C | 2.08 | −0.93 | * | . | F | 0.95 | 0.85 |
| Thr | 407 | . | A | . | . | . | . | C | 1.67 | −0.53 | * | . | F | 1.44 | 2.73 |
| Glu | 408 | A | A | . | . | . | . | . | 1.67 | −0.71 | . | * | F | 1.58 | 2.28 |
| Glu | 409 | A | A | . | . | . | . | . | 2.33 | −1.11 | * | . | F | 1.92 | 4.61 |
| Gln | 410 | . | A | . | . | T | . | . | 1.52 | −1.33 | * | . | F | 2.66 | 5.13 |
| Ser | 411 | . | . | . | . | T | T | . | 1.46 | −1.13 | * | . | F | 3.40 | 2.44 |
| Lys | 412 | . | . | . | . | T | T | . | 1.77 | −0.56 | * | . | F | 2.91 | 0.76 |
| Asn | 413 | . | . | . | . | . | T | C | 1.47 | −0.56 | * | . | F | 2.62 | 0.76 |
| Leu | 414 | . | . | . | . | . | T | C | 0.88 | −0.57 | * | . | . | 2.38 | 0.76 |
| Cys | 415 | . | . | . | . | T | . | . | 0.88 | −0.46 | * | . | . | 1.99 | 0.38 |
| Glu | 416 | . | . | . | . | T | . | . | 0.83 | −0.46 | * | . | F | 2.05 | 0.40 |
| Ser | 417 | . | . | . | . | T | T | . | −0.10 | −0.43 | * | . | F | 2.50 | 0.48 |
| Ala | 418 | . | . | . | . | T | T | . | −0.91 | −0.43 | * | . | F | 2.25 | 0.62 |
| Asp | 419 | . | . | . | . | T | T | . | −0.77 | −0.31 | * | . | F | 2.00 | 0.30 |
| Gly | 420 | . | . | . | . | T | T | . | −0.40 | 0.26 | * | . | . | 1.00 | 0.12 |
| Ile | 421 | . | . | B | . | . | . | . | −0.74 | 0.26 | * | . | . | 0.15 | 0.16 |
| Leu | 422 | . | . | B | . | . | . | . | −0.40 | 0.19 | * | * | . | 0.15 | 0.09 |
| Cys | 423 | . | . | . | . | T | T | . | −0.16 | 0.19 | * | * | . | 1.00 | 0.19 |
| Ser | 424 | . | . | . | . | T | T | . | −0.46 | 0.19 | * | * | F | 1.40 | 0.27 |
| Gly | 425 | . | . | . | . | T | T | . | −0.78 | −0.11 | . | * | F | 2.25 | 0.43 |
| Lys | 426 | . | . | . | . | T | T | . | 0.08 | −0.23 | . | * | F | 2.50 | 0.43 |
| Gly | 427 | . | . | . | . | T | . | . | 0.22 | −0.30 | . | * | F | 2.05 | 0.44 |
| Ser | 428 | . | . | . | . | T | . | . | 0.54 | −0.11 | * | * | F | 1.80 | 0.24 |
| Cys | 429 | . | . | . | . | T | . | . | 0.89 | −0.11 | * | * | . | 1.40 | 0.12 |
| His | 430 | . | . | . | . | T | T | . | 0.57 | −0.11 | * | . | . | 1.35 | 0.24 |
| Cys | 431 | . | . | . | . | T | T | . | −0.37 | 0.03 | * | . | . | 0.50 | 0.10 |
| Gly | 432 | . | . | . | . | T | T | . | −0.69 | 0.33 | * | . | . | 0.50 | 0.12 |
| Lys | 433 | . | . | . | . | T | T | . | −0.69 | 0.33 | * | . | . | 0.50 | 0.05 |
| Cys | 434 | . | . | . | . | T | . | . | −0.61 | 0.21 | * | . | . | 0.30 | 0.12 |
| Ile | 435 | . | A | . | . | T | . | . | −0.58 | 0.14 | * | . | . | 0.10 | 0.13 |
| Cys | 436 | . | A | B | . | . | . | . | 0.09 | −0.29 | * | . | . | 0.30 | 0.11 |
| Ser | 437 | . | A | . | . | . | . | C | 0.14 | −0.29 | * | . | . | 0.50 | 0.35 |
| Ala | 438 | . | A | . | . | . | . | C | −0.14 | 0.06 | * | . | . | −0.10 | 0.52 |
| Glu | 439 | . | A | . | . | T | . | . | −0.37 | 0.13 | . | . | . | 0.25 | 1.53 |
| Glu | 440 | . | A | . | B | T | . | . | 0.22 | 0.24 | . | . | . | 0.10 | 0.80 |
| Trp | 441 | . | A | . | B | T | . | . | 0.54 | 0.24 | . | * | . | 0.25 | 1.06 |
| Tyr | 442 | . | A | . | B | T | . | . | 0.84 | 0.17 | . | * | . | 0.10 | 0.61 |
| Ile | 443 | . | . | . | B | T | . | . | 0.73 | 0.17 | . | * | . | 0.10 | 0.61 |
| Ser | 444 | . | . | . | B | T | . | . | 0.07 | 0.96 | . | * | . | −0.20 | 0.50 |
| Gly | 445 | . | . | . | . | T | . | . | 0.07 | 0.61 | . | * | F | 0.15 | 0.17 |
| Glu | 446 | . | . | . | . | T | . | . | −0.31 | −0.14 | . | * | . | 0.90 | 0.41 |
| Phe | 447 | . | . | . | . | T | . | . | −0.07 | −0.26 | * | . | . | 1.24 | 0.16 |
| Cys | 448 | . | . | . | . | T | T | . | 0.82 | −0.64 | * | * | . | 2.08 | 0.28 |
| Asp | 449 | . | . | . | . | T | T | . | 1.23 | −1.07 | * | . | . | 2.42 | 0.27 |
| Cys | 450 | . | . | . | . | T | T | . | 1.58 | −1.07 | * | . | . | 2.76 | 0.60 |
| Asp | 451 | . | . | . | . | T | T | . | 0.91 | −1.86 | * | . | F | 3.40 | 1.87 |
| Asp | 452 | . | . | . | . | T | T | . | 1.61 | −1.86 | * | . | F | 2.91 | 0.60 |
| Arg | 453 | . | . | . | . | T | T | . | 2.32 | −1.86 | * | * | F | 2.72 | 1.87 |
| Asp | 454 | . | . | . | . | T | T | . | 2.29 | −2.43 | * | * | F | 2.72 | 2.24 |
| Cys | 455 | . | . | . | . | T | T | . | 2.96 | −1.93 | . | . | F | 2.72 | 1.83 |
| Asp | 456 | . | . | . | . | T | . | . | 2.61 | −1.93 | . | . | F | 2.52 | 1.56 |
| Lys | 457 | . | . | . | . | T | . | . | 1.80 | −1.50 | * | . | F | 2.71 | 0.92 |
| His | 458 | . | . | . | . | T | T | . | 0.80 | −0.81 | * | . | F | 3.40 | 1.42 |
| Asp | 459 | . | . | . | . | T | T | . | 0.13 | −0.70 | . | . | F | 2.91 | 0.60 |
| Gly | 460 | . | . | . | . | T | T | . | 0.49 | −0.13 | . | . | . | 2.12 | 0.16 |
| Leu | 461 | . | . | B | . | . | T | . | 0.14 | 0.36 | . | . | . | 0.78 | 0.17 |
| Ile | 462 | . | . | B | . | . | . | . | 0.10 | 0.29 | . | . | . | 0.24 | 0.10 |
| Cys | 463 | . | . | . | . | T | T | . | −0.21 | 0.69 | * | . | . | 0.20 | 0.16 |
| Thr | 464 | . | . | . | . | T | T | . | −1.10 | 0.69 | * | . | F | 0.35 | 0.20 |

TABLE II-continued

| Res | | I | II | III | IV | V | VI | VII | VIII | IX | X | XI | XII | XIII | XIV |
|---|---|---|---|---|---|---|---|---|---|---|---|---|---|---|---|
| Gly | 465 | . | . | . | . | T | T | . | −1.42 | 0.69 | * | . | F | 0.35 | 0.20 |
| Asn | 466 | . | . | . | . | T | T | . | −0.91 | 0.57 | * | . | F | 0.35 | 0.20 |
| Gly | 467 | . | . | . | . | T | . | . | −0.69 | 0.39 | . | . | F | 0.45 | 0.18 |
| Ile | 468 | . | . | . | . | T | . | . | −0.37 | 0.47 | * | . | . | 0.00 | 0.10 |
| Cys | 469 | . | . | . | . | T | T | . | −0.06 | 0.47 | * | . | . | 0.42 | 0.06 |
| Ser | 470 | . | . | . | . | T | T | . | −0.38 | 0.47 | * | . | . | 0.64 | 0.10 |
| Cys | 471 | . | . | . | . | T | T | . | −0.38 | 0.61 | . | . | . | 0.86 | 0.08 |
| Gly | 472 | . | . | . | . | T | T | . | −0.70 | −0.07 | . | . | . | 1.98 | 0.24 |
| Asn | 473 | . | . | . | . | T | T | . | −0.10 | −0.07 | . | . | . | 2.20 | 0.10 |
| Cys | 474 | . | . | . | . | T | T | . | 0.57 | 0.46 | . | . | . | 1.08 | 0.19 |
| Glu | 475 | . | . | . | . | T | T | . | 0.52 | −0.11 | . | . | . | 1.76 | 0.32 |
| Cys | 476 | . | . | . | . | T | T | . | 0.90 | −0.11 | . | . | . | 1.54 | 0.20 |
| Trp | 477 | . | . | . | . | T | T | . | 1.24 | 0.40 | . | . | . | 0.42 | 0.39 |
| Asp | 478 | . | . | . | . | T | T | . | 0.90 | 0.23 | . | . | . | 0.50 | 0.36 |
| Gly | 479 | . | . | . | . | T | T | . | 1.57 | 0.66 | . | . | F | 0.35 | 0.67 |
| Trp | 480 | . | . | . | . | T | T | . | 0.98 | 0.49 | . | . | F | 0.50 | 1.02 |
| Asn | 481 | . | . | . | . | . | T | C | 0.98 | 0.07 | . | . | F | 0.45 | 0.62 |
| Gly | 482 | . | . | . | . | . | T | C | 1.27 | 0.64 | * | . | F | 0.15 | 0.33 |
| Asn | 483 | . | . | . | . | . | T | C | 0.38 | 0.21 | * | . | . | 0.30 | 0.55 |
| Ala | 484 | . | . | . | . | . | T | C | 0.43 | −0.01 | . | . | . | 0.90 | 0.24 |
| Cys | 485 | . | A | . | . | T | . | . | −0.09 | 0.50 | . | . | . | −0.20 | 0.25 |
| Glu | 486 | . | A | B | . | . | . | . | −0.43 | 0.76 | . | . | . | −0.60 | 0.13 |
| Ile | 487 | . | A | . | . | T | . | . | −0.39 | 0.79 | . | . | . | −0.20 | 0.13 |
| Trp | 488 | . | A | . | . | T | . | . | −0.39 | 0.67 | . | . | . | −0.20 | 0.32 |
| Leu | 489 | . | A | . | . | . | . | C | −0.04 | 0.10 | . | . | . | −0.10 | 0.32 |
| Gly | 490 | . | . | . | . | T | T | . | 0.41 | 0.86 | . | * | F | 0.56 | 0.72 |
| Ser | 491 | . | . | . | . | . | T | C | 0.02 | 0.60 | . | . | F | 0.72 | 1.05 |
| Glu | 492 | . | . | . | . | . | T | C | 0.52 | 0.11 | . | . | F | 1.23 | 1.63 |
| Tyr | 493 | . | . | . | . | . | T | C | 0.42 | −0.14 | . | . | . | 1.89 | 2.11 |
| Pro | 494 | . | . | . | . | T | . | . | 0.84 | −0.14 | . | . | . | 2.10 | 2.01 |

TABLE III

| Res | | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | 0.10 | −0.19 | . | . | . | 0.30 | 0.92 |
| Glu | 2 | A | A | . | . | . | . | . | −0.32 | −0.11 | * | * | . | 0.30 | 0.72 |
| Thr | 3 | A | A | . | . | . | . | . | 0.18 | 0.14 | * | . | . | −0.30 | 0.47 |
| Gly | 4 | A | A | . | . | . | . | . | 0.68 | −0.29 | * | . | . | 0.30 | 0.93 |
| Ala | 5 | A | A | . | . | . | . | . | 0.86 | −0.90 | * | . | F | 0.90 | 1.05 |
| Leu | 6 | A | A | . | . | . | . | . | 1.46 | −0.47 | . | . | F | 0.60 | 1.12 |
| Arg | 7 | . | A | B | . | . | . | . | 0.64 | −0.56 | . | . | F | 0.90 | 1.96 |
| Arg | 8 | . | . | B | . | . | . | . | 0.14 | −0.30 | * | . | F | 0.80 | 1.60 |
| Pro | 9 | . | A | B | . | . | . | . | 0.28 | −0.11 | . | . | F | 0.60 | 1.60 |
| Gln | 10 | . | A | B | . | . | . | . | 0.06 | −0.37 | . | . | F | 0.60 | 1.26 |
| Leu | 11 | . | A | B | . | . | . | . | 0.06 | 0.31 | * | . | . | −0.30 | 0.53 |
| Leu | 12 | . | A | B | . | . | . | . | −0.87 | 1.00 | . | . | . | −0.60 | 0.28 |
| Pro | 13 | . | A | B | . | . | . | . | −1.79 | 1.26 | . | * | . | −0.60 | 0.14 |
| Leu | 14 | . | A | B | . | . | . | . | −2.39 | 1.54 | . | . | . | −0.60 | 0.14 |
| Leu | 15 | . | A | B | . | . | . | . | −3.06 | 1.54 | . | . | . | −0.60 | 0.14 |
| Leu | 16 | . | A | B | . | . | . | . | −2.59 | 1.43 | . | . | . | −0.60 | 0.05 |
| Leu | 17 | . | A | B | . | . | . | . | −2.12 | 1.43 | . | . | . | −0.60 | 0.06 |
| Leu | 18 | . | A | B | . | . | . | . | −2.58 | 1.17 | . | . | . | −0.60 | 0.07 |
| Cys | 19 | . | . | B | . | . | T | . | −1.98 | 1.06 | * | * | . | −0.20 | 0.04 |
| Gly | 20 | . | . | . | . | T | T | . | −1.06 | 0.80 | * | * | . | 0.20 | 0.08 |
| Gly | 21 | . | . | . | . | T | T | . | −0.83 | 0.11 | . | * | F | 0.65 | 0.20 |
| Cys | 22 | . | . | B | . | . | T | . | −0.37 | −0.07 | . | * | F | 0.85 | 0.37 |
| Pro | 23 | . | . | B | . | . | . | . | 0.10 | −0.21 | * | * | F | 0.96 | 0.37 |
| Arg | 24 | . | . | . | . | T | T | . | 0.10 | −0.21 | . | * | F | 1.87 | 0.37 |
| Ala | 25 | . | . | . | . | T | T | . | 0.44 | −0.07 | . | * | F | 2.18 | 0.37 |
| Gly | 26 | . | . | . | . | T | T | . | 0.79 | −0.24 | . | * | F | 2.49 | 0.38 |
| Gly | 27 | . | . | . | . | T | T | . | 1.14 | −0.67 | . | * | F | 3.10 | 0.34 |
| Cys | 28 | . | . | . | . | T | . | . | 1.01 | −0.19 | . | * | F | 2.29 | 0.48 |
| Asn | 29 | . | . | . | . | . | T | C | 0.30 | −0.26 | . | * | F | 1.98 | 0.48 |
| Glu | 30 | . | . | B | . | . | T | . | 0.08 | −0.07 | . | . | F | 1.47 | 0.48 |
| Thr | 31 | . | . | B | . | . | T | . | 0.42 | 0.19 | * | . | F | 0.56 | 0.74 |
| Gly | 32 | . | . | B | . | . | T | . | 0.88 | −0.39 | * | . | F | 0.85 | 0.80 |
| Met | 33 | A | A | . | . | . | . | . | 0.73 | −0.79 | * | . | . | 0.60 | 0.91 |
| Leu | 34 | A | A | . | . | . | . | . | 0.52 | −0.10 | * | * | . | 0.30 | 0.52 |
| Glu | 35 | A | A | . | . | . | . | . | −0.29 | −0.16 | . | * | . | 0.30 | 0.81 |
| Arg | 36 | A | A | . | . | . | . | . | −0.64 | 0.10 | * | * | . | −0.30 | 0.67 |
| Leu | 37 | A | A | . | . | . | . | . | −0.64 | 0.06 | * | * | . | −0.30 | 0.44 |
| Pro | 38 | A | A | . | . | . | . | . | 0.00 | −0.20 | * | * | . | 0.30 | 0.25 |
| Leu | 39 | A | A | . | . | . | . | . | 0.22 | −0.20 | * | * | . | 0.30 | 0.26 |

TABLE III-continued

| Res | | I | II | III | IV | V | VI | VII | VIII | IX | X | XI | XII | XIII | XIV |
|---|---|---|---|---|---|---|---|---|---|---|---|---|---|---|---|
| Cys | 40 | A | A | . | . | . | . | . | −0.48 | 0.30 | * | * | . | −0.30 | 0.31 |
| Gly | 41 | A | A | . | . | . | . | . | −1.18 | 0.40 | * | * | . | −0.30 | 0.18 |
| Lys | 42 | A | A | . | . | . | . | . | −0.37 | 0.47 | * | * | . | −0.60 | 0.21 |
| Ala | 43 | A | A | . | . | . | . | . | −0.76 | −0.21 | * | * | . | 0.30 | 0.67 |
| Phe | 44 | A | A | . | . | . | . | . | −0.54 | −0.17 | * | * | . | 0.30 | 0.67 |
| Ala | 45 | A | A | . | . | . | . | . | −0.22 | 0.01 | * | * | . | −0.30 | 0.33 |
| Asp | 46 | A | A | . | . | . | . | . | 0.17 | 0.44 | * | * | . | −0.60 | 0.32 |
| Met | 47 | A | A | . | . | . | . | . | −0.73 | −0.06 | * | * | . | 0.30 | 0.75 |
| Met | 48 | A | A | . | . | . | . | . | −0.14 | −0.20 | * | * | . | 0.30 | 0.55 |
| Gly | 49 | A | A | . | . | . | . | . | −0.30 | −0.70 | * | * | . | 0.60 | 0.55 |
| Lys | 50 | A | . | . | B | . | . | . | 0.00 | −0.06 | . | * | . | 0.30 | 0.41 |
| Val | 51 | A | . | . | B | . | . | . | 0.04 | 0.24 | . | * | . | −0.30 | 0.44 |
| Asp | 52 | A | . | . | B | . | . | . | 0.36 | −0.37 | . | * | . | 0.30 | 0.89 |
| Val | 53 | A | . | . | B | . | . | . | 0.29 | 0.11 | . | * | . | −0.30 | 0.47 |
| Trp | 54 | A | . | . | B | . | . | . | 0.63 | 0.69 | . | * | . | −0.60 | 0.34 |
| Lys | 55 | A | . | . | B | . | . | . | −0.22 | 0.44 | . | * | . | −0.60 | 0.32 |
| Trp | 56 | A | . | . | B | . | . | . | 0.33 | 1.13 | . | . | . | −0.60 | 0.36 |
| Cys | 57 | A | . | . | B | . | . | . | 0.33 | 0.87 | . | . | . | −0.60 | 0.46 |
| Asn | 58 | . | . | . | B | . | . | C | 0.49 | −0.04 | * | . | . | 0.50 | 0.40 |
| Leu | 59 | . | . | . | B | . | . | C | −0.11 | 0.74 | * | . | . | −0.40 | 0.33 |
| Ser | 60 | . | . | . | B | . | . | C | −1.01 | 0.51 | * | . | . | −0.40 | 0.43 |
| Glu | 61 | . | . | B | B | . | . | . | −0.97 | 0.59 | * | . | . | −0.60 | 0.20 |
| Phe | 62 | . | . | B | B | . | . | . | −0.54 | 0.94 | . | . | . | −0.60 | 0.38 |
| Ile | 63 | . | . | B | B | . | . | . | −0.54 | 1.01 | * | . | . | −0.60 | 0.44 |
| Val | 64 | . | . | B | B | . | . | . | −0.03 | 0.63 | * | . | . | −0.60 | 0.44 |
| Tyr | 65 | . | . | B | B | . | . | . | −0.43 | 1.01 | . | . | . | −0.60 | 0.68 |
| Tyr | 66 | . | . | B | B | . | . | . | −0.74 | 1.01 | * | . | . | −0.60 | 0.84 |
| Glu | 67 | . | . | . | B | T | . | . | −0.04 | 0.81 | * | . | . | −0.05 | 1.63 |
| Ser | 68 | . | . | . | B | T | . | . | 0.18 | 0.57 | . | . | . | −0.05 | 1.68 |
| Phe | 69 | . | . | . | . | T | T | . | 0.72 | 0.39 | * | . | . | 0.50 | 0.57 |
| Thr | 70 | . | . | . | . | T | T | . | 0.97 | 0.11 | * | . | F | 0.65 | 0.48 |
| Asn | 71 | . | . | . | . | . | T | C | 0.61 | 0.11 | . | . | F | 0.45 | 0.62 |
| Cys | 72 | A | . | . | . | . | T | . | 0.61 | 0.34 | . | * | F | 0.25 | 0.71 |
| Thr | 73 | A | A | . | . | . | . | . | 0.32 | −0.44 | . | * | F | 0.45 | 0.85 |
| Glu | 74 | A | A | . | . | . | . | . | 1.02 | −0.43 | * | * | . | 0.30 | 0.53 |
| Met | 75 | A | A | . | . | . | . | . | 0.48 | −0.43 | . | * | . | 0.45 | 1.60 |
| Glu | 76 | A | A | . | . | . | . | . | −0.38 | −0.36 | . | * | . | 0.30 | 0.82 |
| Ala | 77 | A | A | . | . | . | . | . | −0.06 | −0.20 | . | * | . | 0.30 | 0.35 |
| Asn | 78 | A | A | . | . | . | . | . | −0.41 | 0.23 | . | * | . | −0.30 | 0.35 |
| Val | 79 | . | A | B | . | . | . | . | −0.66 | 0.19 | . | * | . | −0.30 | 0.11 |
| Val | 80 | . | A | B | . | . | . | . | −0.34 | 0.94 | . | * | . | −0.60 | 0.17 |
| Gly | 81 | . | A | B | . | . | . | . | −0.56 | 1.36 | . | * | . | −0.60 | 0.11 |
| Cys | 82 | . | . | . | . | T | . | . | 0.03 | 1.39 | * | . | . | 0.00 | 0.23 |
| Tyr | 83 | . | . | . | . | T | . | . | −0.18 | 1.14 | * | . | . | 0.00 | 0.50 |
| Trp | 84 | . | . | B | . | . | T | . | −0.13 | 0.93 | . | . | . | −0.20 | 0.78 |
| Pro | 85 | . | . | . | . | . | T | C | 0.13 | 1.19 | * | . | F | 0.30 | 1.20 |
| Asn | 86 | . | . | . | . | . | T | C | 0.48 | 1.11 | * | . | F | 0.15 | 0.77 |
| Pro | 87 | . | . | . | . | . | T | C | 0.80 | 0.76 | * | . | F | 0.30 | 1.27 |
| Leu | 88 | . | . | . | . | . | . | C | 0.34 | 0.27 | * | . | F | 0.25 | 0.81 |
| Ala | 89 | . | . | . | . | . | . | C | −0.26 | 0.63 | * | . | F | −0.05 | 0.44 |
| Gln | 90 | . | . | B | B | . | . | . | −0.36 | 0.91 | * | . | . | −0.60 | 0.20 |
| Gly | 91 | . | . | B | B | . | . | . | −0.70 | 0.97 | * | . | . | −0.60 | 0.35 |
| Phe | 92 | . | . | B | B | . | . | . | −1.38 | 0.71 | * | . | . | −0.60 | 0.34 |
| Ile | 93 | . | . | B | B | . | . | . | −0.60 | 0.90 | * | . | . | −0.60 | 0.14 |
| Thr | 94 | . | . | B | B | . | . | . | 0.10 | 1.00 | * | . | . | −0.60 | 0.19 |
| Gly | 95 | . | . | B | B | . | . | . | 0.10 | 0.57 | * | . | . | −0.60 | 0.43 |
| Ile | 96 | . | . | B | B | . | . | . | −0.26 | 0.19 | * | . | . | −0.15 | 1.06 |
| His | 97 | . | . | B | B | . | . | . | −0.26 | 0.29 | * | . | . | −0.30 | 0.64 |
| Arg | 98 | . | . | . | B | T | . | . | 0.33 | 0.59 | * | . | . | −0.20 | 0.56 |
| Gln | 99 | . | . | . | B | T | . | . | 0.64 | 0.54 | * | . | . | −0.05 | 1.06 |
| Phe | 100 | . | . | . | B | T | . | . | 0.32 | 0.26 | * | . | . | 0.25 | 1.26 |
| Phe | 101 | . | . | . | . | T | T | . | 0.90 | 0.33 | * | . | . | 0.50 | 0.34 |
| Ser | 102 | . | . | . | . | T | T | . | 0.08 | 0.81 | . | * | . | 0.20 | 0.29 |
| Asn | 103 | . | . | . | . | T | T | . | −0.03 | 1.06 | . | . | . | 0.20 | 0.25 |
| Cys | 104 | . | . | . | . | T | T | . | 0.08 | 0.27 | . | * | . | 0.50 | 0.47 |
| Thr | 105 | . | . | . | . | T | . | . | −0.08 | −0.51 | . | . | . | 1.20 | 0.69 |
| Val | 106 | . | A | . | . | T | . | . | 0.59 | −0.26 | . | * | . | 0.70 | 0.32 |
| Asp | 107 | . | A | B | . | . | . | . | 0.08 | −0.16 | . | * | . | 0.30 | 0.81 |
| Arg | 108 | . | A | B | . | . | . | . | 0.08 | −0.04 | . | * | . | 0.30 | 0.46 |
| Val | 109 | . | A | B | . | . | . | . | 0.74 | −0.53 | . | * | . | 0.75 | 1.08 |
| His | 110 | . | A | B | . | . | . | . | 0.84 | −1.17 | . | * | . | 0.75 | 1.08 |
| Leu | 111 | . | A | . | . | . | . | C | 1.49 | −0.74 | . | * | . | 0.80 | 0.85 |
| Glu | 112 | . | A | . | . | . | . | C | 1.49 | −0.31 | . | * | F | 0.80 | 1.78 |
| Asp | 113 | . | A | . | . | . | . | C | 1.38 | −0.96 | * | * | F | 1.10 | 2.18 |
| Pro | 114 | . | . | . | . | . | T | C | 1.38 | −1.46 | * | * | F | 1.50 | 4.58 |
| Pro | 115 | . | . | . | . | T | T | . | 0.60 | −1.50 | * | . | F | 1.70 | 1.96 |
| Asp | 116 | A | . | . | . | . | T | . | 0.52 | −0.81 | * | . | F | 1.15 | 0.97 |

TABLE III-continued

| Res | | I | II | III | IV | V | VI | VII | VIII | IX | X | XI | XII | XIII | XIV |
|---|---|---|---|---|---|---|---|---|---|---|---|---|---|---|---|
| Glu | 117 | A | . | . | . | . | T | . | 0.31 | −0.13 | * | * | . | 0.70 | 0.44 |
| Val | 118 | A | . | . | B | . | . | . | −0.50 | −0.13 | * | . | . | 0.30 | 0.44 |
| Leu | 119 | . | . | B | B | . | . | . | −1.18 | 0.13 | . | . | . | −0.30 | 0.22 |
| Ile | 120 | . | . | B | B | . | . | . | −1.82 | 0.81 | . | . | . | −0.60 | 0.09 |
| Pro | 121 | . | . | B | B | . | . | . | −2.71 | 1.46 | . | . | . | −0.60 | 0.09 |
| Leu | 122 | . | . | B | B | . | . | . | −2.92 | 1.50 | . | * | . | −0.60 | 0.07 |
| Ile | 123 | . | . | B | B | . | . | . | −2.92 | 1.24 | . | . | . | −0.60 | 0.16 |
| Val | 124 | . | . | B | B | . | . | . | −2.97 | 1.20 | . | . | . | −0.60 | 0.08 |
| Ile | 125 | . | . | B | B | . | . | . | −2.89 | 1.41 | . | . | . | −0.60 | 0.07 |
| Pro | 126 | . | . | B | B | . | . | . | −2.99 | 1.41 | . | * | . | −0.60 | 0.08 |
| Val | 127 | . | . | B | B | . | . | . | −3.03 | 1.21 | . | . | . | −0.60 | 0.16 |
| Val | 128 | . | . | B | B | . | . | . | −2.73 | 1.21 | . | * | . | −0.60 | 0.17 |
| Leu | 129 | . | . | B | B | . | . | . | −2.48 | 1.03 | . | . | . | −0.60 | 0.11 |
| Thr | 130 | . | . | B | B | . | . | . | −2.18 | 1.21 | . | * | . | −0.60 | 0.15 |
| Val | 131 | . | . | B | B | . | . | . | −2.31 | 1.07 | . | . | . | −0.60 | 0.20 |
| Ala | 132 | A | . | . | B | . | . | . | −2.27 | 0.86 | . | . | . | −0.60 | 0.25 |
| Met | 133 | A | . | . | B | . | . | . | −2.27 | 0.86 | . | . | . | −0.60 | 0.14 |
| Ala | 134 | A | . | . | B | . | . | . | −2.31 | 1.01 | . | . | . | −0.60 | 0.14 |
| Gly | 135 | A | . | . | B | . | . | . | −2.29 | 1.01 | * | * | . | −0.60 | 0.10 |
| Leu | 136 | A | . | . | B | . | . | . | −1.32 | 1.43 | * | * | . | −0.60 | 0.11 |
| Val | 137 | A | . | . | B | . | . | . | −1.03 | 0.81 | . | * | . | −0.60 | 0.21 |
| Val | 138 | A | . | . | B | . | . | . | −0.39 | 0.70 | * | . | . | −0.26 | 0.29 |
| Trp | 139 | . | . | B | B | . | . | . | 0.31 | 0.27 | * | . | . | 0.38 | 0.70 |
| Arg | 140 | . | . | B | B | . | . | . | 0.34 | −0.41 | . | . | F | 1.62 | 1.84 |
| Ser | 141 | . | . | B | . | . | T | . | 1.16 | −0.57 | . | . | F | 2.66 | 3.58 |
| Lys | 142 | . | . | . | . | T | T | . | 1.70 | −1.21 | . | * | F | 3.40 | 5.68 |
| Arg | 143 | . | . | . | . | T | T | . | 1.74 | −1.64 | * | . | F | 3.06 | 4.19 |
| Thr | 144 | . | . | . | . | T | T | . | 1.22 | −0.96 | . | * | F | 2.72 | 2.58 |
| Asp | 145 | . | A | . | . | T | . | . | 0.72 | −0.66 | . | . | F | 1.98 | 1.06 |
| Thr | 146 | . | A | B | . | . | . | . | 0.63 | −0.23 | * | . | F | 0.79 | 0.69 |
| Leu | 147 | . | A | B | . | . | . | . | 0.20 | 0.20 | * | . | . | −0.30 | 0.61 |
| Leu | 148 | . | A | B | . | . | . | . | −0.30 | 0.14 | . | * | . | −0.30 | 0.47 |

TABLE IV

| Res | | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | −0.76 | 0.27 | . | * | . | −0.30 | 0.49 |
| Arg | 2 | A | A | . | . | . | . | . | −1.07 | 0.34 | * | * | . | −0.30 | 0.39 |
| Leu | 3 | A | A | . | . | . | . | . | −1.49 | 0.70 | * | * | . | −0.60 | 0.26 |
| Leu | 4 | A | A | . | . | . | . | . | −1.40 | 0.96 | . | * | . | −0.60 | 0.22 |
| Ala | 5 | A | A | . | . | . | . | . | −1.82 | 0.73 | . | * | . | −0.60 | 0.15 |
| Phe | 6 | A | A | . | . | . | . | . | −2.03 | 1.41 | * | * | . | −0.60 | 0.15 |
| Leu | 7 | A | A | . | . | . | . | . | −2.73 | 1.41 | . | * | . | −0.60 | 0.15 |
| Ser | 8 | A | A | . | . | . | . | . | −2.73 | 1.23 | . | . | . | −0.60 | 0.15 |
| Leu | 9 | A | A | . | . | . | . | . | −2.78 | 1.41 | . | . | . | −0.60 | 0.14 |
| Leu | 10 | A | A | . | . | . | . | . | −3.00 | 1.27 | * | . | . | −0.60 | 0.13 |
| Ala | 11 | A | A | . | . | . | . | . | −2.30 | 1.27 | * | . | . | −0.60 | 0.08 |
| Leu | 12 | A | A | . | . | . | . | . | −1.49 | 1.29 | . | . | . | −0.60 | 0.17 |
| Val | 13 | A | A | . | . | . | . | . | −1.50 | 0.60 | . | . | . | −0.60 | 0.35 |
| Leu | 14 | A | A | . | . | . | . | . | −1.03 | 0.40 | . | . | . | −0.02 | 0.50 |
| Gln | 15 | A | A | B | . | . | . | . | −0.53 | 0.33 | . | . | F | 0.41 | 0.60 |
| Glu | 16 | A | . | . | . | . | T | . | −0.53 | 0.13 | . | . | F | 1.24 | 1.17 |
| Thr | 17 | A | . | . | . | . | T | . | −0.02 | −0.01 | . | * | F | 2.12 | 1.43 |
| Gly | 18 | . | . | . | . | T | T | . | 0.02 | −0.31 | . | . | F | 2.80 | 1.11 |
| Thr | 19 | A | . | . | . | . | T | . | 0.62 | −0.03 | * | * | F | 1.97 | 0.53 |
| Ala | 20 | A | . | . | . | . | . | . | 0.73 | 0.40 | . | . | F | 0.89 | 0.57 |
| Ser | 21 | . | . | . | . | . | . | C | 0.78 | −0.09 | . | . | F | 1.56 | 1.12 |
| Leu | 22 | . | A | . | . | . | . | C | 1.09 | −0.51 | * | . | F | 1.38 | 1.55 |
| Pro | 23 | A | A | . | . | . | . | . | 1.54 | −1.00 | * | . | F | 0.90 | 2.66 |
| Arg | 24 | A | A | . | . | . | . | . | 1.90 | −1.50 | * | * | F | 0.90 | 3.88 |
| Lys | 25 | A | A | . | . | . | . | . | 2.60 | −1.89 | . | . | F | 0.90 | 9.42 |
| Glu | 26 | A | A | . | . | . | . | . | 3.01 | −2.57 | . | . | F | 0.90 | 11.93 |
| Arg | 27 | A | A | . | . | . | . | . | 3.82 | −3.00 | . | . | F | 0.90 | 11.93 |
| Lys | 28 | A | A | . | . | . | . | . | 4.03 | −3.00 | . | . | F | 0.90 | 10.33 |
| Arg | 29 | A | A | . | . | . | . | . | 3.92 | −3.00 | . | . | F | 0.90 | 10.33 |
| Arg | 30 | A | A | . | . | . | . | . | 3.28 | −2.60 | . | * | F | 0.90 | 9.13 |
| Glu | 31 | A | A | . | . | . | . | . | 3.07 | −1.99 | * | . | F | 0.90 | 4.52 |
| Glu | 32 | A | A | . | . | . | . | . | 3.07 | −1.56 | . | . | F | 1.24 | 3.57 |
| Gln | 33 | A | A | . | . | . | . | . | 3.02 | −1.56 | * | . | F | 1.58 | 3.57 |
| Met | 34 | . | A | . | . | . | . | C | 2.57 | −1.56 | * | . | F | 2.12 | 3.57 |
| Pro | 35 | A | . | . | . | . | T | . | 2.46 | −1.13 | * | . | F | 2.66 | 2.04 |
| Arg | 36 | . | . | . | . | T | T | . | 2.16 | −1.13 | * | . | F | 3.40 | 1.97 |
| Glu | 37 | A | . | . | . | . | T | . | 1.46 | −1.14 | * | . | F | 2.66 | 2.66 |

TABLE IV-continued

| Res | | I | II | III | IV | V | VI | VII | VIII | IX | X | XI | XII | XIII | XIV |
|---|---|---|---|---|---|---|---|---|---|---|---|---|---|---|---|
| Gly | 38 | . | . | . | . | T | T | . | 1.46 | −0.97 | * | * | F | 2.72 | 1.49 |
| Asp | 39 | A | . | . | . | . | . | . | 1.20 | −1.40 | * | . | F | 1.78 | 1.32 |
| Ser | 40 | A | . | . | . | . | . | . | 0.60 | −0.76 | * | . | F | 1.29 | 0.57 |
| Phe | 41 | . | . | B | . | . | . | . | 0.28 | −0.07 | . | . | . | 0.50 | 0.47 |
| Glu | 42 | . | . | B | . | . | . | . | −0.53 | −0.07 | . | . | . | 0.50 | 0.44 |
| Val | 43 | . | . | B | . | . | . | . | −0.08 | 0.61 | . | . | . | −0.40 | 0.27 |
| Leu | 44 | . | . | B | . | . | . | . | −0.08 | 0.23 | . | * | . | −0.10 | 0.61 |
| Pro | 45 | A | . | . | . | . | . | . | 0.22 | −0.16 | . | * | . | 0.50 | 0.56 |
| Leu | 46 | A | . | . | . | . | T | . | 0.07 | −0.16 | . | * | . | 0.85 | 1.27 |
| Arg | 47 | A | . | . | . | . | T | . | −0.74 | −0.16 | . | * | F | 1.00 | 1.14 |
| Asn | 48 | . | . | B | . | T | T | . | 0.11 | −0.16 | . | * | F | 1.25 | 0.61 |
| Asp | 49 | . | . | B | . | . | T | . | 0.71 | −0.19 | . | * | F | 1.00 | 1.19 |
| Val | 50 | . | . | B | . | . | . | . | 0.92 | −0.44 | . | * | F | 0.65 | 0.94 |
| Leu | 51 | . | . | B | . | . | . | . | 1.73 | −0.44 | . | * | F | 0.95 | 0.97 |
| Asn | 52 | . | . | B | . | . | T | . | 1.38 | −0.44 | . | . | F | 1.45 | 0.94 |
| Pro | 53 | . | . | . | . | . | T | C | 1.03 | 0.31 | . | . | F | 1.50 | 1.98 |
| Asp | 54 | . | . | . | . | T | T | . | 1.03 | 0.10 | . | * | F | 2.00 | 2.37 |
| Asn | 55 | . | . | . | . | . | T | C | 1.03 | −0.59 | . | . | F | 3.00 | 2.56 |
| Tyr | 56 | . | . | B | B | . | . | . | 0.96 | −0.34 | . | * | F | 1.80 | 1.23 |
| Gly | 57 | . | . | B | B | . | . | . | 0.96 | −0.09 | . | . | . | 1.20 | 0.52 |
| Glu | 58 | . | . | B | B | . | . | . | 0.36 | −0.09 | * | . | . | 0.90 | 0.53 |
| Val | 59 | . | . | B | B | . | . | . | 0.06 | 0.20 | * | . | . | 0.00 | 0.28 |
| Ile | 60 | . | . | B | B | . | . | . | 0.06 | −0.17 | . | . | . | 0.30 | 0.38 |
| Asp | 61 | . | . | B | B | . | . | . | 0.06 | −0.20 | . | . | . | 0.30 | 0.35 |
| Leu | 62 | . | . | B | . | . | T | . | 0.40 | 0.56 | . | . | . | −0.20 | 0.75 |
| Ser | 63 | . | . | . | . | . | T | C | 0.40 | −0.09 | . | . | . | 1.05 | 1.85 |
| Asn | 64 | . | . | . | . | . | T | C | 0.44 | −0.77 | . | . | F | 1.50 | 1.91 |
| Tyr | 65 | A | . | . | . | . | T | . | 1.02 | −0.09 | . | * | F | 1.34 | 1.91 |
| Glu | 66 | A | . | . | . | . | . | . | 1.02 | −0.29 | . | . | F | 1.48 | 2.06 |
| Glu | 67 | A | . | . | . | . | . | . | 1.59 | −0.67 | * | . | F | 2.12 | 2.14 |
| Leu | 68 | . | . | B | . | . | . | . | 1.54 | −0.31 | * | . | F | 2.16 | 2.14 |
| Thr | 69 | . | . | . | . | T | T | . | 1.54 | −0.64 | * | . | F | 3.40 | 1.22 |
| Asp | 70 | . | . | . | . | T | T | . | 1.79 | −0.64 | * | . | F | 3.06 | 1.18 |
| Tyr | 71 | . | . | . | . | T | T | . | 0.98 | −0.24 | * | . | F | 2.42 | 2.48 |
| Gly | 72 | . | . | . | . | T | T | . | 0.77 | −0.24 | * | . | F | 2.08 | 1.42 |
| Asp | 73 | A | . | . | . | . | . | . | 1.58 | −0.30 | * | . | F | 1.23 | 1.31 |
| Gln | 74 | A | . | . | . | . | . | . | 1.03 | −0.30 | * | * | F | 0.98 | 1.45 |
| Leu | 75 | . | . | B | . | . | . | . | 1.08 | −0.41 | . | * | F | 1.07 | 1.09 |
| Pro | 76 | . | . | B | . | . | . | . | 0.47 | −0.84 | . | * | F | 1.46 | 1.30 |
| Glu | 77 | . | . | B | B | . | . | . | 0.50 | −0.20 | . | * | F | 0.90 | 0.56 |
| Val | 78 | . | . | B | B | . | . | . | 0.20 | −0.11 | . | * | F | 0.81 | 0.98 |
| Lys | 79 | . | . | B | B | . | . | . | −0.61 | −0.41 | . | * | F | 0.72 | 0.85 |
| Val | 80 | . | . | B | B | . | . | . | −0.39 | −0.16 | . | * | F | 0.63 | 0.40 |
| Thr | 81 | . | . | B | B | . | . | . | −0.39 | 0.34 | . | * | F | −0.06 | 0.55 |
| Ser | 82 | . | . | B | . | . | . | . | −0.98 | 0.13 | . | * | F | 0.05 | 0.42 |
| Leu | 83 | . | . | B | . | . | . | . | −0.43 | 0.63 | . | * | . | −0.40 | 0.58 |
| Ala | 84 | . | . | B | . | . | . | . | −0.78 | 0.47 | . | * | . | −0.40 | 0.58 |
| Pro | 85 | A | . | . | . | . | . | . | −0.81 | 0.37 | . | . | . | −0.10 | 0.58 |
| Ala | 86 | . | . | B | B | . | . | . | −0.80 | 0.67 | . | . | F | −0.45 | 0.49 |
| Thr | 87 | . | . | B | B | . | . | . | −0.71 | 0.37 | . | . | F | −0.15 | 0.65 |
| Ser | 88 | . | . | B | B | . | . | . | −0.49 | 0.30 | . | . | F | 0.13 | 0.65 |
| Ile | 89 | . | . | B | B | . | . | . | 0.14 | 0.37 | . | . | F | 0.41 | 0.65 |
| Ser | 90 | . | . | B | . | . | T | . | 0.06 | −0.13 | . | . | F | 1.69 | 0.90 |
| Pro | 91 | . | . | . | . | . | T | C | 0.33 | −0.23 | . | . | F | 2.17 | 0.90 |
| Ala | 92 | . | . | . | . | T | T | . | 0.33 | −0.13 | . | . | F | 2.80 | 1.86 |
| Lys | 93 | . | . | B | . | . | T | . | 0.04 | −0.33 | . | . | F | 2.12 | 2.00 |
| Ser | 94 | . | . | B | . | . | . | . | 0.72 | −0.21 | . | . | F | 1.64 | 1.31 |
| Thr | 95 | . | . | B | . | . | . | . | 0.68 | −0.21 | . | . | F | 1.36 | 2.00 |
| Thr | 96 | . | . | B | . | . | . | . | 0.58 | −0.29 | . | . | F | 0.93 | 0.99 |
| Ala | 97 | . | . | B | . | . | . | . | 0.96 | 0.20 | . | . | F | 0.20 | 1.07 |
| Pro | 98 | . | . | B | . | . | . | . | 0.61 | 0.24 | . | . | F | 0.48 | 1.14 |
| Gly | 99 | . | . | . | . | T | . | . | 0.61 | 0.14 | . | . | F | 1.16 | 1.06 |
| Thr | 100 | . | . | . | . | . | T | C | 0.92 | 0.04 | . | . | F | 1.44 | 1.41 |
| Pro | 101 | . | . | . | . | . | T | C | 1.02 | −0.06 | . | . | F | 2.32 | 1.46 |
| Ser | 102 | . | . | . | . | T | T | . | 1.30 | −0.06 | . | . | F | 2.80 | 2.28 |
| Ser | 103 | . | . | . | . | . | T | C | 0.91 | 0.00 | . | . | F | 2.32 | 2.28 |
| Asn | 104 | . | . | . | . | . | T | C | 0.94 | 0.13 | . | . | F | 1.44 | 1.46 |
| Pro | 105 | . | . | . | . | . | T | C | 1.37 | 0.19 | . | . | F | 1.36 | 1.57 |
| Thr | 106 | . | . | . | . | T | T | . | 1.37 | −0.20 | . | . | F | 2.08 | 2.30 |
| Met | 107 | . | . | B | . | . | T | . | 1.36 | −0.16 | . | . | F | 1.60 | 2.21 |
| Thr | 108 | . | . | B | . | . | . | . | 1.34 | −0.07 | . | . | F | 1.60 | 2.07 |
| Arg | 109 | . | . | B | . | . | T | . | 0.76 | −0.01 | . | . | F | 2.00 | 2.07 |
| Pro | 110 | . | . | B | . | . | T | . | 0.62 | 0.00 | * | . | F | 1.80 | 2.11 |
| Thr | 111 | . | . | B | . | . | T | . | 0.12 | −0.19 | . | . | F | 1.60 | 1.45 |
| Thr | 112 | . | . | B | . | . | T | . | −0.09 | 0.01 | . | . | F | 0.65 | 0.61 |
| Ala | 113 | . | A | B | . | . | . | . | −0.59 | 0.70 | . | . | F | −0.25 | 0.32 |
| Gly | 114 | . | A | B | . | . | . | . | −1.00 | 0.96 | . | . | . | −0.60 | 0.19 |

TABLE IV-continued

| Res | | I | II | III | IV | V | VI | VII | VIII | IX | X | XI | XII | XIII | XIV |
|---|---|---|---|---|---|---|---|---|---|---|---|---|---|---|---|
| Leu | 115 | . | A | B | . | . | . | . | −1.09 | 0.86 | . | . | . | −0.60 | 0.17 |
| Leu | 116 | . | A | B | . | . | . | . | −0.78 | 0.76 | . | . | . | −0.60 | 0.23 |
| Leu | 117 | . | A | B | . | . | . | . | −0.68 | 0.66 | . | * | F | −0.45 | 0.40 |
| Ser | 118 | . | A | B | . | . | . | . | −0.09 | 0.66 | . | . | F | −0.29 | 0.75 |
| Ser | 119 | . | . | B | . | . | . | . | 0.22 | 0.37 | . | . | F | 0.52 | 1.46 |
| Gln | 120 | . | . | B | . | . | T | . | 0.69 | 0.19 | . | . | F | 0.88 | 2.41 |
| Pro | 121 | . | . | . | . | T | T | . | 0.69 | −0.07 | . | . | F | 2.04 | 1.78 |
| Asn | 122 | . | . | . | . | T | T | . | 1.29 | 0.23 | . | * | F | 1.60 | 1.10 |
| His | 123 | . | . | . | . | T | T | . | 1.28 | 0.27 | . | . | F | 1.29 | 0.98 |
| Gly | 124 | . | . | . | . | T | . | . | 0.91 | 0.36 | . | . | . | 0.78 | 0.91 |
| Leu | 125 | . | . | . | . | . | T | C | 0.10 | 0.50 | . | . | . | 0.32 | 0.30 |
| Pro | 126 | . | . | . | . | T | T | . | −0.54 | 0.79 | . | . | . | 0.36 | 0.18 |
| Thr | 127 | . | . | . | . | T | T | . | −1.21 | 0.93 | . | . | . | 0.20 | 0.14 |
| Cys | 128 | . | . | B | . | . | T | . | −2.03 | 1.07 | . | . | . | −0.20 | 0.09 |
| Leu | 129 | . | . | B | B | . | . | . | −2.36 | 1.03 | . | . | . | −0.60 | 0.04 |
| Val | 130 | . | . | B | B | . | . | . | −2.36 | 1.17 | . | . | . | −0.60 | 0.02 |
| Cys | 131 | . | . | B | B | . | . | . | −2.49 | 1.37 | . | . | . | −0.60 | 0.02 |
| Val | 132 | . | . | B | B | . | . | . | −2.48 | 1.23 | . | . | . | −0.60 | 0.03 |
| Cys | 133 | . | . | B | B | . | . | . | −2.11 | 0.93 | . | . | . | −0.60 | 0.05 |
| Leu | 134 | . | . | B | B | . | . | . | −2.16 | 0.67 | . | . | . | −0.60 | 0.13 |
| Gly | 135 | . | . | . | . | T | T | . | −1.54 | 0.74 | . | * | F | 0.35 | 0.13 |
| Ser | 136 | . | . | . | . | T | T | . | −1.54 | 0.86 | . | * | F | 0.35 | 0.39 |
| Ser | 137 | . | . | B | . | . | T | . | −0.69 | 0.86 | . | . | F | −0.05 | 0.25 |
| Val | 138 | . | . | B | . | . | T | . | −0.02 | 0.17 | . | . | . | 0.10 | 0.43 |
| Tyr | 139 | . | . | B | . | . | . | . | −0.10 | −0.26 | . | . | . | 0.50 | 0.53 |
| Cys | 140 | . | . | B | . | . | T | . | 0.24 | 0.04 | . | * | . | 0.10 | 0.28 |
| Asp | 141 | . | . | B | . | . | T | . | −0.27 | −0.34 | . | * | . | 0.70 | 0.63 |
| Asp | 142 | . | . | B | . | . | T | . | 0.03 | −0.30 | . | * | F | 0.85 | 0.33 |
| Ile | 143 | . | . | B | . | . | T | . | 0.89 | −1.06 | . | . | F | 1.30 | 1.07 |
| Asp | 144 | . | A | B | . | . | . | . | 0.24 | −1.63 | . | . | F | 0.90 | 1.07 |
| Leu | 145 | . | A | B | . | . | . | . | 0.70 | −0.94 | . | . | F | 0.75 | 0.45 |
| Glu | 146 | . | A | B | . | . | . | . | 0.49 | −0.51 | . | * | F | 0.75 | 0.99 |
| Asp | 147 | . | A | B | . | . | . | . | −0.32 | −0.77 | . | * | F | 0.99 | 0.92 |
| Ile | 148 | . | A | B | . | . | . | . | 0.36 | −0.09 | * | * | F | 0.93 | 0.92 |
| Pro | 149 | . | . | . | . | . | . | C | 0.47 | −0.34 | * | . | F | 1.57 | 0.82 |
| Pro | 150 | . | . | . | . | . | . | C | 1.39 | −0.34 | * | . | F | 1.81 | 0.96 |
| Leu | 151 | . | . | . | . | . | T | C | 1.08 | −0.34 | * | . | F | 2.40 | 2.68 |
| Pro | 152 | . | . | B | . | . | T | . | 0.49 | −0.54 | * | . | F | 2.26 | 2.50 |
| Arg | 153 | . | . | . | . | T | T | . | 1.13 | −0.47 | * | . | F | 2.12 | 1.63 |
| Arg | 154 | . | . | B | . | . | T | . | 0.53 | −0.14 | * | . | F | 1.48 | 3.11 |
| Thr | 155 | . | . | B | B | . | . | . | 0.50 | −0.14 | * | . | . | 0.69 | 1.66 |
| Ala | 156 | . | . | B | B | . | . | . | 0.72 | 0.19 | * | * | . | −0.15 | 1.33 |
| Tyr | 157 | . | . | B | B | . | . | . | 1.04 | 0.69 | * | * | . | −0.60 | 0.68 |
| Leu | 158 | . | . | B | B | . | . | . | 0.23 | 0.69 | * | * | . | −0.60 | 0.93 |
| Tyr | 159 | . | . | B | B | . | . | . | 0.12 | 0.99 | * | * | . | −0.60 | 0.80 |
| Ala | 160 | . | . | B | B | . | . | . | 0.54 | 0.89 | * | * | . | −0.60 | 0.82 |
| Arg | 161 | . | . | B | B | . | . | . | 0.24 | 0.13 | * | * | . | −0.15 | 1.94 |
| Phe | 162 | . | . | B | B | . | . | . | 0.19 | 0.13 | * | * | . | −0.30 | 0.87 |
| Asn | 163 | . | . | B | B | . | . | . | 1.11 | −0.24 | * | * | . | 0.45 | 1.15 |
| Arg | 164 | . | . | B | B | . | . | . | 0.47 | −0.74 | . | * | F | 1.08 | 1.15 |
| Ile | 165 | . | . | B | B | . | . | . | 1.17 | −0.06 | . | * | F | 0.81 | 0.93 |
| Ser | 166 | . | . | . | B | . | . | C | 0.47 | −0.84 | * | * | F | 1.64 | 1.13 |
| Arg | 167 | . | . | B | B | . | . | . | 1.17 | −0.74 | * | * | F | 1.47 | 0.59 |
| Ile | 168 | . | . | B | B | . | . | . | 1.17 | −0.74 | * | * | F | 1.80 | 1.45 |
| Arg | 169 | . | . | B | B | . | . | . | 0.36 | −1.43 | * | . | . | 1.47 | 1.80 |
| Ala | 170 | A | A | . | . | . | . | . | 1.29 | −1.03 | * | * | F | 1.29 | 0.80 |
| Glu | 171 | A | A | . | . | . | . | . | 1.24 | −1.03 | . | * | F | 1.26 | 2.27 |
| Asp | 172 | A | A | . | . | . | . | . | 0.32 | −1.29 | . | * | F | 1.08 | 1.15 |
| Phe | 173 | A | A | . | . | . | . | . | 0.90 | −0.60 | . | * | F | 0.75 | 0.94 |
| Lys | 174 | A | A | . | . | . | . | . | 0.83 | −0.61 | . | * | F | 0.75 | 0.78 |
| Gly | 175 | A | A | . | . | . | . | . | 0.61 | −0.61 | * | * | F | 0.75 | 0.94 |
| Leu | 176 | A | A | . | . | . | . | . | 0.66 | 0.07 | * | * | F | −0.15 | 0.89 |
| Thr | 177 | A | A | . | . | . | . | . | 0.77 | −0.71 | * | * | F | 0.75 | 0.89 |
| Lys | 178 | A | A | . | . | . | . | . | 0.58 | −0.71 | * | * | F | 0.90 | 1.76 |
| Leu | 179 | A | A | . | . | . | . | . | 0.53 | −0.46 | * | * | F | 0.60 | 1.50 |
| Lys | 180 | . | A | B | . | . | . | . | 0.07 | −1.14 | * | * | F | 0.90 | 1.73 |
| Arg | 181 | . | A | B | . | . | . | . | 0.58 | −0.94 | * | * | F | 0.75 | 0.71 |
| Ile | 182 | . | A | B | . | . | . | . | 0.89 | −0.56 | . | * | F | 0.90 | 1.16 |
| Asp | 183 | . | A | B | . | . | . | . | 0.84 | −0.84 | . | * | . | 0.60 | 0.93 |
| Leu | 184 | . | . | B | . | . | T | . | 0.84 | −0.44 | * | * | F | 0.85 | 0.77 |
| Ser | 185 | . | . | B | . | . | T | . | −0.09 | 0.24 | * | * | F | 0.25 | 0.90 |
| Asn | 186 | . | . | . | . | . | T | C | −0.50 | 0.24 | . | * | F | 0.45 | 0.38 |
| Asn | 187 | . | . | . | . | . | T | C | 0.09 | 0.63 | * | * | F | 0.15 | 0.62 |
| Leu | 188 | . | . | B | . | . | . | . | −0.80 | 0.33 | * | * | . | −0.10 | 0.62 |
| Ile | 189 | . | . | B | . | . | . | . | 0.01 | 0.63 | * | . | . | −0.40 | 0.27 |
| Ser | 190 | . | . | B | . | . | . | . | 0.31 | 0.23 | * | . | F | 0.05 | 0.28 |
| Ser | 191 | . | . | B | . | . | . | . | 0.31 | 0.23 | * | * | F | 0.05 | 0.54 |

TABLE IV-continued

| Res | | I | II | III | IV | V | VI | VII | VIII | IX | X | XI | XII | XIII | XIV |
|---|---|---|---|---|---|---|---|---|---|---|---|---|---|---|---|
| Ile | 192 | . | . | B | . | . | . | . | −0.28 | −0.46 | * | . | F | 0.80 | 1.29 |
| Asp | 193 | . | . | B | . | . | T | . | −0.17 | −0.64 | * | . | F | 1.15 | 0.98 |
| Asn | 194 | A | . | . | . | . | T | . | 0.83 | −0.24 | * | * | F | 0.85 | 0.63 |
| Asp | 195 | A | . | . | . | . | T | . | 0.32 | −0.63 | * | . | F | 1.30 | 1.76 |
| Ala | 196 | A | . | . | . | . | T | . | −0.19 | −0.63 | * | . | . | 1.00 | 0.87 |
| Phe | 197 | A | A | . | . | . | . | . | 0.67 | 0.06 | * | . | . | −0.30 | 0.45 |
| Arg | 198 | A | A | . | . | . | . | . | 0.08 | 0.16 | * | . | . | −0.30 | 0.36 |
| Leu | 199 | A | A | . | . | . | . | . | −0.73 | 0.66 | * | * | . | −0.60 | 0.36 |
| Leu | 200 | A | A | . | . | . | . | . | −0.73 | 0.84 | * | . | . | −0.60 | 0.35 |
| His | 201 | A | A | . | . | . | . | . | −0.14 | 0.46 | * | * | . | −0.60 | 0.31 |
| Ala | 202 | A | A | . | . | . | . | . | −0.26 | 0.46 | * | * | . | −0.60 | 0.62 |
| Leu | 203 | A | A | . | . | . | . | . | −1.26 | 0.46 | * | * | . | −0.60 | 0.62 |
| Gln | 204 | A | A | . | . | . | . | . | −1.26 | 0.46 | * | . | . | −0.60 | 0.32 |
| Asp | 205 | . | A | B | . | . | . | . | −0.66 | 0.64 | . | . | . | −0.60 | 0.26 |
| Leu | 206 | . | A | B | . | . | . | . | −0.62 | 0.57 | . | . | . | −0.60 | 0.49 |
| Ile | 207 | . | A | B | . | . | . | . | −0.03 | −0.11 | . | . | . | 0.30 | 0.49 |
| Leu | 208 | . | . | B | . | . | T | . | 0.78 | −0.11 | * | . | F | 0.85 | 0.47 |
| Pro | 209 | A | . | . | . | . | T | . | −0.03 | 0.29 | . | . | F | 0.25 | 0.99 |
| Glu | 210 | A | . | . | . | . | T | . | −0.03 | 0.29 | . | * | F | 0.40 | 1.16 |
| Asn | 211 | A | . | . | . | . | T | . | 0.19 | −0.40 | . | . | F | 1.00 | 2.44 |
| Gln | 212 | A | A | . | . | . | . | . | 0.27 | −0.59 | . | * | F | 0.90 | 1.60 |
| Leu | 213 | A | A | . | . | . | . | . | 0.87 | −0.33 | . | . | . | 0.30 | 0.76 |
| Glu | 214 | A | A | . | . | . | . | . | 0.22 | 0.10 | . | . | . | −0.30 | 0.73 |
| Ala | 215 | . | A | B | . | . | . | . | −0.59 | 0.34 | . | . | . | −0.30 | 0.31 |
| Leu | 216 | . | A | B | . | . | . | . | −0.80 | 0.63 | . | . | . | −0.60 | 0.31 |
| Pro | 217 | . | . | B | . | . | . | . | −1.10 | 0.37 | . | . | . | −0.10 | 0.28 |
| Val | 218 | . | . | B | . | . | . | . | −0.63 | 0.76 | * | . | . | −0.40 | 0.37 |
| Leu | 219 | . | . | B | . | . | T | . | −1.52 | 0.69 | * | . | F | −0.05 | 0.44 |
| Pro | 220 | . | . | . | . | . | T | C | −0.93 | 0.69 | * | * | F | 0.15 | 0.20 |
| Ser | 221 | . | . | . | . | . | T | C | −0.82 | 0.26 | * | . | F | 0.45 | 0.47 |
| Gly | 222 | . | . | B | . | . | T | . | −1.42 | 0.40 | * | . | F | 0.25 | 0.49 |
| Ile | 223 | . | A | B | . | . | . | . | −0.57 | 0.40 | * | . | F | −0.15 | 0.26 |
| Glu | 224 | . | A | B | . | . | . | . | −0.61 | −0.03 | . | * | . | 0.30 | 0.33 |
| Phe | 225 | . | A | B | . | . | . | . | −0.29 | 0.23 | . | * | . | −0.30 | 0.25 |
| Leu | 226 | . | A | B | . | . | . | . | −0.80 | −0.20 | . | * | . | 0.30 | 0.69 |
| Asp | 227 | A | A | . | . | . | . | . | −0.46 | −0.20 | * | * | . | 0.30 | 0.33 |
| Val | 228 | A | A | . | . | . | . | . | 0.54 | 0.20 | * | . | . | −0.30 | 0.61 |
| Arg | 229 | A | A | . | . | . | . | . | −0.27 | −0.59 | . | * | . | 0.75 | 1.45 |
| Leu | 230 | A | A | . | . | . | . | . | 0.43 | −0.59 | . | * | . | 0.88 | 0.71 |
| Asn | 231 | A | A | . | . | . | . | . | 0.94 | −0.19 | * | * | . | 1.01 | 1.67 |
| Arg | 232 | . | A | . | . | T | . | . | 0.64 | −0.44 | * | * | F | 1.84 | 1.14 |
| Leu | 233 | . | A | . | . | T | . | . | 1.16 | −0.06 | * | . | F | 2.12 | 1.85 |
| Gln | 234 | . | . | . | . | T | T | . | 0.16 | −0.31 | * | . | F | 2.80 | 1.14 |
| Ser | 235 | . | . | . | . | T | T | . | 0.97 | −0.03 | * | . | F | 2.37 | 0.41 |
| Ser | 236 | . | . | . | . | . | T | C | 0.76 | 0.37 | * | * | F | 1.29 | 0.86 |
| Gly | 237 | . | . | . | . | T | T | . | 0.06 | 0.11 | * | * | F | 1.21 | 0.76 |
| Ile | 238 | . | A | B | . | . | . | . | 0.28 | 0.21 | . | . | F | 0.13 | 0.58 |
| Gln | 239 | . | A | B | . | . | . | . | −0.42 | 0.33 | . | . | F | −0.15 | 0.43 |
| Pro | 240 | . | A | B | . | . | . | . | −0.01 | 0.73 | * | * | F | −0.45 | 0.38 |
| Ala | 241 | A | A | . | . | . | . | . | −0.30 | 0.30 | * | * | . | −0.15 | 1.06 |
| Ala | 242 | A | A | . | . | . | . | . | −0.56 | 0.11 | * | . | . | −0.30 | 0.62 |
| Phe | 243 | A | A | . | . | . | . | . | 0.33 | 0.33 | * | * | . | −0.30 | 0.40 |
| Arg | 244 | A | A | . | . | . | . | . | 0.38 | −0.10 | * | * | . | 0.30 | 0.68 |
| Ala | 245 | A | A | . | . | . | . | . | −0.22 | −0.60 | * | * | . | 0.75 | 1.35 |
| Met | 246 | A | A | . | . | . | . | . | 0.37 | −0.41 | * | * | . | 0.45 | 1.28 |
| Glu | 247 | A | A | . | . | . | . | . | 0.26 | −0.80 | * | * | . | 0.75 | 1.13 |
| Lys | 248 | A | A | . | . | . | . | . | 0.14 | −0.01 | * | * | . | 0.30 | 0.97 |
| Leu | 249 | A | A | . | . | . | . | . | −0.21 | 0.17 | * | * | . | −0.30 | 0.81 |
| Gln | 250 | A | A | . | . | . | . | . | −0.43 | 0.31 | . | . | . | −0.30 | 0.73 |
| Phe | 251 | A | A | . | . | . | . | . | −0.13 | 1.00 | . | . | . | −0.60 | 0.30 |
| Leu | 252 | . | A | B | . | . | . | . | −0.13 | 1.39 | . | * | . | −0.60 | 0.49 |
| Tyr | 253 | . | . | B | . | . | . | . | −0.18 | 0.70 | . | * | . | −0.40 | 0.47 |
| Leu | 254 | . | . | B | . | . | . | . | −0.18 | 0.70 | * | . | . | −0.23 | 0.88 |
| Ser | 255 | . | . | B | . | . | T | . | −0.99 | 0.60 | * | . | . | 0.14 | 0.88 |
| Asp | 256 | . | . | . | . | T | T | . | −0.29 | 0.60 | * | . | . | 0.71 | 0.46 |
| Asn | 257 | . | . | . | . | T | T | . | 0.22 | −0.16 | * | . | F | 1.93 | 0.94 |
| Leu | 258 | . | . | B | . | . | T | . | −0.42 | −0.46 | * | . | F | 1.70 | 0.94 |
| Leu | 259 | . | . | B | . | . | . | . | 0.18 | −0.16 | * | . | F | 1.33 | 0.39 |
| Asp | 260 | . | . | B | . | . | . | . | 0.13 | 0.27 | * | . | F | 0.56 | 0.38 |
| Ser | 261 | . | . | B | . | . | . | . | −0.08 | 0.30 | * | . | F | 0.39 | 0.45 |
| Ile | 262 | . | . | B | . | . | T | . | −0.89 | 0.04 | * | . | F | 0.42 | 0.85 |
| Pro | 263 | . | . | B | . | . | T | . | −0.29 | 0.04 | * | . | F | 0.25 | 0.42 |
| Gly | 264 | . | . | . | . | . | T | C | 0.31 | 0.47 | * | . | F | 0.15 | 0.48 |
| Pro | 265 | . | . | . | . | . | T | C | 0.01 | 0.51 | . | * | F | 0.30 | 1.07 |
| Leu | 266 | . | . | . | . | . | . | C | −0.50 | 0.21 | * | * | F | 0.42 | 0.93 |
| Pro | 267 | . | . | . | . | . | T | C | 0.50 | 0.47 | * | * | F | 0.49 | 0.77 |
| Pro | 268 | . | . | . | . | T | T | . | 0.41 | 0.04 | * | * | F | 1.16 | 0.98 |

TABLE IV-continued

| Res | | I | II | III | IV | V | VI | VII | VIII | IX | X | XI | XII | XIII | XIV |
|---|---|---|---|---|---|---|---|---|---|---|---|---|---|---|---|
| Ser | 269 | . | . | B | . | . | T | . | −0.10 | 0.00 | * | * | F | 1.68 | 1.59 |
| Leu | 270 | . | . | B | . | . | T | . | 0.08 | −0.04 | * | * | F | 1.70 | 0.76 |
| Arg | 271 | . | . | B | . | . | . | . | 0.08 | 0.03 | * | * | F | 0.73 | 0.67 |
| Ser | 272 | . | . | B | . | . | . | . | 0.29 | 0.29 | . | . | . | 0.41 | 0.41 |
| Val | 273 | . | . | B | . | . | . | . | 0.50 | 0.30 | . | * | . | 0.24 | 0.87 |
| His | 274 | . | . | B | . | . | . | . | 0.80 | 0.01 | . | * | . | 0.07 | 0.71 |
| Leu | 275 | . | . | B | . | . | T | . | 0.80 | 0.41 | * | . | . | −0.20 | 0.86 |
| Gln | 276 | . | . | . | . | . | T | C | −0.20 | 0.71 | * | . | F | 0.15 | 0.95 |
| Asn | 277 | . | . | . | . | . | T | C | 0.10 | 0.76 | . | * | F | 0.15 | 0.49 |
| Asn | 278 | . | . | . | . | . | T | C | 0.64 | 0.26 | * | * | F | 0.60 | 1.03 |
| Leu | 279 | A | A | . | . | . | . | . | 0.08 | 0.06 | * | . | . | −0.30 | 0.86 |
| Ile | 280 | A | A | . | . | . | . | . | 0.89 | 0.27 | * | * | . | −0.30 | 0.53 |
| Glu | 281 | . | A | B | . | . | . | . | 1.00 | 0.27 | * | . | . | −0.30 | 0.57 |
| Thr | 282 | A | A | . | . | . | . | . | 1.00 | −0.13 | * | . | . | 0.45 | 1.35 |
| Met | 283 | . | A | B | . | . | . | . | 0.14 | −0.81 | * | . | F | 0.90 | 3.21 |
| Gln | 284 | . | A | B | . | . | . | . | 0.26 | −0.86 | * | . | F | 0.90 | 1.38 |
| Arg | 285 | . | A | B | . | . | . | . | 0.48 | −0.07 | * | . | F | 0.45 | 0.83 |
| Asp | 286 | . | A | . | . | T | . | . | 0.48 | 0.01 | * | . | . | 0.10 | 0.45 |
| Val | 287 | . | A | B | . | . | . | . | 0.58 | −0.60 | * | . | . | 0.60 | 0.43 |
| Phe | 288 | A | A | . | . | . | . | . | 1.18 | −0.57 | * | . | . | 0.60 | 0.34 |
| Cys | 289 | A | A | . | . | . | . | . | 1.18 | −0.57 | * | . | . | 0.60 | 0.35 |
| Asp | 290 | A | A | . | . | . | . | . | 1.03 | −0.57 | * | . | F | 0.75 | 0.82 |
| Pro | 291 | A | A | . | . | . | . | . | 1.08 | −0.71 | . | . | F | 0.90 | 1.30 |
| Glu | 292 | A | A | . | . | . | . | . | 1.90 | −1.50 | . | . | F | 0.90 | 4.83 |
| Glu | 293 | A | A | . | . | . | . | . | 2.29 | −1.57 | . | . | F | 0.90 | 3.94 |
| His | 294 | A | A | . | . | . | . | . | 3.07 | −1.09 | * | . | F | 0.90 | 3.67 |
| Lys | 295 | A | A | . | . | . | . | . | 3.18 | −1.51 | . | . | F | 0.90 | 4.16 |
| His | 296 | A | A | . | . | . | . | . | 3.39 | −1.51 | * | . | F | 0.90 | 4.70 |
| Thr | 297 | A | A | . | . | . | . | . | 2.58 | −1.11 | * | . | F | 0.90 | 5.98 |
| Arg | 298 | A | A | . | . | . | . | . | 2.58 | −0.93 | * | . | F | 0.90 | 2.47 |
| Arg | 299 | A | A | . | . | . | . | . | 2.61 | −0.93 | * | . | F | 0.90 | 3.14 |
| Gln | 300 | A | A | . | . | . | . | . | 1.68 | −1.43 | * | * | F | 0.90 | 3.63 |
| Leu | 301 | A | A | . | . | . | . | . | 1.82 | −1.23 | * | * | F | 0.90 | 1.30 |
| Glu | 302 | . | A | B | . | . | . | . | 1.32 | −1.23 | * | * | F | 0.90 | 1.30 |
| Asp | 303 | . | A | B | . | . | . | . | 1.21 | −0.54 | * | * | F | 0.75 | 0.62 |
| Ile | 304 | . | A | B | . | . | . | . | 0.76 | −0.94 | * | * | F | 1.11 | 1.25 |
| Arg | 305 | . | A | B | . | . | . | . | 0.76 | −1.20 | . | * | F | 1.17 | 0.72 |
| Leu | 306 | . | A | B | . | . | . | . | 1.36 | −0.80 | * | * | F | 1.38 | 0.69 |
| Asp | 307 | . | . | . | . | T | T | . | 0.47 | −0.37 | * | * | F | 2.24 | 1.52 |
| Gly | 308 | . | . | . | . | . | T | C | 0.47 | −0.37 | . | * | F | 2.10 | 0.54 |
| Asn | 309 | . | . | . | . | . | T | C | 0.54 | 0.03 | * | * | F | 1.44 | 1.06 |
| Pro | 310 | . | . | . | . | . | T | C | 0.13 | 0.03 | * | * | F | 1.08 | 0.52 |
| Ile | 311 | . | . | B | . | . | . | . | 0.13 | 0.41 | . | . | F | 0.17 | 0.71 |
| Asn | 312 | . | . | B | . | . | . | . | −0.57 | 0.67 | . | . | . | −0.19 | 0.36 |
| Leu | 313 | . | . | B | . | . | . | . | −0.43 | 1.06 | . | * | . | −0.40 | 0.20 |
| Ser | 314 | . | . | B | . | . | . | . | −0.73 | 1.06 | . | * | . | −0.40 | 0.45 |
| Leu | 315 | . | . | B | . | . | . | . | −1.11 | 0.76 | . | * | . | −0.40 | 0.37 |
| Phe | 316 | . | . | B | . | . | T | . | −0.47 | 0.86 | . | * | . | −0.20 | 0.46 |
| Pro | 317 | . | . | . | . | T | T | . | −1.17 | 0.93 | . | * | . | 0.20 | 0.54 |
| Ser | 318 | . | . | . | . | T | T | . | −1.02 | 1.33 | . | * | . | 0.20 | 0.56 |
| Ala | 319 | . | . | B | . | . | T | . | −1.53 | 1.21 | . | . | . | −0.20 | 0.35 |
| Tyr | 320 | . | . | B | . | . | . | . | −0.93 | 1.11 | * | . | . | −0.40 | 0.19 |
| Phe | 321 | . | . | B | . | . | . | . | −0.12 | 1.11 | * | . | . | −0.40 | 0.21 |
| Cys | 322 | . | . | B | . | . | . | . | −0.72 | 0.73 | * | . | . | −0.40 | 0.42 |
| Leu | 323 | . | . | B | . | . | . | . | −0.63 | 0.91 | . | * | . | −0.40 | 0.22 |
| Pro | 324 | . | . | B | . | . | . | . | −0.93 | 0.59 | . | * | . | −0.40 | 0.39 |
| Arg | 325 | . | . | B | B | . | . | . | −1.03 | 0.49 | . | . | . | −0.60 | 0.51 |
| Leu | 326 | . | . | B | B | . | . | . | −0.22 | 0.34 | . | . | . | −0.30 | 0.61 |
| Pro | 327 | . | . | . | B | T | . | . | −0.26 | −0.34 | . | * | . | 0.70 | 0.78 |
| Ile | 328 | . | . | . | B | T | . | . | 0.24 | 0.01 | . | . | . | 0.10 | 0.34 |
| Gly | 329 | . | . | B | B | . | . | . | 0.07 | 0.50 | . | * | F | −0.60 | 0.60 |
| Arg | 330 | . | . | B | B | . | . | . | −0.43 | 0.24 | . | * | F | −0.15 | 0.50 |
| Phe | 331 | . | . | B | B | . | . | . | −0.01 | 0.24 | * | . | . | −0.30 | 0.91 |
| Thr | 332 | . | . | B | B | . | . | . | −0.19 | −0.01 | * | * | . | 0.45 | 1.17 |

TABLE V

| Res | | I | II | III | IV | V | VI | VII | VIII | IX | X | XI | XII | XIII | XIV |
|---|---|---|---|---|---|---|---|---|---|---|---|---|---|---|---|
| Met | 1 | . | A | B | . | . | . | . | −1.30 | 0.70 | . | . | . | −0.60 | 0.39 |
| Leu | 2 | . | A | B | . | . | . | . | −1.72 | 0.96 | . | . | . | −0.60 | 0.25 |
| Leu | 3 | . | A | B | . | . | . | . | −2.14 | 1.21 | . | . | . | −0.60 | 0.16 |
| Pro | 4 | . | A | B | . | . | . | . | −2.06 | 1.47 | . | . | . | −0.60 | 0.14 |
| Leu | 5 | . | A | B | . | . | . | . | −1.97 | 1.24 | * | . | . | −0.60 | 0.22 |

TABLE V-continued

| Res | | I | II | III | IV | V | VI | VII | VIII | IX | X | XI | XII | XIII | XIV |
|---|---|---|---|---|---|---|---|---|---|---|---|---|---|---|---|
| Leu | 6 | . | A | B | . | . | . | . | −2.18 | 0.94 | . | . | . | −0.60 | 0.36 |
| Leu | 7 | . | A | B | . | . | . | . | −2.18 | 0.94 | . | . | . | −0.60 | 0.19 |
| Ser | 8 | . | A | B | . | . | . | . | −1.71 | 1.20 | * | . | . | −0.60 | 0.19 |
| Ser | 9 | . | . | B | B | . | . | . | −1.84 | 0.94 | . | . | F | −0.45 | 0.23 |
| Leu | 10 | . | . | B | B | . | . | . | −1.33 | 0.69 | . | . | F | −0.45 | 0.27 |
| Leu | 11 | . | . | . | B | . | . | C | −0.52 | 0.39 | * | . | F | 0.05 | 0.27 |
| Gly | 12 | . | . | . | . | . | T | C | −0.30 | 0.40 | . | . | F | 0.45 | 0.35 |
| Gly | 13 | . | . | . | . | . | T | C | −0.60 | 0.51 | . | . | F | 0.15 | 0.43 |
| Ser | 14 | . | . | B | . | . | T | . | −0.30 | 0.44 | . | . | F | 0.12 | 0.52 |
| Gln | 15 | . | . | B | . | . | T | . | 0.17 | −0.24 | . | * | F | 1.19 | 0.88 |
| Ala | 16 | . | . | B | . | . | . | . | 1.09 | −0.24 | . | * | F | 1.16 | 0.88 |
| Met | 17 | . | . | B | . | . | T | . | 0.73 | −0.67 | . | * | F | 1.98 | 1.28 |
| Asp | 18 | . | . | B | . | . | T | . | 0.79 | −0.27 | . | * | F | 1.70 | 0.64 |
| Gly | 19 | . | . | . | . | T | T | . | 0.20 | 0.24 | * | * | F | 1.33 | 0.67 |
| Arg | 20 | . | . | . | . | T | T | . | 0.31 | 0.43 | * | * | . | 0.71 | 0.47 |
| Phe | 21 | . | . | B | B | . | . | . | 0.04 | −0.19 | * | * | . | 0.64 | 0.56 |
| Trp | 22 | . | . | B | B | . | . | . | 0.64 | 0.46 | * | * | . | −0.43 | 0.42 |
| Ile | 23 | . | . | B | B | . | . | . | 0.64 | 0.43 | * | * | . | −0.60 | 0.37 |
| Arg | 24 | . | . | B | B | . | . | . | 0.69 | 0.43 | * | * | . | −0.60 | 0.74 |
| Val | 25 | . | . | B | B | . | . | . | −0.28 | 0.03 | * | * | . | −0.30 | 0.94 |
| Gln | 26 | . | . | . | B | . | . | C | −0.18 | −0.24 | * | * | F | 0.65 | 0.99 |
| Glu | 27 | . | . | . | B | . | . | C | −0.74 | −0.31 | * | * | F | 0.65 | 0.50 |
| Ser | 28 | . | . | . | B | T | . | . | −0.07 | 0.33 | . | * | . | 0.10 | 0.50 |
| Val | 29 | . | . | B | B | . | . | . | −0.18 | 0.11 | . | * | . | −0.30 | 0.45 |
| Met | 30 | . | . | B | B | . | . | . | 0.09 | −0.29 | . | . | . | 0.30 | 0.45 |
| Val | 31 | . | . | B | B | . | . | . | −0.58 | 0.21 | . | . | . | −0.30 | 0.34 |
| Pro | 32 | . | . | B | B | . | . | . | −0.58 | 0.40 | . | . | . | −0.30 | 0.24 |
| Glu | 33 | . | . | B | . | . | . | . | −1.17 | −0.24 | . | . | . | 0.50 | 0.41 |
| Ala | 34 | . | . | . | . | T | . | . | −0.61 | −0.17 | . | . | . | 0.90 | 0.39 |
| Cys | 35 | . | . | B | . | . | . | . | −0.87 | −0.43 | * | . | . | 0.50 | 0.34 |
| Asp | 36 | . | . | . | B | T | . | . | −0.22 | −0.21 | * | . | . | 0.70 | 0.14 |
| Ile | 37 | . | . | B | B | . | . | . | −0.68 | 0.21 | . | . | . | −0.30 | 0.22 |
| Ser | 38 | . | . | B | B | . | . | . | −0.98 | 0.29 | . | * | . | −0.30 | 0.22 |
| Val | 39 | . | . | B | . | . | T | . | −1.09 | 0.10 | . | * | . | 0.10 | 0.18 |
| Pro | 40 | . | . | B | . | . | T | . | −0.72 | 0.89 | . | * | . | −0.20 | 0.22 |
| Cys | 41 | . | . | . | . | T | T | . | −0.97 | 0.59 | . | * | . | 0.20 | 0.22 |
| Ser | 42 | . | . | . | . | T | T | . | −0.29 | 0.96 | . | * | . | 0.20 | 0.46 |
| Phe | 43 | . | . | . | . | T | . | . | 0.12 | 0.74 | * | . | . | 0.28 | 0.46 |
| Ser | 44 | . | . | B | . | . | . | . | 0.98 | 0.31 | . | . | . | 0.61 | 1.69 |
| Tyr | 45 | . | . | B | . | . | T | . | 1.19 | 0.14 | . | . | . | 1.09 | 2.19 |
| Pro | 46 | . | . | . | . | T | T | . | 1.57 | −0.24 | . | . | F | 2.52 | 4.22 |
| Arg | 47 | . | . | . | . | T | T | . | 1.56 | −0.11 | . | . | F | 2.80 | 3.31 |
| Gln | 48 | . | . | . | . | T | T | . | 1.91 | −0.01 | . | . | F | 2.52 | 3.05 |
| Asp | 49 | . | . | . | . | T | . | . | 1.91 | −0.34 | . | * | F | 2.04 | 1.95 |
| Trp | 50 | . | . | . | . | T | T | . | 1.84 | −0.39 | . | * | F | 1.96 | 1.33 |
| Thr | 51 | . | . | . | . | . | T | C | 1.84 | 0.10 | . | * | F | 0.88 | 1.11 |
| Gly | 52 | . | . | . | . | T | T | . | 1.14 | 0.13 | . | * | F | 0.80 | 1.03 |
| Ser | 53 | . | . | . | . | . | T | C | 0.90 | 0.63 | . | . | F | 0.15 | 0.99 |
| Thr | 54 | . | . | . | . | . | . | C | 0.56 | 0.47 | . | . | F | 0.10 | 1.07 |
| Pro | 55 | . | . | . | . | . | T | C | 0.60 | 0.41 | . | . | F | 0.30 | 1.07 |
| Ala | 56 | . | . | . | . | T | T | . | 0.62 | 0.74 | . | . | . | 0.35 | 1.26 |
| Tyr | 57 | . | . | . | . | T | T | . | 0.27 | 1.27 | . | . | . | 0.20 | 0.91 |
| Gly | 58 | . | . | . | . | T | T | . | 0.61 | 1.57 | . | . | . | 0.20 | 0.51 |
| Tyr | 59 | . | . | B | B | . | . | . | 0.33 | 1.14 | * | . | . | −0.45 | 1.01 |
| Trp | 60 | . | . | B | B | . | . | . | −0.31 | 1.14 | * | . | . | −0.60 | 0.65 |
| Phe | 61 | . | . | B | B | . | . | . | −0.03 | 1.03 | * | . | . | −0.60 | 0.49 |
| Lys | 62 | . | . | B | B | . | . | . | 0.21 | 1.09 | * | . | . | −0.60 | 0.45 |
| Ala | 63 | . | . | B | B | . | . | . | 0.24 | 0.33 | * | . | . | −0.30 | 0.74 |
| Val | 64 | . | . | B | B | . | . | . | 0.18 | −0.10 | * | . | . | 0.79 | 1.24 |
| Thr | 65 | . | . | B | B | . | . | . | 0.51 | −0.40 | * | . | F | 1.13 | 0.89 |
| Glu | 66 | . | . | B | B | . | . | . | 0.87 | −0.40 | * | . | F | 1.62 | 1.77 |
| Thr | 67 | . | . | . | B | T | . | . | 0.23 | −0.47 | * | . | F | 2.36 | 2.36 |
| Thr | 68 | . | . | . | . | T | T | . | 0.61 | −0.61 | * | . | F | 3.40 | 1.65 |
| Lys | 69 | . | . | . | . | T | T | . | 0.61 | −0.67 | * | . | F | 3.06 | 1.48 |
| Gly | 70 | . | . | . | . | . | T | C | 0.33 | −0.03 | . | . | F | 2.07 | 0.76 |
| Ala | 71 | . | . | . | . | . | T | C | 0.02 | −0.01 | * | . | F | 1.73 | 0.53 |
| Pro | 72 | . | . | B | . | . | . | . | 0.33 | −0.01 | * | . | . | 0.84 | 0.38 |
| Val | 73 | . | . | B | . | . | . | . | 0.61 | 0.39 | . | . | . | −0.10 | 0.62 |
| Ala | 74 | . | . | B | . | . | . | . | 0.57 | 0.46 | . | . | . | −0.10 | 0.84 |
| Thr | 75 | . | . | B | . | . | . | . | 0.61 | 0.36 | * | . | . | 0.50 | 0.94 |
| Asn | 76 | . | . | . | . | . | . | C | 1.31 | 0.31 | . | . | F | 1.30 | 1.70 |
| His | 77 | . | . | . | . | . | T | C | 1.52 | −0.33 | * | . | F | 2.40 | 3.29 |
| Gln | 78 | . | . | . | . | . | T | C | 1.52 | −0.83 | * | . | F | 3.00 | 3.95 |
| Ser | 79 | . | . | . | . | . | T | C | 2.11 | −0.67 | * | . | F | 2.70 | 1.82 |
| Arg | 80 | . | . | B | . | . | T | . | 1.82 | −1.07 | * | . | F | 2.20 | 2.32 |
| Glu | 81 | . | A | B | . | . | . | . | 1.52 | −0.96 | * | . | F | 1.50 | 1.33 |
| Val | 82 | . | A | B | . | . | . | . | 1.24 | −0.97 | * | * | F | 1.54 | 1.33 |

TABLE V-continued

| Res | | I | II | III | IV | V | VI | VII | VIII | IX | X | XI | XII | XIII | XIV |
|---|---|---|---|---|---|---|---|---|---|---|---|---|---|---|---|
| Glu | 83 | . | A | B | . | . | . | . | 1.36 | −0.87 | * | * | . | 1.28 | 0.98 |
| Met | 84 | . | A | B | . | . | . | . | 1.31 | −0.87 | * | * | . | 1.77 | 1.10 |
| Ser | 85 | . | . | . | . | . | T | C | 1.31 | −0.44 | * | * | F | 2.56 | 1.47 |
| Thr | 86 | . | . | . | . | T | T | . | 0.61 | −1.09 | . | * | F | 3.40 | 1.67 |
| Arg | 87 | . | . | . | . | T | T | . | 1.47 | −0.30 | . | * | F | 2.76 | 1.46 |
| Gly | 88 | . | . | . | . | T | T | . | 0.66 | −0.51 | . | * | F | 2.72 | 1.88 |
| Arg | 89 | . | . | B | B | . | . | . | 0.94 | −0.21 | . | * | F | 1.28 | 1.08 |
| Phe | 90 | . | . | B | B | . | . | . | 0.90 | −0.21 | . | * | . | 0.64 | 0.79 |
| Gln | 91 | . | . | B | B | . | . | . | 1.21 | 0.21 | . | * | . | −0.30 | 0.79 |
| Leu | 92 | . | . | B | B | . | . | . | 0.89 | −0.21 | . | * | . | 0.30 | 0.68 |
| Thr | 93 | . | . | B | B | . | . | . | 0.64 | 0.21 | . | * | F | 0.34 | 1.21 |
| Gly | 94 | . | . | . | B | . | . | C | 0.58 | −0.07 | . | * | F | 1.33 | 0.70 |
| Asp | 95 | . | . | . | . | . | T | C | 0.93 | −0.47 | * | * | F | 2.22 | 1.71 |
| Pro | 96 | . | . | . | . | . | T | C | 0.93 | −0.73 | . | * | F | 2.86 | 1.17 |
| Ala | 97 | . | . | . | . | T | T | . | 1.08 | −0.81 | . | . | F | 3.40 | 1.90 |
| Lys | 98 | . | . | . | . | T | T | . | 1.09 | −0.67 | . | * | F | 2.91 | 0.61 |
| Gly | 99 | . | . | . | . | T | T | . | 0.62 | −0.29 | * | . | F | 2.27 | 0.53 |
| Asn | 100 | . | . | B | . | T | T | . | −0.23 | −0.03 | . | * | F | 1.93 | 0.43 |
| Cys | 101 | . | . | B | . | . | T | . | −0.91 | 0.11 | * | * | . | 0.44 | 0.16 |
| Ser | 102 | . | . | B | . | . | T | . | −0.21 | 0.80 | * | * | . | −0.20 | 0.11 |
| Leu | 103 | . | A | B | B | . | . | . | −0.26 | 0.37 | * | * | . | −0.30 | 0.14 |
| Val | 104 | . | A | B | B | . | . | . | −0.50 | −0.03 | * | * | . | 0.30 | 0.43 |
| Ile | 105 | . | A | B | B | . | . | . | −0.50 | −0.10 | * | . | . | 0.30 | 0.33 |
| Arg | 106 | . | A | B | B | . | . | . | −0.43 | −0.09 | * | . | . | 0.30 | 0.68 |
| Asp | 107 | . | A | B | B | . | . | . | −0.13 | −0.16 | * | . | . | 0.30 | 0.91 |
| Ala | 108 | . | A | B | . | . | . | . | 0.68 | −0.40 | * | . | . | 0.45 | 2.25 |
| Gln | 109 | . | A | B | . | . | . | . | 1.53 | −1.09 | * | . | . | 1.03 | 1.92 |
| Met | 110 | . | A | . | . | . | . | C | 2.12 | −1.09 | . | . | . | 1.51 | 1.99 |
| Gln | 111 | . | A | B | . | . | . | . | 2.01 | −0.70 | . | . | F | 1.74 | 2.64 |
| Asp | 112 | . | . | . | . | T | T | . | 1.77 | −0.80 | . | * | F | 2.82 | 2.64 |
| Glu | 113 | . | . | . | . | T | T | . | 1.66 | −0.44 | * | . | F | 2.80 | 4.18 |
| Ser | 114 | . | . | . | . | T | T | . | 0.96 | −0.27 | * | * | F | 2.52 | 2.09 |
| Gln | 115 | . | . | . | . | T | T | . | 1.67 | 0.11 | * | * | F | 1.64 | 1.08 |
| Tyr | 116 | . | . | B | B | . | . | . | 0.81 | 0.11 | * | * | . | 0.41 | 1.22 |
| Phe | 117 | . | . | B | B | . | . | . | 0.81 | 0.76 | * | . | . | −0.32 | 0.68 |
| Phe | 118 | . | . | B | B | . | . | . | 0.92 | 0.37 | * | * | . | 0.04 | 0.68 |
| Arg | 119 | . | . | B | B | . | . | . | 0.88 | −0.03 | * | . | . | 0.98 | 0.85 |
| Val | 120 | . | . | B | B | . | . | . | 0.58 | −0.36 | * | . | . | 1.32 | 0.97 |
| Glu | 121 | . | . | . | . | T | T | . | 0.58 | −0.76 | * | . | F | 3.06 | 1.50 |
| Arg | 122 | . | . | . | . | T | T | . | 0.42 | −0.79 | * | . | F | 3.40 | 1.20 |
| Gly | 123 | . | . | . | . | T | T | . | 1.23 | −0.14 | * | * | F | 2.76 | 1.20 |
| Ser | 124 | . | . | . | . | T | T | . | 0.88 | −0.79 | * | * | F | 2.72 | 1.36 |
| Tyr | 125 | . | . | B | . | . | . | . | 1.73 | −0.03 | . | * | . | 1.33 | 1.09 |
| Val | 126 | . | . | B | . | . | . | . | 1.03 | 0.37 | . | * | . | 0.39 | 1.76 |
| Arg | 127 | . | . | B | . | . | . | . | 0.32 | 0.73 | . | . | . | −0.25 | 1.14 |
| Tyr | 128 | . | . | B | . | . | . | . | 0.67 | 0.96 | . | * | . | −0.40 | 0.72 |
| Asn | 129 | . | . | B | . | . | . | . | 0.97 | 0.60 | . | * | . | −0.25 | 1.56 |
| Phe | 130 | . | . | B | . | . | . | . | 0.87 | −0.04 | . | * | . | 0.65 | 1.33 |
| Met | 131 | . | . | B | . | . | . | . | 1.02 | 0.39 | . | * | . | −0.10 | 0.84 |
| Asn | 132 | . | . | . | . | T | T | . | 0.21 | 0.41 | . | * | . | 0.20 | 0.45 |
| Asp | 133 | . | . | . | . | T | T | . | −0.36 | 0.80 | . | . | . | 0.20 | 0.45 |
| Gly | 134 | . | . | . | . | T | T | . | −0.31 | 0.70 | . | * | . | 0.20 | 0.38 |
| Phe | 135 | . | . | B | . | . | T | . | −0.47 | 0.09 | . | . | . | 0.10 | 0.47 |
| Phe | 136 | . | . | B | B | . | . | . | −0.18 | 0.33 | . | * | . | −0.30 | 0.21 |
| Leu | 137 | . | . | B | B | . | . | . | −1.03 | 0.81 | . | . | . | −0.60 | 0.30 |
| Lys | 138 | . | . | B | B | . | . | . | −1.84 | 1.03 | . | . | . | −0.60 | 0.26 |
| Val | 139 | . | . | B | B | . | . | . | −1.80 | 0.93 | . | . | . | −0.60 | 0.25 |
| Thr | 140 | . | . | B | B | . | . | . | −1.80 | 0.53 | . | * | . | −0.60 | 0.40 |
| Val | 141 | . | . | B | B | . | . | . | −1.41 | 0.63 | . | . | . | −0.60 | 0.17 |
| Leu | 142 | . | . | B | B | . | . | . | −0.81 | 1.11 | . | * | . | −0.60 | 0.34 |
| Ser | 143 | . | . | B | B | . | . | . | −0.74 | 0.90 | . | * | . | −0.60 | 0.36 |
| Phe | 144 | . | . | B | B | . | . | . | −0.10 | 0.41 | * | * | . | −0.26 | 0.96 |
| Thr | 145 | . | . | . | . | . | T | C | 0.21 | 0.20 | * | * | F | 1.28 | 1.80 |
| Pro | 146 | . | . | . | . | . | T | C | 1.07 | −0.09 | * | * | F | 2.22 | 2.32 |
| Arg | 147 | . | . | . | . | . | T | C | 1.84 | −0.47 | . | * | F | 2.56 | 4.48 |
| Pro | 148 | . | . | . | . | T | T | . | 2.14 | −0.76 | . | * | F | 3.40 | 4.22 |
| Gln | 149 | . | . | . | . | T | . | . | 2.53 | −0.84 | * | * | F | 2.86 | 4.39 |
| Asp | 150 | . | . | . | . | T | . | . | 2.84 | −0.79 | * | . | F | 2.52 | 3.24 |
| His | 151 | . | . | . | . | T | . | . | 2.24 | −0.79 | * | . | F | 2.18 | 3.50 |
| Asn | 152 | . | . | . | . | T | T | . | 1.82 | −0.53 | * | * | F | 2.04 | 1.67 |
| Thr | 153 | . | . | . | . | T | T | . | 1.37 | −0.44 | . | . | F | 1.40 | 1.44 |
| Asp | 154 | . | . | . | . | T | T | . | 1.33 | 0.13 | . | * | F | 0.65 | 0.57 |
| Leu | 155 | . | . | B | . | . | T | . | 0.48 | 0.13 | * | * | . | 0.10 | 0.48 |
| Thr | 156 | . | . | B | B | . | . | . | 0.51 | 0.37 | . | * | . | −0.30 | 0.25 |
| Cys | 157 | . | . | B | B | . | . | . | −0.19 | −0.11 | . | * | . | 0.49 | 0.25 |
| His | 158 | . | . | B | B | . | . | . | −0.18 | 0.67 | * | * | . | −0.22 | 0.26 |
| Val | 159 | . | . | B | B | . | . | . | −0.07 | 0.37 | * | * | . | 0.27 | 0.24 |

TABLE V-continued

| Res | | I | II | III | IV | V | VI | VII | VIII | IX | X | XI | XII | XIII | XIV |
|---|---|---|---|---|---|---|---|---|---|---|---|---|---|---|---|
| Asp | 160 | . | . | B | B | . | . | . | 0.79 | −0.11 | * | * | . | 1.06 | 0.88 |
| Phe | 161 | . | . | B | . | . | . | . | 0.76 | −0.69 | * | . | . | 1.90 | 1.29 |
| Ser | 162 | . | . | . | . | T | T | . | 0.57 | −0.76 | * | . | F | 2.46 | 1.72 |
| Arg | 163 | . | . | . | . | T | T | . | 0.30 | −0.76 | * | . | F | 2.12 | 0.77 |
| Lys | 164 | . | . | . | . | T | T | . | 0.57 | −0.37 | * | . | F | 1.78 | 1.18 |
| Gly | 165 | . | . | . | . | T | T | . | 0.57 | −0.66 | * | . | F | 1.74 | 0.89 |
| Val | 166 | . | . | . | B | . | . | C | 1.38 | −0.64 | * | . | F | 0.95 | 0.79 |
| Ser | 167 | . | . | . | B | . | . | C | 1.37 | −0.64 | * | . | F | 0.95 | 0.77 |
| Ala | 168 | . | . | B | B | . | . | . | 0.40 | −0.16 | * | . | F | 0.60 | 1.13 |
| Gln | 169 | . | . | B | B | . | . | . | 0.47 | 0.06 | * | * | F | 0.00 | 1.13 |
| Arg | 170 | . | . | B | B | . | . | . | 0.00 | −0.59 | . | * | F | 0.90 | 1.65 |
| Thr | 171 | . | . | B | B | . | . | . | 0.97 | −0.29 | . | * | F | 0.60 | 1.35 |
| Val | 172 | . | . | B | B | . | . | . | 0.41 | −0.79 | * | * | . | 0.75 | 1.52 |
| Arg | 173 | . | . | B | B | . | . | . | 0.41 | −0.54 | * | * | . | 0.60 | 0.58 |
| Leu | 174 | . | . | B | B | . | . | . | 0.17 | −0.04 | * | * | . | 0.30 | 0.40 |
| Arg | 175 | . | . | B | B | . | . | . | −0.53 | 0.23 | * | * | . | −0.30 | 0.85 |
| Val | 176 | . | . | B | B | . | . | . | −0.43 | 0.09 | * | * | . | −0.30 | 0.44 |
| Ala | 177 | . | . | B | B | . | . | . | 0.53 | 0.51 | * | * | . | −0.60 | 0.82 |
| Tyr | 178 | . | . | B | B | . | . | . | 0.42 | −0.17 | * | * | . | 0.30 | 0.82 |
| Ala | 179 | . | . | B | . | . | T | . | 0.42 | −0.17 | * | * | . | 0.85 | 1.85 |
| Pro | 180 | . | . | B | . | . | T | . | −0.54 | −0.13 | * | * | . | 0.85 | 1.51 |
| Arg | 181 | . | . | B | . | . | T | . | −0.58 | 0.01 | * | . | F | 0.25 | 0.72 |
| Asp | 182 | . | . | B | . | . | T | . | −0.29 | −0.06 | * | . | F | 0.85 | 0.50 |
| Leu | 183 | . | . | B | B | . | . | . | −0.93 | −0.17 | * | . | . | 0.30 | 0.43 |
| Val | 184 | . | . | B | B | . | . | . | −0.64 | 0.09 | * | . | . | −0.30 | 0.15 |
| Ile | 185 | . | . | B | B | . | . | . | −0.32 | 0.47 | * | . | . | −0.26 | 0.12 |
| Ser | 186 | . | . | B | B | . | . | . | −0.43 | 0.47 | * | . | . | 0.08 | 0.29 |
| Ile | 187 | . | . | B | B | . | . | . | −0.43 | −0.21 | * | . | . | 1.32 | 0.66 |
| Ser | 188 | . | . | B | . | . | T | . | 0.07 | −0.46 | * | . | F | 2.36 | 1.52 |
| Arg | 189 | . | . | . | . | T | T | . | 0.71 | −0.66 | * | . | F | 3.40 | 1.63 |
| Asp | 190 | . | . | . | . | T | T | . | 1.01 | −0.61 | * | . | F | 3.06 | 3.61 |
| Asn | 191 | . | . | . | . | . | T | C | 0.50 | −0.80 | * | . | F | 2.52 | 2.72 |
| Thr | 192 | . | . | . | . | . | . | C | 1.39 | −0.50 | * | . | F | 1.98 | 1.14 |
| Pro | 193 | . | . | . | . | . | . | C | 1.48 | −0.50 | . | . | F | 1.64 | 1.19 |
| Ala | 194 | . | . | . | . | T | . | . | 1.37 | −0.07 | * | . | F | 1.20 | 1.14 |
| Leu | 195 | . | . | B | . | . | . | . | 1.16 | −0.07 | . | . | F | 1.14 | 1.37 |
| Glu | 196 | . | . | B | . | . | . | . | 1.16 | −0.13 | . | * | F | 1.48 | 1.37 |
| Pro | 197 | . | . | B | . | . | . | . | 1.12 | −0.16 | . | * | F | 1.82 | 2.35 |
| Gln | 198 | . | . | . | . | . | . | C | 1.33 | −0.23 | . | * | F | 2.36 | 2.82 |
| Pro | 199 | . | . | . | . | T | T | . | 1.07 | −0.51 | . | * | F | 3.40 | 2.62 |
| Gln | 200 | . | . | . | . | T | T | . | 1.67 | 0.13 | . | * | F | 2.16 | 1.26 |
| Gly | 201 | . | . | . | . | T | T | . | 1.42 | 0.13 | . | * | F | 1.82 | 1.12 |
| Asn | 202 | . | . | . | . | . | T | C | 0.82 | 0.49 | . | * | F | 0.98 | 1.14 |
| Val | 203 | . | . | B | . | . | . | . | 0.82 | 0.74 | . | * | F | 0.09 | 0.54 |
| Pro | 204 | . | A | B | . | . | . | . | 0.44 | 0.34 | . | . | . | −0.30 | 0.95 |
| Tyr | 205 | . | A | B | . | . | . | . | 0.44 | 0.41 | . | . | . | −0.60 | 0.59 |
| Leu | 206 | . | A | B | . | . | . | . | 0.83 | 0.41 | . | . | . | −0.17 | 1.39 |
| Glu | 207 | . | A | B | . | . | . | . | 0.49 | −0.23 | . | . | . | 1.01 | 1.79 |
| Ala | 208 | . | A | B | . | . | . | . | 1.34 | −0.23 | . | . | F | 1.44 | 1.13 |
| Gln | 209 | . | . | B | . | . | T | . | 0.86 | −0.59 | . | . | F | 2.42 | 2.38 |
| Lys | 210 | . | . | . | . | T | T | . | 0.29 | −0.49 | * | . | F | 2.80 | 1.19 |
| Gly | 211 | . | . | . | . | T | T | . | 1.21 | 0.20 | * | . | F | 1.77 | 0.97 |
| Gln | 212 | . | . | B | . | . | T | . | 0.40 | −0.30 | * | . | F | 1.84 | 1.10 |
| Phe | 213 | . | A | B | . | . | . | . | 0.18 | −0.01 | * | . | . | 0.86 | 0.45 |
| Leu | 214 | . | A | B | . | . | . | . | −0.49 | 0.67 | * | . | . | −0.32 | 0.38 |
| Arg | 215 | . | A | B | . | . | . | . | −1.12 | 0.81 | * | . | . | −0.60 | 0.12 |
| Leu | 216 | . | A | B | . | . | . | . | −1.37 | 0.91 | * | . | . | −0.60 | 0.14 |
| Leu | 217 | . | A | B | . | . | . | . | −1.37 | 0.63 | * | . | . | −0.60 | 0.17 |
| Cys | 218 | . | A | B | . | . | . | . | −0.97 | −0.06 | * | * | . | 0.54 | 0.14 |
| Ala | 219 | . | A | . | . | T | . | . | −0.16 | 0.33 | * | * | . | 0.58 | 0.23 |
| Ala | 220 | . | . | . | . | T | T | . | −0.48 | 0.04 | * | * | F | 1.37 | 0.49 |
| Asp | 221 | . | . | . | . | T | T | . | 0.12 | −0.21 | . | . | F | 2.36 | 1.40 |
| Ser | 222 | . | . | . | . | . | T | C | 0.34 | −0.36 | . | . | F | 2.40 | 2.15 |
| Gln | 223 | . | . | . | . | . | T | C | 0.70 | −0.36 | . | . | F | 2.16 | 2.15 |
| Pro | 224 | . | . | . | . | . | T | C | 0.48 | −0.37 | . | . | F | 1.92 | 1.85 |
| Pro | 225 | . | . | . | . | T | T | . | 0.77 | 0.31 | . | * | F | 1.28 | 1.14 |
| Ala | 226 | . | . | . | . | T | T | . | 0.48 | 0.31 | . | . | F | 0.89 | 0.88 |
| Thr | 227 | . | . | B | . | . | T | . | −0.08 | 0.83 | . | . | . | −0.20 | 0.60 |
| Leu | 228 | . | . | B | B | . | . | . | −0.89 | 1.04 | * | * | . | −0.60 | 0.29 |
| Ser | 229 | . | . | B | B | . | . | . | −0.68 | 1.30 | . | . | . | −0.60 | 0.24 |
| Trp | 230 | . | . | B | B | . | . | . | −0.47 | 1.20 | . | * | . | −0.60 | 0.28 |
| Val | 231 | . | . | B | B | . | . | . | 0.23 | 1.11 | . | * | . | −0.60 | 0.55 |
| Leu | 232 | . | . | B | B | . | . | . | −0.31 | 0.43 | . | * | . | −0.60 | 0.80 |
| Gln | 233 | . | . | B | B | . | . | . | −0.31 | 0.69 | . | * | F | −0.45 | 0.57 |
| Asn | 234 | . | . | B | B | . | . | . | −0.31 | 0.46 | . | * | F | −0.45 | 0.63 |
| Arg | 235 | . | . | B | B | . | . | . | −0.32 | 0.20 | . | . | F | 0.00 | 1.03 |
| Val | 236 | . | . | B | B | . | . | . | 0.23 | −0.10 | . | . | F | 0.45 | 0.79 |

TABLE V-continued

| Res | | I | II | III | IV | V | VI | VII | VIII | IX | X | XI | XII | XIII | XIV |
|---|---|---|---|---|---|---|---|---|---|---|---|---|---|---|---|
| Leu | 237 | . | . | B | . | . | T | . | 1.01 | −0.11 | * | * | F | 0.85 | 0.66 |
| Ser | 238 | . | . | B | . | . | T | . | 0.80 | −0.01 | * | . | F | 0.85 | 0.46 |
| Ser | 239 | . | . | . | . | T | T | . | 0.51 | 0.41 | * | . | F | 0.35 | 0.96 |
| Ser | 240 | . | . | . | . | . | T | C | 0.06 | 0.69 | * | . | F | 0.30 | 1.22 |
| His | 241 | . | . | . | . | . | T | C | 0.70 | 0.43 | * | . | F | 0.15 | 0.90 |
| Pro | 242 | . | . | . | . | T | T | . | 1.62 | 0.47 | * | . | . | 0.35 | 1.04 |
| Trp | 243 | . | . | . | . | T | T | . | 1.71 | 0.09 | * | . | . | 0.65 | 1.52 |
| Gly | 244 | . | . | . | . | . | T | C | 1.20 | 0.13 | * | . | F | 0.60 | 1.73 |
| Pro | 245 | . | . | . | . | . | . | C | 1.16 | 0.31 | . | . | F | 0.25 | 0.92 |
| Arg | 246 | . | . | . | . | . | T | C | 0.38 | 0.31 | . | . | F | 0.45 | 0.87 |
| Pro | 247 | . | . | . | . | . | T | C | 0.59 | 0.09 | * | . | F | 0.45 | 0.72 |
| Leu | 248 | . | . | B | . | . | T | . | 0.07 | −0.34 | * | . | . | 0.70 | 0.81 |
| Gly | 249 | . | . | B | . | . | T | . | 0.20 | −0.09 | * | . | . | 0.70 | 0.34 |
| Leu | 250 | . | . | B | . | . | . | . | 0.07 | 0.34 | * | . | . | −0.10 | 0.34 |
| Glu | 251 | . | . | B | . | . | . | . | −0.90 | 0.34 | * | . | . | −0.10 | 0.41 |
| Leu | 252 | . | . | B | . | . | . | . | −0.64 | 0.30 | . | . | . | −0.10 | 0.31 |
| Pro | 253 | . | . | B | . | . | . | . | −0.42 | −0.13 | . | . | F | 0.65 | 0.74 |
| Gly | 254 | . | . | B | . | . | . | . | −0.42 | −0.31 | . | . | F | 0.65 | 0.43 |
| Val | 255 | . | . | B | . | . | . | . | 0.39 | 0.11 | * | . | F | 0.05 | 0.52 |
| Lys | 256 | . | . | B | . | . | . | . | 0.09 | −0.57 | . | . | F | 1.29 | 0.56 |
| Ala | 257 | . | . | B | . | . | . | . | 0.56 | −0.61 | * | * | F | 1.63 | 0.76 |
| Gly | 258 | . | . | . | . | T | . | . | 0.88 | −0.61 | * | * | F | 2.52 | 1.02 |
| Asp | 259 | . | . | . | . | T | T | . | 0.98 | −1.26 | * | * | F | 2.91 | 0.99 |
| Ser | 260 | . | . | . | . | T | T | . | 1.52 | −0.50 | * | * | F | 3.40 | 1.54 |
| Gly | 261 | . | . | . | . | T | T | . | 0.81 | −0.51 | * | * | F | 3.06 | 2.25 |
| Arg | 262 | . | . | B | . | . | T | . | 1.51 | −0.37 | * | * | F | 1.87 | 0.72 |
| Tyr | 263 | . | . | B | B | . | . | . | 1.27 | −0.37 | * | * | F | 1.28 | 1.05 |
| Thr | 264 | . | . | B | B | . | . | . | 1.27 | −0.26 | * | * | . | 0.79 | 1.08 |
| Cys | 265 | . | . | B | B | . | . | . | 1.57 | −0.69 | * | * | . | 0.94 | 0.95 |
| Arg | 266 | . | . | B | B | . | . | . | 2.02 | −0.29 | * | * | . | 0.98 | 0.98 |
| Ala | 267 | . | . | B | . | . | . | . | 1.10 | −1.04 | * | * | F | 2.12 | 1.33 |
| Glu | 268 | . | . | B | . | . | . | . | 1.00 | −0.84 | * | * | F | 2.46 | 2.04 |
| Asn | 269 | . | . | . | . | T | T | . | 1.01 | −0.99 | * | * | F | 3.40 | 1.03 |
| Arg | 270 | . | . | . | . | T | T | . | 1.68 | −0.60 | * | * | F | 3.06 | 1.37 |
| Leu | 271 | . | . | . | . | T | T | . | 1.57 | −0.70 | * | * | F | 2.72 | 1.37 |
| Gly | 272 | . | . | . | . | T | T | . | 2.27 | −0.30 | * | * | F | 2.08 | 1.47 |
| Ser | 273 | . | . | . | . | . | . | C | 1.68 | −0.70 | * | * | F | 1.64 | 1.47 |
| Gln | 274 | . | A | B | . | . | . | . | 0.87 | −0.20 | * | * | F | 0.60 | 1.80 |
| Gln | 275 | . | A | B | . | . | . | . | 0.76 | −0.20 | . | * | F | 0.60 | 1.50 |
| Arg | 276 | . | A | B | . | . | . | . | 0.76 | −0.63 | * | . | F | 0.90 | 1.87 |
| Ala | 277 | . | A | B | . | . | . | . | 0.80 | −0.33 | * | . | F | 0.45 | 0.89 |
| Leu | 278 | . | A | B | . | . | . | . | 0.24 | −0.34 | * | * | . | 0.30 | 0.69 |
| Asp | 279 | . | A | B | . | . | . | . | 0.24 | −0.10 | * | * | . | 0.30 | 0.26 |
| Leu | 280 | . | A | B | . | . | . | . | 0.00 | 0.30 | * | * | . | −0.30 | 0.45 |
| Ser | 281 | . | . | B | . | . | . | . | −0.32 | 0.56 | * | * | . | −0.40 | 0.85 |
| Val | 282 | . | . | B | . | . | . | . | 0.06 | 0.30 | * | * | . | −0.10 | 0.79 |
| Gln | 283 | . | . | B | . | . | . | . | 0.87 | 0.73 | . | * | . | −0.25 | 1.48 |
| Tyr | 284 | . | . | B | . | . | . | . | 0.87 | 0.04 | . | * | . | 0.25 | 1.91 |
| Pro | 285 | . | . | . | . | . | T | C | 0.87 | 0.06 | * | * | F | 1.00 | 4.14 |
| Pro | 286 | . | . | . | . | . | T | C | 1.28 | 0.10 | * | * | F | 1.20 | 1.97 |
| Glu | 287 | . | . | . | . | T | T | . | 1.28 | −0.30 | * | * | F | 2.20 | 2.47 |
| Asn | 288 | . | . | B | . | . | T | . | 0.68 | −0.41 | * | * | F | 2.00 | 2.18 |
| Leu | 289 | . | . | B | B | . | . | . | 0.07 | −0.23 | * | * | . | 1.10 | 0.76 |
| Arg | 290 | . | . | B | B | . | . | . | −0.02 | −0.01 | * | * | . | 0.90 | 0.32 |
| Val | 291 | . | . | B | B | . | . | . | 0.19 | 0.37 | * | * | . | 0.10 | 0.27 |
| Met | 292 | . | . | B | B | . | . | . | −0.40 | 0.37 | * | * | . | −0.10 | 0.57 |
| Val | 293 | . | . | B | B | . | . | . | −0.40 | 0.19 | * | * | . | −0.30 | 0.29 |
| Ser | 294 | . | . | B | . | . | . | . | 0.52 | 0.59 | * | * | . | −0.40 | 0.63 |
| Gln | 295 | . | . | B | . | . | . | . | 0.10 | −0.06 | * | * | F | 0.80 | 1.26 |
| Ala | 296 | . | . | B | . | . | . | . | 0.10 | −0.19 | * | . | F | 0.80 | 2.44 |
| Asn | 297 | . | . | B | . | . | . | . | −0.11 | −0.19 | * | . | F | 0.80 | 1.35 |
| Arg | 298 | . | . | B | . | . | . | . | 0.74 | 0.11 | * | . | F | 0.05 | 0.64 |
| Thr | 299 | . | . | B | . | . | . | . | 1.04 | −0.29 | * | . | F | 0.80 | 1.10 |
| Val | 300 | . | . | B | . | . | . | . | 0.23 | −0.39 | * | . | . | 0.65 | 1.10 |
| Leu | 301 | . | . | B | . | . | . | . | 0.48 | −0.10 | * | . | . | 0.50 | 0.47 |
| Glu | 302 | . | . | B | . | . | . | . | 0.48 | 0.33 | * | . | . | 0.03 | 0.32 |
| Asn | 303 | . | . | B | . | . | . | . | 0.02 | 0.24 | * | . | F | 0.31 | 0.69 |
| Leu | 304 | . | . | . | . | T | T | . | 0.02 | 0.03 | * | . | F | 1.04 | 0.83 |
| Gly | 305 | . | . | . | . | T | T | . | 0.58 | −0.17 | * | . | F | 1.77 | 0.69 |
| Asn | 306 | . | . | . | . | T | T | . | 0.58 | 0.21 | * | . | F | 1.30 | 0.58 |
| Gly | 307 | . | . | . | . | . | T | C | 0.37 | 0.50 | * | . | F | 0.67 | 0.58 |
| Thr | 308 | . | . | . | . | . | . | C | −0.49 | 0.24 | . | . | F | 0.64 | 0.90 |
| Ser | 309 | . | . | B | . | . | . | . | −0.49 | 0.46 | . | . | F | 0.01 | 0.42 |
| Leu | 310 | . | . | B | . | . | . | . | −0.14 | 0.74 | . | . | . | −0.27 | 0.35 |
| Pro | 311 | . | . | B | . | . | . | . | −0.49 | 0.31 | . | . | . | −0.10 | 0.42 |
| Val | 312 | . | . | B | . | . | . | . | −0.14 | 0.26 | . | . | . | −0.10 | 0.31 |
| Leu | 313 | . | . | B | . | . | . | . | −0.13 | 0.27 | . | . | F | 0.05 | 0.64 |

TABLE V-continued

| Res | | I | II | III | IV | V | VI | VII | VIII | IX | X | XI | XII | XIII | XIV |
|---|---|---|---|---|---|---|---|---|---|---|---|---|---|---|---|
| Glu | 314 | . | . | B | . | . | . | . | −0.64 | −0.03 | . | . | F | 0.65 | 0.56 |
| Gly | 315 | . | . | . | . | T | T | . | −0.50 | 0.23 | . | . | F | 0.65 | 0.62 |
| Gln | 316 | . | . | . | . | T | T | . | −1.10 | 0.16 | . | . | F | 0.65 | 0.40 |
| Ser | 317 | . | . | . | . | T | T | . | −1.10 | 0.16 | . | . | F | 0.65 | 0.19 |
| Leu | 318 | . | . | B | . | . | T | . | −0.96 | 0.80 | . | . | . | −0.20 | 0.14 |
| Cys | 319 | . | . | B | B | . | . | . | −1.81 | 0.94 | . | . | . | −0.60 | 0.04 |
| Leu | 320 | . | . | B | B | . | . | . | −1.78 | 1.19 | . | . | . | −0.60 | 0.02 |
| Val | 321 | . | . | B | B | . | . | . | −1.81 | 1.29 | . | . | . | −0.60 | 0.04 |
| Cys | 322 | . | . | B | B | . | . | . | −1.81 | 1.10 | . | . | . | −0.60 | 0.11 |
| Val | 323 | . | . | B | B | . | . | . | −1.30 | 0.91 | . | . | . | −0.60 | 0.18 |
| Thr | 324 | . | . | B | B | . | . | . | −0.84 | 0.61 | . | . | . | −0.60 | 0.32 |
| His | 325 | . | . | . | . | T | T | . | −0.24 | 0.40 | . | . | F | 0.89 | 0.93 |
| Ser | 326 | . | . | . | . | . | T | C | 0.02 | 0.26 | * | * | F | 1.08 | 1.93 |
| Ser | 327 | . | . | . | . | . | T | C | 0.80 | 0.11 | * | * | F | 1.32 | 1.35 |
| Pro | 328 | . | . | . | . | . | T | C | 0.84 | −0.37 | . | * | F | 2.16 | 1.95 |
| Pro | 329 | . | . | . | . | T | . | . | 0.86 | −0.19 | . | * | F | 2.40 | 1.20 |
| Ala | 330 | . | . | . | . | T | . | . | 0.60 | −0.19 | . | * | F | 2.16 | 1.20 |
| Arg | 331 | . | . | B | B | . | . | . | 0.59 | 0.34 | . | * | . | 0.42 | 0.82 |
| Leu | 332 | . | . | B | B | . | . | . | 0.89 | 0.40 | . | * | . | 0.18 | 0.76 |
| Ser | 333 | . | . | B | B | . | . | . | 1.21 | 0.37 | . | * | . | 0.09 | 1.30 |
| Trp | 334 | . | . | B | B | . | . | . | 1.08 | −0.13 | . | * | . | 0.45 | 1.30 |
| Thr | 335 | . | . | B | B | . | . | . | 1.67 | 0.30 | . | * | F | 0.00 | 1.56 |
| Gln | 336 | . | . | B | . | . | T | . | 0.70 | 0.01 | . | * | F | 0.40 | 2.02 |
| Arg | 337 | . | . | B | . | . | T | . | 0.70 | 0.27 | . | * | F | 0.40 | 1.43 |
| Gly | 338 | . | . | . | . | T | T | . | 0.70 | 0.04 | . | * | F | 0.65 | 0.82 |
| Gln | 339 | . | . | B | . | . | T | . | 0.78 | −0.06 | . | * | F | 0.85 | 0.63 |
| Val | 340 | . | . | B | . | . | . | . | 0.79 | −0.03 | . | . | F | 0.65 | 0.50 |
| Leu | 341 | . | . | B | . | . | . | . | 0.79 | 0.36 | . | . | F | 0.05 | 0.67 |
| Ser | 342 | . | . | B | . | . | T | . | 0.47 | 0.33 | . | * | F | 0.55 | 0.67 |
| Pro | 343 | . | . | . | . | T | T | . | 0.51 | 0.36 | . | . | F | 1.40 | 1.41 |
| Ser | 344 | . | . | . | . | T | T | . | 0.51 | 0.10 | . | . | F | 1.70 | 2.28 |
| Gln | 345 | . | . | . | . | . | T | C | 1.16 | −0.59 | . | . | F | 2.70 | 2.85 |
| Pro | 346 | . | . | . | . | T | . | . | 1.62 | −0.54 | . | . | F | 3.00 | 2.85 |
| Ser | 347 | . | . | . | . | . | . | C | 1.07 | −0.54 | . | . | F | 2.50 | 2.10 |
| Asp | 348 | . | . | . | . | . | T | C | 0.47 | −0.29 | . | . | F | 1.95 | 0.90 |
| Pro | 349 | . | . | B | . | . | T | . | 0.77 | 0.00 | . | . | F | 1.45 | 0.48 |
| Gly | 350 | . | . | B | . | . | T | . | −0.04 | −0.43 | . | . | F | 1.15 | 0.62 |
| Val | 351 | . | . | B | . | . | T | . | −0.04 | −0.13 | * | . | . | 0.70 | 0.31 |
| Leu | 352 | . | . | B | . | . | . | . | 0.37 | 0.30 | * | . | . | −0.10 | 0.31 |
| Glu | 353 | . | . | B | . | . | . | . | −0.49 | −0.13 | * | . | . | 0.50 | 0.61 |
| Leu | 354 | . | . | B | B | . | . | . | −0.28 | 0.09 | * | * | . | −0.30 | 0.61 |
| Pro | 355 | . | . | B | B | . | . | . | −0.79 | −0.16 | * | * | F | 0.60 | 1.27 |
| Arg | 356 | . | A | B | B | . | . | . | 0.07 | −0.20 | * | * | . | 0.30 | 0.55 |
| Val | 357 | . | A | B | B | . | . | . | 0.84 | −0.20 | . | * | . | 0.45 | 1.15 |
| Gln | 358 | . | A | B | B | . | . | . | 0.84 | −0.39 | . | * | . | 0.45 | 1.01 |
| Val | 359 | . | A | B | B | . | . | . | 1.31 | −0.81 | . | * | . | 0.60 | 0.89 |
| Glu | 360 | . | A | B | B | . | . | . | 1.52 | −0.39 | . | * | . | 0.45 | 1.19 |
| His | 361 | . | A | . | . | . | . | C | 0.71 | −1.03 | . | * | F | 1.10 | 1.19 |
| Glu | 362 | . | A | . | . | T | . | . | 1.26 | −0.64 | . | * | F | 1.30 | 1.39 |
| Gly | 363 | . | A | . | . | T | . | . | 0.59 | −0.80 | . | * | F | 1.30 | 1.16 |
| Glu | 364 | . | A | . | . | T | . | . | 1.41 | −0.23 | * | * | F | 0.85 | 0.46 |
| Phe | 365 | . | A | . | . | T | . | . | 0.82 | −0.23 | * | * | . | 0.70 | 0.36 |
| Thr | 366 | A | A | . | . | . | . | . | 0.97 | 0.27 | . | * | . | −0.30 | 0.37 |
| Cys | 367 | . | A | . | . | T | . | . | 0.93 | −0.16 | * | * | . | 0.70 | 0.41 |
| His | 368 | . | A | B | . | . | . | . | 1.07 | 0.34 | * | * | . | −0.30 | 0.65 |
| Ala | 369 | . | A | . | . | T | . | . | 0.26 | −0.01 | * | * | . | 0.95 | 0.70 |
| Arg | 370 | . | A | . | . | . | . | C | 0.61 | 0.19 | * | * | . | 0.55 | 1.07 |
| His | 371 | . | . | . | . | . | T | C | 0.62 | 0.04 | . | * | . | 1.05 | 0.78 |
| Pro | 372 | . | . | . | . | T | T | . | 1.29 | −0.07 | . | * | . | 2.25 | 1.03 |
| Leu | 373 | . | . | . | . | T | T | . | 1.29 | −0.17 | . | * | F | 2.50 | 0.91 |
| Gly | 374 | . | . | . | . | T | T | . | 1.02 | 0.33 | . | * | F | 1.65 | 0.91 |
| Ser | 375 | . | . | B | B | . | . | . | 0.61 | 0.47 | . | * | F | 0.30 | 0.44 |
| Gln | 376 | . | . | B | B | . | . | . | −0.17 | 0.43 | . | . | F | 0.05 | 0.71 |
| His | 377 | . | . | B | B | . | . | . | −0.26 | 0.43 | . | * | . | −0.35 | 0.59 |
| Val | 378 | . | . | B | B | . | . | . | −0.26 | 0.39 | . | * | . | −0.30 | 0.59 |
| Ser | 379 | . | . | B | B | . | . | . | −0.21 | 0.69 | . | * | . | −0.60 | 0.28 |
| Leu | 380 | . | . | B | B | . | . | . | −0.77 | 0.67 | . | * | . | −0.60 | 0.28 |
| Ser | 381 | . | . | B | B | . | . | . | −0.80 | 0.81 | . | * | . | −0.60 | 0.28 |
| Leu | 382 | . | . | B | B | . | . | . | −1.01 | 0.67 | . | * | . | −0.60 | 0.28 |
| Ser | 383 | . | . | B | B | . | . | . | −0.46 | 1.04 | . | * | . | −0.60 | 0.54 |
| Val | 384 | . | . | B | B | . | . | . | −0.37 | 0.74 | . | * | . | −0.60 | 0.54 |
| His | 385 | . | . | B | B | . | . | . | 0.49 | 0.79 | * | * | . | −0.45 | 1.01 |
| Tyr | 386 | . | . | B | B | . | . | . | −0.02 | 0.10 | * | * | . | −0.15 | 1.50 |
| Ser | 387 | . | . | B | . | . | T | . | −0.02 | 0.40 | . | * | . | 0.25 | 1.67 |
| Pro | 388 | . | . | B | . | . | T | . | −0.07 | 0.44 | * | * | F | 0.10 | 1.01 |
| Lys | 389 | . | . | . | . | T | T | . | 0.58 | 0.37 | * | * | F | 0.65 | 0.64 |
| Leu | 390 | . | . | . | . | T | T | . | 0.31 | 0.04 | * | . | F | 0.65 | 0.74 |

TABLE V-continued

| Res | | I | II | III | IV | V | VI | VII | VIII | IX | X | XI | XII | XIII | XIV |
|---|---|---|---|---|---|---|---|---|---|---|---|---|---|---|---|
| Leu | 391 | . | . | B | . | . | . | . | −0.11 | 0.04 | . | . | F | 0.05 | 0.64 |
| Gly | 392 | . | . | . | . | . | T | C | −0.11 | 0.19 | . | . | F | 0.45 | 0.17 |
| Pro | 393 | . | . | . | . | . | T | C | −0.19 | 0.57 | . | . | F | 0.15 | 0.28 |
| Ser | 394 | . | . | . | . | . | T | C | −0.23 | 0.80 | . | . | F | 0.15 | 0.36 |
| Cys | 395 | . | . | . | . | . | T | C | −0.01 | 0.11 | . | * | . | 0.30 | 0.62 |
| Ser | 396 | . | A | . | . | . | . | C | 0.80 | 0.19 | . | * | . | −0.10 | 0.41 |
| Trp | 397 | . | A | B | . | . | . | . | 0.80 | −0.24 | . | . | . | 0.30 | 0.52 |
| Glu | 398 | . | A | B | . | . | . | . | 0.20 | −0.20 | . | . | . | 0.30 | 0.97 |
| Ala | 399 | . | A | . | . | T | . | . | 0.47 | −0.09 | . | . | . | 0.70 | 0.60 |
| Glu | 400 | . | A | . | . | T | . | . | 0.47 | 0.03 | . | . | F | 0.10 | 0.77 |
| Gly | 401 | . | A | . | . | T | . | . | 0.47 | −0.31 | . | . | . | 0.70 | 0.24 |
| Leu | 402 | . | A | . | . | T | . | . | 0.09 | 0.07 | . | . | . | 0.10 | 0.32 |
| His | 403 | . | A | . | . | T | . | . | −0.21 | 0.14 | . | . | . | 0.10 | 0.10 |
| Cys | 404 | . | . | . | . | T | T | . | 0.08 | 0.53 | . | . | . | 0.20 | 0.13 |
| Ser | 405 | . | . | . | . | T | T | . | 0.08 | 0.49 | . | . | . | 0.20 | 0.22 |
| Cys | 406 | . | . | . | . | T | T | . | −0.17 | 0.20 | . | . | . | 0.50 | 0.27 |
| Ser | 407 | . | . | . | . | T | T | . | 0.34 | 0.20 | . | * | F | 0.65 | 0.52 |
| Ser | 408 | . | . | . | . | T | . | . | 0.17 | 0.01 | . | . | F | 0.45 | 0.52 |
| Gln | 409 | . | . | . | . | T | . | . | 0.24 | 0.06 | . | . | F | 0.60 | 1.49 |
| Ala | 410 | . | . | . | . | . | . | C | 0.33 | −0.01 | . | . | F | 1.24 | 1.13 |
| Ser | 411 | . | . | . | . | . | . | C | 0.70 | 0.03 | . | . | F | 0.88 | 1.30 |
| Pro | 412 | . | . | . | . | . | . | C | 0.19 | 0.03 | . | * | F | 1.12 | 1.00 |
| Ala | 413 | . | . | . | . | . | T | C | 0.60 | 0.31 | . | * | F | 1.41 | 0.82 |
| Pro | 414 | . | . | . | . | . | T | C | 0.31 | −0.19 | * | * | F | 2.40 | 1.20 |
| Ser | 415 | . | . | . | . | . | T | C | 0.61 | 0.34 | * | * | F | 1.41 | 0.82 |
| Leu | 416 | . | . | B | . | . | T | . | 0.10 | 0.83 | * | * | . | 0.52 | 0.85 |
| Arg | 417 | . | . | B | B | . | . | . | −0.03 | 1.01 | * | * | . | −0.12 | 0.45 |
| Trp | 418 | . | . | B | B | . | . | . | 0.56 | 1.01 | . | * | . | −0.36 | 0.33 |
| Trp | 419 | . | A | . | B | . | . | C | 0.77 | 0.63 | . | * | . | −0.40 | 0.70 |
| Leu | 420 | . | A | . | B | . | . | C | 0.26 | −0.06 | . | * | . | 0.50 | 0.62 |
| Gly | 421 | . | A | . | B | . | . | C | 0.26 | 0.63 | . | * | . | −0.40 | 0.49 |
| Glu | 422 | . | A | B | . | . | . | . | 0.14 | 0.40 | . | * | F | −0.15 | 0.38 |
| Glu | 423 | . | A | B | . | . | . | . | 0.09 | −0.51 | . | . | F | 0.75 | 0.80 |
| Leu | 424 | . | A | . | . | . | . | C | 0.38 | −0.77 | * | . | F | 0.95 | 0.80 |
| Leu | 425 | . | A | . | . | . | . | C | 0.89 | −0.80 | * | . | F | 1.25 | 0.74 |
| Glu | 426 | . | A | . | . | T | . | . | 0.93 | −0.41 | . | . | F | 1.45 | 0.58 |
| Gly | 427 | . | A | . | . | T | . | . | 0.93 | −0.03 | . | . | F | 1.75 | 0.94 |
| Asn | 428 | . | . | . | . | T | T | . | 0.93 | −0.31 | . | . | F | 2.60 | 1.97 |
| Ser | 429 | . | . | . | . | . | T | C | 1.44 | −1.00 | . | . | F | 3.00 | 1.89 |
| Ser | 430 | . | . | . | . | . | T | C | 1.56 | −0.61 | . | . | F | 2.70 | 2.57 |
| Gln | 431 | . | . | . | . | . | T | C | 1.56 | −0.26 | . | . | F | 2.10 | 1.38 |
| Asp | 432 | . | A | . | . | . | . | C | 1.04 | −0.66 | * | . | F | 1.70 | 1.79 |
| Ser | 433 | . | A | B | . | . | . | . | 0.73 | −0.40 | * | . | F | 0.75 | 0.99 |
| Phe | 434 | . | A | B | . | . | . | . | 0.82 | −0.30 | . | * | . | 0.30 | 0.82 |
| Glu | 435 | . | A | B | . | . | . | . | 0.82 | −0.27 | . | . | . | 0.43 | 0.76 |
| Val | 436 | . | A | B | . | . | . | . | 0.52 | 0.11 | * | . | F | 0.11 | 0.76 |
| Thr | 437 | . | . | B | . | . | T | . | −0.07 | 0.11 | . | . | F | 0.79 | 1.18 |
| Pro | 438 | . | . | . | . | . | T | C | −0.11 | −0.17 | . | . | F | 1.57 | 0.69 |
| Ser | 439 | . | . | . | . | T | T | . | 0.38 | 0.26 | . | . | F | 1.30 | 0.92 |
| Ser | 440 | . | . | . | . | . | T | C | 0.09 | 0.04 | . | . | F | 0.97 | 0.98 |
| Ala | 441 | . | . | . | . | . | . | C | 0.36 | 0.47 | . | . | F | 0.34 | 0.67 |
| Gly | 442 | . | . | . | . | . | T | C | 0.67 | 0.54 | . | . | F | 0.41 | 0.50 |
| Pro | 443 | . | . | . | . | T | T | . | 0.58 | 0.56 | . | . | F | 0.48 | 0.61 |
| Trp | 444 | . | . | . | . | . | T | C | 0.58 | 0.56 | * | . | F | 0.15 | 0.80 |
| Ala | 445 | . | . | B | . | . | T | . | 0.07 | 0.44 | * | . | F | 0.10 | 1.09 |
| Asn | 446 | . | . | B | . | . | T | . | 0.36 | 0.70 | . | . | F | −0.05 | 0.58 |
| Ser | 447 | . | . | B | . | . | T | . | −0.11 | 0.66 | . | * | F | −0.05 | 0.74 |
| Ser | 448 | . | . | B | . | . | T | . | 0.07 | 0.43 | . | * | F | −0.05 | 0.60 |
| Leu | 449 | . | . | B | . | . | T | . | 0.01 | 0.43 | . | * | . | −0.20 | 0.51 |
| Ser | 450 | . | . | B | . | . | . | . | 0.26 | 0.46 | . | * | . | −0.40 | 0.38 |
| Leu | 451 | . | . | B | . | . | T | . | −0.56 | 0.50 | . | * | . | −0.20 | 0.28 |
| His | 452 | . | . | B | . | . | T | . | −0.56 | 0.80 | . | * | . | −0.20 | 0.28 |
| Gly | 453 | . | . | . | . | T | T | . | −0.56 | 0.50 | . | * | . | 0.20 | 0.28 |
| Gly | 454 | . | . | . | . | . | T | C | −0.09 | 0.50 | . | * | F | 0.15 | 0.45 |
| Leu | 455 | . | . | . | . | . | . | C | −0.60 | 0.24 | * | * | F | 0.39 | 0.33 |
| Ser | 456 | . | . | . | . | . | T | C | 0.32 | 0.43 | * | * | F | 0.43 | 0.27 |
| Ser | 457 | . | . | . | . | T | T | . | −0.46 | 0.00 | . | * | F | 1.67 | 0.54 |
| Gly | 458 | . | . | B | . | . | T | . | 0.00 | 0.26 | . | * | F | 0.81 | 0.54 |
| Leu | 459 | . | . | B | . | . | T | . | −0.32 | −0.43 | * | * | . | 1.40 | 0.79 |
| Arg | 460 | . | A | B | . | . | . | . | 0.49 | −0.24 | * | * | . | 0.86 | 0.32 |
| Leu | 461 | . | A | B | . | . | . | . | 0.20 | −0.63 | * | * | . | 1.02 | 0.56 |
| Arg | 462 | . | A | B | . | . | . | . | 0.21 | −0.56 | * | * | . | 0.88 | 0.68 |
| Cys | 463 | . | A | B | . | . | . | . | 0.56 | −0.33 | * | * | . | 0.44 | 0.37 |
| Glu | 464 | . | A | B | . | . | . | . | 0.51 | 0.07 | . | * | . | −0.30 | 0.71 |
| Ala | 465 | . | A | . | . | T | . | . | 0.37 | 0.03 | * | * | . | 0.10 | 0.27 |
| Trp | 466 | . | A | . | . | T | . | . | 0.83 | 0.53 | * | * | . | −0.20 | 0.68 |
| Asn | 467 | . | . | B | . | . | T | . | 0.13 | 0.39 | . | . | . | 0.10 | 0.39 |

TABLE V-continued

| Res | | I | II | III | IV | V | VI | VII | VIII | IX | X | XI | XII | XIII | XIV |
|---|---|---|---|---|---|---|---|---|---|---|---|---|---|---|---|
| Val | 468 | . | . | B | . | . | T | . | 0.80 | 0.89 | . | . | . | −0.20 | 0.39 |
| His | 469 | . | . | . | . | . | T | C | 0.50 | 0.79 | . | . | . | 0.00 | 0.64 |
| Gly | 470 | . | . | . | . | . | T | C | 0.74 | 0.26 | . | . | . | 0.30 | 0.54 |
| Ala | 471 | . | . | . | . | . | . | C | 0.73 | 0.29 | . | . | F | 0.25 | 0.72 |
| Gln | 472 | . | . | . | . | . | T | C | −0.16 | 0.03 | . | . | F | 0.45 | 0.71 |
| Ser | 473 | . | . | . | . | . | T | C | −0.11 | 0.21 | . | . | F | 0.45 | 0.50 |
| Gly | 474 | . | . | B | . | . | T | . | −0.08 | 0.47 | . | . | F | −0.05 | 0.41 |
| Ser | 475 | . | . | B | . | . | T | . | −0.54 | 0.37 | . | . | F | 0.25 | 0.41 |
| Ile | 476 | . | . | B | . | . | . | . | −0.17 | 0.66 | . | . | . | −0.40 | 0.25 |
| Leu | 477 | . | . | B | . | . | . | . | −0.17 | 0.70 | * | . | . | −0.06 | 0.39 |
| Gln | 478 | . | . | B | . | . | . | . | 0.18 | 0.27 | * | . | . | 0.58 | 0.49 |
| Leu | 479 | . | . | B | . | . | T | . | 0.57 | −0.11 | * | . | . | 1.87 | 1.39 |
| Pro | 480 | . | . | B | . | . | T | . | 0.52 | −0.80 | * | . | F | 2.66 | 3.38 |
| Asp | 481 | . | . | . | . | T | T | . | 0.60 | −1.06 | . | . | F | 3.40 | 1.93 |
| Lys | 482 | . | . | . | . | T | T | . | 0.52 | −0.77 | . | . | F | 3.06 | 1.93 |
| Lys | 483 | . | . | . | B | T | . | . | 0.22 | −0.77 | . | . | F | 2.17 | 0.88 |
| Gly | 484 | . | . | B | B | . | . | . | 0.72 | −0.81 | . | . | F | 1.43 | 0.70 |
| Leu | 485 | . | . | B | B | . | . | . | 0.34 | −0.33 | . | . | F | 0.79 | 0.51 |
| Ile | 486 | . | . | B | B | . | . | . | −0.36 | 0.17 | . | . | . | −0.30 | 0.26 |
| Ser | 487 | . | . | B | B | . | . | . | −0.70 | 0.96 | . | . | . | −0.60 | 0.22 |
| Thr | 488 | . | . | B | B | . | . | . | −0.74 | 0.91 | * | . | . | −0.60 | 0.36 |
| Ala | 489 | . | . | B | B | . | . | . | −0.74 | 0.63 | * | . | . | −0.60 | 0.84 |
| Phe | 490 | . | . | B | . | . | T | . | −0.52 | 0.37 | . | . | F | 0.25 | 0.62 |
| Ser | 491 | . | . | . | . | . | T | C | −0.33 | 0.49 | * | . | F | 0.15 | 0.43 |
| Asn | 492 | . | . | . | . | . | T | C | −0.84 | 0.79 | . | . | F | 0.15 | 0.37 |
| Gly | 493 | . | . | . | . | . | T | C | −0.88 | 0.97 | . | . | F | 0.15 | 0.35 |
| Ala | 494 | . | . | . | B | . | . | C | −1.18 | 0.61 | . | . | . | −0.40 | 0.26 |
| Phe | 495 | . | . | B | B | . | . | . | −0.82 | 0.91 | . | . | . | −0.60 | 0.11 |
| Leu | 496 | . | . | B | B | . | . | . | −1.41 | 0.94 | . | . | . | −0.60 | 0.11 |
| Gly | 497 | . | . | B | B | . | . | . | −1.72 | 1.20 | . | . | . | −0.60 | 0.08 |
| Ile | 498 | . | . | B | B | . | . | . | −1.97 | 1.19 | . | . | . | −0.60 | 0.13 |
| Gly | 499 | . | . | B | B | . | . | . | −2.19 | 0.90 | . | . | . | −0.60 | 0.16 |
| Ile | 500 | . | A | B | . | . | . | . | −2.30 | 0.90 | . | . | . | −0.60 | 0.13 |
| Thr | 501 | . | A | B | . | . | . | . | −2.19 | 1.16 | . | . | . | −0.60 | 0.16 |
| Ala | 502 | . | A | B | . | . | . | . | −2.66 | 1.26 | . | . | . | −0.60 | 0.14 |
| Leu | 503 | . | A | B | . | . | . | . | −2.43 | 1.51 | . | . | . | −0.60 | 0.16 |
| Leu | 504 | . | A | B | . | . | . | . | −2.90 | 1.40 | . | . | . | −0.60 | 0.06 |
| Phe | 505 | . | A | B | . | . | . | . | −2.60 | 1.60 | . | . | . | −0.60 | 0.05 |
| Leu | 506 | . | A | B | . | . | . | . | −3.10 | 1.60 | . | . | . | −0.60 | 0.06 |
| Cys | 507 | A | A | . | . | . | . | . | −3.40 | 1.60 | . | . | . | −0.60 | 0.06 |
| Leu | 508 | A | A | . | . | . | . | . | −3.48 | 1.60 | . | . | . | −0.60 | 0.05 |
| Ala | 509 | A | A | . | . | . | . | . | −3.27 | 1.50 | * | . | . | −0.60 | 0.04 |
| Leu | 510 | A | A | . | . | . | . | . | −2.52 | 1.43 | * | . | . | −0.60 | 0.08 |
| Ile | 511 | . | A | B | . | . | . | . | −2.60 | 0.86 | * | . | . | −0.60 | 0.19 |
| Ile | 512 | . | A | B | . | . | . | . | −2.74 | 0.86 | * | . | . | −0.60 | 0.13 |
| Met | 513 | . | A | B | . | . | . | . | −2.14 | 1.04 | * | . | . | −0.60 | 0.13 |
| Lys | 514 | . | A | B | . | . | . | . | −1.51 | 0.79 | * | . | . | −0.26 | 0.28 |
| Ile | 515 | . | A | B | . | . | . | . | −0.59 | 0.10 | . | . | . | 0.38 | 0.81 |
| Leu | 516 | . | A | B | . | . | . | . | 0.41 | −0.59 | . | * | . | 1.77 | 1.61 |
| Pro | 517 | . | . | . | . | . | T | C | 0.99 | −1.20 | . | . | F | 2.86 | 1.57 |
| Lys | 518 | . | . | . | . | T | T | . | 1.59 | −0.71 | . | * | F | 3.40 | 3.24 |
| Arg | 519 | . | . | . | . | T | T | . | 1.23 | −1.00 | . | * | F | 3.06 | 6.80 |
| Arg | 520 | . | . | . | . | T | T | . | 2.12 | −1.20 | . | . | F | 2.72 | 6.34 |
| Thr | 521 | . | . | . | . | T | . | . | 2.62 | −1.63 | . | . | F | 2.18 | 5.49 |
| Gln | 522 | . | . | B | . | . | . | . | 2.62 | −1.14 | * | . | F | 1.44 | 4.05 |
| Thr | 523 | . | . | B | . | . | . | . | 2.69 | −0.71 | * | . | F | 1.10 | 3.20 |
| Glu | 524 | . | . | B | . | . | . | . | 2.37 | −0.71 | * | * | F | 1.10 | 4.34 |
| Thr | 525 | . | . | B | . | . | T | . | 2.37 | −0.77 | . | * | F | 1.30 | 3.87 |
| Pro | 526 | . | . | . | . | . | T | C | 1.98 | −1.17 | . | * | F | 1.50 | 5.26 |
| Arg | 527 | . | . | . | . | . | T | C | 1.68 | −0.87 | * | * | F | 1.84 | 2.63 |
| Pro | 528 | . | . | . | . | T | T | . | 2.10 | −0.49 | * | * | F | 2.08 | 2.44 |
| Arg | 529 | . | . | . | . | T | . | . | 2.07 | −0.97 | * | * | F | 2.52 | 3.09 |
| Phe | 530 | . | . | . | . | T | . | . | 2.08 | −0.90 | * | * | F | 2.86 | 2.15 |
| Ser | 531 | . | . | . | . | T | T | . | 1.98 | −0.51 | . | * | F | 3.40 | 1.86 |
| Arg | 532 | . | . | B | . | . | T | . | 0.98 | −0.46 | * | * | F | 2.36 | 1.37 |
| His | 533 | . | . | B | . | . | T | . | 0.38 | 0.23 | * | . | F | 1.42 | 1.11 |
| Ser | 534 | . | . | B | . | . | T | . | 0.27 | 0.13 | * | . | F | 0.93 | 0.68 |
| Thr | 535 | . | . | B | B | . | . | . | 0.72 | −0.26 | * | . | . | 0.64 | 0.58 |
| Ile | 536 | . | . | B | B | . | . | . | 0.13 | 0.50 | * | . | . | −0.60 | 0.67 |
| Leu | 537 | . | . | B | B | . | . | . | 0.02 | 0.69 | . | * | . | −0.60 | 0.35 |
| Asp | 538 | . | . | B | B | . | . | . | −0.80 | 0.70 | * | . | . | −0.60 | 0.39 |
| Tyr | 539 | . | . | B | B | . | . | . | −1.36 | 0.86 | * | . | . | −0.60 | 0.41 |
| Ile | 540 | . | . | B | B | . | . | . | −1.26 | 0.81 | * | . | . | −0.60 | 0.37 |
| Asn | 541 | . | . | B | B | . | . | . | −0.68 | 0.56 | * | . | . | −0.60 | 0.34 |
| Val | 542 | . | . | B | B | . | . | . | −0.46 | 1.04 | * | . | . | −0.60 | 0.32 |
| Val | 543 | . | . | B | B | . | . | . | −0.80 | 0.79 | * | . | . | −0.60 | 0.46 |
| Pro | 544 | . | . | B | . | . | . | . | −0.77 | 0.53 | * | . | F | −0.25 | 0.28 |

TABLE V-continued

| Res | | I | II | III | IV | V | VI | VII | VIII | IX | X | XI | XII | XIII | XIV |
|---|---|---|---|---|---|---|---|---|---|---|---|---|---|---|---|
| Thr | 545 | . | . | B | . | . | T | . | −0.69 | 0.56 | * | . | F | −0.05 | 0.59 |
| Ala | 546 | . | . | B | . | . | T | . | −1.28 | 0.60 | * | . | F | −0.05 | 0.65 |
| Gly | 547 | . | . | B | . | . | T | . | −0.42 | 0.46 | * | . | F | −0.05 | 0.43 |
| Pro | 548 | . | . | B | . | . | T | . | 0.48 | 0.43 | * | . | F | 0.21 | 0.51 |
| Leu | 549 | . | . | B | . | . | . | . | 0.80 | −0.06 | . | . | F | 1.32 | 1.01 |
| Ala | 550 | . | . | B | . | . | . | . | 1.11 | −0.56 | . | . | F | 1.88 | 2.00 |
| Gln | 551 | . | . | B | . | . | . | . | 1.70 | −0.59 | . | . | F | 2.14 | 2.08 |
| Lys | 552 | . | . | B | . | . | T | . | 2.09 | −0.61 | * | . | F | 2.60 | 4.38 |
| Arg | 553 | . | . | B | . | . | T | . | 1.71 | −1.30 | . | . | F | 2.34 | 8.66 |
| Asn | 554 | . | . | B | . | . | T | . | 2.21 | −1.30 | . | . | F | 2.08 | 5.05 |
| Gln | 555 | . | . | B | . | . | T | . | 2.59 | −1.21 | * | . | F | 2.10 | 3.65 |
| Lys | 556 | . | . | B | . | . | . | . | 2.59 | −0.79 | * | . | F | 1.92 | 2.88 |
| Ala | 557 | . | . | . | . | . | . | C | 2.24 | −0.39 | * | . | F | 1.84 | 2.88 |
| Thr | 558 | . | . | . | . | . | T | C | 1.92 | −0.40 | * | . | F | 2.32 | 2.23 |
| Pro | 559 | . | . | . | . | T | T | . | 2.03 | −0.37 | * | . | F | 2.80 | 1.72 |
| Asn | 560 | . | . | . | . | T | T | . | 1.72 | −0.37 | * | . | F | 2.52 | 3.34 |
| Ser | 561 | . | . | . | . | . | T | C | 1.47 | −0.39 | * | * | F | 2.04 | 3.34 |
| Pro | 562 | . | . | . | . | T | . | . | 1.24 | −0.44 | * | . | F | 1.76 | 3.34 |
| Arg | 563 | . | . | . | . | T | . | . | 1.34 | −0.19 | * | . | F | 1.48 | 1.71 |
| Thr | 564 | . | . | B | . | . | . | . | 1.34 | −0.16 | * | . | F | 0.80 | 1.98 |
| Pro | 565 | . | . | B | . | . | . | . | 1.00 | −0.11 | * | . | F | 0.80 | 1.98 |
| Leu | 566 | . | . | B | . | . | . | . | 0.71 | −0.11 | . | * | F | 0.65 | 1.00 |
| Pro | 567 | . | . | B | . | . | T | . | 0.71 | 0.39 | . | * | F | 0.25 | 0.70 |
| Pro | 568 | . | . | . | . | T | T | . | 0.30 | 0.33 | . | . | F | 0.65 | 0.70 |
| Gly | 569 | . | . | . | . | . | T | C | 0.40 | 0.29 | . | . | F | 0.60 | 1.14 |
| Ala | 570 | . | . | . | . | . | T | C | 0.61 | 0.03 | . | . | F | 0.94 | 1.14 |
| Pro | 571 | . | . | . | . | . | . | C | 1.12 | −0.40 | . | . | F | 1.68 | 1.27 |
| Ser | 572 | . | . | . | . | . | T | C | 1.38 | −0.44 | . | . | F | 2.22 | 1.72 |
| Pro | 573 | . | . | . | . | . | T | C | 1.63 | −0.87 | . | . | F | 2.86 | 3.41 |
| Glu | 574 | . | . | . | . | T | T | . | 1.98 | −1.37 | . | . | F | 3.40 | 4.41 |
| Ser | 575 | . | . | . | . | T | T | . | 2.57 | −1.40 | . | . | F | 3.06 | 5.29 |
| Lys | 576 | . | . | . | . | T | T | . | 2.82 | −1.39 | . | . | F | 2.94 | 5.93 |
| Lys | 577 | . | . | . | . | T | T | . | 3.17 | −1.81 | . | . | F | 2.82 | 6.84 |
| Asn | 578 | . | . | . | . | T | T | . | 3.38 | −1.81 | . | . | F | 2.70 | 10.21 |
| Gln | 579 | . | . | . | . | T | T | . | 3.13 | −1.80 | * | . | F | 2.58 | 8.84 |
| Lys | 580 | . | . | B | . | . | . | . | 3.43 | −1.04 | * | . | F | 2.20 | 6.93 |
| Lys | 581 | . | . | B | . | . | . | . | 2.58 | −0.64 | * | . | F | 1.98 | 7.46 |
| Gln | 582 | . | . | B | . | . | . | . | 2.32 | −0.36 | * | . | F | 1.46 | 3.55 |
| Tyr | 583 | . | . | B | . | . | . | . | 2.02 | −0.33 | . | . | . | 1.09 | 2.75 |
| Gln | 584 | . | . | B | . | . | . | . | 1.32 | 0.06 | . | . | . | 0.27 | 1.84 |
| Leu | 585 | . | . | B | . | . | T | . | 1.07 | 0.84 | . | . | . | −0.20 | 0.92 |
| Pro | 586 | . | . | B | . | . | T | . | 1.02 | 0.87 | . | . | F | −0.05 | 0.91 |
| Ser | 587 | . | . | B | . | . | T | . | 0.81 | 0.11 | . | . | F | 0.59 | 0.91 |
| Phe | 588 | . | . | B | . | . | T | . | 1.10 | 0.14 | . | . | F | 1.08 | 1.70 |
| Pro | 589 | . | . | . | . | . | . | C | 0.80 | −0.54 | . | . | F | 2.32 | 2.20 |
| Glu | 590 | . | . | . | . | . | . | C | 1.31 | −0.59 | . | . | F | 2.66 | 2.20 |
| Pro | 591 | . | . | . | . | T | T | . | 1.21 | −0.59 | . | . | F | 3.40 | 3.41 |
| Lys | 592 | . | . | . | . | T | T | . | 1.51 | −0.89 | . | . | F | 3.06 | 3.18 |
| Ser | 593 | . | . | . | . | . | T | C | 1.62 | −0.91 | . | . | F | 2.52 | 3.18 |
| Ser | 594 | . | . | . | . | . | T | C | 1.62 | −0.41 | * | . | F | 1.88 | 2.08 |
| Thr | 595 | . | . | . | . | . | . | C | 1.62 | −0.41 | * | . | F | 1.64 | 1.61 |
| Gln | 596 | . | . | . | . | . | . | C | 1.53 | −0.41 | * | . | F | 1.60 | 2.08 |
| Ala | 597 | . | . | . | . | . | T | C | 1.49 | −0.41 | * | . | F | 2.10 | 2.08 |
| Pro | 598 | . | . | . | . | . | T | C | 1.79 | −0.40 | . | . | F | 2.40 | 2.49 |
| Glu | 599 | . | . | . | . | . | T | C | 1.79 | −0.89 | . | . | F | 3.00 | 2.49 |
| Ser | 600 | . | . | . | . | . | T | C | 2.10 | −0.90 | . | . | F | 2.70 | 3.31 |
| Gln | 601 | . | A | . | . | . | . | C | 2.10 | −1.00 | . | . | F | 2.00 | 3.70 |
| Glu | 602 | . | A | . | . | . | . | C | 2.69 | −1.43 | . | . | F | 1.70 | 3.70 |
| Ser | 603 | . | A | . | . | . | . | C | 2.09 | −1.43 | . | . | F | 1.40 | 4.79 |
| Gln | 604 | A | A | . | . | . | . | . | 2.06 | −1.13 | . | . | F | 0.90 | 2.28 |
| Glu | 605 | A | A | . | . | . | . | . | 2.11 | −1.03 | * | . | F | 0.90 | 1.79 |
| Glu | 606 | A | A | . | . | . | . | . | 1.52 | −0.27 | * | . | F | 0.60 | 2.09 |
| Leu | 607 | . | A | B | . | . | . | . | 1.21 | −0.16 | . | . | . | 0.45 | 1.22 |
| His | 608 | . | A | B | . | . | . | . | 0.70 | −0.07 | . | . | . | 0.45 | 1.02 |
| Tyr | 609 | . | A | B | . | . | . | . | 0.70 | 0.61 | . | . | . | −0.60 | 0.48 |
| Ala | 610 | . | A | B | . | . | . | . | 0.00 | 1.01 | * | . | . | −0.60 | 0.95 |
| Thr | 611 | . | A | B | . | . | . | . | −0.21 | 1.11 | . | * | . | −0.60 | 0.60 |
| Leu | 612 | . | A | . | . | T | . | . | 0.26 | 1.04 | . | . | . | −0.20 | 0.59 |
| Asn | 613 | . | A | B | . | . | . | . | −0.57 | 0.71 | * | . | . | −0.60 | 0.58 |
| Phe | 614 | . | . | B | B | . | . | . | −0.21 | 0.86 | . | . | . | −0.60 | 0.30 |
| Pro | 615 | . | . | . | B | T | . | . | 0.17 | 0.37 | . | * | F | 0.25 | 0.71 |
| Gly | 616 | . | . | . | B | T | . | . | 0.59 | 0.11 | . | * | F | 0.25 | 0.68 |
| Val | 617 | . | . | . | B | . | . | C | 1.19 | −0.29 | . | * | F | 0.80 | 1.54 |
| Arg | 618 | . | . | . | . | . | T | C | 1.19 | −0.64 | . | * | F | 1.50 | 1.54 |
| Pro | 619 | . | . | . | . | . | T | C | 1.30 | −1.07 | . | * | F | 1.50 | 2.70 |
| Arg | 620 | . | . | . | . | . | T | C | 1.62 | −1.00 | . | * | F | 1.50 | 3.68 |
| Pro | 621 | . | . | B | . | . | T | . | 1.37 | −1.64 | . | * | F | 1.30 | 3.68 |

TABLE V-continued

| Res | | I | II | III | IV | V | VI | VII | VIII | IX | X | XI | XII | XIII | XIV |
|---|---|---|---|---|---|---|---|---|---|---|---|---|---|---|---|
| Glu | 622 | . | . | . | . | T | . | . | 2.01 | −1.03 | * | * | F | 1.84 | 2.35 |
| Ala | 623 | . | . | B | . | . | . | . | 1.94 | −1.03 | * | * | F | 1.78 | 1.86 |
| Arg | 624 | . | . | B | . | . | . | . | 1.81 | −1.03 | * | * | . | 1.97 | 2.40 |
| Met | 625 | . | . | B | . | . | T | . | 1.39 | −1.03 | * | * | F | 2.66 | 1.37 |
| Pro | 626 | . | . | . | . | T | T | . | 1.60 | −0.54 | . | * | F | 3.40 | 1.96 |
| Lys | 627 | . | . | . | . | T | T | . | 1.01 | −0.64 | . | * | F | 3.06 | 1.74 |
| Gly | 628 | . | . | . | . | . | T | C | 1.60 | −0.14 | * | . | F | 2.22 | 1.77 |
| Thr | 629 | . | A | . | . | . | . | C | 1.24 | −0.76 | * | . | F | 1.78 | 1.91 |
| Gln | 630 | . | A | B | . | . | . | . | 1.26 | −0.43 | . | . | F | 0.94 | 1.50 |
| Ala | 631 | . | A | B | . | . | . | . | 1.47 | 0.07 | . | . | F | 0.00 | 1.53 |
| Asp | 632 | . | A | B | . | . | . | . | 0.57 | −0.36 | . | . | . | 0.45 | 1.84 |
| Tyr | 633 | . | A | B | . | . | . | . | 0.96 | −0.20 | . | * | . | 0.30 | 0.79 |
| Ala | 634 | . | A | B | . | . | . | . | 0.57 | −0.60 | . | * | . | 0.75 | 1.56 |
| Glu | 635 | . | A | B | . | . | . | . | 0.57 | −0.31 | . | * | . | 0.30 | 0.81 |
| Val | 636 | . | A | B | . | . | . | . | 0.77 | 0.09 | . | * | . | −0.30 | 0.89 |
| Lys | 637 | . | A | B | . | . | . | . | 0.38 | −0.24 | . | * | . | 0.45 | 1.13 |
| Phe | 638 | . | A | B | . | . | . | . | 0.23 | −0.31 | . | * | . | 0.30 | 0.83 |
| Gln | 639 | . | A | B | . | . | . | . | 0.43 | 0.11 | . | * | . | −0.15 | 1.44 |

TABLE VI

| Res | | I | II | III | IV | V | VI | VII | VIII | IX | X | XI | XII | XIII | XIV |
|---|---|---|---|---|---|---|---|---|---|---|---|---|---|---|---|
| Met | 1 | . | A | B | . | . | . | . | −1.90 | 0.96 | . | . | . | −0.60 | 0.21 |
| Leu | 2 | . | A | B | . | . | . | . | −2.32 | 1.21 | . | . | . | −0.60 | 0.13 |
| Leu | 3 | . | A | B | . | . | . | . | −2.74 | 1.47 | . | . | . | −0.60 | 0.09 |
| Leu | 4 | . | A | B | . | . | . | . | −2.57 | 1.73 | . | . | . | −0.60 | 0.07 |
| Leu | 5 | . | A | B | . | . | . | . | −2.99 | 1.54 | . | . | . | −0.60 | 0.14 |
| Leu | 6 | . | A | B | . | . | . | . | −3.20 | 1.54 | . | . | . | −0.60 | 0.14 |
| Leu | 7 | . | A | B | . | . | . | . | −2.68 | 1.54 | . | . | . | −0.60 | 0.14 |
| Pro | 8 | . | A | B | . | . | . | . | −2.21 | 1.77 | * | . | . | −0.60 | 0.17 |
| Leu | 9 | . | A | B | . | . | . | . | −1.29 | 1.51 | . | . | . | −0.60 | 0.21 |
| Leu | 10 | . | A | B | . | . | . | . | −0.48 | 0.83 | . | * | . | −0.60 | 0.49 |
| Trp | 11 | . | A | . | . | . | . | C | 0.44 | 0.14 | . | * | . | −0.10 | 0.55 |
| Gly | 12 | . | A | . | . | . | . | C | 0.40 | −0.29 | . | * | F | 0.80 | 1.31 |
| Arg | 13 | . | A | . | . | . | . | C | 0.61 | −0.33 | . | * | F | 0.80 | 1.18 |
| Glu | 14 | . | A | B | . | . | . | . | 1.08 | −1.01 | . | * | F | 0.90 | 1.94 |
| Arg | 15 | . | A | B | . | . | . | . | 1.89 | −1.50 | . | * | F | 1.24 | 1.94 |
| Val | 16 | . | A | B | . | . | . | . | 2.22 | −1.53 | . | * | F | 1.58 | 1.71 |
| Glu | 17 | . | A | . | . | T | . | . | 2.27 | −1.53 | . | * | F | 2.32 | 1.98 |
| Gly | 18 | . | . | . | . | T | . | . | 2.16 | −1.14 | * | * | F | 2.86 | 1.35 |
| Gln | 19 | . | . | . | . | T | T | . | 2.27 | −0.74 | . | * | F | 3.40 | 2.93 |
| Lys | 20 | . | . | . | . | . | T | C | 2.20 | −1.39 | . | * | F | 2.86 | 3.32 |
| Ser | 21 | . | . | . | . | . | T | C | 3.06 | −1.39 | . | . | F | 2.86 | 6.70 |
| Asn | 22 | . | . | . | . | T | T | . | 2.81 | −1.81 | * | . | F | 3.06 | 6.46 |
| Arg | 23 | . | . | . | . | T | T | . | 2.86 | −1.46 | * | . | F | 3.06 | 5.06 |
| Lys | 24 | . | . | . | . | T | T | . | 2.04 | −1.07 | * | . | F | 3.06 | 5.06 |
| Asp | 25 | . | . | . | . | T | T | . | 1.69 | −0.77 | * | . | F | 3.40 | 2.60 |
| Tyr | 26 | . | . | B | . | . | T | . | 1.39 | −0.69 | . | * | . | 2.51 | 1.91 |
| Ser | 27 | . | . | B | B | . | . | . | 1.39 | −0.07 | . | * | . | 1.32 | 0.95 |
| Leu | 28 | . | . | B | B | . | . | . | 0.98 | 0.33 | . | * | . | 0.38 | 0.98 |
| Thr | 29 | . | . | B | B | . | . | . | 0.63 | 0.71 | . | * | . | −0.26 | 0.84 |
| Met | 30 | . | . | B | . | . | T | . | −0.22 | 0.34 | . | * | . | 0.10 | 0.84 |
| Gln | 31 | . | . | B | . | . | T | . | −0.29 | 0.60 | . | * | F | −0.05 | 0.76 |
| Ser | 32 | . | . | B | . | . | T | . | −0.84 | 0.40 | . | * | F | 0.25 | 0.76 |
| Ser | 33 | . | . | B | . | . | T | . | −0.03 | 0.56 | . | * | F | −0.05 | 0.57 |
| Val | 34 | . | . | B | B | . | . | . | 0.28 | 0.34 | . | * | F | −0.15 | 0.57 |
| Thr | 35 | . | . | B | B | . | . | . | 0.53 | −0.06 | . | * | F | 0.45 | 0.73 |
| Val | 36 | . | . | B | B | . | . | . | −0.07 | −0.01 | . | . | F | 0.45 | 0.54 |
| Gln | 37 | . | . | B | B | . | . | . | −0.43 | 0.21 | . | . | F | −0.15 | 0.72 |
| Glu | 38 | . | . | B | B | . | . | . | −0.99 | 0.14 | . | . | F | −0.15 | 0.27 |
| Gly | 39 | . | . | . | B | T | . | . | −0.17 | 0.30 | . | * | . | 0.10 | 0.27 |
| Met | 40 | . | . | B | B | . | . | . | −0.71 | 0.16 | * | * | . | −0.30 | 0.21 |
| Cys | 41 | . | . | B | B | . | . | . | 0.26 | 0.40 | * | * | . | −0.30 | 0.09 |
| Val | 42 | . | . | B | B | . | . | . | −0.41 | 0.40 | * | * | . | −0.30 | 0.18 |
| His | 43 | . | . | B | B | . | . | . | −0.71 | 0.54 | * | * | . | −0.60 | 0.10 |
| Val | 44 | . | . | B | B | . | . | . | −1.07 | 0.31 | . | * | . | −0.30 | 0.24 |
| Arg | 45 | . | . | B | B | . | . | . | −0.77 | 0.53 | . | * | . | −0.60 | 0.28 |
| Cys | 46 | . | . | B | . | . | T | . | −0.34 | 0.27 | . | * | . | 0.10 | 0.28 |
| Ser | 47 | . | . | . | . | T | T | . | 0.30 | 0.53 | . | * | . | 0.20 | 0.59 |
| Phe | 48 | . | . | . | . | T | T | . | −0.52 | 0.31 | * | * | . | 0.50 | 0.46 |
| Ser | 49 | . | . | B | . | . | T | . | 0.33 | 0.96 | * | * | . | −0.20 | 0.64 |
| Tyr | 50 | . | . | B | . | . | . | . | −0.08 | 0.39 | . | * | . | −0.10 | 0.80 |
| Pro | 51 | . | . | B | . | . | T | . | 0.59 | 0.39 | . | * | . | 0.25 | 1.24 |

TABLE VI-continued

| Res | | I | II | III | IV | V | VI | VII | VIII | IX | X | XI | XII | XIII | XIV |
|---|---|---|---|---|---|---|---|---|---|---|---|---|---|---|---|
| Val | 52 | . | . | . | . | T | T | . | 0.58 | 0.00 | * | * | F | 1.40 | 1.60 |
| Asp | 53 | . | . | B | . | . | T | . | 1.28 | 0.10 | * | * | F | 0.74 | 1.47 |
| Ser | 54 | . | . | B | . | . | T | . | 1.28 | −0.66 | . | * | F | 1.98 | 1.59 |
| Gln | 55 | . | . | B | . | . | . | . | 1.52 | −0.70 | . | * | F | 2.12 | 2.87 |
| Thr | 56 | . | . | . | . | T | . | . | 1.52 | −1.34 | . | * | F | 2.86 | 2.87 |
| Asp | 57 | . | . | . | . | T | T | . | 1.52 | −0.91 | . | * | F | 3.40 | 3.31 |
| Ser | 58 | . | . | . | . | . | T | C | 1.49 | −0.66 | . | . | F | 2.86 | 1.42 |
| Asp | 59 | . | . | B | . | . | T | . | 1.44 | −0.56 | . | . | F | 2.32 | 1.34 |
| Pro | 60 | . | . | B | . | . | T | . | 1.20 | −0.61 | . | . | F | 1.83 | 0.79 |
| Val | 61 | . | . | . | . | T | . | . | 1.22 | 0.14 | . | . | . | 0.64 | 0.93 |
| His | 62 | . | . | B | . | . | T | . | 0.52 | 0.67 | * | . | . | −0.20 | 0.58 |
| Gly | 63 | . | . | B | . | . | T | . | 0.93 | 1.46 | * | . | . | −0.20 | 0.33 |
| Tyr | 64 | . | . | B | . | . | T | . | 0.34 | 1.03 | * | . | . | −0.20 | 0.86 |
| Trp | 65 | . | . | B | . | . | T | . | 0.21 | 0.89 | * | . | . | −0.20 | 0.64 |
| Phe | 66 | . | . | B | . | . | . | . | 1.07 | 0.81 | * | . | . | −0.09 | 0.64 |
| Arg | 67 | . | . | B | . | . | T | . | 1.10 | 0.79 | * | * | . | 0.42 | 0.66 |
| Ala | 68 | . | . | . | . | T | T | . | 0.56 | 0.03 | * | * | . | 1.58 | 1.04 |
| Gly | 69 | . | . | . | . | T | T | . | 0.50 | −0.20 | * | * | F | 2.49 | 0.85 |
| Asn | 70 | . | . | . | . | T | T | . | 0.50 | −0.60 | * | * | F | 3.10 | 0.58 |
| Asp | 71 | . | . | . | . | . | . | C | 1.24 | 0.31 | * | * | F | 1.49 | 0.60 |
| Ile | 72 | . | . | . | . | . | . | C | 0.54 | −0.19 | * | * | F | 1.93 | 1.22 |
| Ser | 73 | . | A | . | . | T | . | . | 0.92 | −0.11 | . | * | . | 1.32 | 0.76 |
| Trp | 74 | . | A | B | . | . | . | . | 0.41 | −0.09 | . | * | . | 0.61 | 0.71 |
| Lys | 75 | . | A | B | . | . | . | . | −0.18 | 0.56 | . | * | . | −0.60 | 0.75 |
| Ala | 76 | . | A | B | . | . | . | . | −0.49 | 0.37 | . | * | . | −0.30 | 0.56 |
| Pro | 77 | . | . | B | . | . | . | . | 0.40 | 0.47 | . | * | . | −0.40 | 0.77 |
| Val | 78 | . | . | B | . | . | . | . | 0.70 | −0.04 | . | * | . | 0.50 | 0.62 |
| Ala | 79 | . | . | B | . | . | . | . | 0.78 | 0.36 | . | * | . | −0.10 | 0.99 |
| Thr | 80 | . | . | . | . | . | . | C | 0.14 | 0.29 | . | . | F | 0.25 | 0.99 |
| Asn | 81 | . | . | . | . | . | . | C | 0.44 | 0.36 | . | . | F | 0.40 | 1.35 |
| Asn | 82 | . | . | . | . | . | T | C | 0.07 | 0.63 | . | . | F | 0.30 | 1.41 |
| Pro | 83 | . | . | . | . | . | T | C | 0.07 | 0.63 | . | . | F | 0.15 | 0.98 |
| Ala | 84 | . | . | . | . | T | T | . | 0.66 | 0.79 | * | . | . | 0.20 | 0.45 |
| Trp | 85 | . | . | . | . | . | T | C | 0.97 | 0.79 | . | . | . | 0.00 | 0.49 |
| Ala | 86 | . | A | B | . | . | . | . | 0.97 | 0.39 | . | . | . | −0.30 | 0.55 |
| Val | 87 | . | A | B | . | . | . | . | 0.66 | −0.04 | * | * | . | 0.30 | 0.94 |
| Gln | 88 | . | A | B | . | . | . | . | 0.98 | −0.06 | * | . | F | 0.94 | 1.29 |
| Glu | 89 | . | A | B | . | . | . | . | 1.57 | −0.97 | . | * | F | 1.58 | 2.50 |
| Glu | 90 | . | A | B | . | . | . | . | 1.97 | −1.47 | . | * | F | 1.92 | 5.62 |
| Thr | 91 | . | . | . | . | T | T | . | 1.86 | −2.11 | . | * | F | 3.06 | 6.36 |
| Arg | 92 | . | . | . | . | T | T | . | 2.68 | −1.73 | . | * | F | 3.40 | 3.18 |
| Asp | 93 | . | . | . | . | T | T | . | 1.87 | −1.23 | . | * | F | 3.06 | 2.50 |
| Arg | 94 | . | . | B | . | . | T | . | 1.06 | −0.54 | * | * | . | 2.17 | 1.43 |
| Phe | 95 | . | A | B | . | . | . | . | 0.71 | −0.34 | * | * | . | 0.98 | 0.60 |
| His | 96 | . | A | B | . | . | . | . | 1.02 | 0.09 | * | * | . | 0.04 | 0.36 |
| Leu | 97 | . | A | . | . | . | . | C | 0.70 | 0.09 | . | * | . | −0.10 | 0.30 |
| Leu | 98 | . | A | . | . | T | . | . | 0.70 | 0.51 | . | * | . | −0.20 | 0.54 |
| Gly | 99 | . | A | . | . | T | . | . | 0.28 | 0.13 | * | * | F | 0.59 | 0.69 |
| Asp | 100 | . | . | . | . | . | . | C | 1.02 | 0.11 | * | * | F | 1.08 | 1.21 |
| Pro | 101 | . | . | . | . | T | . | . | 1.06 | −0.57 | . | . | F | 2.52 | 2.93 |
| Gln | 102 | . | . | . | . | T | . | . | 1.20 | −0.86 | . | . | F | 2.86 | 4.76 |
| Thr | 103 | . | . | . | . | T | T | . | 1.70 | −0.71 | . | . | F | 3.40 | 1.53 |
| Lys | 104 | . | . | B | . | . | T | . | 1.23 | −0.23 | . | . | F | 2.36 | 1.43 |
| Asn | 105 | . | . | B | . | . | T | . | 0.93 | 0.03 | . | . | F | 1.27 | 0.68 |
| Cys | 106 | . | . | B | . | . | T | . | 0.26 | 0.01 | * | * | . | 0.78 | 0.63 |
| Thr | 107 | . | . | B | B | . | . | . | 0.37 | 0.21 | * | * | . | 0.04 | 0.22 |
| Leu | 108 | . | . | B | B | . | . | . | 0.68 | 0.21 | * | * | . | −0.30 | 0.27 |
| Ser | 109 | . | . | B | B | . | . | . | 0.04 | −0.19 | * | . | . | 0.30 | 0.84 |
| Ile | 110 | . | . | B | B | . | . | . | 0.16 | −0.26 | * | * | . | 0.30 | 0.59 |
| Arg | 111 | . | . | B | B | . | . | . | 0.22 | −0.74 | * | * | F | 0.90 | 1.39 |
| Asp | 112 | . | A | B | . | . | . | . | 0.23 | −0.81 | * | . | F | 0.90 | 1.03 |
| Ala | 113 | . | A | B | . | . | . | . | 1.04 | −0.81 | * | . | F | 0.90 | 1.97 |
| Arg | 114 | . | A | B | . | . | . | . | 0.76 | −1.50 | * | . | . | 1.03 | 1.68 |
| Met | 115 | . | A | B | . | . | . | . | 1.30 | −1.00 | . | * | F | 1.46 | 1.01 |
| Ser | 116 | . | A | . | . | . | . | C | 1.30 | −0.57 | . | * | F | 1.79 | 0.99 |
| Asp | 117 | . | . | . | . | T | T | . | 1.06 | −1.07 | * | * | F | 2.67 | 0.99 |
| Ala | 118 | . | . | . | . | T | T | . | 0.94 | −0.31 | * | * | F | 2.80 | 1.57 |
| Gly | 119 | . | . | . | . | T | T | . | 0.13 | −0.14 | * | * | F | 2.52 | 1.02 |
| Arg | 120 | . | . | B | . | . | T | . | 0.84 | 0.26 | * | * | . | 0.94 | 0.53 |
| Tyr | 121 | . | . | B | B | . | . | . | 0.54 | 0.26 | * | * | . | 0.41 | 1.02 |
| Phe | 122 | . | . | B | B | . | . | . | 0.54 | 0.37 | * | * | . | 0.13 | 1.02 |
| Phe | 123 | . | . | B | B | . | . | . | 1.18 | −0.06 | * | * | . | 0.30 | 0.90 |
| Arg | 124 | . | . | B | B | . | . | . | 1.18 | −0.06 | * | * | . | 0.79 | 1.15 |
| Met | 125 | . | . | B | . | . | . | . | 1.07 | −0.39 | * | * | . | 1.33 | 1.32 |
| Glu | 126 | . | . | . | . | T | T | . | 0.42 | −0.77 | * | * | F | 2.72 | 2.45 |
| Lys | 127 | . | . | . | . | T | T | . | 1.17 | −0.87 | * | * | F | 2.91 | 0.88 |
| Gly | 128 | . | . | . | . | T | T | . | 1.58 | −0.87 | * | * | F | 3.40 | 1.77 |

TABLE VI-continued

| Res | | I | II | III | IV | V | VI | VII | VIII | IX | X | XI | XII | XIII | XIV |
|---|---|---|---|---|---|---|---|---|---|---|---|---|---|---|---|
| Asn | 129 | . | . | . | . | T | T | . | 1.47 | −0.57 | * | * | F | 3.06 | 1.08 |
| Ile | 130 | . | . | . | . | . | . | C | 1.82 | −0.17 | . | * | F | 1.87 | 0.86 |
| Lys | 131 | . | . | . | . | T | . | . | 1.87 | 0.59 | . | * | . | 0.83 | 1.37 |
| Trp | 132 | . | . | . | . | T | . | . | 1.58 | 0.16 | . | * | . | 0.79 | 1.70 |
| Asn | 133 | . | . | B | . | . | T | . | 1.92 | 0.51 | . | * | . | 0.19 | 3.81 |
| Tyr | 134 | . | . | B | . | . | T | . | 1.92 | −0.17 | . | * | . | 1.33 | 3.18 |
| Lys | 135 | . | . | B | . | . | T | . | 2.00 | 0.23 | * | * | . | 0.97 | 5.23 |
| Tyr | 136 | . | . | . | . | T | T | . | 1.66 | 0.00 | . | * | F | 2.36 | 2.68 |
| Asp | 137 | . | . | . | . | T | . | . | 1.09 | −0.01 | . | * | F | 2.40 | 2.30 |
| Gln | 138 | . | . | B | B | . | . | . | 1.09 | −0.13 | . | * | F | 1.41 | 0.85 |
| Leu | 139 | . | . | B | B | . | . | . | 0.48 | 0.27 | . | * | . | 0.42 | 0.87 |
| Ser | 140 | . | . | B | B | . | . | . | 0.12 | 0.16 | . | * | . | 0.18 | 0.39 |
| Val | 141 | . | . | B | B | . | . | . | −0.22 | 0.64 | * | * | . | −0.36 | 0.32 |
| Asn | 142 | . | . | B | B | . | . | . | −1.03 | 0.74 | . | * | . | −0.60 | 0.40 |
| Val | 143 | . | . | B | B | . | . | . | −1.34 | 0.74 | . | * | . | −0.60 | 0.24 |
| Thr | 144 | . | . | B | B | . | . | . | −0.57 | 0.84 | * | * | . | −0.60 | 0.47 |
| Ala | 145 | . | . | B | B | . | . | . | −0.16 | 0.70 | . | * | . | −0.60 | 0.40 |
| Leu | 146 | . | . | B | B | . | . | . | 0.49 | 0.30 | . | * | . | −0.15 | 1.06 |
| Thr | 147 | . | . | B | B | . | . | . | 0.49 | 0.09 | . | * | . | −0.15 | 1.14 |
| His | 148 | . | . | B | B | . | . | . | 0.46 | 0.00 | . | * | . | 0.45 | 1.81 |
| Arg | 149 | . | . | B | . | . | T | . | −0.04 | 0.19 | . | * | . | 0.25 | 1.54 |
| Pro | 150 | . | . | B | . | . | T | . | −0.34 | 0.19 | . | * | . | 0.10 | 0.88 |
| Asn | 151 | . | . | . | . | T | T | . | 0.26 | 0.39 | . | * | . | 0.50 | 0.45 |
| Ile | 152 | . | . | B | . | . | T | . | 0.22 | 0.31 | . | * | . | 0.10 | 0.36 |
| Leu | 153 | . | . | B | . | . | . | . | −0.06 | 0.74 | . | * | . | −0.40 | 0.23 |
| Ile | 154 | . | . | B | . | . | T | . | −0.98 | 0.80 | * | * | . | −0.20 | 0.21 |
| Pro | 155 | . | . | B | . | . | T | . | −0.77 | 1.09 | . | * | F | −0.05 | 0.24 |
| Gly | 156 | . | . | B | . | . | T | . | −1.07 | 0.40 | . | * | F | 0.25 | 0.51 |
| Thr | 157 | . | . | B | . | . | T | . | −0.52 | 0.10 | . | . | F | 0.25 | 0.97 |
| Leu | 158 | . | . | B | . | . | . | . | −0.38 | −0.16 | . | . | F | 0.65 | 0.62 |
| Glu | 159 | . | . | B | . | . | T | . | −0.19 | −0.01 | . | . | F | 0.85 | 0.34 |
| Ser | 160 | . | . | . | . | T | T | . | 0.02 | 0.34 | . | . | F | 0.65 | 0.20 |
| Gly | 161 | . | . | . | . | T | T | . | 0.37 | 0.26 | . | . | F | 0.61 | 0.42 |
| Cys | 162 | . | . | . | . | T | T | . | −0.13 | −0.03 | . | . | . | 1.02 | 0.39 |
| Phe | 163 | . | . | B | B | . | . | . | 0.37 | 0.66 | . | . | . | −0.72 | 0.24 |
| Gln | 164 | . | . | B | B | . | . | . | −0.30 | 0.76 | . | . | . | −0.76 | 0.35 |
| Asn | 165 | . | . | . | B | T | . | . | −0.30 | 0.90 | * | . | . | −0.40 | 0.35 |
| Leu | 166 | . | . | B | B | . | . | . | −0.81 | 0.71 | * | . | . | −0.76 | 0.55 |
| Thr | 167 | . | . | . | B | T | . | . | −0.36 | 0.57 | * | . | . | −0.32 | 0.23 |
| Cys | 168 | . | . | . | B | T | . | . | 0.06 | 0.60 | * | . | . | −0.28 | 0.22 |
| Ser | 169 | . | . | . | B | T | . | . | −0.53 | 1.11 | * | . | . | −0.24 | 0.29 |
| Val | 170 | . | . | . | B | . | . | C | −1.20 | 0.93 | * | * | . | −0.40 | 0.20 |
| Pro | 171 | . | . | . | . | T | . | . | −0.39 | 1.01 | * | . | . | 0.00 | 0.20 |
| Trp | 172 | . | . | . | . | T | . | . | −0.08 | 0.44 | . | . | . | 0.00 | 0.26 |
| Ala | 173 | . | . | B | . | . | . | . | 0.24 | 0.46 | . | . | . | −0.12 | 0.61 |
| Cys | 174 | . | . | B | . | . | . | . | 0.23 | 0.24 | . | . | . | 0.46 | 0.39 |
| Glu | 175 | . | . | . | . | T | T | . | 0.88 | 0.30 | . | . | F | 1.49 | 0.53 |
| Gln | 176 | . | . | . | . | T | T | . | 0.88 | −0.19 | . | . | F | 2.37 | 0.81 |
| Gly | 177 | . | . | . | . | T | T | . | 0.57 | −0.26 | . | . | F | 2.80 | 2.35 |
| Thr | 178 | . | . | . | . | . | T | C | 0.27 | −0.21 | . | . | F | 2.32 | 1.34 |
| Pro | 179 | . | . | . | . | . | . | C | 0.63 | 0.47 | * | . | F | 0.79 | 0.54 |
| Pro | 180 | . | . | . | B | . | . | C | 0.34 | 0.46 | * | . | F | 0.31 | 0.74 |
| Met | 181 | . | . | B | B | . | . | . | −0.26 | 0.94 | * | . | . | −0.32 | 0.54 |
| Ile | 182 | . | . | B | B | . | . | . | −0.26 | 1.07 | . | . | . | −0.60 | 0.34 |
| Ser | 183 | . | . | B | B | . | . | . | −0.26 | 1.07 | . | . | . | −0.60 | 0.22 |
| Trp | 184 | . | . | B | B | . | . | . | −0.34 | 1.13 | * | . | . | −0.60 | 0.32 |
| Met | 185 | . | . | B | B | . | . | . | −0.99 | 0.90 | * | . | . | −0.60 | 0.61 |
| Gly | 186 | . | . | . | B | T | . | . | −0.69 | 0.86 | * | . | . | −0.20 | 0.34 |
| Thr | 187 | . | . | . | B | . | . | C | −0.01 | 0.86 | * | . | F | −0.25 | 0.43 |
| Ser | 188 | . | . | . | B | . | . | C | −0.52 | 0.37 | * | . | F | 0.05 | 0.67 |
| Val | 189 | . | . | B | B | . | . | . | −0.27 | 0.44 | . | . | F | −0.45 | 0.56 |
| Ser | 190 | . | . | . | . | . | . | C | 0.12 | 0.51 | . | . | F | −0.05 | 0.53 |
| Pro | 191 | . | . | . | . | . | . | C | 0.17 | 0.46 | . | . | F | −0.05 | 0.61 |
| Leu | 192 | . | . | . | . | . | . | C | 0.17 | 0.46 | . | . | F | 0.34 | 1.10 |
| His | 193 | . | . | B | . | . | T | . | 0.16 | 0.30 | * | . | F | 0.88 | 1.19 |
| Pro | 194 | . | . | B | . | . | T | . | 1.12 | 0.40 | * | . | F | 0.82 | 1.11 |
| Ser | 195 | . | . | . | . | T | T | . | 1.12 | −0.03 | * | . | F | 2.36 | 2.64 |
| Thr | 196 | . | . | . | . | . | T | C | 1.03 | −0.33 | . | . | F | 2.40 | 2.60 |
| Thr | 197 | . | . | B | . | . | T | . | 0.99 | −0.44 | . | . | F | 1.96 | 2.25 |
| Arg | 198 | . | . | B | . | . | T | . | 0.21 | −0.23 | . | . | F | 1.72 | 1.25 |
| Ser | 199 | . | . | B | . | . | T | . | 0.11 | 0.07 | . | . | F | 0.73 | 0.71 |
| Ser | 200 | . | . | B | . | . | T | . | −0.40 | 0.07 | . | . | F | 0.49 | 0.71 |
| Val | 201 | . | . | B | B | . | . | . | −0.98 | 0.27 | . | . | . | −0.30 | 0.30 |
| Leu | 202 | . | . | B | B | . | . | . | −0.88 | 0.96 | . | . | . | −0.60 | 0.16 |
| Thr | 203 | . | . | B | B | . | . | . | −0.99 | 1.00 | . | . | . | −0.60 | 0.18 |
| Leu | 204 | . | . | B | B | . | . | . | −0.90 | 1.01 | * | . | . | −0.60 | 0.42 |
| Ile | 205 | . | . | B | B | . | . | . | −0.60 | 0.80 | * | . | . | −0.60 | 0.79 |

TABLE VI-continued

| Res | | I | II | III | IV | V | VI | VII | VIII | IX | X | XI | XII | XIII | XIV |
|---|---|---|---|---|---|---|---|---|---|---|---|---|---|---|---|
| Pro | 206 | . | . | B | B | . | . | . | 0.22 | 0.51 | * | . | F | −0.45 | 0.95 |
| Gln | 207 | . | . | B | . | . | . | . | 1.00 | 0.53 | * | . | F | −0.10 | 1.57 |
| Pro | 208 | . | . | B | . | . | . | . | 0.97 | 0.34 | * | . | F | 0.20 | 3.04 |
| Gln | 209 | . | . | . | . | T | . | . | 1.47 | 0.09 | * | . | F | 0.60 | 1.95 |
| His | 210 | . | . | . | . | T | T | . | 2.06 | 0.14 | * | . | F | 0.80 | 1.62 |
| His | 211 | . | . | . | . | T | T | . | 1.46 | 0.13 | . | . | F | 0.80 | 1.41 |
| Gly | 212 | . | . | . | . | T | T | . | 1.14 | 0.39 | . | . | F | 0.65 | 0.67 |
| Thr | 213 | . | . | . | . | T | T | . | 0.69 | 0.47 | . | . | F | 0.35 | 0.71 |
| Ser | 214 | . | . | . | B | T | . | . | 0.69 | 0.54 | * | . | F | −0.05 | 0.28 |
| Leu | 215 | . | . | B | B | . | . | . | −0.13 | 0.44 | * | . | . | −0.60 | 0.49 |
| Thr | 216 | . | . | B | B | . | . | . | −0.41 | 0.66 | . | * | . | −0.60 | 0.25 |
| Cys | 217 | . | . | B | B | . | . | . | −0.88 | 0.66 | . | * | . | −0.60 | 0.27 |
| Gln | 218 | . | . | B | B | . | . | . | −0.78 | 0.96 | . | * | . | −0.60 | 0.27 |
| Val | 219 | . | . | B | B | . | . | . | −0.82 | 0.70 | . | * | . | −0.60 | 0.29 |
| Thr | 220 | . | . | B | B | . | . | . | −0.60 | 0.64 | . | * | . | −0.60 | 0.54 |
| Leu | 221 | . | . | B | . | . | T | . | −0.63 | 0.57 | . | . | . | −0.20 | 0.31 |
| Pro | 222 | . | . | B | . | . | T | . | −0.82 | 0.60 | . | . | F | −0.05 | 0.42 |
| Gly | 223 | . | . | . | . | T | T | . | −1.13 | 0.60 | . | . | F | 0.35 | 0.21 |
| Ala | 224 | . | . | . | . | . | T | C | −0.59 | 0.60 | . | . | F | 0.35 | 0.38 |
| Gly | 225 | . | . | B | . | . | . | . | −0.28 | 0.40 | * | . | F | 0.15 | 0.35 |
| Val | 226 | . | . | B | . | . | . | . | 0.64 | 0.37 | * | . | F | 0.65 | 0.57 |
| Thr | 227 | . | . | B | . | . | T | . | 0.54 | −0.06 | * | . | F | 1.80 | 1.10 |
| Thr | 228 | . | . | B | . | . | T | . | 0.00 | −0.07 | * | . | F | 2.00 | 1.61 |
| Asn | 229 | . | . | B | . | . | T | . | 0.59 | 0.19 | * | . | F | 1.20 | 1.52 |
| Arg | 230 | . | . | B | . | . | T | . | 0.12 | −0.06 | . | . | F | 1.60 | 1.83 |
| Thr | 231 | . | . | B | B | . | . | . | 0.98 | 0.14 | . | * | F | 0.40 | 1.04 |
| Ile | 232 | . | . | B | B | . | . | . | 0.43 | 0.06 | * | * | . | 0.05 | 1.04 |
| Gln | 233 | . | . | B | B | . | . | . | 0.44 | 0.30 | * | * | . | −0.30 | 0.40 |
| Leu | 234 | . | . | B | B | . | . | . | 0.20 | 0.69 | * | * | . | −0.60 | 0.37 |
| Asn | 235 | . | . | B | . | . | T | . | −0.12 | 0.96 | * | * | . | −0.20 | 0.82 |
| Val | 236 | . | . | B | . | . | T | . | −0.02 | 0.70 | . | * | . | −0.20 | 0.73 |
| Ser | 237 | . | . | . | . | . | T | C | 0.87 | 0.73 | . | * | . | 0.15 | 1.37 |
| Tyr | 238 | . | . | . | . | . | T | C | 0.87 | 0.44 | . | * | F | 0.30 | 1.48 |
| Pro | 239 | . | . | . | . | . | . | C | 0.87 | 0.44 | . | * | F | 0.10 | 3.21 |
| Pro | 240 | . | . | . | . | T | T | . | 0.56 | 0.49 | . | . | F | 0.50 | 1.97 |
| Gln | 241 | . | . | . | . | T | T | . | 0.56 | 0.59 | . | . | F | 0.50 | 1.82 |
| Asn | 242 | . | . | B | . | . | T | . | 0.54 | 0.47 | . | . | F | −0.05 | 0.87 |
| Leu | 243 | . | . | B | . | . | T | . | −0.07 | 0.53 | . | . | . | −0.20 | 0.81 |
| Thr | 244 | . | . | B | B | . | . | . | −0.56 | 0.74 | * | . | . | −0.60 | 0.35 |
| Val | 245 | . | . | B | B | . | . | . | −0.34 | 1.13 | * | . | . | −0.60 | 0.19 |
| Thr | 246 | . | . | B | B | . | . | . | −0.69 | 1.13 | . | . | . | −0.60 | 0.39 |
| Val | 247 | . | . | B | B | . | . | . | −0.69 | 0.87 | . | * | . | −0.60 | 0.27 |
| Phe | 248 | . | . | B | B | . | . | . | −0.22 | 0.39 | . | . | . | −0.30 | 0.63 |
| Gln | 249 | . | . | B | B | . | . | . | −0.22 | 0.17 | . | . | F | 0.09 | 0.43 |
| Gly | 250 | . | . | . | . | . | T | C | 0.04 | 0.17 | . | . | F | 0.93 | 0.84 |
| Glu | 251 | . | . | . | . | . | T | C | 0.06 | 0.03 | . | * | F | 1.17 | 0.98 |
| Gly | 252 | . | . | . | . | . | T | C | 0.60 | −0.37 | . | . | F | 2.01 | 0.76 |
| Thr | 253 | . | . | . | . | . | T | C | 0.71 | −0.29 | . | * | F | 2.40 | 1.11 |
| Ala | 254 | . | . | B | . | . | . | . | −0.10 | −0.21 | . | . | F | 1.61 | 0.65 |
| Ser | 255 | . | . | B | . | . | . | . | −0.10 | 0.47 | . | . | F | 0.47 | 0.54 |
| Thr | 256 | . | . | B | . | . | . | . | −0.10 | 0.47 | . | . | F | 0.23 | 0.37 |
| Ala | 257 | . | . | B | . | . | . | . | −0.06 | 0.39 | . | . | F | 0.29 | 0.59 |
| Leu | 258 | . | . | B | . | . | . | . | −0.04 | 0.27 | . | . | F | 0.05 | 0.59 |
| Gly | 259 | . | . | . | . | T | . | . | 0.24 | 0.27 | . | . | F | 0.45 | 0.55 |
| Asn | 260 | . | . | . | . | . | T | C | −0.27 | 0.17 | . | . | F | 0.45 | 0.72 |
| Ser | 261 | . | . | . | . | . | T | C | −0.26 | 0.36 | . | . | F | 0.45 | 0.72 |
| Ser | 262 | . | . | . | . | . | T | C | −0.52 | 0.06 | . | . | F | 0.45 | 0.98 |
| Ser | 263 | . | . | . | . | . | T | C | −0.52 | 0.27 | . | . | F | 0.45 | 0.45 |
| Leu | 264 | . | A | B | . | . | . | . | −0.18 | 0.56 | . | . | F | −0.45 | 0.28 |
| Ser | 265 | . | A | B | . | . | . | . | −0.52 | 0.17 | . | . | . | −0.30 | 0.36 |
| Val | 266 | . | A | B | . | . | . | . | −0.22 | 0.21 | . | . | . | −0.30 | 0.27 |
| Leu | 267 | . | A | B | . | . | . | . | −0.22 | 0.23 | . | . | . | −0.13 | 0.56 |
| Glu | 268 | . | A | B | . | . | . | . | −0.73 | −0.07 | * | . | F | 0.79 | 0.56 |
| Gly | 269 | . | . | . | . | T | T | . | 0.19 | 0.23 | * | . | F | 1.16 | 0.62 |
| Gln | 270 | . | . | . | . | T | T | . | −0.32 | −0.41 | * | . | F | 2.08 | 1.47 |
| Ser | 271 | . | . | B | . | . | T | . | −0.32 | −0.41 | * | . | F | 1.70 | 0.70 |
| Leu | 272 | . | . | B | . | . | T | . | −0.18 | 0.23 | * | . | F | 0.93 | 0.53 |
| Arg | 273 | . | . | B | B | . | . | . | −0.77 | 0.37 | * | . | . | 0.21 | 0.16 |
| Leu | 274 | . | . | B | B | . | . | . | −1.28 | 0.47 | * | * | . | −0.26 | 0.12 |
| Val | 275 | . | . | B | B | . | . | . | −1.28 | 0.73 | * | * | . | −0.43 | 0.11 |
| Cys | 276 | . | . | B | B | . | . | . | −1.28 | 0.04 | * | * | . | −0.30 | 0.09 |
| Ala | 277 | . | . | B | B | . | . | . | −0.47 | 0.43 | * | * | . | −0.60 | 0.15 |
| Val | 278 | . | . | B | B | . | . | . | −0.79 | 0.14 | * | * | . | 0.00 | 0.33 |
| Asp | 279 | . | . | . | . | T | T | . | −0.19 | −0.07 | . | . | F | 1.85 | 0.96 |
| Ser | 280 | . | . | . | . | . | T | C | 0.08 | −0.21 | . | * | F | 2.10 | 1.46 |
| Asn | 281 | . | . | . | . | . | T | C | 0.86 | −0.21 | . | * | F | 2.40 | 1.99 |
| Pro | 282 | . | . | . | . | . | T | C | 0.63 | −0.86 | . | * | F | 3.00 | 2.34 |

TABLE VI-continued

| Res | | I | II | III | IV | V | VI | VII | VIII | IX | X | XI | XII | XIII | XIV |
|---|---|---|---|---|---|---|---|---|---|---|---|---|---|---|---|
| Pro | 283 | . | . | . | . | T | . | . | 1.19 | −0.17 | . | * | F | 2.40 | 1.44 |
| Ala | 284 | . | . | . | . | T | . | . | 0.90 | −0.17 | . | * | F | 2.10 | 1.20 |
| Arg | 285 | . | . | B | B | . | . | . | 0.89 | 0.34 | * | * | . | 0.30 | 0.82 |
| Leu | 286 | . | . | B | B | . | . | . | 0.60 | 0.40 | * | * | . | −0.30 | 0.76 |
| Ser | 287 | . | . | B | B | . | . | . | 0.92 | 0.89 | * | * | . | −0.60 | 0.79 |
| Trp | 288 | . | . | B | B | . | . | . | 0.83 | 0.39 | * | * | . | −0.30 | 0.79 |
| Thr | 289 | . | . | B | B | . | . | . | 0.61 | 0.77 | * | * | . | −0.45 | 1.29 |
| Trp | 290 | . | . | B | B | . | . | . | 0.19 | 0.77 | * | * | . | −0.60 | 0.79 |
| Arg | 291 | . | . | B | B | . | . | . | 0.19 | 0.87 | * | * | . | −0.45 | 1.09 |
| Ser | 292 | . | . | B | B | . | . | . | 0.24 | 0.64 | * | . | . | −0.60 | 0.62 |
| Leu | 293 | . | . | . | B | T | . | . | 0.32 | 0.91 | * | . | . | −0.20 | 0.93 |
| Thr | 294 | . | . | . | B | T | . | . | 0.33 | 0.43 | * | . | . | −0.20 | 0.73 |
| Leu | 295 | . | . | . | B | . | . | C | 0.62 | 0.81 | * | . | . | −0.40 | 0.73 |
| Tyr | 296 | . | . | B | . | . | T | . | 0.30 | 0.83 | * | . | F | 0.10 | 1.53 |
| Pro | 297 | . | . | . | . | T | T | . | 0.30 | 0.57 | . | . | F | 0.62 | 1.64 |
| Ser | 298 | . | . | . | . | T | T | . | 1.11 | 0.47 | . | . | F | 0.74 | 2.67 |
| Gln | 299 | . | . | . | . | . | T | C | 1.21 | 0.19 | . | . | F | 0.96 | 2.74 |
| Pro | 300 | . | . | . | . | T | T | . | 1.21 | −0.14 | . | . | F | 1.88 | 2.74 |
| Ser | 301 | . | . | . | . | . | T | C | 0.60 | 0.11 | . | . | F | 1.20 | 1.69 |
| Asn | 302 | . | . | . | . | . | T | C | 0.00 | 0.37 | . | . | F | 0.93 | 0.72 |
| Pro | 303 | . | . | B | . | . | T | . | 0.30 | 0.66 | * | . | F | 0.31 | 0.39 |
| Leu | 304 | . | A | B | . | . | . | . | −0.51 | 0.23 | * | * | F | 0.09 | 0.50 |
| Val | 305 | . | A | B | . | . | . | . | −0.30 | 0.53 | . | * | . | −0.48 | 0.26 |
| Leu | 306 | . | A | B | . | . | . | . | −0.86 | 0.53 | . | * | . | −0.60 | 0.29 |
| Glu | 307 | . | A | B | . | . | . | . | −0.89 | 0.74 | . | * | . | −0.60 | 0.26 |
| Leu | 308 | . | A | B | . | . | . | . | −1.49 | 0.56 | . | * | . | −0.60 | 0.47 |
| Gln | 309 | . | A | B | . | . | . | . | −1.02 | 0.60 | * | * | . | −0.60 | 0.47 |
| Val | 310 | . | A | B | . | . | . | . | −0.17 | 0.34 | * | * | . | −0.30 | 0.27 |
| His | 311 | . | A | B | . | . | . | . | 0.64 | 0.34 | * | * | . | −0.30 | 0.55 |
| Leu | 312 | . | A | . | . | . | . | C | 0.30 | −0.34 | * | * | . | 0.84 | 0.55 |
| Gly | 313 | . | . | . | . | . | T | C | 1.11 | −0.31 | . | * | F | 1.73 | 0.73 |
| Asp | 314 | . | . | . | . | T | T | . | 0.41 | −0.96 | . | * | F | 2.57 | 0.93 |
| Glu | 315 | . | . | . | . | T | T | . | 0.96 | −0.67 | . | * | F | 2.91 | 0.97 |
| Gly | 316 | . | . | . | . | T | T | . | 0.32 | −0.87 | * | * | F | 3.40 | 1.42 |
| Glu | 317 | . | A | . | . | T | . | . | 1.24 | −0.73 | * | * | F | 2.51 | 0.46 |
| Phe | 318 | . | A | B | . | . | . | . | 1.00 | −0.73 | * | * | . | 1.62 | 0.52 |
| Thr | 319 | . | A | B | . | . | . | . | 1.00 | −0.23 | * | * | . | 0.98 | 0.53 |
| Cys | 320 | . | A | B | . | . | . | . | 1.00 | −0.26 | * | * | . | 0.89 | 0.53 |
| Arg | 321 | . | A | . | . | T | . | . | 1.04 | 0.14 | * | * | . | 0.60 | 0.98 |
| Ala | 322 | . | A | . | . | T | . | . | 0.23 | −0.26 | * | * | F | 1.60 | 0.91 |
| Gln | 323 | . | A | . | . | T | . | . | 0.59 | −0.06 | * | * | F | 2.00 | 1.40 |
| Asn | 324 | . | . | . | . | T | T | . | 0.60 | −0.20 | * | * | F | 2.50 | 0.71 |
| Ser | 325 | . | . | . | . | . | T | C | 1.27 | 0.19 | * | * | F | 1.45 | 0.94 |
| Leu | 326 | . | . | . | . | . | T | C | 1.12 | 0.09 | * | * | F | 1.20 | 0.94 |
| Gly | 327 | . | . | . | . | T | T | . | 0.86 | 0.19 | . | . | F | 1.15 | 0.79 |
| Ser | 328 | . | . | B | B | . | . | . | 0.56 | 0.43 | . | . | F | −0.20 | 0.44 |
| Gln | 329 | . | . | B | B | . | . | . | −0.26 | 0.43 | . | . | F | −0.45 | 0.71 |
| His | 330 | . | . | B | B | . | . | . | 0.04 | 0.43 | . | * | . | −0.60 | 0.59 |
| Val | 331 | . | . | B | B | . | . | . | 0.04 | 0.40 | . | * | . | −0.60 | 0.71 |
| Ser | 332 | . | A | B | . | . | . | . | 0.09 | 0.70 | . | * | . | −0.60 | 0.34 |
| Leu | 333 | . | A | B | . | . | . | . | −0.42 | 0.69 | . | * | . | −0.60 | 0.33 |
| Asn | 334 | . | A | B | . | . | . | . | −0.42 | 0.87 | . | * | . | −0.60 | 0.37 |
| Leu | 335 | . | A | . | . | . | . | C | −0.39 | 0.63 | . | * | . | −0.40 | 0.48 |
| Ser | 336 | . | A | . | . | . | . | C | 0.47 | 0.64 | . | * | . | −0.25 | 1.01 |
| Leu | 337 | . | A | B | . | . | . | . | 0.52 | −0.04 | . | * | . | 0.45 | 1.09 |
| Gln | 338 | . | A | B | . | . | . | . | 1.02 | 0.31 | . | * | F | 0.00 | 2.06 |
| Gln | 339 | . | A | B | . | . | . | . | 0.68 | 0.11 | . | * | F | 0.34 | 2.22 |
| Glu | 340 | . | A | B | . | . | . | . | 1.53 | 0.16 | . | * | F | 0.68 | 2.66 |
| Tyr | 341 | . | . | B | . | . | T | . | 1.23 | −0.53 | * | * | F | 2.32 | 3.08 |
| Thr | 342 | . | . | . | . | T | T | . | 2.16 | −0.31 | * | * | F | 2.76 | 1.76 |
| Gly | 343 | . | . | . | . | T | T | . | 1.94 | −0.71 | * | * | F | 3.40 | 1.99 |
| Lys | 344 | . | . | . | . | T | T | . | 1.09 | −0.29 | * | * | F | 2.76 | 1.96 |
| Met | 345 | . | . | B | . | . | . | . | 0.79 | −0.40 | . | * | F | 1.82 | 1.01 |
| Arg | 346 | . | . | B | . | . | . | . | 0.69 | −0.50 | * | * | F | 1.48 | 1.37 |
| Pro | 347 | . | . | B | . | . | T | . | 0.14 | −0.50 | * | * | F | 1.19 | 0.68 |
| Val | 348 | . | . | B | . | . | T | . | −0.32 | 0.14 | . | * | F | 0.25 | 0.51 |
| Ser | 349 | . | . | B | . | . | T | . | −1.18 | 0.21 | * | * | F | 0.25 | 0.21 |
| Gly | 350 | . | . | B | . | . | T | . | −0.92 | 0.90 | * | . | . | −0.20 | 0.11 |
| Val | 351 | . | . | B | B | . | . | . | −1.62 | 0.90 | * | . | . | −0.60 | 0.15 |
| Leu | 352 | . | . | B | B | . | . | . | −2.27 | 0.76 | . | . | . | −0.60 | 0.11 |
| Leu | 353 | . | . | B | B | . | . | . | −1.76 | 1.01 | . | . | . | −0.60 | 0.09 |
| Gly | 354 | . | . | B | B | . | . | . | −1.80 | 1.01 | . | . | . | −0.60 | 0.11 |
| Ala | 355 | . | . | B | B | . | . | . | −2.04 | 0.80 | . | . | . | −0.60 | 0.14 |
| Val | 356 | . | . | B | B | . | . | . | −1.53 | 0.61 | . | . | . | −0.60 | 0.17 |
| Gly | 357 | . | . | B | . | . | . | . | −1.31 | 0.36 | . | . | . | −0.10 | 0.17 |
| Gly | 358 | . | . | . | . | . | T | C | −0.81 | 0.43 | . | . | F | 0.15 | 0.17 |
| Ala | 359 | . | . | B | . | . | T | . | −1.06 | 0.41 | . | . | F | −0.05 | 0.33 |

TABLE VI-continued

| Res | | I | II | III | IV | V | VI | VII | VIII | IX | X | XI | XII | XIII | XIV |
|---|---|---|---|---|---|---|---|---|---|---|---|---|---|---|---|
| Gly | 360 | . | . | B | . | . | T | . | −1.28 | 0.27 | . | . | . | 0.10 | 0.33 |
| Ala | 361 | . | . | B | . | . | T | . | −1.28 | 0.53 | . | . | . | −0.20 | 0.28 |
| Thr | 362 | . | . | B | B | . | . | . | −1.63 | 0.74 | . | . | . | −0.60 | 0.20 |
| Ala | 363 | . | . | B | B | . | . | . | −2.10 | 1.03 | . | . | . | −0.60 | 0.18 |
| Leu | 364 | . | . | B | B | . | . | . | −1.81 | 1.29 | . | . | . | −0.60 | 0.15 |
| Val | 365 | . | . | B | B | . | . | . | −2.17 | 1.17 | . | . | . | −0.60 | 0.14 |
| Phe | 366 | . | . | B | B | . | . | . | −2.24 | 1.47 | . | . | . | −0.60 | 0.12 |
| Leu | 367 | . | . | B | B | . | . | . | −2.79 | 1.54 | . | . | . | −0.60 | 0.08 |
| Ser | 368 | . | . | B | B | . | . | . | −3.09 | 1.50 | . | . | . | −0.60 | 0.08 |
| Phe | 369 | . | . | B | B | . | . | . | −2.98 | 1.54 | . | . | . | −0.60 | 0.06 |
| Cys | 370 | . | . | B | B | . | . | . | −3.01 | 1.54 | . | . | . | −0.60 | 0.06 |
| Val | 371 | . | . | B | B | . | . | . | −3.17 | 1.54 | . | . | . | −0.60 | 0.03 |
| Ile | 372 | . | . | B | B | . | . | . | −3.21 | 1.80 | * | * | . | −0.60 | 0.03 |
| Phe | 373 | . | . | B | B | . | . | . | −2.80 | 1.66 | * | . | . | −0.60 | 0.04 |
| Ile | 374 | . | . | B | B | . | . | . | −2.40 | 1.09 | * | . | . | −0.60 | 0.11 |
| Val | 375 | . | . | B | B | . | . | . | −2.40 | 0.83 | * | . | . | −0.26 | 0.20 |
| Val | 376 | . | . | B | B | . | . | . | −1.43 | 0.71 | * | . | . | 0.08 | 0.12 |
| Arg | 377 | . | . | B | . | . | T | . | −0.50 | −0.07 | * | . | . | 1.72 | 0.35 |
| Ser | 378 | . | . | . | . | T | T | . | 0.24 | −0.76 | * | . | F | 2.91 | 0.94 |
| Cys | 379 | . | . | . | . | T | T | . | 0.83 | −1.40 | * | . | F | 3.40 | 2.53 |
| Arg | 380 | . | . | . | . | T | T | . | 1.10 | −1.66 | * | . | F | 3.06 | 1.73 |
| Lys | 381 | . | A | . | . | T | . | . | 2.07 | −1.16 | * | . | F | 2.32 | 1.30 |
| Lys | 382 | . | A | . | . | T | . | . | 1.74 | −1.54 | * | . | F | 1.98 | 4.76 |
| Ser | 383 | . | A | . | . | . | . | C | 1.46 | −1.69 | * | . | F | 1.44 | 3.76 |
| Ala | 384 | . | A | B | . | . | . | . | 1.53 | −1.19 | * | * | F | 0.90 | 1.90 |
| Arg | 385 | . | A | B | . | . | . | . | 1.42 | −0.69 | * | * | F | 0.75 | 0.96 |
| Pro | 386 | . | A | B | . | . | . | . | 0.52 | −0.69 | * | * | F | 0.90 | 1.20 |
| Ala | 387 | . | A | B | . | . | . | . | 0.13 | −0.43 | * | . | . | 0.30 | 0.88 |
| Ala | 388 | . | A | B | . | . | . | . | 0.43 | −0.50 | * | * | . | 0.30 | 0.44 |
| Asp | 389 | . | . | B | . | . | T | . | 0.13 | −0.50 | * | * | . | 0.70 | 0.48 |
| Val | 390 | . | . | B | . | . | T | . | −0.32 | −0.24 | * | * | . | 0.70 | 0.33 |
| Gly | 391 | . | . | B | . | . | T | . | −0.71 | −0.31 | * | . | F | 0.85 | 0.33 |
| Asp | 392 | . | . | B | . | . | T | . | −0.08 | −0.20 | * | . | F | 0.85 | 0.19 |
| Ile | 393 | . | A | B | . | . | . | . | 0.51 | −0.20 | * | . | F | 0.45 | 0.52 |
| Gly | 394 | . | A | B | . | . | . | . | −0.08 | −0.84 | * | . | F | 0.75 | 0.88 |
| Met | 395 | . | A | B | . | . | . | . | 0.78 | −0.77 | * | . | F | 1.01 | 0.53 |
| Lys | 396 | . | A | B | . | . | . | . | 0.81 | −0.37 | * | . | F | 1.12 | 1.22 |
| Asp | 397 | . | . | B | . | . | T | . | −0.08 | −0.57 | * | * | F | 2.08 | 1.78 |
| Ala | 398 | . | . | B | . | . | T | . | 0.92 | −0.31 | * | * | F | 2.04 | 1.26 |
| Asn | 399 | . | . | B | . | . | T | . | 0.92 | −0.93 | * | * | F | 2.60 | 1.23 |
| Thr | 400 | . | . | B | . | . | T | . | 1.22 | −0.50 | * | * | F | 1.89 | 0.73 |
| Ile | 401 | . | . | B | . | . | T | . | 0.59 | −0.11 | * | * | F | 1.63 | 0.97 |
| Arg | 402 | . | . | B | . | . | T | . | 0.29 | −0.11 | * | . | F | 1.61 | 0.61 |
| Gly | 403 | . | . | B | . | . | T | . | 0.88 | −0.13 | * | * | F | 1.59 | 0.57 |
| Ser | 404 | . | . | . | . | . | T | C | 0.53 | −0.21 | * | * | F | 1.92 | 1.40 |
| Ala | 405 | . | . | . | . | . | . | C | 0.84 | −0.47 | * | * | F | 1.81 | 0.71 |
| Ser | 406 | . | . | . | . | . | T | C | 0.92 | −0.07 | * | * | F | 2.40 | 1.15 |
| Gln | 407 | . | . | . | . | . | T | C | 0.50 | 0.19 | * | . | F | 1.41 | 0.71 |
| Gly | 408 | . | . | . | . | . | T | C | 0.84 | 0.29 | . | . | F | 1.32 | 1.01 |
| Asn | 409 | . | . | . | . | . | T | C | 0.84 | −0.21 | . | . | F | 1.68 | 1.30 |
| Leu | 410 | . | . | . | . | . | . | C | 1.14 | −0.21 | . | . | F | 1.58 | 1.01 |
| Thr | 411 | . | . | B | . | . | T | . | 0.86 | 0.30 | * | . | F | 1.08 | 1.07 |
| Glu | 412 | . | . | B | . | . | T | . | 0.86 | 0.37 | * | . | F | 1.27 | 0.67 |
| Ser | 413 | . | . | B | . | . | T | . | 1.20 | −0.03 | * | . | F | 2.36 | 1.36 |
| Trp | 414 | . | . | . | . | T | T | . | 1.20 | −0.71 | * | . | F | 3.40 | 1.58 |
| Ala | 415 | . | . | . | . | . | . | C | 1.80 | −0.80 | * | * | F | 2.66 | 1.46 |
| Asp | 416 | . | . | . | . | T | . | . | 2.22 | −0.37 | * | . | F | 2.56 | 1.69 |
| Asp | 417 | . | . | . | . | . | . | C | 2.19 | −0.76 | * | * | F | 2.66 | 3.15 |
| Asn | 418 | . | . | . | . | . | T | C | 2.46 | −1.17 | * | * | F | 2.86 | 4.24 |
| Pro | 419 | . | . | . | . | . | T | C | 2.40 | −1.17 | . | . | F | 2.86 | 3.45 |
| Arg | 420 | . | . | . | . | T | T | . | 2.18 | −0.74 | . | * | F | 3.40 | 2.05 |
| His | 421 | . | . | . | . | . | T | C | 1.59 | −0.06 | . | . | . | 2.41 | 1.05 |
| His | 422 | . | A | . | . | . | . | C | 1.00 | 0.04 | . | . | . | 0.92 | 0.69 |
| Gly | 423 | . | A | B | . | . | . | . | 0.97 | 0.11 | . | . | . | 0.38 | 0.35 |
| Leu | 424 | . | A | B | . | . | . | . | 0.88 | 0.61 | . | . | . | −0.26 | 0.35 |
| Ala | 425 | . | A | B | . | . | . | . | 0.47 | 0.50 | . | . | . | −0.30 | 0.35 |
| Ala | 426 | . | A | . | . | . | . | C | 0.16 | 0.39 | . | . | . | 0.50 | 0.47 |
| His | 427 | . | . | . | . | . | T | C | 0.19 | 0.39 | . | . | . | 1.20 | 0.57 |
| Ser | 428 | . | . | . | . | . | T | C | 0.53 | −0.30 | . | * | F | 2.25 | 0.97 |
| Ser | 429 | . | . | . | . | . | T | C | 1.46 | −0.80 | . | . | F | 3.00 | 1.66 |
| Gly | 430 | . | . | . | . | . | T | C | 2.04 | −1.30 | . | . | F | 2.70 | 2.39 |
| Glu | 431 | . | A | . | . | . | . | C | 1.74 | −1.80 | . | . | F | 2.00 | 3.09 |
| Glu | 432 | . | A | . | . | . | . | C | 1.78 | −1.50 | * | . | F | 1.70 | 1.62 |
| Arg | 433 | . | A | B | . | . | . | . | 1.83 | −1.49 | * | . | F | 1.20 | 2.83 |
| Glu | 434 | . | A | B | . | . | . | . | 1.54 | −1.16 | * | . | F | 0.90 | 2.56 |
| Ile | 435 | . | A | B | . | . | . | . | 1.68 | −0.66 | . | . | . | 0.75 | 1.49 |
| Gln | 436 | . | A | B | . | . | . | . | 0.87 | −0.23 | * | . | . | 0.45 | 1.18 |

TABLE VI-continued

| Res | | I | II | III | IV | V | VI | VII | VIII | IX | X | XI | XII | XIII | XIV |
|---|---|---|---|---|---|---|---|---|---|---|---|---|---|---|---|
| Tyr | 437 | . | A | B | . | . | . | . | 0.57 | 0.46 | * | . | . | −0.60 | 0.56 |
| Ala | 438 | . | . | . | . | . | . | C | −0.24 | 0.84 | * | . | . | −0.05 | 1.07 |
| Pro | 439 | . | . | B | . | . | . | . | −0.28 | 0.94 | * | . | . | −0.40 | 0.54 |
| Leu | 440 | . | . | B | . | . | . | . | 0.66 | 1.04 | * | . | . | −0.40 | 0.47 |
| Ser | 441 | . | . | . | . | . | . | C | 0.31 | 0.29 | * | . | . | 0.10 | 0.92 |
| Phe | 442 | . | . | . | . | . | . | C | 0.56 | 0.21 | . | . | . | 0.10 | 0.59 |
| His | 443 | . | . | . | . | T | . | . | 0.93 | −0.21 | . | . | . | 1.05 | 1.24 |
| Lys | 444 | . | . | . | . | T | . | . | 1.14 | −0.47 | . | . | F | 1.50 | 1.43 |
| Gly | 445 | . | . | . | . | . | . | C | 1.96 | −0.46 | . | . | F | 1.60 | 2.86 |
| Glu | 446 | . | . | . | . | . | . | C | 1.44 | −1.24 | * | . | F | 2.20 | 3.51 |
| Pro | 447 | . | . | . | . | . | . | C | 1.84 | −1.06 | * | . | F | 2.50 | 1.45 |
| Gln | 448 | . | . | . | . | T | . | . | 1.53 | −0.67 | . | . | F | 3.00 | 1.96 |
| Asp | 449 | . | . | . | . | . | . | C | 1.49 | −0.67 | . | . | F | 2.50 | 1.12 |
| Leu | 450 | . | . | . | . | . | T | C | 1.83 | −0.27 | . | . | F | 2.10 | 1.26 |
| Ser | 451 | . | . | . | . | . | T | C | 1.24 | −0.70 | . | . | F | 2.10 | 1.26 |
| Gly | 452 | . | . | B | . | . | T | . | 1.14 | −0.60 | . | . | F | 1.45 | 0.76 |
| Gln | 453 | . | . | . | . | . | T | C | 1.14 | −0.11 | . | . | F | 1.20 | 1.33 |
| Glu | 454 | . | . | . | . | . | . | C | 1.14 | −0.40 | . | . | F | 1.00 | 1.60 |
| Ala | 455 | . | . | . | . | . | . | C | 1.96 | −0.39 | . | . | F | 1.30 | 2.59 |
| Thr | 456 | . | . | . | . | . | . | C | 2.01 | −0.81 | . | . | F | 1.90 | 2.59 |
| Asn | 457 | . | . | . | . | . | T | C | 2.06 | −0.46 | . | . | F | 2.10 | 2.35 |
| Asn | 458 | . | . | . | . | . | T | C | 2.06 | −0.07 | * | . | F | 2.40 | 3.11 |
| Glu | 459 | . | . | . | . | . | T | C | 1.17 | −0.57 | * | . | F | 3.00 | 3.73 |
| Tyr | 460 | . | . | . | . | T | T | . | 1.80 | −0.37 | . | * | F | 2.60 | 1.63 |
| Ser | 461 | . | . | . | . | T | . | . | 1.22 | −0.77 | . | * | F | 2.40 | 2.02 |
| Glu | 462 | . | . | B | . | . | . | . | 1.01 | −0.49 | . | . | F | 1.25 | 0.82 |
| Ile | 463 | . | . | B | . | . | . | . | 1.06 | −0.06 | . | . | F | 1.22 | 0.81 |
| Lys | 464 | . | . | B | . | . | . | . | 0.67 | −0.81 | . | . | F | 1.64 | 1.21 |
| Ile | 465 | . | . | B | . | . | . | . | 0.52 | −0.77 | . | * | F | 1.76 | 0.89 |
| Pro | 466 | . | . | B | . | . | . | . | 0.43 | −0.34 | . | * | . | 1.73 | 1.62 |
| Lys | 467 | . | . | . | . | T | . | . | 0.04 | −0.60 | . | * | . | 2.70 | 1.04 |

TABLE VII

| Res | | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.43 | 0.01 | * | . | . | −0.10 | 0.79 |
| Asp | 2 | . | . | B | . | . | . | . | 0.48 | −0.41 | * | . | . | 0.65 | 1.21 |
| Leu | 3 | . | . | B | . | . | T | . | 0.06 | −0.41 | * | . | . | 0.70 | 0.94 |
| Pro | 4 | A | . | . | . | . | T | . | −0.41 | −0.16 | * | . | . | 0.70 | 0.78 |
| Arg | 5 | . | . | B | . | . | T | . | −0.88 | −0.13 | * | . | F | 0.85 | 0.35 |
| Gly | 6 | . | . | B | . | . | T | . | −0.87 | 0.51 | * | . | F | −0.05 | 0.31 |
| Leu | 7 | . | . | B | B | . | . | . | −1.16 | 0.33 | * | . | . | −0.30 | 0.20 |
| Val | 8 | . | . | B | B | . | . | . | −0.93 | 0.81 | * | . | . | −0.60 | 0.11 |
| Val | 9 | . | . | B | B | . | . | . | −1.53 | 1.31 | . | . | . | −0.60 | 0.11 |
| Ala | 10 | . | . | B | B | . | . | . | −1.94 | 1.57 | . | * | . | −0.60 | 0.11 |
| Trp | 11 | . | . | B | B | . | . | . | −2.41 | 1.27 | . | . | . | −0.60 | 0.20 |
| Ala | 12 | . | . | B | B | . | . | . | −1.89 | 1.31 | . | . | . | −0.60 | 0.22 |
| Leu | 13 | . | . | B | B | . | . | . | −1.24 | 1.59 | . | . | . | −0.60 | 0.23 |
| Ser | 14 | . | . | . | . | . | . | C | −0.73 | 1.51 | . | . | . | −0.20 | 0.34 |
| Leu | 15 | . | . | . | . | . | . | C | −0.84 | 1.03 | . | . | . | −0.20 | 0.34 |
| Trp | 16 | . | . | . | . | . | T | C | −0.87 | 1.31 | * | . | . | 0.00 | 0.35 |
| Pro | 17 | . | . | . | . | . | T | C | −0.28 | 1.11 | * | . | . | 0.00 | 0.38 |
| Gly | 18 | . | . | . | . | T | T | . | 0.22 | 0.73 | * | . | F | 0.35 | 0.77 |
| Phe | 19 | . | . | . | . | T | T | . | −0.18 | 0.53 | * | . | F | 0.50 | 1.06 |
| Thr | 20 | . | . | . | . | . | . | C | 0.63 | 0.40 | * | . | F | 0.25 | 0.59 |
| Asp | 21 | . | . | . | . | . | . | C | 0.32 | 0.37 | . | * | F | 0.25 | 0.96 |
| Thr | 22 | . | . | . | . | . | . | C | 0.53 | 0.56 | . | * | . | 0.29 | 1.10 |
| Phe | 23 | . | . | B | . | . | . | . | 0.57 | −0.23 | * | * | . | 1.33 | 1.27 |
| Asn | 24 | . | . | B | . | . | T | . | 1.38 | −0.23 | * | * | . | 1.87 | 1.10 |
| Met | 25 | . | . | . | . | T | T | . | 1.73 | −0.23 | * | * | . | 2.61 | 1.49 |
| Asp | 26 | . | . | . | . | T | T | . | 1.52 | −0.71 | * | . | F | 3.40 | 3.44 |
| Thr | 27 | . | . | . | . | T | T | . | 1.94 | −1.07 | * | * | F | 3.06 | 3.31 |
| Arg | 28 | . | . | . | . | T | . | . | 1.79 | −1.47 | * | * | F | 2.52 | 6.55 |
| Lys | 29 | . | . | B | . | . | . | . | 0.90 | −1.44 | * | . | F | 1.78 | 2.91 |
| Pro | 30 | . | . | B | B | . | . | . | 1.29 | −0.76 | * | . | F | 1.24 | 1.41 |
| Arg | 31 | . | . | B | B | . | . | . | 0.94 | −0.81 | . | . | F | 0.90 | 1.12 |
| Val | 32 | . | . | B | B | . | . | . | 0.96 | −0.39 | . | * | . | 0.30 | 0.55 |
| Ile | 33 | . | . | B | . | . | T | . | 0.96 | 0.00 | . | * | F | 0.22 | 0.48 |
| Pro | 34 | . | . | B | . | . | T | . | 0.60 | −0.43 | . | * | F | 0.79 | 0.48 |
| Gly | 35 | . | . | . | . | T | T | . | 0.22 | 0.06 | * | * | F | 0.56 | 0.93 |
| Ser | 36 | . | . | B | . | . | T | . | −0.59 | −0.09 | * | * | F | 0.88 | 1.34 |
| Arg | 37 | . | . | B | B | . | . | . | −0.43 | 0.01 | . | . | F | −0.30 | 0.75 |
| Thr | 38 | . | . | B | B | . | . | . | 0.11 | 0.37 | . | . | F | −0.27 | 0.66 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Ala | 39 | . | . | B | B | . | . | . | 0.08 | 0.37 | . | . | . | −0.39 | 0.49 |
| Phe | 40 | . | . | B | B | . | . | . | 0.11 | 0.74 | . | . | . | −0.66 | 0.39 |
| Phe | 41 | . | . | B | B | . | . | . | −0.44 | 1.23 | . | . | . | −0.63 | 0.39 |
| Gly | 42 | . | . | B | B | . | . | . | −0.56 | 1.39 | . | . | . | −0.60 | 0.29 |
| Tyr | 43 | . | . | B | B | . | . | . | −0.24 | 1.29 | . | . | . | −0.60 | 0.57 |
| Thr | 44 | . | . | B | B | . | . | . | 0.31 | 0.90 | . | . | . | −0.45 | 1.14 |
| Val | 45 | . | . | B | B | . | . | . | 1.01 | 0.61 | . | . | . | −0.45 | 1.57 |
| Gln | 46 | . | . | B | B | . | . | . | 0.82 | 0.19 | . | . | . | −0.15 | 1.67 |
| Gln | 47 | . | . | B | B | . | . | . | 0.87 | 0.11 | . | . | . | −0.30 | 0.81 |
| His | 48 | . | . | B | B | . | . | . | 0.77 | 0.01 | . | . | . | 0.10 | 1.47 |
| Asp | 49 | . | . | B | B | . | . | . | 1.08 | −0.20 | . | . | F | 0.95 | 0.84 |
| Ile | 50 | . | . | . | B | T | . | . | 1.98 | −0.20 | . | . | F | 1.60 | 0.78 |
| Ser | 51 | . | . | . | . | T | T | . | 1.69 | −0.60 | . | . | F | 2.70 | 1.14 |
| Gly | 52 | . | . | . | . | T | T | . | 0.88 | −0.19 | . | . | F | 2.50 | 0.72 |
| Asn | 53 | . | . | . | . | T | T | . | 0.06 | 0.50 | . | . | F | 1.35 | 0.85 |
| Lys | 54 | . | . | . | . | T | T | . | −0.80 | 0.46 | . | . | F | 1.10 | 0.47 |
| Trp | 55 | . | . | B | B | . | . | . | −0.26 | 0.71 | . | . | . | −0.10 | 0.35 |
| Leu | 56 | . | . | B | B | . | . | . | −0.54 | 0.71 | . | . | . | −0.35 | 0.22 |
| Val | 57 | . | . | B | B | . | . | . | −0.41 | 0.81 | . | . | . | −0.60 | 0.11 |
| Val | 58 | . | . | B | B | . | . | . | −1.22 | 1.24 | . | . | . | −0.60 | 0.16 |
| Gly | 59 | . | . | B | B | . | . | . | −1.27 | 1.01 | . | . | . | −0.60 | 0.16 |
| Ala | 60 | . | . | B | . | . | . | . | −1.29 | 0.33 | . | . | . | −0.10 | 0.38 |
| Pro | 61 | . | . | . | . | . | . | C | −0.48 | 0.17 | . | * | . | 0.10 | 0.73 |
| Leu | 62 | . | . | . | . | . | . | C | 0.03 | −0.07 | . | . | F | 1.34 | 1.19 |
| Glu | 63 | A | . | . | . | . | T | . | 0.64 | −0.07 | . | * | F | 1.68 | 1.16 |
| Thr | 64 | . | . | B | . | . | T | . | 0.99 | 0.19 | . | * | F | 1.42 | 1.18 |
| Asn | 65 | . | . | . | . | T | T | . | 1.62 | 0.16 | . | * | F | 2.16 | 2.47 |
| Gly | 66 | . | . | . | . | T | T | . | 1.52 | −0.53 | . | . | F | 3.40 | 2.86 |
| Tyr | 67 | . | . | . | . | T | . | . | 1.99 | −0.04 | . | . | F | 2.56 | 2.86 |
| Gln | 68 | . | . | . | . | T | . | . | 1.99 | −0.10 | . | . | F | 2.48 | 1.76 |
| Lys | 69 | . | . | B | . | T | T | . | 1.44 | −0.50 | * | . | F | 2.60 | 2.97 |
| Thr | 70 | . | . | B | . | . | T | . | 1.20 | −0.29 | * | . | F | 2.12 | 1.41 |
| Gly | 71 | . | . | B | . | . | T | . | 1.59 | −0.29 | * | . | F | 2.04 | 1.27 |
| Asp | 72 | . | . | B | . | . | T | . | 1.17 | −0.69 | * | . | F | 2.60 | 1.27 |
| Val | 73 | . | . | B | . | . | . | . | 0.96 | −0.11 | * | . | F | 1.69 | 0.47 |
| Tyr | 74 | . | . | B | . | . | T | . | 0.06 | −0.17 | . | . | . | 1.48 | 0.74 |
| Lys | 75 | . | . | B | . | . | T | . | −0.52 | 0.04 | . | . | . | 0.62 | 0.33 |
| Cys | 76 | . | . | B | . | . | T | . | −0.21 | 0.73 | . | . | . | 0.06 | 0.31 |
| Pro | 77 | . | . | B | . | . | T | . | −0.56 | 0.59 | . | . | . | −0.20 | 0.27 |
| Val | 78 | . | . | B | . | . | . | . | 0.30 | 0.26 | . | . | . | −0.10 | 0.13 |
| Ile | 79 | . | . | B | . | . | . | . | −0.12 | 0.66 | . | . | . | −0.40 | 0.40 |
| His | 80 | . | . | B | . | . | T | . | −0.48 | 0.66 | . | . | . | −0.20 | 0.14 |
| Gly | 81 | . | . | B | . | . | T | . | 0.23 | 0.71 | . | . | . | −0.20 | 0.27 |
| Asn | 82 | . | . | . | . | T | T | . | −0.37 | 0.07 | . | . | . | 0.50 | 0.77 |
| Cys | 83 | . | . | B | . | . | T | . | 0.49 | 0.07 | . | * | F | 0.25 | 0.47 |
| Thr | 84 | . | . | B | . | . | . | . | 0.57 | −0.03 | . | * | F | 0.65 | 0.76 |
| Lys | 85 | . | . | B | . | . | . | . | 0.26 | 0.23 | . | . | F | 0.05 | 0.39 |
| Leu | 86 | . | . | B | . | . | . | . | 0.71 | 0.26 | . | . | . | −0.10 | 0.72 |
| Asn | 87 | . | . | B | . | . | . | . | −0.14 | −0.31 | . | . | . | 0.50 | 0.97 |
| Leu | 88 | . | . | B | B | . | . | . | 0.21 | −0.16 | . | * | . | 0.30 | 0.36 |
| Gly | 89 | . | . | B | B | . | . | . | −0.29 | 0.33 | . | * | . | −0.30 | 0.63 |
| Arg | 90 | . | . | B | B | . | . | . | −0.63 | 0.33 | . | . | . | −0.30 | 0.32 |
| Val | 91 | . | . | B | B | . | . | . | 0.18 | 0.31 | * | . | . | −0.30 | 0.53 |
| Thr | 92 | . | . | B | B | . | . | . | −0.68 | 0.03 | * | . | . | −0.30 | 0.85 |
| Leu | 93 | . | . | B | B | . | . | . | −0.17 | 0.24 | * | * | . | −0.30 | 0.32 |
| Ser | 94 | . | . | B | B | . | . | . | 0.18 | 0.63 | . | * | . | −0.60 | 0.58 |
| Asn | 95 | . | . | B | B | . | . | . | 0.18 | −0.01 | . | * | F | 0.45 | 0.70 |
| Val | 96 | . | . | B | B | . | . | . | 1.08 | −0.50 | . | . | F | 0.60 | 1.67 |
| Ser | 97 | A | . | . | . | . | . | . | 1.39 | −1.19 | * | . | F | 1.10 | 2.49 |
| Glu | 98 | A | . | . | . | . | . | . | 2.20 | −1.57 | * | . | F | 1.10 | 2.58 |
| Arg | 99 | A | . | . | . | . | T | . | 1.90 | −1.57 | . | * | F | 1.30 | 5.60 |
| Lys | 100 | A | . | . | . | . | T | . | 2.01 | −1.60 | . | * | F | 1.30 | 4.13 |
| Asp | 101 | A | . | . | . | . | T | . | 2.06 | −1.99 | . | * | F | 1.30 | 4.67 |
| Asn | 102 | A | . | . | . | . | T | . | 2.01 | −1.30 | . | * | . | 1.15 | 1.97 |
| Met | 103 | A | . | . | . | . | . | . | 1.20 | −0.87 | . | * | . | 0.80 | 0.97 |
| Arg | 104 | A | . | . | . | . | . | . | 0.79 | −0.19 | . | * | . | 0.50 | 0.48 |
| Leu | 105 | . | . | B | . | . | . | . | −0.07 | 0.20 | * | * | . | −0.10 | 0.40 |
| Gly | 106 | . | . | B | . | . | . | . | −0.66 | 0.49 | * | * | . | −0.40 | 0.33 |
| Leu | 107 | . | . | B | . | . | . | . | −0.97 | 0.37 | * | * | . | −0.10 | 0.17 |
| Ser | 108 | . | . | B | . | . | . | . | −0.37 | 0.86 | * | * | . | −0.40 | 0.30 |
| Leu | 109 | . | . | B | . | . | . | . | −0.69 | 0.57 | * | * | . | −0.06 | 0.49 |
| Ala | 110 | . | . | B | . | . | . | . | 0.17 | 0.57 | . | * | . | 0.28 | 0.92 |
| Thr | 111 | . | . | B | . | . | . | . | 0.51 | −0.11 | . | . | F | 1.82 | 1.37 |
| Asn | 112 | . | . | . | . | . | T | C | 1.32 | −0.50 | . | * | F | 2.56 | 2.78 |
| Pro | 113 | . | . | . | . | T | T | . | 1.32 | −0.79 | . | . | F | 3.40 | 4.42 |
| Lys | 114 | . | . | . | . | T | T | . | 1.43 | −0.90 | . | . | F | 3.06 | 4.10 |
| Asp | 115 | . | . | . | . | T | T | . | 1.21 | −0.60 | . | . | F | 2.72 | 2.21 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Asn | 116 | . | . | . | . | T | T | . | 0.93 | −0.31 | . | . | F | 2.08 | 1.18 |
| Ser | 117 | . | . | B | . | . | T | . | 0.27 | −0.24 | . | . | F | 1.19 | 0.60 |
| Phe | 118 | . | . | B | . | . | T | . | 0.18 | 0.33 | . | . | . | 0.10 | 0.19 |
| Leu | 119 | . | . | B | . | . | T | . | −0.08 | 0.71 | . | . | . | −0.20 | 0.16 |
| Ala | 120 | . | . | B | . | . | . | . | −0.89 | 0.74 | . | . | . | −0.40 | 0.18 |
| Cys | 121 | . | . | B | . | . | . | . | −1.18 | 1.04 | . | . | . | −0.40 | 0.17 |
| Ser | 122 | . | . | . | . | . | T | C | −1.18 | 1.17 | . | . | . | 0.00 | 0.22 |
| Pro | 123 | . | . | . | . | T | T | . | −0.51 | 0.87 | . | . | . | 0.20 | 0.30 |
| Leu | 124 | . | . | . | . | T | T | . | 0.30 | 0.87 | . | . | . | 0.20 | 0.75 |
| Trp | 125 | . | . | . | . | T | T | . | 0.22 | 0.30 | . | . | . | 0.50 | 0.97 |
| Ser | 126 | . | . | B | . | . | . | . | 0.54 | 0.49 | . | . | . | −0.27 | 0.34 |
| His | 127 | . | . | B | . | . | T | . | 0.54 | 0.49 | . | . | . | 0.06 | 0.40 |
| Glu | 128 | . | . | . | . | T | T | . | 0.46 | 0.19 | . | . | . | 0.89 | 0.51 |
| Cys | 129 | . | . | . | . | T | T | . | 1.02 | −0.34 | . | . | F | 1.77 | 0.51 |
| Gly | 130 | . | . | . | . | T | T | . | 1.07 | 0.03 | . | . | F | 1.30 | 0.59 |
| Ser | 131 | . | . | . | . | T | T | . | 1.06 | 0.29 | . | . | F | 1.17 | 0.54 |
| Ser | 132 | . | . | . | . | T | T | . | 0.78 | 0.77 | . | . | F | 0.89 | 1.44 |
| Tyr | 133 | . | . | . | . | T | T | . | 0.43 | 0.69 | . | . | F | 0.76 | 2.11 |
| Tyr | 134 | . | . | B | . | . | T | . | 0.50 | 0.69 | . | . | F | 0.23 | 1.55 |
| Thr | 135 | . | . | B | . | . | . | . | 0.18 | 0.91 | . | . | F | −0.10 | 1.15 |
| Thr | 136 | . | . | B | . | . | . | . | 0.18 | 1.10 | . | . | . | −0.40 | 0.39 |
| Gly | 137 | . | . | B | . | . | T | . | 0.59 | 0.73 | . | * | . | −0.20 | 0.34 |
| Met | 138 | . | . | B | . | . | T | . | −0.02 | −0.03 | . | * | . | 0.70 | 0.46 |
| Cys | 139 | . | . | B | . | . | T | . | 0.22 | 0.13 | . | * | . | 0.10 | 0.23 |
| Ser | 140 | . | . | B | . | . | T | . | 0.23 | 0.04 | . | * | . | 0.10 | 0.38 |
| Arg | 141 | . | . | B | . | . | . | . | 0.54 | 0.00 | * | * | F | 0.05 | 0.52 |
| Val | 142 | . | . | B | . | . | . | . | 0.19 | −0.21 | * | * | F | 0.80 | 1.55 |
| Asn | 143 | . | . | B | . | . | T | . | 0.90 | 0.00 | * | * | F | 0.61 | 1.00 |
| Ser | 144 | . | . | . | . | . | T | C | 0.87 | −0.39 | * | * | F | 1.62 | 1.00 |
| Asn | 145 | . | . | . | . | T | T | . | 0.87 | 0.40 | * | * | F | 1.13 | 1.17 |
| Phe | 146 | . | . | . | . | T | T | . | 0.80 | 0.14 | * | * | . | 1.34 | 0.97 |
| Arg | 147 | . | . | . | . | T | . | . | 1.34 | −0.26 | * | * | . | 2.10 | 1.45 |
| Phe | 148 | . | . | . | B | T | . | . | 0.49 | −0.16 | * | * | . | 1.69 | 1.30 |
| Ser | 149 | . | . | B | B | . | . | . | 0.20 | 0.09 | * | * | F | 0.63 | 1.12 |
| Lys | 150 | . | . | . | B | . | . | C | −0.01 | −0.20 | * | * | F | 1.07 | 0.58 |
| Thr | 151 | . | . | . | B | T | . | . | 0.10 | 0.23 | * | * | F | 0.61 | 1.03 |
| Val | 152 | . | . | . | B | . | . | C | −0.82 | −0.06 | * | . | . | 0.50 | 0.77 |
| Ala | 153 | . | . | B | B | . | . | C | −0.12 | 0.24 | * | . | . | −0.10 | 0.32 |
| Pro | 154 | A | A | . | . | . | . | . | 0.29 | 0.64 | * | . | . | −0.60 | 0.38 |
| Ala | 155 | A | A | . | . | . | . | . | −0.42 | 0.16 | * | . | . | −0.15 | 1.01 |
| Leu | 156 | A | A | . | B | . | . | . | −0.11 | 0.09 | * | . | . | −0.30 | 0.54 |
| Gln | 157 | A | A | . | B | . | . | . | 0.43 | −0.01 | * | . | . | 0.30 | 0.60 |
| Arg | 158 | . | A | B | B | . | . | . | 0.78 | 0.04 | * | . | F | −0.15 | 0.86 |
| Cys | 159 | . | A | B | B | . | . | . | 0.39 | 0.30 | * | * | F | 0.00 | 1.63 |
| Gln | 160 | . | . | B | B | . | . | . | 0.98 | 0.23 | * | * | . | −0.30 | 0.93 |
| Thr | 161 | . | . | B | B | . | . | . | 0.90 | −0.17 | * | * | . | 0.30 | 0.80 |
| Tyr | 162 | . | . | B | B | . | . | . | 0.04 | 0.51 | * | * | . | −0.45 | 1.04 |
| Met | 163 | . | . | B | B | . | . | . | −0.96 | 0.59 | . | * | . | −0.60 | 0.45 |
| Asp | 164 | . | . | B | B | . | . | . | −1.14 | 0.87 | . | * | . | −0.60 | 0.22 |
| Ile | 165 | . | . | B | B | . | . | . | −1.96 | 1.03 | . | * | . | −0.60 | 0.10 |
| Val | 166 | . | . | B | B | . | . | . | −1.64 | 0.96 | . | * | . | −0.60 | 0.09 |
| Ile | 167 | . | . | B | B | . | . | . | −1.74 | 0.34 | . | * | . | −0.30 | 0.09 |
| Val | 168 | . | . | B | B | . | . | . | −1.44 | 0.77 | . | * | . | −0.35 | 0.12 |
| Leu | 169 | . | . | B | B | . | . | . | −1.44 | 0.47 | . | * | . | −0.10 | 0.22 |
| Asp | 170 | . | . | . | B | T | . | . | −0.86 | 0.23 | * | * | F | 1.00 | 0.50 |
| Gly | 171 | . | . | . | . | T | T | . | −0.89 | −0.07 | . | . | F | 2.25 | 0.90 |
| Ser | 172 | . | . | . | . | T | T | . | −0.24 | −0.03 | * | * | F | 2.50 | 0.77 |
| Asn | 173 | . | . | . | . | . | T | C | 0.40 | 0.04 | * | . | F | 1.45 | 0.72 |
| Ser | 174 | . | . | . | . | . | T | C | 0.92 | 0.47 | * | . | F | 1.05 | 1.12 |
| Ile | 175 | . | . | . | B | . | . | C | 0.07 | 0.96 | * | . | . | 0.10 | 0.88 |
| Tyr | 176 | . | . | . | B | . | . | C | 0.41 | 1.21 | * | . | . | −0.15 | 0.41 |
| Pro | 177 | . | . | B | B | . | . | . | −0.14 | 0.81 | . | * | . | −0.60 | 0.53 |
| Trp | 178 | . | . | B | B | . | . | . | −0.14 | 1.07 | . | * | . | −0.60 | 0.56 |
| Val | 179 | . | . | B | B | . | . | . | 0.12 | 0.79 | . | . | . | −0.60 | 0.62 |
| Glu | 180 | . | . | B | B | . | . | . | 0.31 | 0.53 | . | * | . | −0.60 | 0.54 |
| Val | 181 | A | . | . | B | . | . | . | −0.26 | 0.89 | . | . | . | −0.60 | 0.45 |
| Gln | 182 | A | . | . | B | . | . | . | −0.93 | 0.66 | . | . | . | −0.60 | 0.50 |
| His | 183 | A | . | . | B | . | . | . | −0.64 | 0.70 | * | * | . | −0.60 | 0.20 |
| Phe | 184 | A | . | . | B | . | . | . | −0.68 | 1.10 | * | . | . | −0.60 | 0.43 |
| Leu | 185 | A | . | . | B | . | . | . | −1.49 | 1.14 | * | . | . | −0.60 | 0.18 |
| Ile | 186 | A | . | . | B | . | . | . | −0.59 | 1.43 | * | . | . | −0.60 | 0.11 |
| Asn | 187 | A | . | . | B | . | . | . | −0.54 | 0.93 | * | . | . | −0.60 | 0.25 |
| Ile | 188 | A | . | . | B | . | . | . | −1.21 | 0.14 | * | * | . | −0.30 | 0.60 |
| Leu | 189 | A | . | . | B | . | . | . | −0.76 | 0.24 | * | * | . | −0.30 | 0.74 |
| Lys | 190 | . | . | B | B | . | . | . | −0.83 | 0.31 | * | . | . | −0.30 | 0.72 |
| Lys | 191 | . | . | B | B | . | . | . | −0.29 | 0.60 | * | * | . | −0.60 | 0.72 |
| Phe | 192 | . | . | B | B | . | . | . | −0.50 | 0.34 | * | . | . | −0.30 | 0.86 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Tyr | 193 | . | . | B | B | . | . | . | 0.04 | 0.09 | * | . | . | −0.30 | 0.67 |
| Ile | 194 | . | . | B | B | . | . | . | 0.86 | 0.51 | * | . | . | −0.60 | 0.33 |
| Gly | 195 | . | . | . | . | . | T | C | −0.08 | 0.91 | * | . | . | 0.00 | 0.66 |
| Pro | 196 | . | . | . | . | T | T | . | −0.12 | 0.81 | . | * | F | 0.35 | 0.30 |
| Gly | 197 | . | . | . | . | T | T | . | −0.28 | 0.46 | . | * | F | 0.35 | 0.73 |
| Gln | 198 | . | . | B | . | . | T | . | −0.38 | 0.41 | . | * | F | −0.05 | 0.55 |
| Ile | 199 | . | . | B | B | . | . | . | −0.34 | 0.41 | . | * | . | −0.60 | 0.35 |
| Gln | 200 | . | . | B | B | . | . | . | −0.86 | 0.63 | . | * | . | −0.60 | 0.26 |
| Val | 201 | . | . | B | B | . | . | . | −0.64 | 0.84 | . | * | . | −0.60 | 0.11 |
| Gly | 202 | . | . | B | B | . | . | . | −0.54 | 0.84 | . | * | . | −0.60 | 0.28 |
| Val | 203 | . | . | B | B | . | . | . | −0.89 | 0.91 | . | * | . | −0.60 | 0.25 |
| Val | 204 | . | . | B | B | . | . | . | 0.00 | 0.94 | . | . | . | −0.60 | 0.34 |
| Gln | 205 | . | . | B | B | . | . | . | 0.00 | 0.30 | . | . | . | −0.30 | 0.59 |
| Tyr | 206 | . | . | B | B | . | . | . | 0.00 | −0.13 | * | . | . | 0.45 | 1.32 |
| Gly | 207 | . | A | B | B | . | . | . | −0.51 | −0.13 | * | . | F | 0.60 | 1.32 |
| Glu | 208 | A | A | . | B | . | . | . | 0.31 | −0.13 | * | . | F | 0.45 | 0.57 |
| Asp | 209 | A | A | . | B | . | . | . | 1.17 | −0.03 | * | . | F | 0.45 | 0.49 |
| Val | 210 | A | A | . | B | . | . | . | 0.47 | −0.79 | * | . | . | 0.60 | 0.86 |
| Val | 211 | A | A | . | B | . | . | . | 0.68 | −0.43 | * | . | . | 0.30 | 0.43 |
| His | 212 | A | A | . | B | . | . | . | 0.21 | 0.07 | * | * | . | −0.30 | 0.35 |
| Glu | 213 | A | A | . | . | . | . | . | 0.21 | 0.76 | . | . | . | −0.60 | 0.39 |
| Phe | 214 | A | A | . | . | . | . | . | 0.21 | 0.51 | . | * | . | −0.60 | 0.84 |
| His | 215 | A | A | . | . | . | . | . | 0.82 | −0.13 | * | . | . | 0.45 | 1.04 |
| Leu | 216 | A | A | . | . | . | . | . | 1.79 | 0.13 | * | . | . | 0.04 | 0.94 |
| Asn | 217 | A | . | . | . | . | T | . | 1.52 | 0.13 | * | . | . | 0.93 | 2.12 |
| Asp | 218 | A | . | . | . | . | T | . | 0.67 | −0.27 | * | . | F | 2.02 | 2.09 |
| Tyr | 219 | . | . | . | . | T | T | . | 1.41 | −0.13 | * | . | F | 2.76 | 1.88 |
| Arg | 220 | . | . | . | . | T | T | . | 1.44 | −0.81 | * | . | F | 3.40 | 2.34 |
| Ser | 221 | A | . | . | . | . | . | . | 1.40 | −1.21 | * | . | F | 2.46 | 2.34 |
| Val | 222 | . | A | B | . | . | . | . | 0.54 | −0.57 | * | . | F | 1.92 | 1.11 |
| Lys | 223 | . | A | B | . | . | . | . | 0.54 | −0.69 | * | . | F | 1.43 | 0.42 |
| Asp | 224 | . | A | B | . | . | . | . | 0.20 | −0.69 | * | . | F | 1.09 | 0.54 |
| Val | 225 | A | A | . | . | . | . | . | −0.50 | −0.57 | * | . | . | 0.60 | 0.74 |
| Val | 226 | A | A | . | . | . | . | . | −0.50 | −0.71 | * | . | . | 0.60 | 0.37 |
| Glu | 227 | A | A | . | . | . | . | . | 0.32 | −0.33 | * | . | . | 0.30 | 0.30 |
| Ala | 228 | A | A | . | . | . | . | . | −0.61 | 0.17 | * | . | . | −0.30 | 0.55 |
| Ala | 229 | A | A | . | . | . | . | . | −0.61 | 0.21 | * | . | . | −0.30 | 0.52 |
| Ser | 230 | A | A | . | . | . | . | . | 0.24 | −0.43 | * | * | . | 0.30 | 0.52 |
| His | 231 | A | A | . | . | . | . | . | 1.21 | −0.03 | * | * | . | 0.64 | 0.89 |
| Ile | 232 | A | A | . | . | . | . | . | 0.87 | −0.53 | * | * | . | 1.43 | 1.72 |
| Glu | 233 | A | A | . | . | . | . | . | 1.11 | −0.60 | * | * | F | 1.92 | 1.27 |
| Gln | 234 | . | . | . | . | T | T | . | 1.39 | −0.56 | * | * | F | 2.91 | 0.92 |
| Arg | 235 | . | . | . | . | T | T | . | 1.69 | −0.57 | . | * | F | 3.40 | 1.90 |
| Gly | 236 | . | . | . | . | T | T | . | 1.41 | −1.26 | * | * | F | 3.06 | 1.90 |
| Gly | 237 | . | . | . | . | . | T | C | 2.41 | −0.77 | * | * | F | 2.68 | 1.59 |
| Thr | 238 | . | . | . | . | . | . | C | 2.10 | −1.17 | * | * | F | 2.30 | 1.59 |
| Glu | 239 | . | . | . | . | . | . | C | 1.51 | −0.69 | * | * | F | 2.12 | 2.31 |
| Thr | 240 | . | . | B | . | . | . | . | 0.70 | −0.61 | * | * | F | 1.74 | 2.36 |
| Arg | 241 | . | . | B | . | . | . | . | 0.70 | −0.26 | . | * | F | 1.60 | 1.42 |
| Thr | 242 | . | . | B | . | . | . | . | 0.16 | −0.31 | . | * | F | 1.29 | 0.81 |
| Ala | 243 | A | A | . | . | . | . | . | 0.47 | 0.37 | . | * | . | 0.18 | 0.39 |
| Phe | 244 | A | A | . | . | . | . | . | −0.23 | −0.11 | . | * | . | 0.62 | 0.35 |
| Gly | 245 | A | A | . | . | . | . | . | −0.51 | 0.67 | . | * | . | −0.44 | 0.21 |
| Ile | 246 | A | A | . | . | . | . | . | −0.51 | 0.69 | . | * | . | −0.60 | 0.21 |
| Glu | 247 | A | A | . | . | . | . | . | −0.50 | 0.19 | . | . | . | −0.30 | 0.47 |
| Phe | 248 | A | A | . | . | . | . | . | 0.09 | −0.21 | . | . | . | 0.30 | 0.64 |
| Ala | 249 | A | A | . | . | . | . | . | 0.20 | −0.64 | . | . | . | 0.75 | 1.58 |
| Arg | 250 | A | A | . | . | . | . | . | −0.16 | −0.83 | . | . | F | 0.75 | 0.92 |
| Ser | 251 | A | A | . | . | . | . | . | 0.73 | −0.04 | . | . | F | 0.45 | 0.92 |
| Glu | 252 | A | A | . | . | . | . | . | 0.78 | −0.43 | . | . | F | 0.60 | 1.58 |
| Ala | 253 | A | A | . | . | . | . | . | 1.13 | −0.93 | . | . | F | 0.90 | 1.61 |
| Phe | 254 | A | A | . | . | . | . | . | 1.38 | −0.50 | * | * | F | 0.60 | 1.19 |
| Gln | 255 | A | . | . | . | . | T | . | 1.38 | −0.46 | * | . | F | 0.85 | 0.68 |
| Lys | 256 | A | . | . | . | . | T | . | 1.72 | −0.46 | * | . | F | 1.00 | 1.32 |
| Gly | 257 | A | . | . | . | . | T | . | 1.38 | −0.96 | * | . | F | 1.30 | 3.05 |
| Gly | 258 | A | . | . | . | . | T | . | 1.38 | −1.31 | * | . | F | 1.30 | 1.74 |
| Arg | 259 | A | A | . | . | . | . | . | 2.12 | −1.21 | * | . | F | 0.75 | 0.88 |
| Lys | 260 | A | A | . | . | . | . | . | 2.17 | −1.21 | * | . | F | 0.90 | 1.78 |
| Gly | 261 | A | A | . | . | . | . | . | 1.27 | −1.64 | * | . | F | 0.90 | 3.59 |
| Ala | 262 | A | A | . | . | . | . | . | 1.01 | −1.43 | * | . | F | 0.90 | 1.36 |
| Lys | 263 | A | . | . | B | . | . | . | 0.47 | −0.81 | * | . | F | 0.75 | 0.67 |
| Lys | 264 | . | . | B | B | . | . | . | −0.50 | −0.13 | * | . | . | 0.30 | 0.48 |
| Val | 265 | . | . | B | B | . | . | . | −1.43 | 0.09 | * | . | . | −0.30 | 0.35 |
| Met | 266 | . | . | B | B | . | . | . | −1.40 | 0.27 | * | . | . | −0.30 | 0.12 |
| Ile | 267 | . | . | B | B | . | . | . | −0.81 | 0.76 | * | . | . | −0.60 | 0.09 |
| Val | 268 | . | . | B | B | . | . | . | −1.20 | 0.76 | * | . | . | −0.60 | 0.20 |
| Ile | 269 | . | . | B | . | . | T | . | −1.24 | 0.54 | . | . | . | −0.20 | 0.20 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Thr | 270 | . | . | B | . | . | T | . | −0.69 | −0.07 | . | . | F | 0.85 | 0.49 |
| Asp | 271 | . | . | B | . | . | T | . | −0.12 | −0.37 | . | . | F | 0.85 | 0.89 |
| Gly | 272 | . | . | . | . | . | T | C | 0.77 | −0.51 | . | . | F | 1.50 | 1.73 |
| Glu | 273 | . | . | . | . | . | . | C | 1.32 | −1.20 | . | . | F | 1.60 | 2.00 |
| Ser | 274 | . | . | . | . | . | . | C | 2.00 | −1.30 | . | . | F | 1.90 | 1.60 |
| His | 275 | . | . | . | . | . | . | C | 2.31 | −0.87 | . | . | F | 2.20 | 2.51 |
| Asp | 276 | . | . | . | . | . | . | C | 1.50 | −1.30 | . | * | F | 2.50 | 2.42 |
| Ser | 277 | . | . | . | . | . | T | C | 1.84 | −0.61 | . | . | F | 3.00 | 1.49 |
| Pro | 278 | A | . | . | . | . | T | . | 1.89 | −1.00 | . | . | F | 2.50 | 1.89 |
| Asp | 279 | A | . | . | . | . | T | . | 1.33 | −1.50 | * | . | F | 2.20 | 2.27 |
| Leu | 280 | A | . | . | . | . | T | . | 0.48 | −0.86 | * | . | F | 1.90 | 1.25 |
| Glu | 281 | A | A | . | . | . | . | . | 0.48 | −0.56 | * | . | F | 1.05 | 0.57 |
| Lys | 282 | A | A | . | . | . | . | . | 0.78 | −0.59 | * | . | F | 0.75 | 0.59 |
| Val | 283 | A | A | . | . | . | . | . | 0.69 | −0.19 | * | . | . | 0.45 | 1.24 |
| Ile | 284 | A | A | . | . | . | . | . | 0.69 | −0.49 | * | . | F | 0.45 | 0.96 |
| Gln | 285 | . | A | B | . | . | . | . | 1.61 | −0.49 | * | . | F | 0.79 | 0.83 |
| Gln | 286 | A | A | . | . | . | . | . | 1.61 | −0.49 | * | . | F | 1.28 | 2.19 |
| Ser | 287 | A | A | . | . | . | . | . | 1.57 | −1.13 | * | * | F | 1.92 | 5.22 |
| Glu | 288 | . | . | . | . | . | T | C | 1.57 | −1.41 | * | . | F | 2.86 | 4.85 |
| Arg | 289 | . | . | . | . | T | T | . | 2.14 | −1.17 | * | . | F | 3.40 | 2.08 |
| Asp | 290 | . | . | . | . | T | T | . | 2.26 | −1.09 | . | . | F | 3.06 | 2.24 |
| Asn | 291 | . | . | . | . | T | T | . | 2.01 | −1.47 | * | . | F | 2.72 | 2.53 |
| Val | 292 | . | . | B | B | . | . | . | 1.72 | −0.71 | . | . | F | 1.58 | 2.02 |
| Thr | 293 | . | . | B | B | . | . | . | 0.87 | −0.21 | . | . | F | 0.94 | 1.22 |
| Arg | 294 | . | . | B | B | . | . | . | 0.17 | 0.43 | * | . | . | −0.60 | 0.57 |
| Tyr | 295 | . | . | B | B | . | . | . | −0.69 | 0.53 | * | . | . | −0.60 | 0.77 |
| Ala | 296 | . | . | B | B | . | . | . | −1.50 | 0.53 | * | . | . | −0.60 | 0.40 |
| Val | 297 | . | . | B | B | . | . | . | −0.99 | 0.73 | * | . | . | −0.60 | 0.17 |
| Ala | 298 | . | . | B | B | . | . | . | −0.92 | 1.16 | * | . | . | −0.60 | 0.11 |
| Val | 299 | . | . | B | B | . | . | . | −1.28 | 1.16 | * | . | . | −0.60 | 0.16 |
| Leu | 300 | . | . | B | B | . | . | . | −1.03 | 1.41 | * | . | . | −0.60 | 0.34 |
| Gly | 301 | . | . | B | B | . | . | . | −0.33 | 1.17 | * | . | . | −0.60 | 0.55 |
| Tyr | 302 | . | . | B | B | . | . | . | 0.63 | 0.67 | * | . | . | −0.45 | 1.45 |
| Tyr | 303 | . | . | B | . | . | . | . | 0.88 | 0.03 | * | . | . | 0.39 | 3.44 |
| Asn | 304 | . | . | B | . | . | T | . | 0.84 | −0.23 | * | . | . | 1.53 | 3.44 |
| Arg | 305 | . | . | . | . | T | T | . | 1.66 | 0.03 | * | . | F | 1.82 | 1.54 |
| Arg | 306 | . | . | . | . | T | T | . | 1.79 | −0.33 | * | . | F | 2.76 | 1.58 |
| Gly | 307 | . | . | . | . | T | T | . | 2.03 | −0.66 | * | . | F | 3.40 | 1.52 |
| Ile | 308 | . | . | . | . | . | . | C | 1.97 | −1.06 | . | . | F | 2.66 | 1.34 |
| Asn | 309 | . | . | . | . | . | T | C | 1.27 | −0.57 | * | . | F | 2.37 | 0.99 |
| Pro | 310 | . | . | . | . | . | T | C | 0.34 | 0.21 | * | . | F | 1.13 | 0.86 |
| Glu | 311 | . | . | B | . | . | T | . | 0.23 | 0.47 | . | . | F | 0.44 | 1.02 |
| Thr | 312 | . | . | B | . | . | T | . | 0.58 | 0.19 | * | . | F | 0.40 | 1.02 |
| Phe | 313 | A | A | . | . | . | . | . | 0.58 | −0.21 | . | * | . | 0.45 | 1.14 |
| Leu | 314 | A | A | . | . | . | . | . | 0.62 | 0.04 | * | * | . | −0.30 | 0.46 |
| Asn | 315 | A | A | . | . | . | . | . | 0.59 | 0.04 | * | . | . | −0.30 | 0.64 |
| Glu | 316 | A | A | . | . | . | . | . | −0.30 | 0.31 | * | . | F | 0.00 | 1.16 |
| Ile | 317 | A | A | . | . | . | . | . | −0.58 | 0.21 | * | . | . | −0.30 | 0.98 |
| Lys | 318 | A | A | . | . | . | . | . | −0.18 | 0.03 | * | . | . | −0.30 | 0.62 |
| Tyr | 319 | . | A | B | . | . | . | . | 0.63 | 0.01 | * | . | . | −0.30 | 0.48 |
| Ile | 320 | . | A | B | . | . | . | . | 0.42 | 0.01 | * | . | . | −0.15 | 1.14 |
| Ala | 321 | . | A | B | . | . | . | . | 0.42 | −0.24 | * | . | . | 0.64 | 0.88 |
| Ser | 322 | . | A | B | . | . | . | . | 1.31 | −0.24 | * | . | . | 0.98 | 0.94 |
| Asp | 323 | . | . | . | . | . | T | C | 1.31 | −1.00 | . | . | F | 2.52 | 2.23 |
| Pro | 324 | A | . | . | . | . | T | . | 1.52 | −1.69 | . | . | F | 2.66 | 4.42 |
| Asp | 325 | . | . | . | . | T | T | . | 1.71 | −1.69 | . | . | F | 3.40 | 4.49 |
| Asp | 326 | A | . | . | . | . | T | . | 1.60 | −1.29 | . | . | F | 2.66 | 2.33 |
| Lys | 327 | A | A | . | . | . | . | . | 1.90 | −0.50 | . | . | F | 1.62 | 1.30 |
| His | 328 | A | A | . | . | . | . | . | 1.04 | −0.53 | . | * | . | 1.43 | 1.26 |
| Phe | 329 | . | A | B | . | . | . | . | 0.94 | 0.11 | * | . | . | 0.04 | 0.56 |
| Phe | 330 | . | A | B | . | . | . | . | 0.94 | 0.60 | * | . | . | −0.60 | 0.40 |
| Asn | 331 | A | A | . | . | . | . | . | 0.94 | 0.60 | * | . | . | −0.60 | 0.49 |
| Val | 332 | A | A | . | . | . | . | . | 0.31 | 0.10 | * | . | . | −0.30 | 0.99 |
| Thr | 333 | A | A | . | . | . | . | . | −0.24 | −0.19 | * | . | F | 0.60 | 1.15 |
| Asp | 334 | A | A | . | . | . | . | . | −0.36 | −0.47 | * | * | F | 0.45 | 0.72 |
| Glu | 335 | A | A | . | . | . | . | . | 0.39 | −0.19 | . | * | . | 0.30 | 0.81 |
| Ala | 336 | A | A | . | . | . | . | . | 0.39 | −0.83 | . | . | . | 0.75 | 1.12 |
| Ala | 337 | A | A | . | . | . | . | . | 0.36 | −1.31 | . | . | . | 0.75 | 1.12 |
| Leu | 338 | A | A | . | . | . | . | . | −0.19 | −0.63 | * | . | . | 0.60 | 0.45 |
| Lys | 339 | A | A | . | . | . | . | . | −0.19 | 0.01 | * | . | . | −0.30 | 0.33 |
| Asp | 340 | A | A | . | . | . | . | . | −0.78 | −0.49 | * | . | . | 0.30 | 0.55 |
| Ile | 341 | A | A | . | . | . | . | . | −1.00 | −0.49 | * | . | . | 0.30 | 0.67 |
| Val | 342 | A | A | . | . | . | . | . | −0.76 | −0.49 | * | . | . | 0.30 | 0.28 |
| Asp | 343 | A | A | . | . | . | . | . | 0.06 | −0.06 | * | . | . | 0.30 | 0.16 |
| Ala | 344 | A | A | . | . | . | . | . | 0.12 | −0.06 | * | . | . | 0.30 | 0.39 |
| Leu | 345 | A | . | . | . | . | T | . | −0.77 | −0.74 | * | . | . | 1.15 | 1.03 |
| Gly | 346 | A | . | . | . | . | T | . | −0.58 | −0.70 | * | . | . | 1.00 | 0.43 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Asp | 347 | A | . | . | . | . | T | . | −0.02 | 0.09 | * | . | . | 0.10 | 0.37 |
| Arg | 348 | . | . | B | . | . | T | . | −0.83 | −0.03 | * | . | . | 0.70 | 0.60 |
| Ile | 349 | . | . | B | . | . | . | . | −0.24 | −0.03 | * | . | . | 0.50 | 0.50 |
| Phe | 350 | . | . | B | . | . | . | . | 0.22 | −0.46 | * | . | . | 0.50 | 0.52 |
| Ser | 351 | . | . | B | . | . | . | . | 0.26 | −0.03 | * | . | . | 0.50 | 0.26 |
| Leu | 352 | . | . | B | . | . | . | . | 0.26 | 0.46 | . | . | . | −0.10 | 0.54 |
| Glu | 353 | . | . | . | . | . | . | C | 0.19 | 0.17 | . | . | F | 1.00 | 1.01 |
| Gly | 354 | . | . | . | . | . | . | C | 1.08 | −0.61 | . | . | F | 2.20 | 1.50 |
| Thr | 355 | . | . | . | . | . | . | C | 1.78 | −0.60 | . | * | F | 2.50 | 2.93 |
| Asn | 356 | . | . | . | . | . | T | C | 1.77 | −1.29 | . | . | F | 3.00 | 2.93 |
| Lys | 357 | . | . | . | . | . | T | C | 2.28 | −0.80 | . | * | F | 2.70 | 4.28 |
| Asn | 358 | . | . | . | . | . | T | C | 1.58 | −0.84 | . | . | F | 2.40 | 3.97 |
| Glu | 359 | A | . | . | . | . | T | . | 1.58 | −0.54 | . | . | F | 1.90 | 2.14 |
| Thr | 360 | A | . | . | . | . | T | . | 1.08 | −0.51 | . | * | F | 1.60 | 1.06 |
| Ser | 361 | A | . | . | . | . | T | . | 1.08 | 0.17 | . | * | F | 0.25 | 0.54 |
| Phe | 362 | A | . | . | . | . | T | . | 0.43 | −0.23 | . | * | . | 0.70 | 0.54 |
| Gly | 363 | A | . | . | . | . | T | . | 0.13 | 0.39 | . | . | . | 0.10 | 0.37 |
| Leu | 364 | A | . | . | . | . | . | . | 0.13 | 0.29 | . | * | . | −0.10 | 0.37 |
| Glu | 365 | A | . | . | . | . | . | . | 0.13 | 0.30 | . | . | . | −0.10 | 0.74 |
| Met | 366 | A | . | . | . | . | . | . | 0.09 | 0.00 | . | . | . | 0.05 | 1.09 |
| Ser | 367 | A | . | . | . | . | T | . | 0.09 | 0.00 | . | . | F | 0.40 | 1.30 |
| Gln | 368 | A | . | . | . | . | T | . | 0.13 | 0.10 | . | . | F | 0.25 | 0.65 |
| Thr | 369 | . | . | . | . | . | T | C | 0.64 | 0.49 | . | . | F | 0.15 | 0.88 |
| Gly | 370 | . | . | . | . | . | T | C | 0.61 | 0.26 | . | . | F | 0.45 | 0.88 |
| Phe | 371 | . | . | . | . | . | . | C | 0.36 | 0.37 | . | . | F | 0.25 | 0.69 |
| Ser | 372 | . | . | . | B | . | . | C | −0.20 | 0.61 | . | . | F | −0.25 | 0.36 |
| Ser | 373 | . | . | . | B | . | . | C | −0.20 | 0.77 | . | . | . | −0.40 | 0.27 |
| His | 374 | . | . | B | B | . | . | . | 0.11 | 0.34 | . | . | . | −0.30 | 0.53 |
| Val | 375 | . | . | B | B | . | . | . | 0.11 | −0.44 | . | . | . | 0.30 | 0.67 |
| Val | 376 | . | . | B | . | . | T | . | −0.04 | −0.40 | . | . | . | 0.70 | 0.49 |
| Glu | 377 | . | . | B | . | . | T | . | −0.56 | −0.14 | . | . | . | 0.70 | 0.27 |
| Asp | 378 | A | . | . | . | . | T | . | −1.07 | 0.04 | . | . | . | 0.10 | 0.30 |
| Gly | 379 | A | . | . | . | . | T | . | −1.38 | 0.09 | . | . | . | 0.10 | 0.33 |
| Val | 380 | A | A | . | . | . | . | . | −1.11 | −0.13 | . | . | . | 0.30 | 0.19 |
| Leu | 381 | A | A | . | . | . | . | . | −1.11 | 0.37 | . | . | . | −0.30 | 0.11 |
| Leu | 382 | . | A | B | . | . | . | . | −1.46 | 1.01 | . | . | . | −0.60 | 0.09 |
| Gly | 383 | . | A | B | . | . | . | . | −2.04 | 1.01 | . | . | . | −0.60 | 0.11 |
| Ala | 384 | . | A | B | . | . | . | . | −1.94 | 0.87 | . | . | . | −0.60 | 0.14 |
| Val | 385 | . | A | B | . | . | . | . | −1.09 | 0.94 | . | . | . | −0.60 | 0.27 |
| Gly | 386 | . | . | B | . | . | . | . | −0.57 | 0.26 | . | . | . | −0.10 | 0.45 |
| Ala | 387 | . | . | B | . | . | . | . | 0.24 | 0.74 | . | . | . | −0.40 | 0.47 |
| Tyr | 388 | . | . | B | . | . | . | . | 0.24 | 0.64 | . | . | . | −0.25 | 1.01 |
| Asp | 389 | . | . | . | . | T | . | . | 0.24 | 0.43 | . | . | . | 0.15 | 1.01 |
| Trp | 390 | A | . | . | . | . | . | . | 0.24 | 0.50 | . | . | . | −0.25 | 1.01 |
| Asn | 391 | A | . | . | . | . | . | . | −0.22 | 0.64 | * | . | . | −0.40 | 0.48 |
| Gly | 392 | A | A | . | . | . | . | . | 0.41 | 0.57 | * | . | . | −0.60 | 0.24 |
| Ala | 393 | A | A | . | . | . | . | . | 0.66 | 0.57 | . | . | . | −0.60 | 0.45 |
| Val | 394 | A | A | . | . | . | . | . | 0.34 | −0.34 | . | . | . | 0.30 | 0.49 |
| Leu | 395 | A | A | . | . | . | . | . | 0.33 | −0.26 | . | . | F | 0.45 | 0.71 |
| Lys | 396 | A | A | . | . | . | . | . | −0.26 | −0.30 | . | . | F | 0.45 | 0.94 |
| Glu | 397 | A | A | . | . | . | . | . | −0.26 | −0.30 | . | . | F | 0.60 | 1.28 |
| Thr | 398 | A | A | . | . | . | . | . | 0.38 | −0.51 | . | . | F | 0.90 | 1.54 |
| Ser | 399 | A | . | . | . | . | T | . | 0.38 | −1.20 | . | . | F | 1.30 | 1.54 |
| Ala | 400 | A | . | . | . | . | T | . | 0.30 | −0.56 | . | . | F | 1.15 | 0.66 |
| Gly | 401 | A | . | . | . | . | T | . | 0.04 | 0.13 | . | . | F | 0.25 | 0.32 |
| Lys | 402 | . | . | B | . | . | T | . | −0.77 | 0.07 | . | . | F | 0.25 | 0.37 |
| Val | 403 | . | . | B | . | . | . | . | −0.34 | 0.37 | . | . | . | −0.10 | 0.30 |
| Ile | 404 | . | . | B | . | . | . | . | −0.04 | −0.13 | . | . | . | 0.50 | 0.60 |
| Pro | 405 | . | . | B | . | . | . | . | 0.24 | −0.56 | . | . | . | 0.80 | 0.52 |
| Leu | 406 | . | . | B | . | . | . | . | 0.34 | −0.17 | . | . | . | 0.50 | 0.93 |
| Arg | 407 | A | . | . | . | . | . | . | −0.51 | −0.06 | . | . | F | 0.80 | 2.08 |
| Glu | 408 | A | . | . | . | . | . | . | 0.39 | −0.06 | . | . | F | 0.80 | 1.11 |
| Ser | 409 | A | . | . | . | . | . | . | 1.28 | −0.49 | . | * | F | 0.80 | 2.69 |
| Tyr | 410 | A | A | . | . | . | . | . | 0.79 | −1.17 | . | . | F | 0.90 | 2.38 |
| Leu | 411 | A | A | . | . | . | . | . | 1.39 | −0.39 | . | . | F | 0.60 | 1.19 |
| Lys | 412 | A | A | . | . | . | . | . | 1.28 | 0.04 | . | . | F | 0.00 | 1.37 |
| Glu | 413 | A | A | . | . | . | . | . | 1.28 | −0.34 | * | . | F | 0.60 | 1.52 |
| Phe | 414 | A | A | . | . | . | . | . | 0.77 | −1.10 | * | . | F | 0.90 | 3.19 |
| Pro | 415 | A | A | . | . | . | . | . | 1.06 | −1.10 | * | . | F | 0.90 | 1.31 |
| Glu | 416 | A | A | . | . | . | . | . | 1.87 | −1.10 | * | . | F | 0.90 | 1.52 |
| Glu | 417 | A | A | . | . | . | . | . | 1.79 | −0.70 | * | * | F | 0.90 | 2.82 |
| Leu | 418 | A | A | . | . | . | . | . | 1.44 | −0.99 | * | * | F | 0.90 | 2.48 |
| Lys | 419 | A | A | . | . | . | . | . | 1.56 | −0.99 | * | * | F | 0.90 | 1.42 |
| Asn | 420 | A | . | . | . | . | T | . | 1.52 | −0.49 | * | . | . | 0.70 | 0.83 |
| His | 421 | A | . | . | . | . | T | . | 0.71 | 0.27 | * | . | . | 0.25 | 1.57 |
| Gly | 422 | A | . | . | . | . | T | . | 0.37 | 0.27 | . | . | . | 0.10 | 0.65 |
| Ala | 423 | . | . | B | . | . | T | . | 0.93 | 0.70 | . | . | . | −0.20 | 0.40 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Tyr | 424 | . | . | B | B | . | . | . | 0.58 | 1.06 | . | . | . | −0.60 | 0.46 |
| Leu | 425 | . | . | B | B | . | . | . | −0.28 | 1.04 | . | . | . | −0.60 | 0.67 |
| Gly | 426 | . | . | B | B | . | . | . | −0.56 | 1.26 | . | . | . | −0.60 | 0.49 |
| Tyr | 427 | . | . | B | B | . | . | . | −0.51 | 1.24 | . | . | . | −0.60 | 0.45 |
| Thr | 428 | . | . | B | B | . | . | . | −0.78 | 0.87 | . | . | . | −0.60 | 0.74 |
| Val | 429 | . | . | B | B | . | . | . | −1.39 | 0.83 | * | . | . | −0.60 | 0.55 |
| Thr | 430 | . | . | B | B | . | . | . | −0.88 | 1.04 | * | . | . | −0.60 | 0.26 |
| Ser | 431 | . | . | B | B | . | . | . | −0.83 | 0.67 | . | . | . | −0.60 | 0.24 |
| Val | 432 | . | . | B | B | . | . | . | −0.48 | 0.57 | . | . | . | −0.60 | 0.44 |
| Val | 433 | . | . | B | B | . | . | . | −0.17 | −0.07 | . | . | F | 0.79 | 0.60 |
| Ser | 434 | . | . | B | . | . | T | . | 0.34 | −0.16 | . | . | F | 1.53 | 0.77 |
| Ser | 435 | . | . | B | . | . | T | . | 0.77 | −0.11 | . | . | F | 2.02 | 1.03 |
| Arg | 436 | . | . | B | . | . | T | . | 0.21 | −0.76 | . | . | F | 2.66 | 2.71 |
| Gln | 437 | . | . | . | . | T | T | . | 0.82 | −0.76 | . | * | F | 3.40 | 1.50 |
| Gly | 438 | . | . | B | B | . | . | . | 0.82 | −0.39 | * | * | F | 1.96 | 1.75 |
| Arg | 439 | . | . | B | B | . | . | . | 0.53 | −0.13 | * | * | F | 1.47 | 0.66 |
| Val | 440 | . | . | B | B | . | . | . | 0.49 | 0.37 | * | * | . | 0.38 | 0.39 |
| Tyr | 441 | . | . | B | B | . | . | . | −0.21 | 0.40 | * | * | . | −0.26 | 0.39 |
| Val | 442 | . | . | B | B | . | . | . | −0.42 | 0.47 | * | * | . | −0.60 | 0.20 |
| Ala | 443 | . | . | B | B | . | . | . | 0.03 | 0.90 | * | * | . | −0.60 | 0.42 |
| Gly | 444 | . | . | B | B | . | . | . | −0.78 | 0.26 | * | * | . | −0.30 | 0.52 |
| Ala | 445 | . | . | B | . | . | . | . | 0.08 | 0.29 | . | * | . | −0.10 | 0.61 |
| Pro | 446 | . | . | . | . | . | . | C | 0.29 | 0.04 | * | * | F | 0.25 | 0.97 |
| Arg | 447 | . | . | B | . | . | . | . | 0.83 | 0.04 | * | * | F | 0.20 | 1.33 |
| Phe | 448 | . | . | B | . | . | . | . | 1.08 | 0.10 | * | * | . | 0.18 | 1.90 |
| Asn | 449 | . | . | . | . | T | . | . | 1.47 | 0.03 | * | * | . | 0.71 | 1.22 |
| His | 450 | . | . | . | . | T | T | . | 1.20 | −0.40 | * | * | F | 1.79 | 1.24 |
| Thr | 451 | . | . | . | . | . | T | C | 0.52 | 0.24 | * | * | F | 1.12 | 1.06 |
| Gly | 452 | . | . | . | . | T | T | . | −0.40 | 0.14 | * | * | F | 1.30 | 0.46 |
| Lys | 453 | . | . | B | . | . | T | . | −0.40 | 0.43 | * | * | F | 0.47 | 0.28 |
| Val | 454 | . | . | B | B | . | . | . | −0.71 | 0.71 | . | . | . | −0.21 | 0.17 |
| Ile | 455 | . | . | B | B | . | . | . | −1.28 | 0.71 | . | . | . | −0.34 | 0.25 |
| Leu | 456 | . | . | B | B | . | . | . | −1.00 | 0.90 | . | . | . | −0.47 | 0.12 |
| Phe | 457 | . | . | B | B | . | . | . | −0.66 | 1.40 | . | . | . | −0.60 | 0.22 |
| Thr | 458 | . | . | B | B | . | . | . | −0.70 | 1.16 | . | . | . | −0.60 | 0.51 |
| Met | 459 | . | . | B | B | . | . | . | 0.27 | 0.87 | . | . | . | −0.32 | 1.00 |
| His | 460 | . | . | . | . | . | T | C | 0.86 | 0.19 | . | . | . | 1.01 | 2.26 |
| Asn | 461 | . | . | . | . | . | T | C | 0.86 | −0.21 | . | . | F | 2.04 | 2.10 |
| Asn | 462 | . | . | . | . | . | T | C | 1.24 | −0.01 | . | . | F | 2.32 | 1.75 |
| Arg | 463 | . | . | . | . | T | T | . | 0.67 | −0.14 | . | . | F | 2.80 | 1.85 |
| Ser | 464 | . | . | . | . | . | . | C | 1.23 | 0.04 | . | . | F | 1.37 | 0.81 |
| Leu | 465 | A | A | . | . | . | . | . | 1.27 | 0.14 | . | . | . | 0.54 | 0.68 |
| Thr | 466 | . | A | B | . | . | . | . | 0.68 | 0.14 | . | . | . | 0.26 | 0.60 |
| Ile | 467 | . | A | B | . | . | . | . | 0.08 | 0.64 | . | * | . | −0.32 | 0.46 |
| His | 468 | . | A | B | . | . | . | . | 0.08 | 0.87 | . | * | . | −0.60 | 0.55 |
| Gln | 469 | . | A | B | . | . | . | . | 0.03 | 0.19 | * | * | . | −0.30 | 0.74 |
| Ala | 470 | . | A | B | . | . | . | . | 0.84 | 0.13 | * | * | . | 0.02 | 1.05 |
| Met | 471 | . | . | B | . | . | T | . | 1.16 | −0.16 | * | . | . | 1.19 | 1.33 |
| Arg | 472 | . | . | B | . | . | T | . | 1.16 | −0.26 | * | * | F | 1.51 | 1.33 |
| Gly | 473 | . | . | B | . | . | T | . | 0.84 | 0.03 | * | . | F | 0.93 | 0.92 |
| Gln | 474 | . | . | B | . | . | T | . | 0.54 | −0.04 | . | . | F | 1.70 | 0.92 |
| Gln | 475 | . | . | B | . | . | . | . | 0.89 | −0.27 | * | . | F | 1.33 | 0.63 |
| Ile | 476 | . | . | B | . | . | . | . | 0.79 | 0.49 | * | . | F | 0.41 | 1.00 |
| Gly | 477 | . | . | B | . | . | T | . | 0.33 | 0.84 | * | . | F | 0.29 | 0.50 |
| Ser | 478 | . | . | B | . | . | T | . | 0.38 | 0.87 | * | . | F | 0.12 | 0.29 |
| Tyr | 479 | . | . | . | . | . | T | C | 0.38 | 0.86 | * | . | . | 0.00 | 0.55 |
| Phe | 480 | . | . | B | . | . | T | . | −0.51 | 0.17 | * | . | F | 0.25 | 0.96 |
| Gly | 481 | . | . | . | B | . | . | C | 0.07 | 0.43 | * | . | F | −0.25 | 0.50 |
| Ser | 482 | . | . | . | B | . | . | C | 0.11 | 0.53 | * | . | F | −0.25 | 0.46 |
| Glu | 483 | . | . | B | B | . | . | . | −0.44 | 0.16 | * | . | F | −0.15 | 0.71 |
| Ile | 484 | . | . | B | B | . | . | . | −0.20 | 0.01 | . | . | F | −0.15 | 0.54 |
| Thr | 485 | . | . | B | B | . | . | . | −0.39 | −0.41 | . | * | F | 0.45 | 0.67 |
| Ser | 486 | . | . | B | B | . | . | . | −0.04 | −0.11 | . | * | F | 0.45 | 0.27 |
| Val | 487 | . | . | B | B | . | . | . | −0.09 | −0.11 | . | * | F | 0.76 | 0.64 |
| Asp | 488 | . | . | B | B | . | . | . | −0.09 | −0.37 | . | * | F | 1.07 | 0.44 |
| Ile | 489 | . | . | B | . | . | . | . | 0.46 | −0.86 | . | * | F | 1.88 | 0.55 |
| Asp | 490 | . | . | . | . | T | T | . | −0.09 | −0.81 | . | * | F | 2.79 | 0.73 |
| Gly | 491 | . | . | . | . | T | T | . | −0.10 | −0.81 | . | * | F | 3.10 | 0.33 |
| Asp | 492 | . | . | . | . | T | T | . | 0.76 | −0.33 | * | * | F | 2.49 | 0.67 |
| Gly | 493 | . | . | B | . | . | T | . | −0.10 | −1.01 | * | * | F | 2.08 | 0.67 |
| Val | 494 | . | . | B | B | . | . | . | −0.02 | −0.37 | . | * | F | 1.07 | 0.50 |
| Thr | 495 | . | . | B | B | . | . | . | −0.83 | −0.11 | . | . | F | 0.76 | 0.25 |
| Asp | 496 | . | . | B | B | . | . | . | −1.34 | 0.57 | * | . | F | −0.45 | 0.21 |
| Val | 497 | . | . | B | B | . | . | . | −1.69 | 0.79 | * | . | . | −0.60 | 0.21 |
| Leu | 498 | . | . | B | B | . | . | . | −1.93 | 0.57 | . | . | . | −0.60 | 0.14 |
| Leu | 499 | . | . | B | B | . | . | . | −1.29 | 0.59 | . | . | . | −0.60 | 0.09 |
| Val | 500 | . | . | B | B | . | . | . | −1.58 | 1.01 | . | . | . | −0.60 | 0.18 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Gly | 501 | . | . | B | B | . | . | . | −1.82 | 0.99 | . | . | . | −0.60 | 0.21 |
| Ala | 502 | . | . | B | . | . | . | . | −1.67 | 1.06 | . | . | . | −0.40 | 0.41 |
| Pro | 503 | . | . | B | . | . | . | . | −0.86 | 1.16 | . | . | . | −0.40 | 0.48 |
| Met | 504 | . | . | B | . | . | . | . | −0.04 | 0.91 | . | . | . | −0.40 | 0.77 |
| Tyr | 505 | . | . | B | . | . | . | . | 0.47 | 0.49 | . | . | . | −0.25 | 1.33 |
| Phe | 506 | . | . | B | . | . | . | . | 0.92 | 0.41 | * | . | . | −0.40 | 0.85 |
| Asn | 507 | A | . | . | . | . | T | . | 1.51 | −0.01 | . | * | . | 0.85 | 1.68 |
| Glu | 508 | A | . | . | . | . | T | . | 1.83 | −0.63 | . | * | F | 1.30 | 1.86 |
| Gly | 509 | A | . | . | . | . | T | . | 2.09 | −1.39 | . | * | F | 1.30 | 4.20 |
| Arg | 510 | A | . | . | . | . | T | . | 2.38 | −1.74 | . | * | F | 1.30 | 2.58 |
| Glu | 511 | A | . | . | . | . | . | . | 2.22 | −2.14 | . | * | F | 1.10 | 2.98 |
| Arg | 512 | . | . | . | B | T | . | . | 1.98 | −1.50 | . | * | F | 1.30 | 2.24 |
| Gly | 513 | . | . | . | B | T | . | . | 1.12 | −1.17 | . | * | F | 1.30 | 1.79 |
| Lys | 514 | . | . | B | B | . | . | . | 1.22 | −0.53 | . | * | F | 0.75 | 0.77 |
| Val | 515 | . | . | B | B | . | . | . | 1.11 | 0.23 | . | * | . | −0.30 | 0.61 |
| Tyr | 516 | . | . | B | B | . | . | . | 0.30 | 0.23 | . | * | . | −0.15 | 1.07 |
| Val | 517 | . | . | B | B | . | . | . | 0.30 | 0.49 | . | * | . | −0.60 | 0.44 |
| Tyr | 518 | . | . | B | . | . | . | . | 0.64 | 0.49 | * | * | . | 0.01 | 1.17 |
| Glu | 519 | . | . | B | . | . | . | . | 0.60 | 0.24 | * | . | . | 0.57 | 1.29 |
| Leu | 520 | . | . | B | . | . | . | . | 1.57 | −0.11 | . | . | . | 1.43 | 2.80 |
| Arg | 521 | A | . | . | . | . | T | . | 1.11 | −0.76 | . | . | F | 2.34 | 3.50 |
| Gln | 522 | . | . | B | . | . | T | . | 1.11 | −0.73 | . | . | F | 2.60 | 1.75 |
| Asn | 523 | . | . | B | . | . | T | . | 1.11 | −0.09 | * | . | F | 2.04 | 1.57 |
| Arg | 524 | . | . | B | . | . | T | . | 1.11 | −0.01 | * | * | F | 1.78 | 1.26 |
| Phe | 525 | . | . | B | . | . | . | . | 1.58 | 0.39 | * | . | . | 0.57 | 1.17 |
| Val | 526 | . | . | B | . | . | T | . | 1.16 | 0.41 | * | * | . | 0.06 | 0.72 |
| Tyr | 527 | . | . | B | . | . | T | . | 0.34 | 0.50 | . | * | . | −0.20 | 0.53 |
| Asn | 528 | . | . | B | . | . | T | . | 0.39 | 1.19 | . | * | F | 0.29 | 0.50 |
| Gly | 529 | . | . | . | . | T | T | . | 0.28 | 0.40 | * | * | F | 1.18 | 1.36 |
| Thr | 530 | . | . | . | . | . | . | C | 0.68 | −0.24 | . | . | F | 2.02 | 1.45 |
| Leu | 531 | . | . | . | . | . | T | C | 1.50 | −0.61 | . | . | F | 2.86 | 1.21 |
| Lys | 532 | . | . | . | . | T | T | . | 1.44 | −0.51 | . | * | F | 3.40 | 1.66 |
| Asp | 533 | . | . | B | . | . | T | . | 1.20 | −0.56 | . | * | F | 2.66 | 1.54 |
| Ser | 534 | . | . | B | . | . | T | . | 1.54 | −0.29 | . | . | F | 2.02 | 2.93 |
| His | 535 | . | . | B | . | . | T | . | 1.86 | −0.57 | . | . | . | 1.83 | 2.54 |
| Ser | 536 | . | . | B | . | . | T | . | 2.08 | −0.17 | . | * | . | 1.19 | 2.44 |
| Tyr | 537 | . | . | B | . | . | T | . | 2.14 | 0.33 | . | * | . | 0.25 | 1.84 |
| Gln | 538 | . | . | B | . | . | T | . | 1.44 | −0.06 | . | * | . | 0.85 | 2.65 |
| Asn | 539 | . | . | B | . | . | . | . | 1.40 | 0.23 | . | * | . | 0.05 | 1.71 |
| Ala | 540 | . | . | B | . | . | . | . | 1.13 | 0.27 | . | * | . | 0.05 | 1.08 |
| Arg | 541 | . | . | B | . | . | . | . | 1.13 | −0.10 | * | * | . | 0.50 | 0.84 |
| Phe | 542 | . | . | B | . | . | . | . | 0.49 | −0.11 | * | * | F | 0.65 | 0.70 |
| Gly | 543 | . | . | . | . | T | T | . | −0.10 | 0.17 | * | * | F | 0.65 | 0.48 |
| Ser | 544 | . | . | . | . | . | T | C | −0.40 | 0.17 | * | * | F | 0.45 | 0.25 |
| Ser | 545 | . | . | B | . | . | T | . | −0.67 | 0.56 | . | * | F | −0.05 | 0.39 |
| Ile | 546 | . | . | B | . | . | T | . | −0.67 | 0.41 | * | * | . | −0.20 | 0.29 |
| Ala | 547 | . | . | B | B | . | . | . | 0.03 | −0.01 | * | . | . | 0.30 | 0.42 |
| Ser | 548 | . | . | B | B | . | . | . | −0.43 | −0.40 | . | . | . | 0.30 | 0.53 |
| Val | 549 | . | . | B | B | . | . | . | −0.13 | −0.10 | * | . | . | 0.64 | 0.62 |
| Arg | 550 | . | . | B | B | . | . | . | 0.17 | −0.39 | * | . | F | 1.13 | 0.99 |
| Asp | 551 | . | . | B | . | . | . | . | 1.06 | −0.49 | * | . | F | 1.82 | 1.28 |
| Leu | 552 | . | . | B | . | . | . | . | 1.34 | −0.87 | * | . | F | 2.46 | 2.88 |
| Asn | 553 | . | . | . | . | T | T | . | 1.40 | −1.13 | * | . | F | 3.40 | 1.97 |
| Gln | 554 | . | . | . | . | T | T | . | 2.26 | −0.37 | * | . | F | 2.76 | 1.85 |
| Asp | 555 | . | . | . | . | T | T | . | 2.14 | 0.03 | * | . | F | 1.82 | 3.60 |
| Ser | 556 | . | . | . | . | T | T | . | 1.29 | −0.66 | * | . | F | 2.38 | 3.74 |
| Tyr | 557 | . | . | . | B | T | . | . | 1.24 | −0.41 | . | . | F | 1.34 | 1.60 |
| Asn | 558 | . | . | B | B | . | . | . | 0.39 | −0.17 | . | . | F | 0.45 | 0.71 |
| Asp | 559 | . | . | B | B | . | . | . | 0.04 | 0.47 | . | . | . | −0.60 | 0.39 |
| Val | 560 | . | . | B | B | . | . | . | −0.54 | 0.51 | * | . | . | −0.60 | 0.25 |
| Val | 561 | . | . | B | B | . | . | . | −0.46 | 0.26 | . | . | . | −0.30 | 0.16 |
| Val | 562 | . | . | B | B | . | . | . | −1.02 | 0.29 | . | . | . | −0.30 | 0.14 |
| Gly | 563 | . | . | B | B | . | . | . | −1.02 | 0.97 | . | . | . | −0.60 | 0.16 |
| Ala | 564 | . | A | B | . | . | . | . | −1.02 | 0.33 | . | . | . | −0.30 | 0.38 |
| Pro | 565 | A | A | . | . | . | . | . | −0.17 | −0.31 | . | . | . | 0.30 | 0.85 |
| Leu | 566 | A | A | . | . | . | . | . | 0.66 | −0.56 | . | . | . | 0.75 | 1.37 |
| Glu | 567 | A | A | . | . | . | . | . | 0.92 | −0.49 | . | . | F | 0.60 | 1.85 |
| Asp | 568 | A | A | . | . | . | . | . | 0.92 | −0.49 | . | . | . | 0.45 | 1.21 |
| Asn | 569 | A | A | . | . | . | . | . | 0.92 | −0.49 | . | . | . | 0.45 | 1.45 |
| His | 570 | A | A | . | . | . | . | . | 0.24 | −0.67 | . | . | . | 0.60 | 0.85 |
| Ala | 571 | A | . | . | B | . | . | . | 0.81 | 0.01 | . | . | . | −0.30 | 0.36 |
| Gly | 572 | A | . | . | B | . | . | . | −0.08 | 0.77 | . | . | . | −0.60 | 0.35 |
| Ala | 573 | A | . | . | B | . | . | . | −0.78 | 1.06 | . | . | . | −0.60 | 0.18 |
| Ile | 574 | . | . | B | B | . | . | . | −0.81 | 1.34 | . | . | . | −0.60 | 0.15 |
| Tyr | 575 | . | . | B | B | . | . | . | −1.12 | 1.34 | . | . | . | −0.60 | 0.21 |
| Ile | 576 | . | . | B | B | . | . | . | −1.23 | 1.34 | * | * | . | −0.60 | 0.21 |
| Phe | 577 | . | . | B | B | . | . | . | −0.78 | 1.63 | * | * | . | −0.60 | 0.25 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| His | 578 | . | . | B | B | . | . | . | −0.53 | 0.94 | * | * | . | −0.60 | 0.32 |
| Gly | 579 | . | . | . | B | T | . | . | 0.06 | 0.61 | * | * | . | −0.20 | 0.45 |
| Phe | 580 | . | . | . | . | T | T | . | −0.59 | 0.31 | * | * | . | 0.50 | 0.69 |
| Arg | 581 | . | . | . | . | T | T | . | −0.51 | 0.21 | * | * | F | 0.65 | 0.36 |
| Gly | 582 | . | . | . | . | T | T | . | 0.23 | 0.40 | . | . | F | 0.35 | 0.30 |
| Ser | 583 | . | . | . | . | T | T | . | −0.04 | −0.03 | . | . | F | 1.25 | 0.69 |
| Ile | 584 | . | . | . | . | . | . | C | 0.09 | −0.33 | * | * | F | 1.15 | 0.51 |
| Leu | 585 | . | . | . | . | . | . | C | 0.83 | 0.10 | * | * | F | 0.85 | 0.79 |
| Lys | 586 | . | . | . | . | . | . | C | 0.72 | −0.33 | . | * | F | 1.90 | 1.18 |
| Thr | 587 | . | . | . | . | . | T | C | 1.18 | −0.31 | * | * | F | 2.40 | 2.92 |
| Pro | 588 | . | . | . | . | . | T | C | 0.59 | −1.00 | * | * | F | 3.00 | 6.94 |
| Lys | 589 | . | . | B | . | . | T | . | 1.17 | −1.00 | * | * | F | 2.50 | 2.43 |
| Gln | 590 | . | . | B | . | . | T | . | 1.39 | −0.51 | * | * | F | 2.20 | 2.43 |
| Arg | 591 | . | . | B | B | . | . | . | 1.04 | −0.50 | . | * | F | 1.20 | 1.59 |
| Ile | 592 | . | . | B | B | . | . | . | 1.36 | −0.54 | . | * | F | 1.20 | 1.06 |
| Thr | 593 | . | A | B | B | . | . | . | 0.76 | −0.54 | . | * | F | 0.90 | 1.06 |
| Ala | 594 | . | A | B | B | . | . | . | 0.12 | −0.26 | . | * | F | 0.45 | 0.45 |
| Ser | 595 | . | A | B | . | . | . | . | −0.19 | 0.24 | . | . | F | −0.15 | 0.65 |
| Glu | 596 | . | A | B | . | . | . | . | −0.64 | 0.04 | . | * | F | −0.15 | 0.65 |
| Leu | 597 | A | A | . | B | . | . | . | −0.57 | −0.01 | . | . | F | 0.45 | 0.63 |
| Ala | 598 | A | A | . | B | . | . | . | −0.26 | 0.17 | * | . | . | −0.30 | 0.39 |
| Thr | 599 | A | A | . | B | . | . | . | 0.09 | 0.19 | * | . | . | −0.30 | 0.39 |
| Gly | 600 | A | A | . | B | . | . | . | −0.31 | 0.94 | * | . | . | −0.60 | 0.74 |
| Leu | 601 | . | . | B | B | . | . | . | −0.66 | 1.04 | * | . | . | −0.60 | 0.63 |
| Gln | 602 | . | . | B | B | . | . | . | −0.51 | 0.97 | * | . | . | −0.60 | 0.44 |
| Tyr | 603 | . | . | . | . | T | T | . | −0.22 | 1.06 | * | . | . | 0.20 | 0.24 |
| Phe | 604 | . | . | B | . | . | T | . | −0.80 | 1.01 | * | . | . | −0.20 | 0.38 |
| Gly | 605 | . | . | B | . | . | T | . | −0.49 | 1.01 | * | . | . | −0.20 | 0.15 |
| Cys | 606 | . | . | B | . | . | T | . | −0.02 | 1.11 | . | * | . | −0.20 | 0.13 |
| Ser | 607 | . | . | B | B | . | . | . | −0.02 | 0.79 | . | * | . | −0.60 | 0.15 |
| Ile | 608 | . | . | B | B | . | . | . | −0.59 | 0.40 | . | * | . | −0.60 | 0.27 |
| His | 609 | . | . | B | B | . | . | . | 0.11 | 0.66 | . | * | . | −0.60 | 0.41 |
| Gly | 610 | . | . | B | B | . | . | . | −0.36 | 0.09 | . | * | . | −0.30 | 0.52 |
| Gln | 611 | . | . | B | . | . | . | . | 0.31 | 0.39 | . | * | . | −0.10 | 0.61 |
| Leu | 612 | . | . | B | . | . | . | . | 0.61 | 0.10 | . | * | . | −0.10 | 0.72 |
| Asp | 613 | . | . | B | . | . | . | . | 1.50 | −0.40 | . | * | . | 0.65 | 1.26 |
| Leu | 614 | . | . | B | . | . | . | . | 1.19 | −0.83 | . | * | . | 0.95 | 1.21 |
| Asn | 615 | A | . | . | . | . | T | . | 0.72 | −0.80 | . | * | F | 1.30 | 1.45 |
| Glu | 616 | A | . | . | . | . | T | . | −0.17 | −0.80 | . | * | F | 1.15 | 0.72 |
| Asp | 617 | A | . | . | . | . | T | . | 0.64 | −0.11 | . | * | F | 0.85 | 0.61 |
| Gly | 618 | A | . | . | . | . | T | . | −0.17 | −0.80 | . | * | F | 1.15 | 0.63 |
| Leu | 619 | A | . | . | B | . | . | . | 0.06 | −0.51 | . | * | . | 0.60 | 0.30 |
| Ile | 620 | A | . | . | B | . | . | . | −0.80 | −0.01 | . | * | . | 0.30 | 0.18 |
| Asp | 621 | . | . | B | B | . | . | . | −1.14 | 0.63 | . | * | . | −0.60 | 0.14 |
| Leu | 622 | . | . | B | B | . | . | . | −1.73 | 0.63 | * | * | . | −0.60 | 0.16 |
| Ala | 623 | . | . | B | B | . | . | . | −2.20 | 0.44 | . | . | . | −0.60 | 0.24 |
| Val | 624 | A | . | . | B | . | . | . | −1.73 | 0.44 | * | . | . | −0.60 | 0.12 |
| Gly | 625 | A | A | . | . | . | . | . | −0.84 | 0.87 | * | * | . | −0.60 | 0.14 |
| Ala | 626 | A | A | . | . | . | . | . | −1.43 | 0.59 | . | . | . | −0.60 | 0.22 |
| Leu | 627 | A | A | . | . | . | . | . | −1.48 | 0.59 | . | . | . | −0.60 | 0.30 |
| Gly | 628 | A | A | . | . | . | . | . | −1.78 | 0.59 | . | . | . | −0.60 | 0.23 |
| Asn | 629 | . | A | B | B | . | . | . | −1.73 | 0.84 | . | . | . | −0.60 | 0.16 |
| Ala | 630 | . | A | B | B | . | . | . | −1.68 | 1.03 | . | . | . | −0.60 | 0.16 |
| Val | 631 | . | A | B | B | . | . | . | −1.39 | 1.26 | * | . | . | −0.60 | 0.17 |
| Ile | 632 | . | A | B | B | . | . | . | −0.47 | 1.21 | * | . | . | −0.60 | 0.14 |
| Leu | 633 | . | A | B | B | . | . | . | −0.33 | 0.81 | * | . | . | −0.60 | 0.27 |
| Trp | 634 | . | A | B | B | . | . | . | −1.19 | 0.74 | * | . | . | −0.60 | 0.57 |
| Ser | 635 | . | A | B | B | . | . | . | −1.46 | 0.74 | * | . | . | −0.60 | 0.60 |
| Arg | 636 | . | . | B | B | . | . | . | −0.60 | 0.70 | * | * | F | −0.45 | 0.54 |
| Pro | 637 | . | . | B | B | . | . | . | −0.60 | 0.41 | * | * | . | −0.60 | 0.89 |
| Val | 638 | . | . | B | B | . | . | . | 0.21 | 0.19 | * | * | . | −0.30 | 0.46 |
| Val | 639 | . | . | B | B | . | . | . | −0.09 | 0.20 | * | * | . | −0.30 | 0.38 |
| Gln | 640 | . | . | B | B | . | . | . | −0.09 | 0.70 | * | * | . | −0.60 | 0.25 |
| Ile | 641 | . | . | B | B | . | . | . | −1.01 | 0.66 | * | * | . | −0.60 | 0.45 |
| Asn | 642 | . | . | B | . | . | T | . | −0.83 | 0.70 | . | * | . | −0.20 | 0.50 |
| Ala | 643 | . | . | B | . | . | T | . | −0.68 | 0.56 | . | * | . | −0.20 | 0.39 |
| Ser | 644 | . | . | B | . | . | T | . | 0.18 | 0.94 | . | * | . | −0.20 | 0.48 |
| Leu | 645 | A | . | . | . | . | T | . | −0.03 | 0.26 | . | * | . | 0.10 | 0.52 |
| His | 646 | A | . | . | . | . | . | . | 0.56 | 0.29 | . | * | . | 0.18 | 0.80 |
| Phe | 647 | A | . | . | . | . | . | . | 0.60 | 0.17 | . | * | . | 0.46 | 0.80 |
| Glu | 648 | A | . | . | . | . | T | . | 0.30 | −0.21 | . | * | F | 1.84 | 1.94 |
| Pro | 649 | A | . | . | . | . | T | . | 0.60 | −0.21 | . | * | F | 1.97 | 1.00 |
| Ser | 650 | . | . | . | . | T | T | . | 0.52 | −0.31 | . | * | F | 2.80 | 1.85 |
| Lys | 651 | A | . | . | . | . | T | . | −0.14 | −0.41 | . | . | F | 1.97 | 0.75 |
| Ile | 652 | A | . | . | B | . | . | . | 0.52 | 0.37 | * | * | F | 0.69 | 0.42 |
| Asn | 653 | A | . | . | B | . | . | . | 0.63 | 0.44 | * | * | . | −0.04 | 0.43 |
| Ile | 654 | A | . | . | B | . | . | . | 0.84 | 0.06 | * | * | . | −0.02 | 0.42 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Phe | 655 | . | . | B | B | . | . | . | 0.48 | 0.06 | * | * | . | 0.04 | 1.00 |
| His | 656 | . | . | B | . | . | T | . | 0.48 | −0.06 | * | * | . | 1.38 | 0.33 |
| Arg | 657 | . | . | B | . | . | T | . | 1.48 | −0.46 | * | * | . | 1.72 | 0.95 |
| Asp | 658 | . | . | . | . | T | T | . | 1.18 | −1.14 | * | . | F | 3.06 | 2.14 |
| Cys | 659 | . | . | . | . | T | T | . | 1.72 | −1.54 | * | . | F | 3.40 | 2.11 |
| Lys | 660 | . | . | . | . | T | . | . | 2.53 | −1.61 | * | . | F | 2.86 | 1.07 |
| Arg | 661 | . | . | . | . | T | T | . | 2.57 | −1.61 | * | . | F | 3.03 | 1.25 |
| Ser | 662 | . | . | . | . | T | T | . | 1.87 | −1.61 | * | . | F | 3.00 | 3.90 |
| Gly | 663 | . | . | . | . | T | T | . | 1.56 | −1.69 | * | . | F | 2.97 | 1.97 |
| Arg | 664 | . | . | . | . | T | T | . | 1.56 | −1.20 | * | . | F | 2.94 | 1.45 |
| Asp | 665 | . | . | . | . | T | T | . | 0.70 | −0.63 | * | . | F | 3.10 | 0.58 |
| Ala | 666 | . | . | B | . | . | T | . | 0.00 | −0.33 | * | . | F | 2.09 | 0.48 |
| Thr | 667 | . | . | B | . | . | T | . | −0.29 | −0.26 | . | . | . | 1.63 | 0.25 |
| Cys | 668 | . | . | B | . | . | T | . | −0.64 | 0.24 | * | . | . | 0.72 | 0.15 |
| Leu | 669 | A | A | . | . | . | . | . | −1.57 | 1.03 | * | . | . | −0.29 | 0.13 |
| Ala | 670 | A | A | . | . | . | . | . | −2.23 | 1.21 | . | . | . | −0.60 | 0.07 |
| Ala | 671 | A | A | . | . | . | . | . | −2.34 | 1.30 | . | . | . | −0.60 | 0.07 |
| Phe | 672 | A | A | . | . | . | . | . | −2.34 | 1.51 | . | . | . | −0.60 | 0.08 |
| Leu | 673 | A | A | . | . | . | . | . | −1.89 | 1.31 | . | . | . | −0.60 | 0.11 |
| Cys | 674 | . | A | B | . | . | . | . | −1.97 | 1.24 | . | . | . | −0.60 | 0.17 |
| Phe | 675 | . | . | B | B | . | . | . | −2.08 | 1.43 | . | . | . | −0.60 | 0.14 |
| Thr | 676 | . | . | B | B | . | . | . | −2.30 | 1.43 | . | . | . | −0.60 | 0.14 |
| Pro | 677 | . | . | B | B | . | . | . | −2.19 | 1.43 | . | . | . | −0.60 | 0.22 |
| Ile | 678 | . | A | . | B | T | . | . | −1.59 | 1.36 | . | . | . | −0.20 | 0.26 |
| Phe | 679 | . | A | B | B | . | . | . | −0.96 | 1.00 | . | . | . | −0.60 | 0.28 |
| Leu | 680 | . | A | B | B | . | . | . | −0.96 | 1.01 | . | . | . | −0.60 | 0.24 |
| Ala | 681 | . | A | . | B | . | . | C | −0.64 | 1.37 | . | . | . | −0.40 | 0.30 |
| Pro | 682 | . | A | . | B | . | . | C | −0.74 | 1.09 | . | . | . | −0.40 | 0.60 |
| His | 683 | . | A | . | B | T | . | . | −0.17 | 0.79 | . | . | . | −0.05 | 1.05 |
| Phe | 684 | . | A | . | B | T | . | . | 0.22 | 0.59 | . | . | . | −0.05 | 1.51 |
| Gln | 685 | . | A | B | B | . | . | . | 0.18 | 0.57 | . | . | F | −0.30 | 1.41 |
| Thr | 686 | . | A | B | B | . | . | . | 0.42 | 0.79 | . | . | F | −0.45 | 0.77 |
| Thr | 687 | . | . | B | B | . | . | . | −0.26 | 0.71 | * | * | F | −0.45 | 0.88 |
| Thr | 688 | . | . | B | B | . | . | . | −0.11 | 0.61 | * | * | F | −0.45 | 0.35 |
| Val | 689 | . | . | B | B | . | . | . | 0.34 | 0.21 | . | * | . | −0.30 | 0.48 |
| Gly | 690 | . | . | B | B | . | . | . | 0.34 | 0.49 | . | * | . | −0.60 | 0.52 |
| Ile | 691 | . | . | B | B | . | . | . | 0.07 | 0.40 | . | * | . | −0.60 | 0.58 |
| Arg | 692 | . | . | B | B | . | . | . | 0.07 | 0.41 | . | * | . | −0.60 | 0.79 |
| Tyr | 693 | . | . | B | B | . | . | . | −0.22 | 0.26 | . | * | . | −0.15 | 1.16 |
| Asn | 694 | . | A | B | B | . | . | . | 0.63 | 0.44 | . | * | . | −0.45 | 1.63 |
| Ala | 695 | . | A | B | B | . | . | . | 0.98 | −0.24 | * | * | . | 0.45 | 1.39 |
| Thr | 696 | . | A | B | B | . | . | . | 1.98 | −0.24 | . | * | . | 0.45 | 1.54 |
| Met | 697 | . | A | B | B | . | . | . | 1.98 | −1.00 | . | * | F | 0.90 | 1.87 |
| Asp | 698 | . | A | B | . | . | . | . | 1.98 | −1.40 | . | . | F | 0.90 | 3.63 |
| Glu | 699 | . | A | B | . | . | . | . | 1.67 | −1.14 | . | . | F | 1.20 | 3.94 |
| Arg | 700 | . | A | B | . | . | . | . | 2.04 | −1.14 | * | * | F | 1.50 | 5.75 |
| Arg | 701 | . | A | . | . | T | . | . | 2.47 | −1.33 | * | * | F | 2.20 | 5.33 |
| Tyr | 702 | . | A | . | . | T | . | . | 2.48 | −1.33 | * | * | F | 2.50 | 6.02 |
| Thr | 703 | . | . | . | . | . | T | C | 2.44 | −0.83 | . | * | F | 3.00 | 3.11 |
| Pro | 704 | . | . | . | . | . | T | C | 1.63 | −0.33 | . | * | F | 2.40 | 2.16 |
| Arg | 705 | . | . | B | . | . | T | . | 1.52 | 0.36 | . | * | . | 1.15 | 1.14 |
| Ala | 706 | . | . | B | . | . | T | . | 1.41 | −0.40 | * | * | . | 1.45 | 1.31 |
| His | 707 | . | . | B | . | . | . | . | 1.31 | −0.89 | . | * | . | 1.59 | 1.47 |
| Leu | 708 | . | . | B | . | . | . | . | 1.28 | −0.89 | * | * | F | 1.63 | 0.74 |
| Asp | 709 | . | . | B | . | . | T | . | 1.49 | −0.46 | . | * | F | 1.87 | 0.73 |
| Glu | 710 | . | . | . | . | T | T | . | 1.49 | −0.96 | * | * | F | 2.91 | 0.89 |
| Gly | 711 | . | . | . | . | T | T | . | 1.38 | −1.46 | * | * | F | 3.40 | 2.12 |
| Gly | 712 | . | . | . | . | T | T | . | 1.10 | −1.36 | * | . | F | 3.06 | 1.10 |
| Asp | 713 | . | . | . | . | T | . | . | 1.91 | −0.87 | * | * | F | 2.37 | 0.92 |
| Arg | 714 | A | . | . | . | . | . | . | 2.02 | −0.47 | * | * | F | 1.48 | 1.49 |
| Phe | 715 | A | . | . | . | . | . | . | 1.43 | −0.90 | * | * | F | 1.44 | 2.95 |
| Thr | 716 | . | . | B | . | . | . | . | 0.92 | −0.83 | * | * | F | 1.10 | 1.79 |
| Asn | 717 | . | A | B | . | . | . | . | 0.46 | −0.19 | * | * | F | 0.45 | 0.68 |
| Arg | 718 | . | A | B | . | . | . | . | −0.36 | 0.50 | * | * | F | −0.45 | 0.64 |
| Ala | 719 | . | A | B | . | . | . | . | −0.77 | 0.40 | * | * | . | −0.60 | 0.37 |
| Val | 720 | . | A | B | . | . | . | . | −0.37 | 0.30 | . | . | . | −0.06 | 0.31 |
| Leu | 721 | . | A | B | . | . | . | . | −0.40 | 0.29 | . | . | . | 0.18 | 0.21 |
| Leu | 722 | . | A | B | . | . | . | . | −0.40 | 0.71 | . | . | F | 0.27 | 0.21 |
| Ser | 723 | . | . | . | . | . | T | C | −0.51 | 0.61 | . | . | F | 1.11 | 0.48 |
| Ser | 724 | . | . | . | . | . | T | C | −0.73 | −0.03 | . | . | F | 2.40 | 1.01 |
| Gly | 725 | . | . | . | . | . | T | C | −0.54 | −0.03 | * | . | F | 2.16 | 1.01 |
| Gln | 726 | A | . | . | . | . | T | . | 0.27 | −0.14 | * | . | F | 1.57 | 0.40 |
| Glu | 727 | A | A | . | . | . | . | . | 1.19 | −0.53 | * | * | F | 1.23 | 0.52 |
| Leu | 728 | A | A | . | . | . | . | . | 0.60 | −0.91 | * | * | F | 1.14 | 1.03 |
| Cys | 729 | A | A | . | . | . | . | . | 0.90 | −0.66 | * | * | . | 0.60 | 0.42 |
| Glu | 730 | A | A | . | . | . | . | . | 0.54 | −0.66 | * | * | . | 0.60 | 0.39 |
| Arg | 731 | A | A | . | . | . | . | . | 0.51 | 0.13 | * | * | . | −0.30 | 0.41 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Ile | 732 | A | A | . | . | . | . | . | −0.34 | −0.06 | * | * | . | 0.45 | 1.03 |
| Asn | 733 | A | A | . | . | . | . | . | −0.34 | 0.01 | * | * | . | −0.30 | 0.44 |
| Phe | 734 | A | A | . | . | . | . | . | 0.32 | 0.70 | * | * | . | −0.60 | 0.19 |
| His | 735 | . | A | B | . | . | . | . | 0.01 | 0.70 | * | * | . | −0.60 | 0.44 |
| Val | 736 | . | A | B | . | . | . | . | −0.69 | 0.50 | * | * | . | −0.60 | 0.40 |
| Leu | 737 | . | A | B | . | . | . | . | 0.20 | 0.60 | . | * | . | −0.60 | 0.46 |
| Asp | 738 | A | A | . | . | . | . | . | −0.04 | −0.19 | . | . | F | 0.62 | 0.57 |
| Thr | 739 | A | . | . | . | . | T | . | −0.20 | 0.07 | . | . | F | 0.74 | 1.20 |
| Ala | 740 | A | . | . | . | . | T | . | −0.12 | 0.07 | * | . | F | 0.91 | 1.08 |
| Asp | 741 | A | . | . | . | . | T | . | 0.52 | −0.61 | * | . | . | 1.83 | 1.30 |
| Tyr | 742 | . | . | B | . | . | T | . | 0.48 | −0.19 | * | . | . | 1.70 | 1.39 |
| Val | 743 | . | . | B | B | . | . | . | 0.17 | −0.03 | . | . | . | 1.13 | 1.02 |
| Lys | 744 | . | . | B | B | . | . | . | −0.22 | −0.04 | . | . | F | 0.96 | 0.88 |
| Pro | 745 | . | . | B | B | . | . | . | 0.07 | 0.74 | * | . | F | −0.11 | 0.49 |
| Val | 746 | . | . | B | B | . | . | . | −0.79 | 0.37 | * | . | . | −0.13 | 0.88 |
| Thr | 747 | . | . | B | B | . | . | . | −0.54 | 0.37 | * | * | . | −0.30 | 0.33 |
| Phe | 748 | . | . | B | B | . | . | . | 0.07 | 0.37 | . | * | . | −0.30 | 0.37 |
| Ser | 749 | . | . | B | B | . | . | . | −0.28 | 0.70 | . | * | . | −0.60 | 0.77 |
| Val | 750 | . | . | B | B | . | . | . | −0.88 | 0.44 | . | * | . | −0.60 | 0.72 |
| Glu | 751 | . | . | B | B | . | . | . | −0.02 | 0.64 | . | * | . | −0.60 | 0.68 |
| Tyr | 752 | . | . | B | . | . | . | . | 0.29 | −0.14 | . | * | . | 0.50 | 0.88 |
| Ser | 753 | . | . | . | . | . | . | C | 0.78 | −0.53 | . | * | . | 1.49 | 1.99 |
| Leu | 754 | . | . | . | . | T | . | . | 1.08 | −0.74 | * | . | . | 2.03 | 1.78 |
| Glu | 755 | A | . | . | . | . | . | . | 1.90 | −0.74 | * | . | F | 2.12 | 1.89 |
| Asp | 756 | A | . | . | . | . | T | . | 1.56 | −1.00 | . | . | F | 2.66 | 1.92 |
| Pro | 757 | . | . | . | . | T | T | . | 1.59 | −0.96 | . | . | F | 3.40 | 2.31 |
| Asp | 758 | . | . | . | . | T | T | . | 1.29 | −1.21 | . | . | F | 3.06 | 2.06 |
| His | 759 | . | . | . | . | . | T | C | 1.29 | −0.60 | . | . | F | 2.52 | 1.22 |
| Gly | 760 | . | . | . | . | . | . | C | 1.29 | 0.09 | . | . | F | 0.93 | 0.65 |
| Pro | 761 | . | . | B | . | . | . | . | 1.29 | −0.34 | . | . | F | 0.99 | 0.65 |
| Met | 762 | . | . | B | . | . | . | . | 1.16 | −0.34 | * | . | . | 0.50 | 0.80 |
| Leu | 763 | . | . | B | . | . | . | . | 0.87 | −0.41 | * | . | F | 0.89 | 0.80 |
| Asp | 764 | . | . | . | . | T | T | . | 0.69 | 0.07 | . | . | F | 1.13 | 0.54 |
| Asp | 765 | . | . | . | . | T | T | . | 0.72 | 0.07 | . | . | F | 1.37 | 0.85 |
| Gly | 766 | . | . | . | . | T | T | . | 0.62 | −0.06 | . | . | F | 2.36 | 1.48 |
| Trp | 767 | . | . | . | . | . | T | C | 0.41 | −0.26 | * | * | F | 2.40 | 1.28 |
| Pro | 768 | . | . | . | B | . | . | C | 1.33 | 0.43 | * | * | F | 0.71 | 0.63 |
| Thr | 769 | . | . | B | B | . | . | . | 0.48 | 0.43 | * | * | F | 0.42 | 1.25 |
| Thr | 770 | . | . | B | B | . | . | . | 0.18 | 0.64 | * | * | F | 0.03 | 0.89 |
| Leu | 771 | . | . | B | B | . | . | . | −0.33 | 0.11 | . | * | . | −0.06 | 0.77 |
| Arg | 772 | . | . | B | B | . | . | . | −0.26 | 0.33 | * | * | . | −0.30 | 0.39 |
| Val | 773 | . | . | B | B | . | . | . | −0.74 | 0.27 | * | * | . | −0.30 | 0.42 |
| Ser | 774 | . | . | B | B | . | . | . | −0.72 | 0.57 | * | * | . | −0.60 | 0.44 |
| Val | 775 | . | . | B | B | . | . | . | −0.41 | 0.80 | * | * | . | −0.60 | 0.24 |
| Pro | 776 | . | . | B | B | . | . | . | 0.06 | 1.20 | * | * | . | −0.60 | 0.52 |
| Phe | 777 | . | . | . | B | T | . | . | −0.72 | 0.99 | * | * | . | −0.20 | 0.38 |
| Trp | 778 | . | . | . | . | T | T | . | 0.13 | 1.17 | . | . | . | 0.20 | 0.28 |
| Asn | 779 | . | . | . | . | . | T | C | 0.43 | 0.93 | . | . | . | 0.00 | 0.29 |
| Gly | 780 | . | . | . | . | T | T | . | 1.29 | 0.50 | . | . | . | 0.20 | 0.57 |
| Cys | 781 | . | . | . | . | T | T | . | 1.50 | −0.29 | . | . | F | 1.25 | 0.91 |
| Asn | 782 | . | A | . | . | T | . | . | 2.17 | −1.20 | . | . | F | 1.15 | 0.98 |
| Glu | 783 | . | A | . | . | T | . | . | 1.79 | −1.10 | . | . | F | 1.30 | 1.35 |
| Asp | 784 | . | A | . | . | T | . | . | 0.93 | −0.96 | . | . | F | 1.30 | 1.35 |
| Glu | 785 | . | A | . | . | T | . | . | 1.07 | −0.89 | . | . | F | 1.15 | 0.62 |
| His | 786 | . | A | . | . | T | . | . | 1.73 | −0.86 | * | . | . | 1.00 | 0.56 |
| Cys | 787 | A | A | . | . | . | . | . | 0.92 | −0.86 | * | . | . | 0.60 | 0.56 |
| Val | 788 | A | . | . | . | . | . | . | 0.07 | −0.17 | . | . | . | 0.50 | 0.26 |
| Pro | 789 | A | . | . | . | . | . | . | −0.74 | 0.47 | . | . | F | −0.25 | 0.14 |
| Asp | 790 | A | A | . | . | . | . | . | −0.74 | 0.66 | * | . | F | −0.45 | 0.22 |
| Leu | 791 | A | A | . | . | . | . | . | −1.30 | 0.09 | * | * | . | −0.30 | 0.50 |
| Val | 792 | A | A | . | . | . | . | . | −0.52 | −0.06 | * | * | . | 0.30 | 0.33 |
| Leu | 793 | A | A | . | . | . | . | . | 0.03 | −0.49 | * | * | . | 0.30 | 0.38 |
| Asp | 794 | . | A | B | . | . | . | . | 0.24 | −0.10 | . | * | . | 0.30 | 0.62 |
| Ala | 795 | A | A | . | . | . | . | . | −0.57 | −0.79 | . | * | F | 0.90 | 1.40 |
| Arg | 796 | A | . | . | . | . | T | . | 0.03 | −0.74 | . | * | F | 1.30 | 1.40 |
| Ser | 797 | A | . | . | . | . | T | . | 0.58 | −1.00 | . | * | F | 1.30 | 1.29 |
| Asp | 798 | A | . | . | . | . | T | C | 0.80 | −0.51 | . | * | F | 1.50 | 1.85 |
| Leu | 799 | . | . | . | . | . | T | C | 0.20 | −0.51 | * | * | F | 1.35 | 0.95 |
| Pro | 800 | . | A | . | . | . | . | C | 0.79 | 0.10 | * | * | F | 0.05 | 0.70 |
| Thr | 801 | A | A | . | . | . | . | . | 0.43 | −0.29 | . | * | . | 0.30 | 0.73 |
| Ala | 802 | A | A | . | . | . | . | . | 0.07 | 0.47 | . | . | . | −0.45 | 1.39 |
| Met | 803 | A | A | . | . | . | . | . | 0.07 | 0.36 | * | . | . | −0.30 | 0.48 |
| Glu | 804 | A | A | . | . | . | . | . | 0.99 | 0.33 | * | * | . | −0.30 | 0.58 |
| Tyr | 805 | A | . | . | B | . | . | . | 0.34 | −0.16 | * | . | . | 0.45 | 1.12 |
| Cys | 806 | A | . | . | B | . | . | . | −0.16 | −0.01 | * | . | . | 0.30 | 0.84 |
| Gln | 807 | A | . | . | B | . | . | . | 0.54 | 0.06 | * | . | . | −0.30 | 0.40 |
| Arg | 808 | A | . | . | B | . | . | . | 1.19 | 0.06 | * | . | . | −0.30 | 0.50 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Val | 809 | A | . | . | B | . | . | . | 0.98 | −0.70 | * | . | . | 0.75 | 1.86 |
| Leu | 810 | . | . | B | B | . | . | . | 0.63 | −0.84 | * | . | F | 1.20 | 1.66 |
| Arg | 811 | . | . | B | B | . | . | . | 1.30 | −0.74 | * | . | F | 1.35 | 0.86 |
| Lys | 812 | . | . | B | B | . | . | . | 1.30 | −0.34 | * | . | F | 1.50 | 2.00 |
| Pro | 813 | . | . | . | . | T | . | . | 0.52 | −0.99 | * | . | F | 2.70 | 4.06 |
| Ala | 814 | . | . | . | . | T | . | . | 1.08 | −1.10 | * | . | F | 3.00 | 1.11 |
| Gln | 815 | . | . | B | . | . | T | . | 1.30 | −0.71 | * | . | F | 2.35 | 0.74 |
| Asp | 816 | . | . | B | . | . | T | . | 0.94 | −0.21 | * | . | F | 1.75 | 0.49 |
| Cys | 817 | . | . | B | . | . | T | . | 0.59 | 0.11 | . | . | . | 0.70 | 0.75 |
| Ser | 818 | . | . | B | . | . | T | . | −0.01 | 0.10 | . | . | . | 0.40 | 0.63 |
| Ala | 819 | . | . | B | B | . | . | . | 0.28 | 0.39 | . | . | . | −0.30 | 0.31 |
| Tyr | 820 | . | . | B | B | . | . | . | −0.42 | 0.77 | . | . | . | −0.60 | 0.78 |
| Thr | 821 | . | . | B | B | . | . | . | −0.42 | 0.99 | . | . | . | −0.60 | 0.50 |
| Leu | 822 | . | . | B | B | . | . | . | −0.07 | 0.60 | . | . | . | −0.60 | 0.83 |
| Ser | 823 | . | . | B | B | . | . | . | −0.08 | 0.59 | . | * | . | −0.60 | 0.76 |
| Phe | 824 | . | . | B | B | . | . | . | −0.34 | 0.31 | . | * | . | −0.30 | 0.76 |
| Asp | 825 | . | . | B | B | . | . | . | −0.80 | 0.47 | . | * | F | −0.45 | 0.69 |
| Thr | 826 | . | . | B | B | . | . | . | −1.38 | 0.57 | . | * | F | −0.45 | 0.44 |
| Thr | 827 | . | . | B | B | . | . | . | −1.46 | 0.87 | . | * | F | −0.45 | 0.36 |
| Val | 828 | . | . | B | B | . | . | . | −1.16 | 0.77 | . | . | . | −0.60 | 0.15 |
| Phe | 829 | . | . | B | B | . | . | . | −0.76 | 0.77 | . | . | . | −0.60 | 0.18 |
| Ile | 830 | . | . | B | B | . | . | . | −1.07 | 0.67 | . | . | . | −0.60 | 0.17 |
| Ile | 831 | . | . | B | B | . | . | . | −0.64 | 0.67 | . | . | . | −0.60 | 0.33 |
| Glu | 832 | A | . | . | B | . | . | . | −0.33 | 0.03 | . | * | F | −0.15 | 0.74 |
| Ser | 833 | A | . | . | . | . | T | . | 0.63 | −0.36 | . | * | F | 1.00 | 1.83 |
| Thr | 834 | A | . | . | . | . | T | . | 0.48 | −1.04 | . | * | F | 1.30 | 5.10 |
| Arg | 835 | A | . | . | . | . | T | . | 0.78 | −1.09 | . | * | F | 1.30 | 2.19 |
| Gln | 836 | A | . | . | . | . | T | . | 0.81 | −0.59 | . | * | F | 1.30 | 1.65 |
| Arg | 837 | A | A | . | . | . | . | . | 0.81 | −0.33 | . | * | F | 0.45 | 0.85 |
| Val | 838 | . | A | B | . | . | . | . | 0.52 | −0.81 | . | * | . | 0.60 | 0.75 |
| Ala | 839 | . | A | B | . | . | . | . | 0.52 | −0.31 | . | * | . | 0.30 | 0.44 |
| Val | 840 | . | A | B | . | . | . | . | −0.40 | −0.23 | . | * | . | 0.30 | 0.32 |
| Glu | 841 | A | A | . | . | . | . | . | −0.40 | 0.46 | . | * | . | −0.60 | 0.36 |
| Ala | 842 | A | A | . | . | . | . | . | −0.51 | −0.19 | . | * | . | 0.30 | 0.61 |
| Thr | 843 | A | A | . | . | . | . | . | 0.46 | −0.29 | . | * | . | 0.45 | 1.33 |
| Leu | 844 | A | A | . | . | . | . | . | 0.70 | −0.93 | . | * | F | 0.90 | 1.50 |
| Glu | 845 | A | A | . | . | . | . | . | 1.56 | −0.50 | . | * | F | 0.60 | 1.47 |
| Asn | 846 | A | . | . | . | . | T | . | 1.56 | −1.00 | . | * | F | 1.60 | 1.77 |
| Arg | 847 | A | . | . | . | . | T | . | 1.56 | −1.09 | * | * | F | 1.90 | 3.45 |
| Gly | 848 | A | . | . | . | . | T | . | 1.62 | −1.27 | * | * | F | 2.20 | 2.01 |
| Glu | 849 | A | . | . | . | . | T | . | 2.13 | −0.51 | * | * | F | 2.50 | 1.96 |
| Asn | 850 | . | . | . | . | . | T | C | 1.82 | −0.53 | * | . | F | 3.00 | 1.34 |
| Ala | 851 | A | . | . | . | . | T | . | 0.97 | −0.04 | * | . | F | 2.20 | 1.95 |
| Tyr | 852 | . | . | B | . | . | T | . | 0.04 | 0.17 | * | . | . | 1.00 | 0.84 |
| Ser | 853 | . | . | B | . | . | T | . | 0.39 | 0.86 | * | . | . | 0.40 | 0.43 |
| Thr | 854 | . | . | B | B | . | . | . | −0.50 | 0.86 | * | . | . | −0.30 | 0.68 |
| Val | 855 | . | . | B | B | . | . | . | −0.80 | 1.04 | * | . | . | −0.60 | 0.31 |
| Leu | 856 | . | . | B | B | . | . | . | −0.21 | 0.67 | * | . | . | −0.60 | 0.31 |
| Asn | 857 | . | . | B | B | . | . | . | −0.27 | 0.69 | * | . | . | −0.60 | 0.37 |
| Ile | 858 | . | . | B | B | . | . | . | −0.56 | 0.59 | * | . | F | −0.45 | 0.66 |
| Ser | 859 | . | . | B | . | . | . | . | −0.24 | 0.44 | . | * | F | −0.25 | 0.81 |
| Gln | 860 | . | . | B | . | . | . | C | −0.20 | 0.16 | . | * | F | 0.25 | 0.81 |
| Ser | 861 | . | . | . | . | . | T | C | 0.61 | 0.44 | . | * | F | 0.15 | 0.96 |
| Ala | 862 | . | . | B | . | . | T | . | −0.09 | 0.16 | . | * | F | 0.40 | 1.23 |
| Asn | 863 | . | . | B | . | . | T | . | 0.21 | 0.56 | . | * | . | −0.20 | 0.62 |
| Leu | 864 | A | . | . | . | . | T | . | 0.21 | 0.66 | . | . | . | −0.20 | 0.47 |
| Gln | 865 | A | A | . | . | . | . | . | −0.60 | 0.66 | . | * | . | −0.60 | 0.62 |
| Phe | 866 | A | A | . | . | . | . | . | −1.19 | 0.84 | . | * | . | −0.60 | 0.32 |
| Ala | 867 | A | A | . | . | . | . | . | −0.60 | 1.13 | * | * | . | −0.60 | 0.27 |
| Ser | 868 | A | A | . | . | . | . | . | −0.56 | 0.84 | * | * | . | −0.60 | 0.27 |
| Leu | 869 | A | A | . | . | . | . | . | 0.26 | 0.44 | * | . | . | −0.60 | 0.62 |
| Ile | 870 | A | A | . | . | . | . | . | 0.26 | −0.34 | * | . | . | 0.45 | 1.07 |
| Gln | 871 | A | A | . | . | . | . | . | 0.66 | −0.84 | * | . | F | 1.24 | 1.33 |
| Lys | 872 | A | A | . | . | . | . | . | 1.24 | −0.84 | * | . | F | 1.58 | 2.16 |
| Glu | 873 | A | A | . | . | . | . | . | 1.20 | −1.53 | * | . | F | 1.92 | 5.14 |
| Asp | 874 | . | . | . | . | T | T | . | 1.71 | −1.79 | . | * | F | 3.06 | 2.94 |
| Ser | 875 | . | . | . | . | T | T | . | 1.71 | −1.80 | . | * | F | 3.40 | 1.97 |
| Asp | 876 | . | . | . | . | T | T | . | 1.71 | −1.11 | . | * | F | 2.91 | 0.80 |
| Gly | 877 | . | . | . | . | T | T | . | 1.00 | −1.11 | . | * | F | 2.57 | 0.83 |
| Ser | 878 | A | A | . | . | . | . | . | 0.14 | −0.54 | . | . | F | 1.43 | 0.33 |
| Ile | 879 | A | A | . | . | . | . | . | 0.14 | −0.29 | . | * | . | 0.64 | 0.15 |
| Glu | 880 | A | A | . | . | . | . | . | 0.44 | 0.11 | . | . | . | −0.30 | 0.24 |
| Cys | 881 | . | A | B | . | . | . | . | 0.44 | −0.31 | . | * | . | 0.30 | 0.31 |
| Val | 882 | A | A | . | . | . | . | . | 0.90 | −0.70 | * | . | . | 0.60 | 0.76 |
| Asn | 883 | A | A | . | . | . | . | . | 1.31 | −1.39 | * | . | F | 0.75 | 0.86 |
| Glu | 884 | A | A | . | . | . | . | . | 1.39 | −1.39 | * | * | F | 0.90 | 3.15 |
| Glu | 885 | A | A | . | . | . | . | . | 1.39 | −1.27 | * | . | F | 0.90 | 3.50 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Arg | 886 | A | A | . | . | . | . | . | 2.10 | −1.51 | * | . | F | 0.90 | 3.77 |
| Arg | 887 | A | A | . | . | . | . | . | 2.96 | −1.91 | * | * | F | 0.90 | 4.35 |
| Leu | 888 | A | A | . | . | . | . | . | 2.10 | −1.51 | * | . | F | 0.90 | 4.35 |
| Gln | 889 | A | A | . | . | . | . | . | 1.43 | −0.87 | * | . | F | 0.90 | 1.65 |
| Lys | 890 | A | A | . | . | . | . | . | 1.43 | −0.30 | * | . | F | 0.45 | 0.45 |
| Gln | 891 | . | A | B | . | . | . | . | 0.47 | 0.10 | * | . | . | −0.30 | 0.88 |
| Val | 892 | . | A | B | . | . | . | . | 0.06 | 0.06 | * | * | . | −0.30 | 0.38 |
| Cys | 893 | . | A | B | . | . | . | . | 0.62 | 0.04 | * | . | . | −0.30 | 0.25 |
| Asn | 894 | . | . | B | . | . | T | . | 0.41 | 0.80 | * | . | . | −0.20 | 0.23 |
| Val | 895 | . | . | B | . | . | T | . | −0.33 | 0.83 | * | . | . | −0.20 | 0.48 |
| Ser | 896 | . | . | B | . | . | T | . | −1.03 | 0.97 | * | . | . | −0.20 | 0.77 |
| Tyr | 897 | . | . | B | . | . | T | . | −0.07 | 1.19 | * | . | . | −0.20 | 0.41 |
| Pro | 898 | . | . | B | B | . | . | . | 0.01 | 0.79 | * | * | . | −0.45 | 1.09 |
| Phe | 899 | A | A | . | B | . | . | . | 0.06 | 0.64 | * | * | . | −0.60 | 0.82 |
| Phe | 900 | A | A | . | B | . | . | . | 0.32 | 0.26 | * | * | . | −0.15 | 1.05 |
| Arg | 901 | A | A | . | B | . | . | . | 0.67 | 0.00 | * | * | . | −0.30 | 0.69 |
| Ala | 902 | A | A | . | . | . | . | . | 0.06 | −0.43 | * | * | . | 0.45 | 1.59 |
| Lys | 903 | A | A | . | . | . | . | . | −0.32 | −0.57 | * | * | F | 0.90 | 1.36 |
| Ala | 904 | A | A | . | . | . | . | . | −0.32 | −0.86 | * | * | F | 0.75 | 0.70 |
| Lys | 905 | A | A | . | B | . | . | . | 0.49 | −0.07 | * | * | . | 0.30 | 0.60 |
| Val | 906 | A | A | . | B | . | . | . | −0.43 | −0.57 | * | * | . | 0.60 | 0.59 |
| Ala | 907 | A | A | . | B | . | . | . | 0.16 | 0.11 | . | * | . | −0.30 | 0.48 |
| Phe | 908 | A | A | . | B | . | . | . | −0.59 | −0.39 | . | * | . | 0.30 | 0.40 |
| Arg | 909 | A | A | . | B | . | . | . | 0.00 | 0.40 | * | * | . | −0.60 | 0.47 |
| Leu | 910 | A | A | . | . | . | . | . | −0.74 | −0.24 | * | * | . | 0.30 | 0.80 |
| Asp | 911 | A | A | . | . | . | . | . | −0.19 | 0.04 | * | * | . | −0.30 | 0.80 |
| Phe | 912 | A | A | . | . | . | . | . | 0.44 | −0.36 | * | * | . | 0.30 | 0.55 |
| Glu | 913 | A | A | . | . | . | . | . | 0.84 | −0.36 | * | * | . | 0.45 | 1.33 |
| Phe | 914 | A | A | . | . | . | . | . | −0.16 | −0.66 | * | * | . | 0.75 | 1.07 |
| Ser | 915 | A | . | . | . | . | T | . | −0.04 | 0.03 | . | * | F | 0.25 | 0.87 |
| Lys | 916 | A | . | . | . | . | T | . | −0.86 | 0.03 | . | * | F | 0.25 | 0.43 |
| Ser | 917 | A | . | . | . | . | T | . | −0.19 | 0.71 | . | . | . | −0.20 | 0.41 |
| Ile | 918 | A | . | . | . | . | T | . | −0.22 | 0.43 | . | . | . | −0.20 | 0.42 |
| Phe | 919 | A | A | . | . | . | . | . | −0.33 | 0.54 | . | . | . | −0.60 | 0.28 |
| Leu | 920 | A | A | . | . | . | . | . | −0.03 | 1.23 | . | . | . | −0.60 | 0.18 |
| His | 921 | A | A | . | . | . | . | . | −0.97 | 0.84 | . | * | . | −0.60 | 0.43 |
| His | 922 | A | A | . | . | . | . | . | −0.67 | 0.84 | . | * | . | −0.60 | 0.35 |
| Leu | 923 | A | A | . | . | . | . | . | −0.59 | 0.06 | . | * | . | −0.30 | 0.74 |
| Glu | 924 | A | A | . | . | . | . | . | −0.48 | 0.06 | . | * | . | −0.30 | 0.45 |
| Ile | 925 | A | A | . | . | . | . | . | −0.26 | 0.06 | . | * | . | −0.30 | 0.33 |
| Glu | 926 | A | A | . | . | . | . | . | −0.57 | 0.06 | . | * | . | −0.30 | 0.41 |
| Leu | 927 | A | A | . | . | . | . | . | −0.83 | −0.20 | . | * | . | 0.30 | 0.23 |
| Ala | 928 | A | A | . | . | . | . | . | −0.02 | 0.19 | . | * | . | −0.30 | 0.44 |
| Ala | 929 | A | A | . | . | . | . | . | −0.32 | −0.50 | . | * | . | 0.30 | 0.43 |
| Gly | 930 | A | . | . | . | . | T | . | 0.57 | −0.11 | . | * | F | 0.85 | 0.69 |
| Ser | 931 | . | . | . | . | . | T | C | 0.57 | −0.40 | * | * | F | 1.20 | 1.11 |
| Asp | 932 | . | . | . | . | . | T | C | 1.49 | −0.90 | . | . | F | 1.50 | 1.89 |
| Ser | 933 | . | . | . | . | . | T | C | 2.08 | −1.40 | . | . | F | 1.84 | 3.75 |
| Asn | 934 | . | . | . | . | . | . | C | 2.37 | −1.83 | . | . | F | 1.98 | 4.67 |
| Glu | 935 | A | . | . | . | . | . | . | 2.40 | −1.83 | * | * | F | 2.12 | 3.75 |
| Arg | 936 | A | . | . | . | . | . | . | 2.74 | −1.34 | . | . | F | 2.46 | 4.04 |
| Asp | 937 | . | . | . | . | T | T | . | 2.74 | −1.73 | . | * | F | 3.40 | 5.02 |
| Ser | 938 | . | . | . | . | . | T | C | 3.04 | −2.13 | . | . | F | 2.86 | 5.02 |
| Thr | 939 | A | . | . | . | . | T | . | 3.04 | −2.13 | . | . | F | 2.32 | 4.28 |
| Lys | 940 | A | . | . | . | . | T | . | 2.19 | −1.73 | * | . | F | 1.98 | 4.12 |
| Glu | 941 | A | A | . | . | . | . | . | 1.49 | −1.09 | * | . | F | 1.24 | 2.28 |
| Asp | 942 | A | A | . | . | . | . | . | 1.28 | −0.97 | . | . | F | 0.90 | 1.60 |
| Asn | 943 | A | A | . | . | . | . | . | 0.77 | −1.03 | . | * | F | 0.90 | 1.24 |
| Val | 944 | A | A | . | . | . | . | . | 1.19 | −0.34 | . | * | . | 0.30 | 0.59 |
| Ala | 945 | A | A | . | . | . | . | . | 0.44 | −0.34 | . | * | . | 0.30 | 0.69 |
| Pro | 946 | A | A | . | . | . | . | . | 0.41 | 0.44 | . | * | . | −0.60 | 0.37 |
| Leu | 947 | A | A | . | . | . | . | . | −0.40 | 0.54 | . | * | . | −0.60 | 0.68 |
| Arg | 948 | A | A | . | . | . | . | . | −0.36 | 0.59 | . | * | . | −0.60 | 0.56 |
| Phe | 949 | A | A | . | . | . | . | . | 0.26 | 0.09 | . | * | . | −0.30 | 0.72 |
| His | 950 | A | A | . | . | . | . | . | 0.84 | 0.41 | . | * | . | −0.45 | 1.37 |
| Leu | 951 | A | A | . | . | . | . | . | 0.47 | −0.27 | * | * | . | 0.45 | 1.21 |
| Lys | 952 | A | A | . | . | . | . | . | 1.28 | 0.23 | * | * | . | −0.15 | 1.41 |
| Tyr | 953 | A | A | . | . | . | . | . | 0.31 | −0.56 | * | * | . | 0.75 | 1.73 |
| Glu | 954 | A | A | . | . | . | . | . | 0.20 | −0.41 | . | * | . | 0.45 | 1.56 |
| Ala | 955 | A | . | . | B | . | . | . | −0.47 | −0.41 | . | * | . | 0.30 | 0.64 |
| Asp | 956 | A | . | . | B | . | . | . | 0.03 | 0.37 | . | * | . | −0.30 | 0.35 |
| Val | 957 | A | . | . | B | . | . | . | 0.10 | 0.10 | . | * | . | −0.30 | 0.30 |
| Leu | 958 | A | . | . | B | . | . | . | 0.04 | 0.10 | . | . | . | −0.30 | 0.57 |
| Phe | 959 | A | . | . | B | . | . | . | −0.26 | −0.01 | . | . | . | 0.30 | 0.46 |
| Thr | 960 | A | . | . | B | . | . | . | 0.03 | 0.37 | . | . | F | 0.06 | 0.83 |
| Arg | 961 | A | . | . | B | . | . | . | −0.78 | 0.11 | . | . | F | 0.42 | 1.35 |
| Ser | 962 | . | . | . | . | T | T | . | −0.22 | 0.11 | . | . | F | 1.43 | 1.29 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Ser | 963 | . | . | . | . | . | T | C | 0.56 | −0.29 | . | . | F | 2.04 | 1.19 |
| Ser | 964 | . | . | . | . | . | T | C | 1.01 | −0.27 | . | . | F | 2.10 | 0.83 |
| Leu | 965 | . | . | . | . | . | T | C | 1.32 | 0.49 | . | . | F | 0.99 | 0.97 |
| Ser | 966 | . | . | . | . | . | . | C | 0.36 | 0.10 | . | * | . | 0.88 | 1.25 |
| His | 967 | . | . | B | . | . | . | . | 0.70 | 0.36 | . | * | . | 0.32 | 0.69 |
| Tyr | 968 | . | . | B | . | . | . | . | 0.19 | −0.03 | . | * | . | 0.86 | 1.68 |
| Glu | 969 | . | . | B | . | . | . | . | 0.49 | −0.03 | . | * | . | 0.65 | 1.04 |
| Val | 970 | A | . | . | . | . | . | . | 1.00 | −0.01 | . | * | . | 0.65 | 1.22 |
| Lys | 971 | A | . | . | . | . | . | . | 1.00 | −0.13 | . | * | F | 0.80 | 1.05 |
| Leu | 972 | A | . | . | . | . | . | . | 0.22 | −0.50 | . | * | F | 0.65 | 0.81 |
| Asn | 973 | . | . | . | . | . | T | C | 0.47 | 0.19 | * | * | F | 0.45 | 0.90 |
| Ser | 974 | A | . | . | . | . | T | . | 0.58 | −0.46 | * | * | F | 0.85 | 0.78 |
| Ser | 975 | A | . | . | . | . | T | . | 1.19 | −0.46 | * | * | F | 1.00 | 1.85 |
| Leu | 976 | . | . | B | . | . | T | . | 1.14 | −0.39 | * | * | F | 1.31 | 1.80 |
| Glu | 977 | . | . | B | . | . | . | . | 1.61 | −0.79 | * | . | F | 1.72 | 2.25 |
| Arg | 978 | . | . | B | . | . | T | . | 0.72 | −0.74 | * | . | F | 2.23 | 1.66 |
| Tyr | 979 | . | . | B | . | . | T | . | 0.68 | −0.44 | . | . | F | 2.24 | 1.41 |
| Asp | 980 | . | . | . | . | T | T | . | 0.77 | −0.70 | . | . | F | 3.10 | 0.81 |
| Gly | 981 | . | . | . | . | T | T | . | 1.37 | −0.27 | * | . | F | 2.49 | 0.64 |
| Ile | 982 | . | . | . | . | T | . | . | 0.67 | 0.16 | * | . | F | 1.38 | 0.63 |
| Gly | 983 | . | . | . | . | . | . | C | 0.26 | 0.19 | . | * | F | 0.87 | 0.33 |
| Pro | 984 | . | . | . | . | . | T | C | −0.17 | 0.57 | * | . | F | 0.46 | 0.44 |
| Pro | 985 | . | . | . | . | T | T | . | −1.06 | 0.71 | * | . | F | 0.35 | 0.34 |
| Phe | 986 | . | . | . | . | T | T | . | −1.41 | 0.71 | * | * | . | 0.20 | 0.24 |
| Ser | 987 | . | . | B | . | . | T | . | −0.41 | 1.07 | * | * | . | −0.20 | 0.13 |
| Cys | 988 | . | . | B | B | . | . | . | −0.96 | 0.64 | * | * | . | −0.60 | 0.17 |
| Ile | 989 | . | . | B | B | . | . | . | −0.74 | 0.90 | * | * | . | −0.60 | 0.14 |
| Phe | 990 | . | . | B | B | . | . | . | −0.53 | 0.51 | * | * | . | −0.60 | 0.18 |
| Arg | 991 | . | . | B | B | . | . | . | −0.64 | 0.53 | * | * | . | −0.60 | 0.53 |
| Ile | 992 | . | . | B | B | . | . | . | −0.69 | 0.64 | * | * | . | −0.60 | 0.63 |
| Gln | 993 | . | . | B | B | . | . | . | −0.83 | 0.39 | * | * | . | −0.30 | 0.72 |
| Asn | 994 | . | . | . | B | T | . | . | −0.64 | 0.29 | * | * | . | 0.10 | 0.30 |
| Leu | 995 | . | . | . | B | T | . | . | −0.16 | 1.07 | . | * | . | −0.20 | 0.37 |
| Gly | 996 | . | . | . | B | T | . | . | −1.16 | 0.81 | * | * | . | −0.20 | 0.33 |
| Leu | 997 | . | . | . | . | . | . | C | −0.30 | 1.10 | . | . | . | −0.20 | 0.14 |
| Phe | 998 | . | . | B | . | . | . | . | −0.64 | 1.20 | . | . | . | −0.40 | 0.24 |
| Pro | 999 | . | . | B | . | . | . | . | −1.53 | 0.94 | . | . | . | −0.40 | 0.24 |
| Ile | 1000 | A | . | . | B | . | . | . | −1.32 | 1.20 | . | . | . | −0.60 | 0.20 |
| His | 1001 | A | . | . | B | . | . | . | −1.58 | 1.13 | . | . | . | −0.60 | 0.23 |
| Gly | 1002 | A | . | . | B | . | . | . | −0.72 | 0.96 | * | . | . | −0.60 | 0.15 |
| Ile | 1003 | A | . | . | B | . | . | . | −0.91 | 0.53 | . | * | . | −0.60 | 0.42 |
| Met | 1004 | A | . | . | B | . | . | . | −1.01 | 0.53 | . | * | . | −0.60 | 0.22 |
| Met | 1005 | . | . | B | B | . | . | . | −1.01 | 0.51 | . | * | . | −0.60 | 0.32 |
| Lys | 1006 | . | . | B | B | . | . | . | −1.19 | 0.77 | . | * | . | −0.60 | 0.32 |
| Ile | 1007 | . | . | B | B | . | . | . | −1.73 | 0.51 | . | * | . | −0.60 | 0.50 |
| Thr | 1008 | . | . | B | B | . | . | . | −1.43 | 0.59 | . | * | . | −0.60 | 0.35 |
| Ile | 1009 | . | . | B | B | . | . | . | −1.14 | 0.47 | * | * | . | −0.60 | 0.18 |
| Pro | 1010 | . | . | B | B | . | . | . | −0.43 | 0.96 | * | * | . | −0.60 | 0.37 |
| Ile | 1011 | . | . | B | B | . | . | . | −0.78 | 0.27 | * | * | . | 0.04 | 0.50 |
| Ala | 1012 | . | . | B | B | . | . | . | −0.23 | 0.17 | * | * | . | 0.38 | 0.95 |
| Thr | 1013 | . | . | B | . | . | T | . | 0.08 | −0.09 | * | * | F | 1.87 | 0.61 |
| Arg | 1014 | . | . | . | . | T | T | . | 1.08 | −0.11 | * | * | F | 2.76 | 1.40 |
| Ser | 1015 | . | . | . | . | T | T | . | 0.48 | −0.80 | * | * | F | 3.40 | 2.71 |
| Gly | 1016 | . | . | . | . | T | T | . | 0.56 | −0.61 | * | * | F | 3.06 | 1.55 |
| Asn | 1017 | . | A | . | . | T | . | . | 1.19 | −0.41 | * | . | F | 1.87 | 0.65 |
| Arg | 1018 | . | A | B | . | . | . | . | 0.69 | −0.41 | * | * | F | 1.13 | 0.97 |
| Leu | 1019 | . | A | B | . | . | . | . | 0.69 | −0.11 | * | * | F | 0.79 | 0.81 |
| Leu | 1020 | . | A | B | . | . | . | . | 0.99 | −0.54 | . | . | F | 0.75 | 0.99 |
| Lys | 1021 | . | A | B | . | . | . | . | 0.63 | −0.94 | * | . | F | 0.75 | 0.84 |
| Leu | 1022 | . | A | B | . | . | . | . | −0.18 | −0.16 | * | . | F | 0.45 | 0.88 |
| Arg | 1023 | . | A | B | . | . | . | . | −0.60 | −0.16 | * | . | F | 0.45 | 0.88 |
| Asp | 1024 | . | A | B | . | . | . | . | 0.21 | −0.36 | * | * | F | 0.45 | 0.64 |
| Phe | 1025 | . | A | B | . | . | . | . | 1.02 | −0.36 | * | * | . | 0.45 | 1.29 |
| Leu | 1026 | A | A | . | . | . | . | . | 0.12 | −1.04 | * | * | F | 0.90 | 1.14 |
| Thr | 1027 | A | A | . | . | . | . | . | 0.34 | −0.40 | * | . | F | 0.45 | 0.51 |
| Asp | 1028 | A | A | . | . | . | . | . | 0.23 | 0.10 | . | . | F | −0.15 | 0.59 |
| Glu | 1029 | A | A | . | . | . | . | . | −0.08 | −0.29 | * | . | . | 0.45 | 1.15 |
| Val | 1030 | A | A | . | . | . | . | . | 0.32 | −0.49 | . | . | . | 0.45 | 1.15 |
| Ala | 1031 | A | A | . | . | . | . | . | 0.47 | −0.59 | * | . | . | 0.60 | 0.93 |
| Asn | 1032 | . | . | . | . | T | T | . | 0.78 | −0.01 | * | . | F | 1.25 | 0.29 |
| Thr | 1033 | . | . | . | . | T | T | . | −0.11 | 0.39 | * | . | F | 0.65 | 0.62 |
| Ser | 1034 | . | . | B | . | . | T | . | −0.40 | 0.43 | * | . | F | −0.05 | 0.43 |
| Cys | 1035 | . | . | B | . | . | T | . | 0.11 | 0.84 | * | * | . | −0.20 | 0.28 |
| Asn | 1036 | . | . | . | . | T | . | . | 0.70 | 0.87 | . | * | . | 0.16 | 0.19 |
| Ile | 1037 | . | . | . | . | T | . | . | 0.40 | 0.79 | . | * | . | 0.32 | 0.23 |
| Trp | 1038 | . | . | . | . | T | T | . | 0.40 | 0.79 | . | . | . | 0.68 | 0.58 |
| Gly | 1039 | . | . | . | . | . | T | C | 0.70 | 0.70 | . | . | F | 0.79 | 0.52 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Asn | 1040 | . | . | . | . | T | T | . | 1.12 | 0.30 | . | * | F | 1.60 | 1.28 |
| Ser | 1041 | . | . | . | . | . | T | C | 1.23 | 0.37 | . | * | F | 1.24 | 1.91 |
| Thr | 1042 | . | . | . | . | . | . | C | 1.91 | −0.54 | . | * | F | 1.78 | 3.79 |
| Glu | 1043 | . | . | . | . | T | . | . | 1.89 | −0.54 | . | * | F | 1.82 | 3.64 |
| Tyr | 1044 | . | . | . | . | T | . | . | 2.02 | −0.46 | . | . | F | 1.66 | 3.92 |
| Arg | 1045 | . | . | . | . | . | T | C | 1.17 | −0.41 | . | . | F | 1.80 | 4.20 |
| Pro | 1046 | . | . | . | . | . | T | C | 1.47 | −0.26 | . | . | F | 2.10 | 1.80 |
| Thr | 1047 | . | . | . | . | . | T | C | 1.78 | −0.26 | . | . | F | 2.40 | 1.99 |
| Pro | 1048 | . | . | . | . | . | T | C | 1.78 | −1.01 | . | * | F | 3.00 | 1.76 |
| Val | 1049 | A | A | . | . | . | . | . | 1.21 | −1.01 | . | * | F | 2.10 | 1.90 |
| Glu | 1050 | A | A | . | . | . | . | . | 1.21 | −0.76 | * | . | F | 1.80 | 1.09 |
| Glu | 1051 | A | A | . | . | . | . | . | 1.53 | −1.24 | * | . | F | 1.50 | 1.38 |
| Asp | 1052 | A | A | . | . | . | . | . | 1.26 | −1.67 | * | . | F | 1.20 | 3.63 |
| Leu | 1053 | A | A | . | . | . | . | . | 1.26 | −1.81 | * | . | F | 0.90 | 2.12 |
| Arg | 1054 | A | A | . | . | . | . | . | 2.11 | −1.39 | * | * | F | 0.90 | 1.89 |
| Arg | 1055 | A | A | . | . | . | . | . | 1.30 | −0.99 | * | * | F | 0.90 | 1.96 |
| Ala | 1056 | A | A | . | . | . | . | . | 1.30 | −0.30 | * | . | F | 0.60 | 1.96 |
| Pro | 1057 | A | A | . | . | . | . | . | 1.27 | −0.59 | * | * | F | 0.90 | 1.61 |
| Gln | 1058 | A | A | . | . | . | . | . | 1.78 | −0.09 | * | . | F | 0.60 | 1.12 |
| Leu | 1059 | . | A | B | . | . | . | . | 1.67 | 0.30 | * | . | . | 0.13 | 1.48 |
| Asn | 1060 | . | A | . | . | . | . | C | 1.26 | 0.20 | . | . | . | 0.61 | 1.54 |
| His | 1061 | . | . | . | . | . | T | C | 1.84 | 0.16 | . | . | F | 1.44 | 1.19 |
| Ser | 1062 | . | . | . | . | . | T | C | 1.20 | −0.24 | . | . | F | 2.32 | 2.42 |
| Asn | 1063 | . | . | . | . | T | T | . | 0.34 | −0.29 | * | . | F | 2.80 | 1.12 |
| Ser | 1064 | . | . | . | . | T | T | . | 0.86 | −0.04 | * | . | F | 2.37 | 0.61 |
| Asp | 1065 | . | . | B | B | . | . | . | −0.03 | −0.16 | . | . | F | 1.29 | 0.61 |
| Val | 1066 | . | . | B | B | . | . | . | 0.00 | 0.14 | . | . | F | 0.41 | 0.27 |
| Val | 1067 | . | . | B | B | . | . | . | −0.37 | 0.14 | . | . | . | −0.02 | 0.32 |
| Ser | 1068 | . | . | B | . | . | T | . | −0.37 | 0.33 | . | * | . | 0.10 | 0.10 |
| Ile | 1069 | . | . | B | . | . | T | . | −0.96 | 0.73 | * | * | . | −0.20 | 0.22 |
| Asn | 1070 | . | . | B | . | . | T | . | −0.84 | 0.77 | . | * | . | −0.20 | 0.21 |
| Cys | 1071 | . | . | B | . | . | T | . | −0.80 | 0.13 | * | * | . | 0.10 | 0.31 |
| Asn | 1072 | . | . | B | B | . | . | . | −0.80 | 0.43 | * | * | . | −0.60 | 0.36 |
| Ile | 1073 | . | . | B | B | . | . | . | −0.71 | 0.39 | * | * | . | −0.30 | 0.17 |
| Arg | 1074 | . | . | B | B | . | . | . | 0.18 | 0.41 | * | * | . | −0.60 | 0.48 |
| Leu | 1075 | . | . | B | B | . | . | . | 0.18 | 0.24 | * | * | . | −0.30 | 0.48 |
| Val | 1076 | . | . | B | . | . | T | . | 0.84 | 0.24 | . | * | F | 0.40 | 1.18 |
| Pro | 1077 | . | . | . | . | . | T | C | −0.04 | −0.44 | * | * | F | 1.20 | 1.05 |
| Asn | 1078 | . | . | . | . | T | T | . | 0.84 | 0.24 | * | * | F | 0.65 | 0.89 |
| Gln | 1079 | A | . | . | . | . | T | . | 0.03 | −0.04 | * | * | F | 1.00 | 1.93 |
| Glu | 1080 | . | A | B | . | . | . | . | 0.81 | 0.10 | . | * | F | 0.00 | 1.08 |
| Ile | 1081 | . | A | B | . | . | . | . | 0.86 | 0.17 | . | * | F | −0.15 | 0.91 |
| Asn | 1082 | . | A | B | . | . | . | . | 0.26 | 0.46 | . | * | . | −0.60 | 0.43 |
| Phe | 1083 | . | A | B | . | . | . | . | −0.09 | 0.74 | . | * | . | −0.60 | 0.21 |
| His | 1084 | . | A | B | . | . | . | . | −0.09 | 1.17 | . | * | . | −0.60 | 0.29 |
| Leu | 1085 | . | A | B | . | . | . | . | −0.90 | 0.89 | . | * | . | −0.60 | 0.29 |
| Leu | 1086 | . | A | . | . | . | . | C | −0.30 | 1.17 | . | * | . | −0.40 | 0.28 |
| Gly | 1087 | . | A | . | . | T | . | . | −1.11 | 1.30 | * | * | . | −0.20 | 0.22 |
| Asn | 1088 | A | A | . | . | . | . | . | −0.30 | 1.49 | * | * | . | −0.60 | 0.22 |
| Leu | 1089 | A | A | . | . | . | . | . | −0.57 | 0.80 | * | * | . | −0.60 | 0.51 |
| Trp | 1090 | A | A | . | . | . | . | . | −0.57 | 0.50 | * | * | . | −0.60 | 0.69 |
| Leu | 1091 | A | A | . | . | . | . | . | 0.29 | 0.76 | * | . | . | −0.60 | 0.35 |
| Arg | 1092 | A | A | . | . | . | . | . | 0.04 | 0.36 | * | * | . | −0.30 | 0.86 |
| Ser | 1093 | A | A | . | . | . | . | . | −0.77 | 0.17 | * | . | . | −0.30 | 0.83 |
| Leu | 1094 | A | A | . | . | . | . | . | 0.09 | −0.06 | * | . | F | 0.45 | 0.83 |
| Lys | 1095 | A | A | . | . | . | . | . | 0.13 | −0.74 | * | . | F | 0.75 | 0.84 |
| Ala | 1096 | A | A | . | . | . | . | . | 0.99 | 0.01 | * | * | . | −0.30 | 0.99 |
| Leu | 1097 | A | A | . | . | . | . | . | 0.58 | −0.37 | * | . | . | 0.45 | 2.39 |
| Lys | 1098 | A | A | . | . | . | . | . | 0.28 | −0.67 | . | . | F | 0.90 | 1.60 |
| Tyr | 1099 | A | A | . | . | . | . | . | 1.13 | −0.06 | * | . | F | 0.60 | 1.57 |
| Lys | 1100 | A | A | . | . | . | . | . | 0.20 | −0.56 | * | . | F | 0.90 | 3.81 |
| Ser | 1101 | A | A | . | . | . | . | . | 0.19 | −0.56 | . | * | F | 0.90 | 1.34 |
| Met | 1102 | A | A | . | . | . | . | . | 0.14 | 0.06 | . | * | . | −0.30 | 0.84 |
| Lys | 1103 | A | A | . | . | . | . | . | 0.10 | −0.06 | . | * | . | 0.30 | 0.31 |
| Ile | 1104 | . | A | B | . | . | . | . | −0.24 | 0.34 | * | * | . | −0.30 | 0.38 |
| Met | 1105 | A | A | . | . | . | . | . | −0.88 | 0.46 | * | * | . | −0.60 | 0.38 |
| Val | 1106 | A | A | . | . | . | . | . | −1.39 | 0.34 | * | * | . | −0.30 | 0.19 |
| Asn | 1107 | A | A | . | . | . | . | . | −0.79 | 1.03 | . | * | . | −0.60 | 0.23 |
| Ala | 1108 | A | A | . | . | . | . | . | −0.72 | 0.74 | . | * | . | −0.60 | 0.40 |
| Ala | 1109 | A | A | . | . | . | . | . | 0.17 | 0.13 | . | * | . | −0.15 | 1.05 |
| Leu | 1110 | A | A | . | . | . | . | . | 0.07 | −0.11 | * | . | . | 0.45 | 1.13 |
| Gln | 1111 | A | A | . | . | . | . | . | 0.89 | 0.27 | * | . | . | −0.30 | 0.97 |
| Arg | 1112 | A | A | . | . | . | . | . | 0.59 | 0.27 | * | . | . | −0.15 | 1.31 |
| Gln | 1113 | . | A | B | . | . | . | . | 0.97 | 0.16 | * | . | . | −0.15 | 2.13 |
| Phe | 1114 | . | A | . | . | T | . | . | 0.86 | −0.10 | * | . | . | 0.85 | 1.90 |
| His | 1115 | . | A | . | . | . | . | C | 0.78 | 0.29 | * | . | . | −0.10 | 0.84 |
| Ser | 1116 | . | A | . | . | . | . | C | 0.08 | 0.97 | . | * | . | −0.40 | 0.34 |

TABLE VII-continued

| Res | | I | II | III | IV | V | VI | VII | VIII | IX | X | XI | XII | XIII | XIV |
|---|---|---|---|---|---|---|---|---|---|---|---|---|---|---|---|
| Pro | 1117 | . | . | . | B | . | . | C | 0.08 | 1.36 | . | * | . | −0.40 | 0.34 |
| Phe | 1118 | . | A | . | B | . | . | C | 0.08 | 0.57 | . | * | . | −0.40 | 0.49 |
| Ile | 1119 | . | A | B | B | . | . | . | 0.78 | 0.07 | . | * | . | −0.30 | 0.63 |
| Phe | 1120 | . | A | B | B | . | . | . | 0.81 | −0.31 | . | . | . | 0.30 | 0.71 |
| Arg | 1121 | A | A | . | B | . | . | . | 0.90 | −0.74 | . | . | F | 1.24 | 1.37 |
| Glu | 1122 | . | A | . | . | T | . | . | 0.81 | −1.10 | * | * | F | 1.98 | 3.01 |
| Glu | 1123 | . | A | . | . | . | . | C | 1.62 | −1.40 | * | * | F | 2.12 | 4.66 |
| Asp | 1124 | . | . | . | . | . | T | C | 2.51 | −2.19 | * | . | F | 2.86 | 4.66 |
| Pro | 1125 | . | . | . | . | T | T | . | 2.32 | −1.79 | * | * | F | 3.40 | 4.66 |
| Ser | 1126 | . | . | . | . | T | T | . | 1.36 | −1.10 | * | . | F | 3.06 | 1.89 |
| Arg | 1127 | A | . | . | . | . | T | . | 0.66 | −0.46 | . | . | F | 1.87 | 0.84 |
| Gln | 1128 | A | . | . | B | . | . | . | 0.66 | 0.33 | * | . | F | 0.53 | 0.47 |
| Ile | 1129 | A | . | . | B | . | . | . | −0.23 | −0.10 | * | . | . | 0.64 | 0.61 |
| Val | 1130 | A | . | . | B | . | . | . | −0.32 | 0.20 | * | . | . | −0.30 | 0.22 |
| Phe | 1131 | . | . | B | B | . | . | . | 0.02 | 0.59 | * | . | . | −0.60 | 0.17 |
| Glu | 1132 | . | . | B | B | . | . | . | −0.09 | 0.19 | * | . | . | −0.30 | 0.48 |
| Ile | 1133 | . | . | B | B | . | . | . | −0.09 | −0.10 | * | * | F | 0.60 | 1.12 |
| Ser | 1134 | . | A | . | . | . | . | C | 0.80 | −0.74 | . | * | F | 1.10 | 2.24 |
| Lys | 1135 | . | A | . | . | T | . | . | 1.37 | −1.53 | . | . | F | 1.30 | 2.16 |
| Gln | 1136 | . | A | . | . | T | . | . | 2.07 | −0.61 | . | * | F | 1.30 | 3.24 |
| Glu | 1137 | A | A | . | . | . | . | . | 1.21 | −0.90 | . | * | F | 0.90 | 4.18 |
| Asp | 1138 | . | A | . | B | T | . | . | 1.89 | −0.64 | . | * | F | 1.30 | 1.55 |
| Trp | 1139 | . | A | . | B | T | . | . | 1.30 | −0.21 | . | * | . | 0.85 | 1.39 |
| Gln | 1140 | . | A | B | B | . | . | . | 0.97 | 0.07 | . | * | . | −0.30 | 0.56 |
| Val | 1141 | . | A | B | B | . | . | . | 0.08 | 0.99 | . | * | . | −0.60 | 0.35 |
| Pro | 1142 | . | A | B | B | . | . | . | −0.81 | 1.67 | . | * | . | −0.60 | 0.24 |
| Ile | 1143 | . | . | B | B | . | . | . | −1.67 | 1.44 | . | * | . | −0.60 | 0.10 |
| Trp | 1144 | . | . | B | B | . | . | . | −1.72 | 1.69 | . | * | . | −0.60 | 0.10 |
| Ile | 1145 | . | . | B | B | . | . | . | −2.02 | 1.47 | . | . | . | −0.60 | 0.06 |
| Ile | 1146 | . | . | B | B | . | . | . | −1.48 | 1.43 | . | . | . | −0.60 | 0.12 |
| Val | 1147 | . | . | B | B | . | . | . | −2.08 | 1.23 | . | . | . | −0.60 | 0.16 |
| Gly | 1148 | . | . | B | B | . | . | . | −1.53 | 1.00 | . | . | F | −0.45 | 0.19 |
| Ser | 1149 | . | . | . | B | . | . | C | −1.59 | 0.74 | . | . | F | −0.25 | 0.27 |
| Thr | 1150 | . | . | . | B | . | . | C | −1.51 | 0.49 | . | . | F | −0.25 | 0.35 |
| Leu | 1151 | . | . | . | B | . | . | C | −1.43 | 0.53 | . | . | F | −0.25 | 0.30 |
| Gly | 1152 | . | . | . | B | T | . | . | −1.39 | 0.79 | . | . | F | −0.05 | 0.18 |
| Gly | 1153 | . | A | B | B | . | . | . | −1.86 | 1.09 | . | . | . | −0.60 | 0.10 |
| Leu | 1154 | . | A | B | B | . | . | . | −2.14 | 1.29 | . | . | . | −0.60 | 0.10 |
| Leu | 1155 | . | A | B | B | . | . | . | −2.64 | 1.10 | . | . | . | −0.60 | 0.11 |
| Leu | 1156 | A | A | . | B | . | . | . | −2.64 | 1.36 | . | . | . | −0.60 | 0.09 |
| Leu | 1157 | A | A | . | B | . | . | . | −3.16 | 1.61 | . | . | . | −0.60 | 0.09 |
| Ala | 1158 | A | A | . | B | . | . | . | −3.62 | 1.57 | . | . | . | −0.60 | 0.08 |
| Leu | 1159 | A | A | . | B | . | . | . | −3.40 | 1.57 | . | . | . | −0.60 | 0.08 |
| Leu | 1160 | A | A | . | B | . | . | . | −3.40 | 1.39 | . | . | . | −0.60 | 0.10 |
| Val | 1161 | A | A | . | B | . | . | . | −2.88 | 1.39 | . | . | . | −0.60 | 0.08 |
| Leu | 1162 | A | A | . | B | . | . | . | −2.02 | 1.80 | * | . | . | −0.60 | 0.10 |
| Ala | 1163 | A | A | . | B | . | . | . | −2.24 | 1.11 | . | . | . | −0.60 | 0.25 |
| Leu | 1164 | A | A | . | B | . | . | . | −1.78 | 1.11 | . | * | . | −0.60 | 0.27 |
| Trp | 1165 | A | A | . | B | . | . | . | −1.67 | 0.90 | . | . | . | −0.60 | 0.33 |
| Lys | 1166 | A | A | . | B | . | . | . | −1.51 | 1.00 | . | . | . | −0.60 | 0.28 |
| Leu | 1167 | A | A | . | B | . | . | . | −0.59 | 1.29 | . | . | . | −0.60 | 0.29 |
| Gly | 1168 | A | . | . | B | . | . | . | −0.30 | 0.60 | . | . | . | −0.60 | 0.55 |
| Phe | 1169 | . | . | B | B | . | . | . | −0.08 | 0.07 | * | . | . | −0.30 | 0.37 |
| Phe | 1170 | . | . | B | B | . | . | . | 0.32 | 0.57 | * | . | . | −0.60 | 0.45 |
| Arg | 1171 | . | . | B | B | . | . | . | 0.39 | −0.11 | * | . | . | 0.30 | 0.89 |
| Ser | 1172 | . | . | . | B | . | . | C | 1.31 | −0.54 | * | . | F | 1.10 | 2.02 |
| Ala | 1173 | . | . | . | . | . | . | C | 1.77 | −1.33 | * | . | F | 1.30 | 4.57 |
| Arg | 1174 | . | . | . | . | . | . | C | 2.47 | −2.11 | * | . | F | 1.30 | 4.57 |
| Arg | 1175 | . | . | . | . | T | . | . | 2.96 | −2.11 | * | . | F | 1.84 | 5.90 |
| Arg | 1176 | . | . | . | . | T | . | . | 2.50 | −2.07 | * | . | F | 2.18 | 9.03 |
| Arg | 1177 | . | . | . | . | T | . | . | 1.99 | −2.14 | . | . | F | 2.52 | 4.56 |
| Glu | 1178 | . | . | . | . | . | T | C | 2.58 | −1.46 | . | . | F | 2.86 | 1.92 |
| Pro | 1179 | . | . | . | . | T | T | . | 2.26 | −1.46 | . | . | F | 3.40 | 1.64 |
| Gly | 1180 | . | . | . | . | T | T | . | 1.83 | −1.03 | . | . | F | 3.06 | 1.29 |
| Leu | 1181 | . | . | . | . | . | T | C | 1.51 | −0.54 | . | * | F | 2.69 | 1.08 |
| Asp | 1182 | . | . | . | . | . | T | C | 1.44 | −0.11 | . | * | F | 2.22 | 1.08 |
| Pro | 1183 | . | . | . | . | . | T | C | 0.59 | −0.54 | * | * | F | 2.35 | 2.18 |
| Thr | 1184 | . | . | . | . | . | T | C | −0.01 | −0.33 | * | . | F | 1.88 | 1.96 |
| Pro | 1185 | . | . | B | . | . | T | . | 0.33 | −0.33 | * | . | F | 1.70 | 0.97 |
| Lys | 1186 | . | A | B | . | . | . | . | 0.76 | −0.33 | * | * | F | 1.28 | 1.08 |
| Val | 1187 | . | A | B | . | . | . | . | 0.37 | −0.33 | * | . | F | 0.96 | 0.96 |
| Leu | 1188 | A | A | . | . | . | . | . | 0.19 | −0.39 | * | . | . | 0.64 | 0.79 |
| Glu | 1189 | A | A | . | . | . | . | . | 0.11 | −0.39 | * | . | . | 0.47 | 0.51 |

TABLE VIII

| Res | | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | −1.47 | 0.70 | . | . | . | −0.60 | 0.31 |
| Ala | 2 | A | A | . | . | . | . | . | −1.38 | 0.96 | . | . | . | −0.60 | 0.20 |
| Leu | 3 | A | A | . | . | . | . | . | −1.80 | 0.91 | . | . | . | −0.60 | 0.21 |
| Met | 4 | A | A | . | . | . | . | . | −2.27 | 1.17 | . | . | . | −0.60 | 0.17 |
| Leu | 5 | A | A | . | . | . | . | . | −2.69 | 1.20 | . | . | . | −0.60 | 0.13 |
| Ser | 6 | A | A | . | . | . | . | . | −2.39 | 1.39 | . | * | . | −0.60 | 0.13 |
| Leu | 7 | A | A | . | . | . | . | . | −2.61 | 1.09 | . | . | . | −0.60 | 0.17 |
| Val | 8 | A | A | . | . | . | . | . | −2.61 | 1.16 | * | . | . | −0.60 | 0.17 |
| Leu | 9 | A | A | . | . | . | . | . | −1.97 | 1.16 | * | . | . | −0.60 | 0.11 |
| Ser | 10 | A | A | . | . | . | . | . | −1.97 | 0.77 | * | . | . | −0.60 | 0.26 |
| Leu | 11 | . | A | B | . | . | . | . | −2.01 | 0.77 | * | . | . | −0.60 | 0.28 |
| Leu | 12 | . | A | B | . | . | . | . | −1.50 | 0.56 | * | . | . | −0.60 | 0.34 |
| Lys | 13 | . | A | B | . | . | . | . | −0.99 | 0.26 | * | . | F | −0.15 | 0.34 |
| Leu | 14 | . | A | . | . | . | . | C | −0.18 | 0.30 | . | . | F | 0.05 | 0.41 |
| Gly | 15 | . | . | . | . | T | T | . | −0.17 | 0.01 | * | . | F | 0.65 | 0.86 |
| Ser | 16 | . | . | . | . | . | T | C | 0.64 | 0.24 | * | * | F | 0.45 | 0.45 |
| Gly | 17 | . | . | . | . | . | T | C | 0.60 | 0.64 | * | . | F | 0.15 | 0.95 |
| Gln | 18 | . | . | B | . | . | T | . | −0.14 | 0.60 | * | . | F | −0.05 | 0.71 |
| Trp | 19 | . | . | B | B | . | . | . | 0.32 | 0.96 | . | . | . | −0.60 | 0.46 |
| Gln | 20 | . | . | B | B | . | . | . | 0.46 | 1.00 | . | * | . | −0.60 | 0.46 |
| Val | 21 | . | . | B | B | . | . | . | 0.76 | 1.00 | . | * | . | −0.60 | 0.41 |
| Phe | 22 | . | . | B | B | . | . | . | 1.14 | 0.60 | . | * | . | −0.30 | 0.65 |
| Gly | 23 | . | . | . | . | . | T | C | 0.93 | −0.31 | . | . | . | 1.50 | 0.75 |
| Pro | 24 | . | . | . | . | T | T | . | 0.37 | −0.29 | . | . | F | 2.30 | 1.57 |
| Asp | 25 | . | . | . | . | . | T | C | 0.37 | −0.29 | . | . | F | 2.40 | 1.34 |
| Lys | 26 | . | . | . | . | . | T | C | 0.63 | −0.67 | * | . | F | 3.00 | 2.35 |
| Pro | 27 | . | . | . | B | . | . | C | 0.52 | −0.60 | * | . | F | 2.30 | 1.54 |
| Val | 28 | . | . | B | B | . | . | . | 0.01 | −0.34 | * | . | . | 1.20 | 0.76 |
| Gln | 29 | . | . | B | B | . | . | . | −0.12 | 0.30 | * | . | . | 0.30 | 0.28 |
| Ala | 30 | . | . | B | B | . | . | . | −0.12 | 0.73 | . | . | . | −0.30 | 0.18 |
| Leu | 31 | . | . | B | B | . | . | . | −0.17 | 0.30 | . | . | . | −0.30 | 0.42 |
| Val | 32 | . | . | B | B | . | . | . | −0.54 | −0.34 | . | . | . | 0.30 | 0.41 |
| Gly | 33 | A | . | . | B | . | . | . | −0.28 | −0.24 | . | . | F | 0.45 | 0.41 |
| Glu | 34 | A | A | . | . | . | . | . | −0.98 | −0.24 | . | . | F | 0.45 | 0.50 |
| Asp | 35 | A | A | . | . | . | . | . | −0.69 | −0.14 | . | . | F | 0.45 | 0.58 |
| Ala | 36 | A | A | . | . | . | . | . | −0.54 | −0.40 | . | . | . | 0.30 | 0.79 |
| Ala | 37 | A | A | . | B | . | . | . | −0.39 | −0.26 | . | . | . | 0.30 | 0.24 |
| Phe | 38 | A | A | . | B | . | . | . | −0.86 | 0.53 | . | . | . | −0.60 | 0.13 |
| Ser | 39 | A | A | . | B | . | . | . | −1.16 | 1.21 | . | . | . | −0.60 | 0.10 |
| Cys | 40 | A | A | . | B | . | . | . | −1.37 | 1.10 | . | . | . | −0.60 | 0.14 |
| Phe | 41 | A | A | . | B | . | . | . | −0.73 | 1.03 | . | . | . | −0.60 | 0.24 |
| Leu | 42 | . | A | . | B | . | . | C | −0.46 | 0.24 | . | . | . | −0.10 | 0.36 |
| Ser | 43 | . | . | . | . | . | T | C | 0.24 | 0.34 | . | * | F | 0.45 | 0.98 |
| Pro | 44 | . | . | . | . | . | T | C | −0.04 | 0.17 | . | * | F | 0.60 | 1.82 |
| Lys | 45 | . | . | . | . | . | T | C | 0.62 | −0.11 | . | * | F | 1.20 | 2.23 |
| Thr | 46 | A | . | . | . | . | T | . | 0.73 | −0.80 | . | * | F | 1.30 | 2.88 |
| Asn | 47 | A | A | . | . | . | . | . | 0.94 | −0.69 | . | * | F | 0.90 | 1.88 |
| Ala | 48 | A | A | . | . | . | . | . | 1.24 | −0.50 | . | * | . | 0.30 | 0.93 |
| Glu | 49 | A | A | . | . | . | . | . | 0.60 | −0.50 | . | * | . | 0.45 | 1.12 |
| Ala | 50 | A | A | . | . | . | . | . | 0.67 | −0.34 | . | * | . | 0.30 | 0.52 |
| Met | 51 | A | A | . | . | . | . | . | 0.28 | −0.74 | * | * | . | 0.60 | 1.00 |
| Glu | 52 | A | A | . | . | . | . | . | −0.42 | −0.46 | * | . | . | 0.30 | 0.50 |
| Val | 53 | A | A | . | . | . | . | . | 0.28 | 0.33 | * | . | . | −0.30 | 0.43 |
| Arg | 54 | A | A | . | . | . | . | . | −0.07 | −0.17 | * | . | . | 0.30 | 0.85 |
| Phe | 55 | A | A | . | . | . | . | . | 0.52 | −0.36 | * | * | . | 0.30 | 0.48 |
| Phe | 56 | A | . | . | . | . | T | . | 0.42 | 0.04 | * | * | . | 0.25 | 1.13 |
| Arg | 57 | A | . | . | . | . | T | . | 0.12 | 0.19 | * | * | . | 0.10 | 0.50 |
| Gly | 58 | . | . | . | . | T | T | . | 0.68 | 0.57 | * | . | F | 0.35 | 0.77 |
| Gln | 59 | . | . | . | . | T | T | . | −0.29 | 0.17 | * | * | F | 0.80 | 1.20 |
| Phe | 60 | . | . | . | B | . | . | C | −0.44 | 0.03 | * | * | F | 0.05 | 0.45 |
| Ser | 61 | . | . | . | B | . | . | C | 0.22 | 0.67 | * | * | F | −0.25 | 0.34 |
| Ser | 62 | . | . | B | B | . | . | . | −0.70 | 0.74 | * | * | . | −0.60 | 0.27 |
| Val | 63 | . | . | B | B | . | . | . | −0.60 | 1.03 | * | . | . | −0.60 | 0.25 |
| Val | 64 | . | . | B | B | . | . | . | −0.49 | 1.00 | * | . | . | −0.60 | 0.30 |
| His | 65 | . | . | B | B | . | . | . | 0.21 | 0.61 | * | . | . | −0.26 | 0.43 |
| Leu | 66 | . | . | B | B | . | . | . | 0.17 | 0.23 | * | . | . | 0.38 | 0.98 |
| Tyr | 67 | . | . | B | . | . | T | . | 0.51 | 0.01 | * | . | . | 1.27 | 1.30 |
| Arg | 68 | . | . | . | . | T | T | . | 1.37 | −0.63 | * | . | F | 3.06 | 1.92 |
| Asp | 69 | . | . | . | . | T | T | . | 2.22 | −1.13 | * | . | F | 3.40 | 3.88 |
| Gly | 70 | . | . | . | . | T | T | . | 2.04 | −1.41 | * | . | F | 3.06 | 4.29 |
| Lys | 71 | . | . | . | . | T | . | . | 2.16 | −1.74 | * | . | F | 2.52 | 3.39 |
| Asp | 72 | . | . | . | . | . | . | C | 1.80 | −0.96 | . | . | F | 1.98 | 1.76 |
| Gln | 73 | . | . | . | . | . | . | C | 1.69 | −0.34 | . | . | F | 1.34 | 1.76 |
| Pro | 74 | . | . | B | . | . | . | . | 1.09 | −0.37 | . | . | F | 0.80 | 1.52 |
| Phe | 75 | . | . | B | . | . | . | . | 1.22 | 0.24 | . | . | . | −0.10 | 0.90 |
| Met | 76 | . | . | B | . | . | . | . | 1.18 | 0.67 | . | . | . | −0.40 | 0.80 |
| Gln | 77 | . | . | B | . | . | . | . | 0.93 | 0.67 | . | . | . | −0.40 | 0.90 |

TABLE VIII-continued

| Res | | I | II | III | IV | V | VI | VII | VIII | IX | X | XI | XII | XIII | XIV |
|---|---|---|---|---|---|---|---|---|---|---|---|---|---|---|---|
| Met | 78 | . | . | B | . | . | . | . | 0.93 | 1.00 | * | . | . | −0.25 | 1.63 |
| Pro | 79 | . | . | B | . | . | . | . | 0.80 | 0.61 | * | * | . | 0.09 | 2.85 |
| Gln | 80 | . | . | . | . | T | . | . | 1.61 | 0.43 | * | * | F | 0.98 | 1.63 |
| Tyr | 81 | . | . | . | . | T | T | . | 1.90 | 0.03 | . | * | F | 1.82 | 3.23 |
| Gln | 82 | A | . | . | . | . | T | . | 1.94 | −0.10 | . | * | F | 2.36 | 3.01 |
| Gly | 83 | . | . | . | . | T | T | . | 1.73 | −0.53 | . | * | F | 3.40 | 3.48 |
| Arg | 84 | . | . | B | . | . | T | . | 1.09 | −0.24 | . | * | F | 2.36 | 1.83 |
| Thr | 85 | . | . | B | . | . | . | . | 1.13 | −0.36 | . | * | F | 1.90 | 0.78 |
| Lys | 86 | . | . | B | . | . | . | . | 1.38 | −0.76 | . | * | F | 2.24 | 1.59 |
| Leu | 87 | . | . | B | . | . | . | . | 1.08 | −1.19 | * | * | F | 2.13 | 1.35 |
| Val | 88 | . | . | B | . | . | T | . | 0.53 | −0.80 | . | * | F | 2.22 | 1.26 |
| Lys | 89 | . | . | B | . | . | T | . | −0.17 | −0.60 | . | . | F | 2.30 | 0.44 |
| Asp | 90 | . | . | B | . | . | T | . | 0.14 | −0.10 | * | . | F | 1.77 | 0.54 |
| Ser | 91 | . | . | B | . | . | T | . | −0.24 | −0.79 | * | . | . | 1.84 | 1.26 |
| Ile | 92 | A | A | . | . | . | . | . | 0.68 | −1.00 | * | * | . | 1.06 | 0.62 |
| Ala | 93 | A | A | . | . | . | . | . | 0.64 | −1.00 | . | * | F | 0.98 | 0.73 |
| Glu | 94 | A | A | . | . | . | . | . | 0.30 | −0.31 | . | * | F | 0.45 | 0.38 |
| Gly | 95 | A | A | . | . | . | . | . | −0.51 | −0.31 | * | * | F | 0.45 | 0.73 |
| Arg | 96 | A | A | . | . | . | . | . | −0.10 | −0.31 | * | * | F | 0.45 | 0.60 |
| Ile | 97 | A | A | . | . | . | . | . | −0.02 | −0.81 | . | * | F | 0.75 | 0.67 |
| Ser | 98 | A | A | . | . | . | . | . | 0.57 | −0.13 | * | * | . | 0.30 | 0.56 |
| Leu | 99 | A | A | . | . | . | . | . | 0.57 | −0.56 | * | * | . | 0.60 | 0.50 |
| Arg | 100 | A | A | . | . | . | . | . | 0.02 | −0.16 | * | * | . | 0.45 | 1.14 |
| Leu | 101 | A | A | . | . | . | . | . | −0.40 | −0.16 | * | * | . | 0.30 | 0.60 |
| Glu | 102 | . | A | B | . | . | . | . | −0.37 | −0.06 | . | * | . | 0.45 | 1.04 |
| Asn | 103 | . | A | B | . | . | . | . | −0.88 | −0.10 | . | * | . | 0.30 | 0.40 |
| Ile | 104 | . | A | B | . | . | . | . | −0.07 | 0.59 | . | * | . | −0.60 | 0.40 |
| Thr | 105 | . | A | B | . | . | . | . | −0.77 | −0.10 | . | . | . | 0.30 | 0.38 |
| Val | 106 | . | A | B | . | . | . | . | −0.30 | 0.40 | . | . | . | −0.60 | 0.24 |
| Leu | 107 | . | A | B | . | . | . | . | −1.11 | 0.43 | . | . | . | −0.60 | 0.34 |
| Asp | 108 | . | A | B | . | . | . | . | −1.36 | 0.43 | . | . | . | −0.60 | 0.19 |
| Ala | 109 | . | A | B | . | . | . | . | −0.81 | 0.70 | . | . | . | −0.60 | 0.41 |
| Gly | 110 | . | . | . | . | T | . | . | −1.17 | 0.49 | * | . | . | 0.00 | 0.49 |
| Leu | 111 | . | . | B | . | . | T | . | −0.20 | 0.37 | * | . | . | 0.10 | 0.16 |
| Tyr | 112 | . | . | B | . | . | T | . | −0.28 | 0.37 | * | * | . | 0.10 | 0.30 |
| Gly | 113 | . | . | B | . | . | T | . | −0.58 | 0.56 | * | * | . | −0.20 | 0.22 |
| Cys | 114 | . | . | B | . | . | T | . | −0.29 | 0.51 | * | * | . | −0.20 | 0.35 |
| Arg | 115 | . | . | B | B | . | . | . | 0.06 | 0.21 | * | * | . | −0.30 | 0.30 |
| Ile | 116 | . | . | B | B | . | . | . | 0.57 | −0.14 | * | * | F | 0.45 | 0.52 |
| Ser | 117 | . | . | B | B | . | . | . | 0.57 | −0.19 | * | * | F | 0.76 | 1.31 |
| Ser | 118 | . | . | B | . | . | T | . | 0.67 | 0.00 | * | * | F | 1.32 | 1.05 |
| Gln | 119 | . | . | B | . | . | T | . | 1.33 | 0.76 | . | * | F | 0.58 | 2.35 |
| Ser | 120 | . | . | . | . | T | T | . | 1.27 | 0.47 | . | * | F | 1.14 | 3.03 |
| Tyr | 121 | . | . | . | . | T | T | . | 1.57 | 0.09 | . | . | F | 1.60 | 4.52 |
| Tyr | 122 | . | A | . | . | T | . | . | 0.98 | 0.20 | . | . | . | 0.89 | 2.64 |
| Gln | 123 | . | A | B | . | . | . | . | 0.99 | 0.49 | . | . | . | 0.03 | 1.38 |
| Lys | 124 | . | A | B | . | . | . | . | 0.99 | 1.01 | * | . | . | −0.28 | 0.93 |
| Ala | 125 | . | A | B | . | . | . | . | 0.48 | 0.26 | * | . | . | 0.01 | 1.02 |
| Ile | 126 | . | A | B | . | . | . | . | 0.72 | 0.19 | . | * | . | −0.30 | 0.49 |
| Trp | 127 | . | A | B | . | . | . | . | 0.11 | 0.19 | . | * | . | −0.30 | 0.42 |
| Glu | 128 | A | A | . | . | . | . | . | −0.19 | 0.83 | * | * | . | −0.60 | 0.31 |
| Leu | 129 | A | A | . | . | . | . | . | −0.82 | 0.71 | * | * | . | −0.60 | 0.59 |
| Gln | 130 | . | A | B | . | . | . | . | −1.04 | 0.53 | . | * | . | −0.60 | 0.57 |
| Val | 131 | . | A | B | . | . | . | . | −0.50 | 0.30 | . | * | . | −0.30 | 0.27 |
| Ser | 132 | . | A | . | . | . | . | C | −0.51 | 0.73 | . | * | . | −0.40 | 0.33 |
| Ala | 133 | . | A | . | . | . | . | C | −1.37 | 0.43 | . | * | . | −0.40 | 0.25 |
| Leu | 134 | . | A | B | . | . | . | . | −0.77 | 0.67 | . | * | . | −0.60 | 0.25 |
| Gly | 135 | . | A | . | . | T | . | . | −1.58 | 0.46 | . | . | . | −0.20 | 0.29 |
| Ser | 136 | . | . | B | B | . | . | . | −1.61 | 0.76 | . | . | . | −0.60 | 0.24 |
| Val | 137 | . | . | B | B | . | . | . | −1.61 | 0.94 | . | . | . | −0.60 | 0.20 |
| Pro | 138 | . | . | B | B | . | . | . | −1.91 | 0.64 | . | . | . | −0.60 | 0.27 |
| Leu | 139 | . | . | B | B | . | . | . | −1.69 | 0.90 | . | . | . | −0.60 | 0.14 |
| Ile | 140 | . | . | B | B | . | . | . | −1.69 | 1.01 | . | . | . | −0.60 | 0.19 |
| Ser | 141 | . | . | B | B | . | . | . | −1.63 | 0.80 | . | . | . | −0.60 | 0.12 |
| Ile | 142 | . | . | B | B | . | . | . | −1.63 | 1.13 | . | . | . | −0.60 | 0.24 |
| Ala | 143 | . | . | B | B | . | . | . | −1.42 | 1.09 | * | . | . | −0.60 | 0.25 |
| Gly | 144 | . | . | B | B | . | . | . | −0.50 | 0.40 | * | . | . | −0.34 | 0.31 |
| Tyr | 145 | . | . | B | B | . | . | . | 0.39 | 0.01 | * | * | . | 0.22 | 0.87 |
| Val | 146 | . | . | B | B | . | . | . | −0.20 | −0.67 | * | . | . | 1.53 | 1.44 |
| Asp | 147 | . | . | B | . | . | T | . | 0.69 | −0.49 | * | * | F | 2.04 | 1.02 |
| Arg | 148 | . | . | B | . | . | T | . | 0.47 | −0.51 | * | . | F | 2.60 | 1.13 |
| Asp | 149 | . | . | B | . | . | T | . | 0.00 | −0.59 | * | . | F | 2.34 | 1.25 |
| Ile | 150 | . | . | B | . | . | T | . | −0.42 | −0.54 | * | . | . | 1.78 | 0.62 |
| Gln | 151 | . | A | B | . | . | . | . | 0.43 | 0.03 | * | . | . | 0.22 | 0.17 |
| Leu | 152 | . | A | B | . | . | . | . | 0.13 | 0.43 | * | . | . | −0.34 | 0.18 |
| Leu | 153 | . | A | B | . | . | . | . | −0.28 | 0.81 | * | . | . | −0.60 | 0.34 |
| Cys | 154 | . | A | B | . | . | . | . | −0.62 | 0.51 | . | * | . | −0.60 | 0.26 |

TABLE VIII-continued

| Res | | I | II | III | IV | V | VI | VII | VIII | IX | X | XI | XII | XIII | XIV |
|---|---|---|---|---|---|---|---|---|---|---|---|---|---|---|---|
| Gln | 155 | . | A | . | . | T | . | . | −0.02 | 0.54 | * | * | F | −0.05 | 0.31 |
| Ser | 156 | . | . | . | . | T | T | . | −0.72 | 0.77 | * | . | F | 0.35 | 0.40 |
| Ser | 157 | . | . | . | . | T | T | . | −0.12 | 0.87 | * | . | F | 0.35 | 0.64 |
| Gly | 158 | . | . | . | . | T | T | . | 0.80 | 0.73 | * | . | F | 0.35 | 0.57 |
| Trp | 159 | . | . | . | . | T | T | . | 1.26 | 0.33 | * | . | F | 0.65 | 0.84 |
| Phe | 160 | . | . | . | . | . | T | C | 0.94 | 0.37 | * | . | F | 0.45 | 0.97 |
| Pro | 161 | . | . | . | . | . | T | C | 0.66 | 0.47 | * | * | F | 0.30 | 1.41 |
| Arg | 162 | . | . | . | . | . | T | C | 1.00 | 0.54 | * | * | F | 0.30 | 1.36 |
| Pro | 163 | . | . | . | . | T | T | . | 1.06 | −0.37 | * | * | F | 1.40 | 3.13 |
| Thr | 164 | . | . | . | . | T | . | . | 1.39 | −0.24 | * | * | F | 1.20 | 2.13 |
| Ala | 165 | . | . | . | . | T | . | . | 1.74 | −0.67 | * | * | F | 1.50 | 2.17 |
| Lys | 166 | . | . | . | . | T | . | . | 1.74 | −0.24 | . | * | F | 1.20 | 1.39 |
| Trp | 167 | . | . | . | . | T | . | . | 1.63 | −0.24 | . | * | F | 1.54 | 1.49 |
| Lys | 168 | . | . | . | . | . | . | C | 1.50 | −0.33 | . | * | F | 1.68 | 2.55 |
| Gly | 169 | . | . | . | . | . | . | C | 1.81 | −0.40 | . | * | F | 2.02 | 1.26 |
| Pro | 170 | . | . | . | . | . | T | C | 2.40 | 0.00 | . | * | F | 1.96 | 2.08 |
| Gln | 171 | . | . | . | . | T | T | . | 1.54 | −0.91 | . | * | F | 3.40 | 1.74 |
| Gly | 172 | . | . | . | . | . | T | C | 1.53 | −0.23 | . | . | F | 2.56 | 1.45 |
| Gln | 173 | . | . | B | . | . | T | . | 1.18 | −0.27 | . | . | F | 2.02 | 1.26 |
| Asp | 174 | . | . | B | . | . | . | . | 1.52 | −0.21 | . | . | F | 1.82 | 1.05 |
| Leu | 175 | . | . | B | . | . | . | . | 1.43 | −0.61 | * | * | F | 2.12 | 1.77 |
| Ser | 176 | . | . | B | . | . | T | . | 1.54 | −0.66 | * | * | F | 2.32 | 1.37 |
| Thr | 177 | . | . | B | . | . | T | . | 1.58 | −1.06 | * | * | F | 2.66 | 1.60 |
| Asp | 178 | . | . | . | . | T | T | . | 1.58 | −0.57 | * | * | F | 3.40 | 2.80 |
| Ser | 179 | . | . | . | . | . | T | C | 1.69 | −0.86 | * | * | F | 2.86 | 3.37 |
| Arg | 180 | . | . | . | . | T | T | . | 2.50 | −1.24 | * | * | F | 3.06 | 4.57 |
| Thr | 181 | . | . | . | . | T | T | . | 2.20 | −1.73 | * | . | F | 3.06 | 4.57 |
| Asn | 182 | . | . | . | . | T | T | . | 2.48 | −1.11 | * | . | F | 3.06 | 3.37 |
| Arg | 183 | . | . | B | . | . | T | . | 2.13 | −1.00 | * | . | F | 2.66 | 2.34 |
| Asp | 184 | . | . | . | . | T | T | . | 1.62 | −0.57 | * | . | F | 3.40 | 1.61 |
| Met | 185 | . | . | B | . | . | T | . | 0.81 | −0.37 | * | . | . | 2.06 | 0.82 |
| His | 186 | . | . | B | . | . | T | . | 1.12 | 0.01 | * | . | . | 1.12 | 0.36 |
| Gly | 187 | . | . | B | . | . | T | . | 0.27 | 0.01 | * | * | . | 0.78 | 0.36 |
| Leu | 188 | . | . | B | B | . | . | . | 0.16 | 0.66 | * | * | . | −0.26 | 0.27 |
| Phe | 189 | A | . | . | B | . | . | . | −0.73 | 0.04 | . | * | . | −0.30 | 0.35 |
| Asp | 190 | A | . | . | B | . | . | . | −0.43 | 0.23 | . | * | . | −0.30 | 0.25 |
| Val | 191 | A | . | . | B | . | . | . | −1.21 | 0.19 | . | * | . | −0.30 | 0.40 |
| Glu | 192 | A | . | . | B | . | . | . | −1.18 | 0.19 | . | * | . | −0.30 | 0.38 |
| Ile | 193 | A | . | . | B | . | . | . | −1.22 | −0.11 | . | * | . | 0.30 | 0.33 |
| Ser | 194 | A | . | . | B | . | . | . | −0.52 | 0.53 | . | * | . | −0.60 | 0.33 |
| Leu | 195 | A | A | . | B | . | . | . | −0.52 | 0.29 | . | * | . | −0.30 | 0.33 |
| Thr | 196 | A | A | . | B | . | . | . | 0.33 | 0.29 | . | * | . | −0.30 | 0.81 |
| Val | 197 | A | A | . | B | . | . | . | −0.26 | 0.00 | . | * | . | 0.55 | 0.98 |
| Gln | 198 | A | A | . | B | . | . | . | 0.29 | 0.11 | . | * | F | 0.50 | 1.20 |
| Glu | 199 | A | A | . | B | . | . | . | 0.29 | −0.14 | . | . | F | 1.20 | 0.82 |
| Asn | 200 | . | . | . | . | T | T | . | 0.21 | −0.24 | . | . | F | 2.40 | 1.48 |
| Ala | 201 | . | . | . | . | T | T | . | 0.22 | −0.20 | . | . | F | 2.50 | 0.60 |
| Gly | 202 | . | . | . | . | T | T | . | 0.41 | −0.21 | . | . | F | 2.25 | 0.46 |
| Ser | 203 | . | . | . | . | T | T | . | 0.11 | 0.36 | . | . | F | 1.40 | 0.15 |
| Ile | 204 | A | . | . | . | . | . | . | −0.49 | 0.34 | * | * | . | 0.40 | 0.21 |
| Ser | 205 | A | . | . | . | . | . | . | −0.38 | 0.46 | * | * | . | −0.15 | 0.21 |
| Cys | 206 | . | . | B | . | . | . | . | 0.18 | 0.03 | * | * | . | −0.10 | 0.30 |
| Ser | 207 | . | A | B | . | . | . | . | −0.07 | 0.14 | * | * | . | −0.30 | 0.58 |
| Met | 208 | A | A | . | . | . | . | . | 0.20 | −0.04 | * | * | . | 0.30 | 0.44 |
| Arg | 209 | A | A | . | . | . | . | . | 0.28 | 0.07 | * | * | . | −0.15 | 1.11 |
| His | 210 | A | A | . | . | . | . | . | 0.28 | 0.19 | . | . | . | −0.30 | 0.69 |
| Ala | 211 | A | A | . | . | . | . | . | 1.06 | 0.19 | . | . | . | −0.30 | 0.93 |
| His | 212 | A | A | . | . | . | . | . | 1.36 | −0.43 | * | . | . | 0.30 | 0.93 |
| Leu | 213 | A | A | . | . | . | . | . | 1.10 | −0.43 | * | . | . | 0.45 | 1.18 |
| Ser | 214 | A | A | . | . | . | . | . | 0.99 | −0.29 | * | . | . | 0.30 | 0.87 |
| Arg | 215 | A | A | . | . | . | . | . | 0.72 | −0.79 | * | * | F | 0.90 | 1.10 |
| Glu | 216 | A | A | . | . | . | . | . | 1.42 | −0.90 | * | * | F | 0.90 | 1.79 |
| Val | 217 | A | . | . | B | . | . | . | 0.60 | −1.59 | * | * | F | 0.90 | 2.62 |
| Glu | 218 | A | . | . | B | . | . | . | 1.41 | −1.33 | * | * | F | 0.75 | 0.99 |
| Ser | 219 | A | . | . | B | . | . | . | 0.82 | −0.93 | * | * | F | 0.75 | 0.99 |
| Arg | 220 | . | . | B | B | . | . | . | 0.37 | −0.24 | * | * | F | 0.45 | 0.94 |
| Val | 221 | . | . | B | B | . | . | . | 0.37 | −0.46 | . | * | F | 0.45 | 0.54 |
| Gln | 222 | A | . | . | B | . | . | . | 0.93 | −0.46 | . | * | . | 0.64 | 0.67 |
| Ile | 223 | A | . | . | . | . | T | . | 1.04 | 0.07 | * | * | . | 0.78 | 0.36 |
| Gly | 224 | A | . | . | . | . | T | . | 1.46 | 0.07 | * | * | F | 1.27 | 0.95 |
| Asp | 225 | . | . | . | . | T | T | . | 1.39 | −0.57 | . | * | F | 3.06 | 1.07 |
| Trp | 226 | . | . | . | . | T | T | . | 2.21 | −0.97 | . | . | F | 3.40 | 3.06 |
| Arg | 227 | . | . | B | . | . | . | . | 1.87 | −1.16 | * | . | F | 2.46 | 4.20 |
| Arg | 228 | . | . | . | . | T | T | . | 2.76 | −1.16 | * | . | F | 2.72 | 2.49 |
| Lys | 229 | . | . | . | . | T | T | . | 2.51 | −0.76 | * | . | F | 2.38 | 4.10 |
| His | 230 | . | . | . | . | T | T | . | 2.17 | −1.17 | * | . | F | 2.38 | 2.12 |
| Gly | 231 | . | . | . | . | . | T | C | 2.50 | −0.74 | * | . | F | 2.18 | 1.07 |

TABLE VIII-continued

| Res | | I | II | III | IV | V | VI | VII | VIII | IX | X | XI | XII | XIII | XIV |
|---|---|---|---|---|---|---|---|---|---|---|---|---|---|---|---|
| Gln | 232 | . | . | . | . | T | . | . | 2.50 | −0.74 | * | . | F | 2.52 | 1.07 |
| Ala | 233 | . | . | . | . | . | . | C | 2.43 | −0.74 | * | . | F | 2.66 | 1.54 |
| Gly | 234 | . | . | . | . | T | T | . | 2.14 | −1.24 | * | . | F | 3.40 | 3.11 |
| Lys | 235 | . | . | B | . | . | T | . | 1.88 | −0.91 | * | . | F | 2.66 | 2.81 |
| Arg | 236 | . | . | . | . | T | T | . | 1.92 | −0.93 | * | . | F | 2.77 | 3.73 |
| Lys | 237 | . | . | . | . | T | T | . | 1.62 | −1.04 | * | . | F | 2.48 | 5.05 |
| Tyr | 238 | . | . | B | . | . | T | . | 2.18 | −1.09 | . | . | F | 1.79 | 3.39 |
| Ser | 239 | . | . | B | . | . | T | . | 1.63 | −0.59 | . | . | F | 1.50 | 2.35 |
| Ser | 240 | . | . | B | . | . | T | . | 1.34 | 0.10 | . | . | F | 0.50 | 0.82 |
| Ser | 241 | . | . | B | . | . | T | . | 1.23 | 0.86 | . | . | F | 0.15 | 0.82 |
| His | 242 | . | . | B | . | . | . | . | 0.89 | 0.10 | * | . | . | 0.20 | 1.03 |
| Ile | 243 | . | . | B | . | . | . | . | 0.43 | 0.10 | * | . | . | 0.15 | 1.03 |
| Tyr | 244 | . | . | B | . | . | . | . | 0.52 | 0.50 | * | . | . | −0.35 | 0.66 |
| Asp | 245 | . | . | B | . | . | . | . | 0.52 | 0.54 | * | . | . | −0.40 | 0.75 |
| Ser | 246 | . | . | B | . | . | . | . | 0.01 | 0.43 | * | . | F | −0.10 | 1.44 |
| Phe | 247 | . | . | B | . | . | T | . | −0.26 | 0.43 | * | . | F | −0.05 | 0.76 |
| Pro | 248 | . | . | . | . | . | T | C | −0.07 | 0.06 | * | . | F | 0.45 | 0.61 |
| Ser | 249 | . | . | . | . | . | T | C | −0.42 | 0.84 | . | . | F | 0.15 | 0.39 |
| Leu | 250 | . | . | . | . | . | T | C | −0.42 | 1.07 | . | . | . | 0.00 | 0.45 |
| Ser | 251 | . | . | B | . | . | . | . | −0.82 | 0.29 | . | . | . | −0.10 | 0.49 |
| Phe | 252 | . | . | B | B | . | . | . | −0.37 | 0.64 | . | . | . | −0.60 | 0.31 |
| Met | 253 | . | . | B | B | . | . | . | −1.04 | 1.01 | . | . | . | −0.60 | 0.60 |
| Asp | 254 | . | . | B | B | . | . | . | −1.56 | 1.01 | . | . | . | −0.60 | 0.31 |
| Phe | 255 | . | . | B | B | . | . | . | −0.63 | 1.31 | . | . | . | −0.60 | 0.30 |
| Tyr | 256 | . | . | B | B | . | . | . | −0.54 | 0.53 | . | . | . | −0.60 | 0.59 |
| Ile | 257 | . | . | B | B | . | . | . | −0.70 | 0.34 | . | . | . | −0.30 | 0.54 |
| Leu | 258 | . | . | B | B | . | . | . | −0.44 | 0.99 | * | . | . | −0.60 | 0.47 |
| Arg | 259 | . | . | B | B | . | . | . | −0.66 | 0.63 | * | . | . | −0.35 | 0.29 |
| Pro | 260 | . | . | . | B | T | . | . | −0.62 | 0.30 | . | * | F | 0.75 | 0.65 |
| Val | 261 | . | . | . | B | T | . | . | −0.27 | 0.19 | * | * | F | 1.00 | 0.42 |
| Gly | 262 | . | . | . | . | . | T | C | 0.03 | −0.50 | * | * | F | 2.35 | 0.42 |
| Pro | 263 | . | . | . | . | T | T | . | 0.89 | 0.00 | * | * | F | 2.50 | 0.28 |
| Cys | 264 | . | . | B | . | . | T | . | −0.03 | −0.43 | * | * | F | 1.85 | 0.74 |
| Arg | 265 | . | . | B | . | . | T | . | −0.68 | −0.39 | . | * | . | 1.45 | 0.62 |
| Ala | 266 | . | A | B | . | . | . | . | −0.42 | −0.17 | . | * | . | 0.80 | 0.30 |
| Lys | 267 | . | A | B | . | . | . | . | −0.42 | 0.01 | . | * | . | −0.05 | 0.55 |
| Leu | 268 | . | A | B | . | . | . | . | −0.52 | −0.13 | . | * | . | 0.30 | 0.28 |
| Val | 269 | . | A | B | . | . | . | . | −0.67 | 0.36 | . | * | . | −0.30 | 0.40 |
| Met | 270 | A | A | . | . | . | . | . | −0.73 | 0.54 | . | * | . | −0.60 | 0.16 |
| Gly | 271 | A | A | . | . | . | . | . | −0.96 | 0.54 | * | * | . | −0.60 | 0.40 |
| Thr | 272 | A | A | . | . | . | . | . | −1.00 | 0.54 | . | * | . | −0.60 | 0.44 |
| Leu | 273 | A | A | . | . | . | . | . | −1.08 | 0.30 | . | * | . | −0.30 | 0.77 |
| Lys | 274 | A | A | . | . | . | . | . | −1.03 | 0.37 | . | * | . | −0.30 | 0.55 |
| Leu | 275 | A | A | . | . | . | . | . | −0.78 | 0.63 | . | * | . | −0.60 | 0.31 |
| Gln | 276 | A | A | . | . | . | . | . | −0.43 | 0.57 | . | * | . | −0.60 | 0.37 |
| Ile | 277 | . | A | B | . | . | . | . | −0.98 | −0.11 | . | * | . | 0.30 | 0.32 |
| Leu | 278 | A | A | . | . | . | . | . | −0.20 | 0.53 | . | * | . | −0.60 | 0.29 |
| Gly | 279 | A | A | . | . | . | . | . | −0.94 | 0.34 | . | * | . | −0.30 | 0.23 |
| Glu | 280 | A | A | . | . | . | . | . | −0.99 | 0.73 | . | * | . | −0.60 | 0.28 |
| Val | 281 | A | A | . | . | . | . | . | −0.99 | 0.69 | * | * | . | −0.60 | 0.26 |
| His | 282 | A | A | . | . | . | . | . | −0.06 | 0.00 | * | * | . | 0.30 | 0.45 |
| Phe | 283 | A | A | . | . | . | . | . | 0.54 | −0.43 | . | . | . | 0.30 | 0.52 |
| Val | 284 | A | A | . | . | . | . | . | 0.86 | 0.00 | . | * | . | 0.45 | 1.07 |
| Glu | 285 | A | A | . | . | . | . | . | 0.56 | −0.14 | . | . | F | 0.60 | 1.07 |
| Lys | 286 | A | . | . | . | . | T | . | 0.60 | −0.26 | * | . | F | 1.00 | 1.66 |
| Pro | 287 | A | . | . | . | . | T | . | −0.18 | −0.36 | * | . | F | 1.00 | 1.85 |
| His | 288 | A | . | . | . | . | T | . | 0.52 | −0.31 | * | . | F | 0.85 | 0.88 |
| Ser | 289 | A | . | . | . | . | T | . | 0.49 | 0.09 | * | . | . | 0.10 | 0.76 |
| Leu | 290 | A | . | . | B | . | . | . | 0.19 | 0.77 | . | * | . | −0.60 | 0.35 |
| Leu | 291 | . | . | B | B | . | . | . | −0.20 | 0.73 | . | * | . | −0.60 | 0.34 |
| Gln | 292 | . | . | B | B | . | . | . | −0.33 | 0.66 | . | . | . | −0.60 | 0.25 |
| Ile | 293 | . | . | B | B | . | . | . | −0.60 | 0.70 | . | . | F | −0.45 | 0.30 |
| Ser | 294 | . | . | B | . | . | T | . | −0.61 | 0.40 | . | . | F | 0.25 | 0.49 |
| Gly | 295 | . | . | . | . | T | T | . | −0.11 | 0.20 | . | . | F | 0.65 | 0.41 |
| Gly | 296 | . | . | . | . | T | T | . | −0.11 | 0.29 | . | * | F | 0.65 | 0.84 |
| Ser | 297 | . | . | . | . | . | T | C | −0.07 | 0.29 | * | . | F | 0.45 | 0.52 |
| Thr | 298 | . | . | B | B | . | . | . | 0.87 | −0.10 | * | . | F | 0.90 | 1.04 |
| Thr | 299 | . | . | B | B | . | . | . | 0.82 | −0.53 | * | . | F | 1.50 | 2.11 |
| Leu | 300 | . | . | B | B | . | . | . | 0.96 | −0.53 | * | . | F | 1.80 | 1.56 |
| Lys | 301 | . | . | . | B | T | . | . | 1.30 | −0.49 | * | . | F | 2.20 | 1.67 |
| Lys | 302 | . | . | . | . | T | . | . | 1.39 | −0.57 | * | . | F | 3.00 | 1.86 |
| Gly | 303 | . | . | . | . | . | T | C | 1.41 | −0.63 | * | . | F | 2.70 | 3.49 |
| Pro | 304 | . | . | . | . | . | T | C | 1.42 | −0.40 | * | . | F | 2.10 | 1.83 |
| Asn | 305 | . | . | . | . | . | T | C | 1.53 | −0.01 | * | . | F | 1.80 | 1.23 |
| Pro | 306 | . | . | . | . | T | T | . | 1.28 | 0.77 | * | . | F | 0.80 | 1.08 |
| Trp | 307 | . | . | . | . | T | . | . | 0.93 | 0.77 | . | . | . | 0.15 | 1.08 |
| Ser | 308 | . | . | . | . | . | . | C | 1.07 | 0.73 | . | . | . | −0.20 | 0.90 |

TABLE VIII-continued

| Res | | I | II | III | IV | V | VI | VII | VIII | IX | X | XI | XII | XIII | XIV |
|---|---|---|---|---|---|---|---|---|---|---|---|---|---|---|---|
| Phe | 309 | . | . | B | . | . | . | . | 0.61 | 0.76 | . | . | F | −0.25 | 0.90 |
| Pro | 310 | . | . | B | . | . | . | . | 0.02 | 0.90 | . | . | F | −0.25 | 0.46 |
| Ser | 311 | . | . | . | . | . | T | C | −0.58 | 0.49 | . | . | F | 0.15 | 0.34 |
| Pro | 312 | . | . | . | . | T | T | . | −0.99 | 0.79 | . | . | F | 0.35 | 0.33 |
| Cys | 313 | . | . | . | . | T | T | . | −0.90 | 0.79 | . | . | . | 0.20 | 0.18 |
| Ala | 314 | . | . | B | . | T | T | . | −0.51 | 0.79 | . | . | . | 0.20 | 0.21 |
| Leu | 315 | . | . | B | . | . | . | . | −0.69 | 0.89 | . | . | . | −0.40 | 0.20 |
| Phe | 316 | . | . | B | . | . | . | . | −0.78 | 0.89 | . | . | . | −0.40 | 0.47 |
| Pro | 317 | . | . | B | . | . | . | . | −0.96 | 0.74 | . | . | . | −0.40 | 0.60 |
| Thr | 318 | . | . | B | . | . | . | . | −0.68 | 0.67 | . | . | . | −0.40 | 0.93 |

TABLE IX

| Res | | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | −0.69 | 0.51 | . | . | . | −0.40 | 0.26 |
| Ala | 2 | . | . | B | . | . | . | . | −0.64 | 0.51 | . | . | . | −0.40 | 0.31 |
| Gly | 3 | . | . | B | . | . | . | . | −1.07 | 0.51 | . | . | . | −0.40 | 0.24 |
| Ile | 4 | . | . | B | . | . | . | . | −1.49 | 0.77 | . | . | . | −0.40 | 0.20 |
| Pro | 5 | . | . | B | . | . | . | . | −1.80 | 0.84 | . | . | F | −0.25 | 0.17 |
| Gly | 6 | . | . | B | B | . | . | . | −2.01 | 1.13 | . | . | . | −0.60 | 0.14 |
| Leu | 7 | . | . | B | B | . | . | . | −2.23 | 1.39 | . | . | . | −0.60 | 0.17 |
| Leu | 8 | . | . | B | B | . | . | . | −2.59 | 1.39 | . | . | . | −0.60 | 0.09 |
| Phe | 9 | . | . | B | B | . | . | . | −2.40 | 1.74 | . | . | . | −0.60 | 0.08 |
| Leu | 10 | . | . | B | B | . | . | . | −3.00 | 2.10 | . | . | . | −0.60 | 0.08 |
| Leu | 11 | . | . | B | B | . | . | . | −3.47 | 2.10 | . | . | . | −0.60 | 0.08 |
| Phe | 12 | . | . | B | B | . | . | . | −3.32 | 2.10 | . | . | . | −0.60 | 0.08 |
| Phe | 13 | . | . | B | B | . | . | . | −3.10 | 1.89 | . | . | . | −0.60 | 0.05 |
| Leu | 14 | . | . | B | B | . | . | . | −3.26 | 1.70 | . | . | . | −0.60 | 0.06 |
| Leu | 15 | . | . | B | B | . | . | . | −2.79 | 1.66 | . | . | . | −0.60 | 0.05 |
| Cys | 16 | . | . | B | B | . | . | . | −1.98 | 1.30 | * | . | . | −0.60 | 0.06 |
| Ala | 17 | . | . | B | B | T | . | . | −2.13 | 0.91 | . | . | . | −0.20 | 0.13 |
| Val | 18 | . | . | B | B | . | . | . | −1.73 | 0.87 | . | . | . | −0.60 | 0.12 |
| Gly | 19 | . | . | B | B | . | . | . | −1.13 | 0.57 | * | . | . | −0.60 | 0.29 |
| Gln | 20 | . | . | B | B | . | . | . | −0.57 | 0.43 | . | . | F | −0.45 | 0.45 |
| Val | 21 | . | . | B | B | . | . | . | −0.20 | 0.69 | . | . | F | −0.45 | 0.95 |
| Ser | 22 | . | . | B | . | . | T | . | −0.20 | 0.43 | . | . | F | 0.10 | 1.28 |
| Pro | 23 | . | . | B | . | . | T | . | 0.44 | 0.50 | . | . | F | −0.05 | 0.75 |
| Tyr | 24 | . | . | . | . | T | T | . | 0.50 | 0.53 | . | * | . | 0.35 | 1.56 |
| Ser | 25 | . | . | . | . | . | T | C | 0.54 | 0.80 | . | * | . | 0.15 | 1.22 |
| Ala | 26 | . | . | . | . | . | . | C | 1.19 | 0.41 | . | . | . | −0.05 | 1.58 |
| Pro | 27 | . | . | . | . | T | . | . | 1.18 | 0.41 | . | * | . | 0.15 | 1.56 |
| Trp | 28 | . | . | . | . | T | . | . | 1.10 | 0.14 | . | * | . | 0.45 | 1.68 |
| Lys | 29 | . | . | . | . | . | T | C | 1.13 | 0.67 | . | * | F | 0.30 | 1.75 |
| Pro | 30 | . | . | . | . | T | T | . | 0.84 | 0.60 | . | * | F | 0.50 | 1.75 |
| Thr | 31 | . | . | . | . | T | T | . | 1.19 | 0.67 | * | * | F | 0.50 | 1.68 |
| Trp | 32 | . | . | B | . | . | T | . | 1.51 | 0.51 | * | * | . | −0.05 | 1.32 |
| Pro | 33 | . | . | B | . | . | T | . | 0.99 | 0.51 | * | * | . | −0.05 | 1.67 |
| Ala | 34 | . | . | . | . | T | T | . | 0.73 | 0.77 | * | * | . | 0.20 | 0.95 |
| Tyr | 35 | . | . | . | . | T | T | . | 0.09 | 0.71 | . | . | . | 0.35 | 1.40 |
| Arg | 36 | . | . | B | . | . | T | . | −0.46 | 0.44 | . | * | . | −0.20 | 0.67 |
| Leu | 37 | . | . | B | B | . | . | . | −0.98 | 0.66 | . | * | . | −0.60 | 0.49 |
| Pro | 38 | . | . | B | B | . | . | . | −0.98 | 0.84 | * | * | . | −0.60 | 0.26 |
| Val | 39 | . | . | B | B | . | . | . | −0.39 | 0.51 | * | * | . | −0.60 | 0.21 |
| Val | 40 | . | . | B | B | . | . | . | −0.44 | 0.91 | * | * | . | −0.60 | 0.43 |
| Leu | 41 | . | . | B | B | . | . | . | −0.87 | 0.61 | * | * | F | −0.45 | 0.37 |
| Pro | 42 | . | . | B | . | . | T | . | −0.87 | 0.67 | . | . | F | −0.05 | 0.73 |
| Gln | 43 | . | . | B | . | . | T | . | −0.66 | 0.71 | . | * | F | −0.05 | 0.81 |
| Ser | 44 | . | . | B | . | . | T | . | −0.61 | 0.47 | . | . | F | 0.10 | 1.57 |
| Thr | 45 | . | . | B | . | . | T | . | −0.34 | 0.47 | * | . | F | −0.05 | 0.84 |
| Leu | 46 | . | . | B | . | . | . | . | 0.51 | 0.54 | * | . | F | −0.25 | 0.49 |
| Asn | 47 | . | . | B | . | . | . | . | 0.51 | 0.14 | . | . | . | 0.14 | 0.73 |
| Leu | 48 | . | . | B | . | . | . | . | 0.51 | 0.19 | * | * | . | 0.38 | 0.78 |
| Ala | 49 | . | . | B | . | . | . | . | 0.11 | −0.30 | . | . | . | 1.37 | 1.59 |
| Lys | 50 | . | . | . | . | . | T | C | 0.08 | −0.20 | . | . | F | 2.01 | 0.85 |
| Pro | 51 | . | . | . | . | . | T | C | 0.30 | −0.17 | . | * | F | 2.40 | 1.02 |
| Asp | 52 | . | . | . | . | . | T | C | 0.30 | −0.36 | . | * | F | 2.16 | 1.02 |
| Phe | 53 | . | . | B | . | . | T | . | 0.52 | −0.86 | . | * | . | 1.72 | 0.89 |
| Gly | 54 | A | A | . | . | . | . | . | 1.16 | −0.36 | . | * | . | 0.78 | 0.58 |
| Ala | 55 | A | A | . | . | . | . | . | 0.30 | −0.79 | . | * | . | 0.84 | 0.69 |
| Glu | 56 | A | A | . | . | . | . | . | 0.51 | −0.10 | . | * | . | 0.30 | 0.66 |
| Ala | 57 | A | A | . | . | . | . | . | −0.34 | −0.89 | . | * | F | 0.90 | 1.16 |
| Lys | 58 | A | A | . | . | . | . | . | 0.06 | −0.67 | . | * | F | 0.75 | 0.85 |
| Leu | 59 | . | A | B | . | . | . | . | 0.10 | −0.79 | . | * | . | 0.60 | 0.66 |

TABLE IX-continued

| Res | | I | II | III | IV | V | VI | VII | VIII | IX | X | XI | XII | XIII | XIV |
|---|---|---|---|---|---|---|---|---|---|---|---|---|---|---|---|
| Glu | 60 | . | A | B | . | . | . | . | 0.39 | −0.40 | . | * | . | 0.30 | 0.87 |
| Val | 61 | . | A | B | . | . | . | . | −0.28 | −0.51 | . | * | F | 1.00 | 0.58 |
| Ser | 62 | . | A | . | . | T | . | . | −0.03 | 0.06 | . | * | F | 0.75 | 0.38 |
| Ser | 63 | . | . | . | . | T | T | . | −0.29 | −0.20 | . | * | F | 2.00 | 0.22 |
| Ser | 64 | . | . | . | . | T | T | . | 0.52 | 0.23 | . | * | F | 1.65 | 0.45 |
| Cys | 65 | . | . | . | . | T | T | . | −0.14 | −0.01 | . | . | F | 2.50 | 0.58 |
| Gly | 66 | . | . | . | . | . | T | C | 0.68 | 0.17 | . | . | F | 1.45 | 0.23 |
| Pro | 67 | . | . | . | . | T | . | . | 1.02 | 0.29 | . | . | F | 1.45 | 0.24 |
| Gln | 68 | . | . | . | . | T | . | . | 0.98 | −0.10 | . | . | . | 1.90 | 0.89 |
| Cys | 69 | . | . | B | . | . | . | . | 0.97 | −0.24 | . | . | . | 1.50 | 0.89 |
| His | 70 | . | . | . | . | T | T | . | 1.42 | −0.19 | . | . | F | 2.25 | 0.83 |
| Lys | 71 | . | . | . | . | T | T | . | 0.96 | −0.19 | . | . | F | 2.50 | 0.74 |
| Gly | 72 | . | . | . | . | T | T | . | 0.96 | 0.10 | . | . | F | 1.80 | 1.14 |
| Thr | 73 | . | . | . | . | . | T | C | 0.64 | −0.04 | . | . | F | 1.95 | 1.29 |
| Pro | 74 | . | . | . | . | . | . | C | 1.07 | −0.06 | . | . | F | 1.35 | 0.93 |
| Leu | 75 | . | . | . | . | . | . | C | 1.10 | 0.70 | . | . | F | 0.61 | 1.48 |
| Pro | 76 | . | . | . | . | . | T | C | 1.06 | 0.27 | . | . | F | 1.12 | 1.77 |
| Thr | 77 | . | . | B | . | . | T | . | 0.81 | −0.21 | . | . | F | 1.78 | 1.98 |
| Tyr | 78 | . | . | B | . | . | T | . | 1.17 | −0.14 | . | . | F | 2.04 | 2.43 |
| Glu | 79 | . | . | B | . | . | T | . | 1.38 | −0.83 | . | . | F | 2.60 | 3.14 |
| Glu | 80 | . | A | B | . | . | . | . | 1.94 | −0.86 | * | . | F | 1.94 | 3.77 |
| Ala | 81 | A | A | . | . | . | . | . | 1.34 | −0.59 | * | . | F | 1.68 | 3.77 |
| Lys | 82 | . | A | B | . | . | . | . | 1.36 | −0.66 | * | . | F | 1.42 | 1.79 |
| Gln | 83 | . | A | B | . | . | . | . | 1.36 | −0.27 | * | . | F | 0.86 | 1.39 |
| Tyr | 84 | . | A | B | . | . | . | . | 1.36 | 0.49 | . | . | . | −0.45 | 2.15 |
| Leu | 85 | . | . | B | B | . | . | . | 1.04 | −0.01 | . | * | . | 0.45 | 1.87 |
| Ser | 86 | . | . | B | B | . | . | . | 0.82 | 0.47 | . | . | . | −0.45 | 1.55 |
| Tyr | 87 | . | A | B | B | . | . | . | 0.53 | 0.76 | . | . | . | −0.60 | 0.82 |
| Glu | 88 | . | A | B | B | . | . | . | −0.06 | 0.76 | . | . | . | −0.45 | 1.55 |
| Thr | 89 | . | A | B | B | . | . | . | 0.19 | 0.57 | . | . | . | −0.45 | 1.17 |
| Leu | 90 | . | A | B | B | . | . | . | 0.66 | 0.59 | . | . | . | −0.45 | 1.20 |
| Tyr | 91 | . | . | B | . | . | T | . | 0.66 | 0.26 | * | . | . | 0.36 | 0.69 |
| Ala | 92 | . | . | . | . | . | T | C | 1.01 | 0.64 | * | . | . | 0.52 | 0.64 |
| Asn | 93 | . | . | . | . | . | T | C | 0.70 | 0.16 | * | . | F | 1.38 | 1.52 |
| Gly | 94 | . | . | . | . | . | T | C | 1.01 | −0.04 | * | . | F | 2.24 | 1.40 |
| Ser | 95 | . | . | . | . | . | . | C | 1.51 | −0.80 | * | . | F | 2.60 | 2.39 |
| Arg | 96 | . | . | . | B | . | . | C | 1.76 | −0.81 | * | * | F | 2.14 | 2.15 |
| Thr | 97 | . | . | B | B | . | . | . | 1.49 | −0.81 | * | * | F | 1.68 | 3.76 |
| Glu | 98 | . | . | B | B | . | . | . | 1.14 | −0.60 | * | * | F | 1.42 | 2.08 |
| Thr | 99 | . | . | B | B | . | . | . | 0.60 | −0.56 | . | * | F | 1.16 | 1.05 |
| Gln | 100 | . | . | B | B | . | . | . | 0.66 | 0.13 | * | * | F | −0.15 | 0.51 |
| Val | 101 | . | . | B | B | . | . | . | −0.34 | 0.40 | * | * | . | −0.60 | 0.46 |
| Gly | 102 | . | . | B | B | . | . | . | −0.84 | 1.09 | . | * | . | −0.60 | 0.22 |
| Ile | 103 | . | . | B | B | . | . | . | −1.14 | 1.29 | . | * | . | −0.60 | 0.11 |
| Tyr | 104 | . | . | B | B | . | . | . | −1.13 | 1.27 | . | . | . | −0.60 | 0.19 |
| Ile | 105 | . | . | B | B | . | . | . | −1.43 | 1.01 | . | . | . | −0.60 | 0.26 |
| Leu | 106 | . | . | B | B | . | . | . | −0.92 | 0.97 | . | . | . | −0.35 | 0.50 |
| Ser | 107 | . | . | B | . | . | T | . | −0.58 | 0.71 | . | . | F | 0.45 | 0.32 |
| Ser | 108 | . | . | . | . | . | T | C | −0.03 | −0.04 | * | . | F | 1.80 | 0.75 |
| Ser | 109 | . | . | . | . | . | T | C | −0.38 | −0.30 | * | . | F | 2.05 | 0.90 |
| Gly | 110 | . | . | . | . | T | T | . | 0.51 | −0.49 | * | . | F | 2.50 | 0.68 |
| Asp | 111 | . | A | . | . | T | . | . | 1.29 | −0.47 | . | * | F | 1.85 | 0.88 |
| Gly | 112 | . | A | . | . | . | . | C | 1.70 | −0.36 | . | . | F | 1.40 | 0.89 |
| Ala | 113 | . | A | B | . | . | . | . | 2.00 | −0.74 | . | . | F | 1.40 | 1.77 |
| Gln | 114 | . | A | B | . | . | . | . | 2.00 | −1.17 | . | . | . | 1.34 | 1.77 |
| His | 115 | . | A | B | . | . | . | . | 2.00 | −0.79 | . | . | F | 1.58 | 2.39 |
| Arg | 116 | . | A | B | . | . | . | . | 1.70 | −0.79 | . | . | F | 1.92 | 2.34 |
| Asp | 117 | . | . | . | . | T | T | . | 1.74 | −0.90 | . | . | F | 3.06 | 1.81 |
| Ser | 118 | . | . | . | . | T | T | . | 1.99 | −0.91 | . | * | F | 3.40 | 1.79 |
| Gly | 119 | . | . | . | . | T | T | . | 2.03 | −0.99 | * | . | F | 2.91 | 0.90 |
| Ser | 120 | . | . | . | . | T | T | . | 1.77 | −0.99 | . | * | F | 3.02 | 1.08 |
| Ser | 121 | . | . | . | . | . | . | C | 1.77 | −0.60 | . | . | F | 2.58 | 1.08 |
| Gly | 122 | . | . | . | . | . | T | C | 1.88 | −0.99 | . | * | F | 2.74 | 2.14 |
| Lys | 123 | . | . | . | . | T | T | . | 2.22 | −1.41 | . | . | F | 2.90 | 3.13 |
| Ser | 124 | . | . | . | . | . | T | C | 2.68 | −1.80 | . | . | F | 3.00 | 4.66 |
| Arg | 125 | . | . | B | . | . | T | . | 2.98 | −2.19 | . | . | F | 2.50 | 9.23 |
| Arg | 126 | . | . | B | . | . | . | . | 2.39 | −2.21 | . | . | F | 2.00 | 7.99 |
| Lys | 127 | . | . | B | B | . | . | . | 2.49 | −1.53 | . | . | F | 1.50 | 4.18 |
| Arg | 128 | . | . | B | B | . | . | . | 2.10 | −1.16 | . | . | F | 1.20 | 3.35 |
| Gln | 129 | . | . | B | B | . | . | . | 2.16 | −0.73 | . | . | . | 0.75 | 1.69 |
| Ile | 130 | . | . | B | B | . | . | . | 2.04 | 0.03 | . | . | . | −0.15 | 1.32 |
| Tyr | 131 | . | . | B | B | . | . | . | 1.63 | 0.03 | . | . | . | −0.15 | 1.13 |
| Gly | 132 | . | . | B | . | . | . | . | 1.70 | 0.41 | * | * | . | −0.40 | 0.87 |
| Tyr | 133 | . | . | B | . | . | . | . | 0.89 | 0.01 | * | * | . | 0.05 | 2.44 |
| Asp | 134 | . | . | B | . | . | T | . | 0.59 | 0.11 | . | * | F | 0.40 | 1.35 |
| Ser | 135 | . | . | B | . | . | T | . | 0.59 | −0.26 | . | * | F | 1.00 | 1.83 |
| Arg | 136 | . | . | B | . | . | T | . | 0.13 | 0.00 | . | * | F | 0.25 | 0.82 |

TABLE IX-continued

| Res | | I | II | III | IV | V | VI | VII | VIII | IX | X | XI | XII | XIII | XIV |
|---|---|---|---|---|---|---|---|---|---|---|---|---|---|---|---|
| Phe | 137 | . | . | B | . | . | T | . | 0.13 | 0.03 | . | * | . | 0.10 | 0.42 |
| Ser | 138 | . | . | B | B | . | . | . | 0.42 | 0.46 | . | * | . | −0.47 | 0.31 |
| Ile | 139 | . | . | B | B | . | . | . | 0.42 | 0.07 | * | * | . | −0.04 | 0.32 |
| Phe | 140 | . | . | B | B | . | . | . | 0.02 | 0.07 | * | * | . | 0.09 | 0.62 |
| Gly | 141 | . | . | . | . | T | T | . | −0.90 | 0.07 | * | * | . | 1.02 | 0.40 |
| Lys | 142 | . | . | . | . | T | T | . | −1.01 | 0.37 | . | . | F | 1.30 | 0.47 |
| Asp | 143 | . | . | . | . | T | T | . | −0.71 | 0.37 | . | . | F | 1.17 | 0.45 |
| Phe | 144 | . | . | B | . | . | T | . | −0.07 | −0.01 | . | . | . | 1.09 | 0.73 |
| Leu | 145 | . | . | B | . | . | . | . | 0.42 | 0.31 | . | . | . | 0.16 | 0.57 |
| Leu | 146 | . | . | B | . | . | . | . | 0.07 | 0.74 | . | . | . | −0.27 | 0.53 |
| Asn | 147 | . | . | B | . | . | . | . | −0.28 | 1.53 | . | . | . | −0.40 | 0.53 |
| Tyr | 148 | . | . | . | . | . | T | C | −0.59 | 1.13 | . | * | . | 0.00 | 0.85 |
| Pro | 149 | . | . | . | . | T | T | . | −0.19 | 0.93 | . | * | . | 0.35 | 1.50 |
| Phe | 150 | . | . | . | . | T | T | . | −0.23 | 0.63 | * | * | . | 0.35 | 1.25 |
| Ser | 151 | . | . | B | . | . | T | . | 0.62 | 0.87 | * | * | F | −0.05 | 0.59 |
| Thr | 152 | . | . | B | B | . | . | . | −0.19 | 0.11 | . | * | F | −0.15 | 0.76 |
| Ser | 153 | . | . | B | B | . | . | . | −0.24 | 0.37 | . | * | F | −0.15 | 0.73 |
| Val | 154 | . | . | B | B | . | . | . | −0.34 | −0.03 | . | * | F | 0.45 | 0.73 |
| Lys | 155 | . | . | B | B | . | . | . | 0.01 | 0.07 | . | * | F | −0.15 | 0.73 |
| Leu | 156 | . | . | B | B | . | . | . | −0.36 | 0.01 | . | * | F | −0.15 | 0.54 |
| Ser | 157 | . | . | B | . | . | T | . | −0.36 | 0.20 | . | * | F | 0.25 | 0.39 |
| Thr | 158 | . | . | B | . | . | T | . | −0.40 | 0.04 | . | * | F | 0.25 | 0.28 |
| Gly | 159 | . | . | . | . | T | T | . | 0.14 | 0.47 | . | * | F | 0.35 | 0.34 |
| Cys | 160 | . | . | . | . | T | T | . | −0.71 | 0.27 | . | . | F | 0.65 | 0.36 |
| Thr | 161 | . | . | B | . | . | . | . | −0.76 | 0.57 | . | . | F | −0.25 | 0.21 |
| Gly | 162 | . | . | B | . | . | . | . | −1.04 | 0.73 | . | . | F | −0.25 | 0.16 |
| Thr | 163 | . | A | B | . | . | . | . | −0.73 | 0.80 | . | . | F | −0.45 | 0.29 |
| Leu | 164 | . | A | B | . | . | . | . | −0.34 | 0.23 | . | . | . | −0.30 | 0.35 |
| Val | 165 | . | A | B | . | . | . | . | 0.29 | −0.26 | . | . | . | 0.30 | 0.71 |
| Ala | 166 | . | A | B | . | . | . | . | −0.26 | −0.19 | . | . | . | 0.30 | 0.67 |
| Glu | 167 | A | A | . | . | . | . | . | −0.72 | −0.03 | . | . | . | 0.30 | 0.60 |
| Lys | 168 | A | A | . | . | . | . | . | −0.72 | −0.03 | . | . | . | 0.30 | 0.67 |
| His | 169 | A | A | . | . | . | . | . | −0.50 | −0.19 | . | . | . | 0.30 | 0.95 |
| Val | 170 | A | A | . | . | . | . | . | −0.23 | −0.19 | * | . | . | 0.30 | 0.56 |
| Leu | 171 | A | A | . | . | . | . | . | 0.32 | 0.31 | * | . | . | −0.30 | 0.28 |
| Thr | 172 | A | A | . | . | . | . | . | −0.34 | 0.81 | * | . | . | −0.60 | 0.28 |
| Ala | 173 | A | A | . | . | . | . | . | −1.28 | 0.89 | * | . | . | −0.60 | 0.20 |
| Ala | 174 | A | A | . | . | . | . | . | −1.28 | 0.93 | * | . | . | −0.60 | 0.17 |
| His | 175 | . | A | B | . | . | . | . | −0.42 | 0.74 | * | . | . | −0.32 | 0.16 |
| Cys | 176 | . | A | B | . | . | . | . | 0.04 | 0.26 | . | . | . | 0.26 | 0.27 |
| Ile | 177 | . | A | B | . | . | . | . | 0.40 | 0.19 | * | . | . | 0.54 | 0.26 |
| His | 178 | . | . | . | . | T | T | . | 0.68 | −0.31 | * | . | . | 2.22 | 0.39 |
| Asp | 179 | . | . | . | . | T | T | . | 1.02 | −0.33 | * | . | F | 2.80 | 1.04 |
| Gly | 180 | . | . | . | . | T | T | . | 0.20 | −0.14 | * | * | F | 2.52 | 2.33 |
| Lys | 181 | . | . | . | . | T | T | . | 0.91 | −0.19 | * | * | F | 2.24 | 1.27 |
| Thr | 182 | . | . | B | B | . | . | . | 1.46 | −0.69 | * | * | F | 1.46 | 1.52 |
| Tyr | 183 | . | . | B | B | . | . | . | 1.18 | −0.26 | * | * | F | 0.88 | 1.52 |
| Val | 184 | . | . | B | B | . | . | . | 1.18 | −0.20 | * | * | F | 0.60 | 1.10 |
| Lys | 185 | . | . | B | B | . | . | . | 1.57 | 0.20 | * | * | F | 0.12 | 1.32 |
| Gly | 186 | . | . | B | . | . | . | . | 0.71 | −0.29 | * | * | F | 1.04 | 1.68 |
| Thr | 187 | . | . | B | . | . | . | . | 1.13 | −0.36 | . | * | F | 1.16 | 1.87 |
| Gln | 188 | . | . | B | . | . | . | . | 0.52 | −1.00 | * | * | F | 1.58 | 1.83 |
| Lys | 189 | . | . | B | B | . | . | . | 1.03 | −0.36 | * | * | F | 1.20 | 1.37 |
| Leu | 190 | . | . | B | B | . | . | . | 0.29 | −0.36 | * | * | F | 0.93 | 0.94 |
| Arg | 191 | . | . | B | B | . | . | . | −0.18 | −0.06 | * | * | . | 0.66 | 0.47 |
| Val | 192 | . | . | B | B | . | . | . | 0.18 | 0.23 | . | * | . | −0.06 | 0.19 |
| Gly | 193 | . | . | B | B | . | . | . | −0.03 | 0.23 | . | * | . | −0.18 | 0.47 |
| Phe | 194 | . | . | B | B | . | . | . | −0.03 | −0.03 | . | * | . | 0.64 | 0.37 |
| Leu | 195 | . | . | B | B | . | . | . | 0.08 | −0.03 | . | * | . | 1.13 | 1.00 |
| Lys | 196 | . | . | B | . | . | T | . | 0.01 | 0.11 | . | * | F | 1.27 | 0.88 |
| Pro | 197 | . | . | B | . | . | T | . | 0.87 | −0.31 | * | * | F | 2.36 | 2.02 |
| Lys | 198 | . | . | . | . | T | T | . | 0.87 | −1.10 | * | * | F | 3.40 | 4.10 |
| Phe | 199 | . | . | B | . | . | T | . | 1.22 | −1.36 | * | * | F | 2.66 | 2.03 |
| Lys | 200 | . | . | B | . | . | . | . | 2.14 | −0.93 | * | * | F | 2.12 | 1.30 |
| Asp | 201 | . | . | . | . | T | T | . | 1.76 | −1.36 | * | * | F | 2.38 | 1.27 |
| Gly | 202 | . | . | . | . | T | T | . | 1.38 | −0.93 | * | * | F | 2.04 | 1.45 |
| Gly | 203 | . | . | . | . | T | T | . | 1.33 | −1.21 | * | * | F | 1.85 | 0.73 |
| Arg | 204 | . | . | . | . | . | T | C | 2.03 | −0.81 | * | * | F | 1.95 | 0.71 |
| Gly | 205 | . | . | . | . | . | . | C | 1.69 | −0.81 | * | . | F | 2.20 | 1.19 |
| Ala | 206 | . | . | . | . | . | . | C | 1.38 | −0.86 | * | . | F | 2.50 | 1.62 |
| Asn | 207 | . | . | . | . | . | T | C | 1.42 | −0.80 | * | . | F | 3.00 | 1.19 |
| Asp | 208 | . | . | . | . | . | T | C | 1.18 | −0.41 | * | . | F | 2.40 | 1.61 |
| Ser | 209 | . | . | . | . | . | T | C | 0.47 | −0.34 | * | . | F | 2.10 | 1.61 |
| Thr | 210 | . | . | . | . | . | T | C | 0.60 | −0.23 | * | . | F | 1.65 | 0.99 |
| Ser | 211 | . | . | . | . | . | . | C | 1.19 | −0.20 | . | . | F | 1.15 | 0.92 |
| Ala | 212 | . | A | . | . | . | . | C | 1.19 | −0.20 | . | . | F | 0.80 | 1.19 |
| Met | 213 | . | A | B | . | . | . | . | 0.59 | −0.19 | * | . | . | 0.45 | 1.42 |

TABLE IX-continued

| Res | | I | II | III | IV | V | VI | VII | VIII | IX | X | XI | XII | XIII | XIV |
|---|---|---|---|---|---|---|---|---|---|---|---|---|---|---|---|
| Pro | 214 | . | A | . | . | . | . | C | 0.93 | −0.06 | . | * | F | 0.80 | 1.05 |
| Glu | 215 | A | A | . | . | . | . | . | 0.54 | −0.44 | . | * | F | 0.60 | 2.08 |
| Gln | 216 | A | A | . | . | . | . | . | 0.84 | −0.16 | . | * | F | 0.60 | 1.82 |
| Met | 217 | A | A | . | . | . | . | . | 1.14 | −0.37 | . | * | F | 0.60 | 2.04 |
| Lys | 218 | A | . | . | B | . | . | . | 0.86 | 0.11 | * | * | . | −0.15 | 1.24 |
| Phe | 219 | A | . | . | B | . | . | . | 1.18 | 0.80 | * | * | . | −0.60 | 0.50 |
| Gln | 220 | . | . | B | B | . | . | . | 0.32 | 0.40 | . | * | . | −0.60 | 0.99 |
| Trp | 221 | . | . | B | B | . | . | . | 0.37 | 0.43 | * | * | . | −0.60 | 0.37 |
| Ile | 222 | . | . | B | B | . | . | . | 1.08 | 0.43 | * | . | . | −0.37 | 0.85 |
| Arg | 223 | . | . | B | B | . | . | . | 0.72 | −0.36 | . | . | . | 0.76 | 0.96 |
| Val | 224 | . | . | B | B | . | . | . | 1.39 | −0.27 | * | . | . | 1.14 | 1.32 |
| Lys | 225 | . | . | . | B | T | . | . | 0.53 | −0.69 | * | . | F | 2.22 | 2.56 |
| Arg | 226 | . | . | . | B | T | . | . | 0.61 | −0.73 | * | . | F | 2.30 | 0.97 |
| Thr | 227 | . | . | . | B | T | . | . | 1.54 | −0.30 | * | * | F | 1.92 | 2.02 |
| His | 228 | . | . | . | B | . | . | C | 1.09 | −0.94 | * | . | F | 1.79 | 2.02 |
| Val | 229 | . | . | . | B | . | . | C | 1.66 | −0.51 | . | . | F | 1.56 | 1.02 |
| Pro | 230 | . | . | B | . | . | T | . | 0.72 | 0.40 | . | . | F | 0.18 | 0.74 |
| Lys | 231 | . | . | . | . | T | T | . | 0.66 | 0.60 | . | * | F | 0.35 | 0.38 |
| Gly | 232 | . | . | . | . | T | T | . | 0.62 | 0.10 | * | * | F | 0.80 | 1.03 |
| Trp | 233 | . | . | B | . | . | T | . | 0.66 | −0.11 | * | * | F | 0.85 | 0.66 |
| Ile | 234 | . | . | B | . | . | . | . | 0.92 | −0.14 | * | * | F | 0.92 | 0.53 |
| Lys | 235 | . | . | B | . | . | . | . | 1.13 | 0.36 | . | * | F | 0.59 | 0.54 |
| Gly | 236 | . | . | . | . | . | . | C | 1.09 | 0.33 | * | * | F | 1.06 | 0.83 |
| Asn | 237 | . | . | . | . | . | T | C | 0.54 | −0.59 | * | * | F | 2.58 | 1.98 |
| Ala | 238 | . | . | . | . | . | T | C | 0.49 | −0.59 | * | * | F | 2.70 | 0.69 |
| Asn | 239 | . | . | . | . | . | T | C | 0.78 | −0.16 | * | * | F | 2.13 | 0.69 |
| Asp | 240 | . | . | . | . | T | T | . | 0.73 | 0.03 | . | * | F | 1.46 | 0.43 |
| Ile | 241 | . | . | B | . | . | . | . | 0.83 | −0.37 | . | * | . | 1.04 | 0.71 |
| Gly | 242 | . | . | B | . | . | . | . | 0.83 | −0.11 | . | * | . | 0.77 | 0.69 |
| Met | 243 | . | . | B | . | . | . | . | 1.18 | −0.51 | * | . | . | 0.80 | 0.69 |
| Asp | 244 | . | . | B | . | . | T | . | 0.59 | 0.24 | * | * | . | 0.25 | 1.54 |
| Tyr | 245 | . | . | B | . | . | T | . | −0.22 | 0.06 | . | * | . | 0.25 | 1.57 |
| Asp | 246 | . | . | B | . | . | T | . | −0.14 | 0.31 | . | * | . | 0.25 | 1.31 |
| Tyr | 247 | . | . | B | . | . | T | . | 0.20 | 0.39 | . | . | . | 0.10 | 0.65 |
| Ala | 248 | A | A | . | . | . | . | . | −0.01 | 0.39 | . | * | . | −0.30 | 0.71 |
| Leu | 249 | A | A | . | . | . | . | . | 0.03 | 0.31 | * | . | . | −0.30 | 0.35 |
| Leu | 250 | A | A | . | . | . | . | . | 0.32 | 0.31 | * | . | . | −0.30 | 0.45 |
| Glu | 251 | A | A | . | . | . | . | . | 0.11 | −0.44 | * | . | . | 0.30 | 0.89 |
| Leu | 252 | A | A | . | . | . | . | . | 0.32 | −0.51 | * | . | F | 0.90 | 1.67 |
| Lys | 253 | A | A | . | . | . | . | . | 0.96 | −0.70 | * | . | F | 0.90 | 2.76 |
| Lys | 254 | A | . | . | . | . | T | . | 1.88 | −1.39 | * | . | F | 1.30 | 3.18 |
| Pro | 255 | A | . | . | . | . | T | . | 2.73 | −1.39 | * | . | F | 1.30 | 7.56 |
| His | 256 | A | . | . | . | . | T | . | 2.03 | −2.07 | * | . | F | 1.30 | 7.56 |
| Lys | 257 | A | . | . | . | . | T | . | 2.24 | −1.29 | * | . | F | 1.30 | 3.27 |
| Arg | 258 | A | . | . | . | . | . | . | 2.24 | −0.67 | * | . | F | 1.10 | 2.09 |
| Lys | 259 | . | . | B | . | . | . | . | 1.31 | −1.10 | * | . | F | 1.10 | 3.08 |
| Phe | 260 | . | . | B | B | . | . | . | 1.18 | −0.91 | * | . | . | 0.75 | 1.08 |
| Met | 261 | . | . | B | B | . | . | . | 0.36 | −0.49 | * | * | . | 0.30 | 0.55 |
| Lys | 262 | . | . | B | B | . | . | . | 0.01 | 0.16 | * | * | . | −0.30 | 0.20 |
| Ile | 263 | . | . | B | B | . | . | . | −0.31 | 0.54 | * | * | . | −0.60 | 0.31 |
| Gly | 264 | . | . | B | B | . | . | . | −0.57 | 0.19 | * | * | . | −0.02 | 0.49 |
| Val | 265 | . | . | . | B | . | . | C | −0.46 | 0.00 | * | * | F | 0.61 | 0.38 |
| Ser | 266 | . | . | . | B | . | . | C | 0.19 | 0.50 | . | * | F | 0.59 | 0.55 |
| Pro | 267 | . | . | . | . | . | T | C | 0.14 | −0.19 | . | * | F | 2.32 | 1.10 |
| Pro | 268 | . | . | . | . | T | T | . | 0.22 | −0.21 | . | . | F | 2.80 | 2.57 |
| Ala | 269 | . | . | . | . | T | T | . | 0.36 | −0.17 | * | . | F | 2.52 | 1.58 |
| Lys | 270 | . | . | B | . | . | T | . | 0.87 | −0.13 | * | . | F | 1.84 | 1.58 |
| Gln | 271 | . | . | B | . | . | . | . | 0.82 | −0.13 | . | . | F | 1.36 | 1.01 |
| Leu | 272 | . | . | B | . | . | T | . | 1.14 | −0.13 | . | * | F | 1.13 | 0.99 |
| Pro | 273 | . | . | B | . | . | T | . | 0.47 | −0.63 | . | * | F | 1.15 | 0.97 |
| Gly | 274 | . | . | . | . | T | T | . | 1.02 | 0.06 | . | * | F | 0.65 | 0.39 |
| Gly | 275 | . | . | B | . | . | T | . | 0.28 | 0.16 | . | * | F | 0.25 | 0.65 |
| Arg | 276 | . | . | B | B | . | . | . | −0.02 | 0.26 | . | * | F | −0.15 | 0.36 |
| Ile | 277 | . | . | B | B | . | . | . | 0.44 | 0.21 | . | * | . | −0.14 | 0.49 |
| His | 278 | . | . | B | B | . | . | . | 0.41 | 0.21 | * | * | . | 0.02 | 0.49 |
| Phe | 279 | . | . | B | . | . | T | . | 0.76 | 0.54 | * | * | . | 0.28 | 0.39 |
| Ser | 280 | . | . | B | . | . | T | . | 1.10 | 0.54 | . | * | . | 0.44 | 0.94 |
| Gly | 281 | . | . | . | . | T | T | . | 0.99 | 0.26 | * | * | F | 1.60 | 1.11 |
| Tyr | 282 | . | . | . | . | T | T | . | 1.99 | −0.24 | . | * | F | 2.04 | 2.14 |
| Asp | 283 | . | . | . | . | T | . | . | 1.81 | −1.03 | . | . | F | 2.32 | 3.12 |
| Asn | 284 | . | . | . | . | T | . | . | 2.17 | −0.99 | . | . | F | 2.50 | 4.88 |
| Asp | 285 | . | . | . | . | T | . | . | 2.47 | −0.99 | . | . | F | 2.68 | 3.08 |
| Arg | 286 | . | . | . | . | . | T | C | 2.00 | −1.34 | * | . | F | 2.86 | 2.97 |
| Pro | 287 | . | . | . | . | T | T | . | 1.39 | −0.66 | * | . | F | 3.40 | 1.52 |
| Gly | 288 | . | . | . | . | T | T | . | 1.14 | −0.41 | * | . | F | 2.61 | 0.68 |
| Asn | 289 | . | . | B | . | . | T | . | 1.26 | 0.34 | * | * | F | 1.27 | 0.54 |
| Leu | 290 | . | . | B | B | . | . | . | 0.56 | 0.34 | * | * | . | 0.38 | 0.69 |

TABLE IX-continued

| Res | | I | II | III | IV | V | VI | VII | VIII | IX | X | XI | XII | XIII | XIV |
|---|---|---|---|---|---|---|---|---|---|---|---|---|---|---|---|
| Val | 291 | . | . | B | B | . | . | . | −0.22 | 0.70 | * | . | . | −0.26 | 0.60 |
| Tyr | 292 | . | . | B | B | . | . | . | −0.01 | 0.84 | * | * | . | −0.60 | 0.20 |
| Arg | 293 | . | A | B | B | . | . | . | −0.52 | 0.44 | * | * | . | −0.60 | 0.40 |
| Phe | 294 | . | A | B | B | . | . | . | −0.48 | 0.40 | * | . | . | −0.60 | 0.40 |
| Cys | 295 | . | A | B | B | . | . | . | 0.33 | −0.24 | * | . | . | 0.30 | 0.52 |
| Asp | 296 | . | A | B | B | . | . | . | 1.19 | −1.00 | * | . | . | 0.60 | 0.44 |
| Val | 297 | . | A | B | . | . | . | . | 1.12 | −1.00 | * | . | . | 0.60 | 0.88 |
| Lys | 298 | . | A | . | . | T | . | . | 0.77 | −1.30 | * | . | F | 1.30 | 2.37 |
| Asp | 299 | . | A | . | . | T | . | . | 1.47 | −1.11 | * | . | F | 1.30 | 2.23 |
| Glu | 300 | . | A | B | . | T | . | . | 1.32 | −1.11 | * | . | F | 1.30 | 5.01 |
| Thr | 301 | . | A | . | B | T | . | . | 0.51 | −1.07 | * | . | F | 1.30 | 2.06 |
| Tyr | 302 | . | A | . | B | T | . | . | 1.12 | −0.39 | * | . | . | 0.85 | 1.02 |
| Asp | 303 | . | A | B | B | . | . | . | 1.08 | 0.37 | . | . | . | −0.30 | 0.92 |
| Leu | 304 | . | A | B | B | . | . | . | 1.08 | 0.77 | * | . | . | −0.45 | 1.11 |
| Leu | 305 | . | A | B | B | . | . | . | 0.41 | 0.69 | * | . | . | −0.45 | 1.22 |
| Tyr | 306 | . | A | B | B | . | . | . | 0.72 | 0.50 | * | . | . | −0.60 | 0.39 |
| Gln | 307 | . | A | B | B | . | . | . | 0.67 | 0.50 | . | . | . | −0.60 | 0.80 |
| Gln | 308 | . | A | B | B | . | . | . | 0.67 | 0.20 | . | . | F | 0.00 | 1.29 |
| Cys | 309 | . | A | B | B | . | . | . | 1.27 | −0.09 | . | . | F | 0.60 | 1.43 |
| Asp | 310 | . | . | . | B | T | . | . | 1.73 | −0.41 | . | . | F | 1.25 | 1.28 |
| Ser | 311 | . | . | B | . | . | . | . | 1.39 | −0.39 | . | . | F | 1.15 | 0.73 |
| Gln | 312 | . | . | B | . | . | T | . | 1.09 | −0.29 | . | . | F | 1.75 | 1.37 |
| Pro | 313 | . | . | . | . | . | T | C | 0.74 | −0.47 | . | * | F | 2.20 | 1.10 |
| Gly | 314 | . | . | . | . | T | T | . | 1.11 | −0.04 | . | . | F | 2.50 | 0.81 |
| Ala | 315 | . | . | . | . | T | T | C | 0.77 | −0.04 | . | . | F | 2.25 | 0.63 |
| Ser | 316 | . | . | . | . | . | T | C | 0.21 | −0.01 | . | . | F | 1.80 | 0.40 |
| Gly | 317 | . | . | . | . | . | T | C | −0.03 | 0.20 | . | . | F | 0.95 | 0.30 |
| Ser | 318 | . | . | B | . | . | T | . | −0.68 | 0.53 | . | * | F | 0.20 | 0.47 |
| Gly | 319 | . | . | B | . | . | T | . | −0.22 | 0.67 | . | * | F | −0.05 | 0.26 |
| Val | 320 | . | . | B | B | . | . | . | −0.23 | 0.29 | * | * | . | −0.30 | 0.51 |
| Tyr | 321 | . | . | B | B | . | . | . | −0.22 | 0.47 | * | . | . | −0.60 | 0.38 |
| Val | 322 | . | . | B | B | . | . | . | 0.17 | 1.00 | * | * | . | −0.60 | 0.40 |
| Arg | 323 | . | . | B | B | . | . | . | 0.58 | 0.57 | * | * | . | −0.45 | 1.09 |
| Met | 324 | . | . | B | B | . | . | . | 0.92 | −0.07 | * | * | . | 0.45 | 1.36 |
| Trp | 325 | . | . | B | B | . | . | . | 1.74 | −0.43 | * | * | . | 0.45 | 3.17 |
| Lys | 326 | . | . | B | B | . | . | . | 1.99 | −0.57 | * | * | . | 0.75 | 2.20 |
| Arg | 327 | . | A | . | . | T | . | . | 2.89 | −0.17 | * | * | F | 1.00 | 3.85 |
| Gln | 328 | . | A | . | . | . | . | C | 2.49 | −0.79 | * | * | F | 1.10 | 7.33 |
| His | 329 | . | A | . | . | . | . | C | 3.09 | −0.79 | * | . | F | 1.10 | 3.85 |
| Gln | 330 | . | A | . | . | . | . | C | 3.49 | −0.79 | * | . | F | 1.10 | 3.41 |
| Lys | 331 | . | A | . | . | T | . | . | 3.49 | −0.79 | * | . | F | 1.30 | 3.85 |
| Trp | 332 | . | A | . | . | T | . | . | 2.49 | −1.19 | * | * | F | 1.30 | 5.66 |
| Glu | 333 | . | A | . | . | . | . | C | 1.60 | −1.00 | * | . | F | 1.10 | 2.29 |
| Arg | 334 | . | A | B | B | . | . | . | 1.29 | −0.71 | * | . | F | 0.75 | 0.80 |
| Lys | 335 | . | A | B | B | . | . | . | 0.69 | −0.29 | * | . | . | 0.30 | 0.76 |
| Ile | 336 | . | A | B | B | . | . | . | −0.24 | −0.59 | * | . | . | 0.60 | 0.43 |
| Ile | 337 | . | A | B | B | . | . | . | −0.26 | 0.10 | * | . | . | −0.30 | 0.15 |
| Gly | 338 | . | A | B | B | . | . | . | −0.60 | 0.49 | * | . | . | −0.60 | 0.10 |
| Met | 339 | . | . | B | B | . | . | . | −0.74 | 0.91 | * | . | . | −0.60 | 0.15 |
| Ile | 340 | . | . | B | B | . | . | . | −0.79 | 0.73 | . | . | . | −0.60 | 0.28 |
| Ser | 341 | . | . | . | . | . | T | C | −0.19 | 0.44 | . | . | . | 0.00 | 0.50 |
| Gly | 342 | . | . | . | . | . | T | C | −0.16 | 0.93 | . | . | . | 0.00 | 0.53 |
| His | 343 | . | . | . | . | . | T | C | 0.19 | 0.96 | . | . | . | 0.00 | 0.56 |
| Gln | 344 | . | . | B | . | . | T | . | 0.19 | 0.27 | . | * | . | 0.10 | 0.70 |
| Trp | 345 | . | . | B | . | . | . | . | 1.08 | 0.50 | . | * | . | −0.40 | 0.70 |
| Val | 346 | . | . | B | . | . | . | . | 1.03 | 0.07 | . | * | . | 0.20 | 0.86 |
| Asp | 347 | . | . | B | . | . | T | . | 1.08 | 0.00 | . | * | . | 0.70 | 0.49 |
| Met | 348 | . | . | . | . | T | T | . | 0.90 | −0.01 | . | * | F | 2.15 | 0.62 |
| Asp | 349 | . | . | . | . | T | T | . | 0.90 | −0.50 | . | * | F | 2.60 | 1.30 |
| Gly | 350 | . | . | . | . | . | T | C | 1.19 | −0.74 | . | * | F | 3.00 | 1.35 |
| Ser | 351 | . | . | . | . | . | T | C | 1.34 | −0.74 | . | * | F | 2.70 | 2.35 |
| Pro | 352 | . | . | . | . | . | T | C | 1.03 | −0.57 | * | * | F | 2.40 | 1.22 |
| Gln | 353 | . | . | . | . | T | T | . | 1.74 | −0.09 | * | . | F | 2.25 | 1.78 |
| Glu | 354 | . | . | B | . | . | T | . | 1.40 | −0.51 | * | . | F | 2.10 | 2.60 |
| Phe | 355 | . | . | B | . | . | . | . | 1.08 | −0.47 | * | . | F | 1.55 | 1.67 |
| Thr | 356 | . | . | . | . | T | T | . | 1.08 | −0.33 | * | . | F | 2.25 | 0.52 |
| Arg | 357 | . | . | . | . | T | T | . | 1.29 | −0.34 | * | * | F | 2.50 | 0.40 |
| Gly | 358 | . | . | . | . | T | T | . | 0.40 | −0.34 | * | * | F | 2.25 | 0.80 |
| Cys | 359 | . | . | . | . | T | T | . | 0.09 | −0.44 | * | * | F | 2.00 | 0.39 |
| Ser | 360 | . | . | . | B | . | . | C | 0.58 | −0.44 | * | . | F | 1.15 | 0.29 |
| Glu | 361 | . | . | . | B | T | . | . | 0.08 | −0.01 | * | * | F | 1.10 | 0.45 |
| Ile | 362 | . | . | B | B | . | . | . | −0.03 | 0.24 | * | * | F | −0.15 | 0.69 |
| Thr | 363 | . | . | B | B | . | . | . | 0.07 | 0.07 | . | . | F | −0.15 | 0.89 |
| Pro | 364 | . | . | B | B | . | . | . | −0.16 | 0.44 | . | . | F | −0.45 | 0.80 |
| Leu | 365 | . | . | B | B | . | . | . | −0.07 | 1.13 | * | . | . | −0.60 | 0.80 |
| Gln | 366 | . | . | B | B | . | . | . | −0.07 | 0.87 | * | . | . | −0.60 | 0.86 |
| Tyr | 367 | . | . | B | B | . | . | . | −0.07 | 0.39 | * | . | . | −0.30 | 0.93 |

TABLE IX-continued

| Res | | I | II | III | IV | V | VI | VII | VIII | IX | X | XI | XII | XIII | XIV |
|---|---|---|---|---|---|---|---|---|---|---|---|---|---|---|---|
| Ile | 368 | . | . | B | B | . | . | . | −0.06 | 0.64 | * | * | . | −0.60 | 0.79 |
| Pro | 369 | . | . | B | B | . | . | . | −0.73 | 0.34 | . | * | . | −0.30 | 0.61 |
| Asp | 370 | . | . | B | B | . | . | . | −0.27 | 0.63 | * | * | F | −0.45 | 0.27 |
| Ile | 371 | . | . | B | B | . | . | . | −1.12 | 0.30 | * | * | F | −0.15 | 0.39 |
| Ser | 372 | . | . | B | B | . | . | . | −1.27 | 0.26 | . | * | . | −0.30 | 0.19 |
| Ile | 373 | . | . | B | B | . | . | . | −0.77 | 0.26 | . | * | . | −0.30 | 0.14 |
| Gly | 374 | . | . | B | B | . | . | . | −0.94 | 0.69 | . | * | . | −0.60 | 0.26 |
| Val | 375 | . | . | B | B | . | . | . | −1.33 | 0.43 | . | * | . | −0.60 | 0.25 |

TABLE X

| Res | | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | B | . | . | . | −1.26 | 0.43 | . | . | . | −0.60 | 0.37 |
| Ala | 2 | . | . | B | B | . | . | . | −1.68 | 0.64 | . | . | . | −0.60 | 0.22 |
| Ser | 3 | . | . | B | B | . | . | . | −1.50 | 0.90 | . | . | . | −0.60 | 0.14 |
| Val | 4 | . | . | B | B | . | . | . | −1.41 | 0.90 | . | . | . | −0.60 | 0.22 |
| Val | 5 | . | . | B | B | . | . | . | −1.37 | 0.67 | . | . | . | −0.60 | 0.29 |
| Leu | 6 | . | . | B | . | . | T | . | −1.07 | 0.60 | . | . | F | −0.05 | 0.21 |
| Pro | 7 | . | . | . | . | T | T | . | −0.48 | 0.60 | . | . | F | 0.35 | 0.39 |
| Ser | 8 | . | . | . | . | T | T | . | −0.84 | 0.36 | . | . | F | 0.65 | 0.90 |
| Gly | 9 | . | . | . | . | T | T | . | −0.58 | 0.29 | . | . | F | 0.65 | 0.58 |
| Ser | 10 | . | . | . | . | . | T | C | −0.31 | 0.10 | . | . | F | 0.45 | 0.38 |
| Gln | 11 | A | . | . | . | . | T | . | −0.09 | 0.17 | . | . | F | 0.25 | 0.29 |
| Cys | 12 | A | . | . | . | . | T | . | −0.47 | 0.29 | . | . | . | 0.10 | 0.29 |
| Ala | 13 | A | . | . | . | . | T | . | −0.76 | 0.36 | . | . | . | 0.10 | 0.22 |
| Ala | 14 | A | A | . | . | . | . | . | −1.00 | 0.47 | . | . | . | −0.60 | 0.13 |
| Ala | 15 | A | A | . | . | . | . | . | −1.29 | 0.57 | . | . | . | −0.60 | 0.24 |
| Ala | 16 | A | A | . | . | . | . | . | −1.88 | 0.50 | . | . | . | −0.60 | 0.24 |
| Ala | 17 | A | A | . | . | . | . | . | −1.42 | 0.50 | . | . | . | −0.60 | 0.24 |
| Ala | 18 | A | A | . | . | . | . | . | −1.04 | 0.43 | . | . | . | −0.60 | 0.37 |
| Ala | 19 | A | A | . | . | . | . | . | −0.80 | 0.36 | . | . | . | −0.30 | 0.57 |
| Ala | 20 | A | A | . | . | . | . | . | −1.02 | 0.29 | * | * | . | −0.30 | 0.56 |
| Pro | 21 | A | . | . | . | . | T | . | −0.32 | 0.47 | * | * | F | −0.05 | 0.46 |
| Pro | 22 | A | . | . | . | . | T | . | −0.54 | −0.03 | . | * | F | 0.85 | 0.89 |
| Gly | 23 | A | . | . | . | . | T | . | 0.16 | 0.16 | . | * | F | 0.25 | 0.72 |
| Leu | 24 | A | . | . | . | . | T | . | −0.07 | −0.34 | . | * | . | 0.70 | 0.92 |
| Arg | 25 | . | A | B | . | . | . | . | −0.29 | −0.09 | . | * | . | 0.30 | 0.49 |
| Leu | 26 | . | A | B | . | . | . | . | −0.89 | 0.17 | . | * | . | −0.30 | 0.41 |
| Arg | 27 | . | A | B | . | . | . | . | −1.49 | 0.43 | . | * | . | −0.60 | 0.41 |
| Leu | 28 | . | A | B | . | . | . | . | −1.96 | 0.43 | . | * | . | −0.60 | 0.17 |
| Leu | 29 | . | A | B | . | . | . | . | −1.84 | 1.11 | . | * | . | −0.60 | 0.17 |
| Leu | 30 | . | A | B | . | . | . | . | −2.26 | 1.21 | . | * | . | −0.60 | 0.08 |
| Leu | 31 | A | A | . | . | . | . | . | −2.03 | 1.60 | * | * | . | −0.60 | 0.12 |
| Leu | 32 | A | A | . | . | . | . | . | −2.73 | 1.41 | * | * | . | −0.60 | 0.15 |
| Phe | 33 | A | A | . | . | . | . | . | −2.51 | 1.23 | . | . | . | −0.60 | 0.18 |
| Ser | 34 | A | A | . | . | . | . | . | −2.51 | 1.04 | . | . | . | −0.60 | 0.23 |
| Ala | 35 | A | A | . | . | . | . | . | −2.59 | 1.04 | . | . | . | −0.60 | 0.23 |
| Ala | 36 | A | A | . | . | . | . | . | −1.99 | 1.04 | . | . | . | −0.60 | 0.18 |
| Ala | 37 | A | A | . | . | . | . | . | −1.49 | 0.69 | . | . | . | −0.60 | 0.21 |
| Leu | 38 | . | A | B | . | . | . | . | −1.13 | 0.79 | . | . | . | −0.60 | 0.30 |
| Ile | 39 | . | A | B | . | . | . | . | −0.83 | 0.71 | . | . | . | −0.32 | 0.30 |
| Pro | 40 | . | A | B | . | . | . | . | −0.59 | 0.21 | . | . | F | 0.41 | 0.49 |
| Thr | 41 | . | . | . | . | T | . | . | 0.00 | 0.14 | . | . | F | 1.29 | 0.59 |
| Gly | 42 | . | . | . | . | T | T | . | 0.59 | −0.14 | . | . | F | 2.52 | 1.45 |
| Asp | 43 | . | . | . | . | T | T | . | 0.59 | −0.43 | . | . | F | 2.80 | 1.51 |
| Gly | 44 | . | . | . | . | . | T | C | 0.78 | −0.17 | . | . | F | 2.17 | 0.86 |
| Gln | 45 | . | . | B | . | . | T | . | 0.68 | 0.13 | * | . | F | 1.09 | 0.75 |
| Asn | 46 | . | . | B | B | . | . | . | 1.03 | 0.19 | * | . | F | 0.41 | 0.65 |
| Leu | 47 | . | . | B | B | . | . | . | 1.38 | 0.19 | * | . | F | 0.28 | 1.32 |
| Phe | 48 | . | . | B | B | . | . | . | 0.52 | −0.24 | * | . | F | 0.60 | 1.27 |
| Thr | 49 | . | . | B | B | . | . | . | 0.56 | 0.00 | * | . | F | −0.15 | 0.59 |
| Lys | 50 | . | . | B | B | . | . | . | −0.30 | 0.09 | * | . | F | 0.00 | 1.02 |
| Asp | 51 | . | . | B | B | . | . | . | −1.19 | 0.04 | * | . | F | −0.15 | 0.88 |
| Val | 52 | . | . | B | B | . | . | . | −0.38 | −0.06 | * | . | . | 0.30 | 0.43 |
| Thr | 53 | . | . | B | B | . | . | . | −0.02 | −0.54 | * | . | . | 0.60 | 0.37 |
| Val | 54 | . | . | B | B | . | . | . | 0.29 | −0.11 | * | . | . | 0.30 | 0.22 |
| Ile | 55 | A | . | . | B | . | . | . | −0.61 | −0.11 | * | . | . | 0.30 | 0.51 |
| Glu | 56 | A | . | . | B | . | . | . | −1.20 | −0.11 | . | . | F | 0.45 | 0.26 |
| Gly | 57 | A | . | . | . | . | . | . | −0.66 | −0.10 | * | . | F | 0.65 | 0.36 |
| Glu | 58 | A | . | . | B | . | . | . | −1.23 | −0.26 | . | . | F | 0.45 | 0.74 |
| Val | 59 | A | . | . | B | . | . | . | −0.68 | −0.26 | . | . | . | 0.30 | 0.30 |
| Ala | 60 | A | . | . | B | . | . | . | −0.46 | 0.13 | . | * | . | −0.30 | 0.40 |
| Thr | 61 | A | . | . | B | . | . | . | −0.46 | 0.27 | . | * | . | −0.30 | 0.12 |

TABLE X-continued

| Res | | I | II | III | IV | V | VI | VII | VIII | IX | X | XI | XII | XIII | XIV |
|---|---|---|---|---|---|---|---|---|---|---|---|---|---|---|---|
| Ile | 62 | A | . | . | B | . | . | . | −0.97 | 0.67 | . | * | . | −0.60 | 0.29 |
| Ser | 63 | A | . | . | B | . | . | . | −0.97 | 0.67 | * | . | . | −0.60 | 0.21 |
| Cys | 64 | . | . | B | B | . | . | . | −0.07 | 0.57 | * | * | . | −0.60 | 0.24 |
| Gln | 65 | . | . | B | B | . | . | . | 0.22 | 0.09 | . | * | . | 0.04 | 0.68 |
| Val | 66 | . | . | B | B | . | . | . | 0.53 | −0.21 | * | * | . | 0.98 | 0.68 |
| Asn | 67 | . | . | . | B | T | . | . | 1.42 | −0.60 | * | * | F | 2.32 | 2.12 |
| Lys | 68 | . | . | . | B | T | . | . | 1.42 | −1.17 | * | . | F | 2.66 | 2.05 |
| Ser | 69 | . | . | . | . | T | T | . | 1.23 | −1.19 | * | . | F | 3.40 | 3.69 |
| Asp | 70 | . | . | . | . | T | T | . | 0.34 | −1.19 | * | . | F | 3.06 | 1.70 |
| Asp | 71 | . | . | B | . | . | T | . | 1.20 | −0.90 | * | . | F | 2.17 | 0.60 |
| Ser | 72 | . | . | B | . | . | T | . | 0.39 | −0.50 | * | . | . | 1.38 | 0.77 |
| Val | 73 | . | . | B | B | . | . | . | −0.47 | −0.20 | * | . | . | 0.64 | 0.38 |
| Ile | 74 | . | . | B | B | . | . | . | −0.17 | 0.49 | * | . | . | −0.60 | 0.19 |
| Gln | 75 | . | . | B | B | . | . | . | −0.38 | 0.89 | * | . | . | −0.60 | 0.23 |
| Leu | 76 | . | . | B | B | . | . | . | −0.38 | 0.93 | * | . | . | −0.60 | 0.47 |
| Leu | 77 | . | . | B | B | . | . | . | 0.03 | 0.69 | * | . | . | −0.17 | 1.08 |
| Asn | 78 | . | . | . | . | . | T | C | 0.89 | 0.00 | * | . | F | 1.16 | 1.22 |
| Pro | 79 | . | . | . | . | . | T | C | 1.47 | 0.00 | * | . | F | 1.44 | 2.56 |
| Asn | 80 | . | . | . | . | T | T | . | 0.58 | −0.20 | * | . | F | 2.52 | 4.49 |
| Arg | 81 | . | . | . | . | T | T | . | 1.14 | −0.20 | * | . | F | 2.80 | 1.96 |
| Gln | 82 | . | . | B | B | . | . | . | 1.26 | 0.16 | . | * | F | 1.12 | 1.98 |
| Thr | 83 | . | . | B | B | . | . | . | 1.37 | 0.51 | . | * | F | 0.54 | 1.07 |
| Ile | 84 | . | . | B | B | . | . | . | 1.58 | 0.11 | * | * | . | 0.41 | 1.07 |
| Tyr | 85 | . | . | B | B | . | . | . | 0.88 | 0.11 | * | * | . | 0.13 | 1.03 |
| Phe | 86 | . | . | B | B | . | . | . | 0.88 | 0.50 | . | * | . | −0.60 | 0.62 |
| Arg | 87 | . | . | B | B | . | . | . | 0.67 | 0.01 | * | . | . | −0.15 | 1.73 |
| Asp | 88 | . | . | B | B | . | . | . | 0.17 | −0.24 | * | . | F | 0.94 | 1.70 |
| Phe | 89 | . | . | B | . | . | . | . | 1.10 | −0.31 | * | . | F | 1.48 | 1.62 |
| Arg | 90 | . | . | . | . | . | . | C | 1.34 | −1.10 | * | . | F | 2.32 | 1.66 |
| Pro | 91 | . | . | . | . | . | . | C | 1.74 | −1.10 | * | * | F | 2.66 | 1.66 |
| Leu | 92 | . | . | . | . | T | T | . | 1.74 | −0.71 | * | * | F | 3.40 | 2.56 |
| Lys | 93 | . | . | . | . | T | T | . | 1.04 | −1.50 | . | * | F | 3.06 | 2.56 |
| Asp | 94 | . | . | . | . | T | T | . | 1.74 | −0.71 | * | * | F | 2.72 | 1.44 |
| Ser | 95 | A | . | . | . | . | T | . | 0.82 | −0.74 | * | * | F | 1.98 | 3.01 |
| Arg | 96 | . | A | B | . | . | . | . | 0.22 | −0.74 | . | . | F | 1.24 | 1.24 |
| Phe | 97 | . | A | B | . | . | . | . | 1.03 | −0.06 | . | . | . | 0.30 | 0.61 |
| Gln | 98 | . | A | B | . | . | . | . | 0.29 | 0.34 | . | . | . | −0.30 | 0.74 |
| Leu | 99 | . | A | B | . | . | . | . | −0.01 | 0.74 | . | * | . | −0.60 | 0.33 |
| Leu | 100 | . | A | B | . | . | . | . | −0.01 | 1.13 | . | * | . | −0.60 | 0.50 |
| Asn | 101 | . | A | . | . | . | . | C | −0.42 | 0.73 | . | * | . | −0.40 | 0.39 |
| Phe | 102 | . | A | . | . | . | . | C | 0.28 | 0.71 | * | . | F | −0.25 | 0.63 |
| Ser | 103 | . | . | . | . | . | T | C | −0.53 | 0.03 | * | . | F | 0.60 | 1.33 |
| Ser | 104 | A | . | . | . | . | T | . | 0.32 | 0.03 | * | * | F | 0.25 | 0.68 |
| Ser | 105 | A | . | . | . | . | T | . | 0.28 | −0.37 | . | * | F | 1.00 | 1.58 |
| Glu | 106 | A | . | . | . | . | T | . | −0.02 | −0.51 | . | * | F | 1.15 | 0.87 |
| Leu | 107 | A | . | . | B | . | . | . | −0.13 | −0.51 | . | * | F | 0.75 | 0.87 |
| Lys | 108 | A | . | . | B | . | . | . | −0.14 | −0.21 | . | * | F | 0.45 | 0.54 |
| Val | 109 | A | . | . | B | . | . | . | 0.16 | −0.11 | * | * | . | 0.30 | 0.45 |
| Ser | 110 | . | . | B | B | . | . | . | −0.40 | 0.29 | * | * | . | −0.30 | 0.87 |
| Leu | 111 | . | . | B | B | . | . | . | −0.70 | 0.24 | . | * | . | −0.30 | 0.32 |
| Thr | 112 | . | . | B | B | . | . | . | −0.78 | 0.63 | . | * | . | −0.60 | 0.58 |
| Asn | 113 | . | . | B | B | . | . | . | −1.12 | 0.67 | . | . | . | −0.60 | 0.31 |
| Val | 114 | . | . | B | B | . | . | . | −0.27 | 0.67 | . | . | . | −0.60 | 0.50 |
| Ser | 115 | . | . | B | B | . | . | . | 0.03 | −0.01 | . | . | . | 0.64 | 0.58 |
| Ile | 116 | . | . | B | B | . | . | . | 0.50 | −0.50 | . | * | F | 1.13 | 0.62 |
| Ser | 117 | . | . | B | . | . | T | . | 0.92 | −0.47 | * | * | F | 1.87 | 0.83 |
| Asp | 118 | . | . | . | . | T | T | . | 0.68 | −1.11 | * | * | F | 3.06 | 1.21 |
| Glu | 119 | . | . | . | . | T | T | . | 0.83 | −0.74 | * | * | F | 3.40 | 2.70 |
| Gly | 120 | . | . | . | . | T | T | . | 0.47 | −0.64 | * | * | F | 3.06 | 1.74 |
| Arg | 121 | . | . | . | B | T | . | . | 1.36 | −0.46 | * | * | F | 1.87 | 0.56 |
| Tyr | 122 | . | . | . | B | T | . | . | 0.84 | −0.06 | * | * | . | 1.38 | 0.56 |
| Phe | 123 | . | . | B | B | . | . | . | 0.60 | 0.63 | * | * | . | −0.26 | 0.47 |
| Cys | 124 | . | . | B | B | . | . | . | 0.29 | 0.96 | * | * | . | −0.60 | 0.37 |
| Gln | 125 | . | . | B | B | . | . | . | 0.63 | 1.44 | * | * | . | −0.60 | 0.34 |
| Leu | 126 | . | . | B | B | . | . | . | 0.31 | 0.69 | * | * | . | −0.60 | 0.66 |
| Tyr | 127 | . | . | . | . | T | . | . | 0.34 | 0.33 | * | . | . | 0.79 | 1.91 |
| Thr | 128 | . | . | . | . | T | . | . | 1.04 | 0.19 | * | . | F | 1.28 | 1.71 |
| Asp | 129 | . | . | . | . | . | T | C | 1.71 | 0.19 | * | . | F | 1.62 | 3.58 |
| Pro | 130 | . | . | . | . | . | T | C | 1.41 | −0.50 | * | . | F | 2.86 | 3.96 |
| Pro | 131 | . | . | . | . | T | T | . | 1.98 | −0.87 | . | . | F | 3.40 | 3.68 |
| Gln | 132 | . | . | . | . | T | T | . | 1.91 | −0.60 | . | . | F | 3.06 | 3.45 |
| Glu | 133 | . | . | B | B | . | . | . | 1.91 | −0.11 | * | . | F | 1.62 | 3.22 |
| Ser | 134 | . | . | B | B | . | . | . | 1.02 | −0.06 | * | . | F | 1.28 | 3.01 |
| Tyr | 135 | . | . | B | B | . | . | . | 0.92 | 0.20 | . | . | F | 0.34 | 1.22 |
| Thr | 136 | . | . | B | B | . | . | . | 0.28 | 0.29 | . | . | F | 0.00 | 1.01 |
| Thr | 137 | . | . | B | B | . | . | . | −0.53 | 0.93 | * | . | F | −0.45 | 0.56 |
| Ile | 138 | . | . | B | B | . | . | . | −1.39 | 1.23 | . | . | . | −0.60 | 0.30 |

TABLE X-continued

| Res | | I | II | III | IV | V | VI | VII | VIII | IX | X | XI | XII | XIII | XIV |
|---|---|---|---|---|---|---|---|---|---|---|---|---|---|---|---|
| Thr | 139 | . | . | B | B | . | . | . | −1.30 | 1.11 | . | . | . | −0.60 | 0.15 |
| Val | 140 | . | . | B | B | . | . | . | −1.27 | 1.06 | . | * | . | −0.60 | 0.16 |
| Leu | 141 | . | . | B | B | . | . | . | −0.84 | 1.00 | . | * | . | −0.60 | 0.36 |
| Val | 142 | . | . | B | B | . | . | . | −0.53 | 0.31 | . | * | . | −0.30 | 0.49 |
| Pro | 143 | . | . | B | . | . | T | . | −0.46 | 0.23 | . | * | F | 0.40 | 1.06 |
| Pro | 144 | . | . | . | . | T | T | . | −0.74 | 0.27 | . | . | F | 0.80 | 1.06 |
| Arg | 145 | . | . | . | . | T | T | . | −0.78 | 0.20 | . | . | F | 0.80 | 1.41 |
| Asn | 146 | A | . | . | . | . | T | . | 0.03 | 0.24 | . | . | . | 0.10 | 0.64 |
| Leu | 147 | . | A | B | . | . | . | . | 0.00 | −0.19 | * | * | . | 0.30 | 0.69 |
| Met | 148 | . | A | B | . | . | . | . | 0.21 | 0.07 | * | . | . | −0.30 | 0.25 |
| Ile | 149 | . | A | B | . | . | . | . | 0.47 | 0.47 | * | * | . | −0.60 | 0.27 |
| Asp | 150 | . | A | B | . | . | . | . | 0.36 | 0.07 | * | * | . | −0.30 | 0.64 |
| Ile | 151 | A | A | . | . | . | . | . | 0.04 | −0.61 | * | * | . | 0.75 | 1.09 |
| Gln | 152 | A | . | . | . | . | T | . | 0.27 | −0.74 | . | * | F | 1.30 | 2.24 |
| Lys | 153 | A | . | . | . | . | T | . | 0.01 | −0.93 | . | * | F | 1.30 | 1.36 |
| Asp | 154 | A | . | . | . | . | T | . | 0.90 | −0.29 | . | * | F | 1.00 | 1.43 |
| Thr | 155 | A | . | . | . | . | T | . | 0.56 | −0.97 | . | * | F | 1.30 | 1.43 |
| Ala | 156 | A | A | . | . | . | . | . | 1.44 | −0.94 | . | . | F | 0.75 | 0.71 |
| Val | 157 | A | A | . | . | . | . | . | 1.44 | −0.94 | . | . | F | 0.75 | 0.74 |
| Glu | 158 | A | A | . | . | . | . | . | 0.51 | −0.94 | . | . | F | 0.75 | 0.88 |
| Gly | 159 | A | A | . | . | . | . | . | 0.51 | −0.74 | . | * | F | 0.75 | 0.61 |
| Glu | 160 | A | A | . | . | . | . | . | −0.03 | −1.24 | . | * | F | 0.90 | 1.43 |
| Glu | 161 | A | A | . | . | . | . | . | 0.56 | −1.24 | . | * | F | 0.75 | 0.61 |
| Ile | 162 | A | A | . | . | . | . | . | 0.74 | −0.84 | . | * | F | 0.75 | 1.00 |
| Glu | 163 | A | A | . | . | . | . | . | 0.43 | −0.70 | . | * | . | 0.60 | 0.31 |
| Val | 164 | A | A | . | . | . | . | . | 0.19 | −0.21 | . | * | . | 0.30 | 0.26 |
| Asn | 165 | A | A | . | . | . | . | . | −0.41 | 0.29 | . | * | . | −0.30 | 0.37 |
| Cys | 166 | A | A | . | . | . | . | . | −1.00 | 0.21 | . | * | . | −0.30 | 0.21 |
| Thr | 167 | A | A | . | . | . | . | . | −0.41 | 0.71 | . | * | . | −0.60 | 0.29 |
| Ala | 168 | A | A | . | . | . | . | . | −0.37 | 0.46 | . | * | . | −0.60 | 0.24 |
| Met | 169 | A | . | . | . | . | . | . | 0.28 | 0.06 | . | . | . | −0.10 | 0.90 |
| Ala | 170 | A | . | . | . | . | . | . | −0.31 | −0.09 | * | . | . | 0.50 | 0.96 |
| Ser | 171 | A | . | . | . | . | . | . | 0.04 | −0.07 | . | . | F | 0.65 | 0.96 |
| Lys | 172 | A | . | . | . | . | . | . | 0.04 | −0.09 | * | . | F | 0.80 | 1.40 |
| Pro | 173 | A | . | . | B | . | . | . | −0.26 | −0.21 | * | * | F | 0.60 | 2.00 |
| Ala | 174 | A | . | . | B | . | . | . | 0.46 | −0.03 | * | * | F | 0.60 | 1.05 |
| Thr | 175 | . | . | B | B | . | . | . | 0.76 | −0.41 | * | * | F | 0.60 | 1.02 |
| Thr | 176 | . | . | B | B | . | . | . | 0.36 | 0.50 | * | * | F | −0.45 | 0.70 |
| Ile | 177 | . | . | B | B | . | . | . | 0.36 | 0.86 | * | * | . | −0.60 | 0.60 |
| Arg | 178 | . | . | B | B | . | . | . | 0.22 | 0.36 | * | . | . | −0.30 | 0.83 |
| Trp | 179 | . | . | B | B | . | . | . | 0.81 | 0.30 | * | . | . | −0.30 | 0.57 |
| Phe | 180 | . | . | . | . | . | T | C | 0.81 | 0.21 | * | * | . | 0.45 | 1.30 |
| Lys | 181 | . | . | . | . | . | T | C | 1.12 | 0.01 | * | * | F | 0.45 | 0.96 |
| Gly | 182 | . | . | . | . | . | T | C | 1.20 | 0.01 | * | * | F | 0.60 | 1.58 |
| Asn | 183 | . | . | . | . | . | T | C | 1.13 | −0.21 | * | * | F | 1.20 | 1.50 |
| Thr | 184 | . | A | . | . | . | . | C | 1.08 | −1.00 | . | * | F | 1.40 | 1.50 |
| Glu | 185 | A | A | . | . | . | . | . | 1.82 | −0.57 | . | * | F | 1.50 | 1.50 |
| Leu | 186 | A | A | . | . | . | . | . | 1.48 | −1.00 | . | * | F | 1.80 | 1.87 |
| Lys | 187 | A | A | . | . | . | . | . | 1.82 | −1.01 | . | * | F | 2.10 | 1.74 |
| Gly | 188 | . | . | . | . | . | T | C | 0.97 | −1.50 | . | * | F | 3.00 | 1.74 |
| Lys | 189 | . | . | . | . | . | T | C | 1.28 | −0.86 | . | * | F | 2.70 | 1.56 |
| Ser | 190 | A | . | . | . | . | T | . | 1.28 | −1.54 | . | * | F | 2.20 | 1.35 |
| Glu | 191 | A | . | . | . | . | T | . | 1.80 | −1.54 | . | * | F | 1.90 | 2.37 |
| Val | 192 | A | . | . | . | . | . | . | 1.46 | −1.06 | * | * | F | 1.40 | 1.25 |
| Glu | 193 | A | . | . | . | . | . | . | 1.80 | −0.67 | * | * | F | 1.10 | 1.25 |
| Glu | 194 | A | . | . | . | . | . | . | 1.16 | −1.06 | * | . | F | 1.10 | 1.20 |
| Trp | 195 | A | . | . | . | . | T | . | 1.21 | −0.44 | * | . | F | 1.00 | 1.60 |
| Ser | 196 | A | . | . | . | . | T | . | 0.90 | −0.33 | . | . | . | 0.85 | 1.45 |
| Asp | 197 | A | . | . | . | . | T | . | 0.90 | 0.16 | * | . | . | 0.25 | 1.21 |
| Met | 198 | A | . | . | . | . | T | . | 0.59 | 0.80 | . | . | . | −0.20 | 0.85 |
| Tyr | 199 | A | . | . | B | . | . | . | 0.29 | 0.37 | . | . | . | −0.30 | 0.92 |
| Thr | 200 | A | . | . | B | . | . | . | 0.58 | 0.37 | * | . | . | −0.30 | 0.74 |
| Val | 201 | A | . | . | B | . | . | . | 0.07 | 0.77 | * | . | . | −0.45 | 1.29 |
| Thr | 202 | A | . | . | B | . | . | . | −0.53 | 0.84 | . | . | F | −0.45 | 0.68 |
| Ser | 203 | A | A | . | B | . | . | . | −0.74 | 0.70 | . | * | F | −0.45 | 0.47 |
| Gln | 204 | A | A | . | B | . | . | . | −0.46 | 0.90 | * | * | F | −0.45 | 0.52 |
| Leu | 205 | A | A | . | B | . | . | . | −1.00 | 0.26 | . | * | . | −0.30 | 0.72 |
| Met | 206 | A | A | . | B | . | . | . | −0.18 | 0.41 | * | * | . | −0.60 | 0.40 |
| Leu | 207 | A | A | . | B | . | . | . | 0.18 | 0.53 | * | * | . | −0.60 | 0.31 |
| Lys | 208 | A | A | . | B | . | . | . | 0.48 | 0.13 | * | * | . | −0.30 | 0.76 |
| Val | 209 | A | A | . | . | . | . | . | 0.48 | −0.56 | * | * | . | 1.09 | 1.32 |
| His | 210 | A | A | . | . | . | . | . | 1.29 | −1.17 | . | * | F | 1.58 | 2.68 |
| Lys | 211 | A | A | . | . | . | . | . | 1.54 | −1.86 | * | . | F | 1.92 | 2.24 |
| Glu | 212 | A | . | . | . | . | T | . | 1.50 | −1.43 | . | * | F | 2.66 | 2.98 |
| Asp | 213 | . | . | . | . | T | T | . | 1.24 | −1.43 | . | . | F | 3.40 | 1.63 |
| Asp | 214 | . | . | . | . | T | T | . | 1.24 | −1.50 | * | . | F | 3.06 | 1.26 |
| Gly | 215 | . | . | . | . | T | T | . | 0.39 | −0.86 | . | . | F | 2.57 | 0.54 |

TABLE X-continued

| Res | | I | II | III | IV | V | VI | VII | VIII | IX | X | XI | XII | XIII | XIV |
|---|---|---|---|---|---|---|---|---|---|---|---|---|---|---|---|
| Val | 216 | . | . | B | B | . | . | . | −0.32 | −0.17 | * | . | . | 0.98 | 0.23 |
| Pro | 217 | . | . | B | B | . | . | . | −0.32 | 0.40 | * | . | . | −0.26 | 0.07 |
| Val | 218 | . | . | B | B | . | . | . | −1.18 | 0.80 | * | . | . | −0.60 | 0.13 |
| Ile | 219 | . | . | B | B | . | . | . | −1.18 | 1.01 | * | . | . | −0.60 | 0.13 |
| Cys | 220 | . | . | B | B | . | . | . | −0.87 | 0.37 | * | . | . | −0.30 | 0.14 |
| Gln | 221 | . | . | B | B | . | . | . | −0.22 | 0.44 | * | * | . | −0.60 | 0.26 |
| Val | 222 | . | . | B | B | . | . | . | −0.60 | 0.23 | * | . | . | −0.30 | 0.58 |
| Glu | 223 | . | . | B | B | . | . | . | −0.60 | 0.04 | * | . | . | −0.15 | 1.08 |
| His | 224 | . | . | B | . | . | . | . | −0.02 | 0.11 | * | . | . | −0.10 | 0.46 |
| Pro | 225 | . | . | B | . | . | . | . | 0.30 | 0.20 | . | . | . | −0.10 | 0.90 |
| Ala | 226 | . | . | . | . | T | . | . | 0.30 | −0.01 | . | * | . | 0.90 | 0.52 |
| Val | 227 | . | . | . | . | T | T | C | 0.34 | 0.39 | . | * | . | 0.50 | 0.61 |
| Thr | 228 | . | . | . | . | . | T | C | 0.34 | 0.57 | . | * | F | 0.15 | 0.33 |
| Gly | 229 | . | . | . | . | . | T | C | 0.07 | 0.54 | . | * | F | 0.15 | 0.56 |
| Asn | 230 | . | . | . | . | . | T | C | 0.28 | 0.53 | . | * | F | 0.30 | 1.09 |
| Leu | 231 | . | . | B | B | . | . | . | 0.98 | 0.29 | . | . | F | 0.00 | 1.30 |
| Gln | 232 | . | . | B | B | . | . | . | 1.59 | −0.20 | . | * | F | 0.60 | 2.58 |
| Thr | 233 | . | . | B | B | . | . | . | 1.09 | 0.13 | * | . | F | 0.00 | 2.51 |
| Gln | 234 | . | . | B | B | . | . | . | 1.43 | 0.41 | . | . | F | −0.30 | 2.51 |
| Arg | 235 | . | . | B | B | . | . | . | 0.58 | −0.27 | . | * | F | 0.60 | 2.51 |
| Tyr | 236 | . | . | B | B | . | . | . | 1.39 | −0.03 | . | . | . | 0.45 | 1.29 |
| Leu | 237 | . | . | B | B | . | . | . | 1.14 | −0.11 | * | * | . | 0.45 | 1.29 |
| Glu | 238 | . | . | B | B | . | . | . | 1.50 | 0.24 | * | * | . | −0.15 | 1.03 |
| Val | 239 | . | . | B | B | . | . | . | 1.29 | 0.24 | * | * | . | −0.15 | 1.32 |
| Gln | 240 | . | . | . | B | T | . | . | 1.18 | −0.09 | * | * | . | 0.85 | 2.47 |
| Tyr | 241 | . | . | . | B | T | . | . | 0.57 | −0.37 | . | * | . | 0.85 | 2.47 |
| Lys | 242 | . | . | . | B | . | . | C | 1.34 | 0.27 | . | * | F | 0.20 | 2.47 |
| Pro | 243 | A | . | . | B | . | . | . | 0.46 | 0.13 | . | * | F | 0.00 | 1.94 |
| Gln | 244 | . | . | B | B | . | . | . | 1.31 | 0.41 | . | * | . | −0.60 | 0.87 |
| Val | 245 | . | . | B | B | . | . | . | 0.71 | 0.06 | . | * | . | −0.30 | 0.75 |
| His | 246 | . | . | B | B | . | . | . | 0.64 | 0.67 | . | * | . | −0.60 | 0.48 |
| Ile | 247 | . | . | B | B | . | . | . | 0.36 | 0.73 | . | * | . | −0.60 | 0.40 |
| Gln | 248 | . | . | B | B | . | . | . | 0.36 | 1.09 | . | * | . | −0.60 | 0.85 |
| Met | 249 | . | . | B | B | . | . | . | −0.46 | 0.87 | . | * | . | −0.60 | 0.96 |
| Thr | 250 | . | . | B | B | . | . | . | 0.40 | 1.06 | . | * | . | −0.45 | 1.13 |
| Tyr | 251 | . | . | B | . | . | T | . | 0.09 | 0.77 | . | * | . | −0.05 | 1.13 |
| Pro | 252 | . | . | B | . | . | T | . | 0.17 | 0.80 | . | * | . | −0.05 | 1.13 |
| Leu | 253 | . | . | . | . | T | T | . | −0.14 | 0.87 | * | * | . | 0.20 | 0.65 |
| Gln | 254 | . | . | B | . | . | T | . | 0.57 | 0.87 | * | * | . | 0.06 | 0.60 |
| Gly | 255 | . | . | B | . | . | . | . | 0.88 | 0.11 | * | . | F | 0.57 | 0.76 |
| Leu | 256 | . | . | B | . | . | . | . | 0.78 | −0.31 | * | . | F | 1.58 | 1.59 |
| Thr | 257 | . | . | B | . | . | T | . | 0.99 | −0.57 | * | . | F | 2.19 | 0.91 |
| Arg | 258 | . | . | B | . | . | T | . | 1.21 | −0.97 | * | . | F | 2.60 | 1.53 |
| Glu | 259 | A | . | . | . | . | T | . | 0.40 | −0.90 | * | . | F | 2.34 | 1.87 |
| Gly | 260 | A | . | . | . | . | T | . | 0.74 | −0.90 | * | . | F | 2.08 | 1.07 |
| Asp | 261 | A | A | . | . | . | . | . | 0.74 | −1.39 | * | . | F | 1.27 | 0.95 |
| Ala | 262 | A | A | . | . | . | . | . | 0.74 | −0.70 | * | . | F | 1.01 | 0.45 |
| Leu | 263 | A | A | . | . | . | . | . | −0.03 | −0.21 | * | . | . | 0.30 | 0.66 |
| Glu | 264 | A | A | . | . | . | . | . | −0.03 | −0.07 | . | * | . | 0.30 | 0.21 |
| Leu | 265 | A | A | . | . | . | . | . | −0.28 | −0.07 | * | . | . | 0.30 | 0.36 |
| Thr | 266 | A | A | . | . | . | . | . | −1.17 | −0.07 | * | . | . | 0.30 | 0.44 |
| Cys | 267 | A | A | . | . | . | . | . | −0.92 | −0.07 | * | * | . | 0.30 | 0.18 |
| Glu | 268 | A | A | . | . | . | . | . | −0.07 | 0.36 | * | * | . | −0.10 | 0.22 |
| Ala | 269 | A | A | . | . | . | . | . | −0.28 | −0.33 | * | * | . | 0.70 | 0.30 |
| Ile | 270 | A | A | . | . | . | . | . | 0.53 | −0.39 | . | * | . | 0.90 | 0.86 |
| Gly | 271 | . | A | . | . | T | . | . | 0.63 | −0.56 | . | . | F | 1.95 | 0.86 |
| Lys | 272 | . | . | . | . | . | . | C | 0.44 | −0.13 | * | . | F | 2.00 | 1.32 |
| Pro | 273 | . | . | . | . | . | . | C | −0.16 | 0.01 | * | . | F | 1.20 | 1.39 |
| Gln | 274 | . | . | . | B | . | . | C | −0.42 | −0.06 | . | . | F | 1.40 | 1.39 |
| Pro | 275 | . | . | B | B | . | . | . | 0.16 | 0.16 | . | . | F | 0.25 | 0.52 |
| Val | 276 | . | . | B | B | . | . | . | 0.21 | 0.64 | . | . | . | −0.40 | 0.48 |
| Met | 277 | . | . | B | B | . | . | . | −0.69 | 1.13 | * | . | . | −0.60 | 0.29 |
| Val | 278 | . | . | B | B | . | . | . | −0.37 | 1.37 | * | * | . | −0.60 | 0.14 |
| Thr | 279 | . | . | B | B | . | . | . | −1.22 | 0.94 | * | * | . | −0.60 | 0.37 |
| Trp | 280 | . | . | B | B | . | . | . | −1.01 | 0.94 | * | * | . | −0.60 | 0.28 |
| Val | 281 | . | . | B | B | . | . | . | −0.16 | 0.33 | * | * | . | −0.30 | 0.63 |
| Arg | 282 | . | . | B | B | . | . | . | 0.44 | −0.31 | * | * | . | 0.30 | 0.73 |
| Val | 283 | A | . | . | B | . | . | . | 0.70 | −0.80 | * | * | . | 0.75 | 1.19 |
| Asp | 284 | A | . | . | B | . | . | . | 0.80 | −1.10 | * | * | F | 0.90 | 1.59 |
| Asp | 285 | . | A | . | . | T | . | . | 1.09 | −1.31 | * | * | F | 1.30 | 1.26 |
| Glu | 286 | A | A | . | . | . | . | . | 1.91 | −0.91 | * | * | F | 0.90 | 2.93 |
| Met | 287 | A | A | . | . | . | . | . | 1.21 | −1.06 | * | * | F | 0.90 | 2.39 |
| Pro | 288 | A | A | . | . | . | . | . | 1.21 | −0.56 | . | . | F | 0.90 | 1.45 |
| Gln | 289 | A | A | . | B | . | . | . | 0.40 | 0.09 | . | . | . | −0.30 | 0.62 |
| His | 290 | A | A | . | B | . | . | . | 0.10 | 0.77 | . | . | . | −0.60 | 0.52 |
| Ala | 291 | . | A | B | B | . | . | . | −0.24 | 0.54 | . | . | . | −0.60 | 0.45 |
| Val | 292 | . | A | B | B | . | . | . | 0.14 | 0.54 | . | . | . | −0.60 | 0.26 |

TABLE X-continued

| Res | | I | II | III | IV | V | VI | VII | VIII | IX | X | XI | XII | XIII | XIV |
|---|---|---|---|---|---|---|---|---|---|---|---|---|---|---|---|
| Leu | 293 | . | A | B | B | . | . | . | 0.36 | 0.57 | . | . | . | −0.60 | 0.29 |
| Ser | 294 | . | A | . | B | . | . | C | −0.46 | 0.47 | * | . | F | −0.25 | 0.46 |
| Gly | 295 | . | . | . | . | . | T | C | −1.12 | 0.66 | * | . | F | 0.15 | 0.51 |
| Pro | 296 | . | . | . | . | . | T | C | −1.42 | 0.80 | * | . | F | 0.15 | 0.54 |
| Asn | 297 | . | . | . | . | . | T | C | −0.57 | 0.80 | * | . | F | 0.15 | 0.28 |
| Leu | 298 | . | . | B | . | . | T | . | 0.24 | 0.81 | * | . | . | −0.20 | 0.46 |
| Phe | 299 | . | . | B | . | . | . | . | −0.27 | 0.79 | * | . | . | −0.40 | 0.48 |
| Ile | 300 | . | . | B | . | . | . | . | 0.08 | 1.04 | * | . | . | −0.40 | 0.24 |
| Asn | 301 | . | . | B | . | . | . | . | 0.33 | 1.04 | * | . | . | −0.40 | 0.48 |
| Asn | 302 | . | . | B | . | . | . | . | 0.02 | 0.36 | * | . | . | 0.39 | 1.10 |
| Leu | 303 | . | . | . | . | . | . | C | 0.83 | 0.06 | * | . | F | 1.08 | 2.27 |
| Asn | 304 | . | . | . | . | T | . | . | 1.53 | −0.63 | * | . | F | 2.52 | 2.36 |
| Lys | 305 | . | . | . | . | T | . | . | 2.08 | −0.63 | * | . | F | 2.86 | 2.36 |
| Thr | 306 | . | . | . | . | T | T | . | 1.77 | −0.60 | * | . | F | 3.40 | 2.83 |
| Asp | 307 | . | . | . | . | T | T | . | 1.52 | −0.80 | * | * | F | 3.06 | 2.54 |
| Asn | 308 | . | . | . | . | T | T | . | 2.44 | −0.44 | * | * | F | 2.42 | 1.99 |
| Gly | 309 | . | . | . | . | T | T | . | 1.78 | −0.44 | * | * | F | 2.08 | 2.70 |
| Thr | 310 | . | . | B | . | . | . | . | 1.73 | −0.36 | . | * | F | 0.99 | 0.87 |
| Tyr | 311 | . | . | B | . | . | . | . | 1.46 | −0.36 | . | * | . | 0.50 | 0.93 |
| Arg | 312 | . | . | B | . | . | . | . | 1.16 | −0.26 | . | * | . | 0.50 | 0.95 |
| Cys | 313 | . | . | B | . | . | . | . | 1.16 | −0.30 | . | * | . | 0.50 | 0.88 |
| Glu | 314 | . | . | B | . | . | . | . | 0.61 | −0.39 | . | * | . | 0.50 | 0.91 |
| Ala | 315 | A | . | . | . | . | T | . | 0.07 | −0.46 | . | * | . | 0.70 | 0.32 |
| Ser | 316 | A | . | . | . | . | T | . | −0.03 | 0.19 | . | * | . | 0.10 | 0.45 |
| Asn | 317 | A | . | . | . | . | T | . | −0.10 | 0.04 | . | * | . | 0.10 | 0.26 |
| Ile | 318 | A | . | . | . | . | T | . | −0.02 | 0.04 | * | * | . | 0.10 | 0.51 |
| Val | 319 | A | . | . | . | . | . | . | −0.06 | 0.04 | * | . | . | 0.10 | 0.38 |
| Gly | 320 | A | . | . | . | . | . | . | 0.23 | 0.16 | * | * | . | 0.30 | 0.32 |
| Lys | 321 | A | . | . | . | . | . | . | 0.53 | 0.14 | * | * | . | 0.50 | 0.62 |
| Ala | 322 | A | . | . | . | . | . | . | 0.29 | −0.54 | * | * | F | 1.90 | 1.40 |
| His | 323 | . | . | B | . | . | T | . | 0.58 | −0.43 | . | * | F | 2.00 | 2.21 |
| Ser | 324 | . | . | B | . | . | T | . | 0.62 | −0.24 | . | * | . | 1.65 | 1.09 |
| Asp | 325 | . | . | B | . | . | T | . | 0.72 | 0.44 | . | * | . | 0.40 | 0.89 |
| Tyr | 326 | . | . | B | . | . | T | . | −0.18 | 0.70 | . | * | . | 0.35 | 1.03 |
| Met | 327 | . | . | B | B | . | . | . | 0.17 | 0.84 | . | . | . | −0.40 | 0.57 |
| Leu | 328 | . | . | B | B | . | . | . | 0.20 | 1.21 | . | . | . | −0.60 | 0.53 |
| Tyr | 329 | . | . | B | B | . | . | . | 0.29 | 1.21 | . | . | . | −0.60 | 0.57 |
| Val | 330 | . | . | B | B | . | . | . | 0.08 | 0.89 | . | . | . | −0.60 | 0.89 |
| Tyr | 331 | . | . | B | . | . | . | . | 0.01 | 0.70 | . | . | . | −0.25 | 1.67 |
| Asp | 332 | . | . | B | . | . | . | . | 0.30 | 0.50 | * | . | F | −0.10 | 1.54 |
| Pro | 333 | . | . | B | . | . | T | . | 0.22 | 0.23 | . | . | F | 0.40 | 2.99 |
| Pro | 334 | . | . | . | . | T | T | . | 0.26 | 0.27 | * | . | F | 0.80 | 1.34 |
| Thr | 335 | . | . | . | . | T | T | . | 0.90 | −0.06 | * | . | F | 1.40 | 1.24 |
| Thr | 336 | . | . | B | . | . | T | . | 0.93 | 0.37 | . | . | F | 0.40 | 1.24 |
| Ile | 337 | . | . | B | . | . | . | . | 0.62 | 0.37 | . | . | F | 0.32 | 1.24 |
| Pro | 338 | . | . | B | . | . | . | . | 0.52 | 0.43 | . | . | F | 0.14 | 1.24 |
| Pro | 339 | . | . | . | . | . | T | C | 0.42 | 0.43 | . | . | F | 0.66 | 1.24 |
| Pro | 340 | . | . | . | . | . | T | C | 0.42 | 0.43 | . | . | F | 0.78 | 2.55 |
| Thr | 341 | . | . | . | . | . | T | C | 0.42 | 0.23 | . | . | F | 1.20 | 2.38 |
| Thr | 342 | . | . | B | . | . | T | . | 1.00 | 0.29 | . | . | F | 0.88 | 2.22 |
| Thr | 343 | . | . | B | B | . | . | . | 0.90 | 0.34 | . | . | F | 0.36 | 2.07 |
| Thr | 344 | . | . | B | B | . | . | . | 0.80 | 0.40 | . | . | F | −0.06 | 2.07 |
| Thr | 345 | . | . | B | B | . | . | . | 0.70 | 0.40 | . | . | F | −0.18 | 2.07 |
| Thr | 346 | . | . | B | B | . | . | . | 0.70 | 0.40 | . | . | F | −0.30 | 2.07 |
| Thr | 347 | . | . | B | B | . | . | . | 0.70 | 0.40 | . | . | F | −0.30 | 2.07 |
| Thr | 348 | . | . | B | B | . | . | . | 0.70 | 0.40 | . | . | F | −0.30 | 2.07 |
| Thr | 349 | . | . | B | B | . | . | . | 0.70 | 0.40 | . | . | F | −0.30 | 2.07 |
| Thr | 350 | . | . | B | B | . | . | . | 0.12 | 0.40 | . | . | F | −0.30 | 2.07 |
| Thr | 351 | . | . | B | B | . | . | . | −0.38 | 0.60 | . | . | F | −0.30 | 1.01 |
| Thr | 352 | . | . | B | B | . | . | . | −0.38 | 0.80 | . | . | F | −0.45 | 0.57 |
| Thr | 353 | . | . | B | B | . | . | . | −0.96 | 0.80 | * | . | F | −0.45 | 0.57 |
| Ile | 354 | . | . | B | B | . | . | . | −1.53 | 1.00 | * | . | . | −0.60 | 0.28 |
| Leu | 355 | . | . | B | B | . | . | . | −1.53 | 1.20 | * | . | . | −0.60 | 0.14 |
| Thr | 356 | . | . | B | B | . | . | . | −1.22 | 1.20 | * | . | . | −0.60 | 0.14 |
| Ile | 357 | . | . | B | B | . | . | . | −1.21 | 0.71 | * | * | . | −0.60 | 0.32 |
| Ile | 358 | . | . | B | B | . | . | . | −0.79 | 0.41 | . | * | . | −0.26 | 0.53 |
| Thr | 359 | . | . | B | B | . | . | . | −0.49 | −0.27 | . | * | F | 1.13 | 0.71 |
| Asp | 360 | . | . | B | . | . | T | . | 0.43 | −0.26 | . | * | F | 2.02 | 1.03 |
| Ser | 361 | . | . | . | . | . | T | C | 0.36 | −0.94 | . | * | F | 2.86 | 2.87 |
| Arg | 362 | . | . | . | . | T | T | . | 0.86 | −1.20 | . | * | F | 3.40 | 2.54 |
| Ala | 363 | . | . | . | . | T | T | . | 1.36 | −1.26 | . | * | . | 2.91 | 1.95 |
| Arg | 364 | . | . | . | . | T | . | . | 1.28 | −0.83 | . | * | . | 2.37 | 1.86 |

TABLE XI

| Res | | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | . | . | 0.14 | 0.06 | . | . | . | −0.10 | 0.89 |
| Ser | 2 | A | . | . | . | . | T | . | −0.28 | 0.01 | . | . | . | 0.10 | 0.94 |
| Ser | 3 | A | . | . | . | . | T | . | 0.16 | 0.27 | . | . | . | 0.10 | 0.60 |
| Ser | 4 | A | . | . | . | . | T | . | 0.51 | −0.16 | * | . | . | 0.85 | 1.22 |
| Ser | 5 | A | . | . | . | . | T | . | 0.09 | −0.27 | * | . | F | 1.00 | 1.24 |
| Leu | 6 | A | A | . | . | . | . | . | −0.12 | 0.03 | * | . | F | −0.15 | 0.76 |
| Lys | 7 | A | A | . | . | . | . | . | −0.49 | 0.33 | * | . | F | −0.15 | 0.47 |
| His | 8 | A | A | . | . | . | . | . | −0.79 | 0.51 | * | . | . | −0.60 | 0.19 |
| Leu | 9 | A | A | . | . | . | . | . | −1.08 | 0.74 | * | . | . | −0.60 | 0.23 |
| Leu | 10 | A | A | . | . | . | . | . | −1.59 | 0.56 | * | * | . | −0.60 | 0.11 |
| Cys | 11 | A | A | . | . | . | . | . | −1.08 | 1.24 | * | * | . | −0.60 | 0.07 |
| Met | 12 | A | A | . | . | . | . | . | −1.41 | 1.13 | * | . | . | −0.60 | 0.11 |
| Ala | 13 | A | A | . | . | . | . | . | −2.08 | 1.36 | * | . | . | −0.60 | 0.14 |
| Leu | 14 | A | A | . | . | . | . | . | −1.57 | 1.46 | * | . | . | −0.60 | 0.23 |
| Ser | 15 | A | . | . | B | . | . | . | −1.06 | 1.27 | * | . | . | −0.60 | 0.31 |
| Trp | 16 | A | . | . | B | . | . | . | −1.09 | 1.04 | * | . | . | −0.60 | 0.41 |
| Phe | 17 | A | . | . | B | . | . | . | −1.38 | 1.33 | * | . | . | −0.60 | 0.43 |
| Ser | 18 | . | . | . | B | . | . | C | −1.09 | 1.33 | * | . | . | −0.40 | 0.23 |
| Ser | 19 | . | . | . | B | . | . | C | −0.62 | 1.33 | * | . | . | −0.40 | 0.29 |
| Phe | 20 | . | . | . | B | . | . | C | −0.32 | 0.84 | . | . | . | −0.40 | 0.33 |
| Ile | 21 | . | . | . | B | . | . | C | −0.34 | 0.06 | . | . | . | −0.10 | 0.43 |
| Ser | 22 | . | . | . | B | . | . | C | 0.06 | 0.16 | * | * | F | 0.05 | 0.46 |
| Gly | 23 | . | . | . | . | . | . | C | −0.34 | 0.16 | . | * | F | 0.25 | 0.71 |
| Glu | 24 | . | . | . | . | . | . | C | −0.34 | 0.16 | . | * | F | 0.25 | 0.88 |
| Thr | 25 | . | . | . | . | . | . | C | −0.46 | −0.14 | . | * | F | 0.85 | 0.88 |
| Ser | 26 | . | . | . | . | . | . | C | −0.38 | 0.16 | . | * | F | 0.25 | 0.73 |
| Phe | 27 | A | . | . | . | . | . | . | −0.08 | 0.41 | * | * | . | −0.40 | 0.35 |
| Ser | 28 | A | . | . | . | . | . | . | −0.03 | 0.81 | * | * | . | −0.40 | 0.39 |
| Leu | 29 | . | . | . | . | . | . | C | −0.73 | 0.71 | * | . | . | −0.20 | 0.39 |
| Leu | 30 | . | . | . | . | . | . | C | −1.12 | 1.11 | . | . | . | −0.20 | 0.39 |
| Asn | 31 | . | . | . | . | T | T | . | −1.63 | 1.11 | . | . | . | 0.20 | 0.25 |
| Ser | 32 | . | . | . | . | T | T | . | −1.14 | 1.41 | * | . | . | 0.20 | 0.25 |
| Phe | 33 | . | . | . | . | T | T | . | −1.09 | 1.16 | . | . | . | 0.20 | 0.47 |
| Phe | 34 | . | . | B | . | . | T | . | −0.49 | 1.23 | . | . | . | −0.20 | 0.46 |
| Leu | 35 | . | . | . | . | . | . | C | 0.02 | 1.26 | . | . | . | −0.20 | 0.53 |
| Pro | 36 | . | . | . | . | T | . | . | −0.28 | 1.26 | . | . | . | 0.00 | 0.82 |
| Tyr | 37 | . | . | . | . | T | T | . | 0.13 | 0.86 | . | * | F | 0.67 | 1.27 |
| Pro | 38 | . | . | . | . | T | T | . | 0.17 | 0.07 | . | . | F | 1.14 | 3.02 |
| Ser | 39 | . | . | . | . | T | T | . | 0.20 | −0.04 | . | * | F | 1.91 | 1.05 |
| Ser | 40 | . | . | . | . | T | T | . | 0.34 | 0.10 | . | . | F | 1.33 | 0.36 |
| Arg | 41 | . | . | . | B | T | . | . | −0.14 | −0.09 | . | . | F | 1.70 | 0.12 |
| Cys | 42 | . | . | . | B | T | . | . | −0.20 | 0.27 | . | . | . | 0.78 | 0.08 |
| Cys | 43 | . | . | . | B | T | . | . | −0.84 | 0.27 | . | * | . | 0.61 | 0.08 |
| Cys | 44 | . | . | . | B | T | . | . | −0.54 | 0.53 | . | * | . | 0.14 | 0.03 |
| Phe | 45 | . | . | . | B | T | . | . | −0.91 | 0.93 | . | * | . | −0.03 | 0.10 |
| Ser | 46 | . | . | . | B | T | . | . | −1.32 | 0.93 | . | * | . | −0.20 | 0.10 |
| Val | 47 | . | . | . | B | T | . | . | −1.54 | 0.74 | . | * | . | −0.20 | 0.25 |
| Gln | 48 | . | . | . | B | T | . | . | −1.69 | 0.86 | . | * | . | −0.20 | 0.20 |
| Cys | 49 | . | . | . | B | T | . | . | −1.02 | 0.76 | . | * | . | −0.20 | 0.12 |
| Ser | 50 | . | . | . | B | T | . | . | −0.53 | 0.37 | * | * | . | 0.10 | 0.28 |
| Ile | 51 | . | . | . | B | T | . | . | −0.93 | 0.16 | * | * | . | 0.10 | 0.25 |
| Leu | 52 | . | . | . | B | T | . | . | −0.38 | 0.54 | * | * | . | −0.20 | 0.40 |
| Asp | 53 | . | . | . | . | . | T | C | −1.04 | 0.36 | . | . | . | 0.30 | 0.40 |
| Pro | 54 | . | . | . | . | T | T | . | −0.38 | 0.54 | * | . | F | 0.35 | 0.30 |
| Phe | 55 | . | . | . | . | T | T | . | −0.38 | 0.26 | . | . | . | 0.50 | 0.59 |
| Ser | 56 | . | . | . | . | T | T | . | −0.09 | −0.04 | * | . | . | 1.10 | 0.48 |
| Cys | 57 | . | . | . | . | T | T | . | 0.83 | 0.57 | * | * | . | 0.20 | 0.30 |
| Asn | 58 | . | . | . | . | T | T | . | 0.13 | 0.14 | * | * | . | 0.50 | 0.69 |
| Ser | 59 | . | . | . | . | T | T | . | 0.13 | 0.14 | * | * | . | 0.50 | 0.44 |
| Met | 60 | . | . | . | . | T | T | . | 0.54 | 0.19 | * | * | . | 0.86 | 1.28 |
| Arg | 61 | . | . | . | . | . | . | C | 0.84 | 0.53 | * | * | . | 0.22 | 0.84 |
| Phe | 62 | . | . | . | . | . | . | C | 1.51 | 0.13 | * | * | . | 0.88 | 1.08 |
| Pro | 63 | . | . | . | . | T | . | . | 1.12 | 0.14 | * | * | . | 1.29 | 1.76 |
| Trp | 64 | . | . | . | . | T | . | . | 1.03 | −0.04 | . | * | . | 2.10 | 1.15 |
| Glu | 65 | A | . | . | . | . | . | . | 1.24 | 0.39 | . | * | . | 0.89 | 1.70 |
| Asn | 66 | . | . | . | . | T | . | . | 0.74 | 0.03 | . | * | . | 1.08 | 1.40 |

TABLE XII

| Res | | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.97 | −0.71 | * | . | . | 1.64 | 1.91 |
| Ser | 2 | . | . | B | . | . | T | . | 0.76 | −0.76 | . | . | . | 2.07 | 2.00 |
| Arg | 3 | . | . | B | . | . | T | . | 0.33 | −0.57 | . | . | . | 2.30 | 1.55 |

TABLE XII-continued

| Res | | I | II | III | IV | V | VI | VII | VIII | IX | X | XI | XII | XIII | XIV |
|---|---|---|---|---|---|---|---|---|---|---|---|---|---|---|---|
| Arg | 4 | . | . | B | . | . | T | . | −0.09 | −0.31 | . | . | . | 1.77 | 1.29 |
| Ser | 5 | . | . | B | . | . | T | . | −0.29 | −0.24 | . | . | . | 1.39 | 0.79 |
| Met | 6 | . | A | B | . | . | . | . | 0.02 | −0.13 | . | . | . | 0.76 | 0.41 |
| Leu | 7 | . | A | B | . | . | . | . | −0.27 | 0.79 | . | . | . | −0.37 | 0.22 |
| Leu | 8 | . | A | B | . | . | . | . | −1.19 | 1.29 | . | . | . | −0.60 | 0.17 |
| Ala | 9 | . | A | B | . | . | . | . | −1.51 | 1.59 | . | . | . | −0.60 | 0.14 |
| Trp | 10 | . | A | B | . | . | . | . | −1.51 | 1.40 | . | . | . | −0.60 | 0.26 |
| Ala | 11 | . | A | B | . | . | . | . | −1.72 | 1.10 | . | . | . | −0.60 | 0.42 |
| Leu | 12 | . | . | B | . | . | T | . | −1.72 | 1.10 | * | * | . | −0.20 | 0.34 |
| Pro | 13 | . | . | B | . | . | T | . | −0.80 | 1.29 | * | * | . | −0.20 | 0.27 |
| Ser | 14 | . | . | B | . | . | T | . | −1.02 | 0.37 | * | * | . | 0.10 | 0.52 |
| Leu | 15 | . | . | B | . | . | T | . | −1.08 | 0.56 | * | * | . | −0.20 | 0.52 |
| Leu | 16 | . | A | B | . | . | . | . | −1.08 | 0.30 | * | * | . | −0.30 | 0.33 |
| Arg | 17 | . | A | B | . | . | . | . | −0.86 | 0.37 | * | * | . | −0.30 | 0.25 |
| Leu | 18 | . | A | B | . | . | . | . | −0.64 | 0.49 | . | * | . | −0.60 | 0.31 |
| Gly | 19 | . | A | . | . | . | . | C | −0.34 | 0.20 | . | * | . | −0.10 | 0.65 |
| Ala | 20 | . | A | . | . | . | . | C | 0.16 | −0.49 | . | * | . | 0.50 | 0.57 |
| Ala | 21 | . | A | . | . | . | . | C | 0.97 | 0.00 | . | * | . | 0.65 | 1.00 |
| Gln | 22 | . | A | B | . | . | . | . | 0.86 | −0.69 | . | * | F | 1.21 | 1.75 |
| Glu | 23 | . | A | B | . | . | . | . | 1.46 | −1.11 | . | . | F | 1.52 | 2.90 |
| Thr | 24 | . | A | . | . | T | . | . | 1.21 | −1.19 | . | . | F | 2.23 | 4.44 |
| Glu | 25 | . | A | . | . | T | . | . | 1.13 | −1.19 | . | . | F | 2.54 | 2.59 |
| Asp | 26 | . | . | . | . | T | T | . | 1.06 | −1.01 | . | . | F | 3.10 | 0.80 |
| Pro | 27 | . | . | . | . | T | T | . | 0.76 | −0.44 | . | . | F | 2.49 | 0.30 |
| Ala | 28 | . | . | . | . | T | T | . | 0.54 | −0.54 | . | . | . | 2.33 | 0.23 |
| Cys | 29 | . | . | . | . | T | T | . | −0.03 | −0.11 | . | . | . | 1.72 | 0.21 |
| Cys | 30 | . | . | B | B | . | . | . | −0.89 | 0.57 | . | . | . | −0.29 | 0.10 |
| Ser | 31 | . | . | B | B | . | . | . | −1.10 | 0.79 | . | . | . | −0.60 | 0.07 |
| Pro | 32 | . | . | B | B | . | . | . | −0.78 | 0.71 | . | . | . | −0.60 | 0.20 |
| Ile | 33 | . | . | B | B | . | . | . | −0.19 | 0.14 | . | . | . | 0.00 | 0.75 |
| Val | 34 | . | . | B | . | . | T | . | 0.48 | −0.03 | . | * | F | 1.45 | 0.90 |
| Pro | 35 | . | . | B | . | . | T | . | 0.86 | −0.41 | . | * | F | 1.90 | 1.01 |
| Arg | 36 | . | . | . | . | T | T | . | 1.20 | 0.07 | . | * | F | 2.00 | 1.51 |
| Asn | 37 | . | . | . | . | . | T | C | 0.82 | −0.61 | * | * | F | 3.00 | 4.07 |
| Glu | 38 | . | A | . | . | T | . | . | 0.90 | −0.76 | * | * | F | 2.50 | 2.66 |
| Trp | 39 | . | A | . | . | T | . | . | 1.17 | −0.50 | * | * | F | 2.20 | 1.12 |
| Lys | 40 | . | A | . | . | . | . | C | 1.08 | 0.00 | * | * | . | 1.10 | 0.70 |
| Ala | 41 | . | A | . | . | . | . | C | 0.97 | −0.01 | * | * | . | 0.80 | 0.54 |
| Leu | 42 | . | A | . | . | . | . | C | 0.30 | −0.01 | * | . | . | 0.50 | 0.90 |
| Ala | 43 | A | A | . | . | . | . | . | −0.29 | −0.36 | * | * | . | 0.30 | 0.24 |
| Ser | 44 | A | A | . | . | . | . | . | 0.00 | 0.14 | * | . | . | −0.30 | 0.24 |
| Glu | 45 | A | A | . | . | . | . | . | −0.08 | 0.04 | * | . | . | −0.30 | 0.50 |
| Cys | 46 | A | A | . | . | . | . | . | −0.30 | −0.14 | * | . | . | 0.30 | 0.68 |
| Ala | 47 | A | A | . | . | . | . | . | 0.21 | 0.04 | . | . | . | −0.30 | 0.42 |
| Gln | 48 | . | A | B | . | . | . | . | −0.01 | 0.04 | . | . | . | −0.30 | 0.32 |
| His | 49 | . | A | B | . | . | . | . | 0.08 | 0.73 | * | * | . | −0.60 | 0.50 |
| Leu | 50 | . | A | B | . | . | . | . | −0.73 | 0.59 | * | * | . | −0.60 | 0.76 |
| Ser | 51 | . | A | B | . | . | . | . | 0.04 | 0.77 | * | * | . | −0.60 | 0.36 |
| Leu | 52 | . | . | B | . | . | . | . | 0.39 | 0.37 | * | * | . | −0.10 | 0.52 |
| Pro | 53 | . | . | B | B | . | . | . | −0.47 | 0.63 | * | * | . | −0.60 | 0.99 |
| Leu | 54 | . | . | B | B | . | . | . | −1.29 | 0.59 | . | * | . | −0.60 | 0.55 |
| Arg | 55 | . | . | B | B | . | . | . | −1.33 | 0.84 | . | * | . | −0.60 | 0.49 |
| Tyr | 56 | . | . | B | B | . | . | . | −1.33 | 0.80 | . | * | . | −0.60 | 0.24 |
| Val | 57 | . | . | B | B | . | . | . | −0.56 | 0.76 | . | * | . | −0.60 | 0.39 |
| Val | 58 | . | . | B | B | . | . | . | −0.66 | 0.57 | . | * | . | −0.60 | 0.27 |
| Val | 59 | . | . | B | B | . | . | . | −0.43 | 1.06 | . | * | . | −0.60 | 0.25 |
| Ser | 60 | . | . | B | . | . | . | . | −0.89 | 0.80 | . | . | . | −0.40 | 0.34 |
| His | 61 | . | . | B | . | . | . | . | −0.94 | 0.59 | . | . | . | −0.40 | 0.45 |
| Thr | 62 | . | . | B | . | . | . | . | −0.39 | 0.33 | . | . | . | −0.10 | 0.81 |
| Ala | 63 | . | . | . | . | T | . | . | −0.20 | 0.07 | . | . | F | 0.45 | 0.81 |
| Gly | 64 | . | . | . | . | T | T | . | 0.66 | 0.26 | . | . | F | 0.65 | 0.32 |
| Ser | 65 | . | . | . | . | T | T | . | 0.64 | 0.16 | . | . | F | 0.65 | 0.35 |
| Ser | 66 | . | . | . | . | T | T | . | 0.47 | 0.16 | . | . | F | 0.65 | 0.51 |
| Cys | 67 | . | . | . | . | T | T | . | 0.19 | 0.09 | . | . | F | 0.65 | 0.79 |
| Asn | 68 | . | . | . | . | T | . | . | 0.48 | 0.16 | . | . | F | 0.45 | 0.60 |
| Thr | 69 | . | . | . | . | . | . | C | 0.16 | 0.16 | . | . | F | 0.25 | 0.60 |
| Pro | 70 | . | . | . | . | T | T | . | 0.46 | 0.34 | . | . | F | 0.65 | 0.60 |
| Ala | 71 | . | . | . | . | T | T | . | 0.76 | 0.17 | . | * | F | 0.65 | 0.64 |
| Ser | 72 | . | . | B | . | . | T | . | 1.42 | 0.17 | . | * | F | 0.25 | 0.77 |
| Cys | 73 | . | . | B | . | . | T | . | 0.83 | 0.09 | * | * | F | 0.25 | 0.86 |
| Gln | 74 | . | A | B | . | . | . | . | 1.26 | 0.16 | . | * | F | −0.15 | 0.86 |
| Gln | 75 | . | A | B | . | . | . | . | 1.47 | −0.34 | * | * | F | 0.60 | 1.26 |
| Gln | 76 | . | A | B | . | . | . | . | 1.20 | −0.33 | * | * | F | 0.60 | 3.79 |
| Ala | 77 | . | A | B | . | . | . | . | 1.50 | −0.26 | * | . | F | 0.60 | 1.62 |
| Arg | 78 | . | A | B | . | . | . | . | 2.13 | −0.26 | * | . | F | 0.60 | 1.62 |
| Asn | 79 | . | A | B | . | . | . | . | 1.89 | −0.16 | * | . | . | 0.45 | 1.28 |
| Val | 80 | . | A | B | . | . | . | . | 1.86 | 0.20 | * | . | . | −0.15 | 1.98 |

TABLE XII-continued

| Res | | I | II | III | IV | V | VI | VII | VIII | IX | X | XI | XII | XIII | XIV |
|---|---|---|---|---|---|---|---|---|---|---|---|---|---|---|---|
| Gln | 81 | . | A | B | . | . | . | . | 1.26 | 0.20 | * | * | . | −0.15 | 1.37 |
| His | 82 | . | A | B | . | . | . | . | 1.89 | 0.81 | * | * | . | −0.60 | 0.85 |
| Tyr | 83 | . | . | B | . | . | . | . | 1.47 | 0.41 | * | . | . | −0.25 | 2.28 |
| His | 84 | . | . | B | . | . | . | . | 0.66 | 0.26 | . | . | . | 0.05 | 1.90 |
| Met | 85 | . | . | B | B | . | . | . | 1.17 | 0.54 | . | . | . | −0.45 | 1.15 |
| Lys | 86 | . | . | B | B | . | . | . | 0.88 | 0.47 | . | . | . | −0.60 | 0.73 |
| Thr | 87 | . | . | . | B | T | . | . | 0.24 | 0.63 | . | . | . | −0.20 | 0.56 |
| Leu | 88 | . | . | . | B | T | . | . | 0.49 | 0.70 | . | * | . | −0.20 | 0.30 |
| Gly | 89 | . | . | . | B | T | . | . | −0.33 | 0.09 | . | . | . | 0.10 | 0.25 |
| Trp | 90 | . | . | B | B | . | . | . | −0.08 | 0.73 | . | . | . | −0.60 | 0.13 |
| Cys | 91 | . | . | B | B | . | . | . | −0.37 | 0.67 | . | . | . | −0.60 | 0.16 |
| Asp | 92 | . | . | B | . | . | T | . | −0.06 | 0.74 | . | * | . | −0.20 | 0.25 |
| Val | 93 | . | . | B | . | . | T | . | 0.06 | 0.71 | * | . | . | −0.20 | 0.38 |
| Gly | 94 | . | . | B | . | . | T | . | −0.41 | 0.59 | . | * | . | −0.20 | 0.61 |
| Tyr | 95 | . | . | B | . | . | T | . | −1.01 | 0.70 | . | * | . | −0.20 | 0.30 |
| Asn | 96 | . | . | B | B | . | . | . | −0.69 | 1.39 | . | * | . | −0.60 | 0.29 |
| Phe | 97 | . | . | B | B | . | . | . | −0.69 | 1.17 | . | * | . | −0.60 | 0.29 |
| Leu | 98 | . | . | B | B | . | . | . | 0.17 | 0.74 | . | * | . | −0.60 | 0.32 |
| Ile | 99 | . | . | B | B | . | . | . | 0.17 | −0.01 | . | . | . | 0.30 | 0.33 |
| Gly | 100 | . | . | B | . | . | T | . | −0.40 | 0.01 | . | . | . | 0.10 | 0.38 |
| Glu | 101 | . | . | B | . | . | T | . | −1.26 | −0.09 | . | . | F | 0.85 | 0.38 |
| Asp | 102 | . | . | . | . | T | T | . | −0.80 | −0.13 | . | . | F | 1.25 | 0.40 |
| Gly | 103 | . | . | . | . | . | T | C | 0.01 | −0.06 | . | . | F | 1.05 | 0.63 |
| Leu | 104 | . | . | B | . | . | . | . | 0.56 | −0.49 | * | * | . | 0.50 | 0.63 |
| Val | 105 | . | . | B | . | . | . | . | 1.01 | −0.06 | * | * | . | 0.78 | 0.37 |
| Tyr | 106 | . | . | B | . | . | . | . | 0.67 | −0.06 | * | * | . | 1.06 | 0.74 |
| Glu | 107 | . | . | B | . | . | . | . | 0.38 | −0.06 | * | . | F | 1.49 | 0.89 |
| Gly | 108 | . | . | . | . | T | T | . | 0.72 | 0.17 | . | . | F | 1.92 | 1.25 |
| Arg | 109 | . | . | . | . | T | T | . | 0.83 | −0.07 | . | * | F | 2.80 | 1.29 |
| Gly | 110 | . | . | . | . | T | T | . | 1.38 | −0.04 | . | . | F | 2.37 | 0.64 |
| Trp | 111 | . | . | . | . | T | T | . | 1.28 | 0.44 | . | * | . | 1.04 | 0.94 |
| Asn | 112 | . | . | . | . | . | . | C | 0.69 | 0.44 | . | . | . | 0.36 | 0.47 |
| Phe | 113 | . | . | B | . | . | . | . | 1.00 | 0.94 | . | . | . | −0.12 | 0.48 |
| Thr | 114 | . | . | . | . | . | . | C | 0.59 | 1.01 | . | . | . | −0.20 | 0.63 |
| Gly | 115 | . | . | . | . | . | . | C | 0.59 | 0.49 | . | * | . | −0.20 | 0.52 |
| Ala | 116 | . | . | . | . | . | . | C | 0.84 | 0.51 | . | * | . | −0.20 | 0.60 |
| His | 117 | . | . | . | . | . | T | C | 0.03 | 0.23 | . | . | . | 0.30 | 0.56 |
| Ser | 118 | . | . | . | . | . | T | C | 0.44 | 0.43 | . | . | . | 0.00 | 0.47 |
| Gly | 119 | . | . | . | . | . | T | C | 0.76 | 0.91 | . | . | . | 0.00 | 0.49 |
| His | 120 | . | . | . | . | . | T | C | 0.89 | 0.81 | . | . | . | 0.00 | 0.58 |
| Leu | 121 | . | . | . | . | T | . | . | 0.88 | 0.74 | . | . | . | 0.00 | 0.67 |
| Trp | 122 | . | . | . | . | . | . | C | 0.61 | 0.97 | . | . | . | −0.20 | 0.67 |
| Asn | 123 | . | . | . | . | . | . | C | 0.02 | 0.93 | . | . | . | −0.20 | 0.66 |
| Pro | 124 | . | . | B | B | . | . | . | 0.02 | 1.11 | . | * | . | −0.60 | 0.56 |
| Met | 125 | . | . | . | B | T | . | . | −0.83 | 0.86 | * | * | . | −0.20 | 0.52 |
| Ser | 126 | . | . | B | B | . | . | . | −0.32 | 0.63 | . | * | . | −0.60 | 0.23 |
| Ile | 127 | . | . | B | B | . | . | . | −0.73 | 0.61 | . | * | . | −0.60 | 0.20 |
| Gly | 128 | . | . | B | B | . | . | . | −1.33 | 0.97 | . | * | . | −0.60 | 0.17 |
| Ile | 129 | . | . | B | B | . | . | . | −1.47 | 0.97 | . | * | . | −0.60 | 0.13 |
| Ser | 130 | . | . | B | B | . | . | . | −0.87 | 1.01 | . | * | . | −0.60 | 0.18 |
| Phe | 131 | . | . | B | B | . | . | . | −0.81 | 0.73 | . | * | . | −0.60 | 0.29 |
| Met | 132 | . | . | B | . | . | T | . | −0.52 | 1.06 | . | * | . | −0.20 | 0.66 |
| Gly | 133 | . | . | . | . | T | T | . | −0.18 | 0.99 | * | * | . | 0.20 | 0.48 |
| Asn | 134 | . | . | . | . | T | T | . | 0.82 | 0.60 | * | * | . | 0.20 | 0.93 |
| Tyr | 135 | . | . | . | . | T | T | . | 0.27 | −0.19 | * | * | . | 1.25 | 1.85 |
| Met | 136 | . | . | . | . | T | . | . | 0.76 | −0.16 | * | * | . | 1.31 | 1.39 |
| Asp | 137 | . | . | . | . | T | . | . | 1.04 | −0.16 | * | * | . | 1.57 | 1.33 |
| Arg | 138 | . | . | B | . | . | . | . | 1.18 | −0.07 | * | * | F | 1.58 | 1.23 |
| Val | 139 | . | . | B | . | . | T | . | 1.18 | −0.40 | * | . | F | 2.04 | 1.92 |
| Pro | 140 | . | . | B | . | . | T | . | 0.83 | −0.61 | . | . | F | 2.60 | 1.99 |
| Thr | 141 | . | . | . | . | . | T | C | 0.54 | −0.11 | . | * | F | 2.24 | 1.03 |
| Pro | 142 | . | . | B | . | . | T | . | 0.66 | 0.57 | . | * | F | 0.73 | 0.97 |
| Gln | 143 | . | A | B | . | . | . | . | −0.04 | −0.07 | * | * | F | 1.12 | 1.23 |
| Ala | 144 | . | A | B | . | . | . | . | 0.22 | 0.00 | * | . | . | 0.56 | 0.86 |
| Ile | 145 | . | A | B | . | . | . | . | 0.43 | 0.01 | * | . | . | −0.30 | 0.56 |
| Arg | 146 | . | A | B | . | . | . | . | 0.40 | −0.01 | * | . | . | 0.30 | 0.56 |
| Ala | 147 | . | A | B | . | . | . | . | −0.20 | 0.01 | * | . | . | −0.30 | 0.55 |
| Ala | 148 | . | A | B | . | . | . | . | −1.01 | 0.20 | * | . | . | −0.30 | 0.65 |
| Gln | 149 | . | A | B | . | . | . | . | −1.01 | 0.20 | * | * | . | −0.30 | 0.27 |
| Gly | 150 | . | A | B | . | . | . | . | −0.79 | 0.70 | * | * | . | −0.60 | 0.27 |
| Leu | 151 | . | A | B | . | . | . | . | −1.24 | 0.77 | * | . | . | −0.60 | 0.14 |
| Leu | 152 | . | A | B | . | . | . | . | −1.51 | 0.70 | . | . | . | −0.60 | 0.08 |
| Ala | 153 | . | A | B | . | . | . | . | −1.51 | 0.94 | . | . | . | −0.60 | 0.06 |
| Cys | 154 | . | A | B | . | . | . | . | −1.51 | 1.01 | . | . | . | −0.60 | 0.08 |
| Gly | 155 | . | A | B | . | . | . | . | −1.51 | 0.73 | . | . | . | −0.60 | 0.16 |
| Val | 156 | . | A | B | . | . | . | . | −1.29 | 0.47 | . | . | . | −0.60 | 0.16 |
| Ala | 157 | . | A | B | . | . | . | . | −1.29 | 0.47 | * | * | . | −0.60 | 0.29 |

TABLE XII-continued

| Res | | I | II | III | IV | V | VI | VII | VIII | IX | X | XI | XII | XIII | XIV |
|---|---|---|---|---|---|---|---|---|---|---|---|---|---|---|---|
| Gln | 158 | . | A | B | . | . | . | . | −0.59 | 0.59 | * | * | . | −0.60 | 0.25 |
| Gly | 159 | . | A | B | . | . | . | . | −0.22 | 0.16 | * | * | . | −0.30 | 0.65 |
| Ala | 160 | . | A | B | . | . | . | . | 0.12 | −0.10 | * | * | F | 0.45 | 0.86 |
| Leu | 161 | . | A | B | . | . | . | . | 0.73 | −0.20 | * | * | F | 0.45 | 0.80 |
| Arg | 162 | . | . | B | . | . | T | . | 0.47 | 0.16 | * | * | F | 0.40 | 1.26 |
| Ser | 163 | . | . | B | . | . | T | . | −0.34 | 0.37 | * | * | F | 0.25 | 0.93 |
| Asn | 164 | . | . | B | . | . | T | . | 0.04 | 0.56 | . | * | F | −0.05 | 0.93 |
| Tyr | 165 | . | . | B | . | . | T | . | 0.29 | −0.13 | . | * | . | 0.70 | 0.95 |
| Val | 166 | . | . | B | B | . | . | . | 1.07 | 0.30 | . | * | . | −0.12 | 0.70 |
| Leu | 167 | . | . | B | B | . | . | . | 1.07 | 0.41 | * | * | . | −0.24 | 0.59 |
| Lys | 168 | . | . | B | B | . | . | . | 1.37 | 0.01 | * | . | F | 0.39 | 0.74 |
| Gly | 169 | . | . | B | . | . | . | . | 0.51 | −0.74 | * | * | F | 1.82 | 1.67 |
| His | 170 | . | . | B | B | . | . | . | 0.76 | −0.74 | * | . | F | 1.80 | 1.50 |
| Arg | 171 | . | . | B | B | . | . | . | 1.72 | −1.03 | * | . | F | 1.62 | 1.30 |
| Asp | 172 | . | . | B | B | . | . | . | 2.22 | −1.03 | * | . | F | 1.44 | 2.57 |
| Val | 173 | . | . | B | B | . | . | . | 1.37 | −0.97 | * | . | F | 1.26 | 2.72 |
| Gln | 174 | . | . | B | B | . | . | . | 1.41 | −0.79 | * | . | F | 1.08 | 1.15 |
| Arg | 175 | . | . | B | B | . | . | . | 1.23 | −0.40 | * | . | F | 0.57 | 0.92 |
| Thr | 176 | . | . | B | B | . | . | . | 0.78 | 0.03 | * | . | F | 0.24 | 1.92 |
| Leu | 177 | . | . | . | B | . | . | C | 0.78 | −0.19 | * | . | F | 1.16 | 1.10 |
| Ser | 178 | . | . | . | . | . | T | C | 1.63 | −0.19 | * | . | F | 1.53 | 0.90 |
| Pro | 179 | . | . | . | . | . | T | C | 0.82 | 0.21 | * | . | F | 1.20 | 1.08 |
| Gly | 180 | . | . | . | . | T | T | . | 0.47 | 0.41 | * | . | F | 0.98 | 1.08 |
| Asn | 181 | . | . | . | . | T | T | . | 0.74 | 0.49 | . | . | F | 0.86 | 1.26 |
| Gln | 182 | . | A | B | . | . | . | . | 0.74 | 0.60 | * | . | F | −0.06 | 1.11 |
| Leu | 183 | . | A | B | . | . | . | . | 0.16 | 0.86 | * | . | . | −0.48 | 0.93 |
| Tyr | 184 | . | A | B | . | . | . | . | 0.37 | 1.11 | * | . | . | −0.60 | 0.40 |
| His | 185 | . | A | B | . | . | . | . | 0.71 | 1.11 | * | . | . | −0.60 | 0.40 |
| Leu | 186 | . | A | B | . | . | . | . | 0.42 | 1.11 | * | . | . | −0.60 | 0.79 |
| Ile | 187 | . | A | B | . | . | . | . | 0.21 | 1.34 | * | . | . | −0.60 | 0.53 |
| Gln | 188 | . | A | B | . | . | . | . | 0.99 | 1.01 | * | . | . | −0.60 | 0.60 |
| Asn | 189 | . | A | . | . | T | . | . | 0.99 | 1.01 | . | * | . | −0.20 | 0.99 |
| Trp | 190 | . | . | . | . | . | T | C | 1.13 | 1.09 | . | * | . | 0.15 | 2.21 |
| Pro | 191 | . | . | . | . | . | T | C | 1.64 | 0.40 | . | * | . | 0.45 | 2.50 |
| His | 192 | . | . | . | . | T | T | . | 2.32 | 0.39 | . | * | . | 0.86 | 2.09 |
| Tyr | 193 | . | . | . | . | T | T | . | 1.93 | 0.41 | . | . | . | 0.77 | 3.07 |
| Arg | 194 | . | . | . | . | T | . | . | 1.54 | −0.07 | . | . | . | 1.68 | 2.54 |
| Ser | 195 | . | . | . | . | . | . | C | 1.44 | −0.07 | . | . | . | 1.69 | 2.38 |
| Pro | 196 | . | . | . | . | T | . | . | 1.27 | −0.14 | . | * | . | 2.10 | 1.94 |

TABLE XIII

| | | | | | | | | | | | | | | | |
|---|---|---|---|---|---|---|---|---|---|---|---|---|---|---|---|
| Met | 1 | . | A | B | . | . | . | . | −1.30 | 0.70 | . | . | . | −0.60 | 0.39 |
| Leu | 2 | . | A | B | . | . | . | . | −1.72 | 0.96 | . | . | . | −0.60 | 0.25 |
| Leu | 3 | . | A | B | . | . | . | . | −2.14 | 1.21 | . | . | . | −0.60 | 0.16 |
| Pro | 4 | . | A | B | . | . | . | . | −2.06 | 1.47 | . | . | . | −0.60 | 0.14 |
| Leu | 5 | . | A | B | . | . | . | . | −1.97 | 1.24 | * | . | . | −0.60 | 0.22 |
| Leu | 6 | . | A | B | . | . | . | . | −2.18 | 0.94 | . | . | . | −0.60 | 0.36 |
| Leu | 7 | . | A | B | . | . | . | . | −2.18 | 0.94 | . | . | . | −0.60 | 0.19 |
| Ser | 8 | . | A | B | . | . | . | . | −1.71 | 1.20 | * | . | . | −0.60 | 0.19 |
| Ser | 9 | . | . | B | B | . | . | . | −1.84 | 0.94 | . | . | F | −0.45 | 0.23 |
| Leu | 10 | . | . | B | B | . | . | . | −1.33 | 0.69 | . | . | F | −0.45 | 0.27 |
| Leu | 11 | . | . | . | B | . | . | C | −0.52 | 0.39 | * | . | F | 0.05 | 0.27 |
| Gly | 12 | . | . | . | . | . | T | C | −0.30 | 0.40 | . | . | F | 0.45 | 0.35 |
| Gly | 13 | . | . | . | . | . | T | C | −0.60 | 0.51 | . | . | F | 0.15 | 0.43 |
| Ser | 14 | . | . | B | . | . | T | . | −0.30 | 0.44 | . | . | F | 0.12 | 0.52 |
| Gln | 15 | . | . | B | . | . | T | . | 0.17 | −0.24 | . | * | F | 1.19 | 0.88 |
| Ala | 16 | . | . | B | . | . | . | . | 1.09 | −0.24 | . | * | F | 1.16 | 0.88 |
| Met | 17 | . | . | B | . | . | T | . | 0.73 | −0.67 | . | * | F | 1.98 | 1.28 |
| Asp | 18 | . | . | B | . | . | T | . | 0.79 | −0.27 | . | * | F | 1.70 | 0.64 |
| Gly | 19 | . | . | . | . | T | T | . | 0.20 | 0.24 | * | * | F | 1.33 | 0.67 |
| Arg | 20 | . | . | . | . | T | T | . | 0.31 | 0.43 | * | * | . | 0.71 | 0.47 |
| Phe | 21 | . | . | B | B | . | . | . | 0.04 | −0.19 | * | * | . | 0.64 | 0.56 |
| Trp | 22 | . | . | B | B | . | . | . | 0.64 | 0.46 | * | * | . | −0.43 | 0.42 |
| Ile | 23 | . | . | B | B | . | . | . | 0.64 | 0.43 | * | * | . | −0.60 | 0.37 |
| Arg | 24 | . | . | B | B | . | . | . | 0.69 | 0.43 | * | * | . | −0.60 | 0.74 |
| Val | 25 | . | . | B | B | . | . | . | −0.28 | 0.03 | * | * | . | −0.30 | 0.94 |
| Gln | 26 | . | . | B | B | . | . | . | −0.18 | −0.24 | * | * | F | 0.45 | 0.99 |
| Glu | 27 | . | . | . | B | . | . | C | −0.74 | −0.31 | * | * | F | 0.65 | 0.50 |
| Ser | 28 | . | . | . | B | . | . | C | −0.07 | 0.33 | . | * | . | −0.10 | 0.50 |
| Val | 29 | . | . | B | B | . | . | . | −0.18 | 0.11 | . | * | . | −0.30 | 0.45 |
| Met | 30 | . | . | B | B | . | . | . | 0.33 | −0.29 | * | . | . | 0.30 | 0.45 |
| Val | 31 | . | . | B | . | . | T | . | −0.48 | 0.14 | . | . | . | 0.10 | 0.33 |
| Pro | 32 | . | . | B | . | . | T | . | −1.14 | 0.44 | . | . | . | −0.20 | 0.37 |

TABLE XIII-continued

| | | | | | | | | | | | | | | | |
|---|---|---|---|---|---|---|---|---|---|---|---|---|---|---|---|
| Glu | 33 | . | . | . | . | T | T | . | −1.73 | 0.37 | . | . | F | 0.65 | 0.20 |
| Gly | 34 | . | . | . | . | T | T | . | −1.18 | 0.44 | . | . | F | 0.35 | 0.19 |
| Leu | 35 | . | . | B | B | . | . | . | −1.43 | 0.19 | . | . | . | −0.30 | 0.16 |
| Cys | 36 | . | . | B | B | . | . | . | −0.79 | 0.40 | . | . | . | −0.30 | 0.07 |
| Ile | 37 | . | . | B | B | . | . | . | −1.24 | 0.83 | . | . | . | −0.60 | 0.11 |
| Ser | 38 | . | . | B | B | . | . | . | −1.54 | 0.97 | . | * | . | −0.60 | 0.07 |
| Val | 39 | . | . | B | . | . | T | . | −1.90 | 0.67 | . | * | . | −0.20 | 0.18 |
| Pro | 40 | . | . | B | . | . | T | . | −1.39 | 0.89 | . | * | . | −0.20 | 0.22 |
| Cys | 41 | . | . | . | . | T | T | . | −0.97 | 0.59 | . | * | . | 0.20 | 0.22 |
| Ser | 42 | . | . | . | . | T | T | . | −0.29 | 0.96 | . | * | . | 0.20 | 0.46 |
| Phe | 43 | . | . | . | . | T | . | . | 0.12 | 0.74 | * | . | . | 0.28 | 0.46 |
| Ser | 44 | . | . | B | . | . | . | . | 0.98 | 0.31 | . | . | . | 0.61 | 1.69 |
| Tyr | 45 | . | . | B | . | . | T | . | 1.19 | 0.14 | . | . | . | 1.09 | 2.19 |
| Pro | 46 | . | . | . | . | T | T | . | 1.57 | −0.24 | . | . | F | 2.52 | 4.22 |
| Arg | 47 | . | . | . | . | T | T | . | 1.56 | −0.11 | . | . | F | 2.80 | 3.31 |
| Gln | 48 | . | . | . | . | T | T | . | 1.91 | −0.01 | . | * | F | 2.52 | 3.05 |
| Asp | 49 | . | . | . | . | T | . | . | 1.91 | −0.34 | . | * | F | 2.04 | 1.95 |
| Trp | 50 | . | . | . | . | T | T | . | 1.84 | −0.39 | . | * | F | 1.96 | 1.33 |
| Thr | 51 | . | . | . | . | . | T | C | 1.84 | 0.10 | . | * | F | 0.88 | 1.11 |
| Gly | 52 | . | . | . | . | T | T | . | 1.14 | 0.13 | . | * | F | 0.80 | 1.03 |
| Ser | 53 | . | . | . | . | . | T | C | 0.90 | 0.63 | . | . | F | 0.15 | 0.99 |
| Thr | 54 | . | . | . | . | . | . | C | 0.56 | 0.47 | . | . | F | 0.10 | 1.07 |
| Pro | 55 | . | . | . | . | . | T | C | 0.60 | 0.41 | . | . | F | 0.30 | 1.07 |
| Ala | 56 | . | . | . | . | T | T | . | 0.62 | 0.74 | . | . | . | 0.35 | 1.26 |
| Tyr | 57 | . | . | . | . | T | T | . | 0.27 | 1.27 | . | . | . | 0.20 | 0.91 |
| Gly | 58 | . | . | . | . | T | T | . | 0.61 | 1.57 | . | . | . | 0.20 | 0.51 |
| Tyr | 59 | . | . | B | B | . | . | . | 0.33 | 1.14 | * | . | . | −0.45 | 1.01 |
| Trp | 60 | . | . | B | B | . | . | . | −0.31 | 1.14 | * | . | . | −0.60 | 0.65 |
| Phe | 61 | . | . | B | B | . | . | . | −0.03 | 1.03 | * | . | . | −0.60 | 0.49 |
| Lys | 62 | . | . | B | B | . | . | . | 0.21 | 1.09 | * | . | . | −0.60 | 0.45 |
| Ala | 63 | . | . | B | B | . | . | . | 0.24 | 0.33 | * | . | . | −0.30 | 0.74 |
| Val | 64 | . | . | B | B | . | . | . | 0.18 | −0.10 | * | . | . | 0.79 | 1.24 |
| Thr | 65 | . | . | B | B | . | . | . | 0.51 | −0.40 | * | . | F | 1.13 | 0.89 |
| Glu | 66 | . | . | B | B | . | . | . | 0.87 | −0.40 | * | . | F | 1.62 | 1.77 |
| Thr | 67 | . | . | . | B | T | . | . | 0.23 | −0.47 | * | . | F | 2.36 | 2.36 |
| Thr | 68 | . | . | . | . | T | T | . | 0.61 | −0.61 | * | . | F | 3.40 | 1.65 |
| Lys | 69 | . | . | . | . | T | T | . | 0.61 | −0.67 | * | . | F | 3.06 | 1.48 |
| Gly | 70 | . | . | . | . | . | T | C | 0.33 | −0.03 | . | . | F | 2.07 | 0.76 |
| Ala | 71 | . | . | . | . | . | T | C | 0.02 | −0.01 | * | . | F | 1.73 | 0.53 |
| Pro | 72 | . | . | B | . | . | . | . | 0.33 | −0.01 | * | . | . | 0.84 | 0.38 |
| Val | 73 | . | . | B | . | . | . | . | 0.61 | 0.39 | . | . | . | −0.10 | 0.62 |
| Ala | 74 | . | . | B | . | . | . | . | 0.57 | 0.46 | . | . | . | −0.10 | 0.84 |
| Thr | 75 | . | . | B | . | . | . | . | 0.61 | 0.36 | * | * | . | 0.50 | 0.94 |
| Asn | 76 | . | . | . | . | . | . | C | 1.31 | 0.31 | . | . | F | 1.30 | 1.70 |
| His | 77 | . | . | . | . | . | T | C | 1.52 | −0.33 | * | . | F | 2.40 | 3.29 |
| Gln | 78 | . | . | . | . | . | T | C | 1.52 | −0.83 | * | . | F | 3.00 | 3.95 |
| Ser | 79 | . | . | . | . | . | T | C | 2.11 | −0.67 | * | . | F | 2.70 | 1.82 |
| Arg | 80 | . | . | B | . | . | T | . | 1.82 | −1.07 | * | . | F | 2.20 | 2.32 |
| Glu | 81 | . | A | B | . | . | . | . | 1.52 | −0.96 | * | . | F | 1.50 | 1.33 |
| Val | 82 | . | A | B | . | . | . | . | 1.24 | −0.97 | * | * | F | 1.54 | 1.33 |
| Glu | 83 | . | A | B | . | . | . | . | 1.36 | −0.87 | * | * | . | 1.28 | 0.98 |
| Met | 84 | . | A | B | . | . | . | . | 1.31 | −0.87 | * | * | . | 1.77 | 1.10 |
| Ser | 85 | . | . | . | . | . | T | C | 1.31 | −0.44 | * | * | F | 2.56 | 1.47 |
| Thr | 86 | . | . | . | . | T | T | . | 0.61 | −1.09 | . | * | F | 3.40 | 1.67 |
| Arg | 87 | . | . | . | . | T | T | . | 1.47 | −0.30 | . | * | F | 2.76 | 1.46 |
| Gly | 88 | . | . | . | . | T | T | . | 0.66 | −0.51 | . | * | F | 2.72 | 1.88 |
| Arg | 89 | . | . | B | B | . | . | . | 0.94 | −0.21 | . | * | F | 1.28 | 1.08 |
| Phe | 90 | . | . | B | B | . | . | . | 0.90 | −0.21 | . | * | . | 0.64 | 0.79 |
| Gln | 91 | . | . | B | B | . | . | . | 1.21 | 0.21 | . | * | . | −0.30 | 0.79 |
| Leu | 92 | . | . | B | B | . | . | . | 0.89 | −0.21 | . | * | . | 0.30 | 0.68 |
| Thr | 93 | . | . | B | B | . | . | . | 0.64 | 0.21 | . | * | F | 0.34 | 1.21 |
| Gly | 94 | . | . | . | B | . | . | C | 0.58 | −0.07 | . | * | F | 1.33 | 0.70 |
| Asp | 95 | . | . | . | . | . | T | C | 0.93 | −0.47 | * | * | F | 2.22 | 1.71 |
| Pro | 96 | . | . | . | . | . | T | C | 0.93 | −0.73 | . | * | F | 2.86 | 1.17 |
| Ala | 97 | . | . | . | . | T | T | . | 1.08 | −0.81 | . | . | F | 3.40 | 1.90 |
| Lys | 98 | . | . | . | . | T | T | . | 1.09 | −0.67 | . | * | F | 2.91 | 0.61 |
| Gly | 99 | . | . | . | . | T | T | . | 0.62 | −0.29 | * | . | F | 2.27 | 0.53 |
| Asn | 100 | . | . | B | . | T | T | . | −0.23 | −0.03 | . | * | F | 1.93 | 0.43 |
| Cys | 101 | . | . | B | . | . | T | . | −0.91 | 0.11 | * | * | . | 0.44 | 0.16 |
| Ser | 102 | . | . | B | . | . | T | . | −0.21 | 0.80 | * | * | . | −0.20 | 0.11 |
| Leu | 103 | . | A | B | B | . | . | . | −0.26 | 0.37 | * | * | . | −0.30 | 0.14 |
| Val | 104 | . | A | B | B | . | . | . | −0.50 | −0.03 | * | * | . | 0.30 | 0.43 |
| Ile | 105 | . | A | B | B | . | . | . | −0.50 | −0.10 | * | * | . | 0.30 | 0.33 |
| Arg | 106 | . | A | B | B | . | . | . | −0.43 | −0.09 | * | . | . | 0.30 | 0.68 |
| Asp | 107 | . | A | B | B | . | . | . | −0.13 | −0.16 | * | . | . | 0.30 | 0.91 |
| Ala | 108 | . | A | B | . | . | . | . | 0.68 | −0.40 | * | . | . | 0.45 | 2.25 |
| Gln | 109 | . | A | B | . | . | . | . | 1.53 | −1.09 | * | . | . | 1.03 | 1.92 |
| Met | 110 | . | A | . | . | . | . | C | 2.12 | −1.09 | . | . | . | 1.51 | 1.99 |
| Gln | 111 | . | A | B | . | . | . | . | 2.01 | −0.70 | . | . | F | 1.74 | 2.64 |

TABLE XIII-continued

| | | | | | | | | | | | | | | | |
|---|---|---|---|---|---|---|---|---|---|---|---|---|---|---|---|
| Asp | 112 | . | . | . | . | T | T | . | 1.77 | −0.80 | . | * | F | 2.82 | 2.64 |
| Glu | 113 | . | . | . | . | T | T | . | 1.66 | −0.44 | * | . | F | 2.80 | 4.18 |
| Ser | 114 | . | . | . | . | T | T | . | 0.96 | −0.27 | * | * | F | 2.52 | 2.09 |
| Gln | 115 | . | . | . | . | T | T | . | 1.67 | 0.11 | * | * | F | 1.64 | 1.08 |
| Tyr | 116 | . | . | B | B | . | . | . | 0.81 | 0.11 | * | * | . | 0.41 | 1.22 |
| Phe | 117 | . | . | B | B | . | . | . | 0.81 | 0.76 | * | . | . | −0.32 | 0.68 |
| Phe | 118 | . | . | B | B | . | . | . | 0.92 | 0.37 | * | * | . | 0.04 | 0.68 |
| Arg | 119 | . | . | B | B | . | . | . | 0.88 | −0.03 | * | . | . | 0.98 | 0.85 |
| Val | 120 | . | . | B | B | . | . | . | 0.58 | −0.36 | * | . | . | 1.32 | 0.97 |
| Glu | 121 | . | . | . | . | T | T | . | 0.58 | −0.76 | * | . | F | 3.06 | 1.50 |
| Arg | 122 | . | . | . | . | T | T | . | 0.42 | −0.79 | * | * | F | 3.40 | 1.20 |
| Gly | 123 | . | . | . | . | T | T | . | 1.23 | −0.14 | * | * | F | 2.76 | 1.20 |
| Ser | 124 | . | . | . | . | T | T | . | 0.88 | −0.79 | * | * | F | 2.72 | 1.36 |
| Tyr | 125 | . | . | B | . | . | . | . | 1.73 | −0.03 | . | * | . | 1.33 | 1.09 |
| Val | 126 | . | . | B | . | . | . | . | 1.03 | 0.37 | . | * | . | 0.39 | 1.76 |
| Arg | 127 | . | . | B | . | . | . | . | 0.32 | 0.73 | . | . | . | −0.25 | 1.14 |
| Tyr | 128 | . | . | B | . | . | . | . | 0.67 | 0.96 | . | * | . | −0.40 | 0.72 |
| Asn | 129 | . | . | B | . | . | . | . | 0.97 | 0.60 | . | * | . | −0.25 | 1.56 |
| Phe | 130 | . | . | B | . | . | . | . | 0.87 | −0.04 | . | * | . | 0.65 | 1.33 |
| Met | 131 | . | . | B | . | . | . | . | 1.02 | 0.39 | . | * | . | −0.10 | 0.84 |
| Asn | 132 | . | . | . | . | T | T | . | 0.21 | 0.41 | . | * | . | 0.20 | 0.45 |
| Asp | 133 | . | . | . | . | T | T | . | −0.36 | 0.80 | . | . | . | 0.20 | 0.45 |
| Gly | 134 | . | . | . | . | T | T | . | −0.31 | 0.70 | . | * | . | 0.20 | 0.38 |
| Phe | 135 | . | . | B | . | . | T | . | −0.47 | 0.09 | . | . | . | 0.10 | 0.47 |
| Phe | 136 | . | . | B | B | . | . | . | −0.18 | 0.33 | . | * | . | −0.30 | 0.21 |
| Leu | 137 | . | . | B | B | . | . | . | −0.77 | 0.81 | . | . | . | −0.60 | 0.30 |
| Lys | 138 | . | . | B | B | . | . | . | −1.58 | 0.89 | . | . | . | −0.60 | 0.35 |
| Val | 139 | . | . | B | B | . | . | . | −1.54 | 0.79 | . | * | . | −0.60 | 0.34 |
| Thr | 140 | . | . | B | B | . | . | . | −0.84 | 0.49 | * | * | . | −0.60 | 0.59 |
| Ala | 141 | . | . | B | B | . | . | . | −0.10 | 0.20 | * | . | . | −0.30 | 0.51 |
| Leu | 142 | . | . | B | B | . | . | . | 0.50 | 0.20 | . | * | F | 0.00 | 1.38 |
| Thr | 143 | . | . | B | B | . | . | . | 0.46 | −0.01 | . | * | F | 0.85 | 1.48 |
| Gln | 144 | . | . | B | B | . | . | . | 0.46 | −0.50 | . | . | F | 1.40 | 2.44 |
| Lys | 145 | . | . | B | . | . | T | . | 0.52 | −0.36 | . | * | F | 1.75 | 2.20 |
| Pro | 146 | . | . | B | . | . | T | . | 0.22 | −0.29 | . | * | F | 2.00 | 2.38 |
| Asp | 147 | . | . | . | . | T | T | . | 0.82 | −0.09 | * | * | F | 2.50 | 0.97 |
| Val | 148 | . | . | B | . | . | T | . | 1.13 | −0.06 | . | * | . | 1.70 | 0.75 |
| Tyr | 149 | . | . | B | . | . | . | . | 0.82 | −0.06 | * | * | . | 1.25 | 0.84 |
| Ile | 150 | . | . | B | . | . | . | . | −0.03 | 0.00 | * | * | . | 1.00 | 0.72 |
| Pro | 151 | . | . | B | . | . | . | . | 0.18 | 0.69 | . | * | . | 0.15 | 0.80 |
| Glu | 152 | . | . | B | . | . | . | . | −0.03 | 0.04 | . | * | F | 0.65 | 0.89 |
| Thr | 153 | . | . | B | . | . | . | . | 0.48 | −0.29 | * | . | F | 1.70 | 1.96 |
| Leu | 154 | . | . | . | . | . | . | C | 0.72 | −0.54 | * | . | F | 2.50 | 1.25 |
| Glu | 155 | . | . | . | . | . | T | C | 1.40 | −0.57 | * | . | F | 3.00 | 1.25 |
| Pro | 156 | . | . | . | . | T | T | . | 0.76 | −0.14 | * | . | F | 2.60 | 1.34 |
| Gly | 157 | . | . | . | . | T | T | . | 0.44 | 0.01 | . | . | F | 1.70 | 1.21 |
| Gln | 158 | . | . | . | . | . | T | C | −0.10 | −0.19 | . | . | F | 1.80 | 1.01 |
| Pro | 159 | . | . | B | B | . | . | . | −0.18 | 0.46 | . | . | F | −0.15 | 0.48 |
| Val | 160 | . | . | B | B | . | . | . | −0.84 | 0.71 | . | . | F | −0.45 | 0.34 |
| Thr | 161 | . | . | B | B | . | . | . | −1.49 | 0.86 | . | . | . | −0.60 | 0.11 |
| Val | 162 | . | . | B | B | . | . | . | −1.84 | 1.10 | . | . | . | −0.60 | 0.05 |
| Ile | 163 | . | . | B | B | . | . | . | −1.84 | 1.46 | . | . | . | −0.60 | 0.06 |
| Cys | 164 | . | . | B | B | . | . | . | −1.92 | 1.21 | . | . | . | −0.60 | 0.07 |
| Val | 165 | . | . | B | B | . | . | . | −1.66 | 1.64 | . | . | . | −0.60 | 0.09 |
| Phe | 166 | . | A | B | B | . | . | . | −2.04 | 1.50 | * | . | . | −0.60 | 0.13 |
| Asn | 167 | . | A | . | B | T | . | . | −1.19 | 1.60 | * | . | . | −0.20 | 0.22 |
| Trp | 168 | . | A | . | B | T | . | . | −0.30 | 1.03 | * | . | . | −0.20 | 0.51 |
| Ala | 169 | . | A | . | B | . | . | C | −0.30 | 0.39 | * | . | . | 0.05 | 1.02 |
| Phe | 170 | . | A | . | . | T | . | . | 0.34 | 0.17 | * | . | . | 0.10 | 0.34 |
| Glu | 171 | . | A | . | . | T | . | . | 0.83 | 0.20 | * | * | . | 0.10 | 0.50 |
| Glu | 172 | . | A | . | . | T | . | . | 0.62 | −0.29 | . | . | F | 0.95 | 0.76 |
| Cys | 173 | . | A | . | . | . | . | C | 0.61 | −0.36 | . | . | F | 1.00 | 1.36 |
| Pro | 174 | . | A | . | . | . | . | C | 0.50 | −0.76 | . | . | F | 1.40 | 1.05 |
| Pro | 175 | . | . | . | . | . | T | C | 0.90 | 0.03 | * | . | F | 0.85 | 0.53 |
| Pro | 176 | . | . | . | . | T | T | . | 0.61 | 0.41 | . | . | F | 1.00 | 1.32 |
| Ser | 177 | . | . | . | . | T | T | . | 0.30 | 0.76 | . | . | F | 0.75 | 0.90 |
| Phe | 178 | . | . | . | . | T | T | . | 0.62 | 0.81 | . | . | . | 0.50 | 0.84 |
| Ser | 179 | . | . | B | B | . | . | . | 0.24 | 0.81 | . | . | . | −0.40 | 0.54 |
| Trp | 180 | . | . | B | B | . | . | . | −0.13 | 0.89 | . | . | . | −0.50 | 0.40 |
| Thr | 181 | . | . | B | B | . | . | . | −0.73 | 1.00 | . | . | . | −0.60 | 0.47 |
| Gly | 182 | . | . | . | B | . | . | C | −0.73 | 0.90 | . | . | . | −0.40 | 0.29 |
| Ala | 183 | . | . | . | . | . | . | C | −0.33 | 0.90 | . | . | . | −0.20 | 0.37 |
| Ala | 184 | . | . | . | . | . | . | C | −0.03 | 0.37 | . | . | . | 0.10 | 0.34 |
| Leu | 185 | . | . | . | . | . | . | C | −0.09 | 0.29 | . | . | F | 0.53 | 0.60 |
| Ser | 186 | . | . | . | . | . | . | C | −0.09 | 0.29 | * | . | F | 0.81 | 0.59 |
| Ser | 187 | . | . | . | . | T | T | . | 0.30 | 0.27 | * | . | F | 1.49 | 0.84 |
| Gln | 188 | . | . | . | . | T | T | . | 0.68 | −0.23 | . | . | F | 2.52 | 2.04 |
| Gly | 189 | . | . | . | . | T | T | . | 0.96 | −0.49 | * | . | F | 2.80 | 2.35 |
| Thr | 190 | . | . | . | . | . | T | C | 1.46 | −0.39 | * | . | F | 2.32 | 2.53 |

TABLE XIII-continued

| | | | | | | | | | | | | | | | |
|---|---|---|---|---|---|---|---|---|---|---|---|---|---|---|---|
| Lys | 191 | . | . | . | . | . | T | C | 1.46 | −0.29 | . | . | F | 2.04 | 2.11 |
| Pro | 192 | . | . | B | . | . | T | . | 1.72 | −0.30 | * | . | F | 1.56 | 2.86 |
| Thr | 193 | . | . | B | . | . | T | . | 1.02 | −0.23 | * | . | F | 1.28 | 2.69 |
| Thr | 194 | . | . | B | . | . | T | . | 1.07 | 0.07 | . | . | F | 0.40 | 1.17 |
| Ser | 195 | . | . | B | B | . | . | . | 0.52 | 0.46 | * | . | F | −0.30 | 1.01 |
| His | 196 | . | . | B | B | . | . | . | −0.33 | 0.67 | * | . | . | −0.60 | 0.52 |
| Phe | 197 | . | . | B | B | . | . | . | −0.42 | 0.87 | . | . | . | −0.60 | 0.30 |
| Ser | 198 | . | . | B | B | . | . | . | −0.81 | 0.77 | . | . | . | −0.60 | 0.30 |
| Val | 199 | . | . | B | B | . | . | . | −0.81 | 1.17 | . | . | . | −0.60 | 0.19 |
| Leu | 200 | . | . | B | B | . | . | . | −0.72 | 1.16 | * | * | . | −0.60 | 0.31 |
| Ser | 201 | . | . | . | B | T | . | . | −0.58 | 0.80 | * | * | . | −0.20 | 0.36 |
| Phe | 202 | . | . | . | B | . | . | C | −0.09 | 0.41 | * | * | . | −0.06 | 0.96 |
| Thr | 203 | . | . | . | . | . | T | C | 0.21 | 0.20 | * | * | F | 1.28 | 1.80 |
| Pro | 204 | . | . | . | . | . | T | C | 1.07 | −0.09 | * | * | F | 2.22 | 2.32 |
| Arg | 205 | . | . | . | . | . | T | C | 1.84 | −0.47 | . | * | F | 2.56 | 4.48 |
| Pro | 206 | . | . | . | . | T | T | . | 2.14 | −0.76 | . | * | F | 3.40 | 4.22 |
| Gln | 207 | . | . | . | . | T | . | . | 2.53 | −0.84 | * | * | F | 2.86 | 4.39 |
| Asp | 208 | . | . | . | . | T | . | . | 2.84 | −0.79 | * | * | F | 2.52 | 3.24 |
| His | 209 | . | . | . | . | T | . | . | 2.24 | −0.79 | * | * | F | 2.18 | 3.50 |
| Asn | 210 | . | . | . | . | T | T | . | 1.82 | −0.53 | * | * | F | 2.04 | 1.67 |
| Thr | 211 | . | . | . | . | T | T | . | 1.37 | −0.44 | . | . | F | 1.40 | 1.44 |
| Asp | 212 | . | . | . | . | T | T | . | 1.33 | 0.13 | . | * | F | 0.65 | 0.57 |
| Leu | 213 | . | . | B | . | . | T | . | 0.48 | 0.13 | * | * | . | 0.10 | 0.48 |
| Thr | 214 | . | . | B | B | . | . | . | 0.51 | 0.37 | . | * | . | −0.30 | 0.25 |
| Cys | 215 | . | . | B | B | . | . | . | −0.19 | −0.11 | . | * | . | 0.49 | 0.25 |
| His | 216 | . | . | B | B | . | . | . | −0.18 | 0.67 | * | * | . | −0.22 | 0.26 |
| Val | 217 | . | . | B | B | . | . | . | −0.07 | 0.37 | * | * | . | 0.27 | 0.24 |
| Asp | 218 | . | . | B | B | . | . | . | 0.79 | −0.11 | * | * | . | 1.06 | 0.88 |
| Phe | 219 | . | . | B | . | . | . | . | 0.76 | −0.69 | * | . | . | 1.90 | 1.29 |
| Ser | 220 | . | . | . | . | T | T | . | 0.57 | −0.76 | * | . | F | 2.46 | 1.72 |
| Arg | 221 | . | . | . | . | T | T | . | 0.30 | −0.76 | * | . | F | 2.12 | 0.77 |
| Lys | 222 | . | . | . | . | T | T | . | 0.30 | −0.37 | * | * | F | 1.78 | 1.18 |
| Gly | 223 | . | . | . | . | T | T | . | 0.30 | −0.51 | * | . | F | 1.74 | 0.66 |
| Val | 224 | . | . | . | B | . | . | C | 1.11 | −0.50 | * | . | F | 0.95 | 0.58 |
| Ser | 225 | . | . | B | B | . | . | . | 1.10 | −0.50 | * | . | . | 0.60 | 0.57 |
| Val | 226 | . | . | B | B | . | . | . | 0.13 | −0.01 | * | * | . | 0.30 | 0.83 |
| Gln | 227 | . | . | B | B | . | . | . | 0.20 | 0.20 | * | * | F | −0.15 | 0.83 |
| Arg | 228 | . | . | B | B | . | . | . | −0.27 | −0.44 | * | * | F | 0.60 | 1.21 |
| Thr | 229 | . | . | B | B | . | . | . | 0.70 | −0.14 | * | * | F | 0.60 | 1.35 |
| Val | 230 | . | . | B | B | . | . | . | 0.14 | −0.79 | * | * | . | 0.75 | 1.52 |
| Arg | 231 | . | . | B | B | . | . | . | 0.41 | −0.54 | * | * | . | 0.60 | 0.58 |
| Leu | 232 | . | . | B | B | . | . | . | 0.17 | −0.04 | * | * | . | 0.30 | 0.40 |
| Arg | 233 | . | . | B | B | . | . | . | −0.53 | 0.23 | * | * | . | −0.30 | 0.85 |
| Val | 234 | . | . | B | B | . | . | . | −0.43 | 0.09 | * | * | . | −0.30 | 0.44 |
| Ala | 235 | . | . | B | B | . | . | . | 0.53 | 0.51 | * | * | . | −0.60 | 0.82 |
| Tyr | 236 | . | . | B | B | . | . | . | 0.42 | −0.17 | * | * | . | 0.30 | 0.82 |
| Ala | 237 | . | . | B | . | . | T | . | 0.42 | −0.17 | * | * | . | 0.85 | 1.85 |
| Pro | 238 | . | . | B | . | . | T | . | −0.54 | −0.13 | * | * | . | 0.85 | 1.51 |
| Arg | 239 | . | . | B | . | . | T | . | −0.58 | 0.01 | * | . | F | 0.25 | 0.72 |
| Asp | 240 | . | . | B | . | . | T | . | −0.29 | −0.06 | * | . | F | 0.85 | 0.50 |
| Leu | 241 | . | . | B | B | . | . | . | −0.93 | −0.17 | * | . | . | 0.30 | 0.43 |
| Val | 242 | . | . | B | B | . | . | . | −0.64 | 0.09 | * | . | . | −0.30 | 0.15 |
| Ile | 243 | . | . | B | B | . | . | . | −0.32 | 0.47 | * | . | . | −0.26 | 0.12 |
| Ser | 244 | . | . | B | B | . | . | . | −0.43 | 0.47 | * | . | . | 0.08 | 0.29 |
| Ile | 245 | . | . | B | B | . | . | . | −0.43 | −0.21 | * | . | . | 1.32 | 0.66 |
| Ser | 246 | . | . | B | . | . | T | . | 0.07 | −0.46 | * | . | F | 2.36 | 1.52 |
| Arg | 247 | . | . | . | . | T | T | . | 0.71 | −0.66 | * | . | F | 3.40 | 1.63 |
| Asp | 248 | . | . | . | . | T | T | . | 1.01 | −0.61 | * | . | F | 3.06 | 3.61 |
| Asn | 249 | . | . | . | . | . | T | C | 0.50 | −0.80 | * | . | F | 2.52 | 2.72 |
| Thr | 250 | . | . | . | . | . | . | C | 1.39 | −0.50 | * | . | F | 1.98 | 1.14 |
| Pro | 251 | . | . | . | . | . | . | C | 1.48 | −0.50 | . | . | F | 1.64 | 1.19 |
| Ala | 252 | . | . | . | . | T | . | . | 1.37 | −0.07 | * | . | F | 1.20 | 1.14 |
| Leu | 253 | . | . | B | . | . | . | . | 1.16 | −0.07 | . | . | F | 1.14 | 1.37 |
| Glu | 254 | . | . | B | . | . | . | . | 1.16 | −0.13 | . | * | F | 1.48 | 1.37 |
| Pro | 255 | . | . | B | . | . | . | . | 1.12 | −0.16 | . | * | F | 1.82 | 2.35 |
| Gln | 256 | . | . | . | . | . | . | C | 1.33 | −0.23 | . | * | F | 2.36 | 2.82 |
| Pro | 257 | . | . | . | . | T | T | . | 1.07 | −0.51 | . | * | F | 3.40 | 2.62 |
| Gln | 258 | . | . | . | . | T | T | . | 1.67 | 0.13 | . | * | F | 2.16 | 1.26 |
| Gly | 259 | . | . | . | . | T | T | . | 1.42 | 0.13 | . | * | F | 1.82 | 1.12 |
| Asn | 260 | . | . | . | . | . | T | C | 0.82 | 0.49 | . | * | F | 0.98 | 1.14 |
| Val | 261 | . | . | B | . | . | . | . | 0.82 | 0.74 | . | * | F | 0.09 | 0.54 |
| Pro | 262 | . | A | B | . | . | . | . | 0.44 | 0.34 | . | . | . | −0.30 | 0.95 |
| Tyr | 263 | . | A | B | . | . | . | . | 0.44 | 0.41 | . | . | . | −0.60 | 0.59 |
| Leu | 264 | . | A | B | . | . | . | . | 0.83 | 0.41 | . | . | . | −0.17 | 1.39 |
| Glu | 265 | . | A | B | . | . | . | . | 0.49 | −0.23 | . | . | . | 1.01 | 1.79 |
| Ala | 266 | . | A | B | . | . | . | . | 1.34 | −0.23 | . | . | F | 1.44 | 1.13 |
| Gln | 267 | . | . | B | . | . | T | . | 0.86 | −0.59 | . | . | F | 2.42 | 2.38 |
| Lys | 268 | . | . | . | . | T | T | . | 0.29 | −0.49 | * | . | F | 2.80 | 1.19 |
| Gly | 269 | . | . | . | . | T | T | . | 1.21 | 0.20 | * | . | F | 1.77 | 0.97 |

TABLE XIII-continued

| | | | | | | | | | | | | | | | |
|---|---|---|---|---|---|---|---|---|---|---|---|---|---|---|---|
| Gln | 270 | . | . | B | . | . | T | . | 0.40 | −0.30 | * | . | F | 1.84 | 1.10 |
| Phe | 271 | . | A | B | . | . | . | . | 0.18 | −0.01 | * | . | . | 0.86 | 0.45 |
| Leu | 272 | . | A | B | . | . | . | . | −0.49 | 0.67 | * | . | . | −0.32 | 0.38 |
| Arg | 273 | . | A | B | . | . | . | . | −1.12 | 0.81 | * | . | . | −0.60 | 0.12 |
| Leu | 274 | . | A | B | . | . | . | . | −1.37 | 0.91 | * | . | . | −0.60 | 0.14 |
| Leu | 275 | . | A | B | . | . | . | . | −1.37 | 0.63 | * | . | . | −0.60 | 0.17 |
| Cys | 276 | . | A | B | . | . | . | . | −0.97 | −0.06 | * | * | . | 0.54 | 0.14 |
| Ala | 277 | . | A | . | . | T | . | . | −0.16 | 0.33 | * | * | . | 0.58 | 0.23 |
| Ala | 278 | . | . | . | . | T | T | . | −0.48 | 0.04 | * | * | F | 1.37 | 0.49 |
| Asp | 279 | . | . | . | . | T | T | . | 0.12 | −0.21 | . | . | F | 2.36 | 1.40 |
| Ser | 280 | . | . | . | . | . | T | C | 0.34 | −0.36 | . | . | F | 2.40 | 2.15 |
| Gln | 281 | . | . | . | . | . | T | C | 0.70 | −0.36 | . | . | F | 2.16 | 2.15 |
| Pro | 282 | . | . | . | . | . | T | C | 0.48 | −0.37 | . | . | F | 1.92 | 1.85 |
| Pro | 283 | . | . | . | . | T | T | . | 0.77 | 0.31 | . | * | F | 1.28 | 1.14 |
| Ala | 284 | . | . | . | . | T | T | . | 0.48 | 0.31 | . | . | F | 0.89 | 0.88 |
| Thr | 285 | . | . | B | . | . | T | . | −0.08 | 0.83 | . | . | . | −0.20 | 0.60 |
| Leu | 286 | . | . | B | B | . | . | . | −0.89 | 1.04 | * | * | . | −0.60 | 0.29 |
| Ser | 287 | . | . | B | B | . | . | . | −0.68 | 1.30 | . | . | . | −0.60 | 0.24 |
| Trp | 288 | . | . | B | B | . | . | . | −0.47 | 1.20 | . | * | . | −0.60 | 0.28 |
| Val | 289 | . | . | B | B | . | . | . | 0.23 | 1.11 | . | * | . | −0.60 | 0.55 |
| Leu | 290 | . | . | B | B | . | . | . | −0.31 | 0.43 | . | * | . | −0.60 | 0.80 |
| Gln | 291 | . | . | B | B | . | . | . | −0.31 | 0.69 | . | * | F | −0.45 | 0.57 |
| Asn | 292 | . | . | B | B | . | . | . | −0.31 | 0.46 | . | * | F | −0.45 | 0.63 |
| Arg | 293 | . | . | B | B | . | . | . | −0.32 | 0.20 | . | * | F | 0.00 | 1.03 |
| Val | 294 | . | . | B | B | . | . | . | 0.23 | −0.10 | . | . | F | 0.45 | 0.79 |
| Leu | 295 | . | . | B | . | . | T | . | 1.01 | −0.11 | * | * | F | 0.85 | 0.66 |
| Ser | 296 | . | . | B | . | . | T | . | 0.80 | −0.01 | * | . | F | 0.85 | 0.46 |
| Ser | 297 | . | . | . | . | T | T | . | 0.51 | 0.41 | * | . | F | 0.35 | 0.96 |
| Ser | 298 | . | . | . | . | . | T | C | 0.06 | 0.69 | * | . | F | 0.30 | 1.22 |
| His | 299 | . | . | . | . | . | T | C | 0.70 | 0.43 | * | . | F | 0.15 | 0.90 |
| Pro | 300 | . | . | . | . | T | T | . | 1.62 | 0.47 | * | . | . | 0.35 | 1.04 |
| Trp | 301 | . | . | . | . | T | T | . | 1.71 | 0.09 | * | . | . | 0.65 | 1.52 |
| Gly | 302 | . | . | . | . | . | T | C | 1.20 | 0.13 | * | . | F | 0.60 | 1.73 |
| Pro | 303 | . | . | . | . | . | . | C | 1.16 | 0.31 | . | . | F | 0.25 | 0.92 |
| Arg | 304 | . | . | . | . | . | T | C | 0.38 | 0.31 | . | . | F | 0.45 | 0.87 |
| Pro | 305 | . | . | . | . | . | T | C | 0.59 | 0.09 | * | . | F | 0.45 | 0.72 |
| Leu | 306 | . | . | B | . | . | T | . | 0.07 | −0.34 | * | . | . | 0.70 | 0.81 |
| Gly | 307 | . | . | B | . | . | T | . | 0.20 | −0.09 | * | . | . | 0.70 | 0.34 |
| Leu | 308 | . | . | B | . | . | . | . | 0.07 | 0.34 | * | . | . | −0.10 | 0.34 |
| Glu | 309 | . | . | B | . | . | . | . | −0.90 | 0.34 | * | . | . | −0.10 | 0.41 |
| Leu | 310 | . | . | B | . | . | . | . | −0.64 | 0.30 | . | . | . | −0.10 | 0.31 |
| Pro | 311 | . | . | B | . | . | . | . | −0.42 | −0.13 | . | . | F | 0.65 | 0.74 |
| Gly | 312 | . | . | B | . | . | . | . | −0.42 | −0.31 | . | . | F | 0.65 | 0.43 |
| Val | 313 | . | . | B | . | . | . | . | 0.39 | 0.11 | * | . | F | 0.05 | 0.52 |
| Lys | 314 | . | . | B | . | . | . | . | 0.09 | −0.57 | . | . | F | 1.29 | 0.56 |
| Ala | 315 | . | . | B | . | . | . | . | 0.56 | −0.61 | * | * | F | 1.63 | 0.76 |
| Gly | 316 | . | . | . | . | T | . | . | 0.88 | −0.61 | * | * | F | 2.52 | 1.02 |
| Asp | 317 | . | . | . | . | T | T | . | 0.98 | −1.26 | * | * | F | 2.91 | 0.99 |
| Ser | 318 | . | . | . | . | T | T | . | 1.52 | −0.50 | * | * | F | 3.40 | 1.54 |
| Gly | 319 | . | . | . | . | T | T | . | 0.81 | −0.51 | * | * | F | 3.06 | 2.25 |
| Arg | 320 | . | . | B | . | . | T | . | 1.51 | −0.37 | * | * | F | 1.87 | 0.72 |
| Tyr | 321 | . | . | B | B | . | . | . | 1.27 | −0.37 | * | * | F | 1.28 | 1.05 |
| Thr | 322 | . | . | B | B | . | . | . | 1.27 | −0.26 | * | * | . | 0.79 | 1.08 |
| Cys | 323 | . | . | B | B | . | . | . | 1.57 | −0.69 | * | * | . | 0.94 | 0.95 |
| Arg | 324 | . | . | B | B | . | . | . | 2.02 | −0.29 | * | * | . | 0.98 | 0.98 |
| Ala | 325 | . | . | B | . | . | . | . | 1.10 | −1.04 | * | * | F | 2.12 | 1.33 |
| Glu | 326 | . | . | B | . | . | . | . | 1.00 | −0.84 | * | * | F | 2.46 | 2.04 |
| Asn | 327 | . | . | . | . | T | T | . | 1.01 | −0.99 | * | * | F | 3.40 | 1.03 |
| Arg | 328 | . | . | . | . | T | T | . | 1.68 | −0.60 | * | * | F | 3.06 | 1.37 |
| Leu | 329 | . | . | . | . | T | T | . | 1.57 | −0.70 | * | * | F | 2.72 | 1.37 |
| Gly | 330 | . | . | . | . | T | T | . | 2.27 | −0.30 | * | * | F | 2.08 | 1.47 |
| Ser | 331 | . | . | . | . | . | . | C | 1.68 | −0.70 | * | * | F | 1.64 | 1.47 |
| Gln | 332 | . | A | B | . | . | . | . | 0.87 | −0.20 | * | * | F | 0.60 | 1.80 |
| Gln | 333 | . | A | B | . | . | . | . | 0.76 | −0.20 | . | * | F | 0.60 | 1.50 |
| Arg | 334 | . | A | B | . | . | . | . | 0.76 | −0.63 | * | . | F | 0.90 | 1.87 |
| Ala | 335 | . | A | B | . | . | . | . | 0.80 | −0.33 | * | . | F | 0.45 | 0.89 |
| Leu | 336 | . | A | B | . | . | . | . | 0.24 | −0.34 | * | * | . | 0.30 | 0.69 |
| Asp | 337 | . | A | B | . | . | . | . | 0.24 | −0.10 | * | * | . | 0.30 | 0.26 |
| Leu | 338 | . | A | B | . | . | . | . | 0.00 | 0.30 | * | * | . | −0.30 | 0.45 |
| Ser | 339 | . | . | B | . | . | . | . | −0.32 | 0.56 | * | * | . | −0.40 | 0.85 |
| Val | 340 | . | . | B | . | . | . | . | 0.06 | 0.30 | * | * | . | −0.10 | 0.79 |
| Gln | 341 | . | . | B | . | . | . | . | 0.87 | 0.73 | . | * | . | −0.25 | 1.48 |
| Tyr | 342 | . | . | B | . | . | . | . | 0.87 | 0.04 | . | * | . | 0.25 | 1.91 |
| Pro | 343 | . | . | . | . | . | T | C | 0.87 | 0.06 | * | * | F | 1.00 | 4.14 |
| Pro | 344 | . | . | . | . | . | T | C | 1.28 | 0.10 | * | * | F | 1.20 | 1.97 |
| Glu | 345 | . | . | . | . | T | T | . | 1.28 | −0.30 | * | * | F | 2.20 | 2.47 |
| Asn | 346 | . | . | B | . | . | T | . | 0.68 | −0.41 | * | * | F | 2.00 | 1.18 |
| Leu | 347 | . | . | B | B | . | . | . | 0.07 | −0.23 | * | * | . | 1.10 | 0.76 |
| Arg | 348 | . | . | B | B | . | . | . | −0.02 | −0.01 | * | * | . | 0.90 | 0.32 |

TABLE XIII-continued

| | | | | | | | | | | | | | | | |
|---|---|---|---|---|---|---|---|---|---|---|---|---|---|---|---|
| Val | 349 | . | . | B | B | . | . | . | 0.19 | 0.37 | * | * | . | 0.10 | 0.27 |
| Met | 350 | . | . | B | B | . | . | . | −0.40 | 0.37 | * | * | . | −0.10 | 0.57 |
| Val | 351 | . | . | B | B | . | . | . | −0.40 | 0.19 | * | * | . | −0.30 | 0.29 |
| Ser | 352 | . | . | B | . | . | . | . | 0.52 | 0.59 | * | * | . | −0.40 | 0.63 |
| Gln | 353 | . | . | B | . | . | . | . | 0.10 | −0.06 | * | * | F | 0.80 | 1.26 |
| Ala | 354 | . | . | B | . | . | . | . | 0.10 | −0.19 | * | . | F | 0.80 | 2.44 |
| Asn | 355 | . | . | B | . | . | . | . | −0.11 | −0.19 | * | . | F | 0.80 | 1.35 |
| Arg | 356 | . | . | B | . | . | . | . | 0.74 | 0.11 | * | . | F | 0.05 | 0.64 |
| Thr | 357 | . | . | B | . | . | . | . | 1.04 | −0.29 | * | . | F | 0.80 | 1.10 |
| Val | 358 | . | . | B | . | . | . | . | 0.23 | −0.39 | * | . | . | 0.65 | 1.10 |
| Leu | 359 | . | . | B | . | . | . | . | 0.48 | −0.10 | * | . | . | 0.50 | 0.47 |
| Glu | 360 | . | . | B | . | . | . | . | 0.48 | 0.33 | * | . | . | 0.03 | 0.32 |
| Asn | 361 | . | . | B | . | . | . | . | 0.02 | 0.24 | * | . | F | 0.31 | 0.69 |
| Leu | 362 | . | . | . | . | T | T | . | 0.02 | 0.03 | * | . | F | 1.04 | 0.83 |
| Gly | 363 | . | . | . | . | T | T | . | 0.58 | −0.17 | * | . | F | 1.77 | 0.69 |
| Asn | 364 | . | . | . | . | T | T | . | 0.58 | 0.21 | * | . | F | 1.30 | 0.58 |
| Gly | 365 | . | . | . | . | . | T | C | 0.37 | 0.50 | * | . | F | 0.67 | 0.58 |
| Thr | 366 | . | . | . | . | . | . | C | −0.49 | 0.24 | . | . | F | 0.64 | 0.90 |
| Ser | 367 | . | . | B | . | . | . | . | −0.49 | 0.46 | . | . | F | 0.01 | 0.42 |
| Leu | 368 | . | . | B | . | . | . | . | −0.14 | 0.74 | . | . | . | −0.27 | 0.35 |
| Pro | 369 | . | . | B | . | . | . | . | −0.49 | 0.31 | . | . | . | −0.10 | 0.42 |
| Val | 370 | . | . | B | . | . | . | . | −0.14 | 0.26 | . | . | . | −0.10 | 0.31 |
| Leu | 371 | . | . | B | . | . | . | . | −0.13 | 0.27 | . | . | F | 0.05 | 0.64 |
| Glu | 372 | . | . | B | . | . | . | . | −0.64 | −0.03 | . | . | F | 0.65 | 0.56 |
| Gly | 373 | . | . | . | . | T | T | . | −0.50 | 0.23 | . | . | F | 0.65 | 0.62 |
| Gln | 374 | . | . | . | . | T | T | . | −1.10 | 0.16 | . | . | F | 0.65 | 0.40 |
| Ser | 375 | . | . | . | . | T | T | . | −1.10 | 0.16 | . | . | F | 0.65 | 0.19 |
| Leu | 376 | . | . | B | . | . | T | . | −0.96 | 0.80 | . | . | . | −0.20 | 0.14 |
| Cys | 377 | . | . | B | B | . | . | . | −1.81 | 0.94 | . | . | . | −0.60 | 0.04 |
| Leu | 378 | . | . | B | B | . | . | . | −1.78 | 1.19 | . | . | . | −0.60 | 0.02 |
| Val | 379 | . | . | B | B | . | . | . | −1.81 | 1.29 | . | . | . | −0.60 | 0.04 |
| Cys | 380 | . | . | B | B | . | . | . | −1.81 | 1.10 | . | . | . | −0.60 | 0.11 |
| Val | 381 | . | . | B | B | . | . | . | −1.30 | 0.91 | . | . | . | −0.60 | 0.18 |
| Thr | 382 | . | . | B | B | . | . | . | −0.84 | 0.61 | . | . | . | −0.60 | 0.32 |
| His | 383 | . | . | . | . | T | T | . | −0.24 | 0.40 | . | . | F | 0.89 | 0.93 |
| Ser | 384 | . | . | . | . | . | T | C | 0.02 | 0.26 | * | * | F | 1.08 | 1.93 |
| Ser | 385 | . | . | . | . | . | T | C | 0.80 | 0.11 | * | * | F | 1.32 | 1.35 |
| Pro | 386 | . | . | . | . | . | T | C | 0.84 | −0.37 | . | * | F | 2.16 | 1.95 |
| Pro | 387 | . | . | . | . | T | . | . | 0.86 | −0.19 | . | * | F | 2.40 | 1.20 |
| Ala | 388 | . | . | . | . | T | . | . | 0.60 | −0.19 | . | * | F | 2.16 | 1.20 |
| Arg | 389 | . | . | B | B | . | . | . | 0.59 | 0.34 | . | * | . | 0.42 | 0.82 |
| Leu | 390 | . | . | B | B | . | . | . | 0.89 | 0.40 | . | * | . | 0.18 | 0.76 |
| Ser | 391 | . | . | B | B | . | . | . | 1.21 | 0.37 | . | * | . | 0.09 | 1.30 |
| Trp | 392 | . | . | B | B | . | . | . | 1.08 | −0.13 | . | * | . | 0.45 | 1.30 |
| Thr | 393 | . | . | B | B | . | . | . | 1.67 | 0.30 | . | * | F | 0.00 | 1.56 |
| Gln | 394 | . | . | B | . | . | T | . | 0.70 | 0.01 | . | * | F | 0.40 | 2.02 |
| Arg | 395 | . | . | B | . | . | T | . | 0.70 | 0.27 | . | * | F | 0.40 | 1.43 |
| Gly | 396 | . | . | . | . | T | T | . | 0.70 | 0.04 | . | * | F | 0.65 | 0.82 |
| Gln | 397 | . | . | B | . | . | T | . | 0.78 | −0.06 | . | * | F | 0.85 | 0.63 |
| Val | 398 | . | . | B | . | . | . | . | 0.79 | −0.03 | . | . | F | 0.65 | 0.50 |
| Leu | 399 | . | . | B | . | . | . | . | 0.79 | 0.36 | . | . | F | 0.05 | 0.67 |
| Ser | 400 | . | . | B | . | . | T | . | 0.47 | 0.33 | . | * | F | 0.55 | 0.67 |
| Pro | 401 | . | . | . | . | T | T | . | 0.51 | 0.36 | . | . | F | 1.40 | 1.41 |
| Ser | 402 | . | . | . | . | T | T | . | 0.51 | 0.10 | . | . | F | 1.70 | 2.28 |
| Gln | 403 | . | . | . | . | . | T | C | 1.16 | −0.59 | . | . | F | 2.70 | 2.85 |
| Pro | 404 | . | . | . | . | T | . | . | 1.62 | −0.54 | . | . | F | 3.00 | 2.85 |
| Ser | 405 | . | . | . | . | . | . | C | 1.07 | −0.54 | . | . | F | 2.50 | 2.10 |
| Asp | 406 | . | . | . | . | . | T | C | 0.47 | −0.29 | . | . | F | 1.95 | 0.90 |
| Pro | 407 | . | . | B | . | . | T | . | 0.77 | 0.00 | . | . | F | 1.45 | 0.48 |
| Gly | 408 | . | . | B | . | . | T | . | −0.04 | −0.43 | . | . | F | 1.15 | 0.62 |
| Val | 409 | . | . | B | . | . | T | . | −0.04 | −0.13 | * | . | . | 0.70 | 0.31 |
| Leu | 410 | . | . | B | . | . | . | . | 0.37 | 0.30 | * | . | . | −0.10 | 0.31 |
| Glu | 411 | . | . | B | . | . | . | . | −0.49 | −0.13 | * | . | . | 0.50 | 0.61 |
| Leu | 412 | . | . | B | B | . | . | . | −0.28 | 0.09 | * | * | . | −0.30 | 0.61 |
| Pro | 413 | . | . | B | B | . | . | . | −0.79 | −0.16 | * | * | F | 0.60 | 1.27 |
| Arg | 414 | . | A | B | B | . | . | . | 0.07 | −0.20 | * | * | . | 0.30 | 0.55 |
| Val | 415 | . | A | B | B | . | . | . | 0.84 | −0.20 | . | * | . | 0.45 | 1.15 |
| Gln | 416 | . | A | B | B | . | . | . | 0.84 | −0.39 | . | * | . | 0.45 | 1.01 |
| Val | 417 | . | A | B | B | . | . | . | 1.31 | −0.81 | . | * | . | 0.60 | 0.89 |
| Glu | 418 | . | A | B | B | . | . | . | 1.52 | −0.39 | . | * | . | 0.45 | 1.19 |
| His | 419 | . | A | . | . | . | . | C | 0.71 | −1.03 | . | * | F | 1.10 | 1.19 |
| Glu | 420 | . | A | . | . | T | . | . | 1.26 | −0.64 | . | * | F | 1.30 | 1.39 |
| Gly | 421 | . | A | . | . | T | . | . | 0.59 | −0.80 | . | * | F | 1.30 | 1.16 |
| Glu | 422 | . | A | . | . | T | . | . | 1.41 | −0.23 | * | * | F | 0.85 | 0.46 |
| Phe | 423 | . | A | . | . | T | . | . | 0.82 | −0.23 | * | * | . | 0.70 | 0.36 |
| Thr | 424 | A | A | . | . | . | . | . | 0.97 | 0.27 | . | * | . | −0.30 | 0.37 |
| Cys | 425 | . | A | . | . | T | . | . | 0.93 | −0.16 | * | * | . | 0.70 | 0.41 |
| His | 426 | . | A | B | . | . | . | . | 1.07 | 0.34 | * | * | . | −0.30 | 0.65 |
| Ala | 427 | . | A | . | . | T | . | . | 0.26 | −0.01 | * | * | . | 0.95 | 0.70 |

TABLE XIII-continued

| | | | | | | | | | | | | | | | |
|---|---|---|---|---|---|---|---|---|---|---|---|---|---|---|---|
| Arg | 428 | . | A | . | . | . | . | C | 0.61 | 0.19 | * | * | . | 0.55 | 1.07 |
| His | 429 | . | . | . | . | . | T | C | 0.62 | 0.04 | . | * | . | 1.05 | 0.78 |
| Pro | 430 | . | . | . | . | T | T | . | 1.29 | −0.07 | . | * | . | 2.25 | 1.03 |
| Leu | 431 | . | . | . | . | T | T | . | 1.29 | −0.17 | . | * | F | 2.50 | 0.91 |
| Gly | 432 | . | . | . | . | T | T | . | 1.02 | 0.33 | . | * | F | 1.65 | 0.91 |
| Ser | 433 | . | . | B | B | . | . | . | 0.61 | 0.47 | . | * | F | 0.30 | 0.44 |
| Gln | 434 | . | . | B | B | . | . | . | −0.17 | 0.43 | . | . | F | 0.05 | 0.71 |
| His | 435 | . | . | B | B | . | . | . | −0.26 | 0.43 | . | * | . | −0.35 | 0.59 |
| Val | 436 | . | . | B | B | . | . | . | −0.26 | 0.39 | . | * | . | −0.30 | 0.59 |
| Ser | 437 | . | . | B | B | . | . | . | −0.21 | 0.69 | . | * | . | −0.60 | 0.28 |
| Leu | 438 | . | . | B | B | . | . | . | −0.77 | 0.67 | . | * | . | −0.60 | 0.28 |
| Ser | 439 | . | . | B | B | . | . | . | −0.80 | 0.81 | . | * | . | −0.60 | 0.28 |
| Leu | 440 | . | . | B | B | . | . | . | −1.01 | 0.67 | . | * | . | −0.60 | 0.28 |
| Ser | 441 | . | . | B | B | . | . | . | −0.46 | 1.04 | . | * | . | −0.60 | 0.54 |
| Val | 442 | . | . | B | B | . | . | . | −0.37 | 0.74 | . | * | . | −0.60 | 0.54 |
| His | 443 | . | . | B | B | . | . | . | 0.49 | 0.79 | * | * | . | −0.45 | 1.01 |
| Tyr | 444 | . | . | B | B | . | . | . | −0.02 | 0.10 | * | * | . | −0.15 | 1.50 |
| Ser | 445 | . | . | B | . | . | T | . | −0.02 | 0.40 | . | * | . | 0.25 | 1.67 |
| Pro | 446 | . | . | B | . | . | T | . | −0.07 | 0.44 | * | * | F | 0.10 | 1.01 |
| Lys | 447 | . | . | . | . | T | T | . | 0.58 | 0.37 | * | * | F | 0.65 | 0.64 |
| Leu | 448 | . | . | . | . | T | T | . | 0.31 | 0.04 | * | . | F | 0.65 | 0.74 |
| Leu | 449 | . | . | B | . | . | . | . | −0.11 | 0.04 | . | . | F | 0.05 | 0.64 |
| Gly | 450 | . | . | . | . | . | T | C | −0.11 | 0.19 | . | . | F | 0.45 | 0.17 |
| Pro | 451 | . | . | . | . | . | T | C | −0.19 | 0.57 | . | . | F | 0.15 | 0.28 |
| Ser | 452 | . | . | . | . | . | T | C | −0.23 | 0.80 | . | . | F | 0.15 | 0.36 |
| Cys | 453 | . | . | . | . | . | T | C | −0.01 | 0.11 | . | * | . | 0.30 | 0.62 |
| Ser | 454 | . | A | . | . | . | . | C | 0.80 | 0.19 | . | * | . | −0.10 | 0.41 |
| Trp | 455 | . | A | B | . | . | . | . | 0.80 | −0.24 | . | . | . | 0.30 | 0.52 |
| Glu | 456 | . | A | B | . | . | . | . | 0.20 | −0.20 | . | . | . | 0.30 | 0.97 |
| Ala | 457 | . | A | . | . | T | . | . | 0.47 | −0.09 | . | . | . | 0.70 | 0.60 |
| Glu | 458 | . | A | . | . | T | . | . | 0.47 | 0.03 | . | . | F | 0.10 | 0.77 |
| Gly | 459 | . | A | . | . | T | . | . | 0.47 | −0.31 | . | . | . | 0.70 | 0.24 |
| Leu | 460 | . | A | . | . | T | . | . | 0.09 | 0.07 | . | . | . | 0.10 | 0.32 |
| His | 461 | . | A | . | . | T | . | . | −0.21 | 0.14 | . | . | . | 0.10 | 0.10 |
| Cys | 462 | . | . | . | . | T | T | . | 0.08 | 0.53 | . | . | . | 0.20 | 0.13 |
| Ser | 463 | . | . | . | . | T | T | . | 0.08 | 0.49 | . | . | . | 0.20 | 0.22 |
| Cys | 464 | . | . | . | . | T | T | . | −0.17 | 0.20 | . | . | . | 0.50 | 0.27 |
| Ser | 465 | . | . | . | . | T | T | . | 0.34 | 0.20 | . | * | F | 0.65 | 0.52 |
| Ser | 466 | . | . | . | . | T | . | . | 0.17 | 0.01 | . | . | F | 0.45 | 0.52 |
| Gln | 467 | . | . | . | . | T | . | . | 0.24 | 0.06 | . | . | F | 0.60 | 1.49 |
| Ala | 468 | . | . | . | . | . | . | C | 0.33 | −0.01 | . | . | F | 1.24 | 1.13 |
| Ser | 469 | . | . | . | . | . | . | C | 0.70 | 0.03 | . | . | F | 0.88 | 1.30 |
| Pro | 470 | . | . | . | . | . | . | C | 0.19 | 0.03 | . | * | F | 1.12 | 1.00 |
| Ala | 471 | . | . | . | . | . | T | C | 0.60 | 0.31 | . | * | F | 1.41 | 0.82 |
| Pro | 472 | . | . | . | . | . | T | C | 0.31 | −0.19 | * | * | F | 2.40 | 1.20 |
| Ser | 473 | . | . | . | . | . | T | C | 0.61 | 0.34 | * | * | F | 1.41 | 0.82 |
| Leu | 474 | . | . | B | . | . | T | . | 0.10 | 0.83 | * | * | . | 0.52 | 0.85 |
| Arg | 475 | . | . | B | B | . | . | . | −0.03 | 1.01 | * | * | . | −0.12 | 0.45 |
| Trp | 476 | . | . | B | B | . | . | . | 0.56 | 1.01 | . | * | . | −0.36 | 0.33 |
| Trp | 477 | . | A | . | B | . | . | C | 0.77 | 0.63 | . | * | . | −0.40 | 0.70 |
| Leu | 478 | . | A | . | B | . | . | C | 0.26 | −0.06 | . | * | . | 0.50 | 0.62 |
| Gly | 479 | . | A | . | B | . | . | C | 0.26 | 0.63 | . | * | . | −0.40 | 0.49 |
| Glu | 480 | . | A | B | . | . | . | . | 0.14 | 0.40 | . | * | F | −0.15 | 0.38 |
| Glu | 481 | . | A | B | . | . | . | . | 0.09 | −0.51 | . | . | F | 0.75 | 0.80 |
| Leu | 482 | . | A | . | . | . | . | C | 0.38 | −0.77 | * | . | F | 0.95 | 0.80 |
| Leu | 483 | . | A | . | . | . | . | C | 0.89 | −0.80 | * | . | F | 1.25 | 0.74 |
| Glu | 484 | . | A | . | . | T | . | . | 0.93 | −0.41 | . | . | F | 1.45 | 0.58 |
| Gly | 485 | . | A | . | . | T | . | . | 0.93 | −0.03 | . | . | F | 1.75 | 0.94 |
| Asn | 486 | . | . | . | . | T | T | . | 0.93 | −0.31 | . | . | F | 2.60 | 1.97 |
| Ser | 487 | . | . | . | . | . | T | C | 1.44 | −1.00 | . | . | F | 3.00 | 1.89 |
| Ser | 488 | . | . | . | . | . | T | C | 1.56 | −0.61 | . | * | F | 2.70 | 2.57 |
| Gln | 489 | . | . | . | . | . | T | C | 1.56 | −0.26 | . | * | F | 2.10 | 1.38 |
| Asp | 490 | . | A | . | . | . | . | C | 1.04 | −0.66 | * | . | F | 1.70 | 1.79 |
| Ser | 491 | . | A | B | . | . | . | . | 0.73 | −0.40 | * | . | F | 0.75 | 0.99 |
| Phe | 492 | . | A | B | . | . | . | . | 0.82 | −0.30 | . | * | . | 0.30 | 0.82 |
| Glu | 493 | . | A | B | . | . | . | . | 0.82 | −0.27 | . | . | . | 0.43 | 0.76 |
| Val | 494 | . | A | B | . | . | . | . | 0.52 | 0.11 | * | . | F | 0.11 | 0.76 |
| Thr | 495 | . | . | B | . | . | T | . | −0.07 | 0.11 | . | . | F | 0.79 | 1.18 |
| Pro | 496 | . | . | . | . | . | T | C | −0.11 | −0.17 | . | * | F | 1.57 | 0.69 |
| Ser | 497 | . | . | . | . | T | T | . | 0.38 | 0.26 | . | . | F | 1.30 | 0.92 |
| Ser | 498 | . | . | . | . | . | T | C | 0.09 | 0.04 | . | . | F | 0.97 | 0.98 |
| Ala | 499 | . | . | . | . | . | . | C | 0.36 | 0.47 | . | . | F | 0.34 | 0.67 |
| Gly | 500 | . | . | . | . | . | T | C | 0.67 | 0.54 | . | . | F | 0.41 | 0.50 |
| Pro | 501 | . | . | . | . | T | T | . | 0.58 | 0.56 | . | . | F | 0.48 | 0.61 |
| Trp | 502 | . | . | . | . | . | T | C | 0.58 | 0.56 | * | . | F | 0.15 | 0.80 |
| Ala | 503 | . | . | B | . | . | T | . | 0.07 | 0.44 | * | . | F | 0.10 | 1.09 |
| Asn | 504 | . | . | B | . | . | T | . | 0.36 | 0.70 | . | . | F | −0.05 | 0.58 |
| Ser | 505 | . | . | B | . | . | T | . | −0.11 | 0.66 | . | * | F | −0.05 | 0.74 |
| Ser | 506 | . | . | B | . | . | T | . | 0.07 | 0.43 | . | * | F | −0.05 | 0.60 |

TABLE XIII-continued

| | | | | | | | | | | | | | | | |
|---|---|---|---|---|---|---|---|---|---|---|---|---|---|---|---|
| Leu | 507 | . | . | B | . | . | T | . | 0.01 | 0.43 | . | * | . | −0.20 | 0.51 |
| Ser | 508 | . | . | B | . | . | . | . | 0.26 | 0.46 | . | * | . | −0.40 | 0.38 |
| Leu | 509 | . | . | B | . | . | T | . | −0.56 | 0.50 | . | * | . | −0.20 | 0.28 |
| His | 510 | . | . | B | . | . | T | . | −0.56 | 0.80 | . | * | . | −0.20 | 0.28 |
| Gly | 511 | . | . | . | . | T | T | . | −0.56 | 0.50 | . | * | . | 0.20 | 0.28 |
| Gly | 512 | . | . | . | . | . | T | C | −0.09 | 0.50 | . | * | F | 0.15 | 0.45 |
| Leu | 513 | . | . | . | . | . | . | C | −0.60 | 0.24 | * | * | F | 0.39 | 0.33 |
| Ser | 514 | . | . | . | . | . | T | C | 0.32 | 0.43 | * | * | F | 0.43 | 0.27 |
| Ser | 515 | . | . | . | . | T | T | . | −0.46 | 0.00 | . | * | F | 1.67 | 0.54 |
| Gly | 516 | . | . | B | . | . | T | . | 0.00 | 0.26 | . | * | F | 0.81 | 0.54 |
| Leu | 517 | . | . | B | . | . | T | . | −0.32 | −0.43 | * | * | . | 1.40 | 0.79 |
| Arg | 518 | . | A | B | . | . | . | . | 0.49 | −0.24 | * | * | . | 0.86 | 0.32 |
| Leu | 519 | . | A | B | . | . | . | . | 0.20 | −0.63 | * | * | . | 1.02 | 0.56 |
| Arg | 520 | . | A | B | . | . | . | . | 0.21 | −0.56 | * | * | . | 0.88 | 0.68 |
| Cys | 521 | . | A | B | . | . | . | . | 0.56 | −0.33 | * | * | . | 0.44 | 0.37 |
| Glu | 522 | . | A | B | . | . | . | . | 0.51 | 0.07 | . | * | . | −0.30 | 0.71 |
| Ala | 523 | . | A | . | . | T | . | . | 0.37 | 0.03 | * | * | . | 0.10 | 0.27 |
| Trp | 524 | . | A | . | . | T | . | . | 0.83 | 0.53 | * | * | . | −0.20 | 0.68 |
| Asn | 525 | . | . | B | . | . | T | . | 0.13 | 0.39 | . | . | . | 0.10 | 0.39 |
| Val | 526 | . | . | B | . | . | T | . | 0.80 | 0.89 | . | . | . | −0.20 | 0.39 |
| His | 527 | . | . | . | . | . | T | C | 0.50 | 0.79 | . | . | . | 0.00 | 0.64 |
| Gly | 528 | . | . | . | . | . | T | C | 0.74 | 0.26 | . | . | . | 0.30 | 0.54 |
| Ala | 529 | . | . | . | . | . | . | C | 0.73 | 0.29 | . | . | F | 0.25 | 0.72 |
| Gln | 530 | . | . | . | . | . | T | C | −0.16 | 0.03 | . | . | F | 0.45 | 0.71 |
| Ser | 531 | . | . | . | . | . | T | C | −0.11 | 0.21 | . | . | F | 0.45 | 0.50 |
| Gly | 532 | . | . | B | . | . | T | . | −0.08 | 0.47 | . | . | F | −0.05 | 0.41 |
| Ser | 533 | . | . | B | . | . | T | . | −0.54 | 0.37 | . | . | F | 0.25 | 0.41 |
| Ile | 534 | . | . | B | . | . | . | . | −0.17 | 0.66 | . | . | . | −0.40 | 0.25 |
| Leu | 535 | . | . | B | . | . | . | . | −0.17 | 0.70 | * | . | . | −0.06 | 0.39 |
| Gln | 536 | . | . | B | . | . | . | . | 0.18 | 0.27 | * | . | . | 0.58 | 0.49 |
| Leu | 537 | . | . | B | . | . | T | . | 0.57 | −0.11 | * | . | . | 1.87 | 1.39 |
| Pro | 538 | . | . | B | . | . | T | . | 0.52 | −0.80 | * | . | F | 2.66 | 3.38 |
| Asp | 539 | . | . | . | . | T | T | . | 0.60 | −1.06 | . | . | F | 3.40 | 1.93 |
| Lys | 540 | . | . | . | . | T | T | . | 0.52 | −0.77 | . | . | F | 3.06 | 1.93 |
| Lys | 541 | . | . | . | B | T | . | . | 0.22 | −0.77 | . | . | F | 2.17 | 0.88 |
| Gly | 542 | . | . | B | B | . | . | . | 0.72 | −0.81 | . | . | F | 1.43 | 0.70 |
| Leu | 543 | . | . | B | B | . | . | . | 0.34 | −0.33 | . | . | F | 0.79 | 0.51 |
| Ile | 544 | . | . | B | B | . | . | . | −0.36 | 0.17 | . | . | . | −0.30 | 0.26 |
| Ser | 545 | . | . | B | B | . | . | . | −0.70 | 0.96 | . | . | . | −0.60 | 0.22 |
| Thr | 546 | . | . | B | B | . | . | . | −0.74 | 0.91 | * | . | . | −0.60 | 0.36 |
| Ala | 547 | . | . | B | B | . | . | . | −0.74 | 0.63 | * | . | . | −0.60 | 0.84 |
| Phe | 548 | . | . | B | . | . | T | . | −0.52 | 0.37 | . | . | F | 0.25 | 0.62 |
| Ser | 549 | . | . | . | . | . | T | C | −0.33 | 0.49 | * | . | F | 0.15 | 0.43 |
| Asn | 550 | . | . | . | . | . | T | C | −0.84 | 0.79 | . | . | F | 0.15 | 0.37 |
| Gly | 551 | . | . | . | . | . | T | C | −0.88 | 0.97 | . | . | F | 0.15 | 0.35 |
| Ala | 552 | . | . | . | B | . | . | C | −1.18 | 0.61 | . | . | . | −0.40 | 0.26 |
| Phe | 553 | . | . | B | B | . | . | . | −0.82 | 0.91 | . | . | . | −0.60 | 0.11 |
| Leu | 554 | . | . | B | B | . | . | . | −1.41 | 0.94 | . | . | . | −0.60 | 0.11 |
| Gly | 555 | . | . | B | B | . | . | . | −1.72 | 1.20 | . | . | . | −0.60 | 0.08 |
| Ile | 556 | . | . | B | B | . | . | . | −1.97 | 1.19 | . | . | . | −0.60 | 0.13 |
| Gly | 557 | . | . | B | B | . | . | . | −2.19 | 0.90 | . | . | . | −0.60 | 0.16 |
| Ile | 558 | . | A | B | . | . | . | . | −2.30 | 0.90 | . | . | . | −0.60 | 0.13 |
| Thr | 559 | . | A | B | . | . | . | . | −2.19 | 1.16 | . | . | . | −0.60 | 0.16 |
| Ala | 560 | . | A | B | . | . | . | . | −2.66 | 1.26 | . | . | . | −0.60 | 0.14 |
| Leu | 561 | . | A | B | . | . | . | . | −2.43 | 1.51 | . | . | . | −0.60 | 0.16 |
| Leu | 562 | . | A | B | . | . | . | . | −2.90 | 1.40 | . | . | . | −0.60 | 0.06 |
| Phe | 563 | . | A | B | . | . | . | . | −2.60 | 1.60 | . | . | . | −0.60 | 0.05 |
| Leu | 564 | . | A | B | . | . | . | . | −3.10 | 1.60 | . | . | . | −0.60 | 0.06 |
| Cys | 565 | A | A | . | . | . | . | . | −3.40 | 1.60 | . | . | . | −0.60 | 0.06 |
| Leu | 566 | A | A | . | . | . | . | . | −3.48 | 1.60 | . | . | . | −0.60 | 0.05 |
| Ala | 567 | A | A | . | . | . | . | . | −3.27 | 1.50 | * | . | . | −0.60 | 0.04 |
| Leu | 568 | A | A | . | . | . | . | . | −2.52 | 1.43 | * | . | . | −0.60 | 0.08 |
| Ile | 569 | . | A | B | . | . | . | . | −2.60 | 0.86 | * | . | . | −0.60 | 0.19 |
| Ile | 570 | . | A | B | . | . | . | . | −2.74 | 0.86 | * | . | . | −0.60 | 0.13 |
| Met | 571 | . | A | B | . | . | . | . | −2.14 | 1.04 | * | . | . | −0.60 | 0.13 |
| Lys | 572 | . | A | B | . | . | . | . | −1.51 | 0.79 | * | . | . | −0.26 | 0.28 |
| Ile | 573 | . | A | B | . | . | . | . | −0.59 | 0.10 | . | . | . | 0.38 | 0.81 |
| Leu | 574 | . | A | B | . | . | . | . | 0.41 | −0.59 | . | * | . | 1.77 | 1.61 |
| Pro | 575 | . | . | . | . | . | T | C | 0.99 | −1.20 | . | . | F | 2.86 | 1.57 |
| Lys | 576 | . | . | . | . | T | T | . | 1.59 | −0.71 | . | * | F | 3.40 | 3.24 |
| Arg | 577 | . | . | . | . | T | T | . | 1.23 | −1.00 | . | * | F | 3.06 | 6.80 |
| Arg | 578 | . | . | . | . | T | T | . | 2.12 | −1.20 | . | . | F | 2.72 | 6.34 |
| Thr | 579 | . | . | . | . | T | . | . | 2.62 | −1.63 | . | . | F | 2.18 | 5.49 |
| Gln | 580 | . | . | B | . | . | . | . | 2.62 | −1.14 | * | . | F | 1.44 | 4.05 |
| Thr | 581 | . | . | B | . | . | . | . | 2.69 | −0.71 | * | . | F | 1.10 | 3.20 |
| Glu | 582 | . | . | B | . | . | . | . | 2.37 | −0.71 | * | * | F | 1.10 | 4.34 |
| Thr | 583 | . | . | B | . | . | T | . | 2.37 | −0.77 | . | * | F | 1.30 | 3.87 |
| Pro | 584 | . | . | . | . | . | T | C | 1.98 | −1.17 | . | * | F | 1.50 | 5.26 |
| Arg | 585 | . | . | . | . | . | T | C | 1.68 | −0.87 | * | * | F | 1.84 | 2.63 |

TABLE XIII-continued

| | | | | | | | | | | | | | | | |
|---|---|---|---|---|---|---|---|---|---|---|---|---|---|---|---|
| Pro | 586 | . | . | . | . | T | T | . | 2.10 | −0.49 | * | * | F | 2.08 | 2.44 |
| Arg | 587 | . | . | . | . | T | . | . | 2.07 | −0.97 | * | * | F | 2.52 | 3.09 |
| Phe | 588 | . | . | . | . | T | . | . | 2.08 | −0.90 | * | * | F | 2.86 | 2.15 |
| Ser | 589 | . | . | . | . | T | T | . | 1.98 | −0.51 | . | * | F | 3.40 | 1.86 |
| Arg | 590 | . | . | B | . | . | T | . | 0.98 | −0.46 | * | * | F | 2.36 | 1.37 |
| His | 591 | . | . | B | . | . | T | . | 0.38 | 0.23 | * | . | F | 1.42 | 1.11 |
| Ser | 592 | . | . | B | . | . | T | . | 0.27 | 0.13 | * | . | F | 0.93 | 0.68 |
| Thr | 593 | . | . | B | B | . | . | . | 0.72 | −0.26 | * | . | . | 0.64 | 0.58 |
| Ile | 594 | . | . | B | B | . | . | . | 0.13 | 0.50 | * | . | . | −0.60 | 0.67 |
| Leu | 595 | . | . | B | B | . | . | . | 0.02 | 0.69 | . | * | . | −0.60 | 0.35 |
| Asp | 596 | . | . | B | B | . | . | . | −0.80 | 0.70 | * | . | . | −0.60 | 0.39 |
| Tyr | 597 | . | . | B | B | . | . | . | −1.36 | 0.86 | * | . | . | −0.60 | 0.41 |
| Ile | 598 | . | . | B | B | . | . | . | −1.26 | 0.81 | * | . | . | −0.60 | 0.37 |
| Asn | 599 | . | . | B | B | . | . | . | −0.68 | 0.56 | * | . | . | −0.60 | 0.34 |
| Val | 600 | . | . | B | B | . | . | . | −0.46 | 1.04 | * | . | . | −0.60 | 0.32 |
| Val | 601 | . | . | B | B | . | . | . | −0.80 | 0.79 | * | . | . | −0.60 | 0.46 |
| Pro | 602 | . | . | B | . | . | . | . | −0.77 | 0.53 | * | . | F | −0.25 | 0.28 |
| Thr | 603 | . | . | B | . | . | T | . | −0.69 | 0.56 | * | . | F | −0.05 | 0.59 |
| Ala | 604 | . | . | B | . | . | T | . | −1.28 | 0.60 | * | . | F | −0.05 | 0.65 |
| Gly | 605 | . | . | B | . | . | T | . | −0.42 | 0.46 | * | . | F | −0.05 | 0.43 |
| Pro | 606 | . | . | B | . | . | T | . | 0.48 | 0.43 | * | . | F | 0.21 | 0.51 |
| Leu | 607 | . | . | B | . | . | . | . | 0.80 | −0.06 | . | . | F | 1.32 | 1.01 |
| Ala | 608 | . | . | B | . | . | . | . | 1.11 | −0.56 | . | . | F | 1.88 | 2.00 |
| Gln | 609 | . | . | B | . | . | . | . | 1.70 | −0.59 | . | . | F | 2.14 | 2.08 |
| Lys | 610 | . | . | B | . | . | T | . | 2.09 | −0.61 | * | . | F | 2.60 | 4.38 |
| Arg | 611 | . | . | B | . | . | T | . | 1.71 | −1.30 | . | . | F | 2.34 | 8.66 |
| Asn | 612 | . | . | B | . | . | T | . | 2.21 | −1.30 | . | . | F | 2.08 | 5.05 |
| Gln | 613 | . | . | B | . | . | T | . | 2.59 | −1.21 | * | . | F | 2.10 | 3.65 |
| Lys | 614 | . | . | B | . | . | . | . | 2.59 | −0.79 | * | . | F | 1.92 | 2.88 |
| Ala | 615 | . | . | . | . | . | . | C | 2.24 | −0.39 | * | . | F | 1.84 | 2.88 |
| Thr | 616 | . | . | . | . | . | T | C | 1.92 | −0.40 | * | . | F | 2.32 | 2.23 |
| Pro | 617 | . | . | . | . | T | T | . | 2.03 | −0.37 | * | . | F | 2.80 | 1.72 |
| Asn | 618 | . | . | . | . | T | T | . | 1.72 | −0.37 | * | . | F | 2.52 | 3.34 |
| Ser | 619 | . | . | . | . | . | T | C | 1.47 | −0.39 | * | * | F | 2.04 | 3.34 |
| Pro | 620 | . | . | . | . | T | . | . | 1.24 | −0.44 | * | . | F | 1.76 | 3.34 |
| Arg | 621 | . | . | . | . | T | . | . | 1.34 | −0.19 | * | . | F | 1.48 | 1.71 |
| Thr | 622 | . | . | B | . | . | . | . | 1.34 | −0.16 | * | . | F | 0.80 | 1.98 |
| Pro | 623 | . | . | B | . | . | . | . | 1.00 | −0.11 | * | . | F | 0.80 | 1.98 |
| Leu | 624 | . | . | B | . | . | . | . | 0.71 | −0.11 | . | * | F | 0.65 | 1.00 |
| Pro | 625 | . | . | B | . | . | T | . | 0.71 | 0.39 | . | * | F | 0.25 | 0.70 |
| Pro | 626 | . | . | . | . | T | T | . | 0.30 | 0.33 | . | * | F | 0.65 | 0.70 |
| Gly | 627 | . | . | . | . | . | T | C | 0.40 | 0.29 | . | . | F | 0.60 | 1.14 |
| Ala | 628 | . | . | . | . | . | T | C | 0.61 | 0.03 | . | . | F | 0.94 | 1.14 |
| Pro | 629 | . | . | . | . | . | . | C | 1.12 | −0.40 | . | . | F | 1.68 | 1.27 |
| Ser | 630 | . | . | . | . | . | T | C | 1.38 | −0.44 | . | . | F | 2.22 | 1.72 |
| Pro | 631 | . | . | . | . | . | T | C | 1.63 | −0.87 | . | . | F | 2.86 | 3.41 |
| Glu | 632 | . | . | . | . | T | T | . | 1.98 | −1.37 | . | . | F | 3.40 | 4.41 |
| Ser | 633 | . | . | . | . | T | T | . | 2.57 | −1.40 | . | . | F | 3.06 | 5.29 |
| Lys | 634 | . | . | . | . | T | T | . | 2.82 | −1.39 | . | . | F | 2.94 | 5.93 |
| Lys | 635 | . | . | . | . | T | T | . | 3.17 | −1.81 | . | . | F | 2.82 | 6.84 |
| Asn | 636 | . | . | . | . | T | T | . | 3.38 | −1.81 | . | . | F | 2.70 | 10.21 |
| Gln | 637 | . | . | . | . | T | T | . | 3.13 | −1.80 | * | . | F | 2.58 | 8.84 |
| Lys | 638 | . | . | B | . | . | . | . | 3.43 | −1.04 | * | . | F | 2.20 | 6.93 |
| Lys | 639 | . | . | B | . | . | . | . | 2.58 | −0.64 | * | . | F | 1.98 | 7.46 |
| Gln | 640 | . | . | B | . | . | . | . | 2.32 | −0.36 | * | . | F | 1.46 | 3.55 |
| Tyr | 641 | . | . | B | . | . | . | . | 2.02 | −0.33 | . | . | . | 1.09 | 2.75 |
| Gln | 642 | . | . | B | . | . | . | . | 1.32 | 0.06 | . | . | . | 0.27 | 1.84 |
| Leu | 643 | . | . | B | . | . | T | . | 1.07 | 0.84 | . | . | . | −0.20 | 0.92 |
| Pro | 644 | . | . | B | . | . | T | . | 1.02 | 0.87 | . | . | F | −0.05 | 0.91 |
| Ser | 645 | . | . | B | . | . | T | . | 0.81 | 0.11 | . | . | F | 0.59 | 0.91 |
| Phe | 646 | . | . | B | . | . | T | . | 1.10 | 0.14 | . | . | F | 1.08 | 1.70 |
| Pro | 647 | . | . | . | . | . | . | C | 0.80 | −0.54 | . | . | F | 2.32 | 2.20 |
| Glu | 648 | . | . | . | . | . | . | C | 1.31 | −0.59 | . | . | F | 2.66 | 2.20 |
| Pro | 649 | . | . | . | . | T | T | . | 1.21 | −0.59 | . | . | F | 3.40 | 3.41 |
| Lys | 650 | . | . | . | . | T | T | . | 1.51 | −0.89 | . | . | F | 3.06 | 3.18 |
| Ser | 651 | . | . | . | . | . | T | C | 1.62 | −0.91 | . | . | F | 2.52 | 3.18 |
| Ser | 652 | . | . | . | . | . | T | C | 1.62 | −0.41 | * | . | F | 1.88 | 2.08 |
| Thr | 653 | . | . | . | . | . | . | C | 1.62 | −0.41 | * | . | F | 1.64 | 1.61 |
| Gln | 654 | . | . | . | . | . | . | C | 1.53 | −0.41 | * | . | F | 1.60 | 2.08 |
| Ala | 655 | . | . | . | . | . | T | C | 1.49 | −0.41 | * | . | F | 2.10 | 2.08 |
| Pro | 656 | . | . | . | . | . | T | C | 1.79 | −0.40 | . | . | F | 2.40 | 2.49 |
| Glu | 657 | . | . | . | . | . | T | C | 1.79 | −0.89 | . | . | F | 3.00 | 2.49 |
| Ser | 658 | . | . | . | . | . | T | C | 2.10 | −0.90 | . | . | F | 2.70 | 3.31 |
| Gln | 659 | . | A | . | . | . | . | C | 2.10 | −1.00 | . | . | F | 2.00 | 3.70 |
| Glu | 660 | . | A | . | . | . | . | C | 2.69 | −1.43 | . | . | F | 1.70 | 3.70 |
| Ser | 661 | . | A | . | . | . | . | C | 2.09 | −1.43 | . | . | F | 1.40 | 4.79 |
| Gln | 662 | A | A | . | . | . | . | . | 2.06 | −1.13 | . | . | F | 0.90 | 2.28 |
| Glu | 663 | A | A | . | . | . | . | . | 2.11 | −1.03 | * | . | F | 0.90 | 1.79 |
| Glu | 664 | A | A | . | . | . | . | . | 1.52 | −0.27 | * | . | F | 0.60 | 2.09 |

TABLE XIII-continued

| | | | | | | | | | | | | | | | |
|---|---|---|---|---|---|---|---|---|---|---|---|---|---|---|---|
| Leu | 665 | . | A | B | . | . | . | . | 1.21 | −0.16 | . | . | . | 0.45 | 1.22 |
| His | 666 | . | A | B | . | . | . | . | 0.70 | −0.07 | . | . | . | 0.45 | 1.02 |
| Tyr | 667 | . | A | B | . | . | . | . | 0.70 | 0.61 | . | . | . | −0.60 | 0.48 |
| Ala | 668 | . | A | B | . | . | . | . | 0.00 | 1.01 | * | . | . | −0.60 | 0.95 |
| Thr | 669 | . | A | B | . | . | . | . | −0.21 | 1.11 | . | * | . | −0.60 | 0.60 |
| Leu | 670 | . | A | . | . | T | . | . | 0.26 | 1.04 | . | . | . | −0.20 | 0.59 |
| Asn | 671 | . | A | B | . | . | . | . | −0.57 | 0.71 | * | . | . | −0.60 | 0.58 |
| Phe | 672 | . | . | B | B | . | . | . | −0.21 | 0.86 | * | . | . | −0.60 | 0.30 |
| Pro | 673 | . | . | . | B | T | . | . | 0.17 | 0.37 | . | * | F | 0.25 | 0.71 |
| Gly | 674 | . | . | . | B | T | . | . | 0.59 | 0.11 | . | * | F | 0.25 | 0.68 |
| Val | 675 | . | . | . | B | . | . | C | 1.19 | −0.29 | . | * | F | 0.80 | 1.54 |
| Arg | 676 | . | . | . | . | . | T | C | 1.19 | −0.64 | . | * | F | 1.50 | 1.54 |
| Pro | 677 | . | . | . | . | . | T | C | 1.30 | −1.07 | . | * | F | 1.50 | 2.70 |
| Arg | 678 | . | . | . | . | . | T | C | 1.62 | −1.00 | . | * | F | 1.50 | 3.68 |
| Pro | 679 | . | . | B | . | . | T | . | 1.37 | −1.64 | . | * | F | 1.30 | 3.68 |
| Glu | 680 | . | . | . | . | T | . | . | 2.01 | −1.03 | * | * | F | 1.84 | 2.35 |
| Ala | 681 | . | . | B | . | . | . | . | 1.94 | −1.03 | * | * | F | 1.78 | 1.86 |
| Arg | 682 | . | . | B | . | . | . | . | 1.81 | −1.03 | * | * | . | 1.97 | 2.40 |
| Met | 683 | . | . | B | . | . | T | . | 1.39 | −1.03 | * | * | F | 2.66 | 1.37 |
| Pro | 684 | . | . | . | . | T | T | . | 1.60 | −0.54 | . | * | F | 3.40 | 1.96 |
| Lys | 685 | . | . | . | . | T | T | . | 1.01 | −0.64 | . | * | F | 3.06 | 1.74 |
| Gly | 686 | . | . | . | . | . | T | C | 1.60 | −0.14 | * | . | F | 2.22 | 1.77 |
| Thr | 687 | . | A | . | . | . | . | C | 1.24 | −0.76 | * | . | F | 1.78 | 1.91 |
| Gln | 688 | . | A | B | . | . | . | . | 1.26 | −0.43 | . | . | F | 0.94 | 1.50 |
| Ala | 689 | . | A | B | . | . | . | . | 1.47 | 0.07 | . | . | F | 0.00 | 1.53 |
| Asp | 690 | . | A | B | . | . | . | . | 0.57 | −0.36 | . | . | . | 0.45 | 1.84 |
| Tyr | 691 | . | A | B | . | . | . | . | 0.96 | −0.20 | . | * | . | 0.30 | 0.79 |
| Ala | 692 | . | A | B | . | . | . | . | 0.57 | −0.60 | . | * | . | 0.75 | 1.56 |
| Glu | 693 | . | A | B | . | . | . | . | 0.57 | −0.31 | . | * | . | 0.30 | 0.81 |
| Val | 694 | . | A | B | . | . | . | . | 0.77 | 0.09 | . | * | . | −0.30 | 0.89 |
| Lys | 695 | . | A | B | . | . | . | . | 0.38 | −0.24 | . | * | . | 0.45 | 1.13 |
| Phe | 696 | . | A | B | . | . | . | . | 0.23 | −0.31 | . | * | . | 0.30 | 0.83 |
| Gln | 697 | . | A | B | . | . | . | . | 0.43 | 0.11 | . | * | . | −0.15 | 1.44 |

TABLE XIV

| Gene No. | cDNA Clone ID | ATCC Deposit No: Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Sec-reted Portion | Last AA of ORF |
|---|---|---|---|---|---|---|---|---|---|---|---|---|---|---|
| 1 | HAOAB64 | 203484 Nov. 17, 1998 | pSport1 | 11 | 2609 | 1 | 2609 | 599 | 599 | 29 | 1 | 30 | 31 | 529 |
| 2 | HOHCH55 | 203484 Nov. 17, 1998 | pCMVSport 2.0 | 12 | 2499 | 1 | 2499 | 221 | 221 | 30 | 1 | 23 | 24 | 494 |
| 2 | HOHCH55 | 203484 Nov. 17, 1998 | pCMVSport 2.0 | 23 | 2522 | 1 | 2522 | 230 | 230 | 41 | 1 | 23 | 24 | 469 |
| 3 | HTLEW81 | 203484 Nov. 17, 1998 | Uni-ZAP XR | 13 | 1339 | 1 | 1339 | 37 | 37 | 31 | 1 | 27 | 28 | 148 |
| 4 | HARAO44 | 203484 Nov. 17, 1998 | pBluescript SK− | 14 | 1389 | 1 | 1389 | 125 | 125 | 32 | 1 | 21 | 22 | 332 |
| 6 | HDPUW68 | 203484 Nov. 17, 1998 | pCMVSport 3.0 | 16 | 1748 | 1 | 1748 | 40 | 40 | 34 | 1 | 18 | 19 | 467 |
| 7 | HOHBY69 | 203484 Nov. 17, 1998 | pCMVSport 2.0 | 17 | 4995 | 1 | 4995 | 82 | 82 | 35 | 1 | 22 | 23 | 1189 |
| 7 | HOHBY69 | 203484 Nov. 17, 1998 | pCMVSport 2.0 | 25 | 4631 | 1 | 4631 | 84 | 84 | 43 | 1 | 22 | 23 | 1034 |
| 8 | HCDDP40 | 203484 Nov. 17, 1998 | Uni-ZAP XR | 18 | 726 | 1 | 726 | 32 | 32 | 36 | 1 | 21 | 22 | 196 |
| 9 | HTTDB46 | 203484 Nov. 17, 1998 | Uni-ZAP XR | 19 | 3059 | 1 | 3059 | 55 | 55 | 37 | 1 | 17 | 18 | 318 |
| 9 | HTTDB46 | 203484 Nov. 17, 1998 | Uni-ZAP XR | 26 | 2008 | 215 | 2008 | 153 | 153 | 44 | 1 | 17 | 18 | 461 |
| 5 | | | | 148 | 2338 | 165 | 2338 | 201 | 201 | 149 | 1 | 16 | 17 | 697 |
| 5 | HDPCL05 | 203484 Nov. 17, 1998 | pCMVSport 3.0 | 15 | 2295 | 1 | 2295 | 58 | 58 | 33 | 1 | 16 | 17 | 639 |
| 5 | HDPCL05 | 203484 Nov. 17, 1998 | pCMVSport 3.0 | 24 | 1344 | 1 | 1344 | 52 | 52 | 42 | 1 | 16 | 17 | 127 |
| 10 | HUSAQ05 | 203484 Nov. 17, 1998 | Lambda ZAP II | 20 | 1699 | 1 | 1699 | 115 | 115 | 38 | 1 | 19 | 20 | 375 |
| 10 | HUSAQ05 | 203484 Nov. 17, 1998 | Lambda ZAP II | 27 | 1654 | 1 | 1654 | 115 | 115 | 45 | 1 | 19 | 20 | 383 |
| 11 | HOUDJ81 | 203484 Nov. 17, 1998 | Uni-ZAP XR | 21 | 1520 | 1 | 1520 | 26 | 26 | 39 | 1 | 44 | 45 | 364 |

TABLE XIV-continued

| Gene No. | cDNA Clone ID | ATCC Deposit No: Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 11 | HOUDJ81 | 203484 Nov. 17, 1998 | Uni-ZAP XR | 28 | 1508 | 19 | 1508 | 454 | 454 | 46 | 1 | 30 | 31 | 229 |
| 12 | HPWCM76 | 203484 Nov. 17, 1998 | Uni-ZAP XR | 22 | 807 | 1 | 807 | 582 | 582 | 40 | 1 | 23 | 24 | 66 |

Table XIV summarizes the information corresponding to each "Gene No." described above. The nucleotide sequence identified as "NT SEQ ID NO:X" was assembled from partially homologous ("overlapping") sequences obtained from the "cDNA clone ID" identified in Table XIV and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the secreted proteins encoded by the cDNA clones identified in Table XIV.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table XIV. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:X, SEQ ID NO:Y, or a deposited clone, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification , such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using techniques described herein or otherwise known in the art, such as, for example, antibodies of the invention raised against the secreted protein.

The present invention provides a polynucleotide comprising, or alternatively consisting of, the nucleic acid sequence of SEQ ID NO:X and/or a cDNA contained in ATCC deposit Z. The present invention also provides a polypeptide comprising, or alternatively, consisting of, the polypeptide sequence of SEQ ID NO:Y and/or a polypeptide encoded by the cDNA contained in ATCC deposit Z. Polynucleotides encoding a polypeptide comprising, or alternatively consisting of the polypeptide sequence of SEQ ID NO:Y and/or a polypeptide sequence encoded by the cDNA contained in ATCC deposit Z are also encompassed by the invention.

Signal Sequences

The present invention also encompasses mature forms of the polypeptide having the polypeptide sequence of SEQ ID NO:Y and/or the polypeptide sequence encoded by the cDNA in a deposited clone. Polynucleotides encoding the mature forms (such as, for example, the polynucleotide sequence in SEQ ID NO:X and/or the polynucleotide sequence contained in the cDNA of a deposited clone) are also encompassed by the invention. According to the signal hypothesis, proteins secreted by mammalian cells have a signal or secretary leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271-286 (1985), uses the information from a short N-terminal charged region and a subsequent uncharged region of the complete (uncleaved) protein. The method of von Heinje, Nucleic Acids Res. 14:4683-4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75-80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1-6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table XIV.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:X and/or the polynucleotide sequence contained in the cDNA of a deposited clone, in a mammalian cell (e.g., COS cells, as described below). These polypeptides, and the polynucleotides encoding such polypeptides, are contemplated by the present invention.

Polynucleotide and Polypeptide Variants

The present invention is directed to variants of the polynucleotide sequence disclosed in SEQ ID NO:X, the complementary strand thereto, and/or the cDNA sequence contained in a deposited clone.

The present invention also encompasses variants of the polypeptide sequence disclosed in SEQ ID NO:Y and/or encoded by a deposited clone.

"Variant" refers to a polynucleotide or polypeptide differing from the polynucleotide or polypeptide of the present invention, but retaining essential properties thereof Generally, variants are overall closely similar, and, in many regions, identical to the polynucleotide or polypeptide of the present invention.

The present invention is also directed to nucleic acid molecules which comprise, or alternatively consist of, a nucleotide sequence which is at least 80%, 85%, 90%, 95%, 96%, 97%, 98% or 99% identical to, for example, the nucleotide coding sequence in SEQ ID NO:X or the complementary strand thereto, the nucleotide coding sequence contained in a deposited cDNA clone or the complementary strand thereto, a nucleotide sequence encoding the polypeptide of SEQ ID NO:Y, a nucleotide sequence encoding the polypeptide encoded by the cDNA contained in a deposited clone, and/or polynucleotide fragments of any of these nucleic acid molecules (e.g., those fragments described herein). Polynucleotides which hybridize to these nucleic acid molecules under stringent hybridization conditions or lower stringency conditions are also encompassed by the invention, as are polypeptides encoded by these polynucleotides.

The present invention is also directed to polypeptides which comprise, or alternatively consist of an amino acid sequence which is at least 80%, 85%, 90%, 95%, 96%, 97%, 98%, 99% identical to, for example, the polypeptide sequence shown in SEQ ID NO:Y, the polypeptide sequence encoded by the cDNA contained in a deposited clone, and/or polypeptide fragments of any of these polypeptides (e.g., those fragments described herein).

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table XIV, the ORF (open reading frame), or any fragment specified as described herein.

As a practical matter, whether any particular nucleic acid molecule or polypeptide is at least 80%, 85%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, an amino acid sequences shown in Table XIV (SEQ ID NO:Y) or to the amino acid sequence encoded by cDNA contained in a deposited clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245(1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, delete, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268:2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988).)

Moreover, ample evidence demonstrates that variants often retain a biological activity similar to that of the naturally occurring protein. For example, Gayle and coworkers (J. Biol. Chem 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36:838-845 (1987); Cleland et al., Crit. Rev. Therapeutic Drug Carrier Systems 10:307-377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5, 5-10, 5-25, 5-50, 10-50 or 50-150, conservative amino acid substitutions are preferable.

Polynucleotide and Polypeptide Fragments

The present invention is also directed to polynucleotide fragments of the polynucleotides of the invention.

In the present invention, a "polynucleotide fragment" refers to a short polynucleotide having a nucleic acid sequence which: is a portion of that contained in a deposited clone, or encoding the polypeptide encoded by the CDNA in a deposited clone; is a portion of that shown in SEQ ID NO:X or the complementary strand thereto, or is a portion of a polynucleotide sequence encoding the polypeptide of SEQ ID NO:Y. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:X. In this context "about" includes the particularly recited value, a value larger or smaller by several (5, 4, 3, 2, or 1) nucleotides, at either terminus or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401450,451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:X, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

In the present invention, a "polypeptide fragment" refers to an amino acid sequence which is a portion of that contained in SEQ ID NO:Y or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 2140, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1-60, can be deleted from the amino terminus of either the secreted polypeptide or the mature form. Similarly, any number of amino acids, ranging from 1-30, can be deleted from the carboxy terminus of the secreted protein or mature form. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

Preferably, the polynucleotide fragments of the invention encode a polypeptide which demonstrates a functional activity. By a polypeptide demonstrating a "functional activity" is meant, a polypeptide capable of displaying one or more known functional activities associated with a full-length (complete) polypeptide of invention protein. Such functional activities include, but are not limited to, biological activity, antigenicity [ability to bind (or compete with a polypeptide of the invention for binding) to an antibody to the polypeptide of the invention], immunogenicity (ability to generate antibody which binds to a polypeptide of the invention), ability to form multimers with polypeptides of the invention, and ability to bind to a receptor or ligand for a polypeptide of the invention.

The functional activity of polypeptides of the invention, and fragments, variants derivatives, and analogs thereof, can be assayed by various methods.

For example, in one embodiment where one is assaying for the ability to bind or compete with full-length polypeptide of the invention for binding to an antibody of the polypeptide of the invention, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a ligand for a polypeptide of the invention identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94-123. In another embodiment, physiological correlates of binding of a polypeptide of the invention to its substrates (signal transduction) can be assayed.

In addition, assays described herein (see Examples) and otherwise known in the art may routinely be applied to measure the ability of polypeptides of the invention and fragments, variants derivatives and analogs thereof to elicit related biological activity related to that of the polypeptide of the invention (either in vitro or in vivo). Other methods will be known to the skilled artisan and are within the scope of the invention.

Epitopes & Antibodies

The present invention encompasses polypeptides comprising, or alternatively consisting of, an epitope of the polypeptide having an amino acid sequence of SEQ ID NO:Y, or an epitope of the polypeptide sequence encoded by a polynucleotide sequence contained in ATCC deposit No. Z or encoded by a polynucleotide that hybridizes to the complement of the sequence of SEQ ID NO:X or contained in ATCC deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:X), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross- reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in inumunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394, 827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:X and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:Y, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any, animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%/o, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, 10-12 M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85 %, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferrably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4):

1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998) Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N— or C— terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *corynebactenium parvum*. Such adjuvants are also well known in the art.

Monoclonal antibodies can be prepared using a wide variety of techniques known in the art including the use of hybridoma, recombinant, and phage display technologies, or a combination thereof For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 10). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinlonan et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Patent Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:Y.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278:457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also by used to express foreign polypeptides as fusion proteins with glutathione S-transterase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa califomica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non- essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in tum can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through liker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fe region, or portion thereof The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fe portions fused to the polypeptides of the present invention can form dimers through disulfide bonding between the Fe portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP307,434; EP367,166;PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, supra, the polypeptides corresponding to a polypeptide, polypeptide fragment, or a variant of SEQ ID NO:Y may be fused or conjugated to the above antibody portions to increase the in vivo half life of the polypeptides or for use in immunoassays using methods known in the art.

Further, the polypeptides corresponding to SEQ ID NO:Y may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fe part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the “HA” tag, which corresponds to an epitope derived from the influenza hemagglutinin protein (Wilson et al., Cell 37:767 (1984)) and the “flag” tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a protein such as tumor necrosis factor, α-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.,* 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 (“IL-1”), interleukin-2 (“IL-2”), interleukin-6 (“IL-6”), granulocyte macrophage colony stimulating factor (“GM-CSF”), granulocyte colony stimulating factor (“G-CSF”), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., “Monoclonal Antibodies For Immunotargeting Of Drugs In Cancer Therapy”, in Monoclonal Antibodies And Cancer Therapy, Reisfeld et al. (eds.), pp. 243-56 (Alan R. Liss, Inc. 1985); Hellstrom et al., “Antibodies For Drug Delivery”, in Controlled Drug Delivery (2nd Ed.), Robinson et al. (eds.), pp. 623-53 (Marcel Dekker, Inc. 1987); Thorpe, “Antibody Carriers Of Cytotoxic Agents In Cancer Therapy: A Review”, in Monoclonal Antibodies ’84: Biological And Clinical Applications, Pinchera et al. (eds.), pp. 475-506 (1985); “Analysis, Results, And Future Prospective Of The Therapeutic Use Of Radiolabeled Antibody In Cancer Therapy”, in Monoclonal Antibodies For Cancer Detection And Therapy, Baldwin et al.

(eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell,* 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue- specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid- carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publicaiton WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92 m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox- like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell . Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface- bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-O 464 533 (Canadian counterpart 2045869) discloses fusion proteins comprising various portions of constant region of immunoglobulin molecules together with another human protein or part thereof In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fe portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, tip, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNR46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Phannacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller et al., *Nature,* 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymnethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:Y or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymnorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Venma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library) .) Assuming 1 megabase mapping resolution and one gene per 20 kb, a CDNA precisely localized to a chromosomal region associated with the disease could be one of 50-500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the present invention and a suitable container. In a specific embodiment, the kit includes two polynucleotide probes defining an internal region of the polynucleotide of the present invention, where each probe has one strand containing a 31' mer-end internal to the region. In a further embodiment, the probes may be useful as primers for polymerase chain reaction amplification.

Where a diagnosis of a disorder, has already been made according to conventional methods, the present invention is useful as a prognostic indicator, whereby patients exhibiting enhanced or depressed polynucleotide of the present invention expression will experience a worse clinical outcome relative to patients expressing the gene at a level nearer the standard level.

By "measuring the expression level of polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or MRNA level) or relatively (e.g., by comparing to the polypeptide level or mRNA level in a second biological sample). Preferably, the polypeptide level or MRNA level in the first biological sample is measured or estimated and compared to a standard polypeptide level or MRNA level, the standard being taken from a second biological sample obtained from an individual not having the disorder or being determined by averaging levels from a population of individuals not having a disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including cancerous diseases and conditions. Such a method is described in U.S. Pat. Nos. 5,858,659 and 5,856,104. The US Patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybfidization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

The present invention is useful for detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative disorders are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiemiik, P. H. et al. eds., 161-182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types. (Gelmann et al., supra) Indeed, the human counterparts of the oncogenes involved in some animal neoplasias have been amplified or translocated in some cases of human leukemia and carcinoma. (Gelmann et al., supra)

For example, c-myc expression is highly amplified in the non-lymphocytic leukemia cell line HL-60. When HL-60 cells are chemically induced to stop proliferation, the level of c-myc is found to be downregulated. (International Publication Number WO 91/15580) However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication Number WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness would not be limited to treatment of proliferative disorders of hematopoietic cells and tissues, in light of the numerous cells and cell types of varying origins which are known to exhibit proliferative phenotypes.

In addition to the foregoing, a polynucleotide can be used to control gene expression through triple helix formation or antisense DNA or RNA. Antisense techniques are discussed, for example, in Okano, J. Neurochem. 56:560 (1991); "Oligodeoxynucleotides as Antisense Inhibitors of Gene Expression, CRCPress, Boca Raton, Fla. (1988). Triple helix formation is discussed in, for instance Lee et al., Nucleic Acids Research 6:3073 (1979); Cooney et al., Science 241: 456 (1988); and Dervan et al., Science 251:1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ED database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, synovial fluid, amniotic fluid, breast milk, lymph, pulmonary sputum or surfactant,urine,fecal matter, etc., can be amplified using PCR. In one prior art technique, gene sequences amplified from polymorphic loci, such as DQa class 11 HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific MRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976-985 (1985); Jalkanen, M., et al., J. Cell . Biol. 105:3087-3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99 mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99 mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., “Immunopharmacokinetics of Radiolabeled Antibodies and Their Fragments.” (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor supressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207-216 (1993); Ferrantini et al., Cancer Research, 53:107-1112 (1993); Ferrantini et al., J. Immunology 153:4604-4615 (1994); Kaido, T., et al., Int. J. Cancer 60: 221-229 (1995); Ogura et al., Cancer Research 50:5102-5106 (1990); Santodonato, et al., Human Gene Therapy 7:1-10 (1996); Santodonato, et al., Gene Therapy 4:1246-1255 (1997); and Zhang, et al., Cancer Gene Therapy 3:31-38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term “naked” polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the nakednucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the arl, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA , 84:7413-7416 (1987), which is herein incorporated by reference); mRNA (Malone et al., Proc. Natl. Acad. Sci. USA, 86:6077-6081 (1989), which is herein incorporated by reference); and purified transcription factors (Debs et al., J. Biol. Chem., 265:10189-10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA , 84:7413-7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413-7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology , 101:512-527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta, 394:483 (1975); Wilson et al., Cell , 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA , 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartzet al., Am. Rev. Respir. Dis., 109:233-238 (1974)). Finally, adenovirus mediated gene transfer has been demonstrated in a number of instances including transfer of alpha-1-antitrypsin and CFTR to the lungs of cotton rats (Rosenfeld et al., Science, 252:431-434 (1991); Rosenfeld et al., Cell, 68:143-155 (1992)). Furthermore, extensive studies to attempt to establish adenovirus as a causative agent in human cancer were uniformly negative (Green et al. Proc. Natl. Acad. Sci. USA , 76:6606 (1979)).

Suitable adenoviral vectors useful in the present invention are described, for example, in Kozarsky and Wilson, Curr. Opin. Genet. Devel., 3:499-503 (1993); Rosenfeld etal., Cell , 68:143-155 (1992); Engelhardt etal., Human Genet. Ther., 4:759-769 (1993); Yang et al., Nature Genet., 7:362-369 (1994); Wilson et al., Nature, 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express Ela and Elb, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding other angiongenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189: 11277-11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly Biological Activities The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

Polynucleotides, polypeptides, antibodies, and/or agonists or antagonists of the present invention may be useful in treating, preventing, and/or diagnosing diseases, disorders, and/or conditions of the immune system, by, for example, activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer and some autoimmune diseases, acquired (e.g., by chemotherapy or toxins), or infectious. Moreover, polynucleotides, polypeptides, antibodies, and/or agonists or antagonists of the present invention can be used as a marker or detector of a particular immune system disease or disorder.

Polynuclebtides, polypeptides, antibodies, and/or agonists or antagonists of the present invention may be useful in treating, preventing, and/or diagnosing diseases, disorders, and/or conditions of hematopoietic cells. Polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g., agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, polynucleotides, polypeptides, antibodies, and/or agonists or antagonists of the present invention could also be used to modulate hemostatic (the stopping of bleeding) or thrombolytic activity (clot formation). For example, by increasing hemostatic or thrombolytic activity, polynucleotides or polypeptides, and/or agonists or antagonists of the present invention could be used to treat or prevent blood coagulation diseases, disorders, and/or conditions (e.g., afibrinogenemia, factor deficiencies), blood platelet diseases, disorders, and/or conditions (e.g., thrombocytopenia), or wounds resulting from trauma, surgery, or other causes. Alternatively, polynucleotides, polypeptides, antibodies, and/or agonists or antagonists of the present invention that can decrease hemostatic or thrombolytic activity could be used to inhibit or dissolve clotting. These molecules could be important in the treatment or prevention of heart attacks (infarction), strokes, or scarring.

The polynucleotides, polypeptides, antibodies, and/or agonists or antagonists of the present invention may be useful in treating, preventing, and/or diagnosing autoimmune disorders. Many autoimmune disorders result from inappropriate recognition of self as foreign material by immune cells. This inappropriate recognition results in an immune response leading to the destruction of the host tissue. Therefore, the administration of polynucleotides and polypeptides of the invention that can inhibit an immune response, particularly the proliferation, differentiation, or chemotaxis of T-cells, may be an effective therapy in preventing autoimmune disorders.

Autoimmune diseases or disorders that may be treated, prevented, and/or diagnosed by polynucleotides, polypeptides, antibodies, and/or agonists or antagonists of the present invention include, but are not limited to, one or more of the following: autoimmune hemolytic anemia, autoimmune neonatal thrombocytopenia, idiopathic thrombocytopenia purpura, autoimmunocytopenia, hemolytic anemia, antiphospholipid syndrome, demmatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Autism, Guillain-Barre Syndrome, insulin dependent diabetes mellitis, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoinunune hemolytic anemia, autoimmune thrombocytopenic purpura, rheumatoid arthritis, schieroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders.

Additional autoimmune disorders (that are probable) that may be treated, prevented, and/or diagnosed with the compositions of the invention include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using for example, antagonists or agonists, pqlypeptides or polynucleotides, or antibodies of the present invention.

In a preferred embodiment polynucleotides, polypeptides, antibodies, and/or agonists or antagonists of the present invention could be used as an agent to boost immunoresponsiveness among B cell and/or T cell immunodeficient individuals.

B cell immunodeficiencies that may be ameliorated or treated by administering the polypeptides or polynucleotides of the invention, and/or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVI) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymophoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

T cell deficiencies that may be ameliorated or treated by administering the polypeptides or polynucleotides of the invention, and/or agonists thereof include, but are not limited to, for example, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity. In specific embodiments, DiGeorge anomaly or conditions associated with DiGeorge anomaly are ameliorated or treated by, for example, administering the polypeptides or polynucleotides of the invention, or antagonists or agonists thereof.

Other immunodeficiencies that may be ameliorated or treated by administering polypeptides or polynucleotides of the invention, and/or agonists thereof, include, but are not limited to, severe combined immunodeficiency (SCID; e.g., X-linked SCID, autosomal SCID, and adenosine deaminase deficiency), ataxia-telangiectasia, Wiskott-Aldrich syndrome, short-limber dwarfism, X-linked lymphoproliferative syndrome (XLP), Nezelof syndrome (e.g., purine nucleoside phosphorylase deficiency), MHC Class II deficiency. In specific embodiments, ataxia-telangiectasia or conditions associated with ataxia-telangiectasia are ameliorated or treated by administering the polypeptides or polynucleotides of the invention, and/or agonists thereof.

In a specific preferred embodiment, rheumatoid arthritis is treated, prevented, and/or diagnosed using polynucleotides, polypeptides, antibodies, and/or agonists or antagonists of the present invention. In another specific preferred embodiment, systemic lupus erythemosus is treated, prevented, and/or diagnosed using polynucleotides, polypeptides, antibodies, and/or agonists or antagonists of the present invention. In another specific preferred embodiment, idiopathic thrombocytopenia purpura is treated, prevented, and/or diagnosed using polynucleotides, polypeptides, antibodies, and/or agonists or antagonists of the present invention. In another specific preferred embodiment IgA nephropathy is treated, prevented, and/or diagnosed using polynucleotides, polypeptides, antibodies, and/or agonists or antagonists of the present invention. In a preferred embodiment, the autoimmune diseases and disorders and/or conditions associated with the diseases and disorders recited above are treated, prevented, and/or diagnosed using antibodies against the protein of the invention.

Similarly, allergic reactions and conditions, such as asthma (particularly allergic asthma) or other respiratory problems, may also be treated, prevented, and/or diagnosed using polypeptides, antibodies, or polynucleotides of the invention, and/or agonists or antagonists thereof Moreover, these molecules can be used to treat, prevent, and/or diagnose anaphylaxis, hypersensitivity to an antigenic molecule, or blood group incompatibility.

Moreover, inflammatory conditions may also be treated, diagnosed, and/or prevented with polynucleotides, polypeptides, antibodies, and/or agonists or antagonists of the present invention. Such inflammatory conditions include, but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease), AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (B and C), rheumatoid arthritis, gout, trauma, septic shock, pancreatitis, sarcoidosis, dermatitis, renal ischemia-reperfusion injury, Grave's disease, systemic lupus erythematosis, diabetes mellitus (i.e., type 1 diabetes), and allogenic transplant rejection).

In specific embodiments, polypeptides, antibodies, or polynucleotides of the invention, and/or agonists or antagonists thereof, are useful to treat, diagnose, and/or prevent transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE). Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD.

Similarly, polynucleotides, polypeptides, antibodies, and/or agonists or antagonists of the present invention may also be used to modulate and/or diagnose inflammation. For example, since polypeptides, antibodies, or polynucleotides of the invention, and/or agonists or antagonists of the invention may inhibit the activation, proliferation and/or differentiation of cells involved in an inflammatory response, these molecules can be used to treat, diagnose, or prognose, inflammatory conditions, both chronic and acute conditions, including, but not limited to, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Croln's disease, and resulting from over production of cytokines (e.g., TNF or IL-1.).

Polypeptides, antibodies, polynucleotides and/or agonists or antagonists of the invention can be used to treat, detect, and/or prevent infectious agents. For example, by increasing the immune response, particularly increasing the proliferation activation and/or differentiation of B and/or T cells, infectious diseases may be treated, detected, and/or prevented. The immune response may be increased by either enhancing an existing immune response, or by initiating a new immune response. Alternatively, polynucleotides, polypeptides, antibodies, and/or agonists or antagonists of the present invention may also directly inhibit the infectious agent (refer to section of application listing infectious agents, etc), without necessarily eliciting an immune response.

Additional preferred embodiments of the invention include, but are not limited to, the use of polypeptides, antibodies, polynucleotides and/or agonists or antagonists in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741.

A vaccine adjuvant that enhances immune responsiveness to specific antigen.

An adjuvant to enhance tumor-specific immune responses.

An adjuvant to enhance anti-viral immune responses. Antiviral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of- AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of. tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobactenum leprae, Salmonella typhi, Salmonella paratyphi, Meisseria meningitidis, Streptococcus pneumoniae*, Group B *streptococcus, Shigella spp.*, Enterotoxigenic *Escherichia coli*, Enterohemorrhagic *E. coli, Borrelia burgdorferi*, and *Plasmodium* (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria).

As a stimulator of B cell responsiveness to pathogens.

As an activator of T cells.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among individuals having an acquired loss of B cell function. Conditions resulting in an acquired loss of B cell function that may be ameliorated or treated by administering the polypeptides, antibodies, polynucleotides and/or agonists or antagonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the polypeptides, antibodies, polynucleotides and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, and/or B-cells. In one embodiment, polynucleotides, polypeptides, antibodies, and/or agonists or antagonists of the present invention enhance antigen presentation or antagonizes antigen presentation in vitro or in vivo. Moreover, in related embodiments, said enhancement or antagonization of antigen presentation may be useful as an anti-tumor treatment or to modulate the immune system.

As an agent to direct an individuals immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a stimulator of B cell production in pathologies such as AIDS, chronic lymphocyte disorder and/or Common Variable Immunodificiency.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance immune mediated responses against polypeptides of the invention.

As a means of activating T cells.

As a means of activating monocytes/macrophages to defend against parasitic diseases that effect monocytes such as Leshmania.

As pretreatment of bone marrow samples prior to transplant. Such treatment would increase B cell representation and thus accelerate recover.

As a means of regulating secreted cytokines that are elicited by polypeptides of the invention.

Additionally, polypeptides or polynucleotides of the invention, and/or agonists thereof, may be used to treat or prevent IgE-mediated allergic reactions. Such allergic reactions include, but are not limited to, asthma, rhinitis, and eczema.

All of the above described applications as they may apply to veterinary medicine.

Antagonists of the invention include, for example, binding and/or inhibitory antibodies, antisense nucleic acids, ribozymes or soluble forms of the secreted-like receptor(s) (e.g., a secreted-like-Fc fusion protein) (see e.g., Example 9). These would be expected to reverse many of the activities of the ligand described above as well as find clinical or practical application as:

A means of blocking various aspects of immune responses to foreign agents or self Examples include autoimmune disorders such as lupus, and arthritis, as well as immunoresponsiveness to skin allergies, inflammation, bowel disease, injury and pathogens.

A therapy for preventing the B cell proliferation and Ig secretion associated with autoimmune diseases such as idiopathic thrombocytopenic purpura, systemic lupus erythramatosus and MS.

An inhibitor of B and/or T cell migration in endothelial cells. This activity disrupts tissue architecture or cognate responses and is useful, for example in disrupting immune responses, and blocking sepsis.

An inhibitor of graft versus host disease or transplant rejection.

A therapy for B cell and/or T cell malignancies such as ALL, Hodgkins disease, non-Hodgkins lymphoma, Chronic lymphocyte leukemia, plasmacytomas, multiple myeloma, Burkitt's lymphoma, and EBV-transfomed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

Polynucleotides, polypeptides, antibodies, and/or agonists or antagonists of the present invention may be used to modulate IgE concentrations in vitro or in vivo.

In another embodiment, administration of polypeptides, antibodies, polynucleotides and/or agonists or antagonists of the invention, may be used to treat or prevent IgE-mediated allergic reactions including, but not limited to, astluna, rhinitis, and eczema.

The agonists and antagonists may be employed in a composition with a pharmaceutically acceptable carrier, e.g., as described herein.

The agonists or antagonists may be employed for instance to inhibit polypeptide chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of autoimmune diseases are described herein and include multiple sclerosis, and insulin-dependent diabetes. The antagonists or agonists may also be employed to treat infectious diseases including silicosis, sarcoidosis, idiopathic pulmonary fibrosis by, for example, preventing the recruitment and activation of mononuclear phagocytes. They may also be employed to treat idiopathic hyper-eosinophilic syndrome by, for example, preventing eosinophil production and migration. The antagonists or agonists or may also be employed for treating atherosclerosis, for example, by preventing monocyte infiltration in the artery wall.

Antibodies against polypeptides of the invention may be employed to treat ARDS.

Agonists and/or antagonists of the invention also have uses in stimulating wound and tissue repair, stimulating angiogenesis, stimulating the repair of vascular or lymphatic diseases or disorders. Additionally, agonists and antagonists of the invention may be used to stimulate the regeneration of mucosal surfaces.

In a specific embodiment, polynucleotides or polypeptides, and/or agonists thereof are used to treat or prevent a disorder characterized by primary or acquired immunodeficiency, deficient serum immunoglobulin production, recurrent infections, and/or immune system dysfunction. Moreover, polynucleotides or polypeptides, and/or agonists thereof may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pneumocystis camii.

In another embodiment, polynucleotides, polypeptides, antibodies, and/or agonists or antagonists of the present invention are used to treat, and/or diagnose an individual having common variable immunodeficiency disease ("CVID"; also known as "acquired agammaglobulinemia" and "acquired hypogammaglobulinemia") or a subset of this disease.

In a specific embodiment, polynucleotides, polypeptides, antibodies, and/or agonists or antagonists of the present invention may be used to treat, diagnose, and/or prevent (1) cancers or neoplasms and (2) autoimmune cell or tissue-related cancers or neoplasms. In a preferred embodiment, polynucleotides, polypeptides, antibodies, and/or agonists or antagonists of the present invention conjugated to a toxin or a radioactive isotope, as described herein, may be used to treat, diagnose, and/or prevent acute myelogeneous leukemia. In a further preferred embodiment, polynucleotides, polypeptides, antibodies, and/or agonists or antagonists of the present invention conjugated to a toxin or a radioactive isotope, as described herein, may be used to treat, diagnose, and/or prevent, chronic myelogeneous leukemia, multiple myeloma, non-Hodgkins lymphoma, and/or Hodgkins disease.

In another specific embodiment, polynucleotides or polypeptides, and/or agonists or antagonists of the invention may be used to treat, diagnose, prognose, and/or prevent selective IgA deficiency, myeloperoxidase deficiency, C2 deficiency, ataxia-telangiectasia, DiGeorge anomaly, common variable immunodeficiency (CVI), X-linked agammaglobulinemia, severe combined immunodeficiency (SCID), chronic granulomatous disease (CGD), and Wiskott-Aldrich syndrome.

Examples of autoimmune disorders that can be treated or detected are described above and also include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

In a preferred embodiment, the autoimmune diseases and disorders and/or conditions associated with the diseases and disorders recited above are treated, prevented, and/or diagnosed using secreted-like antibodies and/or anti-secreted-like antibodies and/or a soluble secreted-like polypeptide of the invention.

In specific embodiments, the compositions of the invention are used as an agent to boost immunoresponsiveness among B cell immunodeficient individuals, such as, for example, an individual who has undergone a partial or complete splenectomy.

Additionally, polynucleotides, polypeptides, and/or antagonists of the invention may affect apoptosis, and therefore, would be useful in treating a number of diseases associated with increased cell survival or the inhibition of apoptosis. For example, diseases associated with increased cell survival or the inhibition of apoptosis that could be treated or detected by polynucleotides, polypeptides, and/or antagonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, polynucleotides, polypeptides, and/or antagonists of the invention are used to inhibit growth, progression, and/or metastisis of cancers, in particular those listed above.

Additional diseases or conditions associated with increased cell survival that could be treated or detected by polynucleotides, polypeptides, and/or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myclocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by polynucleotides, polypeptides, and/or antagonists of the invention, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemialreperfusion injury, cholestosis (bile duct injury) and liver cancer); toxin-induced liver disease (such as that caused by alcohol), septic shock, cachexia and anorexia.

Hyperproliferative diseases and/or disorders that could be detected and/or treated by polynucleotides, polypeptides, and/or antagonists of the invention, include, but are not limited to neoplasms located in the: liver, abdomen, bone, breast, digestive system, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by polynucleotides, polypeptides, and/or antagonists of the invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Hyperproliferative Disorders

A polynucleotides or polypeptides, or agonists or antagonists of the invention can be used to treat or detect hyperproliferative disorders, including neoplasms. A polynucleotides or polypeptides, or agonists or antagonists of the present invention may inhibit the proliferation of the disorder through direct or indirect interactions. Alliteratively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotides or polypeptides, or agonists or antagonists of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotides or polypeptides, or agonists or antagonists of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating cell proliferative disorders by inserting into an abnormally proliferating cell a polynucleotide of the present invention, wherein said polynucleotide represses said expression.

Another embodiment of the present invention provides a method of treating cell-proliferative disorders in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the poynucleotides of the present invention is inserted into cells to be treated utilizing a retrovirus, or more preferably an adenoviral vector (See G J. Nabel, et. al., PNAS 1999 96:324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating one or more of the described disorders. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating a subject having or developing cell proliferative and/or differentiation disorders as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph IB, et al. J Natl Cancer Inst, 90(21):1648-53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155-61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et.al., Eur J Biochem 254(3):439-59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, antiinflammatory proteins (See for example, Mutat Res 400(1-2):447-55 (1998), Med Hypotheses.50(5):423-33 (1998), Chem Biol Interact. April 24;111-112:23-34 (1998), J Mol Med. 76(6):402-12 (1998), Int J Tissue React; 20(1):3-15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewere herein, or indirectly, such as activating the expression of proteins known to inhibit metastasis, for example alpha 4 integrins, (See, e.g., Curr Top Microbiol Immunol 1998;231: 125-41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodes associated with heterologous polypeptides, heterologous nucleic acids, toxins, or prodrugs) to targeted cells expressing the polypeptide of the present invention. Polypeptides or polypeptide antibodes of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardiumn, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, artenitis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., *Cell* 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630-634 (1991); Folkman et al., *N. Engl. J. Med.,* 333:1757-1763 (1995); Auerbach et al., *J. Microvasc. Res.* 29:401-411 (1985); Folkman, Advances in Cancer Research, eds. Klein and Weinhouse, Academic Press, New York, pp. 175-203 (1985); Patz, *Am. J. Opthalmol.* 94:715-743 (1982); and Folkman et al., Science 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442-447 (1987).

The present invention provides for treatment of diseases or disorders associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincon Co., Philadelphia (1985)). Thus, the present invention provides a method of treating an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat a cancer or tumor. Cancers which may be treated with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating other disorders, besides cancers, which involve angiogenesis. These disorders include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., bums), and is preferably initiated after the proliferative phase has had time to progress (approximately 14 days after the initial injury), but before hypertrophic scar or keloid development. As noted above, the present invention also provides methods for treating neovascular diseases of the eye, including for example, corneal neovascularization, neovascular glaucoma, proliferative diabetic retinopathy, retrolental fibroplasia and macular degeneration.

Moreover, Ocular disorders associated with neovascularization which can be treated with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704-710 (1978) and Gartner et al., *Surv. Ophthal.* 22:291-312 (1978).

Thus, within one aspect of the present invention methods are provided for treating neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of disorders can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali bums, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical bums). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2-3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, disorders which can be treated with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated with be treated with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (Helicobacter pylori), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti- angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alliteratively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl4-chloroanthronilic acid disodium or "CCA"; Takeuchi et al., Agents Actions 36:312-316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated or detected by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection.

In preferred embodiments, the polynucleotides or polypeptides, and/or agonists or antagonists of the invention are used to inhibit growth, progression, and/or metasis of cancers, in particular those listed above.

Additional diseases or conditions associated with increased cell survival that could be treated or detected by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by the polynucleotides or polypeptides, and/or agonists or antagonists of the invention, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfuision injury, cholestosis (bile duct injury) and liver cancer); toxin-induced liver disease (such as that caused by alcohol), septic shock, cachexia and anorexia.

Neural Activity and Neurological Diseases

The polynucleotides, polypeptides and agonists or antagonists of the invention may be used for the diagnosis and/or treatment of diseases, disorders, damage or injury of the brain and/or nervous system. Nervous system disorders that can be treated with the compositions of the invention (e.g., secreted polypeptides, polynucleotides, and/or agonists or antagonists), include, but are not limited to, nervous system injuries, and diseases or disorders which result in either a disconnection of axons, a diminution or degeneration of neurons, or demyelination. Nervous system lesions which may be treated in a patient (including human and non-human mammalian patients) according to the methods of the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, or syphilis; (5) degenerative lesions, in which a portion of the nervous system is destroyed or injured as a result of a degenerative process including but not limited to, degeneration associated with Parkinson's disease, Alzheimer's disease, Huntington's chorea, or amyotrophic lateral sclerosis (ALS); (6) lesions associated with nutritional diseases or disorders, in which a portion of the nervous system is destroyed or injured by a nutritional disorder or disorder of metabolism including, but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In one embodiment, the polypeptides, polynucleotides, or agonists or antagonists of the invention are used to protect neural cells from the damaging effects of hypoxia. In a further preferred embodiment, the polypeptides, polynucleotides, or agonists or antagonists of the invention are used to protect neural cells from the damaging effects of cerebral hypoxia. According to this embodiment, the compositions of the invention are used to treat or prevent neural cell injury associated with cerebral hypoxia. In one non-exclusive aspect of this embodiment, the polypeptides, polynucleotides, or agonists or antagonists of the invention, are used to treat or prevent neural cell injury associated with cerebral ischemia. In another non-exclusive aspect of this embodiment, the polypeptides, polynucleotides, or agonists or antagonists of the invention are used to treat or prevent neural cell injury associated with cerebral infarction.

In another preferred embodiment, the polypeptides, polynucleotides, or agonists or antagonists of the invention are used to treat or prevent neural cell injury associated with a stroke. In a specific embodiment, the polypeptides, polynucleotides, or agonists or antagonists of the invention are used to treat or prevent cerebral neural cell injury associated with a stroke.

In another preferred embodiment, the polypeptides, polynucleotides, or agonists or antagonists of the invention are used to treat or prevent neural cell injury associated with a heart attack. In a specific embodiment, the polypeptides, polynucleotides, or agonists or antagonists of the invention are used to treat or prevent cerebral neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture either in the presence or absence of hypoxia or hypoxic conditions; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, in Zhang et al., *Proc Natl Acad Sci USA* 97:3637-42 (2000) or in Arakawa et al., *J. Neurosci.,* 10:3507-15 (1990); increased sprouting of neurons may be detected by methods known in the art, such as, for example, the methods set forth in Pestronk et al., *Exp. Neurol.,* 70:65-82 (1980), or Brown et al., *Ann. Rev. Neurosci,* 4:17-42 (1981): increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron disorders that may be treated according to the invention include, but are not limited to, disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Further, polypeptides or polynucleotides of the invention may play a role in neuronal survival; synapse formation; conductance; neural differentiation, etc. Thus, compositions of the invention (including secreted polynucleotides, polypeptides, and agonists or antagonists) may be used to diagnose and/or treat or prevent diseases or disorders associated with these roles, including, but not limited to, learning and/or cognition disorders. The compositions of the invention may also be useful in the treatment or prevention of neurodegenerative disease states and/or behavioural disorders. Such neurodegenerative disease states and/or behavioral disorders include, but are not limited to, Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, compositions of the invention may also play a role in the treatment, prevention and/or detection of developmental disorders associated with the developing embryo, or sexually-linked disorders.

Additionally, polypeptides, polynucleotides and/or agonists or antagonists of the invention, may be useful in protecting neural cells from diseases, damage, disorders, or injury, associated with cerebrovascular disorders including, but not limited to, carotid artery diseases (e.g., carotid artery thrombosis, carotid stenosis, or Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis (e.g., carotid artery thrombosis, sinus thrombosis, or Wallenberg's Syndrome), cerebral hemorrhage (e.g., epidural or subdural hematoma, or subarachnoid hemorrhage), cerebral infarction, cerebral ischemia (e.g., transient cerebral ischemia, Subclavian Steal Syndrome, or vertebrobasilar insufficiency), vascular dementia (e.g., multi-infarct), leukomalacia, periventricular, and vascular headache (e.g., cluster headache or migraines).

In accordance with yet a further aspect of the present invention, there is provided a process for utilizing polynucleotides or polypeptides, as well as agonists or antagonists of the present invention, for therapeutic purposes, for example, to stimulate neurological cell proliferation and/or differentiation. Therefore, polynucleotides, polypeptides, agonists and/or antagonists of the invention may be used to treat and/or detect neurologic diseases. Moreover, polynucleotides or polypeptides, or agonists or antagonists of the invention, can be used as a marker or detector of a particular nervous system disease or disorder.

Examples of neurologic diseases which can be treated or detected with polynucleotides, polypeptides, agonists, and/or antagonists of the present invention include brain diseases, such as metabolic brain diseases which includes phenylketonuria such as maternal phenylketonuria, pyruvate carboxylase deficiency, pyruvate dehydrogenase complex deficiency, Wemicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis.

Additional neurologic diseases which can be treated or detected with polynucleotides, polypeptides, agonists, and/or antagonists of the present invention include cerebrovascular disorders (such as carotid artery diseases which include carotid artery thrombosis, carotid stenosis and Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache and migraine.

Additional neurologic diseases which can be treated or detected with polynucleotides, polypeptides, agonists, and/or antagonists of the present invention include dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, and Hallervorden-Spatz Syndrome.

Additional neurologic diseases which can be treated or detected with polynucleotides, polypeptides, agonists, and/or antagonists of the present invention include hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, and cerebral malaria.

Additional neurologic diseases which can be treated or detected with polynucleotides, polypeptides, agonists, and/or antagonists of the present invention include meningitis such as arachnoiditis, aseptic meningtitis such as viral meningtitis which includes lymphocytic choriomeningitis, Bacterial meningtitis which includes Haemophilus Meningtitis, Listeria Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uvemeningoencephalitic syndrome, myelitis such as transverse myelitis, neurosyphilis such as tabes dorsalis, poliomyelitis which includes bulbar poliomyelitis and post-poliomyelitis syndrome, prion diseases (such as Creutzfeldt-Jakob Syndrome, Bovine Spongiform Encephalopathy, Gerstmann-Straussler Syndrome, Kuru, Scrapie), and cerebral toxoplasmosis.

Additional neurologic diseases which can be treated or detected with polynucleotides, polypeptides, agonists, and/or antagonists of the present invention include central nervous system neoplasms such as brain neoplasms that include cerebellar neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyelinating diseases such as Canavan Diseases, diffuse cerebral sceloris which includes adrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffmann Disease, spinal cord compression, spinal cord neoplasms such as epidural neoplasms, syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(MI), Sandhoff Disease, Tay-Sachs Disease, Hartnup Disease, homocystinuria, Laurence-Moon- Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cystica and spina bifida occulta.

Additional neurologic diseases which can be treated or detected with polynucleotides, polypeptides, agonists, and/or antagonists of the present invention include hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative disorders such as hearing disorders that includes deafness, partial hearing loss, loudness recruitment and tinnitus, language disorders such as aphasia which include agraphia, anomia, broca aphasia, and Wemicke Aphasia, Dyslexia such as Acquired Dyslexia, language development disorders, speech disorders such as aphasia which includes anomia, broca aphasia and Wemicke Aphasia, articulation disorders, communicative disorders such as speech disorders which include dysarthria, echolalia, mutism and stuttering, voice disorders such as aphonia and hoarseness, decerebrate state, delirium, fasciculation, hallucinations, meningism, movement disorders such as angelman syndrome, ataxia, athetosis, chorea, dystonia, hypokinesia, muscle hypotonia, myoclonus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, ophthalmoplegia such as diplopia, Duane's Syndrome, Homer's Syndrome, Chronic progressive external ophthalmoplegia such as Keams Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste disorders such as ageusia and dysgeusia, vision disorders such as amblyopia, blindness, color vision defects, diplopia, hemianopsia, scotoma and subnormal vision, sleep disorders such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Homer's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia,Melkersson-Rosenthal Syndrome, ocular motility disorders which includes amblyopia, nystagmnus, oculomotor nerve paralysis, ophthalmoplegia such as Duane's Syndrome, Homer's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, and Diabetic neuropathies such as diabetic foot.

Additional neurologic diseases which can be treated or detected with polynucleotides, polypeptides, agonists, and/or antagonists of the present invention include nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonornia, POEMS Syndrome, Sciatica, Gustatory Sweating and Tetany).

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, bums resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intesting, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and bums, that cause necrosis of the bronchiolar epithelium and alveoli could be effectively treated using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Infectious Disease

A polypeptide or polynucleotide and/or agonist or antagonist of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated or detected by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxovindae, Morbillivirus, Rhabdoviridae), Orthomyxoviridae (e.g., Influenza A, Influenza B, and parainfluenza), Papiloma virus, Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat or detect any of these symptoms or diseases. In specific embodiments, polynucleotides, polypeptides, or agonists or antagonists of the invention are used to treat: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat AIDS.

Similarly, bacterial or fungal agents that can cause disease or symptoms and that can be treated or detected by a polynucleotide or polypeptide and/or agonist or antagonist of the present invention include, but not limited to, include, but not limited to, the following Gram-Negative and Gram-positive bacteria and bacterial families and fungi: Actinomycetales (e.g., Corynebacterium, Mycobacterium, Norcardia), Cryptococcus neofonnans, Aspergillosis, Bacillaceae (e.g., Anthrax, Clostridium), Bacteroidaceae, Blastomycosis, Bordetelia, Borrelia (e.g., Borrelia burgdorferi, Brucellosis, Candidiasis, Campylobacter, Coccidioidomycosis, Cryptococcosis, Dermatocycoses, *E. coli* (e.g., Enterotoxigenic *E. coli* and Enterohemonrhagic *E. coli*), Enterobacteriaceae (*Klebsiella, Salmonella* (e.g., *Salmonella typhi*, and *Salmonella paratyphi*), Serratia, Yersinia), Erysipelothrix, Helicobacter, Legionellosis, Leptospirosis, Listena, Mycoplasmatales, Mycobacterium leprae, Vibrio cholerae, Neisseriaceae (e.g., Acinctobacter, Gonorrhea, Menigococcal), Meisseria meningitidis, Pasteurellacea Infections (e.g., Actinobacillus, Heamophilus (e.g., Heamophilus influenza type B), Pasteurella), Pseudomonas, Rickettsiaceae, Chlamydiaceae, Syphilis, Shigella spp., Staphylococcal, Meningiococcal, Pneumococcal and Streptococcal (e.g., Streptococcus pneumoniae and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat or detect any of these symptoms or diseases. In specific embodiments, Ppolynucleotides, polypeptides, agonists or antagonists of the invention are used to treat: tetanus, Diptheria, botulism, and/or meningitis type B.

Moreover, parasitic agents causing disease or symptoms that can be treated or detected by a polynucleotide or polypeptide and/or agonist or antagonist of the present invention include, but not limited to, the following families or class: Amebiasis, Babesiosis, Coccidiosis, Cryptosporidiosis, Dientarnoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., Plasmodium virax, Plasmodium falciparium, Plasmodium malariae and Plasmodium ovale). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat or detect any of these symptoms or diseases. In specific embodiments, polynucleotides, polypeptides, or agonists or antagonists of the invention are used to treat malaria.

Preferably, treatment using a polypeptide or polynucleotide and/or agonist or antagonist of the present invention could-either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, bums, incisions, or ulcers), age, disease (e.g. osteoporosis, osteocarhritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide and/or agonist or antagonist of the present invention may inhibit chemotactic activity. These molecules could also be used to treat disorders. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which the polypeptide binds, or at least, a fragment of the receptor capable of being bound by the polypeptide (e.g. active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724-33 (1997); Harayama, S. Trends Biotechnol. 16(2):76-82 (1998); Hansson, L. O., et al., J. Mol. Biol. 287:265-76 (1999); and Lorenzo, M. M. and Blasco, R. Biotechniques 24(2):308-13 (1998)(each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, M1S, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thyzmidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a nontoxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense And Ribozyme (Antagonists)

In specific embodiments, antagonists according to the present invention are nucleic acids corresponding to the sequences contained in SEQ ID NO:X, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 MM dithiothreitol (DTT) and 0.2 mM ATP) and then ligated to the EcoRI/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature, 29:304-310 (1981), the promoter contained in the 3' long terminal repeat of Rous sarcoma virus (Yamamoto et al., Cell, 22:787-797 (1980), the herpes thymidine promoter (Wagner et al., Proc. Natl. Acad. Sci. U.S.A., 78:1441-1445 (1981), the regulatory sequences of the metallothionein gene (Brinster et al., Nature, 296:39-42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature,* 372:333-335 (1994). Thus, oligonucleotides complementary to either the 5'-or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'-or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci., 84:648-652 (1987); PCT Publication NO: WO88/09810, published Dec. 15, 1988) or the blood-brain barrier (see, e.g., PCT Publication No: WO89/10134, published Apr. 25, 1988), hybridization-triggered cleavage agents. (See, e.g., Krol et al., BioTechniques, 6:958-976 (1988)) or intercalating agents. (See, e.g., Zon, Pharm. Res., 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcyosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic and methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625-6641 (1987)). The oligonucleotide is a 2-0-methylribonucleotide (Inoue et al., Nucl. Acids Res., 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448-7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222-1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585-591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Thus, the invention provides a method of treating disorders or diseases, including but not limited to the disorders or diseases listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Binding Peptides and Other Molecules

The invention also encompasses screening methods for identifying polypeptides and nonpolypeptides that bind secreted polypeptides, and the secreted binding molecules identified thereby. These binding molecules are useful, for example, as agonists and antagonists of the secreted polypeptides. Such agonists and antagonists can be used, in accordance with the invention, in the therapeutic embodiments described in detail, below.

This method comprises the steps of:

a. contacting secreted polypeptides or secreted-like polypeptides with a plurality of molecules; and b. identifying a molecule that binds the secreted polypeptides or secreted-like polypeptides.

The step of contacting the secreted polypeptides or secreted-like polypeptides with the plurality of molecules may be effected in a number of ways. For example, one may contemplate immobilizing the secreted polypeptides or secreted-like polypeptides on a solid support and bringing a solution of the plurality of molecules in contact with the immobilized secreted polypeptides or secreted-like polypeptides. Such a procedure would be akin to an affinity chromatographic process, with the affinity matrix being comprised of the immobilized secreted polypeptides or secreted-like polypeptides. The molecules having a selective affinity for the secreted polypeptides or secreted-like polypeptides can then be purified by affinity selection. The nature of the solid support, process for attachment of the secreted polypeptides or secreted-like polypeptides to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the secreted polypeptides or secreted-like polypeptides, optionally in the presence of an inducer should one be required for expression, to determine if any selective affinity interaction takes place between the secreted polypeptides or secreted-like polypeptides and the individual clone. Prior to contacting the secreted polypeptides or secreted-like polypeptides with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for secreted polypeptides or secreted-like polypeptides. Furthermore, the amino acid sequence of the polypeptide having a selective affinity for the secreted polypeptides or secreted-like polypeptides can be determined directly by conventional means or the coding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound secreted polypeptides or secreted-like polypeptides, or alternatively, unbound polypeptides, from a mixture of the secreted polypeptides or secreted-like polypeptides and the plurality of polypeptides prior to attempting to determine or to detect the presence of a selective affinity interaction. Such a wash step may be particularly desirable when the secreted polypeptides or secreted-like polypeptides or the plurality of polypeptides is bound to a solid support.

The plurality of molecules provided according to this method may be provided by way of diversity libraries, such as random or combinatorial peptide or nonpeptide libraries which can be screened for molecules that specifically bind secreted polypeptides. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767-773; Houghten et al., 1991, Nature 354:84-86; Lam et al., 1991, Nature 354:82-84; Medynski, 1994, Bio/Technology 12:709-710;Gallop et al., 1994, J. Medicinal Chemistry 37(9):1233-1251; Ohimeyer et al, 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayawickreme et al., 1994, Proc. Natl. Acad. Sci. USA 91:1614-1618; Salmon et al., 1993, Proc. Natl. Acad. Sci. USA 90:11708-11712; PCT Publication No. WO 93/20242; and Brenner and Lemer, 1992, Proc. Natl. Acad. Sci. USA 89:5381-5383.

Examples of phage display libraries are described in Scott and Smith, 1990, Science 249:386-390; Devlin et al. 1990, Science, 249:404-406; Christian, R. B., et al., 1992, J. Mol. Biol. 227:711-718); Lenstra, 1992, J. Immunol. Meth. 152: 149-157; Kay et al., 1993, Gene 128:59-65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022-9026.

By way of examples of nonpeptide libraries, a benzodiazepine library (see e.g., Bunin et al., 1994, Proc. Natl. Acad. Sci. USA 91:4708-4712) can be adapted for use. Peptoid libraries (Simon et al., 1992, Proc. Natl. Acad. Sci. USA 89:9367-9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138-11142).

The variety of non-peptide libraries that are useful in the present invention is great. For example, Ecker and Crooke, 1995, Bio/Technology 13:351-360 list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992; BioTechniques 13:422-427; Oldenburg et al., 1992, Proc. Natl. Acad. Sci. USA 89:5393-5397; Yu et al., 1994, Cell 76:933-945; Staudt et al., 1988, Science 241:577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. Nos. 5,096,815, 5,223,409, and 5,198,346, all to Ladner et al.; Rebar and Pabo, 1993, Science 263:671-673; and CT Publication No. WO 94/18318.

In a specific embodiment, screening to identify a molecule that binds secreted polypeptides can be carried out by contacting the library members with a secreted polypeptides or secreted-like polypeptides immobilized on a solid phase and harvesting those library members that bind to the secreted polypeptides or secreted-like polypeptides. Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318; and in references cited herein.

In another embodiment, the two-hybrid system for selecting interacting proteins in yeast (Fields and Song, 1989, Nature 340:245-246; Chien et al., 1991, Proc. Natl. Acad. Sci. USA 88:9578-9582) can be used to identify molecules that specifically bind to secreted polypeptides or secreted-like polypeptides.

Where the secreted binding molecule is a polypeptide, the polypeptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a secreted binding molecule that is a polypeptide, the polypeptide may have about 6 to less than about 60 amino acid residues, preferably about 6 to about 10 amino acid residues, and most preferably, about 6 to about 22 amino acids. In another embodiment, a secreted binding polypeptide has in the range of 15-100 amino acids, or 20-50 amino acids.

The selected secreted binding polypeptide can be obtained by chemical synthesis or recombinant expression.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat and prevent neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The polypeptide of the invention may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table XIV.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table XIV.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table XIV.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table XIV.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table XIV.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table XIV, which DNA molecule is contained in the material deposited with the American Type Culture Collection and given the ATCC Deposit Number shown in Table XIV for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table XIV, which DNA molecule is contained in the deposit given the ATCC Deposit Number shown in Table XIV.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table XIV; and a nucleotide sequence encoded by a human cDNA clone identified by a cDNA Clone Identifier in Table XIV and contained in the deposit with the ATCC Deposit Number shown for said cDNA clone in Table XIV; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table XIV; and a nucleotide sequence encoded by a human cDNA clone identified by a cDNA Clone Identifier in Table XIV and contained in the deposit with the ATCC Deposit Number shown for said cDNA clone in Table XIV.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table XIV, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table XIV; and a nucleotide sequence encoded by a human cDNA clone identified by a cDNA Clone Identifier in Table XIV and contained in the deposit with the ATCC Deposit Number shown for said cDNA clone in Table XIV.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table XIV; and a nucleotide sequence encoded by a human cDNA clone identified by a cDNA Clone Identifier in Table XIV and contained in the deposit with the ATCC Deposit Number shown for said cDNA clone in Table XIV. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID. NO:Y wherein Y is any integer as defined in Table XIV.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table XIV.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table XIV and contained in the deposit with the ATCC Deposit Number shown for said cDNA clone in Table XIV.

Also preferred is a polypeptide wherein said sequence of contiguous amino acids is included in the amino acid sequence of a secreted portion of the secreted protein encoded by a human cDNA clone identified by a cDNA Clone Identifier in Table XIV and contained in the deposit with the ATCC Deposit Number shown for said cDNA clone in Table XIV.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table XIV and contained in the deposit with the ATCC Deposit Number shown for said cDNA clone in Table XIV.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table XIV and contained in the deposit with the ATCC Deposit Number shown for said cDNA clone in Table XIV.

Also preferred is an isolated polypeptide comprising an amino acid sequence at least 95% identical to the amino acid sequence of the secreted portion of the protein encoded by a human cDNA clone identified by a cDNA Clone Identifier in Table XIV and contained in the deposit with the ATCC Deposit Number shown for said cDNA clone in Table XIV.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table XIV; and a complete amino acid sequence of a protein encoded by a human cDNA clone identified by a cDNA Clone Identifier in Table XIV and contained in the deposit with the ATCC Deposit Number shown for said cDNA clone in Table XIV.

Further preferred is a method for detecting in a biological sample a polypeptide comprising an amino acid sequence which is at least 90% identical to a sequence of at least 10 contiguous amino acids in a sequence selected from the group consisting of an amino acid sequence of SEQ ID NO:Y wherein Y is any integer as defined in Table XIV; and a complete amino acid sequence of a protein encoded by a human cDNA clone identified by a cDNA Clone Identifier in Table XIV and contained in the deposit with the ATCC Deposit Number shown for said cDNA clone in Table XIV; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table XIV; and a complete amino acid sequence of a protein encoded by a human cDNA clone identified by a cDNA Clone Identifier in Table XIV and contained in the deposit with the ATCC Deposit Number shown for said cDNA clone in Table XIV.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table XIV; and a complete amino acid sequence of a secreted protein encoded by a human cDNA clone identified by a cDNA Clone Identifier in Table XIV and contained in the deposit with the ATCC Deposit Number shown for said cDNA clone in Table XIV.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table XIV, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table XIV; and a complete amino acid sequence of a secreted protein encoded by a human cDNA clone identified by a cDNA Clone Identifier in Table XIV and contained in the deposit with the ATCC Deposit Number shown for said cDNA clone in Table XIV.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table XIV; and a complete amino acid sequence of a secreted protein encoded by a human cDNA clone identified by a cDNA Clone Identifier in Table XIV and contained in the deposit with the ATCC Deposit Number shown for said cDNA clone in Table XIV.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table XIV; and a complete amino acid sequence of a secreted protein encoded by a human cDNA clone identified by a cDNA Clone Identifier in Table XIV and contained in the deposit with the ATCC Deposit Number shown for said cDNA clone in Table XIV.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table XIV and said position of the First Amino Acid of the Secreted Portion of SEQ ID NO:Y is defined in Table XIV; and an amino acid sequence of a secreted portion of a protein encoded by a human cDNA clone identified by a cDNA Clone Identifier in Table XIV and contained in the deposit with the ATCC Deposit Number shown for said cDNA clone in Table XIV. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Having generally described the invention, the same will be more readily understood by reference to the following examples, which are provided by way of illustration and are not intended as limiting.

EXAMPLES

Example 1

Isolation of a Selected cDNA Clone From the Deposited Sample

Each cDNA clone in a cited ATCC deposit is contained in a plasmid vector. Table XIV identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table XIV as being isolated in the vector "Lambda Zap," the corresponding deposited clone is in "pBluescript."

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583-7600 (1988); Alting-Mees, M. A. and Short, J. M., Nucleic Acids Res. 17:9494 (1989)) and pBK (Alting-Mees, M. A. et al., Strategies 5:58-61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into *E. coli* strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P.O. Box 6009, Gaithersburg, Md. 20897. All Sport vectors contain an ampicillin resistance gene and may be transformed into *E. coli* strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from Life Technologies. (See, for instance, Clark, J. M., Nuc. Acids Res. 16:9677-9686 (1988) and Mead, D. et al., Bio/Technology 9: (1991).) Preferably, a polynucleotide of the present invention does not comprise the phage vector sequences identified for the particular clone in Table XIV, as well as the corresponding plasmid vector sequences designated above.

The deposited material in the sample assigned the ATCC Deposit Number cited in Table XIV for any given cDNA clone also may contain one or more additional plasmids, each comprising a cDNA clone different from that given clone. Thus, deposits sharing the same ATCC Deposit Number contain at least a plasmid for each cDNA clone identified in Table XIV. Typically, each ATCC deposit sample cited in Table XIV comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table XIV. First, a plasmid is directly isolated by screening the clones using a polynucleotide probe corresponding to SEQ ID NO:X.

Particularly, a specific polynucleotide with 30-40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17-20 nucleotides derived from both ends of the SEQ ID NO:X (i.e., within the region of SEQ ID NO:X bounded by the 5' NT and the 3' NT of the clone defined in Table XIV) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5-5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683-1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70 degree C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds,95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lad repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG (Isopropyl-B-D-thiogalacto pyranoside) is then added to a final concentration of 1 mM. IPTG induces by inactivating the lad repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilo-tri-acetic acid ("Ni—NTA") affinity resin column (available from QIAGEN, Inc., supra). Proteins with a 6× His tag bind to the Ni—NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4 degree C. or frozen at −80 degree C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgamo sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

1 Purification of a Polypeptide from an Inclusion Body

The following alternative method can be used to purify a polypeptide expressed in *E coli* when it is present in the form of inclusion bodies. Unless otherwise specified, all of the following steps are conducted at 4-10 degree C.

Upon completion of the production phase of the *E. coli* fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stining. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 7

Cloning and Exression of a Potypt in a Baculorirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

Specifically, the cDNA sequence contained in the deposited clone, including the AUG initiation codon and the naturally associated leader sequence identified in Table XIV, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Feigner et al., Proc. Natl. Acad. Sci. USA 84:7413-7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438-447 (March, 1985)) plus a fragment of the CMV-enhancer (Boshart et al., Cell 41:521-530 (1985). Multiply cloning sites, e.g., with the restriction enzyme cleavage sites BamHI, XbaI and asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five μg of the expression plasmid pC6 a pC4 is cotransfected with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100-200 uM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84-86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

```
        GGGATCCGGAGCCCAAATCTTCTGACAAAACTCACACATGCCCACCGTGCCCAGCACCTGAATTCGAGG   (SEQ ID NO: 1)

GTGCACCGTCAGTCTTCCTCTTCCCCCCAAAACCCAAGGACACCCTCATGATCTCCCGGACTCCTGAGGTCACATG

CGTGGTGGTGGACGTAAGCCACGAAGACCCTGAGGTCAAGTTCAACTGGTACGTGGACGGCGTGGAGGTGCATAA

TGCCAAGACAAAGCCGCGGGAGGAGCAGTACAACAGCACGTACCGTGTGGTCAGCGTCCTCACCGTCCTGCACCA

GGACTGGCTGAATGGCAAGGAGTACAAGTGCAAGGTCTCCAACAAAGCCCTCCCAACCCCCATCGAGAAAACCAT

CTCCAAAGCCAAAGGGCAGCCCCGAGAACCACAGGTGTACACCCTGCCCCCATCCCGGGATGAGCTGACCAAGAA

CCAGGTCAGCCTGACCTGCCTGGTCAAAGGCTTCTATCCAAGCGACATCGCCGTGGAGTGGGAGAGCAATGGGCA

GCCGGAGAACAACTACAAGACCACGCCTCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGATGCATGAGGCTCTGCACAACCACTAC

ACGCAGAAGAGCCTCTCCCTGTCTCCGGGTAAATGAGTGCGACGGCCGCGACTCTAGAGGAT
```

Example 10

Production of an Antibody from a Polypeptide

The antibodies of the present invention can be prepared by a variety of methods. (See, Current Protocols, Chapter 2.) As one example of such methods, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563-681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production of Secreted Protein for High-Throughput Screening Assays

The following protocol produces a supernatant containing a polypeptide to be tested. This supernatant can then be used in the Screening Assays described in Examples 13-20.

First, dilute Poly-D-Lysine (644 587 Boehringer-Mannheim) stock solution (1 mg/ml in PBS) 1:20 in PBS (w/o calcium or magnesium 17-516 F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM(Dulbecco's Modified Eagle Medium)(with 4.5 G/L glucose and L-glutamine (12-604 F Biowhittaker))/10% heat inactivated FBS(14-503 F Biowhittaker)/1× Penstrep (17-602 E Biowhittaker). Let the cells grow overnight.

The next day, mix together in a sterile solution basin: 300 ul Lipofectamine (18324-012 Gibco/BRL) and 5 ml Optimem 1 (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15-45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5-1 ml PBS. Person A then aspirates off PBS rinse, and person B, using a 12-channel pipetter with tips on every other channel, adds the 200 ul of DNA/Lipofectamine/Optimem 1 complex to the odd wells first, then to the even wells, to each row on the 24-well plates. Incubate at 37 degrees C. for 6 hours.

While cells are incubating, prepare appropriate media, either 1 % BSA in DMEM with 1× penstrep, or CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 of $NaHCO_3$; 62.50 mg/L of $NaH_2PO_4$—$H_2O$; 71.02 mg/L of $Na_2$HPO4; 0.4320 mg/L of $ZnSO_4$-$7H_2O$; 0.002 mg/L of Anachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2H $_2$O; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer, 2.39 mg/L; of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 2 uM of Ethanolamnine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1× penstrep. (BSA (81-068-3 Bayer) 100 gm dissolved in 1L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degrees C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13-20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Damell, Ann. Rev. Biochem. 64:621-51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| | JAKs | | | | | |
|---|---|---|---|---|---|---|
| Ligand | tyk2 | Jak1 | Jak2 | Jak3 | STATS | GAS(elements) or ISRE |
| IFN family | | | | | | |
| IFN-a/B | + | + | − | − | 1, 2, 3 | ISRE |
| IFN-g | | + | + | − | 1 | GAS (IRF1 > Lys6 > IFP) |
| Il-10 | + | ? | ? | − | 1, 3 | |
| gp130 family | | | | | | |
| IL-6 (Pleiotrophic) | + | + | + | ? | 1, 3 | GAS (IRF1 > Lys6 > IFP) |
| Il-11(Pleiotrophic) | ? | + | ? | ? | 1, 3 | |
| OnM(Pleiotrophic) | ? | + | + | ? | 1, 3 | |
| LIF(Pleiotrophic) | ? | + | + | ? | 1, 3 | |
| CNTF(Pleiotrophic) | −/+ | + | + | ? | 1, 3 | |
| G-CSF(Pleiotrophic) | ? | + | ? | ? | 1, 3 | |
| IL-12(Pleiotrophic) | + | − | + | + | 1, 3 | |
| g-C family | | | | | | |
| IL-2 (lymphocytes) | − | + | − | + | 1, 3, 5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone | | | | | | |

-continued

| Ligand | JAKs tyk2 | Jak1 | Jak2 | Jak3 | STATS | GAS(elements) or ISRE |
|---|---|---|---|---|---|---|
| family | | | | | | |
| GH | ? | – | + | – | 5 | |
| PRL | ? | +/– | + | – | 1, 3, 5 | |
| EPO | ? | – | + | – | 5 | GAS(B-CAS > IRF1 = IFP >> Ly6) |
| Receptor Tyrosine Kinases | | | | | | |
| EGF | ? | + | + | – | 1, 3 | GAS (IRF1) |
| PDGF | ? | + | + | – | 1, 3 | |
| CSF-1 | ? | + | + | – | 1, 3 | GAS (not IRF1) |

To construct a synthetic GAS containing promoter element, which is used in the Biological Assays described in Examples 13-14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457-468 (1994).), although other GAS or ISRE elements can be used instead. The 5' primer also contains 18 bp of sequence complementary to the SV40 early promoter sequence and is flanked with an XhoI site. The sequence of the 5' primer is:

```
5':GCGCCTCGAGATTTCCCCGAAATCTAGATTTCCCCGAAATGATTTCCCCGAAATGATTTCCCCGAAATATCTGCC  (SEQ ID NO: 3)

ATCTCAATTAG:3'
```

The downstream primer is complementary to the SV40 promoter and is flanked with a Hind III site:

```
5':GCGGCAAGCTTTTTGCAAAGCCTAGGC:3'  (SEQ ID NO: 4)
```

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

```
    5':CTCGAGATTTCCCCGAAATCTAGATTTCCCCGAAATGATTTCCCCGAAATGATTTCCCCGAAATATCTGC  (SEQ ID NO: 5)

CATCTCAATTAGTCAGCAACCATAGTCCCGCCCCTAACTCCGCCCATCCCGCCCCTAACTCCGCCCAGTTCCGCCC

ATTCTCCGCCCCATGGCTGACTAATTTTTTTTATTTATGCAGAGGCCGAGGCCGCCTCGGCCTCTGAGCTATTCCAG

AAGTAGTGAGGAGGCTTTTTTGGAGGCCTAGGCTTTTGCAAAAAGCTT:3'
```

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13-14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUTVAC (aortic), or Cardiomyocyte.

Example 13

High-Throughput Screening Assay for T-Cell Activity

The following protocol is used to assess T-cell activity by identifying factors, and determining whether supernate containing a polypeptide of the invention proliferates and/or differentiates T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mis of OPTI-MEM (Life Technologies) with 10 ug of plasmid DNA in a T25 flask. Add 2.5 ml OPTI-MEM containing 50 ul of DMRIE-C and incubate at room temperature for 15-45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37 degrees C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing polypeptides of the invention and/or induced polypeptides of the invention as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48-72 hrs). 35 ul samples from each well are then transferred to an opaque 96 well plate using a 12 channel pipette. The opaque plates should be covered (using sellophene covers) and stored at −20 degrees C. until SEAP assays are performed according to Example 17. The plates containing the remaining treated cells are placed at 4 degrees C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14

High-Throughput Screening Assay Identifying Myeloid Activity

The following protocol is used to assess myeloid activity by determining whether polypeptides of the invention proliferates and/or differentiates myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259-265) is used. First, harvest $2\times10e^7$ U 937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37 degrees C. for 45 min.

Wash the cells with RPMI 1640 medium containing 10% FBS and then resuspend in 10 ml complete medium and incubate at 37 degrees C. for 36 hr.

The GAS-SEAP/U937 stable cells are obtained by growing the cells in 400 ug/ml G418. The G418-free medium used for routine growth but every one to two months, the cells should be re-grown in 400 ug/ml G418 for couple of passages.

These cells are tested by harvesting $1\times10^8$ cells (this is enough for ten 96-well plates assay) and wash with PBS. Suspend the cells in 200 ml above described growth medium, with a final density of $5\times10^5$ cells/ml. Plate 200 ul cells per well in the 96-well plate (or $1\times10^5$ cells/well).

Add 50 ul of the supernatant prepared by the protocol described in Example 11. Incubate at 37 degrees C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867-871 (1991)) can be PCR amplified from human genomic DNA using the following primers:

```
5'                                        (SEQ ID NO: 6)
GCGCTCGAGGGATGACAGCGATAGAACCCCGG-3'

5'                                        (SEQ ID NO: 7)
GCGAAGCTTCGCGACTCCCCGGATCCGCCTC-3'
```

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mis of a coating solution (1:30 dilution of collagen type 1 (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 ul of the cell suspension to each well of 96-well plate (equivalent to $1\times10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-Throughput Screening Assay for T-Cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 11. Activators or inhibitors of NF-KB would be useful in treating diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:8), 18 bp of sequence complementary to the 5' end of the SV40 early promoter sequence, and is flanked with an XhoI site:

```
5':GCGGCCTCGAGGGGACTTTCCCGGGGACTTTCCGGGGACTTTCCGGGACTTTCCATCCTGCCATCTCAATTAG:3'   (SEQ ID NO: 9)
```

The downstream primer is complementary to the 3' end of the SV40 promoter and is flanked with a Hind III site:

```
5':GCGGCAAGCTTTTTGCAAAGCCTAGGC:3'   (SEQ ID NO: 4)
```

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

```
5':CTCGAGGGGACTTTCCCGGGGACTTTCCGGGGACTTTCCGGGACTTTCCATCTGCCATCTCAATTAGTCAGCAAC  (SEQ ID NO: 10)

CATAGTCCCGCCCCTAACTCCGCCCATCCCGCCCCTAACTCCGCCCAGTTCCGCCCATTCTCCGCCCCATGGCTGAC

TAATTTTTTTTATTTATGCAGAGGCCGAGGCCGCCTCGGCCTCTGAGCTATTCCAGAAGTAGTGAGGAGGCTTTTTT

GGAGGCCTAGGCTTTTGCAAAAAGCTT:3'
```

Next, replace the SV40 minimal promoter element present in the pSEAP2-promoter plasmid (Clontech) with this NF-KB/SV40 fragment using XhoI and Hindlll. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1,1, 10 ng) is added to wells H9, H10, and H11, with a 5-10 fold activation typically observed.

Example 17

Assay for SEAP Activity

As a reporter molecule for the assays described in Examples 13-16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 ul of 2.5× dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

Reaction Buffer Formulation:

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |

-continued

Reaction Buffer Formulation:

| # of plates | Rxn buffer diluent (ml) | CSPD (ml) |
|---|---|---|
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000-20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37 degrees C. in a $CO_2$ incubator for 60 min. The plate is washed four times in the Biotek washer with HBSS leaving 100 ul of buffer.

For non-adherent cells, the cells are spun down from culture media. Cells are re-suspended to 2-5×$10^6$ cell/ml with HBSS in a 50-ml conical tube. 4 ul of 1 mg/ml fluo-4 solution in 10% pluronic acid DMSO is added to each ml of cell suspension. The tube is then placed in a 37 degrees C. water bath for 30-60 min. The cells are washed twice with HBSS, resuspended to 1×$10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300-800 mW; (2) Exposure time is 0.4 second; (3) Camera F/stop is F/2; (4) Excitation is 488; (5) Emission is 530 nm; and (6) Sample addition is 50 ul. Increased emission at 530 nm indicates an extracellular signaling event which has resulted in an increase in the intracellular $Ca^{++}$ concentration.

Example 19

High-Throughput Screening Assay Identifying Tyrosine Kinase Activity

The Protein Tyrosine Kinases (PTK) represent a diverse group of trarsmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type 1 collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5-20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 4 degrees C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degrees C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6-20 of the cell division kinase cdc2-p34) and PSK2 (corresponding to amino acids 1-17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$ (5 mM ATP/50 mM $MgCl_2$), then 10 ul of 5× Assay Buffer (40 mM imidazole hydrochloride, pH7.3, 40 mM beta-glycerophosphate, 1 mM EGTA, 100 mM $MgCl_2$, 5 mM $MnCl_2$, 0.5 mg/ml BSA), then 5 ul of Sodium Vanadate(1 mM), and then 5 ul of water. Mix the components gently and preincubate the reaction mix at 30 degrees C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degrees C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase(anti-P-Tyr-POD (0.5 u/ml)) to each well and incubate at 37 degrees C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3-5 rinses with PBS, the plates are stored at 4 degrees C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5-20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFLA instrument (time-resolved fluorescence). An increased fluorescent signal over background indicates a phosphorylation.

Example 21

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95 degrees C. for 30 seconds; 60-120 seconds at 52-58 degrees C.; and 60-120 second at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson et al., Methods Cell Biol. 35:73-99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C— and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulation

The invention also provides methods of treatment and/or prevention of diseases or disorders (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrastemal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547-556 (1983)), poly (2-hydroxyethyl methacrylate) (Langer et al., J. Biomed. Mater. Res. 15:167-277 (1981), and Langer, Chem. Tech. 12:98-105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see generally, Langer, *Science* 249:1527-1533 (1990); Treat et al., in *Liposomes in the Therapy of Infectious Disease and Cancer*, Lopez-Berestein and Fidler (eds.), Liss, New York, pp. 317-327 and 353-365 (1989)). Liposomes containing the Therapeutic are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527-1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as marmitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (larnivudine/3TC), and COMBIVIR™ (zidovudine/lamivudine). Non-nucleoside reverse transcriptase inhibitors that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRDCIVAN™ (indinavir), NORVIR™ (ritonavir), INWIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIDETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRBMTHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondli* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAM™, SANDOGLOBULIN™, GAMMAGARD S/D™, and GAMIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1 alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE™ (SARGRAMOSTIM™) and NEUPOGEN™ (FILGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 24

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1-100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy-Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 27

Gene Therapy Using Endogenous Genes Corresponding To Polynucleotides of the Invention Another method of gene therapy according to the present invention involves operably associating the endogenous polynucleotide sequence of the invention with a promoter via homologous recombination as described, for example, in U.S. Pat. No: 5,641,670, issued Jun. 24, 1997; International Publication No: WO 96/29411, published Sep. 26, 1996; International Publication No: WO 94/12650, published Aug. 4, 1994; Koller et al., *Proc. Natl. Acad Sci. USA,* 86:8932-8935 (1989); and Zijlstra et al., *Nature,* 342:435-438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2$ $HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MB1 Fennentas, Amherst, N.Y.) is digested with HindIII. The CMV promoter is amplified by PCR with an XbaI site on the 5' end and a BamHI site on the 3' end. Two non-coding sequences are amplified via PCR: one non-coding sequence (fragment 1) is amplified with a HindIII site at the 5' end and an Xba site at the 3' end; the other non-coding sequence (fragment 2) is amplified with a BamHI site at the 5' end and a HindIII site at the 3' end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5.\times10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 28

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693, 622, 5,705,151, 5,580,859; Tabata et al., Cardiovasc. Res. 35(3):470-479 (1997); Chao et al., Pharmacol. Res. 35(6): 517-522 (1997); Wolff, Neuromuscul. Disord. 7(5): 314-318 (1997); Schwartz et al., Gene Ther. 3(5):405-411 (1996); Tsurumi et al., Circulation 94(12):3281-3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. N.Y. Acad. Sci. 772:126-139 and Abdallab B. et al. (1995) Biol. Cell 85(1):1-7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 29

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, 1983, Mol Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g, head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 30

Knock-Out Animals

Endogenous gene expression can also be reduced by inactivating or "knocking out" the gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g. lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g. by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 31

Isolation of Antibody Fragments Directed Against Polypeptides of the Invention from a Library of scFvs Naturally occurring V-genes isolated from human PBLs are constructed into a large library of antibody fragments which contain reactivities against a polypeptide having the amino acid sequence of SEQ ID NO:Y to which the donor may or may not have been exposed (see e.g., U.S. Pat. No. 5,885,793 incorporated herein in its entirety by reference).

Rescue of the Library.

A library of scFvs is constructed from the RNA of human PBLs as described in WO92/01047. To rescue phage displaying antibody fragments, approximately $10^9$ *E. coli* harboring the phagemid are used to inoculate 50 ml of 2× TY containing 1% glucose and 100 micrograms/ml of ampicillin (2× TY-AMP-GLU) and grown to an O.D. of 0.8 with shaking. Five ml of this culture is used to inoculate 50 ml of 2× TY-AMP-GLU, 2×108 TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of of 2× TY containing 100 micrograms/ml ampicillin and 50 micrograms/ml kanamycin and grown overnight Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells were spun down (IEC-Centra 8, 4000 revs/min for 10 min), resuspended in 300 ml 2× TY both containing 100 micrograms ampicillin/ml and 25 micrograms kanamycin/ml (2× TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 micrometer filter (Minisart NML; Sartorius) to give a final concentration of approximately $10^{13}$ transducing units/ml (ampicillin-resistant clones).

Panning the Library.

Immunotubes (Nunc) are coated overnight in PBS with 4 ml of either 100 micrograms/ml or 10 micrograms/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C.

The *E. coli* are then plated on TYE plates containing 1% glucose and 100 micrograms/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders.

Eluted phage from the third and fourth rounds of selection are used to infect *E. coli* HB 2151 and soluble scFv is produced (Marks, et al., 1991) from single colonies for assay. ELISAs are performed with microtiter plates coated with either 10 picograms/ml of the polypeptide of the present invention in 50 mM bicarbonate pH 9.6. Clones positive in ELISA are further characterized by PCR fingerprinting (see e.g., WO92/01047) and then by sequencing.

Example 32

Assays Detecting Stimulation or Inhibition of B cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL-10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay—Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed Staphylococcus aureus Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5\times10^{-5}$M 2 ME, 100 U/ml penicillin, 10 ug/ml steptomycin, and $10^{-5}$ dilution of SAC) in a total volume of 150 ul. Proliferation or inhibition is quantitated by a 20 h pulse (1 uCi/well)) with 3H-thymidine (6.7 Ci/mM) beginning 72 h post factor addition. The positive and negative controls are IL2 and medium respectively.

In Vivo Assay—BALB/c mice are injected (i.p.) twice per day with buffer only, or 2 mg/Kg of a polypeptide of the invention, or truncated forms thereof Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of periarterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R(B220) dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

The studies described in this example tested activity of a polypeptide of the invention. However, one skilled in the art could easily modify the exemplified studies to test the activity of polynucleotides of the invention (e.g., gene therapy), agonists, and/or antagonists of polynucleotides or polypeptides of the invention.

Example 33

T Cell Proliferation Assay

A CD3-induced proliferation assay is performed on PBMCs and is measured by the uptake of $^3$H-thymidine. The assay is performed as follows. Ninety-six well plates are coated with 100 μl/well of mAb to CD3 (HIT3a, Pharmingen) or isotype-matched control mAb (B33.1) overnight at 4 degrees C. (1 μg/ml in 0.05M bicarbonate buffer, pH 9.5), then washed three times with PBS, PBMC are isolated by F/H gradient centrifugation from human peripheral blood and added to quadruplicate wells ($5\times10^4$/well) of mAb coated plates in RPMI containing 10% FCS and P/S in the presence of varying concentrations of polypeptides of the invention (total volume 200 ul). Relevant protein buffer and medium alone are controls. After 48 hr. culture at 37 degrees C., plates are spun for 2 min. at 1000 rpm and 100 μl of supernatant is removed and stored −20 degrees C. for measurement of IL-2 (or other cytokines) if effect on proliferation is observed. Wells are supplemented with 100 ul of medium containing 0.5 uCi of $^3$H-thymidine and cultured at 37 degrees C. for 18-24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of polypeptides of the invention.

The studies described in this example tested activity of polypeptides of the invention. However, one skilled in the art could easily modify the exemplified studies to test the activity of polynucleotides of the invention (e.g., gene therapy), agonists, and/or antagonists of polynucleotides or polypeptides of the invention.

Example 34

Effect of Polypeptides of the Invention on the Expression of MHC Class II, Costimulatory and Adhesion Molecules and Cell Differentiation of Monocytes and Monocyte—Derived Human Dendritic Cells Dendritic cells are generated by the expansion of proliferating precursors found in the peripheral blood: adherent PBMC or elutriated monocytic fractions are cultured for 7-10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MRC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1-3 days with increasing concentrations of polypeptides of the invention or LPS (positive control), washed with PBS containing 1% BSA and 0.02 mM sodium azide, and then incubated with 1:20 dilution of appropriate FITC— or PE-labeled monoclonal antibodies for 30 minutes at 4 degrees C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fe receptors may correlate with improved monocyte cytotoxic activity, cytokine release and phagocytosis.

FACS analysis is used to examine the surface antigens as follows. Monocytes are treated 1-5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 μg/ml, and then incubated at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of the a polypeptide of the invention and under the same conditions, but in the absence of the polypeptide. For IL-12 production, the cells are primed overnight with IFN (100 U/ml) in presence of a polypeptide of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

Oxidative burst. Purified monocytes are plated in 96-w plate at $2\text{-}1\times10^5$ cell/well. Increasing concentrations of polypeptides of the invention are added to the wells in a total volume of 0.2 ml culture medium (RPMI 1640+10% FCS, glutamine and antibodies) After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 μl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity of a polypeptide of the invention. However, one skilled in the art could easily modify the exemplified studies to test the activity of polypeptides, polynucleotides (e.g., gene therapy), agonists, and/or antagonists of the invention.

Example 35

Biological Effects of Polypeptides of the Invention

Astrocyte and Neuronal Assays

Recombinant polypeptides of the invention, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." *Proc. Natl. Acad Sci USA* 83:3012-3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the invention to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescene reader. For the $PGE_2$ assays, the human lung fibroblasts are cultured at 5,000 cells/well in a 96-well plate for one day.After a medium change to 0.1% BSA basal medium, the cells are incubated with FGF-2 or polypeptides of the invention with or without IL-1$\alpha$ for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or with or without polypeptides of the invention IL-1a for 24 hours. The supernatants are collected and assayed for IL-6 by ELISA kit (Endogen, Cambridge, Mass.).

Human lung fibroblasts are cultured with FGF-2 or polypeptides of the invention for 3 days in basal medium before the addition of Alamar Blue to assess effects on growth of the fibroblasts. FGF-2 should show a stimulation at 10-2500 ng/ml which can be used to compare stimulation with polypeptides of the invention.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4phenyl 1,2,3,6-tetrahydropyridine (MPTP). In the CNS, MPTP is taken-up by astrocytes and catabolized by monoamine oxidase B to 1-methyl-4-phenyl pyridine($MPP^+$) and released. Subsequently $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, polypeptides of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of a polypeptide of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if a polypeptide of the invention acts to prolong the survival of dopaminergic neurons, it would suggest that the polypeptide may be involved in Parkinson's Disease.

The studies described in this example tested activity of a polypeptide of the invention. However, one skilled in the art could easily modify the exemplified studies to test the activity of polynucleotides (e.g., gene therapy), agonists, and/or antagonists of the invention.

Example 36

The Effect of Polypeptides of the Invention on the Growth of Vascular Endothelia Cells On day 1, human umbilical vein endothelial cells (HUVEC) are seeded at 2-5×$10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. A polypeptide having the amino acid sequence of SEQ ID NO:Y, and positive controls, such as VEGF and basic FGF (bFGF) are added, at varying concentrations. On days 4 and 6, the medium is replaced. On day 8, cell number is determined with a Coulter Counter.

An increase in the number of HUEC cells indicates that the polypeptide of the invention may proliferate vascular endothelial cells.

The studies described in this example tested activity of a polypeptide of the invention. However, one skilled in the art could easily modify the exemplified studies to test the activity of polynucleotides (e.g., gene therapy), agonists, and/or antagonists of the invention.

Example 37

Stimulatory Effect of Polypeptides of the Invention on the Proliferation of Vascular Endothelial Cells For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, $VEGF_{165}$ or a polypeptide of the invention in 0.5% FBS) with or without Heparin (8 U/ml) are added to wells for 48 hours. 20 mg of MTS/PMS mixture (1:0:05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512-518 (1994).

The studies described in this example tested activity of a polypeptide of the invention. However, one skilled in the art could easily modify the exemplified studies to test the activity of polynucleotides (e.g., gene therapy), agonists, and/or antagonists of the invention.

Example 38

Inhibition of PDGF—Induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4 degrees C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6:271(36):21985-21992 (1996).

The studies described in this example tested activity of a polypeptide of the invention. However, one skilled in the art could easily modify the exemplified studies to test the activity of polynucleotides (e.g., gene therapy), agonists, and/or antagonists of the invention.

Example 39

Stimulation of Endothelial Migration

This example will be used to explore the possibility that a polypeptide of the invention may stimulate lymphatic endothelial cell migration.

Endothelial cell migration assays are performed using a 48 well microchemotaxis chamber (Neuroprobe Inc., Cabin John, MD; Falk, W., et al., J. Immunological Methods 1980; 33:239-247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2-6) HUVEC or BMEC cultures are washed and trypsinized for the minimum time required to achieve cell detachment. After placing the filter between lower and upper chamber, 2.5×$10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity of a polypeptide of the invention. However, one skilled in the art could easily modify the exemplified studies to test the activity of polynucleotides (e.g., gene therapy), agonists, and/or antagonists of the invention.

Example 40

Stimulation of Nitric Oxide Production by Endothelial Cells

Nitric oxide released by the vascular endothelium is believed to be a mediator of vascular endothelium relaxation. Thus, activity of a polypeptide of the invention can be assayed by determining nitric oxide production by endothelial cells in response to the polypeptide.

Nitric oxide is measured in 96-well plates of confluent microvascular endothelial cells after 24 hours starvation and a subsequent 4 hr exposure to various levels of a positive control (such as VEGF-1) and the polypeptide of the invention. Nitric oxide in the medium is determined by use of the Griess reagent to measure total nitrite after reduction of nitric oxide-derived nitrate by nitrate reductase. The effect of the polypeptide of the invention on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

$$2\ KNO_2+2\ KI+2\ H_2SO_4 6\ 2NO+I_2+2H_2O+2K_2SO_4$$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1\times10^6$ endothelial cells. All values reported are means of four to six measurements in each group (number of cell culture wells). See, Leak et al. *Biochem. and Biophys. Res. Comm.* 217:96-105 (1995).

The studies described in this example tested activity of polypeptides of the invention. However, one skilled in the art could easily modify the exemplified studies to test the activity of polynucleotides (e.g., gene therapy), agonists, and/or antagonists of the invention.

Example 41

Effect of Polypepides of the Invention on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or a polypeptide of the invention (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example tested activity of a polypeptide of the invention. However, one skilled in the art could easily modify the exemplified studies to test the activity of polynucleotides (e.g., gene therapy), agonists, and/or antagonists of the invention.

Example 42

Angiogenic Effect on Chick Chorioallantoic Membrane

Chick chorioallantoic membrane (CAM) is a well-established system to examine angiogenesis. Blood vessel formation on CAM is easily visible and quantifiable. The ability of polypeptides of the invention to stimulate angiogenesis in CAM can be examined.

Fertilized eggs of the White Leghorn chick (*Gallus gallus*) and the Japanese qual (*Coturnix coturnix*) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 43

Angiogenesis Assay Using a Matrigel Implant in Mouse

In vivo angiogenesis assay of a polypeptide of the invention measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with a polypeptide of the invention at 150 ng/ml at 4 degrees C. and drawn into cold 3 ml syringes. Female C57B1/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffm and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example tested activity of a polypeptide of the invention. However, one skilled in the art could easily modify the exemplified studies to test the activity of polynucleotides (e.g., gene therapy), agonists, and/or antagonists of the invention.

Example 44

Rescue of Ischemia in Rabbit Lower Limb Model

To study the in vivo effects of polynucleotides and polypeptides of the invention on ischemia, a rabbit hindlimb ischemia, a rabbit hindlimb ischemia model is created by surgical removal of one femoral arteries as described previously (Takeshita et al., *Am J. Pathol* 147:1649-1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita et al. *Am J. Pathol* 147:1649-1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked expression plasmid containing a polynucleotide of the invention by arterial gene transfer technology using a hydrogel-coated balloon catheter as described (Riessen et al. *Hum Gene Ther.* 4:749-758 (1993); Leclerc et al. *J. Clin. Invest.* 90: 936-944 (1992)). When a polypeptide of the invention is used in the treatment, a single bolus of 500 mg polypeptide of the invention or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity of polynucleotides and polypeptides of the invention. However, one skilled in the art could easily modify the exemplified studies to test the agonists, and/or antagonists of the invention.

Example 45

Effect of Polypeptides of the Invention on Vasodilation

Since dilation of vascular endothelium is important in reducing blood pressure, the ability of polypeptides of the invention to affect the blood pressure in spontaneously hypertensive rats (SHR) is examined. Increasing doses (0, 10, 30, 100, 300, and 900 mg/kg) of the polypeptides of the invention are administered to 13-14 week old spontaneously hypertensive rats (SHR). Data are expressed as the mean±SEM. Statistical analysis are performed with a paired t-test and statistical significance is defined as $p<0.05$ vs. the response to buffer alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 46

Rat Ischemic Skin Flop Model

The evaluation parameters include skin blood flow, skin temperature, and factor VIII immunohistochemistry or endothelial alkaline phosphatase reaction. Expression of polypeptides of the invention, during the skin ischemia, is studied using in situ hybridization.

The study in this model is divided into three parts as follows:

a) Ischemic skin b) Ischemic skin wounds c) Normal wounds

The experimental protocol includes:

a) Raising a 3×4 cm, single pedicle full-thickness random skin flap (myocutaneous flap over the lower back of the animal).

b) An excisional wounding (4-6 mm in diameter) in the ischemic skin (skin-flap).

c) Topical treatment with a polypeptide of the invention of the excisional wounds (day 0, 1, 2, 3, 4 post-wounding) at the following various dosage ranges: 1 mg to 100 mg.

d) Harvesting the wound tissues at day 3, 5, 7, 10, 14 and 21 post-wounding for histological, immunohistochemical, and in situ studies.

The studies described in this example tested activity of a polypeptide of the invention. However, one skilled in the art could easily modify the exemplified studies to test the activity of polynucleotides (e.g., gene therapy), agonists, and/or antagonists of the invention.

Example 47

Peripheral Arterial Disease Model

Angiogenic therapy using a polypeptide of the invention is a novel therapeutic strategy to obtain restoration of blood flow around the ischemia in case of peripheral arterial diseases. The experimental protocol includes:

a) One side of the femoral artery is ligated to create ischemic muscle of the hindlimb, the other side of hindlimb serves as a control.

b) a polypeptide of the invention, in a dosage range of 20 mg-500 mg, is delivered intravenously and/or intramuscularly 3 times (perhaps more) per week for 2-3 weeks.

c) The ischemic muscle tissue is collected after ligation of the femoral artery at 1, 2, and 3 weeks for the analysis of expression of a polypeptide of the invention and histology. Biopsy is also performed on the other side of normal muscle of the contralateral hindlimb.

The studies described in this example tested activity of a polypeptide of the invention. However, one skilled in the art could easily modify the exemplified studies to test the activity of polynucleotides (e.g., gene therapy), agonists, and/or antagonists of the invention.

Example 48

Ischemic Myocardial Disease Model

A polypeptide of the invention is evaluated as a potent mitogen capable of stimulating the development of collateral vessels, and restructuring new vessels after coronary artery occlusion. Alteration of expression of the polypeptide is investigated in situ. The experimental protocol includes:

a) The heart is exposed through a left-side thoracotomy in the rat. Immediately, the left coronary artery is occluded with a thin suture (6-0) and the thorax is closed.

b) a polypeptide of the invention, in a dosage range of 20 mg-500 mg, is delivered intravenously and/or intramuscularly 3 times (perhaps more) per week for 24 weeks.

c) Thirty days after the surgery, the heart is removed and cross-sectioned for morphometric and in situ analyzes.

The studies described in this example tested activity of a polypeptide of the invention. However, one skilled in the art could easily modify the exemplified studies to test the activity of polynucleotides (e.g., gene therapy), agonists, and/or antagonists of the invention.

Example 49

Rat Corneal Wound Healing Model

This animal model shows the effect of a polypeptide of the invention on neovascularization. The experimental protocol includes:

a) Making a 1-1.5 mm long incision from the center of cornea into the stromal layer.

b) Inserting a spatula below the lip of the incision facing the outer corner of the eye.

c) Making a pocket (its base is 1-1.5 mm form the edge of the eye).

d) Positioning a pellet, containing 50 ng-5 ug of a polypeptide of the invention, within the pocket.

e) Treatment with a polypeptide of the invention can also be applied topically to the corneal wounds in a dosage range of 20 mg-500 mg (daily treatment for five days).

The studies described in this example tested activity of a polypeptide of the invention. However, one skilled in the art could easily modify the exemplified studies to test the activity of polynucleotides (e.g., gene therapy), agonists, and/or antagonists of the invention.

Example 50

Diabetic Mouse and Glucocordcoid-Impaired Wound Healing Models

A. Diabetic db+/db+ Mouse Model.

To demonstrate that a polypeptide of the invention accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al, *J. Surg. Res.* 52:389 (1992); Greenhalgh, D. G. et al., *Am. J Pathol.* 136: 1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad Sci. USA* 77:283-293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al, *Clin. Exp. Immunol.* 51(1):1-7 (1983); Leiter et al., *Am. J. of Pathol.* 114:46-55 (1985)). Peripheral neuropathy, myocardial complications, and microvascular lesions, basement membrane thickening and glomerular filtration abnormalities have been described in these animals (Norido, F. et al., *Exp. Neurol.* 83(2):221-232 (1984); Robertson et al., *Diabetes* 29(1):60-67 (1980); Giacomelli et al., *Lab Invest.* 40(4):460-473 (1979); Coleman, D. L., *Diabetes* 31 (Suppl):1-6 (1982)). These homozygous diabetic mice develop hyperglycemia that is resistant to insulin analogous to human type II diabetes (Mandel et al., *J. Immunol.* 120:1375-1377 (1978)).

The characteristics observed in these animals suggests that healing in this model may be similar to the healing observed in human diabetes (Greenhalgh, et al., *Am. J. of Pathol.* 136: 1235-1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245-251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1-5 and on day 8. Wounds are measured horizontally and vertically using a calibrated Jameson caliper. Wounds are considered healed if granulation tissue is no longer visible and the wound is covered by a continuous epithelium.

A polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated group, and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with a polypeptide of the invention. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0-8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, Glucocorticoids and Wound healing. In: Anti-Inflammatory Steroid Action: Basic and Clinical Aspects. 280-302 (1989); Wahlet al., *J. Immunol.* 115: 476-481 (1975); Werb et al., *J Exp. Med.* 147:1684-1694 (1978)). Glucocorticoids retard wound healing by inhibiting angiogenesis, decreasing vascular permeability (Ebert et al., *An. Intern. Med.* 37:701-705 (1952)), fibroblast proliferation, and collagen synthesis (Beck et al., *Growth Factors.* 5: 295-304 (1991); Haynes et al., *J. Clin. Invest.* 61: 703-797 (1978)) and producing a transient reduction of circulating monocytes (Haynes et al., *J. Clin. Invest.* 61: 703-797 (1978); Wahl, "Glucocorticoids and wound healing", In: Antiinflammatory Steroid Action: Basic and Clinical Aspects, Academic Press, New York, pp. 280-302 (1989)). The systemic administration of steroids to impaired wound healing is a well establish phenomenon in rats (Beck et al, *Growth Factors.* 5: 295-304 (1991); Haynes et al., *J. Clin. Invest.* 61: 703-797 (1978); Wahl, "Glucocorticoids and wound healing", In: Antiinflammatory Steroid Action: Basic and Clinical Aspects, Academic Press, New York, pp. 280-302 (1989); Pierce et al., *Proc. Natl. Acad. Sci. USA* 86: 2229-2233 (1989)).

To demonstrate that a polypeptide of the invention can accelerate the healing process, the effects of multiple topical applications of the polypeptide on full thickness excisional skin wounds in rats in which healing has been impaired by the systemic administration of methylprednisolone is assessed.

Young adult male Sprague Dawley rats weighing 250-300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1-5 and on day 8. Wounds are measured horizontally and vertically using a calibrated Jameson caliper. Wounds are considered healed if granulation tissue is no longer visible and the wound is covered by a continuous epithelium.

The polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with a polypeptide of the invention. A calibrated lens micrometer is used by a blinded observer to determine the distance of the wound gap.

Experimental data are analyzed using an unpaired t test. A p value of $<0.05$ is considered significant.

The studies described in this example tested activity of a polypeptide of the invention. However, one skilled in the art could easily modify the exemplified studies to test the activity of polynucleotides (e.g., gene therapy), agonists, and/or antagonists of the invention.

Example 51

Lymphadema Animal Model

The purpose of this experimental approach is to create an appropriate and consistent lymphedema model for testing the therapeutic effects of a polypeptide of the invention in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7-10 days. Perhaps more importantly, the chronic progress of the edema is followed for up to 3-4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5-7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and then at conclusion for total protein and $Ca2+$ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at −80 EC until sectioning. Upon sectioning, the muscle is observed under fluorescent microscopy for lymphatics.

The studies described in this example tested activity of a polypeptide of the invention. However, one skilled in the art could easily modify the exemplified studies to test the activity of polynucleotides (e.g., gene therapy), agonists, and/or antagonists of the invention.

Example 52

Suppression of TNF Alpha-Induced Adhesion Molecule Expression By a Polypeptide of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% $CO_2$. HUVECs are seeded in 96-well plates at concentrations of $1\times10^4$ cells/well in EGM medium at 37 degree C. for 18-24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 µl of 0.1% parafommaldehyde-PBS(with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 µl of diluted primary antibody to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed ×3 with PBS(+Ca, Mg)+0.5% BSA.

Then add 20 µL of diluted ExtrAvidin-Alkaline Phosphotase (1:5,000 dilution) to each well and incubated at 37° C. for 30 min. Wells are washed ×3 with PBS(+Ca,Mg)+0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 1:5,000 $(10^0)>10^{-0.5}>10^{-1}>10^{-1.5}$ 0.5 µl of each dilution is added to triplicate wells and the resulting AP content in each well is 5.50 ng, 1.74 ng, 0.55 ng, 0.18 ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity of a polypeptide of the invention. However, one skilled in the art could easily modify the exemplified studies to test the activity of polynucleotides (e.g., gene therapy), agonists, and/or antagonists of the invention.

Example 53

Cloning, Sequence Analysis and Chromosomal Localization of the Novel Human Integrin Alpha 11 Subunit The integrins are a large family of cell adhesion molecules consisting of noncovalently associated αβ heterodimers. We have cloned and sequenced a novel human integrin α-subunit cDNA, designated α11. The α11 cDNA encodes a protein with a 22 amino acid signal peptide, a large 1120 residue extracellular domain that contains an 1-domain of 207 residues and is linked by a transmembrane domain to a short cytoplasmic domain of 24 amino acids. The deduced α11 protein shows the typical structural features of integrin α-subunits and is similar to a distinct group of α-subunits from collagen-binding integrins. However, it differs from most integrin α-chains by an incompletetely preserved cytoplasmic GFFKR motif. The human ITGA11 gene was located to bands q22.3-23 on chromosome 15, and its transcripts were found predominantly in bone, cartilage as well as in cardiac and skeletal muscle. Expression of the 5.5 kilobase α11 mRNA was also detectable in ovary and small intestine.

Introduction

All vertebrate cells express members of the integrin family of cell adhesion molecules, which mediate cellular adhesion to other cells and extracellular subtratum, cell migration and participate in important physiologic processes from signal transduction to cell proliferation and differentiation {Hynes, 92; Springer, 92}. Integrins are structurally homologous heterodimeric type-I membrane glycoproteins formed by the noncovalent association of one of eight β-subunits with one of the 17 different α-subunits described to date, resulting in at least 22 different αβ complexes. Their binding specificities for cellular and extracellular ligands are determined by both subunits and are dynamically regulated in a cell-type-specific mode by the cellular environment as well as by the developmental and activation state of the cell {Diamond and Springer, 94}. In integrin α-subunits, the aminoterminal region of the large extracellular domain consists of a sevenfold repeated structure which is predicted to fold into a β-propeller domain {Corbi et al., 1987; Springer, 1997}. The three or four C-terminal repeats contain putative divalent cation binding motifs that are thought to be important for ligand binding and subunit association {Diamond and Springer, 94}. The $\alpha^1$, $\alpha^2$, $\alpha^{10}$, $\alpha^D$, $\alpha^E$, $\alpha^L$, $\alpha^M$ and $\alpha^X$-subunits contain an approximately 200 amino acid I-domain inserted between the second and third repeat that is not present in other α-chains {Larson et al., 1989}. Several isolated I-domains have been shown to independently bind the ligands of the parent integrin heterodimer {Kamata and Takada, 1994; Randi and Hogg, 1994}. The $\alpha^3$, $\alpha^{5-8}$, $\alpha^{IIb}$ and $\alpha^V$-subunits are proteolytically processed at a conserved site into disulphide-linked heavy and light chains, while the $\alpha^4$-subunit is cleaved at a more aminoterminal site into two fragments that remain noncovalently associated {Hemler et al., 90}. Additional α-subunit variants are generated by alternative splicing of primary transcripts {Ziober et al., 93; Delwel et al., 95; Leung et al., 98}. The extracellular domains of α-integrin subunits are connected by a single spanning transmembrane domain to short, diverse cytoplasmic domains whose only conserved feature is a membrane-proximal KXGFF(K/R)R motif {Sastry and Horwitz, 1993}. The cytoplasmic domains have been implicated in the cell-type-specific modulation of integrin affinity states {Williams et al., 1994}.

Here we report the cDNA cloning, sequence analysis, expression and chromosomal localization of the human α-integrin subunit.

Materials and Methods

Library Screening and DNA Sequencing.

A human fetal heart cDNA library in λgt10 (Clontech Laboratories, Inc., Palo Alto, Calif., USA) was screened with $^{32}$P-labelled (rediprime, Amersham New Zealand Ltd., Auckland, New Zealand) probes corresponding to the regions 473 to 749 and 2394 to 3189 of the α11 cDNA using standard procedures. Inserts were subcloned from λgt10 into pUC21 and sequenced on both strands according to a successive specific primer strategy on an automated sequencer (Applied Biosystems 373A, The Centre for Gene Technology, School of Biological Sciences, The University of Auckland).

Northern Blot Analysis and Tissue Distribution.

A 1341 bp PCR fragment corresponding to the region 351-1692 of the α cDNA was $^{32}$P-labelled (rediprime) and hybridized with human multiple tissue Northern blots (MTN I and MTN II, Clontech) for 16 h at 60∞C in ExpressHyb solution (Clontech). Filters were washed twice with 0.1× SSC/1% SDS at 50∞C for 30 min, and autoradiographed. Human DNA from 63 tissue-specific cDNA libraries (Express-Check™, American Type Culture Collection, Manassas, Va., USA) was amplified using primers KL120 (5'-GCAGGGATGCCACCTGCC) and KL119 (5'-GATGAAGACTGTGGTGTCGAAGG) according to the manufacturers instructions. PCR-products were resolved by agarose gel electrophoresis and transferred to Hybond C+ (Amersham). Filters were hybridized by standard procedures {Ausubel et al., 98} with a 502 bp $^{32}$P-labelled (rediprime) probe fragment obtained from the cloned "$^{11}$ cDNA with the same oligonucleotides.

Chromosomal Assignment.

500 ng genomic DNA prepared from a panel of 21 human-rodent somatic cell hybrids or from human, mouse and hamster cells {Kelsell et al., 95} was amplified with oligonuleotides KL175 (5'-GGTGCCAGACCTACATGGAC) and KL189 (5'-CGTGCAAATTCAATGCCAAATGCC) in a standard PCR reaction of 30 cycles (94∞C for 1 min, 55∞C for 1 min, 72∞C for 2 min). All PCR reactions were resolved in a 2% agarose gel. Southern hybridization was performed as detailed above, except that the probe fragment was obtained from clone HOHBY69 with oligonucleotides KL175 and KL189. For fluorescent in situ hybridization, metaphase spreads were prepared from phytohemagglutinin-stimulated peripheral blood lymphocytes of a 46,XY male donor using standard cytogenetic procedures. A purified 3.7 kB fragment representing the entire coding region of clone HOHBY69 was labelled with biotin-16-dUTP using the High Prime labelling kit (Roche Molecular Biochemicals, Auckland, NZ). Conditions for hybridization and immunofluorescent detection were essentially as described {Morris et al., 93}, except that $C_0$t-1 suppression was not required, slides were washed to a stringency of 0,1×SSC/60∞C after hybridization, and an additional amplification step was needed because of the small size of the probe. For precise chromosome band localization, DAPI and FITC images were captured using a Photometrics KAF1400 CCD camera and QUIPS Smartcapture FISH software version 1.3 (Vysis Inc., Downers Grove, Ill., USA). QUIPS CGH/Karyotyping software (version 3.0.2) assisted karyotype analysis.

Results

Cloning of a Novel Human α-Integrin Subunit cDNA:

A protein homology search {Altschul et al., 90} of the human expressed sequence tag (EST) databases of Human Genome Sciences, Inc. {Ni et al., 97} and The Institute for Genomic Research {Kirkness and Kerlavage, 97} identified the clones HRDAF83 and HOEAM34 as candidate novel integrin α-subunit cDNAs. Clone HRDAF83 was isolated from a human rhabdomyosarcoma cDNA library and sequenced on both strands. The 1223 bp insert contains largely incompletely processed hnRNA and a 277 bp region that showed homology to the aminoterminal half of the α1-integrin 1-domain. The 2517 bp insert of clone HOEAM34 was derived from a human osteoblast cDNA library. It is homologous to the C-terminal part of the human α1-subunit and contains 1324 nucleotides of 3'-untranslated region. In order to isolate the full-length cDNAs for these integrin α-subunits, a cDNA library prepared from human fetal heart in λgt10 was screened with the 277 bp fragment from clone HRDAF83 homologous to the α1-I-domain. Two clones, λ831 and λ832, were isolated and both strands of their inserts sequenced. Clone λ832 contains the entire 5' half of a novel α-subunit cDNA, while clone λ831 covers the same region, but is 358 bp and 173 bp shorter than λ831 at its 5'-and 3'-ends, respectively. A screening of the same library with a 795 bp fragment from the extreme 5'-terminus of clone HOEAM34 identified clone λ342, which contained essentially the same region as clone HOEAM34 but has a 317 bp shorter 3'-untranslated region. Rescreening the EST databases with the sequences derived from the human fetal heart library led to the identification of clone HOHBY69, which was isolated from a osteoblast cDNA libray. Both strands of the 4681 bp insert of clone HOHBY69 were sequenced. The 5'-region of HOHBY69 was identical to the HRDAF83/λ832/λ831-group, while the 3'-region of HOHBY69 was largely identical to HOEAM34 and λ342, thereby demonstrating that the two groups of partial cDNAs represent the 5'-and 3'-portions of the same cDNA. One major difference between the HOHBY69 and HOEAM34/λ342 is the presence of an additional GTA-triplet at position 3088 in HOHBY69. From the overlapping clones, a total of 4986 bp of cDNA was assembled to the composite sequence shown in FIG. 19A-F and has been submitted to GenBank™ with accession number AF109681. This cDNA encodes a previously unidentifed human integrin α-subunit that was designated α11.

Structure of the Human α11-subunit.

The α11 cDNA contains a 5'-untranslated region of 72 nucleotides and a single open reading frame extending from a predicted translation initiation codon at position +1 to a TGA termination codon at position 3570. This is followed by 1324 nucleotides of 3' untranslated region which contains an AATTAAA polyadenylation signal {Wahle and Keller, 1996} 12 nucleotides upstream of a poly(A) stretch. The deduced amino acid sequence contains a 22 residue N-terminal region with the characteristics of a cleaved signal peptide {von Heijne, 83; Nielsen et al, 97}, a large extracellular domain of 1120 amino acids followed by a 23 amino acid hydrophobic stretch that resembles a transmembrane domain, and a short 24 residue cytoplasmic domain. The molecular weight of the mature 1167 amino acid α11-subunit is predicted to be 131 kDa, but the addition of carbohydrate side chains to any of the 15 potential N-glycosylation sequons [NX(S/T)] within the extracellular domain is likely to increase the molecular weight of the native protein. An I-domain of 207 amino acids is inserted between the second and third repeat. Consistent with the structure of an typical I-domain-containing integrin α-subunit, it lacks a potential dibasic protease cleavage site in the C-terminal region of the extracellular domain.

The α11-subunit is most closely related to the recently discovered α10-subunit (Camper et al, 98, Lehnert et al., in preparation} and the α11-and α2-subunits. Overall, the mature α11-protein is 45% identical to the α10 chain, while the homologies to the α1and α2-subunits are 41% and 39%, respectively. Even greater homology exists between the I-domains of the α10- and α11-subunits which are 60% identical to each other. The high degree of homology seen in the extracellular domains of the subunits is in contrast to the low similarity of their cytoplasmic domains. Interestingly, the KXGFF(K/R)R motif that is absolutely conserved in all other a-subunit cytoplasmic domains is only partially preserved in both subunits. The sequence in α11 is KLGFFRS, while the α10-subunit contains a KLGFFAH motif. A graphical comparison of the similarity between all integrin α-subunits is shown in FIG. 3. Together with the α-subunits from the collagen-binding integrins α1β1, α2β1 and α10β1, the α11-subunit forms a group distinct from the other I-domain-containing integrin subunits.

Tissue Distribution and Expression of the Integrin α11-Subunit.

The tissue distribution of the α11 mRNA was assessed by screening multiple human tissue Northern blots with a probe corresponding to the region 351-1692 of the α11 cDNA. A single transcript of approximately 5.5 kb was found weakly expressed only in ovary and small intestine. Integrin α11-subunit expression was further analyzed by amplification and Southern hybridization of a 502 bp fragment corresponding to the region 1988-2490 in the all cDNA from tissue-specific human cDNA libraries. α11 cDNA was detected in five different cDNA libraries prepared from fetal heart (day 57-75), in two fetal brain libraries, and in a cDNA library from large intestine (not shown). An analysis of the Human Genome Sciences Database revealed eight different α11-related ESTs in human osteoblast libraries, three EST in a human chondrosarcoma cDNA library and two EST in a human stromal osteoclastoma library.

Chromosomal Localization of the Integrin α11-Subunit.

Genomic DNA from a collection af 21 human-rodent somatic cell hybrids {Kelsell et al, 95} was amplified by PCR using oligonucleotide primers directed the region 473 to 749 of the human α11 cDNA. In Southern hybridization, a signal corresponding to a 1,4 kb fragment was detectable only with DNA from a hybrid cell line that contains human chromosome 15. A fragment of the same size was also amplified from human genomic DNA, but not from mouse or hamster DNA (FIG. 5C). Cloning and sequence of the PCR product from chromosome 15 revealed the presence of a 1154 bp intron inserted after cDNA-position 600, thus resulting in a PCR-product of 1431 bp. The ITGA11 gene was also localized by fluorescent in situ hybridization of metaphase chromosomes with the entire coding region from clone HOHBY69. All of 20 metaphase cells analyzed showed fluorescent signal on both chromosomes 15, specifically across bands q22.3-q23. No additional signals were detected on any other chromosome (FIG. 5A).

Discussion:

We have cloned and sequenced a novel cDNA encoding a protein that shares extensive structural homology with integrin α-chains. The aminoterminal 22 amino acids of the deduced protein sequence show the characteristic features of a hydrophobic leader peptide, including a signal peptidase recognition motif at positions −3 and −1 {von Heijne 83}. Proteolytic cleavage of the precursor protein at this position would result in an aminoterminal sequence for the mature α11-chain of FNMD, which is similar to the consensus sequence[(F/Y)N(L/V)D] of all other integrin α11-subunits {Tuckwell et at, 94}. The N— terminal half of the large extracellular region of α11 is composed of seven repeats that each contain FG-GAP-GxxY consensus motifs (FG-GAP repeats). These repeats can be found in all integrin al-subunits and are predicted to fold into a β-propeller domain {Springer, 97}. Inserted between the second and third FG-GAP repeats is a 207 amino acid I-domain spanning from glutamine$^{138}$ to methionine$^{344}$. It contains a divalent cation coordination motif that has been shown to directly bind $Mg^{2+}$ ions in the $\alpha^{M}$ subunit {Michishita et al, 96}. The noncontiguous amino acid side chains involved in the coordination of magnesium or manganese ions have been identified by mutagenesis analysis and from crystal structures of the isolated $\alpha^2$, $\alpha^L$ and $\alpha^M$-subunit I-domains {Emsley et al, 97; Qu and Leahy, 95; Lee et al, 95;}. All residues required for the coordination of the divalent cations in these subunits are preserved in the α11-I-domain. These are the asparagines at positions 148 and 249, the serine residues at position 150 and 152, and the threonine at position 218. The crystal sctructure of the α2-subunit has revealed a small "helix that is not present in the I-domains of the β2-associated α-subunits. Together with the MIDAS sphere, amino acid residues from this C-helix and the adjacent turn region have been proposed to make physical contacts to a collagen triple helix {Emsley et al, 97}. Interestingly, the small C-helix is structurally conserved in the α-subunits of the collagen-binding integrins α1β1, α2β1 and α10β1, and is also present in the α11 I-domain ($G^{279}YYNR^{283}$). In addition, asparagine$^{154}$ and histidine$^{258}$ of the α2-I-domain were predicted to contact the collagen triple helix, and both are preserved in the α1, α10 and α11-I-domains, but not in other integrin α11-subunits. The conservation of structural motifs required for collagen binding suggests that collagen may be a ligand for the α11 integrin. Each of the repeats 5-7 of the α11-subunit accomodates the sequence Dx(D/N)xDxxxD. Three or four copies of these putative divalent cation binding sites are conserved in all integrin α-subunits and their presence is consistent with the divalent cation requirement for the adhesive function of integrins {Larson et al, 89; Fujimura and Phillips, 83; Hynes, 92}. The extracellular domain of the integrin α11-subunit contains 20 cysteine residues. Only the intramolecular disulfide bonds in the "$^{IIb}$subunit have been biochemically characterized {Calvete et al., 89}, but the location of many cysteines is conserved in integrin α-subunits. In the α11-subunit, the cysteine residues 637 and 646, 652 and 707, 759 and 765, and 859 and 871 are homologous to the residues that form the four carboxyterminal disulfide bonds in the heavy chain of"$^{IIb}$ {Calvete et al, 89}. Based on the proposed structure of the integrin α-subunit propeller domain {Springer et al, 97}, additional disulfide bonds within the α11 subunit can be predicted between cysteine residues 54 and 61, 99 and 117, and between 107 and 137. Two additional cysteine residues are found within a short segment (residues 783 to 798) that is unique to the α11-subunit. The integrin cytoplasmic domains play central roles in integrin affinity modulation and in cellular signal transmission. The membrane-proximal sequence KxGFF(K/R)R is strictly conserved among integrin α-subunit cytoplasmic domains {Williams et al., 94}. Within this motif, both phenylalanine residues and the last arginine have been implicated in maintaining the default low affinity state of integrins $\alpha^L\beta_2$ and $\alpha^{IIb}\beta_3$, as their substitution or deletion resulted in constitutively activated ligand binding {O'Toole et al, 94, Lu and Spriner 97}. Interestingly, the last arginine residue is replaced by a serine in the α11 cytoplasmic domain and with a histidine in the α10 subunit, suggesting that both integrins might be in a default "high" affinity state. It will be interesting to analyze whether substitution of these residues with a conserved arginine will affect their affinity status. We have isolated α11 cDNAs from osteoclast, osteoblast, myosarcoma and fetal heart libraries. Amongst the HGS EST databases, integrin α11 transcripts were predominantly found in libraries prepared from osteoblast, osteoclast and chondrosarcoma cells. A search for further "[11]-related sequences in the EST division of the GenBank database revealed two clones (accession numbers Z50157 and Z50167) from primary human myoblasts {Genini et al, 96}, two clones from human trabecular bone cells (AA852614 and AA852615), as well as clones from fibroblast cells (W45078), pancreatic tumor (U53091) and breast tissue (H16112). In contrast, Northern blot analysis detected α11-expression only in ovary and small intestine only fetal heart, fetal brain and large intestine. Of the tissues represented in the tissue-specific cDNA-library panel, only fetal heart, fetal brain and large intestine showed detectable α11-expression. However, bone- and muscle-derived tissues were not included in the Northern blot, and cDNA libraries prepared from these tissues were also not represented in the tissue-specific cDNA panel.

The ITGA11 gene was localized to chromosome 15, bands q22.3-23, by FISH and PCR analysis of human-rodent somatic cell hybrids. This segment is overrepresented in squamous cell carcinomas {Wolff et al., 1998}, but appears to only infrequently affected in other cancers. Genes at this region encode neogenin, a protein expressed ubiquitously expressed in human tissues {Meyerhardt et al., 97}; tropomyosin 1, expressed in cardiac and skeletal muscle tissues {Tiso et al, 97}; and the human homologue of the metalloprotease-disintegrin kuzbanian, which is overexpressed in tumors of sympathoadrenal origin {Yavari et al, 98}. In addition, the region 15q22.3-q23 is linked to Bardet-Biedl syndrome 4, a heterogeneous autosomal disorder characterized by obesity and associated with cardiovascular anomalities {Carmi et al., 95}.

In conclusion, we have cloned and sequenced the cDNA for the novel integrin α11-subunit which is closely related to the "-subunits of the collagen-binding integrins α1β1, α2β1 and α10β1. The high degree of homology of α11 to these subunits suggests that it associates with the integrin β1-subunit, and may function as an additional collagen receptor.

All references referred to above and presented below are hereby incorporated herein by reference:

Altschul S. F., Gish, W., Miller, W, Myers, E. W, and Lipman, D. J (1990). Basic local alignment search tool. *Journal of Molecular Biology* 215: 403-410.

Ausbel, F. A., Brent, R., Kingston, R. E., Moore, D. D., Seidman, J. G., Smith, J. A., and Struhl, K. (1998). "Current protocls in molecular biology" John Wiley & Sons, New York.

Calvete J. J., Henschen, A., and Gonzalez-Rodriguez, J (1989). Complete localization of the intrachain disulphide bonds and the N-glycosylation points in the alpha-subunit of human platelet glycoprotein IIb. *Biochemical Journal* 261: 561-568.

Camper L., Hellman, U., and Lundgren-Akerlund, E. (1998). Isolation, cloning and sequence analysis of the integrin subunit α10, a β1-associated collagen binding integrin expressed on chondrocytes. *Journal of Biological Chemistry* 273:20383-20389.

Carmi K, Rokhlina, T., Kwitek-Black, A. E., Elbedour, K., Nishimura, D., Stone, E. M, and Sheffield, V. C. (1995). Use of a DNA pooling strategy to identify a human obesity syndrome locus on chromosome 15. *Human Molecular Genetics* 4: 9-13.

Corbi A. L., Miller, L. J., O'Connor, K., Larson, R. S., and Springer, T. A. (1987). cDNA cloning and complete primary structure of the alpha subunit of a leukocyte adhesion glycoprotein, p150,95. *EMBO Journal* 6: 4023-4028.

De Melker A. A., Kramer, D., Kuikman, I., and Sonnenberg, A. (1997). The two phenylalanines in the GFFKR motif of the integrin alpha6A subunit are essential for heterodimerization. *Biochemical Journal* 328: 529-537.

Diamond M. S. and Springer, T. A. (1994). The dynamic regulation of integrin adhesiveness. *Current Biology* 4: 506-517.

Emsley J., King, S. L., Bergelson, J. M., and Liddington, R. C. (1997). Crystal structure of the I domain from integrin alpha2beta1. *Journal of Biological Chemistry* 272: 28512-28517.

Fujimura K. and Phillips, D. R. (1983). Calcium cation regulation of glycoprotein IIb-IIIa complex formation in platelet plasma membranes. *Journal of Biological Chemistry* 258: 10247-10252.

Genini M., Schwalbe, P., Scholl, F. A., and Schafer, B. W. (1996). Isolation of genes differentially expressed in human primary myoblasts and embryonal rhabdomyosarcoma. *International Journal of Cancer* 66: 571-577.

Hemler M. E., Elices, M. J., Parker, C., and Takada, Y. (1990). Structure of the integrin VLA-4 and its cell-cell and cell-matrix adhesion functions. *Immunological Reviews* 114: 45-65.

Hynes R. O. (1992). Integrins: versatility, modulation, and signaling in cell adhesion. *Cell* 69: 11-25.

Kelsell D. P., Rooke, L., Warne, D., Bouzyk M., Cullin, L., Cox, West, L., Povey, S., and Spurr, N. K. (1995). Development of a panel of monochromosomal somatic cell hybrids for rapid gene mapping. *Annals of Human Genetics* 59: 233-241.

Kirkness E. F. and Kerlavage, A. R. (1997). The TIGR human cDNA database. *Methods in Molecular Biology* 69: 261-268.

Lee J. O., Rieu, P., Arnaout, M. A., and Liddington, K (1995). Crystal structure of the A domain from the alpha subunit of integrin CR3 (CD11b/CD18). *Cell* 80: 631-638.

Larson R. S., Corbi, A. L., Berman, L., and Springer, T. (1989). Primary structure of the leukocyte function-associated molecule-1-alpha subunit: an integrin with an embedded domain defining a protein superfamily. *Journal of Cell Biology* 108: 703-712.

Leung E., Lim, S. P., Berg R., Yang Y, Ni, J, Wang, S. X., and Krissansen, G. W. (1998). A novel extracellular domain variant of the human integrin alpha 7 subunit generated by alternative intron splicing. *Biochemical & Biophysical Research Communications* 243: 317-325.

Lu C. F. and Springer, T. A. (1997). The alpha subunit cytoplasmic domain regulates the assembly and adhesiveness of integrin lymphocyte function-associated antigen-1. *Journal of Immunology* 159: 268-278.

Michishita M., Videm, V., and Arnaout, M. A. (1993). A novel divalent cation-binding site in the A domain of the beta 2 integrin CR3 (CD11b/CD18) is essential for ligand binding. *Cell* 72: 857-867.

Meyerhardt J. A., Look A. T., Bigner, S. H., and Fearon, E. R. (1997). Identification and characterization of neogenin, a DCC-related gene. *Oncogene* 14: 1129-1136.

Morris C., Courtay, C., Geurts, v. K., ten Hoeve, J., Heisterkamp, N., and Groffen, J. (1993). Localization of a gamma-glutamyl-transferase-related gene family on chromosome 22. *Human Genetics* 91: 31-36.

Ni J., Abrahamson, M., Zhang, M., Fernandez, M., Grubb, A., Su, J., Yu, G.-L., and Li, Y.-L. (1997). Cystatin E is a novel human cysteine proteinase inhibitor with structural resemblance to family 2 cystatins. *Journal of Biological Chemisty* 272:10853-10858.

Nielsen H., Engelbrecht, J., Brunak, S., von, and Heiyne, G. (1997). Identification of prokaryotic and eukaryotic signal peptides and prediction of their cleavage sites. *Protein Engineering* 10: 1-6.

O'Toole T. E., Katagiri, Y., Faull, R. J., Peter, K., Tamura, R., Quaranta, V., Loftus, J. C., Shattil, S. J, and Ginsberg, M. H. (1994). Integrin cytoplasmic domains mediate inside-out signal transduction. *Journal of Cell Biology* 124: 1047-1059.

Qu A. and Leahy, D. J. (1995). Crystal structure of the I-domain from the CD11a/CD18 (LFA-1, alpha L beta 2) integrin. *Proceedings of the National Academy of Sciences of the United States of America* 92: 10277-10281.

Sastry S. K. and Horwitz, A. F. (1993). Integrin cytoplasmic domains: mediators of cytoskeletal linkages and extra- and intracellular initiated transmembrane signaling. *Current Opinion in Cell Biology* 5: 819-831.

Springer T. A. (1997). Folding of the N-terminal, ligand-binding region of integrin alpha-subunits into a beta-propeller domain. *Proceedings of the National Academy of Sciences of the United States of America* 94: 65-72.

Springer T. A. (1990). Adhesion receptors of the immune system. *Nature* 346: 425-434.

Tiso N., Rampoldi, L., Pallavicini, A., Zimbello, R., Pandolfo, Valle, G., Lanfranchi, G., and Danieli, G. A. (1997). Fine mapping of five human skeletal muscle genes: alpha-tropomyosin, beta-tropomyosin, troponin-I slow-twitch, troponin-I fast-twitch, and troponin-C fast. *Biochemical & Biophysical Research Communications* 230: 347-350.

Tuckwell D. S., Humphries, M. J., and Brass, A. (1994). A secondary structure model of the integrin alpha subunit N-terminal domain based on analysis of multiple alignments. *Cell Adhesion & Communication* 2: 385-402.

von Heijne G. (1983). Patterns of amino acids near signal-sequence cleavage sites. *European Journal of Biochemistry* 133: 17-21.

Wahle E. and Keller, W. (1996). The biochemistry of polyadenylation. *Trends in Biochemical Sciences* 21: 247-250.

Williams M. J., Hughes, P. E., O'Toole, T. E., and Ginsberg, M. H. (1998). The inner world of cell adhesion: Integrin cytoplasmic domains. *Trends in Cell Biology* 4: 109-112.

Wolff E., Girod, S., Liehr, T., Vorderwulbecke, U, Ries, J., Steininger, H., Gebhart, E. (1998). Oral squamous cell carcinomas are characterized by a rather uniform pattern of genomic imbalances detected by comparative genomic hybridisation. *Oral Oncology* 34: 186-190.

Ziober B. L., Vu, M. P., Waleh, N., Crawford, J., Lin, C. S., Kramer, and RH (1993). Alternative extracellular and cytoplasmic domains of the integrin alpha 7 subunit are differentially expressed during development. *Journal of Biological Chemistry* 268: 26773-83.

Example 54

Identification and Characterization of a New Member of the Siglec Family of Sialic Acid Binding Immunoglobulin-Like Lectins Summary:

Characterized herein is CD33-likeSV, a new member of the Siglec family of sialic acid binding receptors of the immunoglobulin superfamily. A full length cDNA encoding CD33-likeSV was isolated from a human spleen cDNA library. CD33-likeSV is predicted to contain five extracellular immunoglobulin-like domains, a transmembrane region and a cytoplasmic tail containing three putative tyrosine-based signaling motifs. Overall, CD33-likeSV exhibited a high degree of sequence similarity to genes encoding CD33/Siglec-3, Siglecs-5, -6, -7, -8 and -9 and mapped to the same region, on chromosome 19q13.3. Phylogenetic analysis and sequence comparisons indicated that CD33-likeSV was the most ancient of the CD33-related subgroup and may have given rise to the other CD33-related Siglecs by a process involving exon deletion and gene duplication. When CD33-likeSV was expressed on COS or Chinese hamster ovary cells, it was able to mediate sialic acid dependent binding to human erythrocytes and soluble sialoglycoconjugates. Using flow cytometry of human peripheral blood leukocytes, CD33-likeSV was found to be expressed on eosinophils, monocytes and B cells. Higher levels of CD33-likeSV were found on a minor subset of cells within the lymphocyte gate that expressed the CD16 low affinity Fc receptor but lacked the CD56 antigen.

Introduction:

Siglecs are sialic acid binding members of the Ig superfamily expressed at the cell surface (1). Structurally, they have a characteristic N-terminal V-set Ig-like domain containing the sialic acid binding site (2) followed by varying numbers of C2 set domains. Most Siglecs have one or more immune receptor tyrosine-based inhibitory motifs (ITIMs) in their cytoplasmic tails implicated in negative regulatory signaling functions (3-9). The first Siglecs to be defined were sialoadhesin/Siglec-1, CD22/Siglec-2, CD33/Siglec-3 and myelin associated glycoprotein/Siglec-4 expressed by macrophages, B cells, myeloid cells and myelin forming cells respectively (10-14). Recent studies have revealed the existence of a new subset of human Siglecs that are highly related to CD33/Siglec-3, namely Siglecs-5, -6, -7, -8 and -9 (6, 15-22). Each protein exhibits sialic acid binding properties and is expressed in a characteristic manner. With the exception of Siglec-6, which is found mostly in the placenta (16), the CD33-related group of Siglecs are largely expressed on discrete subsets of hemopoietic cells. Interestingly, the highest levels of expression of these proteins are found on effector cells of the innate immune system, including monocytes (Siglecs-3, -5, -7 and -9), neutrophils (Siglecs-5 and -9), eosinophils (Siglec-8) and natural killer cells (Siglec-7). This observation, together with the common theme of sialic acid recognition and the presence of conserved, putative tyrosine-based inhibitory signaling motifs (4-6, 9), has led to the suggestion that these proteins might be involved in regulating activation of leukocytes via sialic acid recognition (21, 22).

Described herein are the properties of a new member of the Siglec family. This protein has 5 extracellular Ig-like domains and based on phylogenetic comparisons it may represent a precursor of the CD33-related Siglec subgroup. Amongst peripheral blood leukocytes, CD33-likeSV was found to be expressed on eosinophils, monocytes and B cells. Higher levels of this novel Siglec were found on a minor subset of natural killer-like cells characterized by high levels of the CD16 low affinity Fe receptor and an absence of the CD56 antigen.

Experimental Procedures:

Materials

Unless specified otherwise, all reagents and chemicals were purchased from Sigma. $^{125}$I-streptavidin (20-40 mCi/mg) and protein A-Sepharose were obtained from Amersham Pharmacia Biotech. Vibrio cholerae sialidase was purchased from Calbiochem. Biotinylated polyacrylamide (PAA) glycoconjugates carrying either NeuAcα2,3Galβ 1,4Glc (2,3-PAA) or NeuAcα2,6Galβ 1,4Glc (2,6-PAA), were obtained from Syntesome (Munich, Germany). These conjugates have a molecular mass of approximately 30 kDa and contain 20% mol of saccharide and 5% mol of biotin. Phycoerythrin (PE)-conjugated mAbs against the following human CD antigens were purchased from Serotec (Kidlington, UK): CD3, CD4, CD8, CD16, CD19, CD56. FITC-conjugated F(ab)2 anti-mouse IgG was from Dako, (Cambridge, UK).

Identification and Characterization of CD33-likeSV cDNA

Using the amino acid sequence of CD33, a specific homology search was performed against Human Genome Science's database, containing more than one million expressed sequence tags obtained from over 700 different cDNA libraries. 21 clones encoding a potential novel Siglec were identified in cDNA libraries prepared from the following human sources: bone marrow, unstimulated B cells, eosinophils, primary dendritic cells, spleen, chronic lymphocytic leukemia. Inserts from four clones were sequenced: pHEOMH10 (eosinophil), pHEOOV77 (eosinophil), pHDPIB36 (dendritic cell), pHDPCL05 (dendritic cell). Since none of these was found to encode a correctly spliced full-length form of this novel Siglec, a human spleen cDNA library in XZAPII (23) was screened with a KpnI-SacI fragment from HDPCL05. A single positive clone, p2.2, was identified and the phage insert subcloned into pBluescript and sequenced. Since clone 2.2 contained a correctly spliced full-length open reading frame, the insert was subcloned into the mammalian expression vector pcDNA3 (Invitrogen, Groningen, The Netherlands) and used as a template in subsequent molecular characterisation. Based on its sialic acid binding activity, this novel Siglec is hereon referred to as CD33-likeSV. To identify proteins related to CD33-likeSV, a computer search of the GenBank nucleotide and proteinssequence databases was carried out using the Blast GeneSearch (National Center for Biotechnology Information, National Institutes of Health, Bethesda, Md.).

Phylogeny Analysis

Manipulations of sequences and alignments were performed using Baylor College of Medicine molecular biology software available on the internet (Human Genome Center, Baylor College of Medicine, Houston, Tex.). Protein and nucleotide alignments were performed using the SIM alignment program (24). Chromosomal localisation Metaphase spreads prepared from phytohemagglutinin-stimulated human lymphocytes were hybridized with a biotinylated 3.4 kb insert from pHEOMH 10 as described (25). Metaphase spreads from 50 cells were analysed. Northern blot analysis. Two human Multiple Tissue Northern (MTN) blots containing approximately 2 μg of poly $A^+$ RNA per lane from various human tissues were purchased from Clontech (Palo Alto, Calif.) and hybridised with $^{32}$P-labelled insert from HEOMH10 as described previously (15).

Cells

The following cell lines were provided by the ICRF Cell Production Service: COS-1, Balb/c 3T3 A3 1, Chinese hamster ovary KI (CHO), KG 1b, HL-60, U937, TBP-1 and Daudi. The NK-like cell line, YT, was obtained from Dr Gillian Griffiths (Oxford University). Cells were cultured as described previously (17). Human red blood cells (RBC) were obtained from healthy donors and stored at 4° C. in Alsever's solution for up to two weeks. Human blood leukocytes were obtained from whole blood by dextran sedimentation followed by lysis of contaminating RBC. Mononuclear fractions for flow cytometry were obtained by density gradient centrifugation using Ficoll-Paque (Amersham Pharmacia Biotech).

Production of Fc-Proteins

Recombinant chimeras containing the entire extracellular region of CD33-likeSV fused to the Fc region of human IgG1 (CD33-likeSV-Fc) were prepared by PCR amplification of the entire extracellular region of CD33-likeSV using the following forward and reverse primers (5'/3'): ACAAGCTTTGCGCCTCCTATGCGGAGATG and CCCCTCGAGCTTATCTGGCAGCTGCAGGAT. The PCR product was cloned in-frame into the plGplus vector, which encodes a Factor Xa cleavage site between the extracellular region and the Fc hinge region of human IgG1. CD33-likeSV-Fc. was produced in transiently transfected COS cells and purified with protein A Sepharose as described (13).

Generation of Mouse Polyclonal and Monoclonal Antibodies to CD33-LikeSV

Balb/c 3T3 A31 cells were transfected by electroporation with CD33-likeSV cDNA in the pcDNA3 vector. G418 resistant clones expressing CD33-likeSV were identified by their ability to bind human RBC and designated CD33-likeSV-3T3. To generate polyclonal antibodies, Balb/c mice were immunized twice intraperitoneally, at an interval of 14 days, with $10^7$ live CD33-likeSV-3T3 cells. After a final boost, the immune serum was collected, IgG purified by protein G Sepharose and passed over a CD33-likeSV-Fc column prepared by coupling 1.0 mg purified CD33-likeSV-Fc to cyanogen bromide activated Sepharose CL4B. Bound IgG was eluted with 0.1 M glycine buffer pH 2.5 and neutralized with 0.1 volumes of 0.1 M Tris pH 8.0. To generate a monoclonal antibody (mAb), Balb/c mice were immunised with CD33-likeSV-Fc and hybridomas generated by fusing immune spleen cells with the SP2 myeloma following standard methods (28). A positive well reacting specifically with CD33-likeSV-Fc was identifed by enzyme-linked immunosorbent assays as described (21). The hybridoma was cloned three times by limiting dilution and the mAb designated 5G6 (IgGI). 5G6 was used as a tissue culture supernatant in all experiments.

Human RBC Binding Assays to CD33-LikeSV Expressed on CHO Cells and COS Cells

CHO cells stably expressing CD33-likeSV (CD33-likeSV-CHO) were generated by transfecting CHO cells with CD33-likeSV cDNA in the pcDNA3 vector. G418 resistant clones expressing CD33-likeSV were identified by their ability to bind the anti-CD33-likeSV mAb 5G6 and designated CD33-likeSV-CHO. COS cells were transiently transfected with CD33-likeSV cDNA by electroporation. RBC binding assays with CD33-likeSV-transfected COS cells and CD33-likeSV-CHO cells were carried out as described (13).

Binding Assays with Polyacrylamide Glycoconjugates

COS-1 cells were transiently transfected by electroporation with cDNAs encoding CD33-likeSV or CR1 (CD35) as a negative control and binding assays carried out 48-72 hours later, as described previously (17). Briefly, sialidase-treated and control cells were incubated with saturating concentrations (20 gg/ml) of biotinylated 2,3 PAA or 2,6 PAA for 1 h at room temperature, washed and incubated with $^{125}$I-Streptavidin at 0.5 µCi/ml for 1 h at 4° C. Bound radioactivity was counted using a Beckman gamma-counter.

FACS Analysis

Single and double labelling of cells for flow cytometry were performed following standard protocols (30). Following staining, cells were fixed in 2% formaldehyde and analysed on a Becton-Dickinson FACS analyser.

Immunoprecipitation

Wild-type CHO cells, CHO—CD33-likeSV and Daudi cells at 2×107/ml were surface biotinylated and lysates prepared in 1% Triton-X-100. Immunoprecipitations were carried out following standard procedures (28) and precipitated material was run on 4-12% gradient SDS-PAGE gels followed by western blotting on nitrocellulose. The blots were blocked and biotinylated proteins revealed using streptavidin-peroxidase followed by addition of the ECL reagent (Amersham Pharmacia Biotech).

Results and Discussion:

Characterization of CD33-LikeSV 21 unique expressed sequence tags encoding a novel Siglec-like protein were identified in 8 different human cDNA libraries, as follows (frequencies in parentheses): eosinophils (10), primary dendritic cells (6), bone marrow (2), unstimulated B cells (1) tonsils (1), spleen (1). A full-length clone encoding this novel sequence was isolated from a human spleen cDNA library. Based on sequence similarity with other Siglecs (FIG. 37) and its ability to bind sialic acid (see below) this protein has been designated CD33-likeSV. The extracellular region of CD33-likeSV contains a hydrophobic signal peptide and five Ig-like domains that are made up of an N-terminal V-set domain and four C2 set domains containing five potential N-linked glycosylation sites. Following the transmembrane region, there is a cytoplasmic tail of 126 amino acids.

CD33-likeSV contains all of the characteristic features of the Siglec subgroup of Ig superfamily proteins (FIG. 37). These include the critical arginine at position 120 that has been shown in the ligand-bound crystal structure of sialoadhesin to interact with the carboxyl group of sialic acid (2). In addition, CD33-likeSV contains two conserved aromatic residues, Phe$^{26}$ and Y$^{134}$ on the A and G strands of the V-set domain that for sialoadhesin are both tryptophans shown to make hydrophobic interactions with the N-acetyl and glycerol side chains of sialic acid (2). CD33-likeSV exhibits the unusual pattern of cysteines in domains 1 and 2 that form the intra-sheet and inter-domain disulfide bonds (2). Within the cytoplasmic tail there are three potential tyrosine-based motifs. The most membrane proximal of these, LD$^{597}$INV, fits the consensus sequence (Y(L/V/I)N(V/P)) for receptors that bind to the SH2 domain of the Grb2 (26-28). Grb2 is an adaptor molecule that is able to activate the Ras signaling pathway via interactions with the Ras-specific guanine nucleotide exchange factor, Sos (29).

Although this motif has not been observed in CD33-related Siglecs previously, a similar motif is present in CD22/Siglec-2 where it has been shown capable of interacting with Grb2 following tyrosine phosphorylation of the CD22 cytoplasmic tail. The interaction of CD22 with Grb2 was recently found to be important for the formation of a quaternary complex of CD22, SFHP, Grb2 and Shc implicated in the signaling functions of CD22. The other two tyrosine-based motifs in CD33-likeSV are more typical of the CD33-related Siglec subset (FIG. 37). The motif LHY$^{667}$ ATL fits the ITIM consensus, (L/I/V/S)XYXX(L/V), and is similar to the corresponding motif in CD33/Siglec-3, LHYASL, which has been shown to be dominant in tyrosine phosphorylation and recruitment of SHP-1 (4, 5, 9) and SHP-2 (4, 9). Similar to other CD33-related Siglecs, the membrane distal motif, ADY$^{691}$ AEV does not fit the ITIM consensus but is well-conserved amongst the Siglecs. The corresponding phosphopeptide for CD33 has been shown capable of recruiting SHP-2 but not SHP-1 (4, 9). The presence of several potential tyrosine-based motifs in CD33-likeSV therefore indicates that this protein may be involved in signaling functions.

Similarity with Other CD33-Related Siglecs and Phylogenetic Analysis

Database searches showed that CD33-likeSV shares the highest sequence similarity with the CD33-related Siglec subset, namely Siglecs-3, -5, -6, -7, -8 and -9. Within the first two Ig-like domains, CD33-likeSV was found to be 40-48% identical to these proteins (FIG. 37). CD33-likeSV is therefore the least similar of the CD33-related Siglecs which have been shown previously to share between 50 and 80% identity within the first two Ig-like domains (15-19, 21). The database searches also identified a human chromosome 19 clone (CTD-2616J11) from the completed human genome sequence that contains the entire CD33-likeSV gene. This allowed us to accurately map the intron-exon boundaries within the cDNA sequence (FIG. 37). This revealed that, besides an additional Ig-like domain not represented in any of the other CD33-related Siglecs, CD33-likeSV has an extra linker region at the end of domain 3 encoded by a separate exon (FIG. 37). This linker is similar in length (16 amino acids) and sequence (63% identity at the nucleotide level) to the linker at the end of domain 2 which is present in all CD33-related Siglecs (FIG. 37). Since domains 3 and 4 of CD33-likeSV share 46% amino acid sequence identity, it seems likely that this region of the molecule arose by tandem duplication of two exons, encoding a linker and an associated Ig-like domain. Alignment of the CD33-likeSV amino acid sequence with other CD33-related Siglecs showed that domain 3 of Siglecs-5, -6, -7, -8 and -9 is highly related to domain 4 of CD33-likeSV (50-67% identity). Domain 3 of Siglecs-5, -6, -7, -8 and -9 also aligned well with domain 3 of CD33-likeSV (44-49% identity). This further supports the notion that domains 3 and 4 of CD33likeSV arose through a duplication process. The alignment also showed that domain 5 of CD33-likeSV was highly related to domain 4 of Siglec-5 (71% identity).

To further investigate the possible evolutionary relationships between the CD33-related Siglecs, unrooted phylogenetic trees were created using both the amino terminal regions (leader peptide, domain 1+domain 2) and carboxy terminal regions (transmembrane region+cytoplasmic tails) of all CD33-related Siglecs (FIG. 38). Both phylogenetic trees gave very similar results (FIGS. 38A and 38B) and are therefore consistent with the notion that CD33-likeSV represents the most ancient of the CD33-related subset, followed by Siglec-5. Based on the phylogenetic analysis and the sequence comparisons, it is tempting to speculate that CD33-likeSV gave rise to the other CD33-related Siglecs by a process of sequential deletion, each involving a single deletion event (FIG. 39). According to this model, Siglec-5 could have arisen from CD33-likeSV by deletion of the exons encoding domain 3 and its associated linker. Siglec-5 could have then have given rise to a three-domain Siglec (e.g., Siglec-6) by a further deletion of Siglec-5 domain 4. The other three-domain, Siglecs (i.e., Siglecs-7,-8 & -9) could have then been generated by gene duplication events. This would be consistent with the high degree of sequence similarity shared between these three Siglecs (FIG. 1 & FIG. 2). In principle, CD33/Siglec-3 could have arisen from any of the other CD33-related Siglecs by a single deletion event (FIG. 3). It also seems likely based on sequence comparisons that NUG/Siglec 4 and Siglec-5 are derived from a common progenitor, since they have the same number of Ig domains and share low, but significant sequence similarity throughout the extracellular and intracellular regions (Table I).

Chromosomal Localization and Expression of the CD33-likeSV Gene

The CD33-likeSV gene was mapped by in situ hybridization to the long arm of chromosome 19, in the 19q13.3 band (FIG. 40A), closely linked to the other CD33-related Siglecs (15-17, 19, 22, 30). Northern blot analysis (FIG. 40B) revealed presence of a major CD33-likeSV mRNA transcript of approximately 3.0 kb, with highest levels in spleen, lymph node, blood leukocytes and appendix. Readily detectable mRNA could also be seen in several other tissues (FIG. 40B).

CD33-LikeSV Mediates Sialic Acid-Dependent Binding to Human RBC and to Glycoconjugates To investigate the potential sialic acid binding properties of CD33-likeSV, we initially performed binding assays in which native and sialidase-treated human RBC were added to transiently transfected COS cells. Very little binding could be detected with untreated COS cells expressing CD33-likeSV. In contrast, following sialidase-treatment, high levels of RBC binding were seen (data not shown). Similar results were obtained using CHO cells stably transfected with CD33-likeSV (data not shown). Much of the increase in binding seen after treating Siglec expressing cells with sialidase is thought to be due to unmasking the sialic acid binding site on Siglecs from cis interactions with sialic acids at the cell surface (14, 15, 17, 19, 21, 22, 31, 32). All binding of RBC to sialidase-treated cells expressing CD33-likeSV was abolished when the RBC were pretreated with sialidase, demonstrating that the binding was sialic acid-dependent (data not shown).

To determine the sialic acid linkage preference of CD33-likeSV, binding assays were carried out with synthetic polyacrylamide conjugates, carrying either 3' or 6' sialyllactose or lactose. In these experiments, COS cells were transiently transfected with CD33-likeSV or CR1 as a negative control. FACS analysis showed that 20-30% of the cells expressed each molecule three days after the transfection (data not shown). Transfected cells were either untreated or treated with sialidase immediately before the binding assay to remove potentially inhibitory sialic acids in the COS cell glycocalyx (FIG. 41). Very little binding of PAA conjugates could be observed with untreated cells, but after sialidase treatment, CD33-likeSV transfected COS cells bound strongly to glycoconjugates carrying sialic acid in either $\alpha$2,3 or $\alpha$2,6 linkages (FIG. 41). No specific binding was observed with lactose-PAA used as a negative control.

Expression of CD33-LikeSV on Human Peripheral Blood Leukocytes

An affinity purified mouse polyclonal antibody was prepared to the extracellular region of CD33-likeSV and shown by FACS analysis not to cross-react with Siglecs-3, -5, -7, and -8 expressed on CHO cells (data not shown). A monoclonal antibody, 5G6, was also raised against CD33-likeSV and shown not to cross-react with Siglecs-3, -5, -7, -8 and -9 expressed on CHO cells (data not shown). A detailed analysis of the expression of CD33-likeSV was carried out by FACS analysis, using human peripheral blood leukocytes. Indistinguishable results were obtained using either the polyclonal or monoclonal antibodies. First, expression on granulocyte, monocyte, and lymphocyte subsets was compared (FIG. 42A). This revealed low levels of CD33-likeSV on granulocytes and monocytes and a subpopulation of lymphocytes. Since CD33-likeSV transcripts were identified frequently in an eosinophil cDNA library, we asked whether CD33-likeSV was normally expressed on eosinophils. Using anti CD16 mAb to distinguish eosinophils from neutrophils, the CD16-negative eosinophils were found to stain specifically with 5G6 (FIG. 42B). To date, Siglec-8 is the only other Siglec that has been shown to be expressed on eosinophils, although in this case, its expression is highly restricted (19,20).

To characterize the lymphocyte-reactive cells in more detail, double labeling was carried out in which staining for CD33-likeSV was combined with staining for CD3 (pan T cell), CD4 and CD8 (T cell subsets), CD19 (pan B cell), CD16 (NK cells) and CD56 (NK cells) (FIG. 4B). The dominant populations expressing CD33-likeSV were $CD19^+$ B cells which were weakly labeled. Higher levels of CD33-likeSV was detected on a very small subset (0.5%) of cells in the lymphocyte gate that are also strongly positive and carry high levels of CD16 but no detectable CD56 (FIG. 6C). A similar pattern of CD33-likeSV staining was observed in 8 independent experiments with different donors, using either the polyclonal or monoclonal antibody. In a previous study on the expression of Siglec-9, the same population of CD16+ CD56− cells was shown to be labeled at a similar level to the staining shown here with CD33-likeSV. Although these cells constitute only a very minor subset of the total blood leukocytes, it is striking that they express two different Siglecs at relatively high levels. Currently the nature and potential functions of these cells is unclear, but they may correspond to a minor population of CD16+CD56− cells that were previously identified in human blood and shown to have the morphological features of NK cells and exhibit low levels of natural cytotoxicity. CD16+CD56− NK-like cells have been shown to be enriched in fetal cord blood compared with adult blood, and it has been speculated that they may represent an earlier stage of NK cell differentiation than the more normal CD16+ CD56+ NK cells.

Finally, FACS staining of various human cell lines was also performed. Consistent with the staining pattern with blood leukocytes, weak positive labeling was observed with the U937 promonocytic cell line and the Daudi (B cell) line. No staining was seen with HL 60 (myelomonocytic), THP-1 (monocytic) or YT (NK-like) cells (data not shown).

Molecular Characterisation of CD33-LikeSV

To investigate the molecular mass of CD33-likeSV expressed at the cell surface, the protein was immunoprecipitated from CD33-likeSV-CHO cells and from Daudi cells using the affinity purified polyclonal antibody (FIG. 43). In both cases, a single, heterogeneous band was observed of approximately 100 kDa under both reducing and non-reducing conditions, demonstrating that CD33-likeSV is exists as a monomer in the plasma membrane (FIG. 43-*gel* No. 1). No material was precipitated from wild-type CHO cells used as a negative control.

Conclusions:

The results presented here with CD33-likeSV extend our previous work characterizing novel Siglecs related to CD33/Siglec-3. Phylogeny analysis and sequence comparisons indicate that CD33-likeSV is the most ancient of the CD33- related subset that may have given rise to the other members of the subset by exon deletion and gene duplication.

REFERENCES

1. Crocker, P. R., Clark, E. A., Filbin, M., Gordon, S., Jones, Y., Kehrl, J. H., Kelm, S., Le Douarin, N., Powell, L., Roder, J., Schnaar, R. L., Sgroi, D. C., Stamenkovic, K., Schauer, R., Schachner, M., van den Berg, T. K., van der Merwe, P. A., Watt, S. M., and Varki, A. (1998) *Glycobiology* 8, v.
2. May, A. P., Robinson, R. C., Vinson, M., Crocker, P. R., and Jones, E. Y. (1998) *Molecular Cell* 1, 719-28.
3. Nitschke, L., Carsetti, R., Ocker, B., Kohler, G., and Lamers, M. C. (1997) *Curr Biol* 7, 133-43.
4. Taylor, V. C., Buckley, C. D., Douglas, M., Cody, A. J., Simmons, D. L., and Freeman, S. D. (1999) *Journal of Biological Chemistry* 274, 11505-12.
5. Ulyanova, T., Blasioli, J., Woodford-Thomas, T. A., and Thomas, M. L. (1999) Eur. J. Immunol 29, 3440-9.
6. Falco, M., Biassoni, R., Bottino, C., Vitale, M., Sivori, S., Augugliaro, R., Moretta, L., and Moretta, A. (1999) *J. Exp. Med.* 190, 793-802.
7. Vitale, C., Romagnani, C., Falco, M., Ponte, M., Vitale, M., Moretta, A., Bacigalupo, A., Moretta, L., and Mingari, M. C. (1999) *Proc. Natl Acad. Sci. USA* 96, 15091-6.
8. Ferlazzo, G., Spaggiari, G. M., Semino, C., Melioli, G., and Moretta, L. (2000) *Eur J Immunol* 30, 827-33.
9. Paul, S. P., Taylor, L. S., Stansbury, E. K., and McVicar, D. W. (2000) *Blood* 96, 483-90.
10. Crocker, P. R., Mucklow, S., Bouckson, V., McWilliam., A., Willis, A. C., Gordon, S., Milon, G., Kelm, S., and Bradfield, P. (1994) *The EMBO Journal* 13, 4490-503.
11. Powell, L. D., Sgrol, D., Sjoberg, E. R., Stamenkovic, I., and Varki, A. (1993) *Journal of Biological Chemistry* 268, 7019-8.
12. Sgroi, D., Varki, A., Braesch-Andersen, S., and Stamenkovic, I. (1993) *Journal of Biological Chemistry* 268, 7011-8.
13. Kelm, S., Pelz, A., Schauer, R., Filbin, M. T., Tang, S., de Bellard, M. E., Schnaar, R. L., Mahoney, J. A., Hartnell, A., Bradfield, P., and Crocker, P. R. (1994) *Current Biology* 4, 965-72.
14. Freeman, S. D., Kelm, S., Barber, E. K., and Crocker, P. R. (1995) *Blood* 85, 2005-12.
15. Comish, A. L., Freeman, S., Forbes, G., Ni, J., Zhang, M., Cepeda, M., Gentz, R., Augustus, M., Carter, K. C., and Crocker, P. R. (1998) *Blood* 92,2123-32.
16. Patel, N., Linden, E. C., Altmann, S. W., Gish, K., Balasubramanian, S., Timans, J. C., Peterson, D., Bell, M. P., Bazan, J. F., Varki, A., and Kastelein, R. A. (1999) *J. Biol. Chem.* 274, 22729-38.
17. Nicoll, G., Ni, J., Liu, D., Klenerman, P., Munday, J., Dubock, S., Mattei, M. G., and Crocker, P. R. (1999) *J. Biol. Chem.* 274, 34089-34095.
18. Angata, T., and Varki, A. (2000) *Glycobiology* 10, 431-8.
19. Floyd, H., Ni, J., Cornish, A. L., Zeng, Z., Liu, D., Carter, K. C., Steel, J., and Crocker, P. R. (2000) *J. Biol. Chem.* 275, 861-6.
20. Kikly, K. K., Bochner, B. S., Freeman, S. D., Tan, K. B., Gallagher, K. T., D'Alessio K. J., Holmes, S. D., Abrahamson, J. A., Erickson-Miller, C. L., Murdock, P. R., Tachimoto, H., Schleimer, R. P., and White, J. R. (2000) *J. Allergy Clin Immunol* 105, 1093-100.
21. Zhang, J. Q., Nicoll, G., Jones, C., and Crocker, P. R. (2000) *J. Biol Chem* 275,22121-6.
22. Angata, T., and Varki, A. (2000) *J. Biol Chem* 275, 22127-35.
23. Hartnell, A., Steel, J., Turley, H., Jones, M., Jackson, D. G., and Crocker, P. R. (2000) *Blood* in press.
24. Huang, X., and Miller, W. (1991) *Adv. Appl. Math.* 12,337-357.
25. Ollendorff, V., Manei, M., Fournier, E., Adelaide, J., Lopez, M., Rosnet, O., and Bimbaum, D. (1998) *Int. J. Oncol.* 13, 1159-61.
26. Skolnik, E. Y., Lee, C. H., Batzer, A., Vicentini, L. M., Zhou, M., Daly, R., Myers, M. J., Jr., Backer, I M., Ulirich, A., White, M. F., and et al. (1993) *Embo J* 12, 1929-36.
27. Ogura, K., Tsuchiya, S., Terasawa, H., Yuzawa, S., Hatanaka, H., Mandiyan, V., Schiessinger, J., and' Inagaki, F. (1999) *J. Mol Biol* 289, 439-45.
28. Rahuel, J., Gay, B., Erdmann, D., Strauss, A., Garcia-Echeverria, C., Furet, P., Caravatti, G., Fretz, H., Schoepfer, J., and Grutter, M. G. (1996) *Nat Struct Biol* 3, 586-9.
29. Buday, L., and Downward, J. (1993) *Cell* 73, 611-20.
30. Peiper, S. C., Ashmun, R. A., and Look, A. T. (1988) *Blood* 72, 314-21.
31. Braesch-Andersen, S., and Stamenkovic, I. (1994) *Journal of Biological Chemistry* 269, 11783-6.
32. Razi, N., and Varki, A. (1998) *Proceedings of the National Academy of Sciences* 95, 7469-74.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties. Additionally, the specifications and sequence listings of U.S. Provisional Applications Nos. 60/243,792, filed on Oct. 30, 2000, 60/198,407, filed Apr. 19, 2000, and 60/105,971, filed Oct. 28, 1998, of U.S. application Ser. No. 09/836,353, filed Apr. 18, 2001, and of International Application Serial No. PCT/US99/25031, filed Oct. 27, 1999, are all hereby incorporated by reference in their entireties.

What is claimed is:

1. An isolated antibody or fragment thereof that specifically binds to a protein selected from the group consisting of:

(a) a protein whose amino acid sequence consists of amino acid residues 23 to 1189 of SEQ ID NO:35;

(b) a protein whose amino acid sequence consists of amino acid residues 1 to 1189 of SEQ ID NO:35;

(c) a protein whose amino acid sequence consists of a portion of SEQ ID NO:35, wherein said portion is at least 30 contiguous amino acid residues in length; and (d) a protein whose amino acid sequence consists of a portion of SEQ ID NO:35, wherein said portion is at least 50 contiguous amino acid residues in length.

2. The antibody or fragment thereof of claim 1 that specifically binds protein (a).

3. The antibody or fragment thereof of claim 1 at specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 3 wherein said protein bound by said antibody or fragment thereof is glycosylated.

7. The antibody or fragment thereof of claim 3 wherein said antibody or fragment thereof is human.

8. The antibody or fragment thereof of claim 3 wherein said antibody or fragment thereof is polyclonal.

9. The antibody or fragment thereof of claim 3 wherein said antibody or fragment thereof is monoclonal.

10. The antibody or fragment thereof of claim 3 which is selected from the group consisting of:

(a) a chimeric antibody or fragment thereof;

(b) a humanized antibody or fragment thereof;

(c) a single chain antibody; and (d) a Fab fragment.

11. The antibody or fragment thereof of claim 3 which is labeled.

12. The antibody or fragment thereof of claim 3 wherein said antibody or fragment thereof specifically binds to said protein in a Western blot or an ELISA.

13. An isolated cell that produces the antibody or fragment thereof of claim 3.

14. A hybridoma that produces the antibody or fragment thereof of claim 3.

15. A method of detecting an integrin alpha 11 protein, comprising SEQ ID NO:35 in a biological sample comprising:

(a) contacting the biological sample with the antibody or fragment thereof claim 13; and (b) detecting the integrin alpha 11 protein in the biological sample.

16. An isolated antibody or fragment thereof that specifically binds a protein purified from a cell culture wherein said protein is encoded by a polynucleotide encoding amino acids 23 to 1189 of SEQ ID NO:35.

17. The antibody or fragment thereof of claim 16 wherein said antibody or fragment thereof is monoclonal.

18. The antibody or fragment thereof of claim 16 wherein said antibody or fragment thereof is polyclonal.

19. The antibody or fragment thereof of claim 16 wherein said antibody or fragment thereof is human.

20. The antibody or fragment thereof of claim 16 which is selected from the group consisting of:

(a) a chimeric antibody or fragment thereof;

(b) a humanized antibody or fragment thereof;

(c) a single chain antibody; and (d) a Fab fragment.

21. The antibody or fragment thereof of claim 16 wherein said antibody or fragment thereof specifically binds to said protein in a Western blot or an ELISA.

22. The antibody or fragment thereof of claim 16 wherein the amino acid sequence of said protein consists of amino acid residues 1 to 1189 of SEQ ID NO:35.

* * * * *

UNITED STATES PATENT AND TRADEMARK OFFICE

CERTIFICATE OF CORRECTION

PATENT NO. : 7,446,176 B2
APPLICATION NO. : 11/246999
DATED : November 4, 2008
INVENTOR(S) : Ni et al.

It is certified that error appears in the above-identified patent and that said Letters Patent is hereby corrected as shown below:

In the Claims:

At Column 730, Claim 15, line 32, delete “SEQ ID NO:35 in” and insert --SEQ ID NO:35, in--.

At Column 730, Claim 15, line 35, delete “thereof claim 13” and insert --thereof of claim 3--.

Signed and Sealed this

Seventeenth Day of February, 2009

JOHN DOLL

*Acting Director of the United States Patent and Trademark Office*

UNITED STATES PATENT AND TRADEMARK OFFICE

CERTIFICATE OF CORRECTION

PATENT NO. : 7,446,176 B2
APPLICATION NO. : 11/246999
DATED : November 4, 2008
INVENTOR(S) : Ni et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (367) days Delete the phrase “by 367 days” and insert -- by 391 days --

Signed and Sealed this

Twenty-seventh Day of April, 2010

David J. Kappos
*Director of the United States Patent and Trademark Office*

UNITED STATES PATENT AND TRADEMARK OFFICE

CERTIFICATE OF CORRECTION

PATENT NO. : 7,446,176 B2
APPLICATION NO. : 11/246999
DATED : November 4, 2008
INVENTOR(S) : Ni et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (367) days Delete the phrase "by 367 days" and insert -- by 391 days --

Signed and Sealed this

Eighth Day of June, 2010

David J. Kappos
*Director of the United States Patent and Trademark Office*

UNITED STATES PATENT AND TRADEMARK OFFICE

CERTIFICATE OF CORRECTION

PATENT NO. : 7,446,176 B2
APPLICATION NO. : 11/246999
DATED : November 4, 2008
INVENTOR(S) : Jian Ni et al.

It is certified that error appears in the above-identified patent and that said Letters Patent is hereby corrected as shown below:

This certificate vacates the Certificate of Correction issued June 8, 2010. The certificate is a duplicate of the Certificate of Correction issued April 27, 2010. All requested changes were included in the Certificate of Correction issued April 27, 2010.

Signed and Sealed this

Sixth Day of July, 2010

David J. Kappos

David J. Kappos
*Director of the United States Patent and Trademark Office*